(12) United States Patent
Evdokimov et al.

(10) Patent No.: US 7,769,575 B2
(45) Date of Patent: *Aug. 3, 2010

(54) THREE DIMENSIONAL COORDINATES OF HPTPBETA

(75) Inventors: Artem Gennady Evdokimov, Loveland, OH (US); Matthew Eugene Pokross, Loveland, OH (US)

(73) Assignee: Warner Chilcott, LLC, Fajardo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/409,111

(22) Filed: Mar. 23, 2009

(65) Prior Publication Data

US 2010/0030487 A1     Feb. 4, 2010

Related U.S. Application Data

(62) Division of application No. 10/634,027, filed on Aug. 4, 2003, now Pat. No. 7,507,568.

(60) Provisional application No. 60/413,547, filed on Sep. 25, 2002.

(51) Int. Cl.
    *C12N 9/14* (2006.01)
    *G01N 31/00* (2006.01)
    *G06G 7/58* (2006.01)

(52) U.S. Cl. .............................. 703/11; 436/4; 436/195; 703/21

(58) Field of Classification Search ........................ None
    See application file for complete search history.

(56) References Cited

U.S. PATENT DOCUMENTS

| | | |
|---|---|---|
| 4,673,641 A | 6/1987 | George et al. |
| 5,424,398 A | 6/1995 | Middeldorp et al. |
| 5,585,089 A | 12/1996 | Queen et al. |
| 5,807,819 A | 9/1998 | Cheng et al. |
| 5,994,128 A | 11/1999 | Fallaux et al. |
| 6,033,908 A | 3/2000 | Bout et al. |
| 6,342,219 B1 | 1/2002 | Thorpe et al. |
| 6,589,758 B1 | 7/2003 | Zhu |
| 6,596,722 B2 | 7/2003 | Moltzen |
| 7,226,755 B1 | 6/2007 | Peters et al. |
| 7,507,568 B2 | 3/2009 | Evdokimov |
| 7,588,924 B2 | 9/2009 | Evdokimov et al. |
| 7,589,212 B2 | 9/2009 | Gray et al. |
| 2004/0167183 A1 | 8/2004 | Klopfenstein |
| 2004/0204863 A1 | 10/2004 | Kim et al. |
| 2007/0299116 A1 | 12/2007 | Gray |
| 2008/0004267 A1 | 1/2008 | Gray |
| 2008/0076764 A1 | 3/2008 | Peters et al. |
| 2008/0108631 A1 | 5/2008 | Gray |
| 2009/0227639 A1 | 9/2009 | Gray et al. |

FOREIGN PATENT DOCUMENTS

| | | |
|---|---|---|
| WO | WO 00/65085 | 11/2000 |
| WO | WO 00/65088 | 11/2000 |
| WO | WO 02/26774 | 4/2002 |

OTHER PUBLICATIONS

Altschul et al., "Gapped BLAST and PSI-BLAST: A New Generation of Protein Database Search Programs," *Nucleic Acids Res.*, 25(27):3389-3402 (1997).
Annex, "Growth factor-induced therapeutic angiogenesis in the heart: protein therapy," Cardiovascule Research, 65(3):649-655 (2005).
Ardelt, "Estradiol regulates angiopoietin-1 mRNA expression through estrogen receptor- in a rodent experimental," Stroke, 36:337-341 (2005).
Auerbach et al., "Angiogenesis Assays: A Critical Overview," *Clinical Chemistry*, 49:32-40 (2003).
Barany et al., "Solid-phase Peptide Synthesis: A Silver Anniversary Report," *Int. J. Peptide Protein Res.*, 30(6):705-739 (1987).
Bartlett et al., "Molecular Recognition in Chemical and Biological Problems; Cavet: A Program to Facilitate the Structure-Derived Design of Biologically Active Molecules," *Special Pub., Royal Chem. Soc.*, 78:182-196 (1989).
Bohm, "The Computer Program LUDI: A New Method for the De Novo Design of Enzyme Inhibitors," *J. Comuter-Aided. Molec. Design*, 6(1):61-78 (1992).
Bussolino, et al., "Molecular mechanisms of blood vessel formation," *Trends Biochem Sci.* 22(7):251-256 (1997).
Carano, et al, "Angiogenesis and bone repair," *Drug Discov Today* 2003 8(21): 980-9 (2003).
Carvalho, et al., "The role of angiogenesis in a murine tibial model of distraction osteogenesis," *Bone.* 34:849-861 (2004).
Chanteau et al., "Synthesis of Anthropomorphic Molecules: The NanoPutians," *J. Org. Chem.*, 68:8750-8766 (2003).
Cohen et al., "Molecular Modeling Software and Methods for Medicinal Chemistry," *J. Med. Chem.*, 33(3):883-894 (1990).
Fachinger et al., "Functional Interaction of Vascular Endothelial-Protein-Tyrosine Phosphatase with the Angiopoietin Receptor Tie-2," *Oncogene*, 18:5948-5953 (1999).
Flower, "Modelling G-Protein-Coupled Receptors for Drug Design," *Biochimica et Biophysica Acta*, 1422:207-234 (1999).
Folkman, J.,"Tumor angiogenesis," *The Molecular Basis of Cancer* (eds. Mendelsohn, J., Howley, P. M., Israel, M. A. & Liotta, L. A.) 206-232 (1995).
Gaits et al., "Increase in Receptor-like Protein Tyrosine Phosphatase Activity and Express Level on Density-Dependent Growth Arrest of Endothelial Cells," *Biochem J.*, 311:97-103 (1995).
Goodford, "A Computational Procedure for Determining Energetically Favorable Binding Sites on Biologically Important Macromolecules," *J. Med. Chem.*, 28(7):849-57 (1985).

(Continued)

*Primary Examiner*—Suzanne M. Noakes
(74) *Attorney, Agent, or Firm*—Richard S. Echler

(57) ABSTRACT

The crystal structures of catalytic domain of HPTPbeta, both ligand-bound and ligand-free are described. These structures are useful in computer aided drug design for identifying compounds that bind or activate HPTPbeta and thereby modulate angiogenesis mediated disorders or diseases.

10 Claims, 304 Drawing Sheets

OTHER PUBLICATIONS

Goodsell et al., "Automated Docking of Substrates to Proteins by Simulated Annealing," *Proteins Struct. Funct. Genet.* 8:195-202 (1990).

Harder et al., "Characterization and Kinetic Analysis of the Intracellular Domain of Human Protein Tyrosine Phosphatase β (HPTPβ) Using Synthetic Phosphopeptides," *Biochem. J.*, 296:395-401 (1994).

Henikoff et al., "Amino Acid Substitution Matrices from Protein Blocks," *Proc. Natl. Acad. Sci. USA* 89:10915-10919 (1992).

Hopkins et al., "Inhibitors of Kinesin Activity from Structure-Based Computer Screening," *Biochemistry*, 39:2805-2814 (2000).

Huang et al., "HCPTPA, a Protein Tyrosine Phosphatase that Regulates Vascular Endothelial Growth Factor Receptor-Mediated Signal Transduction and Biological Activity," *J. Biol. Chem.*, 53:38183-38188 (1999).

Itoh et al., "Purification and Characterization of the Catalytic Domains of the Human Receptor-Linked Protein Tyrosine Phosphatases HPTPβ, Leukocyte Common Antigen (LCA), and Leukocyte Common Antigen-Related Molecule (LAR)," *Journal of Biological Chemistry*, 267(17):12356-12363 (1992).

Jones et al., "Development and Validation of a Genetic Algorithm for Flexible Docking," *J. Mol. Biol.*, 267:727-748 (1997).

Jones et al., "Molecular Recognition of Receptor Sites Using a Genetic Algorithm with a Description of Desolvation," *J. Mol. Biol.*, 245:43-53 (1995).

Keen, "Radioligand Binding Methods for Membrane Preparations and Intact cells," *Methods in Molecular Biology*, 83:*Receptor Signal Transduction Protocols*, edited Humana Press Inc., Totoway N.J. (1997).

Köhler et al., "Continuous Cultures of Fused Cells Secreting Antibody of Predefined Specificity," *Biotechnolog*, 24:524-526 (1992).

Krueger et al., "Structural Diversity and evolution of Human Receptor-Like Protein Tyrosine Phosphatases," *The EMBO Journal*, 9(10):3241-3252 (1990).

Kugathasan, "Role of angiopoietin-1 in experimental and human pulmonary arterial hypertension," *Chest*, 128:633-642 (2005).

Kuntz et al., "A Geometric Approach to Macromolecule—Ligand Interactions," *J. Mol. Biol.* 161:269-288 (1982).

Lin et al., "Inhibition of Tumor Angiogenesis Using a Soluble Receptor Establishes a Role for Tie2 in Pathologic Vascular Growth," *J. Clinical Invest.*,100(8):2072-2078 (1997).

Ma et al., "RNase Protection Assay," *Methods*, 10(3):273-8 (1996).

Martin, "3D Database Searching in Drug Design," *J. of Medicinal Chemistry*, 35(12):2145-2154 (1992).

Meadows, "Keeping Up with Drug Safety Information," 2006: FDA Consumer Magazine: http://www.fda.gov/fdac/features/2006/306_drugsafety.html, accessed Mar. 17, 2008.

Merrifield, "Solid Phase Peptide Synthesism. I. The Synthesis of a Tetrapeptide," *J. Am. Chem. Soc.*, 85:2149-2154 (1963).

Miranker et al., "Functionality Maps of Binding Sites: A Multiple Copy Simultaneous Search Method," *Proteins: Struc. Func. And Genectics*, 11(1):29-34 (1991).

Navaza, "*AMoRe*: An Automated Package for Molecular Replacement," *J. Acta Cryst.* A50:157-163 (1994).

Nguyen et al., "Cellular Interactions in Vascular Growth and Differentiation," Int. Rev. Cytol., 204:1-48 (2001).

Nishibata et al., "Automatic Creation of Drug Candidate Structures Based on Receptor Structure. Starting Point for Artificial Lead Generation," *Tetrahedron*, 47(43):8985-8990 (1991).

O'Reilly, "Angiostatin: a novel angiogenesis inhibitor that mediates the suppression of metastases by a Lewis lung carcinoma," Cell, 79(2):315-28 (1994).

O'Reilly, "Endostatin: an endogenous inhibitor of angiogenesis and tumor growth," Cell, 88(2):277-85 (1997).

Rarey et al., "A Fast Flexible Docking Method Using an Incremental Construction Algorithm," *J. Mol. Biol.*, 261:470-489 (1996).

Riechmann et al., "Reshaping Human Antibodies for Therapy," Nature, 332:323-327 (1988).

Saliba, "Heparin in the Treatment of Burns: A Review," May 2001; Burn 27(4):349-358; full text edition, pp. 1-16.

Schöneberg et al., "Structural basis of G protein-coupled receptor function," *Molecular and Cellular Endocrinology*, 151:181-193 (1999).

Sexton, "Recent advances in our understanding of peptide hormone receptors and RAMPS," *Current Opinion in Drug Discovery and Development*, 2(5):440-448 (1999).

Shiojima, "Disruption of coordinated cardiac hypertrophy and angiogenesis contributes to the transition to heart failure," J. Clinical Invest., 115(8):2108-18 (2005).

Shoichet et al., "Lead Discovery Using Molecular Docking," *Chem. Biology*, 6:439-446 (2002).

Siddiqui, "Combination of angiopoietin-1 and vascular endothelial growth factor gene therapy enhances arteriogenesis in the ischemic myocardium," Biochem. Biophys. Res. Comm., 310(3):1002-1009 (2003).

Simons, Angiogenesis: where do we stand now? Circulation, 111:1556-1566 (2005).

Simons, "Clinical Trials in Coronary Angiogenesis: Issues, Problems, Consensus," Circulation, 102:e73-e86 (2000).

Stal et al., "Detailed Analysis of Scoring Functions for Virtual Screening," *J. Med. Chem.*, 44:1035-1042 (2001).

Stetler-Stevenson, "The Role of Matrix Metalloproteinases in Tumor Invasion, Metastasis, and Angiogenesis," *Surg. Oncol. Clin. N. Am.*, 10(2):383-392 (2001).

Suri et al., "Increased Vascularization in Mice Overexpressing Angiopoietin-1," *Science*, 282:468-471 (1998).

Takahashi, "Adenoviral-delivered Angiopoietin-1 Reduces the Infarction and Attenuates the Progression of Cardiac Dysfunction in the Rat Model of Acute Myocardial Infarction," Molecular Therapy, 8(4):584-592 (2003).

Teischer, "Potentiation of cytotoxic cancer therapies by TNP-470 alone and with other anti-angiogenic agents," Int. J. Cancer, 57(6)920-925 (1994).

Thurston et al., "Angiopoietin-1 Protects the Adult Vasculature Against Plasma Leakage," *Nature Medicine*, 6(4):460-463 (2000).

Thurston, "Complementary Actions of VEGF and Angiopoietin-1 on Blood Vessel Growth and Leakage," *J. Anat.*, 200(6):575-80 (2002).

Vailhe et al., "In vitro Models of Vasculogenesis and Angiogenesis," *Laboratory Investigation*, 81(4):439-452 (2001).

Wang et al., "Expressions and Characterization of Wild Type, Truncated, and Mutant Forms of the Intracellular Region of the Receptor-Like Protein Tyrosine Phosphatase HPTPβ," *J. of Bio. Chem.*, 267(23):16696-16702 (1992).

Weidner, "Tumor Angiogenesis and Metastasis Correlation in Invasive Breast Carcinoma," *New Eng. J. Med.*, 324(1):108 (1991).

Whitaker et al., "Vascular Endothelial Growth Factor Receptor-2 and Neuropilin-1 Form a Receptor Complex That Is Responsible for the Differential Signaling Potency of VEGF$_{165}$ and VEGF$_{121}$," *Journal of Biological Chemistry*, 276(27):25520-25531 (2001).

Wright et al., "Protein-Tyrosine Phosphatases in the Vessel Wall Differential Expression After Acute Arterial Injury," *Arterioscler Thromb. Vasc.*, 1189-1198 (2000).

Yancopoulos et al., "Vascular-Specific Growth Factors and Blood Vessel Formation," *Nature*, 407(6801):242-248 (2000).

Zhang, "Vascular Endothelial Growth Factor and Angopoietins in Focal Cerebral Ischemia," *Trends Cardio. Med.*, 12(2):62-66 (2002).

Collaborative Computational Project, No. 4, "The CCP4 Suite: Programs for Protein Crystallography," *Acta Cryst.*, D50:760-763 (1994).

Daar, "Perspective: Emerging Resistance Profiles of Newly Approved Antiretroviral Drugs," *Topics in HIV Medicine*, 16(4):110-116 (2008).

Dean, "Recent Advances in Drug Design Methods: Where Will They Lead?" *BioEssays*, 16(9):683-687 (1994).

Jones et al., "Molecular Recognition of Receptor Sites Using a Genetic Algorithm with a Description of Desolvation," *J. Mol. Biol.*, 245:43-53 (1995).

Suggitt et al., "50 Years of Preclinical Anticancer Drug Screening: Empirical to Target-Drive Approaches," *Clinical Cancer Research*, 11:971-981 (2005).

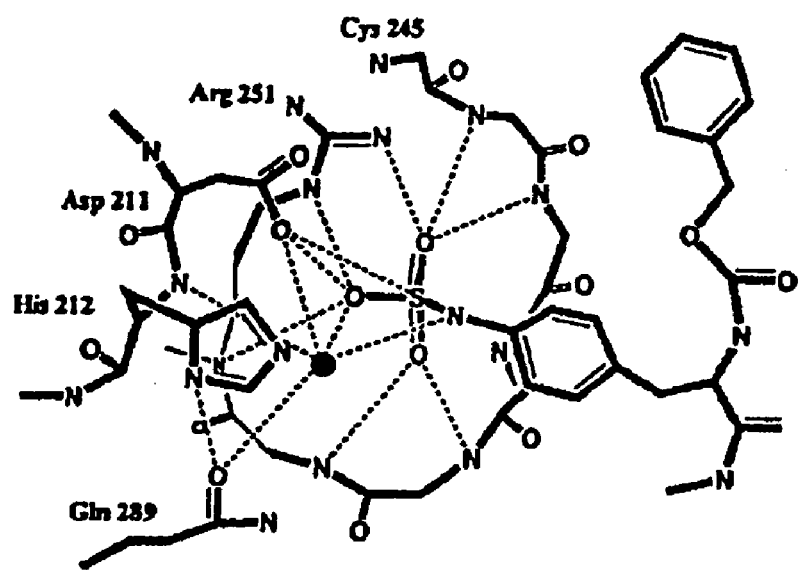
(a)
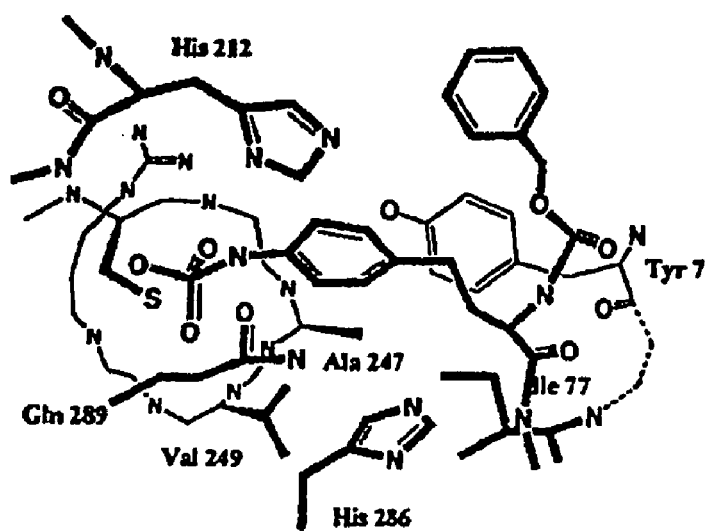
(b)
FIGURE 4

```
CRYST1   61.890    71.535   70.345  90.00  93.25   90.00
ATOM      1    N   LYS A   19      12.885  20.303  21.460 1.000106.97
ATOM      2   CA   LYS A   19      12.939  19.537  20.223 1.000 85.75
ATOM      3   CB   LYS A   19      13.192  20.422  19.007 1.000 87.72
ATOM      4   CG   LYS A   19      11.902  20.923  18.320 1.000 95.27
ATOM      5   CD   LYS A   19      12.014  20.782  16.801 1.000 99.48
ATOM      6   CE   LYS A   19      10.663  21.012  16.143 1.000100.17
ATOM      7   NZ   LYS A   19      10.303  22.523  16.035 1.000102.13
ATOM      8    C   LYS A   19      14.027  18.457  20.298 1.000 78.84
ATOM      9    O   LYS A   19      15.217  18.783  20.327 1.000 93.11
ATOM     10    N   THR A   20      13.573  17.224  20.310 1.000 69.90
ATOM     11   CA   THR A   20      14.257  15.957  20.169 1.000 59.58
ATOM     12   CB   THR A   20      13.713  15.258  18.900 1.000 45.21
ATOM     13  OG1   THR A   20      14.633  14.309  18.358 1.000 57.38
ATOM     14  CG2   THR A   20      13.489  16.286  17.795 1.000 64.36
ATOM     15    C   THR A   20      15.771  16.101  20.107 1.000 59.34
ATOM     16    O   THR A   20      16.304  16.833  19.272 1.000 83.31
ATOM     17    N   SER A   21      16.471  15.408  20.994 1.000 53.48
ATOM     18   CA   SER A   21      17.903  15.206  20.988 1.000 46.96
ATOM     19   CB   SER A   21      18.353  14.742  19.581 1.000 47.66
ATOM     20   OG   SER A   21      19.770  14.620  19.599 1.000 58.97
ATOM     21    C   SER A   21      18.784  16.398  21.346 1.000 41.17
ATOM     22    O   SER A   21      18.538  17.534  20.963 1.000 47.65
ATOM     23    N   CYS A   22      19.843  16.085  22.080 1.000 41.72
ATOM     24   CA   CYS A   22      20.898  16.977  22.509 1.000 43.91
ATOM     25   CB   CYS A   22      20.566  17.726  23.798 1.000 41.39
ATOM     26   SG   CYS A   22      19.635  19.259  23.584 1.000109.59
ATOM     27    C   CYS A   22      22.183  16.174  22.752 1.000 37.65
ATOM     28    O   CYS A   22      22.505  15.999  23.925 1.000 36.88
ATOM     29    N   PRO A   23      22.822  15.731  21.680 1.000 42.64
ATOM     30   CA   PRO A   23      24.007  14.873  21.736 1.000 46.23
ATOM     31   CB   PRO A   23      24.238  14.461  20.277 1.000 45.02
ATOM     32   CG   PRO A   23      23.012  14.867  19.533 1.000 44.64
ATOM     33   CD   PRO A   23      22.447  16.037  20.280 1.000 45.34
ATOM     34    C   PRO A   23      25.254  15.595  22.253 1.000 49.52
ATOM     35    O   PRO A   23      25.409  16.802  22.079 1.000 43.06
ATOM     36    N   ILE A   24      26.145  14.847  22.897 1.000 50.39
ATOM     37   CA   ILE A   24      27.396  15.350  23.436 1.000 45.58
ATOM     38   CB   ILE A   24      27.299  15.718  24.926 1.000 45.32
ATOM     39  CG1   ILE A   24      26.035  16.480  25.330 1.000 43.71
ATOM     40  CD1   ILE A   24      25.222  15.741  26.376 1.000 43.61
ATOM     41  CG2   ILE A   24      28.545  16.488  25.350 1.000 57.16
ATOM     42    C   ILE A   24      28.517  14.327  23.296 1.000 43.32
ATOM     43    O   ILE A   24      28.322  13.140  23.537 1.000 46.87
ATOM     44    N   LYS A   25      29.713  14.766  22.907 1.000 49.84
ATOM     45   CA   LYS A   25      30.820  13.808  22.815 1.000 50.13
ATOM     46   CB   LYS A   25      31.917  14.375  21.922 1.000 59.09
ATOM     47   CG   LYS A   25      31.444  14.757  20.527 1.000 65.03
ATOM     48   CD   LYS A   25      32.307  14.074  19.471 1.000 71.18
ATOM     49   CE   LYS A   25      31.469  13.255  18.493 1.000 72.46
ATOM     50   NZ   LYS A   25      32.328  12.452  17.576 1.000 73.47
ATOM     51    C   LYS A   25      31.346  13.486  24.204 1.000 52.08
```

FIGURE 7

```
ATOM     52  O   LYS A  25      31.294  14.340  25.095  1.000 53.68
ATOM     53  N   ILE A  26      31.849  12.274  24.434  1.000 52.14
ATOM     54  CA  ILE A  26      32.275  11.942  25.793  1.000 63.74
ATOM     55  CB  ILE A  26      32.817  10.504  25.904  1.000 65.16
ATOM     56  CG1 ILE A  26      34.316  10.370  25.624  1.000 65.92
ATOM     57  CD1 ILE A  26      34.847   8.970  25.852  1.000 69.50
ATOM     58  CG2 ILE A  26      32.016   9.561  25.016  1.000 68.17
ATOM     59  C   ILE A  26      33.335  12.911  26.307  1.000 70.34
ATOM     60  O   ILE A  26      33.411  13.146  27.515  1.000 67.42
ATOM     61  N   ASN A  27      34.141  13.465  25.406  1.000 74.12
ATOM     62  CA  ASN A  27      35.231  14.350  25.799  1.000 78.44
ATOM     63  CB  ASN A  27      36.116  14.679  24.588  1.000 86.40
ATOM     64  CG  ASN A  27      36.877  15.980  24.768  1.000 90.22
ATOM     65  OD1 ASN A  27      37.854  16.044  25.515  1.000 84.42
ATOM     66  ND2 ASN A  27      36.432  17.033  24.084  1.000 85.29
ATOM     67  C   ASN A  27      34.740  15.649  26.423  1.000 75.19
ATOM     68  O   ASN A  27      35.473  16.309  27.170  1.000 89.55
ATOM     69  N   GLN A  28      33.507  16.048  26.126  1.000 67.31
ATOM     70  CA  GLN A  28      33.008  17.350  26.550  1.000 57.01
ATOM     71  CB  GLN A  28      32.497  18.097  25.313  1.000 54.35
ATOM     72  CG  GLN A  28      32.204  19.571  25.517  1.000 59.01
ATOM     73  CD  GLN A  28      32.233  20.351  24.213  1.000 66.07
ATOM     74  OE1 GLN A  28      31.315  21.121  23.907  1.000 69.78
ATOM     75  NE2 GLN A  28      33.291  20.154  23.427  1.000 81.02
ATOM     76  C   GLN A  28      31.894  17.263  27.581  1.000 51.77
ATOM     77  O   GLN A  28      31.322  18.300  27.939  1.000 55.71
ATOM     78  N   PHE A  29      31.566  16.061  28.051  1.000 50.17
ATOM     79  CA  PHE A  29      30.395  15.896  28.910  1.000 48.12
ATOM     80  CB  PHE A  29      29.984  14.424  29.031  1.000 47.45
ATOM     81  CG  PHE A  29      28.679  14.209  29.760  1.000 51.71
ATOM     82  CD1 PHE A  29      27.473  14.198  29.076  1.000 47.01
ATOM     83  CE1 PHE A  29      26.272  14.005  29.732  1.000 44.54
ATOM     84  CZ  PHE A  29      26.254  13.826  31.104  1.000 53.70
ATOM     85  CE2 PHE A  29      27.448  13.826  31.808  1.000 58.73
ATOM     86  CD2 PHE A  29      28.641  14.016  31.134  1.000 58.31
ATOM     87  C   PHE A  29      30.633  16.505  30.293  1.000 48.21
ATOM     88  O   PHE A  29      29.805  17.313  30.723  1.000 51.21
ATOM     89  N   GLU A  30      31.725  16.100  30.932  1.000 50.97
ATOM     90  CA  GLU A  30      32.118  16.617  32.243  1.000 40.77
ATOM     91  CB  GLU A  30      33.518  16.157  32.627  1.000 48.14
ATOM     92  CG  GLU A  30      33.957  16.520  34.038  1.000 61.37
ATOM     93  CD  GLU A  30      34.375  15.319  34.871  1.000 63.56
ATOM     94  OE1 GLU A  30      34.907  14.350  34.287  1.000 58.37
ATOM     95  OE2 GLU A  30      34.180  15.327  36.108  1.000 52.10
ATOM     96  C   GLU A  30      32.029  18.136  32.196  1.000 42.41
ATOM     97  O   GLU A  30      31.394  18.780  33.026  1.000 53.55
ATOM     98  N   GLY A  31      32.650  18.719  31.167  1.000 41.84
ATOM     99  CA  GLY A  31      32.510  20.160  31.001  1.000 40.41
ATOM    100  C   GLY A  31      31.063  20.531  30.754  1.000 48.99
ATOM    101  O   GLY A  31      30.515  21.443  31.373  1.000 50.79
ATOM    102  N   HIS A  32      30.407  19.821  29.826  1.000 45.73
ATOM    103  CA  HIS A  32      29.036  20.224  29.519  1.000 40.05
```

FIGURE 8

```
ATOM    104  CB   HIS A  32      28.481  19.370  28.368  1.000 44.33
ATOM    105  CG   HIS A  32      26.991  19.509  28.268  1.000 46.74
ATOM    106  ND1  HIS A  32      26.393  20.629  27.736  1.000 49.67
ATOM    107  CE1  HIS A  32      25.081  20.489  27.779  1.000 47.50
ATOM    108  NE2  HIS A  32      24.803  19.318  28.328  1.000 46.49
ATOM    109  CD2  HIS A  32      25.985  18.688  28.642  1.000 48.61
ATOM    110  C    HIS A  32      28.128  20.126  30.738  1.000 36.48
ATOM    111  O    HIS A  32      27.213  20.935  30.894  1.000 47.25
ATOM    112  N    PHE A  33      28.355  19.146  31.611  1.000 37.04
ATOM    113  CA   PHE A  33      27.466  18.940  32.760  1.000 45.61
ATOM    114  CB   PHE A  33      27.679  17.531  33.322  1.000 44.57
ATOM    115  CG   PHE A  33      26.836  17.160  34.514  1.000 38.23
ATOM    116  CD1  PHE A  33      25.506  17.531  34.598  1.000 30.80
ATOM    117  CE1  PHE A  33      24.748  17.191  35.702  1.000 28.41
ATOM    118  CZ   PHE A  33      25.308  16.468  36.737  1.000 30.68
ATOM    119  CE2  PHE A  33      26.635  16.088  36.669  1.000 27.11
ATOM    120  CD2  PHE A  33      27.378  16.436  35.564  1.000 28.82
ATOM    121  C    PHE A  33      27.652  19.998  33.837  1.000 49.01
ATOM    122  O    PHE A  33      26.723  20.391  34.548  1.000 35.78
ATOM    123  N    MET A  34      28.873  20.503  33.990  1.000 55.36
ATOM    124  CA   MET A  34      29.145  21.595  34.918  1.000 48.73
ATOM    125  CB   MET A  34      30.612  22.002  34.804  1.000 50.55
ATOM    126  CG   MET A  34      31.589  20.956  35.319  1.000 44.00
ATOM    127  SD   MET A  34      31.900  21.178  37.082  1.000 69.37
ATOM    128  CE   MET A  34      32.522  19.553  37.528  1.000157.91
ATOM    129  C    MET A  34      28.257  22.797  34.629  1.000 45.46
ATOM    130  O    MET A  34      27.672  23.409  35.524  1.000 51.08
ATOM    131  N    LYS A  35      28.169  23.133  33.343  1.000 42.34
ATOM    132  CA   LYS A  35      27.337  24.249  32.905  1.000 41.76
ATOM    133  CB   LYS A  35      27.357  24.341  31.387  1.000 48.16
ATOM    134  CG   LYS A  35      28.744  24.409  30.774  1.000 54.19
ATOM    135  CD   LYS A  35      28.745  25.343  29.558  1.000 56.45
ATOM    136  CE   LYS A  35      27.969  26.621  29.849  1.000 59.03
ATOM    137  NZ   LYS A  35      26.532  26.499  29.466  1.000 63.17
ATOM    138  C    LYS A  35      25.902  24.093  33.401  1.000 52.49
ATOM    139  O    LYS A  35      25.341  25.000  34.019  1.000 58.86
ATOM    140  N    LEU A  36      25.323  22.927  33.122  1.000 45.81
ATOM    141  CA   LEU A  36      23.967  22.608  33.538  1.000 38.58
ATOM    142  CB   LEU A  36      23.651  21.126  33.313  1.000 45.57
ATOM    143  CG   LEU A  36      23.288  20.682  31.901  1.000 50.85
ATOM    144  CD1  LEU A  36      24.233  21.277  30.870  1.000 57.32
ATOM    145  CD2  LEU A  36      23.292  19.159  31.799  1.000 59.71
ATOM    146  C    LEU A  36      23.753  22.921  35.011  1.000 35.30
ATOM    147  O    LEU A  36      22.857  23.679  35.382  1.000 53.13
ATOM    148  N    GLN A  37      24.585  22.311  35.857  1.000 36.39
ATOM    149  CA   GLN A  37      24.427  22.527  37.292  1.000 46.18
ATOM    150  CB   GLN A  37      25.238  21.504  38.085  1.000 56.71
ATOM    151  CG   GLN A  37      26.311  20.782  37.289  1.000 59.65
ATOM    152  CD   GLN A  37      26.681  19.440  37.891  1.000 59.86
ATOM    153  OE1  GLN A  37      27.412  18.655  37.285  1.000 76.78
ATOM    154  NE2  GLN A  37      26.190  19.165  39.092  1.000 59.17
ATOM    155  C    GLN A  37      24.844  23.938  37.696  1.000 53.32
```

FIGURE 9

| | | | | | | | | | |
|---|---|---|---|---|---|---|---|---|---|
| ATOM | 156 | O | GLN | A | 37 | 24.407 | 24.448 | 38.730 | 1.000 47.35 |
| ATOM | 157 | N | ALA | A | 38 | 25.684 | 24.560 | 36.876 | 1.000 58.65 |
| ATOM | 158 | CA | ALA | A | 38 | 26.173 | 25.905 | 37.151 | 1.000 68.20 |
| ATOM | 159 | CB | ALA | A | 38 | 27.038 | 26.387 | 35.992 | 1.000 88.29 |
| ATOM | 160 | C | ALA | A | 38 | 25.055 | 26.906 | 37.416 | 1.000 68.67 |
| ATOM | 161 | O | ALA | A | 38 | 24.003 | 26.933 | 36.777 | 1.000 57.74 |
| ATOM | 162 | N | ASP | A | 39 | 25.301 | 27.778 | 38.394 | 1.000 72.20 |
| ATOM | 163 | CA | ASP | A | 39 | 24.314 | 28.796 | 38.736 | 1.000 74.27 |
| ATOM | 164 | CB | ASP | A | 39 | 23.909 | 29.628 | 37.527 | 1.000 85.74 |
| ATOM | 165 | CG | ASP | A | 39 | 25.044 | 30.402 | 36.878 | 1.000 97.59 |
| ATOM | 166 | OD1 | ASP | A | 39 | 24.958 | 30.635 | 35.641 | 1.000113.10 |
| ATOM | 167 | OD2 | ASP | A | 39 | 26.039 | 30.750 | 37.574 | 1.000105.88 |
| ATOM | 168 | C | ASP | A | 39 | 23.087 | 28.123 | 39.343 | 1.000 66.70 |
| ATOM | 169 | O | ASP | A | 39 | 21.999 | 28.689 | 39.281 | 1.000 73.27 |
| ATOM | 170 | N | SER | A | 40 | 23.298 | 26.947 | 39.907 | 1.000 64.44 |
| ATOM | 171 | CA | SER | A | 40 | 22.275 | 26.159 | 40.578 | 1.000 64.68 |
| ATOM | 172 | CB | SER | A | 40 | 21.396 | 27.050 | 41.465 | 1.000 55.65 |
| ATOM | 173 | OG | SER | A | 40 | 22.105 | 28.171 | 41.962 | 1.000 78.01 |
| ATOM | 174 | C | SER | A | 40 | 21.376 | 25.400 | 39.603 | 1.000 62.90 |
| ATOM | 175 | O | SER | A | 40 | 20.184 | 25.716 | 39.507 | 1.000 51.42 |
| ATOM | 176 | N | ASN | A | 41 | 21.912 | 24.422 | 38.883 | 1.000 60.85 |
| ATOM | 177 | CA | ASN | A | 41 | 21.172 | 23.654 | 37.894 | 1.000 61.49 |
| ATOM | 178 | CB | ASN | A | 41 | 20.165 | 22.694 | 38.532 | 1.000 61.83 |
| ATOM | 179 | CG | ASN | A | 41 | 20.762 | 21.620 | 39.402 | 1.000 69.08 |
| ATOM | 180 | OD1 | ASN | A | 41 | 21.917 | 21.225 | 39.250 | 1.000 80.40 |
| ATOM | 181 | ND2 | ASN | A | 41 | 19.957 | 21.130 | 40.339 | 1.000 78.07 |
| ATOM | 182 | C | ASN | A | 41 | 20.361 | 24.555 | 36.966 | 1.000 67.15 |
| ATOM | 183 | O | ASN | A | 41 | 19.289 | 24.130 | 36.528 | 1.000 80.59 |
| ATOM | 184 | N | TYR | A | 42 | 20.825 | 25.767 | 36.685 | 1.000 63.68 |
| ATOM | 185 | CA | TYR | A | 42 | 19.955 | 26.712 | 35.995 | 1.000 58.60 |
| ATOM | 186 | CB | TYR | A | 42 | 20.581 | 28.109 | 35.929 | 1.000 62.78 |
| ATOM | 187 | CG | TYR | A | 42 | 19.713 | 29.057 | 35.134 | 1.000 60.11 |
| ATOM | 188 | CD1 | TYR | A | 42 | 18.414 | 29.333 | 35.553 | 1.000 62.46 |
| ATOM | 189 | CE1 | TYR | A | 42 | 17.603 | 30.195 | 34.844 | 1.000 61.51 |
| ATOM | 190 | CZ | TYR | A | 42 | 18.099 | 30.785 | 33.705 | 1.000 62.86 |
| ATOM | 191 | OH | TYR | A | 42 | 17.300 | 31.648 | 32.990 | 1.000 84.83 |
| ATOM | 192 | CE2 | TYR | A | 42 | 19.378 | 30.523 | 33.263 | 1.000 60.46 |
| ATOM | 193 | CD2 | TYR | A | 42 | 20.186 | 29.658 | 33.976 | 1.000 59.75 |
| ATOM | 194 | C | TYR | A | 42 | 19.631 | 26.234 | 34.584 | 1.000 44.43 |
| ATOM | 195 | O | TYR | A | 42 | 18.468 | 26.109 | 34.216 | 1.000 44.77 |
| ATOM | 196 | N | LEU | A | 43 | 20.701 | 25.982 | 33.847 | 1.000 40.94 |
| ATOM | 197 | CA | LEU | A | 43 | 20.603 | 25.447 | 32.499 | 1.000 53.15 |
| ATOM | 198 | CB | LEU | A | 43 | 21.973 | 25.359 | 31.837 | 1.000 60.19 |
| ATOM | 199 | CG | LEU | A | 43 | 22.899 | 26.570 | 31.920 | 1.000 67.43 |
| ATOM | 200 | CD1 | LEU | A | 43 | 23.839 | 26.600 | 30.724 | 1.000 71.66 |
| ATOM | 201 | CD2 | LEU | A | 43 | 22.126 | 27.871 | 32.003 | 1.000 79.71 |
| ATOM | 202 | C | LEU | A | 43 | 19.934 | 24.068 | 32.542 | 1.000 55.94 |
| ATOM | 203 | O | LEU | A | 43 | 18.895 | 23.893 | 31.904 | 1.000 56.22 |
| ATOM | 204 | N | LEU | A | 44 | 20.523 | 23.138 | 33.277 | 1.000 55.33 |
| ATOM | 205 | CA | LEU | A | 44 | 20.043 | 21.785 | 33.466 | 1.000 57.43 |
| ATOM | 206 | CB | LEU | A | 44 | 20.668 | 21.151 | 34.719 | 1.000 58.28 |
| ATOM | 207 | CG | LEU | A | 44 | 20.333 | 19.672 | 34.935 | 1.000 58.45 |

FIGURE 10

| ATOM | 208 | CD1 | LEU | A | 44 | 21.583 | 18.890 | 35.306 | 1.000 | 66.34 |
| --- | --- | --- | --- | --- | --- | --- | --- | --- | --- | --- |
| ATOM | 209 | CD2 | LEU | A | 44 | 19.259 | 19.509 | 35.999 | 1.000 | 64.52 |
| ATOM | 210 | C | LEU | A | 44 | 18.522 | 21.721 | 33.618 | 1.000 | 58.45 |
| ATOM | 211 | O | LEU | A | 44 | 17.875 | 20.876 | 33.005 | 1.000 | 62.57 |
| ATOM | 212 | N | SER | A | 45 | 18.022 | 22.636 | 34.428 | 1.000 | 58.88 |
| ATOM | 213 | CA | SER | A | 45 | 16.634 | 22.760 | 34.841 | 1.000 | 54.60 |
| ATOM | 214 | CB | SER | A | 45 | 16.564 | 23.645 | 36.093 | 1.000 | 50.24 |
| ATOM | 215 | OG | SER | A | 45 | 15.228 | 23.927 | 36.463 | 1.000 | 55.87 |
| ATOM | 216 | C | SER | A | 45 | 15.745 | 23.315 | 33.743 | 1.000 | 57.32 |
| ATOM | 217 | O | SER | A | 45 | 14.548 | 23.027 | 33.655 | 1.000 | 57.44 |
| ATOM | 218 | N | LYS | A | 46 | 16.303 | 24.131 | 32.849 | 1.000 | 62.62 |
| ATOM | 219 | CA | LYS | A | 46 | 15.432 | 24.625 | 31.776 | 1.000 | 66.95 |
| ATOM | 220 | CB | LYS | A | 46 | 15.937 | 25.962 | 31.242 | 1.000 | 74.26 |
| ATOM | 221 | CG | LYS | A | 46 | 16.359 | 26.942 | 32.327 | 1.000 | 76.81 |
| ATOM | 222 | CD | LYS | A | 46 | 15.163 | 27.555 | 33.036 | 1.000 | 76.98 |
| ATOM | 223 | CE | LYS | A | 46 | 13.919 | 27.533 | 32.159 | 1.000 | 77.01 |
| ATOM | 224 | NZ | LYS | A | 46 | 13.910 | 28.669 | 31.183 | 1.000 | 76.61 |
| ATOM | 225 | C | LYS | A | 46 | 15.324 | 23.574 | 30.673 | 1.000 | 58.56 |
| ATOM | 226 | O | LYS | A | 46 | 14.244 | 23.378 | 30.116 | 1.000 | 75.22 |
| ATOM | 227 | N | GLU | A | 47 | 16.436 | 22.917 | 30.384 | 1.000 | 47.55 |
| ATOM | 228 | CA | GLU | A | 47 | 16.525 | 21.820 | 29.431 | 1.000 | 50.54 |
| ATOM | 229 | CB | GLU | A | 47 | 17.934 | 21.229 | 29.416 | 1.000 | 51.00 |
| ATOM | 230 | CG | GLU | A | 47 | 18.207 | 20.220 | 28.322 | 1.000 | 54.12 |
| ATOM | 231 | CD | GLU | A | 47 | 19.602 | 19.627 | 28.395 | 1.000 | 52.91 |
| ATOM | 232 | OE1 | GLU | A | 47 | 20.500 | 20.053 | 27.631 | 1.000 | 41.94 |
| ATOM | 233 | OE2 | GLU | A | 47 | 19.799 | 18.714 | 29.229 | 1.000 | 49.31 |
| ATOM | 234 | C | GLU | A | 47 | 15.509 | 20.738 | 29.790 | 1.000 | 49.73 |
| ATOM | 235 | O | GLU | A | 47 | 14.803 | 20.208 | 28.939 | 1.000 | 39.85 |
| ATOM | 236 | N | TYR | A | 48 | 15.448 | 20.426 | 31.086 | 1.000 | 44.02 |
| ATOM | 237 | CA | TYR | A | 48 | 14.563 | 19.352 | 31.531 | 1.000 | 41.02 |
| ATOM | 238 | CB | TYR | A | 48 | 14.890 | 18.965 | 32.971 | 1.000 | 38.64 |
| ATOM | 239 | CG | TYR | A | 48 | 13.922 | 17.993 | 33.599 | 1.000 | 36.61 |
| ATOM | 240 | CD1 | TYR | A | 48 | 13.950 | 16.650 | 33.247 | 1.000 | 34.64 |
| ATOM | 241 | CE1 | TYR | A | 48 | 13.073 | 15.745 | 33.809 | 1.000 | 36.45 |
| ATOM | 242 | CZ | TYR | A | 48 | 12.153 | 16.179 | 34.738 | 1.000 | 35.24 |
| ATOM | 243 | OH | TYR | A | 48 | 11.285 | 15.269 | 35.288 | 1.000 | 36.83 |
| ATOM | 244 | CE2 | TYR | A | 48 | 12.098 | 17.506 | 35.108 | 1.000 | 34.92 |
| ATOM | 245 | CD2 | TYR | A | 48 | 12.983 | 18.405 | 34.535 | 1.000 | 38.27 |
| ATOM | 246 | C | TYR | A | 48 | 13.112 | 19.774 | 31.382 | 1.000 | 42.44 |
| ATOM | 247 | O | TYR | A | 48 | 12.227 | 18.943 | 31.170 | 1.000 | 37.58 |
| ATOM | 248 | N | GLU | A | 49 | 12.839 | 21.077 | 31.488 | 1.000 | 34.93 |
| ATOM | 249 | CA | GLU | A | 49 | 11.443 | 21.484 | 31.313 | 1.000 | 36.05 |
| ATOM | 250 | CB | GLU | A | 49 | 11.210 | 22.881 | 31.875 | 1.000 | 45.26 |
| ATOM | 251 | CG | GLU | A | 49 | 11.239 | 22.953 | 33.390 | 1.000 | 56.89 |
| ATOM | 252 | CD | GLU | A | 49 | 10.271 | 21.998 | 34.053 | 1.000 | 65.15 |
| ATOM | 253 | OE1 | GLU | A | 49 | 10.722 | 21.031 | 34.704 | 1.000 | 61.85 |
| ATOM | 254 | OE2 | GLU | A | 49 | 9.047 | 22.220 | 33.926 | 1.000 | 85.66 |
| ATOM | 255 | C | GLU | A | 49 | 11.065 | 21.406 | 29.835 | 1.000 | 40.11 |
| ATOM | 256 | O | GLU | A | 49 | 9.884 | 21.429 | 29.488 | 1.000 | 45.25 |
| ATOM | 257 | N | GLU | A | 50 | 12.071 | 21.304 | 28.972 | 1.000 | 34.88 |
| ATOM | 258 | CA | GLU | A | 50 | 11.897 | 21.219 | 27.536 | 1.000 | 34.15 |
| ATOM | 259 | CB | GLU | A | 50 | 13.225 | 21.224 | 26.784 | 1.000 | 47.42 |

FIGURE 11

| | | | | | | | | | |
|---|---|---|---|---|---|---|---|---|---|
| ATOM | 260 | CG | GLU | A | 50 | 14.193 | 22.357 | 27.039 | 1.000 58.31 |
| ATOM | 261 | CD | GLU | A | 50 | 15.395 | 22.299 | 26.111 | 1.000 72.71 |
| ATOM | 262 | OE1 | GLU | A | 50 | 15.705 | 21.201 | 25.592 | 1.000 84.88 |
| ATOM | 263 | OE2 | GLU | A | 50 | 16.034 | 23.355 | 25.892 | 1.000 89.36 |
| ATOM | 264 | C | GLU | A | 50 | 11.172 | 19.927 | 27.145 | 1.000 41.10 |
| ATOM | 265 | O | GLU | A | 50 | 10.637 | 19.814 | 26.042 | 1.000 48.55 |
| ATOM | 266 | N | LEU | A | 51 | 11.214 | 18.984 | 28.077 | 1.000 37.69 |
| ATOM | 267 | CA | LEU | A | 51 | 10.671 | 17.650 | 27.907 | 1.000 34.93 |
| ATOM | 268 | CB | LEU | A | 51 | 11.632 | 16.647 | 28.554 | 1.000 32.69 |
| ATOM | 269 | CG | LEU | A | 51 | 12.990 | 16.479 | 27.869 | 1.000 27.26 |
| ATOM | 270 | CD1 | LEU | A | 51 | 14.003 | 15.896 | 28.837 | 1.000 30.09 |
| ATOM | 271 | CD2 | LEU | A | 51 | 12.860 | 15.598 | 26.636 | 1.000 25.80 |
| ATOM | 272 | C | LEU | A | 51 | 9.286 | 17.512 | 28.523 | 1.000 39.93 |
| ATOM | 273 | O | LEU | A | 51 | 8.633 | 16.483 | 28.348 | 1.000 32.60 |
| ATOM | 274 | N | LYS | A | 52 | 8.856 | 18.542 | 29.242 | 1.000 35.85 |
| ATOM | 275 | CA | LYS | A | 52 | 7.628 | 18.496 | 30.017 | 1.000 43.68 |
| ATOM | 276 | CB | LYS | A | 52 | 7.282 | 19.881 | 30.584 | 1.000 49.99 |
| ATOM | 277 | CG | LYS | A | 52 | 5.828 | 20.014 | 31.009 | 1.000 50.93 |
| ATOM | 278 | CD | LYS | A | 52 | 5.552 | 21.383 | 31.613 | 1.000 54.40 |
| ATOM | 279 | CE | LYS | A | 52 | 4.187 | 21.908 | 31.183 | 1.000 52.01 |
| ATOM | 280 | NZ | LYS | A | 52 | 4.061 | 23.372 | 31.421 | 1.000 52.88 |
| ATOM | 281 | C | LYS | A | 52 | 6.440 | 17.978 | 29.211 | 1.000 41.72 |
| ATOM | 282 | O | LYS | A | 52 | 5.749 | 17.087 | 29.712 | 1.000 40.74 |
| ATOM | 283 | N | ASP | A | 53 | 6.241 | 18.521 | 28.018 | 1.000 35.76 |
| ATOM | 284 | CA | ASP | A | 53 | 5.074 | 18.259 | 27.196 | 1.000 33.00 |
| ATOM | 285 | CB | ASP | A | 53 | 4.640 | 19.524 | 26.440 | 1.000 35.62 |
| ATOM | 286 | CG | ASP | A | 53 | 4.134 | 20.637 | 27.333 | 1.000 39.83 |
| ATOM | 287 | OD1 | ASP | A | 53 | 4.039 | 21.790 | 26.856 | 1.000 41.69 |
| ATOM | 288 | OD2 | ASP | A | 53 | 3.834 | 20.393 | 28.518 | 1.000 48.93 |
| ATOM | 289 | C | ASP | A | 53 | 5.283 | 17.142 | 26.177 | 1.000 29.06 |
| ATOM | 290 | O | ASP | A | 53 | 4.349 | 16.827 | 25.426 | 1.000 22.95 |
| ATOM | 291 | N | VAL | A | 54 | 6.459 | 16.533 | 26.120 | 1.000 26.91 |
| ATOM | 292 | CA | VAL | A | 54 | 6.661 | 15.454 | 25.148 | 1.000 23.54 |
| ATOM | 293 | CB | VAL | A | 54 | 8.059 | 14.818 | 25.272 | 1.000 30.36 |
| ATOM | 294 | CG1 | VAL | A | 54 | 8.120 | 13.547 | 24.435 | 1.000 21.06 |
| ATOM | 295 | CG2 | VAL | A | 54 | 9.154 | 15.791 | 24.855 | 1.000 31.51 |
| ATOM | 296 | C | VAL | A | 54 | 5.617 | 14.348 | 25.309 | 1.000 29.36 |
| ATOM | 297 | O | VAL | A | 54 | 5.350 | 13.848 | 26.409 | 1.000 28.89 |
| ATOM | 298 | N | GLY | A | 55 | 5.015 | 13.988 | 24.188 | 1.000 23.19 |
| ATOM | 299 | CA | GLY | A | 55 | 4.021 | 12.953 | 24.067 | 1.000 23.74 |
| ATOM | 300 | C | GLY | A | 55 | 2.731 | 13.216 | 24.816 | 1.000 35.64 |
| ATOM | 301 | O | GLY | A | 55 | 1.917 | 12.289 | 24.916 | 1.000 34.29 |
| ATOM | 302 | N | ARG | A | 56 | 2.535 | 14.432 | 25.331 | 1.000 26.60 |
| ATOM | 303 | CA | ARG | A | 56 | 1.351 | 14.736 | 26.122 | 1.000 26.13 |
| ATOM | 304 | CB | ARG | A | 56 | 1.587 | 15.960 | 27.020 | 1.000 28.53 |
| ATOM | 305 | CG | ARG | A | 56 | 2.477 | 15.672 | 28.222 | 1.000 31.24 |
| ATOM | 306 | CD | ARG | A | 56 | 1.970 | 14.486 | 29.030 | 1.000 31.18 |
| ATOM | 307 | NE | ARG | A | 56 | 2.866 | 14.160 | 30.136 | 1.000 39.70 |
| ATOM | 308 | CZ | ARG | A | 56 | 2.724 | 14.463 | 31.417 | 1.000 41.60 |
| ATOM | 309 | NH1 | ARG | A | 56 | 1.683 | 15.139 | 31.879 | 1.000 33.99 |
| ATOM | 310 | NH2 | ARG | A | 56 | 3.650 | 14.082 | 32.292 | 1.000 42.42 |
| ATOM | 311 | C | ARG | A | 56 | 0.123 | 14.966 | 25.250 | 1.000 24.97 |

FIGURE 12

```
ATOM  312  O    ARG A  56   -0.957  15.301  25.741 1.000 29.55
ATOM  313  N    ASN A  57    0.258  14.781  23.944 1.000 24.28
ATOM  314  CA   ASN A  57   -0.895  14.909  23.064 1.000 33.49
ATOM  315  CB   ASN A  57   -0.474  15.189  21.611 1.000 33.93
ATOM  316  CG   ASN A  57    0.605  14.218  21.162 1.000 35.19
ATOM  317  OD1  ASN A  57    1.492  13.907  21.957 1.000 42.76
ATOM  318  ND2  ASN A  57    0.547  13.751  19.918 1.000 35.98
ATOM  319  C    ASN A  57   -1.720  13.635  23.056 1.000 35.77
ATOM  320  O    ASN A  57   -2.865  13.607  22.617 1.000 32.52
ATOM  321  N    GLN A  58   -1.139  12.529  23.521 1.000 35.76
ATOM  322  CA   GLN A  58   -1.864  11.271  23.295 1.000 30.59
ATOM  323  CB   GLN A  58   -0.851  10.129  23.178 1.000 29.64
ATOM  324  CG   GLN A  58    0.201  10.442  22.108 1.000 28.67
ATOM  325  CD   GLN A  58    1.406   9.527  22.230 1.000 31.92
ATOM  326  OE1  GLN A  58    2.330   9.754  23.023 1.000 40.11
ATOM  327  NE2  GLN A  58    1.386   8.474  21.427 1.000 22.80
ATOM  328  C    GLN A  58   -2.899  11.017  24.373 1.000 26.57
ATOM  329  O    GLN A  58   -2.814  11.505  25.494 1.000 28.16
ATOM  330  N    SER A  59   -3.895  10.232  23.996 1.000 21.64
ATOM  331  CA   SER A  59   -5.004   9.889  24.858 1.000 21.49
ATOM  332  CB   SER A  59   -6.312   9.936  24.060 1.000 23.13
ATOM  333  OG   SER A  59   -6.423   8.760  23.266 1.000 50.75
ATOM  334  C    SER A  59   -4.832   8.495  25.465 1.000 27.34
ATOM  335  O    SER A  59   -4.113   7.652  24.915 1.000 28.20
ATOM  336  N    CYS A  60   -5.510   8.289  26.585 1.000 21.68
ATOM  337  CA   CYS A  60   -5.566   7.030  27.307 1.000 19.90
ATOM  338  CB   CYS A  60   -4.841   7.171  28.645 1.000 31.73
ATOM  339  SG   CYS A  60   -3.240   8.002  28.554 1.000 43.81
ATOM  340  C    CYS A  60   -7.008   6.595  27.556 1.000 22.77
ATOM  341  O    CYS A  60   -7.341   6.204  28.678 1.000 20.42
ATOM  342  N    ASP A  61   -7.852   6.663  26.540 1.000 21.77
ATOM  343  CA   ASP A  61   -9.266   6.323  26.610 1.000 30.03
ATOM  344  CB   ASP A  61   -9.915   6.527  25.236 1.000 35.37
ATOM  345  CG   ASP A  61   -9.894   7.936  24.695 1.000 32.99
ATOM  346  OD1  ASP A  61   -9.618   8.909  25.426 1.000 42.37
ATOM  347  OD2  ASP A  61  -10.171   8.083  23.481 1.000 42.70
ATOM  348  C    ASP A  61   -9.529   4.890  27.073 1.000 31.27
ATOM  349  O    ASP A  61  -10.375   4.669  27.946 1.000 26.07
ATOM  350  N    ILE A  62   -8.840   3.896  26.517 1.000 33.57
ATOM  351  CA   ILE A  62   -9.017   2.497  26.889 1.000 26.85
ATOM  352  CB   ILE A  62   -8.021   1.572  26.166 1.000 27.84
ATOM  353  CG1  ILE A  62   -7.987   1.728  24.650 1.000 25.02
ATOM  354  CD1  ILE A  62   -9.326   1.502  23.982 1.000 31.68
ATOM  355  CG2  ILE A  62   -8.284   0.124  26.574 1.000 22.54
ATOM  356  C    ILE A  62   -8.822   2.256  28.381 1.000 32.08
ATOM  357  O    ILE A  62   -9.608   1.599  29.071 1.000 30.72
ATOM  358  N    ALA A  63   -7.724   2.812  28.896 1.000 25.21
ATOM  359  CA   ALA A  63   -7.448   2.650  30.321 1.000 24.51
ATOM  360  CB   ALA A  63   -6.138   3.336  30.687 1.000 24.25
ATOM  361  C    ALA A  63   -8.585   3.208  31.168 1.000 32.19
ATOM  362  O    ALA A  63   -8.795   2.776  32.302 1.000 36.44
ATOM  363  N    LEU A  64   -9.309   4.183  30.622 1.000 29.54
```

FIGURE 13

```
ATOM    364  CA   LEU A  64     -10.325    4.890   31.389  1.000  31.43
ATOM    365  CB   LEU A  64     -10.486    6.331   30.884  1.000  27.77
ATOM    366  CG   LEU A  64      -9.333    7.259   31.283  1.000  27.38
ATOM    367  CD1  LEU A  64      -9.308    8.494   30.399  1.000  15.84
ATOM    368  CD2  LEU A  64      -9.456    7.608   32.760  1.000  25.15
ATOM    369  C    LEU A  64     -11.663    4.180   31.315  1.000  27.53
ATOM    370  O    LEU A  64     -12.640    4.639   31.902  1.000  25.88
ATOM    371  N    LEU A  65     -11.712    3.063   30.594  1.000  24.50
ATOM    372  CA   LEU A  65     -13.005    2.371   30.555  1.000  29.09
ATOM    373  CB   LEU A  65     -12.934    1.238   29.534  1.000  26.20
ATOM    374  CG   LEU A  65     -12.633    1.726   28.112  1.000  32.04
ATOM    375  CD1  LEU A  65     -12.556    0.568   27.137  1.000  26.24
ATOM    376  CD2  LEU A  65     -13.692    2.740   27.692  1.000  42.91
ATOM    377  C    LEU A  65     -13.380    1.876   31.948  1.000  36.19
ATOM    378  O    LEU A  65     -12.506    1.424   32.690  1.000  34.08
ATOM    379  N    PRO A  66     -14.658    1.985   32.302  1.000  38.51
ATOM    380  CA   PRO A  66     -15.156    1.575   33.618  1.000  45.55
ATOM    381  CB   PRO A  66     -16.682    1.595   33.438  1.000  41.37
ATOM    382  CG   PRO A  66     -16.895    2.654   32.411  1.000  38.85
ATOM    383  CD   PRO A  66     -15.733    2.545   31.463  1.000  39.79
ATOM    384  C    PRO A  66     -14.718    0.173   34.026  1.000  45.91
ATOM    385  O    PRO A  66     -14.329   -0.049   35.171  1.000  40.19
ATOM    386  N    GLU A  67     -14.780   -0.764   33.090  1.000  39.45
ATOM    387  CA   GLU A  67     -14.412   -2.143   33.370  1.000  36.99
ATOM    388  CB   GLU A  67     -14.780   -3.022   32.170  1.000  40.26
ATOM    389  CG   GLU A  67     -13.872   -2.765   30.975  1.000  51.03
ATOM    390  CD   GLU A  67     -14.478   -3.329   29.706  1.000  62.19
ATOM    391  OE1  GLU A  67     -15.190   -4.351   29.789  1.000  95.02
ATOM    392  OE2  GLU A  67     -14.229   -2.750   28.629  1.000  48.12
ATOM    393  C    GLU A  67     -12.929   -2.311   33.685  1.000  41.35
ATOM    394  O    GLU A  67     -12.555   -3.306   34.309  1.000  49.39
ATOM    395  N    ASN A  68     -12.105   -1.357   33.266  1.000  44.36
ATOM    396  CA   ASN A  68     -10.668   -1.381   33.488  1.000  35.22
ATOM    397  CB   ASN A  68      -9.938   -0.853   32.244  1.000  30.80
ATOM    398  CG   ASN A  68     -10.071   -1.799   31.070  1.000  26.82
ATOM    399  OD1  ASN A  68     -10.219   -3.004   31.263  1.000  30.94
ATOM    400  ND2  ASN A  68     -10.021   -1.271   29.849  1.000  25.55
ATOM    401  C    ASN A  68     -10.240   -0.570   34.706  1.000  35.99
ATOM    402  O    ASN A  68      -9.074   -0.612   35.110  1.000  34.21
ATOM    403  N    ARG A  69     -11.151    0.170   35.325  1.000  40.53
ATOM    404  CA   ARG A  69     -10.796    1.005   36.475  1.000  35.31
ATOM    405  CB   ARG A  69     -12.060    1.688   36.993  1.000  47.65
ATOM    406  CG   ARG A  69     -11.878    3.089   37.547  1.000  59.36
ATOM    407  CD   ARG A  69     -12.710    3.262   38.819  1.000  65.36
ATOM    408  NE   ARG A  69     -12.615    2.076   39.666  1.000  69.47
ATOM    409  CZ   ARG A  69     -13.019    1.980   40.923  1.000  75.71
ATOM    410  NH1  ARG A  69     -13.586    3.018   41.542  1.000  91.00
ATOM    411  NH2  ARG A  69     -12.880    0.832   41.575  1.000  74.09
ATOM    412  C    ARG A  69     -10.114    0.205   37.572  1.000  33.70
ATOM    413  O    ARG A  69      -9.102    0.634   38.135  1.000  41.23
ATOM    414  N    GLY A  70     -10.641   -0.976   37.890  1.000  34.09
ATOM    415  CA   GLY A  70     -10.030   -1.844   38.877  1.000  29.32
```

FIGURE 14

```
ATOM    416  C   GLY A  70      -8.645  -2.304  38.476  1.000  33.87
ATOM    417  O   GLY A  70      -7.861  -2.788  39.293  1.000  29.15
ATOM    418  N   LYS A  71      -8.269  -2.166  37.200  1.000  28.62
ATOM    419  CA  LYS A  71      -6.975  -2.730  36.805  1.000  28.56
ATOM    420  CB  LYS A  71      -7.145  -3.327  35.403  1.000  26.54
ATOM    421  CG  LYS A  71      -8.206  -4.431  35.340  1.000  22.84
ATOM    422  CD  LYS A  71      -8.540  -4.715  33.880  1.000  25.18
ATOM    423  CE  LYS A  71      -9.766  -5.603  33.744  1.000  26.92
ATOM    424  NZ  LYS A  71     -10.179  -5.703  32.310  1.000  25.36
ATOM    425  C   LYS A  71      -5.825  -1.737  36.871  1.000  24.24
ATOM    426  O   LYS A  71      -4.670  -2.046  36.565  1.000  23.92
ATOM    427  N   ASN A  72      -6.078  -0.506  37.292  1.000  21.36
ATOM    428  CA  ASN A  72      -5.019   0.485  37.438  1.000  22.33
ATOM    429  CB  ASN A  72      -5.431   1.802  36.760  1.000  17.72
ATOM    430  CG  ASN A  72      -5.773   1.557  35.299  1.000  20.67
ATOM    431  OD1 ASN A  72      -4.968   1.023  34.534  1.000  19.13
ATOM    432  ND2 ASN A  72      -6.981   1.935  34.901  1.000  22.56
ATOM    433  C   ASN A  72      -4.691   0.708  38.904  1.000  22.55
ATOM    434  O   ASN A  72      -5.548   0.952  39.747  1.000  27.49
ATOM    435  N   ARG A  73      -3.410   0.626  39.238  1.000  24.79
ATOM    436  CA  ARG A  73      -2.989   0.857  40.612  1.000  22.71
ATOM    437  CB  ARG A  73      -1.523   0.471  40.761  1.000  19.16
ATOM    438  CG  ARG A  73      -1.003   0.559  42.185  1.000  20.59
ATOM    439  CD  ARG A  73       0.456   0.114  42.254  1.000  16.95
ATOM    440  NE  ARG A  73       0.546  -1.347  42.281  1.000  17.30
ATOM    441  CZ  ARG A  73       0.282  -2.041  43.387  1.000  28.69
ATOM    442  NH1 ARG A  73      -0.073  -1.406  44.500  1.000  20.46
ATOM    443  NH2 ARG A  73       0.372  -3.371  43.383  1.000  26.38
ATOM    444  C   ARG A  73      -3.227   2.314  40.990  1.000  29.57
ATOM    445  O   ARG A  73      -3.731   2.609  42.070  1.000  23.74
ATOM    446  N   TYR A  74      -2.864   3.229  40.095  1.000  22.89
ATOM    447  CA  TYR A  74      -3.188   4.640  40.292  1.000  19.10
ATOM    448  CB  TYR A  74      -1.941   5.487  40.496  1.000  29.90
ATOM    449  CG  TYR A  74      -0.889   4.936  41.434  1.000  28.85
ATOM    450  CD1 TYR A  74      -0.948   5.169  42.802  1.000  29.68
ATOM    451  CE1 TYR A  74       0.019   4.668  43.655  1.000  32.91
ATOM    452  CZ  TYR A  74       1.064   3.920  43.146  1.000  32.73
ATOM    453  OH  TYR A  74       2.029   3.415  43.989  1.000  28.80
ATOM    454  CE2 TYR A  74       1.156   3.672  41.791  1.000  20.37
ATOM    455  CD2 TYR A  74       0.182   4.186  40.957  1.000  22.57
ATOM    456  C   TYR A  74      -4.007   5.110  39.095  1.000  33.71
ATOM    457  O   TYR A  74      -3.753   4.819  37.920  1.000  23.30
ATOM    458  N   ASN A  75      -5.062   5.861  39.410  1.000  33.95
ATOM    459  CA  ASN A  75      -6.019   6.213  38.358  1.000  32.58
ATOM    460  CB  ASN A  75      -7.389   6.458  39.014  1.000  35.23
ATOM    461  CG  ASN A  75      -7.716   5.300  39.947  1.000  42.60
ATOM    462  OD1 ASN A  75      -7.925   5.491  41.144  1.000  68.26
ATOM    463  ND2 ASN A  75      -7.745   4.087  39.403  1.000  39.56
ATOM    464  C   ASN A  75      -5.533   7.385  37.534  1.000  30.63
ATOM    465  O   ASN A  75      -6.101   7.736  36.497  1.000  26.15
ATOM    466  N   ASN A  76      -4.440   8.015  37.962  1.000  28.76
ATOM    467  CA  ASN A  76      -3.897   9.102  37.150  1.000  28.13
```

FIGURE 15

```
ATOM    468  CB  ASN A  76      -3.719  10.374  37.979 1.000 27.74
ATOM    469  CG  ASN A  76      -2.648  10.200  39.041 1.000 28.93
ATOM    470  OD1 ASN A  76      -2.497   9.101  39.573 1.000 29.34
ATOM    471  ND2 ASN A  76      -1.937  11.284  39.321 1.000 29.63
ATOM    472  C   ASN A  76      -2.570   8.694  36.526 1.000 29.10
ATOM    473  O   ASN A  76      -1.851   9.557  36.015 1.000 33.33
ATOM    474  N   ILE A  77      -2.273   7.392  36.558 1.000 24.17
ATOM    475  CA  ILE A  77      -1.095   6.908  35.830 1.000 23.94
ATOM    476  CB  ILE A  77       0.024   6.496  36.797 1.000 28.53
ATOM    477  CG1 ILE A  77       0.575   7.663  37.624 1.000 24.03
ATOM    478  CD1 ILE A  77       1.451   7.212  38.776 1.000 35.26
ATOM    479  CG2 ILE A  77       1.137   5.798  36.041 1.000 21.08
ATOM    480  C   ILE A  77      -1.457   5.760  34.900 1.000 22.75
ATOM    481  O   ILE A  77      -1.618   4.597  35.282 1.000 17.56
ATOM    482  N   LEU A  78      -1.605   6.108  33.621 1.000 16.56
ATOM    483  CA  LEU A  78      -2.172   5.202  32.641 1.000 12.89
ATOM    484  CB  LEU A  78      -3.616   5.616  32.310 1.000 17.17
ATOM    485  CG  LEU A  78      -4.457   6.017  33.522 1.000 22.43
ATOM    486  CD1 LEU A  78      -5.794   6.590  33.075 1.000 27.35
ATOM    487  CD2 LEU A  78      -4.637   4.813  34.431 1.000 17.32
ATOM    488  C   LEU A  78      -1.415   5.213  31.326 1.000 17.93
ATOM    489  O   LEU A  78      -0.846   6.221  30.922 1.000 18.95
ATOM    490  N   PRO A  79      -1.459   4.086  30.640 1.000 21.12
ATOM    491  CA  PRO A  79      -0.773   3.971  29.355 1.000 18.86
ATOM    492  CB  PRO A  79      -0.858   2.470  29.068 1.000 18.12
ATOM    493  CG  PRO A  79      -2.148   2.076  29.721 1.000 21.28
ATOM    494  CD  PRO A  79      -2.184   2.858  31.011 1.000 17.43
ATOM    495  C   PRO A  79      -1.532   4.694  28.253 1.000 19.81
ATOM    496  O   PRO A  79      -2.761   4.633  28.249 1.000 19.07
ATOM    497  N   TYR A  80      -0.784   5.317  27.355 1.000 16.14
ATOM    498  CA  TYR A  80      -1.338   5.843  26.117 1.000 15.09
ATOM    499  CB  TYR A  80      -0.216   6.508  25.313 1.000 20.99
ATOM    500  CG  TYR A  80       0.350   7.734  25.993 1.000 20.29
ATOM    501  CD1 TYR A  80      -0.494   8.670  26.577 1.000 20.64
ATOM    502  CE1 TYR A  80       0.019   9.796  27.206 1.000 20.96
ATOM    503  CZ  TYR A  80       1.385   9.986  27.243 1.000 21.66
ATOM    504  OH  TYR A  80       1.903  11.103  27.859 1.000 23.51
ATOM    505  CE2 TYR A  80       2.239   9.071  26.671 1.000 18.25
ATOM    506  CD2 TYR A  80       1.722   7.946  26.047 1.000 21.75
ATOM    507  C   TYR A  80      -1.988   4.755  25.277 1.000 23.46
ATOM    508  O   TYR A  80      -1.471   3.635  25.187 1.000 23.99
ATOM    509  N   ASP A  81      -3.125   5.040  24.637 1.000 22.91
ATOM    510  CA  ASP A  81      -3.735   4.027  23.780 1.000 19.34
ATOM    511  CB  ASP A  81      -5.033   4.518  23.120 1.000 24.22
ATOM    512  CG  ASP A  81      -6.080   4.908  24.143 1.000 34.31
ATOM    513  OD1 ASP A  81      -6.296   4.128  25.094 1.000 27.78
ATOM    514  OD2 ASP A  81      -6.688   5.992  24.010 1.000 35.52
ATOM    515  C   ASP A  81      -2.769   3.610  22.678 1.000 18.44
ATOM    516  O   ASP A  81      -2.722   2.439  22.278 1.000 24.18
ATOM    517  N   ALA A  82      -2.002   4.573  22.161 1.000 16.71
ATOM    518  CA  ALA A  82      -1.164   4.229  21.008 1.000 21.74
ATOM    519  CB  ALA A  82      -0.654   5.520  20.373 1.000 25.83
```

FIGURE 16

```
ATOM    520  C   ALA A  82      -0.010   3.300  21.338 1.000 26.28
ATOM    521  O   ALA A  82       0.556   2.660  20.439 1.000 24.04
ATOM    522  N   THR A  83       0.447   3.140  22.584 1.000 19.03
ATOM    523  CA  THR A  83       1.625   2.280  22.757 1.000 14.68
ATOM    524  CB  THR A  83       2.853   3.095  23.225 1.000 22.79
ATOM    525  OG1 THR A  83       2.464   3.852  24.374 1.000 18.61
ATOM    526  CG2 THR A  83       3.308   4.096  22.168 1.000 17.97
ATOM    527  C   THR A  83       1.412   1.199  23.799 1.000 22.48
ATOM    528  O   THR A  83       2.380   0.580  24.254 1.000 20.29
ATOM    529  N   ARG A  84       0.144   1.005  24.159 1.000 18.73
ATOM    530  CA  ARG A  84      -0.176   0.106  25.257 1.000 22.92
ATOM    531  CB  ARG A  84      -1.621   0.347  25.683 1.000 27.10
ATOM    532  CG  ARG A  84      -2.650  -0.247  24.721 1.000 21.68
ATOM    533  CD  ARG A  84      -4.047   0.092  25.236 1.000 25.76
ATOM    534  NE  ARG A  84      -5.071  -0.515  24.395 1.000 31.14
ATOM    535  CZ  ARG A  84      -5.698  -1.652  24.648 1.000 28.06
ATOM    536  NH1 ARG A  84      -5.426  -2.351  25.741 1.000 15.53
ATOM    537  NH2 ARG A  84      -6.608  -2.073  23.781 1.000 24.30
ATOM    538  C   ARG A  84       0.032  -1.353  24.874 1.000 25.02
ATOM    539  O   ARG A  84      -0.089  -1.712  23.702 1.000 21.04
ATOM    540  N   VAL A  85       0.337  -2.204  25.856 1.000 14.13
ATOM    541  CA  VAL A  85       0.491  -3.624  25.512 1.000 14.38
ATOM    542  CB  VAL A  85       1.464  -4.344  26.455 1.000  9.78
ATOM    543  CG1 VAL A  85       1.425  -5.848  26.218 1.000 17.73
ATOM    544  CG2 VAL A  85       2.881  -3.814  26.306 1.000 12.51
ATOM    545  C   VAL A  85      -0.863  -4.313  25.593 1.000 24.23
ATOM    546  O   VAL A  85      -1.573  -4.163  26.594 1.000 24.70
ATOM    547  N   LYS A  86      -1.270  -5.081  24.590 1.000 22.80
ATOM    548  CA  LYS A  86      -2.572  -5.741  24.686 1.000 22.12
ATOM    549  CB  LYS A  86      -3.307  -5.564  23.347 1.000 31.33
ATOM    550  CG  LYS A  86      -3.256  -4.147  22.803 1.000 27.28
ATOM    551  CD  LYS A  86      -3.691  -4.077  21.352 1.000 33.19
ATOM    552  CE  LYS A  86      -4.193  -2.688  20.990 1.000 43.70
ATOM    553  NZ  LYS A  86      -4.520  -2.549  19.542 1.000 37.64
ATOM    554  C   LYS A  86      -2.483  -7.222  25.020 1.000 24.22
ATOM    555  O   LYS A  86      -1.658  -7.961  24.475 1.000 27.05
ATOM    556  N   LEU A  87      -3.358  -7.682  25.911 1.000 23.05
ATOM    557  CA  LEU A  87      -3.530  -9.107  26.143 1.000 23.37
ATOM    558  CB  LEU A  87      -4.250  -9.392  27.460 1.000 24.62
ATOM    559  CG  LEU A  87      -3.733  -8.696  28.711 1.000 27.34
ATOM    560  CD1 LEU A  87      -4.614  -9.032  29.904 1.000 20.48
ATOM    561  CD2 LEU A  87      -2.284  -9.078  28.973 1.000 32.54
ATOM    562  C   LEU A  87      -4.360  -9.720  25.020 1.000 26.94
ATOM    563  O   LEU A  87      -5.318  -9.094  24.555 1.000 38.77
ATOM    564  N   SER A  88      -4.021 -10.925  24.581 1.000 33.75
ATOM    565  CA  SER A  88      -4.872 -11.557  23.567 1.000 42.66
ATOM    566  CB  SER A  88      -4.317 -12.913  23.154 1.000 46.57
ATOM    567  OG  SER A  88      -4.765 -13.947  24.014 1.000 59.78
ATOM    568  C   SER A  88      -6.292 -11.680  24.113 1.000 52.63
ATOM    569  O   SER A  88      -6.499 -11.777  25.325 1.000 40.47
ATOM    570  N   ASN A  89      -7.274 -11.656  23.225 1.000 65.95
ATOM    571  CA  ASN A  89      -8.680 -11.790  23.586 1.000 71.68
```

FIGURE 17

```
ATOM    572  CB   ASN A  89      -9.528  -11.132  22.496 1.000  75.26
ATOM    573  CG   ASN A  89      -8.793  -11.244  21.163 1.000  78.86
ATOM    574  OD1  ASN A  89      -7.806  -10.546  20.946 1.000  71.99
ATOM    575  ND2  ASN A  89      -9.271  -12.122  20.293 1.000  90.92
ATOM    576  C    ASN A  89      -9.057  -13.256  23.738 1.000  79.05
ATOM    577  O    ASN A  89      -8.808  -14.039  22.811 1.000  73.71
ATOM    578  N    VAL A  90      -9.633  -13.639  24.875 1.000  87.92
ATOM    579  CA   VAL A  90      -9.929  -15.052  25.128 1.000  94.68
ATOM    580  CB   VAL A  90      -8.920  -15.629  26.140 1.000  89.31
ATOM    581  CG1  VAL A  90      -7.494  -15.497  25.590 1.000  54.27
ATOM    582  CG2  VAL A  90      -9.031  -14.923  27.491 1.000 100.28
ATOM    583  C    VAL A  90     -11.354  -15.293  25.619 1.000 102.19
ATOM    584  O    VAL A  90     -12.315  -14.798  25.014 1.000 100.56
ATOM    585  N    ASP A  91     -11.498  -16.059  26.693 1.000 105.22
ATOM    586  CA   ASP A  91     -12.783  -16.447  27.271 1.000 108.70
ATOM    587  CB   ASP A  91     -12.578  -17.068  28.656 1.000 107.42
ATOM    588  CG   ASP A  91     -13.530  -18.205  28.939 1.000 106.43
ATOM    589  OD1  ASP A  91     -13.926  -18.900  27.974 1.000 113.61
ATOM    590  OD2  ASP A  91     -13.894  -18.413  30.116 1.000  86.41
ATOM    591  C    ASP A  91     -13.743  -15.268  27.371 1.000 115.28
ATOM    592  O    ASP A  91     -13.390  -14.223  27.924 1.000 126.76
ATOM    593  N    ASP A  92     -14.952  -15.429  26.834 1.000 116.43
ATOM    594  CA   ASP A  92     -15.914  -14.333  26.741 1.000 116.50
ATOM    595  CB   ASP A  92     -16.500  -13.952  28.090 1.000 111.11
ATOM    596  CG   ASP A  92     -17.029  -15.093  28.929 1.000 103.39
ATOM    597  OD1  ASP A  92     -17.835  -15.908  28.441 1.000  70.91
ATOM    598  OD2  ASP A  92     -16.639  -15.180  30.116 1.000 105.06
ATOM    599  C    ASP A  92     -15.224  -13.122  26.103 1.000 121.44
ATOM    600  O    ASP A  92     -14.846  -13.211  24.935 1.000 119.15
ATOM    601  N    ASP A  93     -15.077  -12.068  26.886 1.000 124.91
ATOM    602  CA   ASP A  93     -14.260  -10.887  26.698 1.000 127.04
ATOM    603  CB   ASP A  93     -13.201  -11.126  25.615 1.000 127.70
ATOM    604  CG   ASP A  93     -13.710  -10.960  24.174 1.000 128.89
ATOM    605  OD1  ASP A  93     -14.877  -11.323  23.869 1.000 136.07
ATOM    606  OD2  ASP A  93     -12.928  -10.464  23.315 1.000 126.93
ATOM    607  C    ASP A  93     -15.055   -9.617  26.384 1.000 125.66
ATOM    608  O    ASP A  93     -15.775   -9.536  25.388 1.000 112.27
ATOM    609  N    PRO A  94     -14.884   -8.640  27.272 1.000 123.81
ATOM    610  CA   PRO A  94     -15.331   -7.253  27.126 1.000 114.77
ATOM    611  CB   PRO A  94     -15.751   -6.908  28.554 1.000 118.39
ATOM    612  CG   PRO A  94     -14.893   -7.760  29.440 1.000 121.09
ATOM    613  CD   PRO A  94     -14.224   -8.799  28.586 1.000 123.81
ATOM    614  C    PRO A  94     -14.172   -6.360  26.685 1.000  99.08
ATOM    615  O    PRO A  94     -14.080   -5.961  25.527 1.000  69.91
ATOM    616  N    CYS A  95     -13.294   -6.071  27.635 1.000  91.61
ATOM    617  CA   CYS A  95     -11.981   -5.485  27.441 1.000  80.21
ATOM    618  CB   CYS A  95     -11.883   -4.014  27.797 1.000  80.05
ATOM    619  SG   CYS A  95     -10.319   -3.186  27.438 1.000  75.64
ATOM    620  C    CYS A  95     -10.991   -6.285  28.303 1.000  67.30
ATOM    621  O    CYS A  95     -10.299   -5.735  29.149 1.000  48.15
ATOM    622  N    SER A  96     -10.993   -7.580  28.030 1.000  62.04
ATOM    623  CA   SER A  96     -10.102   -8.548  28.645 1.000  49.24
```

FIGURE 18

```
ATOM    624  CB  SER A  96     -10.644  -9.959  28.392 1.000 47.34
ATOM    625  OG  SER A  96     -10.772 -10.165  26.989 1.000 35.99
ATOM    626  C   SER A  96      -8.689  -8.404  28.091 1.000 40.83
ATOM    627  O   SER A  96      -7.762  -9.091  28.530 1.000 43.79
ATOM    628  N   ASP A  97      -8.519  -7.503  27.119 1.000 33.54
ATOM    629  CA  ASP A  97      -7.200  -7.260  26.543 1.000 26.97
ATOM    630  CB  ASP A  97      -7.333  -6.817  25.088 1.000 24.79
ATOM    631  CG  ASP A  97      -7.611  -5.353  24.842 1.000 31.75
ATOM    632  OD1 ASP A  97      -7.973  -4.566  25.740 1.000 34.88
ATOM    633  OD2 ASP A  97      -7.473  -4.920  23.667 1.000 32.46
ATOM    634  C   ASP A  97      -6.406  -6.227  27.331 1.000 19.31
ATOM    635  O   ASP A  97      -5.239  -6.008  27.001 1.000 32.90
ATOM    636  N   TYR A  98      -7.001  -5.563  28.319 1.000 21.87
ATOM    637  CA  TYR A  98      -6.317  -4.446  28.958 1.000 24.52
ATOM    638  CB  TYR A  98      -7.294  -3.441  29.604 1.000 22.29
ATOM    639  CG  TYR A  98      -6.556  -2.288  30.277 1.000 21.76
ATOM    640  CD1 TYR A  98      -6.012  -1.275  29.489 1.000 23.46
ATOM    641  CE1 TYR A  98      -5.324  -0.202  30.044 1.000 12.80
ATOM    642  CZ  TYR A  98      -5.184  -0.152  31.415 1.000 16.57
ATOM    643  OH  TYR A  98      -4.516   0.900  32.001 1.000 20.04
ATOM    644  CE2 TYR A  98      -5.710  -1.138  32.234 1.000 21.65
ATOM    645  CD2 TYR A  98      -6.388  -2.192  31.652 1.000 22.47
ATOM    646  C   TYR A  98      -5.329  -4.852  30.045 1.000 23.39
ATOM    647  O   TYR A  98      -5.609  -5.609  30.964 1.000 28.32
ATOM    648  N   ILE A  99      -4.143  -4.250  29.978 1.000 19.82
ATOM    649  CA  ILE A  99      -3.247  -4.242  31.130 1.000 21.08
ATOM    650  CB  ILE A  99      -2.185  -5.354  31.091 1.000 21.45
ATOM    651  CG1 ILE A  99      -1.169  -5.304  32.224 1.000 13.12
ATOM    652  CD1 ILE A  99      -0.466  -6.601  32.573 1.000 15.73
ATOM    653  CG2 ILE A  99      -1.481  -5.344  29.737 1.000 24.91
ATOM    654  C   ILE A  99      -2.593  -2.867  31.218 1.000 17.86
ATOM    655  O   ILE A  99      -2.362  -2.161  30.235 1.000 23.00
ATOM    656  N   ASN A 100      -2.271  -2.426  32.429 1.000 17.97
ATOM    657  CA  ASN A 100      -1.523  -1.168  32.506 1.000 16.53
ATOM    658  CB  ASN A 100      -1.696  -0.583  33.904 1.000 15.17
ATOM    659  CG  ASN A 100      -1.169   0.837  33.940 1.000 17.63
ATOM    660  OD1 ASN A 100      -0.087   1.081  33.409 1.000 19.68
ATOM    661  ND2 ASN A 100      -1.931   1.727  34.566 1.000 19.64
ATOM    662  C   ASN A 100      -0.064  -1.408  32.144 1.000 20.69
ATOM    663  O   ASN A 100       0.784  -1.727  32.977 1.000 13.39
ATOM    664  N   ALA A 101       0.246  -1.268  30.851 1.000 11.73
ATOM    665  CA  ALA A 101       1.586  -1.586  30.370 1.000 13.46
ATOM    666  CB  ALA A 101       1.737  -3.096  30.235 1.000 16.17
ATOM    667  C   ALA A 101       1.842  -0.930  29.026 1.000 14.30
ATOM    668  O   ALA A 101       0.883  -0.739  28.277 1.000 15.61
ATOM    669  N   SER A 102       3.088  -0.603  28.708 1.000 17.77
ATOM    670  CA  SER A 102       3.385   0.102  27.472 1.000 18.13
ATOM    671  CB  SER A 102       3.627   1.593  27.759 1.000 13.36
ATOM    672  OG  SER A 102       2.735   2.076  28.738 1.000 20.39
ATOM    673  C   SER A 102       4.623  -0.444  26.786 1.000 23.90
ATOM    674  O   SER A 102       5.568  -0.832  27.475 1.000 22.19
ATOM    675  N   TYR A 103       4.639  -0.454  25.452 1.000 16.79
```

FIGURE 19

| | | | | | | | | | |
|---|---|---|---|---|---|---|---|---|---|
| ATOM | 676 | CA | TYR | A | 103 | 5.871 | -0.877 | 24.793 | 1.000 10.43 |
| ATOM | 677 | CB | TYR | A | 103 | 5.619 | -1.287 | 23.347 | 1.000 16.27 |
| ATOM | 678 | CG | TYR | A | 103 | 4.840 | -2.567 | 23.157 | 1.000 15.11 |
| ATOM | 679 | CD1 | TYR | A | 103 | 5.421 | -3.802 | 23.412 | 1.000 18.80 |
| ATOM | 680 | CE1 | TYR | A | 103 | 4.704 | -4.978 | 23.232 | 1.000 22.75 |
| ATOM | 681 | CZ | TYR | A | 103 | 3.396 | -4.922 | 22.798 | 1.000 19.98 |
| ATOM | 682 | OH | TYR | A | 103 | 2.689 | -6.094 | 22.625 | 1.000 16.85 |
| ATOM | 683 | CE2 | TYR | A | 103 | 2.797 | -3.704 | 22.536 | 1.000 14.29 |
| ATOM | 684 | CD2 | TYR | A | 103 | 3.517 | -2.540 | 22.714 | 1.000 12.99 |
| ATOM | 685 | C | TYR | A | 103 | 6.847 | 0.293 | 24.853 | 1.000 19.42 |
| ATOM | 686 | O | TYR | A | 103 | 6.398 | 1.440 | 24.787 | 1.000 21.35 |
| ATOM | 687 | N | ILE | A | 104 | 8.143 | 0.039 | 24.983 | 1.000 20.28 |
| ATOM | 688 | CA | ILE | A | 104 | 9.090 | 1.151 | 25.068 | 1.000 18.75 |
| ATOM | 689 | CB | ILE | A | 104 | 9.522 | 1.444 | 26.516 | 1.000 25.72 |
| ATOM | 690 | CG1 | ILE | A | 104 | 8.372 | 1.673 | 27.507 | 1.000 19.54 |
| ATOM | 691 | CD1 | ILE | A | 104 | 7.657 | 2.991 | 27.243 | 1.000 24.18 |
| ATOM | 692 | CG2 | ILE | A | 104 | 10.466 | 2.640 | 26.556 | 1.000 25.08 |
| ATOM | 693 | C | ILE | A | 104 | 10.321 | 0.843 | 24.229 | 1.000 18.91 |
| ATOM | 694 | O | ILE | A | 104 | 10.899 | -0.236 | 24.356 | 1.000 21.99 |
| ATOM | 695 | N | PRO | A | 105 | 10.719 | 1.777 | 23.376 | 1.000 25.40 |
| ATOM | 696 | CA | PRO | A | 105 | 11.854 | 1.513 | 22.482 | 1.000 23.49 |
| ATOM | 697 | CB | PRO | A | 105 | 11.761 | 2.641 | 21.457 | 1.000 25.41 |
| ATOM | 698 | CG | PRO | A | 105 | 11.030 | 3.747 | 22.133 | 1.000 26.30 |
| ATOM | 699 | CD | PRO | A | 105 | 10.166 | 3.121 | 23.187 | 1.000 24.38 |
| ATOM | 700 | C | PRO | A | 105 | 13.165 | 1.602 | 23.249 | 1.000 24.84 |
| ATOM | 701 | O | PRO | A | 105 | 13.255 | 2.321 | 24.246 | 1.000 19.70 |
| ATOM | 702 | N | GLY | A | 106 | 14.176 | 0.872 | 22.788 | 1.000 21.42 |
| ATOM | 703 | CA | GLY | A | 106 | 15.485 | 1.020 | 23.423 | 1.000 28.59 |
| ATOM | 704 | C | GLY | A | 106 | 16.527 | 1.498 | 22.425 | 1.000 30.55 |
| ATOM | 705 | O | GLY | A | 106 | 16.222 | 2.089 | 21.395 | 1.000 20.21 |
| ATOM | 706 | N | ASN | A | 107 | 17.796 | 1.244 | 22.710 | 1.000 32.09 |
| ATOM | 707 | CA | ASN | A | 107 | 18.884 | 1.677 | 21.850 | 1.000 26.56 |
| ATOM | 708 | CB | ASN | A | 107 | 20.219 | 1.386 | 22.552 | 1.000 28.73 |
| ATOM | 709 | CG | ASN | A | 107 | 20.932 | 2.668 | 22.930 | 1.000 36.73 |
| ATOM | 710 | OD1 | ASN | A | 107 | 20.436 | 3.454 | 23.736 | 1.000 67.71 |
| ATOM | 711 | ND2 | ASN | A | 107 | 22.095 | 2.891 | 22.331 | 1.000 51.19 |
| ATOM | 712 | C | ASN | A | 107 | 18.828 | 0.985 | 20.497 | 1.000 33.29 |
| ATOM | 713 | O | ASN | A | 107 | 19.161 | 1.589 | 19.469 | 1.000 31.37 |
| ATOM | 714 | N | ASN | A | 108 | 18.394 | -0.282 | 20.495 | 1.000 25.02 |
| ATOM | 715 | CA | ASN | A | 108 | 18.476 | -1.030 | 19.241 | 1.000 37.28 |
| ATOM | 716 | CB | ASN | A | 108 | 19.377 | -2.255 | 19.480 | 1.000 49.51 |
| ATOM | 717 | CG | ASN | A | 108 | 20.794 | -1.843 | 19.847 | 1.000 47.25 |
| ATOM | 718 | OD1 | ASN | A | 108 | 21.555 | -1.301 | 19.041 | 1.000 51.78 |
| ATOM | 719 | ND2 | ASN | A | 108 | 21.149 | -2.103 | 21.097 | 1.000 32.89 |
| ATOM | 720 | C | ASN | A | 108 | 17.157 | -1.472 | 18.642 | 1.000 41.66 |
| ATOM | 721 | O | ASN | A | 108 | 17.148 | -1.922 | 17.485 | 1.000 47.43 |
| ATOM | 722 | N | PHE | A | 109 | 16.007 | -1.389 | 19.306 | 1.000 28.44 |
| ATOM | 723 | CA | PHE | A | 109 | 14.782 | -1.693 | 18.557 | 1.000 26.26 |
| ATOM | 724 | CB | PHE | A | 109 | 14.575 | -3.179 | 18.334 | 1.000 25.58 |
| ATOM | 725 | CG | PHE | A | 109 | 14.889 | -4.154 | 19.423 | 1.000 33.48 |
| ATOM | 726 | CD1 | PHE | A | 109 | 13.866 | -4.796 | 20.113 | 1.000 34.64 |
| ATOM | 727 | CE1 | PHE | A | 109 | 14.130 | -5.705 | 21.121 | 1.000 41.36 |

FIGURE 20

```
ATOM    728  CZ   PHE A 109      15.442  -5.997  21.459  1.000 37.10
ATOM    729  CE2  PHE A 109      16.469  -5.365  20.782  1.000 39.85
ATOM    730  CD2  PHE A 109      16.198  -4.452  19.778  1.000 33.66
ATOM    731  C    PHE A 109      13.572  -1.059  19.243  1.000 30.59
ATOM    732  O    PHE A 109      13.663  -0.571  20.375  1.000 28.48
ATOM    733  N    ARG A 110      12.446  -1.068  18.531  1.000 21.36
ATOM    734  CA   ARG A 110      11.262  -0.340  18.981  1.000 27.72
ATOM    735  CB   ARG A 110      10.239  -0.271  17.833  1.000 27.18
ATOM    736  CG   ARG A 110      10.751   0.480  16.614  1.000 42.55
ATOM    737  CD   ARG A 110      10.188   1.893  16.543  1.000 49.91
ATOM    738  NE   ARG A 110      11.080   2.835  17.214  1.000 61.23
ATOM    739  CZ   ARG A 110      10.772   4.078  17.551  1.000 65.49
ATOM    740  NH1  ARG A 110       9.569   4.569  17.287  1.000 60.40
ATOM    741  NH2  ARG A 110      11.681   4.823  18.164  1.000 70.08
ATOM    742  C    ARG A 110      10.581  -0.929  20.206  1.000 31.32
ATOM    743  O    ARG A 110      10.063  -0.191  21.048  1.000 19.57
ATOM    744  N    ARG A 111      10.536  -2.256  20.315  1.000 31.03
ATOM    745  CA   ARG A 111       9.825  -2.858  21.447  1.000 28.45
ATOM    746  CB   ARG A 111       8.752  -3.826  20.971  1.000 24.30
ATOM    747  CG   ARG A 111       7.678  -3.274  20.054  1.000 26.60
ATOM    748  CD   ARG A 111       6.895  -4.443  19.432  1.000 26.88
ATOM    749  NE   ARG A 111       5.494  -4.083  19.259  1.000 39.04
ATOM    750  CZ   ARG A 111       4.427  -4.851  19.403  1.000 38.77
ATOM    751  NH1  ARG A 111       4.532  -6.128  19.745  1.000 39.25
ATOM    752  NH2  ARG A 111       3.226  -4.319  19.199  1.000 38.01
ATOM    753  C    ARG A 111      10.821  -3.575  22.352  1.000 27.13
ATOM    754  O    ARG A 111      10.716  -4.761  22.672  1.000 22.92
ATOM    755  N    GLU A 112      11.827  -2.801  22.753  1.000 24.46
ATOM    756  CA   GLU A 112      12.921  -3.388  23.527  1.000 20.04
ATOM    757  CB   GLU A 112      14.147  -2.484  23.425  1.000 26.41
ATOM    758  CG   GLU A 112      15.469  -3.181  23.658  1.000 27.73
ATOM    759  CD   GLU A 112      16.662  -2.423  23.112  1.000 26.53
ATOM    760  OE1  GLU A 112      17.767  -2.676  23.628  1.000 22.28
ATOM    761  OE2  GLU A 112      16.520  -1.592  22.191  1.000 24.96
ATOM    762  C    GLU A 112      12.523  -3.597  24.976  1.000 14.90
ATOM    763  O    GLU A 112      13.092  -4.442  25.668  1.000 19.62
ATOM    764  N    TYR A 113      11.540  -2.823  25.426  1.000 12.89
ATOM    765  CA   TYR A 113      11.084  -2.956  26.807  1.000 16.51
ATOM    766  CB   TYR A 113      11.619  -1.873  27.733  1.000 20.74
ATOM    767  CG   TYR A 113      13.078  -1.515  27.619  1.000 26.13
ATOM    768  CD1  TYR A 113      13.516  -0.557  26.718  1.000 18.47
ATOM    769  CE1  TYR A 113      14.856  -0.215  26.600  1.000 15.41
ATOM    770  CZ   TYR A 113      15.762  -0.861  27.419  1.000 20.13
ATOM    771  OH   TYR A 113      17.101  -0.557  27.351  1.000 18.27
ATOM    772  CE2  TYR A 113      15.348  -1.814  28.327  1.000 21.37
ATOM    773  CD2  TYR A 113      14.015  -2.150  28.439  1.000 19.35
ATOM    774  C    TYR A 113       9.561  -2.892  26.883  1.000 12.89
ATOM    775  O    TYR A 113       8.890  -2.269  26.069  1.000 17.48
ATOM    776  N    ILE A 114       9.052  -3.550  27.919  1.000 15.07
ATOM    777  CA   ILE A 114       7.656  -3.353  28.290  1.000 16.69
ATOM    778  CB   ILE A 114       6.820  -4.639  28.237  1.000 20.07
ATOM    779  CG1  ILE A 114       6.471  -5.095  26.816  1.000 12.15
```

FIGURE 21

```
ATOM    780  CD1 ILE A 114       6.039  -6.546  26.725 1.000  8.94
ATOM    781  CG2 ILE A 114       5.565  -4.473  29.088 1.000  8.30
ATOM    782  C   ILE A 114       7.694  -2.763  29.700 1.000 14.06
ATOM    783  O   ILE A 114       8.303  -3.348  30.598 1.000 21.26
ATOM    784  N   VAL A 115       7.089  -1.596  29.869 1.000 14.01
ATOM    785  CA  VAL A 115       7.062  -0.937  31.174 1.000 13.47
ATOM    786  CB  VAL A 115       7.364   0.562  31.033 1.000 21.33
ATOM    787  CG1 VAL A 115       6.907   1.314  32.276 1.000 36.92
ATOM    788  CG2 VAL A 115       8.848   0.796  30.787 1.000 22.96
ATOM    789  C   VAL A 115       5.679  -1.158  31.777 1.000 17.22
ATOM    790  O   VAL A 115       4.690  -0.963  31.064 1.000 14.66
ATOM    791  N   THR A 116       5.582  -1.561  33.041 1.000 12.85
ATOM    792  CA  THR A 116       4.240  -1.763  33.594 1.000 13.54
ATOM    793  CB  THR A 116       3.847  -3.242  33.400 1.000 21.30
ATOM    794  OG1 THR A 116       2.453  -3.453  33.671 1.000 12.82
ATOM    795  CG2 THR A 116       4.622  -4.140  34.364 1.000 10.46
ATOM    796  C   THR A 116       4.203  -1.329  35.050 1.000 19.71
ATOM    797  O   THR A 116       5.232  -0.961  35.629 1.000 17.41
ATOM    798  N   GLN A 117       3.030  -1.346  35.671 1.000 15.37
ATOM    799  CA  GLN A 117       2.879  -0.940  37.068 1.000 16.82
ATOM    800  CB  GLN A 117       1.431  -0.504  37.325 1.000 15.09
ATOM    801  CG  GLN A 117       0.408  -1.602  37.048 1.000 19.18
ATOM    802  CD  GLN A 117      -1.027  -1.187  37.299 1.000 20.69
ATOM    803  OE1 GLN A 117      -1.353  -0.007  37.405 1.000 25.69
ATOM    804  NE2 GLN A 117      -1.921  -2.158  37.408 1.000 18.66
ATOM    805  C   GLN A 117       3.256  -2.108  37.959 1.000 19.79
ATOM    806  O   GLN A 117       3.305  -3.228  37.431 1.000 16.87
ATOM    807  N   GLY A 118       3.513  -1.947  39.253 1.000 17.49
ATOM    808  CA  GLY A 118       3.594  -3.168  40.078 1.000 15.99
ATOM    809  C   GLY A 118       2.238  -3.855  40.061 1.000 17.56
ATOM    810  O   GLY A 118       1.217  -3.179  40.257 1.000 18.31
ATOM    811  N   PRO A 119       2.182  -5.164  39.834 1.000 24.40
ATOM    812  CA  PRO A 119       0.885  -5.845  39.699 1.000 30.48
ATOM    813  CB  PRO A 119       1.272  -7.296  39.388 1.000 31.82
ATOM    814  CG  PRO A 119       2.683  -7.227  38.899 1.000 29.01
ATOM    815  CD  PRO A 119       3.310  -6.102  39.686 1.000 21.75
ATOM    816  C   PRO A 119       0.033  -5.781  40.966 1.000 34.89
ATOM    817  O   PRO A 119       0.531  -5.756  42.091 1.000 19.13
ATOM    818  N   LEU A 120      -1.288  -5.753  40.778 1.000 30.42
ATOM    819  CA  LEU A 120      -2.231  -5.801  41.886 1.000 18.88
ATOM    820  CB  LEU A 120      -3.467  -4.949  41.613 1.000 22.55
ATOM    821  CG  LEU A 120      -3.264  -3.439  41.494 1.000 24.74
ATOM    822  CD1 LEU A 120      -4.202  -2.849  40.458 1.000 19.55
ATOM    823  CD2 LEU A 120      -3.482  -2.766  42.842 1.000 27.98
ATOM    824  C   LEU A 120      -2.690  -7.241  42.099 1.000 25.27
ATOM    825  O   LEU A 120      -2.588  -8.006  41.139 1.000 22.48
ATOM    826  N   PRO A 121      -3.160  -7.550  43.298 1.000 32.56
ATOM    827  CA  PRO A 121      -3.719  -8.872  43.596 1.000 22.33
ATOM    828  CB  PRO A 121      -4.528  -8.621  44.871 1.000 23.26
ATOM    829  CG  PRO A 121      -3.777  -7.531  45.557 1.000 29.77
ATOM    830  CD  PRO A 121      -3.184  -6.660  44.477 1.000 30.93
ATOM    831  C   PRO A 121      -4.638  -9.339  42.476 1.000 23.80
```

FIGURE 22

| ATOM | 832 | O   | PRO | A | 121 | -4.596 | -10.483 | 42.026 | 1.000 | 34.64 |
|------|-----|-----|-----|---|-----|--------|---------|--------|-------|-------|
| ATOM | 833 | N   | GLY | A | 122 | -5.453 | -8.405  | 41.983 | 1.000 | 24.62 |
| ATOM | 834 | CA  | GLY | A | 122 | -6.344 | -8.742  | 40.887 | 1.000 | 23.65 |
| ATOM | 835 | C   | GLY | A | 122 | -5.751 | -8.605  | 39.505 | 1.000 | 23.11 |
| ATOM | 836 | O   | GLY | A | 122 | -6.478 | -8.836  | 38.533 | 1.000 | 28.12 |
| ATOM | 837 | N   | THR | A | 123 | -4.480 | -8.246  | 39.320 | 1.000 | 20.65 |
| ATOM | 838 | CA  | THR | A | 123 | -3.939 | -8.167  | 37.962 | 1.000 | 21.61 |
| ATOM | 839 | CB  | THR | A | 123 | -3.544 | -6.732  | 37.551 | 1.000 | 26.10 |
| ATOM | 840 | OG1 | THR | A | 123 | -2.505 | -6.195  | 38.380 | 1.000 | 23.39 |
| ATOM | 841 | CG2 | THR | A | 123 | -4.762 | -5.828  | 37.710 | 1.000 | 18.68 |
| ATOM | 842 | C   | THR | A | 123 | -2.713 | -9.052  | 37.765 | 1.000 | 24.76 |
| ATOM | 843 | O   | THR | A | 123 | -2.184 | -9.097  | 36.653 | 1.000 | 25.68 |
| ATOM | 844 | N   | LYS | A | 124 | -2.249 | -9.744  | 38.806 | 1.000 | 23.64 |
| ATOM | 845 | CA  | LYS | A | 124 | -1.015 | -10.520 | 38.633 | 1.000 | 29.85 |
| ATOM | 846 | CB  | LYS | A | 124 | -0.485 | -10.990 | 39.979 | 1.000 | 33.93 |
| ATOM | 847 | CG  | LYS | A | 124 | -1.476 | -11.566 | 40.964 | 1.000 | 33.84 |
| ATOM | 848 | CD  | LYS | A | 124 | -0.857 | -11.618 | 42.358 | 1.000 | 31.42 |
| ATOM | 849 | CE  | LYS | A | 124 | -1.630 | -12.583 | 43.246 | 1.000 | 29.23 |
| ATOM | 850 | NZ  | LYS | A | 124 | -0.899 | -12.844 | 44.518 | 1.000 | 57.02 |
| ATOM | 851 | C   | LYS | A | 124 | -1.209 | -11.674 | 37.656 | 1.000 | 25.22 |
| ATOM | 852 | O   | LYS | A | 124 | -0.283 | -12.089 | 36.954 | 1.000 | 23.70 |
| ATOM | 853 | N   | ASP | A | 125 | -2.412 | -12.221 | 37.545 | 1.000 | 18.28 |
| ATOM | 854 | CA  | ASP | A | 125 | -2.657 | -13.219 | 36.515 | 1.000 | 12.12 |
| ATOM | 855 | CB  | ASP | A | 125 | -4.097 | -13.722 | 36.640 | 1.000 | 22.43 |
| ATOM | 856 | CG  | ASP | A | 125 | -4.249 | -14.657 | 37.831 | 1.000 | 27.90 |
| ATOM | 857 | OD1 | ASP | A | 125 | -3.285 | -14.704 | 38.618 | 1.000 | 29.09 |
| ATOM | 858 | OD2 | ASP | A | 125 | -5.301 | -15.311 | 37.945 | 1.000 | 33.37 |
| ATOM | 859 | C   | ASP | A | 125 | -2.450 | -12.633 | 35.120 | 1.000 | 23.84 |
| ATOM | 860 | O   | ASP | A | 125 | -1.964 | -13.280 | 34.191 | 1.000 | 23.80 |
| ATOM | 861 | N   | ASP | A | 126 | -2.855 | -11.375 | 34.973 | 1.000 | 22.66 |
| ATOM | 862 | CA  | ASP | A | 126 | -2.745 | -10.631 | 33.732 | 1.000 | 16.52 |
| ATOM | 863 | CB  | ASP | A | 126 | -3.480 | -9.297  | 33.831 | 1.000 | 25.64 |
| ATOM | 864 | CG  | ASP | A | 126 | -4.972 | -9.394  | 33.608 | 1.000 | 41.42 |
| ATOM | 865 | OD1 | ASP | A | 126 | -5.419 | -10.439 | 33.084 | 1.000 | 47.26 |
| ATOM | 866 | OD2 | ASP | A | 126 | -5.703 | -8.435  | 33.953 | 1.000 | 43.25 |
| ATOM | 867 | C   | ASP | A | 126 | -1.274 | -10.385 | 33.422 | 1.000 | 17.37 |
| ATOM | 868 | O   | ASP | A | 126 | -0.798 | -10.492 | 32.297 | 1.000 | 16.89 |
| ATOM | 869 | N   | PHE | A | 127 | -0.544 | -10.017 | 34.473 | 1.000 | 17.74 |
| ATOM | 870 | CA  | PHE | A | 127 | 0.871  | -9.707  | 34.284 | 1.000 | 21.41 |
| ATOM | 871 | CB  | PHE | A | 127 | 1.493  | -9.263  | 35.604 | 1.000 | 21.46 |
| ATOM | 872 | CG  | PHE | A | 127 | 3.004  | -9.193  | 35.632 | 1.000 | 22.78 |
| ATOM | 873 | CD1 | PHE | A | 127 | 3.643  | -8.020  | 35.266 | 1.000 | 12.05 |
| ATOM | 874 | CE1 | PHE | A | 127 | 5.024  | -7.924  | 35.292 | 1.000 | 16.72 |
| ATOM | 875 | CZ  | PHE | A | 127 | 5.790  | -9.004  | 35.682 | 1.000 | 21.66 |
| ATOM | 876 | CE2 | PHE | A | 127 | 5.172  | -10.189 | 36.044 | 1.000 | 19.24 |
| ATOM | 877 | CD2 | PHE | A | 127 | 3.794  | -10.266 | 36.036 | 1.000 | 18.50 |
| ATOM | 878 | C   | PHE | A | 127 | 1.578  | -10.931 | 33.700 | 1.000 | 25.45 |
| ATOM | 879 | O   | PHE | A | 127 | 2.374  | -10.786 | 32.784 | 1.000 | 21.87 |
| ATOM | 880 | N   | TRP | A | 128 | 1.280  | -12.107 | 34.243 | 1.000 | 21.42 |
| ATOM | 881 | CA  | TRP | A | 128 | 1.958  | -13.350 | 33.864 | 1.000 | 15.43 |
| ATOM | 882 | CB  | TRP | A | 128 | 1.695  | -14.415 | 34.942 | 1.000 | 17.74 |
| ATOM | 883 | CG  | TRP | A | 128 | 2.565  | -14.200 | 36.157 | 1.000 | 13.35 |

FIGURE 23

```
ATOM    884  CD1 TRP A 128       2.171 -14.021  37.449  1.000 18.06
ATOM    885  NE1 TRP A 128       3.264 -13.857  38.263  1.000 16.29
ATOM    886  CE2 TRP A 128       4.398 -13.927  37.497  1.000 13.72
ATOM    887  CD2 TRP A 128       3.999 -14.142  36.169  1.000 15.37
ATOM    888  CE3 TRP A 128       4.986 -14.251  35.178  1.000 20.85
ATOM    889  CZ3 TRP A 128       6.319 -14.148  35.521  1.000 13.01
ATOM    890  CH2 TRP A 128       6.684 -13.932  36.859  1.000 20.19
ATOM    891  CZ2 TRP A 128       5.744 -13.822  37.849  1.000 22.48
ATOM    892  C   TRP A 128       1.529 -13.783  32.480  1.000 11.86
ATOM    893  O   TRP A 128       2.310 -14.288  31.668  1.000 21.55
ATOM    894  N   LYS A 129       0.267 -13.551  32.155  1.000 16.27
ATOM    895  CA  LYS A 129      -0.214 -13.821  30.798  1.000 20.73
ATOM    896  CB  LYS A 129      -1.732 -13.626  30.741  1.000 17.81
ATOM    897  CG  LYS A 129      -2.314 -13.971  29.375  1.000 25.97
ATOM    898  CD  LYS A 129      -3.752 -13.477  29.289  1.000 37.98
ATOM    899  CE  LYS A 129      -4.458 -14.085  28.083  1.000 38.08
ATOM    900  NZ  LYS A 129      -4.700 -15.547  28.280  1.000 56.47
ATOM    901  C   LYS A 129       0.480 -12.919  29.785  1.000 24.29
ATOM    902  O   LYS A 129       0.862 -13.346  28.692  1.000 28.21
ATOM    903  N   MET A 130       0.668 -11.651  30.143  1.000 19.69
ATOM    904  CA  MET A 130       1.478 -10.735  29.351  1.000 15.73
ATOM    905  CB  MET A 130       1.576  -9.342  29.996  1.000 13.64
ATOM    906  CG  MET A 130       2.430  -8.380  29.162  1.000 18.33
ATOM    907  SD  MET A 130       2.476  -6.702  29.808  1.000 23.04
ATOM    908  CE  MET A 130       3.483  -6.962  31.274  1.000 22.96
ATOM    909  C   MET A 130       2.897 -11.282  29.166  1.000 14.42
ATOM    910  O   MET A 130       3.384 -11.324  28.034  1.000 21.88
ATOM    911  N   VAL A 131       3.537 -11.664  30.266  1.000 11.85
ATOM    912  CA  VAL A 131       4.902 -12.202  30.262  1.000 21.55
ATOM    913  CB  VAL A 131       5.372 -12.557  31.682  1.000 18.65
ATOM    914  CG1 VAL A 131       6.598 -13.458  31.679  1.000 16.39
ATOM    915  CG2 VAL A 131       5.688 -11.303  32.508  1.000 13.87
ATOM    916  C   VAL A 131       4.984 -13.418  29.333  1.000 26.29
ATOM    917  O   VAL A 131       5.892 -13.533  28.500  1.000 16.82
ATOM    918  N   TRP A 132       4.026 -14.334  29.437  1.000 24.10
ATOM    919  CA  TRP A 132       3.985 -15.531  28.598  1.000 23.86
ATOM    920  CB  TRP A 132       2.902 -16.495  29.121  1.000 27.36
ATOM    921  CG  TRP A 132       2.771 -17.754  28.310  1.000 30.80
ATOM    922  CD1 TRP A 132       1.818 -18.027  27.370  1.000 36.86
ATOM    923  NE1 TRP A 132       2.017 -19.278  26.835  1.000 36.99
ATOM    924  CE2 TRP A 132       3.115 -19.844  27.424  1.000 30.56
ATOM    925  CD2 TRP A 132       3.613 -18.914  28.359  1.000 24.79
ATOM    926  CE3 TRP A 132       4.745 -19.267  29.094  1.000 24.86
ATOM    927  CZ3 TRP A 132       5.332 -20.499  28.890  1.000 26.51
ATOM    928  CH2 TRP A 132       4.813 -21.405  27.955  1.000 24.87
ATOM    929  CZ2 TRP A 132       3.706 -21.089  27.215  1.000 30.31
ATOM    930  C   TRP A 132       3.747 -15.207  27.129  1.000 29.34
ATOM    931  O   TRP A 132       4.450 -15.695  26.237  1.000 17.82
ATOM    932  N   GLU A 133       2.744 -14.379  26.835  1.000 23.54
ATOM    933  CA  GLU A 133       2.415 -14.062  25.448  1.000 23.03
ATOM    934  CB  GLU A 133       1.100 -13.274  25.422  1.000 27.10
ATOM    935  CG  GLU A 133      -0.095 -14.176  25.718  1.000 30.65
```

FIGURE 24

```
ATOM    936  CD   GLU A 133      -1.396 -13.399  25.736  1.000 35.26
ATOM    937  OE1  GLU A 133      -1.363 -12.159  25.561  1.000 34.94
ATOM    938  OE2  GLU A 133      -2.444 -14.049  25.925  1.000 35.41
ATOM    939  C    GLU A 133       3.490 -13.262  24.735  1.000 27.45
ATOM    940  O    GLU A 133       3.689 -13.428  23.528  1.000 24.03
ATOM    941  N    GLN A 134       4.197 -12.382  25.449  1.000 21.95
ATOM    942  CA   GLN A 134       5.207 -11.554  24.787  1.000 17.30
ATOM    943  CB   GLN A 134       5.310 -10.184  25.466  1.000 17.87
ATOM    944  CG   GLN A 134       3.998  -9.411  25.524  1.000 15.39
ATOM    945  CD   GLN A 134       3.647  -8.841  24.163  1.000 19.03
ATOM    946  OE1  GLN A 134       4.481  -8.152  23.584  1.000 36.10
ATOM    947  NE2  GLN A 134       2.453  -9.133  23.668  1.000 27.56
ATOM    948  C    GLN A 134       6.576 -12.214  24.782  1.000 21.51
ATOM    949  O    GLN A 134       7.556 -11.579  24.396  1.000 32.24
ATOM    950  N    ASN A 135       6.677 -13.476  25.207  1.000 20.76
ATOM    951  CA   ASN A 135       7.974 -14.146  25.117  1.000 19.02
ATOM    952  CB   ASN A 135       8.406 -14.179  23.644  1.000 24.87
ATOM    953  CG   ASN A 135       7.566 -15.129  22.810  1.000 36.12
ATOM    954  OD1  ASN A 135       7.515 -16.331  23.072  1.000 34.91
ATOM    955  ND2  ASN A 135       6.895 -14.604  21.788  1.000 45.85
ATOM    956  C    ASN A 135       9.026 -13.459  25.974  1.000 21.43
ATOM    957  O    ASN A 135      10.193 -13.337  25.602  1.000 20.37
ATOM    958  N    VAL A 136       8.620 -12.988  27.148  1.000 16.96
ATOM    959  CA   VAL A 136       9.529 -12.287  28.047  1.000 15.79
ATOM    960  CB   VAL A 136       8.719 -11.486  29.093  1.000 11.80
ATOM    961  CG1  VAL A 136       9.587 -11.074  30.260  1.000  9.82
ATOM    962  CG2  VAL A 136       8.053 -10.279  28.431  1.000 16.29
ATOM    963  C    VAL A 136      10.440 -13.264  28.760  1.000 18.01
ATOM    964  O    VAL A 136       9.900 -14.252  29.262  1.000 28.46
ATOM    965  N    HIS A 137      11.747 -13.025  28.820  1.000 17.89
ATOM    966  CA   HIS A 137      12.634 -13.889  29.610  1.000 21.67
ATOM    967  CB   HIS A 137      13.724 -14.513  28.743  1.000 30.48
ATOM    968  CG   HIS A 137      13.253 -15.380  27.621  1.000 42.06
ATOM    969  ND1  HIS A 137      14.124 -16.077  26.808  1.000 53.39
ATOM    970  CE1  HIS A 137      13.449 -16.758  25.899  1.000 51.26
ATOM    971  NE2  HIS A 137      12.159 -16.533  26.088  1.000 49.27
ATOM    972  CD2  HIS A 137      12.018 -15.676  27.154  1.000 48.02
ATOM    973  C    HIS A 137      13.263 -13.116  30.766  1.000 19.36
ATOM    974  O    HIS A 137      13.818 -13.683  31.703  1.000 19.33
ATOM    975  N    ASN A 138      13.190 -11.780  30.748  1.000 23.51
ATOM    976  CA   ASN A 138      13.772 -11.010  31.842  1.000 19.39
ATOM    977  CB   ASN A 138      15.045 -10.301  31.351  1.000 21.07
ATOM    978  CG   ASN A 138      16.123 -11.316  30.999  1.000 26.12
ATOM    979  OD1  ASN A 138      16.514 -11.460  29.841  1.000 27.41
ATOM    980  ND2  ASN A 138      16.606 -12.026  32.011  1.000 23.04
ATOM    981  C    ASN A 138      12.811  -9.974  32.413  1.000 21.29
ATOM    982  O    ASN A 138      12.180  -9.217  31.666  1.000 16.20
ATOM    983  N    ILE A 139      12.718  -9.937  33.737  1.000 17.13
ATOM    984  CA   ILE A 139      11.859  -8.987  34.435  1.000 16.53
ATOM    985  CB   ILE A 139      10.693  -9.655  35.187  1.000 17.07
ATOM    986  CG1  ILE A 139       9.711 -10.424  34.296  1.000 17.67
ATOM    987  CD1  ILE A 139       8.911 -11.494  35.031  1.000 15.33
```

FIGURE 25

| | | | | | | | | |
|---|---|---|---|---|---|---|---|---|
| ATOM | 988 | CG2 | ILE | A 139 | 9.941 | -8.625 | 36.020 | 1.000 12.08 |
| ATOM | 989 | C | ILE | A 139 | 12.694 | -8.169 | 35.412 | 1.000 17.79 |
| ATOM | 990 | O | ILE | A 139 | 13.465 | -8.707 | 36.203 | 1.000 21.50 |
| ATOM | 991 | N | VAL | A 140 | 12.560 | -6.852 | 35.353 | 1.000 19.27 |
| ATOM | 992 | CA | VAL | A 140 | 13.298 | -5.966 | 36.242 | 1.000 20.43 |
| ATOM | 993 | CB | VAL | A 140 | 14.088 | -4.892 | 35.469 | 1.000 23.29 |
| ATOM | 994 | CG1 | VAL | A 140 | 14.892 | -4.018 | 36.427 | 1.000 15.96 |
| ATOM | 995 | CG2 | VAL | A 140 | 14.965 | -5.563 | 34.419 | 1.000 15.64 |
| ATOM | 996 | C | VAL | A 140 | 12.331 | -5.254 | 37.179 | 1.000 17.79 |
| ATOM | 997 | O | VAL | A 140 | 11.385 | -4.619 | 36.709 | 1.000 15.65 |
| ATOM | 998 | N | MET | A 141 | 12.596 | -5.376 | 38.473 | 1.000 19.78 |
| ATOM | 999 | CA | MET | A 141 | 11.718 | -4.726 | 39.452 | 1.000 23.36 |
| ATOM | 1000 | CB | MET | A 141 | 11.016 | -5.796 | 40.283 | 1.000 25.59 |
| ATOM | 1001 | CG | MET | A 141 | 10.199 | -5.282 | 41.461 | 1.000 21.23 |
| ATOM | 1002 | SD | MET | A 141 | 9.408 | -6.648 | 42.325 | 1.000 27.56 |
| ATOM | 1003 | CE | MET | A 141 | 8.617 | -5.832 | 43.707 | 1.000 31.17 |
| ATOM | 1004 | C | MET | A 141 | 12.541 | -3.772 | 40.294 | 1.000 27.26 |
| ATOM | 1005 | O | MET | A 141 | 13.509 | -4.208 | 40.923 | 1.000 19.70 |
| ATOM | 1006 | N | VAL | A 142 | 12.179 | -2.487 | 40.299 | 1.000 22.95 |
| ATOM | 1007 | CA | VAL | A 142 | 12.981 | -1.529 | 41.061 | 1.000 23.51 |
| ATOM | 1008 | CB | VAL | A 142 | 13.642 | -0.457 | 40.171 | 1.000 24.01 |
| ATOM | 1009 | CG1 | VAL | A 142 | 14.774 | -1.104 | 39.384 | 1.000 28.07 |
| ATOM | 1010 | CG2 | VAL | A 142 | 12.631 | 0.200 | 39.250 | 1.000 26.62 |
| ATOM | 1011 | C | VAL | A 142 | 12.151 | -0.832 | 42.134 | 1.000 24.80 |
| ATOM | 1012 | O | VAL | A 142 | 12.092 | 0.396 | 42.186 | 1.000 24.92 |
| ATOM | 1013 | N | THR | A 143 | 11.544 | -1.654 | 42.968 | 1.000 32.06 |
| ATOM | 1014 | CA | THR | A 143 | 10.713 | -1.262 | 44.092 | 1.000 31.60 |
| ATOM | 1015 | CB | THR | A 143 | 9.303 | -0.845 | 43.629 | 1.000 34.01 |
| ATOM | 1016 | OG1 | THR | A 143 | 8.553 | -0.296 | 44.720 | 1.000 32.56 |
| ATOM | 1017 | CG2 | THR | A 143 | 8.489 | -2.040 | 43.150 | 1.000 19.73 |
| ATOM | 1018 | C | THR | A 143 | 10.608 | -2.414 | 45.081 | 1.000 32.84 |
| ATOM | 1019 | O | THR | A 143 | 10.735 | -3.579 | 44.697 | 1.000 27.98 |
| ATOM | 1020 | N | GLN | A 144 | 10.371 | -2.074 | 46.348 | 1.000 33.83 |
| ATOM | 1021 | CA | GLN | A 144 | 9.992 | -3.090 | 47.327 | 1.000 31.46 |
| ATOM | 1022 | CB | GLN | A 144 | 10.464 | -2.772 | 48.733 | 1.000 28.66 |
| ATOM | 1023 | CG | GLN | A 144 | 11.964 | -2.806 | 48.954 | 1.000 39.24 |
| ATOM | 1024 | CD | GLN | A 144 | 12.357 | -2.317 | 50.339 | 1.000 47.09 |
| ATOM | 1025 | OE1 | GLN | A 144 | 12.240 | -3.049 | 51.324 | 1.000 40.08 |
| ATOM | 1026 | NE2 | GLN | A 144 | 12.828 | -1.075 | 50.438 | 1.000 32.97 |
| ATOM | 1027 | C | GLN | A 144 | 8.469 | -3.184 | 47.268 | 1.000 30.87 |
| ATOM | 1028 | O | GLN | A 144 | 7.859 | -2.272 | 46.701 | 1.000 27.64 |
| ATOM | 1029 | N | CYS | A 145 | 7.887 | -4.240 | 47.815 | 1.000 32.97 |
| ATOM | 1030 | CA | CYS | A 145 | 6.434 | -4.376 | 47.762 | 1.000 27.50 |
| ATOM | 1031 | CB | CYS | A 145 | 6.053 | -5.820 | 48.082 | 1.000 24.78 |
| ATOM | 1032 | SG | CYS | A 145 | 6.485 | -6.965 | 46.749 | 1.000 32.93 |
| ATOM | 1033 | C | CYS | A 145 | 5.746 | -3.404 | 48.716 | 1.000 29.39 |
| ATOM | 1034 | O | CYS | A 145 | 4.579 | -3.052 | 48.520 | 1.000 29.75 |
| ATOM | 1035 | N | VAL | A 146 | 6.480 | -2.988 | 49.733 | 1.000 32.17 |
| ATOM | 1036 | CA | VAL | A 146 | 6.060 | -2.022 | 50.744 | 1.000 32.69 |
| ATOM | 1037 | CB | VAL | A 146 | 5.547 | -2.672 | 52.039 | 1.000 35.63 |
| ATOM | 1038 | CG1 | VAL | A 146 | 4.981 | -1.619 | 52.989 | 1.000 28.22 |
| ATOM | 1039 | CG2 | VAL | A 146 | 4.490 | -3.724 | 51.746 | 1.000 39.32 |

FIGURE 26

| ATOM | 1040 | C | VAL | A | 146 | 7.238 | -1.119 | 51.101 | 1.000 | 24.56 |
|------|------|------|-----|---|-----|-------|--------|--------|-------|-------|
| ATOM | 1041 | O | VAL | A | 146 | 8.312 | -1.600 | 51.466 | 1.000 | 30.54 |
| ATOM | 1042 | N | GLU | A | 147 | 7.053 | 0.184 | 50.987 | 1.000 | 26.82 |
| ATOM | 1043 | CA | GLU | A | 147 | 8.128 | 1.123 | 51.322 | 1.000 | 34.58 |
| ATOM | 1044 | CB | GLU | A | 147 | 8.516 | 1.929 | 50.080 | 1.000 | 36.31 |
| ATOM | 1045 | CG | GLU | A | 147 | 8.591 | 1.048 | 48.834 | 1.000 | 43.83 |
| ATOM | 1046 | CD | GLU | A | 147 | 9.589 | 1.535 | 47.809 | 1.000 | 42.03 |
| ATOM | 1047 | OE1 | GLU | A | 147 | 9.517 | 2.715 | 47.414 | 1.000 | 36.27 |
| ATOM | 1048 | OE2 | GLU | A | 147 | 10.460 | 0.748 | 47.383 | 1.000 | 38.56 |
| ATOM | 1049 | C | GLU | A | 147 | 7.682 | 2.020 | 52.466 | 1.000 | 43.00 |
| ATOM | 1050 | O | GLU | A | 147 | 6.842 | 2.895 | 52.262 | 1.000 | 36.39 |
| ATOM | 1051 | N | LYS | A | 148 | 8.228 | 1.770 | 53.651 | 1.000 | 53.50 |
| ATOM | 1052 | CA | LYS | A | 148 | 7.803 | 2.440 | 54.874 | 1.000 | 50.57 |
| ATOM | 1053 | CB | LYS | A | 148 | 8.242 | 3.904 | 54.859 | 1.000 | 53.82 |
| ATOM | 1054 | CG | LYS | A | 148 | 9.487 | 4.175 | 55.693 | 1.000 | 55.76 |
| ATOM | 1055 | CD | LYS | A | 148 | 9.736 | 5.666 | 55.836 | 1.000 | 61.51 |
| ATOM | 1056 | CE | LYS | A | 148 | 11.217 | 5.994 | 55.917 | 1.000 | 64.59 |
| ATOM | 1057 | NZ | LYS | A | 148 | 11.582 | 7.165 | 55.066 | 1.000 | 54.71 |
| ATOM | 1058 | C | LYS | A | 148 | 6.291 | 2.327 | 55.068 | 1.000 | 40.10 |
| ATOM | 1059 | O | LYS | A | 148 | 5.588 | 3.337 | 55.119 | 1.000 | 40.70 |
| ATOM | 1060 | N | GLY | A | 149 | 5.792 | 1.102 | 55.161 | 1.000 | 31.76 |
| ATOM | 1061 | CA | GLY | A | 149 | 4.396 | 0.812 | 55.408 | 1.000 | 38.69 |
| ATOM | 1062 | C | GLY | A | 149 | 3.455 | 1.021 | 54.249 | 1.000 | 45.94 |
| ATOM | 1063 | O | GLY | A | 149 | 2.303 | 0.575 | 54.255 | 1.000 | 42.79 |
| ATOM | 1064 | N | ARG | A | 150 | 3.889 | 1.707 | 53.188 | 1.000 | 44.38 |
| ATOM | 1065 | CA | ARG | A | 150 | 2.967 | 1.932 | 52.076 | 1.000 | 37.05 |
| ATOM | 1066 | CB | ARG | A | 150 | 3.179 | 3.306 | 51.450 | 1.000 | 43.59 |
| ATOM | 1067 | CG | ARG | A | 150 | 2.273 | 4.410 | 51.971 | 1.000 | 52.87 |
| ATOM | 1068 | CD | ARG | A | 150 | 2.530 | 5.696 | 51.196 | 1.000 | 65.25 |
| ATOM | 1069 | NE | ARG | A | 150 | 1.626 | 6.786 | 51.559 | 1.000 | 75.91 |
| ATOM | 1070 | CZ | ARG | A | 150 | 1.738 | 8.024 | 51.087 | 1.000 | 82.71 |
| ATOM | 1071 | NH1 | ARG | A | 150 | 2.708 | 8.322 | 50.240 | 1.000 | 99.14 |
| ATOM | 1072 | NH2 | ARG | A | 150 | 0.886 | 8.969 | 51.456 | 1.000 | 75.70 |
| ATOM | 1073 | C | ARG | A | 150 | 3.144 | 0.849 | 51.015 | 1.000 | 31.26 |
| ATOM | 1074 | O | ARG | A | 150 | 4.266 | 0.643 | 50.541 | 1.000 | 26.56 |
| ATOM | 1075 | N | VAL | A | 151 | 2.039 | 0.197 | 50.671 | 1.000 | 26.68 |
| ATOM | 1076 | CA | VAL | A | 151 | 2.035 | -0.861 | 49.673 | 1.000 | 27.32 |
| ATOM | 1077 | CB | VAL | A | 151 | 0.713 | -1.647 | 49.660 | 1.000 | 35.52 |
| ATOM | 1078 | CG1 | VAL | A | 151 | 0.755 | -2.776 | 48.637 | 1.000 | 33.72 |
| ATOM | 1079 | CG2 | VAL | A | 151 | 0.441 | -2.202 | 51.049 | 1.000 | 18.61 |
| ATOM | 1080 | C | VAL | A | 151 | 2.298 | -0.281 | 48.288 | 1.000 | 28.80 |
| ATOM | 1081 | O | VAL | A | 151 | 1.563 | 0.579 | 47.806 | 1.000 | 38.64 |
| ATOM | 1082 | N | LYS | A | 152 | 3.371 | -0.759 | 47.674 | 1.000 | 33.79 |
| ATOM | 1083 | CA | LYS | A | 152 | 3.788 | -0.282 | 46.358 | 1.000 | 32.44 |
| ATOM | 1084 | CB | LYS | A | 152 | 5.272 | 0.088 | 46.373 | 1.000 | 29.41 |
| ATOM | 1085 | CG | LYS | A | 152 | 5.626 | 1.158 | 47.393 | 1.000 | 38.23 |
| ATOM | 1086 | CD | LYS | A | 152 | 4.469 | 2.111 | 47.631 | 1.000 | 43.28 |
| ATOM | 1087 | CE | LYS | A | 152 | 4.900 | 3.566 | 47.538 | 1.000 | 49.33 |
| ATOM | 1088 | NZ | LYS | A | 152 | 3.834 | 4.403 | 46.910 | 1.000 | 76.06 |
| ATOM | 1089 | C | LYS | A | 152 | 3.528 | -1.344 | 45.298 | 1.000 | 30.77 |
| ATOM | 1090 | O | LYS | A | 152 | 3.227 | -1.024 | 44.149 | 1.000 | 33.84 |
| ATOM | 1091 | N | CYS | A | 153 | 3.648 | -2.611 | 45.697 | 1.000 | 27.03 |

FIGURE 27

| ATOM | 1092 | CA | CYS | A | 153 | 3.476 | -3.698 | 44.729 | 1.000 | 27.81 |
|------|------|-----|-----|---|-----|--------|---------|--------|-------|-------|
| ATOM | 1093 | CB | CYS | A | 153 | 4.776 | -3.878 | 43.946 | 1.000 | 27.07 |
| ATOM | 1094 | SG | CYS | A | 153 | 4.790 | -5.091 | 42.611 | 1.000 | 26.17 |
| ATOM | 1095 | C | CYS | A | 153 | 3.064 | -4.986 | 45.420 | 1.000 | 26.82 |
| ATOM | 1096 | O | CYS | A | 153 | 3.553 | -5.324 | 46.490 | 1.000 | 27.44 |
| ATOM | 1097 | N | ASP | A | 154 | 2.155 | -5.742 | 44.804 | 1.000 | 34.85 |
| ATOM | 1098 | CA | ASP | A | 154 | 1.828 | -7.062 | 45.322 | 1.000 | 37.76 |
| ATOM | 1099 | CB | ASP | A | 154 | 0.584 | -7.638 | 44.645 | 1.000 | 29.89 |
| ATOM | 1100 | CG | ASP | A | 154 | 0.099 | -8.911 | 45.316 | 1.000 | 34.93 |
| ATOM | 1101 | OD1 | ASP | A | 154 | -0.148 | -9.919 | 44.627 | 1.000 | 38.18 |
| ATOM | 1102 | OD2 | ASP | A | 154 | -0.042 | -8.917 | 46.557 | 1.000 | 47.22 |
| ATOM | 1103 | C | ASP | A | 154 | 3.010 | -8.017 | 45.130 | 1.000 | 40.61 |
| ATOM | 1104 | O | ASP | A | 154 | 3.825 | -7.877 | 44.216 | 1.000 | 30.25 |
| ATOM | 1105 | N | HIS | A | 155 | 3.097 | -8.993 | 46.020 | 1.000 | 32.47 |
| ATOM | 1106 | CA | HIS | A | 155 | 4.072 | -10.070 | 45.914 | 1.000 | 30.20 |
| ATOM | 1107 | CB | HIS | A | 155 | 4.312 | -10.721 | 47.282 | 1.000 | 28.22 |
| ATOM | 1108 | CG | HIS | A | 155 | 5.365 | -11.788 | 47.244 | 1.000 | 30.06 |
| ATOM | 1109 | ND1 | HIS | A | 155 | 6.655 | -11.595 | 47.686 | 1.000 | 32.04 |
| ATOM | 1110 | CE1 | HIS | A | 155 | 7.357 | -12.700 | 47.514 | 1.000 | 31.07 |
| ATOM | 1111 | NE2 | HIS | A | 155 | 6.557 | -13.606 | 46.980 | 1.000 | 35.21 |
| ATOM | 1112 | CD2 | HIS | A | 155 | 5.311 | -13.064 | 46.793 | 1.000 | 27.75 |
| ATOM | 1113 | C | HIS | A | 155 | 3.531 | -11.053 | 44.879 | 1.000 | 30.27 |
| ATOM | 1114 | O | HIS | A | 155 | 2.745 | -11.922 | 45.253 | 1.000 | 34.64 |
| ATOM | 1115 | N | TYR | A | 156 | 3.914 | -10.897 | 43.613 | 1.000 | 24.90 |
| ATOM | 1116 | CA | TYR | A | 156 | 3.234 | -11.590 | 42.521 | 1.000 | 22.68 |
| ATOM | 1117 | CB | TYR | A | 156 | 3.093 | -10.621 | 41.340 | 1.000 | 22.68 |
| ATOM | 1118 | CG | TYR | A | 156 | 4.387 | -10.046 | 40.818 | 1.000 | 21.15 |
| ATOM | 1119 | CD1 | TYR | A | 156 | 5.101 | -10.741 | 39.844 | 1.000 | 20.48 |
| ATOM | 1120 | CE1 | TYR | A | 156 | 6.286 | -10.236 | 39.348 | 1.000 | 18.15 |
| ATOM | 1121 | CZ | TYR | A | 156 | 6.755 | -9.037 | 39.824 | 1.000 | 18.02 |
| ATOM | 1122 | OH | TYR | A | 156 | 7.933 | -8.545 | 39.322 | 1.000 | 19.23 |
| ATOM | 1123 | CE2 | TYR | A | 156 | 6.070 | -8.320 | 40.786 | 1.000 | 19.56 |
| ATOM | 1124 | CD2 | TYR | A | 156 | 4.883 | -8.836 | 41.274 | 1.000 | 17.13 |
| ATOM | 1125 | C | TYR | A | 156 | 3.905 | -12.870 | 42.063 | 1.000 | 25.52 |
| ATOM | 1126 | O | TYR | A | 156 | 3.550 | -13.447 | 41.027 | 1.000 | 22.83 |
| ATOM | 1127 | N | TRP | A | 157 | 4.881 | -13.356 | 42.825 | 1.000 | 33.11 |
| ATOM | 1128 | CA | TRP | A | 157 | 5.531 | -14.623 | 42.504 | 1.000 | 31.82 |
| ATOM | 1129 | CB | TRP | A | 157 | 6.985 | -14.383 | 42.092 | 1.000 | 32.50 |
| ATOM | 1130 | CG | TRP | A | 157 | 7.827 | -13.805 | 43.197 | 1.000 | 31.35 |
| ATOM | 1131 | CD1 | TRP | A | 157 | 8.582 | -14.486 | 44.110 | 1.000 | 27.90 |
| ATOM | 1132 | NE1 | TRP | A | 157 | 9.208 | -13.611 | 44.960 | 1.000 | 24.08 |
| ATOM | 1133 | CE2 | TRP | A | 157 | 8.866 | -12.330 | 44.607 | 1.000 | 25.03 |
| ATOM | 1134 | CD2 | TRP | A | 157 | 8.000 | -12.414 | 43.503 | 1.000 | 28.13 |
| ATOM | 1135 | CE3 | TRP | A | 157 | 7.500 | -11.231 | 42.944 | 1.000 | 23.89 |
| ATOM | 1136 | CZ3 | TRP | A | 157 | 7.880 | -10.030 | 43.502 | 1.000 | 22.95 |
| ATOM | 1137 | CH2 | TRP | A | 157 | 8.743 | -9.975 | 44.602 | 1.000 | 25.46 |
| ATOM | 1138 | CZ2 | TRP | A | 157 | 9.251 | -11.113 | 45.172 | 1.000 | 27.53 |
| ATOM | 1139 | C | TRP | A | 157 | 5.490 | -15.556 | 43.706 | 1.000 | 28.64 |
| ATOM | 1140 | O | TRP | A | 157 | 5.361 | -15.056 | 44.828 | 1.000 | 33.96 |
| ATOM | 1141 | N | PRO | A | 158 | 5.623 | -16.858 | 43.503 | 1.000 | 30.31 |
| ATOM | 1142 | CA | PRO | A | 158 | 5.666 | -17.787 | 44.640 | 1.000 | 33.91 |
| ATOM | 1143 | CB | PRO | A | 158 | 5.597 | -19.170 | 44.009 | 1.000 | 24.17 |

FIGURE 28

| ATOM | 1144 | CG  | PRO | A | 158 | 5.988  | -18.987 | 42.583 | 1.000 | 30.62 |
| ATOM | 1145 | CD  | PRO | A | 158 | 5.757  | -17.553 | 42.215 | 1.000 | 28.57 |
| ATOM | 1146 | C   | PRO | A | 158 | 6.990  | -17.602 | 45.391 | 1.000 | 42.64 |
| ATOM | 1147 | O   | PRO | A | 158 | 8.051  | -17.797 | 44.790 | 1.000 | 41.28 |
| ATOM | 1148 | N   | ALA | A | 159 | 6.903  | -17.227 | 46.657 | 1.000 | 44.31 |
| ATOM | 1149 | CA  | ALA | A | 159 | 8.044  | -16.897 | 47.500 | 1.000 | 52.40 |
| ATOM | 1150 | CB  | ALA | A | 159 | 7.567  | -16.083 | 48.701 | 1.000 | 39.50 |
| ATOM | 1151 | C   | ALA | A | 159 | 8.838  | -18.094 | 48.000 | 1.000 | 52.74 |
| ATOM | 1152 | O   | ALA | A | 159 | 9.922  | -17.935 | 48.572 | 1.000 | 69.24 |
| ATOM | 1153 | N   | ASP | A | 160 | 8.338  | -19.307 | 47.809 | 1.000 | 51.47 |
| ATOM | 1154 | CA  | ASP | A | 160 | 9.110  | -20.487 | 48.190 | 1.000 | 60.84 |
| ATOM | 1155 | CB  | ASP | A | 160 | 8.266  | -21.507 | 48.945 | 1.000 | 68.39 |
| ATOM | 1156 | CG  | ASP | A | 160 | 7.989  | -21.175 | 50.394 | 1.000 | 75.02 |
| ATOM | 1157 | OD1 | ASP | A | 160 | 8.838  | -20.519 | 51.035 | 1.000 | 88.56 |
| ATOM | 1158 | OD2 | ASP | A | 160 | 6.913  | -21.574 | 50.891 | 1.000 | 76.88 |
| ATOM | 1159 | C   | ASP | A | 160 | 9.663  | -21.134 | 46.924 | 1.000 | 53.11 |
| ATOM | 1160 | O   | ASP | A | 160 | 9.452  | -20.618 | 45.827 | 1.000 | 52.42 |
| ATOM | 1161 | N   | GLN | A | 161 | 10.327 | -22.273 | 47.064 | 1.000 | 49.61 |
| ATOM | 1162 | CA  | GLN | A | 161 | 10.738 | -23.062 | 45.911 | 1.000 | 54.59 |
| ATOM | 1163 | CB  | GLN | A | 161 | 11.818 | -24.073 | 46.306 | 1.000 | 56.30 |
| ATOM | 1164 | CG  | GLN | A | 161 | 13.239 | -23.547 | 46.201 | 1.000 | 55.95 |
| ATOM | 1165 | CD  | GLN | A | 161 | 13.450 | -22.701 | 44.959 | 1.000 | 53.24 |
| ATOM | 1166 | OE1 | GLN | A | 161 | 13.368 | -23.208 | 43.842 | 1.000 | 49.06 |
| ATOM | 1167 | NE2 | GLN | A | 161 | 13.724 | -21.415 | 45.153 | 1.000 | 41.80 |
| ATOM | 1168 | C   | GLN | A | 161 | 9.543  | -23.794 | 45.301 | 1.000 | 51.44 |
| ATOM | 1169 | O   | GLN | A | 161 | 9.666  | -24.493 | 44.295 | 1.000 | 52.78 |
| ATOM | 1170 | N   | ASP | A | 162 | 8.381  | -23.641 | 45.922 | 1.000 | 45.89 |
| ATOM | 1171 | CA  | ASP | A | 162 | 7.149  | -24.258 | 45.482 | 1.000 | 51.10 |
| ATOM | 1172 | CB  | ASP | A | 162 | 6.101  | -24.204 | 46.603 | 1.000 | 57.35 |
| ATOM | 1173 | CG  | ASP | A | 162 | 5.884  | -22.779 | 47.078 | 1.000 | 65.40 |
| ATOM | 1174 | OD1 | ASP | A | 162 | 6.698  | -21.916 | 46.685 | 1.000 | 69.28 |
| ATOM | 1175 | OD2 | ASP | A | 162 | 4.914  | -22.539 | 47.823 | 1.000 | 75.26 |
| ATOM | 1176 | C   | ASP | A | 162 | 6.603  | -23.596 | 44.219 | 1.000 | 49.85 |
| ATOM | 1177 | O   | ASP | A | 162 | 7.291  | -22.878 | 43.496 | 1.000 | 53.02 |
| ATOM | 1178 | N   | SER | A | 163 | 5.331  | -23.884 | 43.972 | 1.000 | 41.47 |
| ATOM | 1179 | CA  | SER | A | 163 | 4.634  | -23.472 | 42.768 | 1.000 | 32.87 |
| ATOM | 1180 | CB  | SER | A | 163 | 4.486  | -24.685 | 41.840 | 1.000 | 32.47 |
| ATOM | 1181 | OG  | SER | A | 163 | 3.800  | -25.721 | 42.529 | 1.000 | 31.33 |
| ATOM | 1182 | C   | SER | A | 163 | 3.257  | -22.894 | 43.072 | 1.000 | 32.86 |
| ATOM | 1183 | O   | SER | A | 163 | 2.679  | -23.132 | 44.135 | 1.000 | 30.48 |
| ATOM | 1184 | N   | LEU | A | 164 | 2.739  | -22.138 | 42.115 | 1.000 | 28.27 |
| ATOM | 1185 | CA  | LEU | A | 164 | 1.390  | -21.603 | 42.172 | 1.000 | 23.14 |
| ATOM | 1186 | CB  | LEU | A | 164 | 1.320  | -20.222 | 42.813 | 1.000 | 23.52 |
| ATOM | 1187 | CG  | LEU | A | 164 | 1.908  | -20.041 | 44.206 | 1.000 | 37.76 |
| ATOM | 1188 | CD1 | LEU | A | 164 | 1.918  | -18.560 | 44.569 | 1.000 | 36.50 |
| ATOM | 1189 | CD2 | LEU | A | 164 | 1.141  | -20.859 | 45.236 | 1.000 | 38.57 |
| ATOM | 1190 | C   | LEU | A | 164 | 0.833  | -21.459 | 40.757 | 1.000 | 28.03 |
| ATOM | 1191 | O   | LEU | A | 164 | 1.613  | -21.308 | 39.816 | 1.000 | 24.57 |
| ATOM | 1192 | N   | TYR | A | 165 | -0.492 | -21.480 | 40.677 | 1.000 | 28.64 |
| ATOM | 1193 | CA  | TYR | A | 165 | -1.157 | -21.136 | 39.432 | 1.000 | 28.93 |
| ATOM | 1194 | CB  | TYR | A | 165 | -2.517 | -21.817 | 39.316 | 1.000 | 22.72 |
| ATOM | 1195 | CG  | TYR | A | 165 | -2.482 | -23.276 | 38.942 | 1.000 | 18.62 |

FIGURE 29

```
ATOM   1196  CD1 TYR A 165      -2.328 -24.260  39.911  1.000  25.83
ATOM   1197  CE1 TYR A 165      -2.294 -25.603  39.581  1.000  25.94
ATOM   1198  CZ  TYR A 165      -2.418 -25.987  38.262  1.000  26.30
ATOM   1199  OH  TYR A 165      -2.393 -27.324  37.926  1.000  27.99
ATOM   1200  CE2 TYR A 165      -2.577 -25.035  37.287  1.000  21.27
ATOM   1201  CD2 TYR A 165      -2.606 -23.693  37.627  1.000  22.96
ATOM   1202  C   TYR A 165      -1.349 -19.620  39.364  1.000  30.51
ATOM   1203  O   TYR A 165      -1.633 -19.005  40.383  1.000  27.58
ATOM   1204  N   TYR A 166      -1.205 -19.047  38.185  1.000  24.74
ATOM   1205  CA  TYR A 166      -1.612 -17.675  37.914  1.000  24.22
ATOM   1206  CB  TYR A 166      -0.422 -16.731  37.786  1.000  24.27
ATOM   1207  CG  TYR A 166       0.394 -16.584  39.057  1.000  25.75
ATOM   1208  CD1 TYR A 166       0.075 -15.624  40.015  1.000  21.51
ATOM   1209  CE1 TYR A 166       0.820 -15.483  41.177  1.000  23.56
ATOM   1210  CZ  TYR A 166       1.899 -16.316  41.394  1.000  24.64
ATOM   1211  OH  TYR A 166       2.646 -16.197  42.543  1.000  25.20
ATOM   1212  CE2 TYR A 166       2.244 -17.280  40.464  1.000  21.31
ATOM   1213  CD2 TYR A 166       1.492 -17.401  39.306  1.000  28.88
ATOM   1214  C   TYR A 166      -2.449 -17.749  36.642  1.000  28.89
ATOM   1215  O   TYR A 166      -1.923 -17.886  35.535  1.000  28.35
ATOM   1216  N   GLY A 167      -3.775 -17.705  36.793  1.000  30.71
ATOM   1217  CA  GLY A 167      -4.586 -17.861  35.583  1.000  35.47
ATOM   1218  C   GLY A 167      -4.383 -19.271  35.038  1.000  34.48
ATOM   1219  O   GLY A 167      -4.521 -20.213  35.826  1.000  29.66
ATOM   1220  N   ASP A 168      -4.072 -19.391  33.760  1.000  25.86
ATOM   1221  CA  ASP A 168      -3.860 -20.665  33.082  1.000  23.07
ATOM   1222  CB  ASP A 168      -4.216 -20.560  31.601  1.000  22.17
ATOM   1223  CG  ASP A 168      -5.719 -20.526  31.403  1.000  30.38
ATOM   1224  OD1 ASP A 168      -6.422 -20.536  32.432  1.000  44.55
ATOM   1225  OD2 ASP A 168      -6.178 -20.501  30.246  1.000  52.57
ATOM   1226  C   ASP A 168      -2.411 -21.110  33.207  1.000  28.96
ATOM   1227  O   ASP A 168      -1.997 -22.187  32.785  1.000  35.10
ATOM   1228  N   LEU A 169      -1.617 -20.229  33.816  1.000  33.00
ATOM   1229  CA  LEU A 169      -0.197 -20.558  33.927  1.000  32.77
ATOM   1230  CB  LEU A 169       0.652 -19.326  33.571  1.000  25.71
ATOM   1231  CG  LEU A 169       0.116 -18.558  32.353  1.000  24.37
ATOM   1232  CD1 LEU A 169       0.491 -17.088  32.434  1.000  31.21
ATOM   1233  CD2 LEU A 169       0.634 -19.191  31.076  1.000  35.13
ATOM   1234  C   LEU A 169       0.190 -21.063  35.306  1.000  20.10
ATOM   1235  O   LEU A 169      -0.332 -20.698  36.352  1.000  25.85
ATOM   1236  N   ILE A 170       1.186 -21.938  35.253  1.000  23.95
ATOM   1237  CA  ILE A 170       1.792 -22.432  36.482  1.000  30.46
ATOM   1238  CB  ILE A 170       1.748 -23.965  36.556  1.000  29.06
ATOM   1239  CG1 ILE A 170       2.820 -24.536  37.485  1.000  31.61
ATOM   1240  CD1 ILE A 170       2.381 -24.474  38.935  1.000  36.97
ATOM   1241  CG2 ILE A 170       1.824 -24.585  35.175  1.000  61.97
ATOM   1242  C   ILE A 170       3.229 -21.924  36.541  1.000  27.52
ATOM   1243  O   ILE A 170       3.980 -22.051  35.579  1.000  28.50
ATOM   1244  N   LEU A 171       3.581 -21.324  37.663  1.000  33.56
ATOM   1245  CA  LEU A 171       4.899 -20.758  37.889  1.000  23.37
ATOM   1246  CB  LEU A 171       4.752 -19.251  38.120  1.000  35.18
ATOM   1247  CG  LEU A 171       5.997 -18.414  37.823  1.000  43.60
```

FIGURE 30

```
ATOM   1248  CD1 LEU A 171       5.642 -17.121  37.111  1.000 63.91
ATOM   1249  CD2 LEU A 171       6.736 -18.133  39.121  1.000 45.12
ATOM   1250  C   LEU A 171       5.591 -21.435  39.061  1.000 27.57
ATOM   1251  O   LEU A 171       5.001 -21.717  40.109  1.000 26.54
ATOM   1252  N   GLN A 172       6.879 -21.712  38.886  1.000 33.32
ATOM   1253  CA  GLN A 172       7.659 -22.398  39.914  1.000 32.37
ATOM   1254  CB  GLN A 172       7.941 -23.825  39.432  1.000 29.07
ATOM   1255  CG  GLN A 172       8.747 -24.687  40.384  1.000 30.68
ATOM   1256  CD  GLN A 172       9.108 -26.026  39.763  1.000 33.95
ATOM   1257  OE1 GLN A 172       9.084 -26.176  38.543  1.000 34.24
ATOM   1258  NE2 GLN A 172       9.436 -27.007  40.589  1.000 42.96
ATOM   1259  C   GLN A 172       8.953 -21.663  40.192  1.000 26.84
ATOM   1260  O   GLN A 172       9.698 -21.353  39.268  1.000 27.43
ATOM   1261  N   MET A 173       9.304 -21.339  41.437  1.000 32.50
ATOM   1262  CA  MET A 173      10.597 -20.678  41.595  1.000 30.97
ATOM   1263  CB  MET A 173      10.693 -19.860  42.883  1.000 29.94
ATOM   1264  CG  MET A 173      12.132 -19.396  43.134  1.000 34.61
ATOM   1265  SD  MET A 173      12.197 -18.091  44.380  1.000 57.02
ATOM   1266  CE  MET A 173      12.001 -19.065  45.860  1.000 24.26
ATOM   1267  C   MET A 173      11.719 -21.715  41.612  1.000 36.84
ATOM   1268  O   MET A 173      11.649 -22.640  42.427  1.000 50.73
ATOM   1269  N   LEU A 174      12.703 -21.541  40.741  1.000 29.04
ATOM   1270  CA  LEU A 174      13.805 -22.491  40.663  1.000 33.35
ATOM   1271  CB  LEU A 174      14.272 -22.638  39.215  1.000 28.88
ATOM   1272  CG  LEU A 174      13.322 -23.341  38.253  1.000 37.78
ATOM   1273  CD1 LEU A 174      13.953 -23.473  36.869  1.000 27.40
ATOM   1274  CD2 LEU A 174      12.907 -24.710  38.769  1.000 40.70
ATOM   1275  C   LEU A 174      14.990 -22.089  41.532  1.000 40.05
ATOM   1276  O   LEU A 174      15.816 -22.939  41.869  1.000 47.76
ATOM   1277  N   SER A 175      15.096 -20.812  41.884  1.000 40.28
ATOM   1278  CA  SER A 175      16.267 -20.331  42.611  1.000 36.37
ATOM   1279  CB  SER A 175      17.521 -20.496  41.750  1.000 41.94
ATOM   1280  OG  SER A 175      17.651 -19.439  40.814  1.000 42.50
ATOM   1281  C   SER A 175      16.120 -18.877  43.028  1.000 33.27
ATOM   1282  O   SER A 175      15.231 -18.146  42.597  1.000 31.30
ATOM   1283  N   GLU A 176      17.016 -18.426  43.908  1.000 21.04
ATOM   1284  CA  GLU A 176      16.840 -17.086  44.444  1.000 28.91
ATOM   1285  CB  GLU A 176      15.621 -17.013  45.373  1.000 31.33
ATOM   1286  CG  GLU A 176      15.576 -15.684  46.108  1.000 33.37
ATOM   1287  CD  GLU A 176      14.525 -15.568  47.187  1.000 40.95
ATOM   1288  OE1 GLU A 176      14.831 -15.906  48.350  1.000 66.50
ATOM   1289  OE2 GLU A 176      13.390 -15.121  46.900  1.000 42.21
ATOM   1290  C   GLU A 176      18.075 -16.657  45.225  1.000 35.17
ATOM   1291  O   GLU A 176      18.353 -17.212  46.288  1.000 48.02
ATOM   1292  N   SER A 177      18.794 -15.685  44.683  1.000 30.91
ATOM   1293  CA  SER A 177      20.036 -15.232  45.282  1.000 28.08
ATOM   1294  CB  SER A 177      21.182 -15.290  44.263  1.000 26.33
ATOM   1295  OG  SER A 177      21.340 -16.639  43.844  1.000 59.53
ATOM   1296  C   SER A 177      19.908 -13.811  45.804  1.000 28.71
ATOM   1297  O   SER A 177      19.678 -12.900  45.008  1.000 21.80
ATOM   1298  N   VAL A 178      20.078 -13.672  47.112  1.000 28.75
ATOM   1299  CA  VAL A 178      20.081 -12.360  47.739  1.000 33.94
```

FIGURE 31

```
ATOM   1300  CB   VAL A 178      19.564 -12.385  49.185  1.000 36.90
ATOM   1301  CG1  VAL A 178      19.530 -10.966  49.740  1.000 26.11
ATOM   1302  CG2  VAL A 178      18.191 -13.032  49.252  1.000 38.71
ATOM   1303  C    VAL A 178      21.492 -11.768  47.753  1.000 37.69
ATOM   1304  O    VAL A 178      22.404 -12.390  48.298  1.000 42.82
ATOM   1305  N    LEU A 179      21.605 -10.603  47.149  1.000 36.54
ATOM   1306  CA   LEU A 179      22.772  -9.738  47.125  1.000 37.72
ATOM   1307  CB   LEU A 179      23.086  -9.250  45.709  1.000 40.59
ATOM   1308  CG   LEU A 179      23.817 -10.254  44.811  1.000 42.47
ATOM   1309  CD1  LEU A 179      24.258 -11.454  45.634  1.000 49.20
ATOM   1310  CD2  LEU A 179      22.942 -10.672  43.638  1.000 27.98
ATOM   1311  C    LEU A 179      22.522  -8.547  48.041  1.000 36.64
ATOM   1312  O    LEU A 179      21.375  -8.338  48.461  1.000 39.97
ATOM   1313  N    PRO A 180      23.523  -7.750  48.377  1.000 35.66
ATOM   1314  CA   PRO A 180      23.219  -6.610  49.254  1.000 37.77
ATOM   1315  CB   PRO A 180      24.584  -5.934  49.447  1.000 38.49
ATOM   1316  CG   PRO A 180      25.553  -7.049  49.201  1.000 37.57
ATOM   1317  CD   PRO A 180      24.950  -7.802  48.031  1.000 30.63
ATOM   1318  C    PRO A 180      22.228  -5.644  48.617  1.000 33.86
ATOM   1319  O    PRO A 180      21.382  -5.100  49.338  1.000 33.02
ATOM   1320  N    GLU A 181      22.328  -5.430  47.303  1.000 29.48
ATOM   1321  CA   GLU A 181      21.557  -4.357  46.678  1.000 30.49
ATOM   1322  CB   GLU A 181      22.501  -3.428  45.911  1.000 33.66
ATOM   1323  CG   GLU A 181      23.039  -2.275  46.752  1.000 42.87
ATOM   1324  CD   GLU A 181      24.282  -1.678  46.120  1.000 51.54
ATOM   1325  OE1  GLU A 181      25.233  -2.443  45.850  1.000 75.46
ATOM   1326  OE2  GLU A 181      24.303  -0.455  45.890  1.000 75.08
ATOM   1327  C    GLU A 181      20.471  -4.855  45.741  1.000 31.78
ATOM   1328  O    GLU A 181      19.651  -4.082  45.245  1.000 30.15
ATOM   1329  N    TRP A 182      20.469  -6.158  45.486  1.000 30.83
ATOM   1330  CA   TRP A 182      19.412  -6.733  44.667  1.000 29.29
ATOM   1331  CB   TRP A 182      19.582  -6.376  43.197  1.000 28.58
ATOM   1332  CG   TRP A 182      20.858  -6.827  42.567  1.000 33.11
ATOM   1333  CD1  TRP A 182      21.167  -8.066  42.078  1.000 32.78
ATOM   1334  NE1  TRP A 182      22.451  -8.067  41.577  1.000 29.50
ATOM   1335  CE2  TRP A 182      22.991  -6.819  41.738  1.000 29.38
ATOM   1336  CD2  TRP A 182      22.021  -6.010  42.354  1.000 28.84
ATOM   1337  CE3  TRP A 182      22.313  -4.676  42.637  1.000 26.83
ATOM   1338  CZ3  TRP A 182      23.561  -4.198  42.293  1.000 27.97
ATOM   1339  CH2  TRP A 182      24.508  -5.021  41.679  1.000 32.03
ATOM   1340  CZ2  TRP A 182      24.250  -6.333  41.391  1.000 35.86
ATOM   1341  C    TRP A 182      19.363  -8.248  44.842  1.000 29.75
ATOM   1342  O    TRP A 182      20.270  -8.854  45.409  1.000 29.69
ATOM   1343  N    THR A 183      18.273  -8.804  44.338  1.000 23.29
ATOM   1344  CA   THR A 183      17.984 -10.221  44.437  1.000 22.15
ATOM   1345  CB   THR A 183      16.812 -10.506  45.397  1.000 23.41
ATOM   1346  OG1  THR A 183      17.155 -10.024  46.694  1.000 26.52
ATOM   1347  CG2  THR A 183      16.567 -12.004  45.501  1.000 25.62
ATOM   1348  C    THR A 183      17.630 -10.771  43.063  1.000 22.12
ATOM   1349  O    THR A 183      16.748 -10.228  42.399  1.000 27.35
ATOM   1350  N    ILE A 184      18.333 -11.820  42.662  1.000 22.30
ATOM   1351  CA   ILE A 184      18.088 -12.437  41.360  1.000 23.94
```

FIGURE 32

```
ATOM   1352  CB   ILE A 184      19.396  -12.675  40.592  1.000  25.30
ATOM   1353  CG1  ILE A 184      20.199  -11.396  40.326  1.000  22.21
ATOM   1354  CD1  ILE A 184      21.601  -11.696  39.831  1.000  22.92
ATOM   1355  CG2  ILE A 184      19.170  -13.392  39.270  1.000  24.72
ATOM   1356  C    ILE A 184      17.317  -13.730  41.564  1.000  27.42
ATOM   1357  O    ILE A 184      17.775  -14.657  42.235  1.000  27.72
ATOM   1358  N    ARG A 185      16.108  -13.816  41.000  1.000  24.23
ATOM   1359  CA   ARG A 185      15.404  -15.097  41.120  1.000  17.59
ATOM   1360  CB   ARG A 185      14.007  -14.943  41.706  1.000  21.98
ATOM   1361  CG   ARG A 185      13.946  -14.608  43.191  1.000  30.13
ATOM   1362  CD   ARG A 185      12.698  -13.806  43.506  1.000  29.20
ATOM   1363  NE   ARG A 185      12.608  -13.366  44.885  1.000  25.63
ATOM   1364  CZ   ARG A 185      12.669  -12.112  45.309  1.000  25.06
ATOM   1365  NH1  ARG A 185      12.832  -11.112  44.455  1.000  24.55
ATOM   1366  NH2  ARG A 185      12.570  -11.850  46.607  1.000  24.44
ATOM   1367  C    ARG A 185      15.324  -15.729  39.740  1.000  18.32
ATOM   1368  O    ARG A 185      15.468  -15.034  38.737  1.000  27.89
ATOM   1369  N    GLU A 186      15.083  -17.033  39.702  1.000  27.54
ATOM   1370  CA   GLU A 186      14.806  -17.688  38.433  1.000  33.52
ATOM   1371  CB   GLU A 186      15.931  -18.640  38.027  1.000  37.26
ATOM   1372  CG   GLU A 186      15.709  -19.229  36.633  1.000  44.30
ATOM   1373  CD   GLU A 186      16.999  -19.785  36.063  1.000  50.45
ATOM   1374  OE1  GLU A 186      16.974  -20.303  34.930  1.000  68.14
ATOM   1375  OE2  GLU A 186      18.035  -19.694  36.755  1.000  45.57
ATOM   1376  C    GLU A 186      13.496  -18.471  38.501  1.000  35.05
ATOM   1377  O    GLU A 186      13.271  -19.227  39.448  1.000  27.73
ATOM   1378  N    PHE A 187      12.649  -18.294  37.488  1.000  21.89
ATOM   1379  CA   PHE A 187      11.434  -19.091  37.427  1.000  24.39
ATOM   1380  CB   PHE A 187      10.188  -18.203  37.533  1.000  26.13
ATOM   1381  CG   PHE A 187      10.245  -17.205  38.663  1.000  34.20
ATOM   1382  CD1  PHE A 187      10.669  -15.907  38.444  1.000  31.66
ATOM   1383  CE1  PHE A 187      10.727  -14.979  39.465  1.000  27.66
ATOM   1384  CZ   PHE A 187      10.352  -15.353  40.737  1.000  25.23
ATOM   1385  CE2  PHE A 187       9.926  -16.645  40.980  1.000  26.99
ATOM   1386  CD2  PHE A 187       9.875  -17.565  39.952  1.000  33.63
ATOM   1387  C    PHE A 187      11.345  -19.910  36.138  1.000  22.76
ATOM   1388  O    PHE A 187      11.934  -19.600  35.113  1.000  22.84
ATOM   1389  N    LYS A 188      10.568  -20.964  36.254  1.000  24.79
ATOM   1390  CA   LYS A 188      10.099  -21.834  35.200  1.000  26.88
ATOM   1391  CB   LYS A 188      10.353  -23.309  35.515  1.000  29.96
ATOM   1392  CG   LYS A 188      10.069  -24.234  34.340  1.000  40.94
ATOM   1393  CD   LYS A 188      10.185  -25.699  34.726  1.000  36.57
ATOM   1394  CE   LYS A 188       8.857  -26.229  35.244  1.000  36.18
ATOM   1395  NZ   LYS A 188       9.078  -27.265  36.298  1.000  55.70
ATOM   1396  C    LYS A 188       8.602  -21.591  35.044  1.000  24.40
ATOM   1397  O    LYS A 188       7.885  -21.601  36.049  1.000  27.61
ATOM   1398  N    ILE A 189       8.141  -21.364  33.822  1.000  23.95
ATOM   1399  CA   ILE A 189       6.710  -21.109  33.659  1.000  28.81
ATOM   1400  CB   ILE A 189       6.449  -19.639  33.313  1.000  35.20
ATOM   1401  CG1  ILE A 189       4.972  -19.306  33.080  1.000  43.59
ATOM   1402  CD1  ILE A 189       4.692  -17.815  33.127  1.000  51.14
ATOM   1403  CG2  ILE A 189       7.290  -19.208  32.121  1.000  19.65
```

FIGURE 33

```
ATOM   1404  C   ILE A 189       6.141 -22.040  32.594 1.000 30.63
ATOM   1405  O   ILE A 189       6.820 -22.278  31.600 1.000 34.60
ATOM   1406  N   CYS A 190       4.945 -22.551  32.839 1.000 36.44
ATOM   1407  CA  CYS A 190       4.195 -23.466  32.001 1.000 38.23
ATOM   1408  CB  CYS A 190       3.935 -24.832  32.645 1.000 36.83
ATOM   1409  SG  CYS A 190       5.333 -25.621  33.465 1.000 54.28
ATOM   1410  C   CYS A 190       2.836 -22.854  31.647 1.000 40.07
ATOM   1411  O   CYS A 190       2.035 -22.528  32.524 1.000 34.54
ATOM   1412  N   GLY A 191       2.596 -22.714  30.348 1.000 38.67
ATOM   1413  CA  GLY A 191       1.317 -22.192  29.891 1.000 47.19
ATOM   1414  C   GLY A 191       0.665 -23.168  28.937 1.000 57.83
ATOM   1415  O   GLY A 191       1.108 -24.313  28.810 1.000 57.59
ATOM   1416  N   GLU A 192      -0.394 -22.733  28.252 1.000 68.94
ATOM   1417  CA  GLU A 192      -0.950 -23.669  27.264 1.000 77.08
ATOM   1418  CB  GLU A 192      -2.249 -23.139  26.671 1.000 79.72
ATOM   1419  CG  GLU A 192      -3.488 -23.931  27.082 1.000 83.44
ATOM   1420  CD  GLU A 192      -4.763 -23.113  27.103 1.000 88.99
ATOM   1421  OE1 GLU A 192      -4.760 -21.996  27.669 1.000 97.81
ATOM   1422  OE2 GLU A 192      -5.784 -23.582  26.555 1.000 83.85
ATOM   1423  C   GLU A 192       0.137 -23.932  26.222 1.000 79.08
ATOM   1424  O   GLU A 192       0.449 -23.046  25.419 1.000 84.98
ATOM   1425  N   GLU A 193       0.712 -25.136  26.276 1.000 80.23
ATOM   1426  CA  GLU A 193       1.810 -25.537  25.407 1.000 88.15
ATOM   1427  CB  GLU A 193       1.859 -27.061  25.268 1.000 82.57
ATOM   1428  CG  GLU A 193       2.981 -27.559  24.373 1.000 74.69
ATOM   1429  CD  GLU A 193       4.340 -27.361  25.023 1.000 75.38
ATOM   1430  OE1 GLU A 193       4.581 -27.990  26.075 1.000 64.29
ATOM   1431  OE2 GLU A 193       5.153 -26.581  24.488 1.000 79.60
ATOM   1432  C   GLU A 193       1.682 -24.896  24.026 1.000100.09
ATOM   1433  O   GLU A 193       0.956 -25.403  23.166 1.000118.96
ATOM   1434  N   GLN A 194       2.383 -23.782  23.814 1.000102.10
ATOM   1435  CA  GLN A 194       2.277 -23.101  22.520 1.000107.47
ATOM   1436  CB  GLN A 194       1.451 -21.819  22.686 1.000110.48
ATOM   1437  CG  GLN A 194       0.039 -22.092  23.245 1.000111.93
ATOM   1438  CD  GLN A 194      -0.952 -20.989  22.858 1.000112.96
ATOM   1439  OE1 GLN A 194      -0.959 -20.485  21.724 1.000119.77
ATOM   1440  NE2 GLN A 194      -1.812 -20.629  23.805 1.000105.14
ATOM   1441  C   GLN A 194       3.653 -22.834  21.928 1.000110.55
ATOM   1442  O   GLN A 194       4.374 -23.775  21.570 1.000118.12
ATOM   1443  N   LEU A 195       4.067 -21.573  21.796 1.000108.99
ATOM   1444  CA  LEU A 195       5.409 -21.363  21.238 1.000106.04
ATOM   1445  CB  LEU A 195       5.601 -19.930  20.752 1.000103.44
ATOM   1446  CG  LEU A 195       6.025 -19.764  19.285 1.000101.76
ATOM   1447  CD1 LEU A 195       6.636 -18.390  19.041 1.000 93.51
ATOM   1448  CD2 LEU A 195       7.000 -20.865  18.871 1.000 83.67
ATOM   1449  C   LEU A 195       6.462 -21.736  22.276 1.000109.72
ATOM   1450  O   LEU A 195       7.662 -21.740  21.977 1.000128.83
ATOM   1451  N   ASP A 196       6.020 -22.054  23.495 1.000104.75
ATOM   1452  CA  ASP A 196       6.956 -22.505  24.521 1.000 97.46
ATOM   1453  CB  ASP A 196       7.139 -21.463  25.616 1.000 94.37
ATOM   1454  CG  ASP A 196       6.470 -20.133  25.358 1.000 89.89
ATOM   1455  OD1 ASP A 196       5.236 -20.089  25.182 1.000 80.93
```

FIGURE 34

```
ATOM   1456  OD2 ASP A 196       7.206 -19.119  25.348  1.000  73.17
ATOM   1457  C   ASP A 196       6.498 -23.822  25.150  1.000  96.72
ATOM   1458  O   ASP A 196       5.391 -24.300  24.896  1.000 103.69
ATOM   1459  N   ALA A 197       7.366 -24.390  25.976  1.000  95.34
ATOM   1460  CA  ALA A 197       7.113 -25.628  26.703  1.000  92.76
ATOM   1461  CB  ALA A 197       7.661 -26.824  25.949  1.000  80.95
ATOM   1462  C   ALA A 197       7.715 -25.535  28.106  1.000  92.67
ATOM   1463  O   ALA A 197       6.986 -25.567  29.100  1.000 101.36
ATOM   1464  N   HIS A 198       9.035 -25.410  28.190  1.000  90.04
ATOM   1465  CA  HIS A 198       9.720 -25.190  29.464  1.000  83.32
ATOM   1466  CB  HIS A 198      10.618 -26.370  29.813  1.000  84.18
ATOM   1467  CG  HIS A 198      11.844 -26.074  30.617  1.000  84.25
ATOM   1468  ND1 HIS A 198      11.839 -25.834  31.968  1.000  86.44
ATOM   1469  CE1 HIS A 198      13.071 -25.609  32.389  1.000  85.15
ATOM   1470  NE2 HIS A 198      13.884 -25.681  31.348  1.000  81.36
ATOM   1471  CD2 HIS A 198      13.141 -25.969  30.232  1.000  81.88
ATOM   1472  C   HIS A 198      10.489 -23.876  29.379  1.000  70.03
ATOM   1473  O   HIS A 198      11.664 -23.784  29.023  1.000  64.25
ATOM   1474  N   ARG A 199       9.790 -22.781  29.701  1.000  58.16
ATOM   1475  CA  ARG A 199      10.431 -21.480  29.568  1.000  50.11
ATOM   1476  CB  ARG A 199       9.498 -20.464  28.903  1.000  50.90
ATOM   1477  CG  ARG A 199      10.292 -19.446  28.092  1.000  53.59
ATOM   1478  CD  ARG A 199       9.616 -18.087  28.108  1.000  48.39
ATOM   1479  NE  ARG A 199       8.377 -18.120  27.322  1.000  42.37
ATOM   1480  CZ  ARG A 199       7.502 -17.120  27.427  1.000  43.29
ATOM   1481  NH1 ARG A 199       7.751 -16.096  28.241  1.000  31.50
ATOM   1482  NH2 ARG A 199       6.398 -17.186  26.709  1.000  24.97
ATOM   1483  C   ARG A 199      10.900 -20.944  30.918  1.000  37.10
ATOM   1484  O   ARG A 199      10.201 -21.106  31.914  1.000  28.73
ATOM   1485  N   LEU A 200      12.079 -20.336  30.889  1.000  29.92
ATOM   1486  CA  LEU A 200      12.757 -19.865  32.087  1.000  35.35
ATOM   1487  CB  LEU A 200      14.196 -20.394  32.149  1.000  38.39
ATOM   1488  CG  LEU A 200      14.295 -21.881  32.511  1.000  51.57
ATOM   1489  CD1 LEU A 200      15.401 -22.134  33.523  1.000  73.84
ATOM   1490  CD2 LEU A 200      12.963 -22.382  33.052  1.000  69.62
ATOM   1491  C   LEU A 200      12.762 -18.343  32.153  1.000  31.71
ATOM   1492  O   LEU A 200      13.040 -17.681  31.155  1.000  29.83
ATOM   1493  N   ILE A 201      12.446 -17.820  33.333  1.000  23.61
ATOM   1494  CA  ILE A 201      12.371 -16.376  33.510  1.000  23.62
ATOM   1495  CB  ILE A 201      10.962 -15.892  33.903  1.000  25.57
ATOM   1496  CG1 ILE A 201       9.858 -16.232  32.898  1.000  30.41
ATOM   1497  CD1 ILE A 201      10.310 -16.192  31.459  1.000  26.58
ATOM   1498  CG2 ILE A 201      10.964 -14.395  34.171  1.000  23.03
ATOM   1499  C   ILE A 201      13.332 -15.933  34.604  1.000  22.99
ATOM   1500  O   ILE A 201      13.382 -16.507  35.688  1.000  27.49
ATOM   1501  N   ARG A 202      14.088 -14.886  34.299  1.000  19.58
ATOM   1502  CA  ARG A 202      14.960 -14.324  35.320  1.000  17.66
ATOM   1503  CB  ARG A 202      16.361 -14.091  34.768  1.000  25.08
ATOM   1504  CG  ARG A 202      17.450 -14.797  35.562  1.000  39.27
ATOM   1505  CD  ARG A 202      18.605 -15.183  34.654  1.000  48.88
ATOM   1506  NE  ARG A 202      19.385 -16.289  35.220  1.000  55.89
ATOM   1507  CZ  ARG A 202      19.961 -17.201  34.435  1.000  60.48
```

FIGURE 35

| | | | | | | | | | |
|---|---|---|---|---|---|---|---|---|---|
| ATOM | 1508 | NH1 | ARG | A | 202 | 19.812 | -17.100 | 33.119 | 1.000 50.30 |
| ATOM | 1509 | NH2 | ARG | A | 202 | 20.666 | -18.191 | 34.965 | 1.000 77.85 |
| ATOM | 1510 | C | ARG | A | 202 | 14.343 | -13.023 | 35.826 | 1.000 22.83 |
| ATOM | 1511 | O | ARG | A | 202 | 13.885 | -12.219 | 35.007 | 1.000 22.73 |
| ATOM | 1512 | N | HIS | A | 203 | 14.345 | -12.858 | 37.136 | 1.000 18.38 |
| ATOM | 1513 | CA | HIS | A | 203 | 13.794 | -11.690 | 37.815 | 1.000 21.09 |
| ATOM | 1514 | CB | HIS | A | 203 | 12.701 | -12.145 | 38.770 | 1.000 22.13 |
| ATOM | 1515 | CG | HIS | A | 203 | 11.824 | -11.117 | 39.389 | 1.000 24.48 |
| ATOM | 1516 | ND1 | HIS | A | 203 | 12.146 | -10.463 | 40.554 | 1.000 20.07 |
| ATOM | 1517 | CE1 | HIS | A | 203 | 11.186 | -9.616 | 40.875 | 1.000 23.08 |
| ATOM | 1518 | NE2 | HIS | A | 203 | 10.240 | -9.697 | 39.959 | 1.000 27.63 |
| ATOM | 1519 | CD2 | HIS | A | 203 | 10.611 | -10.629 | 39.022 | 1.000 25.25 |
| ATOM | 1520 | C | HIS | A | 203 | 14.894 | -10.952 | 38.579 | 1.000 27.02 |
| ATOM | 1521 | O | HIS | A | 203 | 15.541 | -11.548 | 39.447 | 1.000 18.53 |
| ATOM | 1522 | N | PHE | A | 204 | 15.086 | -9.691 | 38.246 | 1.000 21.78 |
| ATOM | 1523 | CA | PHE | A | 204 | 16.068 | -8.796 | 38.840 | 1.000 16.28 |
| ATOM | 1524 | CB | PHE | A | 204 | 16.891 | -8.101 | 37.742 | 1.000 16.39 |
| ATOM | 1525 | CG | PHE | A | 204 | 17.526 | -9.112 | 36.813 | 1.000 27.16 |
| ATOM | 1526 | CD1 | PHE | A | 204 | 16.899 | -9.466 | 35.632 | 1.000 16.95 |
| ATOM | 1527 | CE1 | PHE | A | 204 | 17.476 | -10.397 | 34.790 | 1.000 26.09 |
| ATOM | 1528 | CZ | PHE | A | 204 | 18.686 | -10.979 | 35.123 | 1.000 31.27 |
| ATOM | 1529 | CE2 | PHE | A | 204 | 19.326 | -10.639 | 36.303 | 1.000 26.75 |
| ATOM | 1530 | CD2 | PHE | A | 204 | 18.744 | -9.699 | 37.136 | 1.000 28.81 |
| ATOM | 1531 | C | PHE | A | 204 | 15.378 | -7.752 | 39.707 | 1.000 16.41 |
| ATOM | 1532 | O | PHE | A | 204 | 14.748 | -6.809 | 39.223 | 1.000 24.46 |
| ATOM | 1533 | N | HIS | A | 205 | 15.514 | -7.930 | 41.006 | 1.000 16.66 |
| ATOM | 1534 | CA | HIS | A | 205 | 14.879 | -7.081 | 41.998 | 1.000 14.51 |
| ATOM | 1535 | CB | HIS | A | 205 | 14.118 | -7.987 | 42.982 | 1.000 14.31 |
| ATOM | 1536 | CG | HIS | A | 205 | 13.201 | -7.221 | 43.887 | 1.000 25.21 |
| ATOM | 1537 | ND1 | HIS | A | 205 | 12.631 | -7.784 | 45.009 | 1.000 24.28 |
| ATOM | 1538 | CE1 | HIS | A | 205 | 11.882 | -6.885 | 45.611 | 1.000 27.88 |
| ATOM | 1539 | NE2 | HIS | A | 205 | 11.939 | -5.756 | 44.927 | 1.000 24.25 |
| ATOM | 1540 | CD2 | HIS | A | 205 | 12.761 | -5.949 | 43.845 | 1.000 28.00 |
| ATOM | 1541 | C | HIS | A | 205 | 15.867 | -6.211 | 42.764 | 1.000 26.42 |
| ATOM | 1542 | O | HIS | A | 205 | 16.535 | -6.668 | 43.697 | 1.000 21.37 |

FIGURE 36

```
ATOM   1543  N    TYR A 206      15.950   -4.954   42.359  1.000  25.43
ATOM   1544  CA   TYR A 206      16.705   -3.918   43.045  1.000  26.77
ATOM   1545  CB   TYR A 206      16.849   -2.707   42.142  1.000  30.54
ATOM   1546  CG   TYR A 206      17.810   -1.643   42.603  1.000  30.50
ATOM   1547  CD1  TYR A 206      19.177   -1.758   42.349  1.000  21.06
ATOM   1548  CE1  TYR A 206      20.048   -0.774   42.779  1.000  26.02
ATOM   1549  CZ   TYR A 206      19.551    0.320   43.457  1.000  28.32
ATOM   1550  OH   TYR A 206      20.406    1.309   43.883  1.000  33.26
ATOM   1551  CE2  TYR A 206      18.201    0.452   43.715  1.000  31.83
ATOM   1552  CD2  TYR A 206      17.330   -0.534   43.289  1.000  30.09
ATOM   1553  C    TYR A 206      15.978   -3.521   44.324  1.000  32.60
ATOM   1554  O    TYR A 206      14.893   -2.942   44.266  1.000  27.05
ATOM   1555  N    THR A 207      16.574   -3.858   45.460  1.000  30.86
ATOM   1556  CA   THR A 207      15.870   -3.793   46.729  1.000  34.19
ATOM   1557  CB   THR A 207      16.205   -5.071   47.535  1.000  35.60
ATOM   1558  OG1  THR A 207      17.627   -5.263   47.486  1.000  37.52
ATOM   1559  CG2  THR A 207      15.545   -6.290   46.917  1.000  40.16
ATOM   1560  C    THR A 207      16.214   -2.599   47.604  1.000  42.95
ATOM   1561  O    THR A 207      15.790   -2.560   48.768  1.000  33.25
ATOM   1562  N    VAL A 208      16.982   -1.633   47.105  1.000  38.87
ATOM   1563  CA   VAL A 208      17.495   -0.587   47.986  1.000  42.20
ATOM   1564  CB   VAL A 208      19.001   -0.829   48.254  1.000  38.89
ATOM   1565  CG1  VAL A 208      19.208   -2.188   48.913  1.000  29.05
ATOM   1566  CG2  VAL A 208      19.810   -0.734   46.973  1.000  32.10
ATOM   1567  C    VAL A 208      17.304    0.826   47.464  1.000  41.85
ATOM   1568  O    VAL A 208      18.055    1.725   47.850  1.000  40.55
ATOM   1569  N    TRP A 209      16.329    1.095   46.602  1.000  38.83
ATOM   1570  CA   TRP A 209      16.039    2.473   46.199  1.000  36.12
ATOM   1571  CB   TRP A 209      15.037    2.480   45.053  1.000  31.43
ATOM   1572  CG   TRP A 209      15.042    3.683   44.170  1.000  31.44
ATOM   1573  CD1  TRP A 209      14.710    4.963   44.509  1.000  26.97
ATOM   1574  NE1  TRP A 209      14.840    5.788   43.417  1.000  29.65
ATOM   1575  CE2  TRP A 209      15.261    5.047   42.342  1.000  23.71
ATOM   1576  CD2  TRP A 209      15.399    3.717   42.779  1.000  28.34
ATOM   1577  CE3  TRP A 209      15.821    2.749   41.862  1.000  32.82
ATOM   1578  CZ3  TRP A 209      16.086    3.142   40.564  1.000  33.95
ATOM   1579  CH2  TRP A 209      15.939    4.478   40.159  1.000  36.07
ATOM   1580  CZ2  TRP A 209      15.527    5.448   41.033  1.000  22.47
ATOM   1581  C    TRP A 209      15.490    3.239   47.397  1.000  36.81
ATOM   1582  O    TRP A 209      14.515    2.795   48.008  1.000  32.77
ATOM   1583  N    PRO A 210      16.069    4.369   47.770  1.000  34.94
ATOM   1584  CA   PRO A 210      15.624    5.061   48.987  1.000  33.09
ATOM   1585  CB   PRO A 210      16.456    6.345   48.988  1.000  32.95
ATOM   1586  CG   PRO A 210      17.633    6.063   48.123  1.000  34.50
ATOM   1587  CD   PRO A 210      17.160    5.078   47.088  1.000  36.07
ATOM   1588  C    PRO A 210      14.140    5.412   48.940  1.000  41.55
ATOM   1589  O    PRO A 210      13.515    5.321   47.882  1.000  42.95
ATOM   1590  N    ASP A 211      13.590    5.820   50.081  1.000  49.64
ATOM   1591  CA   ASP A 211      12.183    6.214   50.158  1.000  54.78
ATOM   1592  CB   ASP A 211      11.720    6.296   51.612  1.000  55.95
ATOM   1593  CG   ASP A 211      11.048    5.030   52.100  1.000  56.96
ATOM   1594  OD1  ASP A 211      10.660    4.976   53.286  1.000  50.78
```

FIGURE 37

```
ATOM   1595  OD2 ASP A 211      10.905   4.079  51.306 1.000 63.04
ATOM   1596  C   ASP A 211      11.959   7.551  49.457 1.000 52.82
ATOM   1597  O   ASP A 211      10.896   7.882  48.937 1.000 45.02
ATOM   1598  N   HIS A 212      13.020   8.351  49.446 1.000 48.03
ATOM   1599  CA  HIS A 212      12.961   9.675  48.845 1.000 53.87
ATOM   1600  CB  HIS A 212      12.846  10.746  49.934 1.000 72.68
ATOM   1601  CG  HIS A 212      12.681  10.177  51.311 1.000 76.92
ATOM   1602  ND1 HIS A 212      11.458  10.093  51.935 1.000 78.57
ATOM   1603  CE1 HIS A 212      11.610   9.555  53.133 1.000 80.63
ATOM   1604  NE2 HIS A 212      12.890   9.277  53.307 1.000 79.40
ATOM   1605  CD2 HIS A 212      13.578   9.660  52.180 1.000 77.05
ATOM   1606  C   HIS A 212      14.197   9.908  47.986 1.000 46.17
ATOM   1607  O   HIS A 212      15.310   9.572  48.392 1.000 42.06
ATOM   1608  N   GLY A 213      13.992  10.472  46.799 1.000 43.66
ATOM   1609  CA  GLY A 213      15.091  10.704  45.885 1.000 43.27
ATOM   1610  C   GLY A 213      15.654   9.421  45.299 1.000 41.13
ATOM   1611  O   GLY A 213      15.050   8.357  45.431 1.000 31.32
ATOM   1612  N   VAL A 214      16.804   9.569  44.663 1.000 40.78
ATOM   1613  CA  VAL A 214      17.476   8.540  43.881 1.000 37.49
ATOM   1614  CB  VAL A 214      18.098   9.200  42.644 1.000 31.11
ATOM   1615  CG1 VAL A 214      17.047  10.031  41.917 1.000 31.20
ATOM   1616  CG2 VAL A 214      19.284  10.056  43.059 1.000 42.36
ATOM   1617  C   VAL A 214      18.526   7.827  44.715 1.000 45.89
ATOM   1618  O   VAL A 214      18.953   8.384  45.729 1.000 57.46
ATOM   1619  N   PRO A 215      18.933   6.624  44.333 1.000 40.93
ATOM   1620  CA  PRO A 215      19.764   5.782  45.188 1.000 34.00
ATOM   1621  CB  PRO A 215      20.251   4.672  44.247 1.000 42.73
ATOM   1622  CG  PRO A 215      19.225   4.606  43.168 1.000 48.15
ATOM   1623  CD  PRO A 215      18.636   5.975  43.041 1.000 45.87
ATOM   1624  C   PRO A 215      21.003   6.478  45.755 1.000 38.07
ATOM   1625  O   PRO A 215      21.508   7.427  45.159 1.000 36.58
ATOM   1626  N   GLU A 216      21.427   5.942  46.886 1.000 51.41
ATOM   1627  CA  GLU A 216      22.569   6.331  47.688 1.000 59.42
ATOM   1628  CB  GLU A 216      23.016   5.168  48.587 1.000 62.22
ATOM   1629  CG  GLU A 216      24.008   5.566  49.666 1.000 66.95
ATOM   1630  CD  GLU A 216      25.143   4.586  49.863 1.000 69.08
ATOM   1631  OE1 GLU A 216      24.891   3.377  50.036 1.000 49.54
ATOM   1632  OE2 GLU A 216      26.314   5.036  49.867 1.000 70.82
ATOM   1633  C   GLU A 216      23.739   6.782  46.818 1.000 54.66
ATOM   1634  O   GLU A 216      24.238   7.895  46.980 1.000 48.01
ATOM   1635  N   THR A 217      24.155   5.905  45.908 1.000 43.30
ATOM   1636  CA  THR A 217      25.239   6.207  44.989 1.000 40.68
ATOM   1637  CB  THR A 217      26.492   5.353  45.264 1.000 40.90
ATOM   1638  OG1 THR A 217      26.180   3.960  45.083 1.000 41.85
ATOM   1639  CG2 THR A 217      26.966   5.527  46.698 1.000 28.03
ATOM   1640  C   THR A 217      24.823   5.970  43.535 1.000 42.76
ATOM   1641  O   THR A 217      23.831   5.299  43.269 1.000 55.29
ATOM   1642  N   THR A 218      25.612   6.524  42.625 1.000 38.69
ATOM   1643  CA  THR A 218      25.506   6.280  41.199 1.000 46.38
ATOM   1644  CB  THR A 218      26.407   7.242  40.399 1.000 48.77
ATOM   1645  OG1 THR A 218      27.771   7.133  40.833 1.000 31.20
ATOM   1646  CG2 THR A 218      26.004   8.690  40.634 1.000 44.45
```

FIGURE 38

```
ATOM   1647  C   THR A 218      25.887   4.831  40.882  1.000  40.27
ATOM   1648  O   THR A 218      25.248   4.124  40.099  1.000  43.37
ATOM   1649  N   GLN A 219      26.962   4.401  41.524  1.000  36.77
ATOM   1650  CA  GLN A 219      27.592   3.095  41.332  1.000  40.35
ATOM   1651  CB  GLN A 219      28.841   3.052  42.215  1.000  46.27
ATOM   1652  CG  GLN A 219      29.392   1.680  42.538  1.000  60.44
ATOM   1653  CD  GLN A 219      30.902   1.629  42.393  1.000  71.25
ATOM   1654  OE1 GLN A 219      31.414   1.573  41.274  1.000  90.40
ATOM   1655  NE2 GLN A 219      31.593   1.640  43.527  1.000  53.90
ATOM   1656  C   GLN A 219      26.621   1.959  41.619  1.000  37.53
ATOM   1657  O   GLN A 219      26.618   0.907  40.977  1.000  32.61
ATOM   1658  N   SER A 220      25.739   2.146  42.596  1.000  33.04
ATOM   1659  CA  SER A 220      24.720   1.164  42.929  1.000  26.50
ATOM   1660  CB  SER A 220      23.845   1.739  44.049  1.000  29.93
ATOM   1661  OG  SER A 220      22.837   0.814  44.413  1.000  35.63
ATOM   1662  C   SER A 220      23.860   0.792  41.727  1.000  34.98
ATOM   1663  O   SER A 220      23.745  -0.378  41.354  1.000  31.36
ATOM   1664  N   LEU A 221      23.247   1.800  41.104  1.000  34.26
ATOM   1665  CA  LEU A 221      22.404   1.571  39.940  1.000  32.25
ATOM   1666  CB  LEU A 221      21.483   2.764  39.648  1.000  25.67
ATOM   1667  CG  LEU A 221      20.313   2.430  38.705  1.000  23.74
ATOM   1668  CD1 LEU A 221      19.468   1.312  39.303  1.000  18.81
ATOM   1669  CD2 LEU A 221      19.490   3.672  38.420  1.000  28.95
ATOM   1670  C   LEU A 221      23.238   1.270  38.700  1.000  36.04
ATOM   1671  O   LEU A 221      22.797   0.534  37.806  1.000  29.22
ATOM   1672  N   ILE A 222      24.446   1.845  38.637  1.000  33.99
ATOM   1673  CA  ILE A 222      25.231   1.532  37.445  1.000  25.77
ATOM   1674  CB  ILE A 222      26.562   2.282  37.364  1.000  24.00
ATOM   1675  CG1 ILE A 222      26.426   3.748  36.963  1.000  25.72
ATOM   1676  CD1 ILE A 222      27.516   4.638  37.512  1.000  30.84
ATOM   1677  CG2 ILE A 222      27.496   1.556  36.405  1.000  31.40
ATOM   1678  C   ILE A 222      25.511   0.027  37.382  1.000  27.84
ATOM   1679  O   ILE A 222      25.444  -0.541  36.293  1.000  29.04
ATOM   1680  N   GLN A 223      25.789  -0.572  38.525  1.000  25.48
ATOM   1681  CA  GLN A 223      26.120  -1.982  38.660  1.000  27.33
ATOM   1682  CB  GLN A 223      26.628  -2.245  40.091  1.000  32.58
ATOM   1683  CG  GLN A 223      28.119  -1.965  40.240  1.000  37.66
ATOM   1684  CD  GLN A 223      28.804  -1.836  38.896  1.000  40.45
ATOM   1685  OE1 GLN A 223      28.765  -2.759  38.076  1.000  70.90
ATOM   1686  NE2 GLN A 223      29.430  -0.693  38.657  1.000  56.51
ATOM   1687  C   GLN A 223      24.952  -2.916  38.387  1.000  25.59
ATOM   1688  O   GLN A 223      25.071  -3.940  37.712  1.000  26.61
ATOM   1689  N   PHE A 224      23.794  -2.560  38.945  1.000  23.53
ATOM   1690  CA  PHE A 224      22.586  -3.328  38.637  1.000  26.71
ATOM   1691  CB  PHE A 224      21.408  -2.714  39.374  1.000  23.63
ATOM   1692  CG  PHE A 224      20.093  -3.429  39.226  1.000  23.65
ATOM   1693  CD1 PHE A 224      19.892  -4.676  39.789  1.000  26.30
ATOM   1694  CE1 PHE A 224      18.688  -5.341  39.670  1.000  23.27
ATOM   1695  CZ  PHE A 224      17.660  -4.747  38.963  1.000  22.78
ATOM   1696  CE2 PHE A 224      17.843  -3.504  38.397  1.000  21.02
ATOM   1697  CD2 PHE A 224      19.050  -2.842  38.529  1.000  17.14
ATOM   1698  C   PHE A 224      22.335  -3.340  37.135  1.000  29.21
```

FIGURE 39

```
ATOM   1699  O    PHE A 224      22.212   -4.385  36.497  1.000  23.28
ATOM   1700  N    VAL A 225      22.272   -2.147  36.539  1.000  29.45
ATOM   1701  CA   VAL A 225      22.003   -2.057  35.103  1.000  23.17
ATOM   1702  CB   VAL A 225      22.017   -0.597  34.616  1.000  27.27
ATOM   1703  CG1  VAL A 225      22.186   -0.539  33.112  1.000  19.10
ATOM   1704  CG2  VAL A 225      20.732    0.108  35.045  1.000  33.43
ATOM   1705  C    VAL A 225      22.985   -2.871  34.273  1.000  28.40
ATOM   1706  O    VAL A 225      22.554   -3.638  33.400  1.000  25.05
ATOM   1707  N    ARG A 226      24.285   -2.724  34.517  1.000  31.38
ATOM   1708  CA   ARG A 226      25.276   -3.513  33.780  1.000  34.53
ATOM   1709  CB   ARG A 226      26.705   -3.147  34.173  1.000  31.80
ATOM   1710  CG   ARG A 226      27.183   -1.771  33.762  1.000  33.34
ATOM   1711  CD   ARG A 226      28.697   -1.716  33.673  1.000  47.45
ATOM   1712  NE   ARG A 226      29.241   -0.365  33.600  1.000  56.24
ATOM   1713  CZ   ARG A 226      29.961    0.232  34.542  1.000  62.79
ATOM   1714  NH1  ARG A 226      30.261   -0.370  35.686  1.000  50.14
ATOM   1715  NH2  ARG A 226      30.401    1.471  34.354  1.000  74.65
ATOM   1716  C    ARG A 226      25.054   -5.011  34.010  1.000  23.44
ATOM   1717  O    ARG A 226      25.301   -5.826  33.118  1.000  30.89
ATOM   1718  N    THR A 227      24.582   -5.377  35.195  1.000  21.86
ATOM   1719  CA   THR A 227      24.250   -6.761  35.521  1.000  31.38
ATOM   1720  CB   THR A 227      23.825   -6.921  36.994  1.000  37.64
ATOM   1721  OG1  THR A 227      24.903   -6.608  37.874  1.000  34.53
ATOM   1722  CG2  THR A 227      23.457   -8.365  37.306  1.000  22.45
ATOM   1723  C    THR A 227      23.108   -7.250  34.627  1.000  32.76
ATOM   1724  O    THR A 227      23.237   -8.240  33.912  1.000  27.21
ATOM   1725  N    VAL A 228      21.985   -6.526  34.679  1.000  22.99
ATOM   1726  CA   VAL A 228      20.814   -6.869  33.886  1.000  22.33
ATOM   1727  CB   VAL A 228      19.627   -5.922  34.162  1.000  22.12
ATOM   1728  CG1  VAL A 228      18.466   -6.213  33.221  1.000  17.66
ATOM   1729  CG2  VAL A 228      19.192   -6.066  35.605  1.000  18.46
ATOM   1730  C    VAL A 228      21.140   -6.859  32.397  1.000  21.49
ATOM   1731  O    VAL A 228      20.766   -7.790  31.686  1.000  22.44
ATOM   1732  N    ARG A 229      21.821   -5.824  31.914  1.000  19.91
ATOM   1733  CA   ARG A 229      22.183   -5.792  30.489  1.000  30.48
ATOM   1734  CB   ARG A 229      22.877   -4.480  30.149  1.000  30.12
ATOM   1735  CG   ARG A 229      23.502   -4.301  28.786  1.000  28.02
ATOM   1736  CD   ARG A 229      22.590   -4.596  27.614  1.000  26.85
ATOM   1737  NE   ARG A 229      21.290   -3.951  27.719  1.000  26.70
ATOM   1738  CZ   ARG A 229      20.267   -4.199  26.913  1.000  27.29
ATOM   1739  NH1  ARG A 229      20.394   -5.079  25.930  1.000  20.12
ATOM   1740  NH2  ARG A 229      19.110   -3.573  27.076  1.000  22.84
ATOM   1741  C    ARG A 229      23.041   -7.010  30.156  1.000  42.31
ATOM   1742  O    ARG A 229      22.988   -7.552  29.053  1.000  34.86
ATOM   1743  N    ASP A 230      23.842   -7.483  31.114  1.000  40.71
ATOM   1744  CA   ASP A 230      24.637   -8.682  30.882  1.000  32.09
ATOM   1745  CB   ASP A 230      25.480   -9.003  32.118  1.000  31.74
ATOM   1746  CG   ASP A 230      26.543  -10.044  31.824  1.000  48.14
ATOM   1747  OD1  ASP A 230      27.577  -10.046  32.528  1.000  73.82
ATOM   1748  OD2  ASP A 230      26.357  -10.865  30.899  1.000  48.16
ATOM   1749  C    ASP A 230      23.761   -9.882  30.547  1.000  32.41
ATOM   1750  O    ASP A 230      24.000  -10.629  29.598  1.000  36.42
```

FIGURE 40

```
ATOM   1751  N    TYR A 231      22.720 -10.093  31.342  1.000  24.93
ATOM   1752  CA   TYR A 231      21.802 -11.200  31.103  1.000  24.73
ATOM   1753  CB   TYR A 231      20.899 -11.375  32.314  1.000  25.55
ATOM   1754  CG   TYR A 231      21.532 -12.058  33.498  1.000  21.52
ATOM   1755  CD1  TYR A 231      22.248 -11.325  34.429  1.000  20.07
ATOM   1756  CE1  TYR A 231      22.826 -11.956  35.516  1.000  25.25
ATOM   1757  CZ   TYR A 231      22.690 -13.315  35.684  1.000  23.69
ATOM   1758  OH   TYR A 231      23.272 -13.934  36.770  1.000  36.60
ATOM   1759  CE2  TYR A 231      21.981 -14.060  34.765  1.000  22.85
ATOM   1760  CD2  TYR A 231      21.406 -13.431  33.678  1.000  23.77
ATOM   1761  C    TYR A 231      20.940 -10.997  29.866  1.000  24.62
ATOM   1762  O    TYR A 231      20.658 -11.948  29.137  1.000  34.40
ATOM   1763  N    ILE A 232      20.502  -9.768  29.602  1.000  26.34
ATOM   1764  CA   ILE A 232      19.713  -9.542  28.388  1.000  29.59
ATOM   1765  CB   ILE A 232      19.309  -8.068  28.191  1.000  19.99
ATOM   1766  CG1  ILE A 232      18.283  -7.551  29.204  1.000  21.05
ATOM   1767  CD1  ILE A 232      18.300  -6.047  29.371  1.000  26.31
ATOM   1768  CG2  ILE A 232      18.811  -7.833  26.772  1.000  16.63
ATOM   1769  C    ILE A 232      20.497  -9.985  27.153  1.000  25.92
ATOM   1770  O    ILE A 232      19.982 -10.719  26.311  1.000  22.41
ATOM   1771  N    ASN A 233      21.741  -9.526  27.075  1.000  21.03
ATOM   1772  CA   ASN A 233      22.573  -9.788  25.900  1.000  32.05
ATOM   1773  CB   ASN A 233      23.931  -9.102  26.027  1.000  31.19
ATOM   1774  CG   ASN A 233      23.891  -7.603  25.830  1.000  35.15
ATOM   1775  OD1  ASN A 233      22.990  -7.064  25.190  1.000  42.73
ATOM   1776  ND2  ASN A 233      24.873  -6.892  26.379  1.000  33.97
ATOM   1777  C    ASN A 233      22.757 -11.289  25.690  1.000  36.07
ATOM   1778  O    ASN A 233      22.998 -11.738  24.575  1.000  43.18
ATOM   1779  N    ARG A 234      22.637 -12.049  26.765  1.000  37.01
ATOM   1780  CA   ARG A 234      22.702 -13.496  26.771  1.000  31.16
ATOM   1781  CB   ARG A 234      23.407 -13.992  28.046  1.000  30.18
ATOM   1782  CG   ARG A 234      24.757 -13.308  28.235  1.000  40.73
ATOM   1783  CD   ARG A 234      25.514 -13.886  29.429  1.000  52.07
ATOM   1784  NE   ARG A 234      26.704 -13.084  29.729  1.000  58.87
ATOM   1785  CZ   ARG A 234      27.879 -13.610  30.055  1.000  65.29
ATOM   1786  NH1  ARG A 234      28.006 -14.931  30.122  1.000  53.28
ATOM   1787  NH2  ARG A 234      28.913 -12.818  30.313  1.000  60.98
ATOM   1788  C    ARG A 234      21.320 -14.122  26.695  1.000  30.94
ATOM   1789  O    ARG A 234      21.130 -15.307  26.977  1.000  24.57
ATOM   1790  N    SER A 235      20.307 -13.346  26.303  1.000  26.15
ATOM   1791  CA   SER A 235      18.990 -13.971  26.162  1.000  23.60
ATOM   1792  CB   SER A 235      17.959 -13.293  27.058  1.000  26.05
ATOM   1793  OG   SER A 235      18.357 -13.227  28.416  1.000  33.56
ATOM   1794  C    SER A 235      18.533 -13.913  24.704  1.000  32.45
ATOM   1795  O    SER A 235      17.616 -13.135  24.420  1.000  33.61
ATOM   1796  N    PRO A 236      19.136 -14.685  23.805  1.000  44.30
ATOM   1797  CA   PRO A 236      18.740 -14.662  22.393  1.000  39.17
ATOM   1798  CB   PRO A 236      19.695 -15.646  21.714  1.000  48.74
ATOM   1799  CG   PRO A 236      20.068 -16.584  22.822  1.000  52.35
ATOM   1800  CD   PRO A 236      20.220 -15.667  24.009  1.000  52.02
ATOM   1801  C    PRO A 236      17.312 -15.175  22.233  1.000  29.65
ATOM   1802  O    PRO A 236      16.908 -16.104  22.941  1.000  30.54
```

FIGURE 41

```
ATOM   1803  N    GLY A 237      16.590  -14.544  21.309 1.000 24.46
ATOM   1804  CA   GLY A 237      15.214  -14.952  21.050 1.000 25.34
ATOM   1805  C    GLY A 237      14.233  -14.388  22.054 1.000 26.14
ATOM   1806  O    GLY A 237      13.035  -14.623  21.905 1.000 33.46
ATOM   1807  N    ALA A 238      14.681  -13.642  23.069 1.000 22.93
ATOM   1808  CA   ALA A 238      13.739  -13.094  24.042 1.000 17.40
ATOM   1809  CB   ALA A 238      14.491  -12.542  25.253 1.000 20.22
ATOM   1810  C    ALA A 238      12.860  -11.987  23.485 1.000 22.13
ATOM   1811  O    ALA A 238      13.305  -11.162  22.683 1.000 22.14
ATOM   1812  N    GLY A 239      11.599  -11.944  23.922 1.000 22.60
ATOM   1813  CA   GLY A 239      10.794  -10.755  23.654 1.000 19.77
ATOM   1814  C    GLY A 239      11.314   -9.578  24.475 1.000 23.04
ATOM   1815  O    GLY A 239      12.456   -9.584  24.931 1.000 22.08
ATOM   1816  N    PRO A 240      10.501   -8.544  24.664 1.000 20.46
ATOM   1817  CA   PRO A 240      10.904   -7.365  25.418 1.000 18.32
ATOM   1818  CB   PRO A 240       9.645   -6.478  25.441 1.000 15.24
ATOM   1819  CG   PRO A 240       8.855   -6.953  24.270 1.000 26.50
ATOM   1820  CD   PRO A 240       9.123   -8.425  24.156 1.000 18.86
ATOM   1821  C    PRO A 240      11.261   -7.689  26.866 1.000 24.79
ATOM   1822  O    PRO A 240      10.775   -8.644  27.466 1.000 18.83
ATOM   1823  N    THR A 241      12.130   -6.846  27.414 1.000 24.76
ATOM   1824  CA   THR A 241      12.452   -6.849  28.822 1.000 19.34
ATOM   1825  CB   THR A 241      13.790   -6.140  29.127 1.000 24.33
ATOM   1826  OG1  THR A 241      14.851   -6.786  28.430 1.000 21.31
ATOM   1827  CG2  THR A 241      14.100   -6.254  30.618 1.000 17.13
ATOM   1828  C    THR A 241      11.352   -6.124  29.598 1.000 19.74
ATOM   1829  O    THR A 241      11.073   -4.964  29.314 1.000 18.65
ATOM   1830  N    VAL A 242      10.731   -6.769  30.576 1.000 19.16
ATOM   1831  CA   VAL A 242       9.738   -6.070  31.381 1.000 24.84
ATOM   1832  CB   VAL A 242       8.698   -7.016  32.012 1.000 25.33
ATOM   1833  CG1  VAL A 242       7.903   -6.283  33.087 1.000 13.96
ATOM   1834  CG2  VAL A 242       7.778   -7.573  30.936 1.000 18.53
ATOM   1835  C    VAL A 242      10.420   -5.311  32.515 1.000 22.81
ATOM   1836  O    VAL A 242      11.202   -5.907  33.245 1.000 15.62
ATOM   1837  N    VAL A 243      10.114   -4.032  32.656 1.000 16.25
ATOM   1838  CA   VAL A 243      10.607   -3.200  33.733 1.000 14.93
ATOM   1839  CB   VAL A 243      11.507   -2.058  33.233 1.000 19.66
ATOM   1840  CG1  VAL A 243      12.145   -1.357  34.424 1.000 17.79
ATOM   1841  CG2  VAL A 243      12.551   -2.600  32.271 1.000 16.83
ATOM   1842  C    VAL A 243       9.437   -2.590  34.489 1.000 18.40
ATOM   1843  O    VAL A 243       8.522   -2.079  33.856 1.000 17.50
ATOM   1844  N    HIS A 244       9.469   -2.655  35.821 1.000 14.50
ATOM   1845  CA   HIS A 244       8.388   -2.005  36.543 1.000 19.33
ATOM   1846  CB   HIS A 244       7.200   -2.952  36.704 1.000 15.76
ATOM   1847  CG   HIS A 244       7.362   -4.005  37.749 1.000 15.99
ATOM   1848  ND1  HIS A 244       7.060   -3.783  39.076 1.000 16.28
ATOM   1849  CE1  HIS A 244       7.293   -4.893  39.761 1.000 23.84
ATOM   1850  NE2  HIS A 244       7.736   -5.820  38.934 1.000 18.37
ATOM   1851  CD2  HIS A 244       7.785   -5.289  37.665 1.000 12.59
ATOM   1852  C    HIS A 244       8.868   -1.514  37.906 1.000 22.68
ATOM   1853  O    HIS A 244       9.879   -1.996  38.398 1.000 22.27
ATOM   1854  N    CYS A 245       8.127   -0.563  38.448 1.000 22.48
```

FIGURE 42

```
ATOM   1855  CA   CYS A 245       8.229  -0.136  39.836 1.000 22.65
ATOM   1856  CB   CYS A 245       8.861   1.241  39.990 1.000 16.47
ATOM   1857  SG   CYS A 245       8.219   2.535  38.895 1.000 26.22
ATOM   1858  C    CYS A 245       6.812  -0.194  40.402 1.000 23.88
ATOM   1859  O    CYS A 245       6.094  -1.173  40.153 1.000 26.38
ATOM   1860  N    SER A 246       6.385   0.833  41.132 1.000 17.80
ATOM   1861  CA   SER A 246       4.995   0.806  41.607 1.000 11.67
ATOM   1862  CB   SER A 246       4.853   1.726  42.821 1.000 26.78
ATOM   1863  OG   SER A 246       3.561   1.643  43.393 1.000 30.47
ATOM   1864  C    SER A 246       4.033   1.208  40.501 1.000 11.21
ATOM   1865  O    SER A 246       3.068   0.510  40.185 1.000 20.25
ATOM   1866  N    ALA A 247       4.286   2.377  39.909 1.000 15.30
ATOM   1867  CA   ALA A 247       3.455   2.947  38.871 1.000 13.07
ATOM   1868  CB   ALA A 247       3.302   4.446  39.102 1.000 23.22
ATOM   1869  C    ALA A 247       4.008   2.710  37.468 1.000 17.09
ATOM   1870  O    ALA A 247       3.286   2.806  36.473 1.000 23.76
ATOM   1871  N    GLY A 248       5.300   2.413  37.353 1.000 15.64
ATOM   1872  CA   GLY A 248       5.920   2.177  36.056 1.000 19.79
ATOM   1873  C    GLY A 248       6.329   3.497  35.413 1.000 28.08
ATOM   1874  O    GLY A 248       6.206   3.654  34.200 1.000 29.60
ATOM   1875  N    VAL A 249       6.828   4.410  36.242 1.000 24.91
ATOM   1876  CA   VAL A 249       7.165   5.771  35.893 1.000 28.97
ATOM   1877  CB   VAL A 249       6.349   6.742  36.799 1.000 36.67
ATOM   1878  CG1  VAL A 249       4.984   6.994  36.192 1.000 26.78
ATOM   1879  CG2  VAL A 249       6.223   6.201  38.219 1.000 28.45
ATOM   1880  C    VAL A 249       8.635   6.167  36.035 1.000 29.09
ATOM   1881  O    VAL A 249       9.456   5.930  35.151 1.000 32.80
ATOM   1882  N    GLY A 250       8.941   6.823  37.144 1.000 24.19
ATOM   1883  CA   GLY A 250      10.149   7.515  37.501 1.000 19.59
ATOM   1884  C    GLY A 250      11.344   6.573  37.577 1.000 14.84
ATOM   1885  O    GLY A 250      12.267   6.702  36.763 1.000 27.35
ATOM   1886  N    ARG A 251      11.280   5.662  38.534 1.000 11.74
ATOM   1887  CA   ARG A 251      12.347   4.688  38.735 1.000 15.59
ATOM   1888  CB   ARG A 251      12.096   3.823  39.969 1.000 21.64
ATOM   1889  CG   ARG A 251      11.869   4.624  41.250 1.000 23.80
ATOM   1890  CD   ARG A 251      11.653   3.670  42.416 1.000 23.58
ATOM   1891  NE   ARG A 251      11.390   4.352  43.679 1.000 22.88
ATOM   1892  CZ   ARG A 251      11.100   3.675  44.791 1.000 22.64
ATOM   1893  NH1  ARG A 251      11.042   2.354  44.756 1.000 26.67
ATOM   1894  NH2  ARG A 251      10.865   4.301  45.931 1.000 21.50
ATOM   1895  C    ARG A 251      12.517   3.790  37.513 1.000 19.15
ATOM   1896  O    ARG A 251      13.649   3.477  37.144 1.000 23.13
ATOM   1897  N    THR A 252      11.409   3.372  36.904 1.000 18.67
ATOM   1898  CA   THR A 252      11.482   2.546  35.702 1.000 18.13
ATOM   1899  CB   THR A 252      10.103   2.014  35.289 1.000 20.50
ATOM   1900  OG1  THR A 252       9.706   1.005  36.228 1.000 22.47
ATOM   1901  CG2  THR A 252      10.127   1.333  33.924 1.000 18.43
ATOM   1902  C    THR A 252      12.101   3.351  34.562 1.000 20.66
ATOM   1903  O    THR A 252      13.001   2.852  33.877 1.000 22.41
ATOM   1904  N    GLY A 253      11.627   4.580  34.377 1.000 19.06
ATOM   1905  CA   GLY A 253      12.124   5.407  33.276 1.000 24.03
ATOM   1906  C    GLY A 253      13.615   5.663  33.423 1.000 26.29
```

FIGURE 43

```
ATOM   1907  O    GLY A 253      14.370    5.727  32.452 1.000 20.33
ATOM   1908  N    THR A 254      14.036    5.811  34.674 1.000 20.94
ATOM   1909  CA   THR A 254      15.433    6.059  35.011 1.000 25.32
ATOM   1910  CB   THR A 254      15.546    6.439  36.505 1.000 23.28
ATOM   1911  OG1  THR A 254      14.879    7.688  36.704 1.000 19.41
ATOM   1912  CG2  THR A 254      16.993    6.642  36.910 1.000 22.36
ATOM   1913  C    THR A 254      16.300    4.847  34.714 1.000 22.06
ATOM   1914  O    THR A 254      17.389    4.928  34.151 1.000 27.89
ATOM   1915  N    PHE A 255      15.811    3.671  35.094 1.000 18.65
ATOM   1916  CA   PHE A 255      16.498    2.433  34.780 1.000 13.27
ATOM   1917  CB   PHE A 255      15.709    1.219  35.277 1.000 13.04
ATOM   1918  CG   PHE A 255      16.305   -0.125  34.923 1.000 21.43
ATOM   1919  CD1  PHE A 255      17.222   -0.717  35.783 1.000 22.29
ATOM   1920  CE1  PHE A 255      17.786   -1.941  35.492 1.000 24.82
ATOM   1921  CZ   PHE A 255      17.476   -2.615  34.325 1.000 20.78
ATOM   1922  CE2  PHE A 255      16.558   -2.054  33.461 1.000 16.57
ATOM   1923  CD2  PHE A 255      15.987   -0.836  33.778 1.000 20.56
ATOM   1924  C    PHE A 255      16.721    2.323  33.277 1.000 23.91
ATOM   1925  O    PHE A 255      17.791    1.918  32.814 1.000 23.04
ATOM   1926  N    ILE A 256      15.665    2.620  32.511 1.000 21.98
ATOM   1927  CA   ILE A 256      15.794    2.334  31.082 1.000 23.48
ATOM   1928  CB   ILE A 256      14.462    2.211  30.336 1.000 22.01
ATOM   1929  CG1  ILE A 256      13.667    0.941  30.657 1.000 26.28
ATOM   1930  CD1  ILE A 256      12.210    1.020  30.221 1.000 23.52
ATOM   1931  CG2  ILE A 256      14.666    2.310  28.823 1.000 17.05
ATOM   1932  C    ILE A 256      16.666    3.412  30.439 1.000 14.97
ATOM   1933  O    ILE A 256      17.470    3.058  29.575 1.000 20.35
ATOM   1934  N    ALA A 257      16.489    4.659  30.864 1.000 16.95
ATOM   1935  CA   ALA A 257      17.365    5.725  30.354 1.000 13.62
ATOM   1936  CB   ALA A 257      16.973    7.077  30.894 1.000 16.03
ATOM   1937  C    ALA A 257      18.811    5.373  30.689 1.000 20.04
ATOM   1938  O    ALA A 257      19.713    5.497  29.866 1.000 24.71
ATOM   1939  N    LEU A 258      19.083    4.886  31.908 1.000 20.59
ATOM   1940  CA   LEU A 258      20.490    4.560  32.186 1.000 25.52
ATOM   1941  CB   LEU A 258      20.723    4.299  33.673 1.000 29.22
ATOM   1942  CG   LEU A 258      22.171    4.177  34.151 1.000 33.36
ATOM   1943  CD1  LEU A 258      23.069    5.186  33.453 1.000 17.44
ATOM   1944  CD2  LEU A 258      22.268    4.363  35.660 1.000 32.48
ATOM   1945  C    LEU A 258      20.931    3.377  31.336 1.000 24.80
ATOM   1946  O    LEU A 258      22.020    3.447  30.768 1.000 31.87
ATOM   1947  N    ASP A 259      20.130    2.316  31.238 1.000 19.82
ATOM   1948  CA   ASP A 259      20.524    1.155  30.439 1.000 21.21
ATOM   1949  CB   ASP A 259      19.441    0.080  30.461 1.000 26.62
ATOM   1950  CG   ASP A 259      19.716   -1.155  29.637 1.000 33.72
ATOM   1951  OD1  ASP A 259      20.883   -1.598  29.573 1.000 35.74
ATOM   1952  OD2  ASP A 259      18.758   -1.719  29.046 1.000 24.80
ATOM   1953  C    ASP A 259      20.832    1.579  29.010 1.000 21.68
ATOM   1954  O    ASP A 259      21.742    1.052  28.372 1.000 28.89
ATOM   1955  N    ARG A 260      20.070    2.539  28.506 1.000 23.42
ATOM   1956  CA   ARG A 260      20.230    3.024  27.138 1.000 25.06
ATOM   1957  CB   ARG A 260      19.028    3.897  26.771 1.000 28.71
ATOM   1958  CG   ARG A 260      17.920    3.218  25.983 1.000 37.83
```

FIGURE 44

```
ATOM   1959  CD   ARG A 260      17.815    3.892   24.612  1.000 40.41
ATOM   1960  NE   ARG A 260      16.447    4.236   24.289  1.000 39.10
ATOM   1961  CZ   ARG A 260      15.997    5.081   23.376  1.000 37.92
ATOM   1962  NH1  ARG A 260      16.820    5.759   22.595  1.000 44.18
ATOM   1963  NH2  ARG A 260      14.682    5.235   23.257  1.000 38.91
ATOM   1964  C    ARG A 260      21.503    3.834   26.932  1.000 28.89
ATOM   1965  O    ARG A 260      22.183    3.707   25.913  1.000 28.43
ATOM   1966  N    ILE A 261      21.850    4.713   27.878  1.000 31.24
ATOM   1967  CA   ILE A 261      23.011    5.568   27.644  1.000 32.00
ATOM   1968  CB   ILE A 261      23.003    6.871   28.463  1.000 30.49
ATOM   1969  CG1  ILE A 261      23.174    6.692   29.969  1.000 33.74
ATOM   1970  CD1  ILE A 261      22.668    7.864   30.782  1.000 47.87
ATOM   1971  CG2  ILE A 261      21.747    7.669   28.142  1.000 38.62
ATOM   1972  C    ILE A 261      24.311    4.827   27.939  1.000 30.43
ATOM   1973  O    ILE A 261      25.293    5.061   27.228  1.000 33.25
ATOM   1974  N    LEU A 262      24.317    3.958   28.951  1.000 22.89
ATOM   1975  CA   LEU A 262      25.541    3.189   29.202  1.000 27.21
ATOM   1976  CB   LEU A 262      25.411    2.219   30.368  1.000 29.63
ATOM   1977  CG   LEU A 262      25.330    2.760   31.793  1.000 38.46
ATOM   1978  CD1  LEU A 262      25.371    1.630   32.815  1.000 28.64
ATOM   1979  CD2  LEU A 262      26.441    3.762   32.059  1.000 34.63
ATOM   1980  C    LEU A 262      25.912    2.424   27.931  1.000 37.42
ATOM   1981  O    LEU A 262      27.090    2.228   27.640  1.000 48.70
ATOM   1982  N    GLN A 263      24.900    1.987   27.183  1.000 40.24
ATOM   1983  CA   GLN A 263      25.151    1.267   25.943  1.000 38.78
ATOM   1984  CB   GLN A 263      23.875    0.706   25.322  1.000 30.36
ATOM   1985  CG   GLN A 263      23.653   -0.767   25.637  1.000 26.81
ATOM   1986  CD   GLN A 263      22.223   -1.212   25.423  1.000 28.10
ATOM   1987  OE1  GLN A 263      21.946   -1.976   24.500  1.000 30.64
ATOM   1988  NE2  GLN A 263      21.304   -0.760   26.273  1.000 33.75
ATOM   1989  C    GLN A 263      25.827    2.190   24.934  1.000 44.56
ATOM   1990  O    GLN A 263      26.667    1.744   24.161  1.000 46.96
ATOM   1991  N    GLN A 264      25.420    3.455   24.977  1.000 42.51
ATOM   1992  CA   GLN A 264      25.954    4.431   24.033  1.000 47.48
ATOM   1993  CB   GLN A 264      25.220    5.773   24.152  1.000 39.34
ATOM   1994  CG   GLN A 264      23.957    5.807   23.303  1.000 37.99
ATOM   1995  CD   GLN A 264      23.060    6.989   23.591  1.000 42.10
ATOM   1996  OE1  GLN A 264      23.477    7.972   24.206  1.000 41.41
ATOM   1997  NE2  GLN A 264      21.814    6.899   23.144  1.000 49.45
ATOM   1998  C    GLN A 264      27.452    4.610   24.256  1.000 50.33
ATOM   1999  O    GLN A 264      28.253    4.493   23.328  1.000 38.61
ATOM   2000  N    LEU A 265      27.777    4.876   25.513  1.000 49.87
ATOM   2001  CA   LEU A 265      29.118    5.176   25.984  1.000 51.23
ATOM   2002  CB   LEU A 265      29.084    5.389   27.503  1.000 48.71
ATOM   2003  CG   LEU A 265      28.256    6.584   27.988  1.000 49.68
ATOM   2004  CD1  LEU A 265      28.263    6.684   29.507  1.000 46.47
ATOM   2005  CD2  LEU A 265      28.757    7.884   27.370  1.000 44.07
ATOM   2006  C    LEU A 265      30.122    4.097   25.607  1.000 59.08
ATOM   2007  O    LEU A 265      31.329    4.351   25.565  1.000 62.01
ATOM   2008  N    ASP A 266      29.656    2.887   25.317  1.000 60.11
ATOM   2009  CA   ASP A 266      30.559    1.815   24.901  1.000 60.82
ATOM   2010  CB   ASP A 266      30.345    0.581   25.776  1.000 68.15
```

FIGURE 45

```
ATOM   2011  CG   ASP A 266      30.603   0.832  27.251  1.000  74.94
ATOM   2012  OD1  ASP A 266      31.286   1.822  27.599  1.000  87.47
ATOM   2013  OD2  ASP A 266      30.117   0.033  28.083  1.000  72.82
ATOM   2014  C    ASP A 266      30.362   1.481  23.428  1.000  56.29
ATOM   2015  O    ASP A 266      30.797   0.449  22.918  1.000  65.03
ATOM   2016  N    SER A 267      29.692   2.373  22.703  1.000  49.36
ATOM   2017  CA   SER A 267      29.450   2.133  21.286  1.000  49.97
ATOM   2018  CB   SER A 267      28.040   1.563  21.092  1.000  47.54
ATOM   2019  OG   SER A 267      28.070   0.147  21.070  1.000  70.07
ATOM   2020  C    SER A 267      29.602   3.403  20.457  1.000  56.45
ATOM   2021  O    SER A 267      29.833   3.345  19.249  1.000  64.11
ATOM   2022  N    LYS A 268      29.457   4.547  21.113  1.000  54.03
ATOM   2023  CA   LYS A 268      29.450   5.851  20.473  1.000  61.77
ATOM   2024  CB   LYS A 268      28.124   6.565  20.747  1.000  73.01
ATOM   2025  CG   LYS A 268      27.792   7.746  19.856  1.000  78.98
ATOM   2026  CD   LYS A 268      26.344   7.687  19.384  1.000  85.20
ATOM   2027  CE   LYS A 268      25.589   8.983  19.679  1.000  87.23
ATOM   2028  NZ   LYS A 268      24.372   8.773  20.503  1.000  77.94
ATOM   2029  C    LYS A 268      30.607   6.721  20.967  1.000  57.67
ATOM   2030  O    LYS A 268      31.288   6.352  21.923  1.000  56.55
ATOM   2031  N    ASP A 269      30.759   7.842  20.289  1.000  51.51
ATOM   2032  CA   ASP A 269      31.664   8.925  20.619  1.000  61.39
ATOM   2033  CB   ASP A 269      32.424   9.415  19.388  1.000  66.41
ATOM   2034  CG   ASP A 269      31.625   9.286  18.106  1.000  74.35
ATOM   2035  OD1  ASP A 269      32.119   8.629  17.162  1.000  91.04
ATOM   2036  OD2  ASP A 269      30.505   9.842  18.044  1.000  81.62
ATOM   2037  C    ASP A 269      30.865  10.067  21.240  1.000  58.72
ATOM   2038  O    ASP A 269      31.369  11.104  21.659  1.000  48.76
ATOM   2039  N    SER A 270      29.551   9.848  21.289  1.000  55.39
ATOM   2040  CA   SER A 270      28.687  10.847  21.910  1.000  53.30
ATOM   2041  CB   SER A 270      27.989  11.679  20.834  1.000  46.93
ATOM   2042  OG   SER A 270      27.692  10.829  19.734  1.000  51.09
ATOM   2043  C    SER A 270      27.674  10.148  22.807  1.000  54.77
ATOM   2044  O    SER A 270      27.500   8.934  22.703  1.000  57.87
ATOM   2045  N    VAL A 271      27.031  10.915  23.668  1.000  51.16
ATOM   2046  CA   VAL A 271      26.025  10.400  24.590  1.000  47.16
ATOM   2047  CB   VAL A 271      26.612  10.189  25.992  1.000  43.33
ATOM   2048  CG1  VAL A 271      27.075  11.525  26.564  1.000  28.98
ATOM   2049  CG2  VAL A 271      25.609   9.523  26.918  1.000  33.32
ATOM   2050  C    VAL A 271      24.851  11.374  24.626  1.000  51.02
ATOM   2051  O    VAL A 271      25.054  12.585  24.754  1.000  45.80
ATOM   2052  N    ASP A 272      23.639  10.841  24.484  1.000  43.19
ATOM   2053  CA   ASP A 272      22.451  11.680  24.350  1.000  34.67
ATOM   2054  CB   ASP A 272      21.819  11.492  22.973  1.000  34.66
ATOM   2055  CG   ASP A 272      20.791  12.553  22.633  1.000  34.78
ATOM   2056  OD1  ASP A 272      20.496  13.413  23.488  1.000  35.05
ATOM   2057  OD2  ASP A 272      20.262  12.537  21.499  1.000  61.92
ATOM   2058  C    ASP A 272      21.450  11.367  25.450  1.000  37.86
ATOM   2059  O    ASP A 272      20.601  10.489  25.312  1.000  33.07
ATOM   2060  N    ILE A 273      21.548  12.095  26.564  1.000  29.66
ATOM   2061  CA   ILE A 273      20.651  11.774  27.671  1.000  30.56
ATOM   2062  CB   ILE A 273      21.245  12.212  29.019  1.000  28.78
```

FIGURE 46

```
ATOM   2063  CG1 ILE A 273      22.562  11.518  29.362  1.000 24.46
ATOM   2064  CD1 ILE A 273      23.227  12.049  30.612  1.000 33.99
ATOM   2065  CG2 ILE A 273      20.228  12.016  30.134  1.000 24.56
ATOM   2066  C   ILE A 273      19.290  12.420  27.450  1.000 36.66
ATOM   2067  O   ILE A 273      18.264  11.844  27.813  1.000 38.74
ATOM   2068  N   TYR A 274      19.301  13.608  26.845  1.000 31.39
ATOM   2069  CA  TYR A 274      18.044  14.276  26.525  1.000 27.62
ATOM   2070  CB  TYR A 274      18.312  15.642  25.908  1.000 26.54
ATOM   2071  CG  TYR A 274      17.119  16.489  25.551  1.000 27.58
ATOM   2072  CD1 TYR A 274      16.633  17.434  26.450  1.000 29.05
ATOM   2073  CE1 TYR A 274      15.544  18.225  26.150  1.000 28.10
ATOM   2074  CZ  TYR A 274      14.913  18.089  24.932  1.000 28.89
ATOM   2075  OH  TYR A 274      13.827  18.881  24.631  1.000 40.18
ATOM   2076  CE2 TYR A 274      15.372  17.169  24.020  1.000 30.70
ATOM   2077  CD2 TYR A 274      16.469  16.377  24.331  1.000 31.75
ATOM   2078  C   TYR A 274      17.228  13.415  25.565  1.000 30.07
ATOM   2079  O   TYR A 274      16.027  13.221  25.735  1.000 27.79
ATOM   2080  N   GLY A 275      17.908  12.908  24.540  1.000 30.84
ATOM   2081  CA  GLY A 275      17.256  12.132  23.499  1.000 38.31
ATOM   2082  C   GLY A 275      16.611  10.863  24.016  1.000 36.93
ATOM   2083  O   GLY A 275      15.515  10.487  23.605  1.000 33.21
ATOM   2084  N   ALA A 276      17.282  10.176  24.930  1.000 26.01
ATOM   2085  CA  ALA A 276      16.728   8.949  25.490  1.000 26.10
ATOM   2086  CB  ALA A 276      17.753   8.300  26.409  1.000 36.77
ATOM   2087  C   ALA A 276      15.440   9.236  26.248  1.000 26.60
ATOM   2088  O   ALA A 276      14.412   8.600  26.061  1.000 21.84
ATOM   2089  N   VAL A 277      15.510  10.227  27.129  1.000 27.46
ATOM   2090  CA  VAL A 277      14.382  10.602  27.971  1.000 26.38
ATOM   2091  CB  VAL A 277      14.829  11.656  29.004  1.000 27.97
ATOM   2092  CG1 VAL A 277      13.661  12.343  29.687  1.000 33.02
ATOM   2093  CG2 VAL A 277      15.720  10.980  30.043  1.000 17.52
ATOM   2094  C   VAL A 277      13.229  11.103  27.113  1.000 26.05
ATOM   2095  O   VAL A 277      12.060  10.837  27.417  1.000 29.47
ATOM   2096  N   HIS A 278      13.556  11.815  26.043  1.000 20.60
ATOM   2097  CA  HIS A 278      12.558  12.336  25.113  1.000 25.33
ATOM   2098  CB  HIS A 278      13.204  13.259  24.087  1.000 27.86
ATOM   2099  CG  HIS A 278      12.276  13.815  23.054  1.000 25.27
ATOM   2100  ND1 HIS A 278      11.807  13.069  21.994  1.000 24.22
ATOM   2101  CE1 HIS A 278      11.015  13.819  21.244  1.000 24.97
ATOM   2102  NE2 HIS A 278      10.961  15.031  21.773  1.000 23.92
ATOM   2103  CD2 HIS A 278      11.746  15.050  22.900  1.000 22.15
ATOM   2104  C   HIS A 278      11.838  11.214  24.370  1.000 23.01
ATOM   2105  O   HIS A 278      10.650  11.288  24.068  1.000 25.09
ATOM   2106  N   ASP A 279      12.571  10.160  24.059  1.000 20.73
ATOM   2107  CA  ASP A 279      11.994   9.026  23.343  1.000 24.89
ATOM   2108  CB  ASP A 279      13.099   8.159  22.746  1.000 30.17
ATOM   2109  CG  ASP A 279      12.727   7.306  21.558  1.000 30.34
ATOM   2110  OD1 ASP A 279      12.077   7.787  20.605  1.000 26.50
ATOM   2111  OD2 ASP A 279      13.096   6.106  21.539  1.000 33.56
ATOM   2112  C   ASP A 279      11.131   8.228  24.309  1.000 19.27
ATOM   2113  O   ASP A 279      10.059   7.720  23.981  1.000 23.16
ATOM   2114  N   LEU A 280      11.627   8.121  25.541  1.000 17.51
```

FIGURE 47

```
ATOM   2115  CA  LEU A 280      10.848    7.371   26.523  1.000  25.22
ATOM   2116  CB  LEU A 280      11.578    7.273   27.857  1.000  22.56
ATOM   2117  CG  LEU A 280      12.948    6.595   27.878  1.000  30.97
ATOM   2118  CD1 LEU A 280      13.309    6.169   29.294  1.000  16.61
ATOM   2119  CD2 LEU A 280      12.998    5.407   26.930  1.000  39.44
ATOM   2120  C   LEU A 280       9.475    8.027   26.702  1.000  28.43
ATOM   2121  O   LEU A 280       8.472    7.315   26.678  1.000  19.82
ATOM   2122  N   ARG A 281       9.480    9.335   26.877  1.000  27.78
ATOM   2123  CA  ARG A 281       8.364   10.230   27.097  1.000  26.26
ATOM   2124  CB  ARG A 281       8.840   11.690   27.129  1.000  27.59
ATOM   2125  CG  ARG A 281       9.597   12.025   28.413  1.000  35.06
ATOM   2126  CD  ARG A 281       8.645   11.966   29.597  1.000  33.64
ATOM   2127  NE  ARG A 281       9.295   12.376   30.831  1.000  36.75
ATOM   2128  CZ  ARG A 281       9.526   13.626   31.204  1.000  40.89
ATOM   2129  NH1 ARG A 281       9.161   14.636   30.435  1.000  32.39
ATOM   2130  NH2 ARG A 281      10.132   13.874   32.361  1.000  61.48
ATOM   2131  C   ARG A 281       7.302   10.096   26.018  1.000  19.40
ATOM   2132  O   ARG A 281       6.104   10.236   26.254  1.000  20.20
ATOM   2133  N   LEU A 282       7.773    9.823   24.805  1.000  20.07
ATOM   2134  CA  LEU A 282       6.823    9.651   23.711  1.000  23.11
ATOM   2135  CB  LEU A 282       7.523    9.589   22.353  1.000  17.59
ATOM   2136  CG  LEU A 282       7.893   10.913   21.688  1.000  27.09
ATOM   2137  CD1 LEU A 282       8.800   10.679   20.489  1.000  27.56
ATOM   2138  CD2 LEU A 282       6.660   11.688   21.243  1.000  20.11
ATOM   2139  C   LEU A 282       5.974    8.404   23.913  1.000  26.60
ATOM   2140  O   LEU A 282       4.880    8.342   23.352  1.000  22.78
ATOM   2141  N   HIS A 283       6.430    7.412   24.678  1.000  25.41
ATOM   2142  CA  HIS A 283       5.698    6.144   24.667  1.000  19.57
ATOM   2143  CB  HIS A 283       6.688    5.008   24.336  1.000  24.33
ATOM   2144  CG  HIS A 283       7.263    5.215   22.965  1.000  22.62
ATOM   2145  ND1 HIS A 283       6.742    4.619   21.841  1.000  26.42
ATOM   2146  CE1 HIS A 283       7.436    4.985   20.775  1.000  25.06
ATOM   2147  NE2 HIS A 283       8.386    5.808   21.174  1.000  24.57
ATOM   2148  CD2 HIS A 283       8.300    5.974   22.536  1.000  21.10
ATOM   2149  C   HIS A 283       4.956    5.861   25.961  1.000  17.31
ATOM   2150  O   HIS A 283       4.101    4.976   26.006  1.000  20.69
ATOM   2151  N   ARG A 284       5.262    6.606   27.011  1.000  16.92
ATOM   2152  CA  ARG A 284       4.594    6.512   28.296  1.000  15.56
ATOM   2153  CB  ARG A 284       5.038    5.279   29.091  1.000  19.52
ATOM   2154  CG  ARG A 284       4.214    5.010   30.355  1.000  16.19
ATOM   2155  CD  ARG A 284       4.569    3.660   30.954  1.000  19.69
ATOM   2156  NE  ARG A 284       4.009    3.428   32.282  1.000  18.76
ATOM   2157  CZ  ARG A 284       2.892    2.731   32.492  1.000  19.76
ATOM   2158  NH1 ARG A 284       2.214    2.207   31.475  1.000  11.48
ATOM   2159  NH2 ARG A 284       2.439    2.553   33.726  1.000  17.29
ATOM   2160  C   ARG A 284       4.845    7.774   29.119  1.000  15.30
ATOM   2161  O   ARG A 284       5.941    8.327   29.076  1.000  25.00
ATOM   2162  N   VAL A 285       3.834    8.221   29.846  1.000  19.78
ATOM   2163  CA  VAL A 285       3.912    9.415   30.685  1.000  26.66
ATOM   2164  CB  VAL A 285       2.507    9.771   31.215  1.000  32.12
ATOM   2165  CG1 VAL A 285       1.981    8.686   32.152  1.000  20.70
ATOM   2166  CG2 VAL A 285       2.503   11.126   31.909  1.000  29.12
```

FIGURE 48

```
ATOM   2167  C    VAL A 285       4.917   9.216  31.814  1.000  20.03
ATOM   2168  O    VAL A 285       5.153   8.085  32.242  1.000  23.27
ATOM   2169  N    HIS A 286       5.510  10.296  32.281  1.000  28.92
ATOM   2170  CA   HIS A 286       6.440  10.404  33.382  1.000  29.32
ATOM   2171  CB   HIS A 286       5.744  10.052  34.718  1.000  33.92
ATOM   2172  CG   HIS A 286       4.476  10.821  34.904  1.000  38.90
ATOM   2173  ND1  HIS A 286       4.430  12.188  34.769  1.000  45.43
ATOM   2174  CE1  HIS A 286       3.197  12.615  34.978  1.000  45.72
ATOM   2175  NE2  HIS A 286       2.439  11.567  35.244  1.000  48.04
ATOM   2176  CD2  HIS A 286       3.216  10.433  35.200  1.000  47.11
ATOM   2177  C    HIS A 286       7.669   9.521  33.267  1.000  24.27
ATOM   2178  O    HIS A 286       8.292   9.259  34.303  1.000  39.87
ATOM   2179  N    MET A 287       8.054   9.038  32.087  1.000  19.82
ATOM   2180  CA   MET A 287       9.326   8.294  32.047  1.000  18.04
ATOM   2181  CB   MET A 287       9.579   7.694  30.679  1.000  19.24
ATOM   2182  CG   MET A 287       8.566   6.647  30.239  1.000  24.10
ATOM   2183  SD   MET A 287       8.699   5.134  31.234  1.000  32.12
ATOM   2184  CE   MET A 287       7.526   5.570  32.521  1.000  32.04
ATOM   2185  C    MET A 287      10.457   9.247  32.459  1.000  32.08
ATOM   2186  O    MET A 287      10.732  10.211  31.741  1.000  32.41
ATOM   2187  N    VAL A 288      11.071   8.981  33.599  1.000  29.73
ATOM   2188  CA   VAL A 288      12.024   9.837  34.294  1.000  22.00
ATOM   2189  CB   VAL A 288      13.229  10.233  33.436  1.000  21.06
ATOM   2190  CG1  VAL A 288      14.167  11.132  34.232  1.000  28.71
ATOM   2191  CG2  VAL A 288      13.961   8.986  32.952  1.000  15.73
ATOM   2192  C    VAL A 288      11.269  11.073  34.787  1.000  30.61
ATOM   2193  O    VAL A 288      11.226  12.112  34.132  1.000  31.06
ATOM   2194  N    GLN A 289      10.675  10.871  35.957  1.000  23.90
ATOM   2195  CA   GLN A 289       9.626  11.709  36.494  1.000  28.48
ATOM   2196  CB   GLN A 289       8.735  10.869  37.427  1.000  27.94
ATOM   2197  CG   GLN A 289       7.406  11.535  37.748  1.000  34.50
ATOM   2198  CD   GLN A 289       6.481  10.661  38.562  1.000  30.01
ATOM   2199  OE1  GLN A 289       6.907   9.646  39.112  1.000  45.90
ATOM   2200  NE2  GLN A 289       5.209  11.026  38.655  1.000  37.56
ATOM   2201  C    GLN A 289      10.123  12.924  37.258  1.000  36.20
ATOM   2202  O    GLN A 289       9.316  13.811  37.536  1.000  32.67
ATOM   2203  N    THR A 290      11.402  12.994  37.619  1.000  33.43
ATOM   2204  CA   THR A 290      11.857  14.147  38.382  1.000  32.24
ATOM   2205  CB   THR A 290      12.078  13.862  39.878  1.000  27.63
ATOM   2206  OG1  THR A 290      13.285  13.106  40.043  1.000  42.04
ATOM   2207  CG2  THR A 290      10.951  13.021  40.456  1.000  35.76
ATOM   2208  C    THR A 290      13.174  14.677  37.822  1.000  42.79
ATOM   2209  O    THR A 290      13.921  13.935  37.191  1.000  31.85
ATOM   2210  N    GLU A 291      13.421  15.963  38.072  1.000  41.73
ATOM   2211  CA   GLU A 291      14.707  16.538  37.692  1.000  33.95
ATOM   2212  CB   GLU A 291      14.749  18.032  37.980  1.000  44.06
ATOM   2213  CG   GLU A 291      16.167  18.595  38.042  1.000  51.27
ATOM   2214  CD   GLU A 291      16.146  20.001  38.627  1.000  50.92
ATOM   2215  OE1  GLU A 291      16.994  20.298  39.487  1.000  46.66
ATOM   2216  OE2  GLU A 291      15.255  20.769  38.205  1.000  44.79
ATOM   2217  C    GLU A 291      15.814  15.826  38.461  1.000  26.05
ATOM   2218  O    GLU A 291      16.890  15.581  37.921  1.000  31.12
```

FIGURE 49

```
ATOM   2219  N    CYS A 292      15.513  15.486  39.714 1.000 27.69
ATOM   2220  CA   CYS A 292      16.460  14.750  40.550 1.000 22.15
ATOM   2221  CB   CYS A 292      15.840  14.409  41.899 1.000 28.25
ATOM   2222  SG   CYS A 292      16.996  13.623  43.050 1.000 68.90
ATOM   2223  C    CYS A 292      16.908  13.477  39.849 1.000 29.87
ATOM   2224  O    CYS A 292      18.079  13.092  39.819 1.000 32.69
ATOM   2225  N    GLN A 293      15.924  12.801  39.246 1.000 28.10
ATOM   2226  CA   GLN A 293      16.294  11.621  38.459 1.000 28.74
ATOM   2227  CB   GLN A 293      15.030  10.845  38.087 1.000 25.18
ATOM   2228  CG   GLN A 293      14.509  10.017  39.250 1.000 22.15
ATOM   2229  CD   GLN A 293      13.034   9.698  39.089 1.000 27.52
ATOM   2230  OE1  GLN A 293      12.412  10.175  38.141 1.000 28.92
ATOM   2231  NE2  GLN A 293      12.503   8.909  40.009 1.000 24.69
ATOM   2232  C    GLN A 293      17.097  12.037  37.235 1.000 29.57
ATOM   2233  O    GLN A 293      18.056  11.373  36.831 1.000 25.56
ATOM   2234  N    TYR A 294      16.706  13.165  36.640 1.000 27.49
ATOM   2235  CA   TYR A 294      17.399  13.690  35.469 1.000 28.60
ATOM   2236  CB   TYR A 294      16.667  14.921  34.934 1.000 26.37
ATOM   2237  CG   TYR A 294      17.095  15.300  33.540 1.000 27.25
ATOM   2238  CD1  TYR A 294      16.934  14.379  32.509 1.000 37.08
ATOM   2239  CE1  TYR A 294      17.311  14.682  31.218 1.000 37.31
ATOM   2240  CZ   TYR A 294      17.861  15.920  30.951 1.000 39.27
ATOM   2241  OH   TYR A 294      18.234  16.214  29.659 1.000 43.06
ATOM   2242  CE2  TYR A 294      18.030  16.846  31.957 1.000 36.04
ATOM   2243  CD2  TYR A 294      17.648  16.535  33.252 1.000 28.82
ATOM   2244  C    TYR A 294      18.844  14.045  35.798 1.000 26.82
ATOM   2245  O    TYR A 294      19.783  13.828  35.040 1.000 34.04
ATOM   2246  N    VAL A 295      19.062  14.611  36.978 1.000 22.51
ATOM   2247  CA   VAL A 295      20.439  14.894  37.384 1.000 32.33
ATOM   2248  CB   VAL A 295      20.466  15.733  38.675 1.000 34.92
ATOM   2249  CG1  VAL A 295      21.858  15.698  39.282 1.000 36.74
ATOM   2250  CG2  VAL A 295      20.006  17.152  38.372 1.000 28.93
ATOM   2251  C    VAL A 295      21.228  13.612  37.608 1.000 27.09
ATOM   2252  O    VAL A 295      22.364  13.460  37.153 1.000 34.90
ATOM   2253  N    TYR A 296      20.606  12.678  38.319 1.000 26.27
ATOM   2254  CA   TYR A 296      21.232  11.378  38.578 1.000 29.32
ATOM   2255  CB   TYR A 296      20.229  10.492  39.314 1.000 28.67
ATOM   2256  CG   TYR A 296      20.761   9.196  39.861 1.000 35.66
ATOM   2257  CD1  TYR A 296      21.638   9.150  40.937 1.000 33.98
ATOM   2258  CE1  TYR A 296      22.119   7.951  41.431 1.000 32.73
ATOM   2259  CZ   TYR A 296      21.722   6.770  40.842 1.000 33.73
ATOM   2260  OH   TYR A 296      22.187   5.561  41.318 1.000 35.73
ATOM   2261  CE2  TYR A 296      20.853   6.786  39.775 1.000 33.85
ATOM   2262  CD2  TYR A 296      20.376   7.987  39.290 1.000 37.49
ATOM   2263  C    TYR A 296      21.742  10.739  37.295 1.000 27.66
ATOM   2264  O    TYR A 296      22.831  10.150  37.266 1.000 32.42
ATOM   2265  N    LEU A 297      21.015  10.840  36.184 1.000 26.94
ATOM   2266  CA   LEU A 297      21.497  10.174  34.968 1.000 28.80
ATOM   2267  CB   LEU A 297      20.459  10.187  33.846 1.000 24.99
ATOM   2268  CG   LEU A 297      19.141   9.462  34.135 1.000 24.86
ATOM   2269  CD1  LEU A 297      18.119   9.734  33.046 1.000 23.89
ATOM   2270  CD2  LEU A 297      19.357   7.966  34.270 1.000 20.37
```

FIGURE 50

```
ATOM   2271  C    LEU A 297      22.795  10.820  34.495  1.000  33.04
ATOM   2272  O    LEU A 297      23.704  10.129  34.036  1.000  49.72
ATOM   2273  N    HIS A 298      22.879  12.139  34.606  1.000  31.51
ATOM   2274  CA   HIS A 298      24.115  12.850  34.291  1.000  35.13
ATOM   2275  CB   HIS A 298      23.871  14.358  34.261  1.000  40.34
ATOM   2276  CG   HIS A 298      22.964  14.791  33.153  1.000  37.19
ATOM   2277  ND1  HIS A 298      21.598  14.646  33.222  1.000  31.89
ATOM   2278  CE1  HIS A 298      21.052  15.109  32.108  1.000  37.29
ATOM   2279  NE2  HIS A 298      22.021  15.545  31.322  1.000  38.18
ATOM   2280  CD2  HIS A 298      23.228  15.356  31.954  1.000  36.75
ATOM   2281  C    HIS A 298      25.202  12.524  35.310  1.000  29.73
ATOM   2282  O    HIS A 298      26.358  12.314  34.945  1.000  36.94
ATOM   2283  N    GLN A 299      24.848  12.470  36.599  1.000  26.95
ATOM   2284  CA   GLN A 299      25.880  12.104  37.579  1.000  34.87
ATOM   2285  CB   GLN A 299      25.339  12.184  39.001  1.000  34.33
ATOM   2286  CG   GLN A 299      24.925  13.584  39.424  1.000  44.04
ATOM   2287  CD   GLN A 299      24.110  13.598  40.702  1.000  49.76
ATOM   2288  OE1  GLN A 299      23.289  12.715  40.953  1.000  45.00
ATOM   2289  NE2  GLN A 299      24.315  14.612  41.540  1.000  34.03
ATOM   2290  C    GLN A 299      26.425  10.712  37.267  1.000  42.34
ATOM   2291  O    GLN A 299      27.602  10.424  37.494  1.000  36.30
ATOM   2292  N    CYS A 300      25.565   9.845  36.732  1.000  40.53
ATOM   2293  CA   CYS A 300      25.967   8.486  36.389  1.000  34.21
ATOM   2294  CB   CYS A 300      24.743   7.622  36.058  1.000  28.55
ATOM   2295  SG   CYS A 300      23.923   6.884  37.493  1.000  33.04
ATOM   2296  C    CYS A 300      26.937   8.476  35.217  1.000  34.71
ATOM   2297  O    CYS A 300      27.937   7.754  35.210  1.000  29.76
ATOM   2298  N    VAL A 301      26.651   9.279  34.193  1.000  43.45
ATOM   2299  CA   VAL A 301      27.534   9.265  33.021  1.000  48.01
ATOM   2300  CB   VAL A 301      26.875   9.944  31.809  1.000  44.81
ATOM   2301  CG1  VAL A 301      27.860  10.046  30.650  1.000  34.28
ATOM   2302  CG2  VAL A 301      25.626   9.187  31.372  1.000  34.53
ATOM   2303  C    VAL A 301      28.865   9.935  33.351  1.000  51.69
ATOM   2304  O    VAL A 301      29.937   9.511  32.918  1.000  43.92
ATOM   2305  N    ARG A 302      28.808  11.008  34.140  1.000  49.27
ATOM   2306  CA   ARG A 302      30.013  11.730  34.519  1.000  45.50
ATOM   2307  CB   ARG A 302      29.670  12.984  35.328  1.000  43.11
ATOM   2308  CG   ARG A 302      30.898  13.642  35.952  1.000  44.65
ATOM   2309  CD   ARG A 302      30.517  14.426  37.200  1.000  42.63
ATOM   2310  NE   ARG A 302      30.239  13.510  38.308  1.000  45.99
ATOM   2311  CZ   ARG A 302      29.458  13.803  39.336  1.000  50.62
ATOM   2312  NH1  ARG A 302      28.871  14.992  39.398  1.000  51.05
ATOM   2313  NH2  ARG A 302      29.264  12.909  40.297  1.000  48.05
ATOM   2314  C    ARG A 302      30.955  10.852  35.332  1.000  44.54
ATOM   2315  O    ARG A 302      32.162  10.831  35.095  1.000  56.02
ATOM   2316  N    ASP A 303      30.409  10.124  36.305  1.000  44.54
ATOM   2317  CA   ASP A 303      31.292   9.270  37.105  1.000  43.81
ATOM   2318  CB   ASP A 303      30.542   8.705  38.312  1.000  34.49
ATOM   2319  CG   ASP A 303      30.053   9.823  39.215  1.000  37.57
ATOM   2320  OD1  ASP A 303      30.540  10.963  39.057  1.000  52.86
ATOM   2321  OD2  ASP A 303      29.183   9.594  40.078  1.000  46.64
ATOM   2322  C    ASP A 303      31.889   8.163  36.248  1.000  48.14
```

FIGURE 51

```
ATOM   2323  O    ASP A 303      33.015   7.724  36.489  1.000  65.82
ATOM   2324  N    VAL A 304      31.151   7.703  35.241  1.000  50.71
ATOM   2325  CA   VAL A 304      31.668   6.631  34.389  1.000  49.88
ATOM   2326  CB   VAL A 304      30.541   5.917  33.628  1.000  51.23
ATOM   2327  CG1  VAL A 304      30.871   5.761  32.150  1.000  50.73
ATOM   2328  CG2  VAL A 304      30.277   4.561  34.263  1.000  34.30
ATOM   2329  C    VAL A 304      32.697   7.175  33.404  1.000  41.63
ATOM   2330  O    VAL A 304      33.656   6.498  33.037  1.000  41.23
ATOM   2331  N    LEU A 305      32.489   8.413  32.981  1.000  46.33
ATOM   2332  CA   LEU A 305      33.442   9.091  32.106  1.000  57.09
ATOM   2333  CB   LEU A 305      32.783  10.338  31.507  1.000  52.07
ATOM   2334  CG   LEU A 305      31.872  10.008  30.314  1.000  47.93
ATOM   2335  CD1  LEU A 305      31.630  11.216  29.427  1.000  48.09
ATOM   2336  CD2  LEU A 305      32.488   8.860  29.529  1.000  30.69
ATOM   2337  C    LEU A 305      34.728   9.439  32.849  1.000  64.87
ATOM   2338  O    LEU A 305      35.814   9.387  32.266  1.000  58.87
ATOM   2339  N    ARG A 306      34.601   9.776  34.127  1.000  68.65
ATOM   2340  CA   ARG A 306      35.714  10.014  35.032  1.000  66.90
ATOM   2341  CB   ARG A 306      35.210  10.407  36.420  1.000  62.97
ATOM   2342  CG   ARG A 306      34.909  11.889  36.584  1.000  63.46
ATOM   2343  CD   ARG A 306      34.233  12.132  37.927  1.000  63.67
ATOM   2344  NE   ARG A 306      33.867  13.537  38.091  1.000  72.26
ATOM   2345  CZ   ARG A 306      33.178  13.982  39.131  1.000  81.44
ATOM   2346  NH1  ARG A 306      32.786  13.132  40.074  1.000  88.77
ATOM   2347  NH2  ARG A 306      32.874  15.266  39.234  1.000  94.65
ATOM   2348  C    ARG A 306      36.601   8.773  35.157  1.000  69.05
ATOM   2349  O    ARG A 306      37.722   8.751  34.650  1.000  60.08
ATOM   2350  N    ALA A 307      36.073   7.760  35.834  1.000  70.13
ATOM   2351  CA   ALA A 307      36.735   6.475  36.013  1.000  72.89
ATOM   2352  CB   ALA A 307      35.766   5.449  36.576  1.000  79.56
ATOM   2353  C    ALA A 307      37.324   5.984  34.694  1.000  75.87
ATOM   2354  O    ALA A 307      38.449   5.491  34.642  1.000  86.48
ATOM   2355  N    ARG A 308      36.535   6.146  33.635  1.000  72.53
ATOM   2356  CA   ARG A 308      36.980   5.843  32.285  1.000  71.87
ATOM   2357  CB   ARG A 308      35.954   6.318  31.260  1.000  72.41
ATOM   2358  CG   ARG A 308      35.892   5.489  29.991  1.000  75.31
ATOM   2359  CD   ARG A 308      34.468   5.480  29.453  1.000  81.76
ATOM   2360  NE   ARG A 308      34.286   4.508  28.381  1.000  82.26
ATOM   2361  CZ   ARG A 308      33.963   4.835  27.136  1.000  81.15
ATOM   2362  NH1  ARG A 308      33.794   6.106  26.802  1.000  66.44
ATOM   2363  NH2  ARG A 308      33.818   3.879  26.222  1.000  98.94
ATOM   2364  C    ARG A 308      38.316   6.522  31.997  1.000  79.31
ATOM   2365  O    ARG A 308      39.323   6.227  32.636  1.000  93.34
ATOM   2366  N    LYS A 309      38.277   7.433  31.039  1.000  83.39
ATOM   2367  CA   LYS A 309      39.434   8.214  30.626  1.000  85.77
ATOM   2368  CB   LYS A 309      39.029   9.196  29.532  1.000  85.52
ATOM   2369  CG   LYS A 309      37.652   8.903  28.934  1.000  85.90
ATOM   2370  CD   LYS A 309      36.903  10.189  28.611  1.000  87.13
ATOM   2371  CE   LYS A 309      37.828  11.241  28.041  1.000  90.18
ATOM   2372  NZ   LYS A 309      37.294  11.834  26.782  1.000  95.87
ATOM   2373  C    LYS A 309      40.045   8.948  31.819  1.000  88.05
ATOM   2374  O    LYS A 309      39.829  10.143  32.007  1.000  83.82
```

FIGURE 52

```
ATOM   2375  N    LEU A 310      40.812    8.199   32.602  1.000 91.25
ATOM   2376  CA   LEU A 310      41.488    8.642   33.803  1.000 89.65
ATOM   2377  CB   LEU A 310      40.575    8.511   35.031  1.000 89.61
ATOM   2378  CG   LEU A 310      41.209    8.874   36.375  1.000 91.78
ATOM   2379  CD1  LEU A 310      41.928   10.213   36.280  1.000 97.42
ATOM   2380  CD2  LEU A 310      40.167    8.896   37.476  1.000 97.23
ATOM   2381  C    LEU A 310      42.772    7.848   34.034  1.000 88.08
ATOM   2382  O    LEU A 310      42.708    6.719   34.516  1.000 91.11
ATOM   2383  N    LYS B  19      45.803   11.373   51.943  1.000103.56
ATOM   2384  CA   LYS B  19      45.533   10.011   51.483  1.000 77.94
ATOM   2385  CB   LYS B  19      46.473    9.008   52.147  1.000 82.60
ATOM   2386  CG   LYS B  19      46.882    7.835   51.255  1.000 87.87
ATOM   2387  CD   LYS B  19      48.286    7.354   51.584  1.000 91.26
ATOM   2388  CE   LYS B  19      49.120    7.117   50.329  1.000 90.51
ATOM   2389  NZ   LYS B  19      50.584    7.099   50.628  1.000 76.07
ATOM   2390  C    LYS B  19      44.082    9.614   51.751  1.000 64.77
ATOM   2391  O    LYS B  19      43.153   10.321   51.368  1.000 54.90
ATOM   2392  N    THR B  20      43.927    8.473   52.402  1.000 58.60
ATOM   2393  CA   THR B  20      42.644    7.870   52.709  1.000 50.23
ATOM   2394  CB   THR B  20      42.853    6.643   53.618  1.000 48.19
ATOM   2395  OG1  THR B  20      41.626    6.256   54.241  1.000 67.26
ATOM   2396  CG2  THR B  20      43.824    6.994   54.737  1.000 41.73
ATOM   2397  C    THR B  20      41.695    8.862   53.376  1.000 54.14
ATOM   2398  O    THR B  20      42.126    9.839   53.992  1.000 48.50
ATOM   2399  N    SER B  21      40.407    8.579   53.235  1.000 57.41
ATOM   2400  CA   SER B  21      39.308    9.335   53.812  1.000 54.62
ATOM   2401  CB   SER B  21      39.008   10.562   52.951  1.000 57.73
ATOM   2402  OG   SER B  21      38.000   10.316   51.989  1.000 61.68
ATOM   2403  C    SER B  21      38.071    8.452   53.980  1.000 51.70
ATOM   2404  O    SER B  21      38.044    7.306   53.523  1.000 45.33
ATOM   2405  N    CYS B  22      37.038    8.961   54.640  1.000 48.54
ATOM   2406  CA   CYS B  22      35.824    8.195   54.908  1.000 41.60
ATOM   2407  CB   CYS B  22      35.884    7.524   56.281  1.000 46.98
ATOM   2408  SG   CYS B  22      36.813    5.974   56.365  1.000 93.30
ATOM   2409  C    CYS B  22      34.590    9.082   54.851  1.000 38.62
ATOM   2410  O    CYS B  22      34.027    9.443   55.887  1.000 49.86
ATOM   2411  N    PRO B  23      34.143    9.447   53.659  1.000 47.14
ATOM   2412  CA   PRO B  23      32.954   10.304   53.566  1.000 56.35
ATOM   2413  CB   PRO B  23      32.868   10.652   52.085  1.000 55.14
ATOM   2414  CG   PRO B  23      34.157   10.216   51.473  1.000 48.26
ATOM   2415  CD   PRO B  23      34.680    9.104   52.334  1.000 45.23
ATOM   2416  C    PRO B  23      31.720    9.529   54.021  1.000 59.08
ATOM   2417  O    PRO B  23      31.566    8.358   53.677  1.000 63.26
ATOM   2418  N    ILE B  24      30.856   10.175   54.800  1.000 57.72
ATOM   2419  CA   ILE B  24      29.645    9.515   55.274  1.000 57.66
ATOM   2420  CB   ILE B  24      29.730    9.129   56.761  1.000 61.40
ATOM   2421  CG1  ILE B  24      30.656    7.951   57.048  1.000 63.99
ATOM   2422  CD1  ILE B  24      31.645    8.269   58.170  1.000 72.75
ATOM   2423  CG2  ILE B  24      28.346    8.849   57.336  1.000 55.60
ATOM   2424  C    ILE B  24      28.423   10.404   55.073  1.000 56.32
ATOM   2425  O    ILE B  24      28.463   11.607   55.319  1.000 56.42
ATOM   2426  N    LYS B  25      27.336    9.790   54.618  1.000 60.08
```

FIGURE 53

```
ATOM   2427  CA   LYS B  25      26.083  10.506  54.431  1.000 69.15
ATOM   2428  CB   LYS B  25      24.998   9.583  53.874  1.000 82.75
ATOM   2429  CG   LYS B  25      25.033   9.350  52.369  1.000 85.99
ATOM   2430  CD   LYS B  25      24.777   7.874  52.048  1.000 85.92
ATOM   2431  CE   LYS B  25      26.083   7.172  51.689  1.000 85.44
ATOM   2432  NZ   LYS B  25      26.510   7.499  50.285  1.000 80.54
ATOM   2433  C    LYS B  25      25.604  11.112  55.747  1.000 63.20
ATOM   2434  O    LYS B  25      25.591  10.438  56.783  1.000 50.64
ATOM   2435  N    ILE B  26      25.195  12.378  55.680  1.000 54.67
ATOM   2436  CA   ILE B  26      24.670  13.059  56.860  1.000 55.87
ATOM   2437  CB   ILE B  26      24.575  14.581  56.678  1.000 58.65
ATOM   2438  CG1  ILE B  26      23.569  15.042  55.620  1.000 60.19
ATOM   2439  CD1  ILE B  26      23.370  16.547  55.610  1.000 57.06
ATOM   2440  CG2  ILE B  26      25.953  15.157  56.389  1.000 63.31
ATOM   2441  C    ILE B  26      23.291  12.498  57.214  1.000 58.06
ATOM   2442  O    ILE B  26      22.810  12.724  58.319  1.000 56.98
ATOM   2443  N    ASN B  27      22.730  11.784  56.260  1.000 61.16
ATOM   2444  CA   ASN B  27      21.489  11.049  56.299  1.000 59.75
ATOM   2445  CB   ASN B  27      21.008  10.743  54.876  1.000 63.07
ATOM   2446  CG   ASN B  27      20.656  12.000  54.106  1.000 65.31
ATOM   2447  OD1  ASN B  27      20.305  11.913  52.930  1.000 50.97
ATOM   2448  ND2  ASN B  27      20.748  13.143  54.774  1.000 75.32
ATOM   2449  C    ASN B  27      21.632   9.724  57.040  1.000 57.11
ATOM   2450  O    ASN B  27      20.646   9.183  57.534  1.000 57.56
ATOM   2451  N    GLN B  28      22.856   9.217  57.094  1.000 57.63
ATOM   2452  CA   GLN B  28      23.130   7.930  57.717  1.000 56.91
ATOM   2453  CB   GLN B  28      23.761   6.988  56.678  1.000 64.21
ATOM   2454  CG   GLN B  28      24.000   5.578  57.192  1.000 66.30
ATOM   2455  CD   GLN B  28      22.771   4.698  57.075  1.000 70.95
ATOM   2456  OE1  GLN B  28      22.005   4.829  56.119  1.000 74.56
ATOM   2457  NE2  GLN B  28      22.580   3.801  58.039  1.000 63.57
ATOM   2458  C    GLN B  28      24.053   8.043  58.917  1.000 44.81
ATOM   2459  O    GLN B  28      24.358   7.034  59.556  1.000 48.39
ATOM   2460  N    PHE B  29      24.526   9.244  59.241  1.000 46.88
ATOM   2461  CA   PHE B  29      25.544   9.393  60.273  1.000 36.76
ATOM   2462  CB   PHE B  29      25.849  10.882  60.532  1.000 43.65
ATOM   2463  CG   PHE B  29      27.092  11.033  61.384  1.000 41.38
ATOM   2464  CD1  PHE B  29      28.348  10.939  60.813  1.000 39.51
ATOM   2465  CE1  PHE B  29      29.493  11.073  61.579  1.000 39.09
ATOM   2466  CZ   PHE B  29      29.383  11.303  62.933  1.000 38.33
ATOM   2467  CE2  PHE B  29      28.131  11.392  63.518  1.000 42.37
ATOM   2468  CD2  PHE B  29      26.995  11.257  62.747  1.000 38.83
ATOM   2469  C    PHE B  29      25.186   8.747  61.601  1.000 37.74
ATOM   2470  O    PHE B  29      26.032   8.087  62.213  1.000 43.72
ATOM   2471  N    GLU B  30      23.960   8.933  62.080  1.000 45.93
ATOM   2472  CA   GLU B  30      23.554   8.292  63.331  1.000 49.96
ATOM   2473  CB   GLU B  30      22.082   8.589  63.614  1.000 61.18
ATOM   2474  CG   GLU B  30      21.655   8.277  65.041  1.000 72.30
ATOM   2475  CD   GLU B  30      22.517   8.965  66.069  1.000 84.23
ATOM   2476  OE1  GLU B  30      23.748   8.742  66.082  1.000104.41
ATOM   2477  OE2  GLU B  30      21.962   9.740  66.892  1.000 90.78
ATOM   2478  C    GLU B  30      23.801   6.785  63.292  1.000 53.76
```

FIGURE 54

```
ATOM   2479  O    GLU B  30      24.396   6.207  64.208  1.000 40.13
ATOM   2480  N    GLY B  31      23.348   6.160  62.207  1.000 50.11
ATOM   2481  CA   GLY B  31      23.552   4.743  61.979  1.000 39.81
ATOM   2482  C    GLY B  31      25.024   4.352  61.975  1.000 42.21
ATOM   2483  O    GLY B  31      25.429   3.569  62.841  1.000 48.72
ATOM   2484  N    HIS B  32      25.786   4.891  61.027  1.000 44.34
ATOM   2485  CA   HIS B  32      27.227   4.682  60.898  1.000 44.47
ATOM   2486  CB   HIS B  32      27.848   5.622  59.865  1.000 46.08
ATOM   2487  CG   HIS B  32      29.339   5.758  59.929  1.000 57.10
ATOM   2488  ND1  HIS B  32      30.199   4.924  59.241  1.000 54.47
ATOM   2489  CE1  HIS B  32      31.451   5.291  59.477  1.000 52.58
ATOM   2490  NE2  HIS B  32      31.440   6.328  60.296  1.000 49.52
ATOM   2491  CD2  HIS B  32      30.140   6.650  60.573  1.000 56.38
ATOM   2492  C    HIS B  32      27.916   4.872  62.244  1.000 43.34
ATOM   2493  O    HIS B  32      28.702   4.051  62.710  1.000 44.29
ATOM   2494  N    PHE B  33      27.608   6.001  62.884  1.000 42.64
ATOM   2495  CA   PHE B  33      28.186   6.230  64.209  1.000 46.60
ATOM   2496  CB   PHE B  33      27.794   7.621  64.705  1.000 45.66
ATOM   2497  CG   PHE B  33      28.411   8.010  66.024  1.000 41.60
ATOM   2498  CD1  PHE B  33      29.639   7.503  66.418  1.000 28.55
ATOM   2499  CE1  PHE B  33      30.180   7.856  67.635  1.000 34.17
ATOM   2500  CZ   PHE B  33      29.502   8.729  68.464  1.000 39.16
ATOM   2501  CE2  PHE B  33      28.282   9.249  68.088  1.000 40.43
ATOM   2502  CD2  PHE B  33      27.743   8.885  66.871  1.000 46.28
ATOM   2503  C    PHE B  33      27.742   5.122  65.157  1.000 49.56
ATOM   2504  O    PHE B  33      28.543   4.568  65.918  1.000 39.50
ATOM   2505  N    MET B  34      26.451   4.782  65.110  1.000 53.61
ATOM   2506  CA   MET B  34      25.979   3.673  65.946  1.000 51.72
ATOM   2507  CB   MET B  34      24.456   3.545  65.882  1.000 51.72
ATOM   2508  CG   MET B  34      23.750   4.565  66.777  1.000 52.01
ATOM   2509  SD   MET B  34      22.105   4.050  67.305  1.000 72.48
ATOM   2510  CE   MET B  34      21.721   2.817  66.063  1.000 45.79
ATOM   2511  C    MET B  34      26.671   2.377  65.554  1.000 52.65
ATOM   2512  O    MET B  34      27.064   1.601  66.433  1.000 63.08
ATOM   2513  N    LYS B  35      26.862   2.114  64.258  1.000 52.00
ATOM   2514  CA   LYS B  35      27.584   0.889  63.905  1.000 54.31
ATOM   2515  CB   LYS B  35      27.570   0.627  62.402  1.000 59.44
ATOM   2516  CG   LYS B  35      26.633   1.515  61.614  1.000 66.12
ATOM   2517  CD   LYS B  35      26.520   1.074  60.166  1.000 69.40
ATOM   2518  CE   LYS B  35      25.639   2.012  59.351  1.000 62.69
ATOM   2519  NZ   LYS B  35      26.251   2.293  58.019  1.000 48.67
ATOM   2520  C    LYS B  35      29.028   0.951  64.404  1.000 56.64
ATOM   2521  O    LYS B  35      29.607  -0.094  64.699  1.000 47.38
ATOM   2522  N    LEU B  36      29.564   2.163  64.485  1.000 61.24
ATOM   2523  CA   LEU B  36      30.933   2.424  64.902  1.000 59.97
ATOM   2524  CB   LEU B  36      31.323   3.874  64.594  1.000 64.56
ATOM   2525  CG   LEU B  36      32.434   4.056  63.557  1.000 65.01
ATOM   2526  CD1  LEU B  36      32.294   3.032  62.440  1.000 65.86
ATOM   2527  CD2  LEU B  36      32.421   5.477  63.006  1.000 46.61
ATOM   2528  C    LEU B  36      31.155   2.157  66.385  1.000 58.41
ATOM   2529  O    LEU B  36      32.238   1.731  66.790  1.000 42.70
ATOM   2530  N    GLN B  37      30.143   2.412  67.207  1.000 64.59
```

FIGURE 55

```
ATOM   2531  CA  GLN B  37      30.253   2.093  68.627  1.000 66.89
ATOM   2532  CB  GLN B  37      29.379   3.009  69.479  1.000 65.39
ATOM   2533  CG  GLN B  37      29.268   4.435  68.963  1.000 71.01
ATOM   2534  CD  GLN B  37      29.402   5.459  70.075  1.000 69.30
ATOM   2535  OE1 GLN B  37      28.554   6.349  70.194  1.000 65.62
ATOM   2536  NE2 GLN B  37      30.448   5.336  70.883  1.000 67.63
ATOM   2537  C   GLN B  37      29.858   0.639  68.887  1.000 64.12
ATOM   2538  O   GLN B  37      30.133   0.109  69.965  1.000 61.41
ATOM   2539  N   ALA B  38      29.211   0.013  67.912  1.000 61.52
ATOM   2540  CA  ALA B  38      28.752  -1.364  68.068  1.000 61.79
ATOM   2541  CB  ALA B  38      27.973  -1.811  66.843  1.000 61.12
ATOM   2542  C   ALA B  38      29.924  -2.304  68.328  1.000 71.64
ATOM   2543  O   ALA B  38      31.070  -1.992  68.000  1.000 88.33
ATOM   2544  N   ASP B  39      29.627  -3.453  68.927  1.000 75.20
ATOM   2545  CA  ASP B  39      30.678  -4.382  69.332  1.000 79.52
ATOM   2546  CB  ASP B  39      31.399  -4.960  68.119  1.000 83.70
ATOM   2547  CG  ASP B  39      31.928  -6.362  68.329  1.000 85.54
ATOM   2548  OD1 ASP B  39      33.151  -6.572  68.165  1.000 77.07
ATOM   2549  OD2 ASP B  39      31.125  -7.261  68.656  1.000 94.95
ATOM   2550  C   ASP B  39      31.654  -3.661  70.262  1.000 80.16
ATOM   2551  O   ASP B  39      32.866  -3.844  70.171  1.000 82.76
ATOM   2552  N   SER B  40      31.091  -2.847  71.149  1.000 80.57
ATOM   2553  CA  SER B  40      31.845  -2.060  72.117  1.000 88.50
ATOM   2554  CB  SER B  40      32.474  -2.960  73.184  1.000 94.68
ATOM   2555  OG  SER B  40      32.154  -2.503  74.493  1.000104.32
ATOM   2556  C   SER B  40      32.923  -1.227  71.430  1.000 88.12
ATOM   2557  O   SER B  40      34.120  -1.492  71.558  1.000101.21
ATOM   2558  N   ASN B  41      32.493  -0.212  70.685  1.000 79.40
ATOM   2559  CA  ASN B  41      33.401   0.680  69.978  1.000 77.46
ATOM   2560  CB  ASN B  41      34.193   1.538  70.973  1.000 73.13
ATOM   2561  CG  ASN B  41      33.910   3.013  70.761  1.000 66.31
ATOM   2562  OD1 ASN B  41      32.852   3.359  70.237  1.000 66.52
ATOM   2563  ND2 ASN B  41      34.853   3.853  71.161  1.000 67.42
ATOM   2564  C   ASN B  41      34.370  -0.080  69.091  1.000 78.31
ATOM   2565  O   ASN B  41      35.499   0.345  68.837  1.000 79.80
ATOM   2566  N   TYR B  42      33.919  -1.239  68.605  1.000 74.28
ATOM   2567  CA  TYR B  42      34.837  -2.034  67.800  1.000 72.73
ATOM   2568  CB  TYR B  42      34.211  -3.377  67.423  1.000 73.56
ATOM   2569  CG  TYR B  42      35.147  -4.228  66.588  1.000 73.21
ATOM   2570  CD1 TYR B  42      36.311  -4.738  67.144  1.000 77.06
ATOM   2571  CE1 TYR B  42      37.173  -5.514  66.388  1.000 78.96
ATOM   2572  CZ  TYR B  42      36.872  -5.773  65.067  1.000 78.31
ATOM   2573  OH  TYR B  42      37.729  -6.541  64.312  1.000 91.83
ATOM   2574  CE2 TYR B  42      35.724  -5.272  64.492  1.000 73.89
ATOM   2575  CD2 TYR B  42      34.868  -4.501  65.256  1.000 72.17
ATOM   2576  C   TYR B  42      35.257  -1.247  66.561  1.000 64.17
ATOM   2577  O   TYR B  42      36.414  -0.843  66.456  1.000 62.76
ATOM   2578  N   LEU B  43      34.312  -1.041  65.653  1.000 59.26
ATOM   2579  CA  LEU B  43      34.589  -0.428  64.362  1.000 59.76
ATOM   2580  CB  LEU B  43      33.310  -0.304  63.528  1.000 63.25
ATOM   2581  CG  LEU B  43      32.890  -1.570  62.775  1.000 63.42
ATOM   2582  CD1 LEU B  43      31.436  -1.480  62.336  1.000 46.05
```

FIGURE 56

```
ATOM   2583  CD2 LEU B  43      33.807  -1.812  61.585 1.000 76.10
ATOM   2584  C   LEU B  43      35.252   0.932  64.522 1.000 54.62
ATOM   2585  O   LEU B  43      36.208   1.237  63.810 1.000 53.46
ATOM   2586  N   LEU B  44      34.760   1.742  65.454 1.000 56.15
ATOM   2587  CA  LEU B  44      35.409   3.030  65.682 1.000 52.24
ATOM   2588  CB  LEU B  44      34.729   3.785  66.826 1.000 48.36
ATOM   2589  CG  LEU B  44      35.293   5.195  67.068 1.000 49.68
ATOM   2590  CD1 LEU B  44      35.267   6.017  65.787 1.000 41.86
ATOM   2591  CD2 LEU B  44      34.522   5.886  68.170 1.000 38.98
ATOM   2592  C   LEU B  44      36.898   2.865  65.975 1.000 48.68
ATOM   2593  O   LEU B  44      37.732   3.549  65.378 1.000 45.89
ATOM   2594  N   SER B  45      37.242   1.962  66.882 1.000 49.23
ATOM   2595  CA  SER B  45      38.619   1.713  67.282 1.000 39.06
ATOM   2596  CB  SER B  45      38.690   0.436  68.127 1.000 39.80
ATOM   2597  OG  SER B  45      39.247   0.727  69.398 1.000 49.93
ATOM   2598  C   SER B  45      39.558   1.552  66.098 1.000 45.56
ATOM   2599  O   SER B  45      40.668   2.082  66.083 1.000 52.78
ATOM   2600  N   LYS B  46      39.087   0.795  65.113 1.000 51.54
ATOM   2601  CA  LYS B  46      39.891   0.470  63.941 1.000 63.73
ATOM   2602  CB  LYS B  46      39.189  -0.575  63.073 1.000 74.89
ATOM   2603  CG  LYS B  46      39.589  -2.009  63.395 1.000 86.82
ATOM   2604  CD  LYS B  46      39.920  -2.808  62.129 1.000 98.47
ATOM   2605  CE  LYS B  46      40.285  -4.250  62.467 1.000105.16
ATOM   2606  NZ  LYS B  46      39.701  -5.221  61.446 1.000118.97
ATOM   2607  C   LYS B  46      40.196   1.720  63.115 1.000 64.75
ATOM   2608  O   LYS B  46      41.369   2.039  62.917 1.000 80.74
ATOM   2609  N   GLU B  47      39.144   2.386  62.661 1.000 60.32
ATOM   2610  CA  GLU B  47      39.214   3.608  61.876 1.000 57.31
ATOM   2611  CB  GLU B  47      37.861   4.317  61.829 1.000 59.96
ATOM   2612  CG  GLU B  47      37.108   4.262  60.513 1.000 64.86
ATOM   2613  CD  GLU B  47      36.069   5.368  60.394 1.000 62.05
ATOM   2614  OE1 GLU B  47      35.086   5.213  59.637 1.000 43.75
ATOM   2615  OE2 GLU B  47      36.243   6.408  61.066 1.000 56.16
ATOM   2616  C   GLU B  47      40.261   4.566  62.445 1.000 52.08
ATOM   2617  O   GLU B  47      40.973   5.207  61.673 1.000 46.49
ATOM   2618  N   TYR B  48      40.331   4.643  63.772 1.000 51.35
ATOM   2619  CA  TYR B  48      41.241   5.559  64.447 1.000 47.41
ATOM   2620  CB  TYR B  48      40.768   5.841  65.876 1.000 43.35
ATOM   2621  CG  TYR B  48      41.664   6.800  66.628 1.000 43.06
ATOM   2622  CD1 TYR B  48      41.634   8.162  66.350 1.000 43.39
ATOM   2623  CE1 TYR B  48      42.446   9.049  67.026 1.000 33.55
ATOM   2624  CZ  TYR B  48      43.301   8.577  67.997 1.000 33.43
ATOM   2625  OH  TYR B  48      44.109   9.457  68.675 1.000 39.28
ATOM   2626  CE2 TYR B  48      43.357   7.232  68.299 1.000 35.45
ATOM   2627  CD2 TYR B  48      42.538   6.354  67.609 1.000 39.88
ATOM   2628  C   TYR B  48      42.666   5.026  64.486 1.000 44.84
ATOM   2629  O   TYR B  48      43.636   5.779  64.556 1.000 38.45
ATOM   2630  N   GLU B  49      42.798   3.704  64.448 1.000 45.22
ATOM   2631  CA  GLU B  49      44.131   3.103  64.459 1.000 46.18
ATOM   2632  CB  GLU B  49      44.027   1.636  64.889 1.000 60.64
ATOM   2633  CG  GLU B  49      43.562   1.476  66.331 1.000 71.11
ATOM   2634  CD  GLU B  49      44.096   2.572  67.234 1.000 79.66
```

FIGURE 57

```
ATOM   2635  OE1 GLU B  49      43.360   2.978  68.161  1.000  77.35
ATOM   2636  OE2 GLU B  49      45.242   3.035  67.029  1.000  85.01
ATOM   2637  C   GLU B  49      44.790   3.234  63.097  1.000  39.20
ATOM   2638  O   GLU B  49      46.009   3.355  62.975  1.000  46.67
ATOM   2639  N   GLU B  50      43.971   3.230  62.044  1.000  35.49
ATOM   2640  CA  GLU B  50      44.513   3.352  60.694  1.000  43.74
ATOM   2641  CB  GLU B  50      43.412   3.174  59.644  1.000  53.39
ATOM   2642  CG  GLU B  50      42.601   1.900  59.756  1.000  64.71
ATOM   2643  CD  GLU B  50      41.686   1.654  58.577  1.000  72.97
ATOM   2644  OE1 GLU B  50      41.888   0.646  57.858  1.000  85.76
ATOM   2645  OE2 GLU B  50      40.752   2.456  58.346  1.000  70.73
ATOM   2646  C   GLU B  50      45.205   4.698  60.485  1.000  41.38
ATOM   2647  O   GLU B  50      45.975   4.860  59.534  1.000  49.75
ATOM   2648  N   LEU B  51      44.932   5.664  61.354  1.000  32.56
ATOM   2649  CA  LEU B  51      45.542   6.982  61.247  1.000  33.23
ATOM   2650  CB  LEU B  51      44.611   8.073  61.767  1.000  28.37
ATOM   2651  CG  LEU B  51      43.377   8.384  60.920  1.000  34.19
ATOM   2652  CD1 LEU B  51      42.246   8.901  61.799  1.000  37.25
ATOM   2653  CD2 LEU B  51      43.720   9.389  59.828  1.000  48.43
ATOM   2654  C   LEU B  51      46.840   7.056  62.042  1.000  38.45
ATOM   2655  O   LEU B  51      47.503   8.091  62.030  1.000  31.93
ATOM   2656  N   LYS B  52      47.146   5.957  62.721  1.000  40.28
ATOM   2657  CA  LYS B  52      48.274   5.912  63.641  1.000  42.24
ATOM   2658  CB  LYS B  52      48.513   4.470  64.104  1.000  40.97
ATOM   2659  CG  LYS B  52      49.510   4.333  65.238  1.000  42.39
ATOM   2660  CD  LYS B  52      49.041   3.361  66.306  1.000  52.34
ATOM   2661  CE  LYS B  52      49.390   3.867  67.700  1.000  61.04
ATOM   2662  NZ  LYS B  52      50.844   4.180  67.830  1.000  76.71
ATOM   2663  C   LYS B  52      49.556   6.482  63.033  1.000  42.33
ATOM   2664  O   LYS B  52      50.231   7.281  63.679  1.000  51.51
ATOM   2665  N   ASP B  53      49.860   6.073  61.826  1.000  38.71
ATOM   2666  CA  ASP B  53      51.069   6.209  61.057  1.000  45.09
ATOM   2667  CB  ASP B  53      51.162   5.010  60.082  1.000  50.29
ATOM   2668  CG  ASP B  53      49.852   4.773  59.352  1.000  58.20
ATOM   2669  OD1 ASP B  53      48.816   4.532  60.008  1.000  47.71
ATOM   2670  OD2 ASP B  53      49.828   4.823  58.101  1.000  71.83
ATOM   2671  C   ASP B  53      51.159   7.483  60.225  1.000  42.44
ATOM   2672  O   ASP B  53      52.242   7.872  59.785  1.000  38.32
ATOM   2673  N   VAL B  54      50.014   8.111  59.996  1.000  33.25
ATOM   2674  CA  VAL B  54      49.943   9.247  59.080  1.000  30.88
ATOM   2675  CB  VAL B  54      48.498   9.764  58.989  1.000  35.26
ATOM   2676  CG1 VAL B  54      48.409  11.060  58.194  1.000  24.09
ATOM   2677  CG2 VAL B  54      47.599   8.696  58.361  1.000  22.83
ATOM   2678  C   VAL B  54      50.917  10.340  59.504  1.000  32.17
ATOM   2679  O   VAL B  54      50.929  10.809  60.638  1.000  25.64
ATOM   2680  N   GLY B  55      51.766  10.722  58.562  1.000  36.64
ATOM   2681  CA  GLY B  55      52.749  11.767  58.654  1.000  34.77
ATOM   2682  C   GLY B  55      53.995  11.423  59.430  1.000  30.37
ATOM   2683  O   GLY B  55      54.923  12.232  59.538  1.000  25.00
ATOM   2684  N   ARG B  56      54.036  10.221  60.001  1.000  27.19
ATOM   2685  CA  ARG B  56      55.133   9.904  60.919  1.000  34.78
ATOM   2686  CB  ARG B  56      54.724   8.753  61.847  1.000  36.03
```

FIGURE 58

```
ATOM   2687  CG   ARG B  56      53.643   9.120  62.851  1.000  31.22
ATOM   2688  CD   ARG B  56      54.128  10.152  63.853  1.000  34.70
ATOM   2689  NE   ARG B  56      53.193  10.340  64.954  1.000  46.39
ATOM   2690  CZ   ARG B  56      53.205   9.786  66.155  1.000  39.08
ATOM   2691  NH1  ARG B  56      54.165   8.935  66.471  1.000  26.47
ATOM   2692  NH2  ARG B  56      52.270  10.066  67.063  1.000  33.87
ATOM   2693  C    ARG B  56      56.425   9.574  60.187  1.000  37.74
ATOM   2694  O    ARG B  56      57.415   9.186  60.808  1.000  41.64
ATOM   2695  N    ASN B  57      56.415   9.743  58.871  1.000  41.17
ATOM   2696  CA   ASN B  57      57.583   9.563  58.028  1.000  38.70
ATOM   2697  CB   ASN B  57      57.146   9.244  56.587  1.000  42.33
ATOM   2698  CG   ASN B  57      56.145  10.235  56.026  1.000  38.45
ATOM   2699  OD1  ASN B  57      55.184  10.631  56.689  1.000  47.13
ATOM   2700  ND2  ASN B  57      56.334  10.662  54.780  1.000  33.73
ATOM   2701  C    ASN B  57      58.478  10.794  58.001  1.000  32.39
ATOM   2702  O    ASN B  57      59.628  10.706  57.573  1.000  32.15
ATOM   2703  N    GLN B  58      57.985  11.955  58.419  1.000  33.50
ATOM   2704  CA   GLN B  58      58.765  13.190  58.281  1.000  32.36
ATOM   2705  CB   GLN B  58      57.838  14.389  58.063  1.000  31.34
ATOM   2706  CG   GLN B  58      57.016  14.302  56.782  1.000  22.41
ATOM   2707  CD   GLN B  58      55.700  15.058  56.891  1.000  23.88
ATOM   2708  OE1  GLN B  58      54.809  14.711  57.668  1.000  33.63
ATOM   2709  NE2  GLN B  58      55.545  16.114  56.113  1.000  22.62
ATOM   2710  C    GLN B  58      59.652  13.445  59.490  1.000  25.07
ATOM   2711  O    GLN B  58      59.327  13.045  60.608  1.000  29.18
ATOM   2712  N    SER B  59      60.773  14.121  59.261  1.000  17.59
ATOM   2713  CA   SER B  59      61.737  14.383  60.317  1.000  24.95
ATOM   2714  CB   SER B  59      63.157  14.310  59.752  1.000  30.84
ATOM   2715  OG   SER B  59      63.355  15.365  58.819  1.000  51.69
ATOM   2716  C    SER B  59      61.503  15.745  60.971  1.000  27.35
ATOM   2717  O    SER B  59      60.751  16.555  60.421  1.000  26.25
ATOM   2718  N    CYS B  60      62.142  15.962  62.108  1.000  20.52
ATOM   2719  CA   CYS B  60      62.088  17.174  62.901  1.000  25.62
ATOM   2720  CB   CYS B  60      61.291  16.938  64.187  1.000  32.28
ATOM   2721  SG   CYS B  60      59.563  16.490  63.935  1.000  44.06
ATOM   2722  C    CYS B  60      63.483  17.658  63.294  1.000  26.82
ATOM   2723  O    CYS B  60      63.697  17.986  64.466  1.000  32.10
ATOM   2724  N    ASP B  61      64.399  17.692  62.342  1.000  27.28
ATOM   2725  CA   ASP B  61      65.796  18.026  62.568  1.000  27.04
ATOM   2726  CB   ASP B  61      66.567  17.889  61.242  1.000  38.19
ATOM   2727  CG   ASP B  61      66.412  16.519  60.605  1.000  50.13
ATOM   2728  OD1  ASP B  61      66.494  15.504  61.335  1.000  46.12
ATOM   2729  OD2  ASP B  61      66.204  16.442  59.370  1.000  33.84
ATOM   2730  C    ASP B  61      66.010  19.431  63.103  1.000  25.10
ATOM   2731  O    ASP B  61      66.821  19.666  63.995  1.000  32.03
ATOM   2732  N    ILE B  62      65.315  20.420  62.536  1.000  31.05
ATOM   2733  CA   ILE B  62      65.582  21.807  62.924  1.000  30.27
ATOM   2734  CB   ILE B  62      64.816  22.824  62.061  1.000  30.17
ATOM   2735  CG1  ILE B  62      65.175  22.724  60.577  1.000  33.67
ATOM   2736  CD1  ILE B  62      66.676  22.691  60.345  1.000  39.64
ATOM   2737  CG2  ILE B  62      65.010  24.244  62.584  1.000  21.41
ATOM   2738  C    ILE B  62      65.202  22.019  64.382  1.000  32.48
```

FIGURE 59

| | | | | | | | | | |
|---|---|---|---|---|---|---|---|---|---|
| ATOM | 2739 | O | ILE | B | 62 | 65.907 | 22.658 | 65.156 | 1.000 29.08 |
| ATOM | 2740 | N | ALA | B | 63 | 64.048 | 21.444 | 64.738 | 1.000 26.00 |
| ATOM | 2741 | CA | ALA | B | 63 | 63.649 | 21.631 | 66.136 | 1.000 26.52 |
| ATOM | 2742 | CB | ALA | B | 63 | 62.232 | 21.116 | 66.313 | 1.000 16.06 |
| ATOM | 2743 | C | ALA | B | 63 | 64.643 | 20.948 | 67.058 | 1.000 26.00 |
| ATOM | 2744 | O | ALA | B | 63 | 64.789 | 21.266 | 68.235 | 1.000 32.44 |
| ATOM | 2745 | N | LEU | B | 64 | 65.380 | 19.963 | 66.558 | 1.000 29.22 |
| ATOM | 2746 | CA | LEU | B | 64 | 66.274 | 19.228 | 67.458 | 1.000 36.10 |
| ATOM | 2747 | CB | LEU | B | 64 | 66.389 | 17.787 | 66.957 | 1.000 34.83 |
| ATOM | 2748 | CG | LEU | B | 64 | 65.227 | 16.867 | 67.351 | 1.000 34.44 |
| ATOM | 2749 | CD1 | LEU | B | 64 | 65.292 | 15.577 | 66.547 | 1.000 29.17 |
| ATOM | 2750 | CD2 | LEU | B | 64 | 65.242 | 16.616 | 68.853 | 1.000 22.34 |
| ATOM | 2751 | C | LEU | B | 64 | 67.641 | 19.880 | 67.584 | 1.000 38.72 |
| ATOM | 2752 | O | LEU | B | 64 | 68.466 | 19.505 | 68.423 | 1.000 33.43 |
| ATOM | 2753 | N | LEU | B | 65 | 67.910 | 20.882 | 66.752 | 1.000 29.69 |
| ATOM | 2754 | CA | LEU | B | 65 | 69.194 | 21.567 | 66.816 | 1.000 24.50 |
| ATOM | 2755 | CB | LEU | B | 65 | 69.248 | 22.693 | 65.788 | 1.000 23.85 |
| ATOM | 2756 | CG | LEU | B | 65 | 69.163 | 22.287 | 64.320 | 1.000 39.84 |
| ATOM | 2757 | CD1 | LEU | B | 65 | 68.898 | 23.516 | 63.459 | 1.000 38.18 |
| ATOM | 2758 | CD2 | LEU | B | 65 | 70.432 | 21.567 | 63.880 | 1.000 36.27 |
| ATOM | 2759 | C | LEU | B | 65 | 69.438 | 22.122 | 68.218 | 1.000 36.38 |
| ATOM | 2760 | O | LEU | B | 65 | 68.526 | 22.606 | 68.883 | 1.000 40.63 |
| ATOM | 2761 | N | PRO | B | 66 | 70.686 | 22.026 | 68.657 | 1.000 45.15 |
| ATOM | 2762 | CA | PRO | B | 66 | 71.066 | 22.422 | 70.011 | 1.000 54.26 |
| ATOM | 2763 | CB | PRO | B | 66 | 72.601 | 22.452 | 69.931 | 1.000 52.68 |
| ATOM | 2764 | CG | PRO | B | 66 | 72.910 | 21.394 | 68.918 | 1.000 46.70 |
| ATOM | 2765 | CD | PRO | B | 66 | 71.831 | 21.512 | 67.881 | 1.000 44.93 |
| ATOM | 2766 | C | PRO | B | 66 | 70.553 | 23.796 | 70.415 | 1.000 50.86 |
| ATOM | 2767 | O | PRO | B | 66 | 70.105 | 23.966 | 71.552 | 1.000 48.53 |
| ATOM | 2768 | N | GLU | B | 67 | 70.616 | 24.767 | 69.510 | 1.000 51.81 |
| ATOM | 2769 | CA | GLU | B | 67 | 70.250 | 26.137 | 69.872 | 1.000 51.43 |
| ATOM | 2770 | CB | GLU | B | 67 | 70.880 | 27.124 | 68.885 | 1.000 55.34 |
| ATOM | 2771 | CG | GLU | B | 67 | 71.814 | 28.138 | 69.522 | 1.000 71.70 |
| ATOM | 2772 | CD | GLU | B | 67 | 71.302 | 28.794 | 70.787 | 1.000 77.75 |
| ATOM | 2773 | OE1 | GLU | B | 67 | 72.110 | 28.959 | 71.733 | 1.000 81.38 |
| ATOM | 2774 | OE2 | GLU | B | 67 | 70.109 | 29.159 | 70.864 | 1.000 60.23 |
| ATOM | 2775 | C | GLU | B | 67 | 68.745 | 26.354 | 69.938 | 1.000 46.00 |
| ATOM | 2776 | O | GLU | B | 67 | 68.296 | 27.474 | 70.196 | 1.000 48.84 |
| ATOM | 2777 | N | ASN | B | 68 | 67.944 | 25.314 | 69.711 | 1.000 40.69 |
| ATOM | 2778 | CA | ASN | B | 68 | 66.494 | 25.487 | 69.755 | 1.000 36.03 |
| ATOM | 2779 | CB | ASN | B | 68 | 65.825 | 24.980 | 68.477 | 1.000 39.69 |
| ATOM | 2780 | CG | ASN | B | 68 | 66.147 | 25.780 | 67.233 | 1.000 33.61 |
| ATOM | 2781 | OD1 | ASN | B | 68 | 66.504 | 26.952 | 67.287 | 1.000 31.83 |
| ATOM | 2782 | ND2 | ASN | B | 68 | 66.038 | 25.160 | 66.060 | 1.000 31.89 |
| ATOM | 2783 | C | ASN | B | 68 | 65.914 | 24.759 | 70.964 | 1.000 34.09 |
| ATOM | 2784 | O | ASN | B | 68 | 64.719 | 24.859 | 71.235 | 1.000 47.57 |
| ATOM | 2785 | N | ARG | B | 69 | 66.765 | 24.038 | 71.685 | 1.000 36.03 |
| ATOM | 2786 | CA | ARG | B | 69 | 66.306 | 23.202 | 72.792 | 1.000 41.44 |
| ATOM | 2787 | CB | ARG | B | 69 | 67.483 | 22.545 | 73.522 | 1.000 43.89 |
| ATOM | 2788 | CG | ARG | B | 69 | 67.790 | 21.126 | 73.075 | 1.000 54.59 |
| ATOM | 2789 | CD | ARG | B | 69 | 68.623 | 21.108 | 71.802 | 1.000 63.54 |
| ATOM | 2790 | NE | ARG | B | 69 | 68.602 | 19.813 | 71.126 | 1.000 68.27 |

FIGURE 60

```
ATOM   2791  CZ   ARG B  69      69.645  18.999  71.016  1.000  73.48
ATOM   2792  NH1  ARG B  69      70.812  19.341  71.551  1.000  75.03
ATOM   2793  NH2  ARG B  69      69.536  17.838  70.378  1.000  71.51
ATOM   2794  C    ARG B  69      65.466  23.990  73.787  1.000  37.64
ATOM   2795  O    ARG B  69      64.448  23.486  74.260  1.000  47.56
ATOM   2796  N    GLY B  70      65.885  25.212  74.117  1.000  32.41
ATOM   2797  CA   GLY B  70      65.107  25.974  75.086  1.000  30.87
ATOM   2798  C    GLY B  70      63.789  26.425  74.495  1.000  31.35
ATOM   2799  O    GLY B  70      62.881  26.880  75.183  1.000  32.44
ATOM   2800  N    LYS B  71      63.642  26.301  73.172  1.000  28.40
ATOM   2801  CA   LYS B  71      62.431  26.876  72.579  1.000  23.17
ATOM   2802  CB   LYS B  71      62.809  27.437  71.205  1.000  24.12
ATOM   2803  CG   LYS B  71      63.920  28.476  71.318  1.000  25.57
ATOM   2804  CD   LYS B  71      64.674  28.583  70.010  1.000  30.17
ATOM   2805  CE   LYS B  71      65.580  29.802  69.994  1.000  37.46
ATOM   2806  NZ   LYS B  71      66.319  29.886  68.700  1.000  51.92
ATOM   2807  C    LYS B  71      61.296  25.876  72.492  1.000  23.16
ATOM   2808  O    LYS B  71      60.205  26.158  71.995  1.000  27.70
ATOM   2809  N    ASN B  72      61.501  24.663  72.997  1.000  19.21
ATOM   2810  CA   ASN B  72      60.414  23.691  72.972  1.000  21.63
ATOM   2811  CB   ASN B  72      60.918  22.370  72.375  1.000  26.16
ATOM   2812  CG   ASN B  72      61.306  22.543  70.916  1.000  31.09
ATOM   2813  OD1  ASN B  72      60.465  22.945  70.109  1.000  26.04
ATOM   2814  ND2  ASN B  72      62.558  22.245  70.577  1.000  24.16
ATOM   2815  C    ASN B  72      59.855  23.481  74.369  1.000  28.90
ATOM   2816  O    ASN B  72      60.603  23.340  75.333  1.000  27.09
ATOM   2817  N    ARG B  73      58.532  23.462  74.504  1.000  29.94
ATOM   2818  CA   ARG B  73      57.950  23.251  75.827  1.000  29.94
ATOM   2819  CB   ARG B  73      56.501  23.738  75.862  1.000  30.13
ATOM   2820  CG   ARG B  73      55.847  23.665  77.239  1.000  26.45
ATOM   2821  CD   ARG B  73      54.393  24.129  77.156  1.000  21.48
ATOM   2822  NE   ARG B  73      54.347  25.597  77.101  1.000  21.98
ATOM   2823  CZ   ARG B  73      54.413  26.305  78.225  1.000  30.47
ATOM   2824  NH1  ARG B  73      54.514  25.676  79.390  1.000  22.83
ATOM   2825  NH2  ARG B  73      54.373  27.624  78.162  1.000  37.96
ATOM   2826  C    ARG B  73      58.047  21.775  76.205  1.000  36.82
ATOM   2827  O    ARG B  73      58.212  21.428  77.375  1.000  27.47
ATOM   2828  N    TYR B  74      57.948  20.904  75.202  1.000  27.29
ATOM   2829  CA   TYR B  74      58.101  19.470  75.416  1.000  24.94
ATOM   2830  CB   TYR B  74      56.774  18.731  75.335  1.000  24.22
ATOM   2831  CG   TYR B  74      55.661  19.265  76.209  1.000  31.66
ATOM   2832  CD1  TYR B  74      55.531  18.876  77.540  1.000  37.63
ATOM   2833  CE1  TYR B  74      54.513  19.366  78.342  1.000  39.66
ATOM   2834  CZ   TYR B  74      53.601  20.258  77.818  1.000  38.75
ATOM   2835  OH   TYR B  74      52.588  20.745  78.608  1.000  34.40
ATOM   2836  CE2  TYR B  74      53.695  20.668  76.503  1.000  25.62
ATOM   2837  CD2  TYR B  74      54.722  20.163  75.724  1.000  27.42
ATOM   2838  C    TYR B  74      59.091  18.944  74.377  1.000  34.07
ATOM   2839  O    TYR B  74      58.878  19.078  73.170  1.000  35.65
ATOM   2840  N    ASN B  75      60.170  18.362  74.871  1.000  32.88
ATOM   2841  CA   ASN B  75      61.260  17.890  74.027  1.000  35.16
ATOM   2842  CB   ASN B  75      62.397  17.415  74.942  1.000  41.15
```

FIGURE 61

```
ATOM  2843  CG   ASN B  75      63.227  18.582  75.448  1.000  49.51
ATOM  2844  OD1  ASN B  75      64.296  18.392  76.032  1.000  62.29
ATOM  2845  ND2  ASN B  75      62.756  19.808  75.230  1.000  47.01
ATOM  2846  C    ASN B  75      60.832  16.813  73.042  1.000  27.77
ATOM  2847  O    ASN B  75      61.544  16.541  72.062  1.000  31.84
ATOM  2848  N    ASN B  76      59.676  16.191  73.248  1.000  24.48
ATOM  2849  CA   ASN B  76      59.194  15.180  72.303  1.000  31.98
ATOM  2850  CB   ASN B  76      58.888  13.857  73.026  1.000  39.45
ATOM  2851  CG   ASN B  76      57.794  14.002  74.065  1.000  36.56
ATOM  2852  OD1  ASN B  76      57.640  15.076  74.643  1.000  29.01
ATOM  2853  ND2  ASN B  76      57.038  12.939  74.311  1.000  28.69
ATOM  2854  C    ASN B  76      57.964  15.646  71.535  1.000  35.01
ATOM  2855  O    ASN B  76      57.304  14.845  70.863  1.000  26.16
ATOM  2856  N    ILE B  77      57.641  16.943  71.608  1.000  28.11
ATOM  2857  CA   ILE B  77      56.567  17.443  70.743  1.000  30.83
ATOM  2858  CB   ILE B  77      55.318  17.839  71.534  1.000  30.03
ATOM  2859  CG1  ILE B  77      54.547  16.646  72.114  1.000  33.86
ATOM  2860  CD1  ILE B  77      53.956  16.931  73.479  1.000  23.65
ATOM  2861  CG2  ILE B  77      54.400  18.697  70.690  1.000  34.46
ATOM  2862  C    ILE B  77      57.078  18.622  69.914  1.000  27.23
ATOM  2863  O    ILE B  77      57.193  19.748  70.388  1.000  22.76
ATOM  2864  N    LEU B  78      57.404  18.308  68.668  1.000  23.21
ATOM  2865  CA   LEU B  78      58.101  19.170  67.741  1.000  24.29
ATOM  2866  CB   LEU B  78      59.571  18.763  67.579  1.000  30.93
ATOM  2867  CG   LEU B  78      60.317  18.344  68.845  1.000  29.39
ATOM  2868  CD1  LEU B  78      61.596  17.606  68.496  1.000  30.84
ATOM  2869  CD2  LEU B  78      60.606  19.563  69.702  1.000  39.96
ATOM  2870  C    LEU B  78      57.477  19.158  66.348  1.000  27.34
ATOM  2871  O    LEU B  78      56.883  18.186  65.883  1.000  22.52
ATOM  2872  N    PRO B  79      57.653  20.300  65.695  1.000  26.68
ATOM  2873  CA   PRO B  79      57.097  20.468  64.351  1.000  19.33
ATOM  2874  CB   PRO B  79      57.244  21.974  64.135  1.000  20.00
ATOM  2875  CG   PRO B  79      58.491  22.309  64.892  1.000  17.51
ATOM  2876  CD   PRO B  79      58.384  21.490  66.156  1.000  17.54
ATOM  2877  C    PRO B  79      57.939  19.691  63.351  1.000  18.83
ATOM  2878  O    PRO B  79      59.161  19.657  63.510  1.000  24.06
ATOM  2879  N    TYR B  80      57.287  19.098  62.367  1.000  18.71
ATOM  2880  CA   TYR B  80      57.911  18.548  61.181  1.000  17.89
ATOM  2881  CB   TYR B  80      56.857  17.886  60.297  1.000  30.40
ATOM  2882  CG   TYR B  80      56.167  16.688  60.900  1.000  29.81
ATOM  2883  CD1  TYR B  80      56.876  15.711  61.589  1.000  27.11
ATOM  2884  CE1  TYR B  80      56.247  14.607  62.147  1.000  26.90
ATOM  2885  CZ   TYR B  80      54.885  14.478  62.004  1.000  27.92
ATOM  2886  OH   TYR B  80      54.233  13.393  62.539  1.000  22.86
ATOM  2887  CE2  TYR B  80      54.162  15.432  61.324  1.000  21.67
ATOM  2888  CD2  TYR B  80      54.794  16.532  60.774  1.000  22.55
ATOM  2889  C    TYR B  80      58.600  19.647  60.373  1.000  26.95
ATOM  2890  O    TYR B  80      58.000  20.703  60.137  1.000  29.85
ATOM  2891  N    ASP B  81      59.836  19.401  59.962  1.000  23.42
ATOM  2892  CA   ASP B  81      60.607  20.320  59.148  1.000  23.41
ATOM  2893  CB   ASP B  81      61.878  19.642  58.613  1.000  34.98
ATOM  2894  CG   ASP B  81      62.914  19.322  59.664  1.000  32.41
```

FIGURE 62

```
ATOM   2895  OD1 ASP B  81      62.951  20.053  60.680  1.000  35.92
ATOM   2896  OD2 ASP B  81      63.686  18.346  59.510  1.000  30.60
ATOM   2897  C   ASP B  81      59.795  20.828  57.959  1.000  25.69
ATOM   2898  O   ASP B  81      59.760  22.011  57.634  1.000  33.08
ATOM   2899  N   ALA B  82      59.122  19.915  57.268  1.000  28.44
ATOM   2900  CA  ALA B  82      58.455  20.249  56.015  1.000  30.21
ATOM   2901  CB  ALA B  82      57.984  18.939  55.373  1.000  26.10
ATOM   2902  C   ALA B  82      57.283  21.200  56.164  1.000  29.54
ATOM   2903  O   ALA B  82      56.790  21.814  55.211  1.000  25.55
ATOM   2904  N   THR B  83      56.753  21.363  57.372  1.000  22.96
ATOM   2905  CA  THR B  83      55.542  22.170  57.495  1.000  22.68
ATOM   2906  CB  THR B  83      54.342  21.270  57.845  1.000  29.40
ATOM   2907  OG1 THR B  83      54.667  20.507  59.014  1.000  20.17
ATOM   2908  CG2 THR B  83      54.087  20.287  56.713  1.000  25.89
ATOM   2909  C   THR B  83      55.677  23.231  58.566  1.000  23.50
ATOM   2910  O   THR B  83      54.681  23.841  58.936  1.000  22.92
ATOM   2911  N   ARG B  84      56.897  23.443  59.056  1.000  25.87
ATOM   2912  CA  ARG B  84      57.050  24.372  60.171  1.000  26.66
ATOM   2913  CB  ARG B  84      58.405  24.149  60.862  1.000  26.13
ATOM   2914  CG  ARG B  84      59.618  24.541  60.040  1.000  22.35
ATOM   2915  CD  ARG B  84      60.929  24.294  60.779  1.000  26.61
ATOM   2916  NE  ARG B  84      62.018  24.933  60.053  1.000  28.50
ATOM   2917  CZ  ARG B  84      62.683  26.031  60.352  1.000  29.24
ATOM   2918  NH1 ARG B  84      62.442  26.754  61.435  1.000  24.43
ATOM   2919  NH2 ARG B  84      63.645  26.433  59.530  1.000  32.59
ATOM   2920  C   ARG B  84      56.890  25.819  59.728  1.000  22.30
ATOM   2921  O   ARG B  84      57.133  26.183  58.583  1.000  23.04
ATOM   2922  N   VAL B  85      56.477  26.663  60.669  1.000  18.94
ATOM   2923  CA  VAL B  85      56.405  28.101  60.424  1.000  21.51
ATOM   2924  CB  VAL B  85      55.322  28.738  61.308  1.000  18.95
ATOM   2925  CG1 VAL B  85      55.256  30.249  61.152  1.000  24.35
ATOM   2926  CG2 VAL B  85      53.967  28.113  60.988  1.000  12.73
ATOM   2927  C   VAL B  85      57.776  28.707  60.699  1.000  25.23
ATOM   2928  O   VAL B  85      58.331  28.435  61.767  1.000  27.46
ATOM   2929  N   LYS B  86      58.320  29.488  59.782  1.000  19.69
ATOM   2930  CA  LYS B  86      59.624  30.120  59.878  1.000  21.25
ATOM   2931  CB  LYS B  86      60.321  30.044  58.509  1.000  26.66
ATOM   2932  CG  LYS B  86      60.905  28.675  58.194  1.000  33.26
ATOM   2933  CD  LYS B  86      60.950  28.412  56.698  1.000  34.06
ATOM   2934  CE  LYS B  86      61.685  27.121  56.377  1.000  41.77
ATOM   2935  NZ  LYS B  86      63.000  27.368  55.715  1.000  51.25
ATOM   2936  C   LYS B  86      59.558  31.584  60.289  1.000  27.93
ATOM   2937  O   LYS B  86      58.723  32.338  59.780  1.000  31.79
ATOM   2938  N   LEU B  87      60.431  32.027  61.194  1.000  31.15
ATOM   2939  CA  LEU B  87      60.507  33.457  61.505  1.000  28.89
ATOM   2940  CB  LEU B  87      61.126  33.736  62.870  1.000  21.77
ATOM   2941  CG  LEU B  87      60.472  33.041  64.066  1.000  30.37
ATOM   2942  CD1 LEU B  87      61.312  33.206  65.321  1.000  35.12
ATOM   2943  CD2 LEU B  87      59.066  33.577  64.279  1.000  22.71
ATOM   2944  C   LEU B  87      61.332  34.163  60.429  1.000  37.83
ATOM   2945  O   LEU B  87      62.297  33.589  59.913  1.000  30.13
ATOM   2946  N   SER B  88      60.944  35.389  60.100  1.000  36.67
```

FIGURE 63

| ATOM | 2947 | CA  | SER B | 88 | 61.678 | 36.147 | 59.095 | 1.000 | 40.88 |
| ATOM | 2948 | CB  | SER B | 88 | 61.145 | 37.572 | 58.969 | 1.000 | 50.96 |
| ATOM | 2949 | OG  | SER B | 88 | 61.924 | 38.447 | 59.787 | 1.000 | 71.49 |
| ATOM | 2950 | C   | SER B | 88 | 63.162 | 36.209 | 59.453 | 1.000 | 53.58 |
| ATOM | 2951 | O   | SER B | 88 | 63.487 | 36.614 | 60.569 | 1.000 | 59.70 |
| ATOM | 2952 | N   | ASN B | 89 | 63.971 | 35.800 | 58.503 | 1.000 | 71.44 |
| ATOM | 2953 | CA  | ASN B | 89 | 65.419 | 35.723 | 58.486 | 1.000 | 85.86 |
| ATOM | 2954 | CB  | ASN B | 89 | 65.871 | 36.099 | 57.064 | 1.000 | 85.53 |
| ATOM | 2955 | CG  | ASN B | 89 | 64.906 | 35.515 | 56.046 | 1.000 | 83.74 |
| ATOM | 2956 | OD1 | ASN B | 89 | 63.714 | 35.820 | 56.022 | 1.000 | 58.06 |
| ATOM | 2957 | ND2 | ASN B | 89 | 65.435 | 34.646 | 55.196 | 1.000 | 94.70 |
| ATOM | 2958 | C   | ASN B | 89 | 66.085 | 36.608 | 59.532 | 1.000 | 95.53 |
| ATOM | 2959 | O   | ASN B | 89 | 66.500 | 37.726 | 59.230 | 1.000 | 106.63 |
| ATOM | 2960 | N   | VAL B | 90 | 66.182 | 36.108 | 60.760 | 1.000 | 99.91 |
| ATOM | 2961 | CA  | VAL B | 90 | 66.604 | 36.863 | 61.925 | 1.000 | 106.49 |
| ATOM | 2962 | CB  | VAL B | 90 | 65.922 | 36.329 | 63.208 | 1.000 | 100.23 |
| ATOM | 2963 | CG1 | VAL B | 90 | 65.594 | 37.484 | 64.140 | 1.000 | 85.61 |
| ATOM | 2964 | CG2 | VAL B | 90 | 64.673 | 35.536 | 62.861 | 1.000 | 93.25 |
| ATOM | 2965 | C   | VAL B | 90 | 68.114 | 36.866 | 62.182 | 1.000 | 113.45 |
| ATOM | 2966 | O   | VAL B | 90 | 68.832 | 35.943 | 61.806 | 1.000 | 122.31 |
| ATOM | 2967 | N   | ASP B | 91 | 68.544 | 37.933 | 62.844 | 1.000 | 114.27 |
| ATOM | 2968 | CA  | ASP B | 91 | 69.897 | 38.277 | 63.228 | 1.000 | 110.66 |
| ATOM | 2969 | CB  | ASP B | 91 | 69.892 | 39.409 | 64.264 | 1.000 | 111.15 |
| ATOM | 2970 | CG  | ASP B | 91 | 71.270 | 40.014 | 64.465 | 1.000 | 110.08 |
| ATOM | 2971 | OD1 | ASP B | 91 | 71.763 | 40.698 | 63.539 | 1.000 | 108.01 |
| ATOM | 2972 | OD2 | ASP B | 91 | 71.864 | 39.800 | 65.540 | 1.000 | 107.80 |
| ATOM | 2973 | C   | ASP B | 91 | 70.667 | 37.090 | 63.802 | 1.000 | 103.90 |
| ATOM | 2974 | O   | ASP B | 91 | 70.062 | 36.112 | 64.251 | 1.000 | 107.40 |
| ATOM | 2975 | N   | ASP B | 92 | 71.989 | 37.191 | 63.769 | 1.000 | 95.56 |
| ATOM | 2976 | CA  | ASP B | 92 | 72.913 | 36.160 | 64.216 | 1.000 | 92.84 |
| ATOM | 2977 | CB  | ASP B | 92 | 72.475 | 35.573 | 65.557 | 1.000 | 96.48 |
| ATOM | 2978 | CG  | ASP B | 92 | 73.473 | 35.776 | 66.676 | 1.000 | 98.09 |
| ATOM | 2979 | OD1 | ASP B | 92 | 73.609 | 34.872 | 67.529 | 1.000 | 84.88 |
| ATOM | 2980 | OD2 | ASP B | 92 | 74.122 | 36.837 | 66.715 | 1.000 | 107.58 |
| ATOM | 2981 | C   | ASP B | 92 | 73.036 | 35.057 | 63.161 | 1.000 | 91.94 |
| ATOM | 2982 | O   | ASP B | 92 | 74.144 | 34.632 | 62.832 | 1.000 | 94.07 |
| ATOM | 2983 | N   | ASP B | 93 | 71.901 | 34.619 | 62.650 | 1.000 | 91.73 |
| ATOM | 2984 | CA  | ASP B | 93 | 71.682 | 33.642 | 61.611 | 1.000 | 95.04 |
| ATOM | 2985 | CB  | ASP B | 93 | 72.393 | 34.073 | 60.319 | 1.000 | 103.17 |
| ATOM | 2986 | CG  | ASP B | 93 | 71.728 | 35.227 | 59.594 | 1.000 | 106.58 |
| ATOM | 2987 | OD1 | ASP B | 93 | 70.954 | 34.993 | 58.638 | 1.000 | 104.63 |
| ATOM | 2988 | OD2 | ASP B | 93 | 71.988 | 36.396 | 59.962 | 1.000 | 107.25 |
| ATOM | 2989 | C   | ASP B | 93 | 72.140 | 32.243 | 62.001 | 1.000 | 91.99 |
| ATOM | 2990 | O   | ASP B | 93 | 72.871 | 31.598 | 61.239 | 1.000 | 105.20 |
| ATOM | 2991 | N   | PRO B | 94 | 71.753 | 31.714 | 63.147 | 1.000 | 86.76 |
| ATOM | 2992 | CA  | PRO B | 94 | 72.111 | 30.328 | 63.491 | 1.000 | 84.05 |
| ATOM | 2993 | CB  | PRO B | 94 | 72.346 | 30.431 | 64.992 | 1.000 | 81.07 |
| ATOM | 2994 | CG  | PRO B | 94 | 71.549 | 31.600 | 65.461 | 1.000 | 79.07 |
| ATOM | 2995 | CD  | PRO B | 94 | 70.967 | 32.274 | 64.262 | 1.000 | 82.73 |
| ATOM | 2996 | C   | PRO B | 94 | 70.930 | 29.403 | 63.184 | 1.000 | 88.17 |
| ATOM | 2997 | O   | PRO B | 94 | 70.886 | 28.767 | 62.140 | 1.000 | 95.17 |
| ATOM | 2998 | N   | CYS B | 95 | 70.014 | 29.396 | 64.129 | 1.000 | 85.15 |

FIGURE 64

| | | | | | | | | | |
|---|---|---|---|---|---|---|---|---|---|
| ATOM | 2999 | CA | CYS | B | 95 | 68.692 | 28.806 | 64.171 | 1.000 71.00 |
| ATOM | 3000 | CB | CYS | B | 95 | 68.676 | 27.559 | 65.048 | 1.000 68.25 |
| ATOM | 3001 | SG | CYS | B | 95 | 70.324 | 27.048 | 65.606 | 1.000 59.08 |
| ATOM | 3002 | C | CYS | B | 95 | 67.724 | 29.872 | 64.691 | 1.000 61.59 |
| ATOM | 3003 | O | CYS | B | 95 | 66.839 | 29.638 | 65.507 | 1.000 45.14 |
| ATOM | 3004 | N | SER | B | 96 | 67.966 | 31.077 | 64.176 | 1.000 54.56 |
| ATOM | 3005 | CA | SER | B | 96 | 67.227 | 32.262 | 64.582 | 1.000 54.51 |
| ATOM | 3006 | CB | SER | B | 96 | 67.962 | 33.527 | 64.131 | 1.000 53.89 |
| ATOM | 3007 | OG | SER | B | 96 | 68.750 | 33.268 | 62.979 | 1.000 64.41 |
| ATOM | 3008 | C | SER | B | 96 | 65.806 | 32.239 | 64.029 | 1.000 47.05 |
| ATOM | 3009 | O | SER | B | 96 | 64.946 | 32.971 | 64.526 | 1.000 50.88 |
| ATOM | 3010 | N | ASP | B | 97 | 65.565 | 31.402 | 63.024 | 1.000 36.23 |
| ATOM | 3011 | CA | ASP | B | 97 | 64.263 | 31.360 | 62.369 | 1.000 27.85 |
| ATOM | 3012 | CB | ASP | B | 97 | 64.461 | 30.914 | 60.911 | 1.000 24.26 |
| ATOM | 3013 | CG | ASP | B | 97 | 64.720 | 29.419 | 60.834 | 1.000 36.82 |
| ATOM | 3014 | OD1 | ASP | B | 97 | 65.206 | 28.822 | 61.819 | 1.000 38.88 |
| ATOM | 3015 | OD2 | ASP | B | 97 | 64.431 | 28.828 | 59.772 | 1.000 52.38 |
| ATOM | 3016 | C | ASP | B | 97 | 63.263 | 30.420 | 63.027 | 1.000 29.64 |
| ATOM | 3017 | O | ASP | B | 97 | 62.132 | 30.313 | 62.537 | 1.000 25.93 |
| ATOM | 3018 | N | TYR | B | 98 | 63.653 | 29.727 | 64.094 | 1.000 31.48 |
| ATOM | 3019 | CA | TYR | B | 98 | 62.830 | 28.686 | 64.683 | 1.000 27.28 |
| ATOM | 3020 | CB | TYR | B | 98 | 63.708 | 27.639 | 65.426 | 1.000 24.83 |
| ATOM | 3021 | CG | TYR | B | 98 | 62.860 | 26.500 | 65.960 | 1.000 19.17 |
| ATOM | 3022 | CD1 | TYR | B | 98 | 62.365 | 25.535 | 65.080 | 1.000 20.66 |
| ATOM | 3023 | CE1 | TYR | B | 98 | 61.587 | 24.485 | 65.523 | 1.000 24.11 |
| ATOM | 3024 | CZ | TYR | B | 98 | 61.285 | 24.380 | 66.864 | 1.000 26.77 |
| ATOM | 3025 | OH | TYR | B | 98 | 60.508 | 23.331 | 67.317 | 1.000 19.75 |
| ATOM | 3026 | CE2 | TYR | B | 98 | 61.760 | 25.324 | 67.751 | 1.000 22.13 |
| ATOM | 3027 | CD2 | TYR | B | 98 | 62.540 | 26.372 | 67.306 | 1.000 20.85 |
| ATOM | 3028 | C | TYR | B | 98 | 61.775 | 29.132 | 65.687 | 1.000 20.04 |
| ATOM | 3029 | O | TYR | B | 98 | 61.972 | 29.920 | 66.608 | 1.000 25.66 |
| ATOM | 3030 | N | ILE | B | 99 | 60.604 | 28.517 | 65.531 | 1.000 20.57 |
| ATOM | 3031 | CA | ILE | B | 99 | 59.546 | 28.552 | 66.532 | 1.000 19.42 |
| ATOM | 3032 | CB | ILE | B | 99 | 58.577 | 29.720 | 66.314 | 1.000 19.96 |
| ATOM | 3033 | CG1 | ILE | B | 99 | 57.447 | 29.790 | 67.336 | 1.000 17.02 |
| ATOM | 3034 | CD1 | ILE | B | 99 | 56.771 | 31.140 | 67.413 | 1.000 19.58 |
| ATOM | 3035 | CG2 | ILE | B | 99 | 58.013 | 29.694 | 64.897 | 1.000 29.56 |
| ATOM | 3036 | C | ILE | B | 99 | 58.773 | 27.240 | 66.500 | 1.000 22.92 |
| ATOM | 3037 | O | ILE | B | 99 | 58.543 | 26.677 | 65.428 | 1.000 23.59 |
| ATOM | 3038 | N | ASN | B | 100 | 58.373 | 26.722 | 67.665 | 1.000 17.01 |
| ATOM | 3039 | CA | ASN | B | 100 | 57.617 | 25.462 | 67.617 | 1.000 20.62 |
| ATOM | 3040 | CB | ASN | B | 100 | 57.574 | 24.797 | 68.989 | 1.000 22.98 |
| ATOM | 3041 | CG | ASN | B | 100 | 56.990 | 23.404 | 68.998 | 1.000 24.77 |
| ATOM | 3042 | OD1 | ASN | B | 100 | 56.001 | 23.116 | 68.319 | 1.000 25.34 |
| ATOM | 3043 | ND2 | ASN | B | 100 | 57.571 | 22.496 | 69.786 | 1.000 18.32 |
| ATOM | 3044 | C | ASN | B | 100 | 56.226 | 25.777 | 67.081 | 1.000 20.30 |
| ATOM | 3045 | O | ASN | B | 100 | 55.361 | 26.152 | 67.888 | 1.000 19.79 |
| ATOM | 3046 | N | ALA | B | 101 | 56.067 | 25.654 | 65.760 | 1.000 21.42 |
| ATOM | 3047 | CA | ALA | B | 101 | 54.782 | 25.946 | 65.121 | 1.000 21.68 |
| ATOM | 3048 | CB | ALA | B | 101 | 54.559 | 27.450 | 65.071 | 1.000 13.80 |
| ATOM | 3049 | C | ALA | B | 101 | 54.696 | 25.326 | 63.732 | 1.000 26.20 |
| ATOM | 3050 | O | ALA | B | 101 | 55.715 | 25.142 | 63.072 | 1.000 18.76 |

FIGURE 65

| | | | | | | | | | |
|---|---|---|---|---|---|---|---|---|---|
| ATOM | 3051 | N | SER | B | 102 | 53.499 | 24.985 | 63.271 | 1.000 29.48 |
| ATOM | 3052 | CA | SER | B | 102 | 53.250 | 24.285 | 62.023 | 1.000 19.07 |
| ATOM | 3053 | CB | SER | B | 102 | 52.919 | 22.808 | 62.271 | 1.000 15.75 |
| ATOM | 3054 | OG | SER | B | 102 | 53.753 | 22.258 | 63.274 | 1.000 21.52 |
| ATOM | 3055 | C | SER | B | 102 | 52.073 | 24.879 | 61.259 | 1.000 19.78 |
| ATOM | 3056 | O | SER | B | 102 | 51.068 | 25.227 | 61.882 | 1.000 21.21 |
| ATOM | 3057 | N | TYR | B | 103 | 52.181 | 24.977 | 59.931 | 1.000 17.66 |
| ATOM | 3058 | CA | TYR | B | 103 | 51.017 | 25.426 | 59.166 | 1.000 18.10 |
| ATOM | 3059 | CB | TYR | B | 103 | 51.373 | 25.982 | 57.794 | 1.000 20.23 |
| ATOM | 3060 | CG | TYR | B | 103 | 52.221 | 27.216 | 57.690 | 1.000 18.78 |
| ATOM | 3061 | CD1 | TYR | B | 103 | 51.692 | 28.498 | 57.841 | 1.000 22.17 |
| ATOM | 3062 | CE1 | TYR | B | 103 | 52.490 | 29.627 | 57.736 | 1.000 21.36 |
| ATOM | 3063 | CZ | TYR | B | 103 | 53.840 | 29.489 | 57.472 | 1.000 23.55 |
| ATOM | 3064 | OH | TYR | B | 103 | 54.656 | 30.597 | 57.367 | 1.000 21.98 |
| ATOM | 3065 | CE2 | TYR | B | 103 | 54.394 | 28.237 | 57.316 | 1.000 20.92 |
| ATOM | 3066 | CD2 | TYR | B | 103 | 53.585 | 27.113 | 57.422 | 1.000 26.09 |
| ATOM | 3067 | C | TYR | B | 103 | 50.054 | 24.256 | 58.995 | 1.000 16.67 |
| ATOM | 3068 | O | TYR | B | 103 | 50.489 | 23.126 | 58.760 | 1.000 22.66 |
| ATOM | 3069 | N | ILE | B | 104 | 48.756 | 24.521 | 59.088 | 1.000 19.23 |
| ATOM | 3070 | CA | ILE | B | 104 | 47.781 | 23.448 | 58.955 | 1.000 24.34 |
| ATOM | 3071 | CB | ILE | B | 104 | 47.099 | 23.127 | 60.304 | 1.000 32.75 |
| ATOM | 3072 | CG1 | ILE | B | 104 | 48.085 | 22.913 | 61.452 | 1.000 27.91 |
| ATOM | 3073 | CD1 | ILE | B | 104 | 48.886 | 21.643 | 61.328 | 1.000 18.81 |
| ATOM | 3074 | CG2 | ILE | B | 104 | 46.164 | 21.938 | 60.144 | 1.000 20.62 |
| ATOM | 3075 | C | ILE | B | 104 | 46.672 | 23.774 | 57.966 | 1.000 24.01 |
| ATOM | 3076 | O | ILE | B | 104 | 46.080 | 24.847 | 58.018 | 1.000 15.86 |
| ATOM | 3077 | N | PRO | B | 105 | 46.370 | 22.829 | 57.086 | 1.000 25.98 |
| ATOM | 3078 | CA | PRO | B | 105 | 45.332 | 23.074 | 56.078 | 1.000 27.95 |
| ATOM | 3079 | CB | PRO | B | 105 | 45.503 | 21.922 | 55.088 | 1.000 18.03 |
| ATOM | 3080 | CG | PRO | B | 105 | 46.582 | 21.035 | 55.586 | 1.000 21.67 |
| ATOM | 3081 | CD | PRO | B | 105 | 46.944 | 21.482 | 56.973 | 1.000 24.89 |
| ATOM | 3082 | C | PRO | B | 105 | 43.940 | 23.045 | 56.698 | 1.000 28.32 |
| ATOM | 3083 | O | PRO | B | 105 | 43.656 | 22.391 | 57.703 | 1.000 36.85 |
| ATOM | 3084 | N | GLY | B | 106 | 43.011 | 23.768 | 56.085 | 1.000 21.37 |
| ATOM | 3085 | CA | GLY | B | 106 | 41.640 | 23.703 | 56.591 | 1.000 21.21 |
| ATOM | 3086 | C | GLY | B | 106 | 40.757 | 23.172 | 55.465 | 1.000 27.66 |
| ATOM | 3087 | O | GLY | B | 106 | 41.280 | 22.580 | 54.521 | 1.000 21.69 |
| ATOM | 3088 | N | ASN | B | 107 | 39.461 | 23.394 | 55.567 | 1.000 27.43 |
| ATOM | 3089 | CA | ASN | B | 107 | 38.490 | 22.979 | 54.572 | 1.000 35.96 |
| ATOM | 3090 | CB | ASN | B | 107 | 37.085 | 23.184 | 55.152 | 1.000 47.76 |
| ATOM | 3091 | CG | ASN | B | 107 | 36.304 | 21.899 | 55.308 | 1.000 49.77 |
| ATOM | 3092 | OD1 | ASN | B | 107 | 35.075 | 21.945 | 55.229 | 1.000 73.31 |
| ATOM | 3093 | ND2 | ASN | B | 107 | 36.983 | 20.777 | 55.521 | 1.000 41.72 |
| ATOM | 3094 | C | ASN | B | 107 | 38.605 | 23.762 | 53.268 | 1.000 40.01 |
| ATOM | 3095 | O | ASN | B | 107 | 38.170 | 23.268 | 52.227 | 1.000 27.43 |
| ATOM | 3096 | N | ASN | B | 108 | 39.172 | 24.962 | 53.316 | 1.000 47.34 |
| ATOM | 3097 | CA | ASN | B | 108 | 39.181 | 25.892 | 52.194 | 1.000 49.18 |
| ATOM | 3098 | CB | ASN | B | 108 | 38.573 | 27.227 | 52.670 | 1.000 53.17 |
| ATOM | 3099 | CG | ASN | B | 108 | 37.444 | 27.012 | 53.664 | 1.000 60.31 |
| ATOM | 3100 | OD1 | ASN | B | 108 | 36.332 | 26.632 | 53.279 | 1.000 45.80 |
| ATOM | 3101 | ND2 | ASN | B | 108 | 37.724 | 27.248 | 54.945 | 1.000 39.45 |
| ATOM | 3102 | C | ASN | B | 108 | 40.545 | 26.159 | 51.574 | 1.000 41.89 |

FIGURE 66

```
ATOM   3103  O    ASN B 108      40.633  26.284  50.347 1.000 48.34
ATOM   3104  N    PHE B 109      41.607  26.266  52.373 1.000 32.76
ATOM   3105  CA   PHE B 109      42.947  26.513  51.844 1.000 22.32
ATOM   3106  CB   PHE B 109      43.245  28.009  51.738 1.000 27.58
ATOM   3107  CG   PHE B 109      42.837  28.902  52.878 1.000 36.26
ATOM   3108  CD1  PHE B 109      43.785  29.482  53.709 1.000 36.93
ATOM   3109  CE1  PHE B 109      43.434  30.318  54.748 1.000 43.65
ATOM   3110  CZ   PHE B 109      42.102  30.599  54.991 1.000 46.87
ATOM   3111  CE2  PHE B 109      41.144  30.029  54.175 1.000 48.29
ATOM   3112  CD2  PHE B 109      41.509  29.191  53.140 1.000 38.59
ATOM   3113  C    PHE B 109      44.009  25.809  52.681 1.000 26.82
ATOM   3114  O    PHE B 109      43.745  25.302  53.775 1.000 33.42
ATOM   3115  N    ARG B 110      45.231  25.760  52.163 1.000 21.41
ATOM   3116  CA   ARG B 110      46.293  24.976  52.783 1.000 29.86
ATOM   3117  CB   ARG B 110      47.331  24.635  51.691 1.000 23.08
ATOM   3118  CG   ARG B 110      46.678  23.836  50.567 1.000 24.73
ATOM   3119  CD   ARG B 110      47.700  23.142  49.690 1.000 35.94
ATOM   3120  NE   ARG B 110      48.602  22.284  50.447 1.000 54.44
ATOM   3121  CZ   ARG B 110      48.689  20.963  50.337 1.000 65.83
ATOM   3122  NH1  ARG B 110      47.907  20.318  49.480 1.000 62.56
ATOM   3123  NH2  ARG B 110      49.562  20.304  51.095 1.000 60.21
ATOM   3124  C    ARG B 110      46.975  25.640  53.960 1.000 33.08
ATOM   3125  O    ARG B 110      47.566  24.963  54.817 1.000 25.95
ATOM   3126  N    ARG B 111      46.949  26.968  54.073 1.000 29.38
ATOM   3127  CA   ARG B 111      47.600  27.571  55.248 1.000 25.02
ATOM   3128  CB   ARG B 111      48.716  28.513  54.839 1.000 22.60
ATOM   3129  CG   ARG B 111      49.940  27.889  54.187 1.000 25.96
ATOM   3130  CD   ARG B 111      51.044  28.951  54.077 1.000 25.11
ATOM   3131  NE   ARG B 111      52.352  28.321  54.010 1.000 31.63
ATOM   3132  CZ   ARG B 111      53.527  28.919  53.942 1.000 26.99
ATOM   3133  NH1  ARG B 111      53.614  30.238  53.935 1.000 28.95
ATOM   3134  NH2  ARG B 111      54.622  28.173  53.884 1.000 31.47
ATOM   3135  C    ARG B 111      46.556  28.306  56.085 1.000 24.94
ATOM   3136  O    ARG B 111      46.687  29.475  56.447 1.000 29.91
ATOM   3137  N    GLU B 112      45.493  27.571  56.391 1.000 23.64
ATOM   3138  CA   GLU B 112      44.323  28.134  57.049 1.000 17.42
ATOM   3139  CB   GLU B 112      43.130  27.204  56.817 1.000 18.28
ATOM   3140  CG   GLU B 112      41.790  27.862  57.105 1.000 24.48
ATOM   3141  CD   GLU B 112      40.654  27.199  56.351 1.000 26.29
ATOM   3142  OE1  GLU B 112      39.501  27.461  56.751 1.000 26.21
ATOM   3143  OE2  GLU B 112      40.909  26.434  55.398 1.000 31.20
ATOM   3144  C    GLU B 112      44.592  28.379  58.528 1.000 17.73
ATOM   3145  O    GLU B 112      44.083  29.339  59.110 1.000 22.88
ATOM   3146  N    TYR B 113      45.416  27.518  59.101 1.000 16.08
ATOM   3147  CA   TYR B 113      45.780  27.574  60.502 1.000 21.42
ATOM   3148  CB   TYR B 113      45.177  26.393  61.277 1.000 23.13
ATOM   3149  CG   TYR B 113      43.707  26.143  61.023 1.000 21.61
ATOM   3150  CD1  TYR B 113      43.282  25.255  60.046 1.000 20.99
ATOM   3151  CE1  TYR B 113      41.933  25.027  59.815 1.000 20.86
ATOM   3152  CZ   TYR B 113      40.987  25.692  60.567 1.000 21.97
ATOM   3153  OH   TYR B 113      39.644  25.476  60.352 1.000 20.75
ATOM   3154  CE2  TYR B 113      41.385  26.582  61.546 1.000 21.97
```

FIGURE 67

```
ATOM  3155  CD2  TYR B 113    42.735  26.804  61.770 1.000 21.68
ATOM  3156  C    TYR B 113    47.295  27.552  60.685 1.000 27.43
ATOM  3157  O    TYR B 113    48.024  26.950  59.899 1.000 18.10
ATOM  3158  N    ILE B 114    47.733  28.214  61.752 1.000 19.17
ATOM  3159  CA   ILE B 114    49.024  27.953  62.338 1.000 17.32
ATOM  3160  CB   ILE B 114    49.919  29.192  62.464 1.000 22.32
ATOM  3161  CG1  ILE B 114    50.399  29.756  61.124 1.000 15.29
ATOM  3162  CD1  ILE B 114    50.784  31.212  61.142 1.000 18.68
ATOM  3163  CG2  ILE B 114    51.079  28.849  63.390 1.000 21.25
ATOM  3164  C    ILE B 114    48.786  27.336  63.725 1.000 21.28
ATOM  3165  O    ILE B 114    48.140  27.927  64.594 1.000 17.78
ATOM  3166  N    VAL B 115    49.305  26.125  63.911 1.000 17.69
ATOM  3167  CA   VAL B 115    49.196  25.470  65.217 1.000 24.09
ATOM  3168  CB   VAL B 115    48.867  23.969  65.081 1.000 25.84
ATOM  3169  CG1  VAL B 115    49.290  23.223  66.338 1.000 28.88
ATOM  3170  CG2  VAL B 115    47.385  23.774  64.788 1.000 23.07
ATOM  3171  C    VAL B 115    50.500  25.641  65.985 1.000 22.51
ATOM  3172  O    VAL B 115    51.594  25.418  65.450 1.000 14.78
ATOM  3173  N    THR B 116    50.429  26.049  67.251 1.000 21.02
ATOM  3174  CA   THR B 116    51.704  26.242  67.962 1.000 19.77
ATOM  3175  CB   THR B 116    52.149  27.711  67.869 1.000 23.82
ATOM  3176  OG1  THR B 116    53.495  27.907  68.350 1.000 16.84
ATOM  3177  CG2  THR B 116    51.242  28.587  68.722 1.000 19.85
ATOM  3178  C    THR B 116    51.552  25.744  69.390 1.000 22.67
ATOM  3179  O    THR B 116    50.467  25.376  69.849 1.000 17.14
ATOM  3180  N    GLN B 117    52.654  25.693  70.119 1.000 23.60
ATOM  3181  CA   GLN B 117    52.679  25.319  71.514 1.000 23.36
ATOM  3182  CB   GLN B 117    54.080  24.807  71.898 1.000 24.62
ATOM  3183  CG   GLN B 117    55.034  25.933  72.239 1.000 18.72
ATOM  3184  CD   GLN B 117    56.479  25.515  72.375 1.000 26.17
ATOM  3185  OE1  GLN B 117    56.812  24.331  72.431 1.000 27.92
ATOM  3186  NE2  GLN B 117    57.357  26.520  72.419 1.000 23.64
ATOM  3187  C    GLN B 117    52.327  26.512  72.391 1.000 23.75
ATOM  3188  O    GLN B 117    52.440  27.656  71.939 1.000 18.82
ATOM  3189  N    GLY B 118    51.927  26.261  73.638 1.000 21.15
ATOM  3190  CA   GLY B 118    51.716  27.416  74.523 1.000 21.52
ATOM  3191  C    GLY B 118    53.050  28.104  74.761 1.000 17.96
ATOM  3192  O    GLY B 118    54.002  27.456  75.207 1.000 23.95
ATOM  3193  N    PRO B 119    53.131  29.390  74.454 1.000 18.88
ATOM  3194  CA   PRO B 119    54.401  30.117  74.548 1.000 23.38
ATOM  3195  CB   PRO B 119    53.993  31.581  74.327 1.000 19.87
ATOM  3196  CG   PRO B 119    52.757  31.486  73.500 1.000 19.60
ATOM  3197  CD   PRO B 119    52.031  30.260  74.000 1.000 17.07
ATOM  3198  C    PRO B 119    55.064  29.980  75.917 1.000 25.74
ATOM  3199  O    PRO B 119    54.414  29.867  76.952 1.000 21.95
ATOM  3200  N    LEU B 120    56.384  29.996  75.884 1.000 24.68
ATOM  3201  CA   LEU B 120    57.259  29.997  77.034 1.000 28.37
ATOM  3202  CB   LEU B 120    58.542  29.210  76.755 1.000 21.91
ATOM  3203  CG   LEU B 120    58.366  27.711  76.511 1.000 23.23
ATOM  3204  CD1  LEU B 120    59.490  27.175  75.642 1.000 25.39
ATOM  3205  CD2  LEU B 120    58.314  26.965  77.837 1.000 31.44
ATOM  3206  C    LEU B 120    57.615  31.439  77.377 1.000 22.77
```

FIGURE 68

```
ATOM   3207  O    LEU B 120      57.514  32.304  76.499 1.000 23.03
ATOM   3208  N    PRO B 121      58.016  31.692  78.615 1.000 26.35
ATOM   3209  CA   PRO B 121      58.561  33.014  78.945 1.000 22.57
ATOM   3210  CB   PRO B 121      59.171  32.787  80.326 1.000 27.81
ATOM   3211  CG   PRO B 121      58.375  31.675  80.918 1.000 32.45
ATOM   3212  CD   PRO B 121      57.975  30.783  79.773 1.000 28.73
ATOM   3213  C    PRO B 121      59.641  33.414  77.943 1.000 28.24
ATOM   3214  O    PRO B 121      59.741  34.555  77.489 1.000 30.29
ATOM   3215  N    GLY B 122      60.489  32.450  77.562 1.000 22.78
ATOM   3216  CA   GLY B 122      61.573  32.788  76.653 1.000 20.37
ATOM   3217  C    GLY B 122      61.178  32.799  75.191 1.000 28.02
ATOM   3218  O    GLY B 122      61.990  33.229  74.365 1.000 28.41
ATOM   3219  N    THR B 123      59.980  32.360  74.810 1.000 27.99
ATOM   3220  CA   THR B 123      59.604  32.385  73.401 1.000 33.24
ATOM   3221  CB   THR B 123      59.259  30.981  72.854 1.000 33.57
ATOM   3222  OG1  THR B 123      58.039  30.554  73.480 1.000 25.65
ATOM   3223  CG2  THR B 123      60.341  29.968  73.169 1.000 20.05
ATOM   3224  C    THR B 123      58.385  33.260  73.106 1.000 29.44
ATOM   3225  O    THR B 123      57.931  33.303  71.961 1.000 25.91
ATOM   3226  N    LYS B 124      57.853  33.950  74.105 1.000 26.51
ATOM   3227  CA   LYS B 124      56.691  34.807  73.893 1.000 28.23
ATOM   3228  CB   LYS B 124      56.273  35.483  75.199 1.000 32.16
ATOM   3229  CG   LYS B 124      57.460  35.814  76.097 1.000 43.91
ATOM   3230  CD   LYS B 124      57.144  37.009  76.981 1.000 56.45
ATOM   3231  CE   LYS B 124      57.277  36.684  78.458 1.000 47.68
ATOM   3232  NZ   LYS B 124      56.082  37.130  79.224 1.000 47.04
ATOM   3233  C    LYS B 124      56.961  35.882  72.845 1.000 31.27
ATOM   3234  O    LYS B 124      56.010  36.336  72.203 1.000 20.04
ATOM   3235  N    ASP B 125      58.221  36.273  72.690 1.000 27.24
ATOM   3236  CA   ASP B 125      58.589  37.344  71.759 1.000 30.97
ATOM   3237  CB   ASP B 125      59.998  37.856  72.044 1.000 30.13
ATOM   3238  CG   ASP B 125      60.063  38.882  73.163 1.000 37.62
ATOM   3239  OD1  ASP B 125      59.010  39.337  73.647 1.000 29.79
ATOM   3240  OD2  ASP B 125      61.180  39.261  73.577 1.000 55.37
ATOM   3241  C    ASP B 125      58.486  36.861  70.313 1.000 29.10
ATOM   3242  O    ASP B 125      58.053  37.590  69.423 1.000 23.13
ATOM   3243  N    ASP B 126      58.894  35.619  70.119 1.000 29.81
ATOM   3244  CA   ASP B 126      58.855  34.917  68.846 1.000 29.93
ATOM   3245  CB   ASP B 126      59.612  33.590  68.923 1.000 33.34
ATOM   3246  CG   ASP B 126      61.095  33.725  69.208 1.000 42.49
ATOM   3247  OD1  ASP B 126      61.684  34.754  68.799 1.000 33.29
ATOM   3248  OD2  ASP B 126      61.666  32.798  69.837 1.000 36.63
ATOM   3249  C    ASP B 126      57.410  34.663  68.425 1.000 29.50
ATOM   3250  O    ASP B 126      57.077  34.759  67.243 1.000 23.31
ATOM   3251  N    PHE B 127      56.556  34.333  69.391 1.000 27.35
ATOM   3252  CA   PHE B 127      55.135  34.135  69.089 1.000 28.78
ATOM   3253  CB   PHE B 127      54.360  33.783  70.363 1.000 25.58
ATOM   3254  CG   PHE B 127      52.860  33.698  70.240 1.000 22.20
ATOM   3255  CD1  PHE B 127      52.255  32.500  69.878 1.000 21.35
ATOM   3256  CE1  PHE B 127      50.881  32.398  69.750 1.000 20.50
ATOM   3257  CZ   PHE B 127      50.087  33.500  70.006 1.000 26.34
ATOM   3258  CE2  PHE B 127      50.667  34.705  70.361 1.000 17.31
```

FIGURE 69

```
ATOM   3259  CD2  PHE B 127     52.039  34.789  70.487 1.000 15.23
ATOM   3260  C    PHE B 127     54.535  35.373  68.426 1.000 22.38
ATOM   3261  O    PHE B 127     53.905  35.276  67.377 1.000 24.96
ATOM   3262  N    TRP B 128     54.685  36.549  69.032 1.000 24.70
ATOM   3263  CA   TRP B 128     54.065  37.773  68.523 1.000 19.09
ATOM   3264  CB   TRP B 128     54.104  38.859  69.604 1.000 17.25
ATOM   3265  CG   TRP B 128     53.145  38.614  70.734 1.000 17.80
ATOM   3266  CD1  TRP B 128     53.470  38.390  72.040 1.000 22.53
ATOM   3267  NE1  TRP B 128     52.331  38.203  72.789 1.000 21.74
ATOM   3268  CE2  TRP B 128     51.240  38.303  71.966 1.000 19.23
ATOM   3269  CD2  TRP B 128     51.714  38.558  70.668 1.000 19.24
ATOM   3270  CE3  TRP B 128     50.778  38.703  69.637 1.000 28.93
ATOM   3271  CZ3  TRP B 128     49.429  38.592  69.915 1.000 22.05
ATOM   3272  CH2  TRP B 128     48.991  38.335  71.226 1.000 17.91
ATOM   3273  CZ2  TRP B 128     49.878  38.187  72.259 1.000 22.46
ATOM   3274  C    TRP B 128     54.735  38.234  67.237 1.000 18.56
ATOM   3275  O    TRP B 128     54.116  38.775  66.322 1.000 21.01
ATOM   3276  N    LYS B 129     56.042  38.016  67.133 1.000 13.97
ATOM   3277  CA   LYS B 129     56.723  38.282  65.866 1.000 15.64
ATOM   3278  CB   LYS B 129     58.217  37.994  65.979 1.000 22.55
ATOM   3279  CG   LYS B 129     58.950  37.985  64.651 1.000 39.82
ATOM   3280  CD   LYS B 129     60.460  38.047  64.814 1.000 48.10
ATOM   3281  CE   LYS B 129     61.160  37.738  63.491 1.000 52.05
ATOM   3282  NZ   LYS B 129     62.627  37.573  63.678 1.000 61.20
ATOM   3283  C    LYS B 129     56.113  37.409  64.776 1.000 27.27
ATOM   3284  O    LYS B 129     55.893  37.876  63.661 1.000 29.01
ATOM   3285  N    MET B 130     55.848  36.148  65.124 1.000 29.80
ATOM   3286  CA   MET B 130     55.154  35.233  64.230 1.000 27.17
ATOM   3287  CB   MET B 130     54.979  33.827  64.845 1.000 19.02
ATOM   3288  CG   MET B 130     54.169  32.925  63.904 1.000 19.86
ATOM   3289  SD   MET B 130     54.092  31.205  64.479 1.000 25.65
ATOM   3290  CE   MET B 130     52.919  31.427  65.833 1.000 14.58
ATOM   3291  C    MET B 130     53.777  35.775  63.863 1.000 17.87
ATOM   3292  O    MET B 130     53.351  35.838  62.715 1.000 21.77
ATOM   3293  N    VAL B 131     53.029  36.170  64.886 1.000 12.63
ATOM   3294  CA   VAL B 131     51.706  36.739  64.639 1.000 19.47
ATOM   3295  CB   VAL B 131     51.028  37.081  65.977 1.000 24.44
ATOM   3296  CG1  VAL B 131     49.870  38.035  65.754 1.000 20.24
ATOM   3297  CG2  VAL B 131     50.586  35.801  66.687 1.000 20.58
ATOM   3298  C    VAL B 131     51.794  37.977  63.748 1.000 29.32
ATOM   3299  O    VAL B 131     50.974  38.203  62.851 1.000 27.58
ATOM   3300  N    TRP B 132     52.810  38.804  63.985 1.000 24.33
ATOM   3301  CA   TRP B 132     52.980  40.015  63.177 1.000 25.60
ATOM   3302  CB   TRP B 132     54.037  40.918  63.807 1.000 21.12
ATOM   3303  CG   TRP B 132     54.280  42.211  63.101 1.000 30.16
ATOM   3304  CD1  TRP B 132     55.382  42.547  62.364 1.000 34.45
ATOM   3305  NE1  TRP B 132     55.258  43.822  61.863 1.000 35.96
ATOM   3306  CE2  TRP B 132     54.059  44.338  62.273 1.000 34.79
ATOM   3307  CD2  TRP B 132     53.417  43.354  63.054 1.000 29.88
ATOM   3308  CE3  TRP B 132     52.159  43.629  63.598 1.000 23.47
ATOM   3309  CZ3  TRP B 132     51.604  44.866  63.343 1.000 29.19
ATOM   3310  CH2  TRP B 132     52.271  45.821  62.564 1.000 30.89
```

FIGURE 70

```
ATOM   3311  CZ2 TRP B 132      53.499  45.590  62.016 1.000 31.90
ATOM   3312  C   TRP B 132      53.348  39.679  61.736 1.000 27.64
ATOM   3313  O   TRP B 132      52.732  40.210  60.809 1.000 25.13
ATOM   3314  N   GLU B 133      54.336  38.817  61.516 1.000 19.97
ATOM   3315  CA  GLU B 133      54.803  38.528  60.167 1.000 21.72
ATOM   3316  CB  GLU B 133      56.122  37.762  60.268 1.000 25.50
ATOM   3317  CG  GLU B 133      57.215  38.565  60.953 1.000 21.80
ATOM   3318  CD  GLU B 133      58.525  37.797  60.960 1.000 30.30
ATOM   3319  OE1 GLU B 133      58.479  36.560  60.767 1.000 25.13
ATOM   3320  OE2 GLU B 133      59.568  38.461  61.151 1.000 35.58
ATOM   3321  C   GLU B 133      53.810  37.732  59.339 1.000 28.77
ATOM   3322  O   GLU B 133      53.729  37.935  58.127 1.000 26.53
ATOM   3323  N   GLN B 134      53.050  36.828  59.957 1.000 25.47
ATOM   3324  CA  GLN B 134      52.103  36.010  59.204 1.000 24.21
ATOM   3325  CB  GLN B 134      51.962  34.639  59.875 1.000 30.73
ATOM   3326  CG  GLN B 134      53.313  33.951  60.093 1.000 29.62
ATOM   3327  CD  GLN B 134      53.852  33.400  58.783 1.000 30.05
ATOM   3328  OE1 GLN B 134      53.182  32.656  58.068 1.000 33.53
ATOM   3329  NE2 GLN B 134      55.080  33.772  58.460 1.000 33.18
ATOM   3330  C   GLN B 134      50.739  36.668  59.092 1.000 26.45
ATOM   3331  O   GLN B 134      49.769  36.050  58.640 1.000 25.94
ATOM   3332  N   ASN B 135      50.646  37.924  59.510 1.000 24.63
ATOM   3333  CA  ASN B 135      49.405  38.687  59.374 1.000 25.47
ATOM   3334  CB  ASN B 135      49.089  38.902  57.885 1.000 27.21
ATOM   3335  CG  ASN B 135      49.300  40.369  57.529 1.000 46.77
ATOM   3336  OD1 ASN B 135      48.353  41.121  57.307 1.000 69.94
ATOM   3337  ND2 ASN B 135      50.565  40.770  57.500 1.000 36.37
ATOM   3338  C   ASN B 135      48.223  38.027  60.069 1.000 31.62
ATOM   3339  O   ASN B 135      47.088  38.019  59.589 1.000 28.84
ATOM   3340  N   VAL B 136      48.484  37.467  61.246 1.000 27.43
ATOM   3341  CA  VAL B 136      47.416  36.859  62.032 1.000 24.98
ATOM   3342  CB  VAL B 136      48.035  36.029  63.179 1.000 20.72
ATOM   3343  CG1 VAL B 136      46.958  35.491  64.102 1.000 26.47
ATOM   3344  CG2 VAL B 136      48.887  34.909  62.599 1.000 13.70
ATOM   3345  C   VAL B 136      46.469  37.891  62.619 1.000 23.98
ATOM   3346  O   VAL B 136      46.875  38.904  63.196 1.000 19.31
ATOM   3347  N   HIS B 137      45.165  37.662  62.502 1.000 24.96
ATOM   3348  CA  HIS B 137      44.208  38.529  63.180 1.000 24.73
ATOM   3349  CB  HIS B 137      43.215  39.124  62.170 1.000 30.08
ATOM   3350  CG  HIS B 137      43.872  40.090  61.240 1.000 35.97
ATOM   3351  ND1 HIS B 137      43.604  41.435  61.247 1.000 47.37
ATOM   3352  CE1 HIS B 137      44.338  42.022  60.314 1.000 50.81
ATOM   3353  NE2 HIS B 137      45.073  41.107  59.706 1.000 44.95
ATOM   3354  CD2 HIS B 137      44.799  39.891  60.275 1.000 40.02
ATOM   3355  C   HIS B 137      43.407  37.801  64.253 1.000 21.29
ATOM   3356  O   HIS B 137      42.727  38.467  65.026 1.000 27.23
ATOM   3357  N   ASN B 138      43.469  36.470  64.274 1.000 22.17
ATOM   3358  CA  ASN B 138      42.685  35.702  65.233 1.000 20.26
ATOM   3359  CB  ASN B 138      41.491  35.030  64.534 1.000 26.81
ATOM   3360  CG  ASN B 138      40.525  36.056  63.968 1.000 33.07
ATOM   3361  OD1 ASN B 138      40.383  36.164  62.750 1.000 31.33
ATOM   3362  ND2 ASN B 138      39.869  36.819  64.842 1.000 20.76
```

FIGURE 71

```
ATOM   3363  C    ASN B 138      43.540  34.655  65.938  1.000  23.24
ATOM   3364  O    ASN B 138      44.238  33.895  65.262  1.000  18.61
ATOM   3365  N    ILE B 139      43.462  34.638  67.266  1.000  19.79
ATOM   3366  CA   ILE B 139      44.122  33.625  68.077  1.000  25.68
ATOM   3367  CB   ILE B 139      45.258  34.217  68.934  1.000  29.82
ATOM   3368  CG1  ILE B 139      46.318  34.945  68.101  1.000  41.20
ATOM   3369  CD1  ILE B 139      47.149  35.964  68.850  1.000  20.87
ATOM   3370  CG2  ILE B 139      45.900  33.146  69.806  1.000  14.95
ATOM   3371  C    ILE B 139      43.126  32.902  68.985  1.000  24.46
ATOM   3372  O    ILE B 139      42.278  33.526  69.624  1.000  24.46
ATOM   3373  N    VAL B 140      43.264  31.585  69.008  1.000  19.79
ATOM   3374  CA   VAL B 140      42.449  30.644  69.744  1.000  20.63
ATOM   3375  CB   VAL B 140      41.747  29.622  68.832  1.000  28.33
ATOM   3376  CG1  VAL B 140      41.044  28.585  69.698  1.000  19.08
ATOM   3377  CG2  VAL B 140      40.773  30.296  67.875  1.000  24.28
ATOM   3378  C    VAL B 140      43.320  29.857  70.731  1.000  24.37
ATOM   3379  O    VAL B 140      44.279  29.223  70.306  1.000  18.12
ATOM   3380  N    MET B 141      42.990  29.911  72.007  1.000  26.02
ATOM   3381  CA   MET B 141      43.681  29.264  73.114  1.000  26.63
ATOM   3382  CB   MET B 141      44.180  30.349  74.076  1.000  21.56
ATOM   3383  CG   MET B 141      44.895  29.837  75.314  1.000  23.47
ATOM   3384  SD   MET B 141      45.830  31.148  76.140  1.000  25.00
ATOM   3385  CE   MET B 141      46.435  30.216  77.558  1.000  23.28
ATOM   3386  C    MET B 141      42.749  28.270  73.801  1.000  21.18
ATOM   3387  O    MET B 141      41.699  28.664  74.320  1.000  21.43
ATOM   3388  N    VAL B 142      43.079  26.991  73.799  1.000  20.95
ATOM   3389  CA   VAL B 142      42.221  25.959  74.364  1.000  24.30
ATOM   3390  CB   VAL B 142      41.813  24.856  73.371  1.000  21.57
ATOM   3391  CG1  VAL B 142      40.925  25.432  72.277  1.000  44.18
ATOM   3392  CG2  VAL B 142      43.039  24.197  72.760  1.000  32.97
ATOM   3393  C    VAL B 142      42.918  25.273  75.538  1.000  24.63
ATOM   3394  O    VAL B 142      42.870  24.057  75.706  1.000  36.20
ATOM   3395  N    THR B 143      43.566  26.104  76.333  1.000  27.52
ATOM   3396  CA   THR B 143      44.179  25.667  77.575  1.000  32.61
ATOM   3397  CB   THR B 143      45.641  25.224  77.402  1.000  33.85
ATOM   3398  OG1  THR B 143      46.111  24.687  78.647  1.000  32.96
ATOM   3399  CG2  THR B 143      46.518  26.417  77.065  1.000  21.18
ATOM   3400  C    THR B 143      44.152  26.815  78.577  1.000  28.98
ATOM   3401  O    THR B 143      44.172  27.975  78.178  1.000  26.70
ATOM   3402  N    GLN B 144      44.115  26.478  79.855  1.000  26.36
ATOM   3403  CA   GLN B 144      44.388  27.496  80.868  1.000  31.26
ATOM   3404  CB   GLN B 144      43.644  27.201  82.158  1.000  36.91
ATOM   3405  CG   GLN B 144      42.161  27.541  82.146  1.000  45.71
ATOM   3406  CD   GLN B 144      41.465  27.010  83.387  1.000  58.10
ATOM   3407  OE1  GLN B 144      41.528  27.640  84.446  1.000  62.95
ATOM   3408  NE2  GLN B 144      40.807  25.859  83.268  1.000  68.48
ATOM   3409  C    GLN B 144      45.899  27.536  81.085  1.000  30.16
ATOM   3410  O    GLN B 144      46.586  26.558  80.764  1.000  23.48
ATOM   3411  N    CYS B 145      46.426  28.637  81.607  1.000  23.70
ATOM   3412  CA   CYS B 145      47.868  28.723  81.803  1.000  23.35
ATOM   3413  CB   CYS B 145      48.244  30.127  82.276  1.000  17.96
ATOM   3414  SG   CYS B 145      48.066  31.371  80.965  1.000  36.78
```

FIGURE 72

```
ATOM   3415  C   CYS B 145      48.383  27.692  82.799 1.000 29.59
ATOM   3416  O   CYS B 145      49.493  27.168  82.657 1.000 29.74
ATOM   3417  N   VAL B 146      47.547  27.437  83.792 1.000 26.86
ATOM   3418  CA  VAL B 146      47.809  26.499  84.877 1.000 25.79
ATOM   3419  CB  VAL B 146      48.125  27.210  86.202 1.000 30.10
ATOM   3420  CG1 VAL B 146      48.824  26.274  87.179 1.000 28.99
ATOM   3421  CG2 VAL B 146      48.980  28.443  85.953 1.000 32.92
ATOM   3422  C   VAL B 146      46.606  25.573  85.059 1.000 20.95
ATOM   3423  O   VAL B 146      45.458  25.979  85.215 1.000 28.86
ATOM   3424  N   GLU B 147      46.878  24.288  85.002 1.000 24.41
ATOM   3425  CA  GLU B 147      45.881  23.235  85.161 1.000 40.57
ATOM   3426  CB  GLU B 147      45.538  22.562  83.839 1.000 35.73
ATOM   3427  CG  GLU B 147      44.603  23.349  82.943 1.000 41.76
ATOM   3428  CD  GLU B 147      44.308  22.690  81.610 1.000 45.31
ATOM   3429  OE1 GLU B 147      44.722  21.531  81.403 1.000 43.78
ATOM   3430  OE2 GLU B 147      43.653  23.322  80.749 1.000 28.21
ATOM   3431  C   GLU B 147      46.496  22.288  86.182 1.000 45.18
ATOM   3432  O   GLU B 147      47.457  21.558  85.926 1.000 48.42
ATOM   3433  N   LYS B 148      45.992  22.325  87.419 1.000 49.18
ATOM   3434  CA  LYS B 148      46.881  21.658  88.390 1.000 54.02
ATOM   3435  CB  LYS B 148      46.836  22.434  89.703 1.000 46.43
ATOM   3436  CG  LYS B 148      48.184  23.017  90.088 1.000 42.28
ATOM   3437  CD  LYS B 148      49.019  23.482  88.921 1.000 48.15
ATOM   3438  CE  LYS B 148      50.503  23.260  89.180 1.000 46.56
ATOM   3439  NZ  LYS B 148      51.361  24.153  88.358 1.000 39.33
ATOM   3440  C   LYS B 148      46.554  20.182  88.515 1.000 54.15
ATOM   3441  O   LYS B 148      45.415  19.737  88.387 1.000 67.03
ATOM   3442  N   GLY B 149      47.628  19.428  88.760 1.000 52.37
ATOM   3443  CA  GLY B 149      48.941  20.037  88.892 1.000 55.56
ATOM   3444  C   GLY B 149      49.697  20.137  87.583 1.000 63.58
ATOM   3445  O   GLY B 149      50.182  19.100  87.123 1.000 62.06
ATOM   3446  N   ARG B 150      49.813  21.330  86.999 1.000 67.43
ATOM   3447  CA  ARG B 150      50.589  21.516  85.780 1.000 68.36
ATOM   3448  CB  ARG B 150      50.037  20.536  84.725 1.000 77.22
ATOM   3449  CG  ARG B 150      50.929  19.341  84.438 1.000 76.56
ATOM   3450  CD  ARG B 150      52.223  19.406  85.233 1.000 73.15
ATOM   3451  NE  ARG B 150      53.346  19.893  84.431 1.000 71.83
ATOM   3452  CZ  ARG B 150      54.098  19.105  83.668 1.000 75.97
ATOM   3453  NH1 ARG B 150      53.840  17.803  83.608 1.000 77.01
ATOM   3454  NH2 ARG B 150      55.103  19.611  82.967 1.000 68.43
ATOM   3455  C   ARG B 150      50.600  22.925  85.204 1.000 53.31
ATOM   3456  O   ARG B 150      49.604  23.442  84.687 1.000 35.27
ATOM   3457  N   VAL B 151      51.750  23.608  85.234 1.000 34.49
ATOM   3458  CA  VAL B 151      51.924  24.799  84.411 1.000 38.16
ATOM   3459  CB  VAL B 151      53.297  25.469  84.557 1.000 41.62
ATOM   3460  CG1 VAL B 151      53.498  26.491  83.437 1.000 40.64
ATOM   3461  CG2 VAL B 151      53.471  26.163  85.899 1.000 39.00
ATOM   3462  C   VAL B 151      51.760  24.387  82.945 1.000 41.12
ATOM   3463  O   VAL B 151      52.372  23.400  82.525 1.000 39.66
ATOM   3464  N   LYS B 152      50.959  25.079  82.142 1.000 33.45
ATOM   3465  CA  LYS B 152      50.754  24.596  80.776 1.000 28.24
ATOM   3466  CB  LYS B 152      49.302  24.144  80.591 1.000 34.13
```

FIGURE 73

```
ATOM   3467  CG  LYS B 152      48.830  23.155  81.645  1.000  34.20
ATOM   3468  CD  LYS B 152      49.804  22.001  81.780  1.000  38.68
ATOM   3469  CE  LYS B 152      49.120  20.664  81.549  1.000  48.80
ATOM   3470  NZ  LYS B 152      50.119  19.577  81.342  1.000  72.66
ATOM   3471  C   LYS B 152      51.098  25.644  79.729  1.000  31.18
ATOM   3472  O   LYS B 152      51.407  25.310  78.584  1.000  33.64
ATOM   3473  N   CYS B 153      51.049  26.923  80.090  1.000  27.35
ATOM   3474  CA  CYS B 153      51.346  27.960  79.093  1.000  22.51
ATOM   3475  CB  CYS B 153      50.165  28.100  78.150  1.000  16.46
ATOM   3476  SG  CYS B 153      50.211  29.416  76.916  1.000  26.45
ATOM   3477  C   CYS B 153      51.678  29.265  79.801  1.000  31.82
ATOM   3478  O   CYS B 153      51.084  29.606  80.822  1.000  28.53
ATOM   3479  N   ASP B 154      52.637  30.023  79.279  1.000  33.07
ATOM   3480  CA  ASP B 154      52.907  31.332  79.858  1.000  35.38
ATOM   3481  CB  ASP B 154      54.191  31.929  79.261  1.000  35.82
ATOM   3482  CG  ASP B 154      54.817  32.947  80.200  1.000  41.73
ATOM   3483  OD1 ASP B 154      56.002  33.296  80.044  1.000  63.43
ATOM   3484  OD2 ASP B 154      54.104  33.398  81.117  1.000  50.87
ATOM   3485  C   ASP B 154      51.735  32.287  79.642  1.000  41.87
ATOM   3486  O   ASP B 154      50.951  32.111  78.703  1.000  33.32
ATOM   3487  N   HIS B 155      51.623  33.296  80.509  1.000  35.60
ATOM   3488  CA  HIS B 155      50.654  34.375  80.304  1.000  37.44
ATOM   3489  CB  HIS B 155      50.312  35.059  81.628  1.000  36.58
ATOM   3490  CG  HIS B 155      49.205  36.062  81.526  1.000  32.90
ATOM   3491  ND1 HIS B 155      47.930  35.814  82.000  1.000  29.00
ATOM   3492  CE1 HIS B 155      47.168  36.872  81.774  1.000  30.32
ATOM   3493  NE2 HIS B 155      47.903  37.796  81.172  1.000  34.71
ATOM   3494  CD2 HIS B 155      49.182  37.312  81.009  1.000  27.70
ATOM   3495  C   HIS B 155      51.236  35.374  79.311  1.000  36.71
ATOM   3496  O   HIS B 155      51.750  36.422  79.691  1.000  42.00
ATOM   3497  N   TYR B 156      51.192  35.068  78.016  1.000  29.11
ATOM   3498  CA  TYR B 156      52.011  35.820  77.081  1.000  24.84
ATOM   3499  CB  TYR B 156      52.303  34.932  75.855  1.000  27.19
ATOM   3500  CG  TYR B 156      51.050  34.394  75.208  1.000  24.09
ATOM   3501  CD1 TYR B 156      50.488  35.051  74.120  1.000  16.98
ATOM   3502  CE1 TYR B 156      49.344  34.554  73.528  1.000  17.14
ATOM   3503  CZ  TYR B 156      48.745  33.407  73.996  1.000  25.77
ATOM   3504  OH  TYR B 156      47.596  32.928  73.387  1.000  23.27
ATOM   3505  CE2 TYR B 156      49.294  32.745  75.074  1.000  27.41
ATOM   3506  CD2 TYR B 156      50.439  33.238  75.672  1.000  27.13
ATOM   3507  C   TYR B 156      51.409  37.129  76.615  1.000  23.96
ATOM   3508  O   TYR B 156      51.948  37.722  75.673  1.000  30.34
ATOM   3509  N   TRP B 157      50.332  37.596  77.228  1.000  29.38
ATOM   3510  CA  TRP B 157      49.801  38.920  76.885  1.000  30.99
ATOM   3511  CB  TRP B 157      48.389  38.798  76.324  1.000  35.30
ATOM   3512  CG  TRP B 157      47.436  38.178  77.304  1.000  37.36
ATOM   3513  CD1 TRP B 157      46.608  38.819  78.180  1.000  32.25
ATOM   3514  NE1 TRP B 157      45.897  37.886  78.896  1.000  33.37
ATOM   3515  CE2 TRP B 157      46.257  36.626  78.495  1.000  24.24
ATOM   3516  CD2 TRP B 157      47.227  36.772  77.488  1.000  31.89
ATOM   3517  CE3 TRP B 157      47.774  35.630  76.894  1.000  32.73
ATOM   3518  CZ3 TRP B 157      47.334  34.394  77.324  1.000  31.61
```

FIGURE 74

```
ATOM   3519  CH2 TRP B 157      46.366  34.269  78.328  1.000  31.07
ATOM   3520  CZ2 TRP B 157      45.819  35.378  78.923  1.000  30.59
ATOM   3521  C   TRP B 157      49.806  39.815  78.116  1.000  33.23
ATOM   3522  O   TRP B 157      50.003  39.308  79.229  1.000  47.58
ATOM   3523  N   PRO B 158      49.613  41.119  77.999  1.000  35.32
ATOM   3524  CA  PRO B 158      49.665  41.957  79.206  1.000  42.97
ATOM   3525  CB  PRO B 158      49.605  43.384  78.670  1.000  36.94
ATOM   3526  CG  PRO B 158      49.779  43.296  77.200  1.000  32.51
ATOM   3527  CD  PRO B 158      49.347  41.916  76.793  1.000  36.20
ATOM   3528  C   PRO B 158      48.468  41.701  80.128  1.000  58.41
ATOM   3529  O   PRO B 158      47.343  41.559  79.645  1.000  65.51
ATOM   3530  N   ALA B 159      48.739  41.658  81.422  1.000  68.74
ATOM   3531  CA  ALA B 159      47.823  41.404  82.518  1.000  64.94
ATOM   3532  CB  ALA B 159      48.387  41.972  83.819  1.000  34.74
ATOM   3533  C   ALA B 159      46.428  41.975  82.282  1.000  65.31
ATOM   3534  O   ALA B 159      45.468  41.222  82.121  1.000  68.71
ATOM   3535  N   ASP B 160      46.330  43.297  82.278  1.000  66.84
ATOM   3536  CA  ASP B 160      45.079  44.010  82.063  1.000  69.30
ATOM   3537  CB  ASP B 160      44.668  44.824  83.286  1.000  73.78
ATOM   3538  CG  ASP B 160      45.671  44.813  84.417  1.000  78.54
ATOM   3539  OD1 ASP B 160      46.696  45.535  84.324  1.000  85.06
ATOM   3540  OD2 ASP B 160      45.449  44.083  85.410  1.000  82.66
ATOM   3541  C   ASP B 160      45.199  44.934  80.850  1.000  70.60
ATOM   3542  O   ASP B 160      45.922  44.612  79.904  1.000  80.81
ATOM   3543  N   GLN B 161      44.503  46.063  80.897  1.000  65.68
ATOM   3544  CA  GLN B 161      44.460  47.034  79.813  1.000  60.98
ATOM   3545  CB  GLN B 161      43.341  48.054  80.079  1.000  66.64
ATOM   3546  CG  GLN B 161      41.977  47.435  80.326  1.000  70.82
ATOM   3547  CD  GLN B 161      41.431  46.682  79.129  1.000  73.10
ATOM   3548  OE1 GLN B 161      41.858  46.906  77.995  1.000  91.18
ATOM   3549  NE2 GLN B 161      40.481  45.781  79.367  1.000  51.42
ATOM   3550  C   GLN B 161      45.774  47.770  79.607  1.000  52.94
ATOM   3551  O   GLN B 161      45.860  48.713  78.819  1.000  46.56
ATOM   3552  N   ASP B 162      46.841  47.376  80.294  1.000  57.53
ATOM   3553  CA  ASP B 162      48.126  48.048  80.111  1.000  53.21
ATOM   3554  CB  ASP B 162      49.080  47.691  81.251  1.000  60.81
ATOM   3555  CG  ASP B 162      49.331  46.204  81.393  1.000  64.03
ATOM   3556  OD1 ASP B 162      48.588  45.415  80.770  1.000  73.29
ATOM   3557  OD2 ASP B 162      50.272  45.829  82.129  1.000  52.70
ATOM   3558  C   ASP B 162      48.742  47.700  78.759  1.000  46.46
ATOM   3559  O   ASP B 162      48.083  47.149  77.874  1.000  52.43
ATOM   3560  N   SER B 163      50.014  48.039  78.604  1.000  36.08
ATOM   3561  CA  SER B 163      50.763  47.761  77.385  1.000  30.11
ATOM   3562  CB  SER B 163      50.905  49.014  76.523  1.000  37.96
ATOM   3563  OG  SER B 163      51.383  50.101  77.295  1.000  38.12
ATOM   3564  C   SER B 163      52.141  47.223  77.724  1.000  31.57
ATOM   3565  O   SER B 163      52.646  47.355  78.838  1.000  35.55
ATOM   3566  N   LEU B 164      52.776  46.591  76.741  1.000  30.19
ATOM   3567  CA  LEU B 164      54.081  46.002  77.023  1.000  21.86
ATOM   3568  CB  LEU B 164      53.918  44.691  77.779  1.000  37.42
ATOM   3569  CG  LEU B 164      53.641  44.732  79.281  1.000  38.91
ATOM   3570  CD1 LEU B 164      53.495  43.319  79.843  1.000  28.89
```

FIGURE 75

```
ATOM   3571  CD2 LEU B 164      54.736  45.470  80.031  1.000  42.72
ATOM   3572  C   LEU B 164      54.822  45.780  75.715  1.000  27.76
ATOM   3573  O   LEU B 164      54.201  45.635  74.660  1.000  28.16
ATOM   3574  N   TYR B 165      56.150  45.767  75.799  1.000  29.39
ATOM   3575  CA  TYR B 165      56.959  45.469  74.631  1.000  27.11
ATOM   3576  CB  TYR B 165      58.338  46.113  74.728  1.000  24.50
ATOM   3577  CG  TYR B 165      58.373  47.576  74.362  1.000  33.29
ATOM   3578  CD1 TYR B 165      58.505  47.926  73.022  1.000  27.89
ATOM   3579  CE1 TYR B 165      58.538  49.248  72.635  1.000  31.36
ATOM   3580  CZ  TYR B 165      58.443  50.244  73.581  1.000  24.85
ATOM   3581  OH  TYR B 165      58.487  51.546  73.139  1.000  26.61
ATOM   3582  CE2 TYR B 165      58.309  49.930  74.915  1.000  28.53
ATOM   3583  CD2 TYR B 165      58.271  48.594  75.307  1.000  28.19
ATOM   3584  C   TYR B 165      57.109  43.955  74.503  1.000  32.17
ATOM   3585  O   TYR B 165      57.195  43.254  75.511  1.000  29.95
ATOM   3586  N   TYR B 166      57.152  43.472  73.271  1.000  28.70
ATOM   3587  CA  TYR B 166      57.498  42.072  73.035  1.000  27.96
ATOM   3588  CB  TYR B 166      56.268  41.232  72.710  1.000  29.27
ATOM   3589  CG  TYR B 166      55.350  41.031  73.899  1.000  32.16
ATOM   3590  CD1 TYR B 166      55.542  39.987  74.805  1.000  27.15
ATOM   3591  CE1 TYR B 166      54.689  39.821  75.884  1.000  26.48
ATOM   3592  CZ  TYR B 166      53.637  40.699  76.065  1.000  31.42
ATOM   3593  OH  TYR B 166      52.780  40.552  77.133  1.000  26.92
ATOM   3594  CE2 TYR B 166      53.427  41.738  75.182  1.000  25.16
ATOM   3595  CD2 TYR B 166      54.282  41.897  74.107  1.000  30.85
ATOM   3596  C   TYR B 166      58.533  42.065  71.926  1.000  23.40
ATOM   3597  O   TYR B 166      58.221  42.038  70.746  1.000  29.44
ATOM   3598  N   GLY B 167      59.815  42.124  72.303  1.000  30.73
ATOM   3599  CA  GLY B 167      60.795  42.293  71.225  1.000  31.29
ATOM   3600  C   GLY B 167      60.629  43.677  70.620  1.000  34.66
ATOM   3601  O   GLY B 167      60.636  44.683  71.340  1.000  26.60
ATOM   3602  N   ASP B 168      60.475  43.757  69.302  1.000  29.65
ATOM   3603  CA  ASP B 168      60.388  45.070  68.660  1.000  31.97
ATOM   3604  CB  ASP B 168      61.050  45.062  67.282  1.000  30.77
ATOM   3605  CG  ASP B 168      62.559  44.932  67.417  1.000  44.29
ATOM   3606  OD1 ASP B 168      63.059  45.103  68.550  1.000  70.44
ATOM   3607  OD2 ASP B 168      63.238  44.655  66.411  1.000  63.44
ATOM   3608  C   ASP B 168      58.935  45.510  68.551  1.000  32.07
ATOM   3609  O   ASP B 168      58.619  46.594  68.076  1.000  32.90
ATOM   3610  N   LEU B 169      58.073  44.613  69.025  1.000  29.35
ATOM   3611  CA  LEU B 169      56.648  44.870  68.984  1.000  33.24
ATOM   3612  CB  LEU B 169      55.877  43.576  68.686  1.000  30.90
ATOM   3613  CG  LEU B 169      56.205  42.932  67.336  1.000  32.40
ATOM   3614  CD1 LEU B 169      55.292  41.738  67.129  1.000  26.83
ATOM   3615  CD2 LEU B 169      56.082  43.955  66.219  1.000  27.58
ATOM   3616  C   LEU B 169      56.111  45.433  70.294  1.000  32.00
ATOM   3617  O   LEU B 169      56.642  45.147  71.365  1.000  27.18
ATOM   3618  N   ILE B 170      55.042  46.205  70.127  1.000  23.43
ATOM   3619  CA  ILE B 170      54.297  46.711  71.263  1.000  37.97
ATOM   3620  CB  ILE B 170      54.333  48.242  71.369  1.000  44.96
ATOM   3621  CG1 ILE B 170      53.206  48.832  72.219  1.000  51.13
ATOM   3622  CD1 ILE B 170      53.662  49.989  73.089  1.000  79.46
```

FIGURE 76

```
ATOM   3623  CG2 ILE B 170      54.345  48.876  69.991 1.000 56.59
ATOM   3624  C   ILE B 170      52.851  46.228  71.147 1.000 36.98
ATOM   3625  O   ILE B 170      52.247  46.337  70.083 1.000 29.48
ATOM   3626  N   LEU B 171      52.367  45.700  72.258 1.000 37.92
ATOM   3627  CA  LEU B 171      51.015  45.200  72.405 1.000 39.12
ATOM   3628  CB  LEU B 171      51.037  43.709  72.767 1.000 46.39
ATOM   3629  CG  LEU B 171      50.043  42.860  71.971 1.000 52.95
ATOM   3630  CD1 LEU B 171      50.694  41.558  71.563 1.000 42.82
ATOM   3631  CD2 LEU B 171      48.783  42.619  72.784 1.000 80.84
ATOM   3632  C   LEU B 171      50.235  45.939  73.482 1.000 37.92
ATOM   3633  O   LEU B 171      50.744  46.261  74.556 1.000 41.84
ATOM   3634  N   GLN B 172      48.962  46.207  73.191 1.000 33.26
ATOM   3635  CA  GLN B 172      48.132  46.767  74.257 1.000 42.90
ATOM   3636  CB  GLN B 172      47.929  48.272  74.095 1.000 43.81
ATOM   3637  CG  GLN B 172      46.841  48.669  73.123 1.000 44.65
ATOM   3638  CD  GLN B 172      46.760  50.170  72.905 1.000 41.71
ATOM   3639  OE1 GLN B 172      47.004  50.675  71.809 1.000 39.38
ATOM   3640  NE2 GLN B 172      46.410  50.886  73.963 1.000 51.04
ATOM   3641  C   GLN B 172      46.800  46.028  74.274 1.000 36.46
ATOM   3642  O   GLN B 172      46.205  45.820  73.214 1.000 30.33
ATOM   3643  N   MET B 173      46.349  45.629  75.460 1.000 34.57
ATOM   3644  CA  MET B 173      45.024  45.020  75.526 1.000 37.82
ATOM   3645  CB  MET B 173      44.827  44.177  76.786 1.000 44.70
ATOM   3646  CG  MET B 173      43.371  44.165  77.243 1.000 48.88
ATOM   3647  SD  MET B 173      43.091  43.051  78.637 1.000 61.82
ATOM   3648  CE  MET B 173      43.023  41.490  77.765 1.000 30.24
ATOM   3649  C   MET B 173      43.960  46.115  75.496 1.000 37.98
ATOM   3650  O   MET B 173      43.913  46.968  76.387 1.000 50.74
ATOM   3651  N   LEU B 174      43.116  46.087  74.476 1.000 39.28
ATOM   3652  CA  LEU B 174      42.041  47.069  74.379 1.000 40.72
ATOM   3653  CB  LEU B 174      41.705  47.353  72.911 1.000 40.97
ATOM   3654  CG  LEU B 174      42.894  47.860  72.084 1.000 48.67
ATOM   3655  CD1 LEU B 174      42.466  48.190  70.666 1.000 63.07
ATOM   3656  CD2 LEU B 174      43.524  49.058  72.778 1.000 40.09
ATOM   3657  C   LEU B 174      40.794  46.608  75.113 1.000 37.13
ATOM   3658  O   LEU B 174      39.994  47.450  75.515 1.000 41.98
ATOM   3659  N   SER B 175      40.613  45.295  75.288 1.000 36.81
ATOM   3660  CA  SER B 175      39.379  44.856  75.936 1.000 37.02
ATOM   3661  CB  SER B 175      38.204  45.077  74.978 1.000 39.53
ATOM   3662  OG  SER B 175      38.164  44.075  73.975 1.000 60.16
ATOM   3663  C   SER B 175      39.419  43.397  76.372 1.000 43.07
ATOM   3664  O   SER B 175      40.144  42.583  75.801 1.000 35.52
ATOM   3665  N   GLU B 176      38.616  43.077  77.387 1.000 36.53
ATOM   3666  CA  GLU B 176      38.525  41.721  77.899 1.000 37.42
ATOM   3667  CB  GLU B 176      39.524  41.528  79.050 1.000 29.90
ATOM   3668  CG  GLU B 176      39.524  40.101  79.570 1.000 36.55
ATOM   3669  CD  GLU B 176      40.377  39.924  80.806 1.000 41.20
ATOM   3670  OE1 GLU B 176      39.808  39.980  81.913 1.000 65.49
ATOM   3671  OE2 GLU B 176      41.602  39.726  80.667 1.000 51.95
ATOM   3672  C   GLU B 176      37.120  41.366  78.371 1.000 42.69
ATOM   3673  O   GLU B 176      36.658  41.868  79.400 1.000 44.27
ATOM   3674  N   SER B 177      36.434  40.496  77.627 1.000 39.90
```

FIGURE 77

```
ATOM   3675  CA   SER B 177      35.073  40.107  77.983  1.000  35.04
ATOM   3676  CB   SER B 177      34.101  40.295  76.816  1.000  36.67
ATOM   3677  OG   SER B 177      34.475  41.395  76.007  1.000  52.82
ATOM   3678  C    SER B 177      35.030  38.658  78.448  1.000  41.90
ATOM   3679  O    SER B 177      35.160  37.715  77.669  1.000  42.75
ATOM   3680  N    VAL B 178      34.840  38.482  79.750  1.000  40.45
ATOM   3681  CA   VAL B 178      34.819  37.128  80.295  1.000  49.91
ATOM   3682  CB   VAL B 178      35.272  37.144  81.768  1.000  56.06
ATOM   3683  CG1  VAL B 178      35.518  35.735  82.276  1.000  36.78
ATOM   3684  CG2  VAL B 178      36.520  38.006  81.909  1.000  58.94
ATOM   3685  C    VAL B 178      33.439  36.509  80.163  1.000  50.01
ATOM   3686  O    VAL B 178      32.445  37.037  80.659  1.000  63.04
ATOM   3687  N    LEU B 179      33.372  35.372  79.478  1.000  45.68
ATOM   3688  CA   LEU B 179      32.098  34.653  79.362  1.000  38.65
ATOM   3689  CB   LEU B 179      31.753  34.401  77.900  1.000  37.56
ATOM   3690  CG   LEU B 179      30.892  35.472  77.222  1.000  42.61
ATOM   3691  CD1  LEU B 179      30.991  36.805  77.946  1.000  33.74
ATOM   3692  CD2  LEU B 179      31.286  35.631  75.766  1.000  47.05
ATOM   3693  C    LEU B 179      32.206  33.383  80.189  1.000  30.01
ATOM   3694  O    LEU B 179      33.317  33.035  80.611  1.000  33.11
ATOM   3695  N    PRO B 180      31.108  32.694  80.467  1.000  44.43
ATOM   3696  CA   PRO B 180      31.210  31.516  81.345  1.000  49.89
ATOM   3697  CB   PRO B 180      29.766  31.004  81.441  1.000  47.48
ATOM   3698  CG   PRO B 180      28.932  32.194  81.096  1.000  47.96
ATOM   3699  CD   PRO B 180      29.720  32.929  80.038  1.000  48.96
ATOM   3700  C    PRO B 180      32.130  30.439  80.793  1.000  43.82
ATOM   3701  O    PRO B 180      32.877  29.834  81.569  1.000  44.36
ATOM   3702  N    GLU B 181      32.144  30.139  79.492  1.000  42.02
ATOM   3703  CA   GLU B 181      33.041  29.044  79.095  1.000  41.65
ATOM   3704  CB   GLU B 181      32.305  28.017  78.245  1.000  42.17
ATOM   3705  CG   GLU B 181      31.191  27.274  78.964  1.000  46.96
ATOM   3706  CD   GLU B 181      30.000  27.055  78.047  1.000  47.94
ATOM   3707  OE1  GLU B 181      29.114  27.932  78.017  1.000  66.99
ATOM   3708  OE2  GLU B 181      29.958  26.017  77.358  1.000  66.16
ATOM   3709  C    GLU B 181      34.270  29.552  78.353  1.000  42.89
ATOM   3710  O    GLU B 181      35.211  28.790  78.114  1.000  45.33
ATOM   3711  N    TRP B 182      34.287  30.831  77.987  1.000  38.96
ATOM   3712  CA   TRP B 182      35.473  31.378  77.343  1.000  34.57
ATOM   3713  CB   TRP B 182      35.493  31.021  75.853  1.000  34.24
ATOM   3714  CG   TRP B 182      34.289  31.453  75.078  1.000  31.49
ATOM   3715  CD1  TRP B 182      34.055  32.679  74.531  1.000  33.21
ATOM   3716  NE1  TRP B 182      32.839  32.683  73.891  1.000  30.07
ATOM   3717  CE2  TRP B 182      32.258  31.451  74.014  1.000  24.47
ATOM   3718  CD2  TRP B 182      33.145  30.644  74.755  1.000  36.54
ATOM   3719  CE3  TRP B 182      32.793  29.317  75.030  1.000  38.44
ATOM   3720  CZ3  TRP B 182      31.582  28.837  74.562  1.000  36.86
ATOM   3721  CH2  TRP B 182      30.725  29.670  73.827  1.000  32.83
ATOM   3722  CZ2  TRP B 182      31.038  30.971  73.543  1.000  25.32
ATOM   3723  C    TRP B 182      35.581  32.890  77.481  1.000  29.73
ATOM   3724  O    TRP B 182      34.637  33.609  77.802  1.000  34.04
ATOM   3725  N    THR B 183      36.786  33.370  77.203  1.000  19.61
ATOM   3726  CA   THR B 183      37.043  34.808  77.245  1.000  24.25
```

FIGURE 78

```
ATOM  3727  CB   THR B 183      38.106  35.096  78.329  1.000  27.46
ATOM  3728  OG1  THR B 183      37.562  34.709  79.589  1.000  35.93
ATOM  3729  CG2  THR B 183      38.446  36.570  78.408  1.000  27.17
ATOM  3730  C    THR B 183      37.539  35.333  75.910  1.000  20.91
ATOM  3731  O    THR B 183      38.454  34.749  75.312  1.000  28.00
ATOM  3732  N    ILE B 184      36.966  36.423  75.422  1.000  26.34
ATOM  3733  CA   ILE B 184      37.472  37.068  74.208  1.000  26.11
ATOM  3734  CB   ILE B 184      36.341  37.420  73.235  1.000  29.02
ATOM  3735  CG1  ILE B 184      35.592  36.198  72.681  1.000  36.60
ATOM  3736  CD1  ILE B 184      34.154  36.545  72.341  1.000  36.57
ATOM  3737  CG2  ILE B 184      36.819  38.293  72.087  1.000  18.36
ATOM  3738  C    ILE B 184      38.232  38.333  74.580  1.000  31.53
ATOM  3739  O    ILE B 184      37.781  39.186  75.345  1.000  38.29
ATOM  3740  N    ARG B 185      39.437  38.501  74.043  1.000  34.57
ATOM  3741  CA   ARG B 185      40.147  39.754  74.292  1.000  25.10
ATOM  3742  CB   ARG B 185      41.417  39.538  75.100  1.000  28.99
ATOM  3743  CG   ARG B 185      41.209  39.034  76.522  1.000  31.53
ATOM  3744  CD   ARG B 185      42.403  38.222  76.976  1.000  25.65
ATOM  3745  NE   ARG B 185      42.343  37.791  78.364  1.000  21.83
ATOM  3746  CZ   ARG B 185      42.092  36.551  78.753  1.000  23.41
ATOM  3747  NH1  ARG B 185      41.864  35.591  77.867  1.000  20.48
ATOM  3748  NH2  ARG B 185      42.064  36.264  80.047  1.000  23.08
ATOM  3749  C    ARG B 185      40.474  40.399  72.952  1.000  34.69
ATOM  3750  O    ARG B 185      40.557  39.744  71.909  1.000  35.97
ATOM  3751  N    GLU B 186      40.657  41.714  72.993  1.000  27.86
ATOM  3752  CA   GLU B 186      41.104  42.376  71.771  1.000  30.56
ATOM  3753  CB   GLU B 186      40.003  43.261  71.200  1.000  27.97
ATOM  3754  CG   GLU B 186      38.651  42.555  71.232  1.000  39.02
ATOM  3755  CD   GLU B 186      37.530  43.456  70.746  1.000  52.48
ATOM  3756  OE1  GLU B 186      37.819  44.357  69.928  1.000  68.25
ATOM  3757  OE2  GLU B 186      36.378  43.243  71.180  1.000  77.37
ATOM  3758  C    GLU B 186      42.373  43.152  72.110  1.000  32.85
ATOM  3759  O    GLU B 186      42.405  43.798  73.154  1.000  31.08
ATOM  3760  N    PHE B 187      43.349  43.031  71.236  1.000  30.67
ATOM  3761  CA   PHE B 187      44.651  43.643  71.332  1.000  28.22
ATOM  3762  CB   PHE B 187      45.761  42.599  71.472  1.000  23.26
ATOM  3763  CG   PHE B 187      45.580  41.563  72.546  1.000  30.99
ATOM  3764  CD1  PHE B 187      45.238  40.260  72.244  1.000  27.35
ATOM  3765  CE1  PHE B 187      45.074  39.304  73.230  1.000  20.96
ATOM  3766  CZ   PHE B 187      45.244  39.654  74.558  1.000  27.74
ATOM  3767  CE2  PHE B 187      45.589  40.951  74.882  1.000  33.31
ATOM  3768  CD2  PHE B 187      45.760  41.891  73.884  1.000  33.33
ATOM  3769  C    PHE B 187      44.937  44.474  70.079  1.000  32.36
ATOM  3770  O    PHE B 187      44.466  44.149  68.989  1.000  24.82
ATOM  3771  N    LYS B 188      45.731  45.502  70.304  1.000  33.51
ATOM  3772  CA   LYS B 188      46.366  46.294  69.265  1.000  39.34
ATOM  3773  CB   LYS B 188      46.107  47.786  69.445  1.000  52.27
ATOM  3774  CG   LYS B 188      47.360  48.631  69.623  1.000  65.67
ATOM  3775  CD   LYS B 188      47.208  49.980  68.916  1.000  71.88
ATOM  3776  CE   LYS B 188      48.299  50.947  69.345  1.000  76.68
ATOM  3777  NZ   LYS B 188      48.492  52.055  68.375  1.000  77.91
ATOM  3778  C    LYS B 188      47.867  46.005  69.285  1.000  31.64
```

FIGURE 79

```
ATOM   3779  O    LYS B 188      48.496  46.016  70.345 1.000 31.25
ATOM   3780  N    ILE B 189      48.432  45.740  68.110 1.000 25.97
ATOM   3781  CA   ILE B 189      49.869  45.521  68.045 1.000 32.80
ATOM   3782  CB   ILE B 189      50.247  44.098  67.612 1.000 38.71
ATOM   3783  CG1  ILE B 189      49.093  43.327  66.974 1.000 46.51
ATOM   3784  CD1  ILE B 189      48.715  43.822  65.594 1.000 39.76
ATOM   3785  CG2  ILE B 189      50.838  43.337  68.787 1.000 53.93
ATOM   3786  C    ILE B 189      50.485  46.515  67.066 1.000 33.72
ATOM   3787  O    ILE B 189      49.888  46.777  66.022 1.000 37.58
ATOM   3788  N    CYS B 190      51.648  47.022  67.450 1.000 30.23
ATOM   3789  CA   CYS B 190      52.400  47.934  66.602 1.000 40.89
ATOM   3790  CB   CYS B 190      52.596  49.307  67.233 1.000 42.64
ATOM   3791  SG   CYS B 190      51.150  50.118  67.926 1.000 58.03
ATOM   3792  C    CYS B 190      53.775  47.334  66.282 1.000 44.57
ATOM   3793  O    CYS B 190      54.446  46.804  67.173 1.000 40.52
ATOM   3794  N    GLY B 191      54.140  47.444  65.011 1.000 36.59
ATOM   3795  CA   GLY B 191      55.407  46.950  64.504 1.000 43.85
ATOM   3796  C    GLY B 191      56.063  48.026  63.654 1.000 51.14
ATOM   3797  O    GLY B 191      55.515  49.122  63.561 1.000 44.72
ATOM   3798  N    GLU B 192      57.206  47.732  63.051 1.000 65.39
ATOM   3799  CA   GLU B 192      57.917  48.729  62.251 1.000 74.92
ATOM   3800  CB   GLU B 192      59.164  48.118  61.620 1.000 80.08
ATOM   3801  CG   GLU B 192      59.486  46.705  62.068 1.000 89.69
ATOM   3802  CD   GLU B 192      60.187  46.619  63.406 1.000 99.45
ATOM   3803  OE1  GLU B 192      59.909  45.653  64.155 1.000109.46
ATOM   3804  OE2  GLU B 192      61.017  47.500  63.734 1.000105.75
ATOM   3805  C    GLU B 192      56.982  49.325  61.190 1.000 77.53
ATOM   3806  O    GLU B 192      57.093  50.520  60.921 1.000 71.90
ATOM   3807  N    GLU B 193      56.119  48.468  60.689 1.000 80.23
ATOM   3808  CA   GLU B 193      55.037  48.642  59.748 1.000 85.66
ATOM   3809  CB   GLU B 193      54.717  50.116  59.508 1.000 94.37
ATOM   3810  CG   GLU B 193      53.928  50.436  58.253 1.000106.40
ATOM   3811  CD   GLU B 193      52.595  49.734  58.174 1.000115.65
ATOM   3812  OE1  GLU B 193      51.537  50.403  58.158 1.000130.32
ATOM   3813  OE2  GLU B 193      52.613  48.478  58.138 1.000120.48
ATOM   3814  C    GLU B 193      55.364  47.949  58.424 1.000 90.24
ATOM   3815  O    GLU B 193      56.248  48.389  57.684 1.000 99.18
ATOM   3816  N    GLN B 194      54.652  46.858  58.146 1.000 94.55
ATOM   3817  CA   GLN B 194      54.801  46.130  56.892 1.000 99.07
ATOM   3818  CB   GLN B 194      55.799  44.984  57.030 1.000 99.47
ATOM   3819  CG   GLN B 194      56.655  45.014  58.284 1.000 99.46
ATOM   3820  CD   GLN B 194      58.097  44.616  58.010 1.000 96.93
ATOM   3821  OE1  GLN B 194      58.678  44.953  56.977 1.000 92.58
ATOM   3822  NE2  GLN B 194      58.682  43.863  58.944 1.000 90.47
ATOM   3823  C    GLN B 194      53.449  45.595  56.413 1.000102.41
ATOM   3824  O    GLN B 194      53.158  44.410  56.574 1.000106.43
ATOM   3825  N    LEU B 195      52.649  46.481  55.833 1.000102.43
ATOM   3826  CA   LEU B 195      51.322  46.214  55.301 1.000100.78
ATOM   3827  CB   LEU B 195      51.291  44.888  54.539 1.000 96.19
ATOM   3828  CG   LEU B 195      51.096  44.962  53.021 1.000 88.64
ATOM   3829  CD1  LEU B 195      51.473  46.333  52.484 1.000 68.61
ATOM   3830  CD2  LEU B 195      51.917  43.868  52.320 1.000 77.73
```

FIGURE 80

```
ATOM   3831  C    LEU B 195      50.270  46.236  56.412  1.000101.84
ATOM   3832  O    LEU B 195      49.132  45.812  56.210  1.000107.43
ATOM   3833  N    ASP B 196      50.667  46.740  57.570  1.000100.14
ATOM   3834  CA   ASP B 196      49.834  46.918  58.754  1.000 95.50
ATOM   3835  CB   ASP B 196      49.258  45.605  59.253  1.000 93.87
ATOM   3836  CG   ASP B 196      50.159  44.699  60.049  1.000 86.73
ATOM   3837  OD1  ASP B 196      51.251  44.300  59.589  1.000 56.18
ATOM   3838  OD2  ASP B 196      49.770  44.325  61.183  1.000 68.86
ATOM   3839  C    ASP B 196      50.665  47.613  59.833  1.000 91.65
ATOM   3840  O    ASP B 196      51.757  47.144  60.157  1.000 97.39
ATOM   3841  N    ALA B 197      50.175  48.732  60.358  1.000 87.23
ATOM   3842  CA   ALA B 197      50.971  49.522  61.291  1.000 84.73
ATOM   3843  CB   ALA B 197      51.043  50.971  60.832  1.000 82.95
ATOM   3844  C    ALA B 197      50.426  49.456  62.716  1.000 82.50
ATOM   3845  O    ALA B 197      51.192  49.650  63.662  1.000 66.61
ATOM   3846  N    HIS B 198      49.132  49.213  62.833  1.000 82.67
ATOM   3847  CA   HIS B 198      48.373  49.029  64.057  1.000 77.93
ATOM   3848  CB   HIS B 198      47.927  50.338  64.697  1.000 77.67
ATOM   3849  CG   HIS B 198      48.200  51.573  63.899  1.000 84.79
ATOM   3850  ND1  HIS B 198      47.669  51.785  62.645  1.000 86.88
ATOM   3851  CE1  HIS B 198      48.085  52.952  62.182  1.000 88.81
ATOM   3852  NE2  HIS B 198      48.869  53.503  63.089  1.000 87.71
ATOM   3853  CD2  HIS B 198      48.959  52.659  64.170  1.000 85.49
ATOM   3854  C    HIS B 198      47.141  48.164  63.752  1.000 75.55
ATOM   3855  O    HIS B 198      46.055  48.678  63.493  1.000 83.33
ATOM   3856  N    ARG B 199      47.365  46.860  63.783  1.000 63.26
ATOM   3857  CA   ARG B 199      46.380  45.839  63.475  1.000 55.42
ATOM   3858  CB   ARG B 199      47.074  44.642  62.808  1.000 56.72
ATOM   3859  CG   ARG B 199      46.181  43.423  62.663  1.000 47.99
ATOM   3860  CD   ARG B 199      46.961  42.174  62.308  1.000 37.39
ATOM   3861  NE   ARG B 199      48.216  42.423  61.614  1.000 35.84
ATOM   3862  CZ   ARG B 199      49.253  41.591  61.677  1.000 43.79
ATOM   3863  NH1  ARG B 199      49.171  40.475  62.398  1.000 20.33
ATOM   3864  NH2  ARG B 199      50.368  41.875  61.018  1.000 25.11
ATOM   3865  C    ARG B 199      45.629  45.376  64.717  1.000 43.83
ATOM   3866  O    ARG B 199      46.181  45.353  65.817  1.000 40.98
ATOM   3867  N    LEU B 200      44.361  45.010  64.551  1.000 35.65
ATOM   3868  CA   LEU B 200      43.571  44.511  65.672  1.000 34.82
ATOM   3869  CB   LEU B 200      42.096  44.866  65.560  1.000 37.89
ATOM   3870  CG   LEU B 200      41.296  45.146  66.831  1.000 47.74
ATOM   3871  CD1  LEU B 200      41.329  43.974  67.800  1.000 44.43
ATOM   3872  CD2  LEU B 200      41.794  46.411  67.514  1.000 55.08
ATOM   3873  C    LEU B 200      43.707  42.991  65.738  1.000 36.55
ATOM   3874  O    LEU B 200      43.563  42.331  64.706  1.000 39.15
ATOM   3875  N    ILE B 201      43.977  42.484  66.938  1.000 29.95
ATOM   3876  CA   ILE B 201      44.033  41.033  67.101  1.000 25.47
ATOM   3877  CB   ILE B 201      45.314  40.531  67.770  1.000 25.78
ATOM   3878  CG1  ILE B 201      46.630  40.929  67.102  1.000 24.11
ATOM   3879  CD1  ILE B 201      46.743  40.486  65.660  1.000 22.88
ATOM   3880  CG2  ILE B 201      45.271  39.009  67.912  1.000 28.86
ATOM   3881  C    ILE B 201      42.824  40.609  67.935  1.000 25.30
ATOM   3882  O    ILE B 201      42.468  41.326  68.864  1.000 36.64
```

FIGURE 81

```
ATOM   3883  N   ARG B 202      42.229  39.478  67.597  1.000  29.04
ATOM   3884  CA  ARG B 202      41.111  38.919  68.353  1.000  28.15
ATOM   3885  CB  ARG B 202      39.928  38.698  67.421  1.000  32.44
ATOM   3886  CG  ARG B 202      38.587  39.177  67.941  1.000  38.49
ATOM   3887  CD  ARG B 202      38.061  40.347  67.121  1.000  51.50
ATOM   3888  NE  ARG B 202      36.996  41.057  67.815  1.000  62.80
ATOM   3889  CZ  ARG B 202      36.709  42.345  67.754  1.000  72.90
ATOM   3890  NH1 ARG B 202      37.410  43.184  67.004  1.000  64.58
ATOM   3891  NH2 ARG B 202      35.690  42.818  68.467  1.000  95.35
ATOM   3892  C   ARG B 202      41.552  37.621  69.013  1.000  24.66
ATOM   3893  O   ARG B 202      41.976  36.706  68.299  1.000  31.26
ATOM   3894  N   HIS B 203      41.479  37.532  70.330  1.000  19.54
ATOM   3895  CA  HIS B 203      41.943  36.336  71.046  1.000  27.13
ATOM   3896  CB  HIS B 203      43.011  36.754  72.047  1.000  23.50
ATOM   3897  CG  HIS B 203      43.762  35.711  72.798  1.000  26.59
ATOM   3898  ND1 HIS B 203      43.264  35.062  73.902  1.000  33.06
ATOM   3899  CE1 HIS B 203      44.154  34.200  74.365  1.000  29.95
ATOM   3900  NE2 HIS B 203      45.231  34.264  73.603  1.000  28.32
ATOM   3901  CD2 HIS B 203      45.012  35.203  72.620  1.000  29.08
ATOM   3902  C   HIS B 203      40.790  35.608  71.729  1.000  29.92
ATOM   3903  O   HIS B 203      40.060  36.152  72.557  1.000  25.16
ATOM   3904  N   PHE B 204      40.599  34.337  71.385  1.000  23.26
ATOM   3905  CA  PHE B 204      39.474  33.561  71.878  1.000  17.30
ATOM   3906  CB  PHE B 204      38.735  32.923  70.702  1.000  21.59
ATOM   3907  CG  PHE B 204      38.310  33.929  69.657  1.000  29.41
ATOM   3908  CD1 PHE B 204      39.097  34.183  68.548  1.000  28.21
ATOM   3909  CE1 PHE B 204      38.720  35.091  67.585  1.000  29.05
ATOM   3910  CZ  PHE B 204      37.537  35.792  67.732  1.000  29.20
ATOM   3911  CE2 PHE B 204      36.737  35.544  68.829  1.000  29.69
ATOM   3912  CD2 PHE B 204      37.114  34.616  69.779  1.000  29.48
ATOM   3913  C   PHE B 204      39.947  32.481  72.844  1.000  28.09
ATOM   3914  O   PHE B 204      40.557  31.502  72.406  1.000  31.26
ATOM   3915  N   HIS B 205      39.676  32.681  74.133  1.000  18.80
ATOM   3916  CA  HIS B 205      40.188  31.784  75.156  1.000  21.65
ATOM   3917  CB  HIS B 205      40.883  32.621  76.249  1.000  23.81
ATOM   3918  CG  HIS B 205      41.692  31.816  77.216  1.000  24.84
ATOM   3919  ND1 HIS B 205      42.280  32.371  78.328  1.000  29.84
ATOM   3920  CE1 HIS B 205      42.931  31.440  78.997  1.000  32.02
ATOM   3921  NE2 HIS B 205      42.793  30.285  78.364  1.000  25.82
ATOM   3922  CD2 HIS B 205      42.029  30.502  77.251  1.000  28.58
ATOM   3923  C   HIS B 205      39.114  30.895  75.778  1.000  28.42
ATOM   3924  O   HIS B 205      38.277  31.351  76.564  1.000  24.92
ATOM   3925  N   TYR B 206      39.190  29.613  75.438  1.000  26.78
ATOM   3926  CA  TYR B 206      38.347  28.572  76.005  1.000  25.27
ATOM   3927  CB  TYR B 206      38.308  27.361  75.091  1.000  25.32
ATOM   3928  CG  TYR B 206      37.302  26.289  75.429  1.000  21.60
ATOM   3929  CD1 TYR B 206      35.946  26.502  75.229  1.000  21.30
ATOM   3930  CE1 TYR B 206      35.027  25.519  75.537  1.000  22.97
ATOM   3931  CZ  TYR B 206      35.457  24.313  76.039  1.000  26.67
ATOM   3932  OH  TYR B 206      34.536  23.336  76.341  1.000  53.16
ATOM   3933  CE2 TYR B 206      36.799  24.073  76.248  1.000  25.66
ATOM   3934  CD2 TYR B 206      37.708  25.067  75.939  1.000  23.88
```

FIGURE 82

```
ATOM   3935  C    TYR B 206      38.850  28.115  77.369  1.000  23.63
ATOM   3936  O    TYR B 206      39.927  27.531  77.442  1.000  22.75
ATOM   3937  N    THR B 207      38.078  28.362  78.419  1.000  28.47
ATOM   3938  CA   THR B 207      38.594  28.239  79.781  1.000  34.58
ATOM   3939  CB   THR B 207      38.251  29.523  80.579  1.000  29.68
ATOM   3940  OG1  THR B 207      36.868  29.844  80.409  1.000  32.12
ATOM   3941  CG2  THR B 207      39.025  30.717  80.039  1.000  27.42
ATOM   3942  C    THR B 207      38.079  27.031  80.540  1.000  38.19
ATOM   3943  O    THR B 207      38.351  26.891  81.740  1.000  46.50
ATOM   3944  N    VAL B 208      37.333  26.118  79.912  1.000  36.23
ATOM   3945  CA   VAL B 208      36.752  25.066  80.760  1.000  32.80
ATOM   3946  CB   VAL B 208      35.226  25.275  80.831  1.000  28.19
ATOM   3947  CG1  VAL B 208      34.942  26.537  81.638  1.000  27.38
ATOM   3948  CG2  VAL B 208      34.601  25.387  79.454  1.000  32.82
ATOM   3949  C    VAL B 208      37.089  23.660  80.314  1.000  39.69
ATOM   3950  O    VAL B 208      36.491  22.707  80.825  1.000  41.93
ATOM   3951  N    TRP B 209      38.039  23.467  79.397  1.000  40.70
ATOM   3952  CA   TRP B 209      38.445  22.102  79.049  1.000  36.47
ATOM   3953  CB   TRP B 209      39.577  22.083  78.032  1.000  31.02
ATOM   3954  CG   TRP B 209      39.652  20.846  77.194  1.000  28.16
ATOM   3955  CD1  TRP B 209      39.949  19.583  77.597  1.000  27.98
ATOM   3956  NE1  TRP B 209      39.921  18.716  76.527  1.000  33.60
ATOM   3957  CE2  TRP B 209      39.600  19.427  75.396  1.000  27.75
ATOM   3958  CD2  TRP B 209      39.426  20.768  75.775  1.000  24.17
ATOM   3959  CE3  TRP B 209      39.092  21.719  74.805  1.000  28.32
ATOM   3960  CZ3  TRP B 209      38.941  21.300  73.496  1.000  34.71
ATOM   3961  CH2  TRP B 209      39.121  19.954  73.151  1.000  31.19
ATOM   3962  CZ2  TRP B 209      39.450  18.999  74.078  1.000  21.94
ATOM   3963  C    TRP B 209      38.888  21.358  80.309  1.000  39.28
ATOM   3964  O    TRP B 209      39.737  21.872  81.039  1.000  33.04
ATOM   3965  N    PRO B 210      38.325  20.185  80.563  1.000  38.49
ATOM   3966  CA   PRO B 210      38.574  19.480  81.825  1.000  33.55
ATOM   3967  CB   PRO B 210      37.657  18.251  81.742  1.000  33.67
ATOM   3968  CG   PRO B 210      36.654  18.591  80.688  1.000  33.65
ATOM   3969  CD   PRO B 210      37.408  19.429  79.689  1.000  31.99
ATOM   3970  C    PRO B 210      40.020  19.024  81.943  1.000  39.20
ATOM   3971  O    PRO B 210      40.737  18.955  80.943  1.000  45.02
ATOM   3972  N    ASP B 211      40.425  18.710  83.167  1.000  42.94
ATOM   3973  CA   ASP B 211      41.772  18.214  83.426  1.000  48.87
ATOM   3974  CB   ASP B 211      42.010  18.080  84.934  1.000  57.39
ATOM   3975  CG   ASP B 211      42.375  19.402  85.586  1.000  66.45
ATOM   3976  OD1  ASP B 211      42.136  20.463  84.966  1.000  52.25
ATOM   3977  OD2  ASP B 211      42.903  19.369  86.721  1.000  87.29
ATOM   3978  C    ASP B 211      42.020  16.872  82.747  1.000  39.83
ATOM   3979  O    ASP B 211      43.122  16.559  82.300  1.000  47.17
ATOM   3980  N    HIS B 212      40.987  16.044  82.672  1.000  40.86
ATOM   3981  CA   HIS B 212      41.117  14.730  82.050  1.000  47.36
ATOM   3982  CB   HIS B 212      41.076  13.599  83.066  1.000  59.57
ATOM   3983  CG   HIS B 212      42.146  13.536  84.102  1.000  71.70
ATOM   3984  ND1  HIS B 212      42.060  14.183  85.313  1.000  74.03
ATOM   3985  CE1  HIS B 212      43.144  13.953  86.032  1.000  77.44
ATOM   3986  NE2  HIS B 212      43.938  13.155  85.336  1.000  79.18
```

FIGURE 83

```
ATOM   3987  CD2 HIS B 212      43.332  12.879  84.131  1.000 78.65
ATOM   3988  C   HIS B 212      39.976  14.556  81.049  1.000 44.25
ATOM   3989  O   HIS B 212      38.865  14.996  81.354  1.000 50.41
ATOM   3990  N   GLY B 213      40.237  13.936  79.906  1.000 43.28
ATOM   3991  CA  GLY B 213      39.210  13.707  78.905  1.000 34.05
ATOM   3992  C   GLY B 213      38.716  14.968  78.223  1.000 36.21
ATOM   3993  O   GLY B 213      39.361  16.015  78.258  1.000 46.36
ATOM   3994  N   VAL B 214      37.550  14.875  77.595  1.000 38.56
ATOM   3995  CA  VAL B 214      36.931  15.933  76.818  1.000 39.41
ATOM   3996  CB  VAL B 214      36.356  15.345  75.510  1.000 40.18
ATOM   3997  CG1 VAL B 214      37.467  14.671  74.725  1.000 35.68
ATOM   3998  CG2 VAL B 214      35.226  14.382  75.831  1.000 48.90
ATOM   3999  C   VAL B 214      35.809  16.620  77.575  1.000 43.12
ATOM   4000  O   VAL B 214      35.366  16.105  78.602  1.000 64.15
ATOM   4001  N   PRO B 215      35.344  17.763  77.089  1.000 42.93
ATOM   4002  CA  PRO B 215      34.151  18.378  77.679  1.000 40.14
ATOM   4003  CB  PRO B 215      33.784  19.448  76.653  1.000 42.40
ATOM   4004  CG  PRO B 215      35.090  19.835  76.040  1.000 41.27
ATOM   4005  CD  PRO B 215      35.888  18.567  75.982  1.000 37.96
ATOM   4006  C   PRO B 215      33.008  17.374  77.800  1.000 45.59
ATOM   4007  O   PRO B 215      32.766  16.617  76.859  1.000 40.94
ATOM   4008  N   GLU B 216      32.333  17.381  78.942  1.000 50.95
ATOM   4009  CA  GLU B 216      31.204  16.498  79.215  1.000 53.03
ATOM   4010  CB  GLU B 216      30.693  16.699  80.643  1.000 59.73
ATOM   4011  CG  GLU B 216      29.489  15.856  81.030  1.000 65.18
ATOM   4012  CD  GLU B 216      28.745  16.402  82.236  1.000 71.96
ATOM   4013  OE1 GLU B 216      29.388  16.616  83.292  1.000 79.59
ATOM   4014  OE2 GLU B 216      27.515  16.622  82.138  1.000 56.48
ATOM   4015  C   GLU B 216      30.083  16.748  78.217  1.000 50.99
ATOM   4016  O   GLU B 216      29.274  15.873  77.907  1.000 49.11
ATOM   4017  N   THR B 217      30.038  17.981  77.699  1.000 46.20
ATOM   4018  CA  THR B 217      29.017  18.266  76.693  1.000 46.03
ATOM   4019  CB  THR B 217      28.092  19.430  77.079  1.000 38.73
ATOM   4020  OG1 THR B 217      26.778  19.154  76.564  1.000 61.70
ATOM   4021  CG2 THR B 217      28.539  20.738  76.440  1.000 30.35
ATOM   4022  C   THR B 217      29.666  18.582  75.347  1.000 49.34
ATOM   4023  O   THR B 217      30.797  19.060  75.290  1.000 48.39
ATOM   4024  N   THR B 218      28.918  18.307  74.287  1.000 45.15
ATOM   4025  CA  THR B 218      29.328  18.657  72.938  1.000 38.83
ATOM   4026  CB  THR B 218      28.599  17.780  71.908  1.000 40.05
ATOM   4027  OG1 THR B 218      27.195  18.052  72.006  1.000 47.92
ATOM   4028  CG2 THR B 218      28.789  16.302  72.204  1.000 37.44
ATOM   4029  C   THR B 218      29.025  20.122  72.648  1.000 40.85
ATOM   4030  O   THR B 218      29.781  20.830  71.985  1.000 49.43
ATOM   4031  N   GLN B 219      27.886  20.590  73.149  1.000 39.19
ATOM   4032  CA  GLN B 219      27.423  21.943  72.863  1.000 40.36
ATOM   4033  CB  GLN B 219      26.112  22.238  73.599  1.000 47.97
ATOM   4034  CG  GLN B 219      25.063  22.954  72.773  1.000 57.22
ATOM   4035  CD  GLN B 219      24.636  24.294  73.334  1.000 65.42
ATOM   4036  OE1 GLN B 219      24.948  24.653  74.471  1.000 76.84
ATOM   4037  NE2 GLN B 219      23.901  25.061  72.531  1.000 73.40
ATOM   4038  C   GLN B 219      28.486  22.976  73.229  1.000 40.36
```

FIGURE 84

```
ATOM   4039  O    GLN B 219      28.610  23.987  72.535  1.000 40.22
ATOM   4040  N    SER B 220      29.229  22.716  74.293  1.000 38.53
ATOM   4041  CA   SER B 220      30.296  23.588  74.774  1.000 40.28
ATOM   4042  CB   SER B 220      31.039  22.897  75.927  1.000 36.16
ATOM   4043  OG   SER B 220      31.787  23.830  76.681  1.000 43.68
ATOM   4044  C    SER B 220      31.282  23.969  73.678  1.000 39.40
ATOM   4045  O    SER B 220      31.451  25.138  73.322  1.000 40.25
ATOM   4046  N    LEU B 221      31.977  22.990  73.102  1.000 42.59
ATOM   4047  CA   LEU B 221      32.991  23.314  72.093  1.000 37.94
ATOM   4048  CB   LEU B 221      33.912  22.118  71.864  1.000 36.81
ATOM   4049  CG   LEU B 221      35.282  22.419  71.247  1.000 44.42
ATOM   4050  CD1  LEU B 221      36.044  23.445  72.073  1.000 31.31
ATOM   4051  CD2  LEU B 221      36.111  21.152  71.101  1.000 39.34
ATOM   4052  C    LEU B 221      32.323  23.778  70.805  1.000 37.27
ATOM   4053  O    LEU B 221      32.776  24.708  70.136  1.000 50.72
ATOM   4054  N    ILE B 222      31.217  23.135  70.456  1.000 35.78
ATOM   4055  CA   ILE B 222      30.451  23.526  69.277  1.000 40.80
ATOM   4056  CB   ILE B 222      29.169  22.678  69.172  1.000 36.72
ATOM   4057  CG1  ILE B 222      29.431  21.240  68.707  1.000 28.35
ATOM   4058  CD1  ILE B 222      28.159  20.425  68.645  1.000 27.69
ATOM   4059  CG2  ILE B 222      28.131  23.351  68.293  1.000 33.22
ATOM   4060  C    ILE B 222      30.103  25.005  69.293  1.000 36.01
ATOM   4061  O    ILE B 222      30.270  25.723  68.300  1.000 32.03
ATOM   4062  N    GLN B 223      29.607  25.516  70.425  1.000 29.32
ATOM   4063  CA   GLN B 223      29.310  26.951  70.415  1.000 35.50
ATOM   4064  CB   GLN B 223      28.535  27.378  71.662  1.000 46.37
ATOM   4065  CG   GLN B 223      27.155  27.943  71.365  1.000 60.65
ATOM   4066  CD   GLN B 223      26.869  29.302  71.968  1.000 64.54
ATOM   4067  OE1  GLN B 223      27.164  30.353  71.390  1.000 52.88
ATOM   4068  NE2  GLN B 223      26.268  29.309  73.157  1.000 64.34
ATOM   4069  C    GLN B 223      30.601  27.759  70.275  1.000 32.82
ATOM   4070  O    GLN B 223      30.633  28.704  69.482  1.000 40.85
ATOM   4071  N    PHE B 224      31.643  27.396  71.019  1.000 25.74
ATOM   4072  CA   PHE B 224      32.907  28.131  70.963  1.000 27.71
ATOM   4073  CB   PHE B 224      33.949  27.479  71.869  1.000 24.79
ATOM   4074  CG   PHE B 224      35.314  28.117  71.858  1.000 25.53
ATOM   4075  CD1  PHE B 224      35.532  29.343  72.466  1.000 23.05
ATOM   4076  CE1  PHE B 224      36.785  29.925  72.476  1.000 27.91
ATOM   4077  CZ   PHE B 224      37.861  29.306  71.869  1.000 21.81
ATOM   4078  CE2  PHE B 224      37.654  28.086  71.253  1.000 21.78
ATOM   4079  CD2  PHE B 224      36.400  27.506  71.255  1.000 21.56
ATOM   4080  C    PHE B 224      33.441  28.175  69.535  1.000 25.15
ATOM   4081  O    PHE B 224      33.832  29.206  68.999  1.000 25.80
ATOM   4082  N    VAL B 225      33.454  27.006  68.903  1.000 26.67
ATOM   4083  CA   VAL B 225      33.933  26.919  67.532  1.000 29.86
ATOM   4084  CB   VAL B 225      33.999  25.467  67.029  1.000 20.12
ATOM   4085  CG1  VAL B 225      34.080  25.457  65.499  1.000 25.23
ATOM   4086  CG2  VAL B 225      35.171  24.740  67.654  1.000 26.39
ATOM   4087  C    VAL B 225      33.042  27.709  66.581  1.000 34.74
ATOM   4088  O    VAL B 225      33.545  28.329  65.644  1.000 35.87
ATOM   4089  N    ARG B 226      31.732  27.673  66.823  1.000 30.68
ATOM   4090  CA   ARG B 226      30.851  28.464  65.957  1.000 28.68
```

FIGURE 85

```
ATOM   4091  CB   ARG B 226      29.398  28.070  66.220  1.00  35.23
ATOM   4092  CG   ARG B 226      29.089  26.678  65.666  1.00  37.49
ATOM   4093  CD   ARG B 226      27.609  26.495  65.389  1.00  45.19
ATOM   4094  NE   ARG B 226      27.284  25.237  64.718  1.00  47.88
ATOM   4095  CZ   ARG B 226      26.232  24.481  65.025  1.00  52.72
ATOM   4096  NH1  ARG B 226      25.394  24.845  65.994  1.00  43.21
ATOM   4097  NH2  ARG B 226      26.003  23.348  64.369  1.00  42.49
ATOM   4098  C    ARG B 226      31.120  29.943  66.166  1.00  34.17
ATOM   4099  O    ARG B 226      31.166  30.741  65.228  1.00  36.74
ATOM   4100  N    THR B 227      31.340  30.366  67.409  1.00  28.96
ATOM   4101  CA   THR B 227      31.672  31.767  67.647  1.00  24.50
ATOM   4102  CB   THR B 227      31.786  32.029  69.165  1.00  34.83
ATOM   4103  OG1  THR B 227      30.553  31.661  69.790  1.00  51.39
ATOM   4104  CG2  THR B 227      32.011  33.502  69.440  1.00  28.79
ATOM   4105  C    THR B 227      32.980  32.179  66.987  1.00  26.81
ATOM   4106  O    THR B 227      33.096  33.245  66.375  1.00  44.96
ATOM   4107  N    VAL B 228      34.011  31.345  67.106  1.00  28.59
ATOM   4108  CA   VAL B 228      35.306  31.681  66.512  1.00  31.86
ATOM   4109  CB   VAL B 228      36.413  30.705  66.949  1.00  36.11
ATOM   4110  CG1  VAL B 228      37.648  30.824  66.068  1.00  29.10
ATOM   4111  CG2  VAL B 228      36.821  30.927  68.408  1.00  24.69
ATOM   4112  C    VAL B 228      35.169  31.706  64.996  1.00  31.35
ATOM   4113  O    VAL B 228      35.760  32.543  64.321  1.00  23.32
ATOM   4114  N    ARG B 229      34.386  30.796  64.422  1.00  32.50
ATOM   4115  CA   ARG B 229      34.313  30.758  62.950  1.00  35.15
ATOM   4116  CB   ARG B 229      33.635  29.463  62.517  1.00  29.29
ATOM   4117  CG   ARG B 229      33.187  29.363  61.077  1.00  32.09
ATOM   4118  CD   ARG B 229      34.246  29.762  60.075  1.00  36.20
ATOM   4119  NE   ARG B 229      35.498  29.024  60.225  1.00  34.10
ATOM   4120  CZ   ARG B 229      36.530  29.145  59.398  1.00  31.12
ATOM   4121  NH1  ARG B 229      36.458  29.976  58.364  1.00  29.99
ATOM   4122  NH2  ARG B 229      37.637  28.440  59.603  1.00  25.49
ATOM   4123  C    ARG B 229      33.634  32.009  62.407  1.00  37.12
ATOM   4124  O    ARG B 229      34.041  32.534  61.363  1.00  38.65
ATOM   4125  N    ASP B 230      32.621  32.517  63.102  1.00  33.49
ATOM   4126  CA   ASP B 230      31.983  33.770  62.716  1.00  34.08
ATOM   4127  CB   ASP B 230      30.892  34.161  63.717  1.00  43.05
ATOM   4128  CG   ASP B 230      29.629  33.328  63.559  1.00  58.43
ATOM   4129  OD1  ASP B 230      29.284  32.975  62.409  1.00  90.62
ATOM   4130  OD2  ASP B 230      28.986  33.029  64.589  1.00  59.92
ATOM   4131  C    ASP B 230      32.996  34.899  62.621  1.00  32.94
ATOM   4132  O    ASP B 230      32.925  35.752  61.737  1.00  48.01
ATOM   4133  N    TYR B 231      33.967  34.941  63.537  1.00  28.38
ATOM   4134  CA   TYR B 231      34.903  36.062  63.457  1.00  31.35
ATOM   4135  CB   TYR B 231      35.624  36.312  64.779  1.00  33.15
ATOM   4136  CG   TYR B 231      34.805  37.080  65.791  1.00  35.44
ATOM   4137  CD1  TYR B 231      33.863  36.439  66.582  1.00  39.03
ATOM   4138  CE1  TYR B 231      33.119  37.148  67.508  1.00  45.49
ATOM   4139  CZ   TYR B 231      33.311  38.506  67.647  1.00  43.26
ATOM   4140  OH   TYR B 231      32.572  39.217  68.563  1.00  57.83
ATOM   4141  CE2  TYR B 231      34.240  39.164  66.874  1.00  37.85
ATOM   4142  CD2  TYR B 231      34.981  38.448  65.951  1.00  38.89
```

FIGURE 86

```
ATOM   4143  C    TYR B 231      35.937  35.836  62.358  1.000  32.28
ATOM   4144  O    TYR B 231      36.404  36.825  61.794  1.000  29.21
ATOM   4145  N    ILE B 232      36.288  34.583  62.079  1.000  29.70
ATOM   4146  CA   ILE B 232      37.274  34.317  61.032  1.000  26.08
ATOM   4147  CB   ILE B 232      37.731  32.855  60.956  1.000  26.12
ATOM   4148  CG1  ILE B 232      38.610  32.387  62.123  1.000  28.07
ATOM   4149  CD1  ILE B 232      38.492  30.888  62.342  1.000  30.24
ATOM   4150  CG2  ILE B 232      38.435  32.591  59.628  1.000  13.37
ATOM   4151  C    ILE B 232      36.664  34.713  59.686  1.000  24.35
ATOM   4152  O    ILE B 232      37.327  35.289  58.829  1.000  42.38
ATOM   4153  N    ASN B 233      35.384  34.401  59.536  1.000  24.49
ATOM   4154  CA   ASN B 233      34.678  34.774  58.310  1.000  35.31
ATOM   4155  CB   ASN B 233      33.288  34.125  58.331  1.000  33.92
ATOM   4156  CG   ASN B 233      33.411  32.644  58.011  1.000  35.63
ATOM   4157  OD1  ASN B 233      34.456  32.194  57.542  1.000  30.58
ATOM   4158  ND2  ASN B 233      32.353  31.889  58.275  1.000  39.02
ATOM   4159  C    ASN B 233      34.602  36.285  58.135  1.000  39.52
ATOM   4160  O    ASN B 233      34.526  36.785  57.012  1.000  35.15
ATOM   4161  N    ARG B 234      34.636  37.051  59.217  1.000  38.25
ATOM   4162  CA   ARG B 234      34.605  38.501  59.186  1.000  36.43
ATOM   4163  CB   ARG B 234      33.826  39.055  60.391  1.000  49.91
ATOM   4164  CG   ARG B 234      32.397  38.562  60.514  1.000  60.74
ATOM   4165  CD   ARG B 234      31.528  39.486  61.349  1.000  58.98
ATOM   4166  NE   ARG B 234      30.847  38.790  62.440  1.000  54.26
ATOM   4167  CZ   ARG B 234      31.260  38.870  63.702  1.000  52.64
ATOM   4168  NH1  ARG B 234      32.325  39.608  63.990  1.000  52.91
ATOM   4169  NH2  ARG B 234      30.626  38.228  64.671  1.000  46.68
ATOM   4170  C    ARG B 234      35.998  39.117  59.211  1.000  33.22
ATOM   4171  O    ARG B 234      36.115  40.331  59.418  1.000  48.40
ATOM   4172  N    SER B 235      37.061  38.347  59.020  1.000  28.34
ATOM   4173  CA   SER B 235      38.421  38.885  59.043  1.000  32.54
ATOM   4174  CB   SER B 235      39.279  38.104  60.042  1.000  34.07
ATOM   4175  OG   SER B 235      38.666  38.004  61.314  1.000  34.54
ATOM   4176  C    SER B 235      39.076  38.841  57.671  1.000  40.54
ATOM   4177  O    SER B 235      40.079  38.152  57.421  1.000  36.22
ATOM   4178  N    PRO B 236      38.561  39.592  56.707  1.000  42.54
ATOM   4179  CA   PRO B 236      39.064  39.383  55.341  1.000  46.53
ATOM   4180  CB   PRO B 236      38.093  40.193  54.494  1.000  50.52
ATOM   4181  CG   PRO B 236      37.658  41.297  55.406  1.000  55.25
ATOM   4182  CD   PRO B 236      37.577  40.675  56.775  1.000  50.10
ATOM   4183  C    PRO B 236      40.491  39.914  55.278  1.000  45.59
ATOM   4184  O    PRO B 236      40.815  40.861  56.008  1.000  34.18
ATOM   4185  N    GLY B 237      41.304  39.292  54.422  1.000  33.61
ATOM   4186  CA   GLY B 237      42.692  39.734  54.313  1.000  30.68
ATOM   4187  C    GLY B 237      43.533  39.226  55.468  1.000  27.98
ATOM   4188  O    GLY B 237      44.720  39.537  55.554  1.000  36.96
ATOM   4189  N    ALA B 238      42.940  38.440  56.365  1.000  31.80
ATOM   4190  CA   ALA B 238      43.680  37.890  57.499  1.000  29.23
ATOM   4191  CB   ALA B 238      42.706  37.471  58.590  1.000  24.93
ATOM   4192  C    ALA B 238      44.543  36.705  57.090  1.000  29.82
ATOM   4193  O    ALA B 238      44.178  35.916  56.220  1.000  23.87
ATOM   4194  N    GLY B 239      45.703  36.544  57.722  1.000  26.54
```

FIGURE 87

```
ATOM   4195  CA   GLY B 239      46.486  35.346  57.425  1.000  26.69
ATOM   4196  C    GLY B 239      45.930  34.157  58.191  1.000  26.81
ATOM   4197  O    GLY B 239      44.747  34.100  58.534  1.000  29.92
ATOM   4198  N    PRO B 240      46.775  33.188  58.496  1.000  20.79
ATOM   4199  CA   PRO B 240      46.306  31.999  59.199  1.000  22.49
ATOM   4200  CB   PRO B 240      47.566  31.135  59.350  1.000  22.87
ATOM   4201  CG   PRO B 240      48.509  31.669  58.321  1.000  27.01
ATOM   4202  CD   PRO B 240      48.223  33.140  58.223  1.000  26.31
ATOM   4203  C    PRO B 240      45.763  32.328  60.583  1.000  25.93
ATOM   4204  O    PRO B 240      46.235  33.194  61.314  1.000  24.16
ATOM   4205  N    THR B 241      44.723  31.581  60.949  1.000  27.93
ATOM   4206  CA   THR B 241      44.224  31.620  62.317  1.000  18.48
ATOM   4207  CB   THR B 241      42.791  31.078  62.389  1.000  20.63
ATOM   4208  OG1  THR B 241      41.906  31.922  61.633  1.000  18.88
ATOM   4209  CG2  THR B 241      42.286  31.088  63.823  1.000  21.94
ATOM   4210  C    THR B 241      45.177  30.793  63.182  1.000  26.66
ATOM   4211  O    THR B 241      45.459  29.624  62.873  1.000  23.21
ATOM   4212  N    VAL B 242      45.693  31.386  64.249  1.000  26.37
ATOM   4213  CA   VAL B 242      46.571  30.686  65.183  1.000  20.09
ATOM   4214  CB   VAL B 242      47.476  31.650  65.969  1.000  17.77
ATOM   4215  CG1  VAL B 242      47.993  30.997  67.245  1.000  24.64
ATOM   4216  CG2  VAL B 242      48.652  32.105  65.118  1.000  18.35
ATOM   4217  C    VAL B 242      45.745  29.871  66.171  1.000  21.82
ATOM   4218  O    VAL B 242      44.763  30.387  66.707  1.000  22.41
ATOM   4219  N    VAL B 243      46.124  28.618  66.415  1.000  24.38
ATOM   4220  CA   VAL B 243      45.444  27.807  67.426  1.000  16.94
ATOM   4221  CB   VAL B 243      44.512  26.759  66.797  1.000  22.95
ATOM   4222  CG1  VAL B 243      43.664  26.072  67.863  1.000  26.25
ATOM   4223  CG2  VAL B 243      43.612  27.396  65.744  1.000  15.21
ATOM   4224  C    VAL B 243      46.477  27.132  68.314  1.000  19.30
ATOM   4225  O    VAL B 243      47.444  26.568  67.807  1.000  19.80
ATOM   4226  N    HIS B 244      46.315  27.189  69.642  1.000  17.73
ATOM   4227  CA   HIS B 244      47.275  26.507  70.500  1.000  23.12
ATOM   4228  CB   HIS B 244      48.487  27.365  70.842  1.000  20.11
ATOM   4229  CG   HIS B 244      48.250  28.450  71.842  1.000  20.40
ATOM   4230  ND1  HIS B 244      48.315  28.263  73.200  1.000  23.45
ATOM   4231  CE1  HIS B 244      48.067  29.396  73.828  1.000  22.23
ATOM   4232  NE2  HIS B 244      47.850  30.330  72.921  1.000  22.87
ATOM   4233  CD2  HIS B 244      47.962  29.762  71.675  1.000  18.95
ATOM   4234  C    HIS B 244      46.582  26.046  71.783  1.000  26.22
ATOM   4235  O    HIS B 244      45.501  26.501  72.131  1.000  23.10
ATOM   4236  N    CYS B 245      47.252  25.119  72.440  1.000  22.02
ATOM   4237  CA   CYS B 245      46.907  24.642  73.777  1.000  19.58
ATOM   4238  CB   CYS B 245      46.233  23.282  73.751  1.000  24.57
ATOM   4239  SG   CYS B 245      47.070  21.959  72.834  1.000  28.98
ATOM   4240  C    CYS B 245      48.229  24.655  74.539  1.000  28.34
ATOM   4241  O    CYS B 245      48.948  25.667  74.457  1.000  29.70
ATOM   4242  N    SER B 246      48.559  23.571  75.231  1.000  25.71
ATOM   4243  CA   SER B 246      49.846  23.537  75.921  1.000  18.89
ATOM   4244  CB   SER B 246      49.839  22.627  77.146  1.000  23.17
ATOM   4245  OG   SER B 246      51.066  22.797  77.853  1.000  25.65
ATOM   4246  C    SER B 246      50.934  23.087  74.951  1.000  24.25
```

FIGURE 88

```
ATOM   4247  O    SER B 246      51.940  23.789  74.856  1.000  33.31
ATOM   4248  N    ALA B 247      50.731  21.962  74.259  1.000  18.83
ATOM   4249  CA   ALA B 247      51.743  21.518  73.314  1.000  15.18
ATOM   4250  CB   ALA B 247      52.036  20.041  73.514  1.000  17.96
ATOM   4251  C    ALA B 247      51.363  21.733  71.851  1.000  26.35
ATOM   4252  O    ALA B 247      52.187  21.474  70.959  1.000  31.41
ATOM   4253  N    GLY B 248      50.146  22.178  71.569  1.000  21.25
ATOM   4254  CA   GLY B 248      49.642  22.228  70.206  1.000  20.49
ATOM   4255  C    GLY B 248      49.312  20.840  69.659  1.000  30.46
ATOM   4256  O    GLY B 248      49.670  20.541  68.517  1.000  41.55
ATOM   4257  N    VAL B 249      48.635  19.983  70.414  1.000  28.50
ATOM   4258  CA   VAL B 249      48.393  18.586  70.073  1.000  34.64
ATOM   4259  CB   VAL B 249      49.048  17.670  71.137  1.000  36.74
ATOM   4260  CG1  VAL B 249      50.523  17.496  70.828  1.000  29.63
ATOM   4261  CG2  VAL B 249      48.858  18.238  72.545  1.000  30.44
ATOM   4262  C    VAL B 249      46.931  18.172  69.964  1.000  33.93
ATOM   4263  O    VAL B 249      46.301  18.395  68.930  1.000  40.05
ATOM   4264  N    GLY B 250      46.392  17.537  71.003  1.000  28.29
ATOM   4265  CA   GLY B 250      45.069  16.957  71.039  1.000  22.14
ATOM   4266  C    GLY B 250      43.943  17.966  70.997  1.000  24.67
ATOM   4267  O    GLY B 250      43.137  17.979  70.063  1.000  30.05
ATOM   4268  N    ARG B 251      43.872  18.828  72.003  1.000  16.63
ATOM   4269  CA   ARG B 251      42.869  19.882  72.038  1.000  19.31
ATOM   4270  CB   ARG B 251      43.124  20.810  73.240  1.000  16.91
ATOM   4271  CG   ARG B 251      43.429  20.052  74.521  1.000  25.85
ATOM   4272  CD   ARG B 251      43.443  21.003  75.708  1.000  27.38
ATOM   4273  NE   ARG B 251      43.437  20.283  76.974  1.000  25.25
ATOM   4274  CZ   ARG B 251      43.500  20.852  78.167  1.000  28.05
ATOM   4275  NH1  ARG B 251      43.577  22.171  78.279  1.000  20.04
ATOM   4276  NH2  ARG B 251      43.485  20.081  79.246  1.000  33.27
ATOM   4277  C    ARG B 251      42.857  20.719  70.764  1.000  22.20
ATOM   4278  O    ARG B 251      41.814  20.925  70.142  1.000  37.10
ATOM   4279  N    THR B 252      44.023  21.228  70.372  1.000  25.42
ATOM   4280  CA   THR B 252      44.120  22.091  69.200  1.000  22.56
ATOM   4281  CB   THR B 252      45.571  22.546  68.965  1.000  23.97
ATOM   4282  OG1  THR B 252      45.903  23.531  69.956  1.000  25.35
ATOM   4283  CG2  THR B 252      45.734  23.196  67.600  1.000  15.93
ATOM   4284  C    THR B 252      43.631  21.357  67.965  1.000  20.90
ATOM   4285  O    THR B 252      42.825  21.833  67.170  1.000  27.79
ATOM   4286  N    GLY B 253      44.161  20.145  67.819  1.000  23.41
ATOM   4287  CA   GLY B 253      43.796  19.353  66.642  1.000  23.12
ATOM   4288  C    GLY B 253      42.313  19.031  66.705  1.000  28.00
ATOM   4289  O    GLY B 253      41.682  18.906  65.663  1.000  25.61
ATOM   4290  N    THR B 254      41.803  18.914  67.932  1.000  30.82
ATOM   4291  CA   THR B 254      40.382  18.631  68.136  1.000  28.89
ATOM   4292  CB   THR B 254      40.052  18.236  69.589  1.000  30.33
ATOM   4293  OG1  THR B 254      40.646  16.971  69.891  1.000  17.84
ATOM   4294  CG2  THR B 254      38.553  18.043  69.764  1.000  23.85
ATOM   4295  C    THR B 254      39.560  19.849  67.750  1.000  24.95
ATOM   4296  O    THR B 254      38.534  19.750  67.093  1.000  25.70
ATOM   4297  N    PHE B 255      40.023  21.033  68.168  1.000  20.14
ATOM   4298  CA   PHE B 255      39.330  22.238  67.761  1.000  18.66
```

FIGURE 89

```
ATOM   4299  CB   PHE B 255      40.055  23.472  68.309 1.000 20.98
ATOM   4300  CG   PHE B 255      39.468  24.795  67.891 1.000 25.32
ATOM   4301  CD1  PHE B 255      38.462  25.342  68.685 1.000 21.68
ATOM   4302  CE1  PHE B 255      37.893  26.550  68.349 1.000 20.94
ATOM   4303  CZ   PHE B 255      38.291  27.240  67.224 1.000 24.52
ATOM   4304  CE2  PHE B 255      39.287  26.713  66.419 1.000 22.92
ATOM   4305  CD2  PHE B 255      39.877  25.519  66.779 1.000 24.05
ATOM   4306  C    PHE B 255      39.255  22.352  66.239 1.000 20.18
ATOM   4307  O    PHE B 255      38.229  22.668  65.647 1.000 23.46
ATOM   4308  N    ILE B 256      40.401  22.192  65.592 1.000 14.95
ATOM   4309  CA   ILE B 256      40.468  22.444  64.155 1.000 19.23
ATOM   4310  CB   ILE B 256      41.923  22.480  63.668 1.000 24.98
ATOM   4311  CG1  ILE B 256      42.735  23.658  64.220 1.000 27.51
ATOM   4312  CD1  ILE B 256      44.198  23.613  63.833 1.000 28.76
ATOM   4313  CG2  ILE B 256      41.988  22.469  62.146 1.000 19.65
ATOM   4314  C    ILE B 256      39.642  21.413  63.395 1.000 21.66
ATOM   4315  O    ILE B 256      38.931  21.770  62.448 1.000 28.91
ATOM   4316  N    ALA B 257      39.699  20.142  63.782 1.000 18.05
ATOM   4317  CA   ALA B 257      38.802  19.169  63.158 1.000 19.47
ATOM   4318  CB   ALA B 257      38.987  17.798  63.775 1.000 21.30
ATOM   4319  C    ALA B 257      37.346  19.600  63.303 1.000 24.28
ATOM   4320  O    ALA B 257      36.588  19.578  62.335 1.000 29.52
ATOM   4321  N    LEU B 258      36.913  19.998  64.506 1.000 19.55
ATOM   4322  CA   LEU B 258      35.511  20.383  64.656 1.000 23.44
ATOM   4323  CB   LEU B 258      35.187  20.725  66.109 1.000 26.54
ATOM   4324  CG   LEU B 258      33.718  21.043  66.402 1.000 26.93
ATOM   4325  CD1  LEU B 258      32.830  19.879  65.989 1.000 33.89
ATOM   4326  CD2  LEU B 258      33.523  21.383  67.874 1.000 26.13
ATOM   4327  C    LEU B 258      35.162  21.561  63.747 1.000 26.19
ATOM   4328  O    LEU B 258      34.104  21.555  63.113 1.000 34.02
ATOM   4329  N    ASP B 259      36.047  22.546  63.699 1.000 24.40
ATOM   4330  CA   ASP B 259      35.925  23.714  62.834 1.000 27.44
ATOM   4331  CB   ASP B 259      37.184  24.585  62.907 1.000 26.51
ATOM   4332  CG   ASP B 259      37.015  25.907  62.185 1.000 31.73
ATOM   4333  OD1  ASP B 259      35.871  26.400  62.144 1.000 33.45
ATOM   4334  OD2  ASP B 259      38.013  26.448  61.664 1.000 25.69
ATOM   4335  C    ASP B 259      35.678  23.286  61.392 1.000 22.95
ATOM   4336  O    ASP B 259      34.813  23.822  60.702 1.000 30.45
ATOM   4337  N    ARG B 260      36.446  22.302  60.950 1.000 26.62
ATOM   4338  CA   ARG B 260      36.361  21.798  59.585 1.000 33.18
ATOM   4339  CB   ARG B 260      37.519  20.835  59.319 1.000 31.29
ATOM   4340  CG   ARG B 260      38.785  21.473  58.778 1.000 30.70
ATOM   4341  CD   ARG B 260      39.239  20.700  57.536 1.000 37.95
ATOM   4342  NE   ARG B 260      40.673  20.498  57.556 1.000 41.13
ATOM   4343  CZ   ARG B 260      41.391  19.709  56.782 1.000 33.80
ATOM   4344  NH1  ARG B 260      40.798  18.979  55.856 1.000 42.79
ATOM   4345  NH2  ARG B 260      42.705  19.660  56.957 1.000 37.06
ATOM   4346  C    ARG B 260      35.055  21.066  59.301 1.000 38.95
ATOM   4347  O    ARG B 260      34.398  21.344  58.296 1.000 34.89
ATOM   4348  N    ILE B 261      34.673  20.123  60.157 1.000 40.78
ATOM   4349  CA   ILE B 261      33.506  19.282  59.888 1.000 36.65
ATOM   4350  CB   ILE B 261      33.512  18.013  60.759 1.000 36.83
```

FIGURE 90

```
ATOM   4351  CG1 ILE B 261      33.172  18.232  62.236 1.000 36.37
ATOM   4352  CD1 ILE B 261      33.788  17.170  63.128 1.000 27.30
ATOM   4353  CG2 ILE B 261      34.851  17.297  60.648 1.000 30.19
ATOM   4354  C   ILE B 261      32.193  20.033  60.076 1.000 37.68
ATOM   4355  O   ILE B 261      31.233  19.779  59.332 1.000 29.23
ATOM   4356  N   LEU B 262      32.121  20.960  61.032 1.000 29.30
ATOM   4357  CA  LEU B 262      30.910  21.778  61.134 1.000 34.05
ATOM   4358  CB  LEU B 262      30.909  22.676  62.372 1.000 34.84
ATOM   4359  CG  LEU B 262      30.865  21.951  63.722 1.000 33.81
ATOM   4360  CD1 LEU B 262      30.907  22.931  64.886 1.000 29.40
ATOM   4361  CD2 LEU B 262      29.628  21.067  63.813 1.000 31.05
ATOM   4362  C   LEU B 262      30.763  22.639  59.882 1.000 49.12
ATOM   4363  O   LEU B 262      29.667  23.081  59.538 1.000 56.67
ATOM   4364  N   GLN B 263      31.888  22.887  59.204 1.000 44.18
ATOM   4365  CA  GLN B 263      31.808  23.682  57.982 1.000 46.28
ATOM   4366  CB  GLN B 263      33.169  24.218  57.542 1.000 42.43
ATOM   4367  CG  GLN B 263      33.463  25.604  58.110 1.000 37.21
ATOM   4368  CD  GLN B 263      34.905  25.991  57.847 1.000 38.82
ATOM   4369  OE1 GLN B 263      35.200  26.564  56.803 1.000 42.28
ATOM   4370  NE2 GLN B 263      35.789  25.670  58.782 1.000 38.53
ATOM   4371  C   GLN B 263      31.207  22.830  56.870 1.000 43.95
ATOM   4372  O   GLN B 263      30.412  23.325  56.083 1.000 46.04
ATOM   4373  N   GLN B 264      31.609  21.563  56.843 1.000 40.32
ATOM   4374  CA  GLN B 264      31.058  20.637  55.859 1.000 43.58
ATOM   4375  CB  GLN B 264      31.776  19.291  55.904 1.000 41.24
ATOM   4376  CG  GLN B 264      33.299  19.353  55.893 1.000 32.42
ATOM   4377  CD  GLN B 264      33.885  17.975  56.138 1.000 34.83
ATOM   4378  OE1 GLN B 264      33.154  16.982  56.114 1.000 49.05
ATOM   4379  NE2 GLN B 264      35.181  17.880  56.386 1.000 36.65
ATOM   4380  C   GLN B 264      29.557  20.453  56.088 1.000 46.84
ATOM   4381  O   GLN B 264      28.787  20.463  55.125 1.000 60.95
ATOM   4382  N   LEU B 265      29.143  20.293  57.339 1.000 44.06
ATOM   4383  CA  LEU B 265      27.744  20.092  57.689 1.000 48.45
ATOM   4384  CB  LEU B 265      27.541  20.198  59.204 1.000 48.90
ATOM   4385  CG  LEU B 265      28.027  19.015  60.044 1.000 49.51
ATOM   4386  CD1 LEU B 265      27.374  19.048  61.416 1.000 39.17
ATOM   4387  CD2 LEU B 265      27.761  17.702  59.326 1.000 46.39
ATOM   4388  C   LEU B 265      26.816  21.098  57.009 1.000 55.29
ATOM   4389  O   LEU B 265      25.738  20.747  56.529 1.000 61.57
ATOM   4390  N   ASP B 266      27.242  22.353  56.989 1.000 56.37
ATOM   4391  CA  ASP B 266      26.489  23.438  56.374 1.000 56.13
ATOM   4392  CB  ASP B 266      26.708  24.734  57.154 1.000 62.09
ATOM   4393  CG  ASP B 266      26.306  24.619  58.612 1.000 68.79
ATOM   4394  OD1 ASP B 266      25.108  24.405  58.894 1.000 79.54
ATOM   4395  OD2 ASP B 266      27.190  24.742  59.489 1.000 81.01
ATOM   4396  C   ASP B 266      26.905  23.610  54.917 1.000 50.88
ATOM   4397  O   ASP B 266      26.597  24.607  54.265 1.000 58.84
ATOM   4398  N   SER B 267      27.632  22.622  54.407 1.000 53.13
ATOM   4399  CA  SER B 267      28.177  22.699  53.056 1.000 64.34
ATOM   4400  CB  SER B 267      29.708  22.798  53.101 1.000 56.46
ATOM   4401  OG  SER B 267      30.143  24.108  52.784 1.000 60.08
ATOM   4402  C   SER B 267      27.759  21.499  52.214 1.000 75.07
```

FIGURE 91

| ATOM | 4403 | O   | SER | B | 267 | 26.653 | 21.444 | 51.677 | 1.000 | 79.48  |
|------|------|-----|-----|---|-----|--------|--------|--------|-------|--------|
| ATOM | 4404 | N   | LYS | B | 268 | 28.656 | 20.523 | 52.092 | 1.000 | 83.42  |
| ATOM | 4405 | CA  | LYS | B | 268 | 28.385 | 19.358 | 51.257 | 1.000 | 86.00  |
| ATOM | 4406 | CB  | LYS | B | 268 | 29.664 | 18.545 | 51.050 | 1.000 | 90.22  |
| ATOM | 4407 | CG  | LYS | B | 268 | 30.899 | 19.402 | 50.804 | 1.000 | 90.85  |
| ATOM | 4408 | CD  | LYS | B | 268 | 31.608 | 19.724 | 52.110 | 1.000 | 87.44  |
| ATOM | 4409 | CE  | LYS | B | 268 | 32.908 | 20.484 | 51.868 | 1.000 | 87.50  |
| ATOM | 4410 | NZ  | LYS | B | 268 | 33.982 | 19.590 | 51.340 | 1.000 | 90.86  |
| ATOM | 4411 | C   | LYS | B | 268 | 27.279 | 18.493 | 51.854 | 1.000 | 79.53  |
| ATOM | 4412 | O   | LYS | B | 268 | 26.697 | 18.840 | 52.883 | 1.000 | 65.16  |
| ATOM | 4413 | N   | ASP | B | 269 | 27.000 | 17.380 | 51.183 | 1.000 | 75.19  |
| ATOM | 4414 | CA  | ASP | B | 269 | 25.948 | 16.453 | 51.576 | 1.000 | 74.46  |
| ATOM | 4415 | CB  | ASP | B | 269 | 25.390 | 15.742 | 50.342 | 1.000 | 83.40  |
| ATOM | 4416 | CG  | ASP | B | 269 | 25.381 | 16.633 | 49.114 | 1.000 | 92.95  |
| ATOM | 4417 | OD1 | ASP | B | 269 | 24.301 | 16.816 | 48.509 | 1.000 | 99.02  |
| ATOM | 4418 | OD2 | ASP | B | 269 | 26.460 | 17.153 | 48.752 | 1.000 | 105.13 |
| ATOM | 4419 | C   | ASP | B | 269 | 26.475 | 15.440 | 52.584 | 1.000 | 69.56  |
| ATOM | 4420 | O   | ASP | B | 269 | 25.755 | 14.571 | 53.071 | 1.000 | 66.15  |
| ATOM | 4421 | N   | SER | B | 270 | 27.763 | 15.573 | 52.883 | 1.000 | 63.01  |
| ATOM | 4422 | CA  | SER | B | 270 | 28.449 | 14.658 | 53.782 | 1.000 | 53.77  |
| ATOM | 4423 | CB  | SER | B | 270 | 29.261 | 13.633 | 52.991 | 1.000 | 58.45  |
| ATOM | 4424 | OG  | SER | B | 270 | 30.230 | 12.983 | 53.797 | 1.000 | 73.26  |
| ATOM | 4425 | C   | SER | B | 270 | 29.357 | 15.436 | 54.734 | 1.000 | 46.99  |
| ATOM | 4426 | O   | SER | B | 270 | 29.393 | 16.664 | 54.654 | 1.000 | 42.15  |
| ATOM | 4427 | N   | VAL | B | 271 | 30.035 | 14.690 | 55.588 | 1.000 | 48.78  |
| ATOM | 4428 | CA  | VAL | B | 271 | 31.029 | 15.141 | 56.544 | 1.000 | 48.00  |
| ATOM | 4429 | CB  | VAL | B | 271 | 30.446 | 15.379 | 57.946 | 1.000 | 49.59  |
| ATOM | 4430 | CG1 | VAL | B | 271 | 29.390 | 14.335 | 58.283 | 1.000 | 49.18  |
| ATOM | 4431 | CG2 | VAL | B | 271 | 31.569 | 15.369 | 58.980 | 1.000 | 36.94  |
| ATOM | 4432 | C   | VAL | B | 271 | 32.145 | 14.100 | 56.637 | 1.000 | 42.78  |
| ATOM | 4433 | O   | VAL | B | 271 | 31.864 | 12.911 | 56.794 | 1.000 | 49.77  |
| ATOM | 4434 | N   | ASP | B | 272 | 33.390 | 14.532 | 56.524 | 1.000 | 38.85  |
| ATOM | 4435 | CA  | ASP | B | 272 | 34.530 | 13.630 | 56.527 | 1.000 | 35.40  |
| ATOM | 4436 | CB  | ASP | B | 272 | 35.438 | 13.862 | 55.314 | 1.000 | 27.29  |
| ATOM | 4437 | CG  | ASP | B | 272 | 36.212 | 12.617 | 54.924 | 1.000 | 35.62  |
| ATOM | 4438 | OD1 | ASP | B | 272 | 36.101 | 11.583 | 55.615 | 1.000 | 37.07  |
| ATOM | 4439 | OD2 | ASP | B | 272 | 36.947 | 12.666 | 53.915 | 1.000 | 50.42  |
| ATOM | 4440 | C   | ASP | B | 272 | 35.359 | 13.795 | 57.792 | 1.000 | 40.21  |
| ATOM | 4441 | O   | ASP | B | 272 | 36.364 | 14.503 | 57.797 | 1.000 | 41.63  |
| ATOM | 4442 | N   | ILE | B | 273 | 34.929 | 13.131 | 58.862 | 1.000 | 40.79  |
| ATOM | 4443 | CA  | ILE | B | 273 | 35.679 | 13.285 | 60.108 | 1.000 | 34.29  |
| ATOM | 4444 | CB  | ILE | B | 273 | 34.909 | 12.721 | 61.310 | 1.000 | 30.34  |
| ATOM | 4445 | CG1 | ILE | B | 273 | 33.565 | 13.409 | 61.576 | 1.000 | 31.83  |
| ATOM | 4446 | CD1 | ILE | B | 273 | 32.766 | 12.740 | 62.679 | 1.000 | 27.01  |
| ATOM | 4447 | CG2 | ILE | B | 273 | 35.768 | 12.761 | 62.563 | 1.000 | 28.54  |
| ATOM | 4448 | C   | ILE | B | 273 | 37.053 | 12.639 | 59.968 | 1.000 | 39.35  |
| ATOM | 4449 | O   | ILE | B | 273 | 38.060 | 13.284 | 60.295 | 1.000 | 37.96  |
| ATOM | 4450 | N   | TYR | B | 274 | 37.080 | 11.404 | 59.482 | 1.000 | 40.06  |
| ATOM | 4451 | CA  | TYR | B | 274 | 38.320 | 10.692 | 59.209 | 1.000 | 36.37  |
| ATOM | 4452 | CB  | TYR | B | 274 | 38.083 | 9.343  | 58.534 | 1.000 | 34.20  |
| ATOM | 4453 | CG  | TYR | B | 274 | 39.288 | 8.485  | 58.221 | 1.000 | 26.44  |
| ATOM | 4454 | CD1 | TYR | B | 274 | 39.691 | 7.499  | 59.115 | 1.000 | 29.38  |

FIGURE 92

```
ATOM   4455  CE1 TYR B 274      40.787   6.698  58.847  1.000 34.20
ATOM   4456  CZ  TYR B 274      41.501   6.863  57.683  1.000 32.34
ATOM   4457  OH  TYR B 274      42.595   6.077  57.401  1.000 45.24
ATOM   4458  CE2 TYR B 274      41.126   7.829  56.774  1.000 32.36
ATOM   4459  CD2 TYR B 274      40.033   8.609  57.056  1.000 26.39
ATOM   4460  C   TYR B 274      39.228  11.528  58.299  1.000 32.63
ATOM   4461  O   TYR B 274      40.436  11.567  58.534  1.000 31.00
ATOM   4462  N   GLY B 275      38.634  12.102  57.266  1.000 39.31
ATOM   4463  CA  GLY B 275      39.375  12.824  56.239  1.000 35.88
ATOM   4464  C   GLY B 275      40.102  14.006  56.865  1.000 40.67
ATOM   4465  O   GLY B 275      41.263  14.270  56.555  1.000 33.84
ATOM   4466  N   ALA B 276      39.376  14.679  57.751  1.000 36.51
ATOM   4467  CA  ALA B 276      39.906  15.849  58.442  1.000 37.26
ATOM   4468  CB  ALA B 276      38.791  16.511  59.244  1.000 29.45
ATOM   4469  C   ALA B 276      41.097  15.502  59.323  1.000 31.12
ATOM   4470  O   ALA B 276      42.147  16.150  59.234  1.000 27.41
ATOM   4471  N   VAL B 277      40.972  14.480  60.169  1.000 28.39
ATOM   4472  CA  VAL B 277      42.049  14.164  61.101  1.000 26.25
ATOM   4473  CB  VAL B 277      41.639  13.101  62.138  1.000 27.10
ATOM   4474  CG1 VAL B 277      42.882  12.558  62.827  1.000 24.03
ATOM   4475  CG2 VAL B 277      40.671  13.681  63.159  1.000 28.27
ATOM   4476  C   VAL B 277      43.306  13.654  60.402  1.000 31.14
ATOM   4477  O   VAL B 277      44.411  13.880  60.897  1.000 29.79
ATOM   4478  N   HIS B 278      43.121  12.975  59.277  1.000 27.18
ATOM   4479  CA  HIS B 278      44.202  12.495  58.431  1.000 25.97
ATOM   4480  CB  HIS B 278      43.601  11.645  57.309  1.000 33.39
ATOM   4481  CG  HIS B 278      44.609  11.055  56.378  1.000 34.11
ATOM   4482  ND1 HIS B 278      45.201  11.773  55.367  1.000 25.09
ATOM   4483  CE1 HIS B 278      46.048  11.002  54.708  1.000 28.44
ATOM   4484  NE2 HIS B 278      46.026   9.801  55.267  1.000 31.16
ATOM   4485  CD2 HIS B 278      45.138   9.806  56.307  1.000 31.49
ATOM   4486  C   HIS B 278      45.001  13.660  57.859  1.000 24.46
ATOM   4487  O   HIS B 278      46.225  13.753  57.928  1.000 25.14
ATOM   4488  N   ASP B 279      44.283  14.603  57.260  1.000 23.15
ATOM   4489  CA  ASP B 279      44.887  15.817  56.715  1.000 24.67
ATOM   4490  CB  ASP B 279      43.776  16.718  56.178  1.000 29.92
ATOM   4491  CG  ASP B 279      44.160  17.578  55.001  1.000 37.07
ATOM   4492  OD1 ASP B 279      45.077  17.212  54.235  1.000 38.06
ATOM   4493  OD2 ASP B 279      43.537  18.648  54.835  1.000 30.88
ATOM   4494  C   ASP B 279      45.706  16.530  57.784  1.000 25.54
ATOM   4495  O   ASP B 279      46.843  16.941  57.550  1.000 21.93
ATOM   4496  N   LEU B 280      45.150  16.673  58.991  1.000 18.66
ATOM   4497  CA  LEU B 280      45.867  17.373  60.061  1.000 27.59
ATOM   4498  CB  LEU B 280      45.025  17.491  61.331  1.000 23.76
ATOM   4499  CG  LEU B 280      43.732  18.302  61.281  1.000 29.33
ATOM   4500  CD1 LEU B 280      43.374  18.821  62.668  1.000 34.75
ATOM   4501  CD2 LEU B 280      43.836  19.450  60.293  1.000 30.06
ATOM   4502  C   LEU B 280      47.181  16.678  60.432  1.000 33.16
ATOM   4503  O   LEU B 280      48.218  17.326  60.576  1.000 22.56
ATOM   4504  N   ARG B 281      47.077  15.363  60.589  1.000 29.37
ATOM   4505  CA  ARG B 281      48.168  14.491  60.979  1.000 31.07
ATOM   4506  CB  ARG B 281      47.675  13.042  61.092  1.000 28.63
```

FIGURE 93

```
ATOM   4507  CG   ARG B 281      46.655  12.833  62.199  1.000  26.35
ATOM   4508  CD   ARG B 281      47.328  12.460  63.506  1.000  27.07
ATOM   4509  NE   ARG B 281      46.350  12.116  64.535  1.000  30.18
ATOM   4510  CZ   ARG B 281      46.041  10.880  64.893  1.000  27.85
ATOM   4511  NH1  ARG B 281      46.628   9.852  64.310  1.000  31.06
ATOM   4512  NH2  ARG B 281      45.138  10.667  65.838  1.000  39.11
ATOM   4513  C    ARG B 281      49.318  14.561  59.985  1.000  29.17
ATOM   4514  O    ARG B 281      50.478  14.363  60.347  1.000  28.56
ATOM   4515  N    LEU B 282      48.986  14.842  58.727  1.000  30.67
ATOM   4516  CA   LEU B 282      50.041  15.001  57.727  1.000  30.29
ATOM   4517  CB   LEU B 282      49.455  15.139  56.327  1.000  24.52
ATOM   4518  CG   LEU B 282      48.830  13.899  55.689  1.000  27.65
ATOM   4519  CD1  LEU B 282      48.201  14.290  54.357  1.000  22.99
ATOM   4520  CD2  LEU B 282      49.859  12.792  55.511  1.000  27.48
ATOM   4521  C    LEU B 282      50.913  16.222  58.014  1.000  27.27
ATOM   4522  O    LEU B 282      52.030  16.277  57.506  1.000  26.46
ATOM   4523  N    HIS B 283      50.418  17.178  58.794  1.000  26.63
ATOM   4524  CA   HIS B 283      51.104  18.459  58.962  1.000  28.55
ATOM   4525  CB   HIS B 283      50.157  19.615  58.551  1.000  26.78
ATOM   4526  CG   HIS B 283      49.852  19.437  57.083  1.000  31.38
ATOM   4527  ND1  HIS B 283      50.669  19.906  56.078  1.000  29.31
ATOM   4528  CE1  HIS B 283      50.164  19.584  54.901  1.000  26.22
ATOM   4529  NE2  HIS B 283      49.048  18.905  55.114  1.000  26.82
ATOM   4530  CD2  HIS B 283      48.838  18.792  56.461  1.000  28.69
ATOM   4531  C    HIS B 283      51.658  18.636  60.359  1.000  26.35
ATOM   4532  O    HIS B 283      52.552  19.465  60.565  1.000  24.96
ATOM   4533  N    ARG B 284      51.186  17.858  61.335  1.000  20.29
ATOM   4534  CA   ARG B 284      51.798  17.980  62.664  1.000  21.12
ATOM   4535  CB   ARG B 284      51.322  19.245  63.391  1.000  20.38
ATOM   4536  CG   ARG B 284      52.150  19.588  64.639  1.000  22.36
ATOM   4537  CD   ARG B 284      51.699  20.875  65.292  1.000  21.53
ATOM   4538  NE   ARG B 284      52.054  21.061  66.698  1.000  19.46
ATOM   4539  CZ   ARG B 284      53.142  21.705  67.107  1.000  25.24
ATOM   4540  NH1  ARG B 284      54.004  22.225  66.238  1.000  24.69
ATOM   4541  NH2  ARG B 284      53.412  21.850  68.402  1.000  27.97
ATOM   4542  C    ARG B 284      51.493  16.731  63.482  1.000  16.74
ATOM   4543  O    ARG B 284      50.383  16.207  63.410  1.000  20.61
ATOM   4544  N    VAL B 285      52.454  16.252  64.253  1.000  21.81
ATOM   4545  CA   VAL B 285      52.238  15.089  65.112  1.000  29.13
ATOM   4546  CB   VAL B 285      53.540  14.760  65.869  1.000  29.57
ATOM   4547  CG1  VAL B 285      53.834  15.855  66.888  1.000  24.27
ATOM   4548  CG2  VAL B 285      53.448  13.399  66.536  1.000  22.96
ATOM   4549  C    VAL B 285      51.105  15.309  66.112  1.000  27.63
ATOM   4550  O    VAL B 285      50.869  16.442  66.513  1.000  21.60
ATOM   4551  N    HIS B 286      50.396  14.271  66.516  1.000  32.06
ATOM   4552  CA   HIS B 286      49.336  14.195  67.498  1.000  25.21
ATOM   4553  CB   HIS B 286      49.885  14.551  68.892  1.000  28.70
ATOM   4554  CG   HIS B 286      51.021  13.664  69.305  1.000  32.98
ATOM   4555  ND1  HIS B 286      51.067  12.319  69.031  1.000  39.17
ATOM   4556  CE1  HIS B 286      52.186  11.799  69.506  1.000  36.14
ATOM   4557  NE2  HIS B 286      52.871  12.769  70.082  1.000  30.56
ATOM   4558  CD2  HIS B 286      52.169  13.944  69.969  1.000  33.55
```

FIGURE 94

```
ATOM  4559  C    HIS B 286      48.127  15.077  67.218  1.000  30.46
ATOM  4560  O    HIS B 286      47.387  15.403  68.154  1.000  40.44
ATOM  4561  N    MET B 287      47.881  15.467  65.973  1.000  22.86
ATOM  4562  CA   MET B 287      46.691  16.259  65.664  1.000  22.17
ATOM  4563  CB   MET B 287      46.756  16.854  64.270  1.000  18.80
ATOM  4564  CG   MET B 287      47.775  17.949  64.042  1.000  29.11
ATOM  4565  SD   MET B 287      47.516  19.438  65.055  1.000  32.43
ATOM  4566  CE   MET B 287      48.661  19.026  66.372  1.000  13.54
ATOM  4567  C    MET B 287      45.457  15.368  65.848  1.000  29.49
ATOM  4568  O    MET B 287      45.182  14.511  65.013  1.000  22.99
ATOM  4569  N    VAL B 288      44.774  15.611  66.952  1.000  34.12
ATOM  4570  CA   VAL B 288      43.740  14.820  67.589  1.000  28.81
ATOM  4571  CB   VAL B 288      42.560  14.478  66.675  1.000  27.58
ATOM  4572  CG1  VAL B 288      41.636  13.502  67.385  1.000  26.91
ATOM  4573  CG2  VAL B 288      41.797  15.726  66.275  1.000  19.05
ATOM  4574  C    VAL B 288      44.390  13.535  68.093  1.000  30.95
ATOM  4575  O    VAL B 288      44.556  12.583  67.334  1.000  40.72
ATOM  4576  N    GLN B 289      44.783  13.526  69.362  1.000  42.21
ATOM  4577  CA   GLN B 289      45.728  12.504  69.827  1.000  40.64
ATOM  4578  CB   GLN B 289      46.907  13.254  70.450  1.000  38.74
ATOM  4579  CG   GLN B 289      47.311  12.901  71.865  1.000  38.30
ATOM  4580  CD   GLN B 289      48.223  13.989  72.413  1.000  37.90
ATOM  4581  OE1  GLN B 289      47.738  15.038  72.837  1.000  34.96
ATOM  4582  NE2  GLN B 289      49.525  13.736  72.392  1.000  42.59
ATOM  4583  C    GLN B 289      45.156  11.454  70.756  1.000  35.16
ATOM  4584  O    GLN B 289      45.899  10.560  71.181  1.000  34.51
ATOM  4585  N    THR B 290      43.869  11.469  71.086  1.000  27.99
ATOM  4586  CA   THR B 290      43.294  10.342  71.819  1.000  34.56
ATOM  4587  CB   THR B 290      42.922  10.643  73.277  1.000  36.69
ATOM  4588  OG1  THR B 290      41.958  11.699  73.369  1.000  39.54
ATOM  4589  CG2  THR B 290      44.140  11.134  74.049  1.000  28.24
ATOM  4590  C    THR B 290      42.053   9.858  71.067  1.000  45.19
ATOM  4591  O    THR B 290      41.423  10.630  70.344  1.000  37.85
ATOM  4592  N    GLU B 291      41.708   8.583  71.228  1.000  40.04
ATOM  4593  CA   GLU B 291      40.514   8.060  70.569  1.000  31.40
ATOM  4594  CB   GLU B 291      40.426   6.549  70.769  1.000  33.20
ATOM  4595  CG   GLU B 291      38.992   6.033  70.734  1.000  54.35
ATOM  4596  CD   GLU B 291      38.936   4.515  70.792  1.000  61.38
ATOM  4597  OE1  GLU B 291      37.831   3.978  71.011  1.000  56.63
ATOM  4598  OE2  GLU B 291      40.009   3.898  70.610  1.000  65.55
ATOM  4599  C    GLU B 291      39.274   8.756  71.108  1.000  27.13
ATOM  4600  O    GLU B 291      38.289   9.026  70.424  1.000  39.02
ATOM  4601  N    CYS B 292      39.330   9.074  72.393  1.000  30.92
ATOM  4602  CA   CYS B 292      38.290   9.823  73.085  1.000  28.64
ATOM  4603  CB   CYS B 292      38.815  10.131  74.493  1.000  36.66
ATOM  4604  SG   CYS B 292      37.722  11.163  75.490  1.000  55.37
ATOM  4605  C    CYS B 292      37.903  11.103  72.351  1.000  31.79
ATOM  4606  O    CYS B 292      36.723  11.332  72.070  1.000  36.92
ATOM  4607  N    GLN B 293      38.892  11.940  72.039  1.000  33.19
ATOM  4608  CA   GLN B 293      38.724  13.169  71.267  1.000  28.60
ATOM  4609  CB   GLN B 293      40.056  13.880  71.039  1.000  27.95
ATOM  4610  CG   GLN B 293      40.532  14.744  72.194  1.000  27.18
```

FIGURE 95

```
ATOM   4611  CD   GLN B 293      42.023  15.015  72.172 1.000 33.21
ATOM   4612  OE1  GLN B 293      42.730  14.694  71.211 1.000 26.74
ATOM   4613  NE2  GLN B 293      42.533  15.611  73.245 1.000 24.69
ATOM   4614  C    GLN B 293      38.076  12.811  69.931 1.000 28.40
ATOM   4615  O    GLN B 293      37.089  13.407  69.513 1.000 41.52
ATOM   4616  N    TYR B 294      38.647  11.795  69.281 1.000 24.64
ATOM   4617  CA   TYR B 294      38.065  11.284  68.041 1.000 29.87
ATOM   4618  CB   TYR B 294      38.826  10.059  67.528 1.000 35.21
ATOM   4619  CG   TYR B 294      38.549   9.719  66.079 1.000 39.63
ATOM   4620  CD1  TYR B 294      38.696  10.672  65.081 1.000 28.61
ATOM   4621  CE1  TYR B 294      38.451  10.386  63.754 1.000 28.44
ATOM   4622  CZ   TYR B 294      38.047   9.119  63.401 1.000 38.28
ATOM   4623  OH   TYR B 294      37.803   8.837  62.078 1.000 41.13
ATOM   4624  CE2  TYR B 294      37.891   8.151  64.368 1.000 40.14
ATOM   4625  CD2  TYR B 294      38.141   8.446  65.695 1.000 38.49
ATOM   4626  C    TYR B 294      36.603  10.923  68.261 1.000 28.62
ATOM   4627  O    TYR B 294      35.741  11.211  67.434 1.000 36.24
ATOM   4628  N    VAL B 295      36.302  10.285  69.396 1.000 34.52
ATOM   4629  CA   VAL B 295      34.910   9.921  69.662 1.000 31.51
ATOM   4630  CB   VAL B 295      34.752   9.065  70.932 1.000 35.21
ATOM   4631  CG1  VAL B 295      33.272   8.911  71.238 1.000 40.28
ATOM   4632  CG2  VAL B 295      35.432   7.720  70.755 1.000 35.85
ATOM   4633  C    VAL B 295      34.043  11.161  69.834 1.000 27.72
ATOM   4634  O    VAL B 295      32.911  11.223  69.360 1.000 36.42
ATOM   4635  N    TYR B 296      34.613  12.139  70.527 1.000 37.43
ATOM   4636  CA   TYR B 296      33.941  13.417  70.761 1.000 36.42
ATOM   4637  CB   TYR B 296      34.866  14.321  71.578 1.000 43.28
ATOM   4638  CG   TYR B 296      34.259  15.599  72.102 1.000 42.68
ATOM   4639  CD1  TYR B 296      33.533  15.620  73.285 1.000 41.40
ATOM   4640  CE1  TYR B 296      32.979  16.794  73.765 1.000 39.34
ATOM   4641  CZ   TYR B 296      33.146  17.964  73.062 1.000 34.82
ATOM   4642  OH   TYR B 296      32.597  19.132  73.530 1.000 27.53
ATOM   4643  CE2  TYR B 296      33.865  17.973  71.884 1.000 41.20
ATOM   4644  CD2  TYR B 296      34.415  16.796  71.415 1.000 43.82
ATOM   4645  C    TYR B 296      33.527  14.083  69.458 1.000 28.58
ATOM   4646  O    TYR B 296      32.421  14.622  69.341 1.000 31.47
ATOM   4647  N    LEU B 297      34.403  14.066  68.453 1.000 30.22
ATOM   4648  CA   LEU B 297      34.076  14.745  67.196 1.000 30.67
ATOM   4649  CB   LEU B 297      35.195  14.583  66.180 1.000 30.58
ATOM   4650  CG   LEU B 297      36.483  15.373  66.375 1.000 32.73
ATOM   4651  CD1  LEU B 297      37.535  14.919  65.367 1.000 29.68
ATOM   4652  CD2  LEU B 297      36.220  16.866  66.250 1.000 27.24
ATOM   4653  C    LEU B 297      32.782  14.187  66.605 1.000 33.83
ATOM   4654  O    LEU B 297      31.891  14.932  66.215 1.000 31.16
ATOM   4655  N    HIS B 298      32.737  12.860  66.570 1.000 41.22
ATOM   4656  CA   HIS B 298      31.562  12.114  66.138 1.000 38.95
ATOM   4657  CB   HIS B 298      31.818  10.612  66.255 1.000 34.71
ATOM   4658  CG   HIS B 298      32.822  10.070  65.285 1.000 34.66
ATOM   4659  ND1  HIS B 298      34.177  10.070  65.531 1.000 40.08
ATOM   4660  CE1  HIS B 298      34.825   9.528  64.511 1.000 38.60
ATOM   4661  NE2  HIS B 298      33.935   9.166  63.602 1.000 36.65
ATOM   4662  CD2  HIS B 298      32.679   9.494  64.071 1.000 35.52
```

FIGURE 96

```
ATOM   4663  C   HIS B 298      30.340  12.523  66.951  1.000  36.47
ATOM   4664  O   HIS B 298      29.314  12.914  66.389  1.000  36.46
ATOM   4665  N   GLN B 299      30.420  12.464  68.280  1.000  33.50
ATOM   4666  CA  GLN B 299      29.250  12.855  69.073  1.000  36.05
ATOM   4667  CB  GLN B 299      29.525  12.674  70.563  1.000  39.72
ATOM   4668  CG  GLN B 299      30.053  11.279  70.887  1.000  48.51
ATOM   4669  CD  GLN B 299      30.367  11.132  72.362  1.000  53.01
ATOM   4670  OE1 GLN B 299      30.932  12.045  72.967  1.000  50.76
ATOM   4671  NE2 GLN B 299      29.999   9.994  72.931  1.000  51.27
ATOM   4672  C   GLN B 299      28.841  14.289  68.782  1.000  38.19
ATOM   4673  O   GLN B 299      27.660  14.644  68.781  1.000  36.44
ATOM   4674  N   CYS B 300      29.837  15.136  68.520  1.000  36.51
ATOM   4675  CA  CYS B 300      29.496  16.519  68.201  1.000  31.01
ATOM   4676  CB  CYS B 300      30.752  17.368  68.017  1.000  32.05
ATOM   4677  SG  CYS B 300      31.545  17.931  69.542  1.000  33.82
ATOM   4678  C   CYS B 300      28.665  16.568  66.925  1.000  30.84
ATOM   4679  O   CYS B 300      27.706  17.327  66.828  1.000  37.19
ATOM   4680  N   VAL B 301      29.042  15.767  65.927  1.000  30.57
ATOM   4681  CA  VAL B 301      28.357  15.877  64.636  1.000  35.77
ATOM   4682  CB  VAL B 301      29.131  15.124  63.542  1.000  37.54
ATOM   4683  CG1 VAL B 301      28.252  14.886  62.327  1.000  28.37
ATOM   4684  CG2 VAL B 301      30.380  15.915  63.165  1.000  38.14
ATOM   4685  C   VAL B 301      26.925  15.369  64.735  1.000  39.26
ATOM   4686  O   VAL B 301      25.977  16.025  64.295  1.000  52.69
ATOM   4687  N   ARG B 302      26.736  14.201  65.327  1.000  38.31
ATOM   4688  CA  ARG B 302      25.403  13.654  65.555  1.000  45.66
ATOM   4689  CB  ARG B 302      25.506  12.385  66.410  1.000  42.74
ATOM   4690  CG  ARG B 302      24.268  12.102  67.240  1.000  46.88
ATOM   4691  CD  ARG B 302      24.579  11.103  68.354  1.000  45.04
ATOM   4692  NE  ARG B 302      25.118  11.799  69.513  1.000  48.32
ATOM   4693  CZ  ARG B 302      25.697  11.252  70.567  1.000  45.65
ATOM   4694  NH1 ARG B 302      25.838   9.937  70.659  1.000  43.04
ATOM   4695  NH2 ARG B 302      26.131  12.057  71.531  1.000  48.35
ATOM   4696  C   ARG B 302      24.480  14.642  66.256  1.000  54.36
ATOM   4697  O   ARG B 302      23.339  14.882  65.856  1.000  40.59
ATOM   4698  N   ASP B 303      24.975  15.234  67.348  1.000  56.40
ATOM   4699  CA  ASP B 303      24.142  16.171  68.100  1.000  55.70
ATOM   4700  CB  ASP B 303      24.898  16.662  69.342  1.000  57.02
ATOM   4701  CG  ASP B 303      25.181  15.521  70.303  1.000  59.83
ATOM   4702  OD1 ASP B 303      24.651  14.412  70.073  1.000  59.82
ATOM   4703  OD2 ASP B 303      25.930  15.724  71.281  1.000  60.83
ATOM   4704  C   ASP B 303      23.688  17.342  67.236  1.000  50.72
ATOM   4705  O   ASP B 303      22.538  17.775  67.357  1.000  47.41
ATOM   4706  N   VAL B 304      24.571  17.839  66.374  1.000  44.96
ATOM   4707  CA  VAL B 304      24.268  18.980  65.512  1.000  47.93
ATOM   4708  CB  VAL B 304      25.515  19.435  64.739  1.000  46.69
ATOM   4709  CG1 VAL B 304      25.147  20.348  63.575  1.000  43.96
ATOM   4710  CG2 VAL B 304      26.484  20.141  65.677  1.000  44.01
ATOM   4711  C   VAL B 304      23.137  18.626  64.546  1.000  53.73
ATOM   4712  O   VAL B 304      22.178  19.375  64.347  1.000  37.08
ATOM   4713  N   LEU B 305      23.286  17.442  63.958  1.000  51.48
ATOM   4714  CA  LEU B 305      22.264  16.852  63.108  1.000  52.53
```

FIGURE 97

```
ATOM   4715  CB   LEU B 305      22.789  15.569  62.455 1.000 39.00
ATOM   4716  CG   LEU B 305      24.083  15.749  61.649 1.000 37.23
ATOM   4717  CD1  LEU B 305      24.587  14.409  61.143 1.000 51.92
ATOM   4718  CD2  LEU B 305      23.868  16.711  60.496 1.000 36.51
ATOM   4719  C    LEU B 305      20.979  16.583  63.901 1.000 53.75
ATOM   4720  O    LEU B 305      19.939  17.100  63.476 1.000 35.65
ATOM   4721  N    ARG B 306      21.076  15.820  64.980 1.000 57.84
ATOM   4722  CA   ARG B 306      20.003  15.505  65.913 1.000 58.04
ATOM   4723  CB   ARG B 306      20.540  15.067  67.268 1.000 54.34
ATOM   4724  CG   ARG B 306      20.660  13.573  67.496 1.000 55.97
ATOM   4725  CD   ARG B 306      21.035  13.272  68.943 1.000 61.19
ATOM   4726  NE   ARG B 306      21.719  11.995  69.097 1.000 68.99
ATOM   4727  CZ   ARG B 306      21.752  11.249  70.190 1.000 74.79
ATOM   4728  NH1  ARG B 306      21.132  11.608  71.304 1.000 69.23
ATOM   4729  NH2  ARG B 306      22.421  10.100  70.183 1.000 80.87
ATOM   4730  C    ARG B 306      19.118  16.738  66.111 1.000 62.20
ATOM   4731  O    ARG B 306      17.971  16.763  65.681 1.000 63.69
ATOM   4732  N    ALA B 307      19.734  17.737  66.728 1.000 65.49
ATOM   4733  CA   ALA B 307      19.143  19.057  66.891 1.000 64.51
ATOM   4734  CB   ALA B 307      20.143  19.994  67.558 1.000 51.87
ATOM   4735  C    ALA B 307      18.680  19.605  65.548 1.000 64.66
ATOM   4736  O    ALA B 307      17.611  20.209  65.423 1.000 65.97
ATOM   4737  N    ARG B 308      19.468  19.412  64.491 1.000 61.42
ATOM   4738  CA   ARG B 308      19.012  19.929  63.193 1.000 70.94
ATOM   4739  CB   ARG B 308      20.088  19.697  62.137 1.000 76.27
ATOM   4740  CG   ARG B 308      19.741  20.209  60.748 1.000 86.23
ATOM   4741  CD   ARG B 308      20.397  21.547  60.456 1.000 95.24
ATOM   4742  NE   ARG B 308      21.821  21.417  60.163 1.000101.38
ATOM   4743  CZ   ARG B 308      22.786  21.666  61.049 1.000107.77
ATOM   4744  NH1  ARG B 308      22.485  22.054  62.288 1.000110.29
ATOM   4745  NH2  ARG B 308      24.056  21.519  60.695 1.000113.92
ATOM   4746  C    ARG B 308      17.685  19.293  62.787 1.000 73.80
ATOM   4747  O    ARG B 308      16.827  19.955  62.197 1.000 73.18
ATOM   4748  N    LYS B 309      17.486  18.015  63.102 1.000 73.43
ATOM   4749  CA   LYS B 309      16.283  17.286  62.718 1.000 76.77
ATOM   4750  CB   LYS B 309      16.472  15.788  62.979 1.000 79.31
ATOM   4751  CG   LYS B 309      17.591  15.149  62.164 1.000 80.69
ATOM   4752  CD   LYS B 309      17.436  13.637  62.104 1.000 82.88
ATOM   4753  CE   LYS B 309      18.186  13.050  60.925 1.000 82.69
ATOM   4754  NZ   LYS B 309      19.523  12.501  61.319 1.000 75.87
ATOM   4755  C    LYS B 309      15.033  17.778  63.442 1.000 74.89
ATOM   4756  O    LYS B 309      14.006  18.014  62.802 1.000 70.03
ATOM   4757  N    LEU B 310      15.106  17.915  64.760 1.000 66.81
ATOM   4758  CA   LEU B 310      13.993  18.391  65.566 1.000 57.56
ATOM   4759  CB   LEU B 310      14.439  18.679  67.003 1.000 58.43
ATOM   4760  CG   LEU B 310      14.439  17.504  67.980 1.000 59.58
ATOM   4761  CD1  LEU B 310      15.451  17.728  69.090 1.000 37.85
ATOM   4762  CD2  LEU B 310      13.055  17.278  68.570 1.000 65.92
ATOM   4763  C    LEU B 310      13.371  19.657  64.978 1.000 57.95
ATOM   4764  O    LEU B 310      12.371  20.157  65.507 1.000 56.97
ATOM   4765  O1   HOH W   1      -3.530  -2.470  27.550 1.000 17.96
ATOM   4766  O1   HOH W   2      60.077  26.796  63.038 1.000 15.33
```

FIGURE 98

| | | | | | | | | | |
|---|---|---|---|---|---|---|---|---|---|
| ATOM | 4767 | O1 | HOH | W | 3 | 55.045 | 17.613 | 63.918 | 1.000 20.66 |
| ATOM | 4768 | O1 | HOH | W | 4 | 10.035 | -6.431 | 48.617 | 1.000 19.03 |
| ATOM | 4769 | O1 | HOH | W | 5 | -2.541 | 7.405 | 22.573 | 1.000 24.15 |
| ATOM | 4770 | O1 | HOH | W | 6 | -1.465 | 3.010 | 37.742 | 1.000 20.37 |
| ATOM | 4771 | O1 | HOH | W | 7 | 1.064 | 6.887 | 29.228 | 1.000 21.37 |
| ATOM | 4772 | O1 | HOH | W | 8 | 12.797 | -10.463 | 28.170 | 1.000 21.33 |
| ATOM | 4773 | O1 | HOH | W | 9 | 44.023 | 30.928 | 82.230 | 1.000 23.35 |
| ATOM | 4774 | O1 | HOH | W | 10 | 15.262 | -6.127 | 25.706 | 1.000 20.03 |
| ATOM | 4775 | O1 | HOH | W | 11 | 41.135 | 13.077 | 75.806 | 1.000 24.83 |
| ATOM | 4776 | O1 | HOH | W | 12 | 44.160 | 35.266 | 61.596 | 1.000 21.20 |
| ATOM | 4777 | O1 | HOH | W | 13 | -2.293 | 13.135 | 27.030 | 1.000 29.16 |
| ATOM | 4778 | O1 | HOH | W | 14 | -1.152 | -4.851 | 36.331 | 1.000 18.92 |
| ATOM | 4779 | O1 | HOH | W | 15 | 12.494 | -9.297 | 20.888 | 1.000 32.44 |
| ATOM | 4780 | O1 | HOH | W | 16 | 10.561 | -4.413 | 17.800 | 1.000 27.50 |
| ATOM | 4781 | O1 | HOH | W | 17 | 12.953 | -1.978 | 15.793 | 1.000 23.51 |
| ATOM | 4782 | O1 | HOH | W | 18 | 54.169 | 29.526 | 70.613 | 1.000 20.32 |
| ATOM | 4783 | O1 | HOH | W | 19 | 13.709 | 11.416 | 42.827 | 1.000 18.88 |
| ATOM | 4784 | O1 | HOH | W | 20 | 55.731 | 28.213 | 80.604 | 1.000 26.83 |
| ATOM | 4785 | O1 | HOH | W | 21 | 4.760 | 11.444 | 27.886 | 1.000 20.66 |
| ATOM | 4786 | O1 | HOH | W | 22 | 56.913 | 29.110 | 71.387 | 1.000 17.72 |
| ATOM | 4787 | O1 | HOH | W | 23 | 18.440 | -8.145 | 47.574 | 1.000 28.67 |
| ATOM | 4788 | O1 | HOH | W | 24 | 51.613 | 13.126 | 62.266 | 1.000 25.40 |
| ATOM | 4789 | O1 | HOH | W | 25 | 56.785 | 21.500 | 72.666 | 1.000 22.09 |
| ATOM | 4790 | O1 | HOH | W | 26 | 46.913 | 32.045 | 55.417 | 1.000 36.86 |
| ATOM | 4791 | O1 | HOH | W | 27 | 10.490 | -7.264 | 21.479 | 1.000 24.68 |
| ATOM | 4792 | O1 | HOH | W | 28 | -4.811 | -5.788 | 33.716 | 1.000 23.37 |
| ATOM | 4793 | O1 | HOH | W | 29 | 58.662 | 11.046 | 62.178 | 1.000 28.32 |
| ATOM | 4794 | O1 | HOH | W | 30 | 40.935 | 36.024 | 75.388 | 1.000 36.78 |
| ATOM | 4795 | O1 | HOH | W | 31 | 56.949 | 30.099 | 57.221 | 1.000 20.47 |
| ATOM | 4796 | O1 | HOH | W | 32 | 45.404 | 15.934 | 74.179 | 1.000 31.95 |
| ATOM | 4797 | O1 | HOH | W | 33 | -6.695 | -5.778 | 43.032 | 1.000 31.77 |
| ATOM | 4798 | O1 | HOH | W | 34 | 46.397 | 21.045 | 76.403 | 1.000 35.06 |
| ATOM | 4799 | O1 | HOH | W | 35 | 60.957 | 30.231 | 69.118 | 1.000 21.63 |
| ATOM | 4800 | O1 | HOH | W | 36 | -3.350 | -17.246 | 31.808 | 1.000 41.60 |
| ATOM | 4801 | O1 | HOH | W | 37 | 55.555 | 12.895 | 71.190 | 1.000 29.48 |
| ATOM | 4802 | O1 | HOH | W | 38 | 1.468 | -5.097 | 35.986 | 1.000 22.35 |
| ATOM | 4803 | O1 | HOH | W | 39 | 15.156 | -9.650 | 27.646 | 1.000 20.92 |
| ATOM | 4804 | O1 | HOH | W | 40 | 38.773 | 25.200 | 57.849 | 1.000 23.39 |
| ATOM | 4805 | O1 | HOH | W | 41 | 10.348 | 17.067 | 32.030 | 1.000 41.46 |
| ATOM | 4806 | O1 | HOH | W | 42 | 1.648 | -14.559 | 44.147 | 1.000 28.83 |
| ATOM | 4807 | O1 | HOH | W | 43 | 61.596 | 20.901 | 62.903 | 1.000 28.38 |
| ATOM | 4808 | O1 | HOH | W | 44 | 14.144 | -11.298 | 42.153 | 1.000 36.30 |
| ATOM | 4809 | O1 | HOH | W | 45 | 59.647 | 17.031 | 57.868 | 1.000 23.78 |
| ATOM | 4810 | O1 | HOH | W | 46 | 53.695 | 23.952 | 54.917 | 1.000 39.83 |
| ATOM | 4811 | O1 | HOH | W | 47 | 27.056 | 31.327 | 66.272 | 1.000 55.85 |
| ATOM | 4812 | O1 | HOH | W | 48 | 37.053 | 41.920 | 74.032 | 1.000 46.26 |
| ATOM | 4813 | O1 | HOH | W | 49 | -2.397 | 0.653 | 20.483 | 1.000 37.18 |
| ATOM | 4814 | O1 | HOH | W | 50 | 41.473 | 15.741 | 75.531 | 1.000 43.52 |
| ATOM | 4815 | O1 | HOH | W | 51 | -2.370 | -15.863 | 33.885 | 1.000 30.41 |
| ATOM | 4816 | O1 | HOH | W | 52 | -12.538 | 6.131 | 27.682 | 1.000 29.52 |
| ATOM | 4817 | O1 | HOH | W | 53 | 53.221 | 16.883 | 55.102 | 1.000 33.14 |
| ATOM | 4818 | O1 | HOH | W | 54 | 14.966 | -8.503 | 24.747 | 1.000 25.12 |

FIGURE 99

```
ATOM  4819  O1  HOH W  55    8.494  -4.831  50.889 1.000 30.18
ATOM  4820  O1  HOH W  56   24.585  -9.942  22.611 1.000 54.01
ATOM  4821  O1  HOH W  57   18.441 -20.771  46.004 1.000 39.24
ATOM  4822  O1  HOH W  58   51.873  22.607  56.086 1.000 29.82
ATOM  4823  O1  HOH W  59    1.396  -6.152  18.909 1.000 47.00
ATOM  4824  O1  HOH W  60   44.607  38.534  81.740 1.000 40.03
ATOM  4825  O1  HOH W  61   18.322  -0.373  24.933 1.000 28.92
ATOM  4826  O1  HOH W  62   39.406  39.382  64.024 1.000 36.75
ATOM  4827  O1  HOH W  63   71.786  42.646  67.354 1.000 38.18
ATOM  4828  O1  HOH W  64   41.387  20.207  52.496 1.000 61.66
ATOM  4829  O1  HOH W  65   58.599  39.944  69.257 1.000 22.54
ATOM  4830  O1  HOH W  66    7.902   0.663  20.612 1.000 25.67
ATOM  4831  O1  HOH W  67   49.818  23.739  54.522 1.000 26.64
ATOM  4832  O1  HOH W  68    0.323  -5.848  22.222 1.000 21.16
ATOM  4833  O1  HOH W  69    8.339  -2.798  16.062 1.000 35.15
ATOM  4834  O1  HOH W  70   10.628  -6.726  18.494 1.000 23.48
ATOM  4835  O1  HOH W  71   34.368   9.766  58.834 1.000 46.05
ATOM  4836  O1  HOH W  72    0.104  -9.966  24.934 1.000 31.25
ATOM  4837  O1  HOH W  73   -3.205  -3.781  34.722 1.000 24.34
ATOM  4838  O1  HOH W  74   40.443  25.217  78.384 1.000 21.19
ATOM  4839  O1  HOH W  75   60.161  17.919  77.858 1.000 43.49
ATOM  4840  O1  HOH W  76   57.383  25.403  56.423 1.000 28.69
ATOM  4841  O1  HOH W  77   -0.918  -4.290  45.708 1.000 23.94
ATOM  4842  O1  HOH W  78   39.671  29.793  57.818 1.000 28.43
ATOM  4843  O1  HOH W  79   -0.151  -0.962  21.277 1.000 31.95
ATOM  4844  O1  HOH W  80    7.936  -8.337  20.044 1.000 31.62
ATOM  4845  O1  HOH W  81   41.764  30.809  59.091 1.000 32.37
ATOM  4846  O1  HOH W  82   16.518  -9.547  23.062 1.000 37.01
ATOM  4847  O1  HOH W  83   30.713  30.994  77.311 1.000 33.53
ATOM  4848  O1  HOH W  84   28.454  -2.369  72.054 1.000 47.39
ATOM  4849  O1  HOH W  85   -5.917  -8.292  22.002 1.000 37.83
ATOM  4850  O1  HOH W  86    7.580 -10.565  21.487 1.000 31.50
ATOM  4851  O1  HOH W  87   13.747   8.631  42.204 1.000 29.91
ATOM  4852  O1  HOH W  88   34.378   8.211  61.163 1.000 35.02
ATOM  4853  O1  HOH W  89   55.698  21.340  61.326 1.000 34.48
ATOM  4854  O1  HOH W  90   -0.448  -6.040  47.787 1.000 38.54
ATOM  4855  O1  HOH W  91   -0.537  -4.018  20.186 1.000 52.78
ATOM  4856  O1  HOH W  92   58.171  28.185  55.468 1.000 35.33
ATOM  4857  O1  HOH W  93   -1.835 -17.836  29.482 1.000 43.68
ATOM  4858  O1  HOH W  94   19.387 -17.439  48.725 1.000 53.98
ATOM  4859  O1  HOH W  95   60.252  41.304  67.862 1.000 40.39
ATOM  4860  O1  HOH W  96   33.297  25.666  61.866 1.000 30.40
ATOM  4861  O1  HOH W  97   -0.856  -8.441  21.984 1.000 40.05
ATOM  4862  O1  HOH W  98    1.309   3.127  26.649 1.000 32.55
ATOM  4863  O1  HOH W  99   -1.694 -18.493  42.845 1.000 43.76
ATOM  4864  O1  HOH W 100   24.060  -6.419  45.384 1.000 40.45
ATOM  4865  O1  HOH W 101  -16.201   0.201  30.012 1.000 60.21
ATOM  4866  O1  HOH W 102   26.465  -8.482  43.564 1.000 39.40
ATOM  4867  O1  HOH W 103   26.382  -4.680  30.946 1.000 37.07
ATOM  4868  O1  HOH W 104   14.152  -0.770  45.187 1.000 31.90
ATOM  4869  O1  HOH W 105   45.353   7.442  65.377 1.000 41.13
ATOM  4870  O1  HOH W 106   61.574  29.765  78.858 1.000 30.33
```

FIGURE 100

```
ATOM   4871  O1  HOH W 107      7.240  13.732  33.506 1.000 51.68
ATOM   4872  O1  HOH W 108     63.827  31.328  67.142 1.000 34.68
ATOM   4873  O1  HOH W 109     27.765   8.197  72.253 1.000 40.60
ATOM   4874  O1  HOH W 110     26.746  31.022  63.432 1.000 78.25
ATOM   4875  O1  HOH W 111      5.779  12.491  31.119 1.000 40.18
ATOM   4876  O1  HOH W 112      0.254  17.249  30.260 1.000 37.62
ATOM   4877  O1  HOH W 113     12.595  10.239  20.359 1.000 35.26
ATOM   4878  O1  HOH W 114    -12.231   8.847  27.346 1.000 34.71
ATOM   4879  O1  HOH W 115      6.080  14.549  28.922 1.000 38.97
ATOM   4880  O1  HOH W 116     42.291  33.445  57.940 1.000 22.41
ATOM   4881  O1  HOH W 117     59.009  28.099  70.085 1.000 25.15
ATOM   4882  O1  HOH W 118     21.222   2.455  47.444 1.000 48.38
ATOM   4883  O1  HOH W 119     15.608 -16.455  31.001 1.000 42.95
ATOM   4884  O1  HOH W 120     -0.125  11.690  36.476 1.000 30.48
ATOM   4885  O1  HOH W 121      1.726  11.454  38.848 1.000 32.74
ATOM   4886  O1  HOH W 122     28.290  -0.445  30.933 1.000 38.16
ATOM   4887  O1  HOH W 123      6.212 -24.378  36.045 1.000 44.15
ATOM   4888  O1  HOH W 124      1.177 -29.065  27.544 1.000 45.02
ATOM   4889  O1  HOH W 125     56.979  34.259  60.005 1.000 48.14
ATOM   4890  O1  HOH W 126     58.730  33.237  57.099 1.000 45.63
ATOM   4891  O1  HOH W 127     15.046  11.322  20.955 1.000 40.69
ATOM   4892  O1  HOH W 128     17.468  -4.910  24.971 1.000 27.77
ATOM   4893  O1  HOH W 129     -7.587  -7.450  31.742 1.000 42.13
ATOM   4894  O1  HOH W 130     62.587  23.632  57.526 1.000 35.90
ATOM   4895  O1  HOH W 131     -1.756   3.962  17.316 1.000 54.25
ATOM   4896  O1  HOH W 132     -7.965  -8.197  36.101 1.000 44.77
ATOM   4897  O1  HOH W 133     24.522 -12.151  40.839 1.000 47.60
ATOM   4898  O1  HOH W 134     41.871  34.231  60.791 1.000 28.90
ATOM   4899  O1  HOH W 135      0.084   1.514  45.812 1.000 36.86
ATOM   4900  O1  HOH W 136     -8.408   3.637  36.615 1.000 38.14
ATOM   4901  O1  HOH W 137     40.900  41.156  64.403 1.000 36.63
ATOM   4902  O1  HOH W 138    -11.020 -17.691  22.512 1.000 75.97
ATOM   4903  O1  HOH W 139      7.850   3.732  42.421 1.000 36.40
ATOM   4904  O1  HOH W 140     26.443 -10.866  28.599 1.000 51.16
ATOM   4905  O1  HOH W 141     23.109   4.111  20.091 1.000 51.94
ATOM   4906  O1  HOH W 142     38.297  16.036  84.787 1.000 45.01
ATOM   4907  O1  HOH W 143     21.913  17.019  28.707 1.000 43.32
ATOM   4908  O1  HOH W 144     59.964  41.572  65.028 1.000 58.77
ATOM   4909  O1  HOH W 145     46.873  21.994  79.174 1.000 40.67
ATOM   4910  O1  HOH W 146     19.058 -16.861  40.797 1.000 48.41
ATOM   4911  O1  HOH W 147     50.103  11.202  73.004 1.000 41.20
ATOM   4912  O1  HOH W 148     -3.801   9.680  21.040 1.000 40.17
ATOM   4913  O1  HOH W 149      0.486   8.561  18.811 1.000 40.75
ATOM   4914  O1  HOH W 150     19.935   8.387  60.381 1.000 53.72
ATOM   4915  O1  HOH W 151     23.477  -0.731  29.783 1.000 32.64
ATOM   4916  O1  HOH W 152     43.876  43.513  55.758 1.000 69.30
ATOM   4917  O1  HOH W 153     -5.161   3.525  27.477 1.000 32.16
ATOM   4918  O1  HOH W 154     41.525  16.199  52.939 1.000 81.81
ATOM   4919  O1  HOH W 155     -4.928 -12.335  20.354 1.000 61.63
ATOM   4920  O1  HOH W 156     13.058   0.354  47.602 1.000 30.77
ATOM   4921  O1  HOH W 157     43.059  17.423  76.789 1.000 45.11
ATOM   4922  O1  HOH W 158     62.494  11.714  59.113 1.000108.46
```

FIGURE 101

```
ATOM   4923  O1  HOH W 159      48.631  10.662  67.791 1.000 38.71
ATOM   4924  O1  HOH W 160      36.309  22.824  83.433 1.000 53.78
ATOM   4925  O1  HOH W 161      34.255  41.203  81.271 1.000 58.61
ATOM   4926  O1  HOH W 162      41.197  23.937  80.959 1.000 34.06
ATOM   4927  O1  HOH W 163      41.828  13.385  50.732 1.000 77.14
ATOM   4928  O1  HOH W 164      31.641  33.672  55.019 1.000 59.40
ATOM   4929  O1  HOH W 165      15.868  14.555  66.209 1.000 65.90
ATOM   4930  O1  HOH W 166      57.742  42.116  78.337 1.000 65.62
ATOM   4931  O1  HOH W 167       4.617 -25.082  27.972 1.000 47.28
ATOM   4932  O1  HOH W 168       2.787  17.721  23.213 1.000 98.79
ATOM   4933  O1  HOH W 169      59.715  23.680  80.391 1.000 59.77
ATOM   4934  O1  HOH W 170      37.169  14.176  35.477 1.000 57.67
ATOM   4935  O1  HOH W 171      15.841 -25.349  41.958 1.000 68.09
ATOM   4936  O1  HOH W 172      69.007  25.633  74.020 1.000 68.84
ATOM   4937  O1  HOH W 173      63.270  32.699  57.782 1.000 41.40
ATOM   4938  O1  HOH W 174      38.069  44.790  79.133 1.000 74.12
ATOM   4939  O1  HOH W 175      74.296  43.345  65.746 1.000 58.77
ATOM   4940  O1  HOH W 176      29.671  29.752  62.465 1.000 48.75
ATOM   4941  O1  HOH W 177      27.349  16.661  41.834 1.000 64.12
ATOM   4942  O1  HOH W 178      68.864  18.200  64.263 1.000 44.37
ATOM   4943  O1  HOH W 179      51.540  25.428  52.448 1.000 52.06
ATOM   4944  O1  HOH W 180      28.343  -0.494  74.952 1.000 90.20
ATOM   4945  O1  HOH W 181     -12.972  -6.360  31.919 1.000 61.07
ATOM   4946  O1  HOH W 182      29.627  16.979  37.935 1.000 63.71
ATOM   4947  O1  HOH W 183      30.147  -2.678  28.953 1.000 52.59
ATOM   4948  O1  HOH W 184      55.934  13.116  53.037 1.000 49.11
ATOM   4949  O1  HOH W 185      -4.863 -11.799  39.588 1.000 42.83
ATOM   4950  O1  HOH W 186      52.756  41.765  58.587 1.000 57.97
ATOM   4951  O1  HOH W 187      27.188  -2.332  27.244 1.000 43.06
ATOM   4952  O1  HOH W 188      30.473   7.380  75.791 1.000 81.10
ATOM   4953  O1  HOH W 189      -7.908 -19.633  34.839 1.000 59.42
ATOM   4954  O1  HOH W 190      28.733  14.583  42.278 1.000 54.80
ATOM   4955  O1  HOH W 191     -13.906  -5.879  34.683 1.000 54.42
ATOM   4956  O1  HOH W 192      60.646  30.561  54.430 1.000103.36
ATOM   4957  O1  HOH W 193      35.855  14.670  80.980 1.000 52.28
ATOM   4958  O1  HOH W 194      19.267  -7.719  50.684 1.000 99.38
ATOM   4959  O1  HOH W 195      17.702 -14.597  31.579 1.000 48.72
ATOM   4960  O1  HOH W 196      25.127   1.357  21.179 1.000 86.89
ATOM   4961  O1  HOH W 197       7.136  23.308  30.331 1.000 67.50
ATOM   4962  O1  HOH W 198      66.979  28.356  73.926 1.000 73.15
ATOM   4963  O1  HOH W 199      58.649  27.550  81.422 1.000 51.44
ATOM   4964  O1  HOH W 200      26.717  16.527  75.237 1.000 49.85
ATOM   4965  O1  HOH W 201      50.540  18.935  78.454 1.000 49.28
END
```

FIGURE 102

```
CRYST1   38.852   69.610  117.777  90.00  90.00  90.00 P 21 21 21
ATOM      1  N   LYS A  19     -13.362  32.383  10.240  1.00 48.36
ATOM      2  CA  LYS A  19     -13.935  33.412   9.318  1.00 47.56
ATOM      3  CB  LYS A  19     -14.789  34.414  10.102  1.00 48.40
ATOM      4  CG  LYS A  19     -16.107  34.813   9.444  1.00 50.42
ATOM      5  CD  LYS A  19     -16.509  36.212   9.896  1.00 51.36
ATOM      6  CE  LYS A  19     -17.815  36.655   9.263  1.00 52.93
ATOM      7  NZ  LYS A  19     -18.963  36.009   9.969  1.00 50.02
ATOM      8  C   LYS A  19     -12.885  34.153   8.487  1.00 45.61
ATOM      9  O   LYS A  19     -12.823  33.994   7.265  1.00 46.13
ATOM     10  N   THR A  20     -12.070  34.966   9.153  1.00 43.56
ATOM     11  CA  THR A  20     -11.312  35.995   8.460  1.00 40.00
ATOM     12  CB  THR A  20     -11.081  37.248   9.348  1.00 41.25
ATOM     13  OG1 THR A  20     -11.320  38.444   8.598  1.00 41.63
ATOM     14  CG2 THR A  20      -9.647  37.393   9.810  1.00 43.82
ATOM     15  C   THR A  20     -10.091  35.385   7.764  1.00 36.65
ATOM     16  O   THR A  20      -9.557  34.349   8.149  1.00 34.08
ATOM     17  N   SER A  21      -9.707  36.004   6.662  1.00 33.82
ATOM     18  CA  SER A  21      -9.158  35.238   5.553  1.00 31.39
ATOM     19  CB  SER A  21     -10.279  34.427   4.900  1.00 32.67
ATOM     20  OG  SER A  21      -9.913  33.919   3.630  1.00 34.27
ATOM     21  C   SER A  21      -8.654  36.302   4.606  1.00 31.16
ATOM     22  O   SER A  21      -9.312  37.328   4.434  1.00 30.44
ATOM     23  N   CYS A  22      -7.494  36.064   4.005  1.00 28.46
ATOM     24  CA  CYS A  22      -6.989  36.913   2.927  1.00 28.63
ATOM     25  CB  CYS A  22      -5.891  37.819   3.465  1.00 28.57
ATOM     26  SG ACYS A  22      -6.413  38.961   4.757  0.50 34.99
ATOM     27  SG BCYS A  22      -5.652  39.300   2.462  0.50 30.02
ATOM     28  C   CYS A  22      -6.377  36.077   1.801  1.00 26.91
ATOM     29  O   CYS A  22      -5.154  35.976   1.717  1.00 26.74
ATOM     30  N   PRO A  23      -7.204  35.459   0.965  1.00 27.39
ATOM     31  CA  PRO A  23      -6.683  34.571  -0.080  1.00 27.48
ATOM     32  CB  PRO A  23      -7.934  33.853  -0.574  1.00 28.38
ATOM     33  CG  PRO A  23      -8.993  34.875  -0.368  1.00 30.20
ATOM     34  CD  PRO A  23      -8.674  35.517   0.952  1.00 27.17
ATOM     35  C   PRO A  23      -6.036  35.395  -1.185  1.00 27.85
ATOM     36  O   PRO A  23      -6.513  36.495  -1.487  1.00 28.68
ATOM     37  N   ILE A  24      -4.929  34.890  -1.723  1.00 25.89
ATOM     38  CA  ILE A  24      -4.148  35.595  -2.723  1.00 24.61
ATOM     39  CB  ILE A  24      -2.747  35.890  -2.154  1.00 25.01
ATOM     40  CG1 ILE A  24      -2.821  36.742  -0.873  1.00 23.94
ATOM     41  CD1 ILE A  24      -3.654  38.013  -1.033  1.00 28.76
ATOM     42  CG2 ILE A  24      -1.845  36.467  -3.229  1.00 24.43
ATOM     43  C   ILE A  24      -4.044  34.641  -3.898  1.00 24.73
ATOM     44  O   ILE A  24      -3.774  33.445  -3.719  1.00 24.14
ATOM     45  N   LYS A  25      -4.262  35.138  -5.112  1.00 23.63
ATOM     46  CA  LYS A  25      -4.158  34.245  -6.261  1.00 23.86
ATOM     47  CB  LYS A  25      -4.639  34.948  -7.538  1.00 25.41
ATOM     48  CG  LYS A  25      -6.138  35.188  -7.552  1.00 29.05
ATOM     49  CD  LYS A  25      -6.540  35.965  -8.799  1.00 35.15
ATOM     50  CE  LYS A  25      -8.054  36.059  -8.951  1.00 40.89
ATOM     51  NZ  LYS A  25      -8.390  36.581 -10.313  1.00 45.05
```

FIGURE 103

```
ATOM     52  C   LYS A  25      -2.688  33.885  -6.407  1.00 22.99
ATOM     53  O   LYS A  25      -1.823  34.725  -6.195  1.00 23.91
ATOM     54  N   ILE A  26      -2.374  32.643  -6.762  1.00 24.14
ATOM     55  CA  ILE A  26      -0.961  32.283  -6.723  1.00 26.45
ATOM     56  CB  ILE A  26      -0.718  30.774  -6.781  1.00 26.63
ATOM     57  CG1 ILE A  26      -1.088  30.233  -8.158  1.00 25.40
ATOM     58  CD1 ILE A  26      -0.405  28.926  -8.497  1.00 33.92
ATOM     59  CG2 ILE A  26      -1.424  30.068  -5.616  1.00 25.53
ATOM     60  C   ILE A  26      -0.148  33.072  -7.745  1.00 28.11
ATOM     61  O   ILE A  26       1.003  33.402  -7.493  1.00 30.02
ATOM     62  N   ASN A  27      -0.770  33.454  -8.855  1.00 30.78
ATOM     63  CA  ASN A  27      -0.033  34.223  -9.862  1.00 35.08
ATOM     64  CB  ASN A  27      -0.710  34.094 -11.236  1.00 34.95
ATOM     65  CG  ASN A  27      -1.552  32.824 -11.347  1.00 40.82
ATOM     66  OD1 ASN A  27      -1.093  31.822 -11.915  1.00 44.00
ATOM     67  ND2 ASN A  27      -2.770  32.844 -10.778  1.00 42.15
ATOM     68  C   ASN A  27       0.174  35.683  -9.455  1.00 34.87
ATOM     69  O   ASN A  27       0.938  36.415 -10.098  1.00 38.32
ATOM     70  N   GLN A  28      -0.491  36.100  -8.379  1.00 33.79
ATOM     71  CA  GLN A  28      -0.283  37.411  -7.776  1.00 33.05
ATOM     72  CB  GLN A  28      -1.633  38.093  -7.546  1.00 34.54
ATOM     73  CG  GLN A  28      -2.004  39.014  -8.699  1.00 40.43
ATOM     74  CD  GLN A  28      -3.422  38.827  -9.172  1.00 46.19
ATOM     75  OE1 GLN A  28      -4.339  38.673  -8.362  1.00 49.62
ATOM     76  NE2 GLN A  28      -3.612  38.845 -10.491  1.00 49.01
ATOM     77  C   GLN A  28       0.520  37.409  -6.478  1.00 31.93
ATOM     78  O   GLN A  28       0.823  38.469  -5.920  1.00 30.78
ATOM     79  N   PHE A  29       0.863  36.216  -5.996  1.00 31.01
ATOM     80  CA  PHE A  29       1.573  36.132  -4.720  1.00 29.71
ATOM     81  CB  PHE A  29       1.805  34.688  -4.249  1.00 29.10
ATOM     82  CG  PHE A  29       2.257  34.608  -2.809  1.00 25.53
ATOM     83  CD1 PHE A  29       1.331  34.519  -1.790  1.00 25.89
ATOM     84  CE1 PHE A  29       1.749  34.470  -0.465  1.00 25.38
ATOM     85  CZ  PHE A  29       3.101  34.545  -0.156  1.00 23.03
ATOM     86  CE2 PHE A  29       4.024  34.658  -1.171  1.00 22.38
ATOM     87  CD2 PHE A  29       3.608  34.678  -2.481  1.00 22.17
ATOM     88  C   PHE A  29       2.872  36.930  -4.662  1.00 31.08
ATOM     89  O   PHE A  29       3.104  37.662  -3.690  1.00 30.41
ATOM     90  N   GLU A  30       3.719  36.779  -5.680  1.00 30.60
ATOM     91  CA  GLU A  30       5.044  37.388  -5.633  1.00 32.65
ATOM     92  CB  GLU A  30       5.766  37.120  -6.953  1.00 33.47
ATOM     93  CG  GLU A  30       7.107  37.828  -7.096  1.00 38.26
ATOM     94  CD  GLU A  30       8.210  37.192  -6.273  1.00 41.01
ATOM     95  OE1 GLU A  30       8.324  35.942  -6.263  1.00 41.31
ATOM     96  OE2 GLU A  30       8.972  37.954  -5.638  1.00 43.55
ATOM     97  C   GLU A  30       4.913  38.890  -5.391  1.00 32.57
ATOM     98  O   GLU A  30       5.570  39.475  -4.523  1.00 31.57
ATOM     99  N   GLY A  31       4.031  39.504  -6.171  1.00 34.44
ATOM    100  CA  GLY A  31       3.688  40.905  -5.986  1.00 35.40
ATOM    101  C   GLY A  31       2.984  41.274  -4.697  1.00 35.45
ATOM    102  O   GLY A  31       3.285  42.311  -4.102  1.00 36.66
ATOM    103  N   HIS A  32       2.040  40.449  -4.250  1.00 35.17
```

FIGURE 104

```
ATOM   104  CA   HIS A  32       1.406  40.666  -2.953  1.00 34.19
ATOM   105  CB   HIS A  32       0.377  39.571  -2.650  1.00 33.45
ATOM   106  CG   HIS A  32      -0.137  39.576  -1.239  1.00 35.35
ATOM   107  ND1  HIS A  32      -1.005  40.533  -0.759  1.00 34.86
ATOM   108  CE1  HIS A  32      -1.294  40.275   0.504  1.00 38.34
ATOM   109  NE2  HIS A  32      -0.667  39.165   0.856  1.00 39.21
ATOM   110  CD2  HIS A  32       0.072  38.714  -0.212  1.00 36.26
ATOM   111  C    HIS A  32       2.471  40.749  -1.861  1.00 33.35
ATOM   112  O    HIS A  32       2.461  41.663  -1.037  1.00 31.23
ATOM   113  N    PHE A  33       3.409  39.806  -1.884  1.00 32.01
ATOM   114  CA   PHE A  33       4.435  39.728  -0.852  1.00 31.66
ATOM   115  CB   PHE A  33       5.168  38.384  -0.942  1.00 32.90
ATOM   116  CG   PHE A  33       6.024  38.057   0.254  1.00 30.75
ATOM   117  CD1  PHE A  33       5.708  38.529   1.524  1.00 34.33
ATOM   118  CE1  PHE A  33       6.507  38.213   2.616  1.00 34.24
ATOM   119  CZ   PHE A  33       7.643  37.424   2.450  1.00 35.46
ATOM   120  CE2  PHE A  33       7.961  36.943   1.186  1.00 32.02
ATOM   121  CD2  PHE A  33       7.145  37.255   0.106  1.00 27.29
ATOM   122  C    PHE A  33       5.395  40.917  -0.953  1.00 31.91
ATOM   123  O    PHE A  33       5.757  41.484   0.077  1.00 30.81
ATOM   124  N    MET A  34       5.784  41.309  -2.170  1.00 31.13
ATOM   125  CA   MET A  34       6.599  42.512  -2.328  1.00 34.10
ATOM   126  CB   MET A  34       6.951  42.790  -3.797  1.00 33.71
ATOM   127  CG   MET A  34       7.918  41.787  -4.410  1.00 36.64
ATOM   128  SD   MET A  34       9.456  41.519  -3.504  1.00 45.35
ATOM   129  CE   MET A  34      10.582  40.969  -4.820  1.00 46.02
ATOM   130  C    MET A  34       5.903  43.709  -1.674  1.00 33.09
ATOM   131  O    MET A  34       6.504  44.406  -0.866  1.00 34.24
ATOM   132  N    LYS A  35       4.629  43.919  -1.996  1.00 35.14
ATOM   133  CA   LYS A  35       3.835  44.999  -1.411  1.00 35.12
ATOM   134  CB   LYS A  35       2.416  44.986  -1.990  1.00 36.58
ATOM   135  CG   LYS A  35       2.372  45.164  -3.500  1.00 39.86
ATOM   136  CD   LYS A  35       1.013  45.684  -3.944  1.00 44.78
ATOM   137  CE   LYS A  35       1.181  46.751  -5.007  1.00 46.40
ATOM   138  NZ   LYS A  35       1.355  46.127  -6.352  1.00 48.36
ATOM   139  C    LYS A  35       3.808  44.960   0.122  1.00 35.83
ATOM   140  O    LYS A  35       4.075  45.958   0.793  1.00 34.45
ATOM   141  N    LEU A  36       3.505  43.799   0.695  1.00 34.49
ATOM   142  CA   LEU A  36       3.546  43.658   2.144  1.00 33.34
ATOM   143  CB   LEU A  36       3.238  42.218   2.534  1.00 33.70
ATOM   144  CG   LEU A  36       1.800  41.748   2.349  1.00 34.08
ATOM   145  CD1  LEU A  36       1.759  40.272   2.714  1.00 39.25
ATOM   146  CD2  LEU A  36       0.827  42.549   3.202  1.00 35.36
ATOM   147  C    LEU A  36       4.908  44.006   2.720  1.00 34.23
ATOM   148  O    LEU A  36       5.017  44.469   3.855  1.00 32.77
ATOM   149  N    GLN A  37       5.952  43.758   1.934  1.00 36.11
ATOM   150  CA   GLN A  37       7.315  43.871   2.434  1.00 38.15
ATOM   151  CB   GLN A  37       8.226  42.852   1.746  1.00 39.69
ATOM   152  CG   GLN A  37       8.393  41.537   2.507  1.00 41.08
ATOM   153  CD   GLN A  37       9.248  40.543   1.750  1.00 42.50
ATOM   154  OE1  GLN A  37      10.228  40.029   2.281  1.00 46.33
ATOM   155  NE2  GLN A  37       8.882  40.274   0.505  1.00 46.39
```

FIGURE 105

```
ATOM    156  C   GLN A  37       7.888  45.280   2.283  1.00 39.26
ATOM    157  O   GLN A  37       8.913  45.600   2.881  1.00 38.73
ATOM    158  N   ALA A  38       7.219  46.099   1.481  1.00 39.85
ATOM    159  CA  ALA A  38       7.634  47.480   1.237  1.00 41.68
ATOM    160  CB  ALA A  38       6.717  48.129   0.200  1.00 40.33
ATOM    161  C   ALA A  38       7.638  48.288   2.538  1.00 42.41
ATOM    162  O   ALA A  38       7.000  47.898   3.515  1.00 42.66
ATOM    163  N   ASP A  39       8.358  49.408   2.545  1.00 43.16
ATOM    164  CA  ASP A  39       8.490  50.253   3.731  1.00 43.58
ATOM    165  CB  ASP A  39       7.222  51.066   3.995  1.00 43.94
ATOM    166  CG  ASP A  39       6.539  51.521   2.733  1.00 46.50
ATOM    167  OD1 ASP A  39       5.474  52.165   2.853  1.00 53.13
ATOM    168  OD2 ASP A  39       6.982  51.279   1.592  1.00 51.25
ATOM    169  C   ASP A  39       8.782  49.487   5.011  1.00 43.69
ATOM    170  O   ASP A  39       8.062  49.653   5.991  1.00 44.78
ATOM    171  N   SER A  40       9.823  48.663   5.025  1.00 44.51
ATOM    172  CA  SER A  40      10.177  47.964   6.256  1.00 44.47
ATOM    173  CB  SER A  40      10.697  48.954   7.308  1.00 45.60
ATOM    174  OG  SER A  40      11.858  49.640   6.852  1.00 45.70
ATOM    175  C   SER A  40       8.934  47.224   6.770  1.00 44.23
ATOM    176  O   SER A  40       8.450  47.477   7.879  1.00 43.64
ATOM    177  N   ASN A  41       8.410  46.338   5.927  1.00 42.57
ATOM    178  CA  ASN A  41       7.313  45.448   6.293  1.00 41.50
ATOM    179  CB  ASN A  41       7.802  44.364   7.264  1.00 42.19
ATOM    180  CG  ASN A  41       8.525  43.225   6.559  1.00 43.25
ATOM    181  OD1 ASN A  41       8.753  43.268   5.350  1.00 47.07
ATOM    182  ND2 ASN A  41       8.897  42.200   7.317  1.00 44.15
ATOM    183  C   ASN A  41       6.051  46.146   6.805  1.00 40.97
ATOM    184  O   ASN A  41       5.262  45.570   7.559  1.00 40.09
ATOM    185  N   TYR A  42       5.842  47.383   6.370  1.00 39.82
ATOM    186  CA  TYR A  42       4.723  48.184   6.859  1.00 40.35
ATOM    187  CB  TYR A  42       4.655  49.528   6.125  1.00 41.74
ATOM    188  CG  TYR A  42       3.461  50.359   6.527  1.00 45.15
ATOM    189  CD1 TYR A  42       3.431  51.021   7.753  1.00 48.34
ATOM    190  CE1 TYR A  42       2.333  51.778   8.137  1.00 51.74
ATOM    191  CZ  TYR A  42       1.246  51.877   7.287  1.00 54.21
ATOM    192  OH  TYR A  42       0.154  52.632   7.659  1.00 55.81
ATOM    193  CE2 TYR A  42       1.250  51.227   6.065  1.00 52.92
ATOM    194  CD2 TYR A  42       2.358  50.472   5.690  1.00 49.40
ATOM    195  C   TYR A  42       3.369  47.472   6.809  1.00 38.41
ATOM    196  O   TYR A  42       2.685  47.355   7.826  1.00 37.47
ATOM    197  N   LEU A  43       2.985  46.978   5.635  1.00 37.22
ATOM    198  CA  LEU A  43       1.667  46.380   5.480  1.00 34.65
ATOM    199  CB  LEU A  43       1.205  46.392   4.021  1.00 36.77
ATOM    200  CG  LEU A  43       0.731  47.739   3.455  1.00 34.94
ATOM    201  CD1 LEU A  43       0.530  47.603   1.962  1.00 38.85
ATOM    202  CD2 LEU A  43      -0.567  48.164   4.139  1.00 37.34
ATOM    203  C   LEU A  43       1.660  44.953   6.016  1.00 34.58
ATOM    204  O   LEU A  43       0.613  44.459   6.441  1.00 33.18
ATOM    205  N   LEU A  44       2.812  44.290   5.972  1.00 32.70
ATOM    206  CA  LEU A  44       2.917  42.976   6.606  1.00 32.37
ATOM    207  CB  LEU A  44       4.316  42.376   6.458  1.00 32.08
```

FIGURE 106

```
ATOM    208  CG  LEU A  44       4.293  40.922   6.948  1.00 30.67
ATOM    209  CD1 LEU A  44       4.884  39.953   5.934  1.00 35.30
ATOM    210  CD2 LEU A  44       4.877  40.746   8.342  1.00 30.73
ATOM    211  C   LEU A  44       2.574  43.078   8.092  1.00 33.04
ATOM    212  O   LEU A  44       1.743  42.326   8.603  1.00 31.84
ATOM    213  N   SER A  45       3.248  43.992   8.784  1.00 32.72
ATOM    214  CA  SER A  45       3.023  44.200  10.211  1.00 32.14
ATOM    215  CB  SER A  45       3.937  45.297  10.761  1.00 32.86
ATOM    216  OG  SER A  45       5.298  44.946  10.616  1.00 33.52
ATOM    217  C   SER A  45       1.579  44.543  10.543  1.00 31.96
ATOM    218  O   SER A  45       1.063  44.085  11.562  1.00 31.93
ATOM    219  N   LYS A  46       0.937  45.378   9.730  1.00 31.67
ATOM    220  CA  LYS A  46      -0.452  45.743   9.983  1.00 32.52
ATOM    221  CB  LYS A  46      -0.907  46.880   9.058  1.00 33.10
ATOM    222  CG  LYS A  46      -0.320  48.247   9.408  1.00 37.46
ATOM    223  CD  LYS A  46      -1.206  49.024  10.362  1.00 43.28
ATOM    224  CE  LYS A  46      -0.660  48.938  11.785  1.00 46.45
ATOM    225  NZ  LYS A  46      -1.645  48.309  12.714  1.00 43.98
ATOM    226  C   LYS A  46      -1.361  44.534   9.819  1.00 31.81
ATOM    227  O   LYS A  46      -2.279  44.313  10.608  1.00 33.52
ATOM    228  N   GLU A  47      -1.108  43.735   8.788  1.00 30.77
ATOM    229  CA  GLU A  47      -1.921  42.546   8.607  1.00 29.42
ATOM    230  CB  GLU A  47      -1.527  41.852   7.317  1.00 29.31
ATOM    231  CG  GLU A  47      -2.261  40.540   7.157  1.00 30.91
ATOM    232  CD  GLU A  47      -2.032  39.991   5.770  1.00 33.04
ATOM    233  OE1 GLU A  47      -2.462  40.656   4.790  1.00 31.27
ATOM    234  OE2 GLU A  47      -1.387  38.923   5.697  1.00 30.22
ATOM    235  C   GLU A  47      -1.745  41.573   9.764  1.00 27.29
ATOM    236  O   GLU A  47      -2.729  41.065  10.317  1.00 28.88
ATOM    237  N   TYR A  48      -0.488  41.316  10.110  1.00 27.52
ATOM    238  CA  TYR A  48      -0.170  40.444  11.234  1.00 28.53
ATOM    239  CB  TYR A  48       1.337  40.327  11.426  1.00 26.41
ATOM    240  CG  TYR A  48       1.697  39.418  12.574  1.00 30.88
ATOM    241  CD1 TYR A  48       1.508  38.039  12.489  1.00 27.50
ATOM    242  CE1 TYR A  48       1.854  37.212  13.547  1.00 26.46
ATOM    243  CZ  TYR A  48       2.341  37.759  14.713  1.00 31.48
ATOM    244  OH  TYR A  48       2.683  36.975  15.797  1.00 33.16
ATOM    245  CE2 TYR A  48       2.539  39.118  14.814  1.00 33.37
ATOM    246  CD2 TYR A  48       2.198  39.937  13.760  1.00 31.15
ATOM    247  C   TYR A  48      -0.807  40.876  12.555  1.00 30.00
ATOM    248  O   TYR A  48      -1.212  40.047  13.374  1.00 29.71
ATOM    249  N   GLU A  49      -0.867  42.179  12.800  1.00 29.94
ATOM    250  CA  GLU A  49      -1.423  42.607  14.082  1.00 29.29
ATOM    251  CB  GLU A  49      -0.863  43.970  14.510  1.00 31.83
ATOM    252  CG  GLU A  49       0.648  43.941  14.759  1.00 34.43
ATOM    253  CD  GLU A  49       1.103  43.090  15.942  1.00 41.82
ATOM    254  OE1 GLU A  49       2.329  42.964  16.146  1.00 45.44
ATOM    255  OE2 GLU A  49       0.267  42.555  16.705  1.00 49.14
ATOM    256  C   GLU A  49      -2.948  42.494  14.156  1.00 28.43
ATOM    257  O   GLU A  49      -3.519  42.445  15.243  1.00 28.47
ATOM    258  N   GLU A  50      -3.597  42.362  13.002  1.00 26.77
ATOM    259  CA  GLU A  50      -5.026  42.129  12.939  1.00 28.42
```

FIGURE 107

```
ATOM    260  CB  GLU A  50      -5.501  42.167  11.493  1.00  29.72
ATOM    261  CG  GLU A  50      -5.695  43.555  10.902  1.00  37.08
ATOM    262  CD  GLU A  50      -6.521  43.494   9.635  1.00  48.22
ATOM    263  OE1 GLU A  50      -7.094  44.536   9.235  1.00  53.56
ATOM    264  OE2 GLU A  50      -6.588  42.394   9.038  1.00  51.31
ATOM    265  C   GLU A  50      -5.369  40.744  13.487  1.00  26.59
ATOM    266  O   GLU A  50      -6.498  40.514  13.903  1.00  28.10
ATOM    267  N   LEU A  51      -4.385  39.855  13.481  1.00  26.25
ATOM    268  CA  LEU A  51      -4.561  38.486  13.994  1.00  23.60
ATOM    269  CB  LEU A  51      -3.585  37.538  13.284  1.00  22.99
ATOM    270  CG  LEU A  51      -3.829  37.234  11.798  1.00  22.34
ATOM    271  CD1 LEU A  51      -2.549  36.611  11.228  1.00  18.21
ATOM    272  CD2 LEU A  51      -5.087  36.385  11.612  1.00  24.13
ATOM    273  C   LEU A  51      -4.370  38.363  15.509  1.00  24.96
ATOM    274  O   LEU A  51      -4.677  37.326  16.111  1.00  22.08
ATOM    275  N   LYS A  52      -3.855  39.417  16.144  1.00  26.20
ATOM    276  CA  LYS A  52      -3.365  39.323  17.514  1.00  26.71
ATOM    277  CB  LYS A  52      -2.860  40.693  17.980  1.00  26.43
ATOM    278  CG  LYS A  52      -2.737  40.861  19.471  1.00  33.28
ATOM    279  CD  LYS A  52      -2.346  42.297  19.849  1.00  36.15
ATOM    280  CE  LYS A  52      -2.370  42.442  21.371  1.00  39.71
ATOM    281  NZ  LYS A  52      -3.746  42.725  21.891  1.00  41.67
ATOM    282  C   LYS A  52      -4.401  38.751  18.487  1.00  25.95
ATOM    283  O   LYS A  52      -4.071  37.922  19.335  1.00  28.87
ATOM    284  N   ASP A  53      -5.647  39.193  18.369  1.00  25.82
ATOM    285  CA  ASP A  53      -6.665  38.840  19.352  1.00  27.69
ATOM    286  CB  ASP A  53      -7.547  40.052  19.677  1.00  29.82
ATOM    287  CG  ASP A  53      -6.811  41.109  20.492  1.00  35.24
ATOM    288  OD1 ASP A  53      -7.138  42.300  20.303  1.00  41.07
ATOM    289  OD2 ASP A  53      -5.893  40.851  21.306  1.00  38.05
ATOM    290  C   ASP A  53      -7.569  37.670  18.980  1.00  25.40
ATOM    291  O   ASP A  53      -8.525  37.364  19.698  1.00  26.92
ATOM    292  N   VAL A  54      -7.297  37.026  17.853  1.00  21.25
ATOM    293  CA  VAL A  54      -8.181  35.958  17.403  1.00  20.37
ATOM    294  CB  VAL A  54      -7.674  35.400  16.059  1.00  20.28
ATOM    295  CG1 VAL A  54      -8.452  34.176  15.627  1.00  20.13
ATOM    296  CG2 VAL A  54      -7.640  36.526  14.988  1.00  20.70
ATOM    297  C   VAL A  54      -8.155  34.888  18.496  1.00  21.34
ATOM    298  O   VAL A  54      -7.068  34.539  18.969  1.00  21.56
ATOM    299  N   GLY A  55      -9.345  34.408  18.857  1.00  19.73
ATOM    300  CA  GLY A  55      -9.501  33.351  19.830  1.00  21.36
ATOM    301  C   GLY A  55      -9.516  33.779  21.284  1.00  25.60
ATOM    302  O   GLY A  55      -9.779  32.934  22.137  1.00  25.18
ATOM    303  N   ARG A  56      -9.243  35.041  21.597  1.00  28.66
ATOM    304  CA  ARG A  56      -8.825  35.351  22.967  1.00  33.28
ATOM    305  CB  ARG A  56      -7.723  36.420  23.019  1.00  34.38
ATOM    306  CG  ARG A  56      -6.566  36.172  22.048  1.00  38.44
ATOM    307  CD  ARG A  56      -5.400  35.366  22.594  1.00  41.11
ATOM    308  NE  ARG A  56      -4.139  35.991  22.211  1.00  47.68
ATOM    309  CZ  ARG A  56      -3.441  36.808  22.989  1.00  51.01
ATOM    310  NH1 ARG A  56      -3.880  37.097  24.206  1.00  50.37
ATOM    311  NH2 ARG A  56      -2.308  37.346  22.551  1.00  48.68
```

FIGURE 108

```
ATOM    312  C   ARG A  56     -10.003  35.704  23.870  1.00 34.09
ATOM    313  O   ARG A  56      -9.826  36.081  25.030  1.00 37.38
ATOM    314  N   ASN A  57     -11.198  35.540  23.319  1.00 34.85
ATOM    315  CA  ASN A  57     -12.448  35.609  24.046  1.00 34.43
ATOM    316  CB  ASN A  57     -13.561  35.897  23.039  1.00 35.95
ATOM    317  CG  ASN A  57     -13.661  34.836  21.944  1.00 40.08
ATOM    318  OD1 ASN A  57     -12.748  34.655  21.124  1.00 42.89
ATOM    319  ND2 ASN A  57     -14.799  34.144  21.912  1.00 40.39
ATOM    320  C   ASN A  57     -12.760  34.309  24.799  1.00 31.67
ATOM    321  O   ASN A  57     -13.767  34.232  25.487  1.00 33.78
ATOM    322  N   GLN A  58     -11.920  33.286  24.653  1.00 27.75
ATOM    323  CA  GLN A  58     -12.243  31.931  25.119  1.00 24.28
ATOM    324  CB  GLN A  58     -11.843  30.903  24.058  1.00 23.90
ATOM    325  CG  GLN A  58     -12.595  31.051  22.743  1.00 25.65
ATOM    326  CD  GLN A  58     -12.102  30.074  21.714  1.00 26.89
ATOM    327  OE1 GLN A  58     -10.971  30.202  21.238  1.00 28.76
ATOM    328  NE2 GLN A  58     -12.933  29.084  21.381  1.00 28.16
ATOM    329  C   GLN A  58     -11.584  31.583  26.458  1.00 23.11
ATOM    330  O   GLN A  58     -10.450  32.001  26.725  1.00 21.96
ATOM    331  N   SER A  59     -12.285  30.801  27.284  1.00 21.91
ATOM    332  CA  SER A  59     -11.880  30.520  28.667  1.00 21.56
ATOM    333  CB  SER A  59     -13.120  30.331  29.548  1.00 25.89
ATOM    334  OG  SER A  59     -13.853  29.160  29.159  1.00 30.06
ATOM    335  C   SER A  59     -10.966  29.293  28.744  1.00 20.75
ATOM    336  O   SER A  59     -11.067  28.413  27.879  1.00 21.59
ATOM    337  N   CYS A  60     -10.045  29.281  29.717  1.00 17.44
ATOM    338  CA  CYS A  60      -9.241  28.110  30.066  1.00 16.53
ATOM    339  CB  CYS A  60      -7.727  28.401  29.837  1.00 16.03
ATOM    340  SG  CYS A  60      -7.335  28.999  28.191  1.00 20.55
ATOM    341  C   CYS A  60      -9.464  27.783  31.540  1.00 15.89
ATOM    342  O   CYS A  60      -8.518  27.605  32.301  1.00 16.90
ATOM    343  N   ASP A  61     -10.724  27.666  31.948  1.00 16.95
ATOM    344  CA  ASP A  61     -11.008  27.467  33.364  1.00 18.02
ATOM    345  CB  ASP A  61     -12.496  27.660  33.610  1.00 19.47
ATOM    346  CG  ASP A  61     -12.954  29.082  33.379  1.00 24.64
ATOM    347  OD1 ASP A  61     -12.160  30.049  33.365  1.00 20.11
ATOM    348  OD2 ASP A  61     -14.155  29.306  33.171  1.00 24.81
ATOM    349  C   ASP A  61     -10.574  26.102  33.887  1.00 20.07
ATOM    350  O   ASP A  61     -10.102  25.997  35.017  1.00 21.40
ATOM    351  N   ILE A  62     -10.679  25.062  33.064  1.00 17.97
ATOM    352  CA  ILE A  62     -10.298  23.747  33.574  1.00 16.98
ATOM    353  CB  ILE A  62     -10.723  22.652  32.564  1.00 14.99
ATOM    354  CG1 ILE A  62     -12.247  22.609  32.414  1.00 19.52
ATOM    355  CD1 ILE A  62     -12.918  22.254  33.696  1.00 24.86
ATOM    356  CG2 ILE A  62     -10.213  21.266  32.987  1.00 18.74
ATOM    357  C   ILE A  62      -8.779  23.712  33.804  1.00 17.57
ATOM    358  O   ILE A  62      -8.295  23.179  34.802  1.00 18.69
ATOM    359  N   ALA A  63      -8.036  24.245  32.841  1.00 16.86
ATOM    360  CA  ALA A  63      -6.570  24.285  32.923  1.00 18.52
ATOM    361  CB  ALA A  63      -5.999  24.905  31.623  1.00 18.66
ATOM    362  C   ALA A  63      -6.075  25.067  34.155  1.00 19.62
ATOM    363  O   ALA A  63      -4.972  24.842  34.653  1.00 20.46
```

FIGURE 109

| | | | | | | | | | |
|---|---|---|---|---|---|---|---|---|---|
| ATOM | 364 | N | LEU | A | 64 | -6.919 | 25.972 | 34.632 | 1.00 20.64 |
| ATOM | 365 | CA | LEU | A | 64 | -6.605 | 26.811 | 35.779 | 1.00 21.59 |
| ATOM | 366 | CB | LEU | A | 64 | -7.316 | 28.157 | 35.640 | 1.00 21.74 |
| ATOM | 367 | CG | LEU | A | 64 | -6.603 | 29.150 | 34.735 | 1.00 22.91 |
| ATOM | 368 | CD1 | LEU | A | 64 | -7.504 | 30.360 | 34.530 | 1.00 26.23 |
| ATOM | 369 | CD2 | LEU | A | 64 | -5.274 | 29.607 | 35.346 | 1.00 20.97 |
| ATOM | 370 | C | LEU | A | 64 | -6.988 | 26.205 | 37.128 | 1.00 23.83 |
| ATOM | 371 | O | LEU | A | 64 | -6.666 | 26.792 | 38.168 | 1.00 24.37 |
| ATOM | 372 | N | LEU | A | 65 | -7.690 | 25.071 | 37.144 | 1.00 23.26 |
| ATOM | 373 | CA | LEU | A | 65 | -8.009 | 24.427 | 38.418 | 1.00 25.30 |
| ATOM | 374 | CB | LEU | A | 65 | -8.892 | 23.199 | 38.218 | 1.00 23.61 |
| ATOM | 375 | CG | LEU | A | 65 | -10.281 | 23.423 | 37.623 | 1.00 25.74 |
| ATOM | 376 | CD1 | LEU | A | 65 | -10.875 | 22.077 | 37.228 | 1.00 27.81 |
| ATOM | 377 | CD2 | LEU | A | 65 | -11.154 | 24.183 | 38.616 | 1.00 27.81 |
| ATOM | 378 | C | LEU | A | 65 | -6.739 | 24.069 | 39.184 | 1.00 25.22 |
| ATOM | 379 | O | LEU | A | 65 | -5.741 | 23.654 | 38.606 | 1.00 23.18 |
| ATOM | 380 | N | PRO | A | 66 | -6.716 | 24.280 | 40.498 | 1.00 26.80 |
| ATOM | 381 | CA | PRO | A | 66 | -5.463 | 24.105 | 41.234 | 1.00 26.96 |
| ATOM | 382 | CB | PRO | A | 66 | -5.830 | 24.483 | 42.678 | 1.00 28.00 |
| ATOM | 383 | CG | PRO | A | 66 | -7.289 | 24.642 | 42.717 | 1.00 27.81 |
| ATOM | 384 | CD | PRO | A | 66 | -7.827 | 24.762 | 41.333 | 1.00 29.27 |
| ATOM | 385 | C | PRO | A | 66 | -4.917 | 22.683 | 41.121 | 1.00 27.13 |
| ATOM | 386 | O | PRO | A | 66 | -3.697 | 22.517 | 41.088 | 1.00 25.29 |
| ATOM | 387 | N | GLU | A | 67 | -5.819 | 21.707 | 41.019 | 1.00 27.81 |
| ATOM | 388 | CA | GLU | A | 67 | -5.504 | 20.294 | 40.825 | 1.00 28.93 |
| ATOM | 389 | CB | GLU | A | 67 | -6.818 | 19.510 | 40.733 | 1.00 30.51 |
| ATOM | 390 | CG A | GLU | A | 67 | -6.790 | 18.040 | 41.147 | 0.50 32.82 |
| ATOM | 391 | CG B | GLU | A | 67 | -7.575 | 19.363 | 42.052 | 0.50 29.81 |
| ATOM | 392 | CD A | GLU | A | 67 | -5.497 | 17.580 | 41.804 | 0.50 34.06 |
| ATOM | 393 | CD B | GLU | A | 67 | -8.575 | 20.471 | 42.362 | 0.50 32.38 |
| ATOM | 394 | OE1A | GLU | A | 67 | -5.465 | 17.473 | 43.049 | 0.50 33.59 |
| ATOM | 395 | OE1B | GLU | A | 67 | -8.580 | 21.554 | 41.729 | 0.50 28.29 |
| ATOM | 396 | OE2A | GLU | A | 67 | -4.523 | 17.281 | 41.077 | 0.50 37.14 |
| ATOM | 397 | OE2B | GLU | A | 67 | -9.376 | 20.260 | 43.298 | 0.50 33.73 |
| ATOM | 398 | C | GLU | A | 67 | -4.681 | 20.052 | 39.557 | 1.00 28.81 |
| ATOM | 399 | O | GLU | A | 67 | -3.896 | 19.100 | 39.474 | 1.00 28.70 |
| ATOM | 400 | N | ASN | A | 68 | -4.841 | 20.938 | 38.577 | 1.00 27.24 |
| ATOM | 401 | CA | ASN | A | 68 | -4.105 | 20.833 | 37.324 | 1.00 26.55 |
| ATOM | 402 | CB | ASN | A | 68 | -5.043 | 21.171 | 36.157 | 1.00 23.97 |
| ATOM | 403 | CG | ASN | A | 68 | -6.154 | 20.139 | 35.977 | 1.00 25.76 |
| ATOM | 404 | OD1 | ASN | A | 68 | -5.976 | 18.936 | 36.227 | 1.00 21.62 |
| ATOM | 405 | ND2 | ASN | A | 68 | -7.312 | 20.596 | 35.510 | 1.00 21.09 |
| ATOM | 406 | C | ASN | A | 68 | -2.780 | 21.602 | 37.228 | 1.00 25.64 |
| ATOM | 407 | O | ASN | A | 68 | -2.087 | 21.528 | 36.213 | 1.00 26.59 |
| ATOM | 408 | N | ARG | A | 69 | -2.397 | 22.344 | 38.269 | 1.00 27.31 |
| ATOM | 409 | CA | ARG | A | 69 | -1.330 | 23.336 | 38.101 | 1.00 26.13 |
| ATOM | 410 | CB | ARG | A | 69 | -1.137 | 24.132 | 39.402 | 1.00 28.24 |
| ATOM | 411 | CG | ARG | A | 69 | 0.208 | 24.842 | 39.456 | 1.00 33.49 |
| ATOM | 412 | CD | ARG | A | 69 | 0.727 | 25.045 | 40.870 | 1.00 45.09 |
| ATOM | 413 | NE | ARG | A | 69 | 2.100 | 24.568 | 41.036 | 1.00 48.71 |
| ATOM | 414 | CZ | ARG | A | 69 | 3.132 | 25.001 | 40.319 | 1.00 51.40 |
| ATOM | 415 | NH1 | ARG | A | 69 | 2.961 | 25.927 | 39.384 | 1.00 45.02 |

FIGURE 110

| | | | | | | | | | |
|---|---|---|---|---|---|---|---|---|---|
| ATOM | 416 | NH2 | ARG | A | 69 | 4.347 | 24.514 | 40.549 | 1.00 54.13 |
| ATOM | 417 | C | ARG | A | 69 | 0.003 | 22.714 | 37.665 | 1.00 26.18 |
| ATOM | 418 | O | ARG | A | 69 | 0.695 | 23.211 | 36.756 | 1.00 27.17 |
| ATOM | 419 | N | GLY | A | 70 | 0.319 | 21.578 | 38.279 | 1.00 24.09 |
| ATOM | 420 | CA | GLY | A | 70 | 1.568 | 20.888 | 37.993 | 1.00 22.34 |
| ATOM | 421 | C | GLY | A | 70 | 1.556 | 20.175 | 36.648 | 1.00 22.09 |
| ATOM | 422 | O | GLY | A | 70 | 2.579 | 19.634 | 36.252 | 1.00 22.14 |
| ATOM | 423 | N | LYS | A | 71 | 0.417 | 20.179 | 35.962 | 1.00 18.88 |
| ATOM | 424 | CA | LYS | A | 71 | 0.261 | 19.527 | 34.658 | 1.00 18.61 |
| ATOM | 425 | CB | LYS | A | 71 | -1.192 | 19.057 | 34.499 | 1.00 18.52 |
| ATOM | 426 | CG | LYS | A | 71 | -1.516 | 18.010 | 35.558 | 1.00 17.03 |
| ATOM | 427 | CD | LYS | A | 71 | -2.862 | 17.421 | 35.371 | 1.00 16.16 |
| ATOM | 428 | CE | LYS | A | 71 | -3.257 | 16.744 | 36.685 | 1.00 19.61 |
| ATOM | 429 | NZ | LYS | A | 71 | -4.691 | 16.331 | 36.616 | 1.00 22.15 |
| ATOM | 430 | C | LYS | A | 71 | 0.589 | 20.487 | 33.527 | 1.00 18.47 |
| ATOM | 431 | O | LYS | A | 71 | 0.596 | 20.124 | 32.341 | 1.00 18.95 |
| ATOM | 432 | N | ASN | A | 72 | 0.790 | 21.743 | 33.885 | 1.00 18.67 |
| ATOM | 433 | CA | ASN | A | 72 | 1.126 | 22.757 | 32.879 | 1.00 19.34 |
| ATOM | 434 | CB | ASN | A | 72 | 0.245 | 23.977 | 33.056 | 1.00 18.51 |
| ATOM | 435 | CG | ASN | A | 72 | -1.206 | 23.648 | 32.847 | 1.00 17.81 |
| ATOM | 436 | OD1 | ASN | A | 72 | -1.576 | 23.040 | 31.838 | 1.00 16.74 |
| ATOM | 437 | ND2 | ASN | A | 72 | -2.035 | 24.037 | 33.801 | 1.00 18.58 |
| ATOM | 438 | C | ASN | A | 72 | 2.591 | 23.158 | 32.922 | 1.00 18.69 |
| ATOM | 439 | O | ASN | A | 72 | 3.075 | 23.556 | 33.981 | 1.00 19.55 |
| ATOM | 440 | N | ARG | A | 73 | 3.298 | 22.983 | 31.806 | 1.00 19.19 |
| ATOM | 441 | CA | ARG | A | 73 | 4.706 | 23.394 | 31.736 | 1.00 18.17 |
| ATOM | 442 | CB | ARG | A | 73 | 5.277 | 23.098 | 30.351 | 1.00 18.40 |
| ATOM | 443 | CG | ARG | A | 73 | 6.735 | 23.539 | 30.185 | 1.00 16.99 |
| ATOM | 444 | CD | ARG | A | 73 | 7.388 | 23.053 | 28.874 | 1.00 16.70 |
| ATOM | 445 | NE | ARG | A | 73 | 7.620 | 21.604 | 28.934 | 1.00 16.40 |
| ATOM | 446 | CZ | ARG | A | 73 | 8.650 | 21.038 | 29.565 | 1.00 19.62 |
| ATOM | 447 | NH1 | ARG | A | 73 | 9.534 | 21.783 | 30.213 | 1.00 21.72 |
| ATOM | 448 | NH2 | ARG | A | 73 | 8.794 | 19.709 | 29.568 | 1.00 20.41 |
| ATOM | 449 | C | ARG | A | 73 | 4.811 | 24.891 | 31.984 | 1.00 19.99 |
| ATOM | 450 | O | ARG | A | 73 | 5.660 | 25.359 | 32.765 | 1.00 21.05 |
| ATOM | 451 | N | TYR | A | 74 | 3.961 | 25.633 | 31.292 | 1.00 18.61 |
| ATOM | 452 | CA | TYR | A | 74 | 3.919 | 27.081 | 31.449 | 1.00 18.09 |
| ATOM | 453 | CB | TYR | A | 74 | 4.190 | 27.726 | 30.102 | 1.00 16.79 |
| ATOM | 454 | CG | TYR | A | 74 | 5.560 | 27.365 | 29.541 | 1.00 16.34 |
| ATOM | 455 | CD1 | TYR | A | 74 | 6.722 | 27.696 | 30.196 | 1.00 20.25 |
| ATOM | 456 | CE1 | TYR | A | 74 | 7.971 | 27.371 | 29.649 | 1.00 21.10 |
| ATOM | 457 | CZ | TYR | A | 74 | 8.034 | 26.643 | 28.469 | 1.00 18.00 |
| ATOM | 458 | OH | TYR | A | 74 | 9.254 | 26.324 | 27.902 | 1.00 18.74 |
| ATOM | 459 | CE2 | TYR | A | 74 | 6.879 | 26.318 | 27.803 | 1.00 20.42 |
| ATOM | 460 | CD2 | TYR | A | 74 | 5.644 | 26.667 | 28.342 | 1.00 17.70 |
| ATOM | 461 | C | TYR | A | 74 | 2.539 | 27.463 | 31.946 | 1.00 20.00 |
| ATOM | 462 | O | TYR | A | 74 | 1.567 | 27.207 | 31.254 | 1.00 19.46 |
| ATOM | 463 | N | ASN | A | 75 | 2.442 | 28.052 | 33.138 | 1.00 19.96 |
| ATOM | 464 | CA | ASN | A | 75 | 1.125 | 28.228 | 33.729 | 1.00 18.71 |
| ATOM | 465 | CB | ASN | A | 75 | 1.218 | 28.665 | 35.186 | 1.00 19.98 |
| ATOM | 466 | CG | ASN | A | 75 | 1.531 | 27.534 | 36.144 | 1.00 28.50 |
| ATOM | 467 | OD1 | ASN | A | 75 | 1.941 | 27.798 | 37.276 | 1.00 41.57 |

FIGURE 111

```
ATOM    468  ND2 ASN A  75       1.291  26.291  35.743  1.00 34.02
ATOM    469  C   ASN A  75       0.300  29.254  32.975  1.00 19.22
ATOM    470  O   ASN A  75      -0.933  29.328  33.123  1.00 19.65
ATOM    471  N   ASN A  76       0.970  30.016  32.122  1.00 17.60
ATOM    472  CA  ASN A  76       0.307  30.963  31.250  1.00 17.67
ATOM    473  CB  ASN A  76       1.089  32.267  31.179  1.00 19.18
ATOM    474  CG  ASN A  76       2.392  32.127  30.427  1.00 19.09
ATOM    475  OD1 ASN A  76       3.099  31.147  30.602  1.00 19.41
ATOM    476  ND2 ASN A  76       2.677  33.069  29.545  1.00 18.60
ATOM    477  C   ASN A  76      -0.027  30.485  29.828  1.00 18.54
ATOM    478  O   ASN A  76      -0.587  31.266  29.046  1.00 20.42
ATOM    479  N   ILE A  77       0.332  29.243  29.499  1.00 17.75
ATOM    480  CA  ILE A  77       0.023  28.679  28.175  1.00 16.98
ATOM    481  CB  ILE A  77       1.267  28.284  27.363  1.00 17.92
ATOM    482  CG1 ILE A  77       2.270  29.429  27.287  1.00 17.69
ATOM    483  CD1 ILE A  77       1.825  30.580  26.477  1.00 24.18
ATOM    484  CG2 ILE A  77       0.802  27.838  25.951  1.00 14.34
ATOM    485  C   ILE A  77      -0.875  27.472  28.359  1.00 16.69
ATOM    486  O   ILE A  77      -0.438  26.387  28.721  1.00 17.71
ATOM    487  N   LEU A  78      -2.171  27.703  28.171  1.00 16.17
ATOM    488  CA  LEU A  78      -3.177  26.760  28.614  1.00 15.63
ATOM    489  CB  LEU A  78      -3.970  27.378  29.782  1.00 17.02
ATOM    490  CG  LEU A  78      -3.103  27.826  30.952  1.00 14.20
ATOM    491  CD1 LEU A  78      -3.971  28.492  32.013  1.00 18.34
ATOM    492  CD2 LEU A  78      -2.351  26.592  31.530  1.00 15.97
ATOM    493  C   LEU A  78      -4.116  26.521  27.448  1.00 16.27
ATOM    494  O   LEU A  78      -4.338  27.415  26.640  1.00 16.45
ATOM    495  N   PRO A  79      -4.676  25.319  27.365  1.00 15.77
ATOM    496  CA  PRO A  79      -5.657  25.005  26.325  1.00 16.37
ATOM    497  CB  PRO A  79      -5.825  23.494  26.465  1.00 15.52
ATOM    498  CG  PRO A  79      -5.511  23.196  27.896  1.00 16.91
ATOM    499  CD  PRO A  79      -4.409  24.186  28.269  1.00 16.37
ATOM    500  C   PRO A  79      -7.001  25.658  26.657  1.00 15.83
ATOM    501  O   PRO A  79      -7.397  25.687  27.824  1.00 16.64
ATOM    502  N   TYR A  80      -7.668  26.191  25.639  1.00 17.68
ATOM    503  CA  TYR A  80      -9.073  26.594  25.776  1.00 16.66
ATOM    504  CB  TYR A  80      -9.571  27.131  24.426  1.00 17.47
ATOM    505  CG  TYR A  80      -8.862  28.405  23.974  1.00 18.71
ATOM    506  CD1 TYR A  80      -8.661  29.469  24.864  1.00 21.72
ATOM    507  CE1 TYR A  80      -8.008  30.612  24.458  1.00 18.65
ATOM    508  CZ  TYR A  80      -7.552  30.728  23.163  1.00 18.69
ATOM    509  OH  TYR A  80      -6.951  31.901  22.794  1.00 19.69
ATOM    510  CE2 TYR A  80      -7.730  29.709  22.252  1.00 19.15
ATOM    511  CD2 TYR A  80      -8.363  28.532  22.676  1.00 18.51
ATOM    512  C   TYR A  80      -9.944  25.419  26.190  1.00 17.71
ATOM    513  O   TYR A  80      -9.835  24.326  25.641  1.00 18.31
ATOM    514  N   ASP A  81     -10.884  25.656  27.098  1.00 17.08
ATOM    515  CA  ASP A  81     -11.881  24.660  27.444  1.00 17.40
ATOM    516  CB  ASP A  81     -12.929  25.314  28.332  1.00 18.47
ATOM    517  CG  ASP A  81     -12.361  25.790  29.649  1.00 22.96
ATOM    518  OD1 ASP A  81     -11.447  25.148  30.229  1.00 20.84
ATOM    519  OD2 ASP A  81     -12.841  26.794  30.205  1.00 19.85
```

FIGURE 112

```
ATOM    520  C   ASP A  81     -12.568  24.065  26.215  1.00 16.40
ATOM    521  O   ASP A  81     -12.790  22.845  26.175  1.00 18.31
ATOM    522  N   ALA A  82     -12.901  24.923  25.248  1.00 18.79
ATOM    523  CA  ALA A  82     -13.714  24.544  24.096  1.00 21.05
ATOM    524  CB  ALA A  82     -14.082  25.787  23.284  1.00 22.15
ATOM    525  C   ALA A  82     -13.065  23.500  23.194  1.00 20.96
ATOM    526  O   ALA A  82     -13.763  22.798  22.459  1.00 19.35
ATOM    527  N   THR A  83     -11.730  23.441  23.203  1.00 18.07
ATOM    528  CA  THR A  83     -11.029  22.560  22.274  1.00 20.13
ATOM    529  CB  THR A  83     -10.260  23.375  21.204  1.00 21.39
ATOM    530  OG1 THR A  83      -9.399  24.306  21.888  1.00 20.87
ATOM    531  CG2 THR A  83     -11.215  24.257  20.373  1.00 22.64
ATOM    532  C   THR A  83     -10.015  21.647  22.962  1.00 19.11
ATOM    533  O   THR A  83      -9.241  21.027  22.255  1.00 18.63
ATOM    534  N   ARG A  84     -10.008  21.543  24.292  1.00 16.72
ATOM    535  CA  ARG A  84      -8.994  20.752  24.973  1.00 18.30
ATOM    536  CB  ARG A  84      -8.977  21.025  26.481  1.00 20.17
ATOM    537  CG  ARG A  84     -10.132  20.412  27.255  1.00 21.69
ATOM    538  CD  ARG A  84     -10.152  20.875  28.716  1.00 21.07
ATOM    539  NE  ARG A  84     -11.233  20.227  29.455  1.00 18.74
ATOM    540  CZ  ARG A  84     -11.068  19.171  30.257  1.00 17.05
ATOM    541  NH1 ARG A  84      -9.857  18.640  30.407  1.00 17.98
ATOM    542  NH2 ARG A  84     -12.125  18.639  30.884  1.00 17.21
ATOM    543  C   ARG A  84      -9.207  19.276  24.702  1.00 18.78
ATOM    544  O   ARG A  84     -10.348  18.839  24.517  1.00 19.49
ATOM    545  N   VAL A  85      -8.108  18.538  24.710  1.00 17.44
ATOM    546  CA  VAL A  85      -8.130  17.081  24.614  1.00 17.40
ATOM    547  CB  VAL A  85      -6.799  16.539  24.064  1.00 18.13
ATOM    548  CG1 VAL A  85      -6.897  15.001  23.926  1.00 17.98
ATOM    549  CG2 VAL A  85      -6.493  17.177  22.686  1.00 19.36
ATOM    550  C   VAL A  85      -8.371  16.488  26.003  1.00 18.79
ATOM    551  O   VAL A  85      -7.719  16.869  26.976  1.00 19.65
ATOM    552  N   LYS A  86      -9.315  15.555  26.094  1.00 18.68
ATOM    553  CA  LYS A  86      -9.613  14.946  27.396  1.00 17.68
ATOM    554  CB  LYS A  86     -11.137  14.942  27.623  1.00 18.74
ATOM    555  CG  LYS A  86     -11.672  16.355  27.728  1.00 22.75
ATOM    556  CD  LYS A  86     -13.167  16.435  27.837  1.00 27.00
ATOM    557  CE  LYS A  86     -13.540  17.906  27.691  1.00 30.36
ATOM    558  NZ  LYS A  86     -14.942  18.132  27.228  1.00 34.08
ATOM    559  C   LYS A  86      -9.118  13.517  27.445  1.00 19.75
ATOM    560  O   LYS A  86      -9.357  12.766  26.489  1.00 22.00
ATOM    561  N   LEU A  87      -8.443  13.188  28.544  1.00 19.49
ATOM    562  CA  LEU A  87      -8.007  11.819  28.836  1.00 21.14
ATOM    563  CB  LEU A  87      -6.883  11.849  29.871  1.00 20.71
ATOM    564  CG  LEU A  87      -5.611  12.606  29.453  1.00 24.00
ATOM    565  CD1 LEU A  87      -4.671  12.651  30.634  1.00 23.82
ATOM    566  CD2 LEU A  87      -4.924  11.964  28.229  1.00 22.65
ATOM    567  C   LEU A  87      -9.214  11.092  29.426  1.00 21.83
ATOM    568  O   LEU A  87     -10.077  11.716  30.069  1.00 21.33
ATOM    569  N   SER A  88      -9.278   9.777  29.239  1.00 22.50
ATOM    570  CA  SER A  88     -10.267   9.015  30.030  1.00 27.20
ATOM    571  CB  SER A  88     -10.199   7.517  29.746  1.00 26.15
```

FIGURE 113

```
ATOM   572  OG   SER A  88      -8.930   6.992  30.099  1.00 27.44
ATOM   573  C    SER A  88     -10.120   9.264  31.527  1.00 29.45
ATOM   574  O    SER A  88      -9.021   9.477  32.035  1.00 28.78
ATOM   575  N    ASN A  89     -11.244   9.263  32.234  1.00 33.66
ATOM   576  CA   ASN A  89     -11.240   9.331  33.697  1.00 38.59
ATOM   577  CB   ASN A  89     -12.675   9.420  34.228  1.00 40.00
ATOM   578  CG   ASN A  89     -13.511  10.437  33.472  1.00 44.74
ATOM   579  OD1  ASN A  89     -13.097  10.948  32.425  1.00 50.87
ATOM   580  ND2  ASN A  89     -14.702  10.725  33.990  1.00 48.81
ATOM   581  C    ASN A  89     -10.510   8.180  34.383  1.00 39.26
ATOM   582  O    ASN A  89     -10.637   7.018  33.977  1.00 40.17
ATOM   583  N    VAL A  90      -9.750   8.521  35.420  1.00 39.03
ATOM   584  CA   VAL A  90      -9.059   7.551  36.267  1.00 39.07
ATOM   585  CB   VAL A  90      -7.579   7.933  36.450  1.00 39.43
ATOM   586  CG1  VAL A  90      -6.890   7.053  37.502  1.00 39.89
ATOM   587  CG2  VAL A  90      -6.848   7.840  35.114  1.00 39.94
ATOM   588  C    VAL A  90      -9.724   7.437  37.641  1.00 39.53
ATOM   589  O    VAL A  90     -10.029   8.446  38.277  1.00 39.69
ATOM   590  N    CYS A  95     -10.123  15.551  38.257  1.00 32.20
ATOM   591  CA   CYS A  95      -9.274  16.239  37.274  1.00 31.56
ATOM   592  CB   CYS A  95      -8.436  17.341  37.923  1.00 32.45
ATOM   593  SG   CYS A  95      -9.470  18.646  38.623  1.00 39.21
ATOM   594  C    CYS A  95      -8.351  15.296  36.529  1.00 29.09
ATOM   595  O    CYS A  95      -7.399  15.760  35.888  1.00 28.47
ATOM   596  N    SER A  96      -8.624  13.992  36.611  1.00 25.31
ATOM   597  CA   SER A  96      -7.816  13.009  35.891  1.00 26.34
ATOM   598  CB   SER A  96      -8.104  11.576  36.380  1.00 26.13
ATOM   599  OG   SER A  96      -9.450  11.210  36.131  1.00 28.38
ATOM   600  C    SER A  96      -7.857  13.149  34.365  1.00 24.83
ATOM   601  O    SER A  96      -6.970  12.661  33.640  1.00 25.70
ATOM   602  N    ASP A  97      -8.863  13.860  33.873  1.00 23.60
ATOM   603  CA   ASP A  97      -9.022  14.004  32.432  1.00 23.00
ATOM   604  CB   ASP A  97     -10.486  14.244  32.031  1.00 23.06
ATOM   605  CG   ASP A  97     -10.939  15.704  32.178  1.00 25.86
ATOM   606  OD1  ASP A  97     -10.131  16.559  32.575  1.00 23.58
ATOM   607  OD2  ASP A  97     -12.113  16.073  31.926  1.00 27.66
ATOM   608  C    ASP A  97      -8.085  15.005  31.779  1.00 20.67
ATOM   609  O    ASP A  97      -8.055  15.123  30.548  1.00 21.87
ATOM   610  N    TYR A  98      -7.333  15.746  32.581  1.00 19.60
ATOM   611  CA   TYR A  98      -6.691  16.926  32.030  1.00 18.52
ATOM   612  CB   TYR A  98      -6.520  18.003  33.104  1.00 18.03
ATOM   613  CG   TYR A  98      -5.822  19.205  32.517  1.00 19.58
ATOM   614  CD1  TYR A  98      -6.534  20.124  31.746  1.00 21.57
ATOM   615  CE1  TYR A  98      -5.904  21.216  31.192  1.00 16.87
ATOM   616  CZ   TYR A  98      -4.536  21.375  31.389  1.00 16.22
ATOM   617  OH   TYR A  98      -3.906  22.447  30.797  1.00 18.85
ATOM   618  CE2  TYR A  98      -3.803  20.475  32.138  1.00 17.86
ATOM   619  CD2  TYR A  98      -4.445  19.385  32.694  1.00 19.81
ATOM   620  C    TYR A  98      -5.338  16.650  31.410  1.00 16.72
ATOM   621  O    TYR A  98      -4.485  16.025  32.040  1.00 19.70
ATOM   622  N    ILE A  99      -5.137  17.179  30.199  1.00 15.99
ATOM   623  CA   ILE A  99      -3.773  17.307  29.653  1.00 15.12
```

FIGURE 114

```
ATOM    624  CB   ILE A  99      -3.485  16.142  28.679  1.00 16.27
ATOM    625  CG1  ILE A  99      -2.013  16.171  28.227  1.00 13.41
ATOM    626  CD1  ILE A  99      -1.501  14.952  27.413  1.00 15.15
ATOM    627  CG2  ILE A  99      -4.516  16.099  27.536  1.00 18.41
ATOM    628  C    ILE A  99      -3.730  18.654  28.924  1.00 14.61
ATOM    629  O    ILE A  99      -4.754  19.134  28.452  1.00 14.64
ATOM    630  N    ASN A 100      -2.549  19.246  28.845  1.00 13.96
ATOM    631  CA   ASN A 100      -2.381  20.522  28.162  1.00 15.20
ATOM    632  CB   ASN A 100      -1.218  21.330  28.763  1.00 15.09
ATOM    633  CG   ASN A 100      -1.167  22.726  28.214  1.00 15.71
ATOM    634  OD1  ASN A 100      -1.374  22.917  27.020  1.00 16.88
ATOM    635  ND2  ASN A 100      -0.873  23.698  29.060  1.00 15.13
ATOM    636  C    ASN A 100      -2.184  20.228  26.679  1.00 14.05
ATOM    637  O    ASN A 100      -1.068  20.052  26.188  1.00 15.61
ATOM    638  N    ALA A 101      -3.321  20.129  26.011  1.00 14.18
ATOM    639  CA   ALA A 101      -3.342  19.806  24.587  1.00 14.86
ATOM    640  CB   ALA A 101      -3.238  18.306  24.435  1.00 14.35
ATOM    641  C    ALA A 101      -4.665  20.251  24.018  1.00 15.17
ATOM    642  O    ALA A 101      -5.669  20.248  24.743  1.00 14.69
ATOM    643  N    SER A 102      -4.679  20.523  22.708  1.00 15.50
ATOM    644  CA   SER A 102      -5.810  21.159  22.047  1.00 15.05
ATOM    645  CB   SER A 102      -5.471  22.629  21.759  1.00 15.31
ATOM    646  OG   SER A 102      -5.151  23.291  22.969  1.00 15.76
ATOM    647  C    SER A 102      -6.060  20.499  20.687  1.00 14.47
ATOM    648  O    SER A 102      -5.122  20.253  19.962  1.00 16.41
ATOM    649  N    TYR A 103      -7.315  20.273  20.310  1.00 14.11
ATOM    650  CA   TYR A 103      -7.625  19.700  18.994  1.00 16.15
ATOM    651  CB   TYR A 103      -9.064  19.128  18.983  1.00 15.58
ATOM    652  CG   TYR A 103      -9.226  17.837  19.738  1.00 17.69
ATOM    653  CD1  TYR A 103      -8.530  16.696  19.331  1.00 21.85
ATOM    654  CE1  TYR A 103      -8.681  15.485  20.004  1.00 18.09
ATOM    655  CZ   TYR A 103      -9.560  15.417  21.070  1.00 23.34
ATOM    656  OH   TYR A 103      -9.763  14.235  21.749  1.00 25.07
ATOM    657  CE2  TYR A 103     -10.281  16.527  21.482  1.00 22.71
ATOM    658  CD2  TYR A 103     -10.123  17.724  20.808  1.00 19.56
ATOM    659  C    TYR A 103      -7.606  20.816  17.968  1.00 17.25
ATOM    660  O    TYR A 103      -8.067  21.930  18.244  1.00 18.82
ATOM    661  N    ILE A 104      -7.125  20.470  16.779  1.00 16.96
ATOM    662  CA   ILE A 104      -7.227  21.292  15.577  1.00 17.89
ATOM    663  CB   ILE A 104      -5.810  21.550  15.040  1.00 18.29
ATOM    664  CG1  ILE A 104      -4.887  21.993  16.154  1.00 19.03
ATOM    665  CD1  ILE A 104      -5.247  23.333  16.819  1.00 21.70
ATOM    666  CG2  ILE A 104      -5.845  22.465  13.784  1.00 22.08
ATOM    667  C    ILE A 104      -8.013  20.483  14.547  1.00 20.87
ATOM    668  O    ILE A 104      -7.582  19.407  14.121  1.00 20.90
ATOM    669  N    PRO A 105      -9.188  20.966  14.154  1.00 21.39
ATOM    670  CA   PRO A 105      -9.980  20.233  13.162  1.00 20.64
ATOM    671  CB   PRO A 105     -11.348  20.918  13.214  1.00 21.14
ATOM    672  CG   PRO A 105     -11.064  22.320  13.696  1.00 25.38
ATOM    673  CD   PRO A 105      -9.836  22.219  14.596  1.00 22.10
ATOM    674  C    PRO A 105      -9.346  20.426  11.786  1.00 20.86
ATOM    675  O    PRO A 105      -8.621  21.420  11.579  1.00 22.00
```

FIGURE 115

```
ATOM    676  N   GLY A 106      -9.603  19.487  10.872  1.00 20.78
ATOM    677  CA  GLY A 106      -9.258  19.643   9.472  1.00 23.04
ATOM    678  C   GLY A 106     -10.329  20.332   8.646  1.00 25.39
ATOM    679  O   GLY A 106     -11.440  20.586   9.124  1.00 24.34
ATOM    680  N   ASN A 107     -10.001  20.603   7.386  1.00 27.36
ATOM    681  CA  ASN A 107     -10.986  21.163   6.458  1.00 29.29
ATOM    682  CB  ASN A 107     -10.336  21.579   5.142  1.00 31.82
ATOM    683  CG  ASN A 107      -9.436  22.795   5.291  1.00 34.51
ATOM    684  OD1 ASN A 107      -8.306  22.792   4.798  1.00 43.42
ATOM    685  ND2 ASN A 107      -9.917  23.824   5.984  1.00 40.29
ATOM    686  C   ASN A 107     -12.080  20.168   6.153  1.00 28.84
ATOM    687  O   ASN A 107     -13.182  20.560   5.772  1.00 29.29
ATOM    688  N   ASN A 108     -11.776  18.881   6.300  1.00 27.42
ATOM    689  CA  ASN A 108     -12.716  17.847   5.886  1.00 28.42
ATOM    690  CB  ASN A 108     -12.020  16.861   4.947  1.00 29.82
ATOM    691  CG  ASN A 108     -11.769  17.438   3.570  1.00 33.34
ATOM    692  OD1 ASN A 108     -10.623  17.630   3.158  1.00 39.32
ATOM    693  ND2 ASN A 108     -12.846  17.710   2.843  1.00 37.81
ATOM    694  C   ASN A 108     -13.325  17.065   7.052  1.00 27.69
ATOM    695  O   ASN A 108     -14.371  16.440   6.895  1.00 28.98
ATOM    696  N   PHE A 109     -12.665  17.078   8.206  1.00 24.03
ATOM    697  CA  PHE A 109     -13.114  16.259   9.339  1.00 21.78
ATOM    698  CB  PHE A 109     -12.718  14.795   9.081  1.00 20.51
ATOM    699  CG  PHE A 109     -13.564  13.780   9.830  1.00 21.38
ATOM    700  CD1 PHE A 109     -13.061  13.110  10.936  1.00 21.50
ATOM    701  CE1 PHE A 109     -13.823  12.180  11.626  1.00 24.12
ATOM    702  CZ  PHE A 109     -15.129  11.909  11.208  1.00 25.45
ATOM    703  CE2 PHE A 109     -15.641  12.561  10.113  1.00 21.35
ATOM    704  CD2 PHE A 109     -14.866  13.493   9.421  1.00 18.54
ATOM    705  C   PHE A 109     -12.452  16.764  10.612  1.00 22.13
ATOM    706  O   PHE A 109     -11.412  17.437  10.545  1.00 21.08
ATOM    707  N   ARG A 110     -13.013  16.358  11.752  1.00 19.50
ATOM    708  CA  ARG A 110     -12.523  16.785  13.054  1.00 21.56
ATOM    709  CB  ARG A 110     -13.472  16.347  14.168  1.00 22.46
ATOM    710  CG  ARG A 110     -13.476  14.851  14.413  1.00 24.80
ATOM    711  CD  ARG A 110     -14.802  14.225  14.822  1.00 32.72
ATOM    712  NE  ARG A 110     -15.236  14.643  16.150  1.00 39.42
ATOM    713  CZ  ARG A 110     -15.044  13.914  17.243  1.00 43.17
ATOM    714  NH1 ARG A 110     -14.400  12.750  17.162  1.00 42.56
ATOM    715  NH2 ARG A 110     -15.474  14.358  18.418  1.00 43.79
ATOM    716  C   ARG A 110     -11.118  16.239  13.310  1.00 20.39
ATOM    717  O   ARG A 110     -10.729  15.220  12.746  1.00 21.44
ATOM    718  N   ARG A 111     -10.436  16.843  14.273  1.00 20.63
ATOM    719  CA  ARG A 111      -9.259  16.240  14.885  1.00 21.26
ATOM    720  CB  ARG A 111      -9.651  15.008  15.728  1.00 20.41
ATOM    721  CG  ARG A 111     -10.650  15.324  16.827  1.00 21.47
ATOM    722  CD  ARG A 111     -10.936  14.151  17.754  1.00 21.72
ATOM    723  NE  ARG A 111     -11.920  14.585  18.729  1.00 22.21
ATOM    724  CZ  ARG A 111     -12.269  13.928  19.825  1.00 27.64
ATOM    725  NH1 ARG A 111     -11.713  12.759  20.119  1.00 30.92
ATOM    726  NH2 ARG A 111     -13.175  14.456  20.633  1.00 26.56
ATOM    727  C   ARG A 111      -8.161  15.872  13.914  1.00 20.16
```

FIGURE 116

```
ATOM    728  O   ARG A 111      -7.612  14.761  13.972  1.00 21.20
ATOM    729  N   GLU A 112      -7.777  16.801  13.043  1.00 18.71
ATOM    730  CA  GLU A 112      -6.651  16.499  12.179  1.00 17.48
ATOM    731  CB  GLU A 112      -6.632  17.426  10.954  1.00 18.75
ATOM    732  CG  GLU A 112      -5.441  17.169  10.049  1.00 16.97
ATOM    733  CD  GLU A 112      -5.437  18.043   8.809  1.00 27.96
ATOM    734  OE1 GLU A 112      -4.889  17.541   7.805  1.00 25.67
ATOM    735  OE2 GLU A 112      -5.919  19.209   8.860  1.00 25.41
ATOM    736  C   GLU A 112      -5.307  16.580  12.906  1.00 16.93
ATOM    737  O   GLU A 112      -4.421  15.771  12.615  1.00 17.02
ATOM    738  N   TYR A 113      -5.168  17.526  13.834  1.00 16.48
ATOM    739  CA  TYR A 113      -3.964  17.632  14.673  1.00 17.06
ATOM    740  CB  TYR A 113      -3.168  18.898  14.387  1.00 15.83
ATOM    741  CG  TYR A 113      -2.779  19.127  12.955  1.00 18.99
ATOM    742  CD1 TYR A 113      -3.606  19.884  12.148  1.00 22.98
ATOM    743  CE1 TYR A 113      -3.290  20.157  10.850  1.00 24.83
ATOM    744  CZ  TYR A 113      -2.089  19.709  10.356  1.00 22.77
ATOM    745  OH  TYR A 113      -1.838  20.017   9.035  1.00 28.70
ATOM    746  CE2 TYR A 113      -1.233  18.945  11.118  1.00 22.82
ATOM    747  CD2 TYR A 113      -1.570  18.678  12.457  1.00 24.11
ATOM    748  C   TYR A 113      -4.327  17.701  16.163  1.00 14.55
ATOM    749  O   TYR A 113      -5.445  18.039  16.533  1.00 16.23
ATOM    750  N   ILE A 114      -3.439  17.251  17.029  1.00 13.11
ATOM    751  CA  ILE A 114      -3.500  17.610  18.439  1.00 13.46
ATOM    752  CB  ILE A 114      -3.501  16.340  19.331  1.00 13.02
ATOM    753  CG1 ILE A 114      -4.859  15.643  19.231  1.00 15.50
ATOM    754  CD1 ILE A 114      -4.796  14.175  19.736  1.00 17.84
ATOM    755  CG2 ILE A 114      -3.233  16.721  20.803  1.00 15.76
ATOM    756  C   ILE A 114      -2.239  18.421  18.708  1.00 15.12
ATOM    757  O   ILE A 114      -1.146  17.951  18.448  1.00 16.55
ATOM    758  N   VAL A 115      -2.407  19.636  19.215  1.00 15.68
ATOM    759  CA  VAL A 115      -1.262  20.440  19.619  1.00 14.96
ATOM    760  CB  VAL A 115      -1.499  21.899  19.277  1.00 15.98
ATOM    761  CG1 VAL A 115      -0.446  22.789  19.895  1.00 18.83
ATOM    762  CG2 VAL A 115      -1.501  22.011  17.767  1.00 19.14
ATOM    763  C   VAL A 115      -1.078  20.282  21.114  1.00 15.79
ATOM    764  O   VAL A 115      -2.039  20.346  21.880  1.00 15.38
ATOM    765  N   THR A 116       0.163  20.062  21.541  1.00 14.14
ATOM    766  CA  THR A 116       0.399  19.938  22.966  1.00 15.23
ATOM    767  CB  THR A 116       0.267  18.421  23.362  1.00 15.94
ATOM    768  OG1 THR A 116       0.282  18.318  24.792  1.00 16.48
ATOM    769  CG2 THR A 116       1.492  17.619  22.906  1.00 20.42
ATOM    770  C   THR A 116       1.737  20.589  23.403  1.00 14.47
ATOM    771  O   THR A 116       2.563  20.939  22.583  1.00 17.79
ATOM    772  N   GLN A 117       1.924  20.762  24.706  1.00 16.11
ATOM    773  CA  GLN A 117       3.181  21.248  25.251  1.00 15.39
ATOM    774  CB  GLN A 117       2.975  21.710  26.716  1.00 14.51
ATOM    775  CG  GLN A 117       2.597  20.569  27.659  1.00 15.32
ATOM    776  CD  GLN A 117       2.327  21.017  29.072  1.00 16.29
ATOM    777  OE1 GLN A 117       2.162  22.202  29.329  1.00 17.89
ATOM    778  NE2 GLN A 117       2.265  20.073  29.987  1.00 15.78
ATOM    779  C   GLN A 117       4.208  20.143  25.228  1.00 16.18
```

FIGURE 117

```
ATOM    780  O    GLN A 117       3.895  18.970  25.110  1.00 16.55
ATOM    781  N    GLY A 118       5.469  20.517  25.375  1.00 16.92
ATOM    782  CA   GLY A 118       6.470  19.495  25.606  1.00 16.65
ATOM    783  C    GLY A 118       6.186  18.761  26.901  1.00 15.21
ATOM    784  O    GLY A 118       6.087  19.352  27.989  1.00 16.22
ATOM    785  N    PRO A 119       6.035  17.445  26.822  1.00 15.88
ATOM    786  CA   PRO A 119       5.791  16.689  28.055  1.00 15.90
ATOM    787  CB   PRO A 119       5.878  15.243  27.582  1.00 17.35
ATOM    788  CG   PRO A 119       5.520  15.281  26.147  1.00 16.27
ATOM    789  CD   PRO A 119       6.092  16.575  25.628  1.00 16.39
ATOM    790  C    PRO A 119       6.768  16.949  29.213  1.00 17.04
ATOM    791  O    PRO A 119       7.972  17.127  28.997  1.00 17.25
ATOM    792  N    LEU A 120       6.230  16.986  30.427  1.00 20.34
ATOM    793  CA   LEU A 120       7.006  17.119  31.660  1.00 20.38
ATOM    794  CB   LEU A 120       6.171  17.875  32.683  1.00 20.80
ATOM    795  CG   LEU A 120       5.899  19.355  32.400  1.00 20.40
ATOM    796  CD1  LEU A 120       4.670  19.772  33.207  1.00 20.65
ATOM    797  CD2  LEU A 120       7.087  20.257  32.655  1.00 22.46
ATOM    798  C    LEU A 120       7.324  15.718  32.190  1.00 22.07
ATOM    799  O    LEU A 120       6.642  14.762  31.824  1.00 19.88
ATOM    800  N    PRO A 121       8.343  15.566  33.032  1.00 22.56
ATOM    801  CA   PRO A 121       8.590  14.265  33.676  1.00 22.53
ATOM    802  CB   PRO A 121       9.586  14.599  34.790  1.00 22.51
ATOM    803  CG   PRO A 121      10.302  15.799  34.270  1.00 24.46
ATOM    804  CD   PRO A 121       9.302  16.594  33.481  1.00 23.40
ATOM    805  C    PRO A 121       7.295  13.766  34.308  1.00 20.90
ATOM    806  O    PRO A 121       7.019  12.575  34.178  1.00 22.13
ATOM    807  N    GLY A 122       6.529  14.643  34.946  1.00 18.52
ATOM    808  CA   GLY A 122       5.267  14.247  35.555  1.00 19.71
ATOM    809  C    GLY A 122       4.050  14.113  34.658  1.00 19.48
ATOM    810  O    GLY A 122       3.008  13.713  35.158  1.00 20.10
ATOM    811  N    THR A 123       4.152  14.463  33.376  1.00 19.70
ATOM    812  CA   THR A 123       3.013  14.300  32.467  1.00 20.05
ATOM    813  CB   THR A 123       2.470  15.643  31.910  1.00 19.02
ATOM    814  OG1  THR A 123       3.417  16.229  31.006  1.00 17.75
ATOM    815  CG2  THR A 123       2.286  16.724  33.011  1.00 21.52
ATOM    816  C    THR A 123       3.305  13.389  31.279  1.00 18.26
ATOM    817  O    THR A 123       2.428  13.238  30.410  1.00 19.28
ATOM    818  N    LYS A 124       4.498  12.810  31.219  1.00 18.95
ATOM    819  CA   LYS A 124       4.788  11.956  30.057  1.00 18.96
ATOM    820  CB   LYS A 124       6.283  11.641  29.950  1.00 20.13
ATOM    821  CG   LYS A 124       6.834  10.806  31.086  1.00 23.04
ATOM    822  CD   LYS A 124       8.336  10.603  30.898  1.00 29.73
ATOM    823  CE   LYS A 124       8.775   9.445  31.787  1.00 36.02
ATOM    824  NZ   LYS A 124      10.152   9.706  32.286  1.00 43.04
ATOM    825  C    LYS A 124       3.876  10.734  29.956  1.00 19.08
ATOM    826  O    LYS A 124       3.538  10.312  28.855  1.00 17.17
ATOM    827  N    ASP A 125       3.454  10.156  31.086  1.00 18.94
ATOM    828  CA   ASP A 125       2.497   9.066  31.016  1.00 19.18
ATOM    829  CB   ASP A 125       2.272   8.426  32.390  1.00 20.53
ATOM    830  CG   ASP A 125       3.531   7.858  32.991  1.00 22.30
ATOM    831  OD1  ASP A 125       4.545   7.684  32.280  1.00 23.89
```

FIGURE 118

```
ATOM    832  OD2 ASP A 125       3.577   7.580  34.216  1.00 25.30
ATOM    833  C   ASP A 125       1.160   9.570  30.460  1.00 18.40
ATOM    834  O   ASP A 125       0.519   8.877  29.670  1.00 19.13
ATOM    835  N   ASP A 126       0.760  10.773  30.871  1.00 17.97
ATOM    836  CA  ASP A 126      -0.453  11.402  30.351  1.00 17.81
ATOM    837  CB  ASP A 126      -0.632  12.804  30.951  1.00 18.50
ATOM    838  CG  ASP A 126      -0.832  12.813  32.447  1.00 24.65
ATOM    839  OD1 ASP A 126      -1.196  11.774  33.046  1.00 22.46
ATOM    840  OD2 ASP A 126      -0.670  13.887  33.085  1.00 24.22
ATOM    841  C   ASP A 126      -0.314  11.606  28.837  1.00 16.85
ATOM    842  O   ASP A 126      -1.256  11.407  28.082  1.00 16.48
ATOM    843  N   PHE A 127       0.868  12.008  28.380  1.00 17.92
ATOM    844  CA  PHE A 127       1.068  12.282  26.958  1.00 16.02
ATOM    845  CB  PHE A 127       2.459  12.901  26.744  1.00 15.67
ATOM    846  CG  PHE A 127       2.886  12.934  25.300  1.00 15.63
ATOM    847  CD1 PHE A 127       2.614  14.040  24.513  1.00 15.34
ATOM    848  CE1 PHE A 127       3.015  14.065  23.170  1.00 18.23
ATOM    849  CZ  PHE A 127       3.682  12.972  22.603  1.00 17.60
ATOM    850  CE2 PHE A 127       3.902  11.819  23.398  1.00 14.91
ATOM    851  CD2 PHE A 127       3.540  11.826  24.721  1.00 15.74
ATOM    852  C   PHE A 127       0.913  10.967  26.199  1.00 15.37
ATOM    853  O   PHE A 127       0.234  10.922  25.167  1.00 15.38
ATOM    854  N   TRP A 128       1.486   9.880  26.710  1.00 15.77
ATOM    855  CA  TRP A 128       1.412   8.643  25.951  1.00 15.30
ATOM    856  CB  TRP A 128       2.416   7.618  26.452  1.00 14.62
ATOM    857  CG  TRP A 128       3.800   7.961  26.004  1.00 15.64
ATOM    858  CD1 TRP A 128       4.848   8.266  26.796  1.00 16.32
ATOM    859  NE1 TRP A 128       5.978   8.498  26.047  1.00 16.04
ATOM    860  CE2 TRP A 128       5.658   8.340  24.721  1.00 17.00
ATOM    861  CD2 TRP A 128       4.275   8.037  24.656  1.00 14.14
ATOM    862  CE3 TRP A 128       3.697   7.798  23.401  1.00 18.83
ATOM    863  CZ3 TRP A 128       4.481   7.947  22.261  1.00 19.71
ATOM    864  CH2 TRP A 128       5.855   8.288  22.362  1.00 18.66
ATOM    865  CZ2 TRP A 128       6.446   8.494  23.583  1.00 17.54
ATOM    866  C   TRP A 128       0.000   8.071  25.981  1.00 14.42
ATOM    867  O   TRP A 128      -0.410   7.416  25.021  1.00 15.80
ATOM    868  N   LYS A 129      -0.671   8.219  27.123  1.00 16.32
ATOM    869  CA  LYS A 129      -2.091   7.905  27.214  1.00 15.35
ATOM    870  CB  LYS A 129      -2.642   8.310  28.588  1.00 18.04
ATOM    871  CG  LYS A 129      -4.131   7.953  28.762  1.00 16.84
ATOM    872  CD  LYS A 129      -4.549   8.066  30.229  1.00 19.80
ATOM    873  CE  LYS A 129      -6.064   8.051  30.343  1.00 21.91
ATOM    874  NZ  LYS A 129      -6.439   8.260  31.807  1.00 25.23
ATOM    875  C   LYS A 129      -2.861   8.607  26.121  1.00 16.69
ATOM    876  O   LYS A 129      -3.713   8.011  25.465  1.00 16.75
ATOM    877  N   MET A 130      -2.618   9.909  25.990  1.00 15.72
ATOM    878  CA  MET A 130      -3.311  10.652  24.957  1.00 16.87
ATOM    879  CB  MET A 130      -3.026  12.145  25.080  1.00 14.45
ATOM    880  CG  MET A 130      -3.608  12.865  23.908  1.00 15.57
ATOM    881  SD  MET A 130      -3.131  14.614  23.936  1.00 17.91
ATOM    882  CE  MET A 130      -1.383  14.608  23.583  1.00 16.03
ATOM    883  C   MET A 130      -3.040  10.117  23.548  1.00 16.34
```

FIGURE 119

```
ATOM    884  O    MET A 130      -3.965   9.899  22.759  1.00 16.31
ATOM    885  N    VAL A 131      -1.783   9.837  23.226  1.00 15.65
ATOM    886  CA   VAL A 131      -1.402   9.283  21.924  1.00 13.92
ATOM    887  CB   VAL A 131       0.120   9.049  21.956  1.00 14.34
ATOM    888  CG1  VAL A 131       0.588   8.212  20.797  1.00 18.45
ATOM    889  CG2  VAL A 131       0.877  10.386  21.984  1.00 18.04
ATOM    890  C    VAL A 131      -2.107   7.948  21.681  1.00 14.86
ATOM    891  O    VAL A 131      -2.609   7.668  20.579  1.00 15.81
ATOM    892  N    TRP A 132      -2.209   7.145  22.732  1.00 14.88
ATOM    893  CA   TRP A 132      -2.840   5.840  22.599  1.00 14.40
ATOM    894  CB   TRP A 132      -2.599   4.996  23.861  1.00 14.68
ATOM    895  CG   TRP A 132      -3.301   3.666  23.747  1.00 16.82
ATOM    896  CD1  TRP A 132      -4.427   3.273  24.402  1.00 17.83
ATOM    897  NE1  TRP A 132      -4.799   2.015  23.980  1.00 16.10
ATOM    898  CE2  TRP A 132      -3.901   1.566  23.049  1.00 19.18
ATOM    899  CD2  TRP A 132      -2.956   2.591  22.852  1.00 18.23
ATOM    900  CE3  TRP A 132      -1.924   2.388  21.930  1.00 16.64
ATOM    901  CZ3  TRP A 132      -1.857   1.165  21.233  1.00 18.77
ATOM    902  CH2  TRP A 132      -2.841   0.177  21.450  1.00 19.47
ATOM    903  CZ2  TRP A 132      -3.857   0.358  22.350  1.00 18.87
ATOM    904  C    TRP A 132      -4.346   6.021  22.375  1.00 14.57
ATOM    905  O    TRP A 132      -4.901   5.489  21.423  1.00 14.81
ATOM    906  N    GLU A 133      -4.977   6.784  23.257  1.00 17.42
ATOM    907  CA   GLU A 133      -6.450   6.895  23.277  1.00 15.50
ATOM    908  CB   GLU A 133      -6.924   7.614  24.526  1.00 15.78
ATOM    909  CG   GLU A 133      -6.669   6.814  25.790  1.00 17.18
ATOM    910  CD   GLU A 133      -7.390   7.374  26.988  1.00 25.51
ATOM    911  OE1  GLU A 133      -7.721   8.585  26.977  1.00 22.92
ATOM    912  OE2  GLU A 133      -7.539   6.592  27.957  1.00 21.86
ATOM    913  C    GLU A 133      -6.990   7.595  22.041  1.00 17.24
ATOM    914  O    GLU A 133      -8.144   7.335  21.609  1.00 16.93
ATOM    915  N    GLN A 134      -6.188   8.513  21.501  1.00 16.12
ATOM    916  CA   GLN A 134      -6.583   9.284  20.326  1.00 16.01
ATOM    917  CB   GLN A 134      -6.136  10.746  20.432  1.00 15.45
ATOM    918  CG   GLN A 134      -6.658  11.461  21.657  1.00 16.97
ATOM    919  CD   GLN A 134      -8.141  11.671  21.576  1.00 21.63
ATOM    920  OE1  GLN A 134      -8.649  12.128  20.548  1.00 30.42
ATOM    921  NE2  GLN A 134      -8.855  11.298  22.636  1.00 24.38
ATOM    922  C    GLN A 134      -6.211   8.681  18.987  1.00 16.29
ATOM    923  O    GLN A 134      -6.418   9.300  17.936  1.00 17.57
ATOM    924  N    ASN A 135      -5.721   7.438  19.007  1.00 16.26
ATOM    925  CA   ASN A 135      -5.338   6.741  17.788  1.00 16.42
ATOM    926  CB   ASN A 135      -6.562   6.516  16.901  1.00 18.03
ATOM    927  CG   ASN A 135      -7.602   5.656  17.580  1.00 22.43
ATOM    928  OD1  ASN A 135      -7.358   4.475  17.849  1.00 28.78
ATOM    929  ND2  ASN A 135      -8.757   6.232  17.865  1.00 27.37
ATOM    930  C    ASN A 135      -4.243   7.426  16.964  1.00 18.21
ATOM    931  O    ASN A 135      -4.199   7.287  15.749  1.00 17.34
ATOM    932  N    VAL A 136      -3.380   8.164  17.651  1.00 18.13
ATOM    933  CA   VAL A 136      -2.276   8.873  17.011  1.00 16.80
ATOM    934  CB   VAL A 136      -1.664   9.866  18.023  1.00 18.00
ATOM    935  CG1  VAL A 136      -0.351  10.461  17.482  1.00 16.01
```

FIGURE 120

```
ATOM    936  CG2 VAL A 136      -2.680  10.930  18.399  1.00 18.19
ATOM    937  C   VAL A 136      -1.229   7.880  16.483  1.00 18.93
ATOM    938  O   VAL A 136      -0.821   6.977  17.211  1.00 19.57
ATOM    939  N   HIS A 137      -0.860   8.013  15.202  1.00 17.50
ATOM    940  CA  HIS A 137       0.264   7.277  14.623  1.00 16.22
ATOM    941  CB  HIS A 137      -0.110   6.473  13.360  1.00 18.79
ATOM    942  CG  HIS A 137      -1.152   5.414  13.571  1.00 19.38
ATOM    943  ND1 HIS A 137      -2.419   5.691  14.034  1.00 20.18
ATOM    944  CE1 HIS A 137      -3.116   4.572  14.115  1.00 22.60
ATOM    945  NE2 HIS A 137      -2.358   3.579  13.680  1.00 22.19
ATOM    946  CD2 HIS A 137      -1.121   4.078  13.344  1.00 20.32
ATOM    947  C   HIS A 137       1.494   8.093  14.295  1.00 17.23
ATOM    948  O   HIS A 137       2.513   7.496  13.947  1.00 17.71
ATOM    949  N   ASN A 138       1.428   9.423  14.394  1.00 16.24
ATOM    950  CA  ASN A 138       2.590  10.238  14.046  1.00 17.25
ATOM    951  CB  ASN A 138       2.470  10.816  12.632  1.00 17.99
ATOM    952  CG  ASN A 138       2.330   9.741  11.562  1.00 18.27
ATOM    953  OD1 ASN A 138       1.219   9.397  11.126  1.00 25.07
ATOM    954  ND2 ASN A 138       3.457   9.169  11.189  1.00 19.74
ATOM    955  C   ASN A 138       2.684  11.382  15.044  1.00 14.09
ATOM    956  O   ASN A 138       1.676  11.996  15.397  1.00 15.42
ATOM    957  N   ILE A 139       3.904  11.633  15.485  1.00 13.67
ATOM    958  CA  ILE A 139       4.204  12.739  16.391  1.00 13.12
ATOM    959  CB  ILE A 139       4.750  12.186  17.716  1.00 14.52
ATOM    960  CG1 ILE A 139       3.714  11.302  18.394  1.00 14.31
ATOM    961  CD1 ILE A 139       4.274  10.494  19.577  1.00 15.81
ATOM    962  CG2 ILE A 139       5.125  13.346  18.653  1.00 15.50
ATOM    963  C   ILE A 139       5.282  13.581  15.752  1.00 15.31
ATOM    964  O   ILE A 139       6.323  13.073  15.333  1.00 16.48
ATOM    965  N   VAL A 140       5.076  14.892  15.788  1.00 14.75
ATOM    966  CA  VAL A 140       6.049  15.831  15.231  1.00 15.93
ATOM    967  CB  VAL A 140       5.367  16.704  14.177  1.00 15.43
ATOM    968  CG1 VAL A 140       6.329  17.788  13.728  1.00 16.73
ATOM    969  CG2 VAL A 140       4.898  15.852  12.985  1.00 17.63
ATOM    970  C   VAL A 140       6.531  16.700  16.377  1.00 16.09
ATOM    971  O   VAL A 140       5.717  17.295  17.053  1.00 18.31
ATOM    972  N   MET A 141       7.839  16.702  16.645  1.00 16.31
ATOM    973  CA  MET A 141       8.421  17.472  17.741  1.00 17.39
ATOM    974  CB  MET A 141       9.226  16.515  18.632  1.00 16.11
ATOM    975  CG  MET A 141      10.082  17.201  19.670  1.00 16.87
ATOM    976  SD  MET A 141      10.679  15.960  20.837  1.00 18.61
ATOM    977  CE  MET A 141      11.650  16.998  21.959  1.00 19.51
ATOM    978  C   MET A 141       9.344  18.530  17.127  1.00 17.17
ATOM    979  O   MET A 141      10.303  18.177  16.439  1.00 17.62
ATOM    980  N   VAL A 142       9.081  19.805  17.364  1.00 16.69
ATOM    981  CA  VAL A 142       9.869  20.876  16.731  1.00 19.57
ATOM    982  CB  VAL A 142       9.050  21.674  15.715  1.00 17.61
ATOM    983  CG1 VAL A 142       8.808  20.820  14.463  1.00 20.20
ATOM    984  CG2 VAL A 142       7.675  22.009  16.283  1.00 19.28
ATOM    985  C   VAL A 142      10.477  21.756  17.829  1.00 21.83
ATOM    986  O   VAL A 142      10.473  22.986  17.763  1.00 24.11
ATOM    987  N   THR A 143      10.993  21.091  18.852  1.00 19.91
```

FIGURE 121

```
ATOM    988  CA   THR A 143      11.845  21.727  19.857  1.00 20.81
ATOM    989  CB   THR A 143      11.042  22.039  21.108  1.00 20.61
ATOM    990  OG1  THR A 143      11.835  22.818  22.014  1.00 20.47
ATOM    991  CG2  THR A 143      10.728  20.749  21.898  1.00 19.53
ATOM    992  C    THR A 143      13.001  20.795  20.195  1.00 21.41
ATOM    993  O    THR A 143      12.919  19.603  19.953  1.00 20.95
ATOM    994  N    GLN A 144      14.096  21.337  20.719  1.00 21.06
ATOM    995  CA   GLN A 144      15.047  20.523  21.456  1.00 21.41
ATOM    996  CB   GLN A 144      16.453  21.107  21.274  1.00 20.22
ATOM    997  CG   GLN A 144      16.883  21.003  19.815  1.00 24.39
ATOM    998  CD   GLN A 144      18.359  21.298  19.583  1.00 35.02
ATOM    999  OE1  GLN A 144      19.223  20.456  19.834  1.00 39.33
ATOM   1000  NE2  GLN A 144      18.645  22.494  19.082  1.00 39.04
ATOM   1001  C    GLN A 144      14.654  20.440  22.930  1.00 21.42
ATOM   1002  O    GLN A 144      13.847  21.248  23.418  1.00 22.29
ATOM   1003  N    CYS A 145      15.180  19.442  23.633  1.00 22.65
ATOM   1004  CA   CYS A 145      14.894  19.289  25.055  1.00 21.56
ATOM   1005  CB   CYS A 145      15.328  17.917  25.563  1.00 24.41
ATOM   1006  SG   CYS A 145      14.340  16.594  24.859  1.00 25.88
ATOM   1007  C    CYS A 145      15.512  20.364  25.934  1.00 22.77
ATOM   1008  O    CYS A 145      14.891  20.755  26.915  1.00 24.26
ATOM   1009  N    VAL A 146      16.719  20.828  25.592  1.00 23.87
ATOM   1010  CA   VAL A 146      17.339  21.968  26.261  1.00 23.79
ATOM   1011  CB   VAL A 146      18.563  21.575  27.130  1.00 24.52
ATOM   1012  CG1  VAL A 146      19.148  22.814  27.803  1.00 25.21
ATOM   1013  CG2  VAL A 146      18.189  20.488  28.141  1.00 23.81
ATOM   1014  C    VAL A 146      17.767  22.977  25.204  1.00 24.71
ATOM   1015  O    VAL A 146      18.313  22.613  24.157  1.00 25.61
ATOM   1016  N    GLU A 147      17.443  24.238  25.459  1.00 25.28
ATOM   1017  CA   GLU A 147      17.691  25.313  24.508  1.00 27.56
ATOM   1018  CB   GLU A 147      16.406  25.661  23.747  1.00 26.39
ATOM   1019  CG   GLU A 147      16.147  24.689  22.609  1.00 27.32
ATOM   1020  CD   GLU A 147      14.780  24.858  21.965  1.00 30.78
ATOM   1021  OE1  GLU A 147      13.981  25.680  22.460  1.00 34.57
ATOM   1022  OE2  GLU A 147      14.494  24.143  20.984  1.00 29.08
ATOM   1023  C    GLU A 147      18.200  26.521  25.286  1.00 29.05
ATOM   1024  O    GLU A 147      17.526  27.046  26.173  1.00 29.89
ATOM   1025  N    LYS A 148      19.419  26.935  24.961  1.00 32.08
ATOM   1026  CA   LYS A 148      20.039  28.057  25.662  1.00 33.87
ATOM   1027  CB   LYS A 148      19.459  29.383  25.157  1.00 34.11
ATOM   1028  CG   LYS A 148      19.601  29.554  23.639  1.00 39.02
ATOM   1029  CD   LYS A 148      19.140  30.923  23.161  1.00 46.18
ATOM   1030  CE   LYS A 148      19.201  31.029  21.638  1.00 46.64
ATOM   1031  NZ   LYS A 148      18.688  32.332  21.111  1.00 48.93
ATOM   1032  C    LYS A 148      19.970  27.934  27.190  1.00 32.87
ATOM   1033  O    LYS A 148      19.718  28.910  27.909  1.00 34.86
ATOM   1034  N    GLY A 149      20.203  26.721  27.676  1.00 32.51
ATOM   1035  CA   GLY A 149      20.364  26.475  29.100  1.00 31.75
ATOM   1036  C    GLY A 149      19.065  26.281  29.850  1.00 32.98
ATOM   1037  O    GLY A 149      19.060  26.224  31.078  1.00 34.77
ATOM   1038  N    ARG A 150      17.960  26.198  29.113  1.00 28.60
ATOM   1039  CA   ARG A 150      16.636  26.155  29.727  1.00 29.87
```

FIGURE 122

```
ATOM   1040  CB   ARG A 150      15.753  27.256  29.140  1.00 27.76
ATOM   1041  CG   ARG A 150      14.682  27.764  30.090  1.00 38.86
ATOM   1042  CD   ARG A 150      13.434  26.895  30.207  1.00 47.60
ATOM   1043  NE   ARG A 150      12.793  27.055  31.514  1.00 53.99
ATOM   1044  CZ   ARG A 150      11.684  27.754  31.725  1.00 57.80
ATOM   1045  NH1  ARG A 150      11.080  28.354  30.708  1.00 60.31
ATOM   1046  NH2  ARG A 150      11.170  27.851  32.947  1.00 59.21
ATOM   1047  C    ARG A 150      16.059  24.827  29.300  1.00 26.37
ATOM   1048  O    ARG A 150      16.204  24.456  28.136  1.00 26.29
ATOM   1049  N    VAL A 151      15.407  24.129  30.226  1.00 27.16
ATOM   1050  CA   VAL A 151      14.784  22.862  29.876  1.00 26.73
ATOM   1051  CB   VAL A 151      14.567  21.979  31.132  1.00 27.55
ATOM   1052  CG1  VAL A 151      13.608  20.849  30.835  1.00 25.30
ATOM   1053  CG2  VAL A 151      15.909  21.399  31.605  1.00 29.25
ATOM   1054  C    VAL A 151      13.486  23.199  29.136  1.00 24.76
ATOM   1055  O    VAL A 151      12.697  24.027  29.612  1.00 28.00
ATOM   1056  N    LYS A 152      13.285  22.595  27.964  1.00 23.05
ATOM   1057  CA   LYS A 152      12.147  22.954  27.114  1.00 23.12
ATOM   1058  CB   LYS A 152      12.622  23.481  25.741  1.00 24.16
ATOM   1059  CG   LYS A 152      13.479  24.753  25.812  1.00 26.71
ATOM   1060  CD   LYS A 152      12.677  26.053  25.966  1.00 31.53
ATOM   1061  CE   LYS A 152      13.274  27.189  25.109  1.00 31.75
ATOM   1062  NZ   LYS A 152      13.081  28.512  25.766  1.00 39.48
ATOM   1063  C    LYS A 152      11.170  21.809  26.923  1.00 22.29
ATOM   1064  O    LYS A 152       9.987  22.029  26.641  1.00 18.68
ATOM   1065  N    CYS A 153      11.677  20.599  27.139  1.00 22.37
ATOM   1066  CA   CYS A 153      10.914  19.385  26.901  1.00 20.12
ATOM   1067  CB   CYS A 153      10.752  19.107  25.412  1.00 19.37
ATOM   1068  SG   CYS A 153       9.611  17.737  25.063  1.00 18.76
ATOM   1069  C    CYS A 153      11.640  18.241  27.567  1.00 20.48
ATOM   1070  O    CYS A 153      12.868  18.148  27.498  1.00 21.39
ATOM   1071  N    ASP A 154      10.892  17.375  28.230  1.00 21.01
ATOM   1072  CA   ASP A 154      11.490  16.164  28.782  1.00 20.95
ATOM   1073  CB   ASP A 154      10.524  15.523  29.772  1.00 21.87
ATOM   1074  CG   ASP A 154      11.150  14.365  30.511  1.00 25.17
ATOM   1075  OD1  ASP A 154      12.202  14.589  31.155  1.00 24.97
ATOM   1076  OD2  ASP A 154      10.662  13.223  30.477  1.00 24.65
ATOM   1077  C    ASP A 154      11.831  15.185  27.650  1.00 20.85
ATOM   1078  O    ASP A 154      11.233  15.218  26.586  1.00 20.84
ATOM   1079  N    HIS A 155      12.838  14.337  27.860  1.00 20.25
ATOM   1080  CA   HIS A 155      13.113  13.265  26.916  1.00 20.35
ATOM   1081  CB   HIS A 155      14.579  12.839  27.069  1.00 21.06
ATOM   1082  CG   HIS A 155      15.056  11.901  26.007  1.00 22.85
ATOM   1083  ND1  HIS A 155      14.630  10.591  25.915  1.00 25.15
ATOM   1084  CE1  HIS A 155      15.237  10.003  24.900  1.00 24.10
ATOM   1085  NE2  HIS A 155      16.056  10.877  24.340  1.00 27.20
ATOM   1086  CD2  HIS A 155      15.975  12.067  25.026  1.00 27.39
ATOM   1087  C    HIS A 155      12.157  12.112  27.240  1.00 20.30
ATOM   1088  O    HIS A 155      12.458  11.225  28.053  1.00 19.64
ATOM   1089  N    TYR A 156      10.960  12.181  26.666  1.00 19.16
ATOM   1090  CA   TYR A 156       9.814  11.436  27.165  1.00 18.36
ATOM   1091  CB   TYR A 156       8.520  12.247  27.004  1.00 18.65
```

FIGURE 123

```
ATOM   1092  CG   TYR A 156       8.250  12.664  25.569  1.00 17.99
ATOM   1093  CD1  TYR A 156       7.624  11.796  24.669  1.00 16.25
ATOM   1094  CE1  TYR A 156       7.427  12.171  23.328  1.00 16.10
ATOM   1095  CZ   TYR A 156       7.776  13.457  22.936  1.00 15.17
ATOM   1096  OH   TYR A 156       7.497  13.806  21.627  1.00 15.03
ATOM   1097  CE2  TYR A 156       8.397  14.321  23.810  1.00 21.32
ATOM   1098  CD2  TYR A 156       8.618  13.922  25.132  1.00 16.85
ATOM   1099  C    TYR A 156       9.678  10.091  26.469  1.00 17.96
ATOM   1100  O    TYR A 156       8.723   9.365  26.730  1.00 18.06
ATOM   1101  N    TRP A 157      10.660   9.764  25.635  1.00 19.28
ATOM   1102  CA   TRP A 157      10.722   8.482  24.933  1.00 20.13
ATOM   1103  CB   TRP A 157      10.668   8.723  23.414  1.00 18.70
ATOM   1104  CG   TRP A 157      11.885   9.431  22.911  1.00 18.38
ATOM   1105  CD1  TRP A 157      13.031   8.858  22.463  1.00 20.53
ATOM   1106  NE1  TRP A 157      13.924   9.827  22.075  1.00 19.49
ATOM   1107  CE2  TRP A 157      13.387  11.061  22.338  1.00 17.77
ATOM   1108  CD2  TRP A 157      12.085  10.848  22.833  1.00 18.54
ATOM   1109  CE3  TRP A 157      11.320  11.955  23.192  1.00 20.35
ATOM   1110  CZ3  TRP A 157      11.836  13.222  23.012  1.00 20.87
ATOM   1111  CH2  TRP A 157      13.145  13.404  22.500  1.00 22.03
ATOM   1112  CZ2  TRP A 157      13.920  12.335  22.150  1.00 20.41
ATOM   1113  C    TRP A 157      11.993   7.755  25.370  1.00 22.07
ATOM   1114  O    TRP A 157      12.912   8.357  25.928  1.00 21.87
ATOM   1115  N    PRO A 158      12.042   6.446  25.173  1.00 23.81
ATOM   1116  CA   PRO A 158      13.207   5.671  25.615  1.00 25.18
ATOM   1117  CB   PRO A 158      12.854   4.227  25.238  1.00 25.31
ATOM   1118  CG   PRO A 158      11.341   4.234  25.220  1.00 24.87
ATOM   1119  CD   PRO A 158      10.976   5.594  24.619  1.00 25.87
ATOM   1120  C    PRO A 158      14.515   6.105  24.973  1.00 24.62
ATOM   1121  O    PRO A 158      14.568   6.599  23.836  1.00 24.33
ATOM   1122  N    ALA A 159      15.567   5.872  25.742  1.00 25.95
ATOM   1123  CA   ALA A 159      16.937   6.192  25.347  1.00 27.03
ATOM   1124  CB   ALA A 159      17.775   6.378  26.592  1.00 26.95
ATOM   1125  C    ALA A 159      17.529   5.113  24.441  1.00 28.60
ATOM   1126  O    ALA A 159      18.512   5.345  23.723  1.00 31.08
ATOM   1127  N    ASP A 160      16.921   3.932  24.461  1.00 26.27
ATOM   1128  CA   ASP A 160      17.429   2.795  23.710  1.00 26.44
ATOM   1129  CB   ASP A 160      18.488   2.056  24.529  1.00 27.67
ATOM   1130  CG   ASP A 160      17.981   1.620  25.873  1.00 28.84
ATOM   1131  OD1  ASP A 160      16.776   1.290  26.014  1.00 26.79
ATOM   1132  OD2  ASP A 160      18.735   1.597  26.865  1.00 32.92
ATOM   1133  C    ASP A 160      16.296   1.855  23.363  1.00 25.36
ATOM   1134  O    ASP A 160      15.141   2.250  23.501  1.00 23.64
ATOM   1135  N    GLN A 161      16.614   0.641  22.915  1.00 23.95
ATOM   1136  CA   GLN A 161      15.585  -0.240  22.365  1.00 24.83
ATOM   1137  CB   GLN A 161      16.094  -1.043  21.164  1.00 26.83
ATOM   1138  CG   GLN A 161      16.563  -0.146  20.012  1.00 32.67
ATOM   1139  CD   GLN A 161      16.766  -0.870  18.682  1.00 42.17
ATOM   1140  OE1  GLN A 161      16.550  -2.078  18.566  1.00 44.45
ATOM   1141  NE2  GLN A 161      17.202  -0.125  17.675  1.00 44.50
ATOM   1142  C    GLN A 161      14.907  -1.126  23.415  1.00 23.64
ATOM   1143  O    GLN A 161      14.058  -1.955  23.069  1.00 26.15
```

FIGURE 124

```
ATOM   1144  N    ASP A 162      15.219   -0.906   24.689  1.00  21.69
ATOM   1145  CA   ASP A 162      14.621   -1.750   25.724  1.00  22.06
ATOM   1146  CB   ASP A 162      15.416   -1.717   27.025  1.00  20.34
ATOM   1147  CG   ASP A 162      16.797   -2.326   26.891  1.00  29.79
ATOM   1148  OD1  ASP A 162      17.083   -2.995   25.878  1.00  31.31
ATOM   1149  OD2  ASP A 162      17.657   -2.177   27.779  1.00  39.34
ATOM   1150  C    ASP A 162      13.240   -1.174   26.011  1.00  20.10
ATOM   1151  O    ASP A 162      13.149    0.028   26.267  1.00  21.67
ATOM   1152  N    SER A 163      12.210   -2.020   26.029  1.00  22.00
ATOM   1153  CA   SER A 163      10.860   -1.555   26.374  1.00  19.52
ATOM   1154  CB   SER A 163       9.797   -2.621   26.127  1.00  19.81
ATOM   1155  OG   SER A 163      10.079   -3.816   26.840  1.00  24.08
ATOM   1156  C    SER A 163      10.742   -0.998   27.791  1.00  20.81
ATOM   1157  O    SER A 163      11.529   -1.343   28.699  1.00  19.79
ATOM   1158  N    LEU A 164       9.765   -0.123   27.987  1.00  20.37
ATOM   1159  CA   LEU A 164       9.525    0.494   29.298  1.00  20.27
ATOM   1160  CB   LEU A 164      10.225    1.847   29.418  1.00  21.91
ATOM   1161  CG   LEU A 164      11.716    2.029   29.730  1.00  28.59
ATOM   1162  CD1  LEU A 164      11.962    3.530   29.619  1.00  32.46
ATOM   1163  CD2  LEU A 164      11.994    1.587   31.160  1.00  29.88
ATOM   1164  C    LEU A 164       8.031    0.814   29.392  1.00  17.64
ATOM   1165  O    LEU A 164       7.400    1.129   28.385  1.00  19.87
ATOM   1166  N    TYR A 165       7.511    0.782   30.613  1.00  18.28
ATOM   1167  CA   TYR A 165       6.148    1.247   30.880  1.00  16.77
ATOM   1168  CB   TYR A 165       5.625    0.605   32.160  1.00  17.12
ATOM   1169  CG   TYR A 165       4.965   -0.711   31.893  1.00  20.15
ATOM   1170  CD1  TYR A 165       3.698   -0.753   31.322  1.00  21.67
ATOM   1171  CE1  TYR A 165       3.081   -1.967   31.054  1.00  19.75
ATOM   1172  CZ   TYR A 165       3.726   -3.137   31.372  1.00  23.95
ATOM   1173  OH   TYR A 165       3.113   -4.342   31.095  1.00  28.45
ATOM   1174  CE2  TYR A 165       4.972   -3.123   31.935  1.00  21.42
ATOM   1175  CD2  TYR A 165       5.587   -1.906   32.230  1.00  21.96
ATOM   1176  C    TYR A 165       6.107    2.749   31.085  1.00  19.28
ATOM   1177  O    TYR A 165       6.948    3.318   31.778  1.00  22.32
ATOM   1178  N    TYR A 166       5.105    3.372   30.480  1.00  19.16
ATOM   1179  CA   TYR A 166       4.668    4.714   30.858  1.00  18.90
ATOM   1180  CB   TYR A 166       4.762    5.650   29.639  1.00  19.56
ATOM   1181  CG   TYR A 166       6.180    5.875   29.174  1.00  18.34
ATOM   1182  CD1  TYR A 166       6.896    6.985   29.601  1.00  16.76
ATOM   1183  CE1  TYR A 166       8.223    7.190   29.153  1.00  18.94
ATOM   1184  CZ   TYR A 166       8.777    6.306   28.245  1.00  22.27
ATOM   1185  OH   TYR A 166      10.067    6.497   27.780  1.00  24.37
ATOM   1186  CE2  TYR A 166       8.067    5.222   27.789  1.00  26.25
ATOM   1187  CD2  TYR A 166       6.768    5.016   28.245  1.00  22.49
ATOM   1188  C    TYR A 166       3.235    4.628   31.372  1.00  19.75
ATOM   1189  O    TYR A 166       2.297    4.549   30.586  1.00  20.21
ATOM   1190  N    GLY A 167       3.032    4.609   32.694  1.00  20.43
ATOM   1191  CA   GLY A 167       1.684    4.310   33.165  1.00  21.54
ATOM   1192  C    GLY A 167       1.209    2.931   32.728  1.00  23.50
ATOM   1193  O    GLY A 167       1.932    1.957   32.943  1.00  23.77
ATOM   1194  N    ASP A 168       0.029    2.885   32.099  1.00  21.81
ATOM   1195  CA   ASP A 168      -0.673    1.718   31.567  1.00  26.70
```

FIGURE 125

```
ATOM   1196  CB   ASP A 168      -2.086   2.171  31.152  1.00  28.49
ATOM   1197  CG   ASP A 168      -3.021   2.345  32.289  1.00  35.95
ATOM   1198  OD1  ASP A 168      -2.581   2.521  33.451  1.00  44.09
ATOM   1199  OD2  ASP A 168      -4.248   2.352  32.078  1.00  36.92
ATOM   1200  C    ASP A 168      -0.150   1.270  30.206  1.00  24.58
ATOM   1201  O    ASP A 168      -0.717   0.345  29.619  1.00  26.11
ATOM   1202  N    LEU A 169       0.840   1.971  29.657  1.00  21.74
ATOM   1203  CA   LEU A 169       1.205   1.797  28.261  1.00  19.33
ATOM   1204  CB   LEU A 169       1.174   3.152  27.567  1.00  19.99
ATOM   1205  CG   LEU A 169       1.541   3.109  26.095  1.00  25.20
ATOM   1206  CD1  LEU A 169       0.471   3.894  25.397  1.00  26.72
ATOM   1207  CD2  LEU A 169       2.886   3.769  25.917  1.00  25.81
ATOM   1208  C    LEU A 169       2.619   1.256  28.197  1.00  20.65
ATOM   1209  O    LEU A 169       3.485   1.740  28.907  1.00  21.93
ATOM   1210  N    ILE A 170       2.857   0.250  27.370  1.00  18.58
ATOM   1211  CA   ILE A 170       4.239  -0.182  27.197  1.00  19.82
ATOM   1212  CB   ILE A 170       4.309  -1.728  27.237  1.00  19.31
ATOM   1213  CG1  ILE A 170       5.746  -2.220  26.983  1.00  22.75
ATOM   1214  CD1  ILE A 170       6.454  -2.519  28.252  1.00  22.15
ATOM   1215  CG2  ILE A 170       3.367  -2.344  26.238  1.00  22.33
ATOM   1216  C    ILE A 170       4.745   0.359  25.870  1.00  19.44
ATOM   1217  O    ILE A 170       4.000   0.382  24.898  1.00  19.22
ATOM   1218  N    LEU A 171       6.009   0.775  25.817  1.00  18.90
ATOM   1219  CA   LEU A 171       6.505   1.440  24.631  1.00  18.91
ATOM   1220  CB   LEU A 171       6.697   2.923  24.954  1.00  19.73
ATOM   1221  CG   LEU A 171       7.108   3.758  23.751  1.00  25.25
ATOM   1222  CD1  LEU A 171       6.670   5.162  24.054  1.00  28.25
ATOM   1223  CD2  LEU A 171       8.618   3.703  23.723  1.00  29.29
ATOM   1224  C    LEU A 171       7.852   0.820  24.354  1.00  19.14
ATOM   1225  O    LEU A 171       8.556   0.467  25.305  1.00  18.74
ATOM   1226  N    GLN A 172       8.174   0.655  23.074  1.00  17.00
ATOM   1227  CA   GLN A 172       9.485   0.117  22.713  1.00  18.63
ATOM   1228  CB   GLN A 172       9.392  -1.379  22.439  1.00  19.29
ATOM   1229  CG   GLN A 172      10.724  -2.109  22.277  1.00  25.23
ATOM   1230  CD   GLN A 172      10.473  -3.552  21.842  1.00  28.98
ATOM   1231  OE1  GLN A 172       9.779  -3.776  20.859  1.00  30.54
ATOM   1232  NE2  GLN A 172      11.024  -4.521  22.559  1.00  24.05
ATOM   1233  C    GLN A 172       9.946   0.820  21.464  1.00  17.56
ATOM   1234  O    GLN A 172       9.242   0.825  20.460  1.00  20.89
ATOM   1235  N    MET A 173      11.166   1.337  21.506  1.00  18.09
ATOM   1236  CA   MET A 173      11.703   2.006  20.315  1.00  19.64
ATOM   1237  CB   MET A 173      12.860   2.934  20.713  1.00  15.61
ATOM   1238  CG   MET A 173      13.415   3.696  19.493  1.00  20.90
ATOM   1239  SD   MET A 173      14.248   5.251  19.921  1.00  22.90
ATOM   1240  CE   MET A 173      15.666   4.695  20.787  1.00  24.34
ATOM   1241  C    MET A 173      12.262   0.942  19.386  1.00  20.45
ATOM   1242  O    MET A 173      13.189   0.219  19.790  1.00  23.02
ATOM   1243  N    LEU A 174      11.783   0.916  18.144  1.00  19.05
ATOM   1244  CA   LEU A 174      12.245  -0.028  17.131  1.00  20.65
ATOM   1245  CB   LEU A 174      11.102  -0.481  16.243  1.00  22.05
ATOM   1246  CG   LEU A 174       9.874  -1.071  16.934  1.00  19.97
ATOM   1247  CD1  LEU A 174       8.825  -1.459  15.899  1.00  25.97
```

FIGURE 126

```
ATOM   1248  CD2 LEU A 174      10.205  -2.246  17.825  1.00 24.09
ATOM   1249  C   LEU A 174      13.385   0.487  16.262  1.00 22.40
ATOM   1250  O   LEU A 174      14.226  -0.290  15.807  1.00 23.87
ATOM   1251  N   SER A 175      13.419   1.794  16.031  1.00 21.05
ATOM   1252  CA  SER A 175      14.501   2.374  15.250  1.00 20.96
ATOM   1253  CB  SER A 175      14.261   2.317  13.743  1.00 19.89
ATOM   1254  OG  SER A 175      13.038   2.900  13.345  1.00 21.43
ATOM   1255  C   SER A 175      14.670   3.819  15.645  1.00 18.88
ATOM   1256  O   SER A 175      13.739   4.466  16.097  1.00 19.35
ATOM   1257  N   GLU A 176      15.880   4.300  15.439  1.00 17.31
ATOM   1258  CA  GLU A 176      16.187   5.707  15.592  1.00 17.56
ATOM   1259  CB  GLU A 176      16.755   5.907  16.988  1.00 19.24
ATOM   1260  CG  GLU A 176      17.299   7.278  17.319  1.00 22.48
ATOM   1261  CD  GLU A 176      17.792   7.337  18.749  1.00 24.54
ATOM   1262  OE1 GLU A 176      18.951   6.933  19.003  1.00 35.75
ATOM   1263  OE2 GLU A 176      17.050   7.813  19.612  1.00 25.21
ATOM   1264  C   GLU A 176      17.141   6.067  14.463  1.00 17.07
ATOM   1265  O   GLU A 176      18.276   5.559  14.397  1.00 19.83
ATOM   1266  N   SER A 177      16.684   6.953  13.579  1.00 18.92
ATOM   1267  CA  SER A 177      17.484   7.339  12.419  1.00 20.17
ATOM   1268  CB  SER A 177      16.766   6.925  11.139  1.00 19.64
ATOM   1269  OG  SER A 177      16.378   5.553  11.196  1.00 26.41
ATOM   1270  C   SER A 177      17.786   8.844  12.477  1.00 18.07
ATOM   1271  O   SER A 177      16.922   9.671  12.295  1.00 16.18
ATOM   1272  N   VAL A 178      19.035   9.210  12.728  1.00 19.19
ATOM   1273  CA  VAL A 178      19.408  10.605  12.863  1.00 18.44
ATOM   1274  CB  VAL A 178      20.648  10.758  13.802  1.00 18.96
ATOM   1275  CG1 VAL A 178      21.063  12.211  13.900  1.00 19.33
ATOM   1276  CG2 VAL A 178      20.350  10.128  15.180  1.00 22.08
ATOM   1277  C   VAL A 178      19.814  11.098  11.472  1.00 17.78
ATOM   1278  O   VAL A 178      20.753  10.578  10.850  1.00 18.38
ATOM   1279  N   LEU A 179      19.070  12.075  10.970  1.00 18.02
ATOM   1280  CA  LEU A 179      19.347  12.663   9.663  1.00 16.64
ATOM   1281  CB  LEU A 179      18.074  12.673   8.777  1.00 17.91
ATOM   1282  CG  LEU A 179      17.193  11.405   8.899  1.00 18.10
ATOM   1283  CD1 LEU A 179      15.925  11.510   8.066  1.00 18.94
ATOM   1284  CD2 LEU A 179      17.912  10.091   8.610  1.00 15.53
ATOM   1285  C   LEU A 179      19.922  14.059   9.914  1.00 17.92
ATOM   1286  O   LEU A 179      20.078  14.486  11.066  1.00 18.05
ATOM   1287  N   PRO A 180      20.307  14.764   8.862  1.00 15.89
ATOM   1288  CA  PRO A 180      20.946  16.077   9.031  1.00 17.67
ATOM   1289  CB  PRO A 180      21.055  16.593   7.609  1.00 16.61
ATOM   1290  CG  PRO A 180      21.283  15.311   6.840  1.00 17.50
ATOM   1291  CD  PRO A 180      20.255  14.354   7.454  1.00 16.79
ATOM   1292  C   PRO A 180      20.190  17.085   9.863  1.00 17.87
ATOM   1293  O   PRO A 180      20.802  17.756  10.702  1.00 19.82
ATOM   1294  N   GLU A 181      18.878  17.189   9.656  1.00 17.72
ATOM   1295  CA  GLU A 181      18.130  18.231  10.335  1.00 19.40
ATOM   1296  CB  GLU A 181      17.737  19.349   9.366  1.00 20.16
ATOM   1297  CG  GLU A 181      18.973  20.058   8.833  1.00 24.30
ATOM   1298  CD  GLU A 181      18.615  21.064   7.765  1.00 30.86
ATOM   1299  OE1 GLU A 181      17.597  20.866   7.057  1.00 33.00
```

FIGURE 127

```
ATOM   1300  OE2 GLU A 181      19.384  22.040   7.641  1.00 39.73
ATOM   1301  C   GLU A 181      16.890  17.704  11.048  1.00 19.38
ATOM   1302  O   GLU A 181      16.209  18.470  11.692  1.00 19.21
ATOM   1303  N   TRP A 182      16.619  16.405  10.942  1.00 16.49
ATOM   1304  CA  TRP A 182      15.667  15.784  11.836  1.00 16.57
ATOM   1305  CB  TRP A 182      14.242  15.924  11.286  1.00 15.22
ATOM   1306  CG  TRP A 182      14.026  15.548   9.833  1.00 13.61
ATOM   1307  CD1 TRP A 182      13.615  14.342   9.354  1.00 15.76
ATOM   1308  NE1 TRP A 182      13.472  14.385   7.987  1.00 16.34
ATOM   1309  CE2 TRP A 182      13.726  15.663   7.565  1.00 13.66
ATOM   1310  CD2 TRP A 182      14.072  16.427   8.713  1.00 14.52
ATOM   1311  CE3 TRP A 182      14.416  17.767   8.547  1.00 16.17
ATOM   1312  CZ3 TRP A 182      14.369  18.307   7.265  1.00 17.28
ATOM   1313  CH2 TRP A 182      14.019  17.520   6.154  1.00 20.20
ATOM   1314  CZ2 TRP A 182      13.697  16.196   6.281  1.00 18.18
ATOM   1315  C   TRP A 182      16.019  14.330  12.118  1.00 17.43
ATOM   1316  O   TRP A 182      16.831  13.721  11.423  1.00 16.83
ATOM   1317  N   THR A 183      15.372  13.776  13.135  1.00 17.91
ATOM   1318  CA  THR A 183      15.570  12.391  13.524  1.00 17.41
ATOM   1319  CB  THR A 183      16.158  12.387  14.941  1.00 17.91
ATOM   1320  OG1 THR A 183      17.508  12.889  14.867  1.00 19.93
ATOM   1321  CG2 THR A 183      16.379  10.952  15.444  1.00 19.10
ATOM   1322  C   THR A 183      14.216  11.704  13.494  1.00 18.88
ATOM   1323  O   THR A 183      13.253  12.259  14.020  1.00 17.96
ATOM   1324  N   ILE A 184      14.159  10.521  12.884  1.00 14.76
ATOM   1325  CA  ILE A 184      12.915   9.770  12.795  1.00 15.33
ATOM   1326  CB  ILE A 184      12.636   9.313  11.362  1.00 15.60
ATOM   1327  CG1 ILE A 184      12.620  10.508  10.410  1.00 14.39
ATOM   1328  CD1 ILE A 184      12.371  10.133   8.960  1.00 16.80
ATOM   1329  CG2 ILE A 184      11.318   8.518  11.307  1.00 18.05
ATOM   1330  C   ILE A 184      13.050   8.539  13.682  1.00 16.19
ATOM   1331  O   ILE A 184      13.965   7.725  13.524  1.00 18.12
ATOM   1332  N   ARG A 185      12.106   8.368  14.592  1.00 16.20
ATOM   1333  CA  ARG A 185      12.083   7.159  15.425  1.00 15.84
ATOM   1334  CB  ARG A 185      12.137   7.551  16.904  1.00 14.71
ATOM   1335  CG  ARG A 185      13.505   8.055  17.326  1.00 14.82
ATOM   1336  CD  ARG A 185      13.468   8.727  18.685  1.00 17.62
ATOM   1337  NE  ARG A 185      14.822   9.174  19.013  1.00 21.26
ATOM   1338  CZ  ARG A 185      15.195  10.448  18.973  1.00 21.83
ATOM   1339  NH1 ARG A 185      14.345  11.379  18.584  1.00 21.65
ATOM   1340  NH2 ARG A 185      16.422  10.807  19.323  1.00 26.56
ATOM   1341  C   ARG A 185      10.808   6.386  15.181  1.00 16.96
ATOM   1342  O   ARG A 185       9.775   6.967  14.866  1.00 18.49
ATOM   1343  N   GLU A 186      10.876   5.063  15.330  1.00 18.06
ATOM   1344  CA  GLU A 186       9.653   4.289  15.251  1.00 18.19
ATOM   1345  CB  GLU A 186       9.729   3.232  14.126  1.00 18.51
ATOM   1346  CG  GLU A 186       8.354   2.622  13.856  1.00 22.77
ATOM   1347  CD  GLU A 186       8.367   1.477  12.851  1.00 31.07
ATOM   1348  OE1 GLU A 186       7.330   1.279  12.179  1.00 37.68
ATOM   1349  OE2 GLU A 186       9.388   0.775  12.730  1.00 33.77
ATOM   1350  C   GLU A 186       9.452   3.600  16.597  1.00 18.63
ATOM   1351  O   GLU A 186      10.411   3.051  17.142  1.00 19.33
```

FIGURE 128

| | | | | | | | | | |
|---|---|---|---|---|---|---|---|---|---|
| ATOM | 1352 | N | PHE | A | 187 | 8.223 | 3.614 | 17.108 | 1.00 18.68 |
| ATOM | 1353 | CA | PHE | A | 187 | 7.927 | 2.978 | 18.399 | 1.00 18.08 |
| ATOM | 1354 | CB | PHE | A | 187 | 7.426 | 4.006 | 19.415 | 1.00 18.99 |
| ATOM | 1355 | CG | PHE | A | 187 | 8.400 | 5.092 | 19.715 | 1.00 19.80 |
| ATOM | 1356 | CD1 | PHE | A | 187 | 8.155 | 6.382 | 19.283 | 1.00 21.67 |
| ATOM | 1357 | CE1 | PHE | A | 187 | 9.066 | 7.403 | 19.559 | 1.00 23.38 |
| ATOM | 1358 | CZ | PHE | A | 187 | 10.242 | 7.106 | 20.223 | 1.00 20.03 |
| ATOM | 1359 | CE2 | PHE | A | 187 | 10.489 | 5.828 | 20.641 | 1.00 25.29 |
| ATOM | 1360 | CD2 | PHE | A | 187 | 9.595 | 4.819 | 20.369 | 1.00 22.12 |
| ATOM | 1361 | C | PHE | A | 187 | 6.815 | 1.954 | 18.257 | 1.00 19.06 |
| ATOM | 1362 | O | PHE | A | 187 | 5.881 | 2.161 | 17.472 | 1.00 18.23 |
| ATOM | 1363 | N | LYS | A | 188 | 6.898 | 0.863 | 19.018 | 1.00 18.39 |
| ATOM | 1364 | CA | LYS | A | 188 | 5.718 | 0.006 | 19.179 | 1.00 19.84 |
| ATOM | 1365 | CB | LYS | A | 188 | 6.146 | -1.466 | 19.179 | 1.00 21.30 |
| ATOM | 1366 | CG | LYS | A | 188 | 4.994 | -2.449 | 19.361 | 1.00 29.28 |
| ATOM | 1367 | CD | LYS | A | 188 | 5.549 | -3.835 | 19.650 | 1.00 39.42 |
| ATOM | 1368 | CE | LYS | A | 188 | 4.535 | -4.915 | 19.312 | 1.00 41.60 |
| ATOM | 1369 | NZ | LYS | A | 188 | 5.247 | -6.141 | 18.830 | 1.00 47.94 |
| ATOM | 1370 | C | LYS | A | 188 | 5.076 | 0.377 | 20.513 | 1.00 17.53 |
| ATOM | 1371 | O | LYS | A | 188 | 5.765 | 0.472 | 21.511 | 1.00 20.08 |
| ATOM | 1372 | N | ILE | A | 189 | 3.761 | 0.584 | 20.551 | 1.00 18.34 |
| ATOM | 1373 | CA | ILE | A | 189 | 3.063 | 0.924 | 21.781 | 1.00 18.37 |
| ATOM | 1374 | CB | ILE | A | 189 | 2.662 | 2.409 | 21.729 | 1.00 17.71 |
| ATOM | 1375 | CG1AILE | A | 189 | 2.140 | 2.932 | 23.051 | 0.50 18.61 | |
| ATOM | 1376 | CG1BILE | A | 189 | 1.794 | 2.771 | 20.521 | 0.50 19.99 | |
| ATOM | 1377 | CD1AILE | A | 189 | 1.758 | 4.385 | 22.938 | 0.50 20.42 | |
| ATOM | 1378 | CD1BILE | A | 189 | 1.063 | 4.085 | 20.730 | 0.50 24.91 | |
| ATOM | 1379 | CG2AILE | A | 189 | 1.579 | 2.616 | 20.661 | 0.50 18.62 | |
| ATOM | 1380 | CG2BILE | A | 189 | 3.921 | 3.269 | 21.880 | 0.50 16.15 | |
| ATOM | 1381 | C | ILE | A | 189 | 1.848 | -0.013 | 21.922 | 1.00 17.83 |
| ATOM | 1382 | O | ILE | A | 189 | 1.239 | -0.400 | 20.918 | 1.00 16.89 |
| ATOM | 1383 | N | CYS | A | 190 | 1.567 | -0.403 | 23.165 | 1.00 19.24 |
| ATOM | 1384 | CA | CYS | A | 190 | 0.313 | -1.068 | 23.547 | 1.00 19.00 |
| ATOM | 1385 | CB | CYS | A | 190 | 0.590 | -2.542 | 23.881 | 1.00 17.53 |
| ATOM | 1386 | SG | CYS | A | 190 | 1.496 | -3.470 | 22.591 | 1.00 25.53 |
| ATOM | 1387 | C | CYS | A | 190 | -0.258 | -0.402 | 24.791 | 1.00 18.76 |
| ATOM | 1388 | O | CYS | A | 190 | 0.428 | -0.293 | 25.789 | 1.00 18.93 |
| ATOM | 1389 | N | GLY | A | 191 | -1.534 | -0.004 | 24.757 | 1.00 18.32 |
| ATOM | 1390 | CA | GLY | A | 191 | -2.213 | 0.527 | 25.930 | 1.00 20.25 |
| ATOM | 1391 | C | GLY | A | 191 | -3.530 | -0.202 | 26.162 | 1.00 20.72 |
| ATOM | 1392 | O | GLY | A | 191 | -3.740 | -1.262 | 25.606 | 1.00 20.46 |
| ATOM | 1393 | N | GLU | A | 192 | -4.386 | 0.359 | 27.002 | 1.00 22.42 |
| ATOM | 1394 | CA | GLU | A | 192 | -5.677 | -0.253 | 27.279 | 1.00 24.91 |
| ATOM | 1395 | CB | GLU | A | 192 | -6.421 | 0.585 | 28.315 | 1.00 23.09 |
| ATOM | 1396 | CG | GLU | A | 192 | -7.854 | 0.111 | 28.537 | 1.00 29.54 |
| ATOM | 1397 | CD | GLU | A | 192 | -8.646 | 0.961 | 29.512 | 1.00 32.49 |
| ATOM | 1398 | OE1 | GLU | A | 192 | -8.290 | 2.150 | 29.745 | 1.00 31.32 |
| ATOM | 1399 | OE2 | GLU | A | 192 | -9.661 | 0.426 | 30.018 | 1.00 34.67 |
| ATOM | 1400 | C | GLU | A | 192 | -6.461 | -0.414 | 25.974 | 1.00 24.14 |
| ATOM | 1401 | O | GLU | A | 192 | -6.810 | 0.567 | 25.289 | 1.00 24.16 |
| ATOM | 1402 | N | GLU | A | 193 | -6.719 | -1.671 | 25.612 | 1.00 25.67 |
| ATOM | 1403 | CA | GLU | A | 193 | -7.236 | -1.978 | 24.284 | 1.00 26.65 |

FIGURE 129

| | | | | | | | | |
|---|---|---|---|---|---|---|---|---|
| ATOM | 1404 | CB  | GLU | A | 193 | -7.337  | -3.489 | 24.068 | 1.00 28.45 |
| ATOM | 1405 | CG  | GLU | A | 193 | -7.767  | -3.843 | 22.648 | 1.00 29.15 |
| ATOM | 1406 | CD  | GLU | A | 193 | -7.780  | -5.342 | 22.405 | 1.00 34.41 |
| ATOM | 1407 | OE1 | GLU | A | 193 | -7.163  | -6.077 | 23.211 | 1.00 33.00 |
| ATOM | 1408 | OE2 | GLU | A | 193 | -8.400  | -5.778 | 21.408 | 1.00 34.70 |
| ATOM | 1409 | C   | GLU | A | 193 | -8.598  | -1.366 | 24.010 | 1.00 30.04 |
| ATOM | 1410 | O   | GLU | A | 193 | -9.510  | -1.555 | 24.810 | 1.00 29.04 |
| ATOM | 1411 | N   | GLN | A | 194 | -8.730  | -0.635 | 22.902 | 1.00 28.72 |
| ATOM | 1412 | CA  | GLN | A | 194 | -10.054 | -0.254 | 22.417 | 1.00 30.57 |
| ATOM | 1413 | CB  | GLN | A | 194 | -10.349 |  1.229 | 22.654 | 1.00 30.30 |
| ATOM | 1414 | CG  | GLN | A | 194 | -10.354 |  1.700 | 24.097 | 1.00 38.21 |
| ATOM | 1415 | CD  | GLN | A | 194 | -10.661 |  3.192 | 24.205 | 1.00 45.81 |
| ATOM | 1416 | OE1 | GLN | A | 194 | -11.766 |  3.629 | 23.868 | 1.00 47.74 |
| ATOM | 1417 | NE2 | GLN | A | 194 | -9.682  |  3.976 | 24.667 | 1.00 48.46 |
| ATOM | 1418 | C   | GLN | A | 194 | -10.138 | -0.612 | 20.937 | 1.00 30.81 |
| ATOM | 1419 | O   | GLN | A | 194 | -10.444 | -1.762 | 20.596 | 1.00 31.43 |
| ATOM | 1420 | N   | LEU | A | 195 | -9.843  |  0.343 | 20.056 | 1.00 30.77 |
| ATOM | 1421 | CA  | LEU | A | 195 | -9.869  |  0.103 | 18.620 | 1.00 31.53 |
| ATOM | 1422 | CB  | LEU | A | 195 | -9.860  |  1.419 | 17.833 | 1.00 32.19 |
| ATOM | 1423 | CG  | LEU | A | 195 | -11.132 |  2.254 | 17.673 | 1.00 37.67 |
| ATOM | 1424 | CD1 | LEU | A | 195 | -10.860 |  3.277 | 16.579 | 1.00 33.54 |
| ATOM | 1425 | CD2 | LEU | A | 195 | -12.359 |  1.404 | 17.322 | 1.00 36.45 |
| ATOM | 1426 | C   | LEU | A | 195 | -8.692  | -0.729 | 18.144 | 1.00 31.71 |
| ATOM | 1427 | O   | LEU | A | 195 | -8.796  | -1.454 | 17.159 | 1.00 32.54 |
| ATOM | 1428 | N   | ASP | A | 196 | -7.554  | -0.607 | 18.821 | 1.00 29.57 |
| ATOM | 1429 | CA  | ASP | A | 196 | -6.442  | -1.492 | 18.533 | 1.00 28.34 |
| ATOM | 1430 | CB  | ASP | A | 196 | -5.424  | -0.868 | 17.558 | 1.00 26.58 |
| ATOM | 1431 | CG  | ASP | A | 196 | -4.815  |  0.420 | 18.063 | 1.00 27.01 |
| ATOM | 1432 | OD1 | ASP | A | 196 | -5.145  |  0.869 | 19.183 | 1.00 27.13 |
| ATOM | 1433 | OD2 | ASP | A | 196 | -3.989  |  1.049 | 17.375 | 1.00 25.88 |
| ATOM | 1434 | C   | ASP | A | 196 | -5.791  | -2.008 | 19.815 | 1.00 27.72 |
| ATOM | 1435 | O   | ASP | A | 196 | -6.099  | -1.550 | 20.915 | 1.00 26.99 |
| ATOM | 1436 | N   | ALA | A | 197 | -4.912  | -2.989 | 19.653 | 1.00 26.66 |
| ATOM | 1437 | CA  | ALA | A | 197 | -4.279  | -3.646 | 20.792 | 1.00 26.48 |
| ATOM | 1438 | CB  | ALA | A | 197 | -4.557  | -5.145 | 20.748 | 1.00 27.66 |
| ATOM | 1439 | C   | ALA | A | 197 | -2.774  | -3.400 | 20.744 | 1.00 24.78 |
| ATOM | 1440 | O   | ALA | A | 197 | -2.122  | -3.483 | 21.779 | 1.00 26.10 |
| ATOM | 1441 | N   | HIS | A | 198 | -2.237  | -3.062 | 19.573 | 1.00 23.60 |
| ATOM | 1442 | CA  | HIS | A | 198 | -0.811  | -2.715 | 19.465 | 1.00 24.08 |
| ATOM | 1443 | CB  | HIS | A | 198 |  0.098  | -3.951 | 19.353 | 1.00 26.63 |
| ATOM | 1444 | CG  | HIS | A | 198 | -0.227  | -4.848 | 18.198 | 1.00 31.90 |
| ATOM | 1445 | ND1 | HIS | A | 198 | -1.094  | -5.914 | 18.300 | 1.00 40.11 |
| ATOM | 1446 | CE1 | HIS | A | 198 | -1.186  | -6.519 | 17.128 | 1.00 38.77 |
| ATOM | 1447 | NE2 | HIS | A | 198 | -0.406  | -5.886 | 16.271 | 1.00 43.28 |
| ATOM | 1448 | CD2 | HIS | A | 198 |  0.215  | -4.844 | 16.918 | 1.00 33.37 |
| ATOM | 1449 | C   | HIS | A | 198 | -0.679  | -1.841 | 18.217 | 1.00 22.55 |
| ATOM | 1450 | O   | HIS | A | 198 | -1.523  | -1.964 | 17.329 | 1.00 24.31 |
| ATOM | 1451 | N   | ARG | A | 199 |  0.343  | -0.980 | 18.167 | 1.00 20.23 |
| ATOM | 1452 | CA  | ARG | A | 199 |  0.416  |  0.062 | 17.138 | 1.00 18.98 |
| ATOM | 1453 | CB  | ARG | A | 199 | -0.341  |  1.295 | 17.651 | 1.00 17.45 |
| ATOM | 1454 | CG  | ARG | A | 199 | -0.566  |  2.347 | 16.560 | 1.00 19.76 |
| ATOM | 1455 | CD  | ARG | A | 199 | -1.165  |  3.621 | 17.129 | 1.00 19.36 |

FIGURE 130

```
ATOM   1456  NE   ARG A 199      -2.420   3.326  17.842  1.00 18.91
ATOM   1457  CZ   ARG A 199      -2.944   4.092  18.798  1.00 18.52
ATOM   1458  NH1  ARG A 199      -2.381   5.247  19.087  1.00 17.08
ATOM   1459  NH2  ARG A 199      -4.066   3.733  19.428  1.00 19.74
ATOM   1460  C    ARG A 199       1.858   0.488  16.894  1.00 19.23
ATOM   1461  O    ARG A 199       2.642   0.507  17.836  1.00 20.70
ATOM   1462  N    LEU A 200       2.183   0.809  15.639  1.00 19.23
ATOM   1463  CA   LEU A 200       3.472   1.424  15.309  1.00 21.60
ATOM   1464  CB   LEU A 200       4.021   0.867  13.984  1.00 22.49
ATOM   1465  CG   LEU A 200       4.201  -0.647  13.999  1.00 27.67
ATOM   1466  CD1  LEU A 200       4.779  -1.119  12.672  1.00 28.09
ATOM   1467  CD2  LEU A 200       5.160  -1.011  15.130  1.00 28.54
ATOM   1468  C    LEU A 200       3.225   2.920  15.166  1.00 21.95
ATOM   1469  O    LEU A 200       2.245   3.324  14.521  1.00 24.40
ATOM   1470  N    ILE A 201       4.088   3.707  15.798  1.00 19.67
ATOM   1471  CA   ILE A 201       4.022   5.165  15.845  1.00 22.82
ATOM   1472  CB   ILE A 201       4.095   5.679  17.309  1.00 24.19
ATOM   1473  CG1  ILE A 201       2.877   5.227  18.090  1.00 31.22
ATOM   1474  CD1  ILE A 201       1.753   4.981  17.178  1.00 26.82
ATOM   1475  CG2  ILE A 201       4.104   7.245  17.358  1.00 27.78
ATOM   1476  C    ILE A 201       5.295   5.667  15.190  1.00 20.99
ATOM   1477  O    ILE A 201       6.374   5.155  15.492  1.00 21.91
ATOM   1478  N    ARG A 202       5.216   6.709  14.376  1.00 19.22
ATOM   1479  CA   ARG A 202       6.473   7.346  13.949  1.00 18.14
ATOM   1480  CB   ARG A 202       6.517   7.524  12.440  1.00 19.80
ATOM   1481  CG   ARG A 202       6.696   6.213  11.693  1.00 25.47
ATOM   1482  CD   ARG A 202       7.194   6.457  10.291  1.00 32.91
ATOM   1483  NE   ARG A 202       7.555   5.237   9.577  1.00 38.14
ATOM   1484  CZ   ARG A 202       8.719   4.609   9.709  1.00 43.78
ATOM   1485  NH1  ARG A 202       9.646   5.051  10.552  1.00 42.73
ATOM   1486  NH2  ARG A 202       8.964   3.520   8.994  1.00 45.94
ATOM   1487  C    ARG A 202       6.600   8.705  14.639  1.00 18.39
ATOM   1488  O    ARG A 202       5.591   9.334  14.917  1.00 19.31
ATOM   1489  N    HIS A 203       7.829   9.072  14.982  1.00 17.24
ATOM   1490  CA   HIS A 203       8.142  10.319  15.694  1.00 16.77
ATOM   1491  CB   HIS A 203       8.729   9.943  17.068  1.00 16.74
ATOM   1492  CG   HIS A 203       8.980  11.095  17.996  1.00 17.60
ATOM   1493  ND1  HIS A 203      10.173  11.794  18.011  1.00 18.12
ATOM   1494  CE1  HIS A 203      10.133  12.706  18.970  1.00 17.49
ATOM   1495  NE2  HIS A 203       8.946  12.647  19.552  1.00 17.63
ATOM   1496  CD2  HIS A 203       8.221  11.629  18.985  1.00 18.26
ATOM   1497  C    HIS A 203       9.178  11.090  14.880  1.00 16.45
ATOM   1498  O    HIS A 203      10.257  10.574  14.537  1.00 16.92
ATOM   1499  N    PHE A 204       8.811  12.326  14.542  1.00 17.22
ATOM   1500  CA   PHE A 204       9.613  13.165  13.656  1.00 17.63
ATOM   1501  CB   PHE A 204       8.780  13.662  12.478  1.00 17.15
ATOM   1502  CG   PHE A 204       8.211  12.569  11.663  1.00 19.02
ATOM   1503  CD1  PHE A 204       6.914  12.146  11.891  1.00 17.04
ATOM   1504  CE1  PHE A 204       6.350  11.116  11.141  1.00 18.50
ATOM   1505  CZ   PHE A 204       7.075  10.508  10.152  1.00 21.34
ATOM   1506  CE2  PHE A 204       8.386  10.932   9.889  1.00 22.09
ATOM   1507  CD2  PHE A 204       8.952  11.967  10.652  1.00 20.96
```

FIGURE 131

```
ATOM   1508  C    PHE A 204      10.142  14.333  14.466  1.00 18.46
ATOM   1509  O    PHE A 204       9.382  15.198  14.850  1.00 19.13
ATOM   1510  N    HIS A 205      11.448  14.343  14.733  1.00 19.90
ATOM   1511  CA   HIS A 205      12.021  15.321  15.644  1.00 19.54
ATOM   1512  CB   HIS A 205      12.825  14.610  16.716  1.00 21.35
ATOM   1513  CG   HIS A 205      13.401  15.519  17.747  1.00 19.20
ATOM   1514  ND1  HIS A 205      14.407  15.127  18.610  1.00 24.56
ATOM   1515  CE1  HIS A 205      14.724  16.142  19.394  1.00 21.30
ATOM   1516  NE2  HIS A 205      13.962  17.173  19.071  1.00 21.10
ATOM   1517  CD2  HIS A 205      13.130  16.813  18.036  1.00 19.44
ATOM   1518  C    HIS A 205      12.960  16.220  14.846  1.00 19.88
ATOM   1519  O    HIS A 205      14.049  15.775  14.443  1.00 18.91
ATOM   1520  N    TYR A 206      12.504  17.456  14.670  1.00 18.79
ATOM   1521  CA   TYR A 206      13.205  18.483  13.897  1.00 18.49
ATOM   1522  CB   TYR A 206      12.172  19.409  13.287  1.00 19.17
ATOM   1523  CG   TYR A 206      12.754  20.435  12.354  1.00 19.28
ATOM   1524  CD1  TYR A 206      13.004  20.115  11.023  1.00 16.50
ATOM   1525  CE1  TYR A 206      13.540  21.052  10.141  1.00 17.88
ATOM   1526  CZ   TYR A 206      13.831  22.327  10.588  1.00 22.43
ATOM   1527  OH   TYR A 206      14.365  23.270   9.715  1.00 25.31
ATOM   1528  CE2  TYR A 206      13.594  22.666  11.904  1.00 23.08
ATOM   1529  CD2  TYR A 206      13.061  21.711  12.794  1.00 23.33
ATOM   1530  C    TYR A 206      14.064  19.229  14.900  1.00 20.26
ATOM   1531  O    TYR A 206      13.578  19.732  15.911  1.00 19.79
ATOM   1532  N    THR A 207      15.368  19.199  14.661  1.00 21.64
ATOM   1533  CA   THR A 207      16.318  19.479  15.717  1.00 23.75
ATOM   1534  CB   THR A 207      17.403  18.361  15.771  1.00 23.14
ATOM   1535  OG1  THR A 207      17.900  18.102  14.449  1.00 24.97
ATOM   1536  CG2  THR A 207      16.813  17.010  16.198  1.00 25.49
ATOM   1537  C    THR A 207      17.005  20.826  15.501  1.00 24.68
ATOM   1538  O    THR A 207      17.894  21.182  16.291  1.00 26.32
ATOM   1539  N    VAL A 208      16.588  21.554  14.473  1.00 24.44
ATOM   1540  CA   VAL A 208      17.279  22.769  14.010  1.00 26.67
ATOM   1541  CB   VAL A 208      17.996  22.597  12.627  1.00 24.93
ATOM   1542  CG1  VAL A 208      19.123  21.595  12.712  1.00 27.87
ATOM   1543  CG2  VAL A 208      17.022  22.243  11.490  1.00 27.01
ATOM   1544  C    VAL A 208      16.420  24.039  14.032  1.00 26.34
ATOM   1545  O    VAL A 208      16.647  24.972  13.252  1.00 29.43
ATOM   1546  N    TRP A 209      15.419  24.083  14.903  1.00 25.54
ATOM   1547  CA   TRP A 209      14.534  25.244  14.967  1.00 24.37
ATOM   1548  CB   TRP A 209      13.080  24.768  14.863  1.00 25.75
ATOM   1549  CG   TRP A 209      12.082  25.820  14.491  1.00 19.87
ATOM   1550  CD1  TRP A 209      12.153  27.174  14.694  1.00 22.45
ATOM   1551  NE1  TRP A 209      11.034  27.786  14.183  1.00 19.81
ATOM   1552  CE2  TRP A 209      10.202  26.822  13.663  1.00 25.00
ATOM   1553  CD2  TRP A 209      10.834  25.575  13.847  1.00 22.65
ATOM   1554  CE3  TRP A 209      10.185  24.414  13.399  1.00 23.01
ATOM   1555  CZ3  TRP A 209       8.951  24.531  12.793  1.00 19.01
ATOM   1556  CH2  TRP A 209       8.354  25.789  12.609  1.00 24.83
ATOM   1557  CZ2  TRP A 209       8.950  26.940  13.068  1.00 22.36
ATOM   1558  C    TRP A 209      14.678  26.021  16.270  1.00 27.04
ATOM   1559  O    TRP A 209      14.201  25.567  17.313  1.00 25.79
```

FIGURE 132

```
ATOM   1560  N    PRO A 210      15.303  27.198  16.230  1.00 28.07
ATOM   1561  CA   PRO A 210      15.452  28.000  17.454  1.00 28.03
ATOM   1562  CB   PRO A 210      16.386  29.140  17.022  1.00 29.50
ATOM   1563  CG   PRO A 210      16.944  28.740  15.657  1.00 31.17
ATOM   1564  CD   PRO A 210      15.880  27.869  15.050  1.00 27.52
ATOM   1565  C    PRO A 210      14.111  28.519  17.998  1.00 28.48
ATOM   1566  O    PRO A 210      13.268  28.944  17.216  1.00 28.98
ATOM   1567  N    ASP A 211      13.932  28.464  19.319  1.00 28.19
ATOM   1568  CA   ASP A 211      12.736  28.971  19.993  1.00 26.86
ATOM   1569  CB   ASP A 211      12.808  28.792  21.508  1.00 27.24
ATOM   1570  CG   ASP A 211      11.451  28.935  22.177  1.00 26.06
ATOM   1571  OD1  ASP A 211      10.461  29.156  21.452  1.00 26.31
ATOM   1572  OD2  ASP A 211      11.288  28.849  23.413  1.00 29.60
ATOM   1573  C    ASP A 211      12.585  30.448  19.661  1.00 28.25
ATOM   1574  O    ASP A 211      13.577  31.180  19.556  1.00 26.45
ATOM   1575  N    HIS A 212      11.348  30.872  19.435  1.00 25.98
ATOM   1576  CA   HIS A 212      11.107  32.260  19.072  1.00 28.34
ATOM   1577  CB   HIS A 212      11.743  33.153  20.145  1.00 29.66
ATOM   1578  CG   HIS A 212      11.094  34.492  20.283  1.00 36.64
ATOM   1579  ND1  HIS A 212       9.878  34.669  20.908  1.00 42.47
ATOM   1580  CE1  HIS A 212       9.553  35.951  20.875  1.00 42.76
ATOM   1581  NE2  HIS A 212      10.521  36.612  20.265  1.00 42.04
ATOM   1582  CD2  HIS A 212      11.501  35.724  19.892  1.00 41.28
ATOM   1583  C    HIS A 212      11.611  32.640  17.680  1.00 28.91
ATOM   1584  O    HIS A 212      11.494  33.799  17.275  1.00 30.92
ATOM   1585  N    GLY A 213      12.144  31.676  16.936  1.00 27.80
ATOM   1586  CA   GLY A 213      12.751  31.971  15.650  1.00 25.99
ATOM   1587  C    GLY A 213      12.192  31.153  14.511  1.00 26.04
ATOM   1588  O    GLY A 213      11.068  30.640  14.565  1.00 24.20
ATOM   1589  N    VAL A 214      13.012  31.066  13.470  1.00 26.25
ATOM   1590  CA   VAL A 214      12.724  30.274  12.296  1.00 26.25
ATOM   1591  CB   VAL A 214      12.213  31.170  11.158  1.00 27.10
ATOM   1592  CG1  VAL A 214      11.042  32.016  11.659  1.00 27.24
ATOM   1593  CG2  VAL A 214      13.347  32.040  10.628  1.00 28.86
ATOM   1594  C    VAL A 214      13.949  29.498  11.855  1.00 24.52
ATOM   1595  O    VAL A 214      15.095  29.866  12.167  1.00 24.97
ATOM   1596  N    PRO A 215      13.711  28.392  11.152  1.00 25.64
ATOM   1597  CA   PRO A 215      14.793  27.622  10.526  1.00 25.48
ATOM   1598  CB   PRO A 215      14.042  26.573   9.706  1.00 26.92
ATOM   1599  CG   PRO A 215      12.732  26.418  10.434  1.00 26.03
ATOM   1600  CD   PRO A 215      12.380  27.805  10.901  1.00 24.12
ATOM   1601  C    PRO A 215      15.609  28.518   9.612  1.00 27.43
ATOM   1602  O    PRO A 215      15.121  29.554   9.158  1.00 27.22
ATOM   1603  N    GLU A 216      16.841  28.111   9.315  1.00 28.05
ATOM   1604  CA   GLU A 216      17.721  28.985   8.553  1.00 28.65
ATOM   1605  CB   GLU A 216      19.161  28.486   8.661  1.00 30.42
ATOM   1606  CG   GLU A 216      19.771  28.747  10.023  1.00 35.56
ATOM   1607  CD   GLU A 216      21.219  29.169   9.904  1.00 42.95
ATOM   1608  OE1  GLU A 216      21.795  28.954   8.814  1.00 48.84
ATOM   1609  OE2  GLU A 216      21.765  29.715  10.889  1.00 45.41
ATOM   1610  C    GLU A 216      17.315  29.114   7.087  1.00 27.95
ATOM   1611  O    GLU A 216      17.649  30.113   6.448  1.00 27.93
```

FIGURE 133

```
ATOM   1612  N   THR A 217      16.652  28.099   6.537  1.00 25.57
ATOM   1613  CA  THR A 217      16.183  28.168   5.158  1.00 24.50
ATOM   1614  CB  THR A 217      16.913  27.146   4.270  1.00 23.44
ATOM   1615  OG1 THR A 217      16.712  25.831   4.821  1.00 23.33
ATOM   1616  CG2 THR A 217      18.430  27.370   4.323  1.00 25.77
ATOM   1617  C   THR A 217      14.697  27.816   5.082  1.00 22.97
ATOM   1618  O   THR A 217      14.161  27.138   5.964  1.00 23.20
ATOM   1619  N   THR A 218      14.037  28.246   4.013  1.00 22.43
ATOM   1620  CA  THR A 218      12.685  27.753   3.753  1.00 21.86
ATOM   1621  CB  THR A 218      12.003  28.563   2.637  1.00 22.40
ATOM   1622  OG1 THR A 218      12.807  28.503   1.448  1.00 23.58
ATOM   1623  CG2 THR A 218      11.911  30.047   3.006  1.00 25.57
ATOM   1624  C   THR A 218      12.759  26.291   3.315  1.00 21.64
ATOM   1625  O   THR A 218      11.897  25.483   3.667  1.00 21.31
ATOM   1626  N   GLN A 219      13.802  25.938   2.562  1.00 21.89
ATOM   1627  CA  GLN A 219      13.850  24.607   1.967  1.00 22.98
ATOM   1628  CB  GLN A 219      15.019  24.424   0.995  1.00 25.47
ATOM   1629  CG  GLN A 219      16.336  23.998   1.575  1.00 35.80
ATOM   1630  CD  GLN A 219      16.446  22.483   1.671  1.00 42.19
ATOM   1631  OE1 GLN A 219      17.144  21.962   2.541  1.00 48.46
ATOM   1632  NE2 GLN A 219      15.751  21.777   0.785  1.00 48.31
ATOM   1633  C   GLN A 219      13.831  23.550   3.060  1.00 22.41
ATOM   1634  O   GLN A 219      13.184  22.523   2.872  1.00 21.59
ATOM   1635  N   SER A 220      14.509  23.809   4.180  1.00 22.02
ATOM   1636  CA  SER A 220      14.554  22.828   5.260  1.00 21.83
ATOM   1637  CB  SER A 220      15.367  23.348   6.442  1.00 24.24
ATOM   1638  OG  SER A 220      15.366  22.396   7.489  1.00 28.06
ATOM   1639  C   SER A 220      13.157  22.477   5.785  1.00 21.60
ATOM   1640  O   SER A 220      12.768  21.309   5.802  1.00 20.80
ATOM   1641  N   LEU A 221      12.441  23.489   6.251  1.00 18.57
ATOM   1642  CA  LEU A 221      11.111  23.186   6.787  1.00 21.03
ATOM   1643  CB  LEU A 221      10.579  24.281   7.708  1.00 22.58
ATOM   1644  CG  LEU A 221       9.389  23.815   8.562  1.00 22.37
ATOM   1645  CD1 LEU A 221       9.934  22.943   9.698  1.00 22.41
ATOM   1646  CD2 LEU A 221       8.700  25.049   9.117  1.00 21.13
ATOM   1647  C   LEU A 221      10.114  22.722   5.737  1.00 21.34
ATOM   1648  O   LEU A 221       9.317  21.822   6.010  1.00 19.35
ATOM   1649  N   ILE A 222      10.165  23.274   4.524  1.00 17.11
ATOM   1650  CA  ILE A 222       9.335  22.740   3.456  1.00 17.94
ATOM   1651  CB  ILE A 222       9.569  23.524   2.130  1.00 17.12
ATOM   1652  CG1 ILE A 222       9.065  24.974   2.276  1.00 19.50
ATOM   1653  CD1 ILE A 222       9.548  25.933   1.171  1.00 19.49
ATOM   1654  CG2 ILE A 222       8.921  22.783   0.968  1.00 21.07
ATOM   1655  C   ILE A 222       9.601  21.260   3.217  1.00 19.20
ATOM   1656  O   ILE A 222       8.673  20.485   3.025  1.00 19.95
ATOM   1657  N   GLN A 223      10.869  20.854   3.207  1.00 16.23
ATOM   1658  CA  GLN A 223      11.123  19.449   2.988  1.00 18.60
ATOM   1659  CB  GLN A 223      12.616  19.228   2.715  1.00 19.15
ATOM   1660  CG  GLN A 223      12.941  17.766   2.467  1.00 22.79
ATOM   1661  CD  GLN A 223      12.643  17.290   1.061  1.00 33.15
ATOM   1662  OE1 GLN A 223      12.155  18.051   0.211  1.00 33.66
ATOM   1663  NE2 GLN A 223      12.917  16.006   0.817  1.00 35.76
```

FIGURE 134

```
ATOM   1664  C    GLN A 223      10.657  18.623   4.188  1.00 16.93
ATOM   1665  O    GLN A 223      10.199  17.502   3.988  1.00 18.36
ATOM   1666  N    PHE A 224      10.797  19.161   5.401  1.00 15.46
ATOM   1667  CA   PHE A 224      10.363  18.423   6.587  1.00 15.62
ATOM   1668  CB   PHE A 224      10.706  19.198   7.848  1.00 17.10
ATOM   1669  CG   PHE A 224      10.337  18.487   9.120  1.00 16.49
ATOM   1670  CD1  PHE A 224      10.836  17.215   9.398  1.00 17.51
ATOM   1671  CE1  PHE A 224      10.531  16.576  10.616  1.00 17.07
ATOM   1672  CZ   PHE A 224       9.717  17.205  11.544  1.00 16.55
ATOM   1673  CE2  PHE A 224       9.212  18.492  11.279  1.00 18.07
ATOM   1674  CD2  PHE A 224       9.544  19.125  10.054  1.00 19.46
ATOM   1675  C    PHE A 224       8.855  18.199   6.531  1.00 16.89
ATOM   1676  O    PHE A 224       8.380  17.078   6.751  1.00 16.66
ATOM   1677  N    VAL A 225       8.122  19.270   6.265  1.00 17.58
ATOM   1678  CA   VAL A 225       6.654  19.197   6.213  1.00 18.48
ATOM   1679  CB   VAL A 225       6.084  20.603   5.951  1.00 19.47
ATOM   1680  CG1  VAL A 225       4.635  20.522   5.473  1.00 20.27
ATOM   1681  CG2  VAL A 225       6.211  21.475   7.199  1.00 17.11
ATOM   1682  C    VAL A 225       6.241  18.203   5.122  1.00 19.13
ATOM   1683  O    VAL A 225       5.402  17.311   5.312  1.00 21.63
ATOM   1684  N    ARG A 226       6.829  18.331   3.941  1.00 19.30
ATOM   1685  CA   ARG A 226       6.514  17.393   2.871  1.00 20.41
ATOM   1686  CB   ARG A 226       7.276  17.776   1.594  1.00 20.66
ATOM   1687  CG   ARG A 226       6.656  18.990   0.916  1.00 22.30
ATOM   1688  CD   ARG A 226       7.410  19.483  -0.302  1.00 24.61
ATOM   1689  NE   ARG A 226       6.694  20.558  -0.983  1.00 24.83
ATOM   1690  CZ   ARG A 226       7.223  21.308  -1.948  1.00 31.14
ATOM   1691  NH1  ARG A 226       8.489  21.146  -2.306  1.00 30.48
ATOM   1692  NH2  ARG A 226       6.500  22.253  -2.526  1.00 34.90
ATOM   1693  C    ARG A 226       6.797  15.932   3.234  1.00 20.34
ATOM   1694  O    ARG A 226       6.060  15.004   2.879  1.00 19.67
ATOM   1695  N    THR A 227       7.910  15.717   3.920  1.00 19.65
ATOM   1696  CA   THR A 227       8.323  14.388   4.338  1.00 20.52
ATOM   1697  CB   THR A 227       9.715  14.485   4.977  1.00 22.22
ATOM   1698  OG1  THR A 227      10.673  14.679   3.930  1.00 22.33
ATOM   1699  CG2  THR A 227      10.110  13.143   5.586  1.00 24.52
ATOM   1700  C    THR A 227       7.310  13.786   5.339  1.00 20.30
ATOM   1701  O    THR A 227       6.886  12.642   5.191  1.00 20.93
ATOM   1702  N    VAL A 228       6.918  14.576   6.335  1.00 19.24
ATOM   1703  CA   VAL A 228       5.954  14.152   7.348  1.00 19.59
ATOM   1704  CB   VAL A 228       5.778  15.216   8.430  1.00 19.58
ATOM   1705  CG1  VAL A 228       4.631  14.832   9.353  1.00 20.61
ATOM   1706  CG2  VAL A 228       7.077  15.408   9.206  1.00 19.73
ATOM   1707  C    VAL A 228       4.609  13.877   6.690  1.00 21.77
ATOM   1708  O    VAL A 228       4.013  12.844   6.938  1.00 21.18
ATOM   1709  N    ARG A 229       4.183  14.774   5.805  1.00 22.98
ATOM   1710  CA   ARG A 229       2.866  14.626   5.179  1.00 25.81
ATOM   1711  CB   ARG A 229       2.546  15.904   4.402  1.00 23.29
ATOM   1712  CG   ARG A 229       1.423  15.881   3.384  1.00 28.30
ATOM   1713  CD   ARG A 229       0.053  15.877   3.972  1.00 30.57
ATOM   1714  NE   ARG A 229      -0.051  16.615   5.222  1.00 30.38
ATOM   1715  CZ   ARG A 229      -0.925  16.290   6.160  1.00 29.65
```

FIGURE 135

```
ATOM  1716  NH1 ARG A 229   -1.763  15.279   5.941  1.00 32.05
ATOM  1717  NH2 ARG A 229   -0.987  16.980   7.291  1.00 29.06
ATOM  1718  C   ARG A 229    2.879  13.378   4.301  1.00 26.73
ATOM  1719  O   ARG A 229    1.879  12.653   4.242  1.00 27.86
ATOM  1720  N   ASP A 230    4.015  13.108   3.658  1.00 26.22
ATOM  1721  CA  ASP A 230    4.251  11.866   2.928  1.00 28.24
ATOM  1722  CB  ASP A 230    5.621  11.877   2.251  1.00 28.67
ATOM  1723  CG  ASP A 230    5.654  12.720   0.982  1.00 34.01
ATOM  1724  OD1 ASP A 230    4.609  13.162   0.469  1.00 39.53
ATOM  1725  OD2 ASP A 230    6.727  13.005   0.420  1.00 41.90
ATOM  1726  C   ASP A 230    4.071  10.598   3.770  1.00 29.04
ATOM  1727  O   ASP A 230    3.401   9.645   3.350  1.00 29.94
ATOM  1728  N   TYR A 231    4.625  10.592   4.979  1.00 25.95
ATOM  1729  CA  TYR A 231    4.433   9.452   5.871  1.00 26.50
ATOM  1730  CB  TYR A 231    5.319   9.550   7.113  1.00 26.14
ATOM  1731  CG  TYR A 231    6.748   9.078   6.927  1.00 23.97
ATOM  1732  CD1 TYR A 231    7.774   9.978   6.647  1.00 19.78
ATOM  1733  CE1 TYR A 231    9.081   9.547   6.522  1.00 22.19
ATOM  1734  CZ  TYR A 231    9.390   8.211   6.654  1.00 23.00
ATOM  1735  OH  TYR A 231   10.701   7.787   6.513  1.00 28.03
ATOM  1736  CE2 TYR A 231    8.401   7.304   6.947  1.00 27.25
ATOM  1737  CD2 TYR A 231    7.086   7.736   7.088  1.00 25.16
ATOM  1738  C   TYR A 231    2.970   9.323   6.291  1.00 27.31
ATOM  1739  O   TYR A 231    2.446   8.209   6.297  1.00 28.55
ATOM  1740  N   ILE A 232    2.347  10.443   6.652  1.00 26.87
ATOM  1741  CA  ILE A 232    0.914  10.502   6.996  1.00 27.98
ATOM  1742  CB  ILE A 232    0.491  11.959   7.360  1.00 25.62
ATOM  1743  CG1 ILE A 232    1.038  12.361   8.727  1.00 26.35
ATOM  1744  CD1 ILE A 232    0.938  13.838   8.996  1.00 27.73
ATOM  1745  CG2 ILE A 232   -1.058  12.159   7.424  1.00 25.67
ATOM  1746  C   ILE A 232    0.046   9.935   5.875  1.00 32.06
ATOM  1747  O   ILE A 232   -0.767   9.022   6.107  1.00 33.57
ATOM  1748  N   ASN A 233    0.245  10.451   4.663  1.00 33.34
ATOM  1749  CA  ASN A 233   -0.580  10.101   3.509  1.00 37.27
ATOM  1750  CB  ASN A 233   -0.320  11.037   2.313  1.00 36.54
ATOM  1751  CG  ASN A 233   -0.932  12.425   2.480  1.00 38.15
ATOM  1752  OD1 ASN A 233   -1.648  12.712   3.442  1.00 42.42
ATOM  1753  ND2 ASN A 233   -0.630  13.309   1.533  1.00 37.50
ATOM  1754  C   ASN A 233   -0.429   8.635   3.090  1.00 39.12
ATOM  1755  O   ASN A 233   -1.332   8.073   2.463  1.00 41.73
ATOM  1756  N   ARG A 234    0.690   8.001   3.431  1.00 40.44
ATOM  1757  CA  ARG A 234    0.962   6.653   2.945  1.00 42.23
ATOM  1758  CB  ARG A 234    2.455   6.462   2.658  1.00 43.61
ATOM  1759  CG  ARG A 234    2.949   7.205   1.408  1.00 43.04
ATOM  1760  CD  ARG A 234    4.330   6.793   0.906  1.00 48.69
ATOM  1761  NE  ARG A 234    5.341   6.796   1.963  1.00 51.23
ATOM  1762  CZ  ARG A 234    6.283   7.724   2.115  1.00 54.19
ATOM  1763  NH1 ARG A 234    6.365   8.748   1.272  1.00 52.70
ATOM  1764  NH2 ARG A 234    7.144   7.630   3.122  1.00 51.22
ATOM  1765  C   ARG A 234    0.400   5.566   3.863  1.00 42.06
ATOM  1766  O   ARG A 234    0.337   4.379   3.512  1.00 42.43
ATOM  1767  N   SER A 235   -0.055   6.003   5.031  1.00 40.54
```

FIGURE 136

```
ATOM   1768  CA   SER A 235      -0.488    5.108    6.087  1.00 39.57
ATOM   1769  CB   SER A 235      -0.193    5.750    7.451  1.00 39.71
ATOM   1770  OG   SER A 235      -1.211    5.554    8.422  1.00 41.17
ATOM   1771  C    SER A 235      -1.964    4.744    5.925  1.00 38.09
ATOM   1772  O    SER A 235      -2.799    5.592    5.590  1.00 36.22
ATOM   1773  N    PRO A 236      -2.278    3.477    6.177  1.00 38.34
ATOM   1774  CA   PRO A 236      -3.661    2.979    6.083  1.00 39.35
ATOM   1775  CB   PRO A 236      -3.537    1.499    6.461  1.00 40.18
ATOM   1776  CG   PRO A 236      -2.214    1.375    7.150  1.00 39.24
ATOM   1777  CD   PRO A 236      -1.322    2.425    6.563  1.00 38.58
ATOM   1778  C    PRO A 236      -4.678    3.691    6.987  1.00 39.63
ATOM   1779  O    PRO A 236      -5.889    3.488    6.852  1.00 42.61
ATOM   1780  N    GLY A 237      -4.208    4.544    7.889  1.00 36.88
ATOM   1781  CA   GLY A 237      -5.069    5.079    8.938  1.00 34.20
ATOM   1782  C    GLY A 237      -4.178    5.738    9.970  1.00 30.76
ATOM   1783  O    GLY A 237      -3.532    5.037   10.733  1.00 29.45
ATOM   1784  N    ALA A 238      -4.150    7.071    9.986  1.00 28.97
ATOM   1785  CA   ALA A 238      -3.119    7.844   10.698  1.00 24.56
ATOM   1786  CB   ALA A 238      -2.656    9.019    9.834  1.00 27.03
ATOM   1787  C    ALA A 238      -3.564    8.342   12.077  1.00 23.45
ATOM   1788  O    ALA A 238      -2.759    8.476   12.986  1.00 21.78
ATOM   1789  N    GLY A 239      -4.853    8.620   12.242  1.00 21.70
ATOM   1790  CA   GLY A 239      -5.342    9.313   13.423  1.00 21.30
ATOM   1791  C    GLY A 239      -4.903   10.766   13.366  1.00 19.24
ATOM   1792  O    GLY A 239      -4.282   11.186   12.388  1.00 18.48
ATOM   1793  N    PRO A 240      -5.233   11.526   14.405  1.00 20.05
ATOM   1794  CA   PRO A 240      -4.740   12.907   14.530  1.00 19.68
ATOM   1795  CB   PRO A 240      -5.327   13.390   15.861  1.00 18.80
ATOM   1796  CG   PRO A 240      -6.393   12.393   16.247  1.00 21.11
ATOM   1797  CD   PRO A 240      -6.041   11.103   15.562  1.00 20.23
ATOM   1798  C    PRO A 240      -3.213   12.834   14.624  1.00 18.33
ATOM   1799  O    PRO A 240      -2.661   11.864   15.141  1.00 19.27
ATOM   1800  N    THR A 241      -2.548   13.832   14.071  1.00 16.60
ATOM   1801  CA   THR A 241      -1.090   13.930   14.185  1.00 15.99
ATOM   1802  CB   THR A 241      -0.593   14.614   12.919  1.00 15.63
ATOM   1803  OG1  THR A 241      -0.797   13.696   11.849  1.00 17.20
ATOM   1804  CG2  THR A 241       0.941   14.788   12.984  1.00 15.00
ATOM   1805  C    THR A 241      -0.829   14.832   15.367  1.00 16.75
ATOM   1806  O    THR A 241      -1.343   15.938   15.418  1.00 17.15
ATOM   1807  N    VAL A 242       0.031   14.387   16.274  1.00 16.56
ATOM   1808  CA   VAL A 242       0.370   15.207   17.413  1.00 15.30
ATOM   1809  CB   VAL A 242       0.777   14.315   18.586  1.00 13.91
ATOM   1810  CG1  VAL A 242       1.584   15.122   19.651  1.00 17.96
ATOM   1811  CG2  VAL A 242      -0.473   13.828   19.205  1.00 14.74
ATOM   1812  C    VAL A 242       1.537   16.089   17.002  1.00 15.85
ATOM   1813  O    VAL A 242       2.491   15.610   16.401  1.00 17.01
ATOM   1814  N    VAL A 243       1.421   17.375   17.295  1.00 15.52
ATOM   1815  CA   VAL A 243       2.525   18.289   17.027  1.00 15.21
ATOM   1816  CB   VAL A 243       2.223   19.311   15.915  1.00 13.92
ATOM   1817  CG1  VAL A 243       3.540   20.039   15.607  1.00 15.53
ATOM   1818  CG2  VAL A 243       1.710   18.648   14.624  1.00 15.61
ATOM   1819  C    VAL A 243       2.848   19.042   18.309  1.00 13.38
```

FIGURE 137

```
ATOM   1820  O    VAL A 243       1.977  19.511  19.006  1.00 15.35
ATOM   1821  N    HIS A 244       4.127  19.115  18.681  1.00 13.84
ATOM   1822  CA   HIS A 244       4.487  19.880  19.875  1.00 13.12
ATOM   1823  CB   HIS A 244       4.399  19.034  21.167  1.00 11.87
ATOM   1824  CG   HIS A 244       5.560  18.115  21.377  1.00 15.41
ATOM   1825  ND1  HIS A 244       6.728  18.524  21.977  1.00 16.81
ATOM   1826  CE1  HIS A 244       7.566  17.503  22.042  1.00 16.27
ATOM   1827  NE2  HIS A 244       6.998  16.461  21.463  1.00 16.52
ATOM   1828  CD2  HIS A 244       5.726  16.808  21.067  1.00 14.38
ATOM   1829  C    HIS A 244       5.856  20.526  19.735  1.00 14.17
ATOM   1830  O    HIS A 244       6.688  20.046  18.970  1.00 16.93
ATOM   1831  N    CYS A 245       6.041  21.611  20.492  1.00 16.57
ATOM   1832  CA   CYS A 245       7.349  22.211  20.652  1.00 17.05
ATOM   1833  CB   CYS A 245       7.396  23.573  19.941  1.00 15.83
ATOM   1834  SG   CYS A 245       5.834  24.486  20.086  1.00 19.56
ATOM   1835  C    CYS A 245       7.521  22.283  22.151  1.00 17.57
ATOM   1836  O    CYS A 245       7.391  21.246  22.839  1.00 17.79
ATOM   1837  N    SER A 246       7.815  23.464  22.693  1.00 18.50
ATOM   1838  CA   SER A 246       7.937  23.554  24.159  1.00 16.87
ATOM   1839  CB   SER A 246       9.020  24.552  24.628  1.00 18.69
ATOM   1840  OG   SER A 246       9.228  24.422  26.031  1.00 18.18
ATOM   1841  C    SER A 246       6.573  23.942  24.722  1.00 17.49
ATOM   1842  O    SER A 246       6.046  23.238  25.580  1.00 17.21
ATOM   1843  N    ALA A 247       6.019  25.049  24.239  1.00 18.04
ATOM   1844  CA   ALA A 247       4.736  25.497  24.749  1.00 19.26
ATOM   1845  CB   ALA A 247       4.710  27.036  24.838  1.00 19.87
ATOM   1846  C    ALA A 247       3.573  25.010  23.903  1.00 17.94
ATOM   1847  O    ALA A 247       2.430  25.177  24.309  1.00 19.75
ATOM   1848  N    GLY A 248       3.848  24.439  22.729  1.00 20.22
ATOM   1849  CA   GLY A 248       2.806  24.174  21.748  1.00 18.63
ATOM   1850  C    GLY A 248       2.132  25.433  21.196  1.00 18.85
ATOM   1851  O    GLY A 248       0.898  25.475  21.017  1.00 19.05
ATOM   1852  N    VAL A 249       2.954  26.427  20.867  1.00 17.12
ATOM   1853  CA   VAL A 249       2.463  27.715  20.358  1.00 16.65
ATOM   1854  CB   VAL A 249       2.562  28.810  21.445  1.00 18.34
ATOM   1855  CG1  VAL A 249       2.075  30.142  20.845  1.00 21.79
ATOM   1856  CG2  VAL A 249       1.744  28.426  22.662  1.00 20.69
ATOM   1857  C    VAL A 249       3.164  28.180  19.070  1.00 17.87
ATOM   1858  O    VAL A 249       2.543  28.251  18.008  1.00 17.85
ATOM   1859  N    GLY A 250       4.453  28.487  19.140  1.00 19.22
ATOM   1860  CA   GLY A 250       5.039  29.253  18.055  1.00 19.94
ATOM   1861  C    GLY A 250       5.491  28.321  16.963  1.00 19.70
ATOM   1862  O    GLY A 250       5.086  28.456  15.808  1.00 19.01
ATOM   1863  N    ARG A 251       6.366  27.389  17.335  1.00 19.14
ATOM   1864  CA   ARG A 251       6.939  26.498  16.347  1.00 19.05
ATOM   1865  CB   ARG A 251       8.195  25.860  16.890  1.00 19.24
ATOM   1866  CG   ARG A 251       9.219  26.952  17.158  1.00 15.81
ATOM   1867  CD   ARG A 251      10.481  26.394  17.775  1.00 16.06
ATOM   1868  NE   ARG A 251      10.226  26.200  19.214  1.00 19.50
ATOM   1869  CZ   ARG A 251      11.094  25.704  20.078  1.00 22.30
ATOM   1870  NH1  ARG A 251      12.290  25.314  19.644  1.00 20.21
ATOM   1871  NH2  ARG A 251      10.758  25.569  21.366  1.00 23.16
```

FIGURE 138

| | | | | | | | | | |
|---|---|---|---|---|---|---|---|---|---|
| ATOM | 1872 | C | ARG | A | 251 | 5.901 | 25.497 | 15.876 | 1.00 18.56 |
| ATOM | 1873 | O | ARG | A | 251 | 5.813 | 25.250 | 14.680 | 1.00 17.43 |
| ATOM | 1874 | N | THR | A | 252 | 5.111 | 24.941 | 16.794 | 1.00 18.19 |
| ATOM | 1875 | CA | THR | A | 252 | 3.982 | 24.106 | 16.377 | 1.00 17.71 |
| ATOM | 1876 | CB | THR | A | 252 | 3.217 | 23.628 | 17.607 | 1.00 17.40 |
| ATOM | 1877 | OG1A | THR | A | 252 | 2.999 | 24.765 | 18.450 | 0.50 23.23 |
| ATOM | 1878 | OG1B | THR | A | 252 | 4.029 | 22.684 | 18.306 | 0.50 13.92 |
| ATOM | 1879 | CG2A | THR | A | 252 | 4.083 | 22.722 | 18.434 | 0.50 15.60 |
| ATOM | 1880 | CG2B | THR | A | 252 | 1.947 | 22.833 | 17.252 | 0.50 10.20 |
| ATOM | 1881 | C | THR | A | 252 | 3.019 | 24.851 | 15.484 | 1.00 17.17 |
| ATOM | 1882 | O | THR | A | 252 | 2.600 | 24.297 | 14.475 | 1.00 15.23 |
| ATOM | 1883 | N | GLY | A | 253 | 2.661 | 26.092 | 15.832 | 1.00 16.60 |
| ATOM | 1884 | CA | GLY | A | 253 | 1.745 | 26.853 | 14.990 | 1.00 16.77 |
| ATOM | 1885 | C | GLY | A | 253 | 2.300 | 27.075 | 13.599 | 1.00 17.58 |
| ATOM | 1886 | O | GLY | A | 253 | 1.597 | 26.966 | 12.604 | 1.00 16.20 |
| ATOM | 1887 | N | THR | A | 254 | 3.608 | 27.343 | 13.507 | 1.00 15.25 |
| ATOM | 1888 | CA | THR | A | 254 | 4.197 | 27.626 | 12.216 | 1.00 14.32 |
| ATOM | 1889 | CB | THR | A | 254 | 5.628 | 28.249 | 12.422 | 1.00 13.48 |
| ATOM | 1890 | OG1 | THR | A | 254 | 5.439 | 29.443 | 13.202 | 1.00 18.67 |
| ATOM | 1891 | CG2 | THR | A | 254 | 6.190 | 28.764 | 11.050 | 1.00 17.19 |
| ATOM | 1892 | C | THR | A | 254 | 4.262 | 26.342 | 11.390 | 1.00 15.60 |
| ATOM | 1893 | O | THR | A | 254 | 4.052 | 26.379 | 10.184 | 1.00 17.10 |
| ATOM | 1894 | N | PHE | A | 255 | 4.576 | 25.222 | 12.032 | 1.00 15.48 |
| ATOM | 1895 | CA | PHE | A | 255 | 4.640 | 23.944 | 11.321 | 1.00 15.29 |
| ATOM | 1896 | CB | PHE | A | 255 | 5.043 | 22.832 | 12.304 | 1.00 17.14 |
| ATOM | 1897 | CG | PHE | A | 255 | 4.977 | 21.465 | 11.674 | 1.00 17.46 |
| ATOM | 1898 | CD1 | PHE | A | 255 | 6.052 | 21.001 | 10.959 | 1.00 20.12 |
| ATOM | 1899 | CE1 | PHE | A | 255 | 6.001 | 19.759 | 10.330 | 1.00 19.80 |
| ATOM | 1900 | CZ | PHE | A | 255 | 4.860 | 19.003 | 10.351 | 1.00 15.16 |
| ATOM | 1901 | CE2 | PHE | A | 255 | 3.755 | 19.457 | 11.013 | 1.00 16.37 |
| ATOM | 1902 | CD2 | PHE | A | 255 | 3.796 | 20.725 | 11.662 | 1.00 15.77 |
| ATOM | 1903 | C | PHE | A | 255 | 3.271 | 23.608 | 10.725 | 1.00 15.30 |
| ATOM | 1904 | O | PHE | A | 255 | 3.145 | 23.207 | 9.548 | 1.00 15.54 |
| ATOM | 1905 | N | ILE | A | 256 | 2.256 | 23.693 | 11.568 | 1.00 13.96 |
| ATOM | 1906 | CA | ILE | A | 256 | 0.914 | 23.321 | 11.106 | 1.00 14.62 |
| ATOM | 1907 | CB | ILE | A | 256 | -0.077 | 23.288 | 12.256 | 1.00 14.78 |
| ATOM | 1908 | CG1 | ILE | A | 256 | 0.284 | 22.166 | 13.221 | 1.00 16.14 |
| ATOM | 1909 | CD1 | ILE | A | 256 | -0.671 | 22.068 | 14.439 | 1.00 16.04 |
| ATOM | 1910 | CG2 | ILE | A | 256 | -1.497 | 23.016 | 11.695 | 1.00 14.89 |
| ATOM | 1911 | C | ILE | A | 256 | 0.465 | 24.282 | 9.993 | 1.00 14.00 |
| ATOM | 1912 | O | ILE | A | 256 | -0.065 | 23.831 | 8.975 | 1.00 15.99 |
| ATOM | 1913 | N | ALA | A | 257 | 0.637 | 25.588 | 10.195 | 1.00 14.29 |
| ATOM | 1914 | CA | ALA | A | 257 | 0.292 | 26.539 | 9.130 | 1.00 13.84 |
| ATOM | 1915 | CB | ALA | A | 257 | 0.571 | 27.988 | 9.530 | 1.00 14.99 |
| ATOM | 1916 | C | ALA | A | 257 | 0.955 | 26.205 | 7.798 | 1.00 14.85 |
| ATOM | 1917 | O | ALA | A | 257 | 0.328 | 26.208 | 6.746 | 1.00 16.25 |
| ATOM | 1918 | N | LEU | A | 258 | 2.258 | 25.958 | 7.833 | 1.00 13.44 |
| ATOM | 1919 | CA | LEU | A | 258 | 2.950 | 25.564 | 6.631 | 1.00 14.78 |
| ATOM | 1920 | CB | LEU | A | 258 | 4.448 | 25.390 | 6.889 | 1.00 13.66 |
| ATOM | 1921 | CG | LEU | A | 258 | 5.247 | 25.137 | 5.615 | 1.00 15.58 |
| ATOM | 1922 | CD1 | LEU | A | 258 | 5.050 | 26.284 | 4.593 | 1.00 17.44 |
| ATOM | 1923 | CD2 | LEU | A | 258 | 6.745 | 25.019 | 5.965 | 1.00 16.74 |

FIGURE 139

```
ATOM   1924  C    LEU A 258       2.391  24.297   6.013  1.00 14.93
ATOM   1925  O    LEU A 258       2.223  24.210   4.805  1.00 14.85
ATOM   1926  N    ASP A 259       2.105  23.290   6.838  1.00 15.85
ATOM   1927  CA   ASP A 259       1.470  22.081   6.314  1.00 16.95
ATOM   1928  CB   ASP A 259       1.186  21.146   7.501  1.00 18.21
ATOM   1929  CG   ASP A 259       0.834  19.718   7.102  1.00 22.66
ATOM   1930  OD1  ASP A 259       1.205  19.202   6.016  1.00 20.07
ATOM   1931  OD2  ASP A 259       0.217  18.996   7.920  1.00 33.57
ATOM   1932  C    ASP A 259       0.173  22.425   5.567  1.00 15.64
ATOM   1933  O    ASP A 259      -0.024  21.963   4.439  1.00 17.43
ATOM   1934  N    ARG A 260      -0.682  23.260   6.148  1.00 16.51
ATOM   1935  CA   ARG A 260      -1.947  23.632   5.504  1.00 16.62
ATOM   1936  CB   ARG A 260      -2.836  24.464   6.425  1.00 18.22
ATOM   1937  CG   ARG A 260      -3.435  23.668   7.571  1.00 25.51
ATOM   1938  CD   ARG A 260      -4.950  23.818   7.664  1.00 40.63
ATOM   1939  NE   ARG A 260      -5.428  25.199   7.581  1.00 49.41
ATOM   1940  CZ   ARG A 260      -5.919  25.797   6.491  1.00 52.56
ATOM   1941  NH1  ARG A 260      -6.025  25.176   5.311  1.00 50.50
ATOM   1942  NH2  ARG A 260      -6.310  27.059   6.592  1.00 53.49
ATOM   1943  C    ARG A 260      -1.685  24.431   4.233  1.00 16.45
ATOM   1944  O    ARG A 260      -2.247  24.131   3.165  1.00 18.96
ATOM   1945  N    ILE A 261      -0.767  25.394   4.310  1.00 15.77
ATOM   1946  CA   ILE A 261      -0.542  26.228   3.138  1.00 18.24
ATOM   1947  CB   ILE A 261       0.206  27.521   3.521  1.00 21.96
ATOM   1948  CG1AILE A 261        1.651  27.329   3.908  0.50 17.99
ATOM   1949  CG1BILE A 261       -0.685  28.609   4.112  0.50 19.62
ATOM   1950  CD1AILE A 261        2.215  28.633   4.442  0.50 20.12
ATOM   1951  CD1BILE A 261        0.000  29.266   5.315  0.50 24.86
ATOM   1952  CG2AILE A 261       -0.604  28.289   4.549  0.50 18.49
ATOM   1953  CG2BILE A 261        1.211  27.966   2.472  0.50 19.26
ATOM   1954  C    ILE A 261       0.067  25.456   1.973  1.00 19.50
ATOM   1955  O    ILE A 261      -0.278  25.684   0.799  1.00 17.34
ATOM   1956  N    LEU A 262       1.002  24.564   2.291  1.00 18.57
ATOM   1957  CA   LEU A 262       1.572  23.704   1.256  1.00 19.04
ATOM   1958  CB   LEU A 262       2.736  22.874   1.776  1.00 17.43
ATOM   1959  CG   LEU A 262       4.004  23.676   2.064  1.00 16.24
ATOM   1960  CD1  LEU A 262       5.114  22.827   2.635  1.00 18.88
ATOM   1961  CD2  LEU A 262       4.509  24.501   0.861  1.00 21.60
ATOM   1962  C    LEU A 262       0.533  22.831   0.568  1.00 18.56
ATOM   1963  O    LEU A 262       0.613  22.605  -0.649  1.00 19.59
ATOM   1964  N    GLN A 263      -0.423  22.344   1.350  1.00 16.77
ATOM   1965  CA   GLN A 263      -1.517  21.572   0.772  1.00 18.98
ATOM   1966  CB   GLN A 263      -2.359  20.878   1.850  1.00 21.56
ATOM   1967  CG   GLN A 263      -1.581  19.736   2.499  1.00 24.14
ATOM   1968  CD   GLN A 263      -2.322  19.083   3.652  1.00 30.60
ATOM   1969  OE1  GLN A 263      -3.120  18.178   3.445  1.00 37.41
ATOM   1970  NE2  GLN A 263      -2.058  19.540   4.868  1.00 34.60
ATOM   1971  C    GLN A 263      -2.383  22.438  -0.124  1.00 18.41
ATOM   1972  O    GLN A 263      -2.861  21.939  -1.165  1.00 19.16
ATOM   1973  N    GLN A 264      -2.585  23.692   0.286  1.00 17.80
ATOM   1974  CA   GLN A 264      -3.284  24.667  -0.547  1.00 19.17
ATOM   1975  CB   GLN A 264      -3.375  26.035   0.130  1.00 21.52
```

FIGURE 140

```
ATOM   1976  CG   GLN A 264      -4.488  26.101   1.152  1.00 22.71
ATOM   1977  CD   GLN A 264      -4.485  27.392   1.924  1.00 27.25
ATOM   1978  OE1  GLN A 264      -3.974  28.404   1.452  1.00 28.01
ATOM   1979  NE2  GLN A 264      -5.062  27.364   3.126  1.00 32.99
ATOM   1980  C    GLN A 264      -2.569  24.866  -1.856  1.00 17.97
ATOM   1981  O    GLN A 264      -3.195  24.854  -2.914  1.00 18.97
ATOM   1982  N    LEU A 265      -1.243  25.044  -1.807  1.00 16.73
ATOM   1983  CA   LEU A 265      -0.524  25.223  -3.059  1.00 15.75
ATOM   1984  CB   LEU A 265       0.944  25.599  -2.792  1.00 16.04
ATOM   1985  CG   LEU A 265       1.177  26.933  -2.072  1.00 16.47
ATOM   1986  CD1  LEU A 265       2.699  27.094  -1.977  1.00 23.16
ATOM   1987  CD2  LEU A 265       0.556  28.085  -2.851  1.00 23.92
ATOM   1988  C    LEU A 265      -0.567  24.006  -3.963  1.00 17.46
ATOM   1989  O    LEU A 265      -0.348  24.116  -5.177  1.00 19.71
ATOM   1990  N    ASP A 266      -0.787  22.828  -3.397  1.00 15.69
ATOM   1991  CA   ASP A 266      -0.767  21.626  -4.210  1.00 16.88
ATOM   1992  CB   ASP A 266      -0.328  20.423  -3.368  1.00 17.44
ATOM   1993  CG   ASP A 266       1.156  20.375  -3.149  1.00 21.62
ATOM   1994  OD1  ASP A 266       1.862  21.159  -3.791  1.00 21.03
ATOM   1995  OD2  ASP A 266       1.680  19.586  -2.335  1.00 25.07
ATOM   1996  C    ASP A 266      -2.163  21.343  -4.768  1.00 16.49
ATOM   1997  O    ASP A 266      -2.320  20.469  -5.624  1.00 18.65
ATOM   1998  N    SER A 267      -3.151  22.112  -4.318  1.00 17.93
ATOM   1999  CA   SER A 267      -4.562  21.826  -4.646  1.00 18.68
ATOM   2000  CB   SER A 267      -5.334  21.390  -3.392  1.00 20.21
ATOM   2001  OG  ASER A 267      -4.827  20.179  -2.869  0.50 22.09
ATOM   2002  OG  BSER A 267      -5.151  22.290  -2.327  0.50 19.41
ATOM   2003  C    SER A 267      -5.375  22.910  -5.354  1.00 19.44
ATOM   2004  O    SER A 267      -6.260  22.591  -6.147  1.00 19.32
ATOM   2005  N    LYS A 268      -5.083  24.164  -5.022  1.00 18.83
ATOM   2006  CA   LYS A 268      -5.848  25.354  -5.377  1.00 20.16
ATOM   2007  CB   LYS A 268      -6.430  25.992  -4.099  1.00 20.65
ATOM   2008  CG   LYS A 268      -7.498  25.094  -3.470  1.00 26.76
ATOM   2009  CD   LYS A 268      -8.104  25.692  -2.209  1.00 35.23
ATOM   2010  CE   LYS A 268      -9.065  26.845  -2.493  1.00 39.80
ATOM   2011  NZ   LYS A 268      -9.302  27.654  -1.258  1.00 42.30
ATOM   2012  C    LYS A 268      -4.995  26.373  -6.115  1.00 20.26
ATOM   2013  O    LYS A 268      -3.762  26.340  -6.077  1.00 20.14
ATOM   2014  N    ASP A 269      -5.653  27.329  -6.766  1.00 20.67
ATOM   2015  CA   ASP A 269      -4.923  28.431  -7.379  1.00 22.23
ATOM   2016  CB   ASP A 269      -5.354  28.695  -8.824  1.00 21.86
ATOM   2017  CG   ASP A 269      -6.802  29.136  -8.948  1.00 24.01
ATOM   2018  OD1  ASP A 269      -7.478  29.270  -7.910  1.00 23.82
ATOM   2019  OD2  ASP A 269      -7.315  29.358 -10.081  1.00 25.17
ATOM   2020  C    ASP A 269      -4.936  29.704  -6.561  1.00 21.37
ATOM   2021  O    ASP A 269      -4.671  30.783  -7.086  1.00 20.35
ATOM   2022  N    SER A 270      -5.235  29.557  -5.272  1.00 22.33
ATOM   2023  CA   SER A 270      -5.009  30.638  -4.323  1.00 20.47
ATOM   2024  CB   SER A 270      -6.278  31.451  -4.075  1.00 24.06
ATOM   2025  OG   SER A 270      -7.314  30.640  -3.578  1.00 26.40
ATOM   2026  C    SER A 270      -4.518  30.042  -3.018  1.00 21.38
ATOM   2027  O    SER A 270      -4.735  28.852  -2.739  1.00 22.73
```

FIGURE 141

```
ATOM   2028  N    VAL A 271      -3.885  30.903  -2.225  1.00 22.36
ATOM   2029  CA   VAL A 271      -3.263  30.508  -0.963  1.00 21.09
ATOM   2030  CB   VAL A 271      -1.709  30.463  -1.115  1.00 19.31
ATOM   2031  CG1  VAL A 271      -1.167  31.865  -1.450  1.00 21.60
ATOM   2032  CG2  VAL A 271      -1.082  29.972   0.200  1.00 21.85
ATOM   2033  C    VAL A 271      -3.688  31.549   0.072  1.00 20.22
ATOM   2034  O    VAL A 271      -3.787  32.736  -0.240  1.00 22.08
ATOM   2035  N    ASP A 272      -3.917  31.112   1.310  1.00 20.16
ATOM   2036  CA   ASP A 272      -4.471  32.003   2.324  1.00 19.60
ATOM   2037  CB   ASP A 272      -5.965  31.714   2.437  1.00 19.30
ATOM   2038  CG   ASP A 272      -6.676  32.598   3.431  1.00 19.17
ATOM   2039  OD1  ASP A 272      -6.077  33.593   3.891  1.00 21.60
ATOM   2040  OD2  ASP A 272      -7.859  32.350   3.783  1.00 24.88
ATOM   2041  C    ASP A 272      -3.744  31.805   3.655  1.00 20.36
ATOM   2042  O    ASP A 272      -4.243  31.163   4.591  1.00 20.38
ATOM   2043  N    ILE A 273      -2.541  32.365   3.720  1.00 19.70
ATOM   2044  CA   ILE A 273      -1.760  32.311   4.942  1.00 19.19
ATOM   2045  CB   ILE A 273      -0.381  32.962   4.720  1.00 18.60
ATOM   2046  CG1  ILE A 273       0.333  32.288   3.548  1.00 21.27
ATOM   2047  CD1  ILE A 273       1.729  32.865   3.275  1.00 22.60
ATOM   2048  CG2  ILE A 273       0.464  32.875   5.999  1.00 20.66
ATOM   2049  C    ILE A 273      -2.477  32.966   6.107  1.00 20.28
ATOM   2050  O    ILE A 273      -2.472  32.424   7.218  1.00 18.55
ATOM   2051  N    TYR A 274      -3.100  34.117   5.869  1.00 18.83
ATOM   2052  CA   TYR A 274      -3.766  34.840   6.953  1.00 21.01
ATOM   2053  CB   TYR A 274      -4.367  36.112   6.356  1.00 19.87
ATOM   2054  CG   TYR A 274      -5.067  36.972   7.358  1.00 18.97
ATOM   2055  CD1  TYR A 274      -4.394  38.025   7.954  1.00 21.35
ATOM   2056  CE1  TYR A 274      -5.029  38.859   8.864  1.00 25.25
ATOM   2057  CZ   TYR A 274      -6.352  38.625   9.157  1.00 28.87
ATOM   2058  OH   TYR A 274      -6.978  39.454  10.070  1.00 34.66
ATOM   2059  CE2  TYR A 274      -7.051  37.579   8.579  1.00 26.00
ATOM   2060  CD2  TYR A 274      -6.413  36.757   7.669  1.00 22.43
ATOM   2061  C    TYR A 274      -4.875  33.977   7.550  1.00 21.55
ATOM   2062  O    TYR A 274      -4.991  33.834   8.776  1.00 22.52
ATOM   2063  N    GLY A 275      -5.625  33.326   6.671  1.00 19.33
ATOM   2064  CA   GLY A 275      -6.741  32.496   7.090  1.00 19.21
ATOM   2065  C    GLY A 275      -6.245  31.272   7.837  1.00 20.79
ATOM   2066  O    GLY A 275      -6.889  30.859   8.796  1.00 22.44
ATOM   2067  N    ALA A 276      -5.125  30.692   7.398  1.00 18.85
ATOM   2068  CA   ALA A 276      -4.558  29.525   8.094  1.00 20.03
ATOM   2069  CB   ALA A 276      -3.324  29.022   7.356  1.00 20.07
ATOM   2070  C    ALA A 276      -4.195  29.870   9.542  1.00 19.85
ATOM   2071  O    ALA A 276      -4.432  29.103  10.479  1.00 20.22
ATOM   2072  N    VAL A 277      -3.537  31.010   9.719  1.00 19.70
ATOM   2073  CA   VAL A 277      -3.115  31.387  11.057  1.00 19.31
ATOM   2074  CB   VAL A 277      -2.121  32.548  11.018  1.00 17.79
ATOM   2075  CG1  VAL A 277      -1.820  32.967  12.458  1.00 18.22
ATOM   2076  CG2  VAL A 277      -0.848  32.152  10.255  1.00 18.41
ATOM   2077  C    VAL A 277      -4.346  31.757  11.868  1.00 19.90
ATOM   2078  O    VAL A 277      -4.474  31.347  13.019  1.00 20.30
ATOM   2079  N    HIS A 278      -5.241  32.548  11.292  1.00 19.02
```

FIGURE 142

```
ATOM   2080  CA  HIS A 278      -6.516  32.865  11.948  1.00 19.17
ATOM   2081  CB  HIS A 278      -7.444  33.619  10.992  1.00 19.25
ATOM   2082  CG  HIS A 278      -8.751  33.994  11.601  1.00 18.26
ATOM   2083  ND1 HIS A 278      -9.794  33.105  11.749  1.00 23.05
ATOM   2084  CE1 HIS A 278     -10.818  33.721  12.311  1.00 21.29
ATOM   2085  NE2 HIS A 278     -10.478  34.980  12.522  1.00 22.86
ATOM   2086  CD2 HIS A 278      -9.189  35.176  12.093  1.00 20.74
ATOM   2087  C   HIS A 278      -7.203  31.605  12.495  1.00 17.84
ATOM   2088  O   HIS A 278      -7.537  31.525  13.680  1.00 18.09
ATOM   2089  N   ASP A 279      -7.350  30.601  11.635  1.00 18.49
ATOM   2090  CA  ASP A 279      -8.101  29.403  11.989  1.00 19.79
ATOM   2091  CB  ASP A 279      -8.327  28.536  10.749  1.00 21.91
ATOM   2092  CG  ASP A 279      -9.382  29.137   9.805  1.00 27.33
ATOM   2093  OD1 ASP A 279     -10.122  30.086  10.181  1.00 32.69
ATOM   2094  OD2 ASP A 279      -9.571  28.698   8.663  1.00 32.10
ATOM   2095  C   ASP A 279      -7.376  28.645  13.092  1.00 19.96
ATOM   2096  O   ASP A 279      -8.023  28.185  14.024  1.00 21.76
ATOM   2097  N   LEU A 280      -6.040  28.527  13.041  1.00 17.01
ATOM   2098  CA  LEU A 280      -5.330  27.942  14.182  1.00 16.07
ATOM   2099  CB  LEU A 280      -3.826  27.947  13.886  1.00 15.00
ATOM   2100  CG  LEU A 280      -3.422  27.038  12.707  1.00 18.81
ATOM   2101  CD1 LEU A 280      -1.913  27.070  12.480  1.00 18.81
ATOM   2102  CD2 LEU A 280      -3.882  25.608  12.945  1.00 25.24
ATOM   2103  C   LEU A 280      -5.569  28.675  15.513  1.00 16.26
ATOM   2104  O   LEU A 280      -5.712  28.053  16.564  1.00 16.85
ATOM   2105  N   ARG A 281      -5.589  30.004  15.476  1.00 15.08
ATOM   2106  CA  ARG A 281      -5.688  30.743  16.716  1.00 17.44
ATOM   2107  CB  ARG A 281      -5.378  32.206  16.447  1.00 17.50
ATOM   2108  CG  ARG A 281      -3.897  32.412  16.278  1.00 17.29
ATOM   2109  CD  ARG A 281      -3.452  33.863  16.134  1.00 16.44
ATOM   2110  NE  ARG A 281      -1.994  33.944  15.966  1.00 16.47
ATOM   2111  CZ  ARG A 281      -1.298  35.076  15.842  1.00 18.10
ATOM   2112  NH1 ARG A 281      -1.939  36.226  15.915  1.00 21.62
ATOM   2113  NH2 ARG A 281       0.034  35.066  15.648  1.00 18.29
ATOM   2114  C   ARG A 281      -7.060  30.626  17.353  1.00 17.49
ATOM   2115  O   ARG A 281      -7.199  30.854  18.553  1.00 19.29
ATOM   2116  N   LEU A 282      -8.062  30.261  16.560  1.00 18.15
ATOM   2117  CA  LEU A 282      -9.358  29.983  17.142  1.00 17.68
ATOM   2118  CB  LEU A 282     -10.396  29.682  16.062  1.00 16.99
ATOM   2119  CG  LEU A 282     -10.801  30.873  15.182  1.00 19.43
ATOM   2120  CD1 LEU A 282     -11.737  30.362  14.090  1.00 25.48
ATOM   2121  CD2 LEU A 282     -11.501  31.952  16.018  1.00 24.65
ATOM   2122  C   LEU A 282      -9.279  28.793  18.102  1.00 19.14
ATOM   2123  O   LEU A 282     -10.141  28.668  18.977  1.00 19.96
ATOM   2124  N   HIS A 283      -8.293  27.918  17.896  1.00 17.18
ATOM   2125  CA  HIS A 283      -8.277  26.637  18.601  1.00 18.07
ATOM   2126  CB  HIS A 283      -8.139  25.490  17.597  1.00 18.24
ATOM   2127  CG  HIS A 283      -9.231  25.476  16.585  1.00 19.11
ATOM   2128  ND1 HIS A 283     -10.466  24.910  16.822  1.00 23.60
ATOM   2129  CE1 HIS A 283     -11.231  25.064  15.756  1.00 19.21
ATOM   2130  NE2 HIS A 283     -10.545  25.722  14.844  1.00 24.32
ATOM   2131  CD2 HIS A 283      -9.296  26.007  15.343  1.00 23.68
```

FIGURE 143

| | | | | | | | | | |
|---|---|---|---|---|---|---|---|---|---|
| ATOM | 2132 | C | | HIS | A | 283 | -7.254 | 26.512 | 19.707 | 1.00 | 17.83 |
| ATOM | 2133 | O | | HIS | A | 283 | -7.428 | 25.694 | 20.622 | 1.00 | 18.19 |
| ATOM | 2134 | N | | ARG | A | 284 | -6.201 | 27.314 | 19.637 | 1.00 | 17.80 |
| ATOM | 2135 | CA | | ARG | A | 284 | -5.240 | 27.348 | 20.746 | 1.00 | 18.49 |
| ATOM | 2136 | CB | | ARG | A | 284 | -4.226 | 26.210 | 20.609 | 1.00 | 18.69 |
| ATOM | 2137 | CG | | ARG | A | 284 | -3.276 | 26.099 | 21.796 | 1.00 | 18.21 |
| ATOM | 2138 | CD | | ARG | A | 284 | -2.402 | 24.878 | 21.679 | 1.00 | 19.61 |
| ATOM | 2139 | NE | | ARG | A | 284 | -1.291 | 24.852 | 22.639 | 1.00 | 17.43 |
| ATOM | 2140 | CZ | | ARG | A | 284 | -1.355 | 24.269 | 23.836 | 1.00 | 15.60 |
| ATOM | 2141 | NH1 | ARG | A | 284 | -2.509 | 23.773 | 24.275 | 1.00 | 16.53 |
| ATOM | 2142 | NH2 | ARG | A | 284 | -0.290 | 24.237 | 24.619 | 1.00 | 17.46 |
| ATOM | 2143 | C | | ARG | A | 284 | -4.530 | 28.695 | 20.752 | 1.00 | 17.37 |
| ATOM | 2144 | O | | ARG | A | 284 | -4.367 | 29.323 | 19.707 | 1.00 | 16.68 |
| ATOM | 2145 | N | | VAL | A | 285 | -4.142 | 29.123 | 21.941 | 1.00 | 16.77 |
| ATOM | 2146 | CA | | VAL | A | 285 | -3.720 | 30.502 | 22.158 | 1.00 | 18.62 |
| ATOM | 2147 | CB | | VAL | A | 285 | -3.294 | 30.774 | 23.616 | 1.00 | 18.24 |
| ATOM | 2148 | CG1 | VAL | A | 285 | -2.160 | 29.860 | 24.061 | 1.00 | 18.15 |
| ATOM | 2149 | CG2 | VAL | A | 285 | -2.946 | 32.249 | 23.792 | 1.00 | 21.76 |
| ATOM | 2150 | C | | VAL | A | 285 | -2.599 | 30.925 | 21.225 | 1.00 | 19.42 |
| ATOM | 2151 | O | | VAL | A | 285 | -1.503 | 30.358 | 21.256 | 1.00 | 20.43 |
| ATOM | 2152 | N | | HIS | A | 286 | -2.914 | 31.919 | 20.395 | 1.00 | 21.27 |
| ATOM | 2153 | CA | | HIS | A | 286 | -1.916 | 32.671 | 19.615 | 1.00 | 22.02 |
| ATOM | 2154 | CB | | HIS | A | 286 | -1.237 | 33.690 | 20.547 | 1.00 | 20.50 |
| ATOM | 2155 | CG | | HIS | A | 286 | -0.509 | 34.803 | 19.848 | 1.00 | 23.00 |
| ATOM | 2156 | ND1 | HIS | A | 286 | 0.558 | 34.583 | 19.001 | 1.00 | 22.19 |
| ATOM | 2157 | CE1 | HIS | A | 286 | 0.997 | 35.742 | 18.539 | 1.00 | 28.42 |
| ATOM | 2158 | NE2 | HIS | A | 286 | 0.299 | 36.711 | 19.104 | 1.00 | 23.08 |
| ATOM | 2159 | CD2 | HIS | A | 286 | -0.660 | 36.149 | 19.920 | 1.00 | 25.08 |
| ATOM | 2160 | C | | HIS | A | 286 | -0.937 | 31.748 | 18.880 | 1.00 | 20.60 |
| ATOM | 2161 | O | | HIS | A | 286 | 0.249 | 32.021 | 18.774 | 1.00 | 22.19 |
| ATOM | 2162 | N | | MET | A | 287 | -1.425 | 30.634 | 18.328 | 1.00 | 19.66 |
| ATOM | 2163 | CA | | MET | A | 287 | -0.622 | 29.854 | 17.395 | 1.00 | 20.00 |
| ATOM | 2164 | CB | | MET | A | 287 | -1.505 | 28.919 | 16.577 | 1.00 | 21.36 |
| ATOM | 2165 | CG | | MET | A | 287 | -2.213 | 27.872 | 17.401 | 1.00 | 22.55 |
| ATOM | 2166 | SD | | MET | A | 287 | -1.075 | 26.566 | 17.823 | 1.00 | 40.15 |
| ATOM | 2167 | CE | | MET | A | 287 | -1.223 | 27.071 | 19.109 | 1.00 | 6.08 |
| ATOM | 2168 | C | | MET | A | 287 | 0.133 | 30.710 | 16.385 | 1.00 | 20.09 |
| ATOM | 2169 | O | | MET | A | 287 | -0.471 | 31.515 | 15.681 | 1.00 | 20.94 |
| ATOM | 2170 | N | | VAL | A | 288 | 1.422 | 30.424 | 16.237 | 1.00 | 19.63 |
| ATOM | 2171 | CA | | VAL | A | 288 | 2.388 | 31.249 | 15.511 | 1.00 | 18.83 |
| ATOM | 2172 | CB | | VAL | A | 288 | 1.962 | 31.725 | 14.093 | 1.00 | 17.58 |
| ATOM | 2173 | CG1 | VAL | A | 288 | 3.180 | 32.328 | 13.410 | 1.00 | 18.31 |
| ATOM | 2174 | CG2 | VAL | A | 288 | 1.542 | 30.563 | 13.204 | 1.00 | 17.78 |
| ATOM | 2175 | C | | VAL | A | 288 | 2.758 | 32.425 | 16.439 | 1.00 | 18.47 |
| ATOM | 2176 | O | | VAL | A | 288 | 1.937 | 33.283 | 16.710 | 1.00 | 20.51 |
| ATOM | 2177 | N | | GLN | A | 289 | 3.970 | 32.397 | 16.978 | 1.00 | 20.96 |
| ATOM | 2178 | CA | | GLN | A | 289 | 4.275 | 33.242 | 18.136 | 1.00 | 22.85 |
| ATOM | 2179 | CB | | GLN | A | 289 | 5.360 | 32.573 | 18.989 | 1.00 | 23.05 |
| ATOM | 2180 | CG | | GLN | A | 289 | 5.711 | 33.382 | 20.255 | 1.00 | 23.08 |
| ATOM | 2181 | CD | | GLN | A | 289 | 6.940 | 32.853 | 20.982 | 1.00 | 24.28 |
| ATOM | 2182 | OE1 | GLN | A | 289 | 7.913 | 32.445 | 20.361 | 1.00 | 27.56 |
| ATOM | 2183 | NE2 | GLN | A | 289 | 6.888 | 32.843 | 22.309 | 1.00 | 23.63 |

FIGURE 144

```
ATOM   2184  C    GLN A 289       4.723  34.660  17.707  1.00  24.40
ATOM   2185  O    GLN A 289       4.391  35.649  18.378  1.00  23.35
ATOM   2186  N    THR A 290       5.492  34.737  16.617  1.00  26.49
ATOM   2187  CA   THR A 290       6.172  35.968  16.207  1.00  25.39
ATOM   2188  CB   THR A 290       7.702  35.856  16.359  1.00  26.91
ATOM   2189  OG1  THR A 290       8.244  35.042  15.307  1.00  28.99
ATOM   2190  CG2  THR A 290       8.109  35.128  17.629  1.00  27.48
ATOM   2191  C    THR A 290       5.866  36.465  14.801  1.00  26.87
ATOM   2192  O    THR A 290       5.512  35.692  13.896  1.00  25.17
ATOM   2193  N    GLU A 291       6.023  37.770  14.595  1.00  25.95
ATOM   2194  CA   GLU A 291       5.904  38.299  13.242  1.00  26.94
ATOM   2195  CB   GLU A 291       6.101  39.818  13.221  1.00  28.49
ATOM   2196  CG   GLU A 291       5.769  40.445  11.874  1.00  26.87
ATOM   2197  CD   GLU A 291       6.009  41.941  11.858  1.00  36.69
ATOM   2198  OE1  GLU A 291       7.008  42.378  11.254  1.00  43.24
ATOM   2199  OE2  GLU A 291       5.212  42.677  12.471  1.00  40.46
ATOM   2200  C    GLU A 291       6.910  37.609  12.314  1.00  26.09
ATOM   2201  O    GLU A 291       6.577  37.275  11.174  1.00  25.81
ATOM   2202  N    CYS A 292       8.123  37.346  12.792  1.00  27.35
ATOM   2203  CA   CYS A 292       9.115  36.718  11.917  1.00  27.95
ATOM   2204  CB   CYS A 292      10.448  36.520  12.615  1.00  29.85
ATOM   2205  SG   CYS A 292      11.241  38.119  12.768  1.00  41.05
ATOM   2206  C    CYS A 292       8.623  35.388  11.374  1.00  24.32
ATOM   2207  O    CYS A 292       8.866  35.043  10.217  1.00  21.58
ATOM   2208  N    GLN A 293       7.928  34.654  12.234  1.00  23.27
ATOM   2209  CA   GLN A 293       7.384  33.358  11.845  1.00  22.22
ATOM   2210  CB   GLN A 293       6.829  32.657  13.092  1.00  23.15
ATOM   2211  CG   GLN A 293       7.935  32.014  13.943  1.00  22.95
ATOM   2212  CD   GLN A 293       7.497  31.584  15.342  1.00  24.04
ATOM   2213  OE1  GLN A 293       6.342  31.765  15.721  1.00  21.47
ATOM   2214  NE2  GLN A 293       8.409  30.964  16.098  1.00  21.01
ATOM   2215  C    GLN A 293       6.316  33.548  10.766  1.00  21.55
ATOM   2216  O    GLN A 293       6.228  32.792   9.791  1.00  20.32
ATOM   2217  N    TYR A 294       5.506  34.586  10.920  1.00  21.97
ATOM   2218  CA   TYR A 294       4.537  34.924   9.888  1.00  21.49
ATOM   2219  CB   TYR A 294       3.670  36.091  10.352  1.00  23.10
ATOM   2220  CG   TYR A 294       2.400  36.319   9.556  1.00  21.89
ATOM   2221  CD1  TYR A 294       1.379  35.379   9.531  1.00  19.98
ATOM   2222  CE1  TYR A 294       0.185  35.606   8.862  1.00  22.15
ATOM   2223  CZ   TYR A 294       0.045  36.772   8.138  1.00  24.71
ATOM   2224  OH   TYR A 294      -1.116  36.991   7.445  1.00  25.08
ATOM   2225  CE2  TYR A 294       1.059  37.703   8.118  1.00  22.86
ATOM   2226  CD2  TYR A 294       2.222  37.489   8.827  1.00  23.52
ATOM   2227  C    TYR A 294       5.239  35.306   8.576  1.00  22.57
ATOM   2228  O    TYR A 294       4.786  34.933   7.491  1.00  20.32
ATOM   2229  N    VAL A 295       6.373  36.001   8.670  1.00  22.24
ATOM   2230  CA   VAL A 295       7.104  36.358   7.454  1.00  20.86
ATOM   2231  CB   VAL A 295       8.267  37.326   7.712  1.00  23.76
ATOM   2232  CG1  VAL A 295       9.018  37.568   6.381  1.00  23.08
ATOM   2233  CG2  VAL A 295       7.749  38.634   8.308  1.00  23.92
ATOM   2234  C    VAL A 295       7.640  35.093   6.790  1.00  19.44
ATOM   2235  O    VAL A 295       7.633  34.973   5.572  1.00  20.82
```

FIGURE 145

```
ATOM   2236  N   TYR A 296       8.078  34.149   7.611  1.00 21.43
ATOM   2237  CA  TYR A 296       8.763  32.971   7.121  1.00 19.39
ATOM   2238  CB  TYR A 296       9.281  32.156   8.298  1.00 19.80
ATOM   2239  CG  TYR A 296       9.911  30.860   7.902  1.00 18.43
ATOM   2240  CD1 TYR A 296      11.208  30.833   7.381  1.00 18.72
ATOM   2241  CE1 TYR A 296      11.823  29.631   7.077  1.00 22.90
ATOM   2242  CZ  TYR A 296      11.154  28.450   7.332  1.00 22.92
ATOM   2243  OH  TYR A 296      11.728  27.247   7.033  1.00 23.22
ATOM   2244  CE2 TYR A 296       9.873  28.447   7.854  1.00 21.43
ATOM   2245  CD2 TYR A 296       9.275  29.644   8.162  1.00 21.11
ATOM   2246  C   TYR A 296       7.771  32.136   6.320  1.00 18.46
ATOM   2247  O   TYR A 296       8.157  31.542   5.319  1.00 19.77
ATOM   2248  N   LEU A 297       6.509  32.096   6.767  1.00 19.80
ATOM   2249  CA  LEU A 297       5.478  31.346   6.056  1.00 17.52
ATOM   2250  CB  LEU A 297       4.148  31.412   6.825  1.00 19.78
ATOM   2251  CG  LEU A 297       4.110  30.542   8.092  1.00 16.59
ATOM   2252  CD1 LEU A 297       2.768  30.733   8.798  1.00 20.00
ATOM   2253  CD2 LEU A 297       4.304  29.063   7.757  1.00 18.37
ATOM   2254  C   LEU A 297       5.311  31.947   4.657  1.00 18.94
ATOM   2255  O   LEU A 297       5.174  31.247   3.654  1.00 19.58
ATOM   2256  N   HIS A 298       5.350  33.270   4.588  1.00 19.76
ATOM   2257  CA  HIS A 298       5.257  33.950   3.290  1.00 19.33
ATOM   2258  CB  HIS A 298       5.120  35.462   3.508  1.00 20.79
ATOM   2259  CG  HIS A 298       3.742  35.888   3.889  1.00 19.70
ATOM   2260  ND1 HIS A 298       3.242  35.727   5.165  1.00 20.71
ATOM   2261  CE1 HIS A 298       1.991  36.153   5.195  1.00 20.63
ATOM   2262  NE2 HIS A 298       1.672  36.608   3.998  1.00 23.44
ATOM   2263  CD2 HIS A 298       2.753  36.453   3.162  1.00 20.17
ATOM   2264  C   HIS A 298       6.475  33.665   2.410  1.00 18.63
ATOM   2265  O   HIS A 298       6.333  33.486   1.200  1.00 20.17
ATOM   2266  N   GLN A 299       7.667  33.627   2.990  1.00 21.31
ATOM   2267  CA  GLN A 299       8.868  33.309   2.226  1.00 20.83
ATOM   2268  CB  GLN A 299      10.128  33.492   3.082  1.00 22.50
ATOM   2269  CG  GLN A 299      10.312  34.954   3.499  1.00 25.27
ATOM   2270  CD  GLN A 299      11.423  35.135   4.525  1.00 28.26
ATOM   2271  OE1 GLN A 299      11.557  34.329   5.445  1.00 29.83
ATOM   2272  NE2 GLN A 299      12.188  36.219   4.403  1.00 26.71
ATOM   2273  C   GLN A 299       8.769  31.887   1.693  1.00 21.19
ATOM   2274  O   GLN A 299       9.147  31.646   0.552  1.00 20.84
ATOM   2275  N   CYS A 300       8.231  30.964   2.490  1.00 19.77
ATOM   2276  CA  CYS A 300       8.097  29.590   2.021  1.00 21.20
ATOM   2277  CB  CYS A 300       7.546  28.649   3.111  1.00 21.59
ATOM   2278  SG  CYS A 300       8.659  28.313   4.496  1.00 21.31
ATOM   2279  C   CYS A 300       7.227  29.549   0.778  1.00 18.38
ATOM   2280  O   CYS A 300       7.572  28.916  -0.213  1.00 19.58
ATOM   2281  N   VAL A 301       6.076  30.207   0.833  1.00 20.07
ATOM   2282  CA  VAL A 301       5.143  30.161  -0.279  1.00 19.34
ATOM   2283  CB  VAL A 301       3.831  30.847   0.087  1.00 19.69
ATOM   2284  CG1 VAL A 301       2.980  31.013  -1.147  1.00 19.02
ATOM   2285  CG2 VAL A 301       3.082  30.041   1.150  1.00 23.02
ATOM   2286  C   VAL A 301       5.730  30.824  -1.522  1.00 18.98
ATOM   2287  O   VAL A 301       5.634  30.294  -2.652  1.00 18.99
```

FIGURE 146

```
ATOM   2288  N    ARG A 302       6.361  31.968  -1.289  1.00 20.60
ATOM   2289  CA   ARG A 302       7.085  32.662  -2.365  1.00 22.52
ATOM   2290  CB   ARG A 302       7.807  33.876  -1.811  1.00 23.52
ATOM   2291  CG   ARG A 302       8.616  34.611  -2.872  1.00 24.32
ATOM   2292  CD   ARG A 302       9.710  35.455  -2.228  1.00 26.13
ATOM   2293  NE   ARG A 302      10.667  34.616  -1.520  1.00 31.05
ATOM   2294  CZ   ARG A 302      11.476  35.050  -0.558  1.00 36.30
ATOM   2295  NH1  ARG A 302      11.460  36.326  -0.192  1.00 37.18
ATOM   2296  NH2  ARG A 302      12.305  34.207   0.041  1.00 34.04
ATOM   2297  C    ARG A 302       8.087  31.777  -3.095  1.00 23.40
ATOM   2298  O    ARG A 302       8.103  31.755  -4.329  1.00 23.55
ATOM   2299  N    ASP A 303       8.903  31.055  -2.328  1.00 22.39
ATOM   2300  CA   ASP A 303       9.904  30.144  -2.863  1.00 22.73
ATOM   2301  CB   ASP A 303      10.892  29.686  -1.773  1.00 21.26
ATOM   2302  CG   ASP A 303      11.711  30.827  -1.192  1.00 28.53
ATOM   2303  OD1  ASP A 303      11.710  31.931  -1.789  1.00 27.62
ATOM   2304  OD2  ASP A 303      12.386  30.699  -0.137  1.00 26.66
ATOM   2305  C    ASP A 303       9.338  28.944  -3.632  1.00 20.36
ATOM   2306  O    ASP A 303       9.838  28.603  -4.712  1.00 21.25
ATOM   2307  N    VAL A 304       8.284  28.318  -3.106  1.00 20.24
ATOM   2308  CA   VAL A 304       7.656  27.200  -3.805  1.00 19.03
ATOM   2309  CB   VAL A 304       6.506  26.614  -2.948  1.00 21.99
ATOM   2310  CG1  VAL A 304       5.687  25.599  -3.724  1.00 21.81
ATOM   2311  CG2  VAL A 304       7.116  25.982  -1.713  1.00 22.11
ATOM   2312  C    VAL A 304       7.141  27.710  -5.149  1.00 19.92
ATOM   2313  O    VAL A 304       7.322  27.066  -6.197  1.00 21.24
ATOM   2314  N    LEU A 305       6.459  28.851  -5.112  1.00 18.22
ATOM   2315  CA   LEU A 305       5.836  29.364  -6.332  1.00 20.56
ATOM   2316  CB   LEU A 305       4.844  30.480  -6.012  1.00 17.57
ATOM   2317  CG   LEU A 305       3.557  30.008  -5.320  1.00 19.17
ATOM   2318  CD1  LEU A 305       2.712  31.253  -4.985  1.00 19.55
ATOM   2319  CD2  LEU A 305       2.691  28.974  -6.082  1.00 20.38
ATOM   2320  C    LEU A 305       6.824  29.794  -7.407  1.00 21.36
ATOM   2321  O    LEU A 305       6.574  29.576  -8.606  1.00 23.65
ATOM   2322  N    ARG A 306       7.947  30.358  -6.969  1.00 23.97
ATOM   2323  CA   ARG A 306       9.014  30.735  -7.913  1.00 23.57
ATOM   2324  CB   ARG A 306      10.171  31.436  -7.207  1.00 23.85
ATOM   2325  CG   ARG A 306       9.941  32.875  -6.733  1.00 26.18
ATOM   2326  CD   ARG A 306      11.158  33.484  -6.039  1.00 35.81
ATOM   2327  NE   ARG A 306      11.010  34.920  -5.779  1.00 36.91
ATOM   2328  CZ   ARG A 306      11.865  35.646  -5.060  1.00 37.77
ATOM   2329  NH1  ARG A 306      12.925  35.079  -4.500  1.00 36.45
ATOM   2330  NH2  ARG A 306      11.658  36.947  -4.882  1.00 37.40
ATOM   2331  C    ARG A 306       9.547  29.478  -8.604  1.00 25.69
ATOM   2332  O    ARG A 306       9.712  29.439  -9.834  1.00 23.35
ATOM   2333  N    ALA A 307       9.792  28.436  -7.811  1.00 23.29
ATOM   2334  CA   ALA A 307      10.314  27.185  -8.349  1.00 24.26
ATOM   2335  CB   ALA A 307      10.556  26.230  -7.205  1.00 24.03
ATOM   2336  C    ALA A 307       9.354  26.565  -9.344  1.00 22.10
ATOM   2337  O    ALA A 307       9.740  26.077 -10.410  1.00 22.72
ATOM   2338  N    ARG A 308       8.068  26.598  -9.008  1.00 20.80
ATOM   2339  CA   ARG A 308       7.092  25.915  -9.835  1.00 20.00
```

FIGURE 147

```
ATOM   2340  CB   ARG A 308       5.774  25.772  -9.075  1.00 21.72
ATOM   2341  CG   ARG A 308       5.870  24.610  -8.109  1.00 22.26
ATOM   2342  CD   ARG A 308       4.618  24.345  -7.299  1.00 19.97
ATOM   2343  NE   ARG A 308       4.902  23.149  -6.503  1.00 24.07
ATOM   2344  CZ   ARG A 308       4.025  22.542  -5.718  1.00 27.19
ATOM   2345  NH1  ARG A 308       2.791  23.003  -5.673  1.00 23.93
ATOM   2346  NH2  ARG A 308       4.377  21.464  -5.012  1.00 28.78
ATOM   2347  C    ARG A 308       6.876  26.662 -11.139  1.00 22.15
ATOM   2348  O    ARG A 308       6.699  26.030 -12.176  1.00 21.30
ATOM   2349  N    LYS A 309       6.953  27.992 -11.082  1.00 21.16
ATOM   2350  CA   LYS A 309       6.685  28.832 -12.253  1.00 22.32
ATOM   2351  CB   LYS A 309       6.801  30.333 -11.901  1.00 24.02
ATOM   2352  CG   LYS A 309       6.508  31.340 -13.040  1.00 29.43
ATOM   2353  CD   LYS A 309       6.215  32.737 -12.484  1.00 37.46
ATOM   2354  CE   LYS A 309       5.642  33.687 -13.538  1.00 44.02
ATOM   2355  NZ   LYS A 309       6.468  34.926 -13.712  1.00 43.80
ATOM   2356  C    LYS A 309       7.656  28.466 -13.367  1.00 22.56
ATOM   2357  O    LYS A 309       7.281  28.420 -14.539  1.00 23.42
ATOM   2358  N    LEU A 310       8.900  28.189 -12.999  1.00 22.00
ATOM   2359  CA   LEU A 310       9.906  27.866 -14.002  1.00 21.73
ATOM   2360  CB   LEU A 310      11.289  28.091 -13.409  1.00 21.13
ATOM   2361  CG   LEU A 310      11.536  29.517 -12.922  1.00 21.73
ATOM   2362  CD1  LEU A 310      12.995  29.640 -12.487  1.00 22.37
ATOM   2363  CD2  LEU A 310      11.167  30.510 -14.011  1.00 28.55
ATOM   2364  C    LEU A 310       9.830  26.446 -14.582  1.00 21.34
ATOM   2365  O    LEU A 310      10.478  26.145 -15.598  1.00 23.36
ATOM   2366  N    ARG A 311       9.067  25.580 -13.915  1.00 19.41
ATOM   2367  CA   ARG A 311       8.862  24.211 -14.373  1.00 19.13
ATOM   2368  CB   ARG A 311       9.162  23.298 -13.191  1.00 20.37
ATOM   2369  CG   ARG A 311      10.653  23.321 -12.863  1.00 21.47
ATOM   2370  CD   ARG A 311      11.008  22.805 -11.476  1.00 24.25
ATOM   2371  NE   ARG A 311      10.520  21.442 -11.254  1.00 23.85
ATOM   2372  CZ   ARG A 311      10.688  20.774 -10.127  1.00 22.32
ATOM   2373  NH1  ARG A 311      11.377  21.330  -9.126  1.00 25.69
ATOM   2374  NH2  ARG A 311      10.204  19.543  -9.993  1.00 18.91
ATOM   2375  C    ARG A 311       7.431  23.931 -14.838  1.00 21.21
ATOM   2376  O    ARG A 311       6.741  24.874 -15.241  1.00 25.92
ATOM   2377  O50  INH Z   1       4.605  33.376  23.736  1.00 26.83
ATOM   2378  C49  INH Z   1       4.231  34.382  24.326  1.00 26.06
ATOM   2379  O51  INH Z   1       2.962  34.991  23.967  1.00 27.49
ATOM   2380  C52  INH Z   1       1.903  34.307  23.285  1.00 26.93
ATOM   2381  C55  INH Z   1       0.784  35.332  23.198  1.00 23.29
ATOM   2382  C54  INH Z   1       2.396  33.902  21.890  1.00 27.36
ATOM   2383  C53  INH Z   1       1.427  33.119  24.127  1.00 26.28
ATOM   2384  N32  INH Z   1       4.935  34.973  25.294  1.00 24.59
ATOM   2385  C31  INH Z   1       6.210  34.438  25.733  1.00 26.22
ATOM   2386  C34  INH Z   1       6.924  35.626  26.369  1.00 30.49
ATOM   2387  C37  INH Z   1       7.645  36.501  25.365  1.00 33.76
ATOM   2388  C39  INH Z   1       7.034  37.645  24.864  1.00 38.94
ATOM   2389  C42  INH Z   1       7.713  38.450  23.950  1.00 41.70
ATOM   2390  C38  INH Z   1       9.011  38.126  23.555  1.00 44.11
ATOM   2391  O47  INH Z   1       9.671  38.890  22.679  1.00 44.40
```

FIGURE 148

```
ATOM   2392  C41  INH Z    1       9.626  36.988  24.070  1.00 42.62
ATOM   2393  C40  INH Z    1       8.945  36.181  24.978  1.00 40.44
ATOM   2394  C28  INH Z    1       5.891  33.469  26.827  1.00 26.18
ATOM   2395  O30  INH Z    1       4.821  33.476  27.419  1.00 28.17
ATOM   2396  N19  INH Z    1       6.822  32.576  27.106  1.00 25.35
ATOM   2397  C11  INH Z    1       6.586  31.591  28.149  1.00 22.00
ATOM   2398  C20  INH Z    1       7.939  31.279  28.733  1.00 28.32
ATOM   2399  N22  INH Z    1       8.016  31.042  30.046  1.00 29.86
ATOM   2400  C23  INH Z    1       9.185  30.716  30.864  1.00 32.68
ATOM   2401  O21  INH Z    1       8.902  31.256  27.987  1.00 30.70
ATOM   2402  C66  INH Z    1       5.982  30.345  27.471  1.00 23.98
ATOM   2403  C7   INH Z    1       6.449  29.951  26.074  1.00 24.27
ATOM   2404  C4   INH Z    1       5.750  30.388  24.950  1.00 22.11
ATOM   2405  C2   INH Z    1       6.147  30.039  23.651  1.00 23.96
ATOM   2406  C3   INH Z    1       7.564  29.129  25.869  1.00 22.36
ATOM   2407  C6   INH Z    1       7.945  28.794  24.569  1.00 19.47
ATOM   2408  C5   INH Z    1       7.273  29.237  23.440  1.00 24.64
ATOM   2409  N9   INH Z    1       7.676  28.877  22.190  1.00 20.59
ATOM   2410  S14  INH Z    1       7.262  27.472  21.482  1.00 19.91
ATOM   2411  O15  INH Z    1       7.837  26.333  22.230  1.00 20.79
ATOM   2412  O16  INH Z    1       7.744  27.509  20.095  1.00 20.74
ATOM   2413  O17  INH Z    1       5.777  27.520  21.588  1.00 19.08
ATOM   2414  O1   HOH W    1     -11.455  19.036  16.241  1.00 11.20
ATOM   2415  O1   HOH W    2      10.092  17.907  -7.247  1.00 15.97
ATOM   2416  O1   HOH W    3       6.980  17.279  36.265  1.00 18.93
ATOM   2417  O1   HOH W    4      12.344  25.665 -10.547  1.00 26.47
ATOM   2418  O1   HOH W    5      -0.391  18.120  30.610  1.00 15.54
ATOM   2419  O1   HOH W    6     -12.910  27.809  25.785  1.00 18.19
ATOM   2420  O1   HOH W    7      16.795  17.314  22.020  1.00 20.81
ATOM   2421  O1   HOH W    8      10.903  18.975  31.456  1.00 19.26
ATOM   2422  O1   HOH W    9      12.441  11.024  16.607  1.00 18.44
ATOM   2423  O1   HOH W   10      -5.476  27.892  24.187  1.00 18.18
ATOM   2424  O1   HOH W   11      -5.638  29.457 -12.183  1.00 22.91
ATOM   2425  O1   HOH W   12      -5.887  32.377  20.291  1.00 20.26
ATOM   2426  O1   HOH W   13      12.670   1.352  23.922  1.00 21.55
ATOM   2427  O1   HOH W   14      -2.209  18.671  -7.515  1.00 17.26
ATOM   2428  O1   HOH W   15      -7.454  18.582  28.843  1.00 18.21
ATOM   2429  O1   HOH W   16      -8.860  24.488  29.900  1.00 19.86
ATOM   2430  O1   HOH W   17      -2.830  35.618   3.268  1.00 21.86
ATOM   2431  O1   HOH W   18      18.579  15.179  13.609  1.00 26.92
ATOM   2432  O1   HOH W   19      -4.688  14.506  34.209  1.00 22.07
ATOM   2433  O1   HOH W   20       2.105  17.068  26.391  1.00 16.42
ATOM   2434  O1   HOH W   21       4.863  29.127  33.970  1.00 21.17
ATOM   2435  O1   HOH W   22      -3.568  19.852   7.077  1.00 22.18
ATOM   2436  O1   HOH W   23      -5.576   3.087  15.955  1.00 26.29
ATOM   2437  O1   HOH W   24     -12.917  17.205  18.619  1.00 22.65
ATOM   2438  O1   HOH W   25      18.698  13.470  17.368  1.00 27.43
ATOM   2439  O1   HOH W   26       1.962  17.321  29.108  1.00 20.96
ATOM   2440  O1   HOH W   27       2.295  24.954  29.144  1.00 19.64
ATOM   2441  O1   HOH W   28      -1.602  16.134  32.029  1.00 21.50
ATOM   2442  O1   HOH W   29      -0.729  38.734  15.728  1.00 29.29
ATOM   2443  O1   HOH W   30      -7.527  23.769  23.695  1.00 24.34
```

FIGURE 149

```
ATOM   2444  O1  HOH W  31     14.282  22.365  16.948  1.00 22.99
ATOM   2445  O1  HOH W  32     -1.604  32.781 -14.649  1.00 27.92
ATOM   2446  O1  HOH W  33     -8.734  34.148  26.134  1.00 25.36
ATOM   2447  O1  HOH W  34      8.370  30.039  18.987  1.00 21.01
ATOM   2448  O1  HOH W  35     14.794   1.864  27.548  1.00 28.16
ATOM   2449  O1  HOH W  36    -10.739  27.532  37.044  1.00 24.62
ATOM   2450  O1  HOH W  37     -7.059   1.474  21.471  1.00 25.62
ATOM   2451  O1  HOH W  38    -11.234  14.555  24.148  1.00 23.76
ATOM   2452  O1  HOH W  39      4.445  10.833  33.936  1.00 24.00
ATOM   2453  O1  HOH W  40      7.644  22.182  -5.700  1.00 31.73
ATOM   2454  O1  HOH W  41     -9.581  18.385  34.798  1.00 27.77
ATOM   2455  O1  HOH W  42     -3.762   2.958  27.993  1.00 25.67
ATOM   2456  O1  HOH W  43     16.682  28.017  20.896  1.00 27.72
ATOM   2457  O1  HOH W  44      1.889  20.014   3.611  1.00 25.02
ATOM   2458  O1  HOH W  45      1.627  25.550  -6.758  1.00 34.05
ATOM   2459  O1  HOH W  46      0.286   7.549   9.166  1.00 38.49
ATOM   2460  O1  HOH W  47     -3.896  24.915  37.139  1.00 26.95
ATOM   2461  O1  HOH W  48     15.746  30.134   2.550  1.00 25.69
ATOM   2462  O1  HOH W  49     -5.568  10.500  33.186  1.00 28.26
ATOM   2463  O1  HOH W  50     -1.650  34.023   1.496  1.00 26.31
ATOM   2464  O1  HOH W  51     -7.652  10.717  25.362  1.00 28.32
ATOM   2465  O1  HOH W  52      0.328   0.370  13.309  1.00 27.61
ATOM   2466  O1  HOH W  53     15.355   1.106  30.215  1.00 30.33
ATOM   2467  O1  HOH W  54     10.015  24.503  30.496  1.00 29.94
ATOM   2468  O1  HOH W  55    -11.943  35.367  17.617  1.00 28.12
ATOM   2469  O1  HOH W  56     -4.357  -4.311  17.098  1.00 30.10
ATOM   2470  O1  HOH W  57     -1.130  26.109  35.655  1.00 35.14
ATOM   2471  O1  HOH W  58      6.603  33.740  -5.667  1.00 34.26
ATOM   2472  O1  HOH W  59    -11.191  21.716  18.000  1.00 28.53
ATOM   2473  O1  HOH W  60      4.005  20.176  -0.974  1.00 28.49
ATOM   2474  O1  HOH W  61     15.234  25.407  33.117  1.00 33.69
ATOM   2475  O1  HOH W  62     16.720  13.787  18.961  1.00 30.06
ATOM   2476  O1  HOH W  63     17.985  26.085  10.889  1.00 35.47
ATOM   2477  O1  HOH W  64     -4.391  35.179  19.227  1.00 26.34
ATOM   2478  O1  HOH W  65    -10.126   3.407  31.678  1.00 37.24
ATOM   2479  O1  HOH W  66     13.041  23.718  -8.522  1.00 26.67
ATOM   2480  O1  HOH W  67     15.808  27.630   0.948  1.00 31.53
ATOM   2481  O1  HOH W  68     -5.194  14.828  38.851  1.00 32.15
ATOM   2482  O1  HOH W  69     -2.993  14.561  10.647  1.00 27.57
ATOM   2483  O1  HOH W  70      4.460  25.794 -13.772  1.00 29.85
ATOM   2484  O1  HOH W  71     -1.043  10.807  12.546  1.00 36.09
ATOM   2485  O1  HOH W  72      5.955  25.591 -17.688  1.00 35.00
ATOM   2486  O1  HOH W  73     -4.797  23.062   3.425  1.00 23.14
ATOM   2487  O1  HOH W  74     12.930  17.207  31.823  1.00 25.65
ATOM   2488  O1  HOH W  75     14.465  31.814   0.729  1.00 29.17
ATOM   2489  O1  HOH W  76     11.351   8.765  29.000  1.00 29.76
ATOM   2490  O1  HOH W  77     -3.463  15.346   8.038  1.00 33.01
ATOM   2491  O1  HOH W  78      9.188  38.767  15.085  1.00 31.31
ATOM   2492  O1  HOH W  79     -2.414   9.596  32.635  1.00 44.49
ATOM   2493  O1  HOH W  80     -4.993  26.536   9.601  1.00 32.37
ATOM   2494  O1  HOH W  81    -15.925  15.529  11.947  1.00 25.86
ATOM   2495  O1  HOH W  82    -12.382  18.790  35.935  1.00 34.44
```

FIGURE 150

```
ATOM   2496  O1   HOH W   83       2.705   48.628   10.273  1.00 40.15
ATOM   2497  O1   HOH W   84     -13.564   21.329   28.598  1.00 31.01
ATOM   2498  O1   HOH W   85       6.479   39.636   16.774  1.00 32.83
ATOM   2499  O1   HOH W   86      14.961    4.598   28.207  1.00 29.83
ATOM   2500  O1   HOH W   87      18.504   19.104   23.863  1.00 28.45
ATOM   2501  O1   HOH W   88      10.773   20.142   -0.695  1.00 35.21
ATOM   2502  O1   HOH W   89       3.708   16.397    0.920  1.00 38.22
ATOM   2503  O1   HOH W   90      -4.973   37.993   -5.374  1.00 31.06
ATOM   2504  O1   HOH W   91      22.103   24.540   26.314  1.00 35.14
ATOM   2505  O1   HOH W   92      10.864   34.785   14.518  1.00 48.98
ATOM   2506  O1   HOH W   93     -12.541   12.084   30.086  1.00 37.23
ATOM   2507  O1   HOH W   94      13.549   -1.341   30.361  1.00 38.12
ATOM   2508  O1   HOH W   95      -3.286   -3.603   24.358  1.00 30.37
ATOM   2509  O1   HOH W   96      -0.950   37.575    3.392  1.00 26.13
ATOM   2510  O1   HOH W   97       2.862   18.800    1.412  1.00 26.47
ATOM   2511  O1   HOH W   98       2.741    4.340   11.947  1.00 42.25
ATOM   2512  O1   HOH W   99       1.437   11.596   33.660  1.00 33.67
ATOM   2513  O1   HOH W  100      -4.898   17.123    5.233  1.00 30.59
ATOM   2514  O1   HOH W  101      -0.328   39.659   22.285  1.00 37.92
ATOM   2515  O1   HOH W  102       0.457   18.578   -0.352  1.00 32.32
ATOM   2516  O1   HOH W  103      15.238   15.465   29.462  1.00 35.78
ATOM   2517  O1   HOH W  104      12.139   22.090   -0.159  1.00 34.03
ATOM   2518  O1   HOH W  105     -14.864   19.163   30.964  1.00 32.43
ATOM   2519  O1   HOH W  106     -14.505   20.555   25.186  1.00 29.82
ATOM   2520  O1   HOH W  107       3.363   34.814   -7.718  1.00 34.48
ATOM   2521  O1   HOH W  108     -13.197   17.085   34.279  1.00 38.85
ATOM   2522  O1   HOH W  109      -1.443    5.382   31.117  1.00 38.54
ATOM   2523  O1   HOH W  110      -0.120   14.286   35.601  1.00 31.88
ATOM   2524  O1   HOH W  111       9.032   -5.844   19.709  1.00 36.70
ATOM   2525  O1   HOH W  112      11.379   24.876   -1.986  1.00 43.81
ATOM   2526  O1   HOH W  113      12.352   38.057    2.063  1.00 31.64
ATOM   2527  O1   HOH W  114      -5.579    7.024    7.334  1.00 39.14
ATOM   2528  O1   HOH W  115      -6.985   29.910   -0.433  1.00 41.07
ATOM   2529  O1   HOH W  116       5.045   33.328   -8.532  1.00 37.73
ATOM   2530  O1   HOH W  117       8.662   12.116    1.108  1.00 39.77
ATOM   2531  O1   HOH W  118      -6.293    5.912   32.542  1.00 30.14
ATOM   2532  O1   HOH W  119     -13.725   11.954   27.110  1.00 39.76
ATOM   2533  O1   HOH W  120      16.415    8.189   22.223  1.00 29.43
ATOM   2534  O1   HOH W  121     -12.645   19.481   23.348  1.00 31.08
ATOM   2535  O1   HOH W  122     -13.636   39.606    9.864  1.00 39.73
ATOM   2536  O1   HOH W  123     -11.065    7.560   40.828  1.00 45.73
ATOM   2537  O1   HOH W  124      -8.777    3.390   20.560  1.00 36.17
ATOM   2538  O1   HOH W  125       3.379   22.820   -2.032  1.00 27.89
ATOM   2539  O1   HOH W  126     -11.598   14.866   35.138  1.00 32.20
ATOM   2540  O1   HOH W  127      -0.940   19.672   39.788  1.00 33.34
ATOM   2541  O1   HOH W  128      15.163   -4.713   22.940  1.00 36.19
ATOM   2542  O1   HOH W  129      -0.987   26.949   -6.156  1.00 36.12
ATOM   2543  O1   HOH W  130      10.863   12.854    1.718  1.00 34.61
ATOM   2544  O1   HOH W  131      14.478   36.267    1.695  1.00 41.25
ATOM   2545  O1   HOH W  132      15.776   23.818   18.687  1.00 35.61
ATOM   2546  O1   HOH W  133      21.161    7.231   12.795  1.00 32.15
ATOM   2547  O1   HOH W  134      22.887   22.904   29.299  1.00 36.68
```

FIGURE 151

```
ATOM   2548  O1   HOH W 135      3.909  17.363  36.196  1.00 35.35
ATOM   2549  O1   HOH W 136    -12.046  11.064  22.456  1.00 35.04
ATOM   2550  O1   HOH W 137    -12.824  27.211  19.118  1.00 38.04
ATOM   2551  O1   HOH W 138     14.969  31.915   7.579  1.00 35.09
ATOM   2552  O1   HOH W 139     13.443  32.417  -3.827  1.00 44.74
ATOM   2553  O1   HOH W 140      2.776  12.732  37.520  1.00 41.66
ATOM   2554  O1   HOH W 141     -1.350  12.666  37.266  1.00 40.38
ATOM   2555  O1   HOH W 142      3.324   6.477  10.524  1.00 37.22
ATOM   2556  O1   HOH W 143    -16.166  29.270  31.100  1.00 36.51
ATOM   2557  O1   HOH W 144     16.001  -2.359  30.645  1.00 44.06
ATOM   2558  O1   HOH W 145      2.861  45.550  14.180  1.00 45.63
ATOM   2559  O1   HOH W 146      4.593  25.045  35.681  1.00 44.05
ATOM   2560  O1   HOH W 147     -5.762   3.453  30.636  1.00 34.95
ATOM   2561  O1   HOH W 148     -8.031  24.355  12.086  1.00 35.62
ATOM   2562  O1   HOH W 149     -6.652  22.984  -0.071  1.00 31.34
ATOM   2563  O1   HOH W 150     -9.852  26.486  11.576  1.00 53.30
ATOM   2564  O1   HOH W 151    -11.032  13.045  39.495  1.00 41.67
ATOM   2565  O1   HOH W 152     -5.662  -6.734  17.860  1.00 50.02
ATOM   2566  O1   HOH W 153    -14.654  10.777  19.722  1.00 39.18
ATOM   2567  O1   HOH W 154     11.452  35.739   9.234  1.00 31.71
ATOM   2568  O1   HOH W 155     -0.977   7.991  -0.542  1.00 45.59
ATOM   2569  O1   HOH W 156     11.447  44.304   4.341  1.00 42.42
ATOM   2570  O1   HOH W 157     20.425  25.089  10.825  1.00 38.33
ATOM   2571  O1   HOH W 158     -0.478  42.056  23.691  1.00 40.14
ATOM   2572  O1   HOH W 159    -13.365  36.694   5.529  1.00 49.14
ATOM   2573  O1   HOH W 160     15.601  29.777  23.845  1.00 36.82
ATOM   2574  O1   HOH W 161     10.807  30.311  34.040  1.00 40.96
ATOM   2575  O1   HOH W 162     -4.239  12.123  10.131  1.00 32.53
ATOM   2576  O1   HOH W 163    -15.155  30.501  26.593  1.00 34.26
ATOM   2577  O1   HOH W 164     17.868  18.293   5.518  1.00 38.35
ATOM   2578  O1   HOH W 165     -3.791   2.469  10.886  1.00 39.48
ATOM   2579  O1   HOH W 166    -13.791  14.215  31.432  1.00 38.00
ATOM   2580  O1   HOH W 167      0.432  17.497  39.137  1.00 42.73
ATOM   2581  O1   HOH W 168    -17.968  15.461  15.749  1.00 41.59
ATOM   2582  O1   HOH W 169      3.057  38.735  -8.809  1.00 36.15
ATOM   2583  O1   HOH W 170    -13.284  32.522  19.061  1.00 43.72
ATOM   2584  O1   HOH W 171      9.161  39.858  11.511  1.00 61.20
ATOM   2585  O1   HOH W 172     -8.076  25.214   1.277  1.00 34.46
ATOM   2586  O1   HOH W 173      2.413  -7.723  17.535  1.00 50.89
ATOM   2587  O1   HOH W 174      7.967  38.224  -3.285  1.00 35.96
ATOM   2588  O1   HOH W 175     10.930  20.638  33.730  1.00 35.38
ATOM   2589  O1   HOH W 176      4.602   2.675  11.036  1.00 36.17
ATOM   2590  O1   HOH W 177      4.229  47.562   3.051  1.00 39.90
ATOM   2591  O1   HOH W 178     15.151  17.822  29.427  1.00 40.53
ATOM   2592  O1   HOH W 179     -1.974  45.545   5.497  1.00 42.30
ATOM   2593  O1   HOH W 180    -11.790   5.702  19.435  1.00 46.01
ATOM   2594  O1   HOH W 181     -3.116  46.090  12.430  1.00 36.56
ATOM   2595  O1   HOH W 182     -2.855  17.252  -3.365  1.00 46.55
ATOM   2596  O1   HOH W 183     16.937  14.782  22.299  1.00 45.85
ATOM   2597  O1   HOH W 184     15.864  28.547  32.612  1.00 52.60
ATOM   2598  O1   HOH W 185    -12.223  41.151  11.021  1.00 46.56
ATOM   2599  O1   HOH W 186     -3.669  35.551 -11.268  1.00 45.80
```

FIGURE 152

```
ATOM   2600  O1   HOH W 187    -13.450   16.205   23.864  1.00 39.99
ATOM   2601  O1   HOH W 188     21.557    8.538    9.074  1.00 32.39
ATOM   2602  O1   HOH W 189      1.733   29.325  -10.520  1.00 44.58
ATOM   2603  O1   HOH W 190     -1.094   24.213   42.979  1.00 44.98
ATOM   2604  O1   HOH W 191     -6.827    4.971    4.805  1.00 47.90
ATOM   2605  O1   HOH W 192    -13.991   33.731   13.221  1.00 40.59
ATOM   2606  O1   HOH W 193     13.588   13.644   -1.450  1.00 40.18
ATOM   2607  O1   HOH W 194     -5.326   32.039   -9.354  1.00 38.33
ATOM   2608  O1   HOH W 195     13.465   33.762  -13.581  1.00 39.35
ATOM   2609  O1   HOH W 196     20.141   -1.476   26.767  1.00 58.47
ATOM   2610  O1   HOH W 197    -13.105   19.480   20.652  1.00 48.59
ATOM   2611  O1   HOH W 198      7.070    7.353   33.532  1.00 49.27
ATOM   2612  O1   HOH W 199      6.799   28.923  -16.944  1.00 51.04
ATOM   2613  O1   HOH W 200      0.389    6.026   29.372  1.00 35.03
ATOM   2614  O1   HOH W 201      8.386   25.655   32.893  1.00 37.20
ATOM   2615  O1   HOH W 202     17.615   -0.073   29.521  1.00 48.46
ATOM   2616  O1   HOH W 203     -6.124   28.880    4.959  1.00 35.61
ATOM   2617  O1   HOH W 204     13.941    6.496   29.759  1.00 53.62
ATOM   2618  O1   HOH W 205     16.954   -0.234   14.375  1.00 37.68
ATOM   2619  O1   HOH W 206      2.522   -7.489   20.961  1.00 44.59
ATOM   2620  O1   HOH W 207      5.703   49.354   10.543  1.00 44.22
ATOM   2621  O1   HOH W 208     -9.111   38.567   12.389  1.00 50.27
ATOM   2622  O1   HOH W 209     -7.236   20.258    6.492  1.00 35.19
ATOM   2623  O1   HOH W 210      8.786    5.463   31.949  1.00 35.74
ATOM   2624  O1   HOH W 211     -7.222   40.672   16.386  1.00 42.49
ATOM   2625  O1   HOH W 212     12.825   34.503    7.617  1.00 38.94
ATOM   2626  O1   HOH W 213      5.590   30.888   31.645  1.00 26.09
ATOM   2627  O1   HOH W 214      9.169   32.503   25.209  1.00 41.71
ATOM   2628  O1   HOH W 215     23.574   26.554   10.071  1.00 56.57
ATOM   2629  O1   HOH W 216     10.056   38.516   -1.760  1.00 38.36
ATOM   2630  O1   HOH W 217     -5.653   23.538   10.071  1.00 39.02
ATOM   2631  O1   HOH W 218     -9.772   39.888   16.597  1.00 39.89
ATOM   2632  O1   HOH W 219     -7.677   22.937    7.244  1.00 48.50
ATOM   2633  O1   HOH W 220     -8.099   10.871   39.914  1.00 44.93
ATOM   2634  O1   HOH W 221      9.902   31.834   22.653  1.00 46.40
ATOM   2635  O1   HOH W 222      3.536   38.208   17.936  1.00 39.89
ATOM   2636  O1   HOH W 223      5.427   12.563   -2.175  1.00 43.37
ATOM   2637  O1   HOH W 224     19.901   17.833    4.495  1.00 39.94
ATOM   2638  O1   HOH W 225    -12.027   36.815   13.817  1.00 44.07
ATOM   2639  O1   HOH W 226     -8.746   32.585   28.696  1.00 48.46
ATOM   2640  O1   HOH W 227     17.914   15.042   24.333  1.00 48.17
ATOM   2641  O1   HOH W 228    -15.428   28.994   22.176  1.00 32.12
ATOM   2642  O1   HOH W 229     -1.184   15.555   39.910  1.00 42.24
ATOM   2643  O1   HOH W 230      1.784   16.997    9.532  1.00 38.28
ATOM   2644  O1   HOH W 231     -4.431    5.259   30.630  1.00 57.46
ATOM   2645  O1   HOH W 232     14.418   34.885   17.296  1.00 49.40
ATOM   2646  O1   HOH W 233    -10.428   31.639    7.906  1.00 38.03
ATOM   2647  O1   HOH W 234     21.073    3.624   22.298  1.00 46.76
ATOM   2648  O1   HOH W 235      9.325   20.879   -6.720  1.00 46.19
ATOM   2649  O1   HOH W 236     10.266   24.192  -17.765  1.00 43.43
ATOM   2650  O1   HOH W 237      2.085   -3.234   15.986  1.00 49.75
ATOM   2651  O1   HOH W 238     -0.063    5.328   10.360  1.00 52.94
```

FIGURE 153

```
ATOM   2652  O1  HOH W 239      10.028  22.924  33.652  1.00 45.99
ATOM   2653  O1  HOH W 240      16.681  32.926  16.387  1.00 43.29
ATOM   2654  O1  HOH W 241       7.871  13.034  37.758  1.00 46.97
ATOM   2655  O1  HOH W 242      -7.500  33.136 -10.047  1.00 53.39
ATOM   2656  O1  HOH W 243      20.580  20.554   3.052  1.00 48.18
ATOM   2657  O1  HOH W 244      17.540  25.077   8.214  1.00 43.50
ATOM   2658  O1  HOH W 245      -5.445  39.439  24.106  1.00 43.55
ATOM   2659  O1  HOH W 246      10.166  40.681  14.159  1.00 41.16
ATOM   2660  O1  HOH W 247      19.127  23.993   6.155  1.00 40.29
ATOM   2661  O1  HOH W 248      -5.962  35.247 -11.325  1.00 64.60
ATOM   2662  O1  HOH W 249     -13.021  14.668   4.628  1.00 58.02
ATOM   2663  O1  HOH W 250     -15.666  12.941  32.852  1.00 45.95
ATOM   2664  O1  HOH W 251      -5.827   4.361  28.098  1.00 39.00
ATOM   2665  O1  HOH W 252      -4.508   4.229   4.028  1.00 58.76
ATOM   2666  O1  HOH W 253      -1.679  36.793 -11.023  1.00 54.88
ATOM   2667  O1  HOH W 254      -3.188  12.850  35.709  1.00 44.15
ATOM   2668  O1  HOH W 255      -4.863  46.499   9.267  1.00 47.64
ATOM   2669  O1  HOH W 256      -8.876  14.076  39.968  1.00 49.77
ATOM   2670  O1  HOH W 257      -7.413  15.403  42.092  1.00 56.43
ATOM   2671  O1  HOH W 258      15.526  32.542  13.982  1.00 38.82
ATOM   2672  O1  HOH W 259      16.627  29.755  30.106  1.00 59.92
ATOM   2673  O1  HOH W 260      -6.350  21.495  10.220  1.00 44.14
ATOM   2674  O1  HOH W 261     -10.475  11.052  40.121  1.00 46.63
ATOM   2675  O1  HOH W 262     -16.169  28.237  33.252  1.00 50.35
ATOM   2676  O1  HOH W 263      21.143  26.244   7.273  1.00 49.50
ATOM   2677  O1  HOH W 264      18.544   3.658  19.522  1.00 54.96
ATOM   2678  O1  HOH W 265     -13.057  36.485  10.921  1.00 57.92
ATOM   2679  O1  HOH W 266     -14.213  30.872   7.965  1.00 55.62
ATOM   2680  O1  HOH W 267      23.105  19.120   9.667  1.00 51.70
ATOM   2681  O1  HOH W 268      19.557  23.525  21.545  1.00 55.10
ATOM   2682  O1  HOH W 269      -6.887   8.335  40.062  1.00 53.82
ATOM   2683  O1  HOH W 270      12.547  34.227  22.521  1.00 60.24
ATOM   2684  O1  HOH W 271      -3.101  -0.406  15.411  1.00 43.16
ATOM   2685  O1  HOH W 272       2.686  50.220   2.020  1.00 56.09
ATOM   2686  O1  HOH W 273     -14.257  29.391  17.420  1.00 56.26
ATOM   2687  O1  HOH W 274      -7.269  25.617  22.970  1.00 58.39
ATOM   2688  O1  HOH W 275      -2.828   0.486   9.670  1.00 60.53
ATOM   2689  O1  HOH W 276       9.879  32.192 -10.785  1.00 50.33
ATOM   2690  O1  HOH W 277     -13.291  27.301  37.675  1.00 47.65
ATOM   2691  O1  HOH W 278       9.031  40.412  -7.375  1.00 59.24
ATOM   2692  O1  HOH W 279      21.333  22.702   9.534  1.00 50.34
ATOM   2693  O1  HOH W 280      10.062   2.181  11.069  1.00 63.85
ATOM   2694  O1  HOH W 281     -11.670  11.608  25.465  1.00 48.90
ATOM   2695  O1  HOH W 282       5.882  36.123  22.042  1.00 58.95
ATOM   2696  O1  HOH W 283      -4.121   5.854  34.338  1.00 54.24
ATOM   2697  O1  HOH W 284      -9.020   5.421  40.050  1.00 56.11
END
```

FIGURE 154

```
CRYST1   39.250   71.126  119.912  90.00  90.00  90.00
ATOM      1  N    LYS A  19     -12.134  41.491  10.114  1.000  47.16
ATOM      2  CA   LYS A  19     -12.088  40.464   9.085  1.000  46.31
ATOM      3  CB   LYS A  19     -11.200  40.822   7.902  1.000  46.34
ATOM      4  CG   LYS A  19      -9.707  40.790   8.149  1.000  42.97
ATOM      5  CD   LYS A  19      -8.945  40.965   6.847  1.000  43.94
ATOM      6  CE   LYS A  19      -7.609  41.670   7.059  1.000  39.13
ATOM      7  NZ   LYS A  19      -6.732  41.562   5.856  1.000  48.25
ATOM      8  C    LYS A  19     -11.602  39.144   9.702  1.000  47.15
ATOM      9  O    LYS A  19     -10.921  39.174  10.723  1.000  50.63
ATOM     10  N    THR A  20     -11.999  38.090   9.024  1.000  38.61
ATOM     11  CA   THR A  20     -11.875  36.698   9.401  1.000  42.80
ATOM     12  CB   THR A  20     -13.310  36.133   9.502  1.000  46.49
ATOM     13  OG1  THR A  20     -13.660  36.080  10.896  1.000  54.76
ATOM     14  CG2  THR A  20     -13.393  34.742   8.933  1.000  40.58
ATOM     15  C    THR A  20     -11.069  35.879   8.414  1.000  38.96
ATOM     16  O    THR A  20     -10.606  34.774   8.695  1.000  26.83
ATOM     17  N    SER A  21     -10.899  36.432   7.211  1.000  27.43
ATOM     18  CA   SER A  21     -10.213  35.731   6.137  1.000  21.10
ATOM     19  CB   SER A  21     -11.193  34.767   5.449  1.000  34.39
ATOM     20  OG   SER A  21     -10.929  34.678   4.055  1.000  44.20
ATOM     21  C    SER A  21      -9.647  36.730   5.144  1.000  25.82
ATOM     22  O    SER A  21     -10.151  37.858   5.158  1.000  39.09
ATOM     23  N    CYS A  22      -8.669  36.373   4.325  1.000  26.63
ATOM     24  CA   CYS A  22      -8.080  37.358   3.404  1.000  29.32
ATOM     25  CB   CYS A  22      -7.041  38.266   4.056  1.000  29.54
ATOM     26  SG   CYS A  22      -6.599  39.770   3.116  1.000  40.23
ATOM     27  C    CYS A  22      -7.445  36.575   2.264  1.000  28.58
ATOM     28  O    CYS A  22      -6.219  36.546   2.161  1.000  36.15
ATOM     29  N    PRO A  23      -8.315  35.942   1.482  1.000  31.23
ATOM     30  CA   PRO A  23      -7.853  35.032   0.450  1.000  28.72
ATOM     31  CB   PRO A  23      -9.120  34.324  -0.025  1.000  32.50
ATOM     32  CG   PRO A  23     -10.228  35.253   0.317  1.000  32.13
ATOM     33  CD   PRO A  23      -9.784  36.062   1.490  1.000  33.79
ATOM     34  C    PRO A  23      -7.229  35.869  -0.664  1.000  27.64
ATOM     35  O    PRO A  23      -7.703  36.980  -0.890  1.000  28.84
ATOM     36  N    ILE A  24      -6.205  35.309  -1.275  1.000  25.07
ATOM     37  CA   ILE A  24      -5.480  35.988  -2.347  1.000  26.87
ATOM     38  CB   ILE A  24      -4.118  36.521  -1.880  1.000  23.03
ATOM     39  CG1  ILE A  24      -4.194  37.387  -0.616  1.000  32.69
ATOM     40  CD1  ILE A  24      -4.803  38.749  -0.870  1.000  36.67
ATOM     41  CG2  ILE A  24      -3.411  37.301  -2.982  1.000  35.11
ATOM     42  C    ILE A  24      -5.297  35.003  -3.489  1.000  23.25
ATOM     43  O    ILE A  24      -4.816  33.891  -3.288  1.000  28.71
ATOM     44  N    LYS A  25      -5.703  35.414  -4.692  1.000  28.16
ATOM     45  CA   LYS A  25      -5.530  34.603  -5.877  1.000  28.40
ATOM     46  CB   LYS A  25      -6.067  35.296  -7.130  1.000  34.65
ATOM     47  CG   LYS A  25      -7.546  35.653  -7.058  1.000  38.17
ATOM     48  CD   LYS A  25      -7.944  36.538  -8.227  1.000  48.55
ATOM     49  CE   LYS A  25      -9.420  36.915  -8.158  1.000  55.62
ATOM     50  NZ   LYS A  25      -9.640  38.251  -7.532  1.000  59.24
ATOM     51  C    LYS A  25      -4.034  34.363  -6.051  1.000  26.23
```

FIGURE 155

```
ATOM    52  O   LYS A  25      -3.283  35.312  -5.797 1.000 35.63
ATOM    53  N   ILE A  26      -3.655  33.153  -6.449 1.000 26.51
ATOM    54  CA  ILE A  26      -2.202  32.943  -6.476 1.000 39.40
ATOM    55  CB  ILE A  26      -1.848  31.483  -6.769 1.000 41.92
ATOM    56  CG1 ILE A  26      -2.538  30.872  -7.986 1.000 55.69
ATOM    57  CD1 ILE A  26      -1.953  29.527  -8.398 1.000 43.15
ATOM    58  CG2 ILE A  26      -2.092  30.645  -5.505 1.000 30.44
ATOM    59  C   ILE A  26      -1.545  33.891  -7.468 1.000 49.89
ATOM    60  O   ILE A  26      -0.403  34.315  -7.258 1.000 61.92
ATOM    61  N   ASN A  27      -2.257  34.261  -8.535 1.000 47.63
ATOM    62  CA  ASN A  27      -1.622  35.182  -9.489 1.000 48.85
ATOM    63  CB  ASN A  27      -2.409  35.259 -10.789 1.000 58.29
ATOM    64  CG  ASN A  27      -3.867  35.634 -10.702 1.000 64.78
ATOM    65  OD1 ASN A  27      -4.735  34.952 -11.257 1.000 66.47
ATOM    66  ND2 ASN A  27      -4.181  36.732 -10.026 1.000 76.39
ATOM    67  C   ASN A  27      -1.419  36.560  -8.875 1.000 42.84
ATOM    68  O   ASN A  27      -0.555  37.314  -9.323 1.000 45.62
ATOM    69  N   GLN A  28      -2.197  36.926  -7.856 1.000 38.86
ATOM    70  CA  GLN A  28      -1.986  38.188  -7.174 1.000 39.38
ATOM    71  CB  GLN A  28      -3.330  38.731  -6.666 1.000 44.68
ATOM    72  CG  GLN A  28      -3.622  40.150  -7.123 1.000 69.70
ATOM    73  CD  GLN A  28      -3.103  40.420  -8.526 1.000 86.93
ATOM    74  OE1 GLN A  28      -3.225  39.566  -9.412 1.000117.05
ATOM    75  NE2 GLN A  28      -2.527  41.600  -8.735 1.000 74.84
ATOM    76  C   GLN A  28      -1.024  38.107  -5.992 1.000 38.67
ATOM    77  O   GLN A  28      -0.763  39.173  -5.416 1.000 27.96
ATOM    78  N   PHE A  29      -0.525  36.933  -5.609 1.000 36.04
ATOM    79  CA  PHE A  29       0.171  36.807  -4.326 1.000 34.34
ATOM    80  CB  PHE A  29       0.531  35.339  -3.998 1.000 30.22
ATOM    81  CG  PHE A  29       0.922  35.274  -2.520 1.000 26.86
ATOM    82  CD1 PHE A  29      -0.074  35.297  -1.554 1.000 29.29
ATOM    83  CE1 PHE A  29       0.225  35.248  -0.203 1.000 28.67
ATOM    84  CZ  PHE A  29       1.560  35.208   0.168 1.000 38.22
ATOM    85  CE2 PHE A  29       2.567  35.166  -0.786 1.000 38.42
ATOM    86  CD2 PHE A  29       2.249  35.197  -2.134 1.000 32.07
ATOM    87  C   PHE A  29       1.448  37.636  -4.193 1.000 33.30
ATOM    88  O   PHE A  29       1.580  38.350  -3.187 1.000 34.15
ATOM    89  N   GLU A  30       2.352  37.531  -5.149 1.000 41.14
ATOM    90  CA  GLU A  30       3.603  38.271  -5.221 1.000 38.75
ATOM    91  CB  GLU A  30       4.200  38.126  -6.629 1.000 41.90
ATOM    92  CG  GLU A  30       5.619  38.657  -6.739 1.000 50.56
ATOM    93  CD  GLU A  30       6.619  37.768  -6.022 1.000 60.13
ATOM    94  OE1 GLU A  30       6.912  36.658  -6.515 1.000 51.89
ATOM    95  OE2 GLU A  30       7.109  38.196  -4.954 1.000 80.65
ATOM    96  C   GLU A  30       3.456  39.755  -4.931 1.000 38.26
ATOM    97  O   GLU A  30       4.217  40.361  -4.169 1.000 39.06
ATOM    98  N   GLY A  31       2.463  40.378  -5.572 1.000 33.74
ATOM    99  CA  GLY A  31       2.321  41.815  -5.409 1.000 29.48
ATOM   100  C   GLY A  31       1.552  42.106  -4.143 1.000 35.24
ATOM   101  O   GLY A  31       1.757  43.141  -3.521 1.000 37.25
ATOM   102  N   HIS A  32       0.678  41.149  -3.786 1.000 36.89
ATOM   103  CA  HIS A  32       0.025  41.293  -2.488 1.000 33.45
```

FIGURE 156

```
ATOM    104  CB   HIS A   32      -0.863  40.102  -2.149  1.000  30.08
ATOM    105  CG   HIS A   32      -1.356  40.057  -0.738  1.000  25.45
ATOM    106  ND1  HIS A   32      -2.309  40.907  -0.234  1.000  36.70
ATOM    107  CE1  HIS A   32      -2.555  40.630   1.038  1.000  39.89
ATOM    108  NE2  HIS A   32      -1.786  39.603   1.379  1.000  36.80
ATOM    109  CD2  HIS A   32      -1.032  39.232   0.292  1.000  26.97
ATOM    110  C    HIS A   32       1.101  41.431  -1.410  1.000  35.73
ATOM    111  O    HIS A   32       1.007  42.277  -0.516  1.000  32.27
ATOM    112  N    PHE A   33       2.090  40.543  -1.556  1.000  34.68
ATOM    113  CA   PHE A   33       3.120  40.431  -0.515  1.000  32.48
ATOM    114  CB   PHE A   33       3.828  39.071  -0.591  1.000  36.84
ATOM    115  CG   PHE A   33       4.751  38.835   0.595  1.000  37.98
ATOM    116  CD1  PHE A   33       4.471  39.433   1.812  1.000  40.95
ATOM    117  CE1  PHE A   33       5.308  39.272   2.895  1.000  43.07
ATOM    118  CZ   PHE A   33       6.440  38.479   2.754  1.000  34.64
ATOM    119  CE2  PHE A   33       6.724  37.866   1.554  1.000  26.60
ATOM    120  CD2  PHE A   33       5.875  38.039   0.472  1.000  32.44
ATOM    121  C    PHE A   33       4.050  41.630  -0.607  1.000  36.33
ATOM    122  O    PHE A   33       4.526  42.116   0.428  1.000  41.59
ATOM    123  N    MET A   34       4.284  42.170  -1.802  1.000  45.92
ATOM    124  CA   MET A   34       5.094  43.397  -1.876  1.000  40.90
ATOM    125  CB   MET A   34       5.460  43.656  -3.336  1.000  48.61
ATOM    126  CG   MET A   34       6.895  43.260  -3.662  1.000  40.86
ATOM    127  SD   MET A   34       6.983  41.845  -4.774  1.000  86.63
ATOM    128  CE   MET A   34       8.572  41.170  -4.254  1.000  72.85
ATOM    129  C    MET A   34       4.383  44.588  -1.259  1.000  42.23
ATOM    130  O    MET A   34       4.968  45.443  -0.568  1.000  50.41
ATOM    131  N    LYS A   35       3.065  44.686  -1.458  1.000  34.55
ATOM    132  CA   LYS A   35       2.351  45.788  -0.795  1.000  45.08
ATOM    133  CB   LYS A   35       0.889  45.809  -1.279  1.000  48.74
ATOM    134  CG   LYS A   35       0.793  46.296  -2.720  1.000  51.47
ATOM    135  CD   LYS A   35      -0.509  45.889  -3.382  1.000  56.83
ATOM    136  CE   LYS A   35      -0.788  46.795  -4.577  1.000  55.04
ATOM    137  NZ   LYS A   35      -0.993  46.020  -5.830  1.000  61.49
ATOM    138  C    LYS A   35       2.417  45.703   0.717  1.000  38.13
ATOM    139  O    LYS A   35       2.575  46.713   1.419  1.000  38.53
ATOM    140  N    LEU A   36       2.293  44.483   1.267  1.000  37.05
ATOM    141  CA   LEU A   36       2.281  44.337   2.720  1.000  33.35
ATOM    142  CB   LEU A   36       1.904  42.922   3.179  1.000  29.64
ATOM    143  CG   LEU A   36       0.453  42.474   3.024  1.000  30.10
ATOM    144  CD1  LEU A   36       0.259  41.052   3.567  1.000  35.30
ATOM    145  CD2  LEU A   36      -0.516  43.409   3.723  1.000  31.56
ATOM    146  C    LEU A   36       3.641  44.718   3.311  1.000  26.53
ATOM    147  O    LEU A   36       3.664  45.268   4.415  1.000  45.90
ATOM    148  N    GLN A   37       4.713  44.426   2.591  1.000  30.34
ATOM    149  CA   GLN A   37       6.073  44.682   3.038  1.000  46.11
ATOM    150  CB   GLN A   37       7.038  43.727   2.321  1.000  45.16
ATOM    151  CG   GLN A   37       7.047  42.323   2.925  1.000  46.46
ATOM    152  CD   GLN A   37       7.963  41.397   2.146  1.000  41.79
ATOM    153  OE1  GLN A   37       8.895  40.818   2.701  1.000  53.12
ATOM    154  NE2  GLN A   37       7.682  41.253   0.854  1.000  59.23
ATOM    155  C    GLN A   37       6.554  46.116   2.816  1.000  58.12
```

FIGURE 157

```
ATOM    156  O    GLN A  37       7.585  46.535   3.366 1.000 44.71
ATOM    157  N    ALA A  38       5.820  46.878   2.014 1.000 51.00
ATOM    158  CA   ALA A  38       6.214  48.252   1.734 1.000 51.95
ATOM    159  CB   ALA A  38       5.334  48.856   0.638 1.000 33.90
ATOM    160  C    ALA A  38       6.155  49.144   2.971 1.000 53.47
ATOM    161  O    ALA A  38       5.408  48.911   3.916 1.000 39.54
ATOM    162  N    ASP A  39       6.967  50.198   2.923 1.000 54.79
ATOM    163  CA   ASP A  39       7.037  51.192   3.990 1.000 41.76
ATOM    164  CB   ASP A  39       5.738  51.973   4.114 1.000 38.24
ATOM    165  CG   ASP A  39       5.127  52.287   2.757 1.000 53.89
ATOM    166  OD1  ASP A  39       4.001  52.837   2.732 1.000 61.68
ATOM    167  OD2  ASP A  39       5.750  52.000   1.707 1.000 55.37
ATOM    168  C    ASP A  39       7.401  50.477   5.289 1.000 41.78
ATOM    169  O    ASP A  39       6.886  50.753   6.369 1.000 42.20
ATOM    170  N    SER A  40       8.339  49.547   5.104 1.000 41.63
ATOM    171  CA   SER A  40       8.819  48.736   6.213 1.000 39.11
ATOM    172  CB   SER A  40       9.331  49.627   7.344 1.000 45.54
ATOM    173  OG   SER A  40      10.507  50.325   6.967 1.000 63.33
ATOM    174  C    SER A  40       7.701  47.838   6.726 1.000 33.78
ATOM    175  O    SER A  40       7.500  47.791   7.939 1.000 44.33
ATOM    176  N    ASN A  41       6.979  47.158   5.831 1.000 36.63
ATOM    177  CA   ASN A  41       5.911  46.290   6.314 1.000 46.11
ATOM    178  CB   ASN A  41       6.386  45.245   7.332 1.000 39.56
ATOM    179  CG   ASN A  41       7.336  44.240   6.734 1.000 39.34
ATOM    180  OD1  ASN A  41       7.679  43.246   7.379 1.000 66.37
ATOM    181  ND2  ASN A  41       7.760  44.503   5.505 1.000 47.43
ATOM    182  C    ASN A  41       4.833  47.097   7.034 1.000 52.00
ATOM    183  O    ASN A  41       4.484  46.727   8.159 1.000 45.88
ATOM    184  N    TYR A  42       4.366  48.150   6.376 1.000 47.78
ATOM    185  CA   TYR A  42       3.394  49.022   7.014 1.000 48.64
ATOM    186  CB   TYR A  42       3.181  50.305   6.197 1.000 50.57
ATOM    187  CG   TYR A  42       2.110  51.181   6.818 1.000 60.30
ATOM    188  CD1  TYR A  42       2.315  51.798   8.049 1.000 73.71
ATOM    189  CE1  TYR A  42       1.345  52.597   8.619 1.000 79.76
ATOM    190  CZ   TYR A  42       0.148  52.779   7.947 1.000 83.87
ATOM    191  OH   TYR A  42      -0.829  53.570   8.494 1.000 96.86
ATOM    192  CE2  TYR A  42      -0.084  52.176   6.728 1.000 77.87
ATOM    193  CD2  TYR A  42       0.899  51.382   6.173 1.000 69.62
ATOM    194  C    TYR A  42       2.080  48.272   7.202 1.000 40.91
ATOM    195  O    TYR A  42       1.518  48.233   8.297 1.000 38.94
ATOM    196  N    LEU A  43       1.628  47.688   6.094 1.000 39.86
ATOM    197  CA   LEU A  43       0.324  47.037   6.065 1.000 38.25
ATOM    198  CB   LEU A  43      -0.240  46.976   4.648 1.000 34.42
ATOM    199  CG   LEU A  43      -0.625  48.329   4.021 1.000 39.05
ATOM    200  CD1  LEU A  43      -0.840  48.146   2.529 1.000 35.82
ATOM    201  CD2  LEU A  43      -1.869  48.904   4.671 1.000 38.28
ATOM    202  C    LEU A  43       0.401  45.628   6.658 1.000 40.26
ATOM    203  O    LEU A  43      -0.571  45.204   7.288 1.000 41.80
ATOM    204  N    LEU A  44       1.531  44.954   6.473 1.000 40.52
ATOM    205  CA   LEU A  44       1.755  43.658   7.118 1.000 40.17
ATOM    206  CB   LEU A  44       3.181  43.148   6.903 1.000 40.11
ATOM    207  CG   LEU A  44       3.410  41.689   7.327 1.000 39.64
```

FIGURE 158

| | | | | | | | | | |
|---|---|---|---|---|---|---|---|---|---|
| ATOM | 208 | CD1 | LEU | A | 44 | 4.236 | 40.957 | 6.288 | 1.000 46.27 |
| ATOM | 209 | CD2 | LEU | A | 44 | 4.073 | 41.640 | 8.693 | 1.000 36.71 |
| ATOM | 210 | C | LEU | A | 44 | 1.490 | 43.724 | 8.616 | 1.000 40.53 |
| ATOM | 211 | O | LEU | A | 44 | 0.821 | 42.859 | 9.180 | 1.000 35.07 |
| ATOM | 212 | N | SER | A | 45 | 2.019 | 44.759 | 9.269 | 1.000 33.52 |
| ATOM | 213 | CA | SER | A | 45 | 1.856 | 44.909 | 10.710 | 1.000 33.03 |
| ATOM | 214 | CB | SER | A | 45 | 2.871 | 45.946 | 11.228 | 1.000 29.94 |
| ATOM | 215 | OG | SER | A | 45 | 4.137 | 45.710 | 10.612 | 1.000 33.78 |
| ATOM | 216 | C | SER | A | 45 | 0.433 | 45.275 | 11.087 | 1.000 36.97 |
| ATOM | 217 | O | SER | A | 45 | -0.131 | 44.758 | 12.058 | 1.000 34.42 |
| ATOM | 218 | N | LYS | A | 46 | -0.211 | 46.176 | 10.345 | 1.000 34.85 |
| ATOM | 219 | CA | LYS | A | 46 | -1.630 | 46.418 | 10.604 | 1.000 31.36 |
| ATOM | 220 | CB | LYS | A | 46 | -2.199 | 47.461 | 9.636 | 1.000 36.80 |
| ATOM | 221 | CG | LYS | A | 46 | -1.400 | 48.758 | 9.630 | 1.000 46.16 |
| ATOM | 222 | CD | LYS | A | 46 | -2.286 | 49.966 | 9.884 | 1.000 50.59 |
| ATOM | 223 | CE | LYS | A | 46 | -1.915 | 50.631 | 11.197 | 1.000 58.31 |
| ATOM | 224 | NZ | LYS | A | 46 | -0.513 | 51.127 | 11.179 | 1.000 66.09 |
| ATOM | 225 | C | LYS | A | 46 | -2.425 | 45.116 | 10.503 | 1.000 31.41 |
| ATOM | 226 | O | LYS | A | 46 | -3.340 | 44.917 | 11.304 | 1.000 42.72 |
| ATOM | 227 | N | GLU | A | 47 | -2.082 | 44.251 | 9.555 | 1.000 27.42 |
| ATOM | 228 | CA | GLU | A | 47 | -2.810 | 43.006 | 9.332 | 1.000 33.85 |
| ATOM | 229 | CB | GLU | A | 47 | -2.437 | 42.314 | 8.018 | 1.000 35.99 |
| ATOM | 230 | CG | GLU | A | 47 | -3.311 | 41.079 | 7.802 | 1.000 36.26 |
| ATOM | 231 | CD | GLU | A | 47 | -3.301 | 40.603 | 6.369 | 1.000 33.51 |
| ATOM | 232 | OE1 | GLU | A | 47 | -4.136 | 41.068 | 5.559 | 1.000 34.52 |
| ATOM | 233 | OE2 | GLU | A | 47 | -2.433 | 39.753 | 6.076 | 1.000 31.53 |
| ATOM | 234 | C | GLU | A | 47 | -2.560 | 41.985 | 10.443 | 1.000 30.28 |
| ATOM | 235 | O | GLU | A | 47 | -3.506 | 41.345 | 10.901 | 1.000 37.61 |
| ATOM | 236 | N | TYR | A | 48 | -1.298 | 41.883 | 10.836 | 1.000 30.47 |
| ATOM | 237 | CA | TYR | A | 48 | -0.931 | 41.057 | 11.983 | 1.000 29.64 |
| ATOM | 238 | CB | TYR | A | 48 | 0.590 | 41.107 | 12.208 | 1.000 34.11 |
| ATOM | 239 | CG | TYR | A | 48 | 1.016 | 40.197 | 13.336 | 1.000 31.94 |
| ATOM | 240 | CD1 | TYR | A | 48 | 0.866 | 38.821 | 13.183 | 1.000 33.96 |
| ATOM | 241 | CE1 | TYR | A | 48 | 1.231 | 37.938 | 14.175 | 1.000 32.68 |
| ATOM | 242 | CZ | TYR | A | 48 | 1.754 | 38.404 | 15.360 | 1.000 35.81 |
| ATOM | 243 | OH | TYR | A | 48 | 2.101 | 37.491 | 16.330 | 1.000 39.47 |
| ATOM | 244 | CE2 | TYR | A | 48 | 1.911 | 39.760 | 15.548 | 1.000 38.83 |
| ATOM | 245 | CD2 | TYR | A | 48 | 1.542 | 40.648 | 14.540 | 1.000 36.26 |
| ATOM | 246 | C | TYR | A | 48 | -1.712 | 41.530 | 13.202 | 1.000 39.70 |
| ATOM | 247 | O | TYR | A | 48 | -2.201 | 40.748 | 14.015 | 1.000 34.67 |
| ATOM | 248 | N | GLU | A | 49 | -1.839 | 42.852 | 13.334 | 1.000 34.55 |
| ATOM | 249 | CA | GLU | A | 49 | -2.480 | 43.503 | 14.469 | 1.000 26.84 |
| ATOM | 250 | CB | GLU | A | 49 | -2.226 | 45.029 | 14.435 | 1.000 31.26 |
| ATOM | 251 | CG | GLU | A | 49 | -0.796 | 45.295 | 14.919 | 1.000 41.28 |
| ATOM | 252 | CD | GLU | A | 49 | -0.707 | 44.824 | 16.368 | 1.000 46.36 |
| ATOM | 253 | OE1 | GLU | A | 49 | 0.167 | 44.004 | 16.694 | 1.000 49.76 |
| ATOM | 254 | OE2 | GLU | A | 49 | -1.540 | 45.294 | 17.171 | 1.000 64.46 |
| ATOM | 255 | C | GLU | A | 49 | -3.968 | 43.243 | 14.489 | 1.000 17.64 |
| ATOM | 256 | O | GLU | A | 49 | -4.611 | 43.212 | 15.530 | 1.000 31.99 |
| ATOM | 257 | N | GLU | A | 50 | -4.527 | 43.054 | 13.298 | 1.000 24.66 |
| ATOM | 258 | CA | GLU | A | 50 | -5.942 | 42.729 | 13.220 | 1.000 33.35 |
| ATOM | 259 | CB | GLU | A | 50 | -6.441 | 42.674 | 11.768 | 1.000 34.57 |

FIGURE 159

```
ATOM    260  CG  GLU A  50      -6.190  43.933  10.956  1.000  42.22
ATOM    261  CD  GLU A  50      -7.128  43.945   9.750  1.000  52.34
ATOM    262  OE1 GLU A  50      -8.357  43.957   9.988  1.000  46.50
ATOM    263  OE2 GLU A  50      -6.639  43.930   8.604  1.000  70.90
ATOM    264  C   GLU A  50      -6.238  41.369  13.861  1.000  25.23
ATOM    265  O   GLU A  50      -7.375  41.121  14.248  1.000  30.99
ATOM    266  N   LEU A  51      -5.239  40.508  13.957  1.000  26.01
ATOM    267  CA  LEU A  51      -5.447  39.194  14.580  1.000  21.27
ATOM    268  CB  LEU A  51      -4.470  38.237  13.898  1.000  22.16
ATOM    269  CG  LEU A  51      -4.752  38.015  12.411  1.000  26.33
ATOM    270  CD1 LEU A  51      -3.531  37.428  11.721  1.000  24.42
ATOM    271  CD2 LEU A  51      -5.938  37.091  12.208  1.000  28.60
ATOM    272  C   LEU A  51      -5.186  39.188  16.068  1.000  28.00
ATOM    273  O   LEU A  51      -5.315  38.171  16.742  1.000  26.46
ATOM    274  N   LYS A  52      -4.767  40.325  16.620  1.000  26.04
ATOM    275  CA  LYS A  52      -4.297  40.372  18.002  1.000  27.42
ATOM    276  CB  LYS A  52      -3.950  41.832  18.319  1.000  30.97
ATOM    277  CG  LYS A  52      -3.602  42.133  19.765  1.000  36.67
ATOM    278  CD  LYS A  52      -2.878  43.478  19.823  1.000  47.93
ATOM    279  CE  LYS A  52      -3.089  44.186  21.148  1.000  54.43
ATOM    280  NZ  LYS A  52      -3.831  45.481  20.963  1.000  76.91
ATOM    281  C   LYS A  52      -5.281  39.803  19.009  1.000  30.56
ATOM    282  O   LYS A  52      -4.866  38.997  19.848  1.000  31.78
ATOM    283  N   ASP A  53      -6.560  40.166  18.951  1.000  22.00
ATOM    284  CA  ASP A  53      -7.502  39.716  19.960  1.000  27.33
ATOM    285  CB  ASP A  53      -8.442  40.858  20.385  1.000  30.10
ATOM    286  CG  ASP A  53      -7.622  42.098  20.721  1.000  47.01
ATOM    287  OD1 ASP A  53      -6.798  42.004  21.657  1.000  67.96
ATOM    288  OD2 ASP A  53      -7.810  43.119  20.027  1.000  65.18
ATOM    289  C   ASP A  53      -8.370  38.541  19.536  1.000  25.20
ATOM    290  O   ASP A  53      -9.268  38.189  20.304  1.000  25.98
ATOM    291  N   VAL A  54      -8.123  37.957  18.372  1.000  23.81
ATOM    292  CA  VAL A  54      -8.897  36.770  17.995  1.000  20.94
ATOM    293  CB  VAL A  54      -8.477  36.258  16.616  1.000  22.31
ATOM    294  CG1 VAL A  54      -9.232  34.978  16.241  1.000  29.30
ATOM    295  CG2 VAL A  54      -8.710  37.323  15.543  1.000  21.16
ATOM    296  C   VAL A  54      -8.722  35.657  19.047  1.000  22.79
ATOM    297  O   VAL A  54      -7.595  35.307  19.395  1.000  24.33
ATOM    298  N   GLY A  55      -9.835  35.135  19.514  1.000  19.38
ATOM    299  CA  GLY A  55     -10.013  34.105  20.496  1.000  21.67
ATOM    300  C   GLY A  55      -9.849  34.607  21.923  1.000  26.11
ATOM    301  O   GLY A  55     -10.150  33.822  22.828  1.000  24.18
ATOM    302  N   ARG A  56      -9.400  35.842  22.115  1.000  28.14
ATOM    303  CA  ARG A  56      -8.976  36.366  23.416  1.000  31.63
ATOM    304  CB  ARG A  56      -8.162  37.661  23.262  1.000  32.19
ATOM    305  CG  ARG A  56      -6.762  37.493  22.699  1.000  31.76
ATOM    306  CD  ARG A  56      -5.957  36.532  23.528  1.000  29.57
ATOM    307  NE  ARG A  56      -4.544  36.431  23.220  1.000  30.87
ATOM    308  CZ  ARG A  56      -3.526  37.074  23.757  1.000  30.34
ATOM    309  NH1 ARG A  56      -3.681  37.983  24.710  1.000  22.02
ATOM    310  NH2 ARG A  56      -2.280  36.828  23.339  1.000  31.11
ATOM    311  C   ARG A  56     -10.110  36.645  24.386  1.000  27.29
```

FIGURE 160

```
ATOM    312  O    ARG A  56      -9.904  37.126  25.512  1.000  30.11
ATOM    313  N    ASN A  57     -11.352  36.365  24.023  1.000  19.89
ATOM    314  CA   ASN A  57     -12.429  36.544  24.990  1.000  21.90
ATOM    315  CB   ASN A  57     -13.713  36.926  24.246  1.000  27.73
ATOM    316  CG   ASN A  57     -14.041  35.852  23.214  1.000  36.94
ATOM    317  OD1  ASN A  57     -13.158  35.389  22.486  1.000  42.61
ATOM    318  ND2  ASN A  57     -15.303  35.449  23.148  1.000  39.27
ATOM    319  C    ASN A  57     -12.594  35.274  25.807  1.000  27.58
ATOM    320  O    ASN A  57     -13.336  35.218  26.785  1.000  32.05
ATOM    321  N    GLN A  58     -11.917  34.193  25.434  1.000  25.93
ATOM    322  CA   GLN A  58     -12.213  32.925  26.103  1.000  23.11
ATOM    323  CB   GLN A  58     -11.975  31.773  25.109  1.000  24.51
ATOM    324  CG   GLN A  58     -12.758  31.911  23.809  1.000  19.93
ATOM    325  CD   GLN A  58     -12.245  30.977  22.712  1.000  21.00
ATOM    326  OE1  GLN A  58     -11.224  31.206  22.055  1.000  21.51
ATOM    327  NE2  GLN A  58     -12.953  29.879  22.484  1.000  21.23
ATOM    328  C    GLN A  58     -11.396  32.695  27.366  1.000  23.30
ATOM    329  O    GLN A  58     -10.242  33.132  27.462  1.000  24.27
ATOM    330  N    SER A  59     -11.981  31.996  28.335  1.000  19.68
ATOM    331  CA   SER A  59     -11.377  31.719  29.620  1.000  20.00
ATOM    332  CB   SER A  59     -12.481  31.570  30.673  1.000  29.01
ATOM    333  OG   SER A  59     -13.222  30.375  30.394  1.000  51.65
ATOM    334  C    SER A  59     -10.565  30.423  29.617  1.000  32.69
ATOM    335  O    SER A  59     -10.792  29.571  28.754  1.000  24.40
ATOM    336  N    CYS A  60      -9.682  30.285  30.596  1.000  21.63
ATOM    337  CA   CYS A  60      -8.872  29.128  30.861  1.000  19.92
ATOM    338  CB   CYS A  60      -7.392  29.346  30.568  1.000  20.33
ATOM    339  SG   CYS A  60      -7.068  30.023  28.934  1.000  23.64
ATOM    340  C    CYS A  60      -8.980  28.736  32.344  1.000  21.45
ATOM    341  O    CYS A  60      -7.941  28.497  32.959  1.000  20.03
ATOM    342  N    ASP A  61     -10.220  28.697  32.804  1.000  22.24
ATOM    343  CA   ASP A  61     -10.439  28.455  34.236  1.000  22.76
ATOM    344  CB   ASP A  61     -11.912  28.676  34.545  1.000  26.65
ATOM    345  CG   ASP A  61     -12.408  30.099  34.398  1.000  27.80
ATOM    346  OD1  ASP A  61     -11.617  31.062  34.345  1.000  25.45
ATOM    347  OD2  ASP A  61     -13.650  30.248  34.356  1.000  28.50
ATOM    348  C    ASP A  61      -9.962  27.065  34.629  1.000  27.73
ATOM    349  O    ASP A  61      -9.345  26.878  35.690  1.000  25.51
ATOM    350  N    ILE A  62     -10.221  26.052  33.792  1.000  24.65
ATOM    351  CA   ILE A  62      -9.809  24.698  34.223  1.000  21.14
ATOM    352  CB   ILE A  62     -10.325  23.659  33.214  1.000  21.34
ATOM    353  CG1  ILE A  62     -11.838  23.755  33.010  1.000  22.01
ATOM    354  CD1  ILE A  62     -12.609  23.524  34.306  1.000  33.06
ATOM    355  CG2  ILE A  62      -9.903  22.258  33.624  1.000  31.17
ATOM    356  C    ILE A  62      -8.309  24.617  34.399  1.000  22.92
ATOM    357  O    ILE A  62      -7.792  24.134  35.422  1.000  26.58
ATOM    358  N    ALA A  63      -7.566  25.123  33.412  1.000  19.57
ATOM    359  CA   ALA A  63      -6.122  25.164  33.470  1.000  19.70
ATOM    360  CB   ALA A  63      -5.549  25.916  32.285  1.000  22.66
ATOM    361  C    ALA A  63      -5.604  25.864  34.733  1.000  27.00
ATOM    362  O    ALA A  63      -4.516  25.553  35.212  1.000  21.30
ATOM    363  N    LEU A  64      -6.404  26.799  35.235  1.000  23.07
```

FIGURE 161

```
ATOM    364  CA   LEU A  64      -6.027  27.582  36.400  1.000  24.35
ATOM    365  CB   LEU A  64      -6.749  28.929  36.297  1.000  23.45
ATOM    366  CG   LEU A  64      -6.102  29.880  35.306  1.000  23.45
ATOM    367  CD1  LEU A  64      -6.952  31.144  35.230  1.000  26.55
ATOM    368  CD2  LEU A  64      -4.677  30.179  35.723  1.000  24.94
ATOM    369  C    LEU A  64      -6.381  26.919  37.713  1.000  31.23
ATOM    370  O    LEU A  64      -6.097  27.521  38.750  1.000  30.60
ATOM    371  N    LEU A  65      -6.982  25.733  37.690  1.000  25.47
ATOM    372  CA   LEU A  65      -7.306  25.047  38.937  1.000  27.75
ATOM    373  CB   LEU A  65      -8.162  23.817  38.624  1.000  29.69
ATOM    374  CG   LEU A  65      -9.587  24.168  38.169  1.000  29.27
ATOM    375  CD1  LEU A  65     -10.317  22.915  37.710  1.000  22.91
ATOM    376  CD2  LEU A  65     -10.326  24.875  39.294  1.000  45.21
ATOM    377  C    LEU A  65      -6.045  24.666  39.697  1.000  32.88
ATOM    378  O    LEU A  65      -5.049  24.217  39.140  1.000  35.70
ATOM    379  N    PRO A  66      -6.075  24.876  41.014  1.000  36.18
ATOM    380  CA   PRO A  66      -4.904  24.635  41.858  1.000  36.18
ATOM    381  CB   PRO A  66      -5.488  24.754  43.275  1.000  47.92
ATOM    382  CG   PRO A  66      -6.648  25.684  43.117  1.000  42.33
ATOM    383  CD   PRO A  66      -7.235  25.378  41.764  1.000  30.77
ATOM    384  C    PRO A  66      -4.302  23.248  41.658  1.000  26.18
ATOM    385  O    PRO A  66      -3.084  23.122  41.569  1.000  37.38
ATOM    386  N    GLU A  67      -5.151  22.242  41.580  1.000  33.07
ATOM    387  CA   GLU A  67      -4.828  20.867  41.244  1.000  38.66
ATOM    388  CB   GLU A  67      -6.138  20.071  41.150  1.000  40.47
ATOM    389  CG   GLU A  67      -7.142  20.605  40.154  1.000  58.25
ATOM    390  CD   GLU A  67      -8.530  20.002  40.228  1.000  70.71
ATOM    391  OE1  GLU A  67      -8.874  19.134  39.390  1.000  47.20
ATOM    392  OE2  GLU A  67      -9.311  20.406  41.123  1.000  81.59
ATOM    393  C    GLU A  67      -4.033  20.762  39.946  1.000  40.21
ATOM    394  O    GLU A  67      -3.232  19.837  39.768  1.000  33.36
ATOM    395  N    ASN A  68      -4.202  21.695  39.001  1.000  27.60
ATOM    396  CA   ASN A  68      -3.494  21.553  37.729  1.000  27.03
ATOM    397  CB   ASN A  68      -4.471  21.891  36.584  1.000  25.75
ATOM    398  CG   ASN A  68      -5.638  20.924  36.530  1.000  27.63
ATOM    399  OD1  ASN A  68      -5.417  19.725  36.763  1.000  27.03
ATOM    400  ND2  ASN A  68      -6.837  21.424  36.223  1.000  20.87
ATOM    401  C    ASN A  68      -2.244  22.400  37.582  1.000  29.26
ATOM    402  O    ASN A  68      -1.561  22.322  36.543  1.000  32.09
ATOM    403  N    ARG A  69      -1.877  23.230  38.550  1.000  39.29
ATOM    404  CA   ARG A  69      -0.765  24.169  38.333  1.000  36.83
ATOM    405  CB   ARG A  69      -0.581  25.036  39.587  1.000  41.69
ATOM    406  CG   ARG A  69       0.072  26.376  39.290  1.000  44.04
ATOM    407  CD   ARG A  69      -0.117  27.331  40.461  1.000  60.35
ATOM    408  NE   ARG A  69      -1.481  27.376  40.972  1.000  61.46
ATOM    409  CZ   ARG A  69      -1.832  27.284  42.248  1.000  67.83
ATOM    410  NH1  ARG A  69      -3.113  27.336  42.599  1.000  61.15
ATOM    411  NH2  ARG A  69      -0.920  27.136  43.202  1.000  84.01
ATOM    412  C    ARG A  69       0.541  23.491  37.948  1.000  31.02
ATOM    413  O    ARG A  69       1.225  23.924  37.009  1.000  34.71
ATOM    414  N    GLY A  70       0.895  22.385  38.603  1.000  27.71
ATOM    415  CA   GLY A  70       2.103  21.679  38.203  1.000  25.00
```

FIGURE 162

| | | | | | | | | | |
|---|---|---|---|---|---|---|---|---|---|
| ATOM | 416 | C | GLY | A | 70 | 2.044 | 21.041 | 36.822 | 1.000 24.89 |
| ATOM | 417 | O | GLY | A | 70 | 3.083 | 20.564 | 36.376 | 1.000 31.72 |
| ATOM | 418 | N | LYS | A | 71 | 0.903 | 21.014 | 36.147 | 1.000 27.08 |
| ATOM | 419 | CA | LYS | A | 71 | 0.763 | 20.318 | 34.866 | 1.000 24.21 |
| ATOM | 420 | CB | LYS | A | 71 | -0.653 | 19.731 | 34.781 | 1.000 21.70 |
| ATOM | 421 | CG | LYS | A | 71 | -0.943 | 18.621 | 35.788 | 1.000 25.95 |
| ATOM | 422 | CD | LYS | A | 71 | -2.404 | 18.202 | 35.750 | 1.000 27.35 |
| ATOM | 423 | CE | LYS | A | 71 | -2.743 | 17.164 | 36.834 | 1.000 26.32 |
| ATOM | 424 | NZ | LYS | A | 71 | -4.227 | 17.045 | 36.994 | 1.000 29.99 |
| ATOM | 425 | C | LYS | A | 71 | 1.003 | 21.230 | 33.678 | 1.000 26.31 |
| ATOM | 426 | O | LYS | A | 71 | 0.999 | 20.826 | 32.508 | 1.000 21.01 |
| ATOM | 427 | N | ASN | A | 72 | 1.209 | 22.517 | 33.974 | 1.000 24.08 |
| ATOM | 428 | CA | ASN | A | 72 | 1.520 | 23.503 | 32.951 | 1.000 24.06 |
| ATOM | 429 | CB | ASN | A | 72 | 0.700 | 24.782 | 33.236 | 1.000 23.98 |
| ATOM | 430 | CG | ASN | A | 72 | -0.782 | 24.508 | 33.170 | 1.000 24.00 |
| ATOM | 431 | OD1 | ASN | A | 72 | -1.229 | 23.905 | 32.180 | 1.000 27.29 |
| ATOM | 432 | ND2 | ASN | A | 72 | -1.564 | 24.932 | 34.139 | 1.000 21.52 |
| ATOM | 433 | C | ASN | A | 72 | 2.999 | 23.855 | 32.902 | 1.000 24.14 |
| ATOM | 434 | O | ASN | A | 72 | 3.539 | 24.242 | 33.952 | 1.000 32.17 |
| ATOM | 435 | N | ARG | A | 73 | 3.669 | 23.767 | 31.763 | 1.000 18.37 |
| ATOM | 436 | CA | ARG | A | 73 | 5.068 | 24.153 | 31.624 | 1.000 20.26 |
| ATOM | 437 | CB | ARG | A | 73 | 5.606 | 23.824 | 30.236 | 1.000 27.07 |
| ATOM | 438 | CG | ARG | A | 73 | 7.082 | 24.137 | 30.020 | 1.000 24.27 |
| ATOM | 439 | CD | ARG | A | 73 | 7.645 | 23.603 | 28.712 | 1.000 22.01 |
| ATOM | 440 | NE | ARG | A | 73 | 7.794 | 22.144 | 28.739 | 1.000 23.84 |
| ATOM | 441 | CZ | ARG | A | 73 | 8.809 | 21.516 | 29.321 | 1.000 33.27 |
| ATOM | 442 | NH1 | ARG | A | 73 | 9.757 | 22.240 | 29.913 | 1.000 21.92 |
| ATOM | 443 | NH2 | ARG | A | 73 | 8.909 | 20.191 | 29.335 | 1.000 23.01 |
| ATOM | 444 | C | ARG | A | 73 | 5.231 | 25.648 | 31.916 | 1.000 30.65 |
| ATOM | 445 | O | ARG | A | 73 | 6.184 | 26.110 | 32.549 | 1.000 32.85 |
| ATOM | 446 | N | TYR | A | 74 | 4.279 | 26.440 | 31.452 | 1.000 27.96 |
| ATOM | 447 | CA | TYR | A | 74 | 4.329 | 27.903 | 31.619 | 1.000 22.72 |
| ATOM | 448 | CB | TYR | A | 74 | 4.778 | 28.577 | 30.343 | 1.000 24.68 |
| ATOM | 449 | CG | TYR | A | 74 | 6.008 | 28.085 | 29.620 | 1.000 40.81 |
| ATOM | 450 | CD1 | TYR | A | 74 | 7.302 | 28.339 | 30.080 | 1.000 42.06 |
| ATOM | 451 | CE1 | TYR | A | 74 | 8.424 | 27.881 | 29.404 | 1.000 30.31 |
| ATOM | 452 | CZ | TYR | A | 74 | 8.304 | 27.155 | 28.238 | 1.000 36.98 |
| ATOM | 453 | OH | TYR | A | 74 | 9.426 | 26.707 | 27.567 | 1.000 31.11 |
| ATOM | 454 | CE2 | TYR | A | 74 | 7.038 | 26.881 | 27.739 | 1.000 33.48 |
| ATOM | 455 | CD2 | TYR | A | 74 | 5.932 | 27.349 | 28.434 | 1.000 32.64 |
| ATOM | 456 | C | TYR | A | 74 | 2.932 | 28.320 | 32.074 | 1.000 35.24 |
| ATOM | 457 | O | TYR | A | 74 | 1.980 | 28.127 | 31.311 | 1.000 28.99 |
| ATOM | 458 | N | ASN | A | 75 | 2.831 | 28.838 | 33.293 | 1.000 34.47 |
| ATOM | 459 | CA | ASN | A | 75 | 1.587 | 29.142 | 33.973 | 1.000 26.33 |
| ATOM | 460 | CB | ASN | A | 75 | 1.844 | 29.654 | 35.396 | 1.000 28.02 |
| ATOM | 461 | CG | ASN | A | 75 | 2.541 | 28.595 | 36.230 | 1.000 47.27 |
| ATOM | 462 | OD1 | ASN | A | 75 | 2.639 | 27.427 | 35.838 | 1.000 38.13 |
| ATOM | 463 | ND2 | ASN | A | 75 | 3.009 | 29.045 | 37.388 | 1.000 58.84 |
| ATOM | 464 | C | ASN | A | 75 | 0.752 | 30.193 | 33.247 | 1.000 19.13 |
| ATOM | 465 | O | ASN | A | 75 | -0.423 | 30.394 | 33.561 | 1.000 27.32 |
| ATOM | 466 | N | ASN | A | 76 | 1.348 | 30.876 | 32.289 | 1.000 18.49 |
| ATOM | 467 | CA | ASN | A | 76 | 0.562 | 31.826 | 31.510 | 1.000 26.54 |

FIGURE 163

```
ATOM    468  CB   ASN A  76       1.244  33.195  31.432  1.000  26.00
ATOM    469  CG   ASN A  76       2.628  33.130  30.821  1.000  27.59
ATOM    470  OD1  ASN A  76       3.295  32.100  30.926  1.000  28.39
ATOM    471  ND2  ASN A  76       3.131  34.186  30.182  1.000  26.81
ATOM    472  C    ASN A  76       0.331  31.297  30.101  1.000  26.92
ATOM    473  O    ASN A  76      -0.145  32.065  29.263  1.000  24.80
ATOM    474  N    ILE A  77       0.659  30.023  29.813  1.000  21.21
ATOM    475  CA   ILE A  77       0.313  29.527  28.477  1.000  20.79
ATOM    476  CB   ILE A  77       1.534  29.187  27.632  1.000  25.15
ATOM    477  CG1  ILE A  77       2.596  30.315  27.595  1.000  31.48
ATOM    478  CD1  ILE A  77       2.862  30.817  26.195  1.000  49.78
ATOM    479  CG2  ILE A  77       1.116  28.793  26.229  1.000  23.01
ATOM    480  C    ILE A  77      -0.604  28.313  28.648  1.000  23.40
ATOM    481  O    ILE A  77      -0.121  27.210  28.877  1.000  24.16
ATOM    482  N    LEU A  78      -1.899  28.584  28.583  1.000  20.25
ATOM    483  CA   LEU A  78      -2.931  27.667  29.035  1.000  19.58
ATOM    484  CB   LEU A  78      -3.621  28.170  30.307  1.000  18.02
ATOM    485  CG   LEU A  78      -2.711  28.581  31.476  1.000  22.60
ATOM    486  CD1  LEU A  78      -3.510  29.136  32.647  1.000  18.50
ATOM    487  CD2  LEU A  78      -1.854  27.424  31.993  1.000  19.12
ATOM    488  C    LEU A  78      -3.946  27.471  27.912  1.000  18.12
ATOM    489  O    LEU A  78      -4.186  28.398  27.142  1.000  19.00
ATOM    490  N    PRO A  79      -4.511  26.269  27.863  1.000  18.26
ATOM    491  CA   PRO A  79      -5.546  26.003  26.858  1.000  16.50
ATOM    492  CB   PRO A  79      -5.707  24.485  26.984  1.000  21.55
ATOM    493  CG   PRO A  79      -5.462  24.228  28.452  1.000  13.29
ATOM    494  CD   PRO A  79      -4.246  25.103  28.705  1.000  14.71
ATOM    495  C    PRO A  79      -6.844  26.703  27.235  1.000  17.47
ATOM    496  O    PRO A  79      -7.176  26.850  28.420  1.000  20.15
ATOM    497  N    TYR A  80      -7.613  27.139  26.237  1.000  15.99
ATOM    498  CA   TYR A  80      -8.958  27.654  26.481  1.000  17.04
ATOM    499  CB   TYR A  80      -9.454  28.253  25.165  1.000  16.02
ATOM    500  CG   TYR A  80      -8.756  29.502  24.697  1.000  17.83
ATOM    501  CD1  TYR A  80      -8.514  30.562  25.574  1.000  17.44
ATOM    502  CE1  TYR A  80      -7.879  31.711  25.143  1.000  18.38
ATOM    503  CZ   TYR A  80      -7.474  31.828  23.837  1.000  17.97
ATOM    504  OH   TYR A  80      -6.845  32.976  23.415  1.000  20.65
ATOM    505  CE2  TYR A  80      -7.700  30.802  22.930  1.000  19.84
ATOM    506  CD2  TYR A  80      -8.338  29.655  23.381  1.000  17.33
ATOM    507  C    TYR A  80      -9.884  26.547  26.977  1.000  18.38
ATOM    508  O    TYR A  80      -9.791  25.404  26.525  1.000  19.85
ATOM    509  N    ASP A  81     -10.785  26.816  27.908  1.000  18.35
ATOM    510  CA   ASP A  81     -11.772  25.824  28.336  1.000  23.15
ATOM    511  CB   ASP A  81     -12.734  26.485  29.337  1.000  20.21
ATOM    512  CG   ASP A  81     -12.050  26.883  30.626  1.000  19.62
ATOM    513  OD1  ASP A  81     -11.107  26.212  31.082  1.000  20.36
ATOM    514  OD2  ASP A  81     -12.437  27.911  31.225  1.000  24.76
ATOM    515  C    ASP A  81     -12.539  25.250  27.153  1.000  19.52
ATOM    516  O    ASP A  81     -12.771  24.029  27.079  1.000  21.17
ATOM    517  N    ALA A  82     -12.910  26.116  26.218  1.000  19.35
ATOM    518  CA   ALA A  82     -13.787  25.780  25.106  1.000  20.79
ATOM    519  CB   ALA A  82     -14.147  27.041  24.318  1.000  21.73
```

FIGURE 164

```
ATOM    520  C    ALA A  82     -13.218  24.780  24.117 1.000 24.48
ATOM    521  O    ALA A  82     -14.017  24.152  23.409 1.000 24.01
ATOM    522  N    THR A  83     -11.910  24.613  24.002 1.000 19.51
ATOM    523  CA   THR A  83     -11.324  23.717  22.995 1.000 17.80
ATOM    524  CB   THR A  83     -10.631  24.588  21.940 1.000 16.46
ATOM    525  OG1  THR A  83      -9.691  25.412  22.665 1.000 18.46
ATOM    526  CG2  THR A  83     -11.616  25.512  21.246 1.000 23.15
ATOM    527  C    THR A  83     -10.302  22.753  23.586 1.000 19.19
ATOM    528  O    THR A  83      -9.519  22.101  22.875 1.000 18.99
ATOM    529  N    ARG A  84     -10.239  22.638  24.919 1.000 15.87
ATOM    530  CA   ARG A  84      -9.214  21.790  25.521 1.000 13.38
ATOM    531  CB   ARG A  84      -9.125  22.053  27.033 1.000 17.35
ATOM    532  CG   ARG A  84     -10.272  21.451  27.842 1.000 15.57
ATOM    533  CD   ARG A  84     -10.161  21.906  29.303 1.000 23.22
ATOM    534  NE   ARG A  84     -11.142  21.257  30.168 1.000 23.41
ATOM    535  CZ   ARG A  84     -10.962  20.204  30.948 1.000 20.47
ATOM    536  NH1  ARG A  84      -9.809  19.561  31.054 1.000 19.35
ATOM    537  NH2  ARG A  84     -11.994  19.773  31.664 1.000 22.12
ATOM    538  C    ARG A  84      -9.470  20.299  25.308 1.000 18.88
ATOM    539  O    ARG A  84     -10.635  19.874  25.268 1.000 22.06
ATOM    540  N    VAL A  85      -8.375  19.551  25.196 1.000 16.89
ATOM    541  CA   VAL A  85      -8.423  18.097  25.114 1.000 16.58
ATOM    542  CB   VAL A  85      -7.184  17.483  24.455 1.000 22.94
ATOM    543  CG1  VAL A  85      -7.356  15.966  24.274 1.000 23.40
ATOM    544  CG2  VAL A  85      -6.893  18.086  23.091 1.000 17.65
ATOM    545  C    VAL A  85      -8.595  17.535  26.523 1.000 19.64
ATOM    546  O    VAL A  85      -7.844  17.914  27.424 1.000 19.96
ATOM    547  N    LYS A  86      -9.550  16.650  26.756 1.000 17.33
ATOM    548  CA   LYS A  86      -9.719  16.095  28.096 1.000 23.43
ATOM    549  CB   LYS A  86     -11.191  16.082  28.526 1.000 27.56
ATOM    550  CG   LYS A  86     -11.884  17.432  28.490 1.000 32.74
ATOM    551  CD   LYS A  86     -13.319  17.288  28.987 1.000 42.78
ATOM    552  CE   LYS A  86     -14.275  18.120  28.145 1.000 53.05
ATOM    553  NZ   LYS A  86     -14.205  19.569  28.476 1.000 47.90
ATOM    554  C    LYS A  86      -9.213  14.660  28.171 1.000 23.69
ATOM    555  O    LYS A  86      -9.417  13.887  27.241 1.000 24.18
ATOM    556  N    LEU A  87      -8.580  14.294  29.273 1.000 21.05
ATOM    557  CA   LEU A  87      -8.225  12.906  29.504 1.000 18.28
ATOM    558  CB   LEU A  87      -7.106  12.861  30.540 1.000 19.01
ATOM    559  CG   LEU A  87      -5.824  13.608  30.146 1.000 24.48
ATOM    560  CD1  LEU A  87      -4.865  13.612  31.326 1.000 21.86
ATOM    561  CD2  LEU A  87      -5.175  12.994  28.916 1.000 21.83
ATOM    562  C    LEU A  87      -9.433  12.132  30.001 1.000 30.80
ATOM    563  O    LEU A  87     -10.293  12.739  30.652 1.000 27.84
ATOM    564  N    SER A  88      -9.561  10.832  29.745 1.000 25.76
ATOM    565  CA   SER A  88     -10.662  10.132  30.429 1.000 30.68
ATOM    566  CB   SER A  88     -10.751   8.668  29.990 1.000 25.39
ATOM    567  OG   SER A  88      -9.581   7.992  30.416 1.000 28.79
ATOM    568  C    SER A  88     -10.554  10.163  31.955 1.000 34.04
ATOM    569  O    SER A  88      -9.497  10.278  32.577 1.000 30.33
ATOM    570  N    ASN A  89     -11.728  10.055  32.566 1.000 43.34
ATOM    571  CA   ASN A  89     -11.976  10.144  33.991 1.000 56.50
```

FIGURE 165

```
ATOM    572  CB  ASN A  89     -13.369    9.595   34.329  1.000 60.50
ATOM    573  CG  ASN A  89     -13.557    8.127   34.024  1.000 66.77
ATOM    574  OD1 ASN A  89     -12.606    7.351   33.952  1.000 60.44
ATOM    575  ND2 ASN A  89     -14.807    7.703   33.844  1.000 70.97
ATOM    576  C   ASN A  89     -10.926    9.410   34.821  1.000 65.63
ATOM    577  O   ASN A  89     -10.996    9.390   36.052  1.000 72.13
ATOM    578  N   SER A  96      -8.513   15.291   37.171  1.000 39.19
ATOM    579  CA  SER A  96      -7.743   14.211   36.560  1.000 29.84
ATOM    580  CB  SER A  96      -8.043   12.853   37.183  1.000 29.33
ATOM    581  OG  SER A  96      -9.336   12.376   36.866  1.000 31.86
ATOM    582  C   SER A  96      -7.971   14.200   35.049  1.000 25.03
ATOM    583  O   SER A  96      -7.285   13.420   34.378  1.000 30.76
ATOM    584  N   ASP A  97      -8.874   15.033   34.527  1.000 26.35
ATOM    585  CA  ASP A  97      -9.072   15.047   33.069  1.000 23.38
ATOM    586  CB  ASP A  97     -10.495   15.418   32.661  1.000 21.60
ATOM    587  CG  ASP A  97     -10.928   16.834   32.933  1.000 26.73
ATOM    588  OD1 ASP A  97     -10.115   17.686   33.354  1.000 26.07
ATOM    589  OD2 ASP A  97     -12.136   17.107   32.701  1.000 29.59
ATOM    590  C   ASP A  97      -8.112   16.015   32.379  1.000 28.59
ATOM    591  O   ASP A  97      -8.144   16.087   31.149  1.000 22.81
ATOM    592  N   TYR A  98      -7.316   16.753   33.150  1.000 24.51
ATOM    593  CA  TYR A  98      -6.573   17.864   32.576  1.000 18.45
ATOM    594  CB  TYR A  98      -6.287   18.947   33.663  1.000 21.47
ATOM    595  CG  TYR A  98      -5.566   20.114   33.013  1.000 18.45
ATOM    596  CD1 TYR A  98      -6.288   21.015   32.223  1.000 20.80
ATOM    597  CE1 TYR A  98      -5.651   22.093   31.617  1.000 19.85
ATOM    598  CZ  TYR A  98      -4.300   22.277   31.775  1.000 20.41
ATOM    599  OH  TYR A  98      -3.617   23.313   31.194  1.000 18.24
ATOM    600  CE2 TYR A  98      -3.554   21.399   32.546  1.000 19.23
ATOM    601  CD2 TYR A  98      -4.206   20.342   33.147  1.000 19.12
ATOM    602  C   TYR A  98      -5.263   17.498   31.918  1.000 19.64
ATOM    603  O   TYR A  98      -4.369   16.840   32.439  1.000 20.66
ATOM    604  N   ILE A  99      -5.119   18.053   30.711  1.000 16.91
ATOM    605  CA  ILE A  99      -3.822   18.176   30.062  1.000 16.84
ATOM    606  CB  ILE A  99      -3.536   17.002   29.113  1.000 17.82
ATOM    607  CG1 ILE A  99      -2.137   16.977   28.518  1.000 15.01
ATOM    608  CD1 ILE A  99      -1.789   15.688   27.785  1.000 15.78
ATOM    609  CG2 ILE A  99      -4.615   16.953   28.023  1.000 17.57
ATOM    610  C   ILE A  99      -3.766   19.520   29.325  1.000 15.16
ATOM    611  O   ILE A  99      -4.767   20.020   28.812  1.000 17.38
ATOM    612  N   ASN A 100      -2.587   20.120   29.308  1.000 17.52
ATOM    613  CA  ASN A 100      -2.392   21.383   28.584  1.000 13.18
ATOM    614  CB  ASN A 100      -1.125   22.085   29.028  1.000 14.04
ATOM    615  CG  ASN A 100      -1.059   23.494   28.450  1.000 15.18
ATOM    616  OD1 ASN A 100      -1.331   23.713   27.280  1.000 18.72
ATOM    617  ND2 ASN A 100      -0.702   24.455   29.274  1.000 16.16
ATOM    618  C   ASN A 100      -2.333   21.054   27.090  1.000 12.55
ATOM    619  O   ASN A 100      -1.244   20.809   26.544  1.000 15.92
ATOM    620  N   ALA A 101      -3.521   21.008   26.492  1.000 15.34
ATOM    621  CA  ALA A 101      -3.655   20.605   25.088  1.000 18.55
ATOM    622  CB  ALA A 101      -3.556   19.090   24.924  1.000 16.55
ATOM    623  C   ALA A 101      -4.971   21.137   24.527  1.000 13.59
```

FIGURE 166

```
ATOM    624  O    ALA A 101      -5.924  21.365  25.274  1.000 16.49
ATOM    625  N    SER A 102      -5.001  21.341  23.211  1.000 13.49
ATOM    626  CA   SER A 102      -6.108  21.993  22.553  1.000 16.27
ATOM    627  CB   SER A 102      -5.855  23.491  22.338  1.000 21.21
ATOM    628  OG   SER A 102      -5.352  24.131  23.503  1.000 17.32
ATOM    629  C    SER A 102      -6.356  21.367  21.169  1.000 14.55
ATOM    630  O    SER A 102      -5.410  21.018  20.464  1.000 15.20
ATOM    631  N    TYR A 103      -7.636  21.254  20.835  1.000 16.64
ATOM    632  CA   TYR A 103      -8.048  20.802  19.512  1.000 14.77
ATOM    633  CB   TYR A 103      -9.467  20.239  19.531  1.000 18.66
ATOM    634  CG   TYR A 103      -9.703  18.944  20.270  1.000 18.68
ATOM    635  CD1  TYR A 103      -9.140  17.745  19.852  1.000 16.61
ATOM    636  CE1  TYR A 103      -9.358  16.546  20.528  1.000 17.11
ATOM    637  CZ   TYR A 103     -10.159  16.548  21.648  1.000 20.45
ATOM    638  OH   TYR A 103     -10.386  15.378  22.329  1.000 23.33
ATOM    639  CE2  TYR A 103     -10.730  17.732  22.079  1.000 22.73
ATOM    640  CD2  TYR A 103     -10.517  18.922  21.410  1.000 19.22
ATOM    641  C    TYR A 103      -7.987  21.941  18.505  1.000 13.95
ATOM    642  O    TYR A 103      -8.391  23.073  18.745  1.000 19.80
ATOM    643  N    ILE A 104      -7.482  21.618  17.316  1.000 18.42
ATOM    644  CA   ILE A 104      -7.360  22.569  16.229  1.000 18.12
ATOM    645  CB   ILE A 104      -5.872  22.884  15.979  1.000 23.14
ATOM    646  CG1  ILE A 104      -5.070  23.233  17.226  1.000 28.92
ATOM    647  CD1  ILE A 104      -5.524  24.493  17.940  1.000 29.26
ATOM    648  CG2  ILE A 104      -5.741  24.005  14.967  1.000 26.42
ATOM    649  C    ILE A 104      -7.946  22.001  14.952  1.000 23.75
ATOM    650  O    ILE A 104      -7.672  20.852  14.601  1.000 21.79
ATOM    651  N    PRO A 105      -8.754  22.779  14.241  1.000 28.20
ATOM    652  CA   PRO A 105      -9.258  22.365  12.917  1.000 23.95
ATOM    653  CB   PRO A 105     -10.391  23.355  12.645  1.000 31.38
ATOM    654  CG   PRO A 105     -10.630  24.049  13.941  1.000 40.77
ATOM    655  CD   PRO A 105      -9.285  24.093  14.643  1.000 28.64
ATOM    656  C    PRO A 105      -8.174  22.464  11.860  1.000 28.29
ATOM    657  O    PRO A 105      -7.183  23.199  11.926  1.000 24.10
ATOM    658  N    GLY A 106      -8.320  21.674  10.798  1.000 25.13
ATOM    659  CA   GLY A 106      -7.343  21.757   9.710  1.000 22.26
ATOM    660  C    GLY A 106      -8.127  21.803   8.403  1.000 28.91
ATOM    661  O    GLY A 106      -9.318  22.118   8.467  1.000 26.90
ATOM    662  N    ASN A 107      -7.481  21.487   7.285  1.000 25.90
ATOM    663  CA   ASN A 107      -8.184  21.653   6.010  1.000 35.70
ATOM    664  CB   ASN A 107      -7.264  21.551   4.794  1.000 32.05
ATOM    665  CG   ASN A 107      -6.326  22.729   4.615  1.000 27.43
ATOM    666  OD1  ASN A 107      -5.615  22.864   3.606  1.000 22.24
ATOM    667  ND2  ASN A 107      -6.328  23.567   5.634  1.000 26.27
ATOM    668  C    ASN A 107      -9.273  20.581   5.877  1.000 38.65
ATOM    669  O    ASN A 107     -10.274  20.887   5.236  1.000 46.02
ATOM    670  N    ASN A 108      -9.002  19.431   6.465  1.000 30.37
ATOM    671  CA   ASN A 108      -9.700  18.170   6.282  1.000 36.09
ATOM    672  CB   ASN A 108      -8.676  17.017   6.195  1.000 40.88
ATOM    673  CG   ASN A 108      -7.647  17.276   5.099  1.000 44.34
ATOM    674  OD1  ASN A 108      -7.988  17.259   3.914  1.000 26.73
ATOM    675  ND2  ASN A 108      -6.392  17.525   5.466  1.000 23.01
```

FIGURE 167

```
ATOM    676  C    ASN A 108     -10.712  17.862   7.369 1.000 27.84
ATOM    677  O    ASN A 108     -11.746  17.240   7.087 1.000 45.47
ATOM    678  N    PHE A 109     -10.515  18.262   8.614 1.000 28.68
ATOM    679  CA   PHE A 109     -11.601  17.986   9.569 1.000 29.14
ATOM    680  CB   PHE A 109     -11.727  16.503   9.837 1.000 33.67
ATOM    681  CG   PHE A 109     -10.501  15.678  10.128 1.000 32.21
ATOM    682  CD1  PHE A 109      -9.720  15.199   9.088 1.000 36.73
ATOM    683  CE1  PHE A 109      -8.604  14.419   9.325 1.000 33.86
ATOM    684  CZ   PHE A 109      -8.275  14.120  10.633 1.000 42.76
ATOM    685  CE2  PHE A 109      -9.036  14.590  11.683 1.000 37.98
ATOM    686  CD2  PHE A 109     -10.143  15.376  11.430 1.000 37.01
ATOM    687  C    PHE A 109     -11.450  18.785  10.856 1.000 28.59
ATOM    688  O    PHE A 109     -10.493  19.529  11.101 1.000 25.57
ATOM    689  N    ARG A 110     -12.457  18.692  11.728 1.000 29.57
ATOM    690  CA   ARG A 110     -12.560  19.633  12.835 1.000 29.56
ATOM    691  CB   ARG A 110     -13.912  19.447  13.560 1.000 39.08
ATOM    692  CG   ARG A 110     -15.115  19.581  12.647 1.000 51.99
ATOM    693  CD   ARG A 110     -15.714  20.978  12.671 1.000 60.61
ATOM    694  NE   ARG A 110     -16.438  21.295  11.439 1.000 56.28
ATOM    695  CZ   ARG A 110     -17.049  22.446  11.187 1.000 59.30
ATOM    696  NH1  ARG A 110     -17.685  22.657  10.040 1.000 45.23
ATOM    697  NH2  ARG A 110     -17.032  23.413  12.100 1.000 84.92
ATOM    698  C    ARG A 110     -11.462  19.550  13.898 1.000 32.92
ATOM    699  O    ARG A 110     -10.952  20.588  14.359 1.000 36.08
ATOM    700  N    ARG A 111     -11.163  18.325  14.281 1.000 28.03
ATOM    701  CA   ARG A 111     -10.152  17.978  15.275 1.000 26.59
ATOM    702  CB   ARG A 111     -10.714  17.032  16.339 1.000 33.75
ATOM    703  CG   ARG A 111     -11.497  17.792  17.422 1.000 39.79
ATOM    704  CD   ARG A 111     -12.543  16.891  18.038 1.000 40.61
ATOM    705  NE   ARG A 111     -13.133  17.383  19.283 1.000 34.63
ATOM    706  CZ   ARG A 111     -13.380  16.499  20.268 1.000 44.09
ATOM    707  NH1  ARG A 111     -13.087  15.209  20.117 1.000 40.26
ATOM    708  NH2  ARG A 111     -13.915  16.924  21.402 1.000 48.99
ATOM    709  C    ARG A 111      -8.977  17.326  14.564 1.000 26.23
ATOM    710  O    ARG A 111      -8.583  16.195  14.813 1.000 22.76
ATOM    711  N    GLU A 112      -8.437  18.086  13.603 1.000 18.42
ATOM    712  CA   GLU A 112      -7.400  17.493  12.752 1.000 19.07
ATOM    713  CB   GLU A 112      -7.339  18.364  11.470 1.000 13.71
ATOM    714  CG   GLU A 112      -6.317  17.831  10.484 1.000 14.61
ATOM    715  CD   GLU A 112      -6.654  18.208   9.049 1.000 20.17
ATOM    716  OE1  GLU A 112      -7.701  18.836   8.814 1.000 23.80
ATOM    717  OE2  GLU A 112      -5.819  17.872   8.184 1.000 20.53
ATOM    718  C    GLU A 112      -6.059  17.425  13.457 1.000 13.05
ATOM    719  O    GLU A 112      -5.177  16.583  13.179 1.000 16.04
ATOM    720  N    TYR A 113      -5.888  18.365  14.392 1.000 14.44
ATOM    721  CA   TYR A 113      -4.660  18.455  15.170 1.000 14.56
ATOM    722  CB   TYR A 113      -3.783  19.667  14.843 1.000 13.32
ATOM    723  CG   TYR A 113      -3.500  19.908  13.376 1.000 17.76
ATOM    724  CD1  TYR A 113      -2.393  19.395  12.721 1.000 18.07
ATOM    725  CE1  TYR A 113      -2.151  19.630  11.364 1.000 14.90
ATOM    726  CZ   TYR A 113      -3.049  20.406  10.658 1.000 18.66
ATOM    727  OH   TYR A 113      -2.860  20.666   9.306 1.000 17.72
```

FIGURE 168

```
ATOM    728  CE2 TYR A 113      -4.162  20.925  11.293 1.000 20.77
ATOM    729  CD2 TYR A 113      -4.392  20.683  12.633 1.000 15.75
ATOM    730  C   TYR A 113      -4.980  18.563  16.668 1.000 15.81
ATOM    731  O   TYR A 113      -5.993  19.136  17.046 1.000 16.02
ATOM    732  N   ILE A 114      -4.051  18.047  17.461 1.000 12.86
ATOM    733  CA  ILE A 114      -4.004  18.364  18.882 1.000 12.93
ATOM    734  CB  ILE A 114      -4.060  17.088  19.740 1.000 17.81
ATOM    735  CG1 ILE A 114      -5.461  16.478  19.730 1.000 20.46
ATOM    736  CD1 ILE A 114      -5.604  15.068  20.250 1.000 18.86
ATOM    737  CG2 ILE A 114      -3.565  17.380  21.156 1.000 18.53
ATOM    738  C   ILE A 114      -2.712  19.118  19.104 1.000 14.86
ATOM    739  O   ILE A 114      -1.650  18.594  18.750 1.000 17.75
ATOM    740  N   VAL A 115      -2.797  20.311  19.631 1.000 16.67
ATOM    741  CA  VAL A 115      -1.600  21.072  19.972 1.000 13.98
ATOM    742  CB  VAL A 115      -1.749  22.543  19.584 1.000 14.73
ATOM    743  CG1 VAL A 115      -0.680  23.353  20.303 1.000 27.44
ATOM    744  CG2 VAL A 115      -1.659  22.643  18.059 1.000 22.61
ATOM    745  C   VAL A 115      -1.360  20.975  21.472 1.000 13.84
ATOM    746  O   VAL A 115      -2.303  21.113  22.246 1.000 17.38
ATOM    747  N   THR A 116      -0.116  20.748  21.863 1.000 13.55
ATOM    748  CA  THR A 116       0.108  20.593  23.304 1.000 17.85
ATOM    749  CB  THR A 116      -0.042  19.101  23.682 1.000 16.90
ATOM    750  OG1 THR A 116      -0.019  18.974  25.104 1.000 16.67
ATOM    751  CG2 THR A 116       1.092  18.252  23.118 1.000 18.44
ATOM    752  C   THR A 116       1.462  21.186  23.681 1.000 14.01
ATOM    753  O   THR A 116       2.258  21.452  22.775 1.000 13.95
ATOM    754  N   GLN A 117       1.702  21.380  24.961 1.000 15.16
ATOM    755  CA  GLN A 117       3.032  21.825  25.403 1.000 20.32
ATOM    756  CB  GLN A 117       2.866  22.383  26.829 1.000 17.18
ATOM    757  CG  GLN A 117       2.751  21.245  27.841 1.000 23.10
ATOM    758  CD  GLN A 117       2.459  21.700  29.254 1.000 22.85
ATOM    759  OE1 GLN A 117       2.255  22.879  29.560 1.000 19.09
ATOM    760  NE2 GLN A 117       2.428  20.740  30.181 1.000 25.28
ATOM    761  C   GLN A 117       4.051  20.714  25.344 1.000 22.35
ATOM    762  O   GLN A 117       3.743  19.524  25.186 1.000 21.90
ATOM    763  N   GLY A 118       5.348  20.995  25.467 1.000 20.42
ATOM    764  CA  GLY A 118       6.280  19.856  25.478 1.000 16.32
ATOM    765  C   GLY A 118       6.111  19.186  26.830 1.000 14.48
ATOM    766  O   GLY A 118       6.206  19.869  27.834 1.000 20.82
ATOM    767  N   PRO A 119       5.850  17.888  26.898 1.000 19.04
ATOM    768  CA  PRO A 119       5.598  17.210  28.158 1.000 17.15
ATOM    769  CB  PRO A 119       5.626  15.716  27.778 1.000 17.56
ATOM    770  CG  PRO A 119       5.109  15.747  26.360 1.000 16.78
ATOM    771  CD  PRO A 119       5.766  16.966  25.749 1.000 16.98
ATOM    772  C   PRO A 119       6.686  17.470  29.215 1.000 14.53
ATOM    773  O   PRO A 119       7.852  17.580  28.857 1.000 20.14
ATOM    774  N   LEU A 120       6.193  17.562  30.436 1.000 20.34
ATOM    775  CA  LEU A 120       7.014  17.632  31.639 1.000 26.17
ATOM    776  CB  LEU A 120       6.259  18.379  32.752 1.000 18.48
ATOM    777  CG  LEU A 120       6.077  19.879  32.495 1.000 23.01
ATOM    778  CD1 LEU A 120       4.937  20.427  33.332 1.000 23.31
ATOM    779  CD2 LEU A 120       7.399  20.586  32.764 1.000 24.84
```

FIGURE 169

```
ATOM    780  C   LEU A 120       7.358  16.227  32.124  1.000  25.96
ATOM    781  O   LEU A 120       6.667  15.274  31.750  1.000  21.42
ATOM    782  N   PRO A 121       8.381  16.072  32.957  1.000  29.05
ATOM    783  CA  PRO A 121       8.595  14.786  33.629  1.000  25.75
ATOM    784  CB  PRO A 121       9.597  15.156  34.739  1.000  25.40
ATOM    785  CG  PRO A 121      10.409  16.244  34.108  1.000  27.02
ATOM    786  CD  PRO A 121       9.405  17.064  33.325  1.000  27.21
ATOM    787  C   PRO A 121       7.317  14.251  34.258  1.000  22.30
ATOM    788  O   PRO A 121       7.004  13.056  34.125  1.000  25.28
ATOM    789  N   GLY A 122       6.557  15.136  34.914  1.000  18.79
ATOM    790  CA  GLY A 122       5.347  14.719  35.583  1.000  16.68
ATOM    791  C   GLY A 122       4.075  14.740  34.751  1.000  28.03
ATOM    792  O   GLY A 122       3.020  14.526  35.376  1.000  24.04
ATOM    793  N   THR A 123       4.110  14.977  33.436  1.000  20.34
ATOM    794  CA  THR A 123       2.930  14.937  32.578  1.000  14.07
ATOM    795  CB  THR A 123       2.534  16.297  31.970  1.000  14.80
ATOM    796  OG1 THR A 123       3.597  16.765  31.130  1.000  20.06
ATOM    797  CG2 THR A 123       2.290  17.355  33.043  1.000  21.03
ATOM    798  C   THR A 123       3.121  13.982  31.401  1.000  17.25
ATOM    799  O   THR A 123       2.189  13.769  30.625  1.000  19.21
ATOM    800  N   LYS A 124       4.290  13.385  31.258  1.000  17.35
ATOM    801  CA  LYS A 124       4.591  12.474  30.157  1.000  20.84
ATOM    802  CB  LYS A 124       6.056  12.057  30.163  1.000  23.80
ATOM    803  CG  LYS A 124       6.574  11.185  31.268  1.000  22.00
ATOM    804  CD  LYS A 124       8.053  10.832  31.082  1.000  30.29
ATOM    805  CE  LYS A 124       8.441   9.720  32.044  1.000  45.34
ATOM    806  NZ  LYS A 124       9.868   9.696  32.452  1.000  41.63
ATOM    807  C   LYS A 124       3.636  11.275  30.163  1.000  19.38
ATOM    808  O   LYS A 124       3.239  10.855  29.071  1.000  19.48
ATOM    809  N   ASP A 125       3.233  10.748  31.314  1.000  20.33
ATOM    810  CA  ASP A 125       2.250   9.666  31.286  1.000  20.85
ATOM    811  CB  ASP A 125       2.042   9.048  32.667  1.000  21.24
ATOM    812  CG  ASP A 125       3.216   8.294  33.256  1.000  23.35
ATOM    813  OD1 ASP A 125       4.196   8.028  32.528  1.000  20.34
ATOM    814  OD2 ASP A 125       3.124   7.972  34.488  1.000  20.58
ATOM    815  C   ASP A 125       0.903  10.155  30.758  1.000  18.95
ATOM    816  O   ASP A 125       0.264   9.434  29.979  1.000  17.28
ATOM    817  N   ASP A 126       0.462  11.327  31.199  1.000  20.58
ATOM    818  CA  ASP A 126      -0.740  11.974  30.672  1.000  16.25
ATOM    819  CB  ASP A 126      -0.971  13.331  31.325  1.000  22.07
ATOM    820  CG  ASP A 126      -1.198  13.393  32.813  1.000  35.20
ATOM    821  OD1 ASP A 126      -1.760  12.424  33.363  1.000  28.11
ATOM    822  OD2 ASP A 126      -0.833  14.421  33.448  1.000  29.77
ATOM    823  C   ASP A 126      -0.636  12.184  29.153  1.000  14.70
ATOM    824  O   ASP A 126      -1.589  11.970  28.403  1.000  17.56
ATOM    825  N   PHE A 127       0.509  12.629  28.658  1.000  16.52
ATOM    826  CA  PHE A 127       0.641  12.855  27.203  1.000  16.00
ATOM    827  CB  PHE A 127       2.039  13.358  26.853  1.000  16.31
ATOM    828  CG  PHE A 127       2.432  13.364  25.376  1.000  15.99
ATOM    829  CD1 PHE A 127       2.178  14.498  24.615  1.000  18.51
ATOM    830  CE1 PHE A 127       2.518  14.549  23.273  1.000  10.71
ATOM    831  CZ  PHE A 127       3.108  13.449  22.681  1.000  15.27
```

FIGURE 170

| | | | | | | | | | |
|---|---|---|---|---|---|---|---|---|---|
| ATOM | 832 | CE2 | PHE | A | 127 | 3.382 | 12.289 | 23.403 | 1.000 19.04 |
| ATOM | 833 | CD2 | PHE | A | 127 | 3.061 | 12.299 | 24.747 | 1.000 16.38 |
| ATOM | 834 | C | PHE | A | 127 | 0.385 | 11.547 | 26.468 | 1.000 22.45 |
| ATOM | 835 | O | PHE | A | 127 | -0.332 | 11.482 | 25.478 | 1.000 16.59 |
| ATOM | 836 | N | TRP | A | 128 | 1.052 | 10.479 | 26.939 | 1.000 15.18 |
| ATOM | 837 | CA | TRP | A | 128 | 0.896 | 9.221 | 26.182 | 1.000 16.47 |
| ATOM | 838 | CB | TRP | A | 128 | 1.938 | 8.201 | 26.653 | 1.000 14.81 |
| ATOM | 839 | CG | TRP | A | 128 | 3.329 | 8.492 | 26.170 | 1.000 17.83 |
| ATOM | 840 | CD1 | TRP | A | 128 | 4.444 | 8.788 | 26.892 | 1.000 15.04 |
| ATOM | 841 | NE1 | TRP | A | 128 | 5.526 | 8.987 | 26.043 | 1.000 16.38 |
| ATOM | 842 | CE2 | TRP | A | 128 | 5.110 | 8.818 | 24.749 | 1.000 15.72 |
| ATOM | 843 | CD2 | TRP | A | 128 | 3.738 | 8.509 | 24.787 | 1.000 15.19 |
| ATOM | 844 | CE3 | TRP | A | 128 | 3.062 | 8.282 | 23.587 | 1.000 16.34 |
| ATOM | 845 | CZ3 | TRP | A | 128 | 3.760 | 8.373 | 22.395 | 1.000 18.84 |
| ATOM | 846 | CH2 | TRP | A | 128 | 5.126 | 8.684 | 22.375 | 1.000 18.88 |
| ATOM | 847 | CZ2 | TRP | A | 128 | 5.797 | 8.906 | 23.544 | 1.000 19.59 |
| ATOM | 848 | C | TRP | A | 128 | -0.516 | 8.680 | 26.335 | 1.000 18.33 |
| ATOM | 849 | O | TRP | A | 128 | -1.095 | 8.039 | 25.441 | 1.000 17.84 |
| ATOM | 850 | N | LYS | A | 129 | -1.136 | 8.925 | 27.490 | 1.000 16.01 |
| ATOM | 851 | CA | LYS | A | 129 | -2.552 | 8.577 | 27.669 | 1.000 15.83 |
| ATOM | 852 | CB | LYS | A | 129 | -2.959 | 8.905 | 29.107 | 1.000 16.11 |
| ATOM | 853 | CG | LYS | A | 129 | -4.428 | 8.639 | 29.383 | 1.000 22.20 |
| ATOM | 854 | CD | LYS | A | 129 | -4.734 | 8.820 | 30.866 | 1.000 21.45 |
| ATOM | 855 | CE | LYS | A | 129 | -6.258 | 8.852 | 31.065 | 1.000 26.32 |
| ATOM | 856 | NZ | LYS | A | 129 | -6.584 | 9.011 | 32.510 | 1.000 34.60 |
| ATOM | 857 | C | LYS | A | 129 | -3.418 | 9.305 | 26.655 | 1.000 22.77 |
| ATOM | 858 | O | LYS | A | 129 | -4.278 | 8.695 | 26.000 | 1.000 18.99 |
| ATOM | 859 | N | MET | A | 130 | -3.188 | 10.621 | 26.479 | 1.000 15.75 |
| ATOM | 860 | CA | MET | A | 130 | -3.893 | 11.366 | 25.434 | 1.000 13.41 |
| ATOM | 861 | CB | MET | A | 130 | -3.416 | 12.840 | 25.476 | 1.000 16.79 |
| ATOM | 862 | CG | MET | A | 130 | -4.077 | 13.682 | 24.379 | 1.000 18.60 |
| ATOM | 863 | SD | MET | A | 130 | -3.548 | 15.406 | 24.457 | 1.000 18.90 |
| ATOM | 864 | CE | MET | A | 130 | -1.867 | 15.262 | 23.906 | 1.000 14.57 |
| ATOM | 865 | C | MET | A | 130 | -3.662 | 10.816 | 24.035 | 1.000 16.03 |
| ATOM | 866 | O | MET | A | 130 | -4.577 | 10.636 | 23.228 | 1.000 21.60 |
| ATOM | 867 | N | VAL | A | 131 | -2.421 | 10.513 | 23.688 | 1.000 16.52 |
| ATOM | 868 | CA | VAL | A | 131 | -2.096 | 9.907 | 22.395 | 1.000 17.62 |
| ATOM | 869 | CB | VAL | A | 131 | -0.576 | 9.659 | 22.293 | 1.000 15.16 |
| ATOM | 870 | CG1 | VAL | A | 131 | -0.228 | 8.757 | 21.118 | 1.000 16.01 |
| ATOM | 871 | CG2 | VAL | A | 131 | 0.162 | 10.996 | 22.200 | 1.000 14.77 |
| ATOM | 872 | C | VAL | A | 131 | -2.891 | 8.614 | 22.198 | 1.000 14.71 |
| ATOM | 873 | O | VAL | A | 131 | -3.480 | 8.392 | 21.126 | 1.000 17.34 |
| ATOM | 874 | N | TRP | A | 132 | -2.952 | 7.787 | 23.223 | 1.000 14.88 |
| ATOM | 875 | CA | TRP | A | 132 | -3.697 | 6.516 | 23.124 | 1.000 22.11 |
| ATOM | 876 | CB | TRP | A | 132 | -3.433 | 5.620 | 24.339 | 1.000 22.48 |
| ATOM | 877 | CG | TRP | A | 132 | -4.168 | 4.301 | 24.280 | 1.000 27.32 |
| ATOM | 878 | CD1 | TRP | A | 132 | -5.262 | 3.909 | 25.019 | 1.000 25.14 |
| ATOM | 879 | NE1 | TRP | A | 132 | -5.611 | 2.623 | 24.645 | 1.000 23.87 |
| ATOM | 880 | CE2 | TRP | A | 132 | -4.763 | 2.172 | 23.681 | 1.000 18.18 |
| ATOM | 881 | CD2 | TRP | A | 132 | -3.834 | 3.198 | 23.418 | 1.000 18.05 |
| ATOM | 882 | CE3 | TRP | A | 132 | -2.840 | 2.999 | 22.460 | 1.000 22.17 |
| ATOM | 883 | CZ3 | TRP | A | 132 | -2.774 | 1.795 | 21.772 | 1.000 28.54 |

FIGURE 171

```
ATOM    884  CH2 TRP A 132      -3.721   0.806  22.066  1.000  23.87
ATOM    885  CZ2 TRP A 132      -4.696   0.966  22.993  1.000  20.35
ATOM    886  C   TRP A 132      -5.193   6.750  22.947  1.000  17.05
ATOM    887  O   TRP A 132      -5.818   6.256  21.987  1.000  20.64
ATOM    888  N   GLU A 133      -5.791   7.519  23.839  1.000  14.90
ATOM    889  CA  GLU A 133      -7.219   7.778  23.820  1.000  17.45
ATOM    890  CB  GLU A 133      -7.610   8.589  25.078  1.000  18.05
ATOM    891  CG  GLU A 133      -7.397   7.760  26.341  1.000  19.08
ATOM    892  CD  GLU A 133      -7.868   8.505  27.588  1.000  27.21
ATOM    893  OE1 GLU A 133      -8.176   9.707  27.515  1.000  24.17
ATOM    894  OE2 GLU A 133      -7.926   7.874  28.661  1.000  32.77
ATOM    895  C   GLU A 133      -7.680   8.510  22.579  1.000  20.80
ATOM    896  O   GLU A 133      -8.825   8.300  22.156  1.000  22.88
ATOM    897  N   GLN A 134      -6.829   9.358  22.026  1.000  17.73
ATOM    898  CA  GLN A 134      -7.237  10.221  20.900  1.000  16.57
ATOM    899  CB  GLN A 134      -6.549  11.579  21.008  1.000  14.29
ATOM    900  CG  GLN A 134      -6.990  12.288  22.299  1.000  16.77
ATOM    901  CD  GLN A 134      -8.452  12.650  22.274  1.000  21.52
ATOM    902  OE1 GLN A 134      -9.006  13.127  21.277  1.000  27.29
ATOM    903  NE2 GLN A 134      -9.111  12.430  23.414  1.000  22.22
ATOM    904  C   GLN A 134      -6.950   9.599  19.542  1.000  19.42
ATOM    905  O   GLN A 134      -7.196  10.269  18.542  1.000  18.38
ATOM    906  N   ASN A 135      -6.467   8.362  19.537  1.000  19.05
ATOM    907  CA  ASN A 135      -6.213   7.579  18.343  1.000  19.16
ATOM    908  CB  ASN A 135      -7.480   7.376  17.494  1.000  20.31
ATOM    909  CG  ASN A 135      -8.541   6.596  18.257  1.000  31.86
ATOM    910  OD1 ASN A 135      -8.283   5.493  18.725  1.000  33.23
ATOM    911  ND2 ASN A 135      -9.742   7.149  18.391  1.000  30.19
ATOM    912  C   ASN A 135      -5.155   8.263  17.482  1.000  17.39
ATOM    913  O   ASN A 135      -5.206   8.264  16.256  1.000  22.39
ATOM    914  N   VAL A 136      -4.196   8.866  18.167  1.000  14.13
ATOM    915  CA  VAL A 136      -3.123   9.563  17.457  1.000  16.02
ATOM    916  CB  VAL A 136      -2.417  10.541  18.433  1.000  18.99
ATOM    917  CG1 VAL A 136      -1.100  11.000  17.793  1.000  20.47
ATOM    918  CG2 VAL A 136      -3.330  11.692  18.794  1.000  13.05
ATOM    919  C   VAL A 136      -2.120   8.585  16.871  1.000  18.76
ATOM    920  O   VAL A 136      -1.653   7.669  17.563  1.000  17.38
ATOM    921  N   HIS A 137      -1.756   8.745  15.591  1.000  15.53
ATOM    922  CA  HIS A 137      -0.715   7.888  15.035  1.000  18.61
ATOM    923  CB  HIS A 137      -1.197   7.109  13.799  1.000  19.72
ATOM    924  CG  HIS A 137      -2.274   6.119  14.090  1.000  22.80
ATOM    925  ND1 HIS A 137      -3.478   6.436  14.669  1.000  26.95
ATOM    926  CE1 HIS A 137      -4.209   5.343  14.795  1.000  30.61
ATOM    927  NE2 HIS A 137      -3.516   4.331  14.319  1.000  27.83
ATOM    928  CD2 HIS A 137      -2.301   4.778  13.869  1.000  31.20
ATOM    929  C   HIS A 137       0.523   8.677  14.620  1.000  19.42
ATOM    930  O   HIS A 137       1.534   8.071  14.287  1.000  19.32
ATOM    931  N   ASN A 138       0.469  10.009  14.624  1.000  18.64
ATOM    932  CA  ASN A 138       1.609  10.809  14.197  1.000  16.59
ATOM    933  CB  ASN A 138       1.368  11.460  12.823  1.000  14.79
ATOM    934  CG  ASN A 138       1.182  10.388  11.774  1.000  14.32
ATOM    935  OD1 ASN A 138       0.070  10.154  11.277  1.000  23.35
```

FIGURE 172

| | | | | | | | | |
|---|---|---|---|---|---|---|---|---|
| ATOM | 936 | ND2 | ASN | A | 138 | 2.272 | 9.719 | 11.442 1.000 15.72 |
| ATOM | 937 | C | ASN | A | 138 | 1.882 | 11.894 | 15.224 1.000 17.49 |
| ATOM | 938 | O | ASN | A | 138 | 0.923 | 12.540 | 15.639 1.000 16.64 |
| ATOM | 939 | N | ILE | A | 139 | 3.138 | 12.081 | 15.595 1.000 13.57 |
| ATOM | 940 | CA | ILE | A | 139 | 3.492 | 13.222 | 16.443 1.000 13.49 |
| ATOM | 941 | CB | ILE | A | 139 | 4.046 | 12.705 | 17.788 1.000 15.96 |
| ATOM | 942 | CG1 | ILE | A | 139 | 3.032 | 11.892 | 18.597 1.000 17.56 |
| ATOM | 943 | CD1 | ILE | A | 139 | 3.647 | 11.054 | 19.710 1.000 16.60 |
| ATOM | 944 | CG2 | ILE | A | 139 | 4.641 | 13.849 | 18.601 1.000 17.93 |
| ATOM | 945 | C | ILE | A | 139 | 4.545 | 14.100 | 15.776 1.000 16.72 |
| ATOM | 946 | O | ILE | A | 139 | 5.507 | 13.555 | 15.211 1.000 18.97 |
| ATOM | 947 | N | VAL | A | 140 | 4.378 | 15.416 | 15.843 1.000 15.29 |
| ATOM | 948 | CA | VAL | A | 140 | 5.330 | 16.361 | 15.282 1.000 15.83 |
| ATOM | 949 | CB | VAL | A | 140 | 4.672 | 17.254 | 14.202 1.000 17.91 |
| ATOM | 950 | CG1 | VAL | A | 140 | 5.691 | 18.249 | 13.647 1.000 18.30 |
| ATOM | 951 | CG2 | VAL | A | 140 | 4.073 | 16.418 | 13.086 1.000 14.97 |
| ATOM | 952 | C | VAL | A | 140 | 5.892 | 17.200 | 16.427 1.000 15.79 |
| ATOM | 953 | O | VAL | A | 140 | 5.144 | 17.816 | 17.200 1.000 16.44 |
| ATOM | 954 | N | MET | A | 141 | 7.208 | 17.203 | 16.579 1.000 16.25 |
| ATOM | 955 | CA | MET | A | 141 | 7.900 | 17.899 | 17.660 1.000 21.24 |
| ATOM | 956 | CB | MET | A | 141 | 8.745 | 16.916 | 18.480 1.000 18.76 |
| ATOM | 957 | CG | MET | A | 141 | 9.555 | 17.528 | 19.619 1.000 15.74 |
| ATOM | 958 | SD | MET | A | 141 | 10.162 | 16.187 | 20.709 1.000 19.42 |
| ATOM | 959 | CE | MET | A | 141 | 11.299 | 17.174 | 21.703 1.000 22.74 |
| ATOM | 960 | C | MET | A | 141 | 8.795 | 18.989 | 17.072 1.000 14.50 |
| ATOM | 961 | O | MET | A | 141 | 9.715 | 18.659 | 16.332 1.000 19.95 |
| ATOM | 962 | N | VAL | A | 142 | 8.551 | 20.246 | 17.347 1.000 18.34 |
| ATOM | 963 | CA | VAL | A | 142 | 9.296 | 21.313 | 16.698 1.000 19.48 |
| ATOM | 964 | CB | VAL | A | 142 | 8.396 | 22.310 | 15.933 1.000 22.88 |
| ATOM | 965 | CG1 | VAL | A | 142 | 9.226 | 22.965 | 14.836 1.000 28.48 |
| ATOM | 966 | CG2 | VAL | A | 142 | 7.180 | 21.668 | 15.294 1.000 30.53 |
| ATOM | 967 | C | VAL | A | 142 | 10.112 | 22.075 | 17.732 1.000 23.04 |
| ATOM | 968 | O | VAL | A | 142 | 9.990 | 23.280 | 17.923 1.000 23.56 |
| ATOM | 969 | N | THR | A | 143 | 10.952 | 21.298 | 18.417 1.000 29.09 |
| ATOM | 970 | CA | THR | A | 143 | 11.788 | 21.805 | 19.501 1.000 28.45 |
| ATOM | 971 | CB | THR | A | 143 | 10.984 | 22.204 | 20.751 1.000 26.09 |
| ATOM | 972 | OG1 | THR | A | 143 | 11.837 | 22.963 | 21.620 1.000 30.17 |
| ATOM | 973 | CG2 | THR | A | 143 | 10.487 | 21.021 | 21.586 1.000 17.97 |
| ATOM | 974 | C | THR | A | 143 | 12.829 | 20.744 | 19.826 1.000 29.90 |
| ATOM | 975 | O | THR | A | 143 | 12.598 | 19.553 | 19.664 1.000 23.69 |
| ATOM | 976 | N | GLN | A | 144 | 14.008 | 21.163 | 20.257 1.000 35.84 |
| ATOM | 977 | CA | GLN | A | 144 | 14.993 | 20.221 | 20.781 1.000 28.60 |
| ATOM | 978 | CB | GLN | A | 144 | 16.415 | 20.692 | 20.494 1.000 27.98 |
| ATOM | 979 | CG | GLN | A | 144 | 16.871 | 20.426 | 19.061 1.000 31.33 |
| ATOM | 980 | CD | GLN | A | 144 | 18.293 | 20.929 | 18.844 1.000 44.78 |
| ATOM | 981 | OE1 | GLN | A | 144 | 19.270 | 20.199 | 19.004 1.000 50.77 |
| ATOM | 982 | NE2 | GLN | A | 144 | 18.424 | 22.197 | 18.474 1.000 34.02 |
| ATOM | 983 | C | GLN | A | 144 | 14.724 | 20.124 | 22.271 1.000 28.09 |
| ATOM | 984 | O | GLN | A | 144 | 14.141 | 21.024 | 22.878 1.000 24.45 |
| ATOM | 985 | N | CYS | A | 145 | 15.115 | 19.032 | 22.927 1.000 30.90 |
| ATOM | 986 | CA | CYS | A | 145 | 14.856 | 18.998 | 24.365 1.000 21.87 |
| ATOM | 987 | CB | CYS | A | 145 | 15.313 | 17.631 | 24.897 1.000 20.92 |

FIGURE 173

```
ATOM    988  SG  CYS A 145      14.184  16.278  24.463  1.000 30.08
ATOM    989  C   CYS A 145      15.601  20.109  25.083  1.000 26.27
ATOM    990  O   CYS A 145      15.152  20.691  26.056  1.000 25.34
ATOM    991  N   VAL A 146      16.795  20.375  24.555  1.000 27.66
ATOM    992  CA  VAL A 146      17.696  21.367  25.097  1.000 30.29
ATOM    993  CB  VAL A 146      18.963  20.721  25.711  1.000 36.55
ATOM    994  CG1 VAL A 146      19.918  21.827  26.139  1.000 34.60
ATOM    995  CG2 VAL A 146      18.601  19.795  26.859  1.000 44.23
ATOM    996  C   VAL A 146      18.213  22.307  24.014  1.000 28.45
ATOM    997  O   VAL A 146      18.841  21.790  23.076  1.000 40.86
ATOM    998  N   GLU A 147      17.971  23.586  24.167  1.000 28.57
ATOM    999  CA  GLU A 147      18.452  24.625  23.258  1.000 37.00
ATOM   1000  CB  GLU A 147      17.283  25.228  22.467  1.000 37.35
ATOM   1001  CG  GLU A 147      16.357  24.218  21.821  1.000 32.42
ATOM   1002  CD  GLU A 147      15.173  24.836  21.097  1.000 36.64
ATOM   1003  OE1 GLU A 147      14.684  25.926  21.465  1.000 28.99
ATOM   1004  OE2 GLU A 147      14.708  24.197  20.129  1.000 29.46
ATOM   1005  C   GLU A 147      19.191  25.727  24.028  1.000 41.02
ATOM   1006  O   GLU A 147      18.682  26.143  25.080  1.000 35.27
ATOM   1007  N   LYS A 148      20.338  26.211  23.559  1.000 49.35
ATOM   1008  CA  LYS A 148      21.141  27.170  24.317  1.000 50.64
ATOM   1009  CB  LYS A 148      20.525  28.547  24.520  1.000 54.31
ATOM   1010  CG  LYS A 148      21.448  29.714  24.766  1.000 56.11
ATOM   1011  CD  LYS A 148      22.091  29.906  26.107  1.000 51.55
ATOM   1012  CE  LYS A 148      23.607  30.019  26.124  1.000 45.10
ATOM   1013  NZ  LYS A 148      24.142  30.959  27.163  1.000 37.78
ATOM   1014  C   LYS A 148      21.369  26.580  25.712  1.000 33.28
ATOM   1015  O   LYS A 148      21.186  27.326  26.676  1.000 40.06
ATOM   1016  N   GLY A 149      21.686  25.282  25.751  1.000 23.87
ATOM   1017  CA  GLY A 149      21.915  24.686  27.061  1.000 33.16
ATOM   1018  C   GLY A 149      20.778  24.925  28.034  1.000 34.12
ATOM   1019  O   GLY A 149      20.966  24.992  29.241  1.000 33.20
ATOM   1020  N   ARG A 150      19.544  25.082  27.560  1.000 43.51
ATOM   1021  CA  ARG A 150      18.420  25.138  28.502  1.000 47.78
ATOM   1022  CB  ARG A 150      17.913  26.553  28.703  1.000 56.08
ATOM   1023  CG  ARG A 150      16.416  26.706  28.896  1.000 63.73
ATOM   1024  CD  ARG A 150      16.066  28.176  29.132  1.000 69.11
ATOM   1025  NE  ARG A 150      16.737  28.703  30.311  1.000 74.23
ATOM   1026  CZ  ARG A 150      16.496  29.840  30.951  1.000 82.40
ATOM   1027  NH1 ARG A 150      15.544  30.672  30.553  1.000 94.75
ATOM   1028  NH2 ARG A 150      17.228  30.148  32.023  1.000 84.24
ATOM   1029  C   ARG A 150      17.319  24.195  28.020  1.000 40.29
ATOM   1030  O   ARG A 150      17.214  23.897  26.826  1.000 44.43
ATOM   1031  N   VAL A 151      16.553  23.714  28.991  1.000 42.19
ATOM   1032  CA  VAL A 151      15.612  22.624  28.731  1.000 40.59
ATOM   1033  CB  VAL A 151      15.397  21.764  29.991  1.000 39.25
ATOM   1034  CG1 VAL A 151      16.743  21.494  30.643  1.000 35.31
ATOM   1035  CG2 VAL A 151      14.448  22.442  30.961  1.000 47.15
ATOM   1036  C   VAL A 151      14.286  23.143  28.204  1.000 34.87
ATOM   1037  O   VAL A 151      13.588  23.974  28.783  1.000 42.34
ATOM   1038  N   LYS A 152      13.921  22.633  27.028  1.000 34.21
ATOM   1039  CA  LYS A 152      12.658  23.089  26.435  1.000 32.45
```

FIGURE 174

```
ATOM   1040  CB   LYS A 152      12.936  23.469  24.983 1.000 29.05
ATOM   1041  CG   LYS A 152      13.723  24.774  24.884 1.000 40.50
ATOM   1042  CD   LYS A 152      13.161  25.824  25.832 1.000 34.61
ATOM   1043  CE   LYS A 152      12.890  27.143  25.135 1.000 41.44
ATOM   1044  NZ   LYS A 152      12.672  28.247  26.118 1.000 47.72
ATOM   1045  C    LYS A 152      11.580  22.023  26.534 1.000 32.08
ATOM   1046  O    LYS A 152      10.386  22.284  26.459 1.000 26.51
ATOM   1047  N    CYS A 153      11.986  20.771  26.708 1.000 26.76
ATOM   1048  CA   CYS A 153      11.021  19.668  26.654 1.000 25.46
ATOM   1049  CB   CYS A 153      10.682  19.380  25.189 1.000 21.77
ATOM   1050  SG   CYS A 153       9.398  18.138  24.927 1.000 22.14
ATOM   1051  C    CYS A 153      11.618  18.432  27.306 1.000 26.32
ATOM   1052  O    CYS A 153      12.824  18.201  27.158 1.000 25.23
ATOM   1053  N    ASP A 154      10.807  17.640  27.999 1.000 23.11
ATOM   1054  CA   ASP A 154      11.355  16.378  28.515 1.000 21.66
ATOM   1055  CB   ASP A 154      10.361  15.731  29.473 1.000 21.13
ATOM   1056  CG   ASP A 154      10.962  14.589  30.267 1.000 28.12
ATOM   1057  OD1  ASP A 154      11.961  14.786  30.981 1.000 33.22
ATOM   1058  OD2  ASP A 154      10.428  13.470  30.165 1.000 29.23
ATOM   1059  C    ASP A 154      11.654  15.413  27.380 1.000 25.41
ATOM   1060  O    ASP A 154      10.996  15.507  26.341 1.000 20.63
ATOM   1061  N    HIS A 155      12.599  14.484  27.555 1.000 22.40
ATOM   1062  CA   HIS A 155      12.785  13.364  26.630 1.000 23.74
ATOM   1063  CB   HIS A 155      14.212  12.842  26.726 1.000 20.26
ATOM   1064  CG   HIS A 155      14.625  11.929  25.619 1.000 22.14
ATOM   1065  ND1  HIS A 155      14.138  10.655  25.468 1.000 22.08
ATOM   1066  CE1  HIS A 155      14.671  10.085  24.412 1.000 22.58
ATOM   1067  NE2  HIS A 155      15.510  10.940  23.845 1.000 19.53
ATOM   1068  CD2  HIS A 155      15.484  12.098  24.594 1.000 24.73
ATOM   1069  C    HIS A 155      11.740  12.307  26.966 1.000 21.85
ATOM   1070  O    HIS A 155      11.993  11.292  27.629 1.000 26.15
ATOM   1071  N    TYR A 156      10.500  12.546  26.561 1.000 21.24
ATOM   1072  CA   TYR A 156       9.346  11.821  27.075 1.000 18.68
ATOM   1073  CB   TYR A 156       8.041  12.643  26.958 1.000 17.87
ATOM   1074  CG   TYR A 156       7.765  13.067  25.525 1.000 18.81
ATOM   1075  CD1  TYR A 156       7.032  12.280  24.647 1.000 23.10
ATOM   1076  CE1  TYR A 156       6.778  12.662  23.333 1.000 19.51
ATOM   1077  CZ   TYR A 156       7.267  13.880  22.886 1.000 17.53
ATOM   1078  OH   TYR A 156       7.003  14.236  21.579 1.000 16.54
ATOM   1079  CE2  TYR A 156       7.997  14.689  23.725 1.000 17.15
ATOM   1080  CD2  TYR A 156       8.247  14.285  25.047 1.000 15.43
ATOM   1081  C    TYR A 156       9.152  10.478  26.379 1.000 17.16
ATOM   1082  O    TYR A 156       8.180   9.801  26.732 1.000 17.59
ATOM   1083  N    TRP A 157      10.005  10.148  25.427 1.000 20.71
ATOM   1084  CA   TRP A 157       9.956   8.852  24.736 1.000 21.44
ATOM   1085  CB   TRP A 157       9.852   9.047  23.221 1.000 17.84
ATOM   1086  CG   TRP A 157      11.092   9.674  22.655 1.000 22.69
ATOM   1087  CD1  TRP A 157      12.153   9.009  22.094 1.000 24.11
ATOM   1088  NE1  TRP A 157      13.100   9.922  21.690 1.000 23.85
ATOM   1089  CE2  TRP A 157      12.655  11.191  21.991 1.000 20.42
ATOM   1090  CD2  TRP A 157      11.390  11.072  22.597 1.000 18.79
ATOM   1091  CE3  TRP A 157      10.724  12.233  22.996 1.000 18.30
```

FIGURE 175

```
ATOM   1092  CZ3 TRP A 157      11.325  13.459  22.787 1.000 18.73
ATOM   1093  CH2 TRP A 157      12.582  13.548  22.179 1.000 19.11
ATOM   1094  CZ2 TRP A 157      13.254  12.423  21.783 1.000 16.74
ATOM   1095  C   TRP A 157      11.180   8.027  25.116 1.000 21.33
ATOM   1096  O   TRP A 157      12.146   8.606  25.626 1.000 22.55
ATOM   1097  N   PRO A 158      11.211   6.722  24.940 1.000 25.25
ATOM   1098  CA  PRO A 158      12.363   5.904  25.331 1.000 23.55
ATOM   1099  CB  PRO A 158      11.959   4.495  24.848 1.000 23.59
ATOM   1100  CG  PRO A 158      10.459   4.540  25.001 1.000 24.03
ATOM   1101  CD  PRO A 158      10.115   5.887  24.391 1.000 24.42
ATOM   1102  C   PRO A 158      13.675   6.254  24.671 1.000 22.71
ATOM   1103  O   PRO A 158      13.804   6.665  23.522 1.000 24.60
ATOM   1104  N   ALA A 159      14.735   6.052  25.470 1.000 25.38
ATOM   1105  CA  ALA A 159      16.057   6.433  24.978 1.000 26.79
ATOM   1106  CB  ALA A 159      16.933   6.787  26.175 1.000 30.60
ATOM   1107  C   ALA A 159      16.686   5.340  24.141 1.000 31.84
ATOM   1108  O   ALA A 159      17.702   5.599  23.481 1.000 37.52
ATOM   1109  N   ASP A 160      16.119   4.135  24.142 1.000 24.95
ATOM   1110  CA  ASP A 160      16.648   3.021  23.361 1.000 29.97
ATOM   1111  CB  ASP A 160      17.725   2.249  24.119 1.000 33.98
ATOM   1112  CG  ASP A 160      17.259   1.971  25.541 1.000 35.26
ATOM   1113  OD1 ASP A 160      16.102   1.530  25.682 1.000 31.88
ATOM   1114  OD2 ASP A 160      18.045   2.209  26.482 1.000 37.41
ATOM   1115  C   ASP A 160      15.522   2.053  23.016 1.000 28.09
ATOM   1116  O   ASP A 160      14.364   2.428  23.164 1.000 25.87
ATOM   1117  N   GLN A 161      15.855   0.834  22.622 1.000 24.92
ATOM   1118  CA  GLN A 161      14.765  -0.040  22.162 1.000 23.89
ATOM   1119  CB  GLN A 161      15.223  -0.925  20.993 1.000 30.92
ATOM   1120  CG  GLN A 161      15.788  -0.089  19.845 1.000 45.69
ATOM   1121  CD  GLN A 161      15.671  -0.678  18.458 1.000 48.73
ATOM   1122  OE1 GLN A 161      15.341  -1.845  18.249 1.000 48.46
ATOM   1123  NE2 GLN A 161      15.952   0.136  17.441 1.000 68.57
ATOM   1124  C   GLN A 161      14.187  -0.899  23.271 1.000 24.30
ATOM   1125  O   GLN A 161      13.413  -1.806  22.956 1.000 25.26
ATOM   1126  N   ASP A 162      14.518  -0.604  24.521 1.000 25.88
ATOM   1127  CA  ASP A 162      13.974  -1.361  25.644 1.000 27.98
ATOM   1128  CB  ASP A 162      14.876  -1.203  26.872 1.000 26.59
ATOM   1129  CG  ASP A 162      16.207  -1.921  26.713 1.000 28.66
ATOM   1130  OD1 ASP A 162      16.491  -2.448  25.628 1.000 31.96
ATOM   1131  OD2 ASP A 162      16.968  -1.953  27.694 1.000 34.72
ATOM   1132  C   ASP A 162      12.569  -0.891  25.982 1.000 26.99
ATOM   1133  O   ASP A 162      12.382   0.304  26.182 1.000 27.57
ATOM   1134  N   SER A 163      11.587  -1.785  26.071 1.000 22.21
ATOM   1135  CA  SER A 163      10.208  -1.323  26.297 1.000 18.32
ATOM   1136  CB  SER A 163       9.239  -2.491  26.111 1.000 19.11
ATOM   1137  OG  SER A 163       9.616  -3.639  26.863 1.000 24.74
ATOM   1138  C   SER A 163      10.065  -0.701  27.671 1.000 19.89
ATOM   1139  O   SER A 163      10.822  -1.039  28.596 1.000 23.48
ATOM   1140  N   LEU A 164       9.115   0.215  27.839 1.000 22.10
ATOM   1141  CA  LEU A 164       8.902   0.835  29.142 1.000 25.88
ATOM   1142  CB  LEU A 164       9.650   2.160  29.279 1.000 23.32
ATOM   1143  CG  LEU A 164      11.081   2.263  29.771 1.000 32.69
```

FIGURE 176

```
ATOM   1144  CD1 LEU A 164      11.536   3.726  29.711 1.000 28.59
ATOM   1145  CD2 LEU A 164      11.280   1.731  31.183 1.000 31.11
ATOM   1146  C   LEU A 164       7.421   1.126  29.396 1.000 27.10
ATOM   1147  O   LEU A 164       6.712   1.554  28.476 1.000 18.26
ATOM   1148  N   TYR A 165       6.948   0.930  30.633 1.000 16.81
ATOM   1149  CA  TYR A 165       5.610   1.374  30.989 1.000 15.66
ATOM   1150  CB  TYR A 165       5.152   0.803  32.324 1.000 17.16
ATOM   1151  CG  TYR A 165       4.704  -0.642  32.238 1.000 22.22
ATOM   1152  CD1 TYR A 165       3.479  -0.947  31.670 1.000 22.09
ATOM   1153  CE1 TYR A 165       3.008  -2.244  31.568 1.000 21.78
ATOM   1154  CZ  TYR A 165       3.812  -3.256  32.062 1.000 20.60
ATOM   1155  OH  TYR A 165       3.338  -4.550  31.950 1.000 25.51
ATOM   1156  CE2 TYR A 165       5.032  -2.978  32.631 1.000 18.30
ATOM   1157  CD2 TYR A 165       5.506  -1.670  32.740 1.000 18.57
ATOM   1158  C   TYR A 165       5.563   2.905  31.134 1.000 20.90
ATOM   1159  O   TYR A 165       6.525   3.443  31.688 1.000 19.46
ATOM   1160  N   TYR A 166       4.495   3.530  30.690 1.000 17.57
ATOM   1161  CA  TYR A 166       4.172   4.933  30.964 1.000 16.74
ATOM   1162  CB  TYR A 166       4.262   5.809  29.718 1.000 17.74
ATOM   1163  CG  TYR A 166       5.648   6.083  29.202 1.000 18.55
ATOM   1164  CD1 TYR A 166       6.318   7.284  29.472 1.000 15.85
ATOM   1165  CE1 TYR A 166       7.589   7.509  28.990 1.000 15.83
ATOM   1166  CZ  TYR A 166       8.236   6.569  28.235 1.000 17.11
ATOM   1167  OH  TYR A 166       9.498   6.772  27.739 1.000 21.34
ATOM   1168  CE2 TYR A 166       7.597   5.380  27.954 1.000 20.45
ATOM   1169  CD2 TYR A 166       6.324   5.153  28.434 1.000 19.30
ATOM   1170  C   TYR A 166       2.755   4.969  31.521 1.000 17.54
ATOM   1171  O   TYR A 166       1.784   4.874  30.773 1.000 18.04
ATOM   1172  N   GLY A 167       2.582   5.076  32.829 1.000 18.81
ATOM   1173  CA  GLY A 167       1.205   4.954  33.330 1.000 22.60
ATOM   1174  C   GLY A 167       0.691   3.555  33.040 1.000 22.40
ATOM   1175  O   GLY A 167       1.404   2.570  33.233 1.000 24.80
ATOM   1176  N   ASP A 168      -0.529   3.434  32.527 1.000 21.14
ATOM   1177  CA  ASP A 168      -1.052   2.125  32.187 1.000 19.46
ATOM   1178  CB  ASP A 168      -2.583   2.105  32.330 1.000 19.01
ATOM   1179  CG  ASP A 168      -2.972   2.233  33.792 1.000 29.38
ATOM   1180  OD1 ASP A 168      -2.199   1.795  34.675 1.000 31.79
ATOM   1181  OD2 ASP A 168      -4.064   2.776  34.047 1.000 41.21
ATOM   1182  C   ASP A 168      -0.707   1.690  30.779 1.000 22.83
ATOM   1183  O   ASP A 168      -1.223   0.665  30.330 1.000 32.53
ATOM   1184  N   LEU A 169       0.113   2.428  30.059 1.000 22.05
ATOM   1185  CA  LEU A 169       0.439   2.054  28.685 1.000 20.08
ATOM   1186  CB  LEU A 169       0.372   3.268  27.736 1.000 19.68
ATOM   1187  CG  LEU A 169      -0.925   4.075  27.798 1.000 38.06
ATOM   1188  CD1 LEU A 169      -0.792   5.463  27.170 1.000 25.80
ATOM   1189  CD2 LEU A 169      -2.049   3.304  27.119 1.000 37.43
ATOM   1190  C   LEU A 169       1.840   1.480  28.619 1.000 21.18
ATOM   1191  O   LEU A 169       2.677   1.776  29.476 1.000 22.88
ATOM   1192  N   ILE A 170       2.110   0.675  27.585 1.000 15.34
ATOM   1193  CA  ILE A 170       3.498   0.257  27.438 1.000 16.78
ATOM   1194  CB  ILE A 170       3.759  -1.248  27.605 1.000 23.77
ATOM   1195  CG1 ILE A 170       5.235  -1.602  27.342 1.000 28.45
```

FIGURE 177

```
ATOM   1196  CD1 ILE A 170       5.709  -2.782  28.165 1.000 28.18
ATOM   1197  CG2 ILE A 170       2.849  -2.102  26.746 1.000 23.17
ATOM   1198  C   ILE A 170       3.966   0.706  26.047 1.000 19.57
ATOM   1199  O   ILE A 170       3.177   0.625  25.107 1.000 18.10
ATOM   1200  N   LEU A 171       5.196   1.186  26.013 1.000 19.57
ATOM   1201  CA  LEU A 171       5.709   1.829  24.789 1.000 23.46
ATOM   1202  CB  LEU A 171       5.723   3.318  25.102 1.000 24.58
ATOM   1203  CG  LEU A 171       6.059   4.395  24.098 1.000 38.61
ATOM   1204  CD1 LEU A 171       4.995   4.543  23.027 1.000 29.72
ATOM   1205  CD2 LEU A 171       6.247   5.726  24.826 1.000 32.91
ATOM   1206  C   LEU A 171       7.042   1.210  24.442 1.000 25.87
ATOM   1207  O   LEU A 171       7.863   0.848  25.294 1.000 22.43
ATOM   1208  N   GLN A 172       7.320   1.018  23.159 1.000 18.94
ATOM   1209  CA  GLN A 172       8.609   0.485  22.749 1.000 18.74
ATOM   1210  CB  GLN A 172       8.516  -1.033  22.548 1.000 25.07
ATOM   1211  CG  GLN A 172       9.801  -1.733  22.146 1.000 23.89
ATOM   1212  CD  GLN A 172       9.639  -3.222  21.918 1.000 32.82
ATOM   1213  OE1 GLN A 172       8.737  -3.720  21.242 1.000 36.92
ATOM   1214  NE2 GLN A 172      10.552  -3.981  22.530 1.000 34.84
ATOM   1215  C   GLN A 172       9.049   1.190  21.475 1.000 20.94
ATOM   1216  O   GLN A 172       8.271   1.224  20.521 1.000 27.01
ATOM   1217  N   MET A 173      10.265   1.709  21.448 1.000 21.76
ATOM   1218  CA  MET A 173      10.771   2.361  20.246 1.000 19.32
ATOM   1219  CB  MET A 173      11.848   3.393  20.622 1.000 20.29
ATOM   1220  CG  MET A 173      12.395   4.082  19.350 1.000 23.01
ATOM   1221  SD  MET A 173      13.333   5.573  19.752 1.000 23.47
ATOM   1222  CE  MET A 173      14.788   4.835  20.498 1.000 34.32
ATOM   1223  C   MET A 173      11.331   1.325  19.286 1.000 21.94
ATOM   1224  O   MET A 173      12.211   0.554  19.678 1.000 25.02
ATOM   1225  N   LEU A 174      10.824   1.300  18.058 1.000 21.94
ATOM   1226  CA  LEU A 174      11.188   0.272  17.086 1.000 26.84
ATOM   1227  CB  LEU A 174       9.993  -0.104  16.224 1.000 29.19
ATOM   1228  CG  LEU A 174       8.732  -0.590  16.934 1.000 33.01
ATOM   1229  CD1 LEU A 174       7.688  -0.964  15.897 1.000 29.01
ATOM   1230  CD2 LEU A 174       9.062  -1.757  17.857 1.000 38.21
ATOM   1231  C   LEU A 174      12.299   0.737  16.159 1.000 27.31
ATOM   1232  O   LEU A 174      13.081  -0.049  15.641 1.000 28.22
ATOM   1233  N   SER A 175      12.364   2.050  15.956 1.000 28.86
ATOM   1234  CA  SER A 175      13.420   2.612  15.111 1.000 30.23
ATOM   1235  CB  SER A 175      13.135   2.372  13.626 1.000 29.79
ATOM   1236  OG  SER A 175      12.320   3.403  13.111 1.000 28.04
ATOM   1237  C   SER A 175      13.595   4.101  15.397 1.000 22.48
ATOM   1238  O   SER A 175      12.690   4.787  15.885 1.000 22.47
ATOM   1239  N   GLU A 176      14.798   4.562  15.104 1.000 20.99
ATOM   1240  CA  GLU A 176      15.204   5.939  15.322 1.000 21.52
ATOM   1241  CB  GLU A 176      15.885   6.109  16.674 1.000 18.41
ATOM   1242  CG  GLU A 176      16.366   7.514  16.976 1.000 22.49
ATOM   1243  CD  GLU A 176      16.890   7.563  18.413 1.000 39.47
ATOM   1244  OE1 GLU A 176      18.041   7.104  18.596 1.000 35.29
ATOM   1245  OE2 GLU A 176      16.182   8.023  19.331 1.000 26.84
ATOM   1246  C   GLU A 176      16.158   6.334  14.203 1.000 35.39
ATOM   1247  O   GLU A 176      17.237   5.756  14.149 1.000 26.11
```

FIGURE 178

```
ATOM   1248  N    SER A 177      15.754   7.260  13.341  1.000 26.10
ATOM   1249  CA   SER A 177      16.562   7.596  12.175  1.000 22.13
ATOM   1250  CB   SER A 177      15.850   7.215  10.880  1.000 24.63
ATOM   1251  OG   SER A 177      15.442   5.858  10.852  1.000 32.57
ATOM   1252  C    SER A 177      16.888   9.079  12.211  1.000 19.74
ATOM   1253  O    SER A 177      16.041   9.955  12.003  1.000 24.72
ATOM   1254  N    VAL A 178      18.142   9.387  12.521  1.000 21.76
ATOM   1255  CA   VAL A 178      18.577  10.766  12.651  1.000 20.70
ATOM   1256  CB   VAL A 178      19.777  10.890  13.604  1.000 30.20
ATOM   1257  CG1  VAL A 178      20.138  12.353  13.823  1.000 22.39
ATOM   1258  CG2  VAL A 178      19.478  10.224  14.943  1.000 30.74
ATOM   1259  C    VAL A 178      18.959  11.311  11.280  1.000 27.01
ATOM   1260  O    VAL A 178      19.885  10.794  10.652  1.000 26.60
ATOM   1261  N    LEU A 179      18.244  12.333  10.828  1.000 23.24
ATOM   1262  CA   LEU A 179      18.550  12.947   9.541  1.000 17.95
ATOM   1263  CB   LEU A 179      17.292  12.950   8.668  1.000 19.90
ATOM   1264  CG   LEU A 179      16.414  11.712   8.694  1.000 19.48
ATOM   1265  CD1  LEU A 179      15.201  11.861   7.765  1.000 20.09
ATOM   1266  CD2  LEU A 179      17.209  10.467   8.304  1.000 23.69
ATOM   1267  C    LEU A 179      19.119  14.337   9.791  1.000 22.68
ATOM   1268  O    LEU A 179      19.079  14.824  10.939  1.000 23.34
ATOM   1269  N    PRO A 180      19.677  15.022   8.798  1.000 26.71
ATOM   1270  CA   PRO A 180      20.320  16.317   9.086  1.000 23.99
ATOM   1271  CB   PRO A 180      20.700  16.849   7.686  1.000 24.76
ATOM   1272  CG   PRO A 180      20.859  15.612   6.863  1.000 30.87
ATOM   1273  CD   PRO A 180      19.801  14.649   7.378  1.000 29.95
ATOM   1274  C    PRO A 180      19.439  17.339   9.771  1.000 23.60
ATOM   1275  O    PRO A 180      19.901  18.080  10.636  1.000 22.88
ATOM   1276  N    GLU A 181      18.151  17.441   9.439  1.000 21.19
ATOM   1277  CA   GLU A 181      17.363  18.480  10.078  1.000 21.28
ATOM   1278  CB   GLU A 181      16.858  19.455   8.991  1.000 24.45
ATOM   1279  CG   GLU A 181      18.003  20.315   8.476  1.000 34.87
ATOM   1280  CD   GLU A 181      17.596  21.325   7.421  1.000 37.86
ATOM   1281  OE1  GLU A 181      16.746  21.008   6.567  1.000 32.02
ATOM   1282  OE2  GLU A 181      18.154  22.440   7.452  1.000 44.17
ATOM   1283  C    GLU A 181      16.178  17.945  10.870  1.000 17.99
ATOM   1284  O    GLU A 181      15.507  18.740  11.537  1.000 19.13
ATOM   1285  N    TRP A 182      15.906  16.648  10.817  1.000 23.72
ATOM   1286  CA   TRP A 182      14.848  16.095  11.672  1.000 20.93
ATOM   1287  CB   TRP A 182      13.432  16.217  11.113  1.000 15.09
ATOM   1288  CG   TRP A 182      13.192  15.913   9.681  1.000 16.03
ATOM   1289  CD1  TRP A 182      12.852  14.727   9.123  1.000 20.35
ATOM   1290  NE1  TRP A 182      12.715  14.821   7.763  1.000 23.86
ATOM   1291  CE2  TRP A 182      12.971  16.112   7.407  1.000 15.42
ATOM   1292  CD2  TRP A 182      13.275  16.826   8.568  1.000 18.32
ATOM   1293  CE3  TRP A 182      13.583  18.197   8.484  1.000 18.38
ATOM   1294  CZ3  TRP A 182      13.571  18.785   7.229  1.000 19.84
ATOM   1295  CH2  TRP A 182      13.261  18.032   6.085  1.000 21.10
ATOM   1296  CZ2  TRP A 182      12.956  16.698   6.134  1.000 18.37
ATOM   1297  C    TRP A 182      15.188  14.629  11.929  1.000 21.61
ATOM   1298  O    TRP A 182      15.996  14.011  11.228  1.000 21.72
ATOM   1299  N    THR A 183      14.549  14.085  12.961  1.000 18.39
```

FIGURE 179

```
ATOM   1300  CA  THR A 183      14.699  12.677  13.292  1.000 20.50
ATOM   1301  CB  THR A 183      15.328  12.553  14.701  1.000 23.44
ATOM   1302  OG1 THR A 183      16.636  13.143  14.619  1.000 24.00
ATOM   1303  CG2 THR A 183      15.453  11.104  15.137  1.000 21.54
ATOM   1304  C   THR A 183      13.349  11.988  13.226  1.000 16.48
ATOM   1305  O   THR A 183      12.354  12.543  13.710  1.000 18.87
ATOM   1306  N   ILE A 184      13.301  10.809  12.641  1.000 15.19
ATOM   1307  CA  ILE A 184      12.051  10.059  12.556  1.000 15.66
ATOM   1308  CB  ILE A 184      11.775   9.676  11.096  1.000 19.83
ATOM   1309  CG1 ILE A 184      11.821  10.921  10.196  1.000 20.74
ATOM   1310  CD1 ILE A 184      11.379  10.717   8.765  1.000 23.01
ATOM   1311  CG2 ILE A 184      10.481   8.900  10.978  1.000 19.48
ATOM   1312  C   ILE A 184      12.134   8.828  13.450  1.000 25.32
ATOM   1313  O   ILE A 184      13.056   8.018  13.311  1.000 28.73
ATOM   1314  N   ARG A 185      11.189   8.678  14.370  1.000 21.95
ATOM   1315  CA  ARG A 185      11.171   7.501  15.231  1.000 19.00
ATOM   1316  CB  ARG A 185      11.381   7.882  16.693  1.000 17.64
ATOM   1317  CG  ARG A 185      12.739   8.478  17.011  1.000 22.12
ATOM   1318  CD  ARG A 185      12.764   9.060  18.407  1.000 22.23
ATOM   1319  NE  ARG A 185      13.977   9.765  18.768  1.000 27.88
ATOM   1320  CZ  ARG A 185      14.318  11.031  18.624  1.000 22.96
ATOM   1321  NH1 ARG A 185      13.515  11.930  18.062  1.000 21.31
ATOM   1322  NH2 ARG A 185      15.513  11.426  19.056  1.000 28.28
ATOM   1323  C   ARG A 185       9.836   6.796  15.067  1.000 20.34
ATOM   1324  O   ARG A 185       8.827   7.415  14.740  1.000 19.60
ATOM   1325  N   GLU A 186       9.842   5.499  15.318  1.000 21.83
ATOM   1326  CA  GLU A 186       8.590   4.756  15.330  1.000 19.84
ATOM   1327  CB  GLU A 186       8.495   3.779  14.165  1.000 27.08
ATOM   1328  CG  GLU A 186       7.086   3.286  13.877  1.000 38.65
ATOM   1329  CD  GLU A 186       6.961   2.255  12.778  1.000 49.85
ATOM   1330  OE1 GLU A 186       7.958   1.554  12.481  1.000 59.07
ATOM   1331  OE2 GLU A 186       5.874   2.119  12.169  1.000 41.81
ATOM   1332  C   GLU A 186       8.507   4.004  16.664  1.000 24.47
ATOM   1333  O   GLU A 186       9.494   3.391  17.085  1.000 28.68
ATOM   1334  N   PHE A 187       7.342   4.092  17.281  1.000 21.26
ATOM   1335  CA  PHE A 187       7.016   3.401  18.513  1.000 17.58
ATOM   1336  CB  PHE A 187       6.609   4.390  19.609  1.000 19.02
ATOM   1337  CG  PHE A 187       7.601   5.542  19.741  1.000 26.16
ATOM   1338  CD1 PHE A 187       7.288   6.798  19.268  1.000 22.44
ATOM   1339  CE1 PHE A 187       8.192   7.832  19.409  1.000 30.77
ATOM   1340  CZ  PHE A 187       9.428   7.634  19.993  1.000 26.12
ATOM   1341  CE2 PHE A 187       9.746   6.376  20.477  1.000 27.12
ATOM   1342  CD2 PHE A 187       8.832   5.341  20.350  1.000 25.25
ATOM   1343  C   PHE A 187       5.836   2.453  18.339  1.000 20.12
ATOM   1344  O   PHE A 187       4.844   2.733  17.687  1.000 23.02
ATOM   1345  N   LYS A 188       5.969   1.320  19.015  1.000 29.00
ATOM   1346  CA  LYS A 188       4.814   0.486  19.315  1.000 23.44
ATOM   1347  CB  LYS A 188       5.229  -0.986  19.280  1.000 29.53
ATOM   1348  CG  LYS A 188       4.064  -1.959  19.180  1.000 41.78
ATOM   1349  CD  LYS A 188       4.560  -3.360  18.830  1.000 46.50
ATOM   1350  CE  LYS A 188       5.255  -3.976  20.036  1.000 45.29
ATOM   1351  NZ  LYS A 188       5.958  -5.246  19.707  1.000 51.18
```

FIGURE 180

| | | | | | | | | | |
|---|---|---|---|---|---|---|---|---|---|
| ATOM | 1352 | C | LYS | A | 188 | 4.247 | 0.908 | 20.669 | 1.000 21.37 |
| ATOM | 1353 | O | LYS | A | 188 | 4.984 | 1.012 | 21.650 | 1.000 20.70 |
| ATOM | 1354 | N | ILE | A | 189 | 2.942 | 1.151 | 20.722 | 1.000 19.68 |
| ATOM | 1355 | CA | ILE | A | 189 | 2.280 | 1.419 | 21.990 | 1.000 20.68 |
| ATOM | 1356 | CB | ILE | A | 189 | 1.712 | 2.853 | 22.019 | 1.000 26.52 |
| ATOM | 1357 | CG1 | ILE | A | 189 | 1.092 | 3.235 | 23.363 | 1.000 22.26 |
| ATOM | 1358 | CD1 | ILE | A | 189 | 0.940 | 4.748 | 23.485 | 1.000 39.28 |
| ATOM | 1359 | CG2 | ILE | A | 189 | 0.721 | 3.104 | 20.879 | 1.000 26.76 |
| ATOM | 1360 | C | ILE | A | 189 | 1.160 | 0.429 | 22.259 | 1.000 25.87 |
| ATOM | 1361 | O | ILE | A | 189 | 0.397 | 0.070 | 21.351 | 1.000 23.56 |
| ATOM | 1362 | N | CYS | A | 190 | 1.032 | -0.021 | 23.514 | 1.000 24.27 |
| ATOM | 1363 | CA | CYS | A | 190 | -0.078 | -0.912 | 23.859 | 1.000 21.00 |
| ATOM | 1364 | CB | CYS | A | 190 | 0.402 | -2.336 | 24.179 | 1.000 28.92 |
| ATOM | 1365 | SG | CYS | A | 190 | 1.318 | -3.174 | 22.867 | 1.000 32.32 |
| ATOM | 1366 | C | CYS | A | 190 | -0.838 | -0.365 | 25.055 | 1.000 26.90 |
| ATOM | 1367 | O | CYS | A | 190 | -0.279 | -0.024 | 26.098 | 1.000 22.81 |
| ATOM | 1368 | N | GLY | A | 191 | -2.159 | -0.270 | 24.946 | 1.000 28.18 |
| ATOM | 1369 | CA | GLY | A | 191 | -2.883 | 0.291 | 26.094 | 1.000 35.73 |
| ATOM | 1370 | C | GLY | A | 191 | -4.150 | -0.485 | 26.348 | 1.000 42.74 |
| ATOM | 1371 | O | GLY | A | 191 | -4.326 | -1.578 | 25.793 | 1.000 32.85 |
| ATOM | 1372 | N | GLU | A | 192 | -5.093 | -0.003 | 27.180 | 1.000 51.55 |
| ATOM | 1373 | CA | GLU | A | 192 | -6.223 | -0.938 | 27.283 | 1.000 66.18 |
| ATOM | 1374 | CB | GLU | A | 192 | -7.133 | -0.742 | 28.489 | 1.000 76.10 |
| ATOM | 1375 | CG | GLU | A | 192 | -7.860 | -2.067 | 28.785 | 1.000 85.72 |
| ATOM | 1376 | CD | GLU | A | 192 | -7.026 | -3.266 | 28.356 | 1.000 87.86 |
| ATOM | 1377 | OE1 | GLU | A | 192 | -6.184 | -3.687 | 29.190 | 1.000106.89 |
| ATOM | 1378 | OE2 | GLU | A | 192 | -7.174 | -3.794 | 27.229 | 1.000 63.79 |
| ATOM | 1379 | C | GLU | A | 192 | -7.019 | -0.844 | 25.974 | 1.000 60.51 |
| ATOM | 1380 | O | GLU | A | 192 | -7.455 | 0.251 | 25.638 | 1.000 49.89 |
| ATOM | 1381 | N | GLU | A | 193 | -7.112 | -1.996 | 25.326 | 1.000 57.69 |
| ATOM | 1382 | CA | GLU | A | 193 | -7.600 | -2.127 | 23.973 | 1.000 58.03 |
| ATOM | 1383 | CB | GLU | A | 193 | -7.726 | -3.604 | 23.546 | 1.000 59.99 |
| ATOM | 1384 | CG | GLU | A | 193 | -8.209 | -3.661 | 22.102 | 1.000 70.62 |
| ATOM | 1385 | CD | GLU | A | 193 | -8.606 | -5.058 | 21.671 | 1.000 69.93 |
| ATOM | 1386 | OE1 | GLU | A | 193 | -9.439 | -5.674 | 22.369 | 1.000 80.76 |
| ATOM | 1387 | OE2 | GLU | A | 193 | -8.081 | -5.511 | 20.636 | 1.000 63.90 |
| ATOM | 1388 | C | GLU | A | 193 | -8.963 | -1.475 | 23.781 | 1.000 64.42 |
| ATOM | 1389 | O | GLU | A | 193 | -9.945 | -1.868 | 24.403 | 1.000100.70 |
| ATOM | 1390 | N | GLN | A | 194 | -9.008 | -0.492 | 22.895 | 1.000 65.44 |
| ATOM | 1391 | CA | GLN | A | 194 | -10.257 | 0.128 | 22.460 | 1.000 65.33 |
| ATOM | 1392 | CB | GLN | A | 194 | -10.256 | 1.622 | 22.773 | 1.000 59.27 |
| ATOM | 1393 | CG | GLN | A | 194 | -8.915 | 2.066 | 23.359 | 1.000 64.93 |
| ATOM | 1394 | CD | GLN | A | 194 | -8.739 | 3.571 | 23.383 | 1.000 63.48 |
| ATOM | 1395 | OE1 | GLN | A | 194 | -8.193 | 4.160 | 22.449 | 1.000 39.84 |
| ATOM | 1396 | NE2 | GLN | A | 194 | -9.206 | 4.183 | 24.467 | 1.000 72.21 |
| ATOM | 1397 | C | GLN | A | 194 | -10.409 | -0.139 | 20.964 | 1.000 65.87 |
| ATOM | 1398 | O | GLN | A | 194 | -10.725 | -1.270 | 20.581 | 1.000 56.74 |
| ATOM | 1399 | N | LEU | A | 195 | -10.151 | 0.891 | 20.161 | 1.000 58.59 |
| ATOM | 1400 | CA | LEU | A | 195 | -10.167 | 0.734 | 18.707 | 1.000 53.57 |
| ATOM | 1401 | CB | LEU | A | 195 | -10.095 | 2.103 | 18.027 | 1.000 34.01 |
| ATOM | 1402 | CG | LEU | A | 195 | -11.473 | 2.711 | 17.749 | 1.000 52.84 |
| ATOM | 1403 | CD1 | LEU | A | 195 | -11.369 | 4.144 | 17.248 | 1.000 64.31 |

FIGURE 181

| | | | | | | | | | |
|---|---|---|---|---|---|---|---|---|---|
| ATOM | 1404 | CD2 | LEU | A | 195 | -12.213 | 1.828 | 16.745 | 1.000 77.61 |
| ATOM | 1405 | C | LEU | A | 195 | -9.029 | -0.175 | 18.251 | 1.000 62.19 |
| ATOM | 1406 | O | LEU | A | 195 | -9.207 | -0.990 | 17.345 | 1.000 74.97 |
| ATOM | 1407 | N | ASP | A | 196 | -7.874 | -0.040 | 18.893 | 1.000 64.63 |
| ATOM | 1408 | CA | ASP | A | 196 | -6.730 | -0.907 | 18.651 | 1.000 71.88 |
| ATOM | 1409 | CB | ASP | A | 196 | -5.616 | -0.149 | 17.929 | 1.000 69.22 |
| ATOM | 1410 | CG | ASP | A | 196 | -5.589 | 1.331 | 18.254 | 1.000 68.85 |
| ATOM | 1411 | OD1 | ASP | A | 196 | -5.984 | 1.716 | 19.374 | 1.000 46.56 |
| ATOM | 1412 | OD2 | ASP | A | 196 | -5.168 | 2.105 | 17.363 | 1.000 68.77 |
| ATOM | 1413 | C | ASP | A | 196 | -6.197 | -1.496 | 19.959 | 1.000 75.55 |
| ATOM | 1414 | O | ASP | A | 196 | -6.396 | -0.908 | 21.026 | 1.000 52.97 |
| ATOM | 1415 | N | ALA | A | 197 | -5.530 | -2.643 | 19.864 | 1.000 77.66 |
| ATOM | 1416 | CA | ALA | A | 197 | -4.895 | -3.267 | 21.020 | 1.000 76.86 |
| ATOM | 1417 | CB | ALA | A | 197 | -5.256 | -4.738 | 21.113 | 1.000 89.29 |
| ATOM | 1418 | C | ALA | A | 197 | -3.376 | -3.077 | 20.976 | 1.000 70.52 |
| ATOM | 1419 | O | ALA | A | 197 | -2.709 | -3.074 | 22.013 | 1.000 40.24 |
| ATOM | 1420 | N | HIS | A | 198 | -2.852 | -2.910 | 19.772 | 1.000 66.05 |
| ATOM | 1421 | CA | HIS | A | 198 | -1.497 | -2.444 | 19.510 | 1.000 70.91 |
| ATOM | 1422 | CB | HIS | A | 198 | -0.565 | -3.597 | 19.162 | 1.000 75.50 |
| ATOM | 1423 | CG | HIS | A | 198 | -1.090 | -4.481 | 18.069 | 1.000 88.48 |
| ATOM | 1424 | ND1 | HIS | A | 198 | -1.492 | -5.779 | 18.290 | 1.000 94.26 |
| ATOM | 1425 | CE1 | HIS | A | 198 | -1.906 | -6.315 | 17.155 | 1.000 93.97 |
| ATOM | 1426 | NE2 | HIS | A | 198 | -1.788 | -5.411 | 16.199 | 1.000 94.98 |
| ATOM | 1427 | CD2 | HIS | A | 198 | -1.280 | -4.259 | 16.747 | 1.000 92.03 |
| ATOM | 1428 | C | HIS | A | 198 | -1.534 | -1.404 | 18.383 | 1.000 71.60 |
| ATOM | 1429 | O | HIS | A | 198 | -2.374 | -1.488 | 17.480 | 1.000 79.54 |
| ATOM | 1430 | N | ARG | A | 199 | -0.649 | -0.416 | 18.408 | 1.000 59.29 |
| ATOM | 1431 | CA | ARG | A | 199 | -0.625 | 0.649 | 17.409 | 1.000 35.48 |
| ATOM | 1432 | CB | ARG | A | 199 | -1.445 | 1.854 | 17.881 | 1.000 27.18 |
| ATOM | 1433 | CG | ARG | A | 199 | -1.499 | 2.997 | 16.876 | 1.000 28.09 |
| ATOM | 1434 | CD | ARG | A | 199 | -2.136 | 4.248 | 17.473 | 1.000 30.52 |
| ATOM | 1435 | NE | ARG | A | 199 | -3.326 | 3.985 | 18.281 | 1.000 24.15 |
| ATOM | 1436 | CZ | ARG | A | 199 | -3.802 | 4.809 | 19.209 | 1.000 28.77 |
| ATOM | 1437 | NH1 | ARG | A | 199 | -3.159 | 5.961 | 19.433 | 1.000 21.27 |
| ATOM | 1438 | NH2 | ARG | A | 199 | -4.894 | 4.481 | 19.891 | 1.000 20.72 |
| ATOM | 1439 | C | ARG | A | 199 | 0.811 | 1.091 | 17.148 | 1.000 34.48 |
| ATOM | 1440 | O | ARG | A | 199 | 1.652 | 1.004 | 18.041 | 1.000 33.43 |
| ATOM | 1441 | N | LEU | A | 200 | 1.073 | 1.574 | 15.945 | 1.000 25.06 |
| ATOM | 1442 | CA | LEU | A | 200 | 2.347 | 2.162 | 15.564 | 1.000 24.44 |
| ATOM | 1443 | CB | LEU | A | 200 | 2.763 | 1.609 | 14.186 | 1.000 33.41 |
| ATOM | 1444 | CG | LEU | A | 200 | 2.956 | 0.076 | 14.187 | 1.000 38.30 |
| ATOM | 1445 | CD1 | LEU | A | 200 | 3.183 | -0.457 | 12.783 | 1.000 34.53 |
| ATOM | 1446 | CD2 | LEU | A | 200 | 4.085 | -0.324 | 15.136 | 1.000 24.70 |
| ATOM | 1447 | C | LEU | A | 200 | 2.247 | 3.680 | 15.530 | 1.000 27.60 |
| ATOM | 1448 | O | LEU | A | 200 | 1.329 | 4.254 | 14.940 | 1.000 27.27 |
| ATOM | 1449 | N | ILE | A | 201 | 3.190 | 4.352 | 16.167 | 1.000 21.65 |
| ATOM | 1450 | CA | ILE | A | 201 | 3.223 | 5.805 | 16.195 | 1.000 19.45 |
| ATOM | 1451 | CB | ILE | A | 201 | 3.243 | 6.350 | 17.634 | 1.000 23.93 |
| ATOM | 1452 | CG1 | ILE | A | 201 | 2.224 | 5.707 | 18.555 | 1.000 27.08 |
| ATOM | 1453 | CD1 | ILE | A | 201 | 0.840 | 6.267 | 18.547 | 1.000 32.15 |
| ATOM | 1454 | CG2 | ILE | A | 201 | 3.105 | 7.874 | 17.627 | 1.000 22.88 |
| ATOM | 1455 | C | ILE | A | 201 | 4.494 | 6.275 | 15.498 | 1.000 16.73 |

FIGURE 182

| | | | | | | | | |
|---|---|---|---|---|---|---|---|---|
| ATOM | 1456 | O | ILE | A 201 | 5.543 | 5.697 | 15.797 | 1.000 21.43 |
| ATOM | 1457 | N | ARG | A 202 | 4.395 | 7.244 | 14.609 | 1.000 15.34 |
| ATOM | 1458 | CA | ARG | A 202 | 5.529 | 7.874 | 13.952 | 1.000 13.92 |
| ATOM | 1459 | CB | ARG | A 202 | 5.344 | 8.052 | 12.442 | 1.000 21.70 |
| ATOM | 1460 | CG | ARG | A 202 | 4.824 | 6.798 | 11.747 | 1.000 37.52 |
| ATOM | 1461 | CD | ARG | A 202 | 5.397 | 6.648 | 10.346 | 1.000 48.86 |
| ATOM | 1462 | NE | ARG | A 202 | 6.613 | 5.885 | 10.269 | 1.000 46.03 |
| ATOM | 1463 | CZ | ARG | A 202 | 7.751 | 6.058 | 9.632 | 1.000 45.70 |
| ATOM | 1464 | NH1 | ARG | A 202 | 8.037 | 7.082 | 8.834 | 1.000 37.98 |
| ATOM | 1465 | NH2 | ARG | A 202 | 8.673 | 5.112 | 9.812 | 1.000 32.36 |
| ATOM | 1466 | C | ARG | A 202 | 5.730 | 9.248 | 14.587 | 1.000 16.51 |
| ATOM | 1467 | O | ARG | A 202 | 4.762 | 9.959 | 14.863 | 1.000 18.08 |
| ATOM | 1468 | N | HIS | A 203 | 6.987 | 9.543 | 14.854 | 1.000 17.20 |
| ATOM | 1469 | CA | HIS | A 203 | 7.433 | 10.725 | 15.560 | 1.000 16.92 |
| ATOM | 1470 | CB | HIS | A 203 | 8.142 | 10.336 | 16.854 | 1.000 20.76 |
| ATOM | 1471 | CG | HIS | A 203 | 8.421 | 11.450 | 17.803 | 1.000 16.82 |
| ATOM | 1472 | ND1 | HIS | A 203 | 9.626 | 12.125 | 17.837 | 1.000 21.78 |
| ATOM | 1473 | CE1 | HIS | A 203 | 9.592 | 13.064 | 18.762 | 1.000 18.85 |
| ATOM | 1474 | NE2 | HIS | A 203 | 8.404 | 13.021 | 19.331 | 1.000 19.59 |
| ATOM | 1475 | CD2 | HIS | A 203 | 7.654 | 12.037 | 18.755 | 1.000 16.71 |
| ATOM | 1476 | C | HIS | A 203 | 8.357 | 11.516 | 14.629 | 1.000 15.29 |
| ATOM | 1477 | O | HIS | A 203 | 9.374 | 10.977 | 14.206 | 1.000 20.50 |
| ATOM | 1478 | N | PHE | A 204 | 7.949 | 12.737 | 14.315 | 1.000 19.40 |
| ATOM | 1479 | CA | PHE | A 204 | 8.668 | 13.627 | 13.398 | 1.000 22.59 |
| ATOM | 1480 | CB | PHE | A 204 | 7.750 | 14.112 | 12.280 | 1.000 16.25 |
| ATOM | 1481 | CG | PHE | A 204 | 7.133 | 12.949 | 11.535 | 1.000 19.17 |
| ATOM | 1482 | CD1 | PHE | A 204 | 5.859 | 12.519 | 11.888 | 1.000 20.80 |
| ATOM | 1483 | CE1 | PHE | A 204 | 5.296 | 11.466 | 11.195 | 1.000 18.80 |
| ATOM | 1484 | CZ | PHE | A 204 | 5.976 | 10.843 | 10.173 | 1.000 24.56 |
| ATOM | 1485 | CE2 | PHE | A 204 | 7.246 | 11.266 | 9.820 | 1.000 23.53 |
| ATOM | 1486 | CD2 | PHE | A 204 | 7.825 | 12.307 | 10.529 | 1.000 21.57 |
| ATOM | 1487 | C | PHE | A 204 | 9.237 | 14.789 | 14.191 | 1.000 15.29 |
| ATOM | 1488 | O | PHE | A 204 | 8.545 | 15.706 | 14.632 | 1.000 18.02 |
| ATOM | 1489 | N | HIS | A 205 | 10.552 | 14.693 | 14.407 | 1.000 17.57 |
| ATOM | 1490 | CA | HIS | A 205 | 11.231 | 15.586 | 15.336 | 1.000 20.77 |
| ATOM | 1491 | CB | HIS | A 205 | 12.017 | 14.705 | 16.297 | 1.000 22.15 |
| ATOM | 1492 | CG | HIS | A 205 | 12.733 | 15.407 | 17.404 | 1.000 23.38 |
| ATOM | 1493 | ND1 | HIS | A 205 | 12.618 | 16.749 | 17.686 | 1.000 28.56 |
| ATOM | 1494 | CE1 | HIS | A 205 | 13.372 | 17.053 | 18.726 | 1.000 22.17 |
| ATOM | 1495 | NE2 | HIS | A 205 | 13.982 | 15.963 | 19.129 | 1.000 23.37 |
| ATOM | 1496 | CD2 | HIS | A 205 | 13.598 | 14.913 | 18.326 | 1.000 19.72 |
| ATOM | 1497 | C | HIS | A 205 | 12.140 | 16.556 | 14.583 | 1.000 20.64 |
| ATOM | 1498 | O | HIS | A 205 | 13.207 | 16.157 | 14.120 | 1.000 20.31 |
| ATOM | 1499 | N | TYR | A 206 | 11.736 | 17.808 | 14.448 | 1.000 20.99 |
| ATOM | 1500 | CA | TYR | A 206 | 12.552 | 18.816 | 13.771 | 1.000 18.48 |
| ATOM | 1501 | CB | TYR | A 206 | 11.683 | 19.944 | 13.305 | 1.000 21.09 |
| ATOM | 1502 | CG | TYR | A 206 | 12.270 | 20.944 | 12.340 | 1.000 17.56 |
| ATOM | 1503 | CD1 | TYR | A 206 | 12.517 | 20.592 | 11.011 | 1.000 16.37 |
| ATOM | 1504 | CE1 | TYR | A 206 | 13.048 | 21.568 | 10.167 | 1.000 22.62 |
| ATOM | 1505 | CZ | TYR | A 206 | 13.294 | 22.833 | 10.665 | 1.000 23.75 |
| ATOM | 1506 | OH | TYR | A 206 | 13.820 | 23.786 | 9.833 | 1.000 24.85 |
| ATOM | 1507 | CE2 | TYR | A 206 | 13.044 | 23.195 | 11.972 | 1.000 25.09 |

FIGURE 183

```
ATOM   1508  CD2 TYR A 206      12.518  22.219  12.812  1.000  22.77
ATOM   1509  C   TYR A 206      13.580  19.341  14.783  1.000  16.12
ATOM   1510  O   TYR A 206      13.165  19.799  15.824  1.000  21.03
ATOM   1511  N   THR A 207      14.855  19.255  14.458  1.000  20.95
ATOM   1512  CA  THR A 207      15.937  19.446  15.406  1.000  25.39
ATOM   1513  CB  THR A 207      16.825  18.181  15.436  1.000  21.21
ATOM   1514  OG1 THR A 207      17.300  17.892  14.110  1.000  24.55
ATOM   1515  CG2 THR A 207      16.034  16.975  15.913  1.000  20.79
ATOM   1516  C   THR A 207      16.791  20.668  15.090  1.000  29.49
ATOM   1517  O   THR A 207      17.837  20.877  15.720  1.000  27.61
ATOM   1518  N   VAL A 208      16.366  21.501  14.140  1.000  24.45
ATOM   1519  CA  VAL A 208      17.216  22.662  13.859  1.000  21.06
ATOM   1520  CB  VAL A 208      17.883  22.496  12.481  1.000  28.39
ATOM   1521  CG1 VAL A 208      18.791  21.272  12.532  1.000  23.56
ATOM   1522  CG2 VAL A 208      16.849  22.387  11.368  1.000  20.57
ATOM   1523  C   VAL A 208      16.523  23.999  13.935  1.000  31.86
ATOM   1524  O   VAL A 208      17.084  24.981  13.417  1.000  27.99
ATOM   1525  N   TRP A 209      15.359  24.144  14.567  1.000  26.72
ATOM   1526  CA  TRP A 209      14.797  25.499  14.665  1.000  30.27
ATOM   1527  CB  TRP A 209      13.424  25.461  15.322  1.000  28.47
ATOM   1528  CG  TRP A 209      12.553  26.652  15.078  1.000  31.11
ATOM   1529  CD1 TRP A 209      12.747  27.933  15.523  1.000  31.15
ATOM   1530  NE1 TRP A 209      11.725  28.752  15.093  1.000  28.46
ATOM   1531  CE2 TRP A 209      10.845  28.000  14.356  1.000  28.45
ATOM   1532  CD2 TRP A 209      11.331  26.678  14.325  1.000  27.55
ATOM   1533  CE3 TRP A 209      10.611  25.704  13.629  1.000  22.81
ATOM   1534  CZ3 TRP A 209       9.445  26.095  13.005  1.000  25.86
ATOM   1535  CH2 TRP A 209       8.973  27.410  13.044  1.000  21.32
ATOM   1536  CZ2 TRP A 209       9.666  28.388  13.720  1.000  25.69
ATOM   1537  C   TRP A 209      15.756  26.384  15.452  1.000  27.61
ATOM   1538  O   TRP A 209      16.199  25.947  16.515  1.000  25.68
ATOM   1539  N   PRO A 210      16.119  27.575  15.000  1.000  24.36
ATOM   1540  CA  PRO A 210      17.083  28.369  15.787  1.000  26.72
ATOM   1541  CB  PRO A 210      17.398  29.537  14.854  1.000  23.52
ATOM   1542  CG  PRO A 210      16.330  29.568  13.828  1.000  30.83
ATOM   1543  CD  PRO A 210      15.721  28.197  13.735  1.000  24.56
ATOM   1544  C   PRO A 210      16.551  28.877  17.112  1.000  29.12
ATOM   1545  O   PRO A 210      15.359  29.056  17.335  1.000  26.48
ATOM   1546  N   ASP A 211      17.443  29.158  18.079  1.000  39.44
ATOM   1547  CA  ASP A 211      17.006  29.720  19.366  1.000  34.21
ATOM   1548  CB  ASP A 211      18.098  29.809  20.429  1.000  42.94
ATOM   1549  CG  ASP A 211      19.528  29.592  20.007  1.000  62.84
ATOM   1550  OD1 ASP A 211      20.028  30.231  19.044  1.000  74.38
ATOM   1551  OD2 ASP A 211      20.212  28.773  20.663  1.000  76.33
ATOM   1552  C   ASP A 211      16.433  31.124  19.187  1.000  35.17
ATOM   1553  O   ASP A 211      15.656  31.640  19.987  1.000  38.20
ATOM   1554  N   HIS A 212      16.818  31.816  18.113  1.000  39.51
ATOM   1555  CA  HIS A 212      16.184  33.125  17.909  1.000  42.28
ATOM   1556  CB  HIS A 212      17.197  34.250  18.143  1.000  51.96
ATOM   1557  CG  HIS A 212      17.690  34.249  19.563  1.000  70.14
ATOM   1558  ND1 HIS A 212      18.969  33.878  19.916  1.000  72.27
ATOM   1559  CE1 HIS A 212      19.109  33.968  21.227  1.000  71.31
```

FIGURE 184

```
ATOM   1560  NE2 HIS A 212      17.962  34.385  21.735 1.000 73.22
ATOM   1561  CD2 HIS A 212      17.056  34.563  20.718 1.000 71.91
ATOM   1562  C   HIS A 212      15.568  33.188  16.521 1.000 35.23
ATOM   1563  O   HIS A 212      16.155  32.711  15.551 1.000 36.51
ATOM   1564  N   GLY A 213      14.380  33.777  16.425 1.000 39.89
ATOM   1565  CA  GLY A 213      13.712  33.934  15.149 1.000 35.59
ATOM   1566  C   GLY A 213      13.306  32.607  14.530 1.000 40.76
ATOM   1567  O   GLY A 213      13.230  31.604  15.240 1.000 29.83
ATOM   1568  N   VAL A 214      13.073  32.661  13.224 1.000 26.99
ATOM   1569  CA  VAL A 214      12.556  31.542  12.457 1.000 23.88
ATOM   1570  CB  VAL A 214      11.489  32.069  11.477 1.000 27.24
ATOM   1571  CG1 VAL A 214      10.282  32.612  12.225 1.000 25.46
ATOM   1572  CG2 VAL A 214      12.081  33.158  10.585 1.000 32.07
ATOM   1573  C   VAL A 214      13.672  30.841  11.701 1.000 33.49
ATOM   1574  O   VAL A 214      14.782  31.393  11.653 1.000 41.50
ATOM   1575  N   PRO A 215      13.433  29.666  11.132 1.000 33.79
ATOM   1576  CA  PRO A 215      14.416  29.011  10.262 1.000 32.45
ATOM   1577  CB  PRO A 215      13.625  27.863   9.628 1.000 27.07
ATOM   1578  CG  PRO A 215      12.646  27.518  10.693 1.000 25.47
ATOM   1579  CD  PRO A 215      12.228  28.835  11.297 1.000 29.25
ATOM   1580  C   PRO A 215      14.948  29.950   9.185 1.000 39.16
ATOM   1581  O   PRO A 215      14.249  30.839   8.704 1.000 42.31
ATOM   1582  N   GLU A 216      16.215  29.755   8.813 1.000 33.87
ATOM   1583  CA  GLU A 216      16.877  30.778   8.004 1.000 44.43
ATOM   1584  CB  GLU A 216      18.392  30.715   8.244 1.000 52.43
ATOM   1585  CG  GLU A 216      18.841  31.700   9.324 1.000 56.31
ATOM   1586  CD  GLU A 216      20.119  32.423   8.940 1.000 68.80
ATOM   1587  OE1 GLU A 216      20.015  33.454   8.242 1.000 80.56
ATOM   1588  OE2 GLU A 216      21.208  31.946   9.333 1.000 68.46
ATOM   1589  C   GLU A 216      16.531  30.688   6.522 1.000 40.23
ATOM   1590  O   GLU A 216      16.633  31.700   5.823 1.000 37.48
ATOM   1591  N   THR A 217      16.112  29.522   6.063 1.000 29.61
ATOM   1592  CA  THR A 217      15.492  29.314   4.778 1.000 32.71
ATOM   1593  CB  THR A 217      16.185  28.187   3.991 1.000 30.46
ATOM   1594  OG1 THR A 217      16.030  26.987   4.770 1.000 35.61
ATOM   1595  CG2 THR A 217      17.669  28.469   3.835 1.000 34.53
ATOM   1596  C   THR A 217      14.031  28.881   4.915 1.000 36.27
ATOM   1597  O   THR A 217      13.686  28.153   5.839 1.000 30.65
ATOM   1598  N   THR A 218      13.176  29.290   3.990 1.000 31.97
ATOM   1599  CA  THR A 218      11.842  28.692   3.901 1.000 22.66
ATOM   1600  CB  THR A 218      10.987  29.433   2.861 1.000 20.62
ATOM   1601  OG1 THR A 218      11.671  29.423   1.600 1.000 24.39
ATOM   1602  CG2 THR A 218      10.804  30.879   3.294 1.000 23.42
ATOM   1603  C   THR A 218      11.951  27.225   3.518 1.000 28.74
ATOM   1604  O   THR A 218      11.142  26.377   3.905 1.000 32.65
ATOM   1605  N   GLN A 219      12.969  26.889   2.721 1.000 25.74
ATOM   1606  CA  GLN A 219      13.056  25.550   2.173 1.000 20.41
ATOM   1607  CB  GLN A 219      14.365  25.386   1.388 1.000 28.06
ATOM   1608  CG  GLN A 219      14.167  24.541   0.137 1.000 47.72
ATOM   1609  CD  GLN A 219      14.872  23.201   0.253 1.000 57.11
ATOM   1610  OE1 GLN A 219      14.297  22.182  -0.133 1.000 42.74
ATOM   1611  NE2 GLN A 219      16.096  23.246   0.779 1.000 56.71
```

FIGURE 185

| | | | | | | | | | |
|---|---|---|---|---|---|---|---|---|---|
|ATOM|1612|C  |GLN|A|219|13.010|24.421|3.211|1.000 22.65|
|ATOM|1613|O  |GLN|A|219|12.351|23.416|3.001|1.000 26.69|
|ATOM|1614|N  |SER|A|220|13.741|24.594|4.294|1.000 26.94|
|ATOM|1615|CA |SER|A|220|13.846|23.658|5.400|1.000 30.86|
|ATOM|1616|CB |SER|A|220|14.660|24.279|6.537|1.000 29.59|
|ATOM|1617|OG |SER|A|220|14.662|23.505|7.717|1.000 28.43|
|ATOM|1618|C  |SER|A|220|12.463|23.280|5.946|1.000 20.04|
|ATOM|1619|O  |SER|A|220|12.135|22.096|5.958|1.000 27.37|
|ATOM|1620|N  |LEU|A|221|11.711|24.297|6.378|1.000 21.52|
|ATOM|1621|CA |LEU|A|221|10.414|23.978|6.996|1.000 19.60|
|ATOM|1622|CB |LEU|A|221|9.875|25.107|7.874|1.000 18.57|
|ATOM|1623|CG |LEU|A|221|8.762|24.639|8.827|1.000 20.88|
|ATOM|1624|CD1|LEU|A|221|9.333|23.645|9.830|1.000 24.60|
|ATOM|1625|CD2|LEU|A|221|8.061|25.779|9.537|1.000 16.09|
|ATOM|1626|C  |LEU|A|221|9.436|23.546|5.914|1.000 21.46|
|ATOM|1627|O  |LEU|A|221|8.613|22.659|6.182|1.000 22.12|
|ATOM|1628|N  |ILE|A|222|9.507|24.112|4.703|1.000 21.43|
|ATOM|1629|CA |ILE|A|222|8.594|23.627|3.661|1.000 19.51|
|ATOM|1630|CB |ILE|A|222|8.782|24.425|2.352|1.000 17.06|
|ATOM|1631|CG1|ILE|A|222|8.267|25.866|2.483|1.000 22.29|
|ATOM|1632|CD1|ILE|A|222|8.545|26.686|1.227|1.000 25.18|
|ATOM|1633|CG2|ILE|A|222|8.150|23.690|1.193|1.000 22.06|
|ATOM|1634|C  |ILE|A|222|8.788|22.150|3.399|1.000 23.90|
|ATOM|1635|O  |ILE|A|222|7.832|21.361|3.253|1.000 19.79|
|ATOM|1636|N  |GLN|A|223|10.049|21.706|3.348|1.000 23.36|
|ATOM|1637|CA |GLN|A|223|10.361|20.297|3.096|1.000 22.31|
|ATOM|1638|CB |GLN|A|223|11.867|20.094|2.866|1.000 27.99|
|ATOM|1639|CG |GLN|A|223|12.297|18.683|2.510|1.000 27.69|
|ATOM|1640|CD |GLN|A|223|11.727|18.170|1.203|1.000 36.04|
|ATOM|1641|OE1|GLN|A|223|11.311|18.929|0.325|1.000 38.77|
|ATOM|1642|NE2|GLN|A|223|11.677|16.854|1.025|1.000 34.81|
|ATOM|1643|C  |GLN|A|223|9.921|19.383|4.245|1.000 22.46|
|ATOM|1644|O  |GLN|A|223|9.447|18.263|3.994|1.000 19.87|
|ATOM|1645|N  |PHE|A|224|10.087|19.878|5.470|1.000 20.95|
|ATOM|1646|CA |PHE|A|224|9.694|19.074|6.635|1.000 20.11|
|ATOM|1647|CB |PHE|A|224|10.163|19.747|7.918|1.000 18.59|
|ATOM|1648|CG |PHE|A|224|9.767|19.057|9.228|1.000 14.91|
|ATOM|1649|CD1|PHE|A|224|10.211|17.795|9.547|1.000 18.83|
|ATOM|1650|CE1|PHE|A|224|9.852|17.187|10.760|1.000 16.08|
|ATOM|1651|CZ |PHE|A|224|9.030|17.866|11.638|1.000 14.76|
|ATOM|1652|CE2|PHE|A|224|8.568|19.140|11.351|1.000 18.06|
|ATOM|1653|CD2|PHE|A|224|8.947|19.716|10.141|1.000 19.42|
|ATOM|1654|C  |PHE|A|224|8.172|18.890|6.630|1.000 16.39|
|ATOM|1655|O  |PHE|A|224|7.689|17.764|6.787|1.000 18.08|
|ATOM|1656|N  |VAL|A|225|7.464|20.012|6.459|1.000 20.25|
|ATOM|1657|CA |VAL|A|225|5.992|19.996|6.408|1.000 17.55|
|ATOM|1658|CB |VAL|A|225|5.419|21.411|6.253|1.000 21.00|
|ATOM|1659|CG1|VAL|A|225|3.947|21.344|5.850|1.000 16.31|
|ATOM|1660|CG2|VAL|A|225|5.626|22.177|7.560|1.000 13.40|
|ATOM|1661|C  |VAL|A|225|5.512|19.084|5.298|1.000 17.64|
|ATOM|1662|O  |VAL|A|225|4.671|18.200|5.484|1.000 18.82|
|ATOM|1663|N  |ARG|A|226|6.062|19.192|4.088|1.000 19.58|

FIGURE 186

```
ATOM   1664  CA   ARG A 226     5.619  18.308   3.009  1.000  20.05
ATOM   1665  CB   ARG A 226     6.285  18.775   1.705  1.000  20.92
ATOM   1666  CG   ARG A 226     5.686  20.090   1.204  1.000  21.90
ATOM   1667  CD   ARG A 226     6.324  20.446  -0.145  1.000  22.66
ATOM   1668  NE   ARG A 226     5.564  21.504  -0.798  1.000  24.99
ATOM   1669  CZ   ARG A 226     6.095  22.322  -1.697  1.000  40.94
ATOM   1670  NH1  ARG A 226     7.381  22.153  -1.994  1.000  28.79
ATOM   1671  NH2  ARG A 226     5.371  23.272  -2.281  1.000  30.57
ATOM   1672  C    ARG A 226     5.923  16.848   3.263  1.000  17.75
ATOM   1673  O    ARG A 226     5.172  15.933   2.955  1.000  19.58
ATOM   1674  N    THR A 227     7.055  16.531   3.881  1.000  19.90
ATOM   1675  CA   THR A 227     7.391  15.168   4.247  1.000  15.51
ATOM   1676  CB   THR A 227     8.835  15.143   4.821  1.000  21.32
ATOM   1677  OG1  THR A 227     9.764  15.609   3.823  1.000  22.05
ATOM   1678  CG2  THR A 227     9.217  13.723   5.189  1.000  20.98
ATOM   1679  C    THR A 227     6.413  14.588   5.271  1.000  15.49
ATOM   1680  O    THR A 227     5.919  13.477   5.141  1.000  19.20
ATOM   1681  N    VAL A 228     6.109  15.318   6.325  1.000  16.11
ATOM   1682  CA   VAL A 228     5.143  14.927   7.341  1.000  18.46
ATOM   1683  CB   VAL A 228     5.031  15.957   8.477  1.000  17.87
ATOM   1684  CG1  VAL A 228     3.887  15.568   9.414  1.000  18.37
ATOM   1685  CG2  VAL A 228     6.318  16.108   9.270  1.000  27.25
ATOM   1686  C    VAL A 228     3.751  14.744   6.713  1.000  17.43
ATOM   1687  O    VAL A 228     3.112  13.723   6.983  1.000  17.33
ATOM   1688  N    ARG A 229     3.338  15.721   5.898  1.000  18.35
ATOM   1689  CA   ARG A 229     2.003  15.683   5.292  1.000  20.21
ATOM   1690  CB   ARG A 229     1.710  16.982   4.560  1.000  20.48
ATOM   1691  CG   ARG A 229     0.475  16.989   3.670  1.000  22.85
ATOM   1692  CD   ARG A 229    -0.750  16.409   4.384  1.000  19.41
ATOM   1693  NE   ARG A 229    -1.031  17.165   5.615  1.000  19.35
ATOM   1694  CZ   ARG A 229    -2.026  16.831   6.444  1.000  19.18
ATOM   1695  NH1  ARG A 229    -2.773  15.784   6.097  1.000  19.75
ATOM   1696  NH2  ARG A 229    -2.266  17.508   7.550  1.000  14.67
ATOM   1697  C    ARG A 229     1.917  14.434   4.421  1.000  25.70
ATOM   1698  O    ARG A 229     0.933  13.683   4.482  1.000  28.00
ATOM   1699  N    ASP A 230     2.949  14.152   3.627  1.000  23.44
ATOM   1700  CA   ASP A 230     3.008  12.884   2.886  1.000  26.19
ATOM   1701  CB   ASP A 230     4.322  12.757   2.098  1.000  25.54
ATOM   1702  CG   ASP A 230     4.325  13.611   0.845  1.000  39.61
ATOM   1703  OD1  ASP A 230     3.251  14.111   0.450  1.000  29.77
ATOM   1704  OD2  ASP A 230     5.398  13.806   0.233  1.000  42.44
ATOM   1705  C    ASP A 230     2.880  11.659   3.771  1.000  30.77
ATOM   1706  O    ASP A 230     2.146  10.713   3.455  1.000  27.25
ATOM   1707  N    TYR A 231     3.596  11.597   4.906  1.000  26.11
ATOM   1708  CA   TYR A 231     3.418  10.399   5.737  1.000  21.69
ATOM   1709  CB   TYR A 231     4.351  10.385   6.946  1.000  30.21
ATOM   1710  CG   TYR A 231     5.747   9.892   6.649  1.000  33.51
ATOM   1711  CD1  TYR A 231     5.992   8.543   6.409  1.000  34.93
ATOM   1712  CE1  TYR A 231     7.275   8.109   6.131  1.000  37.60
ATOM   1713  CZ   TYR A 231     8.331   8.999   6.092  1.000  28.01
ATOM   1714  OH   TYR A 231     9.604   8.546   5.820  1.000  29.93
ATOM   1715  CE2  TYR A 231     8.100  10.334   6.323  1.000  19.51
```

FIGURE 187

```
ATOM   1716  CD2 TYR A 231       6.819  10.771   6.592  1.000  19.51
ATOM   1717  C   TYR A 231       1.994  10.314   6.274  1.000  26.15
ATOM   1718  O   TYR A 231       1.372   9.255   6.320  1.000  30.72
ATOM   1719  N   ILE A 232       1.503  11.467   6.729  1.000  22.90
ATOM   1720  CA  ILE A 232       0.167  11.452   7.319  1.000  24.42
ATOM   1721  CB  ILE A 232      -0.271  12.843   7.788  1.000  28.90
ATOM   1722  CG1 ILE A 232       0.566  13.416   8.935  1.000  17.25
ATOM   1723  CD1 ILE A 232       0.205  14.859   9.204  1.000  22.29
ATOM   1724  CG2 ILE A 232      -1.764  12.825   8.134  1.000  28.46
ATOM   1725  C   ILE A 232      -0.881  10.941   6.329  1.000  26.86
ATOM   1726  O   ILE A 232      -1.758  10.140   6.669  1.000  32.19
ATOM   1727  N   ASN A 233      -0.764  11.429   5.106  1.000  25.93
ATOM   1728  CA  ASN A 233      -1.751  11.166   4.070  1.000  30.21
ATOM   1729  CB  ASN A 233      -1.549  12.124   2.900  1.000  24.13
ATOM   1730  CG  ASN A 233      -2.266  13.446   3.088  1.000  31.27
ATOM   1731  OD1 ASN A 233      -2.889  13.743   4.112  1.000  29.17
ATOM   1732  ND2 ASN A 233      -2.134  14.239   2.035  1.000  30.92
ATOM   1733  C   ASN A 233      -1.671   9.730   3.568  1.000  41.91
ATOM   1734  O   ASN A 233      -2.603   9.199   2.958  1.000  41.91
ATOM   1735  N   ARG A 234      -0.536   9.078   3.791  1.000  45.86
ATOM   1736  CA  ARG A 234      -0.326   7.804   3.086  1.000  50.95
ATOM   1737  CB  ARG A 234       1.109   7.725   2.547  1.000  40.12
ATOM   1738  CG  ARG A 234       1.343   8.844   1.545  1.000  46.93
ATOM   1739  CD  ARG A 234       2.117   8.452   0.310  1.000  57.95
ATOM   1740  NE  ARG A 234       2.532   9.653  -0.429  1.000  68.35
ATOM   1741  CZ  ARG A 234       3.780  10.094  -0.506  1.000  67.12
ATOM   1742  NH1 ARG A 234       4.774   9.450   0.100  1.000  63.01
ATOM   1743  NH2 ARG A 234       4.041  11.192  -1.199  1.000  61.94
ATOM   1744  C   ARG A 234      -0.696   6.676   4.029  1.000  60.20
ATOM   1745  O   ARG A 234      -0.601   5.491   3.730  1.000  87.41
ATOM   1746  N   SER A 235      -1.146   7.142   5.194  1.000  44.81
ATOM   1747  CA  SER A 235      -1.664   6.224   6.191  1.000  50.50
ATOM   1748  CB  SER A 235      -1.332   6.720   7.596  1.000  40.08
ATOM   1749  OG  SER A 235      -2.550   7.165   8.201  1.000  64.20
ATOM   1750  C   SER A 235      -3.184   6.066   6.042  1.000  58.76
ATOM   1751  O   SER A 235      -3.835   6.996   5.553  1.000  38.45
ATOM   1752  N   PRO A 236      -3.665   4.905   6.477  1.000  62.13
ATOM   1753  CA  PRO A 236      -5.059   4.491   6.327  1.000  58.65
ATOM   1754  CB  PRO A 236      -5.065   3.010   6.716  1.000  53.85
ATOM   1755  CG  PRO A 236      -3.634   2.599   6.792  1.000  49.45
ATOM   1756  CD  PRO A 236      -2.898   3.851   7.185  1.000  58.01
ATOM   1757  C   PRO A 236      -5.975   5.258   7.275  1.000  58.23
ATOM   1758  O   PRO A 236      -7.033   5.742   6.887  1.000  62.93
ATOM   1759  N   GLY A 237      -5.535   5.351   8.526  1.000  50.71
ATOM   1760  CA  GLY A 237      -6.297   6.108   9.514  1.000  46.90
ATOM   1761  C   GLY A 237      -5.292   6.580  10.552  1.000  55.40
ATOM   1762  O   GLY A 237      -4.274   5.894  10.681  1.000  60.29
ATOM   1763  N   ALA A 238      -5.566   7.689  11.229  1.000  61.94
ATOM   1764  CA  ALA A 238      -4.552   8.203  12.150  1.000  56.95
ATOM   1765  CB  ALA A 238      -3.434   8.854  11.328  1.000  52.44
ATOM   1766  C   ALA A 238      -5.070   9.174  13.195  1.000  50.99
ATOM   1767  O   ALA A 238      -4.242   9.571  14.033  1.000  57.56
```

FIGURE 188

| | | | | | | | | | |
|---|---|---|---|---|---|---|---|---|---|
| ATOM | 1768 | N | GLY | A | 239 | -6.349 | 9.552 | 13.199 | 1.000 34.51 |
| ATOM | 1769 | CA | GLY | A | 239 | -6.845 | 10.375 | 14.310 | 1.000 33.83 |
| ATOM | 1770 | C | GLY | A | 239 | -6.120 | 11.715 | 14.312 | 1.000 20.85 |
| ATOM | 1771 | O | GLY | A | 239 | -5.394 | 11.963 | 13.335 | 1.000 30.52 |
| ATOM | 1772 | N | PRO | A | 240 | -6.258 | 12.599 | 15.276 | 1.000 28.46 |
| ATOM | 1773 | CA | PRO | A | 240 | -5.589 | 13.905 | 15.105 | 1.000 23.74 |
| ATOM | 1774 | CB | PRO | A | 240 | -6.004 | 14.716 | 16.315 | 1.000 31.69 |
| ATOM | 1775 | CG | PRO | A | 240 | -7.078 | 13.958 | 16.996 | 1.000 36.41 |
| ATOM | 1776 | CD | PRO | A | 240 | -6.964 | 12.527 | 16.559 | 1.000 28.90 |
| ATOM | 1777 | C | PRO | A | 240 | -4.072 | 13.702 | 15.099 | 1.000 25.52 |
| ATOM | 1778 | O | PRO | A | 240 | -3.538 | 12.739 | 15.647 | 1.000 25.98 |
| ATOM | 1779 | N | THR | A | 241 | -3.404 | 14.642 | 14.458 | 1.000 19.16 |
| ATOM | 1780 | CA | THR | A | 241 | -1.954 | 14.695 | 14.504 | 1.000 17.79 |
| ATOM | 1781 | CB | THR | A | 241 | -1.388 | 15.324 | 13.206 | 1.000 16.44 |
| ATOM | 1782 | OG1 | THR | A | 241 | -1.782 | 14.534 | 12.091 | 1.000 18.37 |
| ATOM | 1783 | CG2 | THR | A | 241 | 0.130 | 15.352 | 13.322 | 1.000 18.85 |
| ATOM | 1784 | C | THR | A | 241 | -1.547 | 15.547 | 15.690 | 1.000 16.03 |
| ATOM | 1785 | O | THR | A | 241 | -2.027 | 16.671 | 15.783 | 1.000 14.26 |
| ATOM | 1786 | N | VAL | A | 242 | -0.710 | 15.081 | 16.604 | 1.000 14.89 |
| ATOM | 1787 | CA | VAL | A | 242 | -0.276 | 15.964 | 17.707 | 1.000 12.20 |
| ATOM | 1788 | CB | VAL | A | 242 | 0.120 | 15.076 | 18.909 | 1.000 15.21 |
| ATOM | 1789 | CG1 | VAL | A | 242 | 0.983 | 15.784 | 19.937 | 1.000 15.58 |
| ATOM | 1790 | CG2 | VAL | A | 242 | -1.132 | 14.525 | 19.592 | 1.000 15.20 |
| ATOM | 1791 | C | VAL | A | 242 | 0.896 | 16.806 | 17.253 | 1.000 15.62 |
| ATOM | 1792 | O | VAL | A | 242 | 1.838 | 16.295 | 16.614 | 1.000 16.25 |
| ATOM | 1793 | N | VAL | A | 243 | 0.877 | 18.091 | 17.577 | 1.000 13.63 |
| ATOM | 1794 | CA | VAL | A | 243 | 1.995 | 18.961 | 17.231 | 1.000 14.54 |
| ATOM | 1795 | CB | VAL | A | 243 | 1.707 | 19.938 | 16.086 | 1.000 18.21 |
| ATOM | 1796 | CG1 | VAL | A | 243 | 2.970 | 20.692 | 15.648 | 1.000 15.88 |
| ATOM | 1797 | CG2 | VAL | A | 243 | 1.120 | 19.216 | 14.869 | 1.000 17.94 |
| ATOM | 1798 | C | VAL | A | 243 | 2.377 | 19.709 | 18.502 | 1.000 14.26 |
| ATOM | 1799 | O | VAL | A | 243 | 1.559 | 20.250 | 19.248 | 1.000 16.04 |
| ATOM | 1800 | N | HIS | A | 244 | 3.686 | 19.752 | 18.781 | 1.000 17.37 |
| ATOM | 1801 | CA | HIS | A | 244 | 4.097 | 20.519 | 19.951 | 1.000 14.10 |
| ATOM | 1802 | CB | HIS | A | 244 | 4.022 | 19.648 | 21.202 | 1.000 15.84 |
| ATOM | 1803 | CG | HIS | A | 244 | 5.142 | 18.657 | 21.367 | 1.000 17.02 |
| ATOM | 1804 | ND1 | HIS | A | 244 | 6.351 | 19.001 | 21.955 | 1.000 21.61 |
| ATOM | 1805 | CE1 | HIS | A | 244 | 7.130 | 17.936 | 21.988 | 1.000 17.38 |
| ATOM | 1806 | NE2 | HIS | A | 244 | 6.471 | 16.897 | 21.474 | 1.000 16.96 |
| ATOM | 1807 | CD2 | HIS | A | 244 | 5.226 | 17.346 | 21.099 | 1.000 12.72 |
| ATOM | 1808 | C | HIS | A | 244 | 5.511 | 21.073 | 19.792 | 1.000 15.92 |
| ATOM | 1809 | O | HIS | A | 244 | 6.302 | 20.556 | 18.999 | 1.000 15.50 |
| ATOM | 1810 | N | CYS | A | 245 | 5.762 | 22.123 | 20.572 | 1.000 19.65 |
| ATOM | 1811 | CA | CYS | A | 245 | 7.129 | 22.659 | 20.697 | 1.000 23.91 |
| ATOM | 1812 | CB | CYS | A | 245 | 7.258 | 24.015 | 19.998 | 1.000 21.22 |
| ATOM | 1813 | SG | CYS | A | 245 | 5.939 | 25.207 | 20.299 | 1.000 27.54 |
| ATOM | 1814 | C | CYS | A | 245 | 7.436 | 22.703 | 22.181 | 1.000 25.09 |
| ATOM | 1815 | O | CYS | A | 245 | 7.226 | 21.699 | 22.894 | 1.000 22.16 |
| ATOM | 1816 | N | SER | A | 246 | 7.888 | 23.809 | 22.751 | 1.000 19.84 |
| ATOM | 1817 | CA | SER | A | 246 | 7.969 | 23.838 | 24.223 | 1.000 16.95 |
| ATOM | 1818 | CB | SER | A | 246 | 9.152 | 24.728 | 24.635 | 1.000 22.80 |
| ATOM | 1819 | OG | SER | A | 246 | 9.277 | 24.846 | 26.034 | 1.000 23.37 |

FIGURE 189

```
ATOM   1820  C    SER A 246       6.660  24.303  24.834  1.000  18.58
ATOM   1821  O    SER A 246       6.097  23.705  25.756  1.000  23.44
ATOM   1822  N    ALA A 247       6.105  25.428  24.344  1.000  21.38
ATOM   1823  CA   ALA A 247       4.834  25.878  24.909  1.000  26.84
ATOM   1824  CB   ALA A 247       4.815  27.397  25.044  1.000  30.94
ATOM   1825  C    ALA A 247       3.627  25.429  24.082  1.000  18.61
ATOM   1826  O    ALA A 247       2.500  25.492  24.563  1.000  23.09
ATOM   1827  N    GLY A 248       3.876  24.984  22.867  1.000  20.85
ATOM   1828  CA   GLY A 248       2.846  24.579  21.933  1.000  24.45
ATOM   1829  C    GLY A 248       2.113  25.731  21.278  1.000  30.38
ATOM   1830  O    GLY A 248       0.928  25.550  20.948  1.000  32.96
ATOM   1831  N    VAL A 249       2.794  26.852  21.091  1.000  21.75
ATOM   1832  CA   VAL A 249       2.214  28.061  20.510  1.000  26.90
ATOM   1833  CB   VAL A 249       2.293  29.257  21.504  1.000  35.49
ATOM   1834  CG1  VAL A 249       1.266  29.099  22.616  1.000  56.26
ATOM   1835  CG2  VAL A 249       3.654  29.410  22.145  1.000  24.47
ATOM   1836  C    VAL A 249       2.839  28.525  19.210  1.000  22.79
ATOM   1837  O    VAL A 249       2.200  28.508  18.151  1.000  26.47
ATOM   1838  N    GLY A 250       4.064  29.056  19.197  1.000  24.61
ATOM   1839  CA   GLY A 250       4.490  29.816  18.032  1.000  16.91
ATOM   1840  C    GLY A 250       4.953  28.914  16.917  1.000  21.72
ATOM   1841  O    GLY A 250       4.438  28.910  15.787  1.000  20.15
ATOM   1842  N    ARG A 251       5.967  28.114  17.253  1.000  19.78
ATOM   1843  CA   ARG A 251       6.512  27.182  16.284  1.000  21.28
ATOM   1844  CB   ARG A 251       7.717  26.381  16.767  1.000  26.04
ATOM   1845  CG   ARG A 251       8.878  27.181  17.346  1.000  34.41
ATOM   1846  CD   ARG A 251      10.132  26.322  17.479  1.000  26.22
ATOM   1847  NE   ARG A 251      11.199  27.043  18.161  1.000  30.53
ATOM   1848  CZ   ARG A 251      12.191  26.523  18.874  1.000  32.54
ATOM   1849  NH1  ARG A 251      12.297  25.212  19.033  1.000  22.98
ATOM   1850  NH2  ARG A 251      13.080  27.349  19.428  1.000  27.69
ATOM   1851  C    ARG A 251       5.417  26.194  15.829  1.000  22.23
ATOM   1852  O    ARG A 251       5.358  25.859  14.651  1.000  15.33
ATOM   1853  N    THR A 252       4.631  25.769  16.810  1.000  19.69
ATOM   1854  CA   THR A 252       3.579  24.773  16.547  1.000  20.16
ATOM   1855  CB   THR A 252       2.960  24.322  17.888  1.000  22.57
ATOM   1856  OG1  THR A 252       3.926  23.485  18.569  1.000  20.75
ATOM   1857  CG2  THR A 252       1.709  23.474  17.699  1.000  17.40
ATOM   1858  C    THR A 252       2.554  25.401  15.618  1.000  18.08
ATOM   1859  O    THR A 252       2.136  24.800  14.632  1.000  19.10
ATOM   1860  N    GLY A 253       2.134  26.639  15.924  1.000  17.29
ATOM   1861  CA   GLY A 253       1.142  27.297  15.074  1.000  14.74
ATOM   1862  C    GLY A 253       1.662  27.585  13.675  1.000  23.43
ATOM   1863  O    GLY A 253       0.946  27.483  12.672  1.000  14.99
ATOM   1864  N    THR A 254       2.940  27.949  13.575  1.000  18.08
ATOM   1865  CA   THR A 254       3.601  28.145  12.289  1.000  17.61
ATOM   1866  CB   THR A 254       5.014  28.741  12.533  1.000  16.64
ATOM   1867  OG1  THR A 254       4.873  29.982  13.251  1.000  20.15
ATOM   1868  CG2  THR A 254       5.694  29.043  11.221  1.000  17.02
ATOM   1869  C    THR A 254       3.643  26.845  11.511  1.000  16.81
ATOM   1870  O    THR A 254       3.355  26.769  10.313  1.000  17.03
ATOM   1871  N    PHE A 255       3.981  25.701  12.162  1.000  17.85
```

FIGURE 190

| | | | | | | | | | |
|---|---|---|---|---|---|---|---|---|---|
| ATOM | 1872 | CA | PHE | A | 255 | 3.963 | 24.414 | 11.477 | 1.000 13.47 |
| ATOM | 1873 | CB | PHE | A | 255 | 4.343 | 23.241 | 12.408 | 1.000 13.89 |
| ATOM | 1874 | CG | PHE | A | 255 | 4.219 | 21.881 | 11.732 | 1.000 14.73 |
| ATOM | 1875 | CD1 | PHE | A | 255 | 5.240 | 21.372 | 10.954 | 1.000 12.62 |
| ATOM | 1876 | CE1 | PHE | A | 255 | 5.203 | 20.153 | 10.292 | 1.000 16.48 |
| ATOM | 1877 | CZ | PHE | A | 255 | 4.042 | 19.390 | 10.390 | 1.000 17.68 |
| ATOM | 1878 | CE2 | PHE | A | 255 | 3.012 | 19.881 | 11.182 | 1.000 13.26 |
| ATOM | 1879 | CD2 | PHE | A | 255 | 3.081 | 21.074 | 11.855 | 1.000 16.37 |
| ATOM | 1880 | C | PHE | A | 255 | 2.554 | 24.154 | 10.899 | 1.000 10.19 |
| ATOM | 1881 | O | PHE | A | 255 | 2.385 | 23.771 | 9.748 | 1.000 15.90 |
| ATOM | 1882 | N | ILE | A | 256 | 1.557 | 24.332 | 11.785 | 1.000 12.97 |
| ATOM | 1883 | CA | ILE | A | 256 | 0.188 | 23.972 | 11.333 | 1.000 13.95 |
| ATOM | 1884 | CB | ILE | A | 256 | -0.779 | 23.954 | 12.523 | 1.000 13.52 |
| ATOM | 1885 | CG1 | ILE | A | 256 | -0.475 | 22.759 | 13.451 | 1.000 15.18 |
| ATOM | 1886 | CD1 | ILE | A | 256 | -1.294 | 22.825 | 14.733 | 1.000 19.48 |
| ATOM | 1887 | CG2 | ILE | A | 256 | -2.238 | 23.941 | 12.124 | 1.000 19.86 |
| ATOM | 1888 | C | ILE | A | 256 | -0.290 | 24.885 | 10.223 | 1.000 12.32 |
| ATOM | 1889 | O | ILE | A | 256 | -0.822 | 24.432 | 9.205 | 1.000 16.82 |
| ATOM | 1890 | N | ALA | A | 257 | -0.075 | 26.179 | 10.375 | 1.000 13.56 |
| ATOM | 1891 | CA | ALA | A | 257 | -0.526 | 27.108 | 9.330 | 1.000 13.60 |
| ATOM | 1892 | CB | ALA | A | 257 | -0.232 | 28.522 | 9.818 | 1.000 18.20 |
| ATOM | 1893 | C | ALA | A | 257 | 0.148 | 26.789 | 8.011 | 1.000 17.01 |
| ATOM | 1894 | O | ALA | A | 257 | -0.446 | 26.751 | 6.923 | 1.000 16.67 |
| ATOM | 1895 | N | LEU | A | 258 | 1.461 | 26.519 | 8.059 | 1.000 17.25 |
| ATOM | 1896 | CA | LEU | A | 258 | 2.147 | 26.158 | 6.822 | 1.000 17.53 |
| ATOM | 1897 | CB | LEU | A | 258 | 3.654 | 26.013 | 7.044 | 1.000 17.08 |
| ATOM | 1898 | CG | LEU | A | 258 | 4.507 | 25.868 | 5.780 | 1.000 20.80 |
| ATOM | 1899 | CD1 | LEU | A | 258 | 4.222 | 27.003 | 4.793 | 1.000 15.05 |
| ATOM | 1900 | CD2 | LEU | A | 258 | 5.992 | 25.859 | 6.121 | 1.000 18.82 |
| ATOM | 1901 | C | LEU | A | 258 | 1.622 | 24.850 | 6.248 | 1.000 18.92 |
| ATOM | 1902 | O | LEU | A | 258 | 1.448 | 24.706 | 5.036 | 1.000 18.97 |
| ATOM | 1903 | N | ASP | A | 259 | 1.363 | 23.837 | 7.090 | 1.000 16.07 |
| ATOM | 1904 | CA | ASP | A | 259 | 0.754 | 22.618 | 6.578 | 1.000 10.97 |
| ATOM | 1905 | CB | ASP | A | 259 | 0.551 | 21.650 | 7.742 | 1.000 13.81 |
| ATOM | 1906 | CG | ASP | A | 259 | -0.025 | 20.310 | 7.371 | 1.000 17.58 |
| ATOM | 1907 | OD1 | ASP | A | 259 | 0.282 | 19.727 | 6.307 | 1.000 16.06 |
| ATOM | 1908 | OD2 | ASP | A | 259 | -0.800 | 19.817 | 8.233 | 1.000 19.09 |
| ATOM | 1909 | C | ASP | A | 259 | -0.574 | 22.893 | 5.858 | 1.000 13.42 |
| ATOM | 1910 | O | ASP | A | 259 | -0.784 | 22.386 | 4.764 | 1.000 18.06 |
| ATOM | 1911 | N | ARG | A | 260 | -1.456 | 23.673 | 6.457 | 1.000 15.30 |
| ATOM | 1912 | CA | ARG | A | 260 | -2.741 | 24.034 | 5.845 | 1.000 17.67 |
| ATOM | 1913 | CB | ARG | A | 260 | -3.567 | 24.849 | 6.842 | 1.000 14.27 |
| ATOM | 1914 | CG | ARG | A | 260 | -3.970 | 24.009 | 8.067 | 1.000 12.81 |
| ATOM | 1915 | CD | ARG | A | 260 | -4.923 | 24.884 | 8.885 | 1.000 20.83 |
| ATOM | 1916 | NE | ARG | A | 260 | -6.158 | 25.124 | 8.125 | 1.000 27.40 |
| ATOM | 1917 | CZ | ARG | A | 260 | -7.185 | 25.786 | 8.663 | 1.000 40.82 |
| ATOM | 1918 | NH1 | ARG | A | 260 | -7.082 | 26.236 | 9.907 | 1.000 36.06 |
| ATOM | 1919 | NH2 | ARG | A | 260 | -8.288 | 25.988 | 7.962 | 1.000 39.48 |
| ATOM | 1920 | C | ARG | A | 260 | -2.523 | 24.808 | 4.549 | 1.000 19.93 |
| ATOM | 1921 | O | ARG | A | 260 | -3.148 | 24.535 | 3.519 | 1.000 17.22 |
| ATOM | 1922 | N | ILE | A | 261 | -1.618 | 25.791 | 4.553 | 1.000 16.11 |
| ATOM | 1923 | CA | ILE | A | 261 | -1.516 | 26.628 | 3.338 | 1.000 17.32 |

FIGURE 191

```
ATOM   1924  CB   ILE A 261      -0.841  27.994   3.615 1.000 21.93
ATOM   1925  CG1  ILE A 261       0.658  27.969   3.875 1.000 27.34
ATOM   1926  CD1  ILE A 261       1.186  29.227   4.546 1.000 33.86
ATOM   1927  CG2  ILE A 261      -1.581  28.703   4.758 1.000 18.92
ATOM   1928  C    ILE A 261      -0.851  25.876   2.216 1.000 20.48
ATOM   1929  O    ILE A 261      -1.226  26.009   1.034 1.000 22.32
ATOM   1930  N    LEU A 262       0.143  25.028   2.509 1.000 16.93
ATOM   1931  CA   LEU A 262       0.737  24.302   1.387 1.000 17.22
ATOM   1932  CB   LEU A 262       1.975  23.501   1.820 1.000 16.74
ATOM   1933  CG   LEU A 262       3.194  24.340   2.240 1.000 20.68
ATOM   1934  CD1  LEU A 262       4.319  23.422   2.693 1.000 18.57
ATOM   1935  CD2  LEU A 262       3.634  25.246   1.085 1.000 18.30
ATOM   1936  C    LEU A 262      -0.280  23.362   0.776 1.000 19.77
ATOM   1937  O    LEU A 262      -0.261  23.155  -0.436 1.000 20.56
ATOM   1938  N    GLN A 263      -1.139  22.759   1.613 1.000 19.67
ATOM   1939  CA   GLN A 263      -2.241  21.952   1.056 1.000 19.49
ATOM   1940  CB   GLN A 263      -3.050  21.287   2.170 1.000 17.39
ATOM   1941  CG   GLN A 263      -2.289  20.167   2.891 1.000 15.52
ATOM   1942  CD   GLN A 263      -3.138  19.572   4.012 1.000 20.67
ATOM   1943  OE1  GLN A 263      -3.928  18.638   3.850 1.000 20.81
ATOM   1944  NE2  GLN A 263      -2.956  20.185   5.176 1.000 17.87
ATOM   1945  C    GLN A 263      -3.138  22.833   0.183 1.000 13.70
ATOM   1946  O    GLN A 263      -3.554  22.415  -0.904 1.000 24.55
ATOM   1947  N    GLN A 264      -3.444  24.043   0.641 1.000 15.00
ATOM   1948  CA   GLN A 264      -4.260  24.907  -0.217 1.000 22.95
ATOM   1949  CB   GLN A 264      -4.553  26.223   0.485 1.000 26.53
ATOM   1950  CG   GLN A 264      -5.586  26.136   1.595 1.000 29.68
ATOM   1951  CD   GLN A 264      -5.638  27.472   2.328 1.000 32.15
ATOM   1952  OE1  GLN A 264      -5.197  28.482   1.781 1.000 29.91
ATOM   1953  NE2  GLN A 264      -6.154  27.458   3.550 1.000 38.37
ATOM   1954  C    GLN A 264      -3.583  25.159  -1.559 1.000 21.95
ATOM   1955  O    GLN A 264      -4.225  25.050  -2.610 1.000 24.60
ATOM   1956  N    LEU A 265      -2.293  25.490  -1.552 1.000 16.75
ATOM   1957  CA   LEU A 265      -1.536  25.721  -2.771 1.000 19.81
ATOM   1958  CB   LEU A 265      -0.067  26.053  -2.420 1.000 23.63
ATOM   1959  CG   LEU A 265       0.195  27.420  -1.807 1.000 29.98
ATOM   1960  CD1  LEU A 265       1.682  27.725  -1.734 1.000 26.97
ATOM   1961  CD2  LEU A 265      -0.519  28.505  -2.613 1.000 33.62
ATOM   1962  C    LEU A 265      -1.541  24.553  -3.735 1.000 19.01
ATOM   1963  O    LEU A 265      -1.324  24.723  -4.947 1.000 22.58
ATOM   1964  N    ASP A 266      -1.767  23.324  -3.273 1.000 19.07
ATOM   1965  CA   ASP A 266      -1.801  22.167  -4.139 1.000 16.52
ATOM   1966  CB   ASP A 266      -1.173  20.917  -3.509 1.000 22.85
ATOM   1967  CG   ASP A 266       0.336  21.022  -3.334 1.000 25.04
ATOM   1968  OD1  ASP A 266       0.957  21.963  -3.836 1.000 21.32
ATOM   1969  OD2  ASP A 266       0.899  20.138  -2.658 1.000 26.79
ATOM   1970  C    ASP A 266      -3.227  21.776  -4.570 1.000 17.40
ATOM   1971  O    ASP A 266      -3.354  20.825  -5.337 1.000 24.62
ATOM   1972  N    SER A 267      -4.231  22.487  -4.092 1.000 22.55
ATOM   1973  CA   SER A 267      -5.619  22.129  -4.359 1.000 24.11
ATOM   1974  CB   SER A 267      -6.289  21.776  -3.019 1.000 23.25
ATOM   1975  OG   SER A 267      -6.418  20.374  -2.892 1.000 34.75
```

FIGURE 192

```
ATOM   1976  C    SER A 267      -6.419  23.235  -5.033 1.000 19.22
ATOM   1977  O    SER A 267      -7.300  22.941  -5.859 1.000 20.89
ATOM   1978  N    LYS A 268      -6.137  24.463  -4.684 1.000 21.22
ATOM   1979  CA   LYS A 268      -6.907  25.624  -5.091 1.000 30.13
ATOM   1980  CB   LYS A 268      -7.595  26.250  -3.869 1.000 24.53
ATOM   1981  CG   LYS A 268      -8.563  25.304  -3.175 1.000 30.56
ATOM   1982  CD   LYS A 268      -8.969  25.910  -1.838 1.000 28.63
ATOM   1983  CE   LYS A 268     -10.158  26.834  -1.992 1.000 29.96
ATOM   1984  NZ   LYS A 268     -10.686  27.208  -0.641 1.000 30.06
ATOM   1985  C    LYS A 268      -6.095  26.737  -5.735 1.000 30.67
ATOM   1986  O    LYS A 268      -4.872  26.833  -5.660 1.000 23.21
ATOM   1987  N    ASP A 269      -6.834  27.650  -6.387 1.000 26.00
ATOM   1988  CA   ASP A 269      -6.096  28.750  -7.019 1.000 24.51
ATOM   1989  CB   ASP A 269      -6.616  28.978  -8.444 1.000 36.81
ATOM   1990  CG   ASP A 269      -8.072  29.337  -8.608 1.000 32.33
ATOM   1991  OD1  ASP A 269      -8.854  29.152  -7.660 1.000 26.79
ATOM   1992  OD2  ASP A 269      -8.465  29.822  -9.701 1.000 28.81
ATOM   1993  C    ASP A 269      -6.126  30.000  -6.165 1.000 21.36
ATOM   1994  O    ASP A 269      -5.857  31.124  -6.623 1.000 25.20
ATOM   1995  N    SER A 270      -6.434  29.846  -4.867 1.000 19.08
ATOM   1996  CA   SER A 270      -6.204  30.978  -3.973 1.000 22.27
ATOM   1997  CB   SER A 270      -7.455  31.809  -3.722 1.000 31.53
ATOM   1998  OG   SER A 270      -8.466  31.045  -3.109 1.000 46.83
ATOM   1999  C    SER A 270      -5.632  30.493  -2.626 1.000 17.38
ATOM   2000  O    SER A 270      -5.828  29.315  -2.334 1.000 22.28
ATOM   2001  N    VAL A 271      -5.000  31.394  -1.910 1.000 20.10
ATOM   2002  CA   VAL A 271      -4.413  31.067  -0.596 1.000 21.99
ATOM   2003  CB   VAL A 271      -2.876  31.020  -0.706 1.000 36.16
ATOM   2004  CG1  VAL A 271      -2.305  32.413  -0.921 1.000 35.70
ATOM   2005  CG2  VAL A 271      -2.233  30.370   0.514 1.000 31.05
ATOM   2006  C    VAL A 271      -4.845  32.054   0.464 1.000 23.10
ATOM   2007  O    VAL A 271      -5.012  33.251   0.241 1.000 21.67
ATOM   2008  N    ASP A 272      -5.046  31.547   1.689 1.000 22.69
ATOM   2009  CA   ASP A 272      -5.591  32.427   2.728 1.000 29.48
ATOM   2010  CB   ASP A 272      -7.070  32.095   2.910 1.000 26.70
ATOM   2011  CG   ASP A 272      -7.813  32.991   3.869 1.000 27.37
ATOM   2012  OD1  ASP A 272      -7.274  34.038   4.288 1.000 23.01
ATOM   2013  OD2  ASP A 272      -8.973  32.599   4.175 1.000 25.43
ATOM   2014  C    ASP A 272      -4.807  32.259   4.021 1.000 22.94
ATOM   2015  O    ASP A 272      -5.200  31.536   4.930 1.000 19.80
ATOM   2016  N    ILE A 273      -3.661  32.934   4.069 1.000 24.25
ATOM   2017  CA   ILE A 273      -2.806  32.829   5.255 1.000 22.39
ATOM   2018  CB   ILE A 273      -1.436  33.465   4.962 1.000 25.49
ATOM   2019  CG1  ILE A 273      -0.747  32.812   3.755 1.000 18.59
ATOM   2020  CD1  ILE A 273       0.498  33.584   3.329 1.000 24.40
ATOM   2021  CG2  ILE A 273      -0.532  33.454   6.177 1.000 18.07
ATOM   2022  C    ILE A 273      -3.472  33.457   6.452 1.000 20.71
ATOM   2023  O    ILE A 273      -3.470  32.853   7.530 1.000 17.55
ATOM   2024  N    TYR A 274      -4.038  34.646   6.266 1.000 21.57
ATOM   2025  CA   TYR A 274      -4.765  35.332   7.338 1.000 27.63
ATOM   2026  CB   TYR A 274      -5.414  36.646   6.864 1.000 23.61
ATOM   2027  CG   TYR A 274      -6.110  37.456   7.937 1.000 24.88
```

FIGURE 193

```
ATOM   2028  CD1  TYR A 274      -7.427  37.236   8.347 1.000 25.22
ATOM   2029  CE1  TYR A 274      -8.040  37.979   9.328 1.000 24.84
ATOM   2030  CZ   TYR A 274      -7.346  39.009   9.937 1.000 24.82
ATOM   2031  OH   TYR A 274      -7.979  39.740  10.919 1.000 31.02
ATOM   2032  CE2  TYR A 274      -6.040  39.266   9.571 1.000 24.34
ATOM   2033  CD2  TYR A 274      -5.435  38.503   8.582 1.000 21.36
ATOM   2034  C    TYR A 274      -5.834  34.413   7.922 1.000 22.02
ATOM   2035  O    TYR A 274      -5.962  34.308   9.150 1.000 23.59
ATOM   2036  N    GLY A 275      -6.642  33.818   7.042 1.000 19.06
ATOM   2037  CA   GLY A 275      -7.741  32.997   7.563 1.000 18.44
ATOM   2038  C    GLY A 275      -7.221  31.755   8.284 1.000 18.35
ATOM   2039  O    GLY A 275      -7.789  31.310   9.278 1.000 20.87
ATOM   2040  N    ALA A 276      -6.123  31.168   7.823 1.000 19.89
ATOM   2041  CA   ALA A 276      -5.591  30.008   8.560 1.000 22.21
ATOM   2042  CB   ALA A 276      -4.480  29.371   7.758 1.000 17.74
ATOM   2043  C    ALA A 276      -5.091  30.429   9.932 1.000 24.08
ATOM   2044  O    ALA A 276      -5.321  29.770  10.938 1.000 19.77
ATOM   2045  N    VAL A 277      -4.390  31.569  10.019 1.000 18.02
ATOM   2046  CA   VAL A 277      -3.912  31.978  11.353 1.000 17.46
ATOM   2047  CB   VAL A 277      -2.831  33.079  11.246 1.000 21.08
ATOM   2048  CG1  VAL A 277      -2.405  33.553  12.631 1.000 21.06
ATOM   2049  CG2  VAL A 277      -1.645  32.548  10.467 1.000 16.97
ATOM   2050  C    VAL A 277      -5.084  32.426  12.205 1.000 20.56
ATOM   2051  O    VAL A 277      -5.142  32.112  13.390 1.000 18.55
ATOM   2052  N    HIS A 278      -6.044  33.156  11.644 1.000 18.91
ATOM   2053  CA   HIS A 278      -7.281  33.470  12.314 1.000 16.67
ATOM   2054  CB   HIS A 278      -8.297  34.063  11.303 1.000 18.69
ATOM   2055  CG   HIS A 278      -9.520  34.540  12.036 1.000 22.21
ATOM   2056  ND1  HIS A 278     -10.626  33.756  12.252 1.000 21.90
ATOM   2057  CE1  HIS A 278     -11.535  34.445  12.925 1.000 23.09
ATOM   2058  NE2  HIS A 278     -11.055  35.656  13.150 1.000 23.99
ATOM   2059  CD2  HIS A 278      -9.801  35.745  12.602 1.000 20.21
ATOM   2060  C    HIS A 278      -7.924  32.254  12.971 1.000 19.90
ATOM   2061  O    HIS A 278      -8.255  32.244  14.165 1.000 22.96
ATOM   2062  N    ASP A 279      -8.105  31.202  12.180 1.000 18.82
ATOM   2063  CA   ASP A 279      -8.742  30.004  12.711 1.000 23.67
ATOM   2064  CB   ASP A 279      -8.995  29.015  11.565 1.000 25.00
ATOM   2065  CG   ASP A 279     -10.100  29.571  10.669 1.000 50.27
ATOM   2066  OD1  ASP A 279     -10.713  30.592  11.074 1.000 51.54
ATOM   2067  OD2  ASP A 279     -10.315  28.989   9.582 1.000 44.55
ATOM   2068  C    ASP A 279      -7.914  29.352  13.811 1.000 21.55
ATOM   2069  O    ASP A 279      -8.488  28.905  14.806 1.000 24.05
ATOM   2070  N    LEU A 280      -6.595  29.300  13.681 1.000 17.02
ATOM   2071  CA   LEU A 280      -5.777  28.736  14.760 1.000 15.09
ATOM   2072  CB   LEU A 280      -4.307  28.672  14.339 1.000 16.04
ATOM   2073  CG   LEU A 280      -3.998  27.877  13.066 1.000 25.79
ATOM   2074  CD1  LEU A 280      -2.505  27.860  12.743 1.000 19.03
ATOM   2075  CD2  LEU A 280      -4.512  26.448  13.134 1.000 25.95
ATOM   2076  C    LEU A 280      -5.928  29.541  16.041 1.000 17.95
ATOM   2077  O    LEU A 280      -6.048  28.991  17.142 1.000 16.96
ATOM   2078  N    ARG A 281      -5.940  30.867  15.909 1.000 17.70
ATOM   2079  CA   ARG A 281      -6.048  31.750  17.064 1.000 20.80
```

FIGURE 194

```
ATOM   2080  CB   ARG A 281      -5.937  33.220  16.611  1.000  16.23
ATOM   2081  CG   ARG A 281      -4.518  33.577  16.185  1.000  21.03
ATOM   2082  CD   ARG A 281      -3.551  33.775  17.350  1.000  20.13
ATOM   2083  NE   ARG A 281      -2.333  34.410  16.826  1.000  22.94
ATOM   2084  CZ   ARG A 281      -2.155  35.711  16.631  1.000  25.63
ATOM   2085  NH1  ARG A 281      -3.096  36.606  16.909  1.000  26.26
ATOM   2086  NH2  ARG A 281      -0.990  36.116  16.136  1.000  24.35
ATOM   2087  C    ARG A 281      -7.348  31.512  17.810  1.000  18.17
ATOM   2088  O    ARG A 281      -7.399  31.612  19.040  1.000  16.51
ATOM   2089  N    LEU A 282      -8.411  31.197  17.055  1.000  14.33
ATOM   2090  CA   LEU A 282      -9.670  30.904  17.725  1.000  19.27
ATOM   2091  CB   LEU A 282     -10.750  30.565  16.690  1.000  19.77
ATOM   2092  CG   LEU A 282     -11.369  31.764  15.966  1.000  29.93
ATOM   2093  CD1  LEU A 282     -12.445  31.274  15.006  1.000  21.91
ATOM   2094  CD2  LEU A 282     -11.916  32.785  16.951  1.000  25.11
ATOM   2095  C    LEU A 282      -9.567  29.715  18.673  1.000  15.90
ATOM   2096  O    LEU A 282     -10.343  29.644  19.622  1.000  19.86
ATOM   2097  N    HIS A 283      -8.652  28.771  18.444  1.000  13.25
ATOM   2098  CA   HIS A 283      -8.655  27.556  19.262  1.000  15.14
ATOM   2099  CB   HIS A 283      -8.585  26.315  18.339  1.000  17.23
ATOM   2100  CG   HIS A 283      -9.761  26.332  17.393  1.000  20.06
ATOM   2101  ND1  HIS A 283     -10.931  25.651  17.625  1.000  31.88
ATOM   2102  CE1  HIS A 283     -11.785  25.866  16.626  1.000  22.40
ATOM   2103  NE2  HIS A 283     -11.210  26.665  15.743  1.000  22.21
ATOM   2104  CD2  HIS A 283      -9.959  26.969  16.216  1.000  21.15
ATOM   2105  C    HIS A 283      -7.541  27.484  20.301  1.000  17.70
ATOM   2106  O    HIS A 283      -7.668  26.724  21.286  1.000  18.21
ATOM   2107  N    ARG A 284      -6.460  28.254  20.155  1.000  18.34
ATOM   2108  CA   ARG A 284      -5.462  28.288  21.252  1.000  17.74
ATOM   2109  CB   ARG A 284      -4.494  27.114  21.172  1.000  19.63
ATOM   2110  CG   ARG A 284      -3.445  26.954  22.275  1.000  18.29
ATOM   2111  CD   ARG A 284      -2.651  25.656  22.082  1.000  20.72
ATOM   2112  NE   ARG A 284      -1.458  25.545  22.957  1.000  15.01
ATOM   2113  CZ   ARG A 284      -1.489  25.046  24.189  1.000  14.81
ATOM   2114  NH1  ARG A 284      -2.637  24.611  24.697  1.000  14.36
ATOM   2115  NH2  ARG A 284      -0.419  24.947  24.977  1.000  17.97
ATOM   2116  C    ARG A 284      -4.746  29.631  21.220  1.000  19.40
ATOM   2117  O    ARG A 284      -4.570  30.222  20.158  1.000  18.68
ATOM   2118  N    VAL A 285      -4.331  30.137  22.382  1.000  20.56
ATOM   2119  CA   VAL A 285      -3.577  31.396  22.467  1.000  19.97
ATOM   2120  CB   VAL A 285      -3.329  31.773  23.942  1.000  20.57
ATOM   2121  CG1  VAL A 285      -2.329  30.829  24.584  1.000  17.50
ATOM   2122  CG2  VAL A 285      -2.811  33.203  24.085  1.000  29.47
ATOM   2123  C    VAL A 285      -2.259  31.298  21.714  1.000  17.66
ATOM   2124  O    VAL A 285      -1.641  30.232  21.618  1.000  17.67
ATOM   2125  N    HIS A 286      -1.814  32.423  21.166  1.000  19.91
ATOM   2126  CA   HIS A 286      -0.537  32.572  20.510  1.000  25.50
ATOM   2127  CB   HIS A 286       0.610  32.334  21.518  1.000  24.01
ATOM   2128  CG   HIS A 286       0.534  33.321  22.640  1.000  27.47
ATOM   2129  ND1  HIS A 286       0.673  32.943  23.966  1.000  36.12
ATOM   2130  CE1  HIS A 286       0.544  34.024  24.711  1.000  31.77
ATOM   2131  NE2  HIS A 286       0.333  35.065  23.927  1.000  32.36
```

FIGURE 195

```
ATOM   2132  CD2 HIS A 286       0.312  34.647  22.624 1.000 25.03
ATOM   2133  C   HIS A 286      -0.272  31.626  19.358 1.000 21.57
ATOM   2134  O   HIS A 286       0.915  31.389  19.095 1.000 27.54
ATOM   2135  N   MET A 287      -1.298  31.074  18.700 1.000 20.51
ATOM   2136  CA  MET A 287      -1.005  30.215  17.540 1.000 17.32
ATOM   2137  CB  MET A 287      -2.248  29.446  17.099 1.000 15.20
ATOM   2138  CG  MET A 287      -2.726  28.475  18.174 1.000 18.71
ATOM   2139  SD  MET A 287      -1.588  27.070  18.339 1.000 23.88
ATOM   2140  CE  MET A 287      -2.087  26.118  16.902 1.000 40.45
ATOM   2141  C   MET A 287      -0.449  31.093  16.419 1.000 19.40
ATOM   2142  O   MET A 287      -1.200  31.865  15.805 1.000 23.59
ATOM   2143  N   VAL A 288       0.842  30.986  16.169 1.000 18.22
ATOM   2144  CA  VAL A 288       1.568  31.941  15.322 1.000 22.64
ATOM   2145  CB  VAL A 288       0.926  32.326  13.986 1.000 17.14
ATOM   2146  CG1 VAL A 288       1.879  33.209  13.183 1.000 23.13
ATOM   2147  CG2 VAL A 288       0.607  31.099  13.159 1.000 21.03
ATOM   2148  C   VAL A 288       1.718  33.186  16.211 1.000 25.94
ATOM   2149  O   VAL A 288       0.851  34.046  16.243 1.000 27.22
ATOM   2150  N   GLN A 289       2.824  33.161  16.945 1.000 27.43
ATOM   2151  CA  GLN A 289       3.003  34.056  18.091 1.000 24.77
ATOM   2152  CB  GLN A 289       3.839  33.286  19.112 1.000 23.16
ATOM   2153  CG  GLN A 289       4.041  33.984  20.443 1.000 22.98
ATOM   2154  CD  GLN A 289       4.639  33.050  21.469 1.000 24.02
ATOM   2155  OE1 GLN A 289       5.224  32.012  21.115 1.000 27.34
ATOM   2156  NE2 GLN A 289       4.479  33.454  22.716 1.000 30.58
ATOM   2157  C   GLN A 289       3.664  35.376  17.751 1.000 28.02
ATOM   2158  O   GLN A 289       3.430  36.375  18.436 1.000 35.00
ATOM   2159  N   THR A 290       4.492  35.409  16.717 1.000 22.20
ATOM   2160  CA  THR A 290       5.169  36.667  16.419 1.000 24.68
ATOM   2161  CB  THR A 290       6.682  36.492  16.619 1.000 25.80
ATOM   2162  OG1 THR A 290       7.133  35.616  15.579 1.000 22.41
ATOM   2163  CG2 THR A 290       7.012  35.803  17.932 1.000 28.39
ATOM   2164  C   THR A 290       4.964  37.120  14.984 1.000 35.97
ATOM   2165  O   THR A 290       4.668  36.327  14.090 1.000 25.80
ATOM   2166  N   GLU A 291       5.148  38.416  14.746 1.000 29.48
ATOM   2167  CA  GLU A 291       5.038  38.965  13.403 1.000 28.57
ATOM   2168  CB  GLU A 291       5.285  40.473  13.478 1.000 29.75
ATOM   2169  CG  GLU A 291       5.073  41.210  12.184 1.000 39.81
ATOM   2170  CD  GLU A 291       4.812  42.699  12.387 1.000 39.37
ATOM   2171  OE1 GLU A 291       4.858  43.418  11.371 1.000 42.29
ATOM   2172  OE2 GLU A 291       4.556  43.148  13.519 1.000 40.22
ATOM   2173  C   GLU A 291       6.029  38.283  12.484 1.000 23.04
ATOM   2174  O   GLU A 291       5.824  37.994  11.304 1.000 23.87
ATOM   2175  N   CYS A 292       7.200  37.987  13.054 1.000 24.91
ATOM   2176  CA  CYS A 292       8.230  37.313  12.255 1.000 20.83
ATOM   2177  CB  CYS A 292       9.434  37.106  13.178 1.000 33.84
ATOM   2178  SG  CYS A 292      10.875  36.380  12.364 1.000 50.67
ATOM   2179  C   CYS A 292       7.777  35.977  11.679 1.000 25.36
ATOM   2180  O   CYS A 292       8.056  35.544  10.549 1.000 26.36
ATOM   2181  N   GLN A 293       7.024  35.250  12.515 1.000 23.19
ATOM   2182  CA  GLN A 293       6.425  33.998  12.069 1.000 22.92
ATOM   2183  CB  GLN A 293       5.779  33.269  13.256 1.000 20.65
```

FIGURE 196

| | | | | | | | | |
|---|---|---|---|---|---|---|---|---|
|ATOM|2184|CG|GLN|A|293|6.783|32.437|14.036 1.000 20.24|
|ATOM|2185|CD|GLN|A|293|6.355|32.071|15.433 1.000 17.59|
|ATOM|2186|OE1|GLN|A|293|5.282|32.450|15.901 1.000 18.69|
|ATOM|2187|NE2|GLN|A|293|7.203|31.336|16.150 1.000 25.13|
|ATOM|2188|C|GLN|A|293|5.400|34.266|10.967 1.000 17.64|
|ATOM|2189|O|GLN|A|293|5.398|33.582|9.954 1.000 20.18|
|ATOM|2190|N|TYR|A|294|4.522|35.253|11.178 1.000 20.42|
|ATOM|2191|CA|TYR|A|294|3.526|35.600|10.153 1.000 19.65|
|ATOM|2192|CB|TYR|A|294|2.680|36.758|10.698 1.000 19.00|
|ATOM|2193|CG|TYR|A|294|1.392|36.980|9.943 1.000 21.07|
|ATOM|2194|CD1|TYR|A|294|0.438|35.986|9.843 1.000 19.94|
|ATOM|2195|CE1|TYR|A|294|-0.747|36.155|9.158 1.000 25.08|
|ATOM|2196|CZ|TYR|A|294|-0.978|37.374|8.547 1.000 34.68|
|ATOM|2197|OH|TYR|A|294|-2.148|37.565|7.856 1.000 23.20|
|ATOM|2198|CE2|TYR|A|294|-0.047|38.385|8.622 1.000 26.61|
|ATOM|2199|CD2|TYR|A|294|1.129|38.197|9.316 1.000 23.82|
|ATOM|2200|C|TYR|A|294|4.202|35.931|8.834 1.000 24.14|
|ATOM|2201|O|TYR|A|294|3.860|35.493|7.737 1.000 23.97|
|ATOM|2202|N|VAL|A|295|5.254|36.744|8.919 1.000 25.60|
|ATOM|2203|CA|VAL|A|295|6.065|37.085|7.762 1.000 26.06|
|ATOM|2204|CB|VAL|A|295|7.222|38.039|8.161 1.000 22.22|
|ATOM|2205|CG1|VAL|A|295|8.189|38.107|6.995 1.000 24.48|
|ATOM|2206|CG2|VAL|A|295|6.668|39.400|8.553 1.000 22.52|
|ATOM|2207|C|VAL|A|295|6.648|35.853|7.111 1.000 20.01|
|ATOM|2208|O|VAL|A|295|6.582|35.637|5.897 1.000 23.07|
|ATOM|2209|N|TYR|A|296|7.233|34.941|7.888 1.000 29.06|
|ATOM|2210|CA|TYR|A|296|7.779|33.698|7.342 1.000 20.10|
|ATOM|2211|CB|TYR|A|296|8.307|32.873|8.528 1.000 20.14|
|ATOM|2212|CG|TYR|A|296|9.099|31.652|8.140 1.000 22.62|
|ATOM|2213|CD1|TYR|A|296|10.343|31.723|7.536 1.000 24.11|
|ATOM|2214|CE1|TYR|A|296|11.044|30.582|7.188 1.000 24.78|
|ATOM|2215|CZ|TYR|A|296|10.500|29.338|7.451 1.000 30.65|
|ATOM|2216|OH|TYR|A|296|11.171|28.185|7.115 1.000 25.95|
|ATOM|2217|CE2|TYR|A|296|9.263|29.241|8.048 1.000 21.75|
|ATOM|2218|CD2|TYR|A|296|8.570|30.384|8.389 1.000 22.93|
|ATOM|2219|C|TYR|A|296|6.802|32.832|6.546 1.000 19.59|
|ATOM|2220|O|TYR|A|296|7.163|32.193|5.540 1.000 20.16|
|ATOM|2221|N|LEU|A|297|5.555|32.742|6.984 1.000 21.48|
|ATOM|2222|CA|LEU|A|297|4.501|32.003|6.276 1.000 16.66|
|ATOM|2223|CB|LEU|A|297|3.186|31.985|7.052 1.000 17.75|
|ATOM|2224|CG|LEU|A|297|3.215|31.148|8.360 1.000 16.83|
|ATOM|2225|CD1|LEU|A|297|2.035|31.495|9.235 1.000 17.79|
|ATOM|2226|CD2|LEU|A|297|3.299|29.668|8.014 1.000 17.48|
|ATOM|2227|C|LEU|A|297|4.276|32.654|4.904 1.000 17.96|
|ATOM|2228|O|LEU|A|297|4.156|31.967|3.898 1.000 20.64|
|ATOM|2229|N|HIS|A|298|4.256|33.978|4.931 1.000 22.58|
|ATOM|2230|CA|HIS|A|298|4.152|34.678|3.633 1.000 23.47|
|ATOM|2231|CB|HIS|A|298|3.950|36.157|3.901 1.000 25.50|
|ATOM|2232|CG|HIS|A|298|2.562|36.496|4.341 1.000 26.24|
|ATOM|2233|ND1|HIS|A|298|2.118|36.313|5.625 1.000 22.98|
|ATOM|2234|CE1|HIS|A|298|0.865|36.709|5.744 1.000 24.82|
|ATOM|2235|NE2|HIS|A|298|0.470|37.141|4.565 1.000 27.56|

FIGURE 197

```
ATOM   2236  CD2 HIS A 298       1.512  37.022   3.673 1.000 23.83
ATOM   2237  C   HIS A 298       5.379  34.412   2.785 1.000 20.56
ATOM   2238  O   HIS A 298       5.260  34.132   1.597 1.000 21.25
ATOM   2239  N   GLN A 299       6.602  34.457   3.323 1.000 24.45
ATOM   2240  CA  GLN A 299       7.767  34.186   2.484 1.000 23.57
ATOM   2241  CB  GLN A 299       9.094  34.286   3.248 1.000 24.20
ATOM   2242  CG  GLN A 299       9.618  35.701   3.344 1.000 38.95
ATOM   2243  CD  GLN A 299      10.513  35.927   4.544 1.000 41.27
ATOM   2244  OE1 GLN A 299      10.525  35.111   5.469 1.000 47.05
ATOM   2245  NE2 GLN A 299      11.230  37.044   4.501 1.000 36.99
ATOM   2246  C   GLN A 299       7.706  32.790   1.911 1.000 17.62
ATOM   2247  O   GLN A 299       8.136  32.450   0.809 1.000 25.21
ATOM   2248  N   CYS A 300       7.152  31.871   2.733 1.000 23.78
ATOM   2249  CA  CYS A 300       7.113  30.506   2.245 1.000 15.17
ATOM   2250  CB  CYS A 300       6.555  29.579   3.330 1.000 26.74
ATOM   2251  SG  CYS A 300       7.710  29.138   4.647 1.000 25.71
ATOM   2252  C   CYS A 300       6.212  30.350   1.023 1.000 21.29
ATOM   2253  O   CYS A 300       6.539  29.695   0.050 1.000 24.33
ATOM   2254  N   VAL A 301       5.033  30.956   1.118 1.000 22.72
ATOM   2255  CA  VAL A 301       4.112  30.918  -0.014 1.000 22.06
ATOM   2256  CB  VAL A 301       2.771  31.522   0.407 1.000 23.59
ATOM   2257  CG1 VAL A 301       1.869  31.780  -0.793 1.000 27.41
ATOM   2258  CG2 VAL A 301       2.103  30.549   1.385 1.000 22.39
ATOM   2259  C   VAL A 301       4.739  31.650  -1.213 1.000 26.22
ATOM   2260  O   VAL A 301       4.684  31.075  -2.300 1.000 25.21
ATOM   2261  N   ARG A 302       5.299  32.832  -0.941 1.000 30.33
ATOM   2262  CA  ARG A 302       5.937  33.614  -2.013 1.000 27.54
ATOM   2263  CB  ARG A 302       6.701  34.808  -1.462 1.000 26.63
ATOM   2264  CG  ARG A 302       7.324  35.658  -2.568 1.000 39.21
ATOM   2265  CD  ARG A 302       8.529  36.449  -2.082 1.000 43.43
ATOM   2266  NE  ARG A 302       9.554  35.568  -1.510 1.000 37.14
ATOM   2267  CZ  ARG A 302      10.329  35.931  -0.494 1.000 41.54
ATOM   2268  NH1 ARG A 302      10.197  37.132   0.049 1.000 63.42
ATOM   2269  NH2 ARG A 302      11.233  35.083  -0.027 1.000 50.68
ATOM   2270  C   ARG A 302       6.895  32.701  -2.764 1.000 32.29
ATOM   2271  O   ARG A 302       6.982  32.557  -3.972 1.000 31.68
ATOM   2272  N   ASP A 303       7.670  31.982  -1.931 1.000 27.62
ATOM   2273  CA  ASP A 303       8.736  31.200  -2.547 1.000 23.05
ATOM   2274  CB  ASP A 303       9.749  30.722  -1.496 1.000 29.94
ATOM   2275  CG  ASP A 303      10.561  31.886  -0.934 1.000 44.96
ATOM   2276  OD1 ASP A 303      10.575  33.000  -1.513 1.000 37.48
ATOM   2277  OD2 ASP A 303      11.207  31.698   0.125 1.000 27.41
ATOM   2278  C   ASP A 303       8.159  30.064  -3.366 1.000 32.89
ATOM   2279  O   ASP A 303       8.647  29.887  -4.490 1.000 34.89
ATOM   2280  N   VAL A 304       7.167  29.345  -2.844 1.000 30.50
ATOM   2281  CA  VAL A 304       6.548  28.260  -3.598 1.000 23.94
ATOM   2282  CB  VAL A 304       5.491  27.493  -2.783 1.000 27.62
ATOM   2283  CG1 VAL A 304       4.652  26.589  -3.669 1.000 23.38
ATOM   2284  CG2 VAL A 304       6.165  26.665  -1.692 1.000 24.59
ATOM   2285  C   VAL A 304       5.884  28.774  -4.877 1.000 22.14
ATOM   2286  O   VAL A 304       6.042  28.169  -5.933 1.000 25.47
ATOM   2287  N   LEU A 305       5.140  29.874  -4.827 1.000 27.71
```

FIGURE 198

```
ATOM   2288  CA  LEU A 305       4.558  30.400  -6.073 1.000 29.38
ATOM   2289  CB  LEU A 305       3.555  31.506  -5.706 1.000 38.16
ATOM   2290  CG  LEU A 305       2.392  31.001  -4.830 1.000 35.13
ATOM   2291  CD1 LEU A 305       1.344  32.082  -4.643 1.000 31.50
ATOM   2292  CD2 LEU A 305       1.810  29.740  -5.458 1.000 27.65
ATOM   2293  C   LEU A 305       5.606  30.942  -7.043 1.000 39.73
ATOM   2294  O   LEU A 305       5.477  30.795  -8.267 1.000 34.97
ATOM   2295  N   ARG A 306       6.644  31.587  -6.500 1.000 30.15
ATOM   2296  CA  ARG A 306       7.696  32.191  -7.303 1.000 41.94
ATOM   2297  CB  ARG A 306       8.843  32.715  -6.443 1.000 44.09
ATOM   2298  CG  ARG A 306       9.589  33.889  -7.052 1.000 39.22
ATOM   2299  CD  ARG A 306      10.448  34.547  -5.980 1.000 42.72
ATOM   2300  NE  ARG A 306       9.979  35.884  -5.635 1.000 52.78
ATOM   2301  CZ  ARG A 306      10.606  36.671  -4.767 1.000 54.00
ATOM   2302  NH1 ARG A 306      11.714  36.247  -4.169 1.000 67.12
ATOM   2303  NH2 ARG A 306      10.130  37.875  -4.496 1.000 46.01
ATOM   2304  C   ARG A 306       8.287  31.172  -8.271 1.000 29.94
ATOM   2305  O   ARG A 306       8.462  31.437  -9.450 1.000 37.35
ATOM   2306  N   ALA A 307       8.569  30.025  -7.699 1.000 31.66
ATOM   2307  CA  ALA A 307       9.158  28.861  -8.317 1.000 23.60
ATOM   2308  CB  ALA A 307       9.447  27.819  -7.233 1.000 26.10
ATOM   2309  C   ALA A 307       8.306  28.189  -9.381 1.000 47.11
ATOM   2310  O   ALA A 307       8.799  28.044 -10.499 1.000 44.35
ATOM   2311  N   ARG A 308       7.102  27.762  -9.042 1.000 52.74
ATOM   2312  CA  ARG A 308       6.308  26.829  -9.829 1.000 54.48
ATOM   2313  CB  ARG A 308       4.971  26.558  -9.115 1.000 57.15
ATOM   2314  CG  ARG A 308       5.194  25.951  -7.736 1.000 58.94
ATOM   2315  CD  ARG A 308       4.116  24.969  -7.323 1.000 55.91
ATOM   2316  NE  ARG A 308       2.804  25.598  -7.229 1.000 48.91
ATOM   2317  CZ  ARG A 308       1.773  25.117  -6.536 1.000 51.64
ATOM   2318  NH1 ARG A 308       1.868  23.990  -5.844 1.000 35.99
ATOM   2319  NH2 ARG A 308       0.639  25.806  -6.558 1.000 44.89
ATOM   2320  C   ARG A 308       6.063  27.269 -11.267 1.000 53.61
ATOM   2321  O   ARG A 308       5.807  26.391 -12.115 1.000 48.27
ATOM   2322  N   LYS A 309       6.155  28.565 -11.523 1.000 43.56
ATOM   2323  CA  LYS A 309       6.129  29.126 -12.866 1.000 55.87
ATOM   2324  CB  LYS A 309       6.515  30.617 -12.836 1.000 53.73
ATOM   2325  CG  LYS A 309       5.322  31.519 -12.555 1.000 50.14
ATOM   2326  CD  LYS A 309       5.733  32.861 -11.988 1.000 51.79
ATOM   2327  CE  LYS A 309       5.194  33.994 -12.859 1.000 58.07
ATOM   2328  NZ  LYS A 309       5.302  35.321 -12.188 1.000 68.64
ATOM   2329  C   LYS A 309       7.071  28.394 -13.819 1.000 49.69
ATOM   2330  O   LYS A 309       6.769  28.146 -14.991 1.000 49.16
ATOM   2331  N   LEU A 310       8.259  28.052 -13.326 1.000 28.26
ATOM   2332  CA  LEU A 310       9.179  27.229 -14.104 1.000 38.83
ATOM   2333  CB  LEU A 310      10.617  27.612 -13.747 1.000 55.29
ATOM   2334  CG  LEU A 310      10.793  29.062 -13.278 1.000 62.65
ATOM   2335  CD1 LEU A 310      12.262  29.360 -12.996 1.000 82.48
ATOM   2336  CD2 LEU A 310      10.245  30.039 -14.295 1.000 58.72
ATOM   2337  C   LEU A 310       8.920  25.745 -13.861 1.000 34.79
ATOM   2338  O1  HOH W   1       2.014  17.687  26.597 1.000 14.70
ATOM   2339  O1  HOH W   2      -5.416  28.864  24.748 1.000 14.82
```

FIGURE 199

```
ATOM   2340  O1  HOH W   3      9.941  34.403  15.794 1.000 20.77
ATOM   2341  O1  HOH W   4      1.150  20.544   3.861 1.000 16.32
ATOM   2342  O1  HOH W   5     11.855   1.496  23.723 1.000 20.79
ATOM   2343  O1  HOH W   6     11.026  19.440  31.061 1.000 22.81
ATOM   2344  O1  HOH W   7     -4.100  15.347  34.619 1.000 20.35
ATOM   2345  O1  HOH W   8     -8.502  35.220  27.278 1.000 20.31
ATOM   2346  O1  HOH W   9     10.956   8.876  28.629 1.000 24.20
ATOM   2347  O1  HOH W  10     13.818  22.433  16.330 1.000 21.57
ATOM   2348  O1  HOH W  11     -4.748  20.337   7.520 1.000 18.34
ATOM   2349  O1  HOH W  12      7.144  17.757  36.248 1.000 23.39
ATOM   2350  O1  HOH W  13     -8.500  25.553  30.582 1.000 21.46
ATOM   2351  O1  HOH W  14      1.872  18.169  29.324 1.000 19.74
ATOM   2352  O1  HOH W  15    -12.583  28.920  26.833 1.000 23.46
ATOM   2353  O1  HOH W  16     17.845  15.230  13.268 1.000 25.48
ATOM   2354  O1  HOH W  17      2.522  25.792  29.444 1.000 21.14
ATOM   2355  O1  HOH W  18    -12.414  36.213  18.671 1.000 35.42
ATOM   2356  O1  HOH W  19     -0.308  19.015  30.907 1.000 20.05
ATOM   2357  O1  HOH W  20     -4.507  15.507   8.656 1.000 26.56
ATOM   2358  O1  HOH W  21     -1.463  16.804  32.355 1.000 19.87
ATOM   2359  O1  HOH W  22     -7.774  24.896  24.411 1.000 25.30
ATOM   2360  O1  HOH W  23      2.487  23.390  -2.046 1.000 21.28
ATOM   2361  O1  HOH W  24     -5.084  36.399  19.340 1.000 24.16
ATOM   2362  O1  HOH W  25     11.554  11.480  16.357 1.000 25.31
ATOM   2363  O1  HOH W  26     12.946   5.581  11.917 1.000 24.23
ATOM   2364  O1  HOH W  27    -12.980  20.577  24.368 1.000 27.97
ATOM   2365  O1  HOH W  28     10.212  31.138  15.942 1.000 33.79
ATOM   2366  O1  HOH W  29     14.372   4.995  27.900 1.000 26.39
ATOM   2367  O1  HOH W  30     -2.960  34.484   1.831 1.000 27.40
ATOM   2368  O1  HOH W  31     10.824  30.078  18.289 1.000 25.67
ATOM   2369  O1  HOH W  32     13.982   2.205  27.167 1.000 25.41
ATOM   2370  O1  HOH W  33      1.575  12.107  33.860 1.000 34.16
ATOM   2371  O1  HOH W  34     -3.137  19.220  -7.395 1.000 25.27
ATOM   2372  O1  HOH W  35     -6.170  33.272  20.828 1.000 21.49
ATOM   2373  O1  HOH W  36     -1.632  39.007  16.222 1.000 27.21
ATOM   2374  O1  HOH W  37      7.347  31.206  19.263 1.000 26.77
ATOM   2375  O1  HOH W  38      9.444  26.520  21.341 1.000 29.37
ATOM   2376  O1  HOH W  39     -8.237   9.947  35.385 1.000 47.49
ATOM   2377  O1  HOH W  40     -2.103  38.773  20.445 1.000 27.92
ATOM   2378  O1  HOH W  41     -9.820  28.498  38.052 1.000 26.65
ATOM   2379  O1  HOH W  42     10.051  20.936  -0.828 1.000 26.93
ATOM   2380  O1  HOH W  43    -14.963  17.351  10.401 1.000 37.99
ATOM   2381  O1  HOH W  44     15.436   8.322  21.787 1.000 29.21
ATOM   2382  O1  HOH W  45      1.871  19.354   1.571 1.000 22.03
ATOM   2383  O1  HOH W  46     -7.599  19.535  29.453 1.000 22.96
ATOM   2384  O1  HOH W  47      3.330  17.045   1.103 1.000 26.08
ATOM   2385  O1  HOH W  48     14.921  28.549   0.827 1.000 30.69
ATOM   2386  O1  HOH W  49      4.221  11.439  33.921 1.000 28.27
ATOM   2387  O1  HOH W  50      6.471   7.214  33.313 1.000 30.73
ATOM   2388  O1  HOH W  51      6.997  11.081   3.016 1.000 29.06
ATOM   2389  O1  HOH W  52      9.828  14.413   1.356 1.000 36.16
ATOM   2390  O1  HOH W  53     -2.049   5.578  31.420 1.000 34.40
ATOM   2391  O1  HOH W  54      7.546  28.605  19.653 1.000 38.00
```

FIGURE 200

```
ATOM   2392  O1  HOH W   55     -11.689   15.787   24.708  1.000  27.99
ATOM   2393  O1  HOH W   56      -1.930   38.222    3.832  1.000  26.57
ATOM   2394  O1  HOH W   57       3.629    5.858   35.758  1.000  33.41
ATOM   2395  O1  HOH W   58       2.994   20.770   -0.697  1.000  26.75
ATOM   2396  O1  HOH W   59     -13.363   22.643   29.523  1.000  32.53
ATOM   2397  O1  HOH W   60      -3.967   36.098    3.552  1.000  24.24
ATOM   2398  O1  HOH W   61     -13.003   28.717   20.098  1.000  30.30
ATOM   2399  O1  HOH W   62      -3.571   34.737   21.021  1.000  24.77
ATOM   2400  O1  HOH W   63      -3.353   25.782   37.784  1.000  31.16
ATOM   2401  O1  HOH W   64      -4.181   15.085   11.174  1.000  23.09
ATOM   2402  O1  HOH W   65      14.882    1.430   29.740  1.000  32.36
ATOM   2403  O1  HOH W   66      -2.385   10.919   14.099  1.000  31.04
ATOM   2404  O1  HOH W   67      -2.022   11.997   12.100  1.000  34.23
ATOM   2405  O1  HOH W   68      -0.074    6.701   29.852  1.000  28.84
ATOM   2406  O1  HOH W   69      13.012   17.319   31.049  1.000  34.35
ATOM   2407  O1  HOH W   70      -0.945   -1.322   32.490  1.000  27.87
ATOM   2408  O1  HOH W   71     -14.687   16.999    7.638  1.000  39.15
ATOM   2409  O1  HOH W   72       5.621   40.002   16.979  1.000  36.19
ATOM   2410  O1  HOH W   73       5.019   34.934   -5.124  1.000  30.14
ATOM   2411  O1  HOH W   74     -13.469   20.866   21.275  1.000  35.79
ATOM   2412  O1  HOH W   75      -6.587   38.439   -4.937  1.000  34.64
ATOM   2413  O1  HOH W   76      -6.586   20.943    1.389  1.000  34.28
ATOM   2414  O1  HOH W   77      16.678    2.326   14.116  1.000  34.62
ATOM   2415  O1  HOH W   78      -0.115    2.845   36.291  1.000  30.53
ATOM   2416  O1  HOH W   79      -0.221   19.000   -0.242  1.000  25.17
ATOM   2417  O1  HOH W   80      18.011   13.617   17.062  1.000  28.47
ATOM   2418  O1  HOH W   81       8.378    5.752   31.945  1.000  25.91
ATOM   2419  O1  HOH W   82      -1.655   40.288   22.680  1.000  32.53
ATOM   2420  O1  HOH W   83       6.545   30.062   22.582  1.000  41.03
ATOM   2421  O1  HOH W   84       8.148   39.805   15.692  1.000  35.25
ATOM   2422  O1  HOH W   85     -14.461   20.880   32.244  1.000  35.66
ATOM   2423  O1  HOH W   86       5.851    3.752   34.055  1.000  36.71
ATOM   2424  O1  HOH W   87      -0.955    1.090   13.636  1.000  39.92
ATOM   2425  O1  HOH W   88       8.422   39.414   -0.957  1.000  48.27
ATOM   2426  O1  HOH W   89      10.954   39.318    2.465  1.000  44.33
ATOM   2427  O1  HOH W   90       2.579   50.503    2.300  1.000  54.86
ATOM   2428  O1  HOH W   91       3.085   48.432    3.786  1.000  37.84
ATOM   2429  O1  HOH W   92       6.015   47.673   10.758  1.000  46.93
ATOM   2430  O1  HOH W   93      -4.388   -7.612   19.050  1.000  45.59
ATOM   2431  O1  HOH W   94       0.214   18.775   39.716  1.000  51.95
ATOM   2432  O1  HOH W   95     -12.966   13.296   30.655  1.000  33.33
ATOM   2433  O1  HOH W   96       0.538   14.855   35.881  1.000  40.77
ATOM   2434  O1  HOH W   97      17.070   25.109    3.747  1.000  45.67
ATOM   2435  O1  HOH W   98      11.830   27.957   -0.458  1.000  43.72
ATOM   2436  O1  HOH W   99      -4.616   12.312   11.217  1.000  40.90
ATOM   2437  O1  HOH W  100      11.872   35.092    7.761  1.000  55.45
ATOM   2438  O1  HOH W  101      10.663   36.578    9.005  1.000  38.01
ATOM   2439  O1  HOH W  102      14.787   30.925    2.347  1.000  38.58
ATOM   2440  O1  HOH W  103      -7.639   22.432   -0.126  1.000  30.65
ATOM   2441  O1  HOH W  104      -0.768   39.758   18.325  1.000  32.85
ATOM   2442  O1  HOH W  105      11.805   25.356   22.168  1.000  40.43
ATOM   2443  O1  HOH W  106      20.422   18.338   13.902  1.000  45.59
```

FIGURE 201

```
ATOM   2444  O1  HOH W 107    10.183  24.874  30.453 1.000 38.68
ATOM   2445  O1  HOH W 108    16.785  32.728  12.612 1.000 31.96
ATOM   2446  O1  HOH W 109    13.492  30.752  17.655 1.000 39.37
ATOM   2447  O1  HOH W 110    -3.931  16.862   2.029 1.000 30.36
ATOM   2448  O1  HOH W 111    -7.045  29.232   5.340 1.000 28.48
ATOM   2449  O1  HOH W 112    -7.762  11.786  25.923 1.000 28.04
ATOM   2450  O1  HOH W 113   -13.605  33.677  20.128 1.000 32.20
ATOM   2451  O1  HOH W 114    10.065  39.638   9.803 1.000 38.13
ATOM   2452  O1  HOH W 115    -8.934  24.435   1.974 1.000 31.50
ATOM   2453  O1  HOH W 116    17.216  10.741  21.573 1.000 34.76
ATOM   2454  O1  HOH W 117   -11.923  22.839  19.220 1.000 39.73
ATOM   2455  O1  HOH W 118     7.473  12.705   1.120 1.000 36.05
ATOM   2456  O1  HOH W 119     5.483   8.873   2.549 1.000 43.08
ATOM   2457  O1  HOH W 120   -14.010  13.235  28.254 1.000 43.67
ATOM   2458  O1  HOH W 121    -6.810   4.829  28.513 1.000 38.61
ATOM   2459  O1  HOH W 122   -14.132  10.542  31.339 1.000 58.03
ATOM   2460  O1  HOH W 123     5.390  21.831  37.038 1.000 43.01
ATOM   2461  O1  HOH W 124   -14.479  21.966  26.038 1.000 35.30
ATOM   2462  O1  HOH W 125     4.264  17.945  -1.288 1.000 36.29
ATOM   2463  O1  HOH W 126    23.828  24.174  30.873 1.000 49.73
ATOM   2464  O1  HOH W 127    -6.176  26.450   5.939 1.000 65.00
ATOM   2465  O1  HOH W 128     3.350  34.622  26.589 1.000 39.90
ATOM   2466  O1  HOH W 129    16.916  27.171   7.485 1.000 41.94
ATOM   2467  O1  HOH W 130   -11.189  32.210   8.814 1.000 35.24
ATOM   2468  O1  HOH W 131    -4.460   2.050  29.021 1.000 40.95
ATOM   2469  O1  HOH W 132   -15.621  16.785  16.397 1.000 51.14
ATOM   2470  O1  HOH W 133    13.141  -0.750  30.285 1.000 35.50
ATOM   2471  O1  HOH W 134    16.391  14.131  18.996 1.000 33.72
ATOM   2472  O1  HOH W 135    15.720  23.607  18.037 1.000 36.32
ATOM   2473  O1  HOH W 136    -9.180  28.989   7.435 1.000 51.57
ATOM   2474  O1  HOH W 137   -13.398  18.098  35.125 1.000 52.51
ATOM   2475  O1  HOH W 138   -14.347  26.998  19.051 1.000 43.88
ATOM   2476  O1  HOH W 139    17.167   1.215  28.662 1.000 40.00
ATOM   2477  O1  HOH W 140    -5.468  13.807   7.111 1.000 45.45
ATOM   2478  O1  HOH W 141    -4.475   4.635  29.841 1.000 36.10
ATOM   2479  O1  HOH W 142   -12.828  27.385  13.802 1.000 33.50
ATOM   2480  O1  HOH W 143   -13.938  17.712  24.521 1.000 31.09
ATOM   2481  O1  HOH W 144    16.503  26.254  10.447 1.000 46.13
ATOM   2482  O1  HOH W 145    20.599  20.875  15.821 1.000 41.98
ATOM   2483  O1  HOH W 146    20.503  19.870  22.082 1.000 51.04
ATOM   2484  O1  HOH W 147     4.262  18.175  36.175 1.000 33.32
ATOM   2485  O1  HOH W 148    -0.297  26.441  36.081 1.000 52.28
ATOM   2486  O1  HOH W 149    20.297  28.737  16.671 1.000 44.74
ATOM   2487  O1  HOH W 150     7.203  23.388  35.762 1.000 66.45
ATOM   2488  O1  HOH W 151    10.549   7.398  31.284 1.000 38.68
ATOM   2489  O1  HOH W 152     6.081  38.872  -2.812 1.000 40.08
ATOM   2490  O1  HOH W 153    13.265  33.000   1.040 1.000 36.24
ATOM   2491  O1  HOH W 154   -12.530  39.835  27.125 1.000105.41
ATOM   2492  O1  HOH W 155    11.420  11.430  30.533 1.000 47.78
ATOM   2493  O1  HOH W 156     0.901   8.244  35.852 1.000 33.14
ATOM   2494  O1  HOH W 157    -7.963  29.336  -0.295 1.000 50.61
ATOM   2495  O1  HOH W 158    20.035  12.009  18.471 1.000 34.37
```

FIGURE 202

```
ATOM   2496  O1   HOH W 159    -4.350   3.543  10.491 1.000 84.51
ATOM   2497  O1   HOH W 160     4.286   9.674  36.102 1.000 40.87
ATOM   2498  O1   HOH W 161    -8.003  41.353  17.020 1.000 48.97
ATOM   2499  O1   HOH W 162    15.195  17.562  28.763 1.000 43.23
ATOM   2500  O1   HOH W 163   -10.778   5.540  28.103 1.000 47.36
ATOM   2501  O1   HOH W 164    19.303  31.924  16.796 1.000 51.07
ATOM   2502  O1   HOH W 165    -4.383  19.665  -0.828 1.000 32.47
ATOM   2503  O1   HOH W 166     8.839  24.816  -3.783 1.000 41.71
ATOM   2504  O1   HOH W 167     6.219  15.861  -1.300 1.000 43.10
ATOM   2505  O1   HOH W 168    10.025  33.624  18.562 1.000 40.32
ATOM   2506  O1   HOH W 169     7.836  30.797  27.712 1.000 56.16
ATOM   2507  O1   HOH W 170    -9.946  19.362  35.362 1.000 41.05
ATOM   2508  O1   HOH W 171    22.397  23.179  24.094 1.000 37.17
ATOM   2509  O1   HOH W 172     6.196  31.438  24.998 1.000 39.04
ATOM   2510  O1   HOH W 173     2.656  29.647 -11.398 1.000 69.02
ATOM   2511  O1   HOH W 174    -7.993  19.195   2.017 1.000 51.50
ATOM   2512  O1   HOH W 175    -7.725   9.838  10.116 1.000 41.23
ATOM   2513  O1   HOH W 176    10.217   8.209  35.322 1.000 52.55
ATOM   2514  O1   HOH W 177    22.886  18.048   5.069 1.000 50.22
ATOM   2515  O1   HOH W 178    13.259   6.843  29.204 1.000 37.28
ATOM   2516  O1   HOH W 179   -11.344  39.086  20.797 1.000 63.58
ATOM   2517  O1   HOH W 180    13.661  33.712   7.349 1.000 48.08
ATOM   2518  O1   HOH W 181    -3.554   0.841  36.601 1.000 44.25
ATOM   2519  O1   HOH W 182     2.483  16.905  37.338 1.000 45.30
ATOM   2520  O1   HOH W 183    20.094   7.002  12.783 1.000 44.53
ATOM   2521  O1   HOH W 184    13.549  19.866  -1.559 1.000 51.39
ATOM   2522  O1   HOH W 185    11.649  -2.468  19.869 1.000 58.70
ATOM   2523  O1   HOH W 186   -11.387   9.057  20.869 1.000 50.26
ATOM   2524  O1   HOH W 187     2.270  53.746   3.948 1.000 77.69
ATOM   2525  O1   HOH W 188     7.272  43.089  10.416 1.000 40.06
ATOM   2526  O1   HOH W 189   -10.704  43.630  20.531 1.000 67.96
ATOM   2527  O1   HOH W 190   -10.161  31.212  -6.317 1.000 49.46
ATOM   2528  O1   HOH W 191     9.522   6.064   4.334 1.000 40.34
ATOM   2529  O1   HOH W 192    16.516  16.717  21.174 1.000 20.43
ATOM   2530  O1   HOH W 193    -0.857  36.253  20.284 1.000 32.45
ATOM   2531  O1   HOH W 194    18.504  18.275  22.970 1.000 34.08
ATOM   2532  O1   HOH W 195     5.801  29.116 -17.383 1.000 43.44
ATOM   2533  O1   HOH W 196    -7.990  22.703  42.079 1.000 44.28
ATOM   2534  O1   HOH W 197    -6.632  16.747  36.401 1.000 37.74
ATOM   2535  O1   HOH W 198   -11.815  21.607  16.468 1.000 30.66
ATOM   2536  O1   HOH W 199    -2.843  32.478 -11.634 1.000 33.04
ATOM   2537  O1   HOH W 200   -10.429  21.931   2.610 1.000 43.58
ATOM   2538  O1   HOH W 201   -12.782  11.466  36.315 1.000 64.73
ATOM   2539  O1   HOH W 202    -1.120   8.730   9.515 1.000 39.25
ATOM   2540  O1   HOH W 203     7.752  27.565  23.146 1.000 40.81
ATOM   2541  O1   HOH W 204    -4.173  17.946  -3.218 1.000 40.93
ATOM   2542  O1   HOH W 205   -12.084   5.496  19.653 1.000 41.61
ATOM   2543  O1   HOH W 206     1.514   0.000  33.985 1.000 47.99
ATOM   2544  O1   HOH W 207    -4.358  32.825  -9.953 1.000 43.82
ATOM   2545  O1   HOH W 208    14.414  14.005  29.829 1.000 45.03
ATOM   2546  O1   HOH W 209    22.352  27.139  21.459 1.000 63.00
ATOM   2547  O1   HOH W 210   -12.128  21.274   9.705 1.000 39.35
```

FIGURE 203

```
ATOM   2548  O1  HOH W 211   -15.431  29.589  23.297 1.000 42.10
ATOM   2549  O1  HOH W 212    15.717  21.134   2.051 1.000 44.92
ATOM   2550  O1  HOH W 213    22.149  19.371   9.989 1.000 42.03
ATOM   2551  O1  HOH W 214   -12.478  28.555  38.340 1.000 49.23
ATOM   2552  O1  HOH W 215   -10.373  26.583  11.557 1.000 78.42
ATOM   2553  O1  HOH W 216     5.904  28.076  21.168 1.000 47.47
ATOM   2554  O1  HOH W 217    18.063  28.353  10.622 1.000 39.47
ATOM   2555  O1  HOH W 218     5.741  29.596  34.757 1.000 50.24
ATOM   2556  O1  HOH W 219    23.482  28.211  28.256 1.000 35.92
ATOM   2557  O1  HOH W 220    20.729  22.839  22.289 1.000 47.92
ATOM   2558  O1  HOH W 221   -13.743  23.631  15.768 1.000 56.18
ATOM   2559  O1  HOH W 222     0.808   4.763  11.965 1.000 52.58
ATOM   2560  O1  HOH W 223    19.695  26.083  30.808 1.000 48.34
ATOM   2561  O1  HOH W 224   -10.086  39.766  26.571 1.000 37.07
ATOM   2562  O1  HOH W 225    -8.185  26.002  12.785 1.000 43.04
ATOM   2563  O1  HOH W 226   -15.767  14.896  27.476 1.000 47.84
ATOM   2564  O1  HOH W 227    -8.943  41.210  23.852 1.000 51.44
ATOM   2565  O1  HOH W 228   -13.243  38.293   6.326 1.000 46.48
ATOM   2566  O1  HOH W 229    18.663   0.325  20.946 1.000 45.85
ATOM   2567  O1  HOH W 230    12.773   6.887  31.536 1.000 35.71
ATOM   2568  O1  HOH W 231    -7.081  32.709  -9.020 1.000 54.13
ATOM   2569  O1  HOH W 232   -14.685  24.271  19.574 1.000 44.68
ATOM   2570  O1  HOH W 233     1.541   7.037  10.861 1.000 42.37
ATOM   2571  O1  HOH W 234    17.407  14.624  24.034 1.000 49.34
ATOM   2572  O1  HOH W 235    -8.898  25.154   4.255 1.000 55.39
ATOM   2573  O1  HOH W 236     9.061  28.544  24.947 1.000 39.46
ATOM   2574  O1  HOH W 237   -13.663  15.439  32.214 1.000 45.65
ATOM   2575  O1  HOH W 238    13.791  17.581  34.085 1.000 46.31
ATOM   2576  O1  HOH W 239   -11.961  16.055  13.445 1.000 40.48
ATOM   2577  O1  HOH W 240    15.223   9.544  28.176 1.000 44.69
ATOM   2578  O1  HOH W 241   -13.353  32.529   7.227 1.000 57.27
ATOM   2579  O1  HOH W 242     8.996  26.371 -16.754 1.000 48.64
ATOM   2580  O1  HOH W 243     6.092  23.068  -5.367 1.000 48.87
ATOM   2581  O1  HOH W 244    22.747  32.593  25.452 1.000 44.40
ATOM   2582  O1  HOH W 245    -0.304  32.548 -11.298 1.000 48.96
ATOM   2583  O1  HOH W 246    -4.988  -3.152  23.809 1.000 62.34
ATOM   2584  O1  HOH W 247     1.129  39.597  -7.798 1.000 53.14
ATOM   2585  O1  HOH W 248    -6.772  14.727   4.405 1.000 81.57
ATOM   2586  O1  HOH W 249    17.223  10.068  27.178 1.000 40.37
ATOM   2587  O1  HOH W 250    17.655  12.530  28.719 1.000 50.20
ATOM   2588  O1  HOH W 251     4.037   7.351   8.012 1.000 58.42
ATOM   2589  O1  HOH W 252    -1.828   7.240  33.526 1.000 45.82
ATOM   2590  O1  HOH W 253   -12.257  12.014  23.313 1.000 42.52
ATOM   2591  O1  HOH W 254    18.878  30.723  23.928 1.000 81.96
ATOM   2592  O1  HOH W 255    -2.406  13.001  35.608 1.000 49.36
ATOM   2593  O1  HOH W 256     0.100  42.639  18.634 1.000 42.69
ATOM   2594  O1  HOH W 257     8.781  15.841  -0.776 1.000 42.10
ATOM   2595  O1  HOH W 258     8.836  41.627  14.232 1.000 37.51
ATOM   2596  O1  HOH W 259    10.082  41.227   7.652 1.000 51.86
ATOM   2597  O1  HOH W 260    16.536   4.886  29.969 1.000 46.99
ATOM   2598  O1  HOH W 261     8.904   2.996  11.102 1.000 59.35
ATOM   2599  O1  HOH W 262    17.169  18.558   5.383 1.000 42.46
```

FIGURE 204

```
ATOM   2600  O1   HOH W 263      22.449  12.846   9.882 1.000 39.10
ATOM   2601  O1   HOH W 264      11.441  22.960  -0.297 1.000 46.40
ATOM   2602  O1   HOH W 265      12.891  35.186  -7.958 1.000 59.81
ATOM   2603  O1   HOH W 266     -13.897  24.909  13.026 1.000 45.86
ATOM   2604  O1   HOH W 267      19.060   9.563  25.380 1.000 45.48
ATOM   2605  O1   HOH W 268       3.802  25.392 -14.805 1.000 50.59
ATOM   2606  O1   HOH W 269      16.184  28.549  22.110 1.000 43.02
ATOM   2607  O1   HOH W 270      -1.154  37.399 -12.192 1.000 53.68
ATOM   2608  O1   HOH W 271      -4.123  -5.269  18.602 1.000 79.29
ATOM   2609  O1   HOH W 272      -7.384   2.425  21.048 1.000 57.48
ATOM   2610  O1   HOH W 273      18.456  25.557  18.479 1.000 44.20
ATOM   2611  O1   HOH W 274       6.328   1.205   9.458 1.000 59.21
ATOM   2612  O1   HOH W 275     -14.117   5.491  34.696 1.000 60.85
ATOM   2613  O1   HOH W 276     -10.629  13.583  38.737 1.000 45.87
ATOM   2614  O1   HOH W 277     -11.913  20.085  36.715 1.000 51.46
ATOM   2615  O1   HOH W 278      -8.375  43.387   4.147 1.000 45.52
ATOM   2616  O1   HOH W 279      -9.702  -4.797  28.731 1.000 54.85
ATOM   2617  O1   HOH W 280     -12.340  25.454  10.801 1.000 58.08
ATOM   2618  O1   HOH W 281      -4.825  10.727   8.928 1.000 55.18
ATOM   2619  O1   HOH W 282      -0.469  27.271  21.450 1.000143.86
ATOM   2620  O1   HOH W 283       1.342   6.223  -2.164 1.000 59.20
ATOM   2621  O1   HOH W 284     -13.187   3.566  20.610 1.000 59.09
ATOM   2622  O1   HOH W 285     -10.963  -4.464  24.556 1.000 70.44
ATOM   2623  O1   HOH W 286       2.082   7.263   5.127 1.000 59.07
ATOM   2624  O1   HOH W 287     -14.375  31.030  19.349 1.000 42.90
ATOM   2625  O1   HOH W 288     -13.932  23.344  10.653 1.000 42.75
ATOM   2626  O1   HOH W 289     -10.496  31.449   2.357 1.000 37.15
ATOM   2627  O1   HOH W 290      -5.935  42.393   1.278 1.000 48.92
ATOM   2628  O1   HOH W 291      -2.417  29.064  38.937 1.000 98.13
ATOM   2629  O1   HOH W 292       4.370   7.161   3.591 1.000 54.78
ATOM   2630  O1   HOH W 293     -12.101  29.567  -1.765 1.000 45.21
ATOM   2631  O1   HOH W 294      -2.974  52.167   6.924 1.000 54.46
ATOM   2632  O1   HOH W 295       6.373  24.732 -15.736 1.000 55.54
ATOM   2633  O1   HOH W 296       5.144   2.212  15.505 1.000132.19
ATOM   2634  O1   HOH W 297       4.119  25.540 -18.043 1.000 63.04
ATOM   2635  O1   HOH W 298      -6.584  46.120   5.004 1.000 61.91
ATOM   2636  O1   HOH W 299      17.182  15.542  27.047 1.000 45.04
ATOM   2637  O1   HOH W 300      12.276  33.194  -3.953 1.000 50.26
ATOM   2638  O1   HOH W 301       4.057  25.805  36.737 1.000 51.03
ATOM   2639  O1   HOH W 302      17.210  27.508  26.182 1.000 43.16
ATOM   2640  O1   HOH W 303     -13.383  20.836   7.055 1.000 53.40
ATOM   2641  O1   HOH W 304      19.482  17.276  28.478 1.000 60.44
ATOM   2642  O1   HOH W 305      -6.950  41.249  -1.159 1.000 53.64
ATOM   2643  O1   HOH W 306     -10.165   8.508  39.743 1.000 61.15
ATOM   2644  O1   HOH W 307       4.134  19.769  -3.502 1.000 52.25
ATOM   2645  O1   HOH W 308       3.101  15.563  -2.031 1.000 45.06
ATOM   2646  O1   HOH W 309       8.724  40.739  11.753 1.000 47.08
ATOM   2647  O1   HOH W 310     -10.535   2.414  25.587 1.000 88.70
END
```

FIGURE 205

```
CRYST1    62.186   71.797   70.448  90.00  93.56  90.00
ATOM      1  N   THR A  20      13.220  15.647  19.635  1.00 51.11
ATOM      2  CA  THR A  20      14.046  16.499  20.485  1.00 49.11
ATOM      3  CB  THR A  20      13.219  17.270  21.525  1.00 56.84
ATOM      4  OG1 THR A  20      11.822  17.025  21.318  1.00 82.00
ATOM      5  CG2 THR A  20      13.411  18.771  21.351  1.00 62.78
ATOM      6  C   THR A  20      15.126  15.682  21.189  1.00 47.28
ATOM      7  O   THR A  20      14.920  14.601  21.731  1.00 36.27
ATOM      8  N   SER A  21      16.332  16.238  21.145  1.00 41.80
ATOM      9  CA  SER A  21      17.525  15.585  21.640  1.00 38.45
ATOM     10  CB  SER A  21      18.027  14.556  20.623  1.00 50.01
ATOM     11  OG  SER A  21      18.114  15.125  19.328  1.00 57.39
ATOM     12  C   SER A  21      18.628  16.597  21.924  1.00 40.97
ATOM     13  O   SER A  21      18.818  17.552  21.172  1.00 54.77
ATOM     14  N   CYS A  22      19.351  16.377  23.013  1.00 38.55
ATOM     15  CA  CYS A  22      20.465  17.251  23.365  1.00 41.82
ATOM     16  CB  CYS A  22      20.194  17.972  24.677  1.00 49.07
ATOM     17  SG  CYS A  22      21.184  19.448  24.992  1.00157.91
ATOM     18  C   CYS A  22      21.737  16.416  23.433  1.00 40.34
ATOM     19  O   CYS A  22      22.215  16.085  24.518  1.00 48.60
ATOM     20  N   PRO A  23      22.270  16.062  22.271  1.00 32.99
ATOM     21  CA  PRO A  23      23.464  15.210  22.261  1.00 38.72
ATOM     22  CB  PRO A  23      23.710  14.926  20.790  1.00 42.84
ATOM     23  CG  PRO A  23      22.474  15.348  20.073  1.00 43.60
ATOM     24  CD  PRO A  23      21.836  16.415  20.914  1.00 38.82
ATOM     25  C   PRO A  23      24.615  15.995  22.881  1.00 48.13
ATOM     26  O   PRO A  23      24.711  17.211  22.701  1.00 47.03
ATOM     27  N   ILE A  24      25.460  15.298  23.625  1.00 44.75
ATOM     28  CA  ILE A  24      26.566  15.975  24.297  1.00 44.40
ATOM     29  CB  ILE A  24      26.272  16.206  25.788  1.00 42.81
ATOM     30  CG1 ILE A  24      25.075  17.122  26.057  1.00 46.37
ATOM     31  CD1 ILE A  24      24.076  16.565  27.047  1.00 66.22
ATOM     32  CG2 ILE A  24      27.512  16.726  26.502  1.00 39.08
ATOM     33  C   ILE A  24      27.832  15.154  24.125  1.00 40.83
ATOM     34  O   ILE A  24      27.907  13.977  24.460  1.00 37.86
ATOM     35  N   LYS A  25      28.852  15.794  23.569  1.00 44.53
ATOM     36  CA  LYS A  25      30.123  15.105  23.390  1.00 43.13
ATOM     37  CB  LYS A  25      31.053  15.966  22.534  1.00 53.45
ATOM     38  CG  LYS A  25      30.471  16.274  21.159  1.00 54.09
ATOM     39  CD  LYS A  25      31.401  15.816  20.047  1.00 53.48
ATOM     40  CE  LYS A  25      30.749  14.744  19.184  1.00 52.46
ATOM     41  NZ  LYS A  25      31.611  13.534  19.051  1.00 56.82
ATOM     42  C   LYS A  25      30.742  14.777  24.743  1.00 35.84
ATOM     43  O   LYS A  25      30.676  15.549  25.699  1.00 35.11
ATOM     44  N   ILE A  26      31.342  13.599  24.805  1.00 30.07
ATOM     45  CA  ILE A  26      31.956  13.072  26.009  1.00 44.79
ATOM     46  CB  ILE A  26      32.828  11.842  25.666  1.00 53.22
ATOM     47  CG1 ILE A  26      32.077  10.710  24.967  1.00 52.52
ATOM     48  CD1 ILE A  26      30.646  10.520  25.409  1.00 30.26
ATOM     49  CG2 ILE A  26      33.540  11.331  26.909  1.00 64.21
ATOM     50  C   ILE A  26      32.827  14.089  26.738  1.00 48.16
ATOM     51  O   ILE A  26      32.683  14.275  27.948  1.00 50.00
```

FIGURE 206

```
ATOM     52  N   ASN A  27      33.731  14.732  26.005  1.00 46.06
ATOM     53  CA  ASN A  27      34.745  15.593  26.605  1.00 48.63
ATOM     54  CB  ASN A  27      35.900  15.802  25.627  1.00 60.83
ATOM     55  CG  ASN A  27      35.840  16.989  24.701  1.00 62.73
ATOM     56  OD1 ASN A  27      34.812  17.621  24.451  1.00 61.11
ATOM     57  ND2 ASN A  27      37.003  17.330  24.140  1.00 50.07
ATOM     58  C   ASN A  27      34.158  16.914  27.075  1.00 49.04
ATOM     59  O   ASN A  27      34.843  17.726  27.705  1.00 47.37
ATOM     60  N   GLN A  28      32.878  17.141  26.778  1.00 46.15
ATOM     61  CA  GLN A  28      32.271  18.381  27.266  1.00 49.97
ATOM     62  CB  GLN A  28      31.655  19.163  26.101  1.00 56.77
ATOM     63  CG  GLN A  28      32.595  19.346  24.918  1.00 66.10
ATOM     64  CD  GLN A  28      32.102  20.390  23.934  1.00 71.73
ATOM     65  OE1 GLN A  28      31.403  21.326  24.320  1.00 72.33
ATOM     66  NE2 GLN A  28      32.453  20.244  22.661  1.00 76.09
ATOM     67  C   GLN A  28      31.227  18.109  28.337  1.00 40.82
ATOM     68  O   GLN A  28      30.634  19.039  28.895  1.00 38.64
ATOM     69  N   PHE A  29      30.965  16.838  28.647  1.00 40.55
ATOM     70  CA  PHE A  29      29.821  16.576  29.522  1.00 33.60
ATOM     71  CB  PHE A  29      29.591  15.064  29.660  1.00 39.21
ATOM     72  CG  PHE A  29      28.380  14.777  30.544  1.00 32.38
ATOM     73  CD1 PHE A  29      27.109  14.865  30.005  1.00 33.31
ATOM     74  CE1 PHE A  29      25.985  14.624  30.772  1.00 33.30
ATOM     75  CZ  PHE A  29      26.136  14.282  32.103  1.00 38.62
ATOM     76  CE2 PHE A  29      27.402  14.192  32.648  1.00 37.08
ATOM     77  CD2 PHE A  29      28.520  14.426  31.874  1.00 28.51
ATOM     78  C   PHE A  29      29.981  17.210  30.898  1.00 25.63
ATOM     79  O   PHE A  29      29.074  17.856  31.430  1.00 40.09
ATOM     80  N   GLU A  30      31.161  17.013  31.469  1.00 36.23
ATOM     81  CA  GLU A  30      31.510  17.549  32.778  1.00 43.91
ATOM     82  CB  GLU A  30      33.004  17.328  33.045  1.00 55.32
ATOM     83  CG  GLU A  30      33.738  16.650  31.903  1.00 66.32
ATOM     84  CD  GLU A  30      33.492  15.158  31.798  1.00 75.29
ATOM     85  OE1 GLU A  30      33.517  14.458  32.833  1.00 81.66
ATOM     86  OE2 GLU A  30      33.270  14.685  30.659  1.00 78.35
ATOM     87  C   GLU A  30      31.153  19.024  32.895  1.00 33.72
ATOM     88  O   GLU A  30      30.421  19.428  33.800  1.00 34.69
ATOM     89  N   GLY A  31      31.659  19.845  31.973  1.00 36.69
ATOM     90  CA  GLY A  31      31.407  21.279  32.045  1.00 29.29
ATOM     91  C   GLY A  31      29.939  21.581  31.824  1.00 40.96
ATOM     92  O   GLY A  31      29.333  22.407  32.512  1.00 37.93
ATOM     93  N   HIS A  32      29.401  20.867  30.835  1.00 51.96
ATOM     94  CA  HIS A  32      27.980  20.958  30.502  1.00 44.37
ATOM     95  CB  HIS A  32      27.638  19.919  29.443  1.00 58.95
ATOM     96  CG  HIS A  32      26.265  19.339  29.512  1.00 69.53
ATOM     97  ND1 HIS A  32      25.190  19.878  28.841  1.00 71.46
ATOM     98  CE1 HIS A  32      24.109  19.159  29.083  1.00 73.05
ATOM     99  NE2 HIS A  32      24.441  18.167  29.890  1.00 73.89
ATOM    100  CD2 HIS A  32      25.783  18.259  30.170  1.00 73.95
ATOM    101  C   HIS A  32      27.176  20.784  31.777  1.00 40.30
ATOM    102  O   HIS A  32      26.380  21.635  32.177  1.00 35.23
ATOM    103  N   PHE A  33      27.414  19.655  32.448  1.00 37.93
```

FIGURE 207

```
ATOM    104  CA   PHE A   33      26.660  19.416  33.684  1.00  35.86
ATOM    105  CB   PHE A   33      27.026  18.033  34.233  1.00  30.87
ATOM    106  CG   PHE A   33      26.146  17.593  35.390  1.00  31.86
ATOM    107  CD1  PHE A   33      24.793  17.870  35.387  1.00  30.87
ATOM    108  CE1  PHE A   33      23.998  17.487  36.449  1.00  39.07
ATOM    109  CZ   PHE A   33      24.556  16.815  37.521  1.00  40.71
ATOM    110  CE2  PHE A   33      25.911  16.528  37.534  1.00  33.73
ATOM    111  CD2  PHE A   33      26.694  16.911  36.464  1.00  32.41
ATOM    112  C    PHE A   33      26.888  20.531  34.694  1.00  33.77
ATOM    113  O    PHE A   33      25.952  20.961  35.381  1.00  36.95
ATOM    114  N    MET A   34      28.109  21.054  34.812  1.00  40.28
ATOM    115  CA   MET A   34      28.365  22.163  35.733  1.00  36.53
ATOM    116  CB   MET A   34      29.840  22.550  35.715  1.00  37.70
ATOM    117  CG   MET A   34      30.725  21.619  36.533  1.00  44.64
ATOM    118  SD   MET A   34      32.467  21.981  36.237  1.00  57.03
ATOM    119  CE   MET A   34      32.639  23.515  37.150  1.00  38.10
ATOM    120  C    MET A   34      27.538  23.393  35.382  1.00  32.51
ATOM    121  O    MET A   34      26.955  24.065  36.235  1.00  52.72
ATOM    122  N    LYS A   35      27.508  23.672  34.081  1.00  35.94
ATOM    123  CA   LYS A   35      26.695  24.776  33.583  1.00  42.22
ATOM    124  CB   LYS A   35      26.769  24.818  32.059  1.00  53.72
ATOM    125  CG   LYS A   35      27.490  26.026  31.488  1.00  64.13
ATOM    126  CD   LYS A   35      26.830  26.522  30.211  1.00  73.45
ATOM    127  CE   LYS A   35      25.799  27.603  30.481  1.00  79.66
ATOM    128  NZ   LYS A   35      25.397  28.334  29.244  1.00  65.59
ATOM    129  C    LYS A   35      25.261  24.606  34.072  1.00  42.89
ATOM    130  O    LYS A   35      24.679  25.467  34.733  1.00  40.73
ATOM    131  N    LEU A   36      24.707  23.441  33.733  1.00  35.38
ATOM    132  CA   LEU A   36      23.356  23.091  34.131  1.00  26.66
ATOM    133  CB   LEU A   36      23.027  21.631  33.793  1.00  34.71
ATOM    134  CG   LEU A   36      22.556  21.329  32.373  1.00  35.84
ATOM    135  CD1  LEU A   36      23.700  21.485  31.388  1.00  40.98
ATOM    136  CD2  LEU A   36      21.974  19.922  32.277  1.00  32.82
ATOM    137  C    LEU A   36      23.172  23.283  35.629  1.00  24.20
ATOM    138  O    LEU A   36      22.123  23.748  36.062  1.00  28.20
ATOM    139  N    GLN A   37      24.207  22.901  36.378  1.00  25.36
ATOM    140  CA   GLN A   37      24.143  22.963  37.831  1.00  31.18
ATOM    141  CB   GLN A   37      25.189  22.007  38.420  1.00  38.07
ATOM    142  CG   GLN A   37      24.588  20.611  38.573  1.00  46.59
ATOM    143  CD   GLN A   37      25.546  19.648  39.244  1.00  51.11
ATOM    144  OE1  GLN A   37      26.637  19.410  38.728  1.00  44.66
ATOM    145  NE2  GLN A   37      25.114  19.115  40.378  1.00  36.68
ATOM    146  C    GLN A   37      24.337  24.373  38.379  1.00  40.44
ATOM    147  O    GLN A   37      23.814  24.666  39.455  1.00  35.38
ATOM    148  N    ALA A   38      25.050  25.199  37.630  1.00  45.31
ATOM    149  CA   ALA A   38      25.238  26.608  37.933  1.00  58.11
ATOM    150  CB   ALA A   38      25.738  27.359  36.705  1.00  66.03
ATOM    151  C    ALA A   38      23.953  27.264  38.431  1.00  66.10
ATOM    152  O    ALA A   38      22.853  26.812  38.114  1.00  78.27
ATOM    153  N    ASP A   39      24.121  28.331  39.199  1.00  68.10
ATOM    154  CA   ASP A   39      23.041  29.104  39.794  1.00  71.28
ATOM    155  CB   ASP A   39      22.423  30.060  38.774  1.00  77.06
```

FIGURE 208

```
ATOM    156  CG  ASP A  39      23.365  30.405  37.638  1.00 86.83
ATOM    157  OD1 ASP A  39      23.544  29.551  36.742  1.00105.52
ATOM    158  OD2 ASP A  39      23.932  31.516  37.639  1.00105.04
ATOM    159  C   ASP A  39      21.969  28.188  40.383  1.00 69.59
ATOM    160  O   ASP A  39      20.770  28.436  40.271  1.00 51.64
ATOM    161  N   SER A  40      22.436  27.116  41.014  1.00 72.47
ATOM    162  CA  SER A  40      21.569  26.129  41.639  1.00 73.99
ATOM    163  CB  SER A  40      20.695  26.792  42.708  1.00 78.30
ATOM    164  OG  SER A  40      20.340  25.862  43.718  1.00 96.66
ATOM    165  C   SER A  40      20.698  25.414  40.612  1.00 69.44
ATOM    166  O   SER A  40      19.473  25.380  40.738  1.00 68.61
ATOM    167  N   ASN A  41      21.324  24.836  39.588  1.00 67.73
ATOM    168  CA  ASN A  41      20.564  24.038  38.628  1.00 64.81
ATOM    169  CB  ASN A  41      19.846  22.901  39.367  1.00 61.79
ATOM    170  CG  ASN A  41      20.795  21.929  40.031  1.00 61.73
ATOM    171  OD1 ASN A  41      22.000  21.958  39.789  1.00 69.43
ATOM    172  ND2 ASN A  41      20.260  21.055  40.876  1.00 77.55
ATOM    173  C   ASN A  41      19.542  24.870  37.871  1.00 61.80
ATOM    174  O   ASN A  41      18.448  24.397  37.545  1.00 46.20
ATOM    175  N   TYR A  42      19.871  26.131  37.586  1.00 55.50
ATOM    176  CA  TYR A  42      18.879  26.965  36.907  1.00 53.77
ATOM    177  CB  TYR A  42      19.293  28.437  36.963  1.00 58.34
ATOM    178  CG  TYR A  42      18.328  29.359  36.248  1.00 57.25
ATOM    179  CD1 TYR A  42      17.106  29.704  36.812  1.00 53.13
ATOM    180  CE1 TYR A  42      16.237  30.547  36.143  1.00 55.57
ATOM    181  CZ  TYR A  42      16.586  31.048  34.908  1.00 57.51
ATOM    182  OH  TYR A  42      15.728  31.888  34.236  1.00 77.05
ATOM    183  CE2 TYR A  42      17.792  30.720  34.327  1.00 53.44
ATOM    184  CD2 TYR A  42      18.652  29.878  35.001  1.00 54.42
ATOM    185  C   TYR A  42      18.676  26.523  35.463  1.00 46.65
ATOM    186  O   TYR A  42      17.565  26.523  34.925  1.00 42.26
ATOM    187  N   LEU A  43      19.772  26.135  34.813  1.00 33.69
ATOM    188  CA  LEU A  43      19.638  25.715  33.419  1.00 35.76
ATOM    189  CB  LEU A  43      20.980  25.835  32.706  1.00 39.54
ATOM    190  CG  LEU A  43      21.238  27.199  32.047  1.00 40.56
ATOM    191  CD1 LEU A  43      20.408  28.282  32.714  1.00 40.30
ATOM    192  CD2 LEU A  43      22.709  27.555  32.093  1.00 29.81
ATOM    193  C   LEU A  43      19.077  24.300  33.348  1.00 48.21
ATOM    194  O   LEU A  43      18.421  23.937  32.371  1.00 40.48
ATOM    195  N   LEU A  44      19.326  23.509  34.394  1.00 46.35
ATOM    196  CA  LEU A  44      18.762  22.160  34.438  1.00 44.23
ATOM    197  CB  LEU A  44      19.440  21.300  35.503  1.00 45.17
ATOM    198  CG  LEU A  44      19.102  19.805  35.499  1.00 45.62
ATOM    199  CD1 LEU A  44      20.365  18.965  35.586  1.00 31.11
ATOM    200  CD2 LEU A  44      18.148  19.475  36.638  1.00 39.34
ATOM    201  C   LEU A  44      17.257  22.238  34.682  1.00 40.48
ATOM    202  O   LEU A  44      16.490  21.546  34.017  1.00 46.20
ATOM    203  N   SER A  45      16.833  23.079  35.624  1.00 37.28
ATOM    204  CA  SER A  45      15.412  23.227  35.909  1.00 41.63
ATOM    205  CB  SER A  45      15.183  24.298  36.971  1.00 49.13
ATOM    206  OG  SER A  45      15.258  23.742  38.273  1.00 45.34
ATOM    207  C   SER A  45      14.644  23.557  34.635  1.00 47.28
```

FIGURE 209

```
ATOM    208  O    SER A  45      13.532  23.071  34.420  1.00 56.54
ATOM    209  N    LYS A  46      15.239  24.377  33.775  1.00 48.99
ATOM    210  CA   LYS A  46      14.588  24.708  32.508  1.00 53.30
ATOM    211  CB   LYS A  46      15.228  25.954  31.890  1.00 59.16
ATOM    212  CG   LYS A  46      15.006  27.210  32.725  1.00 63.86
ATOM    213  CD   LYS A  46      15.835  28.379  32.220  1.00 64.48
ATOM    214  CE   LYS A  46      15.039  29.675  32.252  1.00 64.98
ATOM    215  NZ   LYS A  46      15.675  30.745  31.433  1.00 56.04
ATOM    216  C    LYS A  46      14.622  23.533  31.535  1.00 47.85
ATOM    217  O    LYS A  46      13.603  23.266  30.890  1.00 55.12
ATOM    218  N    GLU A  47      15.746  22.834  31.420  1.00 36.87
ATOM    219  CA   GLU A  47      15.840  21.669  30.546  1.00 45.16
ATOM    220  CB   GLU A  47      17.247  21.060  30.588  1.00 47.65
ATOM    221  CG   GLU A  47      17.495  20.034  29.498  1.00 48.46
ATOM    222  CD   GLU A  47      18.919  19.534  29.410  1.00 55.44
ATOM    223  OE1  GLU A  47      19.665  19.977  28.510  1.00 68.33
ATOM    224  OE2  GLU A  47      19.316  18.675  30.229  1.00 55.44
ATOM    225  C    GLU A  47      14.799  20.615  30.918  1.00 39.97
ATOM    226  O    GLU A  47      14.010  20.178  30.080  1.00 39.03
ATOM    227  N    TYR A  48      14.770  20.191  32.177  1.00 35.97
ATOM    228  CA   TYR A  48      13.770  19.221  32.614  1.00 40.19
ATOM    229  CB   TYR A  48      13.910  18.925  34.105  1.00 35.08
ATOM    230  CG   TYR A  48      13.004  17.856  34.671  1.00 32.74
ATOM    231  CD1  TYR A  48      13.165  16.505  34.361  1.00 28.30
ATOM    232  CE1  TYR A  48      12.316  15.553  34.903  1.00 22.32
ATOM    233  CZ   TYR A  48      11.301  15.922  35.753  1.00 30.86
ATOM    234  OH   TYR A  48      10.450  14.983  36.292  1.00 30.54
ATOM    235  CE2  TYR A  48      11.115  17.253  36.080  1.00 26.20
ATOM    236  CD2  TYR A  48      11.970  18.194  35.534  1.00 28.57
ATOM    237  C    TYR A  48      12.369  19.729  32.302  1.00 49.53
ATOM    238  O    TYR A  48      11.526  19.006  31.769  1.00 51.41
ATOM    239  N    GLU A  49      12.105  20.994  32.637  1.00 46.93
ATOM    240  CA   GLU A  49      10.772  21.536  32.378  1.00 42.89
ATOM    241  CB   GLU A  49      10.655  22.963  32.912  1.00 52.01
ATOM    242  CG   GLU A  49       9.269  23.330  33.420  1.00 65.78
ATOM    243  CD   GLU A  49       8.788  22.347  34.472  1.00 79.04
ATOM    244  OE1  GLU A  49       9.560  22.068  35.413  1.00 96.40
ATOM    245  OE2  GLU A  49       7.646  21.856  34.354  1.00 91.96
ATOM    246  C    GLU A  49      10.462  21.493  30.883  1.00 29.38
ATOM    247  O    GLU A  49       9.309  21.423  30.462  1.00 38.63
ATOM    248  N    GLU A  50      11.510  21.544  30.075  1.00 34.87
ATOM    249  CA   GLU A  50      11.357  21.477  28.626  1.00 46.84
ATOM    250  CB   GLU A  50      12.745  21.550  27.998  1.00 52.28
ATOM    251  CG   GLU A  50      12.782  21.554  26.483  1.00 62.44
ATOM    252  CD   GLU A  50      13.712  22.655  25.996  1.00 72.44
ATOM    253  OE1  GLU A  50      14.373  22.454  24.958  1.00 92.62
ATOM    254  OE2  GLU A  50      13.753  23.697  26.686  1.00 72.72
ATOM    255  C    GLU A  50      10.644  20.199  28.208  1.00 52.30
ATOM    256  O    GLU A  50       9.964  20.114  27.186  1.00 54.37
ATOM    257  N    LEU A  51      10.816  19.164  29.028  1.00 44.46
ATOM    258  CA   LEU A  51      10.319  17.841  28.691  1.00 34.94
ATOM    259  CB   LEU A  51      11.233  16.772  29.304  1.00 24.94
```

FIGURE 210

```
ATOM    260  CG  LEU A   51      12.654  16.734  28.754  1.00 21.39
ATOM    261  CD1 LEU A   51      13.621  16.312  29.850  1.00 34.46
ATOM    262  CD2 LEU A   51      12.731  15.811  27.550  1.00 25.27
ATOM    263  C   LEU A   51       8.912  17.588  29.202  1.00 42.88
ATOM    264  O   LEU A   51       8.350  16.541  28.883  1.00 29.33
ATOM    265  N   LYS A   52       8.399  18.530  29.983  1.00 44.99
ATOM    266  CA  LYS A   52       7.115  18.337  30.643  1.00 49.66
ATOM    267  CB  LYS A   52       6.789  19.557  31.513  1.00 57.53
ATOM    268  CG  LYS A   52       6.095  20.683  30.765  1.00 69.23
ATOM    269  CD  LYS A   52       6.543  22.048  31.263  1.00 75.40
ATOM    270  CE  LYS A   52       5.563  23.135  30.850  1.00 81.49
ATOM    271  NZ  LYS A   52       4.161  22.796  31.229  1.00 87.53
ATOM    272  C   LYS A   52       5.973  18.083  29.671  1.00 38.67
ATOM    273  O   LYS A   52       5.052  17.334  29.988  1.00 35.81
ATOM    274  N   ASP A   53       5.984  18.692  28.489  1.00 36.11
ATOM    275  CA  ASP A   53       4.829  18.567  27.605  1.00 40.07
ATOM    276  CB  ASP A   53       4.529  19.928  26.954  1.00 49.22
ATOM    277  CG  ASP A   53       4.334  21.018  27.995  1.00 54.49
ATOM    278  OD1 ASP A   53       5.153  21.961  28.039  1.00 73.06
ATOM    279  OD2 ASP A   53       3.367  20.942  28.782  1.00 35.35
ATOM    280  C   ASP A   53       5.012  17.503  26.537  1.00 32.08
ATOM    281  O   ASP A   53       4.126  17.303  25.702  1.00 27.30
ATOM    282  N   VAL A   54       6.138  16.789  26.531  1.00 23.82
ATOM    283  CA  VAL A   54       6.275  15.745  25.515  1.00 26.43
ATOM    284  CB  VAL A   54       7.644  15.063  25.611  1.00 23.01
ATOM    285  CG1 VAL A   54       7.804  13.986  24.545  1.00 19.26
ATOM    286  CG2 VAL A   54       8.762  16.096  25.487  1.00 34.53
ATOM    287  C   VAL A   54       5.166  14.704  25.659  1.00 26.62
ATOM    288  O   VAL A   54       4.905  14.234  26.761  1.00 17.16
ATOM    289  N   GLY A   55       4.527  14.349  24.554  1.00 21.88
ATOM    290  CA  GLY A   55       3.558  13.282  24.475  1.00 23.39
ATOM    291  C   GLY A   55       2.195  13.617  25.024  1.00 30.22
ATOM    292  O   GLY A   55       1.314  12.758  25.104  1.00 23.51
ATOM    293  N   ARG A   56       1.989  14.875  25.405  1.00 31.50
ATOM    294  CA  ARG A   56       0.782  15.271  26.119  1.00 28.44
ATOM    295  CB  ARG A   56       0.984  16.662  26.743  1.00 36.73
ATOM    296  CG  ARG A   56       1.082  17.789  25.719  1.00 31.99
ATOM    297  CD  ARG A   56       1.004  19.156  26.390  1.00 37.18
ATOM    298  NE  ARG A   56      -0.281  19.323  27.056  1.00 43.75
ATOM    299  CZ  ARG A   56      -0.556  19.932  28.193  1.00 45.89
ATOM    300  NH1 ARG A   56       0.380  20.516  28.923  1.00 38.18
ATOM    301  NH2 ARG A   56      -1.817  19.962  28.623  1.00 39.43
ATOM    302  C   ARG A   56      -0.450  15.279  25.227  1.00 29.67
ATOM    303  O   ARG A   56      -1.567  15.445  25.732  1.00 27.62
ATOM    304  N   ASN A   57      -0.237  15.110  23.922  1.00 26.65
ATOM    305  CA  ASN A   57      -1.345  15.090  22.982  1.00 27.28
ATOM    306  CB  ASN A   57      -0.843  15.400  21.560  1.00 38.20
ATOM    307  CG  ASN A   57       0.466  14.695  21.254  1.00 54.73
ATOM    308  OD1 ASN A   57       1.420  14.764  22.038  1.00 55.09
ATOM    309  ND2 ASN A   57       0.530  14.011  20.113  1.00 53.28
ATOM    310  C   ASN A   57      -2.063  13.752  22.942  1.00 24.18
ATOM    311  O   ASN A   57      -3.083  13.668  22.252  1.00 23.88
```

FIGURE 211

```
ATOM    312  N   GLN A  58      -1.579  12.719  23.623  1.00 27.84
ATOM    313  CA  GLN A  58      -2.119  11.366  23.492  1.00 20.86
ATOM    314  CB  GLN A  58      -0.963  10.339  23.556  1.00 16.18
ATOM    315  CG  GLN A  58      -0.004  10.576  22.386  1.00 19.18
ATOM    316  CD  GLN A  58       1.282   9.797  22.440  1.00 17.89
ATOM    317  OE1 GLN A  58       1.430   8.818  21.702  1.00 27.40
ATOM    318  NE2 GLN A  58       2.226  10.196  23.293  1.00 22.07
ATOM    319  C   GLN A  58      -3.169  11.060  24.540  1.00 24.60
ATOM    320  O   GLN A  58      -3.146  11.517  25.685  1.00 28.29
ATOM    321  N   SER A  59      -4.147  10.253  24.129  1.00 19.50
ATOM    322  CA  SER A  59      -5.255   9.909  25.012  1.00 17.23
ATOM    323  CB  SER A  59      -6.538   9.850  24.170  1.00 25.69
ATOM    324  OG  SER A  59      -6.970  11.173  23.891  1.00 42.05
ATOM    325  C   SER A  59      -5.039   8.570  25.710  1.00 19.80
ATOM    326  O   SER A  59      -4.224   7.784  25.210  1.00 16.72
ATOM    327  N   CYS A  60      -5.766   8.346  26.789  1.00 18.16
ATOM    328  CA  CYS A  60      -5.784   7.104  27.553  1.00 24.60
ATOM    329  CB  CYS A  60      -5.166   7.309  28.946  1.00 22.29
ATOM    330  SG  CYS A  60      -3.478   7.963  28.894  1.00 32.87
ATOM    331  C   CYS A  60      -7.200   6.568  27.701  1.00 24.69
ATOM    332  O   CYS A  60      -7.633   6.163  28.783  1.00 15.41
ATOM    333  N   ASP A  61      -7.989   6.554  26.627  1.00 21.29
ATOM    334  CA  ASP A  61      -9.399   6.222  26.803  1.00 17.62
ATOM    335  CB  ASP A  61     -10.193   6.519  25.524  1.00 24.76
ATOM    336  CG  ASP A  61     -10.158   7.992  25.163  1.00 30.04
ATOM    337  OD1 ASP A  61      -9.946   8.844  26.050  1.00 27.96
ATOM    338  OD2 ASP A  61     -10.334   8.286  23.966  1.00 30.86
ATOM    339  C   ASP A  61      -9.618   4.764  27.165  1.00 22.87
ATOM    340  O   ASP A  61     -10.577   4.424  27.849  1.00 23.80
ATOM    341  N   ILE A  62      -8.760   3.857  26.693  1.00 17.20
ATOM    342  CA  ILE A  62      -9.073   2.454  27.018  1.00 17.76
ATOM    343  CB  ILE A  62      -8.198   1.491  26.203  1.00 19.59
ATOM    344  CG1 ILE A  62      -8.434   1.614  24.694  1.00 30.45
ATOM    345  CD1 ILE A  62      -9.906   1.542  24.325  1.00 29.59
ATOM    346  CG2 ILE A  62      -8.389   0.061  26.685  1.00 19.52
ATOM    347  C   ILE A  62      -8.891   2.209  28.509  1.00 24.81
ATOM    348  O   ILE A  62      -9.671   1.523  29.170  1.00 20.96
ATOM    349  N   ALA A  63      -7.831   2.828  29.030  1.00 18.90
ATOM    350  CA  ALA A  63      -7.515   2.680  30.442  1.00 17.49
ATOM    351  CB  ALA A  63      -6.214   3.420  30.729  1.00 14.17
ATOM    352  C   ALA A  63      -8.646   3.193  31.321  1.00 22.60
ATOM    353  O   ALA A  63      -8.776   2.756  32.467  1.00 21.69
ATOM    354  N   LEU A  64      -9.433   4.106  30.768  1.00 22.09
ATOM    355  CA  LEU A  64     -10.531   4.780  31.447  1.00 24.05
ATOM    356  CB  LEU A  64     -10.635   6.212  30.898  1.00 20.03
ATOM    357  CG  LEU A  64      -9.562   7.184  31.388  1.00 17.09
ATOM    358  CD1 LEU A  64      -9.621   8.500  30.633  1.00 23.40
ATOM    359  CD2 LEU A  64      -9.722   7.431  32.885  1.00 18.46
ATOM    360  C   LEU A  64     -11.867   4.072  31.310  1.00 28.67
ATOM    361  O   LEU A  64     -12.878   4.468  31.898  1.00 24.74
ATOM    362  N   LEU A  65     -11.959   2.988  30.544  1.00 23.30
ATOM    363  CA  LEU A  65     -13.262   2.317  30.495  1.00 26.61
```

FIGURE 212

| | | | | | | | | | |
|---|---|---|---|---|---|---|---|---|---|
| ATOM | 364 | CB | LEU | A | 65 | -13.254 | 1.209 | 29.436 | 1.00 27.54 |
| ATOM | 365 | CG | LEU | A | 65 | -12.864 | 1.722 | 28.042 | 1.00 27.54 |
| ATOM | 366 | CD1 | LEU | A | 65 | -12.668 | 0.573 | 27.069 | 1.00 25.94 |
| ATOM | 367 | CD2 | LEU | A | 65 | -13.911 | 2.707 | 27.542 | 1.00 31.37 |
| ATOM | 368 | C | LEU | A | 65 | -13.622 | 1.772 | 31.869 | 1.00 24.88 |
| ATOM | 369 | O | LEU | A | 65 | -12.743 | 1.361 | 32.617 | 1.00 27.17 |
| ATOM | 370 | N | PRO | A | 66 | -14.907 | 1.798 | 32.204 | 1.00 28.42 |
| ATOM | 371 | CA | PRO | A | 66 | -15.378 | 1.350 | 33.511 | 1.00 32.94 |
| ATOM | 372 | CB | PRO | A | 66 | -16.909 | 1.316 | 33.342 | 1.00 34.08 |
| ATOM | 373 | CG | PRO | A | 66 | -17.188 | 2.301 | 32.262 | 1.00 39.92 |
| ATOM | 374 | CD | PRO | A | 66 | -16.002 | 2.281 | 31.339 | 1.00 35.79 |
| ATOM | 375 | C | PRO | A | 66 | -14.879 | -0.038 | 33.884 | 1.00 25.20 |
| ATOM | 376 | O | PRO | A | 66 | -14.577 | -0.329 | 35.039 | 1.00 30.25 |
| ATOM | 377 | N | GLU | A | 67 | -14.784 | -0.948 | 32.916 | 1.00 26.85 |
| ATOM | 378 | CA | GLU | A | 67 | -14.418 | -2.299 | 33.346 | 1.00 35.73 |
| ATOM | 379 | CB | GLU | A | 67 | -14.879 | -3.321 | 32.308 | 1.00 39.08 |
| ATOM | 380 | CG | GLU | A | 67 | -15.067 | -2.754 | 30.914 | 1.00 48.88 |
| ATOM | 381 | CD | GLU | A | 67 | -14.264 | -3.501 | 29.864 | 1.00 57.56 |
| ATOM | 382 | OE1 | GLU | A | 67 | -14.251 | -4.752 | 29.884 | 1.00 77.10 |
| ATOM | 383 | OE2 | GLU | A | 67 | -13.642 | -2.832 | 29.012 | 1.00 41.80 |
| ATOM | 384 | C | GLU | A | 67 | -12.923 | -2.398 | 33.622 | 1.00 36.25 |
| ATOM | 385 | O | GLU | A | 67 | -12.447 | -3.441 | 34.078 | 1.00 32.32 |
| ATOM | 386 | N | ASN | A | 68 | -12.167 | -1.333 | 33.359 | 1.00 31.47 |
| ATOM | 387 | CA | ASN | A | 68 | -10.724 | -1.380 | 33.588 | 1.00 21.87 |
| ATOM | 388 | CB | ASN | A | 68 | -9.950 | -0.794 | 32.395 | 1.00 22.35 |
| ATOM | 389 | CG | ASN | A | 68 | -10.008 | -1.714 | 31.195 | 1.00 19.79 |
| ATOM | 390 | OD1 | ASN | A | 68 | -10.127 | -2.930 | 31.350 | 1.00 23.52 |
| ATOM | 391 | ND2 | ASN | A | 68 | -9.927 | -1.147 | 29.997 | 1.00 19.33 |
| ATOM | 392 | C | ASN | A | 68 | -10.329 | -0.618 | 34.841 | 1.00 20.30 |
| ATOM | 393 | O | ASN | A | 68 | -9.154 | -0.604 | 35.215 | 1.00 22.70 |
| ATOM | 394 | N | ARG | A | 69 | -11.286 | 0.026 | 35.508 | 1.00 26.70 |
| ATOM | 395 | CA | ARG | A | 69 | -10.894 | 0.889 | 36.623 | 1.00 33.64 |
| ATOM | 396 | CB | ARG | A | 69 | -12.116 | 1.607 | 37.211 | 1.00 44.80 |
| ATOM | 397 | CG | ARG | A | 69 | -11.775 | 2.959 | 37.824 | 1.00 54.18 |
| ATOM | 398 | CD | ARG | A | 69 | -12.982 | 3.581 | 38.508 | 1.00 63.01 |
| ATOM | 399 | NE | ARG | A | 69 | -12.717 | 3.903 | 39.904 | 1.00 71.32 |
| ATOM | 400 | CZ | ARG | A | 69 | -13.573 | 3.781 | 40.910 | 1.00 77.50 |
| ATOM | 401 | NH1 | ARG | A | 69 | -14.801 | 3.330 | 40.694 | 1.00 86.91 |
| ATOM | 402 | NH2 | ARG | A | 69 | -13.203 | 4.108 | 42.144 | 1.00 73.55 |
| ATOM | 403 | C | ARG | A | 69 | -10.153 | 0.129 | 37.715 | 1.00 29.65 |
| ATOM | 404 | O | ARG | A | 69 | -9.113 | 0.604 | 38.189 | 1.00 40.10 |
| ATOM | 405 | N | GLY | A | 70 | -10.644 | -1.040 | 38.113 | 1.00 23.99 |
| ATOM | 406 | CA | GLY | A | 70 | -9.961 | -1.818 | 39.143 | 1.00 19.86 |
| ATOM | 407 | C | GLY | A | 70 | -8.590 | -2.288 | 38.689 | 1.00 24.39 |
| ATOM | 408 | O | GLY | A | 70 | -7.784 | -2.734 | 39.521 | 1.00 22.56 |
| ATOM | 409 | N | LYS | A | 71 | -8.301 | -2.205 | 37.379 | 1.00 19.98 |
| ATOM | 410 | CA | LYS | A | 71 | -7.003 | -2.702 | 36.908 | 1.00 15.60 |
| ATOM | 411 | CB | LYS | A | 71 | -7.123 | -3.252 | 35.480 | 1.00 18.68 |
| ATOM | 412 | CG | LYS | A | 71 | -8.200 | -4.318 | 35.326 | 1.00 15.28 |
| ATOM | 413 | CD | LYS | A | 71 | -8.403 | -4.675 | 33.855 | 1.00 15.32 |
| ATOM | 414 | CE | LYS | A | 71 | -9.713 | -5.448 | 33.703 | 1.00 27.04 |
| ATOM | 415 | NZ | LYS | A | 71 | -10.141 | -5.554 | 32.281 | 1.00 31.96 |

FIGURE 213

```
ATOM    416  C   LYS A  71      -5.890  -1.672  36.944  1.00 14.54
ATOM    417  O   LYS A  71      -4.752  -1.993  36.578  1.00 17.52
ATOM    418  N   ASN A  72      -6.149  -0.439  37.371  1.00 11.96
ATOM    419  CA  ASN A  72      -5.101   0.568  37.479  1.00 11.74
ATOM    420  CB  ASN A  72      -5.545   1.876  36.813  1.00 14.82
ATOM    421  CG  ASN A  72      -5.837   1.654  35.339  1.00 23.46
ATOM    422  OD1 ASN A  72      -5.007   1.128  34.599  1.00 16.09
ATOM    423  ND2 ASN A  72      -7.025   2.057  34.903  1.00 21.08
ATOM    424  C   ASN A  72      -4.753   0.835  38.937  1.00 16.08
ATOM    425  O   ASN A  72      -5.647   1.079  39.741  1.00 18.28
ATOM    426  N   ARG A  73      -3.471   0.788  39.258  1.00 12.51
ATOM    427  CA  ARG A  73      -3.013   1.010  40.621  1.00 20.92
ATOM    428  CB  ARG A  73      -1.525   0.666  40.738  1.00 13.10
ATOM    429  CG  ARG A  73      -0.989   0.829  42.148  1.00  9.31
ATOM    430  CD  ARG A  73       0.454   0.359  42.272  1.00 11.98
ATOM    431  NE  ARG A  73       0.510  -1.117  42.294  1.00  9.41
ATOM    432  CZ  ARG A  73       0.265  -1.768  43.428  1.00 17.50
ATOM    433  NH1 ARG A  73      -0.024  -1.096  44.549  1.00 14.11
ATOM    434  NH2 ARG A  73       0.330  -3.094  43.391  1.00 16.87
ATOM    435  C   ARG A  73      -3.255   2.460  41.041  1.00 25.16
ATOM    436  O   ARG A  73      -3.658   2.737  42.170  1.00 14.89
ATOM    437  N   TYR A  74      -2.991   3.373  40.114  1.00 17.87
ATOM    438  CA  TYR A  74      -3.209   4.806  40.336  1.00 15.26
ATOM    439  CB  TYR A  74      -1.887   5.539  40.348  1.00 18.93
ATOM    440  CG  TYR A  74      -0.898   5.054  41.388  1.00 19.16
ATOM    441  CD1 TYR A  74      -1.081   5.313  42.735  1.00 22.07
ATOM    442  CE1 TYR A  74      -0.174   4.871  43.684  1.00 17.71
ATOM    443  CZ  TYR A  74       0.932   4.160  43.289  1.00 16.94
ATOM    444  OH  TYR A  74       1.851   3.713  44.213  1.00 16.65
ATOM    445  CE2 TYR A  74       1.139   3.891  41.947  1.00 20.51
ATOM    446  CD2 TYR A  74       0.225   4.337  41.009  1.00 14.89
ATOM    447  C   TYR A  74      -4.150   5.322  39.263  1.00 23.96
ATOM    448  O   TYR A  74      -3.994   5.065  38.065  1.00 19.22
ATOM    449  N   ASN A  75      -5.202   6.053  39.641  1.00 18.99
ATOM    450  CA  ASN A  75      -6.220   6.288  38.610  1.00 23.42
ATOM    451  CB  ASN A  75      -7.557   6.585  39.296  1.00 34.45
ATOM    452  CG  ASN A  75      -8.137   5.350  39.975  1.00 51.03
ATOM    453  OD1 ASN A  75      -8.673   5.414  41.085  1.00 50.00
ATOM    454  ND2 ASN A  75      -8.051   4.180  39.342  1.00 38.85
ATOM    455  C   ASN A  75      -5.736   7.353  37.640  1.00 18.82
ATOM    456  O   ASN A  75      -6.317   7.585  36.580  1.00 20.63
ATOM    457  N   ASN A  76      -4.615   7.991  37.977  1.00 16.28
ATOM    458  CA  ASN A  76      -4.105   9.045  37.110  1.00 19.45
ATOM    459  CB  ASN A  76      -3.997  10.339  37.926  1.00 22.45
ATOM    460  CG  ASN A  76      -2.980  10.295  39.044  1.00 33.59
ATOM    461  OD1 ASN A  76      -2.679   9.257  39.636  1.00 26.17
ATOM    462  ND2 ASN A  76      -2.431  11.474  39.344  1.00 29.60
ATOM    463  C   ASN A  76      -2.781   8.692  36.465  1.00 17.17
ATOM    464  O   ASN A  76      -2.066   9.532  35.917  1.00 17.91
ATOM    465  N   ILE A  77      -2.389   7.423  36.475  1.00 20.00
ATOM    466  CA  ILE A  77      -1.171   6.992  35.791  1.00 14.81
ATOM    467  CB  ILE A  77      -0.049   6.504  36.702  1.00 11.59
```

FIGURE 214

| ATOM | 468 | CG1 | ILE | A | 77 | 0.336 | 7.468 | 37.832 | 1.00 | 17.04 |
| ATOM | 469 | CD1 | ILE | A | 77 | 0.986 | 8.713 | 37.282 | 1.00 | 17.56 |
| ATOM | 470 | CG2 | ILE | A | 77 | 1.227 | 6.165 | 35.924 | 1.00 | 15.42 |
| ATOM | 471 | C | ILE | A | 77 | -1.617 | 5.835 | 34.878 | 1.00 | 16.96 |
| ATOM | 472 | O | ILE | A | 77 | -1.733 | 4.718 | 35.381 | 1.00 | 15.55 |
| ATOM | 473 | N | LEU | A | 78 | -1.897 | 6.184 | 33.632 | 1.00 | 12.76 |
| ATOM | 474 | CA | LEU | A | 78 | -2.530 | 5.255 | 32.689 | 1.00 | 10.94 |
| ATOM | 475 | CB | LEU | A | 78 | -3.984 | 5.623 | 32.413 | 1.00 | 12.51 |
| ATOM | 476 | CG | LEU | A | 78 | -4.880 | 5.963 | 33.601 | 1.00 | 19.43 |
| ATOM | 477 | CD1 | LEU | A | 78 | -6.237 | 6.497 | 33.151 | 1.00 | 22.19 |
| ATOM | 478 | CD2 | LEU | A | 78 | -5.082 | 4.744 | 34.486 | 1.00 | 24.35 |
| ATOM | 479 | C | LEU | A | 78 | -1.723 | 5.244 | 31.398 | 1.00 | 17.94 |
| ATOM | 480 | O | LEU | A | 78 | -1.093 | 6.248 | 31.056 | 1.00 | 16.73 |
| ATOM | 481 | N | PRO | A | 79 | -1.711 | 4.123 | 30.692 | 1.00 | 19.09 |
| ATOM | 482 | CA | PRO | A | 79 | -0.920 | 4.050 | 29.450 | 1.00 | 16.12 |
| ATOM | 483 | CB | PRO | A | 79 | -0.870 | 2.539 | 29.199 | 1.00 | 9.23 |
| ATOM | 484 | CG | PRO | A | 79 | -2.204 | 2.074 | 29.718 | 1.00 | 11.75 |
| ATOM | 485 | CD | PRO | A | 79 | -2.411 | 2.860 | 30.988 | 1.00 | 15.77 |
| ATOM | 486 | C | PRO | A | 79 | -1.655 | 4.794 | 28.339 | 1.00 | 15.99 |
| ATOM | 487 | O | PRO | A | 79 | -2.893 | 4.828 | 28.388 | 1.00 | 15.25 |
| ATOM | 488 | N | TYR | A | 80 | -0.926 | 5.362 | 27.389 | 1.00 | 10.13 |
| ATOM | 489 | CA | TYR | A | 80 | -1.502 | 5.993 | 26.206 | 1.00 | 11.18 |
| ATOM | 490 | CB | TYR | A | 80 | -0.451 | 6.764 | 25.423 | 1.00 | 13.27 |
| ATOM | 491 | CG | TYR | A | 80 | 0.146 | 7.959 | 26.117 | 1.00 | 12.63 |
| ATOM | 492 | CD1 | TYR | A | 80 | -0.697 | 8.902 | 26.685 | 1.00 | 18.08 |
| ATOM | 493 | CE1 | TYR | A | 80 | -0.173 | 10.005 | 27.321 | 1.00 | 20.03 |
| ATOM | 494 | CZ | TYR | A | 80 | 1.186 | 10.172 | 27.391 | 1.00 | 16.07 |
| ATOM | 495 | OH | TYR | A | 80 | 1.682 | 11.281 | 28.032 | 1.00 | 21.65 |
| ATOM | 496 | CE2 | TYR | A | 80 | 2.054 | 9.257 | 26.837 | 1.00 | 13.46 |
| ATOM | 497 | CD2 | TYR | A | 80 | 1.507 | 8.150 | 26.198 | 1.00 | 14.05 |
| ATOM | 498 | C | TYR | A | 80 | -2.104 | 4.930 | 25.286 | 1.00 | 18.00 |
| ATOM | 499 | O | TYR | A | 80 | -1.568 | 3.823 | 25.165 | 1.00 | 15.44 |
| ATOM | 500 | N | ASP | A | 81 | -3.222 | 5.206 | 24.625 | 1.00 | 15.66 |
| ATOM | 501 | CA | ASP | A | 81 | -3.849 | 4.129 | 23.846 | 1.00 | 18.95 |
| ATOM | 502 | CB | ASP | A | 81 | -5.184 | 4.541 | 23.239 | 1.00 | 21.06 |
| ATOM | 503 | CG | ASP | A | 81 | -6.217 | 5.004 | 24.239 | 1.00 | 23.24 |
| ATOM | 504 | OD1 | ASP | A | 81 | -6.322 | 4.394 | 25.318 | 1.00 | 20.28 |
| ATOM | 505 | OD2 | ASP | A | 81 | -6.944 | 5.971 | 23.937 | 1.00 | 21.10 |
| ATOM | 506 | C | ASP | A | 81 | -2.919 | 3.699 | 22.717 | 1.00 | 19.22 |
| ATOM | 507 | O | ASP | A | 81 | -2.884 | 2.543 | 22.314 | 1.00 | 24.23 |
| ATOM | 508 | N | ALA | A | 82 | -2.171 | 4.664 | 22.193 | 1.00 | 20.83 |
| ATOM | 509 | CA | ALA | A | 82 | -1.326 | 4.375 | 21.033 | 1.00 | 21.56 |
| ATOM | 510 | CB | ALA | A | 82 | -0.802 | 5.697 | 20.471 | 1.00 | 18.25 |
| ATOM | 511 | C | ALA | A | 82 | -0.179 | 3.424 | 21.333 | 1.00 | 17.70 |
| ATOM | 512 | O | ALA | A | 82 | 0.344 | 2.784 | 20.412 | 1.00 | 24.59 |
| ATOM | 513 | N | THR | A | 83 | 0.291 | 3.282 | 22.570 | 1.00 | 14.11 |
| ATOM | 514 | CA | THR | A | 83 | 1.482 | 2.482 | 22.831 | 1.00 | 15.16 |
| ATOM | 515 | CB | THR | A | 83 | 2.667 | 3.349 | 23.283 | 1.00 | 26.72 |
| ATOM | 516 | OG1 | THR | A | 83 | 2.291 | 4.126 | 24.431 | 1.00 | 20.70 |
| ATOM | 517 | CG2 | THR | A | 83 | 3.076 | 4.358 | 22.213 | 1.00 | 24.85 |
| ATOM | 518 | C | THR | A | 83 | 1.223 | 1.437 | 23.918 | 1.00 | 17.17 |
| ATOM | 519 | O | THR | A | 83 | 2.168 | 0.825 | 24.412 | 1.00 | 17.29 |

FIGURE 215

```
ATOM    520  N    ARG A   84      -0.030   1.226  24.310  1.00 14.78
ATOM    521  CA   ARG A   84      -0.304   0.265  25.377  1.00 14.16
ATOM    522  CB   ARG A   84      -1.752   0.389  25.832  1.00 16.16
ATOM    523  CG   ARG A   84      -2.824  -0.021  24.841  1.00 12.30
ATOM    524  CD   ARG A   84      -4.206   0.035  25.483  1.00 18.81
ATOM    525  NE   ARG A   84      -5.231  -0.504  24.587  1.00 18.67
ATOM    526  CZ   ARG A   84      -5.856  -1.657  24.745  1.00 25.65
ATOM    527  NH1  ARG A   84      -5.570  -2.421  25.794  1.00 18.24
ATOM    528  NH2  ARG A   84      -6.769  -2.038  23.856  1.00 23.18
ATOM    529  C    ARG A   84       0.002  -1.164  24.926  1.00 19.54
ATOM    530  O    ARG A   84      -0.053  -1.498  23.748  1.00 16.47
ATOM    531  N    VAL A   85       0.340  -2.027  25.871  1.00 14.56
ATOM    532  CA   VAL A   85       0.511  -3.453  25.593  1.00 15.91
ATOM    533  CB   VAL A   85       1.516  -4.099  26.552  1.00  9.66
ATOM    534  CG1  VAL A   85       1.595  -5.605  26.279  1.00 26.22
ATOM    535  CG2  VAL A   85       2.900  -3.489  26.419  1.00  8.35
ATOM    536  C    VAL A   85      -0.824  -4.164  25.708  1.00 18.09
ATOM    537  O    VAL A   85      -1.596  -4.001  26.664  1.00 17.84
ATOM    538  N    LYS A   86      -1.170  -4.991  24.713  1.00 17.85
ATOM    539  CA   LYS A   86      -2.481  -5.634  24.797  1.00 16.55
ATOM    540  CB   LYS A   86      -3.270  -5.448  23.499  1.00 22.98
ATOM    541  CG   LYS A   86      -3.353  -4.027  22.972  1.00 25.37
ATOM    542  CD   LYS A   86      -4.093  -3.996  21.641  1.00 35.98
ATOM    543  CE   LYS A   86      -4.302  -2.569  21.152  1.00 41.61
ATOM    544  NZ   LYS A   86      -5.067  -2.535  19.870  1.00 41.47
ATOM    545  C    LYS A   86      -2.354  -7.130  25.073  1.00 17.71
ATOM    546  O    LYS A   86      -1.473  -7.780  24.495  1.00 26.73
ATOM    547  N    LEU A   87      -3.238  -7.641  25.909  1.00 16.65
ATOM    548  CA   LEU A   87      -3.386  -9.070  26.157  1.00 21.87
ATOM    549  CB   LEU A   87      -4.108  -9.340  27.477  1.00 22.56
ATOM    550  CG   LEU A   87      -3.573  -8.679  28.751  1.00 19.45
ATOM    551  CD1  LEU A   87      -4.502  -8.981  29.920  1.00 33.41
ATOM    552  CD2  LEU A   87      -2.155  -9.123  29.057  1.00 19.25
ATOM    553  C    LEU A   87      -4.194  -9.716  25.033  1.00 34.42
ATOM    554  O    LEU A   87      -5.103  -9.087  24.480  1.00 29.92
ATOM    555  N    SER A   88      -3.906 -10.961  24.684  1.00 39.81
ATOM    556  CA   SER A   88      -4.712 -11.686  23.715  1.00 42.02
ATOM    557  CB   SER A   88      -4.153 -13.103  23.509  1.00 45.96
ATOM    558  OG   SER A   88      -4.499 -13.843  24.684  1.00 44.96
ATOM    559  C    SER A   88      -6.154 -11.853  24.182  1.00 39.54
ATOM    560  O    SER A   88      -6.425 -11.712  25.374  1.00 35.93
ATOM    561  N    ASN A   89      -7.041 -12.175  23.251  1.00 58.52
ATOM    562  CA   ASN A   89      -8.435 -12.501  23.518  1.00 76.46
ATOM    563  CB   ASN A   89      -9.366 -11.396  23.017  1.00 82.65
ATOM    564  CG   ASN A   89      -9.457 -11.372  21.501  1.00 93.50
ATOM    565  OD1  ASN A   89     -10.512 -11.100  20.929  1.00104.34
ATOM    566  ND2  ASN A   89      -8.337 -11.659  20.847  1.00109.77
ATOM    567  C    ASN A   89      -8.807 -13.831  22.860  1.00 88.77
ATOM    568  O    ASN A   89      -8.533 -14.011  21.671  1.00 92.19
ATOM    569  N    VAL A   90      -9.407 -14.736  23.621  1.00 99.23
ATOM    570  CA   VAL A   90      -9.793 -16.059  23.144  1.00106.42
ATOM    571  CB   VAL A   90      -8.923 -17.172  23.760  1.00106.95
```

FIGURE 216

```
ATOM    572  CG1 VAL A   90      -9.298 -18.525  23.172  1.00112.12
ATOM    573  CG2 VAL A   90      -7.444 -16.892  23.548  1.00105.34
ATOM    574  C   VAL A   90     -11.258 -16.369  23.451  1.00111.33
ATOM    575  O   VAL A   90     -12.138 -16.117  22.628  1.00105.84
ATOM    576  N   ASP A   91     -11.510 -16.921  24.632  1.00119.26
ATOM    577  CA  ASP A   91     -12.855 -17.239  25.095  1.00128.16
ATOM    578  CB  ASP A   91     -12.828 -18.448  26.031  1.00125.07
ATOM    579  CG  ASP A   91     -14.191 -18.774  26.609  1.00121.16
ATOM    580  OD1 ASP A   91     -15.007 -19.377  25.880  1.00104.75
ATOM    581  OD2 ASP A   91     -14.447 -18.433  27.785  1.00117.18
ATOM    582  C   ASP A   91     -13.482 -16.042  25.807  1.00139.13
ATOM    583  O   ASP A   91     -13.028 -15.676  26.894  1.00148.32
ATOM    584  N   ASP A   92     -14.503 -15.447  25.202  1.00145.93
ATOM    585  CA  ASP A   92     -15.147 -14.241  25.726  1.00149.70
ATOM    586  CB  ASP A   92     -15.415 -14.375  27.225  1.00149.57
ATOM    587  CG  ASP A   92     -16.361 -15.502  27.584  1.00147.36
ATOM    588  OD1 ASP A   92     -17.567 -15.233  27.781  1.00137.75
ATOM    589  OD2 ASP A   92     -15.912 -16.665  27.677  1.00148.40
ATOM    590  C   ASP A   92     -14.286 -13.021  25.419  1.00150.50
ATOM    591  O   ASP A   92     -13.148 -12.934  25.892  1.00155.89
ATOM    592  N   ASP A   93     -14.778 -12.068  24.620  1.00148.19
ATOM    593  CA  ASP A   93     -13.886 -10.998  24.173  1.00145.42
ATOM    594  CB  ASP A   93     -13.545 -11.222  22.687  1.00146.89
ATOM    595  CG  ASP A   93     -14.744 -11.594  21.844  1.00147.24
ATOM    596  OD1 ASP A   93     -15.278 -12.710  22.011  1.00141.98
ATOM    597  OD2 ASP A   93     -15.159 -10.772  21.001  1.00148.93
ATOM    598  C   ASP A   93     -14.404  -9.578  24.346  1.00140.50
ATOM    599  O   ASP A   93     -14.742  -8.922  23.357  1.00135.04
ATOM    600  N   PRO A   94     -14.451  -9.070  25.570  1.00137.75
ATOM    601  CA  PRO A   94     -14.684  -7.638  25.812  1.00134.16
ATOM    602  CB  PRO A   94     -15.340  -7.646  27.190  1.00136.91
ATOM    603  CG  PRO A   94     -14.801  -8.848  27.882  1.00138.06
ATOM    604  CD  PRO A   94     -14.305  -9.803  26.837  1.00139.01
ATOM    605  C   PRO A   94     -13.363  -6.879  25.830  1.00126.58
ATOM    606  O   PRO A   94     -12.437  -7.253  25.099  1.00132.66
ATOM    607  N   CYS A   95     -13.220  -5.827  26.639  1.00114.33
ATOM    608  CA  CYS A   95     -11.898  -5.198  26.765  1.00 95.06
ATOM    609  CB  CYS A   95     -11.947  -3.690  26.961  1.00 97.01
ATOM    610  SG  CYS A   95     -10.323  -2.901  27.121  1.00 74.50
ATOM    611  C   CYS A   95     -11.146  -5.872  27.913  1.00 71.83
ATOM    612  O   CYS A   95     -10.629  -5.311  28.870  1.00 58.75
ATOM    613  N   SER A   96     -11.089  -7.193  27.759  1.00 54.83
ATOM    614  CA  SER A   96     -10.254  -8.038  28.595  1.00 46.09
ATOM    615  CB  SER A   96     -10.848  -9.437  28.720  1.00 49.86
ATOM    616  OG  SER A   96     -10.801 -10.147  27.491  1.00 47.97
ATOM    617  C   SER A   96      -8.854  -8.076  27.988  1.00 31.56
ATOM    618  O   SER A   96      -8.045  -8.933  28.321  1.00 30.50
ATOM    619  N   ASP A   97      -8.562  -7.129  27.085  1.00 25.83
ATOM    620  CA  ASP A   97      -7.233  -7.050  26.495  1.00 17.26
ATOM    621  CB  ASP A   97      -7.317  -6.646  25.029  1.00 22.22
ATOM    622  CG  ASP A   97      -7.590  -5.179  24.772  1.00 32.54
ATOM    623  OD1 ASP A   97      -7.945  -4.404  25.681  1.00 25.44
```

FIGURE 217

```
ATOM    624  OD2 ASP A  97      -7.444  -4.765  23.600  1.00 44.31
ATOM    625  C   ASP A  97      -6.357  -6.065  27.271  1.00 18.88
ATOM    626  O   ASP A  97      -5.194  -5.883  26.902  1.00 18.89
ATOM    627  N   TYR A  98      -6.947  -5.456  28.296  1.00 20.04
ATOM    628  CA  TYR A  98      -6.313  -4.338  28.976  1.00 18.41
ATOM    629  CB  TYR A  98      -7.366  -3.378  29.609  1.00 18.59
ATOM    630  CG  TYR A  98      -6.631  -2.221  30.288  1.00 20.03
ATOM    631  CD1 TYR A  98      -6.043  -1.216  29.522  1.00 16.83
ATOM    632  CE1 TYR A  98      -5.361  -0.144  30.090  1.00 13.49
ATOM    633  CZ  TYR A  98      -5.276  -0.116  31.471  1.00 19.51
ATOM    634  OH  TYR A  98      -4.624   0.908  32.106  1.00 14.09
ATOM    635  CE2 TYR A  98      -5.846  -1.095  32.255  1.00 13.64
ATOM    636  CD2 TYR A  98      -6.528  -2.145  31.673  1.00 17.45
ATOM    637  C   TYR A  98      -5.343  -4.746  30.066  1.00 18.17
ATOM    638  O   TYR A  98      -5.664  -5.449  31.020  1.00 22.86
ATOM    639  N   ILE A  99      -4.130  -4.218  29.989  1.00 14.66
ATOM    640  CA  ILE A  99      -3.274  -4.175  31.172  1.00 17.87
ATOM    641  CB  ILE A  99      -2.221  -5.290  31.223  1.00 17.34
ATOM    642  CG1 ILE A  99      -1.274  -5.190  32.428  1.00 13.76
ATOM    643  CD1 ILE A  99      -0.492  -6.481  32.633  1.00 14.80
ATOM    644  CG2 ILE A  99      -1.443  -5.348  29.924  1.00 15.59
ATOM    645  C   ILE A  99      -2.594  -2.807  31.227  1.00 14.26
ATOM    646  O   ILE A  99      -2.353  -2.191  30.183  1.00 16.44
ATOM    647  N   ASN A 100      -2.315  -2.334  32.435  1.00 14.80
ATOM    648  CA  ASN A 100      -1.609  -1.054  32.562  1.00 12.64
ATOM    649  CB  ASN A 100      -1.818  -0.440  33.951  1.00 11.26
ATOM    650  CG  ASN A 100      -1.326   0.997  33.976  1.00 13.09
ATOM    651  OD1 ASN A 100      -0.260   1.278  33.456  1.00 13.19
ATOM    652  ND2 ASN A 100      -2.099   1.903  34.579  1.00 15.88
ATOM    653  C   ASN A 100      -0.134  -1.242  32.244  1.00 10.03
ATOM    654  O   ASN A 100       0.698  -1.477  33.119  1.00 12.85
ATOM    655  N   ALA A 101       0.193  -1.152  30.946  1.00 10.66
ATOM    656  CA  ALA A 101       1.550  -1.361  30.488  1.00  9.30
ATOM    657  CB  ALA A 101       1.839  -2.863  30.397  1.00 13.80
ATOM    658  C   ALA A 101       1.777  -0.712  29.125  1.00  6.85
ATOM    659  O   ALA A 101       0.809  -0.539  28.394  1.00 12.08
ATOM    660  N   SER A 102       3.026  -0.393  28.829  1.00  9.92
ATOM    661  CA  SER A 102       3.389   0.362  27.641  1.00 14.73
ATOM    662  CB  SER A 102       3.650   1.831  28.010  1.00 11.60
ATOM    663  OG  SER A 102       2.561   2.407  28.691  1.00 11.12
ATOM    664  C   SER A 102       4.644  -0.211  26.986  1.00 15.69
ATOM    665  O   SER A 102       5.563  -0.654  27.686  1.00 12.17
ATOM    666  N   TYR A 103       4.680  -0.176  25.652  1.00  9.06
ATOM    667  CA  TYR A 103       5.889  -0.530  24.933  1.00  9.07
ATOM    668  CB  TYR A 103       5.549  -0.917  23.486  1.00  9.50
ATOM    669  CG  TYR A 103       4.870  -2.239  23.265  1.00 12.57
ATOM    670  CD1 TYR A 103       5.544  -3.435  23.487  1.00 12.90
ATOM    671  CE1 TYR A 103       4.895  -4.640  23.272  1.00 20.46
ATOM    672  CZ  TYR A 103       3.592  -4.680  22.839  1.00 22.70
ATOM    673  OH  TYR A 103       2.962  -5.894  22.627  1.00 18.14
ATOM    674  CE2 TYR A 103       2.903  -3.500  22.608  1.00 18.79
ATOM    675  CD2 TYR A 103       3.551  -2.304  22.825  1.00 15.94
```

FIGURE 218

```
ATOM    676  C   TYR A 103       6.867   0.630  24.891  1.00 18.09
ATOM    677  O   TYR A 103       6.457   1.768  24.641  1.00 20.48
ATOM    678  N   ILE A 104       8.155   0.358  25.111  1.00 15.21
ATOM    679  CA  ILE A 104       9.108   1.466  25.121  1.00 15.90
ATOM    680  CB  ILE A 104       9.608   1.785  26.545  1.00 22.38
ATOM    681  CG1 ILE A 104       8.496   1.941  27.585  1.00 20.69
ATOM    682  CD1 ILE A 104       7.599   3.126  27.276  1.00 17.88
ATOM    683  CG2 ILE A 104      10.476   3.034  26.538  1.00 22.81
ATOM    684  C   ILE A 104      10.309   1.146  24.243  1.00 17.74
ATOM    685  O   ILE A 104      10.911   0.086  24.357  1.00 16.43
ATOM    686  N   PRO A 105      10.677   2.062  23.352  1.00 17.30
ATOM    687  CA  PRO A 105      11.894   1.894  22.563  1.00 16.76
ATOM    688  CB  PRO A 105      11.837   3.088  21.592  1.00 24.69
ATOM    689  CG  PRO A 105      10.418   3.563  21.626  1.00 25.93
ATOM    690  CD  PRO A 105       9.941   3.295  23.030  1.00 21.65
ATOM    691  C   PRO A 105      13.174   2.007  23.372  1.00 21.81
ATOM    692  O   PRO A 105      13.286   2.726  24.368  1.00 21.23
ATOM    693  N   GLY A 106      14.205   1.282  22.935  1.00 17.97
ATOM    694  CA  GLY A 106      15.504   1.436  23.569  1.00 16.53
ATOM    695  C   GLY A 106      16.557   1.885  22.578  1.00 24.48
ATOM    696  O   GLY A 106      16.248   2.474  21.543  1.00 24.56
ATOM    697  N   ASN A 107      17.824   1.595  22.858  1.00 24.62
ATOM    698  CA  ASN A 107      18.889   2.049  21.971  1.00 31.26
ATOM    699  CB  ASN A 107      20.249   1.899  22.661  1.00 38.05
ATOM    700  CG  ASN A 107      20.775   3.221  23.184  1.00 50.06
ATOM    701  OD1 ASN A 107      20.008   4.143  23.476  1.00 66.78
ATOM    702  ND2 ASN A 107      22.094   3.313  23.301  1.00 52.90
ATOM    703  C   ASN A 107      18.917   1.269  20.663  1.00 30.81
ATOM    704  O   ASN A 107      19.482   1.767  19.693  1.00 28.48
ATOM    705  N   ASN A 108      18.329   0.080  20.679  1.00 32.22
ATOM    706  CA  ASN A 108      18.512  -0.922  19.640  1.00 32.10
ATOM    707  CB  ASN A 108      19.098  -2.184  20.305  1.00 37.07
ATOM    708  CG  ASN A 108      20.233  -1.830  21.251  1.00 46.06
ATOM    709  OD1 ASN A 108      21.309  -1.443  20.780  1.00 27.30
ATOM    710  ND2 ASN A 108      20.005  -1.966  22.559  1.00 28.03
ATOM    711  C   ASN A 108      17.262  -1.291  18.863  1.00 34.62
ATOM    712  O   ASN A 108      17.392  -1.721  17.708  1.00 34.88
ATOM    713  N   PHE A 109      16.060  -1.168  19.423  1.00 25.20
ATOM    714  CA  PHE A 109      14.840  -1.500  18.690  1.00 22.97
ATOM    715  CB  PHE A 109      14.603  -2.993  18.522  1.00 22.47
ATOM    716  CG  PHE A 109      14.885  -3.951  19.661  1.00 28.29
ATOM    717  CD1 PHE A 109      13.849  -4.560  20.357  1.00 24.27
ATOM    718  CE1 PHE A 109      14.113  -5.455  21.391  1.00 22.67
ATOM    719  CZ  PHE A 109      15.414  -5.748  21.750  1.00 19.40
ATOM    720  CE2 PHE A 109      16.451  -5.143  21.061  1.00 34.44
ATOM    721  CD2 PHE A 109      16.183  -4.259  20.033  1.00 33.01
ATOM    722  C   PHE A 109      13.620  -0.886  19.383  1.00 19.13
ATOM    723  O   PHE A 109      13.686  -0.531  20.559  1.00 20.41
ATOM    724  N   ARG A 110      12.538  -0.787  18.641  1.00 16.32
ATOM    725  CA  ARG A 110      11.318  -0.110  19.048  1.00 23.52
ATOM    726  CB  ARG A 110      10.342  -0.036  17.853  1.00 22.40
ATOM    727  CG  ARG A 110      10.918   0.753  16.688  1.00 29.99
```

FIGURE 219

```
ATOM    728  CD   ARG A 110       9.987   1.901  16.317  1.00 44.00
ATOM    729  NE   ARG A 110      10.461   3.122  16.971  1.00 64.93
ATOM    730  CZ   ARG A 110      10.694   4.269  16.352  1.00 72.68
ATOM    731  NH1  ARG A 110      10.494   4.368  15.044  1.00 62.39
ATOM    732  NH2  ARG A 110      11.125   5.318  17.045  1.00 82.09
ATOM    733  C    ARG A 110      10.607  -0.783  20.197  1.00 28.20
ATOM    734  O    ARG A 110       9.959  -0.177  21.052  1.00 29.57
ATOM    735  N    ARG A 111      10.665  -2.120  20.269  1.00 19.46
ATOM    736  CA   ARG A 111       9.868  -2.607  21.432  1.00 19.03
ATOM    737  CB   ARG A 111       8.795  -3.563  20.962  1.00 15.07
ATOM    738  CG   ARG A 111       7.581  -2.905  20.332  1.00 22.11
ATOM    739  CD   ARG A 111       6.553  -3.962  19.940  1.00 34.64
ATOM    740  NE   ARG A 111       5.295  -3.339  19.524  1.00 33.18
ATOM    741  CZ   ARG A 111       4.166  -4.022  19.393  1.00 25.21
ATOM    742  NH1  ARG A 111       4.172  -5.327  19.654  1.00 22.23
ATOM    743  NH2  ARG A 111       3.074  -3.380  19.012  1.00 32.75
ATOM    744  C    ARG A 111      10.831  -3.241  22.417  1.00 17.42
ATOM    745  O    ARG A 111      10.720  -4.425  22.726  1.00 18.84
ATOM    746  N    GLU A 112      11.800  -2.432  22.855  1.00 12.49
ATOM    747  CA   GLU A 112      12.900  -2.998  23.629  1.00 13.99
ATOM    748  CB   GLU A 112      14.070  -2.005  23.581  1.00 15.59
ATOM    749  CG   GLU A 112      15.378  -2.703  23.860  1.00 21.33
ATOM    750  CD   GLU A 112      16.623  -2.023  23.352  1.00 27.40
ATOM    751  OE1  GLU A 112      17.658  -2.284  23.998  1.00 26.38
ATOM    752  OE2  GLU A 112      16.619  -1.264  22.363  1.00 25.78
ATOM    753  C    GLU A 112      12.516  -3.334  25.062  1.00 18.95
ATOM    754  O    GLU A 112      13.022  -4.273  25.693  1.00 14.06
ATOM    755  N    TYR A 113      11.576  -2.551  25.570  1.00 17.52
ATOM    756  CA   TYR A 113      11.060  -2.731  26.911  1.00 15.61
ATOM    757  CB   TYR A 113      11.542  -1.629  27.858  1.00 17.96
ATOM    758  CG   TYR A 113      12.990  -1.237  27.756  1.00 14.87
ATOM    759  CD1  TYR A 113      13.405  -0.255  26.878  1.00 17.71
ATOM    760  CE1  TYR A 113      14.734   0.114  26.781  1.00 16.32
ATOM    761  CZ   TYR A 113      15.671  -0.495  27.574  1.00 15.65
ATOM    762  OH   TYR A 113      17.002  -0.145  27.493  1.00 18.69
ATOM    763  CE2  TYR A 113      15.289  -1.484  28.467  1.00 14.44
ATOM    764  CD2  TYR A 113      13.959  -1.844  28.553  1.00 14.04
ATOM    765  C    TYR A 113       9.551  -2.702  26.926  1.00  9.51
ATOM    766  O    TYR A 113       8.855  -2.122  26.096  1.00 11.17
ATOM    767  N    ILE A 114       9.031  -3.382  27.957  1.00 12.36
ATOM    768  CA   ILE A 114       7.655  -3.187  28.333  1.00  9.29
ATOM    769  CB   ILE A 114       6.831  -4.487  28.322  1.00 13.67
ATOM    770  CG1  ILE A 114       6.425  -4.912  26.904  1.00 14.89
ATOM    771  CD1  ILE A 114       5.910  -6.337  26.844  1.00 15.51
ATOM    772  CG2  ILE A 114       5.623  -4.377  29.232  1.00  8.31
ATOM    773  C    ILE A 114       7.674  -2.598  29.746  1.00 16.23
ATOM    774  O    ILE A 114       8.249  -3.182  30.662  1.00 15.28
ATOM    775  N    VAL A 115       7.060  -1.438  29.910  1.00 14.17
ATOM    776  CA   VAL A 115       7.015  -0.801  31.225  1.00 15.15
ATOM    777  CB   VAL A 115       7.294   0.710  31.084  1.00 20.35
ATOM    778  CG1  VAL A 115       6.761   1.465  32.288  1.00 29.43
ATOM    779  CG2  VAL A 115       8.792   0.932  30.901  1.00 19.15
```

FIGURE 220

```
ATOM    780  C   VAL A 115       5.645  -1.011  31.821  1.00 13.67
ATOM    781  O   VAL A 115       4.631  -0.945  31.114  1.00 12.23
ATOM    782  N   THR A 116       5.556  -1.291  33.122  1.00 13.19
ATOM    783  CA  THR A 116       4.208  -1.553  33.635  1.00 12.05
ATOM    784  CB  THR A 116       3.828  -3.042  33.478  1.00 14.77
ATOM    785  OG1 THR A 116       2.432  -3.257  33.750  1.00 13.69
ATOM    786  CG2 THR A 116       4.589  -3.936  34.458  1.00 17.06
ATOM    787  C   THR A 116       4.173  -1.057  35.072  1.00  9.33
ATOM    788  O   THR A 116       5.221  -0.780  35.652  1.00  8.64
ATOM    789  N   GLN A 117       2.982  -0.942  35.626  1.00 10.66
ATOM    790  CA  GLN A 117       2.843  -0.618  37.039  1.00  8.65
ATOM    791  CB  GLN A 117       1.384  -0.239  37.297  1.00  9.54
ATOM    792  CG  GLN A 117       0.384  -1.351  37.114  1.00 12.18
ATOM    793  CD  GLN A 117      -1.071  -1.010  37.307  1.00 19.05
ATOM    794  OE1 GLN A 117      -1.506   0.143  37.314  1.00 13.39
ATOM    795  NE2 GLN A 117      -1.918  -2.025  37.476  1.00  9.71
ATOM    796  C   GLN A 117       3.215  -1.826  37.895  1.00 11.64
ATOM    797  O   GLN A 117       3.347  -2.918  37.345  1.00 15.93
ATOM    798  N   GLY A 118       3.356  -1.703  39.207  1.00 11.16
ATOM    799  CA  GLY A 118       3.499  -2.903  40.060  1.00 10.85
ATOM    800  C   GLY A 118       2.157  -3.620  40.096  1.00 13.55
ATOM    801  O   GLY A 118       1.119  -3.034  40.400  1.00 15.26
ATOM    802  N   PRO A 119       2.148  -4.916  39.758  1.00 12.96
ATOM    803  CA  PRO A 119       0.901  -5.678  39.674  1.00  9.13
ATOM    804  CB  PRO A 119       1.408  -7.119  39.531  1.00 18.59
ATOM    805  CG  PRO A 119       2.720  -6.964  38.824  1.00 19.31
ATOM    806  CD  PRO A 119       3.341  -5.706  39.396  1.00 15.37
ATOM    807  C   PRO A 119       0.079  -5.567  40.953  1.00  8.91
ATOM    808  O   PRO A 119       0.680  -5.487  42.027  1.00 19.14
ATOM    809  N   LEU A 120      -1.228  -5.555  40.787  1.00 13.32
ATOM    810  CA  LEU A 120      -2.126  -5.581  41.935  1.00 15.54
ATOM    811  CB  LEU A 120      -3.388  -4.787  41.631  1.00 19.85
ATOM    812  CG  LEU A 120      -3.158  -3.297  41.331  1.00 20.01
ATOM    813  CD1 LEU A 120      -4.225  -2.766  40.392  1.00 17.81
ATOM    814  CD2 LEU A 120      -3.135  -2.537  42.646  1.00 24.41
ATOM    815  C   LEU A 120      -2.481  -7.038  42.220  1.00 19.68
ATOM    816  O   LEU A 120      -2.257  -7.863  41.327  1.00 18.35
ATOM    817  N   PRO A 121      -3.030  -7.304  43.390  1.00 24.41
ATOM    818  CA  PRO A 121      -3.516  -8.674  43.666  1.00 25.78
ATOM    819  CB  PRO A 121      -4.280  -8.500  44.981  1.00 26.53
ATOM    820  CG  PRO A 121      -3.702  -7.283  45.633  1.00 23.83
ATOM    821  CD  PRO A 121      -3.243  -6.377  44.519  1.00 22.44
ATOM    822  C   PRO A 121      -4.419  -9.154  42.533  1.00 25.28
ATOM    823  O   PRO A 121      -4.338 -10.302  42.074  1.00 26.89
ATOM    824  N   GLY A 122      -5.292  -8.281  42.027  1.00 28.95
ATOM    825  CA  GLY A 122      -6.226  -8.601  40.969  1.00 25.36
ATOM    826  C   GLY A 122      -5.706  -8.512  39.557  1.00 27.04
ATOM    827  O   GLY A 122      -6.422  -8.858  38.606  1.00 25.16
ATOM    828  N   THR A 123      -4.472  -8.062  39.322  1.00 18.42
ATOM    829  CA  THR A 123      -3.944  -8.084  37.954  1.00 17.40
ATOM    830  CB  THR A 123      -3.607  -6.662  37.448  1.00 16.82
ATOM    831  OG1 THR A 123      -2.539  -6.104  38.220  1.00 16.41
```

FIGURE 221

```
ATOM    832  CG2 THR A 123      -4.828  -5.762  37.609  1.00 13.52
ATOM    833  C   THR A 123      -2.691  -8.924  37.831  1.00 15.59
ATOM    834  O   THR A 123      -2.040  -8.987  36.787  1.00 20.37
ATOM    835  N   LYS A 124      -2.242  -9.614  38.888  1.00 15.84
ATOM    836  CA  LYS A 124      -0.996 -10.357  38.635  1.00 17.87
ATOM    837  CB  LYS A 124      -0.395 -10.888  39.928  1.00 14.86
ATOM    838  CG  LYS A 124      -1.274 -11.701  40.840  1.00 15.78
ATOM    839  CD  LYS A 124      -0.510 -11.950  42.138  1.00 23.39
ATOM    840  CE  LYS A 124      -1.394 -12.535  43.232  1.00 25.01
ATOM    841  NZ  LYS A 124      -0.522 -12.822  44.422  1.00 30.58
ATOM    842  C   LYS A 124      -1.169 -11.500  37.639  1.00 13.08
ATOM    843  O   LYS A 124      -0.190 -11.858  36.969  1.00 18.52
ATOM    844  N   ASP A 125      -2.359 -12.084  37.537  1.00 16.39
ATOM    845  CA  ASP A 125      -2.521 -13.172  36.561  1.00 18.39
ATOM    846  CB  ASP A 125      -3.854 -13.887  36.710  1.00 25.32
ATOM    847  CG  ASP A 125      -3.975 -14.629  38.028  1.00 28.44
ATOM    848  OD1 ASP A 125      -2.925 -14.835  38.666  1.00 26.58
ATOM    849  OD2 ASP A 125      -5.108 -14.987  38.393  1.00 36.95
ATOM    850  C   ASP A 125      -2.397 -12.588  35.160  1.00 17.43
ATOM    851  O   ASP A 125      -1.848 -13.215  34.260  1.00 22.46
ATOM    852  N   ASP A 126      -2.906 -11.376  35.006  1.00 18.42
ATOM    853  CA  ASP A 126      -2.740 -10.637  33.754  1.00 17.99
ATOM    854  CB  ASP A 126      -3.494  -9.310  33.841  1.00 20.62
ATOM    855  CG  ASP A 126      -4.982  -9.448  34.061  1.00 38.88
ATOM    856  OD1 ASP A 126      -5.618 -10.322  33.434  1.00 37.14
ATOM    857  OD2 ASP A 126      -5.512  -8.656  34.867  1.00 50.50
ATOM    858  C   ASP A 126      -1.278 -10.346  33.451  1.00 19.58
ATOM    859  O   ASP A 126      -0.763 -10.451  32.338  1.00 19.76
ATOM    860  N   PHE A 127      -0.558  -9.916  34.485  1.00 20.86
ATOM    861  CA  PHE A 127       0.860  -9.628  34.340  1.00 14.49
ATOM    862  CB  PHE A 127       1.450  -9.238  35.698  1.00 12.42
ATOM    863  CG  PHE A 127       2.959  -9.103  35.725  1.00 16.56
ATOM    864  CD1 PHE A 127       3.522  -7.877  35.359  1.00 14.21
ATOM    865  CE1 PHE A 127       4.879  -7.705  35.354  1.00 16.34
ATOM    866  CZ  PHE A 127       5.727  -8.740  35.709  1.00 23.61
ATOM    867  CE2 PHE A 127       5.187  -9.955  36.082  1.00 17.94
ATOM    868  CD2 PHE A 127       3.820 -10.126  36.094  1.00 10.35
ATOM    869  C   PHE A 127       1.581 -10.861  33.812  1.00 17.74
ATOM    870  O   PHE A 127       2.410 -10.836  32.917  1.00 13.35
ATOM    871  N   TRP A 128       1.311 -12.025  34.435  1.00 11.40
ATOM    872  CA  TRP A 128       2.102 -13.181  33.987  1.00 15.21
ATOM    873  CB  TRP A 128       1.989 -14.340  34.993  1.00 10.56
ATOM    874  CG  TRP A 128       2.845 -14.116  36.205  1.00  8.09
ATOM    875  CD1 TRP A 128       2.376 -13.938  37.463  1.00 11.21
ATOM    876  NE1 TRP A 128       3.421 -13.764  38.325  1.00  8.52
ATOM    877  CE2 TRP A 128       4.594 -13.825  37.643  1.00 13.75
ATOM    878  CD2 TRP A 128       4.266 -14.046  36.298  1.00 12.80
ATOM    879  CE3 TRP A 128       5.315 -14.155  35.373  1.00 11.11
ATOM    880  CZ3 TRP A 128       6.605 -14.034  35.821  1.00 11.38
ATOM    881  CH2 TRP A 128       6.893 -13.810  37.181  1.00 16.48
ATOM    882  CZ2 TRP A 128       5.902 -13.701  38.112  1.00 15.53
ATOM    883  C   TRP A 128       1.654 -13.612  32.601  1.00 12.30
```

FIGURE 222

| | | | | | | | | | |
|---|---|---|---|---|---|---|---|---|---|
| ATOM | 884 | O | TRP | A | 128 | 2.460 | -14.098 | 31.798 | 1.00 20.27 |
| ATOM | 885 | N | LYS | A | 129 | 0.386 | -13.432 | 32.287 | 1.00 14.47 |
| ATOM | 886 | CA | LYS | A | 129 | -0.123 | -13.666 | 30.937 | 1.00 19.61 |
| ATOM | 887 | CB | LYS | A | 129 | -1.619 | -13.344 | 30.895 | 1.00 17.71 |
| ATOM | 888 | CG | LYS | A | 129 | -2.234 | -13.587 | 29.519 | 1.00 25.76 |
| ATOM | 889 | CD | LYS | A | 129 | -3.746 | -13.768 | 29.659 | 1.00 30.81 |
| ATOM | 890 | CE | LYS | A | 129 | -4.330 | -14.309 | 28.366 | 1.00 42.38 |
| ATOM | 891 | NZ | LYS | A | 129 | -5.236 | -13.325 | 27.707 | 1.00 64.19 |
| ATOM | 892 | C | LYS | A | 129 | 0.600 | -12.834 | 29.884 | 1.00 20.15 |
| ATOM | 893 | O | LYS | A | 129 | 0.974 | -13.321 | 28.816 | 1.00 19.90 |
| ATOM | 894 | N | MET | A | 130 | 0.803 | -11.553 | 30.185 | 1.00 15.51 |
| ATOM | 895 | CA | MET | A | 130 | 1.625 | -10.693 | 29.342 | 1.00 12.30 |
| ATOM | 896 | CB | MET | A | 130 | 1.651 | -9.264 | 29.941 | 1.00 13.90 |
| ATOM | 897 | CG | MET | A | 130 | 2.496 | -8.310 | 29.089 | 1.00 21.15 |
| ATOM | 898 | SD | MET | A | 130 | 2.449 | -6.632 | 29.804 | 1.00 18.25 |
| ATOM | 899 | CE | MET | A | 130 | 3.476 | -6.963 | 31.261 | 1.00 9.99 |
| ATOM | 900 | C | MET | A | 130 | 3.032 | -11.212 | 29.173 | 1.00 12.39 |
| ATOM | 901 | O | MET | A | 130 | 3.562 | -11.277 | 28.043 | 1.00 16.98 |
| ATOM | 902 | N | VAL | A | 131 | 3.694 | -11.586 | 30.273 | 1.00 12.09 |
| ATOM | 903 | CA | VAL | A | 131 | 5.070 | -12.076 | 30.234 | 1.00 11.97 |
| ATOM | 904 | CB | VAL | A | 131 | 5.538 | -12.430 | 31.659 | 1.00 16.20 |
| ATOM | 905 | CG1 | VAL | A | 131 | 6.799 | -13.282 | 31.685 | 1.00 15.59 |
| ATOM | 906 | CG2 | VAL | A | 131 | 5.769 | -11.144 | 32.455 | 1.00 15.38 |
| ATOM | 907 | C | VAL | A | 131 | 5.163 | -13.304 | 29.317 | 1.00 15.84 |
| ATOM | 908 | O | VAL | A | 131 | 6.079 | -13.467 | 28.514 | 1.00 16.14 |
| ATOM | 909 | N | TRP | A | 132 | 4.164 | -14.167 | 29.469 | 1.00 14.48 |
| ATOM | 910 | CA | TRP | A | 132 | 4.080 | -15.371 | 28.632 | 1.00 22.42 |
| ATOM | 911 | CB | TRP | A | 132 | 2.932 | -16.265 | 29.104 | 1.00 21.06 |
| ATOM | 912 | CG | TRP | A | 132 | 2.745 | -17.494 | 28.255 | 1.00 22.35 |
| ATOM | 913 | CD1 | TRP | A | 132 | 1.874 | -17.689 | 27.232 | 1.00 23.78 |
| ATOM | 914 | NE1 | TRP | A | 132 | 2.025 | -18.958 | 26.719 | 1.00 33.60 |
| ATOM | 915 | CE2 | TRP | A | 132 | 3.010 | -19.603 | 27.414 | 1.00 33.31 |
| ATOM | 916 | CD2 | TRP | A | 132 | 3.490 | -18.709 | 28.393 | 1.00 28.48 |
| ATOM | 917 | CE3 | TRP | A | 132 | 4.512 | -19.117 | 29.253 | 1.00 28.47 |
| ATOM | 918 | CZ3 | TRP | A | 132 | 5.026 | -20.393 | 29.117 | 1.00 36.09 |
| ATOM | 919 | CH2 | TRP | A | 132 | 4.526 | -21.255 | 28.134 | 1.00 36.28 |
| ATOM | 920 | CZ2 | TRP | A | 132 | 3.528 | -20.889 | 27.277 | 1.00 36.96 |
| ATOM | 921 | C | TRP | A | 132 | 3.856 | -15.027 | 27.164 | 1.00 20.60 |
| ATOM | 922 | O | TRP | A | 132 | 4.646 | -15.362 | 26.287 | 1.00 21.95 |
| ATOM | 923 | N | GLU | A | 133 | 2.758 | -14.324 | 26.879 | 1.00 25.53 |
| ATOM | 924 | CA | GLU | A | 133 | 2.457 | -13.988 | 25.485 | 1.00 19.74 |
| ATOM | 925 | CB | GLU | A | 133 | 1.135 | -13.223 | 25.431 | 1.00 18.87 |
| ATOM | 926 | CG | GLU | A | 133 | -0.060 | -14.082 | 25.806 | 1.00 25.68 |
| ATOM | 927 | CD | GLU | A | 133 | -1.358 | -13.302 | 25.838 | 1.00 29.70 |
| ATOM | 928 | OE1 | GLU | A | 133 | -1.312 | -12.052 | 25.763 | 1.00 30.46 |
| ATOM | 929 | OE2 | GLU | A | 133 | -2.414 | -13.968 | 25.938 | 1.00 36.60 |
| ATOM | 930 | C | GLU | A | 133 | 3.539 | -13.175 | 24.804 | 1.00 28.51 |
| ATOM | 931 | O | GLU | A | 133 | 3.674 | -13.293 | 23.581 | 1.00 21.96 |
| ATOM | 932 | N | GLN | A | 134 | 4.290 | -12.351 | 25.538 | 1.00 19.31 |
| ATOM | 933 | CA | GLN | A | 134 | 5.274 | -11.491 | 24.889 | 1.00 19.87 |
| ATOM | 934 | CB | GLN | A | 134 | 5.351 | -10.130 | 25.608 | 1.00 17.70 |
| ATOM | 935 | CG | GLN | A | 134 | 4.018 | -9.384 | 25.508 | 1.00 16.42 |

FIGURE 223

```
ATOM    936  CD   GLN A 134       3.914  -8.755  24.122  1.00 23.73
ATOM    937  OE1  GLN A 134       4.912  -8.253  23.602  1.00 28.15
ATOM    938  NE2  GLN A 134       2.717  -8.831  23.569  1.00 32.92
ATOM    939  C    GLN A 134       6.657 -12.107  24.865  1.00 20.31
ATOM    940  O    GLN A 134       7.638 -11.458  24.496  1.00 17.95
ATOM    941  N    ASN A 135       6.778 -13.370  25.276  1.00 19.01
ATOM    942  CA   ASN A 135       8.098 -13.993  25.193  1.00 21.67
ATOM    943  CB   ASN A 135       8.553 -13.988  23.723  1.00 21.93
ATOM    944  CG   ASN A 135       7.716 -14.985  22.931  1.00 35.97
ATOM    945  OD1  ASN A 135       7.987 -16.184  23.006  1.00 58.93
ATOM    946  ND2  ASN A 135       6.729 -14.503  22.186  1.00 42.17
ATOM    947  C    ASN A 135       9.119 -13.307  26.077  1.00 19.81
ATOM    948  O    ASN A 135      10.309 -13.220  25.769  1.00 16.12
ATOM    949  N    VAL A 136       8.655 -12.799  27.229  1.00 20.36
ATOM    950  CA   VAL A 136       9.581 -12.111  28.122  1.00 15.08
ATOM    951  CB   VAL A 136       8.778 -11.340  29.200  1.00 15.13
ATOM    952  CG1  VAL A 136       9.745 -10.779  30.232  1.00 12.04
ATOM    953  CG2  VAL A 136       7.926 -10.264  28.538  1.00 15.49
ATOM    954  C    VAL A 136      10.502 -13.092  28.836  1.00 14.70
ATOM    955  O    VAL A 136       9.982 -14.072  29.366  1.00 16.57
ATOM    956  N    HIS A 137      11.802 -12.874  28.906  1.00 14.74
ATOM    957  CA   HIS A 137      12.674 -13.744  29.696  1.00 21.99
ATOM    958  CB   HIS A 137      13.779 -14.320  28.813  1.00 29.85
ATOM    959  CG   HIS A 137      13.243 -15.085  27.643  1.00 41.77
ATOM    960  ND1  HIS A 137      12.224 -14.609  26.847  1.00 47.82
ATOM    961  CE1  HIS A 137      11.951 -15.483  25.894  1.00 50.67
ATOM    962  NE2  HIS A 137      12.762 -16.515  26.043  1.00 51.38
ATOM    963  CD2  HIS A 137      13.575 -16.290  27.131  1.00 52.47
ATOM    964  C    HIS A 137      13.278 -12.993  30.881  1.00 19.04
ATOM    965  O    HIS A 137      13.809 -13.584  31.822  1.00 20.60
ATOM    966  N    ASN A 138      13.193 -11.663  30.864  1.00 14.47
ATOM    967  CA   ASN A 138      13.841 -10.854  31.884  1.00 13.33
ATOM    968  CB   ASN A 138      15.068 -10.147  31.291  1.00 17.70
ATOM    969  CG   ASN A 138      16.167 -11.101  30.874  1.00 22.71
ATOM    970  OD1  ASN A 138      16.544 -11.199  29.699  1.00 22.97
ATOM    971  ND2  ASN A 138      16.701 -11.826  31.845  1.00 11.98
ATOM    972  C    ASN A 138      12.881  -9.806  32.455  1.00 19.07
ATOM    973  O    ASN A 138      12.306  -9.048  31.668  1.00 14.29
ATOM    974  N    ILE A 139      12.750  -9.775  33.771  1.00 13.58
ATOM    975  CA   ILE A 139      11.914  -8.814  34.474  1.00 17.38
ATOM    976  CB   ILE A 139      10.769  -9.506  35.247  1.00 14.95
ATOM    977  CG1  ILE A 139       9.801 -10.303  34.371  1.00 16.27
ATOM    978  CD1  ILE A 139       8.895 -11.256  35.154  1.00 11.30
ATOM    979  CG2  ILE A 139      10.015  -8.481  36.087  1.00 10.83
ATOM    980  C    ILE A 139      12.749  -7.985  35.446  1.00 22.75
ATOM    981  O    ILE A 139      13.512  -8.536  36.247  1.00 19.39
ATOM    982  N    VAL A 140      12.624  -6.663  35.401  1.00 11.65
ATOM    983  CA   VAL A 140      13.383  -5.800  36.301  1.00  8.08
ATOM    984  CB   VAL A 140      14.205  -4.745  35.542  1.00 17.09
ATOM    985  CG1  VAL A 140      14.949  -3.802  36.480  1.00 11.40
ATOM    986  CG2  VAL A 140      15.188  -5.436  34.593  1.00 15.24
ATOM    987  C    VAL A 140      12.387  -5.094  37.211  1.00 15.07
```

FIGURE 224

```
ATOM    988  O   VAL A 140      11.457  -4.455  36.710  1.00 14.02
ATOM    989  N   MET A 141      12.575  -5.238  38.515  1.00 14.68
ATOM    990  CA  MET A 141      11.685  -4.587  39.483  1.00 13.84
ATOM    991  CB  MET A 141      11.042  -5.664  40.363  1.00 10.75
ATOM    992  CG  MET A 141      10.187  -5.130  41.494  1.00 13.65
ATOM    993  SD  MET A 141       9.374  -6.486  42.348  1.00 17.62
ATOM    994  CE  MET A 141       8.443  -5.608  43.606  1.00 16.36
ATOM    995  C   MET A 141      12.481  -3.580  40.309  1.00 15.95
ATOM    996  O   MET A 141      13.483  -3.948  40.946  1.00 13.08
ATOM    997  N   VAL A 142      12.088  -2.304  40.318  1.00 11.30
ATOM    998  CA  VAL A 142      12.946  -1.331  41.013  1.00  9.46
ATOM    999  CB  VAL A 142      13.600  -0.291  40.092  1.00 13.94
ATOM   1000  CG1 VAL A 142      14.741  -0.924  39.288  1.00 13.37
ATOM   1001  CG2 VAL A 142      12.590   0.342  39.149  1.00 17.83
ATOM   1002  C   VAL A 142      12.140  -0.611  42.099  1.00 17.41
ATOM   1003  O   VAL A 142      12.299   0.591  42.303  1.00 23.87
ATOM   1004  N   THR A 143      11.299  -1.355  42.791  1.00 14.35
ATOM   1005  CA  THR A 143      10.552  -0.929  43.977  1.00 16.41
ATOM   1006  CB  THR A 143       9.117  -0.509  43.638  1.00 23.66
ATOM   1007  OG1 THR A 143       8.452   0.041  44.789  1.00 20.68
ATOM   1008  CG2 THR A 143       8.267  -1.698  43.207  1.00  9.56
ATOM   1009  C   THR A 143      10.561  -2.079  44.982  1.00 22.05
ATOM   1010  O   THR A 143      10.851  -3.218  44.614  1.00 15.75
ATOM   1011  N   GLN A 144      10.262  -1.792  46.241  1.00 15.62
ATOM   1012  CA  GLN A 144       9.910  -2.851  47.187  1.00 19.93
ATOM   1013  CB  GLN A 144      10.410  -2.626  48.609  1.00 17.14
ATOM   1014  CG  GLN A 144      11.927  -2.605  48.704  1.00 20.52
ATOM   1015  CD  GLN A 144      12.348  -2.080  50.072  1.00 35.53
ATOM   1016  OE1 GLN A 144      12.254  -2.790  51.068  1.00 40.58
ATOM   1017  NE2 GLN A 144      12.801  -0.835  50.111  1.00 40.58
ATOM   1018  C   GLN A 144       8.384  -2.911  47.180  1.00 22.04
ATOM   1019  O   GLN A 144       7.791  -1.911  46.762  1.00 16.80
ATOM   1020  N   CYS A 145       7.844  -4.039  47.614  1.00 15.58
ATOM   1021  CA  CYS A 145       6.417  -4.249  47.637  1.00 12.91
ATOM   1022  CB  CYS A 145       6.103  -5.685  48.076  1.00 16.62
ATOM   1023  SG  CYS A 145       6.632  -6.849  46.778  1.00 21.90
ATOM   1024  C   CYS A 145       5.740  -3.273  48.598  1.00 16.44
ATOM   1025  O   CYS A 145       4.638  -2.796  48.381  1.00 16.10
ATOM   1026  N   VAL A 146       6.468  -3.025  49.680  1.00 17.59
ATOM   1027  CA  VAL A 146       5.917  -2.095  50.680  1.00 20.28
ATOM   1028  CB  VAL A 146       5.285  -2.784  51.889  1.00 22.74
ATOM   1029  CG1 VAL A 146       4.932  -1.757  52.972  1.00 22.42
ATOM   1030  CG2 VAL A 146       4.037  -3.548  51.478  1.00 22.17
ATOM   1031  C   VAL A 146       7.070  -1.198  51.104  1.00 16.66
ATOM   1032  O   VAL A 146       8.171  -1.704  51.357  1.00 18.81
ATOM   1033  N   GLU A 147       6.824   0.111  51.141  1.00 13.43
ATOM   1034  CA  GLU A 147       7.898   0.995  51.588  1.00 16.86
ATOM   1035  CB  GLU A 147       8.417   1.873  50.447  1.00 21.49
ATOM   1036  CG  GLU A 147       9.145   1.028  49.405  1.00 26.38
ATOM   1037  CD  GLU A 147       9.550   1.808  48.172  1.00 37.10
ATOM   1038  OE1 GLU A 147       9.453   3.051  48.188  1.00 32.89
ATOM   1039  OE2 GLU A 147       9.980   1.139  47.206  1.00 27.53
```

FIGURE 225

```
ATOM   1040  C    GLU A 147       7.403   1.850  52.761  1.00 19.26
ATOM   1041  O    GLU A 147       6.402   2.535  52.577  1.00 27.69
ATOM   1042  N    LYS A 148       8.115   1.732  53.874  1.00 26.96
ATOM   1043  CA   LYS A 148       7.743   2.395  55.125  1.00 26.67
ATOM   1044  CB   LYS A 148       8.105   3.878  55.092  1.00 33.37
ATOM   1045  CG   LYS A 148       9.582   4.143  55.371  1.00 42.34
ATOM   1046  CD   LYS A 148      10.220   4.913  54.226  1.00 49.37
ATOM   1047  CE   LYS A 148      11.467   5.651  54.685  1.00 56.84
ATOM   1048  NZ   LYS A 148      11.213   7.114  54.810  1.00 51.81
ATOM   1049  C    LYS A 148       6.261   2.210  55.380  1.00 29.22
ATOM   1050  O    LYS A 148       5.510   3.102  55.771  1.00 34.85
ATOM   1051  N    GLY A 149       5.788   0.979  55.133  1.00 21.30
ATOM   1052  CA   GLY A 149       4.379   0.765  55.390  1.00 23.12
ATOM   1053  C    GLY A 149       3.451   1.142  54.264  1.00 28.88
ATOM   1054  O    GLY A 149       2.288   0.724  54.322  1.00 23.12
ATOM   1055  N    ARG A 150       3.892   1.910  53.264  1.00 23.43
ATOM   1056  CA   ARG A 150       2.967   2.235  52.172  1.00 19.35
ATOM   1057  CB   ARG A 150       3.237   3.651  51.657  1.00 27.51
ATOM   1058  CG   ARG A 150       3.022   4.689  52.755  1.00 36.85
ATOM   1059  CD   ARG A 150       3.433   6.085  52.332  1.00 46.96
ATOM   1060  NE   ARG A 150       4.879   6.252  52.377  1.00 54.45
ATOM   1061  CZ   ARG A 150       5.541   7.218  52.990  1.00 55.25
ATOM   1062  NH1  ARG A 150       4.899   8.166  53.652  1.00 47.81
ATOM   1063  NH2  ARG A 150       6.868   7.238  52.944  1.00 64.89
ATOM   1064  C    ARG A 150       3.097   1.201  51.060  1.00 17.74
ATOM   1065  O    ARG A 150       4.206   0.894  50.604  1.00 20.32
ATOM   1066  N    VAL A 151       1.980   0.628  50.655  1.00 18.03
ATOM   1067  CA   VAL A 151       1.948  -0.432  49.654  1.00 23.37
ATOM   1068  CB   VAL A 151       0.528  -1.030  49.571  1.00 28.77
ATOM   1069  CG1  VAL A 151       0.412  -2.015  48.412  1.00 18.49
ATOM   1070  CG2  VAL A 151       0.162  -1.691  50.895  1.00 20.07
ATOM   1071  C    VAL A 151       2.351   0.114  48.294  1.00 20.37
ATOM   1072  O    VAL A 151       1.847   1.164  47.899  1.00 19.29
ATOM   1073  N    LYS A 152       3.209  -0.566  47.557  1.00 18.81
ATOM   1074  CA   LYS A 152       3.673  -0.055  46.270  1.00 16.66
ATOM   1075  CB   LYS A 152       5.157   0.303  46.308  1.00 10.31
ATOM   1076  CG   LYS A 152       5.629   1.240  47.419  1.00 16.94
ATOM   1077  CD   LYS A 152       5.089   2.652  47.170  1.00 19.08
ATOM   1078  CE   LYS A 152       5.831   3.663  48.050  1.00 16.36
ATOM   1079  NZ   LYS A 152       5.565   5.051  47.592  1.00 31.76
ATOM   1080  C    LYS A 152       3.460  -1.111  45.189  1.00 18.63
ATOM   1081  O    LYS A 152       3.313  -0.808  44.006  1.00 14.72
ATOM   1082  N    CYS A 153       3.472  -2.381  45.605  1.00 10.99
ATOM   1083  CA   CYS A 153       3.426  -3.447  44.599  1.00 14.85
ATOM   1084  CB   CYS A 153       4.777  -3.577  43.886  1.00 10.33
ATOM   1085  SG   CYS A 153       4.784  -4.845  42.573  1.00 15.08
ATOM   1086  C    CYS A 153       3.025  -4.752  45.279  1.00 19.72
ATOM   1087  O    CYS A 153       3.429  -5.011  46.409  1.00 17.06
ATOM   1088  N    ASP A 154       2.207  -5.564  44.633  1.00 14.81
ATOM   1089  CA   ASP A 154       1.872  -6.852  45.241  1.00 15.17
ATOM   1090  CB   ASP A 154       0.662  -7.429  44.514  1.00 12.59
ATOM   1091  CG   ASP A 154       0.186  -8.745  45.101  1.00 24.42
```

FIGURE 226

| | | | | | | | | |
|---|---|---|---|---|---|---|---|---|
| ATOM | 1092 | OD1 | ASP | A | 154 | 0.232 | -9.777 | 44.397 | 1.00 33.37 |
| ATOM | 1093 | OD2 | ASP | A | 154 | -0.223 | -8.736 | 46.278 | 1.00 26.94 |
| ATOM | 1094 | C | ASP | A | 154 | 3.083 | -7.782 | 45.165 | 1.00 21.36 |
| ATOM | 1095 | O | ASP | A | 154 | 3.914 | -7.662 | 44.252 | 1.00 23.22 |
| ATOM | 1096 | N | HIS | A | 155 | 3.228 | -8.717 | 46.091 | 1.00 15.03 |
| ATOM | 1097 | CA | HIS | A | 155 | 4.241 | -9.766 | 46.046 | 1.00 19.74 |
| ATOM | 1098 | CB | HIS | A | 155 | 4.479 | -10.390 | 47.434 | 1.00 18.44 |
| ATOM | 1099 | CG | HIS | A | 155 | 5.718 | -11.249 | 47.473 | 1.00 16.91 |
| ATOM | 1100 | ND1 | HIS | A | 155 | 5.772 | -12.503 | 46.910 | 1.00 21.58 |
| ATOM | 1101 | CE1 | HIS | A | 155 | 6.975 | -13.028 | 47.088 | 1.00 15.22 |
| ATOM | 1102 | NE2 | HIS | A | 155 | 7.719 | -12.158 | 47.752 | 1.00 21.40 |
| ATOM | 1103 | CD2 | HIS | A | 155 | 6.946 | -11.046 | 47.997 | 1.00 13.16 |
| ATOM | 1104 | C | HIS | A | 155 | 3.765 | -10.828 | 45.054 | 1.00 25.16 |
| ATOM | 1105 | O | HIS | A | 155 | 3.222 | -11.863 | 45.434 | 1.00 22.33 |
| ATOM | 1106 | N | TYR | A | 156 | 3.935 | -10.543 | 43.764 | 1.00 14.86 |
| ATOM | 1107 | CA | TYR | A | 156 | 3.238 | -11.265 | 42.715 | 1.00 14.13 |
| ATOM | 1108 | CB | TYR | A | 156 | 3.055 | -10.354 | 41.479 | 1.00 13.04 |
| ATOM | 1109 | CG | TYR | A | 156 | 4.342 | -9.814 | 40.905 | 1.00 13.16 |
| ATOM | 1110 | CD1 | TYR | A | 156 | 5.071 | -10.496 | 39.932 | 1.00 10.49 |
| ATOM | 1111 | CE1 | TYR | A | 156 | 6.239 | -10.006 | 39.407 | 1.00 17.75 |
| ATOM | 1112 | CZ | TYR | A | 156 | 6.718 | -8.786 | 39.842 | 1.00 15.46 |
| ATOM | 1113 | OH | TYR | A | 156 | 7.895 | -8.286 | 39.320 | 1.00 14.59 |
| ATOM | 1114 | CE2 | TYR | A | 156 | 6.021 | -8.087 | 40.801 | 1.00 14.68 |
| ATOM | 1115 | CD2 | TYR | A | 156 | 4.843 | -8.585 | 41.331 | 1.00 12.40 |
| ATOM | 1116 | C | TYR | A | 156 | 3.959 | -12.526 | 42.265 | 1.00 17.42 |
| ATOM | 1117 | O | TYR | A | 156 | 3.533 | -13.067 | 41.242 | 1.00 15.62 |
| ATOM | 1118 | N | TRP | A | 157 | 4.994 | -12.933 | 42.972 | 1.00 21.73 |
| ATOM | 1119 | CA | TRP | A | 157 | 5.722 | -14.154 | 42.677 | 1.00 16.38 |
| ATOM | 1120 | CB | TRP | A | 157 | 7.152 | -13.878 | 42.223 | 1.00 14.65 |
| ATOM | 1121 | CG | TRP | A | 157 | 7.993 | -13.290 | 43.317 | 1.00 20.93 |
| ATOM | 1122 | CD1 | TRP | A | 157 | 8.817 | -13.924 | 44.200 | 1.00 19.30 |
| ATOM | 1123 | NE1 | TRP | A | 157 | 9.401 | -13.009 | 45.041 | 1.00 18.29 |
| ATOM | 1124 | CE2 | TRP | A | 157 | 8.956 | -11.758 | 44.703 | 1.00 20.37 |
| ATOM | 1125 | CD2 | TRP | A | 157 | 8.070 | -11.895 | 43.622 | 1.00 12.37 |
| ATOM | 1126 | CE3 | TRP | A | 157 | 7.469 | -10.759 | 43.083 | 1.00 15.46 |
| ATOM | 1127 | CZ3 | TRP | A | 157 | 7.772 | -9.522 | 43.635 | 1.00 13.34 |
| ATOM | 1128 | CH2 | TRP | A | 157 | 8.657 | -9.418 | 44.709 | 1.00 18.59 |
| ATOM | 1129 | CZ2 | TRP | A | 157 | 9.262 | -10.519 | 45.259 | 1.00 21.33 |
| ATOM | 1130 | C | TRP | A | 157 | 5.728 | -15.029 | 43.926 | 1.00 30.00 |
| ATOM | 1131 | O | TRP | A | 157 | 5.456 | -14.475 | 44.994 | 1.00 24.21 |
| ATOM | 1132 | N | PRO | A | 158 | 6.007 | -16.316 | 43.798 | 1.00 29.81 |
| ATOM | 1133 | CA | PRO | A | 158 | 6.016 | -17.206 | 44.965 | 1.00 32.16 |
| ATOM | 1134 | CB | PRO | A | 158 | 6.531 | -18.527 | 44.371 | 1.00 30.44 |
| ATOM | 1135 | CG | PRO | A | 158 | 6.069 | -18.476 | 42.946 | 1.00 26.74 |
| ATOM | 1136 | CD | PRO | A | 158 | 6.307 | -17.040 | 42.542 | 1.00 22.30 |
| ATOM | 1137 | C | PRO | A | 158 | 6.961 | -16.803 | 46.089 | 1.00 29.52 |
| ATOM | 1138 | O | PRO | A | 158 | 8.088 | -16.362 | 45.866 | 1.00 43.48 |
| ATOM | 1139 | N | ALA | A | 159 | 6.502 | -16.986 | 47.322 | 1.00 34.03 |
| ATOM | 1140 | CA | ALA | A | 159 | 7.303 | -16.748 | 48.519 | 1.00 33.58 |
| ATOM | 1141 | CB | ALA | A | 159 | 6.444 | -16.986 | 49.760 | 1.00 34.30 |
| ATOM | 1142 | C | ALA | A | 159 | 8.547 | -17.621 | 48.576 | 1.00 32.85 |
| ATOM | 1143 | O | ALA | A | 159 | 9.602 | -17.201 | 49.045 | 1.00 40.76 |

FIGURE 227

```
ATOM   1144  N    ASP A 160       8.427 -18.858  48.101  1.00 29.96
ATOM   1145  CA   ASP A 160       9.520 -19.826  48.164  1.00 28.99
ATOM   1146  CB   ASP A 160       9.468 -20.587  49.485  1.00 27.85
ATOM   1147  CG   ASP A 160       8.150 -21.298  49.727  1.00 33.73
ATOM   1148  OD1  ASP A 160       7.767 -21.452  50.910  1.00 36.35
ATOM   1149  OD2  ASP A 160       7.486 -21.709  48.750  1.00 38.51
ATOM   1150  C    ASP A 160       9.449 -20.784  46.983  1.00 24.92
ATOM   1151  O    ASP A 160       8.857 -20.443  45.951  1.00 29.16
ATOM   1152  N    GLN A 161      10.025 -21.975  47.125  1.00 19.70
ATOM   1153  CA   GLN A 161      10.089 -22.904  46.006  1.00 29.75
ATOM   1154  CB   GLN A 161      11.241 -23.901  46.254  1.00 33.52
ATOM   1155  CG   GLN A 161      12.575 -23.383  45.720  1.00 41.43
ATOM   1156  CD   GLN A 161      13.754 -23.856  46.547  1.00 53.65
ATOM   1157  OE1  GLN A 161      14.390 -24.865  46.229  1.00 54.16
ATOM   1158  NE2  GLN A 161      14.053 -23.128  47.619  1.00 75.55
ATOM   1159  C    GLN A 161       8.798 -23.664  45.760  1.00 32.87
ATOM   1160  O    GLN A 161       8.730 -24.481  44.833  1.00 27.15
ATOM   1161  N    ASP A 162       7.759 -23.443  46.559  1.00 32.19
ATOM   1162  CA   ASP A 162       6.508 -24.162  46.313  1.00 25.87
ATOM   1163  CB   ASP A 162       5.547 -24.078  47.488  1.00 27.76
ATOM   1164  CG   ASP A 162       5.916 -24.971  48.652  1.00 40.60
ATOM   1165  OD1  ASP A 162       7.006 -25.582  48.628  1.00 39.74
ATOM   1166  OD2  ASP A 162       5.099 -25.049  49.598  1.00 66.88
ATOM   1167  C    ASP A 162       5.855 -23.557  45.072  1.00 29.94
ATOM   1168  O    ASP A 162       5.977 -22.348  44.880  1.00 36.10
ATOM   1169  N    SER A 163       5.201 -24.359  44.249  1.00 23.42
ATOM   1170  CA   SER A 163       4.656 -23.839  42.997  1.00 21.05
ATOM   1171  CB   SER A 163       4.556 -24.994  41.988  1.00 26.60
ATOM   1172  OG   SER A 163       3.896 -26.074  42.630  1.00 25.84
ATOM   1173  C    SER A 163       3.306 -23.190  43.194  1.00 17.83
ATOM   1174  O    SER A 163       2.600 -23.381  44.183  1.00 21.12
ATOM   1175  N    LEU A 164       2.909 -22.379  42.208  1.00 22.53
ATOM   1176  CA   LEU A 164       1.618 -21.708  42.296  1.00 17.81
ATOM   1177  CB   LEU A 164       1.770 -20.333  42.942  1.00 22.42
ATOM   1178  CG   LEU A 164       1.717 -20.210  44.457  1.00 30.71
ATOM   1179  CD1  LEU A 164       1.783 -18.736  44.854  1.00 38.32
ATOM   1180  CD2  LEU A 164       0.464 -20.862  45.021  1.00 31.30
ATOM   1181  C    LEU A 164       1.042 -21.526  40.897  1.00 16.82
ATOM   1182  O    LEU A 164       1.843 -21.285  39.990  1.00 20.87
ATOM   1183  N    TYR A 165      -0.269 -21.616  40.758  1.00 15.24
ATOM   1184  CA   TYR A 165      -0.942 -21.169  39.550  1.00 22.53
ATOM   1185  CB   TYR A 165      -2.365 -21.741  39.489  1.00 16.95
ATOM   1186  CG   TYR A 165      -2.417 -23.194  39.073  1.00 20.26
ATOM   1187  CD1  TYR A 165      -2.541 -24.180  40.038  1.00 15.27
ATOM   1188  CE1  TYR A 165      -2.593 -25.515  39.711  1.00 15.03
ATOM   1189  CZ   TYR A 165      -2.522 -25.882  38.390  1.00 19.11
ATOM   1190  OH   TYR A 165      -2.579 -27.227  38.066  1.00 25.32
ATOM   1191  CE2  TYR A 165      -2.402 -24.928  37.410  1.00 19.58
ATOM   1192  CD2  TYR A 165      -2.348 -23.582  37.740  1.00 25.42
ATOM   1193  C    TYR A 165      -1.076 -19.646  39.464  1.00 25.11
ATOM   1194  O    TYR A 165      -1.337 -18.969  40.459  1.00 19.81
ATOM   1195  N    TYR A 166      -0.938 -19.095  38.264  1.00 18.82
```

FIGURE 228

| | | | | | | | | |
|---|---|---|---|---|---|---|---|---|
| ATOM | 1196 | CA  | TYR | A | 166 | -1.373 | -17.719 | 38.014 | 1.00 | 23.86 |
| ATOM | 1197 | CB  | TYR | A | 166 | -0.202 | -16.754 | 37.949 | 1.00 | 25.11 |
| ATOM | 1198 | CG  | TYR | A | 166 |  0.652 | -16.636 | 39.182 | 1.00 | 17.66 |
| ATOM | 1199 | CD1 | TYR | A | 166 |  0.365 | -15.669 | 40.134 | 1.00 | 17.33 |
| ATOM | 1200 | CE1 | TYR | A | 166 |  1.133 | -15.541 | 41.265 | 1.00 | 20.35 |
| ATOM | 1201 | CZ  | TYR | A | 166 |  2.205 | -16.369 | 41.485 | 1.00 | 26.41 |
| ATOM | 1202 | OH  | TYR | A | 166 |  2.943 | -16.198 | 42.636 | 1.00 | 24.80 |
| ATOM | 1203 | CE2 | TYR | A | 166 |  2.521 | -17.338 | 40.561 | 1.00 | 24.56 |
| ATOM | 1204 | CD2 | TYR | A | 166 |  1.738 | -17.457 | 39.421 | 1.00 | 19.47 |
| ATOM | 1205 | C   | TYR | A | 166 | -2.168 | -17.720 | 36.706 | 1.00 | 15.43 |
| ATOM | 1206 | O   | TYR | A | 166 | -1.541 | -17.809 | 35.655 | 1.00 | 16.56 |
| ATOM | 1207 | N   | GLY | A | 167 | -3.474 | -17.641 | 36.810 | 1.00 | 17.70 |
| ATOM | 1208 | CA  | GLY | A | 167 | -4.449 | -17.953 | 35.792 | 1.00 | 24.28 |
| ATOM | 1209 | C   | GLY | A | 167 | -4.211 | -19.347 | 35.220 | 1.00 | 31.57 |
| ATOM | 1210 | O   | GLY | A | 167 | -4.329 | -20.338 | 35.943 | 1.00 | 28.31 |
| ATOM | 1211 | N   | ASP | A | 168 | -3.856 | -19.435 | 33.943 | 1.00 | 24.61 |
| ATOM | 1212 | CA  | ASP | A | 168 | -3.616 | -20.695 | 33.265 | 1.00 | 28.49 |
| ATOM | 1213 | CB  | ASP | A | 168 | -4.089 | -20.622 | 31.802 | 1.00 | 29.53 |
| ATOM | 1214 | CG  | ASP | A | 168 | -5.587 | -20.382 | 31.765 | 1.00 | 33.69 |
| ATOM | 1215 | OD1 | ASP | A | 168 | -6.283 | -21.001 | 32.589 | 1.00 | 33.30 |
| ATOM | 1216 | OD2 | ASP | A | 168 | -6.063 | -19.582 | 30.947 | 1.00 | 43.14 |
| ATOM | 1217 | C   | ASP | A | 168 | -2.152 | -21.097 | 33.273 | 1.00 | 28.68 |
| ATOM | 1218 | O   | ASP | A | 168 | -1.802 | -22.113 | 32.667 | 1.00 | 34.81 |
| ATOM | 1219 | N   | LEU | A | 169 | -1.310 | -20.309 | 33.937 | 1.00 | 22.13 |
| ATOM | 1220 | CA  | LEU | A | 169 |  0.109 | -20.623 | 33.989 | 1.00 | 18.47 |
| ATOM | 1221 | CB  | LEU | A | 169 |  0.958 | -19.356 | 33.795 | 1.00 | 21.38 |
| ATOM | 1222 | CG  | LEU | A | 169 |  0.732 | -18.594 | 32.489 | 1.00 | 25.30 |
| ATOM | 1223 | CD1 | LEU | A | 169 |  1.565 | -17.313 | 32.456 | 1.00 | 21.42 |
| ATOM | 1224 | CD2 | LEU | A | 169 |  1.043 | -19.474 | 31.290 | 1.00 | 27.51 |
| ATOM | 1225 | C   | LEU | A | 169 |  0.470 | -21.268 | 35.322 | 1.00 | 19.04 |
| ATOM | 1226 | O   | LEU | A | 169 | -0.213 | -21.003 | 36.309 | 1.00 | 21.82 |
| ATOM | 1227 | N   | ILE | A | 170 |  1.516 | -22.084 | 35.337 | 1.00 | 20.12 |
| ATOM | 1228 | CA  | ILE | A | 170 |  2.068 | -22.592 | 36.587 | 1.00 | 21.11 |
| ATOM | 1229 | CB  | ILE | A | 170 |  2.138 | -24.120 | 36.675 | 1.00 | 20.24 |
| ATOM | 1230 | CG1 | ILE | A | 170 |  0.783 | -24.795 | 36.514 | 1.00 | 27.42 |
| ATOM | 1231 | CD1 | ILE | A | 170 |  0.840 | -26.292 | 36.777 | 1.00 | 29.31 |
| ATOM | 1232 | CG2 | ILE | A | 170 |  2.804 | -24.547 | 37.980 | 1.00 | 23.61 |
| ATOM | 1233 | C   | ILE | A | 170 |  3.478 | -22.031 | 36.736 | 1.00 | 20.55 |
| ATOM | 1234 | O   | ILE | A | 170 |  4.251 | -22.062 | 35.786 | 1.00 | 28.78 |
| ATOM | 1235 | N   | LEU | A | 171 |  3.763 | -21.531 | 37.926 | 1.00 | 22.31 |
| ATOM | 1236 | CA  | LEU | A | 171 |  5.044 | -20.881 | 38.181 | 1.00 | 24.43 |
| ATOM | 1237 | CB  | LEU | A | 171 |  4.758 | -19.393 | 38.433 | 1.00 | 27.91 |
| ATOM | 1238 | CG  | LEU | A | 171 |  5.910 | -18.408 | 38.278 | 1.00 | 37.79 |
| ATOM | 1239 | CD1 | LEU | A | 171 |  5.400 | -17.017 | 37.942 | 1.00 | 44.63 |
| ATOM | 1240 | CD2 | LEU | A | 171 |  6.747 | -18.374 | 39.551 | 1.00 | 34.65 |
| ATOM | 1241 | C   | LEU | A | 171 |  5.774 | -21.519 | 39.352 | 1.00 | 19.86 |
| ATOM | 1242 | O   | LEU | A | 171 |  5.179 | -21.847 | 40.382 | 1.00 | 20.05 |
| ATOM | 1243 | N   | GLN | A | 172 |  7.077 | -21.692 | 39.203 | 1.00 | 21.32 |
| ATOM | 1244 | CA  | GLN | A | 172 |  7.936 | -22.247 | 40.234 | 1.00 | 29.54 |
| ATOM | 1245 | CB  | GLN | A | 172 |  8.315 | -23.689 | 39.862 | 1.00 | 43.33 |
| ATOM | 1246 | CG  | GLN | A | 172 |  7.514 | -24.770 | 40.555 | 1.00 | 53.47 |
| ATOM | 1247 | CD  | GLN | A | 172 |  8.301 | -26.042 | 40.814 | 1.00 | 63.05 |

FIGURE 229

```
ATOM   1248  OE1 GLN A 172       9.068 -26.503  39.964  1.00 39.02
ATOM   1249  NE2 GLN A 172       8.114 -26.624  41.998  1.00 64.69
ATOM   1250  C   GLN A 172       9.211 -21.440  40.411  1.00 19.61
ATOM   1251  O   GLN A 172       9.974 -21.265  39.457  1.00 19.10
ATOM   1252  N   MET A 173       9.497 -20.971  41.628  1.00 16.88
ATOM   1253  CA  MET A 173      10.792 -20.353  41.863  1.00 19.35
ATOM   1254  CB  MET A 173      10.808 -19.485  43.130  1.00 24.60
ATOM   1255  CG  MET A 173      12.118 -18.710  43.277  1.00 27.16
ATOM   1256  SD  MET A 173      11.885 -17.267  44.349  1.00 39.15
ATOM   1257  CE  MET A 173      11.807 -18.102  45.934  1.00 35.39
ATOM   1258  C   MET A 173      11.914 -21.384  42.027  1.00 24.07
ATOM   1259  O   MET A 173      11.953 -22.072  43.043  1.00 31.47
ATOM   1260  N   LEU A 174      12.782 -21.438  41.036  1.00 23.52
ATOM   1261  CA  LEU A 174      13.945 -22.311  40.998  1.00 33.03
ATOM   1262  CB  LEU A 174      14.403 -22.478  39.543  1.00 27.30
ATOM   1263  CG  LEU A 174      13.369 -23.075  38.590  1.00 32.33
ATOM   1264  CD1 LEU A 174      14.023 -23.477  37.276  1.00 44.31
ATOM   1265  CD2 LEU A 174      12.665 -24.270  39.214  1.00 40.73
ATOM   1266  C   LEU A 174      15.096 -21.796  41.841  1.00 33.13
ATOM   1267  O   LEU A 174      15.857 -22.565  42.431  1.00 36.31
ATOM   1268  N   SER A 175      15.271 -20.475  41.923  1.00 32.25
ATOM   1269  CA  SER A 175      16.386 -19.961  42.712  1.00 28.55
ATOM   1270  CB  SER A 175      17.696 -20.148  41.952  1.00 36.29
ATOM   1271  OG  SER A 175      17.775 -19.299  40.825  1.00 30.88
ATOM   1272  C   SER A 175      16.199 -18.488  43.069  1.00 34.24
ATOM   1273  O   SER A 175      15.445 -17.778  42.404  1.00 23.93
ATOM   1274  N   GLU A 176      16.909 -18.101  44.118  1.00 24.79
ATOM   1275  CA  GLU A 176      16.841 -16.777  44.717  1.00 24.84
ATOM   1276  CB  GLU A 176      15.678 -16.730  45.704  1.00 29.85
ATOM   1277  CG  GLU A 176      15.447 -15.387  46.377  1.00 32.22
ATOM   1278  CD  GLU A 176      14.223 -15.390  47.270  1.00 34.82
ATOM   1279  OE1 GLU A 176      14.358 -15.795  48.447  1.00 50.78
ATOM   1280  OE2 GLU A 176      13.135 -14.988  46.806  1.00 39.74
ATOM   1281  C   GLU A 176      18.166 -16.441  45.398  1.00 35.34
ATOM   1282  O   GLU A 176      18.519 -17.072  46.397  1.00 33.01
ATOM   1283  N   SER A 177      18.884 -15.477  44.837  1.00 29.77
ATOM   1284  CA  SER A 177      20.151 -14.997  45.367  1.00 25.28
ATOM   1285  CB  SER A 177      21.299 -15.094  44.377  1.00 27.96
ATOM   1286  OG  SER A 177      21.253 -16.278  43.606  1.00 51.47
ATOM   1287  C   SER A 177      20.003 -13.547  45.831  1.00 30.74
ATOM   1288  O   SER A 177      19.856 -12.591  45.070  1.00 23.11
ATOM   1289  N   VAL A 178      20.042 -13.454  47.153  1.00 31.26
ATOM   1290  CA  VAL A 178      19.964 -12.168  47.825  1.00 31.69
ATOM   1291  CB  VAL A 178      19.343 -12.317  49.218  1.00 34.41
ATOM   1292  CG1 VAL A 178      19.192 -10.964  49.903  1.00 48.17
ATOM   1293  CG2 VAL A 178      17.989 -13.008  49.117  1.00 26.99
ATOM   1294  C   VAL A 178      21.367 -11.579  47.885  1.00 39.05
ATOM   1295  O   VAL A 178      22.306 -12.239  48.333  1.00 45.15
ATOM   1296  N   LEU A 179      21.484 -10.351  47.400  1.00 29.28
ATOM   1297  CA  LEU A 179      22.713  -9.567  47.511  1.00 24.54
ATOM   1298  CB  LEU A 179      23.278  -9.294  46.122  1.00 27.13
ATOM   1299  CG  LEU A 179      23.427 -10.559  45.262  1.00 39.41
```

FIGURE 230

```
ATOM   1300  CD1 LEU A 179      23.571 -10.210  43.793  1.00 56.70
ATOM   1301  CD2 LEU A 179      24.604 -11.381  45.760  1.00 42.38
ATOM   1302  C   LEU A 179      22.370  -8.317  48.298  1.00 32.59
ATOM   1303  O   LEU A 179      21.180  -8.081  48.548  1.00 37.75
ATOM   1304  N   PRO A 180      23.330  -7.522  48.737  1.00 39.11
ATOM   1305  CA  PRO A 180      22.960  -6.390  49.597  1.00 42.52
ATOM   1306  CB  PRO A 180      24.299  -5.699  49.872  1.00 48.91
ATOM   1307  CG  PRO A 180      25.323  -6.759  49.636  1.00 51.16
ATOM   1308  CD  PRO A 180      24.778  -7.596  48.511  1.00 44.82
ATOM   1309  C   PRO A 180      22.012  -5.425  48.910  1.00 35.13
ATOM   1310  O   PRO A 180      21.144  -4.829  49.553  1.00 43.71
ATOM   1311  N   GLU A 181      22.138  -5.225  47.594  1.00 25.87
ATOM   1312  CA  GLU A 181      21.282  -4.161  47.054  1.00 26.32
ATOM   1313  CB  GLU A 181      22.162  -3.079  46.420  1.00 29.01
ATOM   1314  CG  GLU A 181      22.810  -2.178  47.465  1.00 30.02
ATOM   1315  CD  GLU A 181      24.001  -1.472  46.840  1.00 32.75
ATOM   1316  OE1 GLU A 181      24.714  -2.135  46.060  1.00 55.04
ATOM   1317  OE2 GLU A 181      24.190  -0.279  47.144  1.00 78.18
ATOM   1318  C   GLU A 181      20.279  -4.658  46.035  1.00 19.68
ATOM   1319  O   GLU A 181      19.432  -3.890  45.579  1.00 22.96
ATOM   1320  N   TRP A 182      20.393  -5.937  45.683  1.00 23.62
ATOM   1321  CA  TRP A 182      19.378  -6.504  44.799  1.00 20.73
ATOM   1322  CB  TRP A 182      19.626  -6.134  43.344  1.00 22.35
ATOM   1323  CG  TRP A 182      21.019  -6.447  42.864  1.00 21.68
ATOM   1324  CD1 TRP A 182      21.493  -7.660  42.455  1.00 20.02
ATOM   1325  NE1 TRP A 182      22.813  -7.552  42.089  1.00 24.79
ATOM   1326  CE2 TRP A 182      23.214  -6.252  42.256  1.00 33.15
ATOM   1327  CD2 TRP A 182      22.107  -5.528  42.743  1.00 28.28
ATOM   1328  CE3 TRP A 182      22.241  -4.160  43.006  1.00 26.77
ATOM   1329  CZ3 TRP A 182      23.476  -3.579  42.767  1.00 34.39
ATOM   1330  CH2 TRP A 182      24.560  -4.324  42.281  1.00 31.42
ATOM   1331  CZ2 TRP A 182      24.460  -5.664  42.018  1.00 30.61
ATOM   1332  C   TRP A 182      19.349  -8.017  44.977  1.00 23.48
ATOM   1333  O   TRP A 182      20.281  -8.619  45.513  1.00 24.37
ATOM   1334  N   THR A 183      18.240  -8.569  44.517  1.00 20.84
ATOM   1335  CA  THR A 183      17.987 -10.000  44.561  1.00 22.33
ATOM   1336  CB  THR A 183      16.773 -10.266  45.471  1.00 20.04
ATOM   1337  OG1 THR A 183      17.130  -9.789  46.776  1.00 26.68
ATOM   1338  CG2 THR A 183      16.466 -11.751  45.577  1.00 20.82
ATOM   1339  C   THR A 183      17.725 -10.538  43.168  1.00 26.38
ATOM   1340  O   THR A 183      16.949  -9.925  42.429  1.00 23.46
ATOM   1341  N   ILE A 184      18.351 -11.655  42.819  1.00 16.60
ATOM   1342  CA  ILE A 184      18.094 -12.248  41.505  1.00 14.97
ATOM   1343  CB  ILE A 184      19.399 -12.402  40.716  1.00 20.49
ATOM   1344  CG1 ILE A 184      20.113 -11.053  40.565  1.00 22.48
ATOM   1345  CD1 ILE A 184      21.400 -11.102  39.778  1.00 24.88
ATOM   1346  CG2 ILE A 184      19.181 -13.048  39.360  1.00 15.87
ATOM   1347  C   ILE A 184      17.374 -13.570  41.711  1.00 19.06
ATOM   1348  O   ILE A 184      17.874 -14.392  42.481  1.00 22.71
ATOM   1349  N   ARG A 185      16.228 -13.724  41.066  1.00 17.97
ATOM   1350  CA  ARG A 185      15.419 -14.931  41.157  1.00 18.52
ATOM   1351  CB  ARG A 185      14.031 -14.667  41.733  1.00 15.90
```

FIGURE 231

```
ATOM   1352  CG  ARG A 185      14.102 -14.003  43.105  1.00 20.67
ATOM   1353  CD  ARG A 185      12.739 -13.580  43.574  1.00 23.49
ATOM   1354  NE  ARG A 185      12.620 -13.167  44.962  1.00 21.66
ATOM   1355  CZ  ARG A 185      12.709 -11.898  45.350  1.00 25.33
ATOM   1356  NH1 ARG A 185      12.934 -10.945  44.455  1.00 22.07
ATOM   1357  NH2 ARG A 185      12.581 -11.547  46.624  1.00 27.50
ATOM   1358  C   ARG A 185      15.285 -15.562  39.776  1.00 22.74
ATOM   1359  O   ARG A 185      15.369 -14.866  38.768  1.00 20.98
ATOM   1360  N   GLU A 186      15.113 -16.874  39.766  1.00 23.54
ATOM   1361  CA  GLU A 186      14.810 -17.562  38.512  1.00 27.25
ATOM   1362  CB  GLU A 186      15.910 -18.545  38.151  1.00 26.23
ATOM   1363  CG  GLU A 186      16.337 -18.573  36.696  1.00 29.12
ATOM   1364  CD  GLU A 186      17.731 -19.181  36.591  1.00 39.66
ATOM   1365  OE1 GLU A 186      18.272 -19.548  37.660  1.00 56.70
ATOM   1366  OE2 GLU A 186      18.262 -19.282  35.470  1.00 48.51
ATOM   1367  C   GLU A 186      13.463 -18.273  38.668  1.00 22.29
ATOM   1368  O   GLU A 186      13.280 -18.945  39.685  1.00 18.10
ATOM   1369  N   PHE A 187      12.578 -18.097  37.695  1.00 18.63
ATOM   1370  CA  PHE A 187      11.303 -18.785  37.643  1.00 16.57
ATOM   1371  CB  PHE A 187      10.106 -17.835  37.663  1.00 17.31
ATOM   1372  CG  PHE A 187      10.225 -16.820  38.799  1.00 28.29
ATOM   1373  CD1 PHE A 187      10.561 -15.507  38.521  1.00 35.36
ATOM   1374  CE1 PHE A 187      10.660 -14.575  39.550  1.00 25.40
ATOM   1375  CZ  PHE A 187      10.448 -14.987  40.849  1.00 21.30
ATOM   1376  CE2 PHE A 187      10.104 -16.285  41.143  1.00 18.72
ATOM   1377  CD2 PHE A 187       9.991 -17.207  40.113  1.00 25.67
ATOM   1378  C   PHE A 187      11.210 -19.663  36.381  1.00 26.48
ATOM   1379  O   PHE A 187      11.754 -19.296  35.347  1.00 22.46
ATOM   1380  N   LYS A 188      10.530 -20.777  36.559  1.00 27.77
ATOM   1381  CA  LYS A 188      10.122 -21.741  35.559  1.00 29.70
ATOM   1382  CB  LYS A 188      10.530 -23.158  35.948  1.00 39.93
ATOM   1383  CG  LYS A 188       9.420 -24.194  35.867  1.00 49.03
ATOM   1384  CD  LYS A 188       9.938 -25.587  36.210  1.00 53.96
ATOM   1385  CE  LYS A 188       8.835 -26.451  36.802  1.00 55.37
ATOM   1386  NZ  LYS A 188       8.767 -27.803  36.178  1.00 45.26
ATOM   1387  C   LYS A 188       8.603 -21.640  35.400  1.00 23.00
ATOM   1388  O   LYS A 188       7.888 -21.828  36.378  1.00 26.46
ATOM   1389  N   ILE A 189       8.132 -21.324  34.203  1.00 23.28
ATOM   1390  CA  ILE A 189       6.734 -21.106  33.898  1.00 25.13
ATOM   1391  CB  ILE A 189       6.489 -19.717  33.278  1.00 37.23
ATOM   1392  CG1 ILE A 189       6.899 -18.538  34.159  1.00 42.70
ATOM   1393  CD1 ILE A 189       6.097 -17.286  33.840  1.00 58.33
ATOM   1394  CG2 ILE A 189       5.029 -19.569  32.866  1.00 42.16
ATOM   1395  C   ILE A 189       6.228 -22.144  32.895  1.00 28.65
ATOM   1396  O   ILE A 189       6.897 -22.279  31.869  1.00 28.97
ATOM   1397  N   CYS A 190       5.129 -22.799  33.219  1.00 28.96
ATOM   1398  CA  CYS A 190       4.509 -23.828  32.396  1.00 35.44
ATOM   1399  CB  CYS A 190       4.306 -25.127  33.185  1.00 38.00
ATOM   1400  SG  CYS A 190       5.768 -25.627  34.128  1.00 68.71
ATOM   1401  C   CYS A 190       3.178 -23.331  31.836  1.00 40.13
ATOM   1402  O   CYS A 190       2.263 -22.985  32.586  1.00 32.30
ATOM   1403  N   GLY A 191       3.122 -23.308  30.510  1.00 37.25
```

FIGURE 232

```
ATOM   1404  CA   GLY A 191       2.017 -22.800  29.737  1.00 41.56
ATOM   1405  C    GLY A 191       1.357 -23.872  28.890  1.00 48.56
ATOM   1406  O    GLY A 191       1.577 -25.066  29.095  1.00 45.07
ATOM   1407  N    GLU A 192       0.549 -23.428  27.936  1.00 54.18
ATOM   1408  CA   GLU A 192      -0.200 -24.305  27.048  1.00 69.22
ATOM   1409  CB   GLU A 192      -1.434 -23.566  26.522  1.00 74.04
ATOM   1410  CG   GLU A 192      -2.761 -24.220  26.866  1.00 80.18
ATOM   1411  CD   GLU A 192      -3.579 -23.505  27.916  1.00 81.21
ATOM   1412  OE1  GLU A 192      -3.733 -24.045  29.033  1.00 64.52
ATOM   1413  OE2  GLU A 192      -4.092 -22.396  27.649  1.00 98.21
ATOM   1414  C    GLU A 192       0.670 -24.817  25.901  1.00 77.66
ATOM   1415  O    GLU A 192       0.153 -25.106  24.821  1.00 91.62
ATOM   1416  N    GLU A 193       1.963 -24.929  26.155  1.00 83.58
ATOM   1417  CA   GLU A 193       3.011 -25.361  25.250  1.00 93.54
ATOM   1418  CB   GLU A 193       2.953 -26.877  25.035  1.00 96.89
ATOM   1419  CG   GLU A 193       4.249 -27.604  25.348  1.00 98.33
ATOM   1420  CD   GLU A 193       4.432 -28.893  24.572  1.00 96.49
ATOM   1421  OE1  GLU A 193       3.518 -29.278  23.811  1.00 93.16
ATOM   1422  OE2  GLU A 193       5.494 -29.536  24.722  1.00 88.57
ATOM   1423  C    GLU A 193       2.918 -24.636  23.910  1.00 99.98
ATOM   1424  O    GLU A 193       2.701 -25.271  22.877  1.00108.24
ATOM   1425  N    GLN A 194       3.077 -23.317  23.931  1.00102.55
ATOM   1426  CA   GLN A 194       2.938 -22.499  22.728  1.00105.80
ATOM   1427  CB   GLN A 194       2.358 -21.129  23.088  1.00108.21
ATOM   1428  CG   GLN A 194       0.857 -21.133  23.330  1.00106.39
ATOM   1429  CD   GLN A 194       0.501 -21.310  24.793  1.00103.56
ATOM   1430  OE1  GLN A 194       1.330 -21.724  25.602  1.00 98.95
ATOM   1431  NE2  GLN A 194      -0.741 -20.994  25.143  1.00 99.79
ATOM   1432  C    GLN A 194       4.267 -22.341  21.999  1.00105.62
ATOM   1433  O    GLN A 194       4.998 -23.324  21.847  1.00116.12
ATOM   1434  N    LEU A 195       4.582 -21.125  21.553  1.00101.17
ATOM   1435  CA   LEU A 195       5.860 -20.881  20.883  1.00 95.89
ATOM   1436  CB   LEU A 195       6.034 -19.411  20.507  1.00 88.27
ATOM   1437  CG   LEU A 195       6.093 -19.063  19.016  1.00 76.59
ATOM   1438  CD1  LEU A 195       6.613 -17.648  18.786  1.00 35.43
ATOM   1439  CD2  LEU A 195       6.948 -20.068  18.254  1.00 62.06
ATOM   1440  C    LEU A 195       7.001 -21.372  21.776  1.00 95.74
ATOM   1441  O    LEU A 195       8.005 -21.890  21.287  1.00104.53
ATOM   1442  N    ASP A 196       6.831 -21.227  23.085  1.00 93.29
ATOM   1443  CA   ASP A 196       7.763 -21.771  24.069  1.00 89.45
ATOM   1444  CB   ASP A 196       8.450 -20.660  24.857  1.00 83.52
ATOM   1445  CG   ASP A 196       7.556 -19.912  25.817  1.00 71.43
ATOM   1446  OD1  ASP A 196       6.442 -19.474  25.450  1.00 46.66
ATOM   1447  OD2  ASP A 196       7.964 -19.724  26.984  1.00 45.20
ATOM   1448  C    ASP A 196       7.029 -22.731  25.002  1.00 89.72
ATOM   1449  O    ASP A 196       5.897 -22.456  25.409  1.00 82.68
ATOM   1450  N    ALA A 197       7.657 -23.857  25.335  1.00 93.55
ATOM   1451  CA   ALA A 197       7.020 -24.842  26.208  1.00 94.35
ATOM   1452  CB   ALA A 197       7.240 -26.255  25.691  1.00 80.84
ATOM   1453  C    ALA A 197       7.520 -24.718  27.644  1.00 94.80
ATOM   1454  O    ALA A 197       6.712 -24.641  28.574  1.00 92.09
ATOM   1455  N    HIS A 198       8.839 -24.700  27.838  1.00 92.53
```

FIGURE 233

```
ATOM   1456  CA   HIS A 198       9.370  -24.519  29.182  1.00  88.28
ATOM   1457  CB   HIS A 198      10.131  -25.748  29.703  1.00  89.87
ATOM   1458  CG   HIS A 198      10.859  -25.377  30.967  1.00  91.21
ATOM   1459  ND1  HIS A 198      10.190  -24.902  32.073  1.00  94.03
ATOM   1460  CE1  HIS A 198      11.057  -24.649  33.038  1.00  94.08
ATOM   1461  NE2  HIS A 198      12.268  -24.939  32.593  1.00  94.64
ATOM   1462  CD2  HIS A 198      12.167  -25.392  31.299  1.00  92.48
ATOM   1463  C    HIS A 198      10.316  -23.322  29.267  1.00  77.76
ATOM   1464  O    HIS A 198      11.500  -23.417  28.954  1.00  88.55
ATOM   1465  N    ARG A 199       9.769  -22.197  29.709  1.00  65.70
ATOM   1466  CA   ARG A 199      10.523  -20.957  29.782  1.00  47.47
ATOM   1467  CB   ARG A 199       9.612  -19.780  29.400  1.00  44.67
ATOM   1468  CG   ARG A 199      10.165  -18.453  29.889  1.00  53.42
ATOM   1469  CD   ARG A 199       9.994  -17.331  28.879  1.00  46.83
ATOM   1470  NE   ARG A 199       8.914  -17.624  27.941  1.00  46.19
ATOM   1471  CZ   ARG A 199       7.852  -16.844  27.777  1.00  51.98
ATOM   1472  NH1  ARG A 199       7.744  -15.728  28.495  1.00  21.30
ATOM   1473  NH2  ARG A 199       6.920  -17.196  26.901  1.00  32.81
ATOM   1474  C    ARG A 199      11.133  -20.718  31.161  1.00  32.26
ATOM   1475  O    ARG A 199      10.541  -21.045  32.190  1.00  25.30
ATOM   1476  N    LEU A 200      12.327  -20.133  31.142  1.00  25.66
ATOM   1477  CA   LEU A 200      13.010  -19.678  32.340  1.00  25.37
ATOM   1478  CB   LEU A 200      14.414  -20.256  32.468  1.00  37.98
ATOM   1479  CG   LEU A 200      14.511  -21.782  32.585  1.00  50.45
ATOM   1480  CD1  LEU A 200      15.956  -22.239  32.447  1.00  66.02
ATOM   1481  CD2  LEU A 200      13.911  -22.270  33.899  1.00  46.72
ATOM   1482  C    LEU A 200      13.058  -18.146  32.323  1.00  26.91
ATOM   1483  O    LEU A 200      13.521  -17.544  31.358  1.00  22.85
ATOM   1484  N    ILE A 201      12.549  -17.552  33.391  1.00  23.54
ATOM   1485  CA   ILE A 201      12.463  -16.102  33.528  1.00  16.69
ATOM   1486  CB   ILE A 201      11.023  -15.688  33.897  1.00  18.39
ATOM   1487  CG1  ILE A 201       9.983  -16.468  33.096  1.00  32.11
ATOM   1488  CD1  ILE A 201       9.613  -15.818  31.788  1.00  38.11
ATOM   1489  CG2  ILE A 201      10.814  -14.183  33.790  1.00  26.56
ATOM   1490  C    ILE A 201      13.394  -15.625  34.626  1.00  17.67
ATOM   1491  O    ILE A 201      13.380  -16.158  35.732  1.00  23.89
ATOM   1492  N    ARG A 202      14.218  -14.617  34.353  1.00  16.91
ATOM   1493  CA   ARG A 202      15.020  -14.076  35.443  1.00  13.64
ATOM   1494  CB   ARG A 202      16.465  -13.807  35.065  1.00  20.15
ATOM   1495  CG   ARG A 202      17.322  -15.053  34.928  1.00  33.93
ATOM   1496  CD   ARG A 202      18.698  -14.896  35.558  1.00  44.89
ATOM   1497  NE   ARG A 202      19.494  -16.112  35.342  1.00  57.70
ATOM   1498  CZ   ARG A 202      19.879  -16.510  34.134  1.00  61.66
ATOM   1499  NH1  ARG A 202      19.549  -15.798  33.063  1.00  39.90
ATOM   1500  NH2  ARG A 202      20.596  -17.615  33.984  1.00  69.32
ATOM   1501  C    ARG A 202      14.351  -12.781  35.905  1.00  20.61
ATOM   1502  O    ARG A 202      13.802  -12.033  35.094  1.00  14.26
ATOM   1503  N    HIS A 203      14.431  -12.604  37.207  1.00  18.91
ATOM   1504  CA   HIS A 203      13.836  -11.436  37.870  1.00  18.64
ATOM   1505  CB   HIS A 203      12.711  -11.896  38.765  1.00  13.88
ATOM   1506  CG   HIS A 203      11.813  -10.917  39.426  1.00  22.44
ATOM   1507  ND1  HIS A 203      12.104  -10.321  40.633  1.00  23.99
```

FIGURE 234

| ATOM | 1508 | CE1 | HIS | A | 203 | 11.127 | -9.510 | 40.981 | 1.00 | 23.53 |
| ATOM | 1509 | NE2 | HIS | A | 203 | 10.189 | -9.558 | 40.046 | 1.00 | 17.09 |
| ATOM | 1510 | CD2 | HIS | A | 203 | 10.604 | -10.429 | 39.065 | 1.00 | 18.86 |
| ATOM | 1511 | C | HIS | A | 203 | 14.961 | -10.731 | 38.626 | 1.00 | 17.56 |
| ATOM | 1512 | O | HIS | A | 203 | 15.649 | -11.341 | 39.451 | 1.00 | 18.34 |
| ATOM | 1513 | N | PHE | A | 204 | 15.146 | -9.457 | 38.314 | 1.00 | 15.90 |
| ATOM | 1514 | CA | PHE | A | 204 | 16.181 | -8.621 | 38.906 | 1.00 | 15.46 |
| ATOM | 1515 | CB | PHE | A | 204 | 17.037 | -7.984 | 37.819 | 1.00 | 15.83 |
| ATOM | 1516 | CG | PHE | A | 204 | 17.538 | -8.995 | 36.783 | 1.00 | 15.57 |
| ATOM | 1517 | CD1 | PHE | A | 204 | 16.751 | -9.377 | 35.717 | 1.00 | 12.76 |
| ATOM | 1518 | CE1 | PHE | A | 204 | 17.208 | -10.292 | 34.785 | 1.00 | 23.10 |
| ATOM | 1519 | CZ | PHE | A | 204 | 18.474 | -10.839 | 34.923 | 1.00 | 22.35 |
| ATOM | 1520 | CE2 | PHE | A | 204 | 19.277 | -10.461 | 35.989 | 1.00 | 21.53 |
| ATOM | 1521 | CD2 | PHE | A | 204 | 18.807 | -9.538 | 36.904 | 1.00 | 20.18 |
| ATOM | 1522 | C | PHE | A | 204 | 15.527 | -7.556 | 39.785 | 1.00 | 20.25 |
| ATOM | 1523 | O | PHE | A | 204 | 14.885 | -6.620 | 39.312 | 1.00 | 17.21 |
| ATOM | 1524 | N | HIS | A | 205 | 15.672 | -7.713 | 41.097 | 1.00 | 17.28 |
| ATOM | 1525 | CA | HIS | A | 205 | 14.949 | -6.855 | 42.035 | 1.00 | 14.35 |
| ATOM | 1526 | CB | HIS | A | 205 | 14.203 | -7.745 | 43.021 | 1.00 | 20.27 |
| ATOM | 1527 | CG | HIS | A | 205 | 13.221 | -7.056 | 43.900 | 1.00 | 17.93 |
| ATOM | 1528 | ND1 | HIS | A | 205 | 12.549 | -7.729 | 44.905 | 1.00 | 19.18 |
| ATOM | 1529 | CE1 | HIS | A | 205 | 11.738 | -6.874 | 45.516 | 1.00 | 22.04 |
| ATOM | 1530 | NE2 | HIS | A | 205 | 11.866 | -5.681 | 44.947 | 1.00 | 17.85 |
| ATOM | 1531 | CD2 | HIS | A | 205 | 12.788 | -5.771 | 43.928 | 1.00 | 12.88 |
| ATOM | 1532 | C | HIS | A | 205 | 15.896 | -5.931 | 42.782 | 1.00 | 17.06 |
| ATOM | 1533 | O | HIS | A | 205 | 16.635 | -6.400 | 43.658 | 1.00 | 21.06 |
| ATOM | 1534 | N | TYR | A | 206 | 15.883 | -4.660 | 42.429 | 1.00 | 13.61 |
| ATOM | 1535 | CA | TYR | A | 206 | 16.715 | -3.648 | 43.082 | 1.00 | 11.14 |
| ATOM | 1536 | CB | TYR | A | 206 | 17.008 | -2.490 | 42.141 | 1.00 | 12.43 |
| ATOM | 1537 | CG | TYR | A | 206 | 18.011 | -1.486 | 42.668 | 1.00 | 17.70 |
| ATOM | 1538 | CD1 | TYR | A | 206 | 19.376 | -1.745 | 42.568 | 1.00 | 14.03 |
| ATOM | 1539 | CE1 | TYR | A | 206 | 20.334 | -0.866 | 43.027 | 1.00 | 20.29 |
| ATOM | 1540 | CZ | TYR | A | 206 | 19.892 | 0.318 | 43.602 | 1.00 | 22.75 |
| ATOM | 1541 | OH | TYR | A | 206 | 20.839 | 1.200 | 44.070 | 1.00 | 25.15 |
| ATOM | 1542 | CE2 | TYR | A | 206 | 18.553 | 0.609 | 43.718 | 1.00 | 19.11 |
| ATOM | 1543 | CD2 | TYR | A | 206 | 17.596 | -0.287 | 43.249 | 1.00 | 18.90 |
| ATOM | 1544 | C | TYR | A | 206 | 15.953 | -3.189 | 44.315 | 1.00 | 15.80 |
| ATOM | 1545 | O | TYR | A | 206 | 14.828 | -2.701 | 44.188 | 1.00 | 19.33 |
| ATOM | 1546 | N | THR | A | 207 | 16.503 | -3.371 | 45.520 | 1.00 | 16.37 |
| ATOM | 1547 | CA | THR | A | 207 | 15.652 | -3.191 | 46.691 | 1.00 | 18.59 |
| ATOM | 1548 | CB | THR | A | 207 | 15.789 | -4.385 | 47.669 | 1.00 | 18.47 |
| ATOM | 1549 | OG1 | THR | A | 207 | 17.175 | -4.639 | 47.895 | 1.00 | 23.23 |
| ATOM | 1550 | CG2 | THR | A | 207 | 15.217 | -5.655 | 47.056 | 1.00 | 23.19 |
| ATOM | 1551 | C | THR | A | 207 | 15.955 | -1.923 | 47.481 | 1.00 | 23.83 |
| ATOM | 1552 | O | THR | A | 207 | 15.371 | -1.745 | 48.556 | 1.00 | 24.21 |
| ATOM | 1553 | N | VAL | A | 208 | 16.848 | -1.060 | 47.004 | 1.00 | 22.88 |
| ATOM | 1554 | CA | VAL | A | 208 | 17.156 | 0.123 | 47.814 | 1.00 | 23.02 |
| ATOM | 1555 | CB | VAL | A | 208 | 18.604 | 0.059 | 48.325 | 1.00 | 22.02 |
| ATOM | 1556 | CG1 | VAL | A | 208 | 18.747 | -1.128 | 49.276 | 1.00 | 31.63 |
| ATOM | 1557 | CG2 | VAL | A | 208 | 19.599 | -0.045 | 47.185 | 1.00 | 23.30 |
| ATOM | 1558 | C | VAL | A | 208 | 16.951 | 1.425 | 47.059 | 1.00 | 16.29 |
| ATOM | 1559 | O | VAL | A | 208 | 17.782 | 2.331 | 47.160 | 1.00 | 26.60 |

FIGURE 235

```
ATOM   1560  N    TRP A 209      15.861   1.525  46.321  1.00 14.67
ATOM   1561  CA   TRP A 209      15.522   2.734  45.570  1.00 21.23
ATOM   1562  CB   TRP A 209      15.364   2.460  44.075  1.00 23.37
ATOM   1563  CG   TRP A 209      15.364   3.656  43.171  1.00 17.61
ATOM   1564  CD1  TRP A 209      15.121   4.978  43.419  1.00 16.97
ATOM   1565  NE1  TRP A 209      15.236   5.726  42.271  1.00 24.39
ATOM   1566  CE2  TRP A 209      15.560   4.876  41.238  1.00 22.16
ATOM   1567  CD2  TRP A 209      15.649   3.568  41.766  1.00 16.31
ATOM   1568  CE3  TRP A 209      15.969   2.508  40.918  1.00 20.86
ATOM   1569  CZ3  TRP A 209      16.190   2.771  39.578  1.00 24.91
ATOM   1570  CH2  TRP A 209      16.095   4.077  39.075  1.00 20.45
ATOM   1571  CZ2  TRP A 209      15.785   5.131  39.888  1.00 19.42
ATOM   1572  C    TRP A 209      14.212   3.314  46.101  1.00 23.30
ATOM   1573  O    TRP A 209      13.164   2.827  45.672  1.00 25.49
ATOM   1574  N    PRO A 210      14.299   4.324  46.963  1.00 23.84
ATOM   1575  CA   PRO A 210      13.107   4.901  47.582  1.00 18.86
ATOM   1576  CB   PRO A 210      13.655   5.980  48.508  1.00 26.38
ATOM   1577  CG   PRO A 210      15.115   5.736  48.620  1.00 29.41
ATOM   1578  CD   PRO A 210      15.540   4.996  47.383  1.00 23.17
ATOM   1579  C    PRO A 210      12.199   5.553  46.536  1.00 24.85
ATOM   1580  O    PRO A 210      12.696   6.304  45.689  1.00 25.87
ATOM   1581  N    ASP A 211      10.901   5.271  46.601  1.00 19.16
ATOM   1582  CA   ASP A 211       9.942   5.886  45.698  1.00 23.36
ATOM   1583  CB   ASP A 211       8.499   5.590  46.126  1.00 25.37
ATOM   1584  CG   ASP A 211       7.576   5.865  44.943  1.00 24.78
ATOM   1585  OD1  ASP A 211       6.379   5.571  45.094  1.00 26.65
ATOM   1586  OD2  ASP A 211       8.078   6.348  43.899  1.00 23.48
ATOM   1587  C    ASP A 211      10.124   7.395  45.610  1.00 29.53
ATOM   1588  O    ASP A 211      10.525   8.061  46.573  1.00 32.57
ATOM   1589  N    HIS A 212       9.888   7.977  44.442  1.00 28.91
ATOM   1590  CA   HIS A 212      10.051   9.398  44.175  1.00 28.03
ATOM   1591  CB   HIS A 212       9.080  10.227  45.032  1.00 21.33
ATOM   1592  CG   HIS A 212       7.681   9.700  44.958  1.00 26.06
ATOM   1593  ND1  HIS A 212       6.939   9.760  43.801  1.00 23.57
ATOM   1594  CE1  HIS A 212       5.754   9.219  44.023  1.00 25.96
ATOM   1595  NE2  HIS A 212       5.703   8.814  45.279  1.00 26.25
ATOM   1596  CD2  HIS A 212       6.902   9.100  45.884  1.00 27.02
ATOM   1597  C    HIS A 212      11.460   9.932  44.425  1.00 34.91
ATOM   1598  O    HIS A 212      11.653  11.152  44.346  1.00 42.93
ATOM   1599  N    GLY A 213      12.418   9.071  44.709  1.00 25.41
ATOM   1600  CA   GLY A 213      13.772   9.392  45.079  1.00 25.24
ATOM   1601  C    GLY A 213      14.771   8.747  44.143  1.00 27.01
ATOM   1602  O    GLY A 213      14.471   8.336  43.027  1.00 22.02
ATOM   1603  N    VAL A 214      16.012   8.697  44.602  1.00 26.65
ATOM   1604  CA   VAL A 214      17.102   8.144  43.810  1.00 31.35
ATOM   1605  CB   VAL A 214      17.945   9.250  43.163  1.00 35.53
ATOM   1606  CG1  VAL A 214      17.091  10.182  42.307  1.00 27.84
ATOM   1607  CG2  VAL A 214      18.668  10.055  44.234  1.00 40.38
ATOM   1608  C    VAL A 214      17.953   7.295  44.742  1.00 28.56
ATOM   1609  O    VAL A 214      17.887   7.492  45.959  1.00 28.51
ATOM   1610  N    PRO A 215      18.720   6.349  44.228  1.00 23.57
ATOM   1611  CA   PRO A 215      19.542   5.511  45.116  1.00 29.45
```

FIGURE 236

```
ATOM   1612  CB   PRO A 215      20.192   4.526  44.146  1.00 29.52
ATOM   1613  CG   PRO A 215      19.235   4.515  42.984  1.00 28.93
ATOM   1614  CD   PRO A 215      18.865   5.974  42.820  1.00 23.13
ATOM   1615  C    PRO A 215      20.601   6.338  45.842  1.00 35.63
ATOM   1616  O    PRO A 215      20.990   7.415  45.396  1.00 30.87
ATOM   1617  N    GLU A 216      21.073   5.828  46.972  1.00 35.49
ATOM   1618  CA   GLU A 216      22.063   6.538  47.780  1.00 35.03
ATOM   1619  CB   GLU A 216      22.254   5.768  49.090  1.00 36.48
ATOM   1620  CG   GLU A 216      23.661   5.715  49.649  1.00 52.93
ATOM   1621  CD   GLU A 216      23.844   4.606  50.672  1.00 63.63
ATOM   1622  OE1  GLU A 216      24.879   3.902  50.618  1.00 59.31
ATOM   1623  OE2  GLU A 216      22.952   4.437  51.532  1.00 69.52
ATOM   1624  C    GLU A 216      23.368   6.751  47.032  1.00 33.10
ATOM   1625  O    GLU A 216      24.121   7.675  47.370  1.00 39.10
ATOM   1626  N    THR A 217      23.711   5.964  46.014  1.00 32.88
ATOM   1627  CA   THR A 217      24.924   6.230  45.242  1.00 34.43
ATOM   1628  CB   THR A 217      26.135   5.360  45.635  1.00 41.56
ATOM   1629  OG1  THR A 217      25.910   4.010  45.183  1.00 31.22
ATOM   1630  CG2  THR A 217      26.341   5.329  47.138  1.00 44.45
ATOM   1631  C    THR A 217      24.711   5.979  43.748  1.00 30.56
ATOM   1632  O    THR A 217      23.787   5.258  43.382  1.00 25.88
ATOM   1633  N    THR A 218      25.578   6.530  42.901  1.00 26.73
ATOM   1634  CA   THR A 218      25.494   6.239  41.469  1.00 30.02
ATOM   1635  CB   THR A 218      26.251   7.270  40.615  1.00 29.46
ATOM   1636  OG1  THR A 218      27.594   7.382  41.105  1.00 27.79
ATOM   1637  CG2  THR A 218      25.616   8.644  40.740  1.00 30.31
ATOM   1638  C    THR A 218      26.045   4.846  41.171  1.00 27.66
ATOM   1639  O    THR A 218      25.499   4.105  40.348  1.00 23.92
ATOM   1640  N    GLN A 219      27.123   4.478  41.848  1.00 26.54
ATOM   1641  CA   GLN A 219      27.764   3.182  41.661  1.00 25.35
ATOM   1642  CB   GLN A 219      28.845   2.982  42.729  1.00 35.12
ATOM   1643  CG   GLN A 219      30.230   3.445  42.313  1.00 50.76
ATOM   1644  CD   GLN A 219      31.311   2.472  42.754  1.00 70.22
ATOM   1645  OE1  GLN A 219      31.350   1.331  42.286  1.00 92.23
ATOM   1646  NE2  GLN A 219      32.187   2.921  43.650  1.00 63.32
ATOM   1647  C    GLN A 219      26.783   2.013  41.730  1.00 26.20
ATOM   1648  O    GLN A 219      26.802   1.112  40.897  1.00 29.61
ATOM   1649  N    SER A 220      25.929   2.027  42.746  1.00 26.43
ATOM   1650  CA   SER A 220      24.978   0.956  42.997  1.00 31.59
ATOM   1651  CB   SER A 220      24.116   1.337  44.205  1.00 38.90
ATOM   1652  OG   SER A 220      23.043   0.429  44.379  1.00 33.12
ATOM   1653  C    SER A 220      24.097   0.682  41.788  1.00 31.15
ATOM   1654  O    SER A 220      23.995  -0.428  41.264  1.00 22.82
ATOM   1655  N    LEU A 221      23.421   1.736  41.316  1.00 26.37
ATOM   1656  CA   LEU A 221      22.527   1.511  40.181  1.00 22.50
ATOM   1657  CB   LEU A 221      21.564   2.696  40.002  1.00 25.48
ATOM   1658  CG   LEU A 221      20.346   2.374  39.125  1.00 27.75
ATOM   1659  CD1  LEU A 221      19.596   1.169  39.683  1.00 24.04
ATOM   1660  CD2  LEU A 221      19.428   3.572  39.007  1.00 26.75
ATOM   1661  C    LEU A 221      23.311   1.255  38.907  1.00 16.37
ATOM   1662  O    LEU A 221      22.870   0.452  38.078  1.00 25.76
ATOM   1663  N    ILE A 222      24.462   1.917  38.728  1.00 17.23
```

FIGURE 237

```
ATOM   1664  CA   ILE A 222      25.230   1.662  37.507  1.00 21.02
ATOM   1665  CB   ILE A 222      26.510   2.506  37.436  1.00 23.08
ATOM   1666  CG1  ILE A 222      26.245   3.966  37.060  1.00 23.12
ATOM   1667  CD1  ILE A 222      27.289   4.943  37.546  1.00 25.12
ATOM   1668  CG2  ILE A 222      27.498   1.864  36.473  1.00 26.15
ATOM   1669  C    ILE A 222      25.573   0.179  37.422  1.00 20.38
ATOM   1670  O    ILE A 222      25.462  -0.473  36.385  1.00 18.34
ATOM   1671  N    GLN A 223      26.005  -0.362  38.558  1.00 24.24
ATOM   1672  CA   GLN A 223      26.401  -1.763  38.598  1.00 23.96
ATOM   1673  CB   GLN A 223      27.058  -2.162  39.919  1.00 26.95
ATOM   1674  CG   GLN A 223      28.327  -1.426  40.293  1.00 37.08
ATOM   1675  CD   GLN A 223      29.119  -0.836  39.150  1.00 56.97
ATOM   1676  OE1  GLN A 223      29.337  -1.473  38.116  1.00 84.38
ATOM   1677  NE2  GLN A 223      29.581   0.404  39.315  1.00 54.63
ATOM   1678  C    GLN A 223      25.163  -2.627  38.391  1.00 24.09
ATOM   1679  O    GLN A 223      25.262  -3.654  37.737  1.00 19.87
ATOM   1680  N    PHE A 224      24.017  -2.212  38.943  1.00 20.92
ATOM   1681  CA   PHE A 224      22.831  -3.055  38.717  1.00 22.52
ATOM   1682  CB   PHE A 224      21.658  -2.527  39.529  1.00 21.20
ATOM   1683  CG   PHE A 224      20.330  -3.222  39.302  1.00 23.79
ATOM   1684  CD1  PHE A 224      20.105  -4.505  39.792  1.00 21.63
ATOM   1685  CE1  PHE A 224      18.881  -5.123  39.606  1.00 15.71
ATOM   1686  CZ   PHE A 224      17.867  -4.481  38.919  1.00 16.76
ATOM   1687  CE2  PHE A 224      18.074  -3.204  38.415  1.00 13.56
ATOM   1688  CD2  PHE A 224      19.306  -2.589  38.609  1.00 16.88
ATOM   1689  C    PHE A 224      22.477  -3.104  37.240  1.00 26.00
ATOM   1690  O    PHE A 224      22.266  -4.142  36.617  1.00 17.57
ATOM   1691  N    VAL A 225      22.406  -1.916  36.636  1.00 17.86
ATOM   1692  CA   VAL A 225      22.097  -1.855  35.214  1.00 14.81
ATOM   1693  CB   VAL A 225      22.100  -0.383  34.764  1.00 15.04
ATOM   1694  CG1  VAL A 225      22.090  -0.273  33.250  1.00 17.94
ATOM   1695  CG2  VAL A 225      20.903   0.328  35.391  1.00 19.94
ATOM   1696  C    VAL A 225      23.068  -2.668  34.378  1.00 17.19
ATOM   1697  O    VAL A 225      22.674  -3.427  33.481  1.00 19.92
ATOM   1698  N    ARG A 226      24.371  -2.550  34.632  1.00 18.63
ATOM   1699  CA   ARG A 226      25.295  -3.342  33.809  1.00 24.02
ATOM   1700  CB   ARG A 226      26.735  -2.935  34.122  1.00 26.46
ATOM   1701  CG   ARG A 226      27.107  -1.562  33.582  1.00 23.91
ATOM   1702  CD   ARG A 226      28.568  -1.275  33.905  1.00 30.68
ATOM   1703  NE   ARG A 226      28.977   0.040  33.425  1.00 37.38
ATOM   1704  CZ   ARG A 226      29.848   0.828  34.046  1.00 45.40
ATOM   1705  NH1  ARG A 226      30.416   0.454  35.185  1.00 41.82
ATOM   1706  NH2  ARG A 226      30.154   2.009  33.522  1.00 45.68
ATOM   1707  C    ARG A 226      25.094  -4.836  34.022  1.00 22.36
ATOM   1708  O    ARG A 226      25.220  -5.649  33.106  1.00 24.97
ATOM   1709  N    THR A 227      24.762  -5.258  35.243  1.00 21.54
ATOM   1710  CA   THR A 227      24.427  -6.660  35.455  1.00 21.82
ATOM   1711  CB   THR A 227      24.206  -6.945  36.957  1.00 29.96
ATOM   1712  OG1  THR A 227      25.358  -6.463  37.648  1.00 28.79
ATOM   1713  CG2  THR A 227      24.081  -8.437  37.182  1.00 29.12
ATOM   1714  C    THR A 227      23.182  -7.107  34.713  1.00 19.03
ATOM   1715  O    THR A 227      23.188  -8.158  34.074  1.00 26.29
```

FIGURE 238

```
ATOM   1716  N    VAL A 228      22.097  -6.336  34.778  1.00 17.49
ATOM   1717  CA   VAL A 228      20.926  -6.679  33.967  1.00 17.38
ATOM   1718  CB   VAL A 228      19.784  -5.686  34.259  1.00 18.18
ATOM   1719  CG1  VAL A 228      18.550  -5.978  33.411  1.00 19.51
ATOM   1720  CG2  VAL A 228      19.437  -5.770  35.741  1.00 15.24
ATOM   1721  C    VAL A 228      21.238  -6.711  32.477  1.00 17.43
ATOM   1722  O    VAL A 228      20.849  -7.647  31.766  1.00 19.11
ATOM   1723  N    ARG A 229      21.943  -5.703  31.972  1.00 17.01
ATOM   1724  CA   ARG A 229      22.204  -5.651  30.527  1.00 21.03
ATOM   1725  CB   ARG A 229      22.833  -4.291  30.221  1.00 17.71
ATOM   1726  CG   ARG A 229      23.465  -4.129  28.873  1.00 18.28
ATOM   1727  CD   ARG A 229      22.589  -3.886  27.687  1.00 26.78
ATOM   1728  NE   ARG A 229      21.245  -3.355  27.849  1.00 22.41
ATOM   1729  CZ   ARG A 229      20.263  -3.671  27.008  1.00 26.65
ATOM   1730  NH1  ARG A 229      20.514  -4.494  25.992  1.00 28.43
ATOM   1731  NH2  ARG A 229      19.031  -3.197  27.144  1.00 22.64
ATOM   1732  C    ARG A 229      23.052  -6.833  30.076  1.00 26.78
ATOM   1733  O    ARG A 229      22.914  -7.389  28.974  1.00 22.93
ATOM   1734  N    ASP A 230      23.970  -7.282  30.931  1.00 22.22
ATOM   1735  CA   ASP A 230      24.761  -8.474  30.615  1.00 19.37
ATOM   1736  CB   ASP A 230      25.720  -8.746  31.770  1.00 26.22
ATOM   1737  CG   ASP A 230      26.764  -9.808  31.496  1.00 37.14
ATOM   1738  OD1  ASP A 230      27.772  -9.830  32.234  1.00 43.30
ATOM   1739  OD2  ASP A 230      26.579 -10.609  30.558  1.00 48.34
ATOM   1740  C    ASP A 230      23.856  -9.667  30.369  1.00 24.85
ATOM   1741  O    ASP A 230      24.007 -10.389  29.383  1.00 27.24
ATOM   1742  N    TYR A 231      22.897  -9.868  31.276  1.00 24.39
ATOM   1743  CA   TYR A 231      21.924 -10.943  31.156  1.00 17.89
ATOM   1744  CB   TYR A 231      21.011 -10.999  32.384  1.00 18.72
ATOM   1745  CG   TYR A 231      21.604 -11.752  33.540  1.00 21.03
ATOM   1746  CD1  TYR A 231      22.218 -11.040  34.559  1.00 27.60
ATOM   1747  CE1  TYR A 231      22.770 -11.713  35.627  1.00 32.43
ATOM   1748  CZ   TYR A 231      22.716 -13.085  35.692  1.00 25.45
ATOM   1749  OH   TYR A 231      23.283 -13.694  36.789  1.00 36.71
ATOM   1750  CE2  TYR A 231      22.116 -13.815  34.698  1.00 23.54
ATOM   1751  CD2  TYR A 231      21.561 -13.136  33.622  1.00 30.94
ATOM   1752  C    TYR A 231      21.006 -10.771  29.954  1.00 21.66
ATOM   1753  O    TYR A 231      20.659 -11.726  29.269  1.00 23.21
ATOM   1754  N    ILE A 232      20.581  -9.527  29.718  1.00 16.63
ATOM   1755  CA   ILE A 232      19.785  -9.280  28.517  1.00 19.85
ATOM   1756  CB   ILE A 232      19.349  -7.808  28.395  1.00 18.50
ATOM   1757  CG1  ILE A 232      18.391  -7.370  29.499  1.00 22.29
ATOM   1758  CD1  ILE A 232      18.084  -5.901  29.616  1.00 17.14
ATOM   1759  CG2  ILE A 232      18.773  -7.570  26.999  1.00 22.60
ATOM   1760  C    ILE A 232      20.574  -9.652  27.262  1.00 21.88
ATOM   1761  O    ILE A 232      20.066 -10.308  26.358  1.00 24.41
ATOM   1762  N    ASN A 233      21.840  -9.242  27.197  1.00 23.34
ATOM   1763  CA   ASN A 233      22.592  -9.555  25.975  1.00 30.61
ATOM   1764  CB   ASN A 233      23.963  -8.883  25.996  1.00 27.03
ATOM   1765  CG   ASN A 233      23.869  -7.379  25.800  1.00 29.17
ATOM   1766  OD1  ASN A 233      22.902  -6.849  25.248  1.00 36.95
ATOM   1767  ND2  ASN A 233      24.882  -6.648  26.251  1.00 36.00
```

FIGURE 239

```
ATOM   1768  C   ASN A 233      22.705 -11.062  25.808  1.00 31.90
ATOM   1769  O   ASN A 233      22.823 -11.595  24.711  1.00 37.58
ATOM   1770  N   ARG A 234      22.659 -11.778  26.927  1.00 29.26
ATOM   1771  CA  ARG A 234      22.766 -13.225  26.874  1.00 31.78
ATOM   1772  CB  ARG A 234      23.465 -13.746  28.129  1.00 38.80
ATOM   1773  CG  ARG A 234      24.878 -13.216  28.320  1.00 43.23
ATOM   1774  CD  ARG A 234      25.391 -13.632  29.692  1.00 51.48
ATOM   1775  NE  ARG A 234      26.840 -13.511  29.800  1.00 58.62
ATOM   1776  CZ  ARG A 234      27.670 -14.516  30.055  1.00 57.56
ATOM   1777  NH1 ARG A 234      27.201 -15.746  30.232  1.00 60.00
ATOM   1778  NH2 ARG A 234      28.975 -14.277  30.128  1.00 30.80
ATOM   1779  C   ARG A 234      21.407 -13.890  26.747  1.00 34.88
ATOM   1780  O   ARG A 234      21.304 -15.085  27.031  1.00 32.66
ATOM   1781  N   SER A 235      20.351 -13.186  26.337  1.00 24.05
ATOM   1782  CA  SER A 235      19.065 -13.884  26.273  1.00 27.03
ATOM   1783  CB  SER A 235      17.992 -13.249  27.156  1.00 26.67
ATOM   1784  OG  SER A 235      18.396 -13.237  28.520  1.00 34.69
ATOM   1785  C   SER A 235      18.578 -13.933  24.827  1.00 31.92
ATOM   1786  O   SER A 235      17.770 -13.103  24.425  1.00 28.81
ATOM   1787  N   PRO A 236      19.099 -14.914  24.105  1.00 37.48
ATOM   1788  CA  PRO A 236      18.765 -15.087  22.693  1.00 39.12
ATOM   1789  CB  PRO A 236      19.584 -16.312  22.269  1.00 46.32
ATOM   1790  CG  PRO A 236      19.866 -17.038  23.546  1.00 44.02
ATOM   1791  CD  PRO A 236      20.033 -15.957  24.580  1.00 42.48
ATOM   1792  C   PRO A 236      17.279 -15.378  22.517  1.00 34.00
ATOM   1793  O   PRO A 236      16.696 -16.221  23.207  1.00 43.89
ATOM   1794  N   GLY A 237      16.668 -14.660  21.577  1.00 27.25
ATOM   1795  CA  GLY A 237      15.280 -14.912  21.249  1.00 25.75
ATOM   1796  C   GLY A 237      14.296 -14.183  22.132  1.00 21.94
ATOM   1797  O   GLY A 237      13.109 -14.257  21.848  1.00 21.04
ATOM   1798  N   ALA A 238      14.739 -13.494  23.181  1.00 22.86
ATOM   1799  CA  ALA A 238      13.836 -12.838  24.112  1.00 20.89
ATOM   1800  CB  ALA A 238      14.669 -12.130  25.194  1.00 22.60
ATOM   1801  C   ALA A 238      12.923 -11.807  23.470  1.00 20.68
ATOM   1802  O   ALA A 238      13.361 -11.132  22.539  1.00 27.83
ATOM   1803  N   GLY A 239      11.712 -11.670  23.986  1.00 18.60
ATOM   1804  CA  GLY A 239      10.829 -10.549  23.700  1.00 18.19
ATOM   1805  C   GLY A 239      11.346  -9.351  24.497  1.00 15.46
ATOM   1806  O   GLY A 239      12.521  -9.353  24.887  1.00 18.43
ATOM   1807  N   PRO A 240      10.484  -8.378  24.743  1.00 17.13
ATOM   1808  CA  PRO A 240      10.889  -7.184  25.496  1.00 15.73
ATOM   1809  CB  PRO A 240       9.626  -6.323  25.550  1.00 18.54
ATOM   1810  CG  PRO A 240       8.740  -6.868  24.479  1.00 25.69
ATOM   1811  CD  PRO A 240       9.073  -8.329  24.350  1.00 13.87
ATOM   1812  C   PRO A 240      11.306  -7.518  26.923  1.00 14.71
ATOM   1813  O   PRO A 240      10.867  -8.502  27.508  1.00 14.52
ATOM   1814  N   THR A 241      12.179  -6.683  27.461  1.00 13.92
ATOM   1815  CA  THR A 241      12.533  -6.674  28.869  1.00 14.60
ATOM   1816  CB  THR A 241      13.890  -5.989  29.061  1.00 14.17
ATOM   1817  OG1 THR A 241      14.893  -6.769  28.389  1.00 18.17
ATOM   1818  CG2 THR A 241      14.291  -5.941  30.536  1.00 17.28
ATOM   1819  C   THR A 241      11.441  -5.931  29.639  1.00 16.58
```

FIGURE 240

| | | | | | | | | | |
|---|---|---|---|---|---|---|---|---|---|
|ATOM|1820|O|THR|A|241|11.124|-4.784|29.305|1.00 13.03|
|ATOM|1821|N|VAL|A|242|10.856|-6.571|30.646|1.00 12.88|
|ATOM|1822|CA|VAL|A|242|9.842|-5.913|31.464|1.00 9.81|
|ATOM|1823|CB|VAL|A|242|8.866|-6.900|32.116|1.00 14.04|
|ATOM|1824|CG1|VAL|A|242|8.019|-6.223|33.179|1.00 16.00|
|ATOM|1825|CG2|VAL|A|242|7.942|-7.536|31.081|1.00 15.42|
|ATOM|1826|C|VAL|A|242|10.564|-5.128|32.554|1.00 12.01|
|ATOM|1827|O|VAL|A|242|11.501|-5.623|33.171|1.00 15.03|
|ATOM|1828|N|VAL|A|243|10.107|-3.893|32.785|1.00 11.17|
|ATOM|1829|CA|VAL|A|243|10.668|-3.065|33.838|1.00 9.13|
|ATOM|1830|CB|VAL|A|243|11.575|-1.931|33.352|1.00 15.38|
|ATOM|1831|CG1|VAL|A|243|12.196|-1.213|34.555|1.00 10.88|
|ATOM|1832|CG2|VAL|A|243|12.666|-2.463|32.442|1.00 12.02|
|ATOM|1833|C|VAL|A|243|9.482|-2.452|34.574|1.00 12.00|
|ATOM|1834|O|VAL|A|243|8.576|-1.930|33.932|1.00 9.88|
|ATOM|1835|N|HIS|A|244|9.484|-2.539|35.899|1.00 11.09|
|ATOM|1836|CA|HIS|A|244|8.412|-1.896|36.618|1.00 8.29|
|ATOM|1837|CB|HIS|A|244|7.205|-2.846|36.762|1.00 7.72|
|ATOM|1838|CG|HIS|A|244|7.327|-3.897|37.824|1.00 15.86|
|ATOM|1839|ND1|HIS|A|244|7.058|-3.666|39.160|1.00 14.99|
|ATOM|1840|CE1|HIS|A|244|7.236|-4.775|39.871|1.00 13.71|
|ATOM|1841|NE2|HIS|A|244|7.617|-5.753|39.039|1.00 16.24|
|ATOM|1842|CD2|HIS|A|244|7.666|-5.215|37.766|1.00 15.19|
|ATOM|1843|C|HIS|A|244|8.890|-1.434|37.999|1.00 11.45|
|ATOM|1844|O|HIS|A|244|9.917|-1.896|38.509|1.00 12.61|
|ATOM|1845|N|CYS|A|245|8.085|-0.528|38.539|1.00 18.46|
|ATOM|1846|CA|CYS|A|245|8.250|-0.016|39.911|1.00 14.56|
|ATOM|1847|CB|CYS|A|245|9.019|1.304|39.865|1.00 10.22|
|ATOM|1848|SG|CYS|A|245|8.326|2.556|38.746|1.00 14.87|
|ATOM|1849|C|CYS|A|245|6.876|0.022|40.549|1.00 15.86|
|ATOM|1850|O|CYS|A|245|6.192|-1.015|40.537|1.00 13.86|
|ATOM|1851|N|SER|A|246|6.376|1.128|41.113|1.00 9.56|
|ATOM|1852|CA|SER|A|246|4.987|1.073|41.577|1.00 9.76|
|ATOM|1853|CB|SER|A|246|4.844|1.783|42.926|1.00 7.75|
|ATOM|1854|OG|SER|A|246|3.495|1.651|43.398|1.00 9.89|
|ATOM|1855|C|SER|A|246|4.052|1.626|40.505|1.00 9.69|
|ATOM|1856|O|SER|A|246|3.099|0.947|40.088|1.00 10.94|
|ATOM|1857|N|ALA|A|247|4.265|2.853|40.014|1.00 15.37|
|ATOM|1858|CA|ALA|A|247|3.443|3.430|38.976|1.00 12.59|
|ATOM|1859|CB|ALA|A|247|3.411|4.964|38.966|1.00 11.87|
|ATOM|1860|C|ALA|A|247|3.960|3.046|37.583|1.00 10.49|
|ATOM|1861|O|ALA|A|247|3.242|3.172|36.600|1.00 15.72|
|ATOM|1862|N|GLY|A|248|5.216|2.627|37.542|1.00 9.25|
|ATOM|1863|CA|GLY|A|248|5.870|2.318|36.284|1.00 13.53|
|ATOM|1864|C|GLY|A|248|6.210|3.615|35.570|1.00 20.73|
|ATOM|1865|O|GLY|A|248|6.104|3.656|34.349|1.00 15.35|
|ATOM|1866|N|VAL|A|249|6.616|4.653|36.301|1.00 14.47|
|ATOM|1867|CA|VAL|A|249|7.031|5.853|35.561|1.00 23.41|
|ATOM|1868|CB|VAL|A|249|5.942|6.948|35.534|1.00 27.80|
|ATOM|1869|CG1|VAL|A|249|4.675|6.441|34.850|1.00 10.99|
|ATOM|1870|CG2|VAL|A|249|5.615|7.470|36.930|1.00 21.36|
|ATOM|1871|C|VAL|A|249|8.342|6.437|36.071|1.00 18.78|

FIGURE 241

| | | | | | | | | |
|---|---|---|---|---|---|---|---|---|
| ATOM | 1872 | O | VAL | A | 249 | 9.252 | 6.752 | 35.288 | 1.00 | 16.76 |
| ATOM | 1873 | N | GLY | A | 250 | 8.505 | 6.625 | 37.372 | 1.00 | 17.57 |
| ATOM | 1874 | CA | GLY | A | 250 | 9.695 | 7.363 | 37.801 | 1.00 | 15.55 |
| ATOM | 1875 | C | GLY | A | 250 | 10.939 | 6.526 | 37.860 | 1.00 | 11.84 |
| ATOM | 1876 | O | GLY | A | 250 | 11.945 | 6.720 | 37.165 | 1.00 | 17.28 |
| ATOM | 1877 | N | ARG | A | 251 | 10.945 | 5.519 | 38.740 | 1.00 | 11.43 |
| ATOM | 1878 | CA | ARG | A | 251 | 12.141 | 4.687 | 38.866 | 1.00 | 10.27 |
| ATOM | 1879 | CB | ARG | A | 251 | 12.050 | 3.844 | 40.148 | 1.00 | 14.41 |
| ATOM | 1880 | CG | ARG | A | 251 | 12.082 | 4.786 | 41.366 | 1.00 | 15.59 |
| ATOM | 1881 | CD | ARG | A | 251 | 11.706 | 4.068 | 42.647 | 1.00 | 10.84 |
| ATOM | 1882 | NE | ARG | A | 251 | 10.278 | 3.795 | 42.721 | 1.00 | 15.91 |
| ATOM | 1883 | CZ | ARG | A | 251 | 9.729 | 3.085 | 43.709 | 1.00 | 22.05 |
| ATOM | 1884 | NH1 | ARG | A | 251 | 10.528 | 2.610 | 44.665 | 1.00 | 12.86 |
| ATOM | 1885 | NH2 | ARG | A | 251 | 8.413 | 2.887 | 43.697 | 1.00 | 19.96 |
| ATOM | 1886 | C | ARG | A | 251 | 12.319 | 3.826 | 37.620 | 1.00 | 7.84 |
| ATOM | 1887 | O | ARG | A | 251 | 13.444 | 3.643 | 37.141 | 1.00 | 13.49 |
| ATOM | 1888 | N | THR | A | 252 | 11.189 | 3.332 | 37.112 | 1.00 | 10.86 |
| ATOM | 1889 | CA | THR | A | 252 | 11.278 | 2.605 | 35.826 | 1.00 | 8.96 |
| ATOM | 1890 | CB | THR | A | 252 | 9.877 | 2.125 | 35.429 | 1.00 | 16.98 |
| ATOM | 1891 | OG1 | THR | A | 252 | 9.509 | 1.052 | 36.311 | 1.00 | 15.33 |
| ATOM | 1892 | CG2 | THR | A | 252 | 9.847 | 1.560 | 34.015 | 1.00 | 18.22 |
| ATOM | 1893 | C | THR | A | 252 | 11.901 | 3.464 | 34.745 | 1.00 | 13.54 |
| ATOM | 1894 | O | THR | A | 252 | 12.828 | 3.103 | 34.003 | 1.00 | 14.11 |
| ATOM | 1895 | N | GLY | A | 253 | 11.410 | 4.690 | 34.594 | 1.00 | 14.04 |
| ATOM | 1896 | CA | GLY | A | 253 | 11.976 | 5.531 | 33.532 | 1.00 | 16.89 |
| ATOM | 1897 | C | GLY | A | 253 | 13.426 | 5.881 | 33.711 | 1.00 | 11.18 |
| ATOM | 1898 | O | GLY | A | 253 | 14.233 | 5.937 | 32.777 | 1.00 | 14.06 |
| ATOM | 1899 | N | THR | A | 254 | 13.831 | 6.138 | 34.965 | 1.00 | 12.53 |
| ATOM | 1900 | CA | THR | A | 254 | 15.235 | 6.408 | 35.233 | 1.00 | 13.37 |
| ATOM | 1901 | CB | THR | A | 254 | 15.455 | 6.837 | 36.695 | 1.00 | 16.96 |
| ATOM | 1902 | OG1 | THR | A | 254 | 14.606 | 7.960 | 36.960 | 1.00 | 17.14 |
| ATOM | 1903 | CG2 | THR | A | 254 | 16.884 | 7.294 | 36.923 | 1.00 | 17.26 |
| ATOM | 1904 | C | THR | A | 254 | 16.108 | 5.200 | 34.937 | 1.00 | 18.94 |
| ATOM | 1905 | O | THR | A | 254 | 17.217 | 5.344 | 34.409 | 1.00 | 17.66 |
| ATOM | 1906 | N | PHE | A | 255 | 15.602 | 4.014 | 35.263 | 1.00 | 11.19 |
| ATOM | 1907 | CA | PHE | A | 255 | 16.362 | 2.796 | 34.987 | 1.00 | 10.10 |
| ATOM | 1908 | CB | PHE | A | 255 | 15.617 | 1.534 | 35.479 | 1.00 | 12.68 |
| ATOM | 1909 | CG | PHE | A | 255 | 16.273 | 0.217 | 35.051 | 1.00 | 13.42 |
| ATOM | 1910 | CD1 | PHE | A | 255 | 17.258 | -0.329 | 35.873 | 1.00 | 14.10 |
| ATOM | 1911 | CE1 | PHE | A | 255 | 17.901 | -1.509 | 35.535 | 1.00 | 15.64 |
| ATOM | 1912 | CZ | PHE | A | 255 | 17.592 | -2.156 | 34.345 | 1.00 | 14.48 |
| ATOM | 1913 | CE2 | PHE | A | 255 | 16.600 | -1.645 | 33.523 | 1.00 | 15.99 |
| ATOM | 1914 | CD2 | PHE | A | 255 | 15.937 | -0.487 | 33.898 | 1.00 | 19.84 |
| ATOM | 1915 | C | PHE | A | 255 | 16.626 | 2.687 | 33.493 | 1.00 | 11.10 |
| ATOM | 1916 | O | PHE | A | 255 | 17.732 | 2.397 | 33.060 | 1.00 | 14.84 |
| ATOM | 1917 | N | ILE | A | 256 | 15.561 | 2.863 | 32.704 | 1.00 | 14.82 |
| ATOM | 1918 | CA | ILE | A | 256 | 15.726 | 2.641 | 31.264 | 1.00 | 10.00 |
| ATOM | 1919 | CB | ILE | A | 256 | 14.352 | 2.607 | 30.589 | 1.00 | 12.80 |
| ATOM | 1920 | CG1 | ILE | A | 256 | 13.558 | 1.345 | 30.943 | 1.00 | 11.66 |
| ATOM | 1921 | CD1 | ILE | A | 256 | 12.084 | 1.457 | 30.602 | 1.00 | 12.54 |
| ATOM | 1922 | CG2 | ILE | A | 256 | 14.463 | 2.826 | 29.091 | 1.00 | 14.64 |
| ATOM | 1923 | C | ILE | A | 256 | 16.584 | 3.736 | 30.662 | 1.00 | 14.37 |

FIGURE 242

```
ATOM   1924  O    ILE A 256      17.387    3.496   29.766  1.00 20.73
ATOM   1925  N    ALA A 257      16.399    4.970   31.154  1.00 16.70
ATOM   1926  CA   ALA A 257      17.236    6.040   30.612  1.00 12.87
ATOM   1927  CB   ALA A 257      16.865    7.389   31.209  1.00 18.47
ATOM   1928  C    ALA A 257      18.699    5.703   30.858  1.00 19.90
ATOM   1929  O    ALA A 257      19.567    5.851   29.993  1.00 19.76
ATOM   1930  N    LEU A 258      18.967    5.203   32.071  1.00 15.65
ATOM   1931  CA   LEU A 258      20.358    4.894   32.395  1.00 16.29
ATOM   1932  CB   LEU A 258      20.501    4.631   33.901  1.00 18.82
ATOM   1933  CG   LEU A 258      21.938    4.343   34.350  1.00 18.09
ATOM   1934  CD1  LEU A 258      22.864    5.426   33.809  1.00 16.26
ATOM   1935  CD2  LEU A 258      22.000    4.251   35.864  1.00 19.56
ATOM   1936  C    LEU A 258      20.840    3.708   31.580  1.00 21.01
ATOM   1937  O    LEU A 258      21.974    3.651   31.110  1.00 23.61
ATOM   1938  N    ASP A 259      19.972    2.715   31.377  1.00 14.03
ATOM   1939  CA   ASP A 259      20.372    1.573   30.549  1.00 19.00
ATOM   1940  CB   ASP A 259      19.247    0.544   30.512  1.00 16.27
ATOM   1941  CG   ASP A 259      19.491   -0.692   29.670  1.00 16.85
ATOM   1942  OD1  ASP A 259      20.621   -1.227   29.689  1.00 22.41
ATOM   1943  OD2  ASP A 259      18.564   -1.164   28.976  1.00 22.35
ATOM   1944  C    ASP A 259      20.732    2.051   29.142  1.00 24.46
ATOM   1945  O    ASP A 259      21.715    1.611   28.532  1.00 22.50
ATOM   1946  N    ARG A 260      19.915    2.967   28.624  1.00 18.68
ATOM   1947  CA   ARG A 260      20.166    3.492   27.277  1.00 21.73
ATOM   1948  CB   ARG A 260      18.965    4.302   26.759  1.00 19.52
ATOM   1949  CG   ARG A 260      17.772    3.420   26.379  1.00 21.69
ATOM   1950  CD   ARG A 260      16.687    4.238   25.678  1.00 27.46
ATOM   1951  NE   ARG A 260      17.207    4.867   24.479  1.00 35.48
ATOM   1952  CZ   ARG A 260      16.651    5.618   23.551  1.00 36.55
ATOM   1953  NH1  ARG A 260      15.372    5.944   23.580  1.00 47.22
ATOM   1954  NH2  ARG A 260      17.404    6.063   22.548  1.00 36.27
ATOM   1955  C    ARG A 260      21.432    4.331   27.217  1.00 26.15
ATOM   1956  O    ARG A 260      22.192    4.165   26.256  1.00 23.92
ATOM   1957  N    ILE A 261      21.688    5.215   28.182  1.00 26.20
ATOM   1958  CA   ILE A 261      22.842    6.103   28.059  1.00 22.09
ATOM   1959  CB   ILE A 261      22.764    7.376   28.922  1.00 23.64
ATOM   1960  CG1  ILE A 261      23.001    7.148   30.418  1.00 30.05
ATOM   1961  CD1  ILE A 261      22.191    8.055   31.328  1.00 30.61
ATOM   1962  CG2  ILE A 261      21.452    8.105   28.674  1.00 18.34
ATOM   1963  C    ILE A 261      24.146    5.381   28.394  1.00 28.75
ATOM   1964  O    ILE A 261      25.206    5.722   27.854  1.00 36.26
ATOM   1965  N    LEU A 262      24.110    4.384   29.276  1.00 25.96
ATOM   1966  CA   LEU A 262      25.364    3.663   29.544  1.00 24.13
ATOM   1967  CB   LEU A 262      25.207    2.686   30.699  1.00 24.26
ATOM   1968  CG   LEU A 262      25.112    3.236   32.123  1.00 20.71
ATOM   1969  CD1  LEU A 262      25.079    2.071   33.101  1.00 24.55
ATOM   1970  CD2  LEU A 262      26.257    4.176   32.453  1.00 23.31
ATOM   1971  C    LEU A 262      25.812    2.958   28.271  1.00 29.49
ATOM   1972  O    LEU A 262      27.004    2.863   27.968  1.00 38.42
ATOM   1973  N    GLN A 263      24.851    2.454   27.494  1.00 29.52
ATOM   1974  CA   GLN A 263      25.225    1.863   26.204  1.00 35.18
ATOM   1975  CB   GLN A 263      24.015    1.216   25.545  1.00 34.97
```

FIGURE 243

```
ATOM   1976  CG   GLN A 263      23.632   -0.140   26.125  1.00 36.78
ATOM   1977  CD   GLN A 263      22.277   -0.630   25.661  1.00 34.45
ATOM   1978  OE1  GLN A 263      22.167   -1.327   24.653  1.00 32.02
ATOM   1979  NE2  GLN A 263      21.219   -0.276   26.388  1.00 29.68
ATOM   1980  C    GLN A 263      25.867    2.912   25.300  1.00 38.62
ATOM   1981  O    GLN A 263      26.927    2.694   24.702  1.00 44.23
ATOM   1982  N    GLN A 264      25.255    4.084   25.187  1.00 40.04
ATOM   1983  CA   GLN A 264      25.848    5.189   24.439  1.00 37.35
ATOM   1984  CB   GLN A 264      25.018    6.461   24.597  1.00 30.80
ATOM   1985  CG   GLN A 264      23.739    6.499   23.777  1.00 28.49
ATOM   1986  CD   GLN A 264      22.842    7.650   24.195  1.00 36.13
ATOM   1987  OE1  GLN A 264      23.318    8.630   24.778  1.00 35.61
ATOM   1988  NE2  GLN A 264      21.552    7.519   23.905  1.00 30.19
ATOM   1989  C    GLN A 264      27.280    5.460   24.900  1.00 46.87
ATOM   1990  O    GLN A 264      28.192    5.539   24.076  1.00 59.11
ATOM   1991  N    LEU A 265      27.474    5.599   26.210  1.00 44.30
ATOM   1992  CA   LEU A 265      28.805    5.808   26.774  1.00 44.22
ATOM   1993  CB   LEU A 265      28.794    5.779   28.295  1.00 47.83
ATOM   1994  CG   LEU A 265      28.082    6.900   29.043  1.00 50.56
ATOM   1995  CD1  LEU A 265      28.140    6.641   30.544  1.00 39.48
ATOM   1996  CD2  LEU A 265      28.678    8.255   28.696  1.00 54.16
ATOM   1997  C    LEU A 265      29.763    4.736   26.265  1.00 45.05
ATOM   1998  O    LEU A 265      30.912    5.011   25.925  1.00 54.65
ATOM   1999  N    ASP A 266      29.280    3.495   26.209  1.00 40.79
ATOM   2000  CA   ASP A 266      30.137    2.440   25.670  1.00 47.27
ATOM   2001  CB   ASP A 266      29.739    1.083   26.257  1.00 43.47
ATOM   2002  CG   ASP A 266      30.102    0.960   27.721  1.00 44.36
ATOM   2003  OD1  ASP A 266      31.196    1.428   28.101  1.00 58.24
ATOM   2004  OD2  ASP A 266      29.297    0.391   28.488  1.00 53.34
ATOM   2005  C    ASP A 266      30.066    2.396   24.154  1.00 58.50
ATOM   2006  O    ASP A 266      30.476    1.429   23.506  1.00 56.64
ATOM   2007  N    SER A 267      29.538    3.434   23.497  1.00 67.18
ATOM   2008  CA   SER A 267      29.465    3.282   22.038  1.00 73.64
ATOM   2009  CB   SER A 267      28.110    2.671   21.667  1.00 75.02
ATOM   2010  OG   SER A 267      28.161    1.258   21.786  1.00 72.08
ATOM   2011  C    SER A 267      29.693    4.592   21.301  1.00 81.56
ATOM   2012  O    SER A 267      30.504    4.666   20.376  1.00 96.45
ATOM   2013  N    LYS A 268      28.971    5.630   21.705  1.00 82.73
ATOM   2014  CA   LYS A 268      29.039    6.931   21.064  1.00 81.39
ATOM   2015  CB   LYS A 268      27.736    7.709   21.286  1.00 92.60
ATOM   2016  CG   LYS A 268      26.518    7.115   20.597  1.00 98.30
ATOM   2017  CD   LYS A 268      25.516    8.187   20.194  1.00 99.41
ATOM   2018  CE   LYS A 268      25.288    9.191   21.312  1.00 97.43
ATOM   2019  NZ   LYS A 268      23.896    9.151   21.836  1.00 86.39
ATOM   2020  C    LYS A 268      30.209    7.766   21.583  1.00 67.12
ATOM   2021  O    LYS A 268      30.930    7.340   22.478  1.00 61.30
ATOM   2022  N    ASP A 269      30.340    8.941   20.995  1.00 57.55
ATOM   2023  CA   ASP A 269      31.277    9.986   21.380  1.00 61.48
ATOM   2024  CB   ASP A 269      31.994   10.514   20.137  1.00 71.27
ATOM   2025  CG   ASP A 269      31.482    9.789   18.899  1.00 80.60
ATOM   2026  OD1  ASP A 269      32.270    9.060   18.261  1.00 87.05
```

FIGURE 244

```
ATOM   2027  OD2 ASP A 269      30.283   9.954  18.585  1.00 82.09
ATOM   2028  C   ASP A 269      30.498  11.081  22.096  1.00 54.39
ATOM   2029  O   ASP A 269      30.997  12.070  22.621  1.00 37.16
ATOM   2030  N   SER A 270      29.183  10.843  22.108  1.00 44.05
ATOM   2031  CA  SER A 270      28.290  11.754  22.805  1.00 48.15
ATOM   2032  CB  SER A 270      27.593  12.687  21.814  1.00 54.66
ATOM   2033  OG  SER A 270      27.367  12.009  20.588  1.00 61.37
ATOM   2034  C   SER A 270      27.261  10.971  23.609  1.00 44.27
ATOM   2035  O   SER A 270      27.045   9.781  23.410  1.00 33.61
ATOM   2036  N   VAL A 271      26.613  11.652  24.544  1.00 41.56
ATOM   2037  CA  VAL A 271      25.550  10.966  25.288  1.00 44.74
ATOM   2038  CB  VAL A 271      25.984  10.636  26.722  1.00 43.78
ATOM   2039  CG1 VAL A 271      26.585  11.844  27.428  1.00 22.16
ATOM   2040  CG2 VAL A 271      24.822  10.084  27.544  1.00 24.65
ATOM   2041  C   VAL A 271      24.316  11.852  25.185  1.00 43.38
ATOM   2042  O   VAL A 271      24.418  13.084  25.177  1.00 32.23
ATOM   2043  N   ASP A 272      23.146  11.232  25.058  1.00 35.09
ATOM   2044  CA  ASP A 272      21.929  12.022  24.874  1.00 36.34
ATOM   2045  CB  ASP A 272      21.317  11.723  23.500  1.00 28.68
ATOM   2046  CG  ASP A 272      20.345  12.806  23.075  1.00 25.29
ATOM   2047  OD1 ASP A 272      20.363  13.875  23.726  1.00 33.02
ATOM   2048  OD2 ASP A 272      19.581  12.595  22.112  1.00 37.57
ATOM   2049  C   ASP A 272      20.936  11.754  25.993  1.00 33.69
ATOM   2050  O   ASP A 272      19.969  11.023  25.818  1.00 35.34
ATOM   2051  N   ILE A 273      21.171  12.338  27.166  1.00 29.39
ATOM   2052  CA  ILE A 273      20.262  12.106  28.281  1.00 31.17
ATOM   2053  CB  ILE A 273      20.840  12.632  29.611  1.00 33.58
ATOM   2054  CG1 ILE A 273      22.112  11.900  30.045  1.00 34.59
ATOM   2055  CD1 ILE A 273      22.785  12.475  31.270  1.00 32.68
ATOM   2056  CG2 ILE A 273      19.793  12.604  30.714  1.00 21.45
ATOM   2057  C   ILE A 273      18.909  12.754  28.018  1.00 36.45
ATOM   2058  O   ILE A 273      17.873  12.152  28.319  1.00 29.72
ATOM   2059  N   TYR A 274      18.921  13.967  27.465  1.00 23.18
ATOM   2060  CA  TYR A 274      17.658  14.663  27.204  1.00 23.24
ATOM   2061  CB  TYR A 274      17.927  16.065  26.659  1.00 21.30
ATOM   2062  CG  TYR A 274      16.720  16.885  26.286  1.00 28.11
ATOM   2063  CD1 TYR A 274      16.099  17.722  27.205  1.00 30.12
ATOM   2064  CE1 TYR A 274      14.991  18.475  26.855  1.00 36.51
ATOM   2065  CZ  TYR A 274      14.486  18.401  25.576  1.00 39.07
ATOM   2066  OH  TYR A 274      13.384  19.137  25.206  1.00 39.75
ATOM   2067  CE2 TYR A 274      15.082  17.578  24.641  1.00 33.12
ATOM   2068  CD2 TYR A 274      16.183  16.837  25.003  1.00 30.11
ATOM   2069  C   TYR A 274      16.810  13.851  26.229  1.00 23.51
ATOM   2070  O   TYR A 274      15.604  13.715  26.425  1.00 26.03
ATOM   2071  N   GLY A 275      17.435  13.350  25.181  1.00 21.12
ATOM   2072  CA  GLY A 275      16.774  12.633  24.100  1.00 24.69
ATOM   2073  C   GLY A 275      16.230  11.296  24.575  1.00 30.05
ATOM   2074  O   GLY A 275      15.206  10.793  24.115  1.00 26.82
ATOM   2075  N   ALA A 276      16.950  10.705  25.531  1.00 28.67
ATOM   2076  CA  ALA A 276      16.477   9.436  26.087  1.00 28.22
ATOM   2077  CB  ALA A 276      17.538   8.828  26.980  1.00 23.79
ATOM   2078  C   ALA A 276      15.165   9.685  26.816  1.00 25.48
```

FIGURE 245

| | | | | | | | | |
|---|---|---|---|---|---|---|---|---|
| ATOM | 2079 | O | ALA | A | 276 | 14.174 | 8.993 | 26.612 | 1.00 | 21.68 |
| ATOM | 2080 | N | VAL | A | 277 | 15.134 | 10.709 | 27.669 | 1.00 | 19.63 |
| ATOM | 2081 | CA | VAL | A | 277 | 13.928 | 10.960 | 28.450 | 1.00 | 18.94 |
| ATOM | 2082 | CB | VAL | A | 277 | 14.184 | 11.957 | 29.592 | 1.00 | 18.63 |
| ATOM | 2083 | CG1 | VAL | A | 277 | 12.919 | 12.193 | 30.417 | 1.00 | 19.37 |
| ATOM | 2084 | CG2 | VAL | A | 277 | 15.308 | 11.457 | 30.497 | 1.00 | 23.87 |
| ATOM | 2085 | C | VAL | A | 277 | 12.820 | 11.458 | 27.538 | 1.00 | 22.49 |
| ATOM | 2086 | O | VAL | A | 277 | 11.642 | 11.184 | 27.731 | 1.00 | 18.77 |
| ATOM | 2087 | N | HIS | A | 278 | 13.225 | 12.224 | 26.522 | 1.00 | 20.21 |
| ATOM | 2088 | CA | HIS | A | 278 | 12.220 | 12.729 | 25.587 | 1.00 | 20.77 |
| ATOM | 2089 | CB | HIS | A | 278 | 12.888 | 13.637 | 24.538 | 1.00 | 19.46 |
| ATOM | 2090 | CG | HIS | A | 278 | 11.915 | 14.109 | 23.501 | 1.00 | 27.73 |
| ATOM | 2091 | ND1 | HIS | A | 278 | 11.599 | 13.361 | 22.387 | 1.00 | 25.43 |
| ATOM | 2092 | CE1 | HIS | A | 278 | 10.714 | 14.023 | 21.661 | 1.00 | 26.78 |
| ATOM | 2093 | NE2 | HIS | A | 278 | 10.441 | 15.169 | 22.258 | 1.00 | 30.40 |
| ATOM | 2094 | CD2 | HIS | A | 278 | 11.180 | 15.243 | 23.412 | 1.00 | 29.32 |
| ATOM | 2095 | C | HIS | A | 278 | 11.505 | 11.529 | 24.958 | 1.00 | 17.28 |
| ATOM | 2096 | O | HIS | A | 278 | 10.282 | 11.474 | 24.934 | 1.00 | 19.03 |
| ATOM | 2097 | N | ASP | A | 279 | 12.283 | 10.576 | 24.448 | 1.00 | 19.78 |
| ATOM | 2098 | CA | ASP | A | 279 | 11.736 | 9.408 | 23.766 | 1.00 | 23.11 |
| ATOM | 2099 | CB | ASP | A | 279 | 12.830 | 8.508 | 23.192 | 1.00 | 31.32 |
| ATOM | 2100 | CG | ASP | A | 279 | 12.445 | 7.760 | 21.931 | 1.00 | 41.53 |
| ATOM | 2101 | OD1 | ASP | A | 279 | 11.649 | 8.288 | 21.124 | 1.00 | 44.27 |
| ATOM | 2102 | OD2 | ASP | A | 279 | 12.924 | 6.627 | 21.689 | 1.00 | 31.21 |
| ATOM | 2103 | C | ASP | A | 279 | 10.860 | 8.613 | 24.733 | 1.00 | 16.22 |
| ATOM | 2104 | O | ASP | A | 279 | 9.794 | 8.139 | 24.359 | 1.00 | 17.27 |
| ATOM | 2105 | N | LEU | A | 280 | 11.327 | 8.486 | 25.974 | 1.00 | 18.29 |
| ATOM | 2106 | CA | LEU | A | 280 | 10.517 | 7.786 | 26.974 | 1.00 | 19.74 |
| ATOM | 2107 | CB | LEU | A | 280 | 11.270 | 7.751 | 28.301 | 1.00 | 15.55 |
| ATOM | 2108 | CG | LEU | A | 280 | 12.388 | 6.723 | 28.463 | 1.00 | 26.78 |
| ATOM | 2109 | CD1 | LEU | A | 280 | 13.190 | 6.944 | 29.734 | 1.00 | 23.32 |
| ATOM | 2110 | CD2 | LEU | A | 280 | 11.836 | 5.303 | 28.501 | 1.00 | 32.51 |
| ATOM | 2111 | C | LEU | A | 280 | 9.162 | 8.456 | 27.109 | 1.00 | 19.74 |
| ATOM | 2112 | O | LEU | A | 280 | 8.100 | 7.831 | 27.099 | 1.00 | 15.47 |
| ATOM | 2113 | N | ARG | A | 281 | 9.152 | 9.785 | 27.240 | 1.00 | 17.32 |
| ATOM | 2114 | CA | ARG | A | 281 | 7.931 | 10.535 | 27.402 | 1.00 | 18.47 |
| ATOM | 2115 | CB | ARG | A | 281 | 8.195 | 12.047 | 27.522 | 1.00 | 21.28 |
| ATOM | 2116 | CG | ARG | A | 281 | 9.115 | 12.436 | 28.661 | 1.00 | 29.75 |
| ATOM | 2117 | CD | ARG | A | 281 | 8.318 | 12.580 | 29.951 | 1.00 | 34.02 |
| ATOM | 2118 | NE | ARG | A | 281 | 9.199 | 13.015 | 31.026 | 1.00 | 37.36 |
| ATOM | 2119 | CZ | ARG | A | 281 | 8.851 | 13.737 | 32.071 | 1.00 | 39.23 |
| ATOM | 2120 | NH1 | ARG | A | 281 | 7.595 | 14.129 | 32.206 | 1.00 | 60.17 |
| ATOM | 2121 | NH2 | ARG | A | 281 | 9.769 | 14.055 | 32.972 | 1.00 | 36.32 |
| ATOM | 2122 | C | ARG | A | 281 | 6.987 | 10.381 | 26.220 | 1.00 | 16.87 |
| ATOM | 2123 | O | ARG | A | 281 | 5.785 | 10.568 | 26.424 | 1.00 | 18.99 |
| ATOM | 2124 | N | LEU | A | 282 | 7.549 | 10.111 | 25.034 | 1.00 | 15.85 |
| ATOM | 2125 | CA | LEU | A | 282 | 6.620 | 9.977 | 23.899 | 1.00 | 17.78 |
| ATOM | 2126 | CB | LEU | A | 282 | 7.338 | 9.907 | 22.559 | 1.00 | 21.15 |
| ATOM | 2127 | CG | LEU | A | 282 | 8.060 | 11.126 | 21.997 | 1.00 | 32.88 |
| ATOM | 2128 | CD1 | LEU | A | 282 | 8.732 | 10.767 | 20.673 | 1.00 | 28.74 |
| ATOM | 2129 | CD2 | LEU | A | 282 | 7.133 | 12.311 | 21.783 | 1.00 | 24.88 |
| ATOM | 2130 | C | LEU | A | 282 | 5.763 | 8.721 | 24.078 | 1.00 | 18.42 |

FIGURE 246

```
ATOM   2131  O    LEU A 282       4.658   8.631  23.532  1.00 21.04
ATOM   2132  N    HIS A 283       6.263   7.739  24.823  1.00 16.75
ATOM   2133  CA   HIS A 283       5.574   6.450  24.905  1.00 17.03
ATOM   2134  CB   HIS A 283       6.621   5.350  24.644  1.00 17.45
ATOM   2135  CG   HIS A 283       7.133   5.464  23.234  1.00 19.75
ATOM   2136  ND1  HIS A 283       6.502   4.868  22.169  1.00 24.70
ATOM   2137  CE1  HIS A 283       7.156   5.149  21.056  1.00 24.61
ATOM   2138  NE2  HIS A 283       8.191   5.913  21.353  1.00 23.33
ATOM   2139  CD2  HIS A 283       8.186   6.126  22.714  1.00 25.41
ATOM   2140  C    HIS A 283       4.831   6.199  26.209  1.00 17.38
ATOM   2141  O    HIS A 283       3.932   5.336  26.249  1.00 12.95
ATOM   2142  N    ARG A 284       5.125   6.923  27.282  1.00 12.46
ATOM   2143  CA   ARG A 284       4.367   6.792  28.527  1.00 12.55
ATOM   2144  CB   ARG A 284       4.869   5.622  29.366  1.00 13.17
ATOM   2145  CG   ARG A 284       4.072   5.322  30.633  1.00 10.87
ATOM   2146  CD   ARG A 284       4.464   3.909  31.097  1.00 17.92
ATOM   2147  NE   ARG A 284       3.933   3.546  32.404  1.00 11.92
ATOM   2148  CZ   ARG A 284       2.752   2.965  32.601  1.00 15.19
ATOM   2149  NH1  ARG A 284       1.953   2.675  31.577  1.00 12.14
ATOM   2150  NH2  ARG A 284       2.348   2.666  33.837  1.00 11.55
ATOM   2151  C    ARG A 284       4.496   8.059  29.372  1.00 12.80
ATOM   2152  O    ARG A 284       5.555   8.665  29.370  1.00 13.52
ATOM   2153  N    VAL A 285       3.435   8.425  30.059  1.00 17.40
ATOM   2154  CA   VAL A 285       3.419   9.665  30.847  1.00 15.70
ATOM   2155  CB   VAL A 285       1.998   9.930  31.379  1.00 18.07
ATOM   2156  CG1  VAL A 285       1.657   8.972  32.521  1.00 14.53
ATOM   2157  CG2  VAL A 285       1.848  11.380  31.837  1.00 21.60
ATOM   2158  C    VAL A 285       4.429   9.640  31.982  1.00 24.82
ATOM   2159  O    VAL A 285       4.767   8.581  32.511  1.00 18.02
ATOM   2160  N    HIS A 286       4.926  10.823  32.336  1.00 22.81
ATOM   2161  CA   HIS A 286       5.818  11.084  33.440  1.00 20.84
ATOM   2162  CB   HIS A 286       5.069  10.872  34.768  1.00 24.11
ATOM   2163  CG   HIS A 286       3.818  11.663  34.965  1.00 28.34
ATOM   2164  ND1  HIS A 286       3.763  13.039  34.936  1.00 28.84
ATOM   2165  CE1  HIS A 286       2.526  13.448  35.147  1.00 28.83
ATOM   2166  NE2  HIS A 286       1.766  12.380  35.317  1.00 32.75
ATOM   2167  CD2  HIS A 286       2.548  11.255  35.216  1.00 26.94
ATOM   2168  C    HIS A 286       7.084  10.232  33.510  1.00 21.64
ATOM   2169  O    HIS A 286       7.661  10.218  34.615  1.00 26.93
ATOM   2170  N    MET A 287       7.550   9.548  32.468  1.00 13.96
ATOM   2171  CA   MET A 287       8.792   8.783  32.560  1.00 13.56
ATOM   2172  CB   MET A 287       9.223   8.171  31.264  1.00 16.67
ATOM   2173  CG   MET A 287       8.741   6.954  30.564  1.00 32.18
ATOM   2174  SD   MET A 287       8.371   5.520  31.623  1.00 31.45
ATOM   2175  CE   MET A 287       6.873   6.119  32.287  1.00 12.41
ATOM   2176  C    MET A 287       9.919   9.708  33.070  1.00 31.47
ATOM   2177  O    MET A 287      10.136  10.813  32.556  1.00 27.35
ATOM   2178  N    VAL A 288      10.581   9.213  34.107  1.00 19.43
ATOM   2179  CA   VAL A 288      11.539   9.968  34.906  1.00 20.51
ATOM   2180  CB   VAL A 288      12.719  10.500  34.089  1.00 18.73
ATOM   2181  CG1  VAL A 288      13.598  11.361  34.989  1.00 27.60
ATOM   2182  CG2  VAL A 288      13.506   9.344  33.475  1.00 16.71
```

FIGURE 247

```
ATOM   2183  C   VAL A 288      10.780  11.107  35.584  1.00  24.09
ATOM   2184  O   VAL A 288      10.586  12.174  35.013  1.00  30.01
ATOM   2185  N   GLN A 289      10.325  10.820  36.799  1.00  20.54
ATOM   2186  CA  GLN A 289       9.237  11.559  37.407  1.00  28.07
ATOM   2187  CB  GLN A 289       8.381  10.595  38.239  1.00  31.79
ATOM   2188  CG  GLN A 289       7.078  11.185  38.754  1.00  34.58
ATOM   2189  CD  GLN A 289       7.101  11.363  40.266  1.00  35.98
ATOM   2190  OE1 GLN A 289       7.791  10.623  40.972  1.00  26.51
ATOM   2191  NE2 GLN A 289       6.346  12.347  40.753  1.00  36.09
ATOM   2192  C   GLN A 289       9.689  12.720  38.278  1.00  33.05
ATOM   2193  O   GLN A 289       8.858  13.599  38.525  1.00  35.10
ATOM   2194  N   THR A 290      10.936  12.736  38.736  1.00  30.88
ATOM   2195  CA  THR A 290      11.372  13.920  39.491  1.00  28.02
ATOM   2196  CB  THR A 290      11.590  13.611  40.984  1.00  29.29
ATOM   2197  OG1 THR A 290      12.661  12.677  41.160  1.00  35.40
ATOM   2198  CG2 THR A 290      10.331  12.980  41.563  1.00  24.35
ATOM   2199  C   THR A 290      12.639  14.518  38.909  1.00  23.50
ATOM   2200  O   THR A 290      13.496  13.903  38.287  1.00  21.72
ATOM   2201  N   GLU A 291      12.806  15.830  39.108  1.00  33.06
ATOM   2202  CA  GLU A 291      13.996  16.481  38.534  1.00  26.38
ATOM   2203  CB  GLU A 291      13.849  17.986  38.728  1.00  36.13
ATOM   2204  CG  GLU A 291      14.794  18.656  39.697  1.00  47.55
ATOM   2205  CD  GLU A 291      15.133  20.079  39.279  1.00  50.62
ATOM   2206  OE1 GLU A 291      16.237  20.541  39.645  1.00  58.58
ATOM   2207  OE2 GLU A 291      14.306  20.719  38.593  1.00  33.56
ATOM   2208  C   GLU A 291      15.255  15.901  39.151  1.00  20.43
ATOM   2209  O   GLU A 291      16.325  15.881  38.543  1.00  24.26
ATOM   2210  N   CYS A 292      15.139  15.407  40.386  1.00  20.50
ATOM   2211  CA  CYS A 292      16.308  14.825  41.039  1.00  19.18
ATOM   2212  CB  CYS A 292      16.040  14.535  42.517  1.00  31.41
ATOM   2213  SG  CYS A 292      17.552  14.159  43.444  1.00 101.20
ATOM   2214  C   CYS A 292      16.721  13.542  40.335  1.00  20.87
ATOM   2215  O   CYS A 292      17.899  13.219  40.202  1.00  24.99
ATOM   2216  N   GLN A 293      15.718  12.795  39.862  1.00  26.29
ATOM   2217  CA  GLN A 293      16.062  11.613  39.055  1.00  22.01
ATOM   2218  CB  GLN A 293      14.785  10.827  38.720  1.00  22.44
ATOM   2219  CG  GLN A 293      14.242  10.156  39.972  1.00  21.37
ATOM   2220  CD  GLN A 293      12.831   9.628  39.838  1.00  24.27
ATOM   2221  OE1 GLN A 293      12.134   9.855  38.848  1.00  23.20
ATOM   2222  NE2 GLN A 293      12.439   8.904  40.884  1.00  18.53
ATOM   2223  C   GLN A 293      16.816  12.029  37.805  1.00  18.20
ATOM   2224  O   GLN A 293      17.797  11.408  37.389  1.00  21.10
ATOM   2225  N   TYR A 294      16.355  13.121  37.196  1.00  20.29
ATOM   2226  CA  TYR A 294      17.034  13.649  36.006  1.00  17.93
ATOM   2227  CB  TYR A 294      16.239  14.824  35.456  1.00  20.72
ATOM   2228  CG  TYR A 294      16.600  15.299  34.066  1.00  22.13
ATOM   2229  CD1 TYR A 294      16.441  14.487  32.949  1.00  22.03
ATOM   2230  CE1 TYR A 294      16.767  14.926  31.680  1.00  27.01
ATOM   2231  CZ  TYR A 294      17.259  16.212  31.527  1.00  31.26
ATOM   2232  OH  TYR A 294      17.590  16.669  30.275  1.00  31.95
ATOM   2233  CE2 TYR A 294      17.426  17.043  32.614  1.00  24.60
ATOM   2234  CD2 TYR A 294      17.093  16.581  33.871  1.00  24.21
```

FIGURE 248

```
ATOM   2235  C   TYR A 294      18.457  14.063  36.353  1.00 26.00
ATOM   2236  O   TYR A 294      19.401  13.726  35.643  1.00 24.45
ATOM   2237  N   VAL A 295      18.626  14.790  37.467  1.00 27.38
ATOM   2238  CA  VAL A 295      19.981  15.130  37.908  1.00 26.38
ATOM   2239  CB  VAL A 295      19.989  15.931  39.225  1.00 21.43
ATOM   2240  CG1 VAL A 295      21.402  15.984  39.784  1.00 28.13
ATOM   2241  CG2 VAL A 295      19.428  17.326  39.000  1.00 34.94
ATOM   2242  C   VAL A 295      20.839  13.888  38.136  1.00 21.34
ATOM   2243  O   VAL A 295      21.991  13.837  37.730  1.00 23.60
ATOM   2244  N   TYR A 296      20.296  12.876  38.792  1.00 22.55
ATOM   2245  CA  TYR A 296      20.976  11.609  39.039  1.00 27.13
ATOM   2246  CB  TYR A 296      20.011  10.665  39.773  1.00 19.15
ATOM   2247  CG  TYR A 296      20.587   9.329  40.167  1.00 22.85
ATOM   2248  CD1 TYR A 296      21.493   9.191  41.211  1.00 21.56
ATOM   2249  CE1 TYR A 296      22.022   7.967  41.576  1.00 20.08
ATOM   2250  CZ  TYR A 296      21.628   6.841  40.876  1.00 22.87
ATOM   2251  OH  TYR A 296      22.136   5.601  41.213  1.00 22.11
ATOM   2252  CE2 TYR A 296      20.734   6.954  39.842  1.00 23.68
ATOM   2253  CD2 TYR A 296      20.211   8.179  39.483  1.00 25.13
ATOM   2254  C   TYR A 296      21.495  10.947  37.771  1.00 22.49
ATOM   2255  O   TYR A 296      22.607  10.406  37.752  1.00 24.52
ATOM   2256  N   LEU A 297      20.734  10.960  36.675  1.00 24.50
ATOM   2257  CA  LEU A 297      21.265  10.390  35.437  1.00 19.36
ATOM   2258  CB  LEU A 297      20.278  10.510  34.275  1.00 22.49
ATOM   2259  CG  LEU A 297      18.987   9.697  34.406  1.00 21.19
ATOM   2260  CD1 LEU A 297      17.931  10.172  33.424  1.00 18.99
ATOM   2261  CD2 LEU A 297      19.330   8.224  34.235  1.00 22.58
ATOM   2262  C   LEU A 297      22.563  11.092  35.039  1.00 22.83
ATOM   2263  O   LEU A 297      23.545  10.455  34.672  1.00 26.28
ATOM   2264  N   HIS A 298      22.539  12.432  35.118  1.00 27.23
ATOM   2265  CA  HIS A 298      23.760  13.165  34.773  1.00 26.75
ATOM   2266  CB  HIS A 298      23.526  14.672  34.793  1.00 25.81
ATOM   2267  CG  HIS A 298      22.724  15.186  33.644  1.00 24.47
ATOM   2268  ND1 HIS A 298      21.358  15.061  33.562  1.00 26.77
ATOM   2269  CE1 HIS A 298      20.938  15.617  32.434  1.00 31.41
ATOM   2270  NE2 HIS A 298      21.982  16.099  31.780  1.00 22.95
ATOM   2271  CD2 HIS A 298      23.105  15.841  32.519  1.00 26.28
ATOM   2272  C   HIS A 298      24.877  12.814  35.749  1.00 24.86
ATOM   2273  O   HIS A 298      26.009  12.584  35.342  1.00 32.20
ATOM   2274  N   GLN A 299      24.555  12.775  37.044  1.00 20.61
ATOM   2275  CA  GLN A 299      25.600  12.405  38.005  1.00 27.30
ATOM   2276  CB  GLN A 299      25.077  12.420  39.440  1.00 29.89
ATOM   2277  CG  GLN A 299      24.644  13.789  39.945  1.00 29.83
ATOM   2278  CD  GLN A 299      24.030  13.768  41.327  1.00 39.67
ATOM   2279  OE1 GLN A 299      23.233  12.894  41.678  1.00 50.54
ATOM   2280  NE2 GLN A 299      24.382  14.755  42.148  1.00 42.66
ATOM   2281  C   GLN A 299      26.174  11.033  37.665  1.00 30.62
ATOM   2282  O   GLN A 299      27.380  10.808  37.781  1.00 24.65
ATOM   2283  N   CYS A 300      25.311  10.110  37.244  1.00 32.98
ATOM   2284  CA  CYS A 300      25.750   8.773  36.865  1.00 31.19
ATOM   2285  CB  CYS A 300      24.539   7.921  36.453  1.00 27.79
ATOM   2286  SG  CYS A 300      23.647   7.209  37.864  1.00 24.58
```

FIGURE 249

```
ATOM   2287  C    CYS A 300      26.765   8.828  35.727  1.00 34.76
ATOM   2288  O    CYS A 300      27.822   8.196  35.729  1.00 23.29
ATOM   2289  N    VAL A 301      26.420   9.615  34.708  1.00 32.86
ATOM   2290  CA   VAL A 301      27.302   9.758  33.561  1.00 33.82
ATOM   2291  CB   VAL A 301      26.630  10.582  32.444  1.00 31.77
ATOM   2292  CG1  VAL A 301      27.618  10.894  31.330  1.00 32.91
ATOM   2293  CG2  VAL A 301      25.418   9.821  31.923  1.00 36.31
ATOM   2294  C    VAL A 301      28.618  10.429  33.941  1.00 30.73
ATOM   2295  O    VAL A 301      29.692  10.022  33.501  1.00 35.82
ATOM   2296  N    ARG A 302      28.541  11.468  34.763  1.00 31.17
ATOM   2297  CA   ARG A 302      29.790  12.172  35.086  1.00 30.26
ATOM   2298  CB   ARG A 302      29.484  13.422  35.894  1.00 32.62
ATOM   2299  CG   ARG A 302      30.689  14.073  36.564  1.00 30.76
ATOM   2300  CD   ARG A 302      30.203  14.793  37.826  1.00 35.56
ATOM   2301  NE   ARG A 302      29.679  13.851  38.796  1.00 36.12
ATOM   2302  CZ   ARG A 302      28.999  14.106  39.898  1.00 43.20
ATOM   2303  NH1  ARG A 302      28.702  15.351  40.255  1.00 58.84
ATOM   2304  NH2  ARG A 302      28.601  13.098  40.671  1.00 37.42
ATOM   2305  C    ARG A 302      30.720  11.213  35.811  1.00 38.00
ATOM   2306  O    ARG A 302      31.934  11.187  35.602  1.00 46.79
ATOM   2307  N    ASP A 303      30.137  10.376  36.668  1.00 34.78
ATOM   2308  CA   ASP A 303      30.980   9.431  37.404  1.00 31.64
ATOM   2309  CB   ASP A 303      30.186   8.844  38.579  1.00 32.29
ATOM   2310  CG   ASP A 303      29.766   9.934  39.553  1.00 41.64
ATOM   2311  OD1  ASP A 303      30.143  11.104  39.315  1.00 48.79
ATOM   2312  OD2  ASP A 303      29.060   9.645  40.542  1.00 39.40
ATOM   2313  C    ASP A 303      31.529   8.359  36.484  1.00 33.95
ATOM   2314  O    ASP A 303      32.681   7.925  36.612  1.00 41.56
ATOM   2315  N    VAL A 304      30.755   7.875  35.510  1.00 31.21
ATOM   2316  CA   VAL A 304      31.349   6.840  34.658  1.00 39.08
ATOM   2317  CB   VAL A 304      30.371   6.167  33.685  1.00 44.47
ATOM   2318  CG1  VAL A 304      31.089   5.084  32.889  1.00 27.60
ATOM   2319  CG2  VAL A 304      29.173   5.541  34.381  1.00 27.78
ATOM   2320  C    VAL A 304      32.485   7.483  33.859  1.00 39.60
ATOM   2321  O    VAL A 304      33.515   6.865  33.615  1.00 37.42
ATOM   2322  N    LEU A 305      32.257   8.736  33.484  1.00 36.24
ATOM   2323  CA   LEU A 305      33.241   9.491  32.714  1.00 42.98
ATOM   2324  CB   LEU A 305      32.620  10.746  32.093  1.00 39.34
ATOM   2325  CG   LEU A 305      31.658  10.512  30.929  1.00 34.01
ATOM   2326  CD1  LEU A 305      31.183  11.828  30.327  1.00 28.76
ATOM   2327  CD2  LEU A 305      32.315   9.625  29.876  1.00 34.10
ATOM   2328  C    LEU A 305      34.425   9.863  33.598  1.00 42.82
ATOM   2329  O    LEU A 305      35.578   9.705  33.198  1.00 54.32
ATOM   2330  N    ARG A 306      34.150  10.353  34.805  1.00 41.87
ATOM   2331  CA   ARG A 306      35.253  10.741  35.681  1.00 51.42
ATOM   2332  CB   ARG A 306      34.725  11.361  36.979  1.00 50.76
ATOM   2333  CG   ARG A 306      34.163  12.761  36.809  1.00 57.18
ATOM   2334  CD   ARG A 306      33.547  13.297  38.093  1.00 63.89
ATOM   2335  NE   ARG A 306      33.871  14.701  38.302  1.00 65.68
ATOM   2336  CZ   ARG A 306      33.491  15.494  39.287  1.00 66.42
ATOM   2337  NH1  ARG A 306      32.710  15.080  40.276  1.00 39.94
ATOM   2338  NH2  ARG A 306      33.906  16.759  39.290  1.00 95.50
```

FIGURE 250

```
ATOM   2339  C   ARG A 306      36.161   9.553  35.988  1.00 65.39
ATOM   2340  O   ARG A 306      37.371   9.710  36.183  1.00 79.48
ATOM   2341  N   ALA A 307      35.593   8.350  36.039  1.00 63.13
ATOM   2342  CA  ALA A 307      36.358   7.181  36.463  1.00 59.88
ATOM   2343  CB  ALA A 307      35.424   6.123  37.032  1.00 62.57
ATOM   2344  C   ALA A 307      37.190   6.603  35.327  1.00 63.48
ATOM   2345  O   ALA A 307      38.185   5.922  35.576  1.00 71.07
ATOM   2346  N   ARG A 308      36.778   6.878  34.095  1.00 66.80
ATOM   2347  CA  ARG A 308      37.460   6.357  32.916  1.00 63.53
ATOM   2348  CB  ARG A 308      36.431   5.843  31.910  1.00 64.58
ATOM   2349  CG  ARG A 308      35.909   6.905  30.956  1.00 73.99
ATOM   2350  CD  ARG A 308      34.390   6.946  30.959  1.00 81.85
ATOM   2351  NE  ARG A 308      33.814   5.939  30.070  1.00 85.42
ATOM   2352  CZ  ARG A 308      33.523   6.167  28.794  1.00 82.34
ATOM   2353  NH1 ARG A 308      33.757   7.365  28.275  1.00 72.00
ATOM   2354  NH2 ARG A 308      33.001   5.198  28.053  1.00 74.84
ATOM   2355  C   ARG A 308      38.356   7.408  32.272  1.00 66.32
ATOM   2356  O   ARG A 308      39.461   7.117  31.813  1.00 55.04
ATOM   2357  N   THR B  20      44.023   9.553  52.894  1.00 44.19
ATOM   2358  CA  THR B  20      43.083   8.735  53.658  1.00 52.64
ATOM   2359  CB  THR B  20      43.790   7.980  54.795  1.00 59.51
ATOM   2360  OG1 THR B  20      45.173   7.808  54.450  1.00 74.31
ATOM   2361  CG2 THR B  20      43.208   6.590  54.985  1.00 67.07
ATOM   2362  C   THR B  20      41.947   9.580  54.229  1.00 46.00
ATOM   2363  O   THR B  20      42.162  10.580  54.911  1.00 47.42
ATOM   2364  N   SER B  21      40.725   9.158  53.926  1.00 41.46
ATOM   2365  CA  SER B  21      39.496   9.819  54.320  1.00 39.05
ATOM   2366  CB  SER B  21      39.040  10.796  53.232  1.00 49.38
ATOM   2367  OG  SER B  21      37.654  10.651  52.968  1.00 64.42
ATOM   2368  C   SER B  21      38.381   8.816  54.580  1.00 45.97
ATOM   2369  O   SER B  21      38.392   7.690  54.078  1.00 58.15
ATOM   2370  N   CYS B  22      37.384   9.218  55.363  1.00 49.85
ATOM   2371  CA  CYS B  22      36.237   8.334  55.572  1.00 50.77
ATOM   2372  CB  CYS B  22      36.423   7.465  56.816  1.00 55.65
ATOM   2373  SG  CYS B  22      35.067   6.307  57.123  1.00 88.47
ATOM   2374  C   CYS B  22      34.951   9.143  55.677  1.00 45.29
ATOM   2375  O   CYS B  22      34.411   9.331  56.767  1.00 58.34
ATOM   2376  N   PRO B  23      34.467   9.632  54.543  1.00 39.55
ATOM   2377  CA  PRO B  23      33.212  10.389  54.528  1.00 41.51
ATOM   2378  CB  PRO B  23      33.049  10.758  53.050  1.00 40.09
ATOM   2379  CG  PRO B  23      34.441  10.713  52.503  1.00 41.78
ATOM   2380  CD  PRO B  23      35.072   9.531  53.203  1.00 44.99
ATOM   2381  C   PRO B  23      32.027   9.552  55.000  1.00 44.21
ATOM   2382  O   PRO B  23      31.963   8.335  54.814  1.00 52.40
ATOM   2383  N   ILE B  24      31.065  10.223  55.624  1.00 44.34
ATOM   2384  CA  ILE B  24      29.827   9.587  56.044  1.00 48.20
ATOM   2385  CB  ILE B  24      29.721   9.319  57.555  1.00 45.03
ATOM   2386  CG1 ILE B  24      31.043   9.095  58.282  1.00 44.77
ATOM   2387  CD1 ILE B  24      31.305  10.113  59.373  1.00 61.25
ATOM   2388  CG2 ILE B  24      28.778   8.151  57.813  1.00 56.04
ATOM   2389  C   ILE B  24      28.646  10.483  55.663  1.00 48.34
ATOM   2390  O   ILE B  24      28.590  11.626  56.128  1.00 36.96
```

FIGURE 251

```
ATOM   2391  N    LYS B  25      27.747    9.948   54.848  1.00  44.27
ATOM   2392  CA   LYS B  25      26.540   10.698   54.492  1.00  52.98
ATOM   2393  CB   LYS B  25      25.594    9.846   53.655  1.00  62.63
ATOM   2394  CG   LYS B  25      25.908    9.737   52.176  1.00  62.43
ATOM   2395  CD   LYS B  25      27.378    9.486   51.908  1.00  63.27
ATOM   2396  CE   LYS B  25      27.772    8.047   52.197  1.00  62.30
ATOM   2397  NZ   LYS B  25      29.243    7.842   52.072  1.00  60.67
ATOM   2398  C    LYS B  25      25.859   11.181   55.772  1.00  48.94
ATOM   2399  O    LYS B  25      25.679   10.387   56.698  1.00  46.18
ATOM   2400  N    ILE B  26      25.523   12.466   55.828  1.00  51.90
ATOM   2401  CA   ILE B  26      24.977   13.025   57.066  1.00  54.24
ATOM   2402  CB   ILE B  26      24.660   14.523   56.951  1.00  63.05
ATOM   2403  CG1  ILE B  26      23.589   14.879   55.916  1.00  68.15
ATOM   2404  CD1  ILE B  26      22.545   15.837   56.460  1.00  71.59
ATOM   2405  CG2  ILE B  26      25.929   15.325   56.685  1.00  65.12
ATOM   2406  C    ILE B  26      23.733   12.241   57.465  1.00  51.02
ATOM   2407  O    ILE B  26      23.573   11.830   58.614  1.00  47.65
ATOM   2408  N    ASN B  27      22.870   12.003   56.483  1.00  51.44
ATOM   2409  CA   ASN B  27      21.666   11.219   56.721  1.00  61.45
ATOM   2410  CB   ASN B  27      20.899   10.993   55.415  1.00  75.84
ATOM   2411  CG   ASN B  27      20.870   12.209   54.511  1.00  85.31
ATOM   2412  OD1  ASN B  27      21.910   12.672   54.041  1.00  99.97
ATOM   2413  ND2  ASN B  27      19.672   12.729   54.262  1.00  93.77
ATOM   2414  C    ASN B  27      21.985    9.885   57.379  1.00  55.35
ATOM   2415  O    ASN B  27      21.135    9.336   58.089  1.00  88.25
ATOM   2416  N    GLN B  28      23.176    9.311   57.195  1.00  48.45
ATOM   2417  CA   GLN B  28      23.415    8.047   57.894  1.00  52.09
ATOM   2418  CB   GLN B  28      24.024    6.974   56.990  1.00  57.63
ATOM   2419  CG   GLN B  28      24.654    7.430   55.694  1.00  63.93
ATOM   2420  CD   GLN B  28      24.174    6.638   54.490  1.00  71.84
ATOM   2421  OE1  GLN B  28      24.797    5.657   54.074  1.00  79.09
ATOM   2422  NE2  GLN B  28      23.051    7.067   53.920  1.00  63.99
ATOM   2423  C    GLN B  28      24.321    8.227   59.103  1.00  48.62
ATOM   2424  O    GLN B  28      24.763    7.214   59.654  1.00  48.29
ATOM   2425  N    PHE B  29      24.617    9.452   59.529  1.00  55.12
ATOM   2426  CA   PHE B  29      25.569    9.586   60.626  1.00  55.39
ATOM   2427  CB   PHE B  29      25.852   11.055   61.000  1.00  55.09
ATOM   2428  CG   PHE B  29      27.126   11.084   61.852  1.00  51.70
ATOM   2429  CD1  PHE B  29      28.363   11.038   61.233  1.00  54.80
ATOM   2430  CE1  PHE B  29      29.521   11.046   61.984  1.00  57.30
ATOM   2431  CZ   PHE B  29      29.458   11.100   63.365  1.00  54.61
ATOM   2432  CE2  PHE B  29      28.227   11.150   63.988  1.00  44.82
ATOM   2433  CD2  PHE B  29      27.071   11.145   63.230  1.00  41.09
ATOM   2434  C    PHE B  29      25.123    8.850   61.890  1.00  57.59
ATOM   2435  O    PHE B  29      25.964    8.281   62.594  1.00  47.92
ATOM   2436  N    GLU B  30      23.828    8.867   62.167  1.00  63.38
ATOM   2437  CA   GLU B  30      23.280    8.207   63.344  1.00  62.77
ATOM   2438  CB   GLU B  30      21.748    8.203   63.264  1.00  73.02
ATOM   2439  CG   GLU B  30      21.122    9.397   63.971  1.00  77.36
ATOM   2440  CD   GLU B  30      21.462    9.438   65.448  1.00  78.77
ATOM   2441  OE1  GLU B  30      20.929   10.329   66.141  1.00  79.79
ATOM   2442  OE2  GLU B  30      22.251    8.592   65.918  1.00  84.00
```

FIGURE 252

```
ATOM   2443  C    GLU  B   30      23.793   6.783  63.519  1.00 54.87
ATOM   2444  O    GLU  B   30      24.369   6.475  64.563  1.00 35.09
ATOM   2445  N    GLY  B   31      23.595   5.938  62.517  1.00 59.10
ATOM   2446  CA   GLY  B   31      23.994   4.545  62.525  1.00 56.95
ATOM   2447  C    GLY  B   31      25.493   4.331  62.443  1.00 59.39
ATOM   2448  O    GLY  B   31      26.019   3.379  63.037  1.00 42.38
ATOM   2449  N    HIS  B   32      26.167   5.215  61.710  1.00 59.10
ATOM   2450  CA   HIS  B   32      27.629   5.216  61.649  1.00 51.48
ATOM   2451  CB   HIS  B   32      28.127   6.437  60.888  1.00 51.68
ATOM   2452  CG   HIS  B   32      29.593   6.534  60.618  1.00 64.14
ATOM   2453  ND1  HIS  B   32      30.445   7.321  61.368  1.00 66.96
ATOM   2454  CE1  HIS  B   32      31.680   7.223  60.917  1.00 64.66
ATOM   2455  NE2  HIS  B   32      31.669   6.399  59.884  1.00 69.62
ATOM   2456  CD2  HIS  B   32      30.382   5.959  59.681  1.00 69.44
ATOM   2457  C    HIS  B   32      28.174   5.164  63.071  1.00 48.27
ATOM   2458  O    HIS  B   32      28.812   4.198  63.493  1.00 43.02
ATOM   2459  N    PHE  B   33      27.893   6.215  63.836  1.00 52.78
ATOM   2460  CA   PHE  B   33      28.398   6.300  65.205  1.00 56.25
ATOM   2461  CB   PHE  B   33      27.898   7.596  65.853  1.00 58.42
ATOM   2462  CG   PHE  B   33      28.693   8.008  67.083  1.00 52.11
ATOM   2463  CD1  PHE  B   33      30.015   7.634  67.229  1.00 40.98
ATOM   2464  CE1  PHE  B   33      30.727   8.001  68.354  1.00 46.43
ATOM   2465  CZ   PHE  B   33      30.127   8.753  69.348  1.00 46.14
ATOM   2466  CE2  PHE  B   33      28.806   9.135  69.208  1.00 46.50
ATOM   2467  CD2  PHE  B   33      28.101   8.767  68.079  1.00 53.38
ATOM   2468  C    PHE  B   33      28.022   5.075  66.032  1.00 55.13
ATOM   2469  O    PHE  B   33      28.890   4.473  66.675  1.00 37.79
ATOM   2470  N    MET  B   34      26.755   4.681  66.032  1.00 65.84
ATOM   2471  CA   MET  B   34      26.316   3.484  66.751  1.00 75.38
ATOM   2472  CB   MET  B   34      24.841   3.195  66.464  1.00 80.09
ATOM   2473  CG   MET  B   34      23.886   3.798  67.480  1.00 84.30
ATOM   2474  SD   MET  B   34      22.339   4.405  66.779  1.00 87.53
ATOM   2475  CE   MET  B   34      21.767   2.952  65.905  1.00 52.16
ATOM   2476  C    MET  B   34      27.188   2.284  66.383  1.00 75.48
ATOM   2477  O    MET  B   34      27.588   1.495  67.238  1.00 66.38
ATOM   2478  N    LYS  B   35      27.503   2.192  65.096  1.00 75.62
ATOM   2479  CA   LYS  B   35      28.410   1.192  64.561  1.00 70.36
ATOM   2480  CB   LYS  B   35      28.646   1.437  63.066  1.00 73.89
ATOM   2481  CG   LYS  B   35      27.460   1.150  62.169  1.00 77.64
ATOM   2482  CD   LYS  B   35      27.860   0.247  61.008  1.00 79.39
ATOM   2483  CE   LYS  B   35      27.676  -1.218  61.371  1.00 81.96
ATOM   2484  NZ   LYS  B   35      28.542  -1.629  62.510  1.00 89.41
ATOM   2485  C    LYS  B   35      29.760   1.199  65.265  1.00 64.44
ATOM   2486  O    LYS  B   35      30.185   0.235  65.901  1.00 37.91
ATOM   2487  N    LEU  B   36      30.485   2.316  65.147  1.00 63.16
ATOM   2488  CA   LEU  B   36      31.841   2.334  65.693  1.00 63.09
ATOM   2489  CB   LEU  B   36      32.573   3.624  65.324  1.00 65.24
ATOM   2490  CG   LEU  B   36      32.842   3.848  63.836  1.00 68.40
ATOM   2491  CD1  LEU  B   36      31.931   4.933  63.279  1.00 66.79
ATOM   2492  CD2  LEU  B   36      34.303   4.199  63.599  1.00 81.44
ATOM   2493  C    LEU  B   36      31.826   2.156  67.209  1.00 56.96
ATOM   2494  O    LEU  B   36      32.833   1.728  67.774  1.00 56.27
```

FIGURE 253

```
ATOM   2495  N    GLN B  37      30.691   2.487  67.805  1.00 53.43
ATOM   2496  CA   GLN B  37      30.459   2.414  69.236  1.00 69.43
ATOM   2497  CB   GLN B  37      29.331   3.386  69.619  1.00 68.76
ATOM   2498  CG   GLN B  37      29.831   4.826  69.657  1.00 75.93
ATOM   2499  CD   GLN B  37      28.722   5.824  69.917  1.00 77.13
ATOM   2500  OE1  GLN B  37      27.936   6.137  69.020  1.00 87.89
ATOM   2501  NE2  GLN B  37      28.671   6.319  71.147  1.00 60.96
ATOM   2502  C    GLN B  37      30.117   1.006  69.706  1.00 79.22
ATOM   2503  O    GLN B  37      30.388   0.635  70.850  1.00 73.11
ATOM   2504  N    ALA B  38      29.518   0.228  68.808  1.00 83.91
ATOM   2505  CA   ALA B  38      29.154  -1.148  69.119  1.00 85.90
ATOM   2506  CB   ALA B  38      28.533  -1.809  67.896  1.00 73.44
ATOM   2507  C    ALA B  38      30.354  -1.952  69.612  1.00 87.80
ATOM   2508  O    ALA B  38      31.504  -1.707  69.247  1.00 77.48
ATOM   2509  N    ASP B  39      30.073  -2.936  70.462  1.00 88.62
ATOM   2510  CA   ASP B  39      31.113  -3.821  70.969  1.00 85.89
ATOM   2511  CB   ASP B  39      31.626  -4.719  69.837  1.00 87.42
ATOM   2512  CG   ASP B  39      30.689  -5.885  69.586  1.00 90.49
ATOM   2513  OD1  ASP B  39      30.455  -6.223  68.408  1.00 97.09
ATOM   2514  OD2  ASP B  39      30.188  -6.455  70.579  1.00 93.16
ATOM   2515  C    ASP B  39      32.267  -3.044  71.587  1.00 82.50
ATOM   2516  O    ASP B  39      33.429  -3.298  71.271  1.00 76.36
ATOM   2517  N    SER B  40      31.940  -2.102  72.465  1.00 82.73
ATOM   2518  CA   SER B  40      32.957  -1.326  73.165  1.00 79.40
ATOM   2519  CB   SER B  40      33.839  -2.246  74.009  1.00 75.80
ATOM   2520  OG   SER B  40      34.651  -3.081  73.205  1.00 54.94
ATOM   2521  C    SER B  40      33.807  -0.518  72.180  1.00 76.46
ATOM   2522  O    SER B  40      35.024  -0.714  72.131  1.00 64.01
ATOM   2523  N    ASN B  41      33.121   0.352  71.454  1.00 73.19
ATOM   2524  CA   ASN B  41      33.647   1.191  70.394  1.00 71.55
ATOM   2525  CB   ASN B  41      34.253   2.492  70.912  1.00 67.00
ATOM   2526  CG   ASN B  41      33.360   3.337  71.784  1.00 65.98
ATOM   2527  OD1  ASN B  41      32.134   3.225  71.788  1.00 77.13
ATOM   2528  ND2  ASN B  41      33.976   4.224  72.563  1.00 62.14
ATOM   2529  C    ASN B  41      34.710   0.429  69.603  1.00 74.40
ATOM   2530  O    ASN B  41      35.806   0.941  69.376  1.00 81.24
ATOM   2531  N    TYR B  42      34.393  -0.804  69.212  1.00 74.86
ATOM   2532  CA   TYR B  42      35.405  -1.610  68.534  1.00 74.76
ATOM   2533  CB   TYR B  42      34.880  -3.002  68.168  1.00 75.15
ATOM   2534  CG   TYR B  42      35.907  -3.795  67.386  1.00 75.66
ATOM   2535  CD1  TYR B  42      37.017  -4.332  68.023  1.00 78.98
ATOM   2536  CE1  TYR B  42      37.961  -5.054  67.316  1.00 81.79
ATOM   2537  CZ   TYR B  42      37.804  -5.243  65.959  1.00 81.37
ATOM   2538  OH   TYR B  42      38.747  -5.962  65.258  1.00 80.99
ATOM   2539  CE2  TYR B  42      36.713  -4.717  65.304  1.00 76.53
ATOM   2540  CD2  TYR B  42      35.775  -3.996  66.019  1.00 75.88
ATOM   2541  C    TYR B  42      35.914  -0.906  67.277  1.00 72.94
ATOM   2542  O    TYR B  42      37.119  -0.676  67.155  1.00 61.94
ATOM   2543  N    LEU B  43      35.004  -0.570  66.366  1.00 68.88
ATOM   2544  CA   LEU B  43      35.396   0.092  65.128  1.00 70.56
ATOM   2545  CB   LEU B  43      34.188   0.493  64.286  1.00 72.58
ATOM   2546  CG   LEU B  43      33.017  -0.487  64.224  1.00 76.87
```

FIGURE 254

```
ATOM   2547  CD1 LEU B  43      31.993  -0.053  63.184  1.00 62.51
ATOM   2548  CD2 LEU B  43      33.520  -1.895  63.937  1.00 77.97
ATOM   2549  C   LEU B  43      36.248   1.336  65.417  1.00 67.14
ATOM   2550  O   LEU B  43      37.449   1.316  65.140  1.00 50.41
ATOM   2551  N   LEU B  44      35.580   2.345  65.951  1.00 66.03
ATOM   2552  CA  LEU B  44      36.109   3.651  66.304  1.00 61.62
ATOM   2553  CB  LEU B  44      35.238   4.313  67.375  1.00 62.58
ATOM   2554  CG  LEU B  44      35.741   5.640  67.946  1.00 58.19
ATOM   2555  CD1 LEU B  44      34.587   6.622  68.088  1.00 55.67
ATOM   2556  CD2 LEU B  44      36.446   5.433  69.276  1.00 48.14
ATOM   2557  C   LEU B  44      37.551   3.568  66.793  1.00 59.86
ATOM   2558  O   LEU B  44      38.446   4.143  66.175  1.00 48.99
ATOM   2559  N   SER B  45      37.750   2.840  67.887  1.00 64.48
ATOM   2560  CA  SER B  45      39.072   2.646  68.456  1.00 71.61
ATOM   2561  CB  SER B  45      39.047   1.584  69.560  1.00 73.68
ATOM   2562  OG  SER B  45      40.284   0.883  69.574  1.00 76.78
ATOM   2563  C   SER B  45      40.089   2.224  67.396  1.00 71.36
ATOM   2564  O   SER B  45      41.209   2.728  67.377  1.00 52.39
ATOM   2565  N   LYS B  46      39.662   1.295  66.549  1.00 78.57
ATOM   2566  CA  LYS B  46      40.501   0.742  65.494  1.00 84.31
ATOM   2567  CB  LYS B  46      39.848  -0.499  64.885  1.00 89.10
ATOM   2568  CG  LYS B  46      40.772  -1.693  64.707  1.00 85.70
ATOM   2569  CD  LYS B  46      40.699  -2.236  63.288  1.00 83.59
ATOM   2570  CE  LYS B  46      41.199  -3.666  63.201  1.00 84.74
ATOM   2571  NZ  LYS B  46      40.192  -4.641  63.706  1.00 92.84
ATOM   2572  C   LYS B  46      40.773   1.795  64.420  1.00 81.13
ATOM   2573  O   LYS B  46      41.920   1.966  64.005  1.00 84.85
ATOM   2574  N   GLU B  47      39.718   2.485  64.012  1.00 74.35
ATOM   2575  CA  GLU B  47      39.755   3.570  63.041  1.00 70.19
ATOM   2576  CB  GLU B  47      38.323   3.963  62.661  1.00 66.52
ATOM   2577  CG  GLU B  47      38.025   5.446  62.668  1.00 62.55
ATOM   2578  CD  GLU B  47      36.885   5.861  61.763  1.00 59.88
ATOM   2579  OE1 GLU B  47      36.350   5.017  61.015  1.00 48.61
ATOM   2580  OE2 GLU B  47      36.514   7.057  61.794  1.00 47.49
ATOM   2581  C   GLU B  47      40.536   4.777  63.555  1.00 65.98
ATOM   2582  O   GLU B  47      40.806   5.729  62.818  1.00 61.94
ATOM   2583  N   TYR B  48      40.929   4.759  64.822  1.00 59.02
ATOM   2584  CA  TYR B  48      41.740   5.813  65.412  1.00 54.32
ATOM   2585  CB  TYR B  48      41.164   6.221  66.766  1.00 47.04
ATOM   2586  CG  TYR B  48      41.966   7.305  67.448  1.00 43.40
ATOM   2587  CD1 TYR B  48      41.837   8.629  67.048  1.00 39.64
ATOM   2588  CE1 TYR B  48      42.565   9.622  67.667  1.00 35.48
ATOM   2589  CZ  TYR B  48      43.426   9.313  68.688  1.00 33.02
ATOM   2590  OH  TYR B  48      44.149  10.314  69.302  1.00 49.28
ATOM   2591  CE2 TYR B  48      43.570   8.007  69.103  1.00 43.77
ATOM   2592  CD2 TYR B  48      42.842   7.011  68.481  1.00 38.80
ATOM   2593  C   TYR B  48      43.182   5.374  65.585  1.00 59.37
ATOM   2594  O   TYR B  48      44.124   6.169  65.563  1.00 53.93
ATOM   2595  N   GLU B  49      43.427   4.067  65.759  1.00 56.83
ATOM   2596  CA  GLU B  49      44.857   3.719  65.788  1.00 52.72
ATOM   2597  CB  GLU B  49      45.118   2.439  66.568  1.00 61.99
ATOM   2598  CG  GLU B  49      46.098   2.586  67.723  1.00 66.59
```

FIGURE 255

```
ATOM   2599  CD   GLU B  49      45.724   3.661  68.723  1.00 68.99
ATOM   2600  OE1  GLU B  49      44.737   3.486  69.468  1.00 71.09
ATOM   2601  OE2  GLU B  49      46.424   4.699  68.778  1.00 64.67
ATOM   2602  C    GLU B  49      45.353   3.635  64.349  1.00 43.12
ATOM   2603  O    GLU B  49      46.539   3.492  64.069  1.00 46.58
ATOM   2604  N    GLU B  50      44.424   3.733  63.404  1.00 35.51
ATOM   2605  CA   GLU B  50      44.790   3.731  61.992  1.00 48.92
ATOM   2606  CB   GLU B  50      43.546   3.509  61.132  1.00 55.98
ATOM   2607  CG   GLU B  50      43.820   2.894  59.769  1.00 62.45
ATOM   2608  CD   GLU B  50      42.672   3.111  58.802  1.00 72.64
ATOM   2609  OE1  GLU B  50      42.932   3.465  57.632  1.00 97.10
ATOM   2610  OE2  GLU B  50      41.505   2.932  59.214  1.00 90.89
ATOM   2611  C    GLU B  50      45.484   5.036  61.609  1.00 51.81
ATOM   2612  O    GLU B  50      46.447   5.031  60.840  1.00 60.14
ATOM   2613  N    LEU B  51      44.993   6.142  62.157  1.00 45.17
ATOM   2614  CA   LEU B  51      45.544   7.474  61.921  1.00 36.37
ATOM   2615  CB   LEU B  51      44.599   8.527  62.511  1.00 31.85
ATOM   2616  CG   LEU B  51      43.381   8.867  61.656  1.00 28.95
ATOM   2617  CD1  LEU B  51      42.269   9.488  62.490  1.00 29.93
ATOM   2618  CD2  LEU B  51      43.770   9.789  60.507  1.00 38.39
ATOM   2619  C    LEU B  51      46.931   7.623  62.529  1.00 40.25
ATOM   2620  O    LEU B  51      47.666   8.567  62.254  1.00 43.39
ATOM   2621  N    LYS B  52      47.288   6.661  63.367  1.00 39.11
ATOM   2622  CA   LYS B  52      48.486   6.628  64.172  1.00 41.30
ATOM   2623  CB   LYS B  52      48.607   5.228  64.795  1.00 38.29
ATOM   2624  CG   LYS B  52      49.077   5.211  66.234  1.00 41.48
ATOM   2625  CD   LYS B  52      49.745   3.871  66.543  1.00 42.51
ATOM   2626  CE   LYS B  52      49.996   3.752  68.036  1.00 44.45
ATOM   2627  NZ   LYS B  52      48.720   3.710  68.803  1.00 54.34
ATOM   2628  C    LYS B  52      49.776   6.939  63.433  1.00 43.04
ATOM   2629  O    LYS B  52      50.637   7.651  63.963  1.00 51.42
ATOM   2630  N    ASP B  53      49.981   6.421  62.225  1.00 35.92
ATOM   2631  CA   ASP B  53      51.272   6.646  61.580  1.00 36.34
ATOM   2632  CB   ASP B  53      51.714   5.388  60.823  1.00 46.86
ATOM   2633  CG   ASP B  53      51.520   4.136  61.665  1.00 60.28
ATOM   2634  OD1  ASP B  53      50.750   3.258  61.221  1.00 74.44
ATOM   2635  OD2  ASP B  53      52.132   4.051  62.753  1.00 57.58
ATOM   2636  C    ASP B  53      51.267   7.819  60.606  1.00 25.54
ATOM   2637  O    ASP B  53      52.315   8.092  60.019  1.00 31.31
ATOM   2638  N    VAL B  54      50.126   8.459  60.444  1.00 25.37
ATOM   2639  CA   VAL B  54      50.004   9.549  59.477  1.00 28.87
ATOM   2640  CB   VAL B  54      48.603  10.168  59.522  1.00 32.29
ATOM   2641  CG1  VAL B  54      48.397  11.175  58.399  1.00 27.43
ATOM   2642  CG2  VAL B  54      47.541   9.073  59.433  1.00 35.45
ATOM   2643  C    VAL B  54      51.089  10.587  59.747  1.00 35.40
ATOM   2644  O    VAL B  54      51.266  11.007  60.887  1.00 28.36
ATOM   2645  N    GLY B  55      51.818  10.950  58.704  1.00 30.35
ATOM   2646  CA   GLY B  55      52.888  11.904  58.678  1.00 26.77
ATOM   2647  C    GLY B  55      54.129  11.566  59.459  1.00 31.10
ATOM   2648  O    GLY B  55      54.988  12.440  59.618  1.00 28.63
ATOM   2649  N    ARG B  56      54.281  10.344  59.959  1.00 31.74
ATOM   2650  CA   ARG B  56      55.404   9.997  60.827  1.00 37.30
```

FIGURE 256

```
ATOM   2651  CB   ARG B  56      55.077   8.697  61.573  1.00  46.87
ATOM   2652  CG   ARG B  56      55.107   7.449  60.705  1.00  56.15
ATOM   2653  CD   ARG B  56      55.129   6.169  61.530  1.00  51.35
ATOM   2654  NE   ARG B  56      56.387   5.999  62.253  1.00  46.32
ATOM   2655  CZ   ARG B  56      56.583   5.142  63.245  1.00  43.24
ATOM   2656  NH1  ARG B  56      55.595   4.357  63.646  1.00  38.49
ATOM   2657  NH2  ARG B  56      57.771   5.074  63.831  1.00  37.94
ATOM   2658  C    ARG B  56      56.729   9.869  60.089  1.00  44.81
ATOM   2659  O    ARG B  56      57.782   9.586  60.675  1.00  33.22
ATOM   2660  N    ASN B  57      56.702  10.084  58.779  1.00  40.44
ATOM   2661  CA   ASN B  57      57.876  10.023  57.931  1.00  33.30
ATOM   2662  CB   ASN B  57      57.436   9.773  56.482  1.00  44.90
ATOM   2663  CG   ASN B  57      56.483  10.848  55.987  1.00  53.38
ATOM   2664  OD1  ASN B  57      56.798  11.576  55.040  1.00  73.52
ATOM   2665  ND2  ASN B  57      55.311  10.971  56.602  1.00  38.90
ATOM   2666  C    ASN B  57      58.691  11.308  57.972  1.00  31.80
ATOM   2667  O    ASN B  57      59.810  11.344  57.465  1.00  31.72
ATOM   2668  N    GLN B  58      58.129  12.357  58.569  1.00  28.77
ATOM   2669  CA   GLN B  58      58.736  13.681  58.549  1.00  24.41
ATOM   2670  CB   GLN B  58      57.611  14.729  58.466  1.00  27.17
ATOM   2671  CG   GLN B  58      56.688  14.411  57.292  1.00  28.52
ATOM   2672  CD   GLN B  58      55.494  15.335  57.233  1.00  31.70
ATOM   2673  OE1  GLN B  58      55.513  16.340  56.520  1.00  30.23
ATOM   2674  NE2  GLN B  58      54.460  14.991  57.992  1.00  28.20
ATOM   2675  C    GLN B  58      59.621  13.965  59.743  1.00  26.40
ATOM   2676  O    GLN B  58      59.307  13.588  60.865  1.00  32.07
ATOM   2677  N    SER B  59      60.750  14.633  59.494  1.00  21.54
ATOM   2678  CA   SER B  59      61.713  14.878  60.552  1.00  25.17
ATOM   2679  CB   SER B  59      63.136  14.784  60.000  1.00  31.63
ATOM   2680  OG   SER B  59      63.435  15.925  59.212  1.00  43.09
ATOM   2681  C    SER B  59      61.470  16.250  61.193  1.00  29.30
ATOM   2682  O    SER B  59      60.674  17.010  60.635  1.00  24.20
ATOM   2683  N    CYS B  60      62.166  16.479  62.290  1.00  25.59
ATOM   2684  CA   CYS B  60      62.116  17.647  63.149  1.00  30.08
ATOM   2685  CB   CYS B  60      61.390  17.257  64.451  1.00  26.43
ATOM   2686  SG   CYS B  60      59.647  16.884  64.130  1.00  33.04
ATOM   2687  C    CYS B  60      63.489  18.201  63.472  1.00  33.64
ATOM   2688  O    CYS B  60      63.790  18.632  64.592  1.00  25.31
ATOM   2689  N    ASP B  61      64.361  18.193  62.463  1.00  23.90
ATOM   2690  CA   ASP B  61      65.744  18.559  62.696  1.00  19.83
ATOM   2691  CB   ASP B  61      66.538  18.374  61.392  1.00  28.21
ATOM   2692  CG   ASP B  61      66.602  16.912  60.974  1.00  37.45
ATOM   2693  OD1  ASP B  61      66.668  16.033  61.857  1.00  46.92
ATOM   2694  OD2  ASP B  61      66.585  16.633  59.756  1.00  39.28
ATOM   2695  C    ASP B  61      65.931  19.978  63.202  1.00  18.89
ATOM   2696  O    ASP B  61      66.742  20.234  64.100  1.00  26.23
ATOM   2697  N    ILE B  62      65.208  20.944  62.642  1.00  17.76
ATOM   2698  CA   ILE B  62      65.463  22.312  63.098  1.00  16.77
ATOM   2699  CB   ILE B  62      64.737  23.351  62.222  1.00  26.79
ATOM   2700  CG1  ILE B  62      65.028  23.219  60.729  1.00  30.78
ATOM   2701  CD1  ILE B  62      66.350  22.561  60.400  1.00  49.88
ATOM   2702  CG2  ILE B  62      65.029  24.761  62.731  1.00  20.53
```

FIGURE 257

```
ATOM   2703  C    ILE  B   62      65.015  22.503  64.540  1.00  21.81
ATOM   2704  O    ILE  B   62      65.635  23.218  65.328  1.00  26.45
ATOM   2705  N    ALA  B   63      63.903  21.860  64.890  1.00  22.22
ATOM   2706  CA   ALA  B   63      63.421  22.042  66.267  1.00  23.49
ATOM   2707  CB   ALA  B   63      62.039  21.427  66.404  1.00  13.73
ATOM   2708  C    ALA  B   63      64.438  21.456  67.235  1.00  32.72
ATOM   2709  O    ALA  B   63      64.621  21.898  68.366  1.00  29.49
ATOM   2710  N    LEU  B   64      65.142  20.427  66.770  1.00  26.75
ATOM   2711  CA   LEU  B   64      66.097  19.704  67.590  1.00  24.87
ATOM   2712  CB   LEU  B   64      66.248  18.272  67.035  1.00  30.01
ATOM   2713  CG   LEU  B   64      65.032  17.393  67.356  1.00  30.13
ATOM   2714  CD1  LEU  B   64      65.068  16.082  66.591  1.00  23.61
ATOM   2715  CD2  LEU  B   64      64.982  17.171  68.862  1.00  35.44
ATOM   2716  C    LEU  B   64      67.454  20.371  67.657  1.00  28.99
ATOM   2717  O    LEU  B   64      68.343  19.889  68.367  1.00  41.07
ATOM   2718  N    LEU  B   65      67.636  21.470  66.927  1.00  26.97
ATOM   2719  CA   LEU  B   65      68.925  22.152  66.964  1.00  25.83
ATOM   2720  CB   LEU  B   65      68.955  23.340  66.001  1.00  29.04
ATOM   2721  CG   LEU  B   65      69.017  23.002  64.513  1.00  33.55
ATOM   2722  CD1  LEU  B   65      68.843  24.264  63.679  1.00  36.14
ATOM   2723  CD2  LEU  B   65      70.327  22.301  64.180  1.00  39.25
ATOM   2724  C    LEU  B   65      69.234  22.654  68.373  1.00  30.40
ATOM   2725  O    LEU  B   65      68.329  23.174  69.021  1.00  31.08
ATOM   2726  N    PRO  B   66      70.470  22.487  68.809  1.00  33.09
ATOM   2727  CA   PRO  B   66      70.935  22.972  70.112  1.00  41.49
ATOM   2728  CB   PRO  B   66      72.456  23.052  69.889  1.00  43.28
ATOM   2729  CG   PRO  B   66      72.722  21.860  69.020  1.00  38.43
ATOM   2730  CD   PRO  B   66      71.543  21.766  68.091  1.00  35.99
ATOM   2731  C    PRO  B   66      70.390  24.336  70.511  1.00  44.08
ATOM   2732  O    PRO  B   66      69.735  24.440  71.557  1.00  50.98
ATOM   2733  N    GLU  B   67      70.636  25.375  69.722  1.00  35.08
ATOM   2734  CA   GLU  B   67      70.246  26.724  70.105  1.00  39.35
ATOM   2735  CB   GLU  B   67      70.775  27.730  69.068  1.00  38.98
ATOM   2736  CG   GLU  B   67      71.059  27.062  67.732  1.00  52.87
ATOM   2737  CD   GLU  B   67      70.712  27.954  66.555  1.00  59.99
ATOM   2738  OE1  GLU  B   67      71.040  29.158  66.611  1.00  78.27
ATOM   2739  OE2  GLU  B   67      70.119  27.433  65.586  1.00  46.11
ATOM   2740  C    GLU  B   67      68.744  26.916  70.246  1.00  38.16
ATOM   2741  O    GLU  B   67      68.327  27.971  70.736  1.00  36.75
ATOM   2742  N    ASN  B   68      67.935  25.950  69.821  1.00  29.98
ATOM   2743  CA   ASN  B   68      66.493  26.069  69.927  1.00  24.34
ATOM   2744  CB   ASN  B   68      65.775  25.589  68.662  1.00  22.49
ATOM   2745  CG   ASN  B   68      66.037  26.469  67.459  1.00  23.36
ATOM   2746  OD1  ASN  B   68      66.205  27.674  67.613  1.00  24.40
ATOM   2747  ND2  ASN  B   68      66.092  25.871  66.273  1.00  19.47
ATOM   2748  C    ASN  B   68      65.957  25.255  71.100  1.00  28.35
ATOM   2749  O    ASN  B   68      64.733  25.161  71.233  1.00  31.84
ATOM   2750  N    ARG  B   69      66.821  24.667  71.924  1.00  28.07
ATOM   2751  CA   ARG  B   69      66.284  23.759  72.950  1.00  39.17
ATOM   2752  CB   ARG  B   69      67.429  23.142  73.757  1.00  53.87
ATOM   2753  CG   ARG  B   69      66.997  22.065  74.739  1.00  67.65
ATOM   2754  CD   ARG  B   69      68.095  21.761  75.748  1.00  84.00
```

FIGURE 258

```
ATOM   2755  NE   ARG B  69      67.751  22.204  77.096  1.00 97.13
ATOM   2756  CZ   ARG B  69      68.057  21.573  78.220  1.00102.06
ATOM   2757  NH1  ARG B  69      68.733  20.432  78.192  1.00107.87
ATOM   2758  NH2  ARG B  69      67.686  22.083  79.390  1.00 97.89
ATOM   2759  C    ARG B  69      65.290  24.445  73.877  1.00 34.20
ATOM   2760  O    ARG B  69      64.217  23.908  74.184  1.00 35.41
ATOM   2761  N    GLY B  70      65.616  25.659  74.328  1.00 21.83
ATOM   2762  CA   GLY B  70      64.720  26.300  75.284  1.00 24.46
ATOM   2763  C    GLY B  70      63.455  26.843  74.655  1.00 27.71
ATOM   2764  O    GLY B  70      62.569  27.348  75.354  1.00 27.30
ATOM   2765  N    LYS B  71      63.327  26.770  73.329  1.00 24.69
ATOM   2766  CA   LYS B  71      62.166  27.353  72.655  1.00 22.38
ATOM   2767  CB   LYS B  71      62.587  27.893  71.274  1.00 24.49
ATOM   2768  CG   LYS B  71      63.764  28.870  71.323  1.00 19.45
ATOM   2769  CD   LYS B  71      64.184  29.275  69.921  1.00 23.88
ATOM   2770  CE   LYS B  71      65.345  30.261  69.951  1.00 28.97
ATOM   2771  NZ   LYS B  71      66.081  30.241  68.653  1.00 31.46
ATOM   2772  C    LYS B  71      61.010  26.379  72.521  1.00 17.66
ATOM   2773  O    LYS B  71      59.934  26.726  72.014  1.00 18.84
ATOM   2774  N    ASN B  72      61.211  25.140  72.984  1.00 15.08
ATOM   2775  CA   ASN B  72      60.162  24.136  72.990  1.00 14.64
ATOM   2776  CB   ASN B  72      60.706  22.823  72.400  1.00 18.63
ATOM   2777  CG   ASN B  72      61.196  23.022  70.977  1.00 21.72
ATOM   2778  OD1  ASN B  72      60.464  23.572  70.157  1.00 19.84
ATOM   2779  ND2  ASN B  72      62.409  22.607  70.663  1.00 16.01
ATOM   2780  C    ASN B  72      59.640  23.891  74.408  1.00 14.08
ATOM   2781  O    ASN B  72      60.429  23.667  75.324  1.00 19.73
ATOM   2782  N    ARG B  73      58.334  23.951  74.601  1.00 15.40
ATOM   2783  CA   ARG B  73      57.720  23.714  75.893  1.00 23.30
ATOM   2784  CB   ARG B  73      56.221  23.993  75.832  1.00 17.66
ATOM   2785  CG   ARG B  73      55.551  23.888  77.187  1.00 14.92
ATOM   2786  CD   ARG B  73      54.140  24.412  77.108  1.00 14.81
ATOM   2787  NE   ARG B  73      54.131  25.882  77.110  1.00 17.20
ATOM   2788  CZ   ARG B  73      54.259  26.568  78.241  1.00 22.34
ATOM   2789  NH1  ARG B  73      54.403  25.967  79.421  1.00 13.10
ATOM   2790  NH2  ARG B  73      54.229  27.883  78.127  1.00 19.63
ATOM   2791  C    ARG B  73      57.917  22.253  76.319  1.00 28.40
ATOM   2792  O    ARG B  73      58.144  21.962  77.484  1.00 19.38
ATOM   2793  N    TYR B  74      57.810  21.373  75.335  1.00 22.53
ATOM   2794  CA   TYR B  74      57.930  19.925  75.513  1.00 16.28
ATOM   2795  CB   TYR B  74      56.580  19.271  75.323  1.00 19.24
ATOM   2796  CG   TYR B  74      55.438  19.771  76.176  1.00 19.80
ATOM   2797  CD1  TYR B  74      55.345  19.402  77.515  1.00 21.42
ATOM   2798  CE1  TYR B  74      54.301  19.844  78.304  1.00 21.50
ATOM   2799  CZ   TYR B  74      53.324  20.663  77.785  1.00 18.77
ATOM   2800  OH   TYR B  74      52.288  21.098  78.587  1.00 23.74
ATOM   2801  CE2  TYR B  74      53.379  21.045  76.460  1.00 12.51
ATOM   2802  CD2  TYR B  74      54.439  20.586  75.681  1.00 13.12
ATOM   2803  C    TYR B  74      58.958  19.399  74.521  1.00 22.96
ATOM   2804  O    TYR B  74      58.901  19.662  73.319  1.00 22.52
ATOM   2805  N    ASN B  75      59.951  18.640  74.966  1.00 26.45
ATOM   2806  CA   ASN B  75      61.042  18.268  74.058  1.00 23.82
```

FIGURE 259

| ATOM | 2807 | CB | ASN | B | 75 | 62.205 | 17.736 | 74.904 | 1.00 | 32.86 |
| ATOM | 2808 | CG | ASN | B | 75 | 62.817 | 18.860 | 75.726 | 1.00 | 45.64 |
| ATOM | 2809 | OD1 | ASN | B | 75 | 63.098 | 18.687 | 76.911 | 1.00 | 76.89 |
| ATOM | 2810 | ND2 | ASN | B | 75 | 63.024 | 20.023 | 75.113 | 1.00 | 56.37 |
| ATOM | 2811 | C | ASN | B | 75 | 60.615 | 17.280 | 72.990 | 1.00 | 17.41 |
| ATOM | 2812 | O | ASN | B | 75 | 61.316 | 17.091 | 71.993 | 1.00 | 28.78 |
| ATOM | 2813 | N | ASN | B | 76 | 59.458 | 16.656 | 73.144 | 1.00 | 23.38 |
| ATOM | 2814 | CA | ASN | B | 76 | 58.985 | 15.644 | 72.207 | 1.00 | 29.72 |
| ATOM | 2815 | CB | ASN | B | 76 | 58.807 | 14.310 | 72.941 | 1.00 | 30.87 |
| ATOM | 2816 | CG | ASN | B | 76 | 57.687 | 14.316 | 73.956 | 1.00 | 32.40 |
| ATOM | 2817 | OD1 | ASN | B | 76 | 57.263 | 15.350 | 74.472 | 1.00 | 30.85 |
| ATOM | 2818 | ND2 | ASN | B | 76 | 57.182 | 13.123 | 74.264 | 1.00 | 26.52 |
| ATOM | 2819 | C | ASN | B | 76 | 57.695 | 16.072 | 71.529 | 1.00 | 27.58 |
| ATOM | 2820 | O | ASN | B | 76 | 56.906 | 15.286 | 71.002 | 1.00 | 20.64 |
| ATOM | 2821 | N | ILE | B | 77 | 57.457 | 17.394 | 71.539 | 1.00 | 21.12 |
| ATOM | 2822 | CA | ILE | B | 77 | 56.355 | 17.899 | 70.728 | 1.00 | 21.78 |
| ATOM | 2823 | CB | ILE | B | 77 | 55.141 | 18.381 | 71.519 | 1.00 | 18.13 |
| ATOM | 2824 | CG1 | ILE | B | 77 | 54.513 | 17.334 | 72.446 | 1.00 | 20.08 |
| ATOM | 2825 | CD1 | ILE | B | 77 | 53.650 | 16.337 | 71.722 | 1.00 | 23.88 |
| ATOM | 2826 | CG2 | ILE | B | 77 | 54.103 | 18.928 | 70.552 | 1.00 | 17.41 |
| ATOM | 2827 | C | ILE | B | 77 | 56.919 | 19.048 | 69.880 | 1.00 | 21.40 |
| ATOM | 2828 | O | ILE | B | 77 | 56.994 | 20.175 | 70.348 | 1.00 | 16.51 |
| ATOM | 2829 | N | LEU | B | 78 | 57.354 | 18.703 | 68.682 | 1.00 | 17.91 |
| ATOM | 2830 | CA | LEU | B | 78 | 58.074 | 19.610 | 67.792 | 1.00 | 14.62 |
| ATOM | 2831 | CB | LEU | B | 78 | 59.558 | 19.235 | 67.683 | 1.00 | 19.22 |
| ATOM | 2832 | CG | LEU | B | 78 | 60.190 | 18.709 | 68.980 | 1.00 | 24.19 |
| ATOM | 2833 | CD1 | LEU | B | 78 | 61.387 | 17.832 | 68.669 | 1.00 | 25.60 |
| ATOM | 2834 | CD2 | LEU | B | 78 | 60.571 | 19.861 | 69.903 | 1.00 | 24.35 |
| ATOM | 2835 | C | LEU | B | 78 | 57.435 | 19.608 | 66.409 | 1.00 | 18.54 |
| ATOM | 2836 | O | LEU | B | 78 | 56.815 | 18.637 | 65.968 | 1.00 | 20.82 |
| ATOM | 2837 | N | PRO | B | 79 | 57.571 | 20.731 | 65.709 | 1.00 | 20.55 |
| ATOM | 2838 | CA | PRO | B | 79 | 56.989 | 20.844 | 64.367 | 1.00 | 19.22 |
| ATOM | 2839 | CB | PRO | B | 79 | 57.039 | 22.345 | 64.119 | 1.00 | 13.66 |
| ATOM | 2840 | CG | PRO | B | 79 | 58.250 | 22.790 | 64.870 | 1.00 | 15.94 |
| ATOM | 2841 | CD | PRO | B | 79 | 58.277 | 21.944 | 66.121 | 1.00 | 16.86 |
| ATOM | 2842 | C | PRO | B | 79 | 57.883 | 20.131 | 63.351 | 1.00 | 11.53 |
| ATOM | 2843 | O | PRO | B | 79 | 59.095 | 20.108 | 63.519 | 1.00 | 19.21 |
| ATOM | 2844 | N | TYR | B | 80 | 57.241 | 19.570 | 62.352 | 1.00 | 16.10 |
| ATOM | 2845 | CA | TYR | B | 80 | 57.888 | 18.998 | 61.189 | 1.00 | 18.42 |
| ATOM | 2846 | CB | TYR | B | 80 | 56.838 | 18.332 | 60.309 | 1.00 | 19.59 |
| ATOM | 2847 | CG | TYR | B | 80 | 56.182 | 17.120 | 60.923 | 1.00 | 16.10 |
| ATOM | 2848 | CD1 | TYR | B | 80 | 56.947 | 16.162 | 61.577 | 1.00 | 18.02 |
| ATOM | 2849 | CE1 | TYR | B | 80 | 56.303 | 15.060 | 62.124 | 1.00 | 17.97 |
| ATOM | 2850 | CZ | TYR | B | 80 | 54.947 | 14.908 | 62.021 | 1.00 | 19.16 |
| ATOM | 2851 | OH | TYR | B | 80 | 54.319 | 13.807 | 62.575 | 1.00 | 29.70 |
| ATOM | 2852 | CE2 | TYR | B | 80 | 54.174 | 15.848 | 61.375 | 1.00 | 23.11 |
| ATOM | 2853 | CD2 | TYR | B | 80 | 54.816 | 16.945 | 60.831 | 1.00 | 16.60 |
| ATOM | 2854 | C | TYR | B | 80 | 58.596 | 20.101 | 60.399 | 1.00 | 23.17 |
| ATOM | 2855 | O | TYR | B | 80 | 58.013 | 21.187 | 60.227 | 1.00 | 20.07 |
| ATOM | 2856 | N | ASP | B | 81 | 59.813 | 19.801 | 59.961 | 1.00 | 18.92 |
| ATOM | 2857 | CA | ASP | B | 81 | 60.613 | 20.748 | 59.186 | 1.00 | 25.46 |
| ATOM | 2858 | CB | ASP | B | 81 | 61.883 | 20.083 | 58.649 | 1.00 | 35.12 |

FIGURE 260

```
ATOM   2859  CG   ASP B  81      62.912  19.827  59.726  1.00 34.96
ATOM   2860  OD1  ASP B  81      62.916  20.589  60.714  1.00 26.58
ATOM   2861  OD2  ASP B  81      63.711  18.878  59.602  1.00 34.17
ATOM   2862  C    ASP B  81      59.815  21.292  58.006  1.00 24.68
ATOM   2863  O    ASP B  81      59.877  22.476  57.667  1.00 30.63
ATOM   2864  N    ALA B  82      59.076  20.393  57.377  1.00 21.31
ATOM   2865  CA   ALA B  82      58.381  20.689  56.123  1.00 26.95
ATOM   2866  CB   ALA B  82      57.912  19.386  55.477  1.00 20.31
ATOM   2867  C    ALA B  82      57.202  21.637  56.283  1.00 33.87
ATOM   2868  O    ALA B  82      56.749  22.267  55.323  1.00 20.97
ATOM   2869  N    THR B  83      56.636  21.770  57.486  1.00 28.89
ATOM   2870  CA   THR B  83      55.445  22.602  57.616  1.00 17.68
ATOM   2871  CB   THR B  83      54.208  21.738  57.906  1.00 21.79
ATOM   2872  OG1  THR B  83      54.406  21.013  59.135  1.00 23.91
ATOM   2873  CG2  THR B  83      54.006  20.709  56.804  1.00 19.27
ATOM   2874  C    THR B  83      55.581  23.645  58.723  1.00 17.70
ATOM   2875  O    THR B  83      54.598  24.307  59.062  1.00 19.85
ATOM   2876  N    ARG B  84      56.768  23.799  59.299  1.00 17.15
ATOM   2877  CA   ARG B  84      56.880  24.747  60.406  1.00 21.26
ATOM   2878  CB   ARG B  84      58.224  24.629  61.116  1.00 18.18
ATOM   2879  CG   ARG B  84      59.419  25.008  60.264  1.00 19.29
ATOM   2880  CD   ARG B  84      60.737  24.812  60.999  1.00 26.01
ATOM   2881  NE   ARG B  84      61.852  25.270  60.167  1.00 27.31
ATOM   2882  CZ   ARG B  84      62.526  26.386  60.390  1.00 21.69
ATOM   2883  NH1  ARG B  84      62.193  27.161  61.422  1.00 22.24
ATOM   2884  NH2  ARG B  84      63.521  26.738  59.595  1.00 19.19
ATOM   2885  C    ARG B  84      56.677  26.175  59.897  1.00 24.93
ATOM   2886  O    ARG B  84      56.868  26.452  58.713  1.00 16.17
ATOM   2887  N    VAL B  85      56.283  27.055  60.809  1.00 19.84
ATOM   2888  CA   VAL B  85      56.219  28.487  60.544  1.00 18.69
ATOM   2889  CB   VAL B  85      55.146  29.192  61.386  1.00 16.28
ATOM   2890  CG1  VAL B  85      55.102  30.685  61.039  1.00 23.59
ATOM   2891  CG2  VAL B  85      53.777  28.590  61.148  1.00 12.01
ATOM   2892  C    VAL B  85      57.571  29.131  60.815  1.00 17.55
ATOM   2893  O    VAL B  85      58.203  28.908  61.852  1.00 25.85
ATOM   2894  N    LYS B  86      58.044  29.941  59.868  1.00 18.16
ATOM   2895  CA   LYS B  86      59.348  30.575  60.022  1.00 22.13
ATOM   2896  CB   LYS B  86      60.149  30.469  58.717  1.00 23.96
ATOM   2897  CG   LYS B  86      60.650  29.070  58.416  1.00 23.28
ATOM   2898  CD   LYS B  86      60.864  28.859  56.929  1.00 35.17
ATOM   2899  CE   LYS B  86      61.343  27.446  56.630  1.00 42.63
ATOM   2900  NZ   LYS B  86      62.795  27.284  56.931  1.00 62.83
ATOM   2901  C    LYS B  86      59.240  32.051  60.400  1.00 25.13
ATOM   2902  O    LYS B  86      58.381  32.768  59.867  1.00 22.58
ATOM   2903  N    LEU B  87      60.112  32.497  61.294  1.00 23.50
ATOM   2904  CA   LEU B  87      60.204  33.921  61.604  1.00 27.10
ATOM   2905  CB   LEU B  87      60.653  34.189  63.033  1.00 25.75
ATOM   2906  CG   LEU B  87      59.927  33.453  64.164  1.00 30.29
ATOM   2907  CD1  LEU B  87      60.620  33.695  65.499  1.00 34.70
ATOM   2908  CD2  LEU B  87      58.467  33.866  64.258  1.00 17.70
ATOM   2909  C    LEU B  87      61.205  34.550  60.631  1.00 35.83
ATOM   2910  O    LEU B  87      62.080  33.839  60.127  1.00 31.73
```

FIGURE 261

```
ATOM   2911  N    SER B  88      61.082  35.842  60.383  1.00 37.78
ATOM   2912  CA   SER B  88      62.022  36.595  59.565  1.00 39.22
ATOM   2913  CB   SER B  88      61.501  38.024  59.360  1.00 37.70
ATOM   2914  OG   SER B  88      62.058  38.842  60.384  1.00 56.30
ATOM   2915  C    SER B  88      63.405  36.685  60.202  1.00 54.75
ATOM   2916  O    SER B  88      63.540  36.552  61.419  1.00 56.41
ATOM   2917  N    ASN B  89      64.420  36.927  59.382  1.00 75.33
ATOM   2918  CA   ASN B  89      65.802  37.090  59.812  1.00 89.87
ATOM   2919  CB   ASN B  89      66.720  37.253  58.599  1.00 90.11
ATOM   2920  CG   ASN B  89      66.156  38.159  57.525  1.00 90.26
ATOM   2921  OD1  ASN B  89      65.038  38.666  57.636  1.00 84.88
ATOM   2922  ND2  ASN B  89      66.932  38.372  56.466  1.00 89.32
ATOM   2923  C    ASN B  89      65.966  38.281  60.749  1.00104.61
ATOM   2924  O    ASN B  89      65.046  39.100  60.888  1.00106.28
ATOM   2925  N    VAL B  90      67.134  38.404  61.376  1.00117.38
ATOM   2926  CA   VAL B  90      67.381  39.480  62.324  1.00128.11
ATOM   2927  CB   VAL B  90      66.614  39.227  63.643  1.00131.44
ATOM   2928  CG1  VAL B  90      65.182  39.743  63.544  1.00127.66
ATOM   2929  CG2  VAL B  90      66.623  37.744  64.000  1.00133.27
ATOM   2930  C    VAL B  90      68.865  39.654  62.644  1.00131.59
ATOM   2931  O    VAL B  90      69.731  39.301  61.846  1.00124.37
ATOM   2932  N    ASP B  91      69.146  40.207  63.826  1.00135.31
ATOM   2933  CA   ASP B  91      70.502  40.379  64.339  1.00137.26
ATOM   2934  CB   ASP B  91      70.482  40.895  65.775  1.00133.67
ATOM   2935  CG   ASP B  91      71.529  41.944  66.104  1.00129.34
ATOM   2936  OD1  ASP B  91      72.177  42.475  65.180  1.00133.28
ATOM   2937  OD2  ASP B  91      71.709  42.256  67.303  1.00105.69
ATOM   2938  C    ASP B  91      71.250  39.050  64.250  1.00141.41
ATOM   2939  O    ASP B  91      70.663  38.007  64.553  1.00146.90
ATOM   2940  N    ASP B  92      72.513  39.087  63.838  1.00141.54
ATOM   2941  CA   ASP B  92      73.278  37.858  63.613  1.00138.38
ATOM   2942  CB   ASP B  92      73.621  37.167  64.928  1.00136.13
ATOM   2943  CG   ASP B  92      75.034  37.428  65.408  1.00132.67
ATOM   2944  OD1  ASP B  92      75.913  37.722  64.570  1.00132.34
ATOM   2945  OD2  ASP B  92      75.280  37.340  66.632  1.00122.69
ATOM   2946  C    ASP B  92      72.468  36.947  62.696  1.00135.79
ATOM   2947  O    ASP B  92      71.582  37.442  61.988  1.00127.98
ATOM   2948  N    ASP B  93      72.728  35.641  62.690  1.00134.71
ATOM   2949  CA   ASP B  93      71.890  34.782  61.848  1.00133.27
ATOM   2950  CB   ASP B  93      72.308  34.930  60.381  1.00139.50
ATOM   2951  CG   ASP B  93      71.490  35.955  59.623  1.00143.40
ATOM   2952  OD1  ASP B  93      70.243  35.893  59.679  1.00148.49
ATOM   2953  OD2  ASP B  93      72.087  36.837  58.963  1.00144.76
ATOM   2954  C    ASP B  93      71.922  33.319  62.260  1.00125.52
ATOM   2955  O    ASP B  93      72.239  32.451  61.438  1.00114.55
ATOM   2956  N    PRO B  94      71.590  32.989  63.500  1.00122.86
ATOM   2957  CA   PRO B  94      71.432  31.573  63.874  1.00118.08
ATOM   2958  CB   PRO B  94      71.775  31.592  65.361  1.00119.79
ATOM   2959  CG   PRO B  94      71.314  32.928  65.833  1.00121.96
ATOM   2960  CD   PRO B  94      71.339  33.859  64.657  1.00123.38
ATOM   2961  C    PRO B  94      69.991  31.145  63.644  1.00109.34
ATOM   2962  O    PRO B  94      69.324  31.674  62.746  1.00 96.86
```

FIGURE 262

```
ATOM   2963  N    CYS B  95      69.466  30.208  64.436  1.00101.66
ATOM   2964  CA   CYS B  95      68.051  29.878  64.254  1.00 88.82
ATOM   2965  CB   CYS B  95      67.674  28.484  64.735  1.00 90.50
ATOM   2966  SG   CYS B  95      66.393  27.656  63.760  1.00135.13
ATOM   2967  C    CYS B  95      67.191  30.918  64.979  1.00 70.52
ATOM   2968  O    CYS B  95      66.476  30.585  65.919  1.00 43.58
ATOM   2969  N    SER B  96      67.296  32.147  64.494  1.00 60.87
ATOM   2970  CA   SER B  96      66.446  33.248  64.919  1.00 51.63
ATOM   2971  CB   SER B  96      67.101  34.608  64.689  1.00 54.58
ATOM   2972  OG   SER B  96      67.550  34.751  63.352  1.00 59.05
ATOM   2973  C    SER B  96      65.124  33.166  64.152  1.00 37.78
ATOM   2974  O    SER B  96      64.267  34.025  64.352  1.00 49.18
ATOM   2975  N    ASP B  97      65.021  32.137  63.309  1.00 31.64
ATOM   2976  CA   ASP B  97      63.824  31.873  62.516  1.00 27.57
ATOM   2977  CB   ASP B  97      64.227  31.446  61.103  1.00 23.15
ATOM   2978  CG   ASP B  97      64.442  29.970  60.866  1.00 34.09
ATOM   2979  OD1  ASP B  97      64.645  29.151  61.783  1.00 28.80
ATOM   2980  OD2  ASP B  97      64.413  29.585  59.675  1.00 47.02
ATOM   2981  C    ASP B  97      62.890  30.840  63.150  1.00 18.50
ATOM   2982  O    ASP B  97      61.800  30.601  62.619  1.00 19.32
ATOM   2983  N    TYR B  98      63.315  30.229  64.254  1.00 22.52
ATOM   2984  CA   TYR B  98      62.577  29.112  64.817  1.00 19.25
ATOM   2985  CB   TYR B  98      63.509  28.066  65.493  1.00 21.90
ATOM   2986  CG   TYR B  98      62.669  26.947  66.087  1.00 23.21
ATOM   2987  CD1  TYR B  98      62.108  26.015  65.211  1.00 18.81
ATOM   2988  CE1  TYR B  98      61.328  24.979  65.683  1.00 18.20
ATOM   2989  CZ   TYR B  98      61.098  24.872  67.048  1.00 27.42
ATOM   2990  OH   TYR B  98      60.311  23.833  67.506  1.00 16.71
ATOM   2991  CE2  TYR B  98      61.630  25.785  67.929  1.00 16.10
ATOM   2992  CD2  TYR B  98      62.415  26.819  67.453  1.00 15.44
ATOM   2993  C    TYR B  98      61.524  29.537  65.833  1.00 21.92
ATOM   2994  O    TYR B  98      61.779  30.233  66.820  1.00 22.98
ATOM   2995  N    ILE B  99      60.320  29.031  65.582  1.00 16.17
ATOM   2996  CA   ILE B  99      59.284  29.019  66.598  1.00 17.96
ATOM   2997  CB   ILE B  99      58.282  30.173  66.466  1.00 18.22
ATOM   2998  CG1  ILE B  99      57.208  30.134  67.564  1.00 17.54
ATOM   2999  CD1  ILE B  99      56.327  31.368  67.580  1.00 25.26
ATOM   3000  CG2  ILE B  99      57.629  30.221  65.094  1.00 17.90
ATOM   3001  C    ILE B  99      58.551  27.679  66.534  1.00 23.11
ATOM   3002  O    ILE B  99      58.319  27.138  65.454  1.00 19.27
ATOM   3003  N    ASN B 100      58.185  27.139  67.694  1.00 23.62
ATOM   3004  CA   ASN B 100      57.381  25.908  67.687  1.00 17.64
ATOM   3005  CB   ASN B 100      57.354  25.270  69.079  1.00 18.48
ATOM   3006  CG   ASN B 100      56.794  23.863  69.078  1.00 13.37
ATOM   3007  OD1  ASN B 100      55.775  23.626  68.446  1.00 18.56
ATOM   3008  ND2  ASN B 100      57.453  22.935  69.780  1.00 17.03
ATOM   3009  C    ASN B 100      55.995  26.223  67.175  1.00 17.36
ATOM   3010  O    ASN B 100      55.058  26.498  67.938  1.00 16.80
ATOM   3011  N    ALA B 101      55.867  26.172  65.839  1.00 13.82
ATOM   3012  CA   ALA B 101      54.584  26.447  65.209  1.00  8.38
ATOM   3013  CB   ALA B 101      54.344  27.949  65.090  1.00 14.14
ATOM   3014  C    ALA B 101      54.488  25.803  63.815  1.00 10.67
```

FIGURE 263

```
ATOM   3015  O    ALA B 101      55.532  25.598  63.187  1.00 17.26
ATOM   3016  N    SER B 102      53.268  25.514  63.375  1.00 10.49
ATOM   3017  CA   SER B 102      53.065  24.791  62.119  1.00 15.63
ATOM   3018  CB   SER B 102      52.782  23.308  62.372  1.00 17.37
ATOM   3019  OG   SER B 102      53.658  22.704  63.287  1.00 15.04
ATOM   3020  C    SER B 102      51.879  25.328  61.337  1.00 17.17
ATOM   3021  O    SER B 102      50.844  25.684  61.902  1.00 18.22
ATOM   3022  N    TYR B 103      51.990  25.368  60.011  1.00 16.28
ATOM   3023  CA   TYR B 103      50.851  25.708  59.172  1.00 17.81
ATOM   3024  CB   TYR B 103      51.321  26.133  57.778  1.00 18.72
ATOM   3025  CG   TYR B 103      52.139  27.398  57.701  1.00 12.87
ATOM   3026  CD1  TYR B 103      51.547  28.633  57.956  1.00 23.49
ATOM   3027  CE1  TYR B 103      52.288  29.795  57.886  1.00 21.55
ATOM   3028  CZ   TYR B 103      53.619  29.769  57.564  1.00 22.19
ATOM   3029  OH   TYR B 103      54.334  30.948  57.499  1.00 32.87
ATOM   3030  CE2  TYR B 103      54.238  28.562  57.303  1.00 23.02
ATOM   3031  CD2  TYR B 103      53.483  27.400  57.377  1.00 19.58
ATOM   3032  C    TYR B 103      49.915  24.504  59.015  1.00 24.37
ATOM   3033  O    TYR B 103      50.388  23.378  58.803  1.00 20.89
ATOM   3034  N    ILE B 104      48.612  24.720  59.106  1.00 17.36
ATOM   3035  CA   ILE B 104      47.596  23.693  58.951  1.00 20.36
ATOM   3036  CB   ILE B 104      46.894  23.397  60.301  1.00 24.05
ATOM   3037  CG1  ILE B 104      47.859  23.206  61.472  1.00 23.04
ATOM   3038  CD1  ILE B 104      48.755  21.992  61.352  1.00 23.46
ATOM   3039  CG2  ILE B 104      45.961  22.211  60.187  1.00 28.18
ATOM   3040  C    ILE B 104      46.532  24.093  57.945  1.00 23.59
ATOM   3041  O    ILE B 104      45.944  25.175  58.016  1.00 20.30
ATOM   3042  N    PRO B 105      46.247  23.225  56.979  1.00 20.21
ATOM   3043  CA   PRO B 105      45.145  23.455  56.051  1.00 17.40
ATOM   3044  CB   PRO B 105      45.259  22.284  55.052  1.00 20.56
ATOM   3045  CG   PRO B 105      46.684  21.880  55.173  1.00 22.00
ATOM   3046  CD   PRO B 105      46.978  21.979  56.663  1.00 22.12
ATOM   3047  C    PRO B 105      43.779  23.370  56.704  1.00 23.93
ATOM   3048  O    PRO B 105      43.584  22.625  57.664  1.00 32.98
ATOM   3049  N    GLY B 106      42.850  24.133  56.156  1.00 21.83
ATOM   3050  CA   GLY B 106      41.473  24.095  56.614  1.00 27.14
ATOM   3051  C    GLY B 106      40.541  23.642  55.502  1.00 26.84
ATOM   3052  O    GLY B 106      40.994  23.136  54.472  1.00 26.33
ATOM   3053  N    ASN B 107      39.234  23.821  55.689  1.00 23.33
ATOM   3054  CA   ASN B 107      38.309  23.403  54.648  1.00 33.39
ATOM   3055  CB   ASN B 107      36.859  23.587  55.104  1.00 40.50
ATOM   3056  CG   ASN B 107      36.393  22.414  55.950  1.00 42.30
ATOM   3057  OD1  ASN B 107      37.022  21.357  55.975  1.00 50.74
ATOM   3058  ND2  ASN B 107      35.282  22.645  56.633  1.00 52.70
ATOM   3059  C    ASN B 107      38.485  24.195  53.354  1.00 41.23
ATOM   3060  O    ASN B 107      38.042  23.711  52.312  1.00 34.23
ATOM   3061  N    ASN B 108      39.085  25.371  53.459  1.00 40.92
ATOM   3062  CA   ASN B 108      39.051  26.395  52.426  1.00 31.26
ATOM   3063  CB   ASN B 108      38.527  27.684  53.085  1.00 41.62
ATOM   3064  CG   ASN B 108      37.199  27.416  53.777  1.00 52.11
ATOM   3065  OD1  ASN B 108      36.227  27.042  53.112  1.00 34.83
ATOM   3066  ND2  ASN B 108      37.163  27.598  55.094  1.00 31.17
```

FIGURE 264

| | | | | | | | | | |
|---|---|---|---|---|---|---|---|---|---|
| ATOM | 3067 | C | ASN | B | 108 | 40.386 | 26.637 | 51.756 | 1.00 31.83 |
| ATOM | 3068 | O | ASN | B | 108 | 40.482 | 26.772 | 50.534 | 1.00 39.22 |
| ATOM | 3069 | N | PHE | B | 109 | 41.468 | 26.703 | 52.531 | 1.00 30.33 |
| ATOM | 3070 | CA | PHE | B | 109 | 42.774 | 26.919 | 51.911 | 1.00 21.96 |
| ATOM | 3071 | CB | PHE | B | 109 | 43.085 | 28.400 | 51.749 | 1.00 20.80 |
| ATOM | 3072 | CG | PHE | B | 109 | 42.708 | 29.329 | 52.890 | 1.00 28.79 |
| ATOM | 3073 | CD1 | PHE | B | 109 | 43.692 | 29.911 | 53.674 | 1.00 25.92 |
| ATOM | 3074 | CE1 | PHE | B | 109 | 43.376 | 30.759 | 54.718 | 1.00 31.45 |
| ATOM | 3075 | CZ | PHE | B | 109 | 42.054 | 31.055 | 54.993 | 1.00 37.19 |
| ATOM | 3076 | CE2 | PHE | B | 109 | 41.064 | 30.476 | 54.218 | 1.00 41.01 |
| ATOM | 3077 | CD2 | PHE | B | 109 | 41.386 | 29.628 | 53.175 | 1.00 32.74 |
| ATOM | 3078 | C | PHE | B | 109 | 43.860 | 26.236 | 52.741 | 1.00 20.75 |
| ATOM | 3079 | O | PHE | B | 109 | 43.593 | 25.834 | 53.871 | 1.00 23.61 |
| ATOM | 3080 | N | ARG | B | 110 | 45.045 | 26.137 | 52.178 | 1.00 19.49 |
| ATOM | 3081 | CA | ARG | B | 110 | 46.176 | 25.416 | 52.710 | 1.00 22.84 |
| ATOM | 3082 | CB | ARG | B | 110 | 47.210 | 25.227 | 51.575 | 1.00 21.99 |
| ATOM | 3083 | CG | ARG | B | 110 | 46.634 | 24.284 | 50.511 | 1.00 30.90 |
| ATOM | 3084 | CD | ARG | B | 110 | 47.726 | 23.349 | 50.019 | 1.00 39.83 |
| ATOM | 3085 | NE | ARG | B | 110 | 47.226 | 22.405 | 49.014 | 1.00 54.08 |
| ATOM | 3086 | CZ | ARG | B | 110 | 47.347 | 21.087 | 49.185 | 1.00 72.63 |
| ATOM | 3087 | NH1 | ARG | B | 110 | 47.930 | 20.619 | 50.282 | 1.00 79.88 |
| ATOM | 3088 | NH2 | ARG | B | 110 | 46.889 | 20.253 | 48.262 | 1.00 87.83 |
| ATOM | 3089 | C | ARG | B | 110 | 46.863 | 26.073 | 53.890 | 1.00 29.52 |
| ATOM | 3090 | O | ARG | B | 110 | 47.454 | 25.377 | 54.728 | 1.00 28.77 |
| ATOM | 3091 | N | ARG | B | 111 | 46.847 | 27.402 | 53.997 | 1.00 20.01 |
| ATOM | 3092 | CA | ARG | B | 111 | 47.476 | 27.910 | 55.233 | 1.00 24.11 |
| ATOM | 3093 | CB | ARG | B | 111 | 48.635 | 28.837 | 54.943 | 1.00 22.68 |
| ATOM | 3094 | CG | ARG | B | 111 | 49.880 | 28.255 | 54.313 | 1.00 19.86 |
| ATOM | 3095 | CD | ARG | B | 111 | 50.961 | 29.325 | 54.127 | 1.00 25.94 |
| ATOM | 3096 | NE | ARG | B | 111 | 52.272 | 28.701 | 53.923 | 1.00 30.60 |
| ATOM | 3097 | CZ | ARG | B | 111 | 53.449 | 29.295 | 54.017 | 1.00 21.38 |
| ATOM | 3098 | NH1 | ARG | B | 111 | 53.524 | 30.583 | 54.324 | 1.00 42.58 |
| ATOM | 3099 | NH2 | ARG | B | 111 | 54.570 | 28.620 | 53.808 | 1.00 29.00 |
| ATOM | 3100 | C | ARG | B | 111 | 46.398 | 28.613 | 56.060 | 1.00 21.97 |
| ATOM | 3101 | O | ARG | B | 111 | 46.481 | 29.791 | 56.388 | 1.00 19.77 |
| ATOM | 3102 | N | GLU | B | 112 | 45.354 | 27.865 | 56.383 | 1.00 16.17 |
| ATOM | 3103 | CA | GLU | B | 112 | 44.185 | 28.417 | 57.045 | 1.00 16.65 |
| ATOM | 3104 | CB | GLU | B | 112 | 42.994 | 27.458 | 56.911 | 1.00 17.98 |
| ATOM | 3105 | CG | GLU | B | 112 | 41.678 | 28.188 | 57.126 | 1.00 27.35 |
| ATOM | 3106 | CD | GLU | B | 112 | 40.479 | 27.519 | 56.495 | 1.00 27.95 |
| ATOM | 3107 | OE1 | GLU | B | 112 | 39.370 | 27.881 | 56.934 | 1.00 28.26 |
| ATOM | 3108 | OE2 | GLU | B | 112 | 40.609 | 26.665 | 55.596 | 1.00 25.50 |
| ATOM | 3109 | C | GLU | B | 112 | 44.461 | 28.700 | 58.518 | 1.00 23.99 |
| ATOM | 3110 | O | GLU | B | 112 | 43.974 | 29.662 | 59.122 | 1.00 19.68 |
| ATOM | 3111 | N | TYR | B | 113 | 45.280 | 27.832 | 59.107 | 1.00 19.82 |
| ATOM | 3112 | CA | TYR | B | 113 | 45.597 | 28.015 | 60.522 | 1.00 17.80 |
| ATOM | 3113 | CB | TYR | B | 113 | 44.940 | 26.997 | 61.450 | 1.00 25.68 |
| ATOM | 3114 | CG | TYR | B | 113 | 43.505 | 26.647 | 61.175 | 1.00 20.88 |
| ATOM | 3115 | CD1 | TYR | B | 113 | 43.208 | 25.633 | 60.274 | 1.00 19.21 |
| ATOM | 3116 | CE1 | TYR | B | 113 | 41.902 | 25.283 | 60.002 | 1.00 20.32 |
| ATOM | 3117 | CZ | TYR | B | 113 | 40.871 | 25.942 | 60.626 | 1.00 20.68 |
| ATOM | 3118 | OH | TYR | B | 113 | 39.572 | 25.584 | 60.345 | 1.00 24.62 |

FIGURE 265

| ATOM | 3119 | CE2 | TYR | B | 113 | 41.133 | 26.956 | 61.534 | 1.00 | 14.80 |
| ATOM | 3120 | CD2 | TYR | B | 113 | 42.450 | 27.300 | 61.802 | 1.00 | 15.14 |
| ATOM | 3121 | C | TYR | B | 113 | 47.090 | 27.916 | 60.726 | 1.00 | 11.85 |
| ATOM | 3122 | O | TYR | B | 113 | 47.865 | 27.314 | 59.989 | 1.00 | 18.08 |
| ATOM | 3123 | N | ILE | B | 114 | 47.491 | 28.590 | 61.805 | 1.00 | 17.37 |
| ATOM | 3124 | CA | ILE | B | 114 | 48.801 | 28.423 | 62.389 | 1.00 | 12.30 |
| ATOM | 3125 | CB | ILE | B | 114 | 49.576 | 29.751 | 62.490 | 1.00 | 19.28 |
| ATOM | 3126 | CG1 | ILE | B | 114 | 50.011 | 30.240 | 61.102 | 1.00 | 19.55 |
| ATOM | 3127 | CD1 | ILE | B | 114 | 51.019 | 31.347 | 61.037 | 1.00 | 18.32 |
| ATOM | 3128 | CG2 | ILE | B | 114 | 50.722 | 29.619 | 63.473 | 1.00 | 10.43 |
| ATOM | 3129 | C | ILE | B | 114 | 48.607 | 27.809 | 63.771 | 1.00 | 13.65 |
| ATOM | 3130 | O | ILE | B | 114 | 47.920 | 28.374 | 64.607 | 1.00 | 20.47 |
| ATOM | 3131 | N | VAL | B | 115 | 49.207 | 26.630 | 63.960 | 1.00 | 18.21 |
| ATOM | 3132 | CA | VAL | B | 115 | 49.068 | 25.982 | 65.260 | 1.00 | 21.54 |
| ATOM | 3133 | CB | VAL | B | 115 | 48.724 | 24.487 | 65.134 | 1.00 | 26.76 |
| ATOM | 3134 | CG1 | VAL | B | 115 | 49.151 | 23.747 | 66.394 | 1.00 | 21.17 |
| ATOM | 3135 | CG2 | VAL | B | 115 | 47.236 | 24.353 | 64.859 | 1.00 | 23.83 |
| ATOM | 3136 | C | VAL | B | 115 | 50.366 | 26.144 | 66.018 | 1.00 | 15.13 |
| ATOM | 3137 | O | VAL | B | 115 | 51.470 | 26.092 | 65.484 | 1.00 | 15.47 |
| ATOM | 3138 | N | THR | B | 116 | 50.255 | 26.378 | 67.328 | 1.00 | 14.92 |
| ATOM | 3139 | CA | THR | B | 116 | 51.530 | 26.594 | 68.022 | 1.00 | 12.65 |
| ATOM | 3140 | CB | THR | B | 116 | 51.927 | 28.078 | 67.913 | 1.00 | 16.69 |
| ATOM | 3141 | OG1 | THR | B | 116 | 53.253 | 28.333 | 68.385 | 1.00 | 15.71 |
| ATOM | 3142 | CG2 | THR | B | 116 | 50.956 | 28.910 | 68.764 | 1.00 | 17.43 |
| ATOM | 3143 | C | THR | B | 116 | 51.360 | 26.112 | 69.463 | 1.00 | 11.03 |
| ATOM | 3144 | O | THR | B | 116 | 50.246 | 25.848 | 69.902 | 1.00 | 11.09 |
| ATOM | 3145 | N | GLN | B | 117 | 52.459 | 25.961 | 70.161 | 1.00 | 12.28 |
| ATOM | 3146 | CA | GLN | B | 117 | 52.444 | 25.635 | 71.579 | 1.00 | 13.83 |
| ATOM | 3147 | CB | GLN | B | 117 | 53.863 | 25.230 | 71.985 | 1.00 | 14.30 |
| ATOM | 3148 | CG | GLN | B | 117 | 54.898 | 26.324 | 71.994 | 1.00 | 10.96 |
| ATOM | 3149 | CD | GLN | B | 117 | 56.300 | 25.936 | 72.377 | 1.00 | 19.11 |
| ATOM | 3150 | OE1 | GLN | B | 117 | 56.676 | 24.759 | 72.435 | 1.00 | 18.55 |
| ATOM | 3151 | NE2 | GLN | B | 117 | 57.164 | 26.915 | 72.649 | 1.00 | 17.68 |
| ATOM | 3152 | C | GLN | B | 117 | 51.991 | 26.834 | 72.400 | 1.00 | 20.95 |
| ATOM | 3153 | O | GLN | B | 117 | 52.025 | 27.946 | 71.859 | 1.00 | 14.87 |
| ATOM | 3154 | N | GLY | B | 118 | 51.630 | 26.648 | 73.666 | 1.00 | 14.16 |
| ATOM | 3155 | CA | GLY | B | 118 | 51.461 | 27.815 | 74.553 | 1.00 | 11.25 |
| ATOM | 3156 | C | GLY | B | 118 | 52.809 | 28.483 | 74.732 | 1.00 | 11.67 |
| ATOM | 3157 | O | GLY | B | 118 | 53.804 | 27.871 | 75.122 | 1.00 | 18.12 |
| ATOM | 3158 | N | PRO | B | 119 | 52.897 | 29.771 | 74.383 | 1.00 | 15.72 |
| ATOM | 3159 | CA | PRO | B | 119 | 54.165 | 30.499 | 74.473 | 1.00 | 17.34 |
| ATOM | 3160 | CB | PRO | B | 119 | 53.761 | 31.941 | 74.150 | 1.00 | 18.05 |
| ATOM | 3161 | CG | PRO | B | 119 | 52.540 | 31.802 | 73.307 | 1.00 | 16.94 |
| ATOM | 3162 | CD | PRO | B | 119 | 51.802 | 30.606 | 73.862 | 1.00 | 18.02 |
| ATOM | 3163 | C | PRO | B | 119 | 54.767 | 30.441 | 75.878 | 1.00 | 12.82 |
| ATOM | 3164 | O | PRO | B | 119 | 54.020 | 30.432 | 76.865 | 1.00 | 17.29 |
| ATOM | 3165 | N | LEU | B | 120 | 56.088 | 30.366 | 75.889 | 1.00 | 22.15 |
| ATOM | 3166 | CA | LEU | B | 120 | 56.900 | 30.382 | 77.094 | 1.00 | 25.66 |
| ATOM | 3167 | CB | LEU | B | 120 | 58.171 | 29.551 | 76.952 | 1.00 | 21.93 |
| ATOM | 3168 | CG | LEU | B | 120 | 57.984 | 28.079 | 76.585 | 1.00 | 26.05 |
| ATOM | 3169 | CD1 | LEU | B | 120 | 59.239 | 27.508 | 75.941 | 1.00 | 24.09 |
| ATOM | 3170 | CD2 | LEU | B | 120 | 57.592 | 27.308 | 77.828 | 1.00 | 25.20 |

FIGURE 266

```
ATOM   3171  C   LEU B 120      57.275  31.832  77.417  1.00 23.76
ATOM   3172  O   LEU B 120      57.201  32.682  76.533  1.00 21.98
ATOM   3173  N   PRO B 121      57.659  32.087  78.659  1.00 19.89
ATOM   3174  CA  PRO B 121      58.151  33.418  79.028  1.00 22.32
ATOM   3175  CB  PRO B 121      58.751  33.181  80.415  1.00 25.42
ATOM   3176  CG  PRO B 121      57.957  32.033  80.964  1.00 28.77
ATOM   3177  CD  PRO B 121      57.648  31.145  79.793  1.00 23.68
ATOM   3178  C   PRO B 121      59.228  33.871  78.048  1.00 24.84
ATOM   3179  O   PRO B 121      59.278  35.032  77.646  1.00 28.28
ATOM   3180  N   GLY B 122      60.083  32.929  77.647  1.00 24.79
ATOM   3181  CA  GLY B 122      61.164  33.214  76.738  1.00 26.40
ATOM   3182  C   GLY B 122      60.850  33.227  75.260  1.00 19.61
ATOM   3183  O   GLY B 122      61.744  33.609  74.493  1.00 26.22
ATOM   3184  N   THR B 123      59.660  32.849  74.813  1.00 19.28
ATOM   3185  CA  THR B 123      59.353  32.851  73.388  1.00 21.38
ATOM   3186  CB  THR B 123      59.009  31.450  72.839  1.00 17.49
ATOM   3187  OG1 THR B 123      57.825  30.952  73.499  1.00 18.47
ATOM   3188  CG2 THR B 123      60.136  30.465  73.099  1.00 21.69
ATOM   3189  C   THR B 123      58.182  33.770  73.092  1.00 18.63
ATOM   3190  O   THR B 123      57.760  33.895  71.942  1.00 21.10
ATOM   3191  N   LYS B 124      57.616  34.408  74.128  1.00 17.85
ATOM   3192  CA  LYS B 124      56.401  35.150  73.790  1.00 19.83
ATOM   3193  CB  LYS B 124      55.659  35.684  74.999  1.00 20.67
ATOM   3194  CG  LYS B 124      56.454  36.481  76.010  1.00 22.46
ATOM   3195  CD  LYS B 124      55.540  36.754  77.204  1.00 32.02
ATOM   3196  CE  LYS B 124      56.234  37.523  78.317  1.00 34.93
ATOM   3197  NZ  LYS B 124      55.312  37.592  79.499  1.00 34.71
ATOM   3198  C   LYS B 124      56.716  36.320  72.843  1.00 17.31
ATOM   3199  O   LYS B 124      55.797  36.775  72.162  1.00 18.88
ATOM   3200  N   ASP B 125      57.972  36.753  72.843  1.00 22.11
ATOM   3201  CA  ASP B 125      58.311  37.850  71.919  1.00 32.47
ATOM   3202  CB  ASP B 125      59.648  38.486  72.278  1.00 25.76
ATOM   3203  CG  ASP B 125      59.590  39.330  73.544  1.00 26.93
ATOM   3204  OD1 ASP B 125      58.487  39.534  74.093  1.00 23.69
ATOM   3205  OD2 ASP B 125      60.656  39.797  73.994  1.00 34.33
ATOM   3206  C   ASP B 125      58.275  37.287  70.500  1.00 25.35
ATOM   3207  O   ASP B 125      57.755  37.900  69.568  1.00 20.65
ATOM   3208  N   ASP B 126      58.823  36.085  70.361  1.00 23.45
ATOM   3209  CA  ASP B 126      58.740  35.345  69.103  1.00 28.27
ATOM   3210  CB  ASP B 126      59.416  33.982  69.251  1.00 31.70
ATOM   3211  CG  ASP B 126      60.912  34.025  69.453  1.00 37.78
ATOM   3212  OD1 ASP B 126      61.567  34.998  69.021  1.00 35.70
ATOM   3213  OD2 ASP B 126      61.452  33.065  70.055  1.00 41.12
ATOM   3214  C   ASP B 126      57.297  35.155  68.655  1.00 24.03
ATOM   3215  O   ASP B 126      56.928  35.305  67.484  1.00 21.60
ATOM   3216  N   PHE B 127      56.418  34.780  69.586  1.00 19.45
ATOM   3217  CA  PHE B 127      55.017  34.576  69.246  1.00 18.59
ATOM   3218  CB  PHE B 127      54.220  34.196  70.505  1.00 15.64
ATOM   3219  CG  PHE B 127      52.714  34.146  70.345  1.00 18.56
ATOM   3220  CD1 PHE B 127      52.137  32.939  69.936  1.00 16.99
ATOM   3221  CE1 PHE B 127      50.771  32.846  69.790  1.00 15.74
ATOM   3222  CZ  PHE B 127      49.941  33.925  70.023  1.00 21.60
```

FIGURE 267

| ATOM | 3223 | CE2 | PHE | B | 127 | 50.506 | 35.127 | 70.433 | 1.00 | 14.92 |
| ATOM | 3224 | CD2 | PHE | B | 127 | 51.865 | 35.219 | 70.593 | 1.00 | 11.80 |
| ATOM | 3225 | C | PHE | B | 127 | 54.417 | 35.835 | 68.628 | 1.00 | 15.63 |
| ATOM | 3226 | O | PHE | B | 127 | 53.711 | 35.819 | 67.627 | 1.00 | 14.92 |
| ATOM | 3227 | N | TRP | B | 128 | 54.630 | 36.977 | 69.295 | 1.00 | 14.67 |
| ATOM | 3228 | CA | TRP | B | 128 | 53.959 | 38.186 | 68.805 | 1.00 | 16.59 |
| ATOM | 3229 | CB | TRP | B | 128 | 53.990 | 39.330 | 69.835 | 1.00 | 14.86 |
| ATOM | 3230 | CG | TRP | B | 128 | 52.966 | 39.089 | 70.927 | 1.00 | 13.08 |
| ATOM | 3231 | CD1 | TRP | B | 128 | 53.298 | 38.867 | 72.240 | 1.00 | 14.73 |
| ATOM | 3232 | NE1 | TRP | B | 128 | 52.169 | 38.677 | 72.995 | 1.00 | 12.11 |
| ATOM | 3233 | CE2 | TRP | B | 128 | 51.074 | 38.775 | 72.179 | 1.00 | 13.55 |
| ATOM | 3234 | CD2 | TRP | B | 128 | 51.542 | 39.029 | 70.874 | 1.00 | 12.42 |
| ATOM | 3235 | CE3 | TRP | B | 128 | 50.575 | 39.166 | 69.868 | 1.00 | 13.65 |
| ATOM | 3236 | CZ3 | TRP | B | 128 | 49.246 | 39.052 | 70.168 | 1.00 | 19.72 |
| ATOM | 3237 | CH2 | TRP | B | 128 | 48.814 | 38.796 | 71.482 | 1.00 | 22.04 |
| ATOM | 3238 | CZ2 | TRP | B | 128 | 49.725 | 38.655 | 72.495 | 1.00 | 19.42 |
| ATOM | 3239 | C | TRP | B | 128 | 54.577 | 38.581 | 67.460 | 1.00 | 13.73 |
| ATOM | 3240 | O | TRP | B | 128 | 53.849 | 39.046 | 66.583 | 1.00 | 22.69 |
| ATOM | 3241 | N | LYS | B | 129 | 55.877 | 38.373 | 67.292 | 1.00 | 16.55 |
| ATOM | 3242 | CA | LYS | B | 129 | 56.523 | 38.666 | 66.013 | 1.00 | 19.71 |
| ATOM | 3243 | CB | LYS | B | 129 | 58.015 | 38.363 | 66.108 | 1.00 | 22.40 |
| ATOM | 3244 | CG | LYS | B | 129 | 58.811 | 38.769 | 64.883 | 1.00 | 25.13 |
| ATOM | 3245 | CD | LYS | B | 129 | 60.267 | 38.316 | 64.882 | 1.00 | 28.99 |
| ATOM | 3246 | CE | LYS | B | 129 | 60.695 | 38.135 | 63.426 | 1.00 | 37.78 |
| ATOM | 3247 | NZ | LYS | B | 129 | 62.137 | 37.915 | 63.203 | 1.00 | 37.99 |
| ATOM | 3248 | C | LYS | B | 129 | 55.856 | 37.871 | 64.893 | 1.00 | 32.26 |
| ATOM | 3249 | O | LYS | B | 129 | 55.560 | 38.383 | 63.811 | 1.00 | 23.65 |
| ATOM | 3250 | N | MET | B | 130 | 55.586 | 36.593 | 65.147 | 1.00 | 23.24 |
| ATOM | 3251 | CA | MET | B | 130 | 54.908 | 35.732 | 64.180 | 1.00 | 23.01 |
| ATOM | 3252 | CB | MET | B | 130 | 54.804 | 34.277 | 64.673 | 1.00 | 20.78 |
| ATOM | 3253 | CG | MET | B | 130 | 53.968 | 33.376 | 63.751 | 1.00 | 16.92 |
| ATOM | 3254 | SD | MET | B | 130 | 53.852 | 31.724 | 64.483 | 1.00 | 24.92 |
| ATOM | 3255 | CE | MET | B | 130 | 52.612 | 31.968 | 65.746 | 1.00 | 15.70 |
| ATOM | 3256 | C | MET | B | 130 | 53.516 | 36.249 | 63.878 | 1.00 | 16.75 |
| ATOM | 3257 | O | MET | B | 130 | 53.068 | 36.268 | 62.733 | 1.00 | 21.38 |
| ATOM | 3258 | N | VAL | B | 131 | 52.799 | 36.648 | 64.923 | 1.00 | 14.58 |
| ATOM | 3259 | CA | VAL | B | 131 | 51.451 | 37.179 | 64.697 | 1.00 | 11.14 |
| ATOM | 3260 | CB | VAL | B | 131 | 50.818 | 37.503 | 66.056 | 1.00 | 24.53 |
| ATOM | 3261 | CG1 | VAL | B | 131 | 49.602 | 38.413 | 65.954 | 1.00 | 18.70 |
| ATOM | 3262 | CG2 | VAL | B | 131 | 50.452 | 36.195 | 66.761 | 1.00 | 13.43 |
| ATOM | 3263 | C | VAL | B | 131 | 51.546 | 38.398 | 63.773 | 1.00 | 16.31 |
| ATOM | 3264 | O | VAL | B | 131 | 50.746 | 38.556 | 62.845 | 1.00 | 23.18 |
| ATOM | 3265 | N | TRP | B | 132 | 52.527 | 39.248 | 64.033 | 1.00 | 21.92 |
| ATOM | 3266 | CA | TRP | B | 132 | 52.707 | 40.480 | 63.256 | 1.00 | 28.19 |
| ATOM | 3267 | CB | TRP | B | 132 | 53.735 | 41.385 | 63.925 | 1.00 | 16.64 |
| ATOM | 3268 | CG | TRP | B | 132 | 54.047 | 42.651 | 63.178 | 1.00 | 32.79 |
| ATOM | 3269 | CD1 | TRP | B | 132 | 55.127 | 42.862 | 62.368 | 1.00 | 31.98 |
| ATOM | 3270 | NE1 | TRP | B | 132 | 55.094 | 44.132 | 61.851 | 1.00 | 28.50 |
| ATOM | 3271 | CE2 | TRP | B | 132 | 53.983 | 44.776 | 62.318 | 1.00 | 33.94 |
| ATOM | 3272 | CD2 | TRP | B | 132 | 53.299 | 43.876 | 63.159 | 1.00 | 30.28 |
| ATOM | 3273 | CE3 | TRP | B | 132 | 52.112 | 44.298 | 63.769 | 1.00 | 34.50 |
| ATOM | 3274 | CZ3 | TRP | B | 132 | 51.663 | 45.586 | 63.522 | 1.00 | 38.33 |

FIGURE 268

| ATOM | 3275 | CH2 | TRP | B | 132 | 52.373 | 46.450 | 62.681 | 1.00 | 35.73 |
| --- | --- | --- | --- | --- | --- | --- | --- | --- | --- | --- |
| ATOM | 3276 | CZ2 | TRP | B | 132 | 53.535 | 46.073 | 62.065 | 1.00 | 39.63 |
| ATOM | 3277 | C | TRP | B | 132 | 53.126 | 40.162 | 61.823 | 1.00 | 30.15 |
| ATOM | 3278 | O | TRP | B | 132 | 52.480 | 40.618 | 60.883 | 1.00 | 22.50 |
| ATOM | 3279 | N | GLU | B | 133 | 54.185 | 39.377 | 61.636 | 1.00 | 27.59 |
| ATOM | 3280 | CA | GLU | B | 133 | 54.620 | 39.019 | 60.289 | 1.00 | 24.71 |
| ATOM | 3281 | CB | GLU | B | 133 | 55.914 | 38.198 | 60.359 | 1.00 | 21.40 |
| ATOM | 3282 | CG | GLU | B | 133 | 56.932 | 38.826 | 61.304 | 1.00 | 27.89 |
| ATOM | 3283 | CD | GLU | B | 133 | 58.303 | 38.200 | 61.158 | 1.00 | 32.83 |
| ATOM | 3284 | OE1 | GLU | B | 133 | 58.377 | 36.959 | 61.046 | 1.00 | 36.49 |
| ATOM | 3285 | OE2 | GLU | B | 133 | 59.287 | 38.963 | 61.157 | 1.00 | 38.19 |
| ATOM | 3286 | C | GLU | B | 133 | 53.583 | 38.245 | 59.492 | 1.00 | 28.74 |
| ATOM | 3287 | O | GLU | B | 133 | 53.540 | 38.416 | 58.266 | 1.00 | 22.81 |
| ATOM | 3288 | N | GLN | B | 134 | 52.763 | 37.406 | 60.128 | 1.00 | 20.49 |
| ATOM | 3289 | CA | GLN | B | 134 | 51.817 | 36.563 | 59.392 | 1.00 | 16.15 |
| ATOM | 3290 | CB | GLN | B | 134 | 51.619 | 35.216 | 60.088 | 1.00 | 20.39 |
| ATOM | 3291 | CG | GLN | B | 134 | 52.869 | 34.348 | 60.135 | 1.00 | 23.00 |
| ATOM | 3292 | CD | GLN | B | 134 | 53.168 | 33.663 | 58.815 | 1.00 | 29.61 |
| ATOM | 3293 | OE1 | GLN | B | 134 | 52.258 | 33.147 | 58.166 | 1.00 | 37.61 |
| ATOM | 3294 | NE2 | GLN | B | 134 | 54.437 | 33.658 | 58.425 | 1.00 | 26.32 |
| ATOM | 3295 | C | GLN | B | 134 | 50.466 | 37.236 | 59.220 | 1.00 | 19.93 |
| ATOM | 3296 | O | GLN | B | 134 | 49.519 | 36.586 | 58.783 | 1.00 | 24.92 |
| ATOM | 3297 | N | ASN | B | 135 | 50.372 | 38.515 | 59.575 | 1.00 | 20.36 |
| ATOM | 3298 | CA | ASN | B | 135 | 49.118 | 39.244 | 59.402 | 1.00 | 18.42 |
| ATOM | 3299 | CB | ASN | B | 135 | 48.860 | 39.385 | 57.893 | 1.00 | 28.65 |
| ATOM | 3300 | CG | ASN | B | 135 | 50.072 | 40.027 | 57.229 | 1.00 | 39.16 |
| ATOM | 3301 | OD1 | ASN | B | 135 | 50.454 | 41.140 | 57.596 | 1.00 | 35.15 |
| ATOM | 3302 | ND2 | ASN | B | 135 | 50.693 | 39.350 | 56.271 | 1.00 | 39.15 |
| ATOM | 3303 | C | ASN | B | 135 | 47.956 | 38.565 | 60.092 | 1.00 | 21.37 |
| ATOM | 3304 | O | ASN | B | 135 | 46.828 | 38.506 | 59.609 | 1.00 | 20.97 |
| ATOM | 3305 | N | VAL | B | 136 | 48.226 | 38.024 | 61.282 | 1.00 | 23.56 |
| ATOM | 3306 | CA | VAL | B | 136 | 47.159 | 37.346 | 62.021 | 1.00 | 22.94 |
| ATOM | 3307 | CB | VAL | B | 136 | 47.773 | 36.475 | 63.134 | 1.00 | 19.22 |
| ATOM | 3308 | CG1 | VAL | B | 136 | 46.690 | 35.933 | 64.043 | 1.00 | 20.50 |
| ATOM | 3309 | CG2 | VAL | B | 136 | 48.621 | 35.365 | 62.511 | 1.00 | 13.95 |
| ATOM | 3310 | C | VAL | B | 136 | 46.210 | 38.363 | 62.640 | 1.00 | 19.65 |
| ATOM | 3311 | O | VAL | B | 136 | 46.679 | 39.369 | 63.195 | 1.00 | 23.44 |
| ATOM | 3312 | N | HIS | B | 137 | 44.914 | 38.117 | 62.542 | 1.00 | 15.94 |
| ATOM | 3313 | CA | HIS | B | 137 | 43.919 | 38.956 | 63.175 | 1.00 | 22.68 |
| ATOM | 3314 | CB | HIS | B | 137 | 42.921 | 39.537 | 62.162 | 1.00 | 32.34 |
| ATOM | 3315 | CG | HIS | B | 137 | 43.539 | 40.472 | 61.174 | 1.00 | 50.91 |
| ATOM | 3316 | ND1 | HIS | B | 137 | 42.795 | 41.144 | 60.227 | 1.00 | 62.67 |
| ATOM | 3317 | CE1 | HIS | B | 137 | 43.597 | 41.891 | 59.487 | 1.00 | 61.13 |
| ATOM | 3318 | NE2 | HIS | B | 137 | 44.835 | 41.728 | 59.922 | 1.00 | 55.36 |
| ATOM | 3319 | CD2 | HIS | B | 137 | 44.823 | 40.845 | 60.971 | 1.00 | 46.21 |
| ATOM | 3320 | C | HIS | B | 137 | 43.129 | 38.192 | 64.237 | 1.00 | 21.18 |
| ATOM | 3321 | O | HIS | B | 137 | 42.446 | 38.847 | 65.029 | 1.00 | 25.91 |
| ATOM | 3322 | N | ASN | B | 138 | 43.200 | 36.861 | 64.239 | 1.00 | 20.71 |
| ATOM | 3323 | CA | ASN | B | 138 | 42.435 | 36.117 | 65.251 | 1.00 | 20.35 |
| ATOM | 3324 | CB | ASN | B | 138 | 41.167 | 35.466 | 64.683 | 1.00 | 19.57 |
| ATOM | 3325 | CG | ASN | B | 138 | 40.246 | 36.482 | 64.038 | 1.00 | 25.55 |
| ATOM | 3326 | OD1 | ASN | B | 138 | 40.149 | 36.530 | 62.809 | 1.00 | 32.78 |

FIGURE 269

```
ATOM   3327  ND2 ASN B 138      39.593  37.321  64.827  1.00 15.27
ATOM   3328  C   ASN B 138      43.316  35.057  65.905  1.00 16.32
ATOM   3329  O   ASN B 138      44.016  34.315  65.217  1.00 22.33
ATOM   3330  N   ILE B 139      43.256  35.021  67.224  1.00 12.38
ATOM   3331  CA  ILE B 139      43.981  34.065  68.039  1.00 13.90
ATOM   3332  CB  ILE B 139      45.010  34.736  68.966  1.00 17.37
ATOM   3333  CG1 ILE B 139      46.050  35.606  68.246  1.00 18.49
ATOM   3334  CD1 ILE B 139      47.007  36.323  69.166  1.00 12.78
ATOM   3335  CG2 ILE B 139      45.702  33.693  69.832  1.00 17.74
ATOM   3336  C   ILE B 139      43.005  33.252  68.883  1.00 21.32
ATOM   3337  O   ILE B 139      42.141  33.824  69.551  1.00 17.35
ATOM   3338  N   VAL B 140      43.161  31.923  68.805  1.00 13.24
ATOM   3339  CA  VAL B 140      42.268  31.051  69.568  1.00 16.27
ATOM   3340  CB  VAL B 140      41.494  30.072  68.677  1.00 27.64
ATOM   3341  CG1 VAL B 140      40.663  29.111  69.518  1.00 15.58
ATOM   3342  CG2 VAL B 140      40.592  30.819  67.697  1.00 23.20
ATOM   3343  C   VAL B 140      43.114  30.311  70.610  1.00 18.13
ATOM   3344  O   VAL B 140      44.176  29.761  70.291  1.00 14.05
ATOM   3345  N   MET B 141      42.658  30.324  71.870  1.00 13.85
ATOM   3346  CA  MET B 141      43.424  29.744  72.969  1.00 17.23
ATOM   3347  CB  MET B 141      43.894  30.844  73.939  1.00 16.81
ATOM   3348  CG  MET B 141      44.730  30.340  75.094  1.00 16.69
ATOM   3349  SD  MET B 141      45.484  31.660  76.071  1.00 18.21
ATOM   3350  CE  MET B 141      46.209  30.676  77.403  1.00 22.43
ATOM   3351  C   MET B 141      42.539  28.740  73.681  1.00 18.04
ATOM   3352  O   MET B 141      41.502  29.159  74.204  1.00 23.03
ATOM   3353  N   VAL B 142      42.894  27.450  73.708  1.00 13.36
ATOM   3354  CA  VAL B 142      41.913  26.540  74.325  1.00 13.57
ATOM   3355  CB  VAL B 142      41.368  25.488  73.342  1.00 16.78
ATOM   3356  CG1 VAL B 142      40.352  26.126  72.403  1.00 25.66
ATOM   3357  CG2 VAL B 142      42.526  24.857  72.591  1.00 22.06
ATOM   3358  C   VAL B 142      42.536  25.823  75.513  1.00 15.54
ATOM   3359  O   VAL B 142      42.224  24.690  75.854  1.00 36.13
ATOM   3360  N   THR B 143      43.443  26.538  76.161  1.00 19.81
ATOM   3361  CA  THR B 143      44.013  26.054  77.415  1.00 23.30
ATOM   3362  CB  THR B 143      45.474  25.625  77.268  1.00 20.98
ATOM   3363  OG1 THR B 143      45.916  24.941  78.455  1.00 20.64
ATOM   3364  CG2 THR B 143      46.363  26.856  77.104  1.00 18.59
ATOM   3365  C   THR B 143      43.915  27.174  78.445  1.00 27.90
ATOM   3366  O   THR B 143      43.801  28.343  78.083  1.00 18.82
ATOM   3367  N   GLN B 144      43.972  26.814  79.720  1.00 24.18
ATOM   3368  CA  GLN B 144      44.194  27.849  80.726  1.00 26.49
ATOM   3369  CB  GLN B 144      43.490  27.554  82.038  1.00 25.93
ATOM   3370  CG  GLN B 144      41.973  27.692  81.972  1.00 31.81
ATOM   3371  CD  GLN B 144      41.409  27.232  83.315  1.00 43.70
ATOM   3372  OE1 GLN B 144      41.157  28.059  84.185  1.00 50.17
ATOM   3373  NE2 GLN B 144      41.251  25.923  83.447  1.00 42.17
ATOM   3374  C   GLN B 144      45.701  27.911  80.950  1.00 21.88
ATOM   3375  O   GLN B 144      46.371  26.926  80.618  1.00 18.20
ATOM   3376  N   CYS B 145      46.176  29.017  81.502  1.00 17.45
ATOM   3377  CA  CYS B 145      47.594  29.207  81.718  1.00 13.43
ATOM   3378  CB  CYS B 145      47.853  30.629  82.221  1.00 20.41
```

FIGURE 270

```
ATOM   3379  SG  CYS B 145      47.629  31.851  80.891  1.00 23.38
ATOM   3380  C   CYS B 145      48.151  28.198  82.726  1.00 13.94
ATOM   3381  O   CYS B 145      49.278  27.738  82.611  1.00 14.73
ATOM   3382  N   VAL B 146      47.320  27.912  83.716  1.00 19.10
ATOM   3383  CA  VAL B 146      47.674  26.994  84.798  1.00 21.25
ATOM   3384  CB  VAL B 146      48.116  27.718  86.081  1.00 23.42
ATOM   3385  CG1 VAL B 146      48.515  26.713  87.163  1.00 17.61
ATOM   3386  CG2 VAL B 146      49.270  28.661  85.793  1.00 20.80
ATOM   3387  C   VAL B 146      46.449  26.145  85.081  1.00 19.88
ATOM   3388  O   VAL B 146      45.355  26.702  85.219  1.00 21.18
ATOM   3389  N   GLU B 147      46.590  24.824  85.132  1.00 18.68
ATOM   3390  CA  GLU B 147      45.398  24.012  85.422  1.00 18.49
ATOM   3391  CB  GLU B 147      45.048  23.119  84.225  1.00 21.59
ATOM   3392  CG  GLU B 147      44.374  23.905  83.116  1.00 23.43
ATOM   3393  CD  GLU B 147      44.162  23.234  81.785  1.00 38.61
ATOM   3394  OE1 GLU B 147      44.493  22.040  81.618  1.00 34.89
ATOM   3395  OE2 GLU B 147      43.636  23.926  80.870  1.00 30.39
ATOM   3396  C   GLU B 147      45.675  23.194  86.675  1.00 22.32
ATOM   3397  O   GLU B 147      46.589  22.361  86.632  1.00 27.28
ATOM   3398  N   LYS B 148      44.956  23.423  87.767  1.00 30.22
ATOM   3399  CA  LYS B 148      45.226  22.630  88.976  1.00 32.97
ATOM   3400  CB  LYS B 148      44.850  21.169  88.720  1.00 39.67
ATOM   3401  CG  LYS B 148      43.346  20.947  88.598  1.00 44.29
ATOM   3402  CD  LYS B 148      43.029  19.958  87.489  1.00 44.33
ATOM   3403  CE  LYS B 148      41.527  19.780  87.325  1.00 49.46
ATOM   3404  NZ  LYS B 148      41.028  20.351  86.043  1.00 61.43
ATOM   3405  C   LYS B 148      46.681  22.757  89.395  1.00 28.17
ATOM   3406  O   LYS B 148      47.401  21.830  89.761  1.00 28.44
ATOM   3407  N   GLY B 149      47.163  24.001  89.303  1.00 19.82
ATOM   3408  CA  GLY B 149      48.533  24.259  89.642  1.00 14.78
ATOM   3409  C   GLY B 149      49.550  23.826  88.611  1.00 25.79
ATOM   3410  O   GLY B 149      50.723  24.180  88.775  1.00 24.43
ATOM   3411  N   ARG B 150      49.192  23.090  87.559  1.00 24.49
ATOM   3412  CA  ARG B 150      50.193  22.668  86.579  1.00 21.93
ATOM   3413  CB  ARG B 150      49.803  21.317  85.965  1.00 24.07
ATOM   3414  CG  ARG B 150      49.775  20.179  86.980  1.00 28.42
ATOM   3415  CD  ARG B 150      49.328  18.870  86.341  1.00 38.83
ATOM   3416  NE  ARG B 150      48.126  18.371  87.014  1.00 49.80
ATOM   3417  CZ  ARG B 150      46.904  18.817  86.738  1.00 54.11
ATOM   3418  NH1 ARG B 150      46.718  19.752  85.811  1.00 48.84
ATOM   3419  NH2 ARG B 150      45.865  18.319  87.394  1.00 45.18
ATOM   3420  C   ARG B 150      50.346  23.708  85.467  1.00 15.49
ATOM   3421  O   ARG B 150      49.325  24.039  84.872  1.00 23.49
ATOM   3422  N   VAL B 151      51.543  24.202  85.215  1.00 18.22
ATOM   3423  CA  VAL B 151      51.760  25.224  84.188  1.00 20.43
ATOM   3424  CB  VAL B 151      53.188  25.789  84.283  1.00 27.81
ATOM   3425  CG1 VAL B 151      53.440  26.853  83.216  1.00 35.66
ATOM   3426  CG2 VAL B 151      53.439  26.378  85.667  1.00 24.07
ATOM   3427  C   VAL B 151      51.513  24.667  82.790  1.00 23.20
ATOM   3428  O   VAL B 151      52.059  23.622  82.440  1.00 19.63
ATOM   3429  N   LYS B 152      50.707  25.370  82.006  1.00 24.64
ATOM   3430  CA  LYS B 152      50.357  24.963  80.651  1.00 14.29
```

FIGURE 271

| ATOM | 3431 | CB  | LYS B 152 | 48.860 | 24.691 | 80.517 | 1.00 | 10.40 |
|------|------|-----|-----------|--------|--------|--------|------|-------|
| ATOM | 3432 | CG  | LYS B 152 | 48.253 | 23.776 | 81.578 | 1.00 | 17.03 |
| ATOM | 3433 | CD  | LYS B 152 | 48.788 | 22.349 | 81.417 | 1.00 | 21.83 |
| ATOM | 3434 | CE  | LYS B 152 | 47.958 | 21.386 | 82.264 | 1.00 | 22.06 |
| ATOM | 3435 | NZ  | LYS B 152 | 48.298 | 19.972 | 81.959 | 1.00 | 36.68 |
| ATOM | 3436 | C   | LYS B 152 | 50.754 | 26.040 | 79.644 | 1.00 | 24.64 |
| ATOM | 3437 | O   | LYS B 152 | 51.009 | 25.763 | 78.468 | 1.00 | 18.65 |
| ATOM | 3438 | N   | CYS B 153 | 50.803 | 27.314 | 80.047 | 1.00 | 11.48 |
| ATOM | 3439 | CA  | CYS B 153 | 51.051 | 28.334 | 79.016 | 1.00 | 12.40 |
| ATOM | 3440 | CB  | CYS B 153 | 49.804 | 28.484 | 78.135 | 1.00 | 12.34 |
| ATOM | 3441 | SG  | CYS B 153 | 49.930 | 29.808 | 76.878 | 1.00 | 18.57 |
| ATOM | 3442 | C   | CYS B 153 | 51.402 | 29.647 | 79.697 | 1.00 | 21.82 |
| ATOM | 3443 | O   | CYS B 153 | 50.893 | 29.972 | 80.777 | 1.00 | 18.60 |
| ATOM | 3444 | N   | ASP B 154 | 52.295 | 30.439 | 79.135 | 1.00 | 16.73 |
| ATOM | 3445 | CA  | ASP B 154 | 52.588 | 31.722 | 79.807 | 1.00 | 16.66 |
| ATOM | 3446 | CB  | ASP B 154 | 53.893 | 32.268 | 79.253 | 1.00 | 17.86 |
| ATOM | 3447 | CG  | ASP B 154 | 54.346 | 33.504 | 80.006 | 1.00 | 28.26 |
| ATOM | 3448 | OD1 | ASP B 154 | 54.311 | 34.561 | 79.347 | 1.00 | 32.47 |
| ATOM | 3449 | OD2 | ASP B 154 | 54.693 | 33.396 | 81.199 | 1.00 | 26.75 |
| ATOM | 3450 | C   | ASP B 154 | 51.417 | 32.676 | 79.644 | 1.00 | 19.16 |
| ATOM | 3451 | O   | ASP B 154 | 50.633 | 32.566 | 78.696 | 1.00 | 19.76 |
| ATOM | 3452 | N   | HIS B 155 | 51.254 | 33.609 | 80.583 | 1.00 | 18.37 |
| ATOM | 3453 | CA  | HIS B 155 | 50.258 | 34.666 | 80.434 | 1.00 | 19.93 |
| ATOM | 3454 | CB  | HIS B 155 | 49.911 | 35.303 | 81.787 | 1.00 | 13.95 |
| ATOM | 3455 | CG  | HIS B 155 | 48.744 | 36.236 | 81.679 | 1.00 | 17.38 |
| ATOM | 3456 | ND1 | HIS B 155 | 47.470 | 35.952 | 82.137 | 1.00 | 21.90 |
| ATOM | 3457 | CE1 | HIS B 155 | 46.665 | 36.975 | 81.889 | 1.00 | 23.51 |
| ATOM | 3458 | NE2 | HIS B 155 | 47.376 | 37.912 | 81.278 | 1.00 | 25.28 |
| ATOM | 3459 | CD2 | HIS B 155 | 48.669 | 37.476 | 81.135 | 1.00 | 15.32 |
| ATOM | 3460 | C   | HIS B 155 | 50.871 | 35.672 | 79.468 | 1.00 | 23.82 |
| ATOM | 3461 | O   | HIS B 155 | 51.437 | 36.664 | 79.913 | 1.00 | 26.73 |
| ATOM | 3462 | N   | TYR B 156 | 50.820 | 35.411 | 78.158 | 1.00 | 12.99 |
| ATOM | 3463 | CA  | TYR B 156 | 51.669 | 36.173 | 77.258 | 1.00 | 17.64 |
| ATOM | 3464 | CB  | TYR B 156 | 51.996 | 35.306 | 76.025 | 1.00 | 17.34 |
| ATOM | 3465 | CG  | TYR B 156 | 50.780 | 34.829 | 75.270 | 1.00 | 14.33 |
| ATOM | 3466 | CD1 | TYR B 156 | 50.206 | 35.541 | 74.233 | 1.00 |  9.88 |
| ATOM | 3467 | CE1 | TYR B 156 | 49.095 | 35.057 | 73.566 | 1.00 | 17.37 |
| ATOM | 3468 | CZ  | TYR B 156 | 48.537 | 33.843 | 73.912 | 1.00 | 16.91 |
| ATOM | 3469 | OH  | TYR B 156 | 47.427 | 33.352 | 73.252 | 1.00 | 16.15 |
| ATOM | 3470 | CE2 | TYR B 156 | 49.095 | 33.107 | 74.941 | 1.00 | 16.17 |
| ATOM | 3471 | CD2 | TYR B 156 | 50.202 | 33.597 | 75.603 | 1.00 | 19.17 |
| ATOM | 3472 | C   | TYR B 156 | 51.099 | 37.488 | 76.740 | 1.00 | 15.11 |
| ATOM | 3473 | O   | TYR B 156 | 51.731 | 38.066 | 75.839 | 1.00 | 17.69 |
| ATOM | 3474 | N   | TRP B 157 | 49.973 | 37.913 | 77.257 | 1.00 | 20.44 |
| ATOM | 3475 | CA  | TRP B 157 | 49.317 | 39.185 | 76.948 | 1.00 | 22.51 |
| ATOM | 3476 | CB  | TRP B 157 | 47.941 | 38.916 | 76.355 | 1.00 | 19.87 |
| ATOM | 3477 | CG  | TRP B 157 | 46.985 | 38.298 | 77.330 | 1.00 | 19.72 |
| ATOM | 3478 | CD1 | TRP B 157 | 46.114 | 38.986 | 78.133 | 1.00 | 21.12 |
| ATOM | 3479 | NE1 | TRP B 157 | 45.393 | 38.102 | 78.898 | 1.00 | 21.03 |
| ATOM | 3480 | CE2 | TRP B 157 | 45.787 | 36.823 | 78.596 | 1.00 | 22.01 |
| ATOM | 3481 | CD2 | TRP B 157 | 46.788 | 36.910 | 77.612 | 1.00 | 21.27 |
| ATOM | 3482 | CE3 | TRP B 157 | 47.353 | 35.722 | 77.140 | 1.00 | 15.87 |

FIGURE 272

| | | | | | | | | |
|---|---|---|---|---|---|---|---|---|
| ATOM | 3483 | CZ3 | TRP B 157 | 46.911 | 34.519 | 77.650 | 1.00 | 21.70 |
| ATOM | 3484 | CH2 | TRP B 157 | 45.909 | 34.468 | 78.629 | 1.00 | 22.88 |
| ATOM | 3485 | CZ2 | TRP B 157 | 45.339 | 35.614 | 79.114 | 1.00 | 25.47 |
| ATOM | 3486 | C | TRP B 157 | 49.245 | 40.010 | 78.227 | 1.00 | 31.95 |
| ATOM | 3487 | O | TRP B 157 | 49.455 | 39.413 | 79.292 | 1.00 | 26.71 |
| ATOM | 3488 | N | PRO B 158 | 48.992 | 41.310 | 78.208 | 1.00 | 31.73 |
| ATOM | 3489 | CA | PRO B 158 | 49.055 | 42.131 | 79.423 | 1.00 | 27.67 |
| ATOM | 3490 | CB | PRO B 158 | 48.882 | 43.564 | 78.893 | 1.00 | 33.72 |
| ATOM | 3491 | CG | PRO B 158 | 49.181 | 43.472 | 77.432 | 1.00 | 33.76 |
| ATOM | 3492 | CD | PRO B 158 | 48.645 | 42.119 | 77.021 | 1.00 | 35.38 |
| ATOM | 3493 | C | PRO B 158 | 47.944 | 41.845 | 80.427 | 1.00 | 34.39 |
| ATOM | 3494 | O | PRO B 158 | 46.852 | 41.408 | 80.064 | 1.00 | 43.08 |
| ATOM | 3495 | N | ALA B 159 | 48.213 | 42.100 | 81.706 | 1.00 | 42.13 |
| ATOM | 3496 | CA | ALA B 159 | 47.276 | 41.840 | 82.796 | 1.00 | 36.27 |
| ATOM | 3497 | CB | ALA B 159 | 47.929 | 42.175 | 84.134 | 1.00 | 24.16 |
| ATOM | 3498 | C | ALA B 159 | 45.986 | 42.624 | 82.659 | 1.00 | 36.43 |
| ATOM | 3499 | O | ALA B 159 | 44.871 | 42.160 | 82.889 | 1.00 | 36.44 |
| ATOM | 3500 | N | ASP B 160 | 46.124 | 43.889 | 82.264 | 1.00 | 30.03 |
| ATOM | 3501 | CA | ASP B 160 | 44.940 | 44.748 | 82.237 | 1.00 | 35.84 |
| ATOM | 3502 | CB | ASP B 160 | 44.838 | 45.506 | 83.566 | 1.00 | 38.86 |
| ATOM | 3503 | CG | ASP B 160 | 46.127 | 46.268 | 83.835 | 1.00 | 40.84 |
| ATOM | 3504 | OD1 | ASP B 160 | 46.496 | 47.091 | 82.969 | 1.00 | 44.84 |
| ATOM | 3505 | OD2 | ASP B 160 | 46.760 | 46.038 | 84.883 | 1.00 | 45.44 |
| ATOM | 3506 | C | ASP B 160 | 45.033 | 45.682 | 81.045 | 1.00 | 34.03 |
| ATOM | 3507 | O | ASP B 160 | 45.484 | 45.251 | 79.981 | 1.00 | 35.16 |
| ATOM | 3508 | N | GLN B 161 | 44.646 | 46.947 | 81.174 | 1.00 | 31.44 |
| ATOM | 3509 | CA | GLN B 161 | 44.665 | 47.795 | 79.971 | 1.00 | 37.31 |
| ATOM | 3510 | CB | GLN B 161 | 43.443 | 48.713 | 79.958 | 1.00 | 48.77 |
| ATOM | 3511 | CG | GLN B 161 | 42.113 | 48.002 | 80.141 | 1.00 | 63.63 |
| ATOM | 3512 | CD | GLN B 161 | 41.545 | 47.351 | 78.898 | 1.00 | 66.46 |
| ATOM | 3513 | OE1 | GLN B 161 | 41.702 | 47.819 | 77.769 | 1.00 | 73.28 |
| ATOM | 3514 | NE2 | GLN B 161 | 40.851 | 46.230 | 79.085 | 1.00 | 44.47 |
| ATOM | 3515 | C | GLN B 161 | 45.959 | 48.574 | 79.868 | 1.00 | 30.80 |
| ATOM | 3516 | O | GLN B 161 | 46.164 | 49.414 | 78.991 | 1.00 | 30.61 |
| ATOM | 3517 | N | ASP B 162 | 46.927 | 48.325 | 80.752 | 1.00 | 31.03 |
| ATOM | 3518 | CA | ASP B 162 | 48.201 | 49.018 | 80.507 | 1.00 | 39.93 |
| ATOM | 3519 | CB | ASP B 162 | 49.077 | 49.016 | 81.756 | 1.00 | 50.93 |
| ATOM | 3520 | CG | ASP B 162 | 49.441 | 47.616 | 82.213 | 1.00 | 68.18 |
| ATOM | 3521 | OD1 | ASP B 162 | 48.998 | 46.637 | 81.574 | 1.00 | 86.94 |
| ATOM | 3522 | OD2 | ASP B 162 | 50.176 | 47.492 | 83.218 | 1.00 | 99.89 |
| ATOM | 3523 | C | ASP B 162 | 48.904 | 48.357 | 79.324 | 1.00 | 39.36 |
| ATOM | 3524 | O | ASP B 162 | 48.627 | 47.197 | 79.014 | 1.00 | 54.50 |
| ATOM | 3525 | N | SER B 163 | 49.796 | 49.081 | 78.659 | 1.00 | 29.38 |
| ATOM | 3526 | CA | SER B 163 | 50.522 | 48.555 | 77.510 | 1.00 | 24.30 |
| ATOM | 3527 | CB | SER B 163 | 50.671 | 49.686 | 76.476 | 1.00 | 24.27 |
| ATOM | 3528 | OG | SER B 163 | 51.323 | 50.772 | 77.118 | 1.00 | 33.50 |
| ATOM | 3529 | C | SER B 163 | 51.887 | 47.999 | 77.867 | 1.00 | 27.40 |
| ATOM | 3530 | O | SER B 163 | 52.500 | 48.320 | 78.886 | 1.00 | 30.35 |
| ATOM | 3531 | N | LEU B 164 | 52.412 | 47.131 | 77.004 | 1.00 | 22.69 |
| ATOM | 3532 | CA | LEU B 164 | 53.721 | 46.549 | 77.197 | 1.00 | 23.41 |
| ATOM | 3533 | CB | LEU B 164 | 53.666 | 45.205 | 77.926 | 1.00 | 32.71 |
| ATOM | 3534 | CG | LEU B 164 | 53.276 | 45.168 | 79.401 | 1.00 | 41.07 |

FIGURE 273

```
ATOM  3535  CD1 LEU B 164    52.777 43.780 79.796 1.00 39.52
ATOM  3536  CD2 LEU B 164    54.432 45.565 80.311 1.00 34.59
ATOM  3537  C   LEU B 164    54.400 46.334 75.839 1.00 19.77
ATOM  3538  O   LEU B 164    53.727 46.182 74.820 1.00 25.31
ATOM  3539  N   TYR B 165    55.717 46.327 75.881 1.00 22.94
ATOM  3540  CA  TYR B 165    56.537 45.961 74.752 1.00 22.36
ATOM  3541  CB  TYR B 165    57.888 46.643 74.765 1.00 18.40
ATOM  3542  CG  TYR B 165    57.974 48.100 74.409 1.00 29.19
ATOM  3543  CD1 TYR B 165    57.965 49.067 75.410 1.00 33.88
ATOM  3544  CE1 TYR B 165    58.049 50.410 75.103 1.00 30.20
ATOM  3545  CZ  TYR B 165    58.150 50.803 73.792 1.00 29.95
ATOM  3546  OH  TYR B 165    58.232 52.144 73.492 1.00 23.81
ATOM  3547  CE2 TYR B 165    58.167 49.866 72.780 1.00 32.37
ATOM  3548  CD2 TYR B 165    58.082 48.525 73.091 1.00 29.59
ATOM  3549  C   TYR B 165    56.812 44.448 74.759 1.00 28.65
ATOM  3550  O   TYR B 165    57.094 43.855 75.793 1.00 27.24
ATOM  3551  N   TYR B 166    56.752 43.893 73.562 1.00 26.38
ATOM  3552  CA  TYR B 166    57.169 42.527 73.276 1.00 23.90
ATOM  3553  CB  TYR B 166    55.962 41.650 73.008 1.00 20.88
ATOM  3554  CG  TYR B 166    54.973 41.508 74.140 1.00 22.61
ATOM  3555  CD1 TYR B 166    55.113 40.482 75.076 1.00 21.82
ATOM  3556  CE1 TYR B 166    54.199 40.362 76.101 1.00 17.08
ATOM  3557  CZ  TYR B 166    53.148 41.235 76.224 1.00 19.26
ATOM  3558  OH  TYR B 166    52.255 41.100 77.248 1.00 19.82
ATOM  3559  CE2 TYR B 166    52.976 42.262 75.313 1.00 22.80
ATOM  3560  CD2 TYR B 166    53.901 42.367 74.291 1.00 23.91
ATOM  3561  C   TYR B 166    58.105 42.598 72.069 1.00 15.01
ATOM  3562  O   TYR B 166    57.616 42.676 70.943 1.00 23.20
ATOM  3563  N   GLY B 167    59.399 42.596 72.328 1.00 23.31
ATOM  3564  CA  GLY B 167    60.399 42.819 71.301 1.00 30.99
ATOM  3565  C   GLY B 167    60.278 44.237 70.754 1.00 32.92
ATOM  3566  O   GLY B 167    60.252 45.223 71.498 1.00 31.28
ATOM  3567  N   ASP B 168    60.195 44.348 69.432 1.00 24.47
ATOM  3568  CA  ASP B 168    60.036 45.656 68.810 1.00 30.37
ATOM  3569  CB  ASP B 168    60.661 45.694 67.414 1.00 35.10
ATOM  3570  CG  ASP B 168    62.142 45.378 67.460 1.00 42.09
ATOM  3571  OD1 ASP B 168    62.723 45.550 68.550 1.00 47.47
ATOM  3572  OD2 ASP B 168    62.684 44.966 66.414 1.00 47.31
ATOM  3573  C   ASP B 168    58.570 46.022 68.666 1.00 29.02
ATOM  3574  O   ASP B 168    58.240 46.976 67.967 1.00 37.58
ATOM  3575  N   LEU B 169    57.674 45.259 69.296 1.00 24.88
ATOM  3576  CA  LEU B 169    56.265 45.583 69.132 1.00 19.15
ATOM  3577  CB  LEU B 169    55.436 44.377 68.702 1.00 29.37
ATOM  3578  CG  LEU B 169    55.736 43.693 67.375 1.00 33.58
ATOM  3579  CD1 LEU B 169    55.206 42.262 67.367 1.00 22.11
ATOM  3580  CD2 LEU B 169    55.145 44.492 66.220 1.00 40.24
ATOM  3581  C   LEU B 169    55.705 46.081 70.461 1.00 18.08
ATOM  3582  O   LEU B 169    56.260 45.744 71.498 1.00 30.36
ATOM  3583  N   ILE B 170    54.625 46.828 70.374 1.00 23.85
ATOM  3584  CA  ILE B 170    53.900 47.229 71.571 1.00 29.93
ATOM  3585  CB  ILE B 170    53.947 48.744 71.817 1.00 31.71
ATOM  3586  CG1 ILE B 170    53.316 49.167 73.144 1.00 36.34
```

FIGURE 274

| | | | | | | | | | |
|---|---|---|---|---|---|---|---|---|---|
| ATOM | 3587 | CD1 | ILE | B | 170 | 54.269 | 49.867 | 74.084 | 1.00 48.77 |
| ATOM | 3588 | CG2 | ILE | B | 170 | 53.304 | 49.482 | 70.662 | 1.00 37.89 |
| ATOM | 3589 | C | ILE | B | 170 | 52.460 | 46.757 | 71.433 | 1.00 30.07 |
| ATOM | 3590 | O | ILE | B | 170 | 51.841 | 46.853 | 70.374 | 1.00 29.12 |
| ATOM | 3591 | N | LEU | B | 171 | 51.955 | 46.223 | 72.535 | 1.00 25.46 |
| ATOM | 3592 | CA | LEU | B | 171 | 50.604 | 45.701 | 72.589 | 1.00 21.46 |
| ATOM | 3593 | CB | LEU | B | 171 | 50.612 | 44.200 | 72.895 | 1.00 29.41 |
| ATOM | 3594 | CG | LEU | B | 171 | 50.226 | 43.287 | 71.727 | 1.00 39.01 |
| ATOM | 3595 | CD1 | LEU | B | 171 | 51.391 | 43.140 | 70.758 | 1.00 43.97 |
| ATOM | 3596 | CD2 | LEU | B | 171 | 49.774 | 41.940 | 72.246 | 1.00 47.22 |
| ATOM | 3597 | C | LEU | B | 171 | 49.805 | 46.423 | 73.668 | 1.00 25.20 |
| ATOM | 3598 | O | LEU | B | 171 | 50.337 | 46.746 | 74.734 | 1.00 26.76 |
| ATOM | 3599 | N | GLN | B | 172 | 48.536 | 46.660 | 73.377 | 1.00 22.79 |
| ATOM | 3600 | CA | GLN | B | 172 | 47.630 | 47.237 | 74.358 | 1.00 37.17 |
| ATOM | 3601 | CB | GLN | B | 172 | 47.376 | 48.734 | 74.126 | 1.00 40.40 |
| ATOM | 3602 | CG | GLN | B | 172 | 46.844 | 49.424 | 75.378 | 1.00 50.87 |
| ATOM | 3603 | CD | GLN | B | 172 | 46.684 | 50.924 | 75.272 | 1.00 51.56 |
| ATOM | 3604 | OE1 | GLN | B | 172 | 46.258 | 51.440 | 74.240 | 1.00 46.34 |
| ATOM | 3605 | NE2 | GLN | B | 172 | 47.013 | 51.651 | 76.339 | 1.00 33.78 |
| ATOM | 3606 | C | GLN | B | 172 | 46.300 | 46.486 | 74.342 | 1.00 38.38 |
| ATOM | 3607 | O | GLN | B | 172 | 45.611 | 46.417 | 73.322 | 1.00 24.25 |
| ATOM | 3608 | N | MET | B | 173 | 45.967 | 45.927 | 75.511 | 1.00 30.63 |
| ATOM | 3609 | CA | MET | B | 173 | 44.650 | 45.325 | 75.643 | 1.00 25.80 |
| ATOM | 3610 | CB | MET | B | 173 | 44.534 | 44.392 | 76.853 | 1.00 20.42 |
| ATOM | 3611 | CG | MET | B | 173 | 43.257 | 43.557 | 76.754 | 1.00 26.50 |
| ATOM | 3612 | SD | MET | B | 173 | 43.176 | 42.237 | 77.997 | 1.00 36.50 |
| ATOM | 3613 | CE | MET | B | 173 | 42.811 | 43.236 | 79.442 | 1.00 44.10 |
| ATOM | 3614 | C | MET | B | 173 | 43.598 | 46.437 | 75.729 | 1.00 38.57 |
| ATOM | 3615 | O | MET | B | 173 | 43.630 | 47.252 | 76.654 | 1.00 49.37 |
| ATOM | 3616 | N | LEU | B | 174 | 42.707 | 46.443 | 74.754 | 1.00 32.34 |
| ATOM | 3617 | CA | LEU | B | 174 | 41.663 | 47.434 | 74.587 | 1.00 32.40 |
| ATOM | 3618 | CB | LEU | B | 174 | 41.355 | 47.609 | 73.093 | 1.00 27.63 |
| ATOM | 3619 | CG | LEU | B | 174 | 41.749 | 48.955 | 72.490 | 1.00 42.29 |
| ATOM | 3620 | CD1 | LEU | B | 174 | 42.587 | 48.766 | 71.239 | 1.00 52.03 |
| ATOM | 3621 | CD2 | LEU | B | 174 | 40.490 | 49.769 | 72.215 | 1.00 46.08 |
| ATOM | 3622 | C | LEU | B | 174 | 40.384 | 47.037 | 75.305 | 1.00 41.65 |
| ATOM | 3623 | O | LEU | B | 174 | 39.616 | 47.862 | 75.795 | 1.00 43.69 |
| ATOM | 3624 | N | SER | B | 175 | 40.165 | 45.721 | 75.328 | 1.00 28.31 |
| ATOM | 3625 | CA | SER | B | 175 | 38.911 | 45.204 | 75.845 | 1.00 21.60 |
| ATOM | 3626 | CB | SER | B | 175 | 37.807 | 45.343 | 74.801 | 1.00 21.97 |
| ATOM | 3627 | OG | SER | B | 175 | 37.672 | 44.133 | 74.073 | 1.00 61.12 |
| ATOM | 3628 | C | SER | B | 175 | 39.059 | 43.732 | 76.238 | 1.00 31.76 |
| ATOM | 3629 | O | SER | B | 175 | 39.831 | 43.018 | 75.598 | 1.00 21.28 |
| ATOM | 3630 | N | GLU | B | 176 | 38.305 | 43.370 | 77.266 | 1.00 32.04 |
| ATOM | 3631 | CA | GLU | B | 176 | 38.286 | 42.031 | 77.838 | 1.00 33.85 |
| ATOM | 3632 | CB | GLU | B | 176 | 39.330 | 41.927 | 78.969 | 1.00 27.59 |
| ATOM | 3633 | CG | GLU | B | 176 | 39.308 | 40.570 | 79.654 | 1.00 29.03 |
| ATOM | 3634 | CD | GLU | B | 176 | 40.283 | 40.373 | 80.782 | 1.00 40.65 |
| ATOM | 3635 | OE1 | GLU | B | 176 | 39.972 | 40.727 | 81.940 | 1.00 49.86 |
| ATOM | 3636 | OE2 | GLU | B | 176 | 41.389 | 39.838 | 80.534 | 1.00 40.12 |
| ATOM | 3637 | C | GLU | B | 176 | 36.889 | 41.675 | 78.328 | 1.00 39.65 |
| ATOM | 3638 | O | GLU | B | 176 | 36.400 | 42.226 | 79.318 | 1.00 44.09 |

FIGURE 275

| | | | | | | | | | |
|---|---|---|---|---|---|---|---|---|---|
| ATOM | 3639 | N | SER | B | 177 | 36.195 | 40.757 | 77.654 | 1.00 38.39 |
| ATOM | 3640 | CA | SER | B | 177 | 34.858 | 40.361 | 78.111 | 1.00 40.70 |
| ATOM | 3641 | CB | SER | B | 177 | 33.787 | 40.649 | 77.069 | 1.00 44.75 |
| ATOM | 3642 | OG | SER | B | 177 | 33.979 | 39.939 | 75.863 | 1.00 61.24 |
| ATOM | 3643 | C | SER | B | 177 | 34.856 | 38.884 | 78.518 | 1.00 38.46 |
| ATOM | 3644 | O | SER | B | 177 | 35.006 | 37.984 | 77.695 | 1.00 25.34 |
| ATOM | 3645 | N | VAL | B | 178 | 34.692 | 38.696 | 79.815 | 1.00 35.33 |
| ATOM | 3646 | CA | VAL | B | 178 | 34.780 | 37.440 | 80.534 | 1.00 44.36 |
| ATOM | 3647 | CB | VAL | B | 178 | 35.355 | 37.668 | 81.947 | 1.00 47.13 |
| ATOM | 3648 | CG1 | VAL | B | 178 | 35.862 | 36.376 | 82.570 | 1.00 47.45 |
| ATOM | 3649 | CG2 | VAL | B | 178 | 36.477 | 38.698 | 81.898 | 1.00 51.70 |
| ATOM | 3650 | C | VAL | B | 178 | 33.419 | 36.763 | 80.621 | 1.00 45.86 |
| ATOM | 3651 | O | VAL | B | 178 | 32.512 | 37.204 | 81.327 | 1.00 51.44 |
| ATOM | 3652 | N | LEU | B | 179 | 33.283 | 35.674 | 79.872 | 1.00 37.27 |
| ATOM | 3653 | CA | LEU | B | 179 | 32.036 | 34.908 | 79.851 | 1.00 34.97 |
| ATOM | 3654 | CB | LEU | B | 179 | 31.628 | 34.661 | 78.400 | 1.00 37.51 |
| ATOM | 3655 | CG | LEU | B | 179 | 30.834 | 35.785 | 77.730 | 1.00 43.44 |
| ATOM | 3656 | CD1 | LEU | B | 179 | 31.470 | 37.140 | 77.989 | 1.00 54.18 |
| ATOM | 3657 | CD2 | LEU | B | 179 | 30.704 | 35.528 | 76.237 | 1.00 54.36 |
| ATOM | 3658 | C | LEU | B | 179 | 32.193 | 33.620 | 80.645 | 1.00 34.28 |
| ATOM | 3659 | O | LEU | B | 179 | 33.309 | 33.220 | 81.010 | 1.00 36.89 |
| ATOM | 3660 | N | PRO | B | 180 | 31.101 | 32.937 | 80.970 | 1.00 45.49 |
| ATOM | 3661 | CA | PRO | B | 180 | 31.209 | 31.705 | 81.756 | 1.00 42.82 |
| ATOM | 3662 | CB | PRO | B | 180 | 29.774 | 31.148 | 81.733 | 1.00 47.75 |
| ATOM | 3663 | CG | PRO | B | 180 | 28.932 | 32.376 | 81.617 | 1.00 51.41 |
| ATOM | 3664 | CD | PRO | B | 180 | 29.695 | 33.258 | 80.665 | 1.00 53.24 |
| ATOM | 3665 | C | PRO | B | 180 | 32.153 | 30.666 | 81.176 | 1.00 31.68 |
| ATOM | 3666 | O | PRO | B | 180 | 32.821 | 29.985 | 81.963 | 1.00 42.99 |
| ATOM | 3667 | N | GLU | B | 181 | 32.242 | 30.482 | 79.858 | 1.00 28.10 |
| ATOM | 3668 | CA | GLU | B | 181 | 33.166 | 29.435 | 79.396 | 1.00 30.70 |
| ATOM | 3669 | CB | GLU | B | 181 | 32.420 | 28.305 | 78.697 | 1.00 24.19 |
| ATOM | 3670 | CG | GLU | B | 181 | 31.130 | 27.923 | 79.409 | 1.00 35.82 |
| ATOM | 3671 | CD | GLU | B | 181 | 30.054 | 27.533 | 78.413 | 1.00 40.31 |
| ATOM | 3672 | OE1 | GLU | B | 181 | 29.358 | 28.440 | 77.912 | 1.00 49.12 |
| ATOM | 3673 | OE2 | GLU | B | 181 | 29.924 | 26.323 | 78.142 | 1.00 45.80 |
| ATOM | 3674 | C | GLU | B | 181 | 34.229 | 29.976 | 78.447 | 1.00 33.02 |
| ATOM | 3675 | O | GLU | B | 181 | 35.127 | 29.240 | 78.043 | 1.00 34.02 |
| ATOM | 3676 | N | TRP | B | 182 | 34.139 | 31.254 | 78.085 | 1.00 26.28 |
| ATOM | 3677 | CA | TRP | B | 182 | 35.215 | 31.807 | 77.263 | 1.00 25.54 |
| ATOM | 3678 | CB | TRP | B | 182 | 35.049 | 31.542 | 75.780 | 1.00 25.17 |
| ATOM | 3679 | CG | TRP | B | 182 | 33.799 | 31.961 | 75.090 | 1.00 23.98 |
| ATOM | 3680 | CD1 | TRP | B | 182 | 33.495 | 33.162 | 74.507 | 1.00 27.11 |
| ATOM | 3681 | NE1 | TRP | B | 182 | 32.228 | 33.126 | 73.975 | 1.00 26.38 |
| ATOM | 3682 | CE2 | TRP | B | 182 | 31.689 | 31.888 | 74.210 | 1.00 29.12 |
| ATOM | 3683 | CD2 | TRP | B | 182 | 32.649 | 31.127 | 74.905 | 1.00 25.63 |
| ATOM | 3684 | CE3 | TRP | B | 182 | 32.372 | 29.806 | 75.280 | 1.00 26.46 |
| ATOM | 3685 | CZ3 | TRP | B | 182 | 31.130 | 29.299 | 74.938 | 1.00 31.22 |
| ATOM | 3686 | CH2 | TRP | B | 182 | 30.191 | 30.079 | 74.244 | 1.00 33.39 |
| ATOM | 3687 | CZ2 | TRP | B | 182 | 30.441 | 31.371 | 73.869 | 1.00 31.20 |
| ATOM | 3688 | C | TRP | B | 182 | 35.337 | 33.308 | 77.529 | 1.00 27.72 |
| ATOM | 3689 | O | TRP | B | 182 | 34.418 | 33.935 | 78.055 | 1.00 30.24 |
| ATOM | 3690 | N | THR | B | 183 | 36.493 | 33.818 | 77.150 | 1.00 24.75 |

FIGURE 276

```
ATOM   3691  CA   THR B 183      36.809  35.234  77.261  1.00 29.67
ATOM   3692  CB   THR B 183      37.897  35.481  78.320  1.00 36.72
ATOM   3693  OG1  THR B 183      37.419  35.055  79.606  1.00 30.73
ATOM   3694  CG2  THR B 183      38.218  36.961  78.455  1.00 25.96
ATOM   3695  C    THR B 183      37.263  35.756  75.903  1.00 23.78
ATOM   3696  O    THR B 183      38.157  35.191  75.276  1.00 16.05
ATOM   3697  N    ILE B 184      36.649  36.838  75.455  1.00 21.97
ATOM   3698  CA   ILE B 184      37.110  37.497  74.227  1.00 26.63
ATOM   3699  CB   ILE B 184      35.918  37.735  73.288  1.00 30.23
ATOM   3700  CG1  ILE B 184      35.305  36.415  72.797  1.00 29.99
ATOM   3701  CD1  ILE B 184      33.881  36.539  72.305  1.00 36.01
ATOM   3702  CG2  ILE B 184      36.293  38.648  72.133  1.00 24.86
ATOM   3703  C    ILE B 184      37.843  38.782  74.573  1.00 26.33
ATOM   3704  O    ILE B 184      37.296  39.625  75.285  1.00 27.53
ATOM   3705  N    ARG B 185      39.072  38.936  74.095  1.00 21.56
ATOM   3706  CA   ARG B 185      39.876  40.127  74.341  1.00 21.72
ATOM   3707  CB   ARG B 185      41.151  39.785  75.111  1.00 18.90
ATOM   3708  CG   ARG B 185      40.884  39.061  76.431  1.00 20.33
ATOM   3709  CD   ARG B 185      42.207  38.540  76.980  1.00 31.19
ATOM   3710  NE   ARG B 185      42.119  38.235  78.404  1.00 29.95
ATOM   3711  CZ   ARG B 185      41.905  37.012  78.867  1.00 30.90
ATOM   3712  NH1  ARG B 185      41.770  36.026  77.993  1.00 28.15
ATOM   3713  NH2  ARG B 185      41.831  36.768  80.165  1.00 26.93
ATOM   3714  C    ARG B 185      40.246  40.824  73.038  1.00 24.49
ATOM   3715  O    ARG B 185      40.342  40.197  71.990  1.00 22.11
ATOM   3716  N    GLU B 186      40.440  42.137  73.098  1.00 23.85
ATOM   3717  CA   GLU B 186      40.858  42.852  71.895  1.00 23.99
ATOM   3718  CB   GLU B 186      39.831  43.906  71.499  1.00 32.77
ATOM   3719  CG   GLU B 186      38.961  43.556  70.303  1.00 49.41
ATOM   3720  CD   GLU B 186      38.376  44.815  69.677  1.00 57.85
ATOM   3721  OE1  GLU B 186      38.831  45.212  68.585  1.00 58.65
ATOM   3722  OE2  GLU B 186      37.465  45.405  70.295  1.00 46.66
ATOM   3723  C    GLU B 186      42.215  43.486  72.141  1.00 20.03
ATOM   3724  O    GLU B 186      42.426  44.138  73.165  1.00 28.24
ATOM   3725  N    PHE B 187      43.151  43.295  71.214  1.00 19.91
ATOM   3726  CA   PHE B 187      44.452  43.922  71.357  1.00 17.69
ATOM   3727  CB   PHE B 187      45.562  42.872  71.461  1.00 24.10
ATOM   3728  CG   PHE B 187      45.394  41.859  72.581  1.00 26.73
ATOM   3729  CD1  PHE B 187      45.114  40.535  72.294  1.00 32.91
ATOM   3730  CE1  PHE B 187      44.967  39.593  73.304  1.00 27.10
ATOM   3731  CZ   PHE B 187      45.089  39.989  74.620  1.00 21.98
ATOM   3732  CE2  PHE B 187      45.369  41.308  74.928  1.00 27.08
ATOM   3733  CD2  PHE B 187      45.539  42.233  73.907  1.00 28.39
ATOM   3734  C    PHE B 187      44.809  44.842  70.189  1.00 27.70
ATOM   3735  O    PHE B 187      44.560  44.562  69.019  1.00 24.34
ATOM   3736  N    LYS B 188      45.446  45.953  70.538  1.00 29.92
ATOM   3737  CA   LYS B 188      46.049  46.816  69.521  1.00 36.57
ATOM   3738  CB   LYS B 188      45.678  48.276  69.774  1.00 42.75
ATOM   3739  CG   LYS B 188      46.817  49.269  69.641  1.00 52.83
ATOM   3740  CD   LYS B 188      46.349  50.713  69.711  1.00 58.55
ATOM   3741  CE   LYS B 188      46.124  51.181  71.139  1.00 59.40
ATOM   3742  NZ   LYS B 188      47.298  50.947  72.026  1.00 34.15
```

FIGURE 277

```
ATOM   3743  C    LYS B 188      47.553  46.584  69.518  1.00 30.49
ATOM   3744  O    LYS B 188      48.240  46.624  70.539  1.00 22.92
ATOM   3745  N    ILE B 189      48.136  46.304  68.350  1.00 24.79
ATOM   3746  CA   ILE B 189      49.581  46.144  68.310  1.00 26.54
ATOM   3747  CB   ILE B 189      49.992  44.714  67.933  1.00 29.28
ATOM   3748  CG1  ILE B 189      51.461  44.597  67.523  1.00 33.98
ATOM   3749  CD1  ILE B 189      51.848  43.205  67.067  1.00 52.63
ATOM   3750  CG2  ILE B 189      49.079  44.160  66.853  1.00 36.95
ATOM   3751  C    ILE B 189      50.175  47.152  67.321  1.00 26.97
ATOM   3752  O    ILE B 189      49.539  47.447  66.312  1.00 25.84
ATOM   3753  N    CYS B 190      51.344  47.657  67.659  1.00 32.86
ATOM   3754  CA   CYS B 190      52.103  48.607  66.874  1.00 31.79
ATOM   3755  CB   CYS B 190      52.243  49.961  67.577  1.00 35.55
ATOM   3756  SG   CYS B 190      50.732  50.549  68.369  1.00 48.07
ATOM   3757  C    CYS B 190      53.492  48.052  66.576  1.00 32.84
ATOM   3758  O    CYS B 190      54.208  47.629  67.478  1.00 29.87
ATOM   3759  N    GLY B 191      53.858  48.065  65.295  1.00 35.69
ATOM   3760  CA   GLY B 191      55.151  47.519  64.910  1.00 46.05
ATOM   3761  C    GLY B 191      55.917  48.502  64.045  1.00 51.49
ATOM   3762  O    GLY B 191      55.540  49.677  64.025  1.00 57.04
ATOM   3763  N    GLU B 192      56.944  48.025  63.353  1.00 53.82
ATOM   3764  CA   GLU B 192      57.794  48.872  62.522  1.00 71.96
ATOM   3765  CB   GLU B 192      58.741  48.013  61.681  1.00 79.49
ATOM   3766  CG   GLU B 192      60.088  48.655  61.399  1.00 83.42
ATOM   3767  CD   GLU B 192      61.126  48.395  62.472  1.00 90.04
ATOM   3768  OE1  GLU B 192      60.759  48.211  63.654  1.00 98.44
ATOM   3769  OE2  GLU B 192      62.329  48.371  62.130  1.00 89.90
ATOM   3770  C    GLU B 192      56.969  49.797  61.622  1.00 79.73
ATOM   3771  O    GLU B 192      57.359  50.943  61.396  1.00 81.84
ATOM   3772  N    GLU B 193      55.861  49.274  61.154  1.00 88.39
ATOM   3773  CA   GLU B 193      54.815  49.806  60.317  1.00 96.64
ATOM   3774  CB   GLU B 193      54.932  51.307  60.055  1.00 98.26
ATOM   3775  CG   GLU B 193      53.693  51.905  59.401  1.00 98.54
ATOM   3776  CD   GLU B 193      53.567  53.404  59.562  1.00 97.01
ATOM   3777  OE1  GLU B 193      52.688  53.853  60.336  1.00 83.43
ATOM   3778  OE2  GLU B 193      54.330  54.154  58.911  1.00 98.66
ATOM   3779  C    GLU B 193      54.823  49.030  58.991  1.00102.76
ATOM   3780  O    GLU B 193      54.656  49.612  57.926  1.00116.30
ATOM   3781  N    GLN B 194      55.029  47.726  59.137  1.00102.86
ATOM   3782  CA   GLN B 194      55.067  46.786  58.022  1.00100.17
ATOM   3783  CB   GLN B 194      55.150  45.351  58.544  1.00 94.78
ATOM   3784  CG   GLN B 194      56.548  44.913  58.944  1.00 90.58
ATOM   3785  CD   GLN B 194      57.076  45.627  60.173  1.00 89.36
ATOM   3786  OE1  GLN B 194      56.393  46.444  60.792  1.00 75.86
ATOM   3787  NE2  GLN B 194      58.314  45.317  60.547  1.00 97.42
ATOM   3788  C    GLN B 194      53.848  46.979  57.135  1.00100.06
ATOM   3789  O    GLN B 194      53.618  48.060  56.588  1.00106.59
ATOM   3790  N    LEU B 195      53.019  45.946  56.971  1.00 96.75
ATOM   3791  CA   LEU B 195      51.800  46.199  56.191  1.00 92.05
ATOM   3792  CB   LEU B 195      51.420  44.991  55.342  1.00 85.63
ATOM   3793  CG   LEU B 195      51.792  45.085  53.856  1.00 78.28
ATOM   3794  CD1  LEU B 195      53.216  44.593  53.634  1.00 84.54
```

FIGURE 278

```
ATOM   3795  CD2 LEU B 195      50.811  44.310  52.989  1.00 43.11
ATOM   3796  C   LEU B 195      50.684  46.623  57.141  1.00 93.25
ATOM   3797  O   LEU B 195      49.499  46.559  56.823  1.00106.23
ATOM   3798  N   ASP B 196      51.100  47.071  58.323  1.00 88.54
ATOM   3799  CA  ASP B 196      50.208  47.654  59.311  1.00 85.36
ATOM   3800  CB  ASP B 196      49.937  46.706  60.472  1.00 77.13
ATOM   3801  CG  ASP B 196      50.263  45.256  60.196  1.00 69.71
ATOM   3802  OD1 ASP B 196      51.435  44.924  59.922  1.00 56.81
ATOM   3803  OD2 ASP B 196      49.318  44.442  60.267  1.00 49.34
ATOM   3804  C   ASP B 196      50.795  48.962  59.853  1.00 86.61
ATOM   3805  O   ASP B 196      52.000  49.194  59.771  1.00 72.64
ATOM   3806  N   ALA B 197      49.924  49.797  60.398  1.00 87.67
ATOM   3807  CA  ALA B 197      50.287  51.051  61.042  1.00 89.69
ATOM   3808  CB  ALA B 197      50.135  52.222  60.096  1.00 83.48
ATOM   3809  C   ALA B 197      49.426  51.223  62.302  1.00 94.67
ATOM   3810  O   ALA B 197      49.317  52.318  62.843  1.00100.04
ATOM   3811  N   HIS B 198      48.864  50.096  62.692  1.00 93.88
ATOM   3812  CA  HIS B 198      47.955  49.838  63.785  1.00 88.36
ATOM   3813  CB  HIS B 198      47.173  51.099  64.161  1.00 92.99
ATOM   3814  CG  HIS B 198      45.965  50.823  64.998  1.00104.14
ATOM   3815  ND1 HIS B 198      46.045  50.478  66.329  1.00108.50
ATOM   3816  CE1 HIS B 198      44.830  50.292  66.813  1.00111.40
ATOM   3817  NE2 HIS B 198      43.960  50.506  65.840  1.00112.45
ATOM   3818  CD2 HIS B 198      44.647  50.839  64.696  1.00109.03
ATOM   3819  C   HIS B 198      46.988  48.711  63.416  1.00 81.60
ATOM   3820  O   HIS B 198      46.100  48.902  62.581  1.00 85.74
ATOM   3821  N   ARG B 199      47.151  47.537  64.020  1.00 68.93
ATOM   3822  CA  ARG B 199      46.278  46.398  63.754  1.00 51.46
ATOM   3823  CB  ARG B 199      47.089  45.192  63.265  1.00 49.03
ATOM   3824  CG  ARG B 199      46.204  44.080  62.716  1.00 46.46
ATOM   3825  CD  ARG B 199      46.953  42.775  62.585  1.00 51.43
ATOM   3826  NE  ARG B 199      48.202  42.873  61.850  1.00 58.26
ATOM   3827  CZ  ARG B 199      49.185  41.980  61.891  1.00 57.04
ATOM   3828  NH1 ARG B 199      49.068  40.896  62.649  1.00 28.91
ATOM   3829  NH2 ARG B 199      50.288  42.168  61.174  1.00 39.20
ATOM   3830  C   ARG B 199      45.464  46.004  64.987  1.00 33.01
ATOM   3831  O   ARG B 199      45.928  46.200  66.112  1.00 29.63
ATOM   3832  N   LEU B 200      44.268  45.459  64.781  1.00 24.89
ATOM   3833  CA  LEU B 200      43.422  45.004  65.880  1.00 27.88
ATOM   3834  CB  LEU B 200      42.010  45.570  65.783  1.00 34.27
ATOM   3835  CG  LEU B 200      41.523  46.288  67.047  1.00 42.11
ATOM   3836  CD1 LEU B 200      41.605  45.366  68.249  1.00 45.77
ATOM   3837  CD2 LEU B 200      42.333  47.553  67.292  1.00 51.38
ATOM   3838  C   LEU B 200      43.353  43.477  65.913  1.00 30.00
ATOM   3839  O   LEU B 200      42.871  42.868  64.959  1.00 32.82
ATOM   3840  N   ILE B 201      43.834  42.882  67.003  1.00 28.87
ATOM   3841  CA  ILE B 201      43.821  41.425  67.118  1.00 24.18
ATOM   3842  CB  ILE B 201      45.174  40.900  67.623  1.00 24.29
ATOM   3843  CG1 ILE B 201      46.350  41.222  66.696  1.00 28.49
ATOM   3844  CD1 ILE B 201      45.941  41.124  65.247  1.00 39.78
ATOM   3845  CG2 ILE B 201      45.105  39.401  67.873  1.00 25.71
ATOM   3846  C   ILE B 201      42.717  40.972  68.059  1.00 22.16
```

FIGURE 279

```
ATOM   3847  O    ILE B 201      42.640  41.494  69.168  1.00  23.92
ATOM   3848  N    ARG B 202      41.883  40.037  67.647  1.00  18.44
ATOM   3849  CA   ARG B 202      40.849  39.447  68.478  1.00  22.50
ATOM   3850  CB   ARG B 202      39.585  39.119  67.693  1.00  33.06
ATOM   3851  CG   ARG B 202      38.305  39.726  68.233  1.00  52.62
ATOM   3852  CD   ARG B 202      37.344  40.048  67.098  1.00  66.81
ATOM   3853  NE   ARG B 202      36.728  41.358  67.260  1.00  75.75
ATOM   3854  CZ   ARG B 202      37.372  42.512  67.362  1.00  85.03
ATOM   3855  NH1  ARG B 202      38.698  42.553  67.322  1.00  98.51
ATOM   3856  NH2  ARG B 202      36.677  43.635  67.506  1.00  92.03
ATOM   3857  C    ARG B 202      41.359  38.141  69.099  1.00  26.96
ATOM   3858  O    ARG B 202      41.955  37.319  68.410  1.00  18.58
ATOM   3859  N    HIS B 203      41.120  37.977  70.384  1.00  28.22
ATOM   3860  CA   HIS B 203      41.595  36.823  71.148  1.00  23.47
ATOM   3861  CB   HIS B 203      42.637  37.287  72.150  1.00  18.39
ATOM   3862  CG   HIS B 203      43.392  36.213  72.850  1.00  20.01
ATOM   3863  ND1  HIS B 203      42.935  35.618  73.999  1.00  22.68
ATOM   3864  CE1  HIS B 203      43.797  34.707  74.400  1.00  22.72
ATOM   3865  NE2  HIS B 203      44.809  34.694  73.548  1.00  18.58
ATOM   3866  CD2  HIS B 203      44.580  35.624  72.563  1.00  22.68
ATOM   3867  C    HIS B 203      40.398  36.148  71.813  1.00  23.95
ATOM   3868  O    HIS B 203      39.651  36.785  72.562  1.00  18.73
ATOM   3869  N    PHE B 204      40.248  34.876  71.479  1.00  17.03
ATOM   3870  CA   PHE B 204      39.161  33.994  71.840  1.00  16.70
ATOM   3871  CB   PHE B 204      38.534  33.311  70.614  1.00  22.28
ATOM   3872  CG   PHE B 204      38.026  34.329  69.604  1.00  24.33
ATOM   3873  CD1  PHE B 204      38.876  34.813  68.622  1.00  22.40
ATOM   3874  CE1  PHE B 204      38.411  35.764  67.735  1.00  18.80
ATOM   3875  CZ   PHE B 204      37.103  36.205  67.847  1.00  19.32
ATOM   3876  CE2  PHE B 204      36.244  35.727  68.811  1.00  25.22
ATOM   3877  CD2  PHE B 204      36.716  34.768  69.694  1.00  26.02
ATOM   3878  C    PHE B 204      39.702  32.924  72.788  1.00  22.01
ATOM   3879  O    PHE B 204      40.366  31.995  72.324  1.00  24.15
ATOM   3880  N    HIS B 205      39.416  33.083  74.068  1.00  17.87
ATOM   3881  CA   HIS B 205      40.000  32.212  75.077  1.00  18.30
ATOM   3882  CB   HIS B 205      40.620  33.068  76.193  1.00  17.58
ATOM   3883  CG   HIS B 205      41.469  32.282  77.137  1.00  20.30
ATOM   3884  ND1  HIS B 205      41.954  32.812  78.310  1.00  22.02
ATOM   3885  CE1  HIS B 205      42.670  31.902  78.946  1.00  21.93
ATOM   3886  NE2  HIS B 205      42.663  30.786  78.227  1.00  22.68
ATOM   3887  CD2  HIS B 205      41.915  31.001  77.092  1.00  15.40
ATOM   3888  C    HIS B 205      38.958  31.270  75.658  1.00  23.56
ATOM   3889  O    HIS B 205      38.102  31.697  76.438  1.00  19.47
ATOM   3890  N    TYR B 206      39.032  29.996  75.287  1.00  18.88
ATOM   3891  CA   TYR B 206      38.073  29.022  75.836  1.00  22.05
ATOM   3892  CB   TYR B 206      37.855  27.895  74.846  1.00  20.72
ATOM   3893  CG   TYR B 206      36.757  26.923  75.209  1.00  18.73
ATOM   3894  CD1  TYR B 206      35.420  27.266  75.039  1.00  20.87
ATOM   3895  CE1  TYR B 206      34.413  26.376  75.372  1.00  26.51
ATOM   3896  CZ   TYR B 206      34.752  25.135  75.870  1.00  28.96
ATOM   3897  OH   TYR B 206      33.753  24.244  76.205  1.00  33.83
ATOM   3898  CE2  TYR B 206      36.067  24.773  76.049  1.00  30.27
```

FIGURE 280

```
ATOM   3899  CD2  TYR B 206      37.073  25.671  75.719  1.00 28.39
ATOM   3900  C    TYR B 206      38.613  28.499  77.156  1.00 24.76
ATOM   3901  O    TYR B 206      39.717  27.943  77.181  1.00 19.80
ATOM   3902  N    THR B 207      37.887  28.679  78.261  1.00 20.66
ATOM   3903  CA   THR B 207      38.554  28.426  79.533  1.00 20.59
ATOM   3904  CB   THR B 207      38.343  29.630  80.477  1.00 23.62
ATOM   3905  OG1  THR B 207      36.964  30.008  80.399  1.00 20.08
ATOM   3906  CG2  THR B 207      39.198  30.803  80.014  1.00 30.98
ATOM   3907  C    THR B 207      38.084  27.179  80.263  1.00 23.84
ATOM   3908  O    THR B 207      38.498  26.972  81.414  1.00 22.22
ATOM   3909  N    VAL B 208      37.254  26.345  79.643  1.00 23.82
ATOM   3910  CA   VAL B 208      36.825  25.167  80.402  1.00 28.06
ATOM   3911  CB   VAL B 208      35.322  25.266  80.749  1.00 27.30
ATOM   3912  CG1  VAL B 208      35.074  26.517  81.590  1.00 32.43
ATOM   3913  CG2  VAL B 208      34.465  25.241  79.494  1.00 27.40
ATOM   3914  C    VAL B 208      37.116  23.851  79.698  1.00 30.84
ATOM   3915  O    VAL B 208      36.320  22.909  79.773  1.00 35.95
ATOM   3916  N    TRP B 209      38.255  23.743  79.031  1.00 26.26
ATOM   3917  CA   TRP B 209      38.657  22.486  78.391  1.00 24.69
ATOM   3918  CB   TRP B 209      38.976  22.685  76.918  1.00 30.19
ATOM   3919  CG   TRP B 209      39.163  21.465  76.068  1.00 24.30
ATOM   3920  CD1  TRP B 209      39.449  20.169  76.361  1.00 26.73
ATOM   3921  NE1  TRP B 209      39.526  19.394  75.229  1.00 27.16
ATOM   3922  CE2  TRP B 209      39.278  20.210  74.148  1.00 34.57
ATOM   3923  CD2  TRP B 209      39.048  21.513  74.632  1.00 23.58
ATOM   3924  CE3  TRP B 209      38.768  22.558  73.746  1.00 24.70
ATOM   3925  CZ3  TRP B 209      38.731  22.256  72.395  1.00 35.51
ATOM   3926  CH2  TRP B 209      38.964  20.951  71.930  1.00 33.08
ATOM   3927  CZ2  TRP B 209      39.236  19.917  72.782  1.00 32.65
ATOM   3928  C    TRP B 209      39.889  21.934  79.099  1.00 26.90
ATOM   3929  O    TRP B 209      40.981  22.462  78.880  1.00 24.25
ATOM   3930  N    PRO B 210      39.733  20.881  79.886  1.00 30.43
ATOM   3931  CA   PRO B 210      40.872  20.308  80.611  1.00 22.74
ATOM   3932  CB   PRO B 210      40.241  19.228  81.492  1.00 26.14
ATOM   3933  CG   PRO B 210      38.776  19.517  81.488  1.00 31.27
ATOM   3934  CD   PRO B 210      38.486  20.136  80.147  1.00 27.01
ATOM   3935  C    PRO B 210      41.871  19.648  79.668  1.00 22.10
ATOM   3936  O    PRO B 210      41.475  19.064  78.662  1.00 34.64
ATOM   3937  N    ASP B 211      43.153  19.724  80.001  1.00 15.18
ATOM   3938  CA   ASP B 211      44.183  19.090  79.209  1.00 21.45
ATOM   3939  CB   ASP B 211      45.565  19.247  79.849  1.00 28.68
ATOM   3940  CG   ASP B 211      46.648  19.134  78.790  1.00 26.69
ATOM   3941  OD1  ASP B 211      47.820  19.370  79.138  1.00 34.33
ATOM   3942  OD2  ASP B 211      46.281  18.819  77.638  1.00 25.77
ATOM   3943  C    ASP B 211      43.901  17.600  79.038  1.00 40.98
ATOM   3944  O    ASP B 211      43.349  16.940  79.926  1.00 28.43
ATOM   3945  N    HIS B 212      44.254  17.081  77.868  1.00 34.69
ATOM   3946  CA   HIS B 212      44.020  15.705  77.459  1.00 29.07
ATOM   3947  CB   HIS B 212      44.864  14.770  78.328  1.00 22.05
ATOM   3948  CG   HIS B 212      46.266  15.247  78.527  1.00 23.98
ATOM   3949  ND1  HIS B 212      47.183  15.323  77.504  1.00 29.39
ATOM   3950  CE1  HIS B 212      48.329  15.777  77.969  1.00 33.66
```

FIGURE 281

```
ATOM   3951  NE2 HIS B 212      48.187  15.996  79.268  1.00 32.42
ATOM   3952  CD2 HIS B 212      46.906  15.670  79.637  1.00 23.94
ATOM   3953  C   HIS B 212      42.564  15.267  77.538  1.00 39.31
ATOM   3954  O   HIS B 212      42.251  14.074  77.466  1.00 50.27
ATOM   3955  N   GLY B 213      41.642  16.207  77.683  1.00 40.41
ATOM   3956  CA  GLY B 213      40.245  15.925  77.912  1.00 30.96
ATOM   3957  C   GLY B 213      39.401  16.580  76.835  1.00 33.95
ATOM   3958  O   GLY B 213      39.938  17.004  75.817  1.00 33.78
ATOM   3959  N   VAL B 214      38.120  16.610  77.144  1.00 31.79
ATOM   3960  CA  VAL B 214      37.081  17.170  76.303  1.00 31.65
ATOM   3961  CB  VAL B 214      36.238  16.035  75.701  1.00 35.28
ATOM   3962  CG1 VAL B 214      37.120  15.151  74.832  1.00 45.38
ATOM   3963  CG2 VAL B 214      35.582  15.230  76.815  1.00 24.44
ATOM   3964  C   VAL B 214      36.205  18.070  77.150  1.00 36.18
ATOM   3965  O   VAL B 214      36.097  17.826  78.358  1.00 35.44
ATOM   3966  N   PRO B 215      35.582  19.094  76.597  1.00 32.79
ATOM   3967  CA  PRO B 215      34.679  19.888  77.449  1.00 35.01
ATOM   3968  CB  PRO B 215      34.113  20.923  76.488  1.00 32.92
ATOM   3969  CG  PRO B 215      35.146  21.018  75.406  1.00 39.93
ATOM   3970  CD  PRO B 215      35.654  19.604  75.225  1.00 33.73
ATOM   3971  C   PRO B 215      33.574  18.999  78.031  1.00 40.15
ATOM   3972  O   PRO B 215      33.366  17.872  77.581  1.00 31.33
ATOM   3973  N   GLU B 216      32.896  19.532  79.028  1.00 39.88
ATOM   3974  CA  GLU B 216      31.810  18.913  79.763  1.00 43.51
ATOM   3975  CB  GLU B 216      31.406  19.850  80.906  1.00 52.27
ATOM   3976  CG  GLU B 216      31.040  19.159  82.203  1.00 67.80
ATOM   3977  CD  GLU B 216      31.677  19.781  83.429  1.00 77.24
ATOM   3978  OE1 GLU B 216      31.550  19.193  84.527  1.00 81.69
ATOM   3979  OE2 GLU B 216      32.302  20.857  83.300  1.00 89.24
ATOM   3980  C   GLU B 216      30.617  18.606  78.864  1.00 40.84
ATOM   3981  O   GLU B 216      30.010  17.536  78.967  1.00 53.80
ATOM   3982  N   THR B 217      30.269  19.531  77.983  1.00 38.95
ATOM   3983  CA  THR B 217      29.204  19.383  77.008  1.00 42.02
ATOM   3984  CB  THR B 217      28.040  20.379  77.205  1.00 45.29
ATOM   3985  OG1 THR B 217      28.483  21.708  76.887  1.00 35.12
ATOM   3986  CG2 THR B 217      27.573  20.406  78.649  1.00 41.50
ATOM   3987  C   THR B 217      29.708  19.600  75.580  1.00 41.46
ATOM   3988  O   THR B 217      30.806  20.088  75.328  1.00 31.75
ATOM   3989  N   THR B 218      28.852  19.241  74.631  1.00 44.21
ATOM   3990  CA  THR B 218      29.157  19.469  73.222  1.00 46.58
ATOM   3991  CB  THR B 218      28.428  18.436  72.347  1.00 50.20
ATOM   3992  OG1 THR B 218      27.030  18.755  72.322  1.00 60.14
ATOM   3993  CG2 THR B 218      28.539  17.047  72.953  1.00 48.45
ATOM   3994  C   THR B 218      28.751  20.877  72.807  1.00 39.87
ATOM   3995  O   THR B 218      29.472  21.575  72.100  1.00 33.12
ATOM   3996  N   GLN B 219      27.581  21.301  73.262  1.00 42.47
ATOM   3997  CA  GLN B 219      27.023  22.603  72.942  1.00 48.42
ATOM   3998  CB  GLN B 219      25.735  22.859  73.734  1.00 61.04
ATOM   3999  CG  GLN B 219      24.465  22.396  73.043  1.00 75.20
ATOM   4000  CD  GLN B 219      23.709  21.356  73.846  1.00 86.54
ATOM   4001  OE1 GLN B 219      24.156  20.217  73.990  1.00100.39
ATOM   4002  NE2 GLN B 219      22.552  21.750  74.373  1.00 96.05
```

FIGURE 282

```
ATOM   4003  C    GLN B 219      27.988  23.745  73.241  1.00 42.13
ATOM   4004  O    GLN B 219      27.912  24.784  72.588  1.00 38.02
ATOM   4005  N    SER B 220      28.856  23.557  74.230  1.00 41.58
ATOM   4006  CA   SER B 220      29.702  24.652  74.687  1.00 41.47
ATOM   4007  CB   SER B 220      30.377  24.324  76.022  1.00 40.77
ATOM   4008  OG   SER B 220      31.170  25.425  76.432  1.00 52.01
ATOM   4009  C    SER B 220      30.781  24.985  73.661  1.00 32.19
ATOM   4010  O    SER B 220      30.948  26.137  73.270  1.00 34.50
ATOM   4011  N    LEU B 221      31.491  23.939  73.262  1.00 32.63
ATOM   4012  CA   LEU B 221      32.578  24.130  72.312  1.00 30.11
ATOM   4013  CB   LEU B 221      33.532  22.934  72.268  1.00 31.66
ATOM   4014  CG   LEU B 221      34.848  23.244  71.525  1.00 33.07
ATOM   4015  CD1  LEU B 221      35.653  24.288  72.290  1.00 29.11
ATOM   4016  CD2  LEU B 221      35.641  21.978  71.284  1.00 29.80
ATOM   4017  C    LEU B 221      31.970  24.416  70.944  1.00 30.52
ATOM   4018  O    LEU B 221      32.479  25.263  70.210  1.00 31.28
ATOM   4019  N    ILE B 222      30.879  23.712  70.649  1.00 30.64
ATOM   4020  CA   ILE B 222      30.208  23.955  69.364  1.00 35.39
ATOM   4021  CB   ILE B 222      28.961  23.069  69.244  1.00 28.31
ATOM   4022  CG1  ILE B 222      29.280  21.656  68.733  1.00 23.30
ATOM   4023  CD1  ILE B 222      28.138  20.695  68.988  1.00 31.06
ATOM   4024  CG2  ILE B 222      27.871  23.684  68.394  1.00 30.00
ATOM   4025  C    ILE B 222      29.871  25.433  69.215  1.00 31.09
ATOM   4026  O    ILE B 222      30.088  26.049  68.169  1.00 30.29
ATOM   4027  N    GLN B 223      29.352  26.009  70.296  1.00 31.17
ATOM   4028  CA   GLN B 223      28.973  27.416  70.289  1.00 33.58
ATOM   4029  CB   GLN B 223      28.201  27.804  71.554  1.00 39.47
ATOM   4030  CG   GLN B 223      27.198  28.916  71.237  1.00 56.44
ATOM   4031  CD   GLN B 223      26.886  28.937  69.747  1.00 72.62
ATOM   4032  OE1  GLN B 223      26.007  28.216  69.269  1.00 73.13
ATOM   4033  NE2  GLN B 223      27.618  29.765  69.008  1.00 86.88
ATOM   4034  C    GLN B 223      30.210  28.300  70.151  1.00 27.54
ATOM   4035  O    GLN B 223      30.195  29.217  69.338  1.00 28.05
ATOM   4036  N    PHE B 224      31.238  27.991  70.934  1.00 26.93
ATOM   4037  CA   PHE B 224      32.529  28.675  70.816  1.00 21.53
ATOM   4038  CB   PHE B 224      33.554  28.029  71.726  1.00 22.20
ATOM   4039  CG   PHE B 224      34.930  28.683  71.736  1.00 25.50
ATOM   4040  CD1  PHE B 224      35.141  29.892  72.381  1.00 24.49
ATOM   4041  CE1  PHE B 224      36.398  30.465  72.413  1.00 22.79
ATOM   4042  CZ   PHE B 224      37.451  29.853  71.766  1.00 14.40
ATOM   4043  CE2  PHE B 224      37.260  28.650  71.125  1.00 22.52
ATOM   4044  CD2  PHE B 224      36.000  28.071  71.113  1.00 23.70
ATOM   4045  C    PHE B 224      33.033  28.659  69.372  1.00 25.07
ATOM   4046  O    PHE B 224      33.291  29.707  68.770  1.00 33.29
ATOM   4047  N    VAL B 225      33.166  27.464  68.800  1.00 21.05
ATOM   4048  CA   VAL B 225      33.655  27.335  67.431  1.00 21.13
ATOM   4049  CB   VAL B 225      33.656  25.868  66.962  1.00 20.06
ATOM   4050  CG1  VAL B 225      33.778  25.769  65.448  1.00 21.52
ATOM   4051  CG2  VAL B 225      34.796  25.101  67.607  1.00 23.47
ATOM   4052  C    VAL B 225      32.826  28.179  66.470  1.00 34.08
ATOM   4053  O    VAL B 225      33.395  28.901  65.641  1.00 30.78
ATOM   4054  N    ARG B 226      31.498  28.088  66.584  1.00 33.79
```

FIGURE 283

```
ATOM   4055  CA   ARG B 226      30.663  28.875  65.670  1.00 32.97
ATOM   4056  CB   ARG B 226      29.185  28.551  65.852  1.00 36.13
ATOM   4057  CG   ARG B 226      28.846  27.076  65.682  1.00 38.26
ATOM   4058  CD   ARG B 226      27.340  26.867  65.634  1.00 43.64
ATOM   4059  NE   ARG B 226      26.967  25.743  64.773  1.00 52.04
ATOM   4060  CZ   ARG B 226      25.960  24.913  65.031  1.00 56.46
ATOM   4061  NH1  ARG B 226      25.229  25.084  66.127  1.00 38.23
ATOM   4062  NH2  ARG B 226      25.688  23.917  64.197  1.00 53.92
ATOM   4063  C    ARG B 226      30.933  30.356  65.886  1.00 38.04
ATOM   4064  O    ARG B 226      31.031  31.144  64.947  1.00 40.50
ATOM   4065  N    THR B 227      31.077  30.745  67.151  1.00 32.88
ATOM   4066  CA   THR B 227      31.406  32.146  67.425  1.00 34.79
ATOM   4067  CB   THR B 227      31.474  32.430  68.937  1.00 37.87
ATOM   4068  OG1  THR B 227      30.160  32.368  69.504  1.00 44.90
ATOM   4069  CG2  THR B 227      31.977  33.840  69.194  1.00 37.73
ATOM   4070  C    THR B 227      32.728  32.514  66.772  1.00 33.01
ATOM   4071  O    THR B 227      32.879  33.558  66.136  1.00 29.02
ATOM   4072  N    VAL B 228      33.737  31.645  66.903  1.00 29.04
ATOM   4073  CA   VAL B 228      35.022  32.021  66.300  1.00 25.89
ATOM   4074  CB   VAL B 228      36.125  31.038  66.728  1.00 27.50
ATOM   4075  CG1  VAL B 228      37.419  31.376  66.005  1.00 25.74
ATOM   4076  CG2  VAL B 228      36.316  31.066  68.244  1.00 22.05
ATOM   4077  C    VAL B 228      34.929  32.108  64.779  1.00 25.85
ATOM   4078  O    VAL B 228      35.454  33.028  64.145  1.00 26.36
ATOM   4079  N    ARG B 229      34.253  31.163  64.145  1.00 30.24
ATOM   4080  CA   ARG B 229      34.172  31.158  62.678  1.00 30.97
ATOM   4081  CB   ARG B 229      33.486  29.872  62.232  1.00 35.10
ATOM   4082  CG   ARG B 229      33.083  29.811  60.772  1.00 37.64
ATOM   4083  CD   ARG B 229      34.250  30.014  59.828  1.00 31.83
ATOM   4084  NE   ARG B 229      35.361  29.082  60.089  1.00 32.88
ATOM   4085  CZ   ARG B 229      36.512  29.276  59.439  1.00 32.94
ATOM   4086  NH1  ARG B 229      36.535  30.304  58.602  1.00 27.58
ATOM   4087  NH2  ARG B 229      37.576  28.513  59.590  1.00 33.74
ATOM   4088  C    ARG B 229      33.459  32.398  62.160  1.00 38.61
ATOM   4089  O    ARG B 229      33.809  32.946  61.105  1.00 36.42
ATOM   4090  N    ASP B 230      32.458  32.876  62.897  1.00 30.67
ATOM   4091  CA   ASP B 230      31.792  34.128  62.548  1.00 40.26
ATOM   4092  CB   ASP B 230      30.693  34.455  63.561  1.00 50.06
ATOM   4093  CG   ASP B 230      29.903  35.704  63.234  1.00 61.05
ATOM   4094  OD1  ASP B 230      30.234  36.779  63.781  1.00 62.97
ATOM   4095  OD2  ASP B 230      28.939  35.635  62.438  1.00 74.52
ATOM   4096  C    ASP B 230      32.777  35.287  62.469  1.00 38.62
ATOM   4097  O    ASP B 230      32.680  36.128  61.574  1.00 42.73
ATOM   4098  N    TYR B 231      33.732  35.352  63.398  1.00 33.95
ATOM   4099  CA   TYR B 231      34.680  36.464  63.395  1.00 30.28
ATOM   4100  CB   TYR B 231      35.391  36.596  64.743  1.00 28.40
ATOM   4101  CG   TYR B 231      34.545  37.304  65.783  1.00 31.94
ATOM   4102  CD1  TYR B 231      33.721  36.575  66.632  1.00 31.04
ATOM   4103  CE1  TYR B 231      32.953  37.221  67.582  1.00 39.71
ATOM   4104  CZ   TYR B 231      33.006  38.593  67.685  1.00 44.93
ATOM   4105  OH   TYR B 231      32.237  39.231  68.633  1.00 67.37
ATOM   4106  CE2  TYR B 231      33.819  39.333  66.854  1.00 41.23
```

FIGURE 284

```
ATOM   4107  CD2 TYR B 231      34.587  38.684  65.905  1.00 39.54
ATOM   4108  C   TYR B 231      35.726  36.297  62.305  1.00 28.70
ATOM   4109  O   TYR B 231      36.213  37.238  61.692  1.00 29.85
ATOM   4110  N   ILE B 232      36.093  35.038  62.062  1.00 24.82
ATOM   4111  CA  ILE B 232      37.053  34.819  60.989  1.00 25.65
ATOM   4112  CB  ILE B 232      37.473  33.341  60.961  1.00 22.20
ATOM   4113  CG1 ILE B 232      38.346  32.951  62.164  1.00 25.46
ATOM   4114  CD1 ILE B 232      38.402  31.452  62.401  1.00 22.19
ATOM   4115  CG2 ILE B 232      38.159  32.987  59.653  1.00 26.03
ATOM   4116  C   ILE B 232      36.450  35.262  59.657  1.00 29.68
ATOM   4117  O   ILE B 232      37.061  35.995  58.876  1.00 29.18
ATOM   4118  N   ASN B 233      35.229  34.806  59.410  1.00 29.88
ATOM   4119  CA  ASN B 233      34.545  35.100  58.151  1.00 43.60
ATOM   4120  CB  ASN B 233      33.148  34.472  58.179  1.00 35.22
ATOM   4121  CG  ASN B 233      33.220  32.979  57.909  1.00 32.42
ATOM   4122  OD1 ASN B 233      34.221  32.501  57.366  1.00 44.01
ATOM   4123  ND2 ASN B 233      32.188  32.220  58.277  1.00 29.47
ATOM   4124  C   ASN B 233      34.512  36.604  57.892  1.00 43.88
ATOM   4125  O   ASN B 233      34.637  37.078  56.762  1.00 42.08
ATOM   4126  N   ARG B 234      34.368  37.357  58.967  1.00 40.25
ATOM   4127  CA  ARG B 234      34.313  38.803  58.982  1.00 36.71
ATOM   4128  CB  ARG B 234      33.385  39.259  60.130  1.00 40.64
ATOM   4129  CG  ARG B 234      31.918  39.153  59.733  1.00 50.04
ATOM   4130  CD  ARG B 234      30.963  39.234  60.907  1.00 52.66
ATOM   4131  NE  ARG B 234      31.267  40.346  61.795  1.00 61.93
ATOM   4132  CZ  ARG B 234      31.331  40.270  63.116  1.00 64.33
ATOM   4133  NH1 ARG B 234      31.107  39.119  63.732  1.00 53.92
ATOM   4134  NH2 ARG B 234      31.619  41.352  63.825  1.00 74.42
ATOM   4135  C   ARG B 234      35.685  39.434  59.137  1.00 37.82
ATOM   4136  O   ARG B 234      35.784  40.545  59.659  1.00 49.54
ATOM   4137  N   SER B 235      36.743  38.756  58.701  1.00 31.78
ATOM   4138  CA  SER B 235      38.087  39.304  58.815  1.00 29.31
ATOM   4139  CB  SER B 235      38.901  38.548  59.875  1.00 32.90
ATOM   4140  OG  SER B 235      38.135  38.323  61.045  1.00 44.62
ATOM   4141  C   SER B 235      38.846  39.252  57.494  1.00 35.75
ATOM   4142  O   SER B 235      39.935  38.678  57.421  1.00 35.41
ATOM   4143  N   PRO B 236      38.319  39.848  56.436  1.00 47.17
ATOM   4144  CA  PRO B 236      38.933  39.718  55.109  1.00 44.13
ATOM   4145  CB  PRO B 236      38.008  40.545  54.210  1.00 50.97
ATOM   4146  CG  PRO B 236      37.355  41.506  55.150  1.00 56.25
ATOM   4147  CD  PRO B 236      37.121  40.705  56.408  1.00 56.24
ATOM   4148  C   PRO B 236      40.345  40.289  55.070  1.00 37.49
ATOM   4149  O   PRO B 236      40.660  41.313  55.678  1.00 43.03
ATOM   4150  N   GLY B 237      41.209  39.586  54.341  1.00 33.65
ATOM   4151  CA  GLY B 237      42.601  39.994  54.248  1.00 33.46
ATOM   4152  C   GLY B 237      43.421  39.477  55.407  1.00 26.07
ATOM   4153  O   GLY B 237      44.630  39.670  55.500  1.00 25.20
ATOM   4154  N   ALA B 238      42.775  38.780  56.352  1.00 26.17
ATOM   4155  CA  ALA B 238      43.611  38.252  57.430  1.00 26.70
ATOM   4156  CB  ALA B 238      42.759  37.864  58.628  1.00 26.33
ATOM   4157  C   ALA B 238      44.430  37.058  56.946  1.00 32.60
ATOM   4158  O   ALA B 238      44.004  36.279  56.094  1.00 20.91
```

FIGURE 285

```
ATOM   4159  N    GLY B 239      45.618  36.924  57.534  1.00  28.56
ATOM   4160  CA   GLY B 239      46.374  35.691  57.339  1.00  28.75
ATOM   4161  C    GLY B 239      45.729  34.583  58.179  1.00  23.57
ATOM   4162  O    GLY B 239      44.556  34.686  58.553  1.00  18.99
ATOM   4163  N    PRO B 240      46.550  33.575  58.437  1.00  19.16
ATOM   4164  CA   PRO B 240      46.088  32.396  59.170  1.00  19.17
ATOM   4165  CB   PRO B 240      47.379  31.599  59.391  1.00  21.18
ATOM   4166  CG   PRO B 240      48.234  32.001  58.234  1.00  25.38
ATOM   4167  CD   PRO B 240      47.974  33.480  58.072  1.00  25.67
ATOM   4168  C    PRO B 240      45.451  32.781  60.494  1.00  19.52
ATOM   4169  O    PRO B 240      45.740  33.818  61.093  1.00  24.13
ATOM   4170  N    THR B 241      44.550  31.928  60.942  1.00  18.39
ATOM   4171  CA   THR B 241      43.980  32.007  62.281  1.00  20.07
ATOM   4172  CB   THR B 241      42.583  31.387  62.332  1.00  20.89
ATOM   4173  OG1  THR B 241      41.622  32.194  61.631  1.00  19.78
ATOM   4174  CG2  THR B 241      42.096  31.306  63.780  1.00  20.55
ATOM   4175  C    THR B 241      44.926  31.258  63.221  1.00  23.29
ATOM   4176  O    THR B 241      45.272  30.103  62.927  1.00  13.70
ATOM   4177  N    VAL B 242      45.381  31.875  64.316  1.00  18.05
ATOM   4178  CA   VAL B 242      46.289  31.126  65.197  1.00  19.59
ATOM   4179  CB   VAL B 242      47.234  32.049  65.978  1.00  19.99
ATOM   4180  CG1  VAL B 242      47.973  31.281  67.071  1.00  22.26
ATOM   4181  CG2  VAL B 242      48.256  32.701  65.060  1.00  15.38
ATOM   4182  C    VAL B 242      45.478  30.266  66.157  1.00  17.32
ATOM   4183  O    VAL B 242      44.453  30.702  66.663  1.00  14.54
ATOM   4184  N    VAL B 243      45.897  29.019  66.424  1.00  16.24
ATOM   4185  CA   VAL B 243      45.166  28.247  67.444  1.00  13.16
ATOM   4186  CB   VAL B 243      44.275  27.150  66.860  1.00  15.05
ATOM   4187  CG1  VAL B 243      43.399  26.461  67.922  1.00  13.07
ATOM   4188  CG2  VAL B 243      43.389  27.729  65.760  1.00  10.83
ATOM   4189  C    VAL B 243      46.218  27.641  68.355  1.00  12.85
ATOM   4190  O    VAL B 243      47.232  27.116  67.875  1.00  13.00
ATOM   4191  N    HIS B 244      46.034  27.683  69.667  1.00  17.27
ATOM   4192  CA   HIS B 244      47.023  27.037  70.522  1.00  14.69
ATOM   4193  CB   HIS B 244      48.209  27.931  70.868  1.00  17.49
ATOM   4194  CG   HIS B 244      47.942  28.983  71.909  1.00  22.46
ATOM   4195  ND1  HIS B 244      48.065  28.773  73.260  1.00  18.81
ATOM   4196  CE1  HIS B 244      47.778  29.877  73.925  1.00  16.49
ATOM   4197  NE2  HIS B 244      47.471  30.820  73.044  1.00  20.57
ATOM   4198  CD2  HIS B 244      47.576  30.286  71.781  1.00  22.25
ATOM   4199  C    HIS B 244      46.349  26.574  71.821  1.00  12.09
ATOM   4200  O    HIS B 244      45.286  27.061  72.168  1.00  14.03
ATOM   4201  N    CYS B 245      47.029  25.631  72.434  1.00  16.27
ATOM   4202  CA   CYS B 245      46.655  25.083  73.747  1.00  15.96
ATOM   4203  CB   CYS B 245      45.929  23.756  73.577  1.00  24.17
ATOM   4204  SG   CYS B 245      46.767  22.530  72.540  1.00  19.97  1
ATOM   4205  C    CYS B 245      47.952  25.010  74.536  1.00  23.79
ATOM   4206  O    CYS B 245      48.651  26.039  74.621  1.00  17.71
ATOM   4207  N    SER B 246      48.357  23.869  75.088  1.00  15.26
ATOM   4208  CA   SER B 246      49.645  23.864  75.785  1.00  15.41
ATOM   4209  CB   SER B 246      49.587  23.047  77.091  1.00   8.58
ATOM   4210  OG   SER B 246      50.839  23.185  77.745  1.00  14.15
```

FIGURE 286

```
ATOM   4211  C    SER B 246      50.725  23.332  74.858  1.00 19.97
ATOM   4212  O    SER B 246      51.746  23.963  74.592  1.00 14.07
ATOM   4213  N    ALA B 247      50.505  22.130  74.328  1.00 17.84
ATOM   4214  CA   ALA B 247      51.486  21.562  73.428  1.00 12.20
ATOM   4215  CB   ALA B 247      51.563  20.047  73.532  1.00 18.43
ATOM   4216  C    ALA B 247      51.157  21.898  71.970  1.00 13.39
ATOM   4217  O    ALA B 247      52.039  21.689  71.133  1.00 21.82
ATOM   4218  N    GLY B 248      49.949  22.376  71.712  1.00 11.10
ATOM   4219  CA   GLY B 248      49.513  22.677  70.361  1.00 14.48
ATOM   4220  C    GLY B 248      49.114  21.449  69.571  1.00 26.17
ATOM   4221  O    GLY B 248      49.288  21.419  68.350  1.00 26.33
ATOM   4222  N    VAL B 249      48.574  20.398  70.200  1.00 19.25
ATOM   4223  CA   VAL B 249      48.239  19.232  69.365  1.00 19.23
ATOM   4224  CB   VAL B 249      49.293  18.114  69.401  1.00 18.92
ATOM   4225  CG1  VAL B 249      50.682  18.568  68.977  1.00 15.44
ATOM   4226  CG2  VAL B 249      49.432  17.478  70.794  1.00 20.80
ATOM   4227  C    VAL B 249      46.884  18.672  69.748  1.00 16.22
ATOM   4228  O    VAL B 249      46.010  18.434  68.890  1.00 22.29
ATOM   4229  N    GLY B 250      46.602  18.422  71.030  1.00 21.24
ATOM   4230  CA   GLY B 250      45.334  17.751  71.313  1.00 23.25
ATOM   4231  C    GLY B 250      44.109  18.612  71.266  1.00 24.10
ATOM   4232  O    GLY B 250      43.159  18.477  70.484  1.00 21.30
ATOM   4233  N    ARG B 251      44.071  19.606  72.170  1.00 12.60
ATOM   4234  CA   ARG B 251      42.891  20.459  72.174  1.00 14.08
ATOM   4235  CB   ARG B 251      42.941  21.317  73.449  1.00 17.84
ATOM   4236  CG   ARG B 251      42.681  20.419  74.664  1.00 18.30
ATOM   4237  CD   ARG B 251      42.862  21.184  75.963  1.00 15.33
ATOM   4238  NE   ARG B 251      44.280  21.335  76.262  1.00 21.24
ATOM   4239  CZ   ARG B 251      44.713  22.030  77.317  1.00 22.30
ATOM   4240  NH1  ARG B 251      43.820  22.588  78.124  1.00 18.21
ATOM   4241  NH2  ARG B 251      46.013  22.129  77.516  1.00 17.67
ATOM   4242  C    ARG B 251      42.869  21.322  70.928  1.00 18.05
ATOM   4243  O    ARG B 251      41.815  21.598  70.358  1.00 21.59
ATOM   4244  N    THR B 252      44.086  21.740  70.545  1.00 14.56
ATOM   4245  CA   THR B 252      44.135  22.560  69.328  1.00 21.90
ATOM   4246  CB   THR B 252      45.580  23.025  69.081  1.00 21.05
ATOM   4247  OG1  THR B 252      45.872  24.089  70.001  1.00 21.60
ATOM   4248  CG2  THR B 252      45.705  23.561  67.670  1.00 19.25
ATOM   4249  C    THR B 252      43.600  21.794  68.120  1.00 21.20
ATOM   4250  O    THR B 252      42.811  22.292  67.312  1.00 19.48
ATOM   4251  N    GLY B 253      44.043  20.545  68.002  1.00 22.67
ATOM   4252  CA   GLY B 253      43.671  19.713  66.862  1.00 16.29
ATOM   4253  C    GLY B 253      42.198  19.395  66.821  1.00 22.35
ATOM   4254  O    GLY B 253      41.587  19.330  65.747  1.00 19.39
ATOM   4255  N    THR B 254      41.634  19.191  68.022  1.00 25.18
ATOM   4256  CA   THR B 254      40.194  18.939  68.106  1.00 15.84
ATOM   4257  CB   THR B 254      39.805  18.402  69.499  1.00 21.21
ATOM   4258  OG1  THR B 254      40.624  17.266  69.796  1.00 19.04
ATOM   4259  CG2  THR B 254      38.361  17.943  69.525  1.00 24.29
ATOM   4260  C    THR B 254      39.422  20.198  67.781  1.00 19.07
ATOM   4261  O    THR B 254      38.352  20.162  67.182  1.00 21.18
ATOM   4262  N    PHE B 255      39.931  21.367  68.178  1.00 21.95
```

FIGURE 287

```
ATOM   4263  CA   PHE B 255      39.225  22.595  67.821  1.00  22.07
ATOM   4264  CB   PHE B 255      39.910  23.855  68.368  1.00  20.64
ATOM   4265  CG   PHE B 255      39.280  25.177  67.939  1.00  16.94
ATOM   4266  CD1  PHE B 255      38.222  25.716  68.650  1.00  17.36
ATOM   4267  CE1  PHE B 255      37.628  26.901  68.272  1.00  16.83
ATOM   4268  CZ   PHE B 255      38.079  27.576  67.156  1.00  20.63
ATOM   4269  CE2  PHE B 255      39.141  27.067  66.427  1.00  15.59
ATOM   4270  CD2  PHE B 255      39.730  25.892  66.841  1.00  26.52
ATOM   4271  C    PHE B 255      39.148  22.712  66.298  1.00  16.89
ATOM   4272  O    PHE B 255      38.114  23.045  65.727  1.00  22.55
ATOM   4273  N    ILE B 256      40.305  22.497  65.682  1.00  22.37
ATOM   4274  CA   ILE B 256      40.393  22.694  64.232  1.00  26.45
ATOM   4275  CB   ILE B 256      41.841  22.644  63.742  1.00  22.17
ATOM   4276  CG1  ILE B 256      42.717  23.802  64.245  1.00  19.09
ATOM   4277  CD1  ILE B 256      44.182  23.636  63.845  1.00  17.45
ATOM   4278  CG2  ILE B 256      41.861  22.570  62.218  1.00  25.40
ATOM   4279  C    ILE B 256      39.556  21.645  63.513  1.00  25.61
ATOM   4280  O    ILE B 256      38.871  21.935  62.537  1.00  32.43
ATOM   4281  N    ALA B 257      39.588  20.418  64.006  1.00  22.52
ATOM   4282  CA   ALA B 257      38.740  19.395  63.390  1.00  28.35
ATOM   4283  CB   ALA B 257      39.011  18.049  64.057  1.00  23.53
ATOM   4284  C    ALA B 257      37.271  19.768  63.462  1.00  31.55
ATOM   4285  O    ALA B 257      36.495  19.520  62.536  1.00  36.42
ATOM   4286  N    LEU B 258      36.833  20.366  64.568  1.00  27.78
ATOM   4287  CA   LEU B 258      35.425  20.714  64.735  1.00  25.99
ATOM   4288  CB   LEU B 258      35.101  21.046  66.201  1.00  29.85
ATOM   4289  CG   LEU B 258      33.612  21.160  66.530  1.00  31.93
ATOM   4290  CD1  LEU B 258      32.852  19.931  66.050  1.00  21.42
ATOM   4291  CD2  LEU B 258      33.381  21.372  68.020  1.00  29.92
ATOM   4292  C    LEU B 258      35.049  21.898  63.862  1.00  28.98
ATOM   4293  O    LEU B 258      33.955  21.967  63.306  1.00  33.28
ATOM   4294  N    ASP B 259      35.976  22.850  63.743  1.00  25.38
ATOM   4295  CA   ASP B 259      35.725  23.991  62.856  1.00  26.70
ATOM   4296  CB   ASP B 259      36.911  24.943  62.895  1.00  25.83
ATOM   4297  CG   ASP B 259      36.704  26.266  62.193  1.00  34.39
ATOM   4298  OD1  ASP B 259      35.615  26.855  62.335  1.00  28.39
ATOM   4299  OD2  ASP B 259      37.650  26.717  61.505  1.00  32.58
ATOM   4300  C    ASP B 259      35.466  23.504  61.433  1.00  19.95
ATOM   4301  O    ASP B 259      34.559  23.983  60.753  1.00  32.03
ATOM   4302  N    ARG B 260      36.261  22.532  60.984  1.00  24.53
ATOM   4303  CA   ARG B 260      36.087  22.057  59.603  1.00  25.87
ATOM   4304  CB   ARG B 260      37.297  21.239  59.169  1.00  26.24
ATOM   4305  CG   ARG B 260      38.591  22.045  59.058  1.00  28.14
ATOM   4306  CD   ARG B 260      39.709  21.131  58.569  1.00  24.62
ATOM   4307  NE   ARG B 260      39.311  20.472  57.320  1.00  31.53
ATOM   4308  CZ   ARG B 260      40.177  20.214  56.345  1.00  39.36
ATOM   4309  NH1  ARG B 260      41.447  20.563  56.493  1.00  41.26
ATOM   4310  NH2  ARG B 260      39.778  19.617  55.231  1.00  56.76
ATOM   4311  C    ARG B 260      34.822  21.239  59.447  1.00  31.74
ATOM   4312  O    ARG B 260      34.189  21.251  58.392  1.00  39.13
ATOM   4313  N    ILE B 261      34.381  20.492  60.468  1.00  30.98
ATOM   4314  CA   ILE B 261      33.208  19.657  60.165  1.00  35.76
```

FIGURE 288

```
ATOM   4315  CB   ILE B 261      33.146  18.381  61.023  1.00 33.31
ATOM   4316  CG1  ILE B 261      32.912  18.576  62.521  1.00 27.49
ATOM   4317  CD1  ILE B 261      33.493  17.459  63.368  1.00 32.91
ATOM   4318  CG2  ILE B 261      34.414  17.561  60.796  1.00 33.85
ATOM   4319  C    ILE B 261      31.938  20.476  60.307  1.00 41.61
ATOM   4320  O    ILE B 261      30.932  20.212  59.641  1.00 42.61
ATOM   4321  N    LEU B 262      31.977  21.494  61.170  1.00 36.25
ATOM   4322  CA   LEU B 262      30.747  22.281  61.321  1.00 37.79
ATOM   4323  CB   LEU B 262      30.868  23.297  62.448  1.00 33.16
ATOM   4324  CG   LEU B 262      30.867  22.707  63.865  1.00 34.98
ATOM   4325  CD1  LEU B 262      30.730  23.791  64.918  1.00 35.24
ATOM   4326  CD2  LEU B 262      29.751  21.680  64.011  1.00 39.50
ATOM   4327  C    LEU B 262      30.444  22.945  59.982  1.00 48.10
ATOM   4328  O    LEU B 262      29.297  23.137  59.592  1.00 54.41
ATOM   4329  N    GLN B 263      31.536  23.268  59.294  1.00 42.55
ATOM   4330  CA   GLN B 263      31.446  23.852  57.963  1.00 45.39
ATOM   4331  CB   GLN B 263      32.819  24.403  57.562  1.00 47.06
ATOM   4332  CG   GLN B 263      33.160  25.695  58.293  1.00 52.92
ATOM   4333  CD   GLN B 263      34.546  26.217  57.972  1.00 51.62
ATOM   4334  OE1  GLN B 263      34.689  27.171  57.208  1.00 48.47
ATOM   4335  NE2  GLN B 263      35.575  25.609  58.552  1.00 34.73
ATOM   4336  C    GLN B 263      30.935  22.825  56.961  1.00 37.20
ATOM   4337  O    GLN B 263      29.987  23.076  56.223  1.00 36.52
ATOM   4338  N    GLN B 264      31.551  21.651  56.930  1.00 48.77
ATOM   4339  CA   GLN B 264      31.089  20.583  56.052  1.00 54.55
ATOM   4340  CB   GLN B 264      31.890  19.305  56.289  1.00 51.39
ATOM   4341  CG   GLN B 264      33.377  19.395  55.996  1.00 45.82
ATOM   4342  CD   GLN B 264      34.080  18.072  56.248  1.00 49.30
ATOM   4343  OE1  GLN B 264      33.426  17.046  56.440  1.00 54.85
ATOM   4344  NE2  GLN B 264      35.410  18.093  56.256  1.00 42.52
ATOM   4345  C    GLN B 264      29.602  20.309  56.268  1.00 65.82
ATOM   4346  O    GLN B 264      28.854  20.101  55.312  1.00 71.36
ATOM   4347  N    LEU B 265      29.169  20.311  57.529  1.00 66.58
ATOM   4348  CA   LEU B 265      27.766  20.033  57.816  1.00 67.06
ATOM   4349  CB   LEU B 265      27.465  20.150  59.309  1.00 67.27
ATOM   4350  CG   LEU B 265      27.604  18.870  60.130  1.00 71.80
ATOM   4351  CD1  LEU B 265      27.000  19.066  61.515  1.00 69.10
ATOM   4352  CD2  LEU B 265      26.955  17.695  59.409  1.00 78.85
ATOM   4353  C    LEU B 265      26.858  20.996  57.055  1.00 65.79
ATOM   4354  O    LEU B 265      25.951  20.581  56.340  1.00 62.34
ATOM   4355  N    ASP B 266      27.140  22.278  57.242  1.00 61.77
ATOM   4356  CA   ASP B 266      26.333  23.341  56.663  1.00 64.82
ATOM   4357  CB   ASP B 266      26.740  24.673  57.312  1.00 71.48
ATOM   4358  CG   ASP B 266      26.589  24.603  58.822  1.00 82.79
ATOM   4359  OD1  ASP B 266      26.033  23.597  59.312  1.00 89.00
ATOM   4360  OD2  ASP B 266      27.021  25.562  59.500  1.00104.58
ATOM   4361  C    ASP B 266      26.454  23.433  55.152  1.00 62.69
ATOM   4362  O    ASP B 266      25.779  24.251  54.519  1.00 61.16
ATOM   4363  N    SER B 267      27.294  22.612  54.520  1.00 56.01
ATOM   4364  CA   SER B 267      27.375  22.733  53.063  1.00 54.60
ATOM   4365  CB   SER B 267      28.557  23.647  52.720  1.00 53.27
ATOM   4366  OG   SER B 267      29.698  23.231  53.454  1.00 48.03
```

FIGURE 289

```
ATOM   4367  C   SER B 267      27.529  21.401  52.353  1.00 61.19
ATOM   4368  O   SER B 267      27.489  21.325  51.121  1.00 78.99
ATOM   4369  N   LYS B 268      27.711  20.321  53.101  1.00 66.12
ATOM   4370  CA  LYS B 268      27.946  19.017  52.481  1.00 67.60
ATOM   4371  CB  LYS B 268      29.387  18.583  52.742  1.00 73.63
ATOM   4372  CG  LYS B 268      29.798  17.277  52.087  1.00 76.35
ATOM   4373  CD  LYS B 268      31.310  17.139  52.000  1.00 69.59
ATOM   4374  CE  LYS B 268      31.983  17.228  53.356  1.00 57.88
ATOM   4375  NZ  LYS B 268      32.516  15.916  53.815  1.00 46.13
ATOM   4376  C   LYS B 268      26.957  17.982  52.997  1.00 59.94
ATOM   4377  O   LYS B 268      26.428  18.102  54.100  1.00 64.53
ATOM   4378  N   ASP B 269      26.692  16.955  52.201  1.00 56.14
ATOM   4379  CA  ASP B 269      25.749  15.913  52.591  1.00 60.87
ATOM   4380  CB  ASP B 269      24.980  15.392  51.377  1.00 71.26
ATOM   4381  CG  ASP B 269      25.670  15.678  50.060  1.00 82.48
ATOM   4382  OD1 ASP B 269      26.027  16.846  49.797  1.00101.89
ATOM   4383  OD2 ASP B 269      25.856  14.725  49.273  1.00103.90
ATOM   4384  C   ASP B 269      26.479  14.771  53.294  1.00 57.30
ATOM   4385  O   ASP B 269      25.869  13.797  53.732  1.00 54.94
ATOM   4386  N   SER B 270      27.797  14.922  53.393  1.00 44.67
ATOM   4387  CA  SER B 270      28.633  13.990  54.132  1.00 41.73
ATOM   4388  CB  SER B 270      29.526  13.168  53.206  1.00 43.00
ATOM   4389  OG  SER B 270      28.790  12.556  52.162  1.00 51.47
ATOM   4390  C   SER B 270      29.487  14.760  55.142  1.00 42.93
ATOM   4391  O   SER B 270      29.563  15.988  55.100  1.00 44.44
ATOM   4392  N   VAL B 271      30.122  14.024  56.045  1.00 39.47
ATOM   4393  CA  VAL B 271      31.033  14.606  57.020  1.00 42.42
ATOM   4394  CB  VAL B 271      30.399  14.754  58.412  1.00 43.26
ATOM   4395  CG1 VAL B 271      29.733  13.460  58.864  1.00 32.79
ATOM   4396  CG2 VAL B 271      31.460  15.183  59.417  1.00 35.29
ATOM   4397  C   VAL B 271      32.282  13.735  57.095  1.00 48.99
ATOM   4398  O   VAL B 271      32.184  12.509  57.041  1.00 58.21
ATOM   4399  N   ASP B 272      33.444  14.367  57.209  1.00 45.99
ATOM   4400  CA  ASP B 272      34.707  13.648  57.135  1.00 35.10
ATOM   4401  CB  ASP B 272      35.417  14.055  55.832  1.00 36.44
ATOM   4402  CG  ASP B 272      36.191  12.901  55.232  1.00 35.96
ATOM   4403  OD1 ASP B 272      36.367  11.892  55.943  1.00 46.07
ATOM   4404  OD2 ASP B 272      36.621  13.010  54.067  1.00 60.29
ATOM   4405  C   ASP B 272      35.605  13.897  58.334  1.00 38.48
ATOM   4406  O   ASP B 272      36.631  14.567  58.238  1.00 37.38
ATOM   4407  N   ILE B 273      35.225  13.349  59.485  1.00 44.55
ATOM   4408  CA  ILE B 273      36.018  13.484  60.706  1.00 42.80
ATOM   4409  CB  ILE B 273      35.239  12.986  61.941  1.00 44.89
ATOM   4410  CG1 ILE B 273      34.010  13.836  62.283  1.00 43.95
ATOM   4411  CD1 ILE B 273      32.873  13.080  62.950  1.00 28.68
ATOM   4412  CG2 ILE B 273      36.135  12.859  63.164  1.00 35.00
ATOM   4413  C   ILE B 273      37.341  12.749  60.554  1.00 43.03
ATOM   4414  O   ILE B 273      38.397  13.283  60.903  1.00 47.22
ATOM   4415  N   TYR B 274      37.333  11.528  60.019  1.00 33.68
ATOM   4416  CA  TYR B 274      38.587  10.824  59.758  1.00 33.83
ATOM   4417  CB  TYR B 274      38.323   9.463  59.101  1.00 31.32
ATOM   4418  CG  TYR B 274      39.536   8.615  58.815  1.00 34.21
```

FIGURE 290

```
ATOM   4419  CD1 TYR B 274      40.011   7.706  59.752  1.00 27.81
ATOM   4420  CE1 TYR B 274      41.124   6.936  59.481  1.00 33.31
ATOM   4421  CZ  TYR B 274      41.783   7.051  58.280  1.00 38.03
ATOM   4422  OH  TYR B 274      42.894   6.287  57.994  1.00 74.99
ATOM   4423  CE2 TYR B 274      41.334   7.942  57.338  1.00 34.20
ATOM   4424  CD2 TYR B 274      40.227   8.704  57.615  1.00 30.48
ATOM   4425  C   TYR B 274      39.499  11.654  58.857  1.00 30.77
ATOM   4426  O   TYR B 274      40.699  11.762  59.091  1.00 42.32
ATOM   4427  N   GLY B 275      38.914  12.201  57.796  1.00 33.93
ATOM   4428  CA  GLY B 275      39.661  12.924  56.786  1.00 34.96
ATOM   4429  C   GLY B 275      40.242  14.213  57.340  1.00 28.44
ATOM   4430  O   GLY B 275      41.328  14.628  56.928  1.00 26.09
ATOM   4431  N   ALA B 276      39.508  14.838  58.264  1.00 30.51
ATOM   4432  CA  ALA B 276      40.037  16.083  58.849  1.00 32.53
ATOM   4433  CB  ALA B 276      38.977  16.819  59.633  1.00 28.84
ATOM   4434  C   ALA B 276      41.233  15.754  59.724  1.00 28.27
ATOM   4435  O   ALA B 276      42.298  16.355  59.634  1.00 27.29
ATOM   4436  N   VAL B 277      41.052  14.745  60.587  1.00 22.62
ATOM   4437  CA  VAL B 277      42.157  14.409  61.478  1.00 22.13
ATOM   4438  CB  VAL B 277      41.713  13.420  62.569  1.00 25.76
ATOM   4439  CG1 VAL B 277      42.931  12.861  63.293  1.00 33.74
ATOM   4440  CG2 VAL B 277      40.769  14.087  63.561  1.00 22.07
ATOM   4441  C   VAL B 277      43.342  13.846  60.712  1.00 31.87
ATOM   4442  O   VAL B 277      44.512  14.018  61.076  1.00 30.97
ATOM   4443  N   HIS B 278      43.053  13.141  59.616  1.00 26.49
ATOM   4444  CA  HIS B 278      44.180  12.632  58.831  1.00 24.97
ATOM   4445  CB  HIS B 278      43.663  11.735  57.699  1.00 26.29
ATOM   4446  CG  HIS B 278      44.716  11.393  56.689  1.00 35.64
ATOM   4447  ND1 HIS B 278      45.145  12.273  55.723  1.00 32.18
ATOM   4448  CE1 HIS B 278      46.077  11.699  54.986  1.00 36.91
ATOM   4449  NE2 HIS B 278      46.280  10.473  55.443  1.00 39.75
ATOM   4450  CD2 HIS B 278      45.440  10.261  56.509  1.00 40.27
ATOM   4451  C   HIS B 278      44.988  13.809  58.294  1.00 17.49
ATOM   4452  O   HIS B 278      46.212  13.862  58.377  1.00 21.10
ATOM   4453  N   ASP B 279      44.262  14.777  57.736  1.00 23.86
ATOM   4454  CA  ASP B 279      44.908  15.964  57.171  1.00 33.69
ATOM   4455  CB  ASP B 279      43.864  16.870  56.522  1.00 34.31
ATOM   4456  CG  ASP B 279      44.369  17.652  55.325  1.00 49.90
ATOM   4457  OD1 ASP B 279      45.255  17.163  54.584  1.00 38.05
ATOM   4458  OD2 ASP B 279      43.867  18.782  55.115  1.00 40.80
ATOM   4459  C   ASP B 279      45.697  16.716  58.238  1.00 26.60
ATOM   4460  O   ASP B 279      46.841  17.124  58.034  1.00 28.11
ATOM   4461  N   LEU B 280      45.088  16.895  59.408  1.00 25.81
ATOM   4462  CA  LEU B 280      45.801  17.538  60.510  1.00 28.08
ATOM   4463  CB  LEU B 280      44.955  17.535  61.782  1.00 24.40
ATOM   4464  CG  LEU B 280      43.689  18.389  61.749  1.00 26.95
ATOM   4465  CD1 LEU B 280      43.088  18.489  63.138  1.00 30.65
ATOM   4466  CD2 LEU B 280      43.987  19.757  61.164  1.00 49.17
ATOM   4467  C   LEU B 280      47.117  16.834  60.804  1.00 32.98
ATOM   4468  O   LEU B 280      48.141  17.483  61.022  1.00 28.16
ATOM   4469  N   ARG B 281      47.078  15.503  60.816  1.00 21.92
ATOM   4470  CA  ARG B 281      48.252  14.703  61.134  1.00 14.30
```

FIGURE 291

```
ATOM   4471  CB  ARG B 281      47.854  13.212  61.199  1.00 15.59
ATOM   4472  CG  ARG B 281      46.856  12.946  62.326  1.00 30.08
ATOM   4473  CD  ARG B 281      47.580  12.419  63.554  1.00 35.07
ATOM   4474  NE  ARG B 281      46.665  12.288  64.685  1.00 41.36
ATOM   4475  CZ  ARG B 281      46.356  11.125  65.243  1.00 44.73
ATOM   4476  NH1 ARG B 281      46.894  10.010  64.769  1.00 39.14
ATOM   4477  NH2 ARG B 281      45.515  11.092  66.268  1.00 40.94
ATOM   4478  C   ARG B 281      49.378  14.834  60.141  1.00 16.56
ATOM   4479  O   ARG B 281      50.574  14.692  60.430  1.00 23.41
ATOM   4480  N   LEU B 282      49.000  15.098  58.885  1.00 21.94
ATOM   4481  CA  LEU B 282      50.085  15.295  57.919  1.00 22.08
ATOM   4482  CB  LEU B 282      49.505  15.415  56.508  1.00 30.24
ATOM   4483  CG  LEU B 282      48.946  14.129  55.895  1.00 38.66
ATOM   4484  CD1 LEU B 282      48.260  14.402  54.563  1.00 35.05
ATOM   4485  CD2 LEU B 282      50.055  13.099  55.724  1.00 35.97
ATOM   4486  C   LEU B 282      50.921  16.528  58.246  1.00 22.11
ATOM   4487  O   LEU B 282      52.089  16.605  57.854  1.00 27.03
ATOM   4488  N   HIS B 283      50.359  17.509  58.949  1.00 19.17
ATOM   4489  CA  HIS B 283      51.085  18.767  59.129  1.00 22.40
ATOM   4490  CB  HIS B 283      50.140  19.931  58.762  1.00 28.15
ATOM   4491  CG  HIS B 283      49.775  19.824  57.305  1.00 27.86
ATOM   4492  ND1 HIS B 283      48.636  19.183  56.872  1.00 29.65
ATOM   4493  CE1 HIS B 283      48.585  19.229  55.549  1.00 28.25
ATOM   4494  NE2 HIS B 283      49.648  19.884  55.115  1.00 28.83
ATOM   4495  CD2 HIS B 283      50.417  20.257  56.193  1.00 25.31
ATOM   4496  C   HIS B 283      51.683  18.946  60.513  1.00 16.39
ATOM   4497  O   HIS B 283      52.619  19.732  60.696  1.00 19.23
ATOM   4498  N   ARG B 284      51.215  18.186  61.499  1.00 14.42
ATOM   4499  CA  ARG B 284      51.851  18.254  62.811  1.00 16.63
ATOM   4500  CB  ARG B 284      51.353  19.503  63.539  1.00 17.04
ATOM   4501  CG  ARG B 284      51.990  19.779  64.894  1.00 20.73
ATOM   4502  CD  ARG B 284      51.670  21.227  65.288  1.00 19.31
ATOM   4503  NE  ARG B 284      51.932  21.473  66.705  1.00 16.50
ATOM   4504  CZ  ARG B 284      53.027  22.065  67.155  1.00 18.89
ATOM   4505  NH1 ARG B 284      53.961  22.471  66.295  1.00 16.50
ATOM   4506  NH2 ARG B 284      53.184  22.249  68.464  1.00 12.75
ATOM   4507  C   ARG B 284      51.515  17.002  63.621  1.00 15.24
ATOM   4508  O   ARG B 284      50.395  16.503  63.515  1.00 21.78
ATOM   4509  N   VAL B 285      52.472  16.553  64.400  1.00 22.07
ATOM   4510  CA  VAL B 285      52.309  15.357  65.228  1.00 18.47
ATOM   4511  CB  VAL B 285      53.643  15.032  65.919  1.00 22.85
ATOM   4512  CG1 VAL B 285      53.931  15.996  67.065  1.00 21.98
ATOM   4513  CG2 VAL B 285      53.647  13.591  66.415  1.00 31.56
ATOM   4514  C   VAL B 285      51.181  15.513  66.237  1.00 31.62
ATOM   4515  O   VAL B 285      50.887  16.594  66.739  1.00 20.75
ATOM   4516  N   HIS B 286      50.511  14.404  66.519  1.00 35.82
ATOM   4517  CA  HIS B 286      49.576  14.183  67.598  1.00 24.99
ATOM   4518  CB  HIS B 286      50.264  14.498  68.941  1.00 23.90
ATOM   4519  CG  HIS B 286      51.337  13.511  69.289  1.00 30.81
ATOM   4520  ND1 HIS B 286      51.236  12.162  69.015  1.00 39.23
ATOM   4521  CE1 HIS B 286      52.326  11.537  69.425  1.00 40.25
ATOM   4522  NE2 HIS B 286      53.144  12.431  69.963  1.00 40.87
```

FIGURE 292

| | | | | | | | | | |
|---|---|---|---|---|---|---|---|---|---|
| ATOM | 4523 | CD2 | HIS | B | 286 | 52.543 | 13.669 | 69.883 | 1.00 30.11 |
| ATOM | 4524 | C | HIS | B | 286 | 48.282 | 14.973 | 67.520 | 1.00 28.12 |
| ATOM | 4525 | O | HIS | B | 286 | 47.543 | 15.026 | 68.515 | 1.00 34.48 |
| ATOM | 4526 | N | MET | B | 287 | 47.981 | 15.578 | 66.382 | 1.00 19.24 |
| ATOM | 4527 | CA | MET | B | 287 | 46.741 | 16.320 | 66.214 | 1.00 22.67 |
| ATOM | 4528 | CB | MET | B | 287 | 46.545 | 16.759 | 64.771 | 1.00 29.06 |
| ATOM | 4529 | CG | MET | B | 287 | 47.551 | 17.692 | 64.153 | 1.00 26.09 |
| ATOM | 4530 | SD | MET | B | 287 | 47.319 | 19.403 | 64.727 | 1.00 57.61 1 |
| ATOM | 4531 | CE | MET | B | 287 | 48.486 | 19.307 | 66.054 | 1.00  8.09 |
| ATOM | 4532 | C | MET | B | 287 | 45.535 | 15.468 | 66.623 | 1.00 35.86 |
| ATOM | 4533 | O | MET | B | 287 | 45.367 | 14.357 | 66.108 | 1.00 33.56 |
| ATOM | 4534 | N | VAL | B | 288 | 44.728 | 16.000 | 67.527 | 1.00 31.94 |
| ATOM | 4535 | CA | VAL | B | 288 | 43.671 | 15.249 | 68.206 | 1.00 29.58 |
| ATOM | 4536 | CB | VAL | B | 288 | 42.591 | 14.724 | 67.262 | 1.00 25.44 |
| ATOM | 4537 | CG1 | VAL | B | 288 | 41.504 | 13.994 | 68.051 | 1.00 27.03 |
| ATOM | 4538 | CG2 | VAL | B | 288 | 41.978 | 15.870 | 66.483 | 1.00 25.23 |
| ATOM | 4539 | C | VAL | B | 288 | 44.331 | 14.102 | 68.975 | 1.00 28.49 |
| ATOM | 4540 | O | VAL | B | 288 | 44.486 | 12.998 | 68.463 | 1.00 31.96 |
| ATOM | 4541 | N | GLN | B | 289 | 44.734 | 14.434 | 70.194 | 1.00 22.07 |
| ATOM | 4542 | CA | GLN | B | 289 | 45.722 | 13.703 | 70.953 | 1.00 30.99 |
| ATOM | 4543 | CB | GLN | B | 289 | 46.399 | 14.641 | 71.955 | 1.00 32.52 |
| ATOM | 4544 | CG | GLN | B | 289 | 47.584 | 14.032 | 72.686 | 1.00 31.56 |
| ATOM | 4545 | CD | GLN | B | 289 | 47.342 | 13.990 | 74.187 | 1.00 46.43 |
| ATOM | 4546 | OE1 | GLN | B | 289 | 46.897 | 14.972 | 74.782 | 1.00 45.11 |
| ATOM | 4547 | NE2 | GLN | B | 289 | 47.639 | 12.848 | 74.795 | 1.00 56.32 |
| ATOM | 4548 | C | GLN | B | 289 | 45.165 | 12.495 | 71.695 | 1.00 34.06 |
| ATOM | 4549 | O | GLN | B | 289 | 45.949 | 11.582 | 71.976 | 1.00 37.74 |
| ATOM | 4550 | N | THR | B | 290 | 43.874 | 12.473 | 71.997 | 1.00 34.47 |
| ATOM | 4551 | CA | THR | B | 290 | 43.323 | 11.278 | 72.636 | 1.00 38.23 |
| ATOM | 4552 | CB | THR | B | 290 | 42.869 | 11.533 | 74.089 | 1.00 29.88 |
| ATOM | 4553 | OG1 | THR | B | 290 | 41.723 | 12.396 | 74.064 | 1.00 32.43 |
| ATOM | 4554 | CG2 | THR | B | 290 | 43.954 | 12.209 | 74.903 | 1.00 30.96 |
| ATOM | 4555 | C | THR | B | 290 | 42.131 | 10.704 | 71.879 | 1.00 38.89 |
| ATOM | 4556 | O | THR | B | 290 | 41.394 | 11.381 | 71.170 | 1.00 37.95 |
| ATOM | 4557 | N | GLU | B | 291 | 41.927 |  9.397 | 72.062 | 1.00 40.68 |
| ATOM | 4558 | CA | GLU | B | 291 | 40.760 |  8.735 | 71.494 | 1.00 35.35 |
| ATOM | 4559 | CB | GLU | B | 291 | 40.764 |  7.261 | 71.915 | 1.00 46.96 |
| ATOM | 4560 | CG | GLU | B | 291 | 39.750 |  6.391 | 71.186 | 1.00 52.82 |
| ATOM | 4561 | CD | GLU | B | 291 | 39.890 |  4.935 | 71.603 | 1.00 55.59 |
| ATOM | 4562 | OE1 | GLU | B | 291 | 38.878 |  4.210 | 71.644 | 1.00 67.94 |
| ATOM | 4563 | OE2 | GLU | B | 291 | 41.035 |  4.536 | 71.899 | 1.00 48.99 |
| ATOM | 4564 | C | GLU | B | 291 | 39.465 |  9.394 | 71.939 | 1.00 29.83 |
| ATOM | 4565 | O | GLU | B | 291 | 38.487 |  9.486 | 71.192 | 1.00 34.01 |
| ATOM | 4566 | N | CYS | B | 292 | 39.421 |  9.874 | 73.194 | 1.00 31.22 |
| ATOM | 4567 | CA | CYS | B | 292 | 38.144 | 10.429 | 73.647 | 1.00 30.43 |
| ATOM | 4568 | CB | CYS | B | 292 | 38.112 | 10.562 | 75.169 | 1.00 36.01 |
| ATOM | 4569 | SG | CYS | B | 292 | 39.681 | 11.083 | 75.904 | 1.00131.76 1 |
| ATOM | 4570 | C | CYS | B | 292 | 37.862 | 11.764 | 72.979 | 1.00 24.32 |
| ATOM | 4571 | O | CYS | B | 292 | 36.720 | 12.200 | 72.903 | 1.00 28.29 |
| ATOM | 4572 | N | GLN | B | 293 | 38.915 | 12.415 | 72.489 | 1.00 33.10 |
| ATOM | 4573 | CA | GLN | B | 293 | 38.751 | 13.630 | 71.694 | 1.00 30.62 |
| ATOM | 4574 | CB | GLN | B | 293 | 40.117 | 14.322 | 71.527 | 1.00 28.49 |

FIGURE 293

```
ATOM   4575  CG   GLN B 293      40.470  15.209  72.711  1.00 27.02
ATOM   4576  CD   GLN B 293      41.904  15.666  72.787  1.00 29.40
ATOM   4577  OE1  GLN B 293      42.722  15.395  71.907  1.00 31.27
ATOM   4578  NE2  GLN B 293      42.261  16.375  73.858  1.00 29.27
ATOM   4579  C    GLN B 293      38.132  13.286  70.347  1.00 26.72
ATOM   4580  O    GLN B 293      37.224  13.930  69.828  1.00 39.00
ATOM   4581  N    TYR B 294      38.662  12.203  69.763  1.00 28.45
ATOM   4582  CA   TYR B 294      38.117  11.677  68.512  1.00 24.87
ATOM   4583  CB   TYR B 294      38.861  10.398  68.098  1.00 32.22
ATOM   4584  CG   TYR B 294      38.628  10.021  66.650  1.00 42.38
ATOM   4585  CD1  TYR B 294      39.072  10.848  65.621  1.00 43.00
ATOM   4586  CE1  TYR B 294      38.867  10.520  64.294  1.00 47.37
ATOM   4587  CZ   TYR B 294      38.207   9.350  63.975  1.00 48.16
ATOM   4588  OH   TYR B 294      38.001   9.025  62.651  1.00 34.98
ATOM   4589  CE2  TYR B 294      37.756   8.516  64.976  1.00 41.30
ATOM   4590  CD2  TYR B 294      37.966   8.851  66.302  1.00 40.38
ATOM   4591  C    TYR B 294      36.628  11.405  68.664  1.00 32.24
ATOM   4592  O    TYR B 294      35.800  11.862  67.885  1.00 38.08
ATOM   4593  N    VAL B 295      36.302  10.647  69.711  1.00 45.53
ATOM   4594  CA   VAL B 295      34.926  10.315  70.045  1.00 44.59
ATOM   4595  CB   VAL B 295      34.844   9.467  71.331  1.00 40.45
ATOM   4596  CG1  VAL B 295      33.478   9.640  71.975  1.00 39.76
ATOM   4597  CG2  VAL B 295      35.134   8.009  71.030  1.00 42.13
ATOM   4598  C    VAL B 295      34.096  11.573  70.258  1.00 43.22
ATOM   4599  O    VAL B 295      32.963  11.696  69.798  1.00 39.21
ATOM   4600  N    TYR B 296      34.680  12.529  70.983  1.00 39.28
ATOM   4601  CA   TYR B 296      33.973  13.791  71.204  1.00 38.11
ATOM   4602  CB   TYR B 296      34.866  14.740  72.004  1.00 36.49
ATOM   4603  CG   TYR B 296      34.235  16.065  72.341  1.00 29.43
ATOM   4604  CD1  TYR B 296      33.274  16.182  73.337  1.00 26.96
ATOM   4605  CE1  TYR B 296      32.688  17.392  73.655  1.00 26.29
ATOM   4606  CZ   TYR B 296      33.072  18.524  72.963  1.00 36.48
ATOM   4607  OH   TYR B 296      32.503  19.739  73.267  1.00 28.44
ATOM   4608  CE2  TYR B 296      34.023  18.443  71.970  1.00 34.08
ATOM   4609  CD2  TYR B 296      34.602  17.224  71.661  1.00 38.40
ATOM   4610  C    TYR B 296      33.582  14.431  69.883  1.00 30.28
ATOM   4611  O    TYR B 296      32.516  15.027  69.739  1.00 28.21
ATOM   4612  N    LEU B 297      34.477  14.309  68.896  1.00 32.45
ATOM   4613  CA   LEU B 297      34.172  14.905  67.592  1.00 29.13
ATOM   4614  CB   LEU B 297      35.329  14.627  66.633  1.00 28.47
ATOM   4615  CG   LEU B 297      36.560  15.523  66.842  1.00 31.47
ATOM   4616  CD1  LEU B 297      37.742  14.998  66.052  1.00 24.45
ATOM   4617  CD2  LEU B 297      36.235  16.958  66.462  1.00 26.38
ATOM   4618  C    LEU B 297      32.852  14.378  67.039  1.00 34.78
ATOM   4619  O    LEU B 297      31.967  15.133  66.639  1.00 26.92
ATOM   4620  N    HIS B 298      32.719  13.055  67.036  1.00 42.39
ATOM   4621  CA   HIS B 298      31.505  12.405  66.536  1.00 42.94
ATOM   4622  CB   HIS B 298      31.714  10.888  66.528  1.00 40.75
ATOM   4623  CG   HIS B 298      32.747  10.427  65.545  1.00 42.36
ATOM   4624  ND1  HIS B 298      34.085  10.309  65.850  1.00 43.84
ATOM   4625  CE1  HIS B 298      34.758   9.881  64.795  1.00 39.31
ATOM   4626  NE2  HIS B 298      33.901   9.708  63.804  1.00 42.05
```

FIGURE 294

```
ATOM   4627  CD2 HIS B 298      32.640  10.043  64.249  1.00 43.47
ATOM   4628  C   HIS B 298      30.278  12.791  67.348  1.00 35.51
ATOM   4629  O   HIS B 298      29.192  12.997  66.800  1.00 32.51
ATOM   4630  N   GLN B 299      30.409  12.916  68.669  1.00 33.21
ATOM   4631  CA  GLN B 299      29.266  13.336  69.483  1.00 33.23
ATOM   4632  CB  GLN B 299      29.581  13.264  70.982  1.00 40.20
ATOM   4633  CG  GLN B 299      30.119  11.919  71.443  1.00 49.41
ATOM   4634  CD  GLN B 299      30.348  11.829  72.937  1.00 54.91
ATOM   4635  OE1 GLN B 299      31.345  12.313  73.477  1.00 54.96
ATOM   4636  NE2 GLN B 299      29.412  11.192  73.633  1.00 62.12
ATOM   4637  C   GLN B 299      28.826  14.743  69.114  1.00 32.95
ATOM   4638  O   GLN B 299      27.638  15.068  69.089  1.00 41.61
ATOM   4639  N   CYS B 300      29.787  15.623  68.810  1.00 32.51
ATOM   4640  CA  CYS B 300      29.370  16.967  68.419  1.00 25.41
ATOM   4641  CB  CYS B 300      30.603  17.848  68.163  1.00 23.71
ATOM   4642  SG  CYS B 300      31.486  18.320  69.679  1.00 41.45  1
ATOM   4643  C   CYS B 300      28.493  16.946  67.175  1.00 29.79
ATOM   4644  O   CYS B 300      27.472  17.628  67.074  1.00 30.90
ATOM   4645  N   VAL B 301      28.920  16.157  66.190  1.00 37.78
ATOM   4646  CA  VAL B 301      28.176  16.043  64.943  1.00 31.92
ATOM   4647  CB  VAL B 301      28.938  15.212  63.899  1.00 35.00
ATOM   4648  CG1 VAL B 301      28.024  14.868  62.728  1.00 40.94
ATOM   4649  CG2 VAL B 301      30.179  15.957  63.430  1.00 37.17
ATOM   4650  C   VAL B 301      26.819  15.404  65.220  1.00 27.85
ATOM   4651  O   VAL B 301      25.795  15.854  64.720  1.00 36.79
ATOM   4652  N   ARG B 302      26.825  14.349  66.036  1.00 42.30
ATOM   4653  CA  ARG B 302      25.557  13.697  66.370  1.00 48.19
ATOM   4654  CB  ARG B 302      25.771  12.523  67.322  1.00 48.82
ATOM   4655  CG  ARG B 302      24.477  11.943  67.886  1.00 51.72
ATOM   4656  CD  ARG B 302      24.723  11.322  69.253  1.00 57.09
ATOM   4657  NE  ARG B 302      24.895  12.340  70.291  1.00 63.02
ATOM   4658  CZ  ARG B 302      25.940  12.384  71.110  1.00 68.57
ATOM   4659  NH1 ARG B 302      26.895  11.472  71.013  1.00 88.06
ATOM   4660  NH2 ARG B 302      26.046  13.329  72.036  1.00 62.92
ATOM   4661  C   ARG B 302      24.599  14.715  66.979  1.00 52.02
ATOM   4662  O   ARG B 302      23.481  14.911  66.506  1.00 55.97
ATOM   4663  N   ASP B 303      25.064  15.381  68.036  1.00 43.78
ATOM   4664  CA  ASP B 303      24.206  16.380  68.673  1.00 41.33
ATOM   4665  CB  ASP B 303      24.923  16.943  69.911  1.00 45.65
ATOM   4666  CG  ASP B 303      25.039  15.864  70.980  1.00 50.16
ATOM   4667  OD1 ASP B 303      24.298  14.861  70.855  1.00 45.98
ATOM   4668  OD2 ASP B 303      25.846  15.982  71.927  1.00 34.68
ATOM   4669  C   ASP B 303      23.795  17.459  67.691  1.00 40.46
ATOM   4670  O   ASP B 303      22.662  17.955  67.734  1.00 56.09
ATOM   4671  N   VAL B 304      24.662  17.874  66.763  1.00 34.45
ATOM   4672  CA  VAL B 304      24.201  18.942  65.868  1.00 48.95
ATOM   4673  CB  VAL B 304      25.351  19.587  65.075  1.00 49.79
ATOM   4674  CG1 VAL B 304      24.862  20.185  63.765  1.00 28.51
ATOM   4675  CG2 VAL B 304      26.027  20.662  65.919  1.00 59.44
ATOM   4676  C   VAL B 304      23.143  18.410  64.907  1.00 54.85
ATOM   4677  O   VAL B 304      22.147  19.072  64.611  1.00 47.47
ATOM   4678  N   LEU B 305      23.356  17.194  64.408  1.00 51.63
```

FIGURE 295

```
ATOM   4679  CA   LEU B 305      22.375  16.636  63.478  1.00 51.67
ATOM   4680  CB   LEU B 305      22.844  15.260  62.996  1.00 41.22
ATOM   4681  CG   LEU B 305      24.018  15.265  62.015  1.00 34.32
ATOM   4682  CD1  LEU B 305      24.215  13.904  61.375  1.00 47.80
ATOM   4683  CD2  LEU B 305      23.809  16.325  60.944  1.00 28.65
ATOM   4684  C    LEU B 305      21.001  16.567  64.128  1.00 56.67
ATOM   4685  O    LEU B 305      20.041  17.177  63.650  1.00 54.42
ATOM   4686  N    ARG B 306      20.874  15.835  65.235  1.00 57.52
ATOM   4687  CA   ARG B 306      19.539  15.658  65.806  1.00 66.45
ATOM   4688  CB   ARG B 306      19.575  14.723  67.019  1.00 67.88
ATOM   4689  CG   ARG B 306      20.951  14.533  67.625  1.00 72.91
ATOM   4690  CD   ARG B 306      20.877  14.354  69.133  1.00 75.55
ATOM   4691  NE   ARG B 306      21.300  13.007  69.521  1.00 78.32
ATOM   4692  CZ   ARG B 306      21.914  12.752  70.670  1.00 79.74
ATOM   4693  NH1  ARG B 306      22.161  13.748  71.509  1.00 73.02
ATOM   4694  NH2  ARG B 306      22.275  11.514  70.971  1.00 90.52
ATOM   4695  C    ARG B 306      18.884  16.972  66.211  1.00 65.71
ATOM   4696  O    ARG B 306      17.651  17.050  66.270  1.00 60.57
ATOM   4697  N    ALA B 307      19.674  18.000  66.503  1.00 63.41
ATOM   4698  CA   ALA B 307      19.082  19.268  66.929  1.00 60.95
ATOM   4699  CB   ALA B 307      20.137  20.143  67.585  1.00 47.72
ATOM   4700  C    ALA B 307      18.413  19.987  65.760  1.00 65.50
ATOM   4701  O    ALA B 307      17.285  20.470  65.877  1.00 57.65
ATOM   4702  N    ARG B 308      19.113  20.054  64.634  1.00 73.88
ATOM   4703  CA   ARG B 308      18.601  20.681  63.421  1.00 83.95
ATOM   4704  CB   ARG B 308      19.685  20.718  62.342  1.00 82.20
ATOM   4705  CG   ARG B 308      21.069  21.087  62.860  1.00 81.07
ATOM   4706  CD   ARG B 308      22.138  20.840  61.803  1.00 76.97
ATOM   4707  NE   ARG B 308      21.546  20.677  60.482  1.00 76.87
ATOM   4708  CZ   ARG B 308      22.159  20.442  59.337  1.00 74.18
ATOM   4709  NH1  ARG B 308      23.476  20.316  59.248  1.00 57.78
ATOM   4710  NH2  ARG B 308      21.427  20.324  58.233  1.00 64.71
ATOM   4711  C    ARG B 308      17.365  19.943  62.917  1.00 92.86
ATOM   4712  O    ARG B 308      16.278  20.515  62.815  1.00 85.75
ATOM   4713  N    LYS B 309      17.535  18.658  62.606  1.00 97.18
ATOM   4714  CA   LYS B 309      16.407  17.851  62.152  1.00101.48
ATOM   4715  CB   LYS B 309      16.828  16.414  61.850  1.00103.32
ATOM   4716  CG   LYS B 309      15.687  15.410  61.805  1.00104.02
ATOM   4717  CD   LYS B 309      15.273  15.077  60.382  1.00104.29
ATOM   4718  CE   LYS B 309      13.920  14.382  60.342  1.00101.24
ATOM   4719  NZ   LYS B 309      13.811  13.409  59.216  1.00 84.67
ATOM   4720  C    LYS B 309      15.292  17.866  63.202  1.00101.41
ATOM   4721  O    LYS B 309      15.282  16.996  64.071  1.00109.20
ATOM   4722  N    LEU B 310      14.415  18.846  63.079  1.00 97.60
ATOM   4723  CA   LEU B 310      13.251  19.077  63.916  1.00 95.62
ATOM   4724  CB   LEU B 310      13.533  18.739  65.380  1.00 95.83
ATOM   4725  CG   LEU B 310      13.082  17.359  65.866  1.00 98.74
ATOM   4726  CD1  LEU B 310      12.607  16.487  64.713  1.00 84.93
ATOM   4727  CD2  LEU B 310      14.202  16.667  66.632  1.00113.56
ATOM   4728  C    LEU B 310      12.786  20.528  63.789  1.00 92.71
ATOM   4729  O    LEU B 310      12.515  21.222  64.765  1.00 74.63
ATOM   4730  O14  INH Z   2      55.288  16.173  78.572  1.00 68.22
```

FIGURE 296

| | | | | | | | | | | |
|---|---|---|---|---|---|---|---|---|---|---|
| ATOM | 4731 | O4 | INH | Z | 2 | 48.070 | 20.932 | 75.258 | 1.00 | 24.37 |
| ATOM | 4732 | S1 | INH | Z | 2 | 47.385 | 19.830 | 74.500 | 1.00 | 29.84 1 |
| ATOM | 4733 | O2 | INH | Z | 2 | 48.097 | 19.600 | 73.249 | 1.00 | 23.28 |
| ATOM | 4734 | O3 | INH | Z | 2 | 45.976 | 19.785 | 74.420 | 1.00 | 19.75 |
| ATOM | 4735 | N1 | INH | Z | 2 | 47.628 | 18.601 | 75.423 | 1.00 | 29.61 |
| ATOM | 4736 | C2 | INH | Z | 2 | 48.913 | 18.097 | 75.576 | 1.00 | 22.41 |
| ATOM | 4737 | C1 | INH | Z | 2 | 49.706 | 18.569 | 76.616 | 1.00 | 17.58 |
| ATOM | 4738 | C3 | INH | Z | 2 | 49.439 | 17.157 | 74.694 | 1.00 | 25.75 |
| ATOM | 4739 | C4 | INH | Z | 2 | 50.726 | 16.698 | 74.879 | 1.00 | 21.37 |
| ATOM | 4740 | C5 | INH | Z | 2 | 51.537 | 17.205 | 75.894 | 1.00 | 28.97 |
| ATOM | 4741 | C6 | INH | Z | 2 | 50.996 | 18.159 | 76.786 | 1.00 | 18.78 |
| ATOM | 4742 | C8 | INH | Z | 2 | 52.976 | 16.759 | 76.061 | 1.00 | 30.10 |
| ATOM | 4743 | C7 | INH | Z | 2 | 53.147 | 15.585 | 77.076 | 1.00 | 38.47 |
| ATOM | 4744 | C9 | INH | Z | 2 | 52.112 | 14.479 | 76.942 | 1.00 | 50.15 |
| ATOM | 4745 | N2 | INH | Z | 2 | 52.210 | 13.593 | 75.955 | 1.00 | 46.78 |
| ATOM | 4746 | C10 | INH | Z | 2 | 51.114 | 12.942 | 75.276 | 1.00 | 48.01 |
| ATOM | 4747 | O1 | INH | Z | 2 | 51.204 | 14.431 | 77.757 | 1.00 | 53.75 |
| ATOM | 4748 | N11 | INH | Z | 2 | 53.037 | 16.040 | 78.545 | 1.00 | 43.33 |
| ATOM | 4749 | C12 | INH | Z | 2 | 54.320 | 16.516 | 79.194 | 1.00 | 55.88 |
| ATOM | 4750 | O6 | INH | Z | 2 | 54.055 | 17.245 | 80.374 | 1.00 | 62.18 |
| ATOM | 4751 | C13 | INH | Z | 2 | 55.182 | 17.437 | 81.254 | 1.00 | 68.88 |
| ATOM | 4752 | C14 | INH | Z | 2 | 55.890 | 18.762 | 81.044 | 1.00 | 69.79 |
| ATOM | 4753 | C15 | INH | Z | 2 | 57.051 | 18.833 | 80.275 | 1.00 | 67.74 |
| ATOM | 4754 | C16 | INH | Z | 2 | 57.681 | 20.064 | 80.042 | 1.00 | 70.03 |
| ATOM | 4755 | C17 | INH | Z | 2 | 57.152 | 21.249 | 80.558 | 1.00 | 70.11 |
| ATOM | 4756 | C18 | INH | Z | 2 | 55.999 | 21.166 | 81.352 | 1.00 | 69.36 |
| ATOM | 4757 | C19 | INH | Z | 2 | 55.377 | 19.934 | 81.606 | 1.00 | 69.79 |
| ATOM | 4758 | O14 | INH | Z | 1 | -1.113 | 8.871 | 44.215 | 1.00 | 38.80 |
| ATOM | 4759 | O4 | INH | Z | 1 | 6.622 | 4.171 | 41.248 | 1.00 | 25.08 |
| ATOM | 4760 | S1 | INH | Z | 1 | 7.335 | 5.325 | 40.618 | 1.00 | 22.22 1 |
| ATOM | 4761 | O2 | INH | Z | 1 | 6.828 | 5.548 | 39.260 | 1.00 | 16.51 |
| ATOM | 4762 | O3 | INH | Z | 1 | 8.747 | 5.431 | 40.711 | 1.00 | 19.75 |
| ATOM | 4763 | N1 | INH | Z | 1 | 6.835 | 6.493 | 41.497 | 1.00 | 20.76 |
| ATOM | 4764 | C2 | INH | Z | 1 | 5.527 | 6.957 | 41.421 | 1.00 | 21.28 |
| ATOM | 4765 | C1 | INH | Z | 1 | 4.584 | 6.427 | 42.291 | 1.00 | 13.44 |
| ATOM | 4766 | C3 | INH | Z | 1 | 5.132 | 7.960 | 40.530 | 1.00 | 21.95 |
| ATOM | 4767 | C4 | INH | Z | 1 | 3.817 | 8.382 | 40.524 | 1.00 | 18.36 |
| ATOM | 4768 | C5 | INH | Z | 1 | 2.870 | 7.861 | 41.415 | 1.00 | 23.03 |
| ATOM | 4769 | C6 | INH | Z | 1 | 3.283 | 6.862 | 42.323 | 1.00 | 16.81 |
| ATOM | 4770 | C8 | INH | Z | 1 | 1.429 | 8.323 | 41.430 | 1.00 | 24.83 |
| ATOM | 4771 | C7 | INH | Z | 1 | 1.120 | 9.380 | 42.549 | 1.00 | 39.39 |
| ATOM | 4772 | C9 | INH | Z | 1 | 2.120 | 10.521 | 42.630 | 1.00 | 40.58 |
| ATOM | 4773 | N2 | INH | Z | 1 | 2.202 | 11.436 | 41.667 | 1.00 | 41.79 |
| ATOM | 4774 | C10 | INH | Z | 1 | 3.287 | 12.393 | 41.566 | 1.00 | 43.35 |
| ATOM | 4775 | O1 | INH | Z | 1 | 2.868 | 10.605 | 43.592 | 1.00 | 44.71 |
| ATOM | 4776 | N11 | INH | Z | 1 | 1.157 | 8.742 | 43.948 | 1.00 | 50.75 |
| ATOM | 4777 | C12 | INH | Z | 1 | -0.086 | 8.670 | 44.797 | 1.00 | 50.71 |
| ATOM | 4778 | O6 | INH | Z | 1 | 0.284 | 8.365 | 46.128 | 1.00 | 57.94 |
| ATOM | 4779 | C13 | INH | Z | 1 | -0.788 | 8.005 | 47.016 | 1.00 | 62.79 |
| ATOM | 4780 | C14 | INH | Z | 1 | -1.038 | 6.513 | 47.116 | 1.00 | 58.14 |
| ATOM | 4781 | C15 | INH | Z | 1 | -2.097 | 5.926 | 46.420 | 1.00 | 57.59 |
| ATOM | 4782 | C16 | INH | Z | 1 | -2.357 | 4.551 | 46.525 | 1.00 | 58.75 |

FIGURE 297

```
ATOM   4783  C17  INH Z   1      -1.560    3.742   47.338  1.00  55.57
ATOM   4784  C18  INH Z   1      -0.493    4.337   48.028  1.00  55.37
ATOM   4785  C19  INH Z   1      -0.220    5.707   47.913  1.00  55.41
ATOM   4786  O1   HOH W   1      10.045   -6.206   48.501  1.00   9.70
ATOM   4787  O1   HOH W   2      44.009   31.332   82.099  1.00  12.76
ATOM   4788  O1   HOH W   3      -1.504    3.025   37.601  1.00  14.12
ATOM   4789  O1   HOH W   4      56.634   21.887   72.619  1.00  18.84
ATOM   4790  O1   HOH W   5      -3.336   -2.466   27.653  1.00  16.96
ATOM   4791  O1   HOH W   6      59.893   27.230   63.111  1.00  20.75
ATOM   4792  O1   HOH W   7       0.940    7.097   29.426  1.00  15.51
ATOM   4793  O1   HOH W   8      56.585   29.393   71.563  1.00  17.34
ATOM   4794  O1   HOH W   9      -3.244   -3.725   34.798  1.00  13.56
ATOM   4795  O1   HOH W  10       1.553   -4.822   35.953  1.00  13.15
ATOM   4796  O1   HOH W  11      -4.895   -5.747   33.816  1.00  16.00
ATOM   4797  O1   HOH W  12      55.065   17.796   64.150  1.00  18.78
ATOM   4798  O1   HOH W  13      -2.710    7.632   22.526  1.00  25.85
ATOM   4799  O1   HOH W  14      -1.058   -4.632   36.416  1.00  16.59
ATOM   4800  O1   HOH W  15      58.883   28.512   70.102  1.00  17.41
ATOM   4801  O1   HOH W  16      14.129  -11.346   42.224  1.00  25.25
ATOM   4802  O1   HOH W  17      15.198   -5.722   25.861  1.00  17.95
ATOM   4803  O1   HOH W  18      -5.309    3.570   27.477  1.00  17.89
ATOM   4804  O1   HOH W  19      59.756   17.517   57.776  1.00  24.77
ATOM   4805  O1   HOH W  20      -6.619   -5.980   43.124  1.00  18.09
ATOM   4806  O1   HOH W  21      54.142   29.809   70.726  1.00  17.84
ATOM   4807  O1   HOH W  22       0.201   -5.367   22.242  1.00  20.61
ATOM   4808  O1   HOH W  23       4.276   11.648   28.034  1.00  21.90
ATOM   4809  O1   HOH W  24      51.995   13.231   62.486  1.00  21.98
ATOM   4810  O1   HOH W  25      -2.328   13.484   27.320  1.00  20.24
ATOM   4811  O1   HOH W  26      41.283   24.669   80.924  1.00  23.47
ATOM   4812  O1   HOH W  27      13.869   -0.367   45.406  1.00  23.14
ATOM   4813  O1   HOH W  28      15.304   -9.348   27.802  1.00  21.59
ATOM   4814  O1   HOH W  29      12.631  -10.292   28.093  1.00  20.50
ATOM   4815  O1   HOH W  30      44.431   39.247   81.240  1.00  25.13
ATOM   4816  O1   HOH W  31      -0.865   -4.102   45.807  1.00  17.03
ATOM   4817  O1   HOH W  32      56.944   30.639   57.225  1.00  27.48
ATOM   4818  O1   HOH W  33      44.974   29.800   84.482  1.00  24.66
ATOM   4819  O1   HOH W  34      40.344   25.679   78.385  1.00  25.40
ATOM   4820  O1   HOH W  35      -0.817   11.896   36.268  1.00  27.05
ATOM   4821  O1   HOH W  36      45.813   26.347   88.982  1.00  29.74
ATOM   4822  O1   HOH W  37      61.459   21.495   62.950  1.00  24.86
ATOM   4823  O1   HOH W  38      61.161   30.493   78.889  1.00  24.20
ATOM   4824  O1   HOH W  39      18.380   -0.097   25.182  1.00  20.65
ATOM   4825  O1   HOH W  40      51.721   30.553   83.500  1.00  23.95
ATOM   4826  O1   HOH W  41      44.911   34.060   54.571  1.00  25.17
ATOM   4827  O1   HOH W  42      55.088   28.823   80.613  1.00  20.78
ATOM   4828  O1   HOH W  43      38.439   25.424   57.676  1.00  24.32
ATOM   4829  O1   HOH W  44      17.651   -4.708   24.960  1.00  23.35
ATOM   4830  O1   HOH W  45      60.668   30.480   69.410  1.00  20.33
ATOM   4831  O1   HOH W  46      10.176  -14.189   47.531  1.00  30.12
ATOM   4832  O1   HOH W  47      -0.430   -5.789   47.698  1.00  31.64
ATOM   4833  O1   HOH W  48      49.454   24.259   54.551  1.00  24.40
ATOM   4834  O1   HOH W  49       8.659   -4.775   50.631  1.00  26.30
```

FIGURE 298

```
ATOM   4835  O1  HOH W   50      8.016 -21.216  43.873  1.00 28.15
ATOM   4836  O1  HOH W   51     41.695  31.267  59.043  1.00 30.73
ATOM   4837  O1  HOH W   52      0.050   1.522  45.671  1.00 24.08
ATOM   4838  O1  HOH W   53      9.328   8.423  41.215  1.00 24.60
ATOM   4839  O1  HOH W   54     18.246  -7.424  47.752  1.00 27.95
ATOM   4840  O1  HOH W   55     17.680 -18.968  48.425  1.00 49.05
ATOM   4841  O1  HOH W   56     63.663  32.033  67.334  1.00 33.07
ATOM   4842  O1  HOH W   57     12.879  -8.580  21.032  1.00 30.73
ATOM   4843  O1  HOH W   58     43.952  35.751  61.678  1.00 24.11
ATOM   4844  O1  HOH W   59      5.457   2.609  21.937  1.00 33.95
ATOM   4845  O1  HOH W   60     41.656  34.732  60.883  1.00 26.67
ATOM   4846  O1  HOH W   61     10.826  -7.011  21.512  1.00 26.24
ATOM   4847  O1  HOH W   62     46.866  32.271  55.142  1.00 28.91
ATOM   4848  O1  HOH W   63     -4.848 -11.748  39.346  1.00 22.84
ATOM   4849  O1  HOH W   64     -1.807 -15.828  33.871  1.00 27.34
ATOM   4850  O1  HOH W   65     15.309  -8.364  24.800  1.00 25.02
ATOM   4851  O1  HOH W   66     10.589  -3.957  17.825  1.00 26.51
ATOM   4852  O1  HOH W   67     53.967  24.496  54.681  1.00 44.06
ATOM   4853  O1  HOH W   68     24.990 -11.936  38.629  1.00 28.80
ATOM   4854  O1  HOH W   69      7.664   0.885  20.675  1.00 28.07
ATOM   4855  O1  HOH W   70     59.900  18.836  77.896  1.00 40.35
ATOM   4856  O1  HOH W   71     45.172  16.962  74.854  1.00 28.34
ATOM   4857  O1  HOH W   72     -7.743  -7.173  31.484  1.00 26.07
ATOM   4858  O1  HOH W   73     62.769  33.034  57.586  1.00 26.41
ATOM   4859  O1  HOH W   74      1.944 -14.302  44.406  1.00 26.86
ATOM   4860  O1  HOH W   75     23.222  -0.340  29.959  1.00 22.19
ATOM   4861  O1  HOH W   76     -0.197  -0.646  21.222  1.00 27.09
ATOM   4862  O1  HOH W   77     42.078  33.736  57.956  1.00 26.98
ATOM   4863  O1  HOH W   78     57.402  25.819  56.138  1.00 32.63
ATOM   4864  O1  HOH W   79     55.439  12.986  71.228  1.00 29.87
ATOM   4865  O1  HOH W   80     34.396   8.529  61.576  1.00 43.51
ATOM   4866  O1  HOH W   81     47.286  29.177  51.681  1.00 31.35
ATOM   4867  O1  HOH W   82     30.677  31.060  77.998  1.00 47.26
ATOM   4868  O1  HOH W   83     41.588  15.444  81.328  1.00 41.21
ATOM   4869  O1  HOH W   84      2.486   5.248  46.367  1.00 34.85
ATOM   4870  O1  HOH W   85     63.709  21.021  72.928  1.00 28.76
ATOM   4871  O1  HOH W   86     27.619   8.328  44.050  1.00 31.73
ATOM   4872  O1  HOH W   87     -5.332 -10.734  36.523  1.00 25.53
ATOM   4873  O1  HOH W   88     62.256  24.240  57.795  1.00 27.98
ATOM   4874  O1  HOH W   89      7.339  -1.362  55.174  1.00 27.75
ATOM   4875  O1  HOH W   90     -3.541  -2.818  46.374  1.00 29.31
ATOM   4876  O1  HOH W   91     12.753   0.559  47.705  1.00 25.52
ATOM   4877  O1  HOH W   92     52.949  39.174  79.040  1.00 31.30
ATOM   4878  O1  HOH W   93     36.070  32.961  80.601  1.00 30.93
ATOM   4879  O1  HOH W   94     59.810  36.762  74.769  1.00 30.79
ATOM   4880  O1  HOH W   95    -12.875   5.864  27.849  1.00 26.59
ATOM   4881  O1  HOH W   96     53.121  29.855  85.728  1.00 31.07
ATOM   4882  O1  HOH W   97     51.540  25.787  52.492  1.00 31.52
ATOM   4883  O1  HOH W   98     18.594 -19.849  45.929  1.00 43.83
ATOM   4884  O1  HOH W   99     -1.532 -18.000  43.060  1.00 30.93
ATOM   4885  O1  HOH W  100     42.535  36.857  53.627  1.00 38.22
ATOM   4886  O1  HOH W  101     56.933  34.861  60.367  1.00 32.82
```

FIGURE 299

```
ATOM   4887  O1   HOH W 102     25.851  -1.470  29.859  1.00 36.64
ATOM   4888  O1   HOH W 103      0.077 -10.003  25.584  1.00 32.46
ATOM   4889  O1   HOH W 104      6.037  -0.243  18.292  1.00 42.47
ATOM   4890  O1   HOH W 105     -5.627  -8.277  21.845  1.00 34.15
ATOM   4891  O1   HOH W 106      4.857  13.360  30.883  1.00 31.69
ATOM   4892  O1   HOH W 107      5.308  15.537  21.988  1.00 25.42
ATOM   4893  O1   HOH W 108      6.752  -6.565  51.673  1.00 33.36
ATOM   4894  O1   HOH W 109     58.057  40.591  69.174  1.00 29.89
ATOM   4895  O1   HOH W 110     58.754   7.470  62.072  1.00 35.42
ATOM   4896  O1   HOH W 111      3.972   1.588  20.509  1.00 37.26
ATOM   4897  O1   HOH W 112     53.197  17.249  55.411  1.00 35.13
ATOM   4898  O1   HOH W 113     36.243  21.471  51.543  1.00 48.69
ATOM   4899  O1   HOH W 114     -0.096  -4.011  20.309  1.00 39.42
ATOM   4900  O1   HOH W 115     49.696  32.306  84.528  1.00 35.44
ATOM   4901  O1   HOH W 116     16.010 -16.452  31.337  1.00 44.52
ATOM   4902  O1   HOH W 117     54.391  30.745  82.842  1.00 30.52
ATOM   4903  O1   HOH W 118     69.018  18.815  64.039  1.00 33.34
ATOM   4904  O1   HOH W 119     39.522  30.110  57.759  1.00 23.80
ATOM   4905  O1   HOH W 120    -10.594   2.764  34.249  1.00 29.91
ATOM   4906  O1   HOH W 121      3.787  -7.512  50.278  1.00 24.62
ATOM   4907  O1   HOH W 122     53.957  23.288  80.378  1.00 30.02
ATOM   4908  O1   HOH W 123     18.987 -16.652  40.990  1.00 30.01
ATOM   4909  O1   HOH W 124      3.080   7.934  45.807  1.00 36.85
ATOM   4910  O1   HOH W 125     55.436   7.031  65.054  1.00 41.50
ATOM   4911  O1   HOH W 126     12.352   9.382  48.476  1.00 33.99
ATOM   4912  O1   HOH W 127     14.471   6.265  26.018  1.00 42.81
ATOM   4913  O1   HOH W 128     43.330  38.653  51.761  1.00 46.93
ATOM   4914  O1   HOH W 129     -5.913 -20.550  38.143  1.00 33.89
ATOM   4915  O1   HOH W 130     20.250   3.300  47.738  1.00 34.00
ATOM   4916  O1   HOH W 131      7.970  -2.668  16.219  1.00 35.55
ATOM   4917  O1   HOH W 132     61.696  45.509  74.227  1.00 35.13
ATOM   4918  O1   HOH W 133     53.846  13.143  73.631  1.00 39.37
ATOM   4919  O1   HOH W 134     29.945  17.996  36.926  1.00 46.09
ATOM   4920  O1   HOH W 135     58.559  11.600  62.402  1.00 26.91
ATOM   4921  O1   HOH W 136     -7.418  -5.438  40.009  1.00 30.49
ATOM   4922  O1   HOH W 137     40.559  41.165  64.176  1.00 45.19
ATOM   4923  O1   HOH W 138     49.766  27.636  50.150  1.00 29.35
ATOM   4924  O1   HOH W 139     65.075  22.379  57.198  1.00 35.09
ATOM   4925  O1   HOH W 140     -8.508   3.715  36.930  1.00 34.08
ATOM   4926  O1   HOH W 141     58.237  33.281  56.920  1.00 33.91
ATOM   4927  O1   HOH W 142     59.723  42.167  67.906  1.00 31.58
ATOM   4928  O1   HOH W 143     62.056  30.740  54.701  1.00 46.78
ATOM   4929  O1   HOH W 144      1.919   3.683  26.777  1.00 58.65
ATOM   4930  O1   HOH W 145      0.229   8.607  19.127  1.00 28.35
ATOM   4931  O1   HOH W 146     12.101  11.343  20.627  1.00 49.67
ATOM   4932  O1   HOH W 147     23.889  -5.655  45.864  1.00 40.68
ATOM   4933  O1   HOH W 148     41.109  26.972  47.802  1.00 38.59
ATOM   4934  O1   HOH W 149     61.067  15.824  56.464  1.00 36.37
ATOM   4935  O1   HOH W 150     53.684  36.619  56.025  1.00 38.94
ATOM   4936  O1   HOH W 151      9.718   4.642  49.998  1.00 29.80
ATOM   4937  O1   HOH W 152     15.016 -11.381  20.564  1.00 35.94
ATOM   4938  O1   HOH W 153     -8.503   6.204  36.690  1.00 33.15
```

FIGURE 300

```
ATOM   4939  O1   HOH W 154      52.945   32.067   87.165  1.00 38.96
ATOM   4940  O1   HOH W 155      -3.303  -17.298   32.155  1.00 30.64
ATOM   4941  O1   HOH W 156      43.328   22.392   52.292  1.00 47.87
ATOM   4942  O1   HOH W 157      28.970    3.140   30.250  1.00 36.23
ATOM   4943  O1   HOH W 158      26.533   -4.056   30.628  1.00 35.32
ATOM   4944  O1   HOH W 159       3.437    3.324   18.731  1.00 37.41
ATOM   4945  O1   HOH W 160      12.257    5.668   24.272  1.00 33.12
ATOM   4946  O1   HOH W 161      28.150    0.298   30.479  1.00 34.00
ATOM   4947  O1   HOH W 162     -17.348  -19.031   28.122  1.00 36.82
ATOM   4948  O1   HOH W 163      -0.825   -8.283   21.905  1.00 38.81
ATOM   4949  O1   HOH W 164      33.831   22.123   80.266  1.00 41.38
ATOM   4950  O1   HOH W 165      49.420   49.137   70.663  1.00 48.62
ATOM   4951  O1   HOH W 166      50.346   11.884   65.231  1.00 44.32
ATOM   4952  O1   HOH W 167       6.773   13.068   43.904  1.00 50.36
ATOM   4953  O1   HOH W 168      56.962   16.533   53.665  1.00 38.99
ATOM   4954  O1   HOH W 169      19.408    8.728   24.340  1.00 35.51
ATOM   4955  O1   HOH W 170      -5.185    6.989   42.383  1.00 48.15
ATOM   4956  O1   HOH W 171      33.871    8.380   22.002  1.00 42.56
ATOM   4957  O1   HOH W 172      32.356   27.890   84.104  1.00 38.54
ATOM   4958  O1   HOH W 173      -1.961    0.606   20.306  1.00 37.03
ATOM   4959  O1   HOH W 174      62.208   29.832   76.581  1.00 55.22
ATOM   4960  O1   HOH W 175      33.040   26.033   62.143  1.00 33.40
ATOM   4961  O1   HOH W 176      17.532  -14.378   31.456  1.00 33.99
ATOM   4962  O1   HOH W 177      37.206    7.422   74.312  1.00 38.76
ATOM   4963  O1   HOH W 178      29.817   29.620   62.244  1.00 43.78
ATOM   4964  O1   HOH W 179       2.238   -5.806   48.797  1.00 24.11
ATOM   4965  O1   HOH W 180      50.166   25.503   48.673  1.00 31.60
ATOM   4966  O1   HOH W 181      58.506   42.575   64.866  1.00 35.82
ATOM   4967  O1   HOH W 182      66.265   21.921   70.420  1.00 39.64
ATOM   4968  O1   HOH W 183       0.671   -9.941   18.215  1.00 52.37
ATOM   4969  O1   HOH W 184       5.293   12.702   45.868  1.00 64.96
ATOM   4970  O1   HOH W 185      26.178   16.910   42.036  1.00 39.26
ATOM   4971  O1   HOH W 186       1.316   -1.635   54.945  1.00 32.69
ATOM   4972  O1   HOH W 187      15.079   11.723   21.275  1.00 48.90
ATOM   4973  O1   HOH W 188      58.780    8.778   52.598  1.00 55.31
ATOM   4974  O1   HOH W 189      -1.566  -17.744   29.231  1.00 40.69
ATOM   4975  O1   HOH W 190      -1.443  -20.552   29.054  1.00 36.00
ATOM   4976  O1   HOH W 191      40.753   36.433   75.429  1.00 40.90
ATOM   4977  O1   HOH W 192      43.705   20.194   83.394  1.00 38.59
ATOM   4978  O1   HOH W 193      13.952    8.216   50.830  1.00 55.41
ATOM   4979  O1   HOH W 194      17.477   -1.718   14.946  1.00 30.24
ATOM   4980  O1   HOH W 195      32.069    3.048   36.009  1.00 37.45
ATOM   4981  O1   HOH W 196      49.867   21.149   90.949  1.00 40.22
ATOM   4982  O1   HOH W 197      31.011   39.913   82.015  1.00 44.40
ATOM   4983  O1   HOH W 198       3.768    7.854   20.763  1.00 37.31
ATOM   4984  O1   HOH W 199      36.080   45.674   78.448  1.00 51.48
ATOM   4985  O1   HOH W 200      41.126    8.733   35.756  1.00 45.43
ATOM   4986  O1   HOH W 201      -3.605    9.194   21.065  1.00 42.26
ATOM   4987  O1   HOH W 202      45.411   20.667   52.071  1.00 47.75
ATOM   4988  O1   HOH W 203      22.572   -2.433   51.460  1.00 51.25
ATOM   4989  O1   HOH W 204      -2.340   18.437   23.217  1.00 35.94
ATOM   4990  O1   HOH W 205       4.213    5.779   19.058  1.00 42.01
```

FIGURE 301

```
ATOM   4991  O1   HOH W 206    -0.746    1.998   51.309  1.00 32.75
ATOM   4992  O1   HOH W 207    28.139   33.211   71.066  1.00 52.64
ATOM   4993  O1   HOH W 208    45.744    7.612   66.653  1.00 41.29
ATOM   4994  O1   HOH W 209    36.066   48.240   71.868  1.00 37.65
ATOM   4995  O1   HOH W 210    27.068   31.927   66.243  1.00 45.28
ATOM   4996  O1   HOH W 211     6.224    6.872   49.187  1.00 28.10
ATOM   4997  O1   HOH W 212    -4.674    3.941   19.505  1.00 49.63
ATOM   4998  O1   HOH W 213    36.180   26.038   50.897  1.00 39.62
ATOM   4999  O1   HOH W 214    43.768   26.501   91.776  1.00 47.54
ATOM   5000  O1   HOH W 215    23.227  -12.725   42.616  1.00 47.18
ATOM   5001  O1   HOH W 216    -5.818  -21.605   40.616  1.00 37.05
ATOM   5002  O1   HOH W 217    31.418   -0.721   30.887  1.00 50.68
ATOM   5003  O1   HOH W 218    30.636   27.485   62.006  1.00 46.74
ATOM   5004  O1   HOH W 219    26.116   18.310   75.358  1.00 48.38
ATOM   5005  O1   HOH W 220     1.345   -9.074   48.599  1.00 38.50
ATOM   5006  O1   HOH W 221     0.416   -1.086   17.311  1.00 48.92
ATOM   5007  O1   HOH W 222    54.434   21.262   61.419  1.00 42.93
ATOM   5008  O1   HOH W 223    51.386    9.817   55.916  1.00 33.89
ATOM   5009  O1   HOH W 224    47.376   31.902   85.186  1.00 47.01
ATOM   5010  O1   HOH W 225    14.573    9.677   49.224  1.00 33.72
ATOM   5011  O1   HOH W 226    53.818   34.420   83.299  1.00 40.34
ATOM   5012  O1   HOH W 227    11.775    4.191   51.814  1.00 46.81
ATOM   5013  O1   HOH W 228    36.320   19.863   21.440  1.00 41.37
ATOM   5014  O1   HOH W 229    15.790   10.248   47.362  1.00 37.82
ATOM   5015  O1   HOH W 230     1.272   11.705   38.927  1.00 32.13
ATOM   5016  O1   HOH W 231    -7.721    2.573   21.097  1.00 38.10
ATOM   5017  O1   HOH W 232    53.283   19.471   53.553  1.00 38.71
ATOM   5018  O1   HOH W 233    51.950   32.548   55.051  1.00 30.33
ATOM   5019  O1   HOH W 234    58.877   41.394   62.179  1.00 45.27
ATOM   5020  O1   HOH W 235    -8.538   -1.081   21.839  1.00 39.11
ATOM   5021  O1   HOH W 236    -0.733    4.812   51.216  1.00 41.83
ATOM   5022  O1   HOH W 237    60.623   35.681   72.217  1.00 39.90
ATOM   5023  O1   HOH W 238    57.744   28.339   55.220  1.00 37.07
ATOM   5024  O1   HOH W 239    59.092   12.614   50.910  1.00 48.79
ATOM   5025  O1   HOH W 240    68.091   31.724   68.601  1.00 34.66
ATOM   5026  O1   HOH W 241    63.691   18.438   72.638  1.00 33.62
ATOM   5027  O1   HOH W 242    53.127   41.929   58.612  1.00 47.21
ATOM   5028  O1   HOH W 243     1.457  -17.227   23.707  1.00 48.59
ATOM   5029  O1   HOH W 244    44.599    4.374   53.989  1.00 55.66
ATOM   5030  O1   HOH W 245    -2.827   19.837   25.584  1.00 44.10
ATOM   5031  O1   HOH W 246    22.401   -9.408   51.289  1.00 46.21
ATOM   5032  O1   HOH W 247    -7.242  -11.447   30.436  1.00 45.75
ATOM   5033  O1   HOH W 248    35.419   11.112   74.634  1.00 40.36
ATOM   5034  O1   HOH W 249    49.132    5.615   57.803  1.00 41.51
ATOM   5035  O1   HOH W 250   -12.594    4.646   35.004  1.00 44.27
ATOM   5036  O1   HOH W 251   -12.226    3.502   24.096  1.00 53.57
ATOM   5037  O1   HOH W 252    49.280   12.394   79.591  1.00 54.74
ATOM   5038  O1   HOH W 253    44.128   17.693   48.227  1.00 50.05
ATOM   5039  O1   HOH W 254     2.013   -8.971   51.042  1.00 34.88
ATOM   5040  O1   HOH W 255    29.402   -6.675   32.345  1.00 54.78
ATOM   5041  O1   HOH W 256    43.680   17.273   82.570  1.00 36.27
ATOM   5042  O1   HOH W 257    31.835   -0.971   66.953  1.00 53.67
```

FIGURE 302

```
ATOM   5043  O1   HOH W 258      34.738   9.985  59.599  1.00 38.24
ATOM   5044  O1   HOH W 259      52.495  11.009  53.739  1.00 47.65
ATOM   5045  O1   HOH W 260       0.140  -7.165  52.324  1.00 48.04
ATOM   5046  O1   HOH W 261      64.908  25.810  56.847  1.00 47.20
ATOM   5047  O1   HOH W 262      54.501  32.978  55.500  1.00 42.65
ATOM   5048  O1   HOH W 263      38.723  39.573  64.125  1.00 44.25
ATOM   5049  O1   HOH W 264      60.016   5.683  60.372  1.00 39.48
ATOM   5050  O1   HOH W 265      41.596  40.187  50.813  1.00 39.03
ATOM   5051  O1   HOH W 266       9.560  17.462  32.534  1.00 35.34
ATOM   5052  O1   HOH W 267       3.163 -20.952  48.609  1.00 33.97
ATOM   5053  O1   HOH W 268      16.265  18.009  17.553  1.00 51.71
ATOM   5054  O1   HOH W 269      22.132  26.469  35.632  1.00 49.25
ATOM   5055  O1   HOH W 270       0.202  17.702  30.444  1.00 39.18
ATOM   5056  O1   HOH W 271      28.128  10.379  42.510  1.00 41.98
ATOM   5057  O1   HOH W 272      19.729 -16.688  38.739  1.00 29.83
ATOM   5058  O1   HOH W 273      37.288  16.310  56.333  1.00 54.08
ATOM   5059  O1   HOH W 274      26.953  23.484  61.752  1.00 50.25
ATOM   5060  O1   HOH W 275      44.052  42.974  56.507  1.00 45.06
ATOM   5061  O1   HOH W 276      25.652   3.648  70.742  1.00 42.16
ATOM   5062  O1   HOH W 277       1.252   3.132  54.632  1.00 46.31
ATOM   5063  O1   HOH W 278      52.770  49.829  63.294  1.00 42.77
ATOM   5064  O1   HOH W 279      -2.597   8.623  42.111  1.00 42.65
ATOM   5065  O1   HOH W 280       2.122  -5.441  52.479  1.00 50.02
ATOM   5066  O1   HOH W 281      51.073  19.397  80.420  1.00 48.41
ATOM   5067  O1   HOH W 282      22.162  16.861  29.165  1.00 44.50
ATOM   5068  O1   HOH W 283      11.469  25.200  29.589  1.00 50.84
ATOM   5069  O1   HOH W 284      23.699   3.262  46.867  1.00 46.89
ATOM   5070  O1   HOH W 285      45.993   9.491  73.544  1.00 47.59
ATOM   5071  O1   HOH W 286      34.089  35.336  54.479  1.00 49.25
ATOM   5072  O1   HOH W 287      27.009 -10.733  37.488  1.00 33.68
ATOM   5073  O1   HOH W 288      52.692  21.442  83.608  1.00 42.65
ATOM   5074  O1   HOH W 289      31.129  22.350  28.703  1.00 42.85
ATOM   5075  O1   HOH W 290      36.979  25.478  48.592  1.00 35.15
ATOM   5076  O1   HOH W 291      59.056  24.357  55.498  1.00 42.95
ATOM   5077  O1   HOH W 292      45.058  19.677  57.915  1.00 35.81
ATOM   5078  O1   HOH W 293      27.531  31.666  63.768  1.00 55.59
ATOM   5079  O1   HOH W 294      15.733   8.228  20.545  1.00 55.53
ATOM   5080  O1   HOH W 295      21.402   1.241  51.437  1.00 51.66
ATOM   5081  O1   HOH W 296      24.337  -2.308  23.410  1.00 40.84
ATOM   5082  O1   HOH W 297      45.597  49.644  86.607  1.00 60.74
ATOM   5083  O1   HOH W 298      48.392   7.844  54.894  1.00 40.30
ATOM   5084  O1   HOH W 299      10.706  -0.247  53.887  1.00 36.83
ATOM   5085  O1   HOH W 300      30.841   6.772  42.114  1.00 46.90
ATOM   5086  O1   HOH W 301      56.984  31.594  84.598  1.00 64.61
ATOM   5087  O1   HOH W 302      23.975   0.753  21.900  1.00 58.72
ATOM   5088  O1   HOH W 303      25.943  -3.970  26.011  1.00 34.27
ATOM   5089  O1   HOH W 304      57.745  27.571  81.771  1.00 39.39
ATOM   5090  O1   HOH W 305       8.725  13.816  46.139  1.00 62.61
ATOM   5091  O1   HOH W 306       9.642  -2.831  53.313  1.00 48.15
ATOM   5092  O1   HOH W 307     -12.355  -6.712  32.342  1.00 40.12
ATOM   5093  O1   HOH W 308      10.024   7.396  49.256  1.00 37.70
ATOM   5094  O1   HOH W 309      41.071   3.104  32.909  1.00 61.81
```

FIGURE 303

```
ATOM   5095  O1   HOH W 310      60.474  28.281  80.505  1.00 58.55
ATOM   5096  O1   HOH W 311      -0.719   1.660  54.184  1.00 46.99
ATOM   5097  O1   HOH W 312      42.157   0.641  32.043  1.00 61.15
ATOM   5098  O1   HOH W 313      26.844  31.094  74.091  1.00 57.31
ATOM   5099  O1   HOH W 314       7.696  11.428  47.893  1.00 49.96
ATOM   5100  O1   HOH W 315      54.048  21.906  53.414  1.00 50.41
ATOM   5101  O1   HOH W 316      47.093   3.308  57.181  1.00 49.89
ATOM   5102  O1   HOH W 317       0.538  11.547  46.107  1.00 65.71
ATOM   5103  O1   HOH W 318       8.860  16.730  39.751  1.00 67.14
ATOM   5104  O1   HOH W 319      17.788 -19.138  29.587  1.00 65.65
ATOM   5105  O1   HOH W 320      19.712  14.524  17.149  1.00 66.48
ATOM   5106  O1   HOH W 321      -1.219 -11.550  22.358  1.00 64.74
ATOM   5107  O1   HOH W 322       6.040  14.352  34.149  1.00 62.82
ATOM   5108  O1   HOH W 323      65.030  28.876  55.181  1.00 54.52
ATOM   5109  O1   HOH W 324      41.175   4.830  36.570  1.00 59.29
ATOM   5110  O1   HOH W 325      15.916  -2.843  51.316  1.00 58.50
ATOM   5111  O1   HOH W 326      21.478  17.683  70.720  1.00 50.48
END
```

THREE DIMENSIONAL COORDINATES OF HPTPBETA

The disclosure of U.S. Provisional Application Ser. No. 60/413,547 filed Sep. 25, 2002, which is herein incorporated by reference in its entirety.

CROSS REFERENCE TO RELATED APPLICATIONS

This application is a Divisional Application of and claims the benefit of priority to U.S. Utility application Ser. No. 10/634,027 filed Aug. 4, 2003, issued as U.S. Pat. No. 7,507,568 the disclosure of which is incorporated herein by reference in its entirety.

FIELD OF THE INVENTION

The present invention relates to three-dimensional structures of the catalytic domain of HPTPbeta [SEQ ID NO:7], and structures derived therefrom.

BACKGROUND OF THE INVENTION

HPTPbeta (Kruegar et al., EMBO J., 9, (1990)) has been suggested inter alia for modulating the activity of angiopoietin receptor-type tyrosine kinase Tie-2. See PCT Patent Application WO 00/65088. Inventors have shown in the present and concurrently filed patent applications that modulation of HPTPbeta modulates activities of both Tie-2 and VEGFR2. Therefore, HPTPbeta could be a target for the treatment of angiogenesis mediated disorders. However, the crystal structure of HPTPbeta has not been described. High-resolution 3D experimental models are needed to obtain insight into the mechanisms of HPTPbeta activation, the source of interactions between specific ligands and HPTPbeta, and to design better agonists and antagonists of HPTPbeta. Thus, there is a need for crystal structure of HPTPbeta.

SUMMARY OF THE INVENTION

The present invention attempts to address this need by providing a 3D structure of the catalytic domain of human HPTPbeta [SEQ ID NO:7], and suitable means to design and identify potent and selective agonists or antagonist of the HPTPbeta for the treatment of angiogenesis mediated disorders.

In one aspect the invention provides for crystalline forms of the HPTPbeta catalytic domain [SEQ ID NO:7] having unit cell dimensions of a=62±1 Å, b=72±1 Å, and c=70±1 Å, α=90°, β=93±3°, γ=90° in the space group P2$_1$ (monoclinic form) and unit cell dimensions of a=39±1 Å, b=71±1 Å, and c=120±2 Å, α=90°, β=90°, γ=90° in the space group P2$_1$2$_1$2$_1$ (orthorhombic form).

In another aspect the invention provides for a method of identifying a compound useful for the treatment of an angiogenesis mediated disorder, comprising the steps of using a three-dimensional (3D) structure of HPTPbeta as defined by the atomic coordinates of FIGS. 7-304, or combination thereof; and employing said 3D structure to design, modify, or select a compound that binds HPTPbeta in silico.

A method of identifying a compound useful for the treatment of an angiogenesis mediated disorder, comprising the steps of: providing a crystal of the complex between HPTPbeta and compound, or alternately exposing a crystal of HPTPbeta with a compound in aqueous media; exposing the complex to X-rays to generate a diffraction pattern; capturing the pattern to a recording device to generate diffraction data; processing the data to solve the complex structure; determining the location of compound within complex structure; wherein the compound binding to the binding site of HPTPbeta, wherein the binding site is selected from the group consisting of P0, P+1, P−1, or mixtures thereof, indicates the compound is useful for the treatment of the HPTPbeta mediated disorder.

A method of identifying a compound useful for the treatment of an angiogenesis mediated disorder, comprising the steps of: selecting the compounds based on computer-aided drug design (CADD) using the coordinates from FIGS. 7-304; further analyzing if the compound binds HPTPbeta or modulates HPTPbeta activity in an in vitro, in vivo, or ex vivo assay; and identifying those compounds that bind HPTPbeta or modulate HPTPbeta activity as compounds useful for the treatment of an angiogenesis mediated disorder.

These and other objects, features, and advantages will become apparent to those of ordinary skill in the art from a reading of the following detailed description and the appended claims.

BRIEF DESCRIPTION OF THE DRAWINGS AND TABLES

FIG. 4 schematically represents interactions between Compound 1 and the HPTPbeta catalytic domain [SEQ ID NO:7]: (a) hydrogen bonding and (b) Van der Waals interactions. The ligand is shown in magenta, the main body of the protein is colored blue, and the WPD loop residues are colored red.

Figure 5:
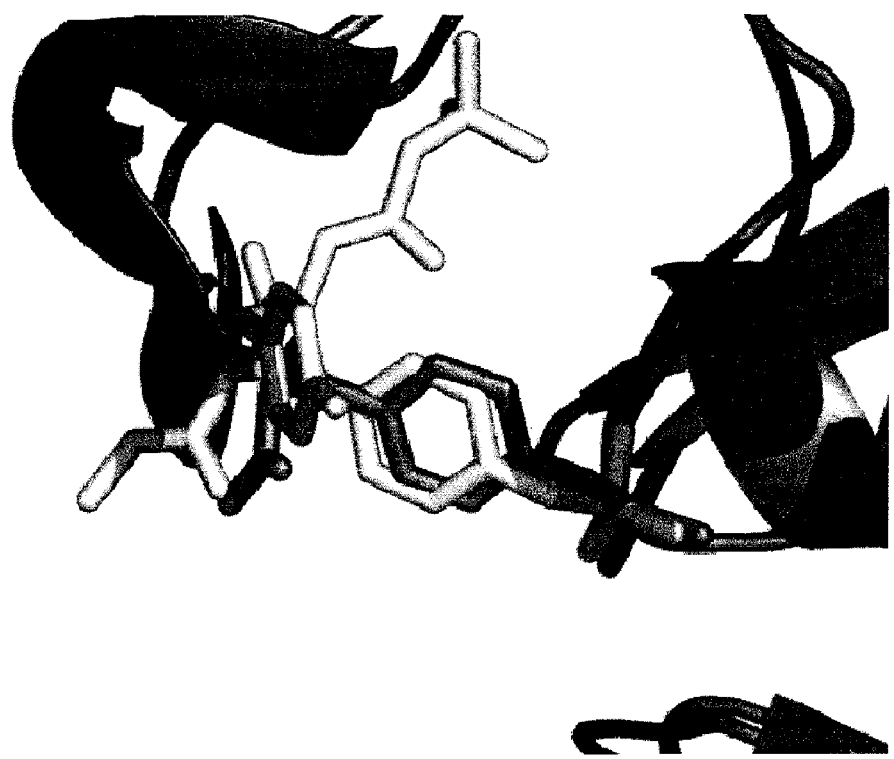

FIG. 5 shows an overlay of the phosphotyrosine (darker) bound to PTP-1B trap mutant and Compound 1 (lighter) bound to the HPTPbeta catalytic domain [SEQ ID NO:7].

Figure 6:
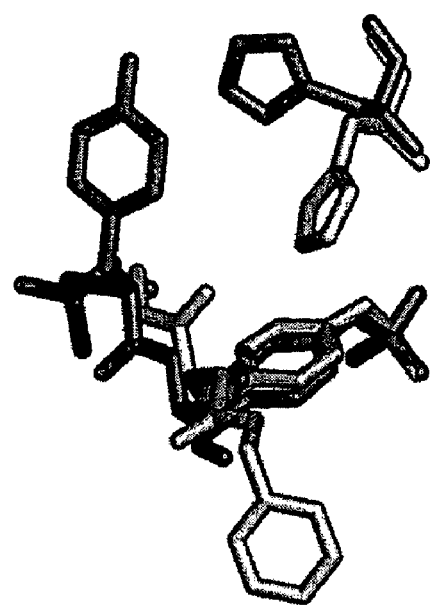

FIG. 6 shows Tyr212 conformation in enzyme complex with Compound 1 (lighter) and Compound 2 (darker).

FIG. 7-102 show the atomic structure coordinates for HPTPbeta as derived from a monoclinic crystal of ligand-free HPTPbeta catalytic domain [SEQ ID NO:7] polypeptide.

FIG. 103-201 show the atomic structure coordinates for HPTPbeta and the inhibitor molecule as derived from a monoclinic crystal of HPTPbeta bound to the inhibitor Compound 1.

FIG. 202-252 show the atomic structure coordinates for HPTPbeta as derived from an orthorhombic crystal of ligand-free HPTPbeta catalytic domain [SEQ ID NO:7] polypeptide.

FIG. 253-304 show the atomic structure coordinates for HPTPbeta and the inhibitor molecule as derived from an orthorhombic crystal of HPTPbeta bound to the inhibitor Compound 2.

The data shown in FIGS. 7-304 are expressed based on the Protein Data Bank (PDB) format: The PDB format is a format containing coordinates (X, Y, Z), etc. of individual atoms, and is the standard formats in expressing coordinates of biopolymers. In FIGS. 7-304, the "ATOM" appearing in the utmost left column (1st column) denotes each atom of the atomic coordinates. The numbers (1, 2, 3, . . . etc.) appearing in the next column (2nd column) are serial numbers of individual atoms. Subsequently, in the left to right direction in these Figures, there are denoted the type of each atom and its position in the amino acid to which it belongs (e.g., "CB", "CG", "SD") (in the 3rd column); the amino acid residue to which each atom belongs (three-letter abbreviations for amino acids, e.g. "MET", "ASN") (in the 4th column); the sequence number of the residue counted from the N-terminal (in the 5th column); X-coordinate (in angstrom (Å) unit) (in the 6th column); Y-coordinate (in angstrom (Å) unit) (in the 7th column); Z-coordinate (in angstrom (Å) unit) (in the 8th column).

SEQUENCE LISTING DESCRIPTION

Each of the nucleotide or amino acid sequences in the sequence listing is shown in Table A.

monoclinic crystal form having unit cell dimensions of a=61.89 Å, b=71.53 Å, and c=70.35 Å, $\alpha=90°$, $\beta=93.25°$, $\gamma=90°$ in the space group $P2_1$.

FIGS. 103-201 show coordinates of HPTPbeta in complex with Compound 1 in the monoclinic crystal form having unit cell dimensions of a=62.19 Å, b=71.80 Å, and c=70.45 Å, $\alpha=90°$, $\beta=93.56°$, $\gamma=90°$ in the space group $P2_1$.

FIGS. 202-252 show coordinates of HPTPbeta in the orthorhombic crystal form having unit cell dimensions of a=39.25 Å, b=71.13 Å, and c=19.91 Å, $\alpha=90°$, $\beta=90°$, $\gamma=90°$ in the space group $P2_12_12_1$.

FIGS. 253-304 show coordinates of HPTPbeta in complex with Compound 2 in the orthorhombic crystal form having unit cell dimensions of a=38.85 Å, b=69.61 Å, and c=117.78 Å, $\alpha=90°$, $\beta=90°$, $\gamma=90°$ in the space group $P2_12_12_1$. The structural data according to FIGS. 7-102; 103-201; 202-252; and 253-304 are at approximately 1.9, 1.8, 1.75, and 1.65 Angstrom (Å) resolution, respectively.

TABLE A

| Sequence Description | SEQ ID NO: Nucleotide, Amino Acid | Species | Genbank (GB) or Derwent (D) Accession No. for Nucleotide Sequence | Related Genbank (GB) or Derwent (D) Accession Nos. |
|---|---|---|---|---|
| HPTPbeta (HPTP-beta, PTPRB, PTPbeta, PTPB, R-PTP-beta) | 1 (nucleotide) | Homo Sapiens | X54131 | NM_002837 |
| HPTPbeta (HPTP-beta, PTPRB, PTPbeta, PTPB, R-PTP-beta) | 2 (amino acid) | Homo Sapiens | X54131 | NM_002837 |
| HPTPbeta intracellular domain (ICD) | 3 (nucleotide) | Homo Sapiens | | NM_002837 |
| HPTPbeta intracellular domain (ICD) | 4 (amino acid) | Homo Sapiens | | NM_002837 |
| HPTPbeta truncated ICD | 5 (nucleotide) | Homo Sapiens | | NM_002837 |
| HPTPbeta truncated ICD | 6 (amino acid) | Homo Sapiens | | NM_002837 |
| HPTPbeta crystallized ICD | 7 (amino acid) | Homo Sapiens | | NM_002837 |
| Intracellular domain forward primer | 8 | | | |
| Intracellular domain reverse primer | 9 | | | |
| Crystal domain forward primer | 10 | | | |
| Crystal domain reverse primer | 11 | | | |
| Crystal, His-tag forward primer | 12 | | | |
| Crystal, His-tag reverse primer | 13 | | | |
| Crystal TEV-site, forward primer | 14 | | | |
| Crystal TEV-site, reverse primer | 15 | | | |

DETAILED DESCRIPTION OF THE INVENTION

The present invention is directed to identifying or obtaining compounds useful for modulating HPTPbeta activity. Crystal structure information presented herein is useful in designing compounds and modeling them or their potential interaction with binding site(s) of HPTPbeta. Actual compounds may be identified from following design and model work performed in silico. A compound identified using the present invention may be effective for the treatment of an angiogenesis mediated disorder. These and other aspects and embodiments of the present invention are discussed below.

One aspect of the invention provides for the crystalline form of HPTPbeta. Four crystal structures of HPTPbeta are presented. FIGS. 7-102 show coordinates of HPTPbeta in the The coordinates of FIGS. 7-304 provide a measure of atomic location in Angstroms, to a first decimal place. The coordinates are a relative set of positions that define a shape in three dimensions. It is possible that an entirely different set of coordinates having a different origin and/or axes could define a similar or identical shape. Furthermore, varying the relative atomic positions of the atoms of the structure so that the root mean square deviation of the conserved residue backbone atoms (i.e. the nitrogen-carbon-carbon backbone atoms of the protein amino acid residues) is less than 1.5 Å, preferably less than 1.0 Å and more preferably less than 0.5 Å, when superimposed on the coordinates provided in FIGS. 7-304 for the conserved residue backbone atoms, will generally result in a structures which are substantially the same as the structures of FIGS. 7-304 in terms of both its structural characteristics and potency for structure-based drug design of HPTPbeta modulators. Likewise changing the number and/or positions of the water molecules of FIGS. 7-304 will not generally affect the potency of the structure for structure-based drug design of HPTPbeta modulators. Thus for the purposes described herein as being aspects of the present invention, it is within the scope of the invention if: the coordinates of FIGS. 7-304 are transposed to a different origin and/or axes; the relative atomic positions of the atoms of the structure are varied so that the root mean square deviation of conserved residue backbone atoms is less than 1.5 Å (preferably less than 1.0 Å and more preferably less than 0.5 Å) when superimposed on the coordinates provided in FIGS. 7-304, respectively, for the conserved residue backbone atoms; and/or the number and/or positions of water molecules is varied. Reference herein to the coordinates of FIGS. 7-304 thus includes the coordinates in which one or more individual values of the Figures are varied in this way.

Also, modifications in the HPTPbeta crystal structure due to e.g. mutations, additions, substitutions, and/or deletions of amino acid residues could account for variations in the HPTPbeta atomic coordinates. However, atomic coordinate data of HPTPbeta modified so that a ligand that bound to one or more binding sites of the HPTPbeta binding pocket would also be expected to bind to the corresponding binding sites of the modified HPTPbeta, and therefore are, for the purposes described herein as being aspects of the present invention, also within the scope of the invention. References herein to the coordinates of FIGS. 7-304 thus include the coordinates modified in this way. Preferably, the modified coordinate data define at least one HPTPbeta binding site.

Another aspect of the invention provides for the HPTPbeta binding pocket, wherein the binding pocket comprises at least the P(0), P(1) and P(−1) binding sites. The nomenclature of the binding sites is based on binding of phosphorylated peptides to PTPases, for example: P(0) is the active site of the enzyme, which accommodates the phosphotyrosine residue of the phosphopeptide; P(+1) is the site which accommodates the amino acid of the phosphopeptide that is adjacent to the phosphotyrosine in the direction of the carboxy terminus of the phosphopeptide; P(−1) accommodates the amino acid of the phosphopeptide that is adjacent to the phosphotyrosine in the direction of the amino terminus of the phosphopeptide. In HPTPbeta, P(0) is characterized by at least amino acid residues 152, 74-77, 209-214, 244-253, 288-290, and 293 of SEQ ID NO: 7; P(+1) is characterized by at least amino acid residues 76-80, 48-66, 284-292, and 212-214 of SEQ ID NO: 7; P−1 is characterized by at least amino acid residues 69-76, 119-123, and 149-154 of SEQ ID NO: 7.

In Silico Drug Design

For the first time, the present invention permits the use of virtual design techniques (i.e., computer modeling or "in silico") to design, select, and synthesize compounds capable of inhibiting/stimulating or binding HPTPbeta. In turn, these drug candidates may be effective in the treatment of an angiogenesis mediated disorder.

The term "angiogenesis mediated disorder" is defined as a disorder that involves a modulation in angiogenic activity resulting in the biological manifestation of a disease, disorder, and/or condition; in the biological cascade leading to the disorder; or as a symptom of the disorder. The Applicants have shown that the process of angiogenesis is modulated by HPTPbeta. This "involvement" of HPTPbeta in an angiogenesis mediated disorder includes, but is not limited to, the following: (1) The modulation of HPTPbeta activity as a "cause" of the angiogenesis mediated disorder or biological manifestation, whether the HPTPbeta is modulated genetically, by infection, by autoimmunity, trauma, biomechanical causes, lifestyle, or by some other causes; (2) The modulated HPTPbeta activity is part of the observable manifestation of the disease or disorder. That is, the disease or disorder is measurable in terms of the modulated HPTPbeta activity. From a clinical standpoint, modulated HPTPbeta activity indicates the disease, however, HPTPbeta activity need not be the "hallmark" of the disease or disorder; (3) The modulated HPTPbeta activity is part of the biochemical or cellular cascade that results in the disease or disorder. In this respect, inhibiting or stimulating of HPTPbeta (per the respective therapeutic goal) interrupts the cascade, and thus controls the disease; (4) The angiogenesis mediated disease or disorder is not the result of modulation in HPTPbeta activity, but modulation of the HPTPbeta activity would result in amelioration of the disease. "Modulation in HPTPbeta activity," as used herein, encompasses both unwanted or elevated HPTPbeta activity and desired or reduced HPTPbeta activity. As used herein, "angiogenesis mediated disorders" include: (1) those disorders, diseases and/or unwanted conditions which are characterized by unwanted or elevated angiogenesis, or (2) those disorders, diseases and/or unwanted conditions which are characterized by wanted or reduced angiogenesis.

Treatment of Angiogenesis Mediated Disorders

Treatment of Disorders Mediated by Elevated Angiogenesis

The agents screened by the present invention may be used in a method for the treatment of a disorder mediated by elevated angiogenesis. The agents identified by the present invention may be used to treat diseases like diabetic retinopathy, macular degeneration, sickle cell anemia, sarcoid, syphilis, pseudoxanthoma elasticum, Paget's disease, vein or artery occlusion, carotid obstructive disease, chronic uveitis/vitritis, mycobacterial infections, Lyme's disease, systemic lupus erythematosis, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma, post-laser complications, diseases associated with rubeosis (neovascularization of the angle) and diseases caused by the abnormal proliferation of fibrovascular or fibrous tissue including all forms of proliferative vitreoretinopathy. Agents screened by of the present invention can also treat diseases associated with chronic inflammation such as Crohn's disease and ulcerative colitis, psoriasis, sarcoidosis and rheumatoid arthritis. Other diseases that can be treated according to the present invention are hemangiomas, Osler-Weber-Rendu disease, or hereditary hemorrhagic telangiectasia, solid or blood borne tumors and acquired immune deficiency syndrome.

Treatment of Disorders Mediated by Reduced Angiogenesis

In one aspect, an agent may be used in a method for the treatment of a disorder mediated by reduced angiogenesis. As expected, this involves stimulated angiogenesis to treat a disease, disorder, or condition. It is likely that an agent that inhibits HPTPbeta would be used for treatment of an angiogenesis mediated disorder. The disorder is one characterized by tissue that is suffering from or is at risk of suffering from ischemic damage, infection, and/or poor healing, which results when the tissue is deprived of an adequate supply of oxygenated blood due to inadequate circulation (ischemic tissue).

In Silico Screening of Compounds

In the present invention, it is possible to carry out virtual screening for drugs using the above-described atomic coordinates or coordinates derived therefrom.

Briefly, the atomic coordinates of the three-dimensional structure elucidated by the invention are input into a computer so that images of the structure and various parameters are shown on the display. Then, the resultant data are input into a virtual compound library. Since a virtual compound library is contained in a virtual screening software such as DOCK-4 (Kuntz, UCSF), the above-described data may be input into such a software. Candidate drugs may be searched for, using a three-dimensional structure database of virtual or non-virtual drug candidate compounds, such as MDDR (Prous Science, Spain).

The potential stimulating/inhibitory or binding effect (i.e., interaction or association) of a compound may be analyzed prior to its actual synthesis and testing by the use of computer modeling techniques. If the theoretical structure of the given compound suggests insufficient interaction and association between it and HPTPbeta, synthesis and testing of the compound may be obviated. However, if computer modeling indicates a strong interaction, the molecule may then be synthesized and tested for its ability to bind to or stimulate/inhibit HPTPbeta using various methods known in the art or as described in the co-pending application. In this manner, synthesis of inoperative compounds may be avoided.

Agonist/antagonist or binding drug candidates of HPTPbeta may be computationally evaluated and designed by means of a series of steps in which chemical entities or fragments are screened and selected for their ability to bind with individual binding sites or combinations thereof (e.g., P0, P+1, and/or P−1) or other areas of HPTPbeta.

One skilled in the art may use any of several methods to screen chemical entities or fragments for their ability to associate with HPTPbeta and more particularly with the specific binding sites. This process may begin by visual inspection of, for example, the active site on the computer screen based on the HPTPbeta coordinates in any of the FIGS. 7-304. Selected fragments or chemical entities may then be positioned in a variety of orientations, or docked, within an individual binding site of HPTPbeta as defined supra. Docking may be accomplished using software such as QUANTA, SYBYL, followed by energy minimization and molecular dynamics with standard molecular mechanics forcefields, such as CHARMM and AMBER.

Specialized computer programs may also assist in the process of selecting fragments or chemical entities. These include: (1) GRID (Goodford, P. J., "A Computational Procedure for Determining Energetically Favorable Binding Sites on Biologically Important Macromolecules" J. Med. Chem., 28, pp. 849-857 (1985)), available from Oxford University, Oxford, UK; (2) MCSS (Miranker, A. and M. Karplus, "Functionality Maps of Binding Sites: A Multiple Copy Simultaneous Search Method" Proteins: Structure, Function and Genetics, 11, pp. 29-34 (1991)), available from Molecular Simulations, Burlington, Mass.; (3) AUTODOCK (Goodsell, D. S. and A. J. Olsen, "Automated Docking of Substrates to Proteins by Simulated Annealing" Proteins: Structure. Function, and Genetics, 8, pp. 195-202 (1990)), available from Scripps Research Institute, La Jolla, Calif.; and (4) DOCK (Kuntz, I. D. et al., "A Geometric Approach to Macromolecule-Ligand Interactions" J. Mol. Biol., 161, pp. 269-288 (1982)), available from University of California, San Francisco, Calif.; (5) GLIDE available from Schrodinger Inc.; (6) FlexX available from Tripos Inc; (7) GOLD (Jones et al., J. Mol. Biol., 245, 43-53, 1995), available from the Cambridge Crystallographic Data Centre.

Once suitable chemical entities or fragments have been selected, they can be assembled in silico or synthesized into a single drug candidate. In silico assembly may proceed by visual inspection of the relationship of the fragments to each other on the three-dimensional image displayed on a computer screen in relation to the structure coordinates of HPTPbeta. This would be followed by manual model building using software such as QUANTA or SYBYL. Chemical syntheses are by those methods well-known in the art.

Useful programs to aid one of skill in the art in connecting the individual chemical entities or fragments include the following: (1) CAVEAT (Bartlett, P. A. et al, "CAVEAT: A Program to Facilitate the Structure-Derived Design of Biologically Active Molecules". In Molecular Recognition in Chemical and Biological Problems", Special Pub., Royal Chem. Soc., 78, pp. 182-196 (1989)), available from the University of California, Berkeley, Calif.; (2) 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992)); and (3) HOOK (available from Molecular Simulations, Burlington, Mass.).

Instead of proceeding to build an HPTPbeta agonist or antagonist in a step-wise fashion one fragment or chemical entity at a time as described above, drug candidates useful for the treatment of angiogenesis mediated disorders may be designed as a whole or "de novo" using either an empty active site or optionally including some portion(s) of a known agonist or antagonist. These methods include the following: (1) LUDI (Bohm, H.-J., "The Computer Program LUDI: A New Method for the De Novo Design of Enzyme Inhibitors", J. ComR. Aid. Molec. Design, 6, pp. 61-78 (1992)), available from Biosym Technologies, San Diego, Calif.; (2) LEGEND (Nishibata, Y. and A. Itai, Tetrahedron, 47, p. 8985 (1991)), available from Molecular Simulations, Burlington, Mass.; (3) LeapFrog (available from Tripos Associates, St. Louis, Mo.). Examples of known agonist or antagonists are described in WO 02/26774 A2.

Once a compound has been designed or selected by the above methods, the efficiency with which that compound may bind to HPTPbeta may be tested and optimized by computational evaluation. For example, an effective HPTPbeta agonist must preferably demonstrate a relatively small difference in energy between its bound and free states (i.e., a small deformation energy of binding). Thus, the most efficient HPTPbeta agonist should preferably be designed with deformation energy of binding of not greater than about 10 kcal/mole, preferably, not greater than 7 kcal/mole. HPTPbeta agonists may interact with the enzyme in more than one conformation that is similar in overall binding energy. In those cases, the deformation energy of binding is taken to be the difference between the energy of the free compound and the average energy of the conformations observed when the agonist binds to the enzyme.

A compound designed or selected, as binding to HPTPbeta may be further computationally optimized so that in its bound state it would preferably lack repulsive electrostatic interaction with the target enzyme. Such non-complementary (e.g., electrostatic) interactions include repulsive charge-charge, dipole-dipole, and charge-dipole interactions. Specifically, the sum of all electrostatic interactions between the compound and the enzyme when the compound is bound to HPTPbeta, preferably make a neutral or favorable contribution to the enthalpy of binding.

Specific computer softwares are available in the art to evaluate compound deformation energy and electrostatic interaction. Examples of programs designed for such uses include: Gaussian 92, revision C [M. J. Frisch, Gaussian, Inc., Pittsburgh, Pa. ©1992]; AMBER, version 4.0 [P. A. Kollman, University of California at San Francisco, ©1994]; QUANTA/CHARMM [Molecular Simulations, Inc., Burlington, Mass. ©1994]; and Insight II/Discover (Biosysm Technologies Inc., San Diego, Calif. ©1994). Other software packages will be known to those skilled in the art.

Once an HPTPbeta-binding compound has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to HPTPbeta by the same computer methods described in detail, above.

Crystallographic Evaluation of Chemical Entities for Binding to HPTPbeta

For the first time, this invention allows one skilled in the art to study the binding of chemical entities to HPTPbeta by exposing either individual compounds or mixtures of compounds (such as may be obtained from combinatorial libraries) into HPTPbeta crystals or, alternatively, by co-crystallization of the substances of interest with HPTPbeta, using methods known to those of ordinary skill in the art, and the crystallization conditions based on those described in the following examples. Acquisition and analysis of X-ray diffraction data from these crystals can be then performed using standard methods. If substance or substances bind to HTPTbeta then positive difference electron density will be observed in the Fourier maps calculated using the X-ray diffraction intensities and phases obtained from the HPTPbeta models presented in FIGS. 7-304. Models of the chemical entities can than be built into the electron density using standard methods and the resulting structures can be refined against the X-ray diffraction data, providing experimental data describing the interaction of the molecules of interest with the enzyme. Those skilled in the art can use these models to design HPTPbeta inhibitors based either on purely structural data or on combination of structural data with enzyme-activity based structure-activity relationship and in silico drug design.

EXAMPLES

1. Cloning and Expression of the Catalytic Domain of HPTPbeta

The intracellular domain (ICD) of HPTPbeta (SEQ ID NO: 3) is cloned from human fetal heart cDNA containing the full gene of HPTPbeta (SEQ ID NO: 1) by PCR using Advantage Polymerase (Clontech) and the primers:

```
Beta-FOR2:
5'-GATCGACCATTATCTGTCCAC-3'      SEQ ID NO: 8

Beta-REV2:
5'-CAGGAGCTCTTCAGGTACAT-3'       SEQ ID NO: 9
``` under the following reaction conditions: 1 cycle at 95° C. for 1 minute, 30 cycles at 94° C. for 30 seconds and 62° C. for 2 minutes, and a final cycle of 62° C. for 3 minutes. PCR products are subcloned into pPCRScript vector (Stratagene) and sequenced, revealing 2 silent mutations in the HPTPbeta ICD clone, one at base pair (bp) 5372 (C to T, a Glycine residue) and the other at bp 5895 (C to T, a Tyrosine residue) (nucleotides are numbered from bp #1 in SEQ ID #1, which means that the initiator methionine in SEQ ID #2 corresponds to the codon beginning at base pair #31 in SEQ ID NO 1).

The sequence [SEQ ID NO: 5] encoding base pairs 5014 to 5949 of SEQ ID NO: 1 is cloned into the vector pMALc2x (New England Biolabs) using the following oligonucleotides:

```
                                          SEQ ID NO: 10
5'primer:  5'-CGAGCATACGTAGATCGACCATTATCTGTCC-3'

SEQ ID NO: 11
3'primer:  5'-CGAGCAAGCTTATTATTGTTCACTCCGTAGC-3'
```

The HPTPbeta truncated gene [SEQ ID NO: 5] (Wang, Y. & Pallen, C. J. The journal of Biological Chemistry, 267(23), pp 16696-16702, 1992) is amplified with these primers by PCR using the pPCRScript plasmid described above as the template, digested with SnaB1 and HindIII and ligated to pMAL-c2x that is pre-digested with Asp700 and HindIII to create plasmid pMAL-c2x-PTPbeta(5014-5949). The protein construct thus encoded is maltose-binding protein from *Escherichia coli* (MBP) followed by a Factor Xa cleavage site followed by base pairs 5014 to 5949 of HPTPbeta SEQ ID NO: 1. A six-histidine tag is added to the carboxy terminus using the QuikChange Site Directed Mutagenesis kit (Stratagene) and the following primers:

```
                                          SEQ ID NO: 12
5'-GAAAGCTACGGAGTGAACAACATCATCATCATCATCATTAATAAGCT
TGGCACTGG-3'

SEQ ID NO: 13
5'-CCAGTGCCAAGCTTATTAATGATGATGATGATGATGTTGTTCACTCC
GTAGCTTTC-3'.
```

The coding sequence of the clone (pMAL-c2x-PTPbeta (5014-5949)His6) is verified by DNA sequence analysis. Finally, the Factor Xa site is changed to a TEV protease cleavage site using the QuikChange Site Directed Mutagenesis kit and the following primers:

```
                                          SEQ ID NO: 14
5'-AACAACAACCTCGGGGAGAATCTTTATTTTCAGGGCGATCGACCATT
ATCTG-3'

SEQ ID NO: 15
5'-CAGATAATGGTCGATCGCCCTGAAAATAAAGATTCTCCCCGAGGTTG
TTGTT-3'.
```

The protein construct thus encoded is maltose-binding protein from *Escherichia coli* (MBP) followed by a TEV protease cleavage site, followed by base pairs 5014 to 5949 of HPTPbeta SEQ ID NO: 1, followed by a six-histidine tag. After TEV protease cleavage, the resulting protein contains a non-native Glycine residue on the amino-terminus and a six-histidine tag on the carboxy-terminus (SEQ ID 7).

The coding sequence of the final clone (pMAL-TEV-PTPbeta(5014-5949)His6) is verified by DNA sequence analysis and used for recombinant protein production. *Escherichia coli* BL21-RIL cells (Stratagene) are used as the host strain. Bacteria are grown in a 10-liter fermenter, using Super Broth medium (30 g tryptone, 20 g yeast extract, 7.5 g NaCl per liter) supplemented with 0.2% glucose and 100 mg/L ampicillin at 22 C to mid-log phase, at which point the bacteria are induced with 0.5 mM β-isopropyl thiogalactopyranoside and harvested by centrifugation 16 hours after induction.

2. Purification of the Catalytic Domain of HPTPbeta 26 grams of cell pellet containing the overexpressed protein are suspended in 287.5 ml of 50 mM $NaH_2PO_4$, 300 mM NaCl, 10 mM imidazole, 5 mM β-mercaptoethanol, pH 8.0 (Buffer A) containing 4 "Complete-EDTA free" protease inhibitor tablets (Roche). Cells are lysed during 2 passes through a French press at 12000 psi, at 4° C. The lysate is centrifuged for 40 minutes at 17000 rpm, using a JA-17 (Sorvall) rotor at 4° C. Resulting supernatant (295 ml) is loaded at 10 ml/min, 4° C. on a 73 ml Ni-NTA column which is pre-equilibrated with Buffer A. The column is washed with 200 ml of 75 mM Imidazole in Buffer A and the protein is eluted with 175 mM of imidazole in Buffer A (6 ml fractions, 10 ml/min). Fractions containing the fusion protein are pooled based on Coomassie Blue-stained SDS-PAGE analysis. The pool is diluted to 515 ml with pure water to final conductivity of 10.42 mS/cm (approximately 125-135 mM NaCl).

Diluted fusion protein is loaded onto a 150 ml Resource Q15 (Pharmacia) column pre-equilibrated with 10 mM Tris.HCl, 2 mM DTT, pH 7.2. The protein is eluted with a 22.5-29% linear gradient of 10 mM Tris.HCl, 2 mM DTT, 1M NaCl, pH 7.2 (10 ml fractions are collected at 10 ml/min flow rate). Fractions are pooled based on SDS-PAGE analysis.

N-Octyl β-glucopyranoside (NOG) and dithiothreitol (DTT) are added to the pool resulting in final concentrations of 0.25% and 2 mM, respectively. Approximately 1.5 mg of recombinant Tobacco Etch Virus protease (TEV protease, Invitrogen) are added to the pool (using ~1/200 weight ratio of protease to substrate) and the reaction mixture is incubated with stirring for 17 hrs at 4° C. SDS-PAGE analysis reveals ~65% cleavage efficiency. Further addition of TEV protease does not result in additional cleavage.

Reaction mixture is adjusted to the final conductivity of 10.4 mS/cm by addition of 10 mM Tris.HCl, 2 mM DTT, 0.25% NOG, pH 7.2 (Buffer B) and loaded on a 150 ml Resource Q15 column pre-equilibrated with Buffer B. Proteins are eluted with a 19-24% linear gradient of 1M NaCl in Buffer B. Unfortunately, the fusion protein and the cleaved PTPβ catalytic domain [SEQ ID NO: 7] do not separate well using this method. Fractions containing the cleaved catalytic domain are pooled based on SDS-PAGE analysis.

The pool containing the PTPbeta catalytic domain [SEQ ID NO: 7] as well as some of the uncleaved fusion protein is concentrated down to 4.5 ml using a YM-10 membrane in an Amicon stirred cell and slowly passed through a 3 ml amylose resin (Quiagen) column pre-equilibrated with Buffer B. Flow-through is collected and the column is washed with 3 ml of Buffer B. Combined flow-through and wash are loaded on a 48×5.0 cm Superdex 75 prep grade column, pre-equilibrated with Buffer B. The column is eluted with Buffer B at 2 ml/min while 10 ml fractions are collected. Two peaks are observed indicating good separation between the full-length fusion protein and the HPTPbeta catalytic domain [SEQ ID NO:7]. Fractions are analyzed by SDS-PAGE and those found to contain pure protein are pooled. HPTPbeta catalytic domain [SEQ ID NO:7] [SEQ ID NO: 7] is concentrated to 9.8 mg/ml using an Amicon stirred cell equipped with YM-10 membrane. Total yield of HPTPbeta catalytic domain [SEQ ID NO:7] is 58.6 mg based on the $OD_{280}$ measured in 6M guanidine-hydrochloride, pH 8.0.

3. Crystallization of the Catalytic Domain of HPTPbeta, Collection of X-Ray Diffraction Data, and Structure Solution HPTPbeta catalytic domain [SEQ ID NO:7] [SEQ ID NO: 7] is crystallized in hanging drops via the sparse-matrix approach using crystallization screens manufactured by Hampton Research and Emerald Biostructures (currently DeCode Genetics). Several polyethylene glycol (PEG)/magnesium chloride conditions are identified as crystallization leads, which are eventually refined to the following condition: 18% PEG8000, 100 mM TRIS-HCl pH 7.5, 1% β-mercaptoethanol (BME), 0.2 M MgCl2 in 6 µl drops containing equal amounts of protein and reservoir solutions. Under these conditions, crystals usually appear after 2-5 days, reach their maximum size of 0.2×0.2×0.3 mm in 6-8 days and decay within 3-4 weeks after set-up. The best crystals are grown by streak-seeding, which results in more reliable nucleation. For structural studies, individual protein crystals are cryoprotected by immersion into Paratone-N oil followed by flash cooling in a stream of nitrogen gas at 100K.

Two clearly different crystal morphologies are observed—one is subsequently identified as orthorhombic and the other as monoclinic crystal form. Laboratory X-ray source equipped with a CCD X-ray detector is used to collect 2.3 Å data from the orthorhombic crystals, which are found to belong to the space group $P2_12_12_1$ with unit cell dimensions of a=39.25 Å, b=71.13 Å, and c=119.91 Å, α=90°, β=90°, γ=90°, and one molecule in the asymmetric unit (a.u.). Programs of the HKL2000 suite are employed to index, integrate, and scale the diffraction data.

The crystal structure is solved via molecular replacement (CCP4 program AMoRe) (Collaborative Computational Project, Number 4. 199 Acta Cryst. D50, 760-763; and Navaza, J. *Acta Cryst*. A50, 157-163 (1994) using the published structure of PTPµ from the Protein Data Bank (PDB), PDB code 1RPM as the search model. After multiple rounds of manual rebuilding (program O) and refinement (programs Refmac and SHELXL) the crystal structure of the enzyme contains residues 24 to 305, as well as 115 water molecules, and had the $R_{work}$ of 21.0%, and $R_{free}$ of 26.2%. Concomitantly we are able to collect high-resolution data for both the orthorhombic and the monoclinic crystal forms of the enzyme using a synchrotron radiation source (beam lines 17-ID and 17-BM of the Advanced Photon Source at the Argonne National Laboratory—APS/ANL). The monoclinic form of the enzyme is found to belong to the space group $P2_1$ with unit cell dimensions of a=61.89 Å, b=71.53 Å, and c=70.35 Å, α=90°, β=93.25°, γ=90°. Using synchrotron data we are able to refine the structure of the enzyme in the orthorhombic crystal form to 1.75 Å resolution ($R_{work}$=19.0%, $R_{free}$=22.0%) and the monoclinic crystal form (which has two protein molecules in the a.u.) to 1.9 Å resolution ($R_{work}$=20.0%, $R_{free}$=24.0%). Validation of structures using programs PROCHECK and SFCHECK does not reveal any geometric abnormalities. Finished structures contain residues 19 to 310 as numerous water molecules.

Proprietary X-ray diffraction data were collected at beamlines 17-ID and 17-BM in the facilities of the Industrial Macromolecular Crystallography Association Collaborative Access Team (IMCA-CAT) at the Advanced Photon Source. These facilities are supported by the companies of the Industrial Macromolecular Crystallography Association through a contract with Illinois Institute of Technology (IIT), executed through IIT's Center for Synchrotron Radiation Research and Instrumentation. Use of the Advanced Photon Source was supported by the U.S. Department of Energy, Basic Energy Sciences, Office of Science, under Contract No. W-31-109-Eng-38.

4. Exposing Inhibitors into HPTPbeta Catalytic Domain [SEQ ID NO:7] Crystals, and Structure Solution of the Resulting Complexes To study the interaction of ligands with PTPβ we expose (soak) various molecules of interest into both the orthorhombic and the monoclinic crystals at a concentration of 1-10 mM in the crystallization buffer, using exposure times from 2 to 24 hours. Monoclinic crystals of the enzyme can be readily soaked (2-4 hours) with compounds of interest—and the resulting soaked crystals usually (with a notable exception that is outlined later) do not deteriorate. True ligands and/or inhibitors can be unambiguously identified, by analyzing electron density maps calculated using X-ray diffraction data collected from the soaked crystals. Interestingly, when molecules that belong to the family of Compound 2 are soaked into the monoclinic crystals, the latter deteriorate to the point where collection of X-ray diffraction data is impossible. Fortunately, the orthorhombic crystals of PTPbeta catalytic domain can be successfully soaked with compounds of this class, which is particularly interesting in view of the fact that the orthorhombic crystals are nigh impossible to soak with many other classes of compounds—even 24-hr soaks do not result in small molecule penetration into the crystal lattice.

X-ray diffraction data from soaked crystals are collected and processed at APS/ANL in the same manner as described above. X-ray crystal structures of the complexes are solved via molecular replacement (AMoRe) using corresponding native structures for each crystal form as search models. Several rounds of manual rebuilding (O) and refinement (Refmac, SHELXL) are employed, after which the inhibitor molecules are built into the electron density (Quanta, SPARTAN) and refined. The geometry of the structures is analyzed using programs PROCHECK and SFCHECK.

5. HPTPbeta Catalytic Domain [SEQ ID NO:7] in Two Space Groups—Overview of the Unliganded Structure The two final models of the protein contain residues 19-310, which are clearly defined in the electron density maps of the orthorhombic and monoclinic forms, respectively. Loop 89-96 is entirely disordered in the orthorhombic form (and therefore is omitted from the final model) and is mostly disordered in the monoclinic form. The orthorhombic crystal form of the PTPbeta catalytic domain contains one protomer in a.u. whereas the monoclinic form contains two protomers in the a.u. Root mean square deviation (rmsd) of the protein backbone atoms of the two molecules found in the monoclinic a.u. is 0.45 Å, whereas rmsd of the orthorhombic PTPbeta catalytic domain and the monoclinic protomers is 0.55-0.66 A. Upon close inspection, it is evident that there are no major structural differences between the three molecules—the changes are confined to minor movements of the loops and rearrangements of conformationally unrestrained side chains of surface-exposed amino-acids. Therefore it is sufficient to supply the overall description of the unliganded PTPbeta catalytic domain performed using the best-defined (highest resolution) protomer—the one found in the orthorhombic crystal form.

PTPbeta belongs to a broad family of PTPases that are extremely dissimilar in terms of their biological function, intracellular localization, and domain structure. These very diverse enzymes have one feature in common, namely their catalytic domain, the fold of which is preserved throughout this whole class of PTPases. Historically, the first human PTPase to be discovered and studied is PTP-1B, which is a soluble single-domain phosphatase that was first identified in human placenta in 1989. Because of its early discovery and biological significance, PTP-1B is the most studied PTPase to-date, with over 40 X-ray crystal structures, both unliganded and liganded, available in the PDB. PTP-1B structure is therefore considered to be an archetype of the catalytic domain of this class of PTPases. Here, we use comparisons between PTPbeta catalytic domain and PTP-1B (PDB code 2HNP) structures to illustrate the relationship between our crystal structure of the PTPbeta catalytic domain and the rest of the PTPases of this class.

Figure 1:
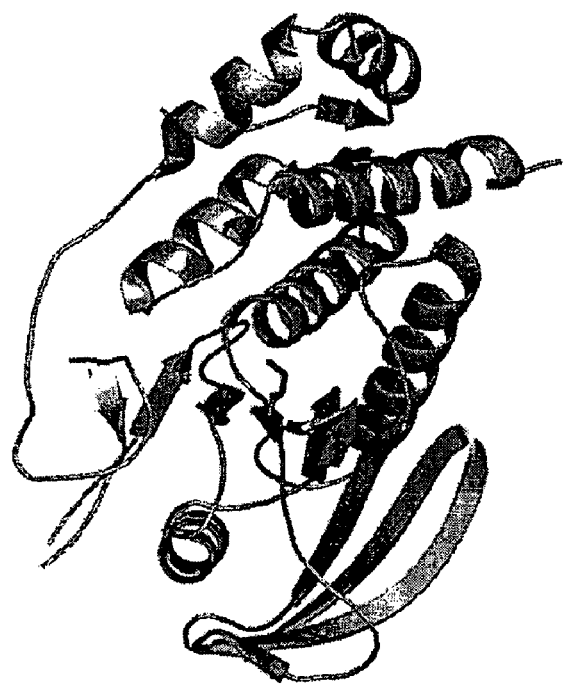
FIG. 1 shows a ribbon representation of the carbon-alpha trace of the HPTPbeta catalytic domain [SEQ ID NO:7].

Similar to PTP-1B, the crystal structure of PTPbeta catalytic domain reveals a common PTPase fold, consisting of two closely-packed compartments: the alpha-helical domain and the beta-sheet one (FIG. 1). When the backbone atoms of the two enzymes are superimposed, the two structures fit with an rmsd of 1.3 A for the matching atoms. In this case, however, the rmsd does not adequately represent the dissimilarity of the two structures. The macroscopic and microscopic differences between PTP-1B and PTPbeta catalytic domain are closely examined below. On the level of backbone, the differences between the two structures are:

- The N-terminus—PTPbeta catalytic domain structure has 12 more ordered residues (residues 19-31) than PTP-1B structure, and the first two alpha-helices (residues 32-55) of the two proteins occupy different positions.
- The 106-111 loop of PTPbeta catalytic domain is placed differently than the corresponding 74-80 loop of PTP-1B.
- The first beta-strand and its beta-turn (residues 161-168 of PTPbeta catalytic domain) are shifted with respect to their PTP-1B analogues (130-139)
- The geometry of the 191-197 loop of PTPbeta catalytic domain is very different from its PTP-1B analogue 162-167.
- Loop 233-238 adopts a radically different conformation from its PTP-1B equivalent 202-209.
- Residues 262-277 and the C-terminal a-helix 291-310 are shifted with respect to the position of their equivalents (residue 252-270 and a-helix 264-282) in PTP-1B.

Figure 2:
FIG. 2 shows the change that occurs in the WPD loop of the HPTPbeta catalytic domain [SEQ ID NO:7] upon ligand binding (ligand-free structure is shown as darker trace).

The active site of the enzyme (residues 152-153, 244-253, 288-290, and 293) is located at the junction of the two domains and is occupied by four water molecules. A characteristic loop, containing a Trp-Pro-Asp triad (the WPD loop, residues 208-214) is located near the binding site. In PTP-1B and other phosphatases this loop is known to adopt a different conformation upon binding of ligands in the active site. As will be shown in the next example this conformation change also takes place when PTPbeta catalytic domain binds to ligands (FIG. 2). The WPD loop of PTPbeta catalytic domain contains a His212 instead of Phe181 in PTP-1B, and the orientation of PTPbeta catalytic domain Trp209 is different from that of its PTP-1B analogue Trp179.

Additional small, but important distinctions between PTPbeta catalytic domain and PTP-1B are further discussed in the example 7.

6. Synthesis of Compounds 1 ((S)-[1-Methylcarbamoyl-2-(4-sulfoamino-phenyl)-ethyl]-carbamic acid benzyl ester) and Compound 2 ({2-(4-Hydroxy-phenyl)-1-[1-methylcarbamoyl-2-(4-sulfoamino-phenyl)-ethylcarbamoyl]-ethyl}-carbamic acid tert-butyl ester)

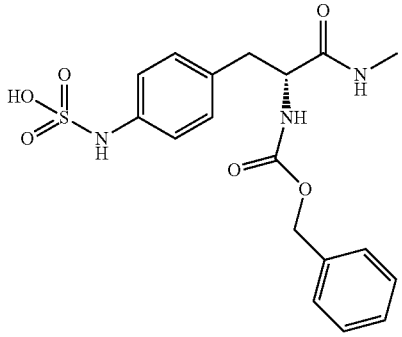

(S)-[1-Methylcarbamoyl-2-(4-sulfoamino-phenyl)-ethyl]-carbamic acid benzyl ester (Compound 1)

Boc-D-Phe(4-NO$_2$)—NMe: Boc-D-Phe(4-NO$_2$)—OH (4.0 g, 12.9 mmol) is dissolved in anhydrous tetrahydrofuran (20 mL) with 4-methylmorpholine (1.56 mL, 14.2 mmol). Isobutylchloroformate (1.84 mL, 14.2 mmol) is dropwise added at 0° C. and the mixture is stirred for 1 hr. at 0° C. Methylamine (12.9 mL, 2.0 M in tetrahydrofuran) is added dropwise at 0° C. and the mixture is stirred for 18 hr. at room temperature. The mixture is then recrystallized from 1:1 DCM:methanol to give a white solid.

H-D-Phe(4-NO$_2$)—NMe: Boc-D-Phe(4-NO$_2$)—NMe (1.5 g, 4.64 mmol) is dissolved in HCl (10 mL, 4.0 M in 1,4-dioxane), and the resulting mixture is stirred at room temperature for 1 hr. Ether (60 mL) is added to the mixture and the resulting precipitate is collected by filtration to yield pure white product.

CBZ-D-Phe(4-NO$_2$)—NMe: H-D-Phe(4-NO$_2$)—NMe (410 mg, 1.84 mmol) is dissolved in anhydrous DCM (10 mL) and diisopropylethylamine (0.352 mL, 2.02 mmol). Benzyl chloroformate (0.263 mL, 1.84 mmol) is added dropwise at 0° C., the mixture is allowed to warm to room temperature and is stirred for 72 hr. The solution is partitioned between DCM and 1N HCl. The organic layer is washed with brine, dried over MgSO$_4$, filtered and evaporated to give crude white solid.

CBZ-D-Phe(4-NH$_2$)—NMe: CBZ-D-Phe(4-NO$_2$)—NMe (80 mg, 0.224 mmol) is dissolved in EtOAc:ethanol (1:1, 2 mL) and tin(II) chloride dihydrate (252 mg, 1.12 mmol) is added. The mixture is stirred at room temperature for 18 h. The reaction is partitioned between EtOAc (25 mL) and 1N NaOH (25 mL). The organic layer is washed twice more with 1N NaOH (25 mL). The combined organics were dried over MgSO$_4$, filtered and evaporated to give pure yellow oil.

(S)-[1-Methylcarbamoyl-2-(4-sulfoamino-phenyl)-ethyl]-carbamic acid benzyl ester: In a dry flask 0.107 g of the aniline compound is dissolved in 2 mL pyridine. To this solution is added 0.156 g of sulfurtrioxide-pyridine complex. The mixture is stirred 5 minutes then diluted with 25 mL of 7% ammonium hydroxide. The mixture is evaporated down to an off-white solid and purified to provide 0.056 g of product as its ammonium salt. $^1$H (D$_2$O): δ7.26-7.20 (m, 3H), 7.11-6.96 (m, 6H), 4.90-4.78 (m, 2H), 4.08 (t, 1H, J=8.3 Hz), 2.84-2.66 (m, 2H) 2.50 (s, 3H)

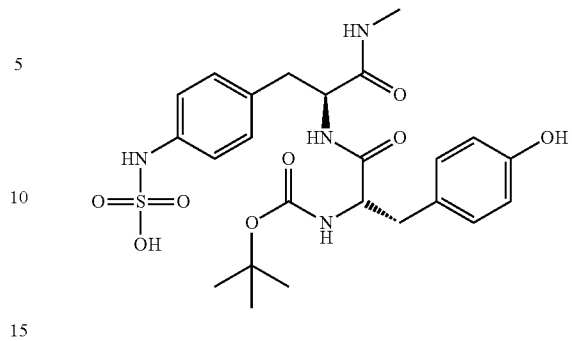

{2-(4-Hydroxy-phenyl)-1-[1-methylcarbamoyl-2-(4-sulfoamino-phenyl)-ethylcarbamoyl]-ethyl}-carbamic acid tert-butyl ester (Compound 2)

Boc-Phe(4-NO$_2$)—NMe: Boc-Phe(4-NO$_2$)—OH (10.0 g, 32.3 mmol) is dissolved in anhydrous tetrahydrofuran (32.2 mL) with 4-methylmorpholine (3.90 mL, 35.4 mmol). Isobutylchloroformate (4.18 mL, 32.3 mmol) is dropwise added at 0° C. and the mixture is stirred for 1 hr. at 0° C. Methylamine (332.3 mL, 2.0 M in tetrahydrofuran) is added dropwise at 0° C. and the mixture is stirred for 18 hr. at room temperature. The mixture is then recrystallized from 1:1 DCM:methanol to give 6.69 g pure white solid.

H-Phe(4-NO$_2$)—NMe: Boc-D-Phe(4-NO$_2$)—NMe (1.5 g, 4.64 mmol) is dissolved in HCl (10 mL, 4.0 M in 1,4-dioxane), and the resulting mixture is stirred at room temperature for 1 hr. Ether (60 mL) is added to the mixture and the resulting precipitate is collected by filtration to yield pure white product.

{2-(4-Hydroxy-phenyl)-1-[1-methylcarbamoyl-2-(4-nitro-phenyl)-ethylcarbamoyl]-ethyl}carbamic acid tert-butyl ester: H-L-Phe(4-NO$_2$)—NMe (200 mg, 0.770 mmol) is dissolved in 1 mL DMF. Diisopropylethylamine (209 mg, 1.62 mmol), EDC (162 mg, 0.847 mmol), HOBt.H$_2$O (130 mg, 0.847 mmol), and Boc-Tyr (238 mg, 0.847 mmol) are added and the mixture is stirred for 18 hr. at 20° C. The mixture is partitioned between water and EtOAc (2×60 mL). The organics are combined and washed with brine, dried over MgSO$_4$, filtered and evaporated to give crude product. Purification by flash chromatography, which is eluted with 97:3 DCM:methanol to give pure white solid.

{2-(4-Hydroxy-phenyl)-1-[1-methylcarbamoyl-2-(4-amino-phenyl)-ethylcarbamoyl]-ethyl}-carbamic acid tert-butyl ester: {2-(4-Hydroxy-phenyl)-1-[1-methylcarbamoyl-2-(4-nitro-phenyl)-ethylcarbamoyl]-ethyl}carbamic acid tert-butyl ester (300, 0.617 mmol) is dissolved in methanol (10 mL). To this was added palladium on carbon (10% by weight, 100 mg). The reaction is placed under a hydrogen atmosphere until reaction is complete (tlc). The catalyst is removed by filtration and the filtrate is concentrated to provide the amine, which is used without purification.

{2-(4-Hydroxy-phenyl) 1-[1-methylcarbamoyl-2-(4-sulfoamino-phenyl)-ethylcarbamoyl]-ethyl}-carbamic acid tert-butyl ester: In a dry flask the aniline compound is dissolved in 2 mL pyridine. To this solution is added 0.295 g of sulfurtrioxide-pyridine complex. The mixture is stirred 5 minutes then diluted with 50 mL of 7% ammonium hydroxide. The mixture is evaporated down to an off-white solid and purified to provide 0.062 g of product as its ammonium salt. $^1$H(D$_2$O): δ7.00-6.87 (m, 6H), 6.69 and 6.66 (d, 2H, J=9.3

Hz), 4.28 (t, 1H, J=8.0), 4.05 (t, 1H, J=8.7 Hz), 2.81-2.65 (m, 4H), 2.47 (s, 3H), 1.21 (s, 9H)

7. HPTPbeta Catalytic Domain [SEQ ID NO:7] in Complex with Ligands

Crystal structures are a very useful tool for design of PTP-beta inhibitors. As an illustration, we describe here two different modes of binding of PTPbeta inhibitors, determined through solving high-resolution crystal structures of PTPbeta catalytic domain complexes with the representative members of these classes—Compound 1 and Compound 2.

Additional similarities and differences between the structure of the ligand-binding site of PTP-1B and PTPbeta catalytic domain become apparent upon comparison of the ligand-bound structures of PTPbeta catalytic domain with the ligand-bound structure of PTP-1B (PDB code 2HNP).

Figure 3:
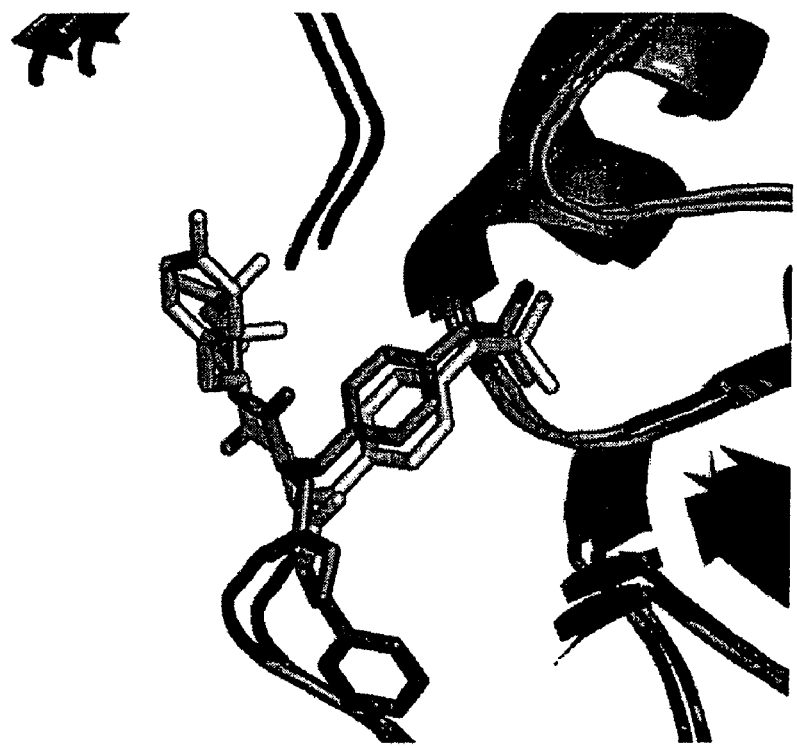
FIG. 3 shows a superposition between Compound 1 ((S)-[1-Methylcarbamoyl-2-(4-sulfoamino-phenyl)-ethyl]-carbamic acid benzyl ester) (darker) and Compound 2 ({2-(4-Hydroxy-phenyl)-1-[1-methylcarbamoyl-2-(4-sulfoamino-phenyl)-ethylcarbamoyl]-ethyl}-carbamic acid tert-butyl ester) (lighter) structures bound to HPTPbeta catalytic domain [SEQ ID NO:7].

On the one hand, as can be seen from FIG. 3, the two sulfamic acid-based inhibitors described here bind with the phenyl sulfamic acid portion of the molecule occupying the P(0) pocket (the active site) of the enzyme. The sulfamic acid moiety is connected to the active site by an extensive network of hydrogen bonds (FIG. 4a), closely resembling the binding of phosphotyrosine phosphate group to previously studied PTPases, as exemplified in FIG. 5 showing superposition of phosphotyrosine bound in the active site of PTP-1B (PDB code 1PTV) with the sulfamic acid bound in the active site of PTPbeta catalytic domain. The binding of sulfamic acids in P(0) pocket is accompanied by the closure of the WPD loop (FIG. 2) which brings Asp211 within hydrogen-bonding distance to sulfamic acid nitrogen and results in sandwiching of the phenyl between residues His212 and Ala247—again, resembling binding of phosphotyrosine to the active site of PTPases (e.g. PTP-1B). The phenyl group of the ligand participates Van der Waal's interactions with residues His286, His212, Ala247, Val249, and Gln289 (FIG. 4b). It is thus easy to assume that the phenyl sulfamic acid mimics the phosphotyrosine side chain that is the natural target of PTPbeta.

On the other hand, there are significant differences in the structure of the binding sites between PTPbeta catalytic domain and PTP-1B. In particular these include:

Orientation of Gln289 is different from that of its PTP-1B analogue Gln262

Orientation of the side chain of His212 is different from that of its PTP-1B analogue Phe182

PTPbeta catalytic domain has Asn76-Asp75 instead of Asp48-Arg47 in PTP-1B, which results in different orientation of both amino acid side chains, as well as slight but significant difference in the geometry of the backbone in that region of the protein In PTPbeta catalytic domain, His286 occupies the mouth of the P(+1) pocket, instead of Gly259 in PTP-1B. This bulky amino acid is likely to modulate access to the P(+1) pocket of the enzyme Differences in the 147-155 stretch conformation as compared to its PTP-1B analogue are likely to result in different specificity of the P(−1) pocket Conformation of the 48-58 region of PTPbeta catalytic domain is different from that of its equivalent in PTP-1B, likely resulting in altered specificity of the P(−1) pocket of the enzyme In both PTPbeta catalytic domain complex structures presented here, the sulfamic acid moiety and the phenyl ring bind to the enzyme in a very similar manner, however the binding mode of the remainder of these two inhibitors to the protein is quite different, as follows:

P(0) pocket: Whereas Compound 1 interacts with His212 through the C-terminal amide carbonyl and through the phenyl ring, in the structure of the Compound 2 complex, His212 side chain is abstracted away from the binding site as a result of an interaction with the tyrosine side chain of the inhibitor (FIG. 6). The N-terminal amide carbonyl of Compound 2 forms a hydrogen bond with the nitrogen of the Asn76 side chain whereas there is no direct interaction between Asn76 and Compound 1.

P(−1) pocket: The N-terminal carbobenzoxy group of Compound 1 participates in extensive Van der Waal's contacts with Arg73 and Tyr74. In contrast, the C-terminal amide of Compound 2 interacts with Tyr74 and to a lesser extent with Arg150.

P(+1) pocket: The only interaction of Compound 1 with this pocket of the enzyme is a superficial VdW contact with Gln289. Compound 2 interacts with the P(+1) pocket through hydrogen bonding of the t-BOC carbonyl with Gln289 side chain, and via extensive VdW interactions of the tert-butyl group with Ile77, Val249, Gln289, Val285, His286, and even Arg56. Notably, His286 is misplaced from its position in the both the unliganded enzyme and in the complex of PTPbeta catalytic domain with Compound 1. In its new position, His286 pi-stacks with the guanidine of Arg281 and forms potential hydrogen bonds with main-chain carbonyls of Val288 and Lys52 or, depending on its protonation state, an ion-pair with Arg56.

In view of the above, it is not surprising that Compound 2, which forms an impressive array of interactions with the enzyme is a more potent inhibitor than Compound 1 which has a much more modest number of interactions with PTPbeta catalytic domain.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited are, in relevant part, incorporated herein by reference; the citation of any document is not to be construed as an admission that it is prior art with respect to the present invention While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope.

What is claimed is:

1. A computer-implemented method of identifying a drug candidate compound for the treatment of an angiogenesis mediated or vascular stabilization disorder, comprising:
   a) providing on a computer readable storage medium X, Y, and Z atomic structure coordinates as set forth in FIGS. 7-304 for Human Protein Tyrosine Phosphatase-beta (HPTP-β) catalytic domain (SEQ ID NO: 7);
   b) generating and/or imaging a three-dimensional structure of all or a portion of the HPTP-β catalytic domain (SEQ ID NO: 7) from the X, Y, and Z coordinates of step (a);
   c) positioning one or more candidate compounds at one or more potential drug candidate compound binding sites of the imaged three-dimensional structure from step (b) by determining the binding mode(s) of said one or more candidate compounds with said site(s) of the imaged-three dimensional structure, wherein the binding sites are selected from the group consisting of: (a) the P(0), P(+1), and/or P(−1) binding sites, (b) amino acids 152, 74-77, 209-214, 244-253, 288-290 and 293 of SEQ ID NO: 7, (c) amino acids 48-66, 76-80, 284-292 and 212-214 of SEQ ID NO: 7, (d) amino acids 69-76, 119-123 and 149-154 of SEQ ID NO: 7, (e) FIGS. 7-102, (f) FIGS. 202-252, and combinations thereof; and
   d) identifying from the one or more candidate compounds those with the best fit and which may bind or modulate HPTP-β as drug candidate compounds useful for the treatment of an angiogenesis mediated or vascular stabilization disorder.

2. The method according to claim 1, further comprising determining the one of more locations or binding geometries of the positioned one or more candidate compounds relative to any of the X, Y, and Z atomic structure coordinates.

3. The method according to claim 1, further comprising assembling fragments of said one or more candidate compounds together to create an assembled compound.

4. The method according to claim 3, further comprising analyzing the ability of the assembled compound to bind or modulate HPTP-β in an in vivo or in vitro assay.

5. The method according to claim 1, wherein the one or more candidate compounds or portion(s) thereof are HPTP-β agonists.

6. The method according to claim 5, further comprising analyzing the ability of the one or more candidate compounds to bind or modulate HPTP-β in an in vivo or in vitro assay.

7. The method according to claim 1, wherein the one or more candidate compounds or portion(s) thereof are HPTP-β as antagonists.

8. The method according to claim 7, further comprising analyzing the ability of the one or more candidate compounds to bind or modulate HPTP-β in an in vivo or in vitro assay.

9. The method of claim 1, wherein the X,Y,Z atomic coordinates have been determined from a crystalline form of a HPTP-β catalytic domain SEQ ID NO: 7 having unit cell dimensions of approximately a=39 Å, b=71 Å, c=120 Å, $\alpha=90°$, $\beta=90°$, $\gamma=90°$ in the space group $P2_12_12_1$.

10. The method of claim 1, wherein the X,Y,Z atomic coordinates have been determined from a crystalline form of a HPTP-β catalytic domain SEQ ID NO: 7 having unit cell dimensions of approximately a=62 Å, b=72 Å, c=70 Å, $\alpha=90°$, $\beta=93°$, $\gamma=90°$ in the space group $P2_1$.

* * * * *

SEQUENCE LISTING

<160> NUMBER OF SEQ ID NOS: 15

<210> SEQ ID NO 1
<211> LENGTH: 6075
<212> TYPE: DNA
<213> ORGANISM: Homo sapiens

```
<220> FEATURE:
<221> NAME/KEY: CDS
<222> LOCATION: (31)..(6024)

<400> SEQUENCE: 1
gtctcctctg gatcttaact actgagcgca atg ctg agc cat gga gcc ggg ttg        54
                                 Met Leu Ser His Gly Ala Gly Leu
                                  1               5 gcc ttg tgg atc aca ctg agc ctg ctg cag act gga ctg gcg gag cca        102
Ala Leu Trp Ile Thr Leu Ser Leu Leu Gln Thr Gly Leu Ala Glu Pro
         10                  15                  20 gag aga tgt aac ttc acc ctg gcg gag tcc aag gcc tcc agc cat tct        150
Glu Arg Cys Asn Phe Thr Leu Ala Glu Ser Lys Ala Ser Ser His Ser
 25                  30                  35                  40 gtg tct atc cag tgg aga att ttg ggc tca ccc tgt aac ttt agc ctc        198
Val Ser Ile Gln Trp Arg Ile Leu Gly Ser Pro Cys Asn Phe Ser Leu
                 45                  50                  55 atc tat agc agt gac acc ctg ggg gcc gcg ttg tgc cct acc ttt cgg        246
Ile Tyr Ser Ser Asp Thr Leu Gly Ala Ala Leu Cys Pro Thr Phe Arg
             60                  65                  70 ata gac aac acc aca tac gga tgt aac ctt caa gat tta caa gca gga        294
Ile Asp Asn Thr Thr Tyr Gly Cys Asn Leu Gln Asp Leu Gln Ala Gly
         75                  80                  85 acc atc tat aac ttc aag att att tct ctg gat gaa gag aga act gtg        342
Thr Ile Tyr Asn Phe Lys Ile Ile Ser Leu Asp Glu Glu Arg Thr Val
     90                  95                 100 gtc ttg caa aca gat cct tta cct cct gct agg ttt gga gtc agt aaa        390
Val Leu Gln Thr Asp Pro Leu Pro Pro Ala Arg Phe Gly Val Ser Lys
105                 110                 115                 120 gag aag acg act tca acc ggc ttg cat gtt tgg tgg act cct tct tcc        438
Glu Lys Thr Thr Ser Thr Gly Leu His Val Trp Trp Thr Pro Ser Ser
                125                 130                 135 gga aaa gtc acc tca tat gag gtg caa tta ttt gat gaa aat aac caa        486
Gly Lys Val Thr Ser Tyr Glu Val Gln Leu Phe Asp Glu Asn Asn Gln
            140                 145                 150 aag ata cag ggg gtt caa att caa gaa agt act tca tgg aat gaa tac        534
Lys Ile Gln Gly Val Gln Ile Gln Glu Ser Thr Ser Trp Asn Glu Tyr
        155                 160                 165 act ttt ttc aat ctc act gct ggt agt aaa tac aat att gcc atc aca        582
Thr Phe Phe Asn Leu Thr Ala Gly Ser Lys Tyr Asn Ile Ala Ile Thr
    170                 175                 180 gct gtt tct gga gga aaa cgt tct ttt tca gtt tat acc aat gga tca        630
Ala Val Ser Gly Gly Lys Arg Ser Phe Ser Val Tyr Thr Asn Gly Ser
185                 190                 195                 200 aca gtg cca tct cca gtg aaa gat att ggt att tcc aca aaa gcc aat        678
Thr Val Pro Ser Pro Val Lys Asp Ile Gly Ile Ser Thr Lys Ala Asn
                205                 210                 215 tct ctc ctg att tcc tgg tcc cat ggt tct ggg aat gtg gaa cga tac        726
Ser Leu Leu Ile Ser Trp Ser His Gly Ser Gly Asn Val Glu Arg Tyr
            220                 225                 230 cgg ctg atg cta atg gat aaa ggg atc cta gtt cat ggc ggt gtt gtg        774
Arg Leu Met Leu Met Asp Lys Gly Ile Leu Val His Gly Gly Val Val
        235                 240                 245 gac aaa cat gct act tcc tat gct ttt cac ggg ctg tcc cct ggc tac        822
Asp Lys His Ala Thr Ser Tyr Ala Phe His Gly Leu Ser Pro Gly Tyr
    250                 255                 260 ctc tac aac ctc act gtt atg act gag gct gca ggg ctg caa aac tac        870
Leu Tyr Asn Leu Thr Val Met Thr Glu Ala Ala Gly Leu Gln Asn Tyr
265                 270                 275                 280 agg tgg aaa cta gtc agg aca gcc ccc atg gaa gtc tca aat ctg aag        918
```

|   |   |   |   |   |   |   |   |   |   |   |   |   |   |   |   |   |
|---|---|---|---|---|---|---|---|---|---|---|---|---|---|---|---|---|
| Arg | Trp | Lys | Leu | Val | Arg | Thr | Ala | Pro | Met | Glu | Val | Ser | Asn | Leu | Lys | |
|     |     |     |     | 285 |     |     |     |     | 290 |     |     |     |     | 295 |     | |

```
gtg aca aat gat ggc agt ttg acc tct cta aaa gtc aaa tgg caa aga     966
Val Thr Asn Asp Gly Ser Leu Thr Ser Leu Lys Val Lys Trp Gln Arg
            300                 305                 310 cct cct gga aat gtg gat tct tac aat atc acc ctg tct cac aaa ggg    1014
Pro Pro Gly Asn Val Asp Ser Tyr Asn Ile Thr Leu Ser His Lys Gly
            315                 320                 325 acc atc aag gaa tcc aga gta tta gca cct tgg att act gaa act cac    1062
Thr Ile Lys Glu Ser Arg Val Leu Ala Pro Trp Ile Thr Glu Thr His
        330                 335                 340 ttt aaa gag tta gtc ccc ggt cga ctt tat caa gtt act gtc agc tgt    1110
Phe Lys Glu Leu Val Pro Gly Arg Leu Tyr Gln Val Thr Val Ser Cys
345                 350                 355                 360 gtc tct ggt gaa ctg tct gct cag aag atg gca gtg ggc aga aca ttt    1158
Val Ser Gly Glu Leu Ser Ala Gln Lys Met Ala Val Gly Arg Thr Phe
                365                 370                 375 cca gac aaa gtt gca aac ctg gag gca aac aat aat ggc agg atg agg    1206
Pro Asp Lys Val Ala Asn Leu Glu Ala Asn Asn Asn Gly Arg Met Arg
            380                 385                 390 tct ctt gta gtg agc tgg tcg ccc cct gct gga gac tgg gag cag tat    1254
Ser Leu Val Val Ser Trp Ser Pro Pro Ala Gly Asp Trp Glu Gln Tyr
            395                 400                 405 cgg atc cta ctc ttc aat gat tct gtg gtg ctc ctc aac atc act gtg    1302
Arg Ile Leu Leu Phe Asn Asp Ser Val Val Leu Leu Asn Ile Thr Val
        410                 415                 420 gga aag gaa gaa aca cag tat gtc atg gat gac acg ggg ctc gta ccg    1350
Gly Lys Glu Glu Thr Gln Tyr Val Met Asp Asp Thr Gly Leu Val Pro
425                 430                 435                 440 gga aga cag tat gag gtg gaa gtc att gtt gag agt gga aat ttg aag    1398
Gly Arg Gln Tyr Glu Val Glu Val Ile Val Glu Ser Gly Asn Leu Lys
                445                 450                 455 aat tct gag cgt tgc caa ggc agg aca gtc ccc ctg gct gtc ctc cag    1446
Asn Ser Glu Arg Cys Gln Gly Arg Thr Val Pro Leu Ala Val Leu Gln
            460                 465                 470 ctt cgt gtc aaa cat gcc aat gaa acc tca ctg agt atc atg tgg cag    1494
Leu Arg Val Lys His Ala Asn Glu Thr Ser Leu Ser Ile Met Trp Gln
            475                 480                 485 acc cct gta gca gaa tgg gag aaa tac atc att tcc cta gct gac aga    1542
Thr Pro Val Ala Glu Trp Glu Lys Tyr Ile Ile Ser Leu Ala Asp Arg
        490                 495                 500 gac ctc tta ctg atc cac aag tca ctc tcc aaa gat gcc aaa gaa ttc    1590
Asp Leu Leu Leu Ile His Lys Ser Leu Ser Lys Asp Ala Lys Glu Phe
505                 510                 515                 520 act ttt act gac ctg gtg cct gga cga aaa tac atg gct aca gtc acc    1638
Thr Phe Thr Asp Leu Val Pro Gly Arg Lys Tyr Met Ala Thr Val Thr
                525                 530                 535 agt att agt gga gac tta aaa aat tcc tct tca gta aaa gga aga aca    1686
Ser Ile Ser Gly Asp Leu Lys Asn Ser Ser Ser Val Lys Gly Arg Thr
            540                 545                 550 gtg cct gcc caa gtg act gac ttg cat gtg gcc aac caa gga atg acc    1734
Val Pro Ala Gln Val Thr Asp Leu His Val Ala Asn Gln Gly Met Thr
            555                 560                 565 agt agt ctg ttt act aac tgg acc cag gca caa gga gac gta gaa ttt    1782
Ser Ser Leu Phe Thr Asn Trp Thr Gln Ala Gln Gly Asp Val Glu Phe
        570                 575                 580 tac caa gtc tta ctg atc cat gaa aat gtg gtc att aaa aat gaa agc    1830
Tyr Gln Val Leu Leu Ile His Glu Asn Val Val Ile Lys Asn Glu Ser
585                 590                 595                 600
```

-continued

| | | | | | | | | | | | | | | | |
|---|---|---|---|---|---|---|---|---|---|---|---|---|---|---|---|
| atc | tcc | agt | gag | acc | agc | aga | tac | agc | ttc | cac | tct | ctc | aag | tcc | ggc | 1878
| Ile | Ser | Ser | Glu | Thr | Ser | Arg | Tyr | Ser | Phe | His | Ser | Leu | Lys | Ser | Gly |
| | | | | 605 | | | | | 610 | | | | | 615 | |

| agc | ctg | tac | tcc | gtg | gtg | gta | aca | aca | gtg | agt | gga | ggg | atc | tct | tcc | 1926
| Ser | Leu | Tyr | Ser | Val | Val | Val | Thr | Thr | Val | Ser | Gly | Gly | Ile | Ser | Ser |
| | | | 620 | | | | | 625 | | | | | 630 | | |

| cga | caa | gtg | gtt | gtg | gag | gga | aga | aca | gtc | cct | tcc | agt | gtg | agt | gga | 1974
| Arg | Gln | Val | Val | Val | Glu | Gly | Arg | Thr | Val | Pro | Ser | Ser | Val | Ser | Gly |
| | | 635 | | | | | 640 | | | | | 645 | | | |

| gta | acg | gtg | aac | aat | tcc | ggt | cgt | aat | gac | tac | ctc | agc | gtt | tcc | tgg | 2022
| Val | Thr | Val | Asn | Asn | Ser | Gly | Arg | Asn | Asp | Tyr | Leu | Ser | Val | Ser | Trp |
| 650 | | | | | 655 | | | | | 660 | | | | | |

| ctc | gtg | gcg | ccc | gga | gat | gtg | gat | aac | tat | gag | gta | aca | ttg | tct | cat | 2070
| Leu | Val | Ala | Pro | Gly | Asp | Val | Asp | Asn | Tyr | Glu | Val | Thr | Leu | Ser | His |
| 665 | | | | 670 | | | | | 675 | | | | | 680 | |

| gac | ggc | aag | gtg | gtt | cag | tcc | ctt | gtc | att | gcc | aag | tct | gtc | aga | gaa | 2118
| Asp | Gly | Lys | Val | Val | Gln | Ser | Leu | Val | Ile | Ala | Lys | Ser | Val | Arg | Glu |
| | | | | 685 | | | | | 690 | | | | | 695 | |

| tgt | tcc | ttc | agc | tcc | ctc | acc | cca | ggc | cgc | ctc | tac | acc | gtg | acc | ata | 2166
| Cys | Ser | Phe | Ser | Ser | Leu | Thr | Pro | Gly | Arg | Leu | Tyr | Thr | Val | Thr | Ile |
| | | | 700 | | | | | 705 | | | | | 710 | | |

| act | aca | agg | agt | ggc | aag | tat | gaa | aat | cac | tcc | ttc | agc | caa | gag | cgg | 2214
| Thr | Thr | Arg | Ser | Gly | Lys | Tyr | Glu | Asn | His | Ser | Phe | Ser | Gln | Glu | Arg |
| | | 715 | | | | | 720 | | | | | 725 | | | |

| aca | gtg | cct | gac | aaa | gtc | cag | gga | gtc | agt | gtt | agc | aac | tca | gcc | agg | 2262
| Thr | Val | Pro | Asp | Lys | Val | Gln | Gly | Val | Ser | Val | Ser | Asn | Ser | Ala | Arg |
| | 730 | | | | | 735 | | | | | 740 | | | | |

| agt | gac | tat | tta | agg | gta | tcc | tgg | gtg | cat | gcc | act | gga | gac | ttt | gat | 2310
| Ser | Asp | Tyr | Leu | Arg | Val | Ser | Trp | Val | His | Ala | Thr | Gly | Asp | Phe | Asp |
| 745 | | | | | 750 | | | | | 755 | | | | | 760 |

| cac | tat | gaa | gtc | acc | att | aaa | aac | aaa | aac | aac | ttc | att | caa | act | aaa | 2358
| His | Tyr | Glu | Val | Thr | Ile | Lys | Asn | Lys | Asn | Asn | Phe | Ile | Gln | Thr | Lys |
| | | | | 765 | | | | | 770 | | | | | 775 | |

| agc | att | ccc | aag | tca | gaa | aac | gaa | tgt | gta | ttt | gtt | cag | cta | gtc | cct | 2406
| Ser | Ile | Pro | Lys | Ser | Glu | Asn | Glu | Cys | Val | Phe | Val | Gln | Leu | Val | Pro |
| | | | 780 | | | | | 785 | | | | | 790 | | |

| gga | cgg | ttg | tac | agt | gtc | act | gtt | act | aca | aaa | agt | gga | caa | tat | gaa | 2454
| Gly | Arg | Leu | Tyr | Ser | Val | Thr | Val | Thr | Thr | Lys | Ser | Gly | Gln | Tyr | Glu |
| | | 795 | | | | | 800 | | | | | 805 | | | |

| gcc | aat | gaa | caa | ggg | aat | ggg | aga | aca | att | cca | gag | cct | gtt | aag | gat | 2502
| Ala | Asn | Glu | Gln | Gly | Asn | Gly | Arg | Thr | Ile | Pro | Glu | Pro | Val | Lys | Asp |
| | 810 | | | | | 815 | | | | | 820 | | | | |

| cta | aca | ttg | cgc | aac | agg | agc | act | gag | gac | ttg | cat | gtg | act | tgg | tca | 2550
| Leu | Thr | Leu | Arg | Asn | Arg | Ser | Thr | Glu | Asp | Leu | His | Val | Thr | Trp | Ser |
| 825 | | | | | 830 | | | | | 835 | | | | | 840 |

| gga | gct | aat | ggg | gat | gtc | gac | caa | tat | gag | atc | cag | ctg | ctc | ttc | aat | 2598
| Gly | Ala | Asn | Gly | Asp | Val | Asp | Gln | Tyr | Glu | Ile | Gln | Leu | Leu | Phe | Asn |
| | | | | 845 | | | | | 850 | | | | | 855 | |

| gac | atg | aaa | gta | ttt | cct | cct | ttt | cac | ctt | gta | aat | acc | gca | acc | gag | 2646
| Asp | Met | Lys | Val | Phe | Pro | Pro | Phe | His | Leu | Val | Asn | Thr | Ala | Thr | Glu |
| | | | 860 | | | | | 865 | | | | | 870 | | |

| tat | cga | ttt | act | tcc | cta | aca | cca | ggc | cgc | caa | tac | aaa | att | ctt | gtc | 2694
| Tyr | Arg | Phe | Thr | Ser | Leu | Thr | Pro | Gly | Arg | Gln | Tyr | Lys | Ile | Leu | Val |
| | | 875 | | | | | 880 | | | | | 885 | | | |

| ttg | acg | att | agc | ggg | gat | gta | cag | cag | tca | gcc | ttc | att | gag | ggc | ttc | 2742
| Leu | Thr | Ile | Ser | Gly | Asp | Val | Gln | Gln | Ser | Ala | Phe | Ile | Glu | Gly | Phe |
| | | | | 890 | | | | | 895 | | | | | 900 | |

| aca | gtt | cct | agt | gct | gtc | aaa | aat | att | cac | att | tct | ccc | aat | gga | gca | 2790
| Thr | Val | Pro | Ser | Ala | Val | Lys | Asn | Ile | His | Ile | Ser | Pro | Asn | Gly | Ala |
| 905 | | | | | 910 | | | | | 915 | | | | | 920 |

```
aca gat agc ctg acg gtg aac tgg act cct ggt ggg gga gac gtt gat    2838
Thr Asp Ser Leu Thr Val Asn Trp Thr Pro Gly Gly Gly Asp Val Asp
            925                 930                 935 tcc tac acg gtg tcg gca ttc agg cac agt caa aag gtt gac tct cag    2886
Ser Tyr Thr Val Ser Ala Phe Arg His Ser Gln Lys Val Asp Ser Gln
            940                 945                 950 act att ccc aag cac gtc ttt gag cac acg ttc cac aga ctg gag gcc    2934
Thr Ile Pro Lys His Val Phe Glu His Thr Phe His Arg Leu Glu Ala
            955                 960                 965 ggg gag cag tac cag atc atg att gcc tca gtc agc ggg tcc ctg aag    2982
Gly Glu Gln Tyr Gln Ile Met Ile Ala Ser Val Ser Gly Ser Leu Lys
970                 975                 980 aat cag ata aat gtg gtt ggg cgg aca gtt cca gca tct gtc caa gga    3030
Asn Gln Ile Asn Val Val Gly Arg Thr Val Pro Ala Ser Val Gln Gly
985                 990                 995                 1000 gta att gca gac aat gca tac agc agt tat tcc tta ata gta agt        3075
Val Ile Ala Asp Asn Ala Tyr Ser Ser Tyr Ser Leu Ile Val Ser
                1005                1010                1015 tgg caa aaa gct gct ggt gtg gca gaa aga tat gat atc ctg ctt        3120
Trp Gln Lys Ala Ala Gly Val Ala Glu Arg Tyr Asp Ile Leu Leu
                1020                1025                1030 cta act gaa aat gga atc ctt ctg cgc aac aca tca gag cca gcc        3165
Leu Thr Glu Asn Gly Ile Leu Leu Arg Asn Thr Ser Glu Pro Ala
                1035                1040                1045 acc act aag caa cac aaa ttt gaa gat cta aca cca ggc aag aaa        3210
Thr Thr Lys Gln His Lys Phe Glu Asp Leu Thr Pro Gly Lys Lys
                1050                1055                1060 tac aag ata cag atc cta act gtc agt gga ggc ctc ttt agc aag        3255
Tyr Lys Ile Gln Ile Leu Thr Val Ser Gly Gly Leu Phe Ser Lys
                1065                1070                1075 gaa gcc cag act gaa ggc cga aca gtc cca gca gct gtc acc gac        3300
Glu Ala Gln Thr Glu Gly Arg Thr Val Pro Ala Ala Val Thr Asp
                1080                1085                1090 ctg agg atc aca gag aac tcc acc agg cac ctg tcc ttc cgc tgg        3345
Leu Arg Ile Thr Glu Asn Ser Thr Arg His Leu Ser Phe Arg Trp
                1095                1100                1105 acc gcc tca gag ggg gag ctc agc tgg tac aac atc ttt ttg tac        3390
Thr Ala Ser Glu Gly Glu Leu Ser Trp Tyr Asn Ile Phe Leu Tyr
                1110                1115                1120 aac cca gat ggg aat ctc cag gag aga gct caa gtt gac cca cta        3435
Asn Pro Asp Gly Asn Leu Gln Glu Arg Ala Gln Val Asp Pro Leu
                1125                1130                1135 gtc cag agc ttc tct ttc cag aac ttg cta caa ggc aga atg tac        3480
Val Gln Ser Phe Ser Phe Gln Asn Leu Leu Gln Gly Arg Met Tyr
                1140                1145                1150 aag atg gtg att gta act cac agt ggg gag ctg tct aat gag tct        3525
Lys Met Val Ile Val Thr His Ser Gly Glu Leu Ser Asn Glu Ser
                1155                1160                1165 ttc ata ttt ggt aga aca gtc cca gcc tct gtg agt cat ctc agg        3570
Phe Ile Phe Gly Arg Thr Val Pro Ala Ser Val Ser His Leu Arg
                1170                1175                1180 ggg tcc aat cgg aac acg aca gac agc ctt tgg ttc aac tgg agt        3615
Gly Ser Asn Arg Asn Thr Thr Asp Ser Leu Trp Phe Asn Trp Ser
                1185                1190                1195 cca gcc tct ggg gac ttt gac ttt tat gag ctg att ctc tat aat        3660
Pro Ala Ser Gly Asp Phe Asp Phe Tyr Glu Leu Ile Leu Tyr Asn
                1200                1205                1210 ccc aat ggc aca aag aag gaa aac tgg aaa gac aag gac ctg acg        3705
Pro Asn Gly Thr Lys Lys Glu Asn Trp Lys Asp Lys Asp Leu Thr
```

-continued

```
                         1215                  1220                   1225
gag tgg cgg ttt caa  ggc ctt gtt cct gga  agg aag tac gtg ctg         3750
Glu Trp Arg Phe Gln  Gly Leu Val Pro Gly  Arg Lys Tyr Val Leu
                1230                 1235                  1240 tgg gtg gta act cac  agt gga gat ctc agc  aat aaa gtc aca gcg         3795
Trp Val Val Thr His  Ser Gly Asp Leu Ser  Asn Lys Val Thr Ala
                1245                 1250                  1255 gag agc aga aca gct  cca agt cct ccc agt  ctt atg tca ttt gct         3840
Glu Ser Arg Thr Ala  Pro Ser Pro Pro Ser  Leu Met Ser Phe Ala
                1260                 1265                  1270 gac att gca aac aca  tcc ttg gcc atc acg  tgg aaa ggg ccc cca         3885
Asp Ile Ala Asn Thr  Ser Leu Ala Ile Thr  Trp Lys Gly Pro Pro
                1275                 1280                  1285 gac tgg aca gac tac  aac gac ttt gag ctg  cag tgg ttg ccc aga         3930
Asp Trp Thr Asp Tyr  Asn Asp Phe Glu Leu  Gln Trp Leu Pro Arg
                1290                 1295                  1300 gat gca ctt act gtc  ttc aac ccc tac aac  aac aga aaa tca gaa         3975
Asp Ala Leu Thr Val  Phe Asn Pro Tyr Asn  Asn Arg Lys Ser Glu
                1305                 1310                  1315 gga cgc att gtg tat  ggt ctt cgt cca ggg  aga tcc tat caa ttc         4020
Gly Arg Ile Val Tyr  Gly Leu Arg Pro Gly  Arg Ser Tyr Gln Phe
                1320                 1325                  1330 aac gtc aag act gtc  agt ggt gat tcc tgg  aaa act tac agc aaa         4065
Asn Val Lys Thr Val  Ser Gly Asp Ser Trp  Lys Thr Tyr Ser Lys
                1335                 1340                  1345 cca att ttt gga tct  gtg agg aca aag cct  gac aag ata caa aac         4110
Pro Ile Phe Gly Ser  Val Arg Thr Lys Pro  Asp Lys Ile Gln Asn
                1350                 1355                  1360 ctg cat tgc cgg cct  cag aac tcc acg gcc  att gcc tgt tct tgg         4155
Leu His Cys Arg Pro  Gln Asn Ser Thr Ala  Ile Ala Cys Ser Trp
                1365                 1370                  1375 atc cct cct gat tct  gac ttt gat ggt tat  agt att gaa tgc cgg         4200
Ile Pro Pro Asp Ser  Asp Phe Asp Gly Tyr  Ser Ile Glu Cys Arg
                1380                 1385                  1390 aaa atg gac acc caa  gaa gtt gag ttt tcc  aga aag ctg gag aaa         4245
Lys Met Asp Thr Gln  Glu Val Glu Phe Ser  Arg Lys Leu Glu Lys
                1395                 1400                  1405 gaa aaa tct ctg ctc  aac atc atg atg cta  gtg ccc cat aag agg         4290
Glu Lys Ser Leu Leu  Asn Ile Met Met Leu  Val Pro His Lys Arg
                1410                 1415                  1420 tac ctg gtg tcc atc  aaa gtg cag tcg gcc  ggc atg acc agc gag         4335
Tyr Leu Val Ser Ile  Lys Val Gln Ser Ala  Gly Met Thr Ser Glu
                1425                 1430                  1435 gtg gtt gaa gac agc  act atc aca atg ata  gac cgc ccc cct cct         4380
Val Val Glu Asp Ser  Thr Ile Thr Met Ile  Asp Arg Pro Pro Pro
                1440                 1445                  1450 cca ccc cca cac att  cgt gtg aat gaa aag  gat gtg cta att agc         4425
Pro Pro Pro His Ile  Arg Val Asn Glu Lys  Asp Val Leu Ile Ser
                1455                 1460                  1465 aag tct tcc atc aac  ttt act gtc aac tgc  agc tgg ttc agc gac         4470
Lys Ser Ser Ile Asn  Phe Thr Val Asn Cys  Ser Trp Phe Ser Asp
                1470                 1475                  1480 acc aat gga gct gtg  aaa tac ttc aca gtg  gtg gtg aga gag gct         4515
Thr Asn Gly Ala Val  Lys Tyr Phe Thr Val  Val Val Arg Glu Ala
                1485                 1490                  1495 gat ggc agt gat gag  ctg aag cca gaa cag  cag cac cct ctc cct         4560
Asp Gly Ser Asp Glu  Leu Lys Pro Glu Gln  Gln His Pro Leu Pro
                1500                 1505                  1510 tcc tac ctg gag tac  agg cac aat gcc tcc  att cgg gtg tat cag         4605
```

```
Ser Tyr Leu Glu Tyr Arg His Asn Ala Ser Ile Arg Val Tyr Gln
        1515                1520                1525 act aat tat ttt gcc agc aaa tgt gcc gaa aat cct aac agc aac       4650
Thr Asn Tyr Phe Ala Ser Lys Cys Ala Glu Asn Pro Asn Ser Asn
        1530                1535                1540 tcc aag agt ttt aac att aag ctt gga gca gag atg gag agc tta       4695
Ser Lys Ser Phe Asn Ile Lys Leu Gly Ala Glu Met Glu Ser Leu
        1545                1550                1555 ggt gga aaa cgc gat ccc act cag caa aaa ttc tgt gat gga cca       4740
Gly Gly Lys Arg Asp Pro Thr Gln Gln Lys Phe Cys Asp Gly Pro
        1560                1565                1570 ctg aag cca cac act gcc tac aga atc agc att cga gct ttt aca       4785
Leu Lys Pro His Thr Ala Tyr Arg Ile Ser Ile Arg Ala Phe Thr
        1575                1580                1585 cag ctc ttt gat gag gac ctg aag gaa ttc aca aag cca ctc tat       4830
Gln Leu Phe Asp Glu Asp Leu Lys Glu Phe Thr Lys Pro Leu Tyr
        1590                1595                1600 tca gac aca ttt ttt tct tta ccc atc act act gaa tca gag ccc       4875
Ser Asp Thr Phe Phe Ser Leu Pro Ile Thr Thr Glu Ser Glu Pro
        1605                1610                1615 ttg ttt gga gct att gaa ggt gtg agt gct ggt ctg ttt tta att       4920
Leu Phe Gly Ala Ile Glu Gly Val Ser Ala Gly Leu Phe Leu Ile
        1620                1625                1630 ggc atg cta gtg gct gtt gtt gcc tta ttg atc tgc aga cag aaa       4965
Gly Met Leu Val Ala Val Val Ala Leu Leu Ile Cys Arg Gln Lys
        1635                1640                1645 gtg agc cat ggt cga gaa aga ccc tct gcc cgt ctg agc att cgt       5010
Val Ser His Gly Arg Glu Arg Pro Ser Ala Arg Leu Ser Ile Arg
        1650                1655                1660 agg gat cga cca tta tct gtc cac tta aac ctg ggc cag aaa ggt       5055
Arg Asp Arg Pro Leu Ser Val His Leu Asn Leu Gly Gln Lys Gly
        1665                1670                1675 aac cgg aaa act tct tgt cca ata aaa ata aat cag ttt gaa ggg       5100
Asn Arg Lys Thr Ser Cys Pro Ile Lys Ile Asn Gln Phe Glu Gly
        1680                1685                1690 cat ttc atg aag cta cag gct gac tcc aac tac ctt cta tcc aag       5145
His Phe Met Lys Leu Gln Ala Asp Ser Asn Tyr Leu Leu Ser Lys
        1695                1700                1705 gaa tac gag gag tta aaa gac gtg ggc cga aac cag tca tgt gac       5190
Glu Tyr Glu Glu Leu Lys Asp Val Gly Arg Asn Gln Ser Cys Asp
        1710                1715                1720 att gca ctc ttg ccg gag aat aga ggg aaa aat cga tac aac aat       5235
Ile Ala Leu Leu Pro Glu Asn Arg Gly Lys Asn Arg Tyr Asn Asn
        1725                1730                1735 ata ttg ccc tat gat gcc acg cga gtg aag ctc tcc aat gta gat       5280
Ile Leu Pro Tyr Asp Ala Thr Arg Val Lys Leu Ser Asn Val Asp
        1740                1745                1750 gat gat cct tgc tct gac tac atc aat gcc agc tac atc cct ggc       5325
Asp Asp Pro Cys Ser Asp Tyr Ile Asn Ala Ser Tyr Ile Pro Gly
        1755                1760                1765 aac aac ttc aga aga gaa tac att gtc act cag gga ccg ctt cct       5370
Asn Asn Phe Arg Arg Glu Tyr Ile Val Thr Gln Gly Pro Leu Pro
        1770                1775                1780 ggc acc aag gat gac ttc tgg aaa atg gtg tgg gaa caa aac gtt       5415
Gly Thr Lys Asp Asp Phe Trp Lys Met Val Trp Glu Gln Asn Val
        1785                1790                1795 cac aac atc gtc atg gtg acc cag tgt gtt gag aag ggc cga gta       5460
His Asn Ile Val Met Val Thr Gln Cys Val Glu Lys Gly Arg Val
        1800                1805                1810
```

```
aag tgt gac cat tac tgg cca gcg gac cag gat tcc ctc tac tat      5505
Lys Cys Asp His Tyr Trp Pro Ala Asp Gln Asp Ser Leu Tyr Tyr
            1815                1820                1825 ggg gac ctc atc ctg cag atg ctc tca gag tcc gtc ctg cct gag      5550
Gly Asp Leu Ile Leu Gln Met Leu Ser Glu Ser Val Leu Pro Glu
        1830                1835                1840 tgg acc atc cgg gag ttt aag ata tgc ggt gag gaa cag ctt gat      5595
Trp Thr Ile Arg Glu Phe Lys Ile Cys Gly Glu Glu Gln Leu Asp
    1845                1850                1855 gca cac aga ctc atc cgc cac ttt cac tat acg gtg tgg cca gac      5640
Ala His Arg Leu Ile Arg His Phe His Tyr Thr Val Trp Pro Asp
1860                1865                1870 cat gga gtc cca gaa acc acc cag tct ctg atc cag ttt gtg aga      5685
His Gly Val Pro Glu Thr Thr Gln Ser Leu Ile Gln Phe Val Arg
            1875                1880                1885 act gtc agg gac tac atc aac aga agc ccg ggt gct ggg ccc act      5730
Thr Val Arg Asp Tyr Ile Asn Arg Ser Pro Gly Ala Gly Pro Thr
        1890                1895                1900 gtg gtg cac tgc agt gct ggt gtg ggt agg act gga acc ttt att      5775
Val Val His Cys Ser Ala Gly Val Gly Arg Thr Gly Thr Phe Ile
    1905                1910                1915 gca ttg gac cga atc ctc cag cag tta gac tcc aaa gac tct gtg      5820
Ala Leu Asp Arg Ile Leu Gln Gln Leu Asp Ser Lys Asp Ser Val
1920                1925                1930 gac att tat gga gca gtg cac gac cta aga ctt cac agg gtt cac      5865
Asp Ile Tyr Gly Ala Val His Asp Leu Arg Leu His Arg Val His
            1935                1940                1945 atg gtc cag act gag tgt cag tat gtc tac cta cat cag tgt gta      5910
Met Val Gln Thr Glu Cys Gln Tyr Val Tyr Leu His Gln Cys Val
        1950                1955                1960 aga gat gtc ctc aga gca aga aag cta cgg agt gaa caa gaa aac      5955
Arg Asp Val Leu Arg Ala Arg Lys Leu Arg Ser Glu Gln Glu Asn
    1965                1970                1975 ccc ttg ttt cca atc tat gaa aat gtg aat cca gag tat cac aga      6000
Pro Leu Phe Pro Ile Tyr Glu Asn Val Asn Pro Glu Tyr His Arg
1980                1985                1990 gat cca gtc tat tca agg cat tga gaatgtacct gaagagctcc tggataaaaa  6054
Asp Pro Val Tyr Ser Arg His
            1995 ttattcactg tgtgatttgt t                                           6075

<210> SEQ ID NO 2
<211> LENGTH: 1997
<212> TYPE: PRT
<213> ORGANISM: Homo sapiens

<400> SEQUENCE: 2

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
            20                  25                  30

Glu Ser Lys Ala Ser Ser His Ser Val Ser Ile Gln Trp Arg Ile Leu
        35                  40                  45

Gly Ser Pro Cys Asn Phe Ser Leu Ile Tyr Ser Ser Asp Thr Leu Gly
    50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95
```

-continued

```
Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Gly Leu
        115                 120                 125

His Val Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240

Ile Leu Val His Gly Val Val Asp Lys His Ala Thr Ser Tyr Ala
                245                 250                 255

Phe His Gly Leu Ser Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
        275                 280                 285

Pro Met Glu Val Ser Asn Leu Lys Val Thr Asn Asp Gly Ser Leu Thr
    290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335

Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
        355                 360                 365

Lys Met Ala Val Gly Arg Thr Phe Pro Asp Lys Val Ala Asn Leu Glu
    370                 375                 380

Ala Asn Asn Asn Gly Arg Met Arg Ser Leu Val Val Ser Trp Ser Pro
385                 390                 395                 400

Pro Ala Gly Asp Trp Glu Gln Tyr Arg Ile Leu Leu Phe Asn Asp Ser
                405                 410                 415

Val Val Leu Leu Asn Ile Thr Val Gly Lys Glu Thr Gln Tyr Val
            420                 425                 430

Met Asp Asp Thr Gly Leu Val Pro Gly Arg Gln Tyr Glu Val Glu Val
        435                 440                 445

Ile Val Glu Ser Gly Asn Leu Lys Asn Ser Glu Arg Cys Gln Gly Arg
    450                 455                 460

Thr Val Pro Leu Ala Val Leu Gln Leu Arg Val Lys His Ala Asn Glu
465                 470                 475                 480

Thr Ser Leu Ser Ile Met Trp Gln Thr Pro Val Ala Glu Trp Glu Lys
                485                 490                 495

Tyr Ile Ile Ser Leu Ala Asp Arg Asp Leu Leu Leu Ile His Lys Ser
            500                 505                 510
```

```
Leu Ser Lys Asp Ala Lys Glu Phe Thr Phe Thr Asp Leu Val Pro Gly
        515                 520                 525

Arg Lys Tyr Met Ala Thr Val Thr Ser Ile Ser Gly Asp Leu Lys Asn
        530                 535                 540

Ser Ser Ser Val Lys Gly Arg Thr Val Pro Ala Gln Val Thr Asp Leu
545                 550                 555                 560

His Val Ala Asn Gln Gly Met Thr Ser Ser Leu Phe Thr Asn Trp Thr
                565                 570                 575

Gln Ala Gln Gly Asp Val Glu Phe Tyr Gln Val Leu Leu Ile His Glu
            580                 585                 590

Asn Val Val Ile Lys Asn Glu Ser Ile Ser Ser Glu Thr Ser Arg Tyr
                595                 600                 605

Ser Phe His Ser Leu Lys Ser Gly Ser Leu Tyr Ser Val Val Val Thr
        610                 615                 620

Thr Val Ser Gly Gly Ile Ser Ser Arg Gln Val Val Val Glu Gly Arg
625                 630                 635                 640

Thr Val Pro Ser Ser Val Ser Gly Val Thr Val Asn Asn Ser Gly Arg
                645                 650                 655

Asn Asp Tyr Leu Ser Val Ser Trp Leu Val Ala Pro Gly Asp Val Asp
                660                 665                 670

Asn Tyr Glu Val Thr Leu Ser His Asp Gly Lys Val Val Gln Ser Leu
        675                 680                 685

Val Ile Ala Lys Ser Val Arg Glu Cys Ser Phe Ser Ser Leu Thr Pro
        690                 695                 700

Gly Arg Leu Tyr Thr Val Thr Ile Thr Thr Arg Ser Gly Lys Tyr Glu
705                 710                 715                 720

Asn His Ser Phe Ser Gln Glu Arg Thr Val Pro Asp Lys Val Gln Gly
                725                 730                 735

Val Ser Val Ser Asn Ser Ala Arg Ser Asp Tyr Leu Arg Val Ser Trp
                740                 745                 750

Val His Ala Thr Gly Asp Phe Asp His Tyr Glu Val Thr Ile Lys Asn
        755                 760                 765

Lys Asn Asn Phe Ile Gln Thr Lys Ser Ile Pro Lys Ser Glu Asn Glu
        770                 775                 780

Cys Val Phe Val Gln Leu Val Pro Gly Arg Leu Tyr Ser Val Thr Val
785                 790                 795                 800

Thr Thr Lys Ser Gly Gln Tyr Glu Ala Asn Glu Gln Gly Asn Gly Arg
                805                 810                 815

Thr Ile Pro Glu Pro Val Lys Asp Leu Thr Leu Arg Asn Arg Ser Thr
                820                 825                 830

Glu Asp Leu His Val Thr Trp Ser Gly Ala Asn Gly Asp Val Asp Gln
        835                 840                 845

Tyr Glu Ile Gln Leu Leu Phe Asn Asp Met Lys Val Phe Pro Pro Phe
        850                 855                 860

His Leu Val Asn Thr Ala Thr Glu Tyr Arg Phe Thr Ser Leu Thr Pro
865                 870                 875                 880

Gly Arg Gln Tyr Lys Ile Leu Val Leu Thr Ile Ser Gly Asp Val Gln
                885                 890                 895

Gln Ser Ala Phe Ile Glu Gly Phe Thr Val Pro Ser Ala Val Lys Asn
            900                 905                 910

Ile His Ile Ser Pro Asn Gly Ala Thr Asp Ser Leu Thr Val Asn Trp
        915                 920                 925

Thr Pro Gly Gly Gly Asp Val Asp Ser Tyr Thr Val Ser Ala Phe Arg
```

-continued

```
            930                 935                 940
His Ser Gln Lys Val Asp Ser Gln Thr Ile Pro Lys His Val Phe Glu
945                 950                 955                 960
His Thr Phe His Arg Leu Glu Ala Gly Glu Gln Tyr Gln Ile Met Ile
                965                 970                 975
Ala Ser Val Ser Gly Ser Leu Lys Asn Gln Ile Asn Val Val Gly Arg
            980                 985                 990
Thr Val Pro Ala Ser Val Gln Gly Val Ile Ala Asp Asn Ala Tyr Ser
                995                1000                1005
Ser Tyr Ser Leu Ile Val Ser Trp Gln Lys Ala Ala Gly Val Ala
        1010                1015                1020
Glu Arg Tyr Asp Ile Leu Leu Leu Thr Glu Asn Gly Ile Leu Leu
        1025                1030                1035
Arg Asn Thr Ser Glu Pro Ala Thr Thr Lys Gln His Lys Phe Glu
        1040                1045                1050
Asp Leu Thr Pro Gly Lys Lys Tyr Lys Ile Gln Ile Leu Thr Val
        1055                1060                1065
Ser Gly Gly Leu Phe Ser Lys Glu Ala Gln Thr Glu Gly Arg Thr
        1070                1075                1080
Val Pro Ala Ala Val Thr Asp Leu Arg Ile Thr Glu Asn Ser Thr
        1085                1090                1095
Arg His Leu Ser Phe Arg Trp Thr Ala Ser Glu Gly Glu Leu Ser
        1100                1105                1110
Trp Tyr Asn Ile Phe Leu Tyr Asn Pro Asp Gly Asn Leu Gln Glu
        1115                1120                1125
Arg Ala Gln Val Asp Pro Leu Val Gln Ser Phe Ser Phe Gln Asn
        1130                1135                1140
Leu Leu Gln Gly Arg Met Tyr Lys Met Val Ile Val Thr His Ser
        1145                1150                1155
Gly Glu Leu Ser Asn Glu Ser Phe Ile Phe Gly Arg Thr Val Pro
        1160                1165                1170
Ala Ser Val Ser His Leu Arg Gly Ser Asn Arg Asn Thr Thr Asp
        1175                1180                1185
Ser Leu Trp Phe Asn Trp Ser Pro Ala Ser Gly Asp Phe Asp Phe
        1190                1195                1200
Tyr Glu Leu Ile Leu Tyr Asn Pro Asn Gly Thr Lys Lys Glu Asn
        1205                1210                1215
Trp Lys Asp Lys Asp Leu Thr Glu Trp Arg Phe Gln Gly Leu Val
        1220                1225                1230
Pro Gly Arg Lys Tyr Val Leu Trp Val Val Thr His Ser Gly Asp
        1235                1240                1245
Leu Ser Asn Lys Val Thr Ala Glu Ser Arg Thr Ala Pro Ser Pro
        1250                1255                1260
Pro Ser Leu Met Ser Phe Ala Asp Ile Ala Asn Thr Ser Leu Ala
        1265                1270                1275
Ile Thr Trp Lys Gly Pro Pro Asp Trp Thr Asp Tyr Asn Asp Phe
        1280                1285                1290
Glu Leu Gln Trp Leu Pro Arg Asp Ala Leu Thr Val Phe Asn Pro
        1295                1300                1305
Tyr Asn Asn Arg Lys Ser Glu Gly Arg Ile Val Tyr Gly Leu Arg
        1310                1315                1320
Pro Gly Arg Ser Tyr Gln Phe Asn Val Lys Thr Val Ser Gly Asp
        1325                1330                1335
```

-continued

```
Ser Trp Lys Thr Tyr Ser Lys Pro Ile Phe Gly Ser Val Arg Thr
    1340                1345                1350
Lys Pro Asp Lys Ile Gln Asn Leu His Cys Arg Pro Gln Asn Ser
    1355                1360                1365
Thr Ala Ile Ala Cys Ser Trp Ile Pro Pro Asp Ser Asp Phe Asp
    1370                1375                1380
Gly Tyr Ser Ile Glu Cys Arg Lys Met Asp Thr Gln Glu Val Glu
    1385                1390                1395
Phe Ser Arg Lys Leu Glu Lys Glu Lys Ser Leu Leu Asn Ile Met
    1400                1405                1410
Met Leu Val Pro His Lys Arg Tyr Leu Val Ser Ile Lys Val Gln
    1415                1420                1425
Ser Ala Gly Met Thr Ser Glu Val Val Glu Asp Ser Thr Ile Thr
    1430                1435                1440
Met Ile Asp Arg Pro Pro Pro Pro Pro His Ile Arg Val Asn
    1445                1450                1455
Glu Lys Asp Val Leu Ile Ser Lys Ser Ser Ile Asn Phe Thr Val
    1460                1465                1470
Asn Cys Ser Trp Phe Ser Asp Thr Asn Gly Ala Val Lys Tyr Phe
    1475                1480                1485
Thr Val Val Val Arg Glu Ala Asp Gly Ser Asp Glu Leu Lys Pro
    1490                1495                1500
Glu Gln Gln His Pro Leu Pro Ser Tyr Leu Glu Tyr Arg His Asn
    1505                1510                1515
Ala Ser Ile Arg Val Tyr Gln Thr Asn Tyr Phe Ala Ser Lys Cys
    1520                1525                1530
Ala Glu Asn Pro Asn Ser Asn Ser Lys Ser Phe Asn Ile Lys Leu
    1535                1540                1545
Gly Ala Glu Met Glu Ser Leu Gly Gly Lys Arg Asp Pro Thr Gln
    1550                1555                1560
Gln Lys Phe Cys Asp Gly Pro Leu Lys Pro His Thr Ala Tyr Arg
    1565                1570                1575
Ile Ser Ile Arg Ala Phe Thr Gln Leu Phe Asp Glu Asp Leu Lys
    1580                1585                1590
Glu Phe Thr Lys Pro Leu Tyr Ser Asp Thr Phe Phe Ser Leu Pro
    1595                1600                1605
Ile Thr Thr Glu Ser Glu Pro Leu Phe Gly Ala Ile Glu Gly Val
    1610                1615                1620
Ser Ala Gly Leu Phe Leu Ile Gly Met Leu Val Ala Val Val Ala
    1625                1630                1635
Leu Leu Ile Cys Arg Gln Lys Val Ser His Gly Arg Glu Arg Pro
    1640                1645                1650
Ser Ala Arg Leu Ser Ile Arg Arg Asp Arg Pro Leu Ser Val His
    1655                1660                1665
Leu Asn Leu Gly Gln Lys Gly Asn Arg Lys Thr Ser Cys Pro Ile
    1670                1675                1680
Lys Ile Asn Gln Phe Glu Gly His Phe Met Lys Leu Gln Ala Asp
    1685                1690                1695
Ser Asn Tyr Leu Leu Ser Lys Glu Tyr Glu Glu Leu Lys Asp Val
    1700                1705                1710
Gly Arg Asn Gln Ser Cys Asp Ile Ala Leu Leu Pro Glu Asn Arg
    1715                1720                1725
```

```
Gly Lys Asn Arg Tyr Asn Asn Ile Leu Pro Tyr Asp Ala Thr Arg
    1730                1735                1740

Val Lys Leu Ser Asn Val Asp Asp Pro Cys Ser Asp Tyr Ile
    1745                1750                1755

Asn Ala Ser Tyr Ile Pro Gly Asn Asn Phe Arg Arg Glu Tyr Ile
    1760                1765                1770

Val Thr Gln Gly Pro Leu Pro Gly Thr Lys Asp Asp Phe Trp Lys
    1775                1780                1785

Met Val Trp Glu Gln Asn Val His Asn Ile Val Met Val Thr Gln
    1790                1795                1800

Cys Val Glu Lys Gly Arg Val Lys Cys Asp His Tyr Trp Pro Ala
    1805                1810                1815

Asp Gln Asp Ser Leu Tyr Tyr Gly Asp Leu Ile Leu Gln Met Leu
    1820                1825                1830

Ser Glu Ser Val Leu Pro Glu Trp Thr Ile Arg Glu Phe Lys Ile
    1835                1840                1845

Cys Gly Glu Glu Gln Leu Asp Ala His Arg Leu Ile Arg His Phe
    1850                1855                1860

His Tyr Thr Val Trp Pro Asp His Gly Val Pro Glu Thr Thr Gln
    1865                1870                1875

Ser Leu Ile Gln Phe Val Arg Thr Val Arg Asp Tyr Ile Asn Arg
    1880                1885                1890

Ser Pro Gly Ala Gly Pro Thr Val Val His Cys Ser Ala Gly Val
    1895                1900                1905

Gly Arg Thr Gly Thr Phe Ile Ala Leu Asp Arg Ile Leu Gln Gln
    1910                1915                1920

Leu Asp Ser Lys Asp Ser Val Asp Ile Tyr Gly Ala Val His Asp
    1925                1930                1935

Leu Arg Leu His Arg Val His Met Val Gln Thr Glu Cys Gln Tyr
    1940                1945                1950

Val Tyr Leu His Gln Cys Val Arg Asp Val Leu Arg Ala Arg Lys
    1955                1960                1965

Leu Arg Ser Glu Gln Glu Asn Pro Leu Phe Pro Ile Tyr Glu Asn
    1970                1975                1980

Val Asn Pro Glu Tyr His Arg Asp Pro Val Tyr Ser Arg His
    1985                1990                1995

<210> SEQ ID NO 3
<211> LENGTH: 1011
<212> TYPE: DNA
<213> ORGANISM: Homo sapiens
<220> FEATURE:
<221> NAME/KEY: CDS
<222> LOCATION: (1)..(1011)

<400> SEQUENCE: 3 gat cga cca tta tct gtc cac tta aac ctg ggc cag aaa ggt aac cgg        48
Asp Arg Pro Leu Ser Val His Leu Asn Leu Gly Gln Lys Gly Asn Arg
1               5                   10                  15 aaa act tct tgt cca ata aaa ata aat cag ttt gaa ggg cat ttc atg        96
Lys Thr Ser Cys Pro Ile Lys Ile Asn Gln Phe Glu Gly His Phe Met
                20                  25                  30 aag cta cag gct gac tcc aac tac ctt cta tcc aag gaa tac gag gag       144
Lys Leu Gln Ala Asp Ser Asn Tyr Leu Leu Ser Lys Glu Tyr Glu Glu
            35                  40                  45 tta aaa gac gtg ggc cga aac cag tca tgt gac att gca ctc ttg ccg       192
Leu Lys Asp Val Gly Arg Asn Gln Ser Cys Asp Ile Ala Leu Leu Pro
```

```
                50                  55                  60
gag aat aga ggg aaa aat cga tac aac aat ata ttg ccc tat gat gcc        240
Glu Asn Arg Gly Lys Asn Arg Tyr Asn Asn Ile Leu Pro Tyr Asp Ala
 65                  70                  75                  80 acg cga gtg aag ctc tcc aat gta gat gat gat cct tgc tct gac tac        288
Thr Arg Val Lys Leu Ser Asn Val Asp Asp Asp Pro Cys Ser Asp Tyr
                     85                  90                  95 atc aat gcc agc tac atc cct ggc aac aac ttc aga aga gaa tac att        336
Ile Asn Ala Ser Tyr Ile Pro Gly Asn Asn Phe Arg Arg Glu Tyr Ile
                100                 105                 110 gtc act cag gga ccg ctt cct ggc acc aag gat gac ttc tgg aaa atg        384
Val Thr Gln Gly Pro Leu Pro Gly Thr Lys Asp Asp Phe Trp Lys Met
            115                 120                 125 gtg tgg gaa caa aac gtt cac aac atc gtc atg gtg acc cag tgt gtt        432
Val Trp Glu Gln Asn Val His Asn Ile Val Met Val Thr Gln Cys Val
        130                 135                 140 gag aag ggc cga gta aag tgt gac cat tac tgg cca gcg gac cag gat        480
Glu Lys Gly Arg Val Lys Cys Asp His Tyr Trp Pro Ala Asp Gln Asp
145                 150                 155                 160 tcc ctc tac tat ggg gac ctc atc ctg cag atg ctc tca gag tcc gtc        528
Ser Leu Tyr Tyr Gly Asp Leu Ile Leu Gln Met Leu Ser Glu Ser Val
                165                 170                 175 ctg cct gag tgg acc atc cgg gag ttt aag ata tgc ggt gag gaa cag        576
Leu Pro Glu Trp Thr Ile Arg Glu Phe Lys Ile Cys Gly Glu Glu Gln
            180                 185                 190 ctt gat gca cac aga ctc atc cgc cac ttt cac tat acg gtg tgg cca        624
Leu Asp Ala His Arg Leu Ile Arg His Phe His Tyr Thr Val Trp Pro
        195                 200                 205 gac cat gga gtc cca gaa acc acc cag tct ctg atc cag ttt gtg aga        672
Asp His Gly Val Pro Glu Thr Thr Gln Ser Leu Ile Gln Phe Val Arg
    210                 215                 220 act gtc agg gac tac atc aac aga agc ccg ggt gct ggg ccc act gtg        720
Thr Val Arg Asp Tyr Ile Asn Arg Ser Pro Gly Ala Gly Pro Thr Val
225                 230                 235                 240 gtg cac tgc agt gct ggt gtg ggt agg act gga acc ttt att gca ttg        768
Val His Cys Ser Ala Gly Val Gly Arg Thr Gly Thr Phe Ile Ala Leu
                245                 250                 255 gac cga atc ctc cag cag tta gac tcc aaa gac tct gtg gac att tat        816
Asp Arg Ile Leu Gln Gln Leu Asp Ser Lys Asp Ser Val Asp Ile Tyr
            260                 265                 270 gga gca gtg cac gac cta aga ctt cac agg gtt cac atg gtc cag act        864
Gly Ala Val His Asp Leu Arg Leu His Arg Val His Met Val Gln Thr
        275                 280                 285 gag tgt cag tat gtc tac cta cat cag tgt gta aga gat gtc ctc aga        912
Glu Cys Gln Tyr Val Tyr Leu His Gln Cys Val Arg Asp Val Leu Arg
    290                 295                 300 gca aga aag cta cgg agt gaa caa gaa aac ccc ttg ttt cca atc tat        960
Ala Arg Lys Leu Arg Ser Glu Gln Glu Asn Pro Leu Phe Pro Ile Tyr
305                 310                 315                 320 gaa aat gtg aat cca gag tat cac aga gat cca gtc tat tca agg cat       1008
Glu Asn Val Asn Pro Glu Tyr His Arg Asp Pro Val Tyr Ser Arg His
                325                 330                 335 tga                                                                    1011

<210> SEQ ID NO 4
<211> LENGTH: 336
<212> TYPE: PRT
<213> ORGANISM: Homo sapiens

<400> SEQUENCE: 4
```

```
Asp Arg Pro Leu Ser Val His Leu Asn Leu Gly Gln Lys Gly Asn Arg
1               5                   10                  15

Lys Thr Ser Cys Pro Ile Lys Ile Asn Gln Phe Glu Gly His Phe Met
            20                  25                  30

Lys Leu Gln Ala Asp Ser Asn Tyr Leu Leu Ser Lys Glu Tyr Glu Glu
        35                  40                  45

Leu Lys Asp Val Gly Arg Asn Gln Ser Cys Asp Ile Ala Leu Leu Pro
    50                  55                  60

Glu Asn Arg Gly Lys Asn Arg Tyr Asn Ile Leu Pro Tyr Asp Ala
65                  70                  75                  80

Thr Arg Val Lys Leu Ser Asn Val Asp Asp Pro Cys Ser Asp Tyr
                85                  90                  95

Ile Asn Ala Ser Tyr Ile Pro Gly Asn Asn Phe Arg Arg Glu Tyr Ile
            100                 105                 110

Val Thr Gln Gly Pro Leu Pro Gly Thr Lys Asp Asp Phe Trp Lys Met
        115                 120                 125

Val Trp Glu Gln Asn Val His Asn Ile Val Met Val Thr Gln Cys Val
    130                 135                 140

Glu Lys Gly Arg Val Lys Cys Asp His Tyr Trp Pro Ala Asp Gln Asp
145                 150                 155                 160

Ser Leu Tyr Tyr Gly Asp Leu Ile Leu Gln Met Leu Ser Glu Ser Val
                165                 170                 175

Leu Pro Glu Trp Thr Ile Arg Glu Phe Lys Ile Cys Gly Glu Glu Gln
            180                 185                 190

Leu Asp Ala His Arg Leu Ile Arg His Phe His Tyr Thr Val Trp Pro
        195                 200                 205

Asp His Gly Val Pro Glu Thr Thr Gln Ser Leu Ile Gln Phe Val Arg
    210                 215                 220

Thr Val Arg Asp Tyr Ile Asn Arg Ser Pro Gly Ala Gly Pro Thr Val
225                 230                 235                 240

Val His Cys Ser Ala Gly Val Gly Arg Thr Gly Thr Phe Ile Ala Leu
                245                 250                 255

Asp Arg Ile Leu Gln Gln Leu Asp Ser Lys Asp Ser Val Asp Ile Tyr
            260                 265                 270

Gly Ala Val His Asp Leu Arg Leu His Arg Val His Met Val Gln Thr
        275                 280                 285

Glu Cys Gln Tyr Val Tyr Leu His Gln Cys Val Arg Asp Val Leu Arg
    290                 295                 300

Ala Arg Lys Leu Arg Ser Glu Gln Glu Asn Pro Leu Phe Pro Ile Tyr
305                 310                 315                 320

Glu Asn Val Asn Pro Glu Tyr His Arg Asp Pro Val Tyr Ser Arg His
                325                 330                 335
```

<210> SEQ ID NO 5
<211> LENGTH: 936
<212> TYPE: DNA
<213> ORGANISM: Homo sapiens
<220> FEATURE:
<221> NAME/KEY: CDS
<222> LOCATION: (1)..(936)

<400> SEQUENCE: 5

```
gat cga cca tta tct gtc cac tta aac ctg ggc cag aaa ggt aac cgg    48
Asp Arg Pro Leu Ser Val His Leu Asn Leu Gly Gln Lys Gly Asn Arg
1               5                   10                  15
```

```
aaa act tct tgt cca ata aaa ata aat cag ttt gaa ggg cat ttc atg      96
Lys Thr Ser Cys Pro Ile Lys Ile Asn Gln Phe Glu Gly His Phe Met
         20                  25                  30 aag cta cag gct gac tcc aac tac ctt cta tcc aag gaa tac gag gag     144
Lys Leu Gln Ala Asp Ser Asn Tyr Leu Leu Ser Lys Glu Tyr Glu Glu
 35                  40                  45 tta aaa gac gtg ggc cga aac cag tca tgt gac att gca ctc ttg ccg     192
Leu Lys Asp Val Gly Arg Asn Gln Ser Cys Asp Ile Ala Leu Leu Pro
     50                  55                  60 gag aat aga ggg aaa aat cga tac aac aat ata ttg ccc tat gat gcc     240
Glu Asn Arg Gly Lys Asn Arg Tyr Asn Asn Ile Leu Pro Tyr Asp Ala
 65                  70                  75                  80 acg cga gtg aag ctc tcc aat gta gat gat gat cct tgc tct gac tac     288
Thr Arg Val Lys Leu Ser Asn Val Asp Asp Asp Pro Cys Ser Asp Tyr
                 85                  90                  95 atc aat gcc agc tac atc cct ggc aac aac ttc aga aga gaa tac att     336
Ile Asn Ala Ser Tyr Ile Pro Gly Asn Asn Phe Arg Arg Glu Tyr Ile
            100                 105                 110 gtc act cag gga ccg ctt cct ggc acc aag gat gac ttc tgg aaa atg     384
Val Thr Gln Gly Pro Leu Pro Gly Thr Lys Asp Asp Phe Trp Lys Met
        115                 120                 125 gtg tgg gaa caa aac gtt cac aac atc gtc atg gtg acc cag tgt gtt     432
Val Trp Glu Gln Asn Val His Asn Ile Val Met Val Thr Gln Cys Val
130                 135                 140 gag aag ggc cga gta aag tgt gac cat tac tgg cca gcg gac cag gat     480
Glu Lys Gly Arg Val Lys Cys Asp His Tyr Trp Pro Ala Asp Gln Asp
145                 150                 155                 160 tcc ctc tac tat ggg gac ctc atc ctg cag atg ctc tca gag tcc gtc     528
Ser Leu Tyr Tyr Gly Asp Leu Ile Leu Gln Met Leu Ser Glu Ser Val
                165                 170                 175 ctg cct gag tgg acc atc cgg gag ttt aag ata tgc ggt gag gaa cag     576
Leu Pro Glu Trp Thr Ile Arg Glu Phe Lys Ile Cys Gly Glu Glu Gln
            180                 185                 190 ctt gat gca cac aga ctc atc cgc cac ttt cac tat acg gtg tgg cca     624
Leu Asp Ala His Arg Leu Ile Arg His Phe His Tyr Thr Val Trp Pro
        195                 200                 205 gac cat gga gtc cca gaa acc acc cag tct ctg atc cag ttt gtg aga     672
Asp His Gly Val Pro Glu Thr Thr Gln Ser Leu Ile Gln Phe Val Arg
    210                 215                 220 act gtc agg gac tac atc aac aga agc ccg ggt gct ggg ccc act gtg     720
Thr Val Arg Asp Tyr Ile Asn Arg Ser Pro Gly Ala Gly Pro Thr Val
225                 230                 235                 240 gtg cac tgc agt gct ggt gtg ggt agg act gga acc ttt att gca ttg     768
Val His Cys Ser Ala Gly Val Gly Arg Thr Gly Thr Phe Ile Ala Leu
                245                 250                 255 gac cga atc ctc cag cag tta gac tcc aaa gac tct gtg gac att tat     816
Asp Arg Ile Leu Gln Gln Leu Asp Ser Lys Asp Ser Val Asp Ile Tyr
            260                 265                 270 gga gca gtg cac gac cta aga ctt cac agg gtt cac atg gtc cag act     864
Gly Ala Val His Asp Leu Arg Leu His Arg Val His Met Val Gln Thr
        275                 280                 285 gag tgt cag tat gtc tac cta cat cag tgt gta aga gat gtc ctc aga     912
Glu Cys Gln Tyr Val Tyr Leu His Gln Cys Val Arg Asp Val Leu Arg
    290                 295                 300 gca aga aag cta cgg agt gaa caa                                     936
Ala Arg Lys Leu Arg Ser Glu Gln
305                 310

<210> SEQ ID NO 6
<211> LENGTH: 312
```

```
<212> TYPE: PRT
<213> ORGANISM: Homo sapiens

<400> SEQUENCE: 6

Asp Arg Pro Leu Ser Val His Leu Asn Leu Gly Gln Lys Gly Asn Arg
1               5                   10                  15

Lys Thr Ser Cys Pro Ile Lys Ile Asn Gln Phe Glu Gly His Phe Met
            20                  25                  30

Lys Leu Gln Ala Asp Ser Asn Tyr Leu Leu Ser Lys Glu Tyr Glu Glu
        35                  40                  45

Leu Lys Asp Val Gly Arg Asn Gln Ser Cys Asp Ile Ala Leu Leu Pro
50                  55                  60

Glu Asn Arg Gly Lys Asn Arg Tyr Asn Asn Ile Leu Pro Tyr Asp Ala
65                  70                  75                  80

Thr Arg Val Lys Leu Ser Asn Val Asp Asp Asp Pro Cys Ser Asp Tyr
                85                  90                  95

Ile Asn Ala Ser Tyr Ile Pro Gly Asn Asn Phe Arg Arg Glu Tyr Ile
            100                 105                 110

Val Thr Gln Gly Pro Leu Pro Gly Thr Lys Asp Asp Phe Trp Lys Met
        115                 120                 125

Val Trp Glu Gln Asn Val His Asn Ile Val Met Val Thr Gln Cys Val
130                 135                 140

Glu Lys Gly Arg Val Lys Cys Asp His Tyr Trp Pro Ala Asp Gln Asp
145                 150                 155                 160

Ser Leu Tyr Tyr Gly Asp Leu Ile Leu Gln Met Leu Ser Glu Ser Val
                165                 170                 175

Leu Pro Glu Trp Thr Ile Arg Glu Phe Lys Ile Cys Gly Glu Glu Gln
            180                 185                 190

Leu Asp Ala His Arg Leu Ile Arg His Phe His Tyr Thr Val Trp Pro
        195                 200                 205

Asp His Gly Val Pro Glu Thr Thr Gln Ser Leu Ile Gln Phe Val Arg
210                 215                 220

Thr Val Arg Asp Tyr Ile Asn Arg Ser Pro Gly Ala Gly Pro Thr Val
225                 230                 235                 240

Val His Cys Ser Ala Gly Val Gly Arg Thr Gly Thr Phe Ile Ala Leu
                245                 250                 255

Asp Arg Ile Leu Gln Gln Leu Asp Ser Lys Asp Ser Val Asp Ile Tyr
            260                 265                 270

Gly Ala Val His Asp Leu Arg Leu His Arg Val His Met Val Gln Thr
        275                 280                 285

Glu Cys Gln Tyr Val Tyr Leu His Gln Cys Val Arg Asp Val Leu Arg
290                 295                 300

Ala Arg Lys Leu Arg Ser Glu Gln
305                 310

<210> SEQ ID NO 7
<211> LENGTH: 319
<212> TYPE: PRT
<213> ORGANISM: Homo sapiens

<400> SEQUENCE: 7

Gly Asp Arg Pro Leu Ser Val His Leu Asn Leu Gly Gln Lys Gly Asn
1               5                   10                  15

Arg Lys Thr Ser Cys Pro Ile Lys Ile Asn Gln Phe Glu Gly His Phe
            20                  25                  30
```

-continued

Met Lys Leu Gln Ala Asp Ser Asn Tyr Leu Leu Ser Lys Glu Tyr Glu
        35                  40                  45

Glu Leu Lys Asp Val Gly Arg Asn Gln Ser Cys Asp Ile Ala Leu Leu
    50                  55                  60

Pro Glu Asn Arg Gly Lys Asn Arg Tyr Asn Asn Ile Leu Pro Tyr Asp
65                  70                  75                  80

Ala Thr Arg Val Lys Leu Ser Asn Val Asp Asp Pro Cys Ser Asp
                85                  90                  95

Tyr Ile Asn Ala Ser Tyr Ile Pro Gly Asn Asn Phe Arg Arg Glu Tyr
                100                 105                 110

Ile Val Thr Gln Gly Pro Leu Pro Gly Thr Lys Asp Phe Trp Lys
                115                 120                 125

Met Val Trp Glu Gln Asn Val His Asn Ile Val Met Val Thr Gln Cys
        130                 135                 140

Val Glu Lys Gly Arg Val Lys Cys Asp His Tyr Trp Pro Ala Asp Gln
145                 150                 155                 160

Asp Ser Leu Tyr Tyr Gly Asp Leu Ile Leu Gln Met Leu Ser Glu Ser
                165                 170                 175

Val Leu Pro Glu Trp Thr Ile Arg Glu Phe Lys Ile Cys Gly Glu Glu
                180                 185                 190

Gln Leu Asp Ala His Arg Leu Ile Arg His Phe His Tyr Thr Val Trp
                195                 200                 205

Pro Asp His Gly Val Pro Glu Thr Thr Gln Ser Leu Ile Gln Phe Val
        210                 215                 220

Arg Thr Val Arg Asp Tyr Ile Asn Arg Ser Pro Gly Ala Gly Pro Thr
225                 230                 235                 240

Val Val His Cys Ser Ala Gly Val Gly Arg Thr Gly Thr Phe Ile Ala
                245                 250                 255

Leu Asp Arg Ile Leu Gln Gln Leu Asp Ser Lys Asp Ser Val Asp Ile
                260                 265                 270

Tyr Gly Ala Val His Asp Leu Arg Leu His Arg Val His Met Val Gln
        275                 280                 285

Thr Glu Cys Gln Tyr Val Tyr Leu His Gln Cys Val Arg Asp Val Leu
        290                 295                 300

Arg Ala Arg Lys Leu Arg Ser Glu Gln His His His His
305                 310                 315

<210> SEQ ID NO 8
<211> LENGTH: 21
<212> TYPE: DNA
<213> ORGANISM: Homo spaiens

<400> SEQUENCE: 8
gatcgaccat tatctgtcca c                                          21

<210> SEQ ID NO 9
<211> LENGTH: 20
<212> TYPE: DNA
<213> ORGANISM: Homo sapiens

<400> SEQUENCE: 9
caggagctct tcaggtacat                                            20

<210> SEQ ID NO 10
<211> LENGTH: 31
<212> TYPE: DNA
<213> ORGANISM: Homo sapiens

```
-continued

<400> SEQUENCE: 10
cgagcatacg tagatcgacc attatctgtc c                              31

<210> SEQ ID NO 11
<211> LENGTH: 31
<212> TYPE: DNA
<213> ORGANISM: Homo sapiens

<400> SEQUENCE: 11
cgagcaagct tattattgtt cactccgtag c                              31

<210> SEQ ID NO 12
<211> LENGTH: 56
<212> TYPE: DNA
<213> ORGANISM: Homo sapiens

<400> SEQUENCE: 12
gaaagctacg gagtgaacaa catcatcatc atcatcatta ataagcttgg cactgg    56

<210> SEQ ID NO 13
<211> LENGTH: 56
<212> TYPE: DNA
<213> ORGANISM: Homo sapiens

<400> SEQUENCE: 13
ccagtgccaa gcttattaat gatgatgatg atgatgttgt tcactccgta gctttc    56

<210> SEQ ID NO 14
<211> LENGTH: 52
<212> TYPE: DNA
<213> ORGANISM: Homo sapiens

<400> SEQUENCE: 14
aacaacaacc tcggggagaa tctttatttt cagggcgatc gaccattatc tg        52

<210> SEQ ID NO 15
<211> LENGTH: 52
<212> TYPE: DNA
<213> ORGANISM: Homo sapiens

<400> SEQUENCE: 15
cagataatgg tcgatcgccc tgaaaataaa gattctcccc gaggttgttg tt        52
```